(12) United States Patent
Njoroge et al.

(10) Patent No.: US 7,592,316 B2
(45) Date of Patent: Sep. 22, 2009

(54) PEPTIDES AS NS3-SERINE PROTEASE INHIBITORS OF HEPATITIS C VIRUS

(75) Inventors: F. George Njoroge, Warren, NJ (US); Ashok Arasappan, Bridgewater, NJ (US); Srikanth Venkatraman, Woodbridge, NJ (US); Stephane L. Bogen, Somerset, NJ (US); Kevin X. Chen, Edison, NJ (US); Frank Bennett, Cranford, NJ (US)

(73) Assignee: Schering Corporation, Kenilworth, NJ (US)

( * ) Notice: Subject to any disclaimer, the term of this patent is extended or adjusted under 35 U.S.C. 154(b) by 83 days.

(21) Appl. No.: 11/714,457

(22) Filed: Mar. 6, 2007

(65) Prior Publication Data

US 2007/0232549 A1 Oct. 4, 2007

Related U.S. Application Data

(60) Division of application No. 10/052,386, filed on Jan. 18, 2002, now Pat. No. 7,244,721, which is a continuation-in-part of application No. 09/908,955, filed on Jul. 19, 2001, now Pat. No. 7,012,066.

(60) Provisional application No. 60/220,108, filed on Jul. 21, 2000.

(51) Int. Cl.
*A61K 38/06* (2006.01)

(52) U.S. Cl. .......................................... 514/18; 530/331
(58) Field of Classification Search ................... 514/18; 530/331

See application file for complete search history.

(56) References Cited

U.S. PATENT DOCUMENTS

| | | | | |
|---|---|---|---|---|
| 5,162,500 A | * | 11/1992 | Takeuchi et al. | 530/330 |
| 5,359,138 A | * | 10/1994 | Takeuchi et al. | 562/567 |
| 5,488,067 A | * | 1/1996 | Hanson | 514/618 |
| 5,496,927 A | * | 3/1996 | Kolb et al. | 530/328 |
| 5,514,694 A | * | 5/1996 | Powers et al. | 514/19 |
| 5,633,388 A | * | 5/1997 | Diana et al. | 548/305.7 |
| 5,739,002 A | * | 4/1998 | De Francesco et al. | 435/23 |
| 5,763,576 A | * | 6/1998 | Powers | 530/330 |
| 5,843,450 A | * | 12/1998 | Dawson et al. | 424/189.1 |
| 5,843,752 A | * | 12/1998 | Dasmahapatra et al. | 435/219 |
| 5,849,866 A | * | 12/1998 | Kolb et al. | 530/323 |
| 5,854,001 A | * | 12/1998 | Casey et al. | 435/7.1 |
| 6,265,380 B1 | * | 7/2001 | Tung et al. | 514/17 |

* cited by examiner

*Primary Examiner*—David Lukton
(74) *Attorney, Agent, or Firm*—Palaiyur S. Kalyanaraman

(57) ABSTRACT

The present invention discloses novel compounds which have HCV protease inhibitory activity as well as methods for preparing such compounds. In another embodiment, the invention discloses pharmaceutical compositions comprising such compounds as well as methods of using them to treat disorders associated with the HCV protease.

6 Claims, No Drawings

PEPTIDES AS NS3-SERINE PROTEASE INHIBITORS OF HEPATITIS C VIRUS

RELATED APPLICATIONS

This application is a divisional of application Ser. No. 10/052,386 filed Jan. 18, 2002, now U.S. Pat. No. 7,244,721, and herein incorporated by reference, which is a continuation-in-part of application Ser. No. 09/908,955 filed Jul. 19, 2001 and now U.S. Pat. No. 7,012,066, which claims priority to U.S. provisional patent application, Ser. No. 60/220,108 filed Jul. 21, 2000.

FIELD OF INVENTION

The present invention relates to novel hepatitis C virus ("HCV") protease inhibitors, pharmaceutical compositions containing one or more such inhibitors, methods of preparing such inhibitors and methods of using such inhibitors to treat hepatitis C and related disorders. This invention specifically discloses novel peptide compounds as inhibitors of the HCV NS3/NS4a serine protease. Priority for the invention is based on U.S. patent applications Ser. No. 60/220,108 filed Jul. 21, 2000, and Ser. No. 09/908,955 filed Jul. 19, 2001.

BACKGROUND OF THE INVENTION

Hepatitis C virus (HCV) is a (+)-sense single-stranded RNA virus that has been implicated as the major causative agent in non-A, non-B hepatitis (NANBH), particularly in blood-associated NANBH (BB-NANBH)(see, International Patent Application Publication No. WO 89/04669 and European Patent Application Publication No. EP 381 216). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliary cirrhosis.

Recently, an HCV protease necessary for polypeptide processing and viral replication has been identified, cloned and expressed; (see, e.g., U.S. Pat. No. 5,712,145). This approximately 3000 amino acid polyprotein contains, from the amino terminus to the carboxy terminus, a nucleocapsid protein (C), envelope proteins (E1 and E2) and several non-structural proteins (NS1, 2, 3, 4a, 5a and 5b). NS3 is an approximately 68 kda protein, encoded by approximately 1893 nucleotides of the HCV genome, and has two distinct domains: (a) a serine protease domain consisting of approximately 200 of the N-terminal amino acids; and (b) an RNA-dependent ATPase domain at the C-terminus of the protein. The NS3 protease is considered a member of the chymotrypsin family because of similarities in protein sequence, overall three-dimensional structure and mechanism of catalysis. Other chymotrypsin-like enzymes are elastase, factor Xa, thrombin, trypsin, plasmin, urokinase, tPA and PSA. The HCV NS3 serine protease is responsible for proteolysis of the polypeptide (polyprotein) at the NS3/NS4a, NS4a/NS4b, NS4b/NS5a and NS5a/NS5b junctions and is thus responsible for generating four viral proteins during viral replication. This has made the HCV NS3 serine protease an attractive target for antiviral chemotherapy.

It has been determined that the NS4a protein, an approximately 6 kda polypeptide, is a co-factor for the serine protease activity of NS3. Autocleavage of the NS3/NS4a junction by the NS3/NS4a serine protease occurs intramolecularly (i.e., cis) while the other cleavage sites are processed intermolecularly (trans).

Analysis of the natural cleavage sites for HCV protease revealed the presence of cysteine at P1 and serine at P1' and that these residues are strictly conserved in the NS4a/NS4b, NS4b/NS5a and NS5a/NS5b junctions. The NS3/NS4a junction contains a threonine at P1 and a serine at P1'. The Cys→Thr substitution at NS3/NS4a is postulated to account for the requirement of cis rather than trans processing at this junction. See, e.g., Pizzi et al. (1994) *Proc. Natl. Acad. Sci. (USA)* 91:888-892, Failla et al. (1996) *Folding & Design* 1:35-42. The NS3/NS4a cleavage site is also more tolerant of mutagenesis than the other sites. See, e.g., Kollykhalov et al. (1994) *J. Virol.* 68:7525-7533. It has also been found that acidic residues in the region upstream of the cleavage site are required for efficient cleavage. See, e.g., Komoda et al. (1994) *J. Virol.* 68:7351-7357.

Inhibitors of HCV protease that have been reported include antioxidants (see, International Patent Application Publication No. WO 98/14181), certain peptides and peptide analogs (see, International Patent Application Publication No. WO 98/17679, Landro et al. (1997) *Biochem.* 36:9340-9348, Ingallinella et al. (1998) *Biochem.* 37:8906-8914, Llinas-Brunet et al. (1998) *Bioorg. Med. Chem. Lett.* 8:1713-1718), inhibitors based on the 70-amino acid polypeptide eglin c (Martin et al. (1998) *Biochem.* 37:11459-11468, inhibitors affinity selected from human pancreatic secretory trypsin inhibitor (hPST1-C3) and minibody repertoires (MBip) (Dimasi et al. (1997) *J. Virol.* 71:7461-7469), $cV_HE2$ (a "camelized" variable domain antibody fragment) (Martin et al. (1997) *Protein Eng.* 10:607-614), and ct1-antichymotrypsin (ACT) (Elzouki et al.) (1997) *J. Hepat.* 27:42-28). A ribozyme designed to selectively destroy hepatitis C virus RNA has recently been disclosed (see, BioWorld Today 9(217): 4 (Nov. 10, 1998)).

Reference is also made to the PCT Publications, No. WO 98/17679, published Apr. 30, 1998 (Vertex Pharmaceuticals Incorporated); WO 98/22496, published May 28, 1998 (F. Hoffmann-La Roche AG); and WO 99/07734, published Feb. 18, 1999 (Boehringer Ingelheim Canada Ltd.).

HCV has been implicated in cirrhosis of the liver and in induction of hepatocellular carcinoma. The prognosis for patients suffering from HCV infection is currently poor. HCV infection is more difficult to treat than other forms of hepatitis due to the lack of immunity or remission associated with HCV infection. Current data indicates a less than 50% survival rate at four years post cirrhosis diagnosis. Patients diagnosed with localized resectable hepatocellular carcinoma have a five-year survival rate of 10-30%, whereas those with localized unresectable hepatocellular carcinoma have a five-year survival rate of less than 1%.

Reference is made to A. Marchetti et al, *Synlett*, S1, 1000-1002 (1999) describing the synthesis of bicylic analogs of an inhibitor of HCV NS3 protease. A compound disclosed therein has the formula:

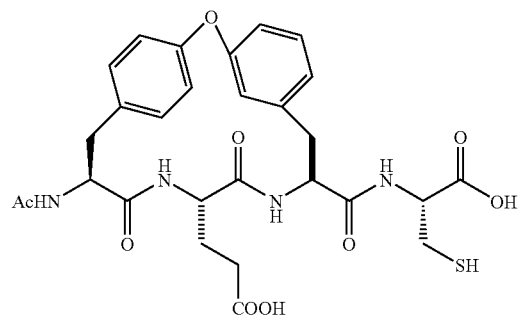

Reference is also made to W. Han et al, *Bioorganic & Medicinal Chem. Lett,* (2000) 10, 711-713, which describes the preparation of certain α-ketoamides, α-ketoesters and α-diketones containing allyl and ethyl functionalities.

Reference is also made to WO 00/09558 (Assignee: Boehringer Ingelheim Limited; Published Feb. 24, 2000) which discloses peptide derivatives of the formula:

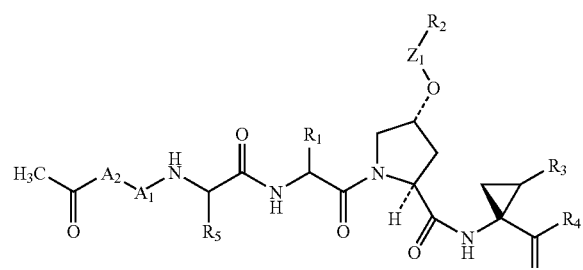

where the various elements are defined therein. An illustrative compound of that series is:

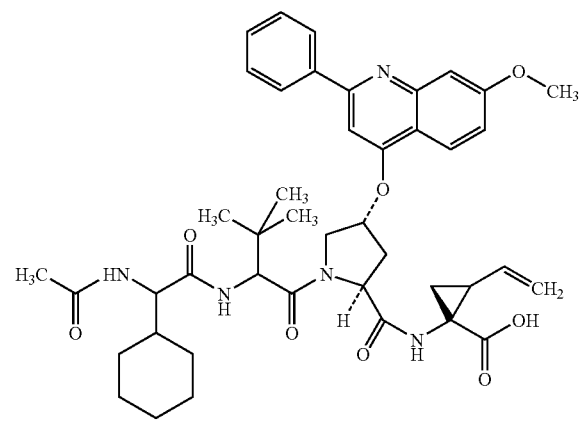

Reference is also made to WO 00/09543 (Assignee: Boehringer Ingelheim Limited; Published Feb. 24, 2000) which discloses peptide derivatives of the formula:

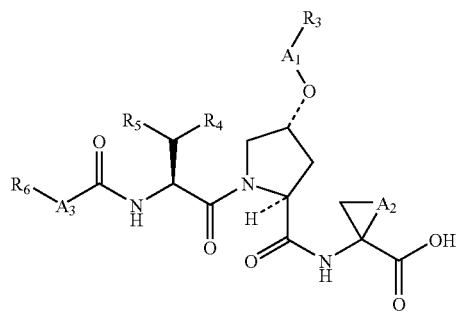

where the various elements are defined therein. An illustrative compound of that series is:

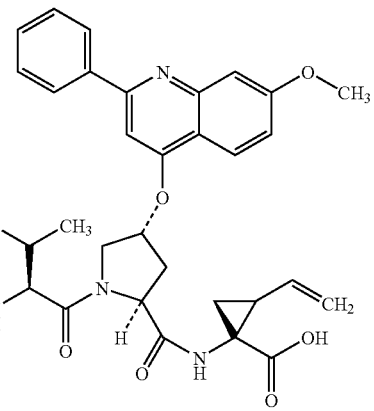

Current therapies for hepatitis C include interferon-α ($INF_\alpha$) and combination therapy with ribavirin and interferon. See, e.g. Beremguer et al. (1998) *Proc. Assoc. Am. Physicians* 110(2):98-112. These therapies suffer from a low sustained response rate and frequent side effects. See, e.g. Hoofnagle et al. (1997) *N. Engl. J. Med.* 336:347. Currently, no vaccine is available for HCV infection.

Pending and copending U.S. patent applications, Ser. No. 60/194,607, filed Apr. 5, 2000, and Ser. No. 60/198,204, filed Apr. 19, 2000, Ser. No. 60/220,110, filed Jul. 21, 2000, Ser. No. 60/220,109, filed Jul. 21, 2000, Ser. No. 60/220,107, filed Jul. 21, 2000, Ser. No. 60/254,869, filed Dec. 12, 2000, and Ser. No. 60/220,101, filed Jul. 21, 2000, disclose various types of peptides and/or other compounds as NS-3 serine protease inhibitors of hepatitis C virus.

There is a need for new treatments and therapies for HCV infection. It is, therefore, an object of this invention to provide compounds useful in the treatment or prevention or amelioration of one or more symptoms of hepatitis C.

It is a further object herein to provide methods of treatment or prevention or amelioration of one or more symptoms of hepatitis C.

A still further object of the present invention is to provide methods for modulating the activity of serine proteases, particularly the HCV NS3/NS4a serine protease, using the compounds provided herein.

Another object herein is to provide methods of modulating the processing of the HCV polypeptide using the compounds provided herein.

SUMMARY OF THE INVENTION

In its many embodiments, the present invention provides a novel class of inhibitors of the HCV protease, pharmaceutical compositions containing one or more of the compounds, methods of preparing pharmaceutical formulations comprising one or more such compounds, and methods of treatment, prevention or amelioration or one or more of the symptoms of hepatitis C. Also provided are methods of modulating the interaction of an HCV polypeptide with HCV protease. Among the compounds provided herein, compounds that inhibit HCV NS3/NS4a serine protease activity are preferred. The present application discloses a compound, including enantiomers, stereoisomers, rotamers, tautomers, racemates and prodrug of said compound, and pharmaceutically acceptable salts or solvates of said compound, or of said prodrug, said compound having the general structure shown in Formula I:

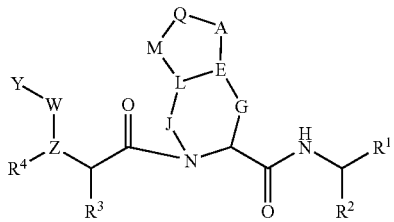

Formula I wherein:

Y is selected from the group consisting of the following moieties: alkyl, alkyl-aryl, heteroalkyl, heteroaryl, aryl-heteroaryl, alkyl-heteroaryl, cycloalkyl, alkyloxy, alkyl-aryloxy, aryloxy, heteroaryloxy, heterocycloalkyloxy, cycloalkyloxy, alkylamino, arylamino, alkyl-arylamino, arylamino, heteroarylamino, cycloalkylamino and heterocycloalkylamino, with the proviso that Y maybe optionally substituted with $X^{11}$ or $X^{12}$;

$X^{11}$ is alkyl, alkenyl, alkynyl, cycloalkyl, cycloalkyl-alkyl, heterocyclyl, heterocyclylalkyl, aryl, alkylaryl, arylalkyl, heteroaryl, alkylheteroaryl, or heteroarylalkyl, with the proviso that $X^{11}$ may be additionally optionally substituted with $X^{12}$;

$X^{12}$ is hydroxy, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, or nitro, with the proviso that said alkyl, alkoxy, and aryl may be additionally optionally substituted with moieties independently selected from $X^{12}$;

$R^1$ is $COR^5$ or $B(OR)_2$, wherein $R^5$ is H, OH, $OR^8$, $NR^9R^{10}$, $CF_3$, $C_2F_5$, $C_3F_7$, $CF_2R^5$, $R^6$, or $COR^7$ wherein $R^7$ is H, OH, $OR^8$, $CHR^9R^{10}$, or $NR^9R^{10}$, wherein $R^6$, $R^8$, $R^9$ and $R^{10}$ are independently selected from the group consisting of H, alkyl, aryl, heteroalkyl, heteroaryl, cycloalkyl, cycloalkyl, arylalkyl, heteroarylalkyl, $[CH(R^{1'})]_p COOR^{11}$, $[CH(R^{1'})]_p CONR^{12}R^{13}$, $[CH(R^{1'})]_p SO_2R^{11}$, $[CH(R^{1'})]_p COR^{11}$, $[CH(R^{1'})]_p CH(OH)R^{11}$, $CH(R^{1'})CONHCH(R^{2'})COO\ R^{11}$, $CH(R^{1'})CONHCH(R^{2'})CONR^{12}R^{13}$, $CH(R^{1'})CONHCH(R^{2'})R'$, $CH(R^{1'})CONHCH(R^{2'})CONHCH(R^{3'})COO\ R^{11}$, $CH(R^{1'})CONHCH(R^{2'})CONHCH(R^{3'})CONR^{12}R^{13}$, $CH(R^{1'})CONHCH(R^{2'})CONHCH(R^{3'})CONHCH(R^{4'})COO\ R^{11}$, $CH(R^{1'})CONHCH(R^{2'})CONHCH(R^{3'})CONHCH(R^{4'})CONR^{12}R^{13}$, $CH(R^{1'})CONHCH(R^{2'})CONHCH(R^{3'})CONHCH(R^{4'})CONHCH(R^{5'})COO\ R^{11}$ and $CH(R^{1'})CONHCH(R^{2'})CONHCH(R^{3'})CONHCH(R^{4'})CONHCH(R^{5'})\ CONR^{12}R^{13}$, wherein $R^{1'}$, $R^{2'}$, $R^{3'}$, $R^{4'}$ $R^{5'}$, $R^{11}$, $R^{12}$, $R^{13}$, and $R'$ are independently selected from the group consisting of H, alkyl, aryl, heteroalkyl, heteroaryl, cycloalkyl, alkyl-aryl, alkyl-heteroaryl, aryl-alkyl and heteroaralkyl;

Z is selected from O, N, CH or CR;

W may be present or absent, and if W is present, W is selected from C=O, C=S, C(=N—CN), or $SO_2$;

Q may be present or absent, and when Q is present, Q is CH, N, P, $(CH_2)_p$, $(CHR)_p$, $(CRR')_p$, O, NR, S, or $SO_2$; and when Q is absent, M may be present or absent; when Q and M are absent, A is directly linked to L;

A is O, $CH_2$, $(CHR)_p$, $(CHR—CHR')_p$, $(CRR')_p$, NR, S, $SO_2$ or a bond;

E is CH, N, CR, or a double bond towards A, L or G;

G may be present or absent, and when G is present, G is $(CH_2)_p$, $(CHR)_p$, or $(CRR')_p$; and when G is absent, J is present and E is directly connected to the carbon atom in Formula I as G is linked to;

J maybe present or absent, and when J is present, J is $(CH_2)_p$, (CHR) p, or $(CRR')_p$, $SO_2$, NH, NR or O; and when J is absent, G is present and E is directly linked to N shown in Formula I as linked to J;

L may be present or absent, and when L is present, L is CH, CR, O, S or NR; and when L is absent, then M may be present or absent; and if M is present with L being absent, then M is directly and independently linked to E, and J is directly and independently linked to E;

M may be present or absent, and when M is present, M is O, NR, S, $SO_2$, $(CH_2)$ p, $(CHR)_p (CHR—CHR')_p$, or $(CRR')_p$;

p is a number from 0 to 6; and

R, $R^1$, $R^2$, $R^3$ and $R^4$ are independently selected from the group consisting of H; $C_1$-$C_{10}$ alkyl; $C_2$-$C_{10}$ alkenyl; $C_3$-$C_8$ cycloalkyl; $C_3$-$C_8$ heterocycloalkyl, alkoxy, aryloxy, alkylthio, arylthio, amino, amido, ester, carboxylic acid, carbamate, urea, ketone, aldehyde, cyano, nitro, halogen; (cycloalkyl)alkyl and (heterocycloalkyl)alkyl, wherein said cycloalkyl is made of three to eight carbon atoms, and zero to six oxygen, nitrogen, sulfur, or phosphorus atoms, and said alkyl is of one to six carbon atoms; aryl; heteroaryl; alkyl-aryl; and alkyl-heteroaryl;

wherein said alkyl, heteroalkyl, alkenyl, heteroalkenyl, aryl, heteroaryl, cycloalkyl and heterocycloalkyl moieties may be optionally and chemically-suitably substituted, with said term "substituted" referring to optional and chemically-suitable substitution with one or more moieties selected from the group consisting of alkyl, alkenyl, alkynyl, aryl, aralkyl, cycloalkyl, heterocyclic, halogen, hydroxy, thio, alkoxy, aryloxy, alkylthio, arylthio, amino, amido, ester, carboxylic acid, carbamate, urea, ketone, aldehyde, cyano, nitro, sulfonamido, sulfoxide, sulfone, sulfonyl urea, hydrazide, and hydroxamate; further wherein said unit N-C-G-E-L-J-N represents a five-membered or six-membered cyclic ring structure with the proviso that when said unit N-C-G-E-L-J-N represents a five-membered cyclic ring structure, or when the bicyclic ring structure in Formula I comprising N, C, G, E, L, J, N, A, Q, and M represents a five-membered cyclic ring structure, then said five-membered cyclic ring structure lacks a carbonyl group as part of the cyclic ring.

Among the above-stated definitions for the various moieties of Formula I, the preferred groups for the various moieties are as follows: Preferred definition for $R^1$ is $COR^5$ with $R^5$ being H, OH, $COOR^8$ or $CONR^9R^{10}$, where $R^8$, $R^9$ and $R^{10}$ are defined above. Still preferred moiety for $R^1$ is $COCONR^9R^{10}$, where $R^9$ is H; and $R^{10}$ is H, $R^{14}$, $[CH(R^{1'})]_p COOR^{11}$, $[CH(R^{1'})]_p CONR^{12}R^{13}$, $[CH(R^{1'})]_p SO_2R^{11}$, $[CH(R^{1'})]_p SO_2NR^{12}R^{13}$, $[CH(R^{1'})]_p COR^{11}$, $CH(R^{1'})CONHCH(R^{2'})COOR^{11}$, $CH(R^{1'})CONHCH(R^{2'})\ CONR^{12}R^{13}$, or $CH(R^{1'})CONHCH(R^{2'})(R')$, wherein $R^{14}$ is H, alkyl, aryl, heteroalkyl, heteroaryl, cycloalkyl, alkyl-aryl, alkyl-heteroaryl, aryl-alkyl, alkenyl, alkynyl or heteroaralkyl. Among the above for $R^{10}$, preferred moieties for $R^{10}$ are: H, $R^{14}$, $CH(R^{1'})COOR^{11}$, $CH(R^{1'})CH(R^{1'})COOR^{11}$, $CH(R^{1'})CONR^{12}R^{13}$, $CH(R^{1'})CH(R^{1'})CONR^{12}R^{13}$, $CH(R^{1'})CH(R^{1'})SO_2R^{11}$, $CH(R^{1'})CH(R^{1'})SO_2NR^{12}R^{13}$, $CH(R^{1'})CH(R^{1'})COR^{11}$, $CH(R^{1'})CONHCH(R^{2'})COOR^{11}$, $CH(R^{1'})CONHCH(R^{2'})\ CONR^{12}R^{13}$, or $CH(R^{1'})CONHCH(R^{2'})(R')$, wherein $R^{1'}$ is H or alkyl, and $R^{2'}$ is phenyl, substituted phenyl, hetero atom-substituted phenyl, thiophenyl, cycloalkyl, piperidyl or pyridyl.

More preferred moieties are: for $R^{1'}$ is H, for $R^{11}$ is H, methyl, ethyl, allyl, tert-butyl, benzyl, α-methylbenzyl, α,α-dimethylbenzyl, 1-methylcyclopropyl or 1-methylcyclopentyl; for R' is hydroxymethyl or $CH_2CONR^{12}R^{13}$ where $NR^{12}R^{13}$ is selected from the group consisting of:

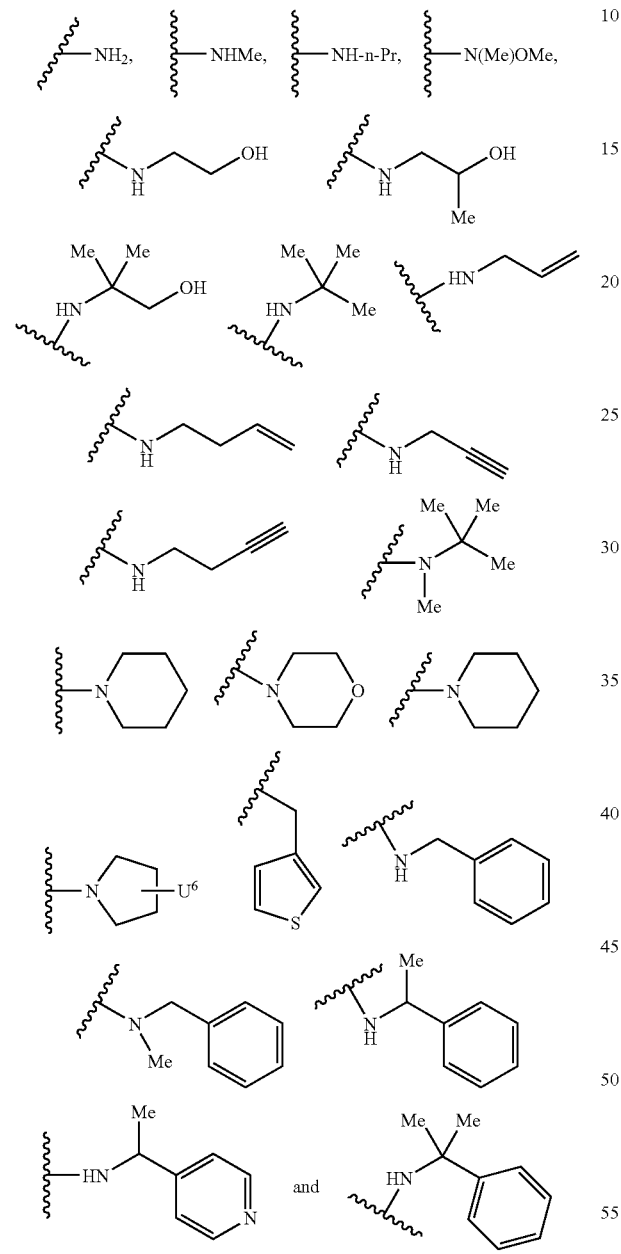

wherein $U^6$ is H, OH, or $CH_2OH$;

$R^{14}$ is preferably selected from the group consisting of: H, Me, Et, n-propyl, methoxy, cyclopropyl, n-butyl, 1-but-3-ynyl, benzyl, α-methylbenzyl, phenethyl, allyl, 1-but-3-enyl, OMe, cyclopropylmethyl;

and $R^{2'}$ is preferably independently selected from the group consisting of:

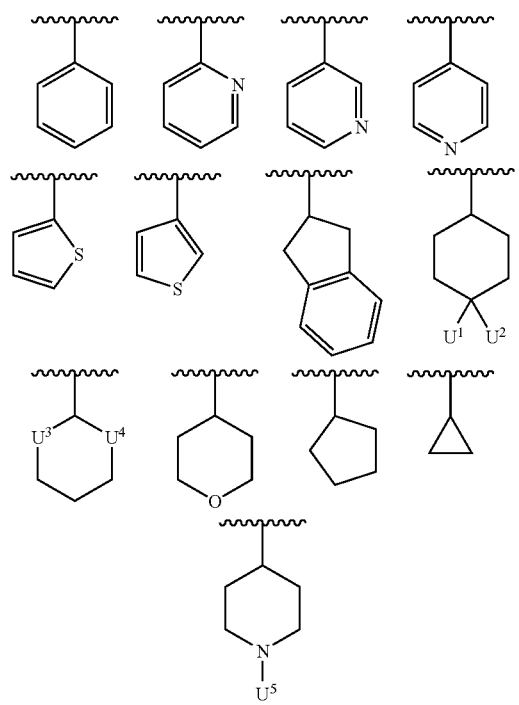

wherein:

$U^1$ and $U^2$ maybe same or different and are selected from H, F, $CH_2COOH$, $CH_2COOMe$, $CH_2CONH_2$, $CH_2CONHMe$, $CH_2CONMe_2$, azido, amino, hydroxyl, substituted amino, substituted hydroxyl;

$U^3$ and $U^4$ maybe same or different and are selected from O and S;

$U^5$ is selected from the moieties consisting of alkyl sulfonyl, aryl sulfonyl, heteroalkyl sulfonyl, heteroaryl sulfonyl, alkyl carbonyl, aryl carbonyl, heteroalkyl carbonyl, heteroaryl carbonyl, alkoxycarbonyl, aryloxycarbonyl, heteroaryloxycarbonyl, alkylaminocarbonyl, arylaminocarbonyl, heteroarylaminocarbonyl or a combination thereof.

Preferred moieties for $R^2$ are:

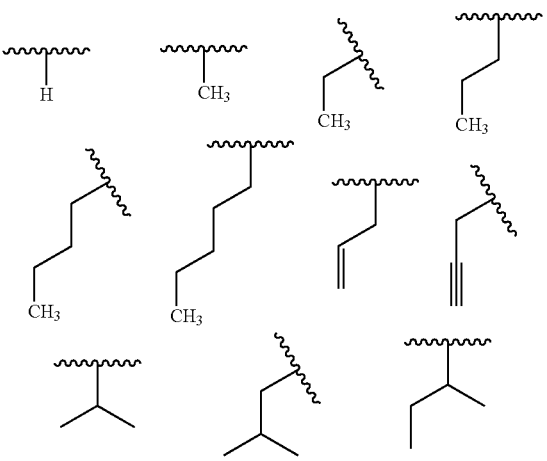

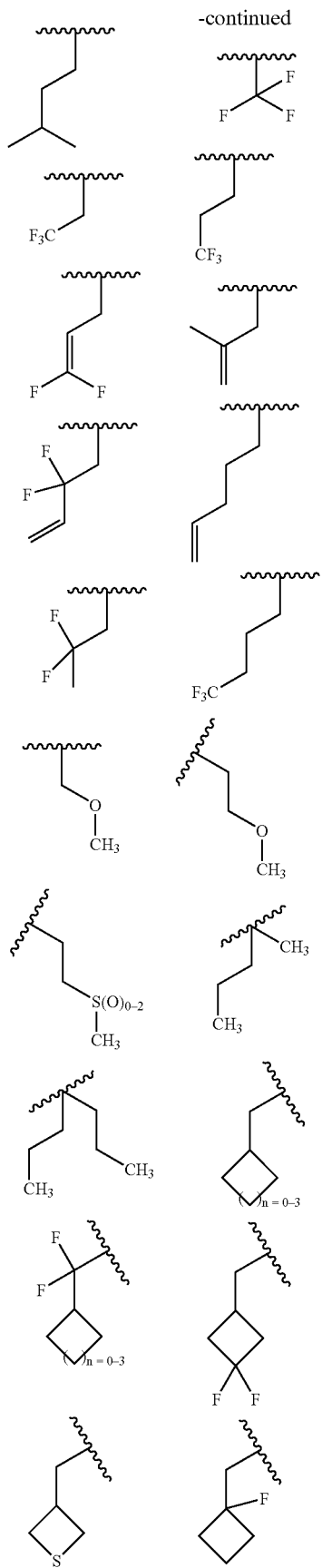
-continued
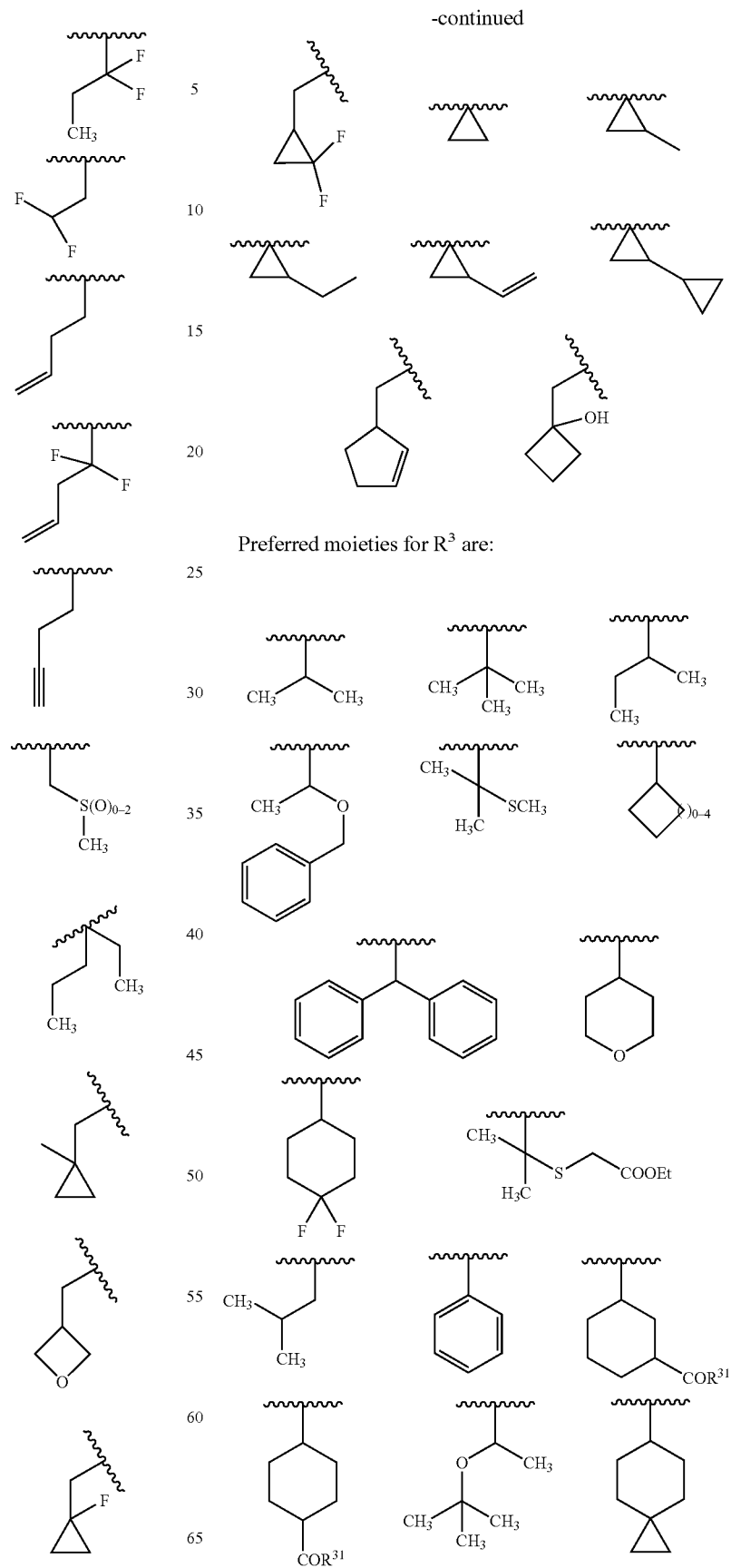
-continued
Preferred moieties for R³ are:

-continued
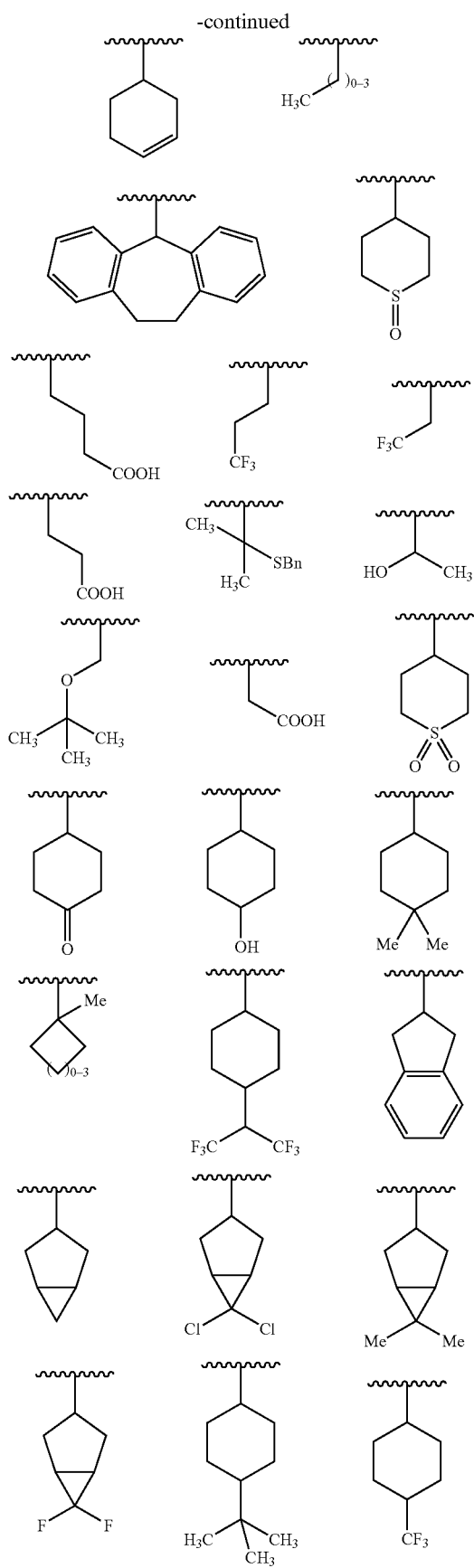
-continued
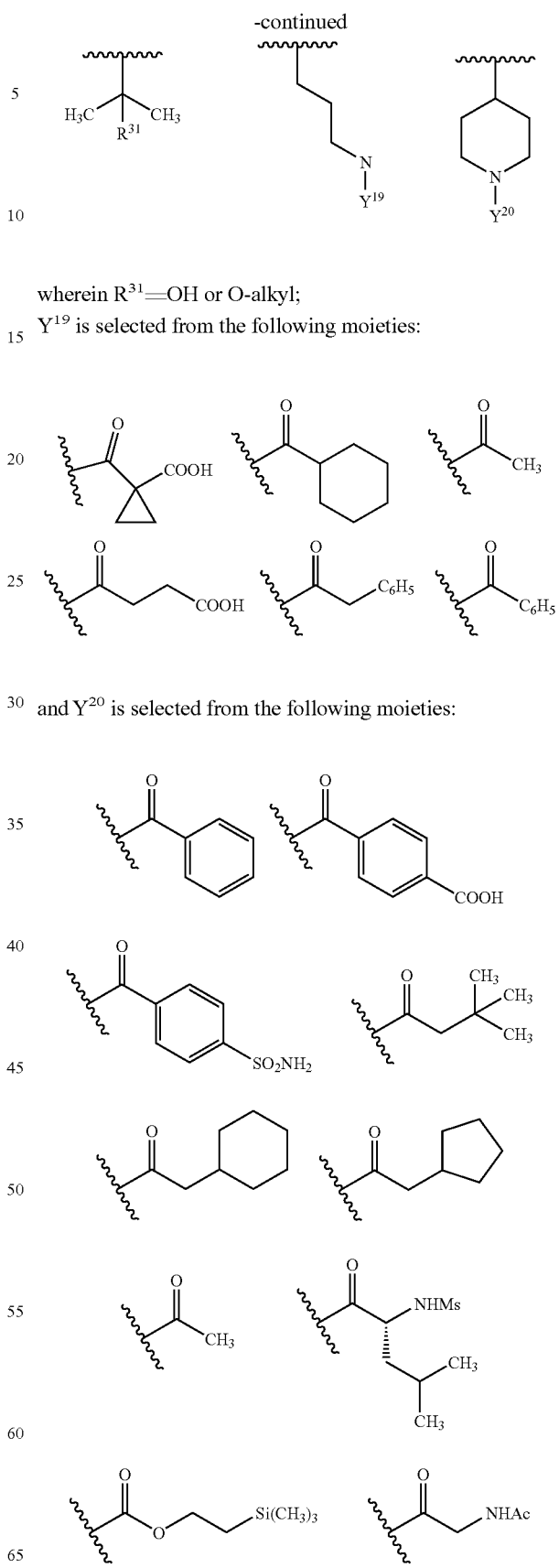
wherein $R^{31}$=OH or O-alkyl;
$Y^{19}$ is selected from the following moieties:
and $Y^{20}$ is selected from the following moieties:

Additional R³ moieties include the following:
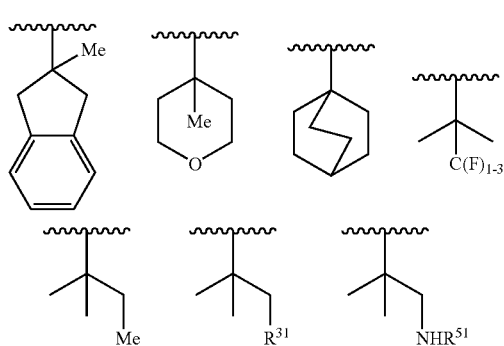
where R⁵¹=H, —COCH₃, —COOtBu or —CONHtBu.
Most preferred moieties for R³ are:
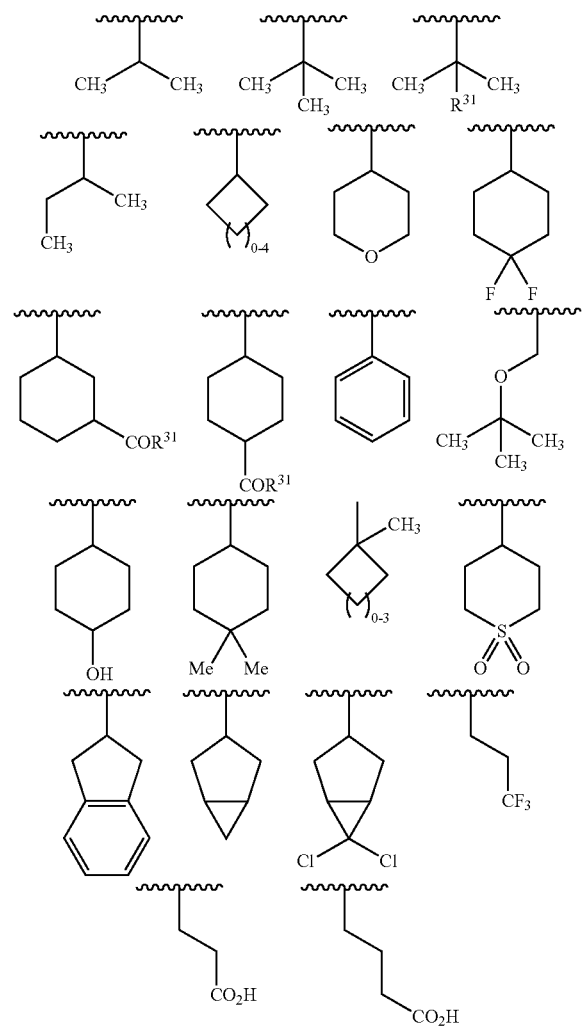
Some other preferred moieties are: for Z it is N, for R⁴ it is H, and for W it is C=O. Additionally, the moiety Z-C—R³ in Formula I, with R⁴ being absent, may be represented by the following structures:
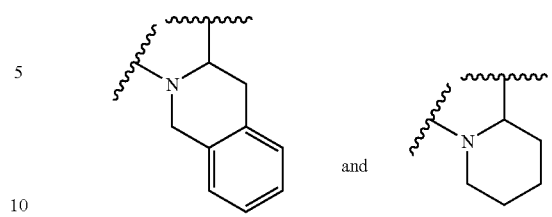
Preferred moieties for Y are:
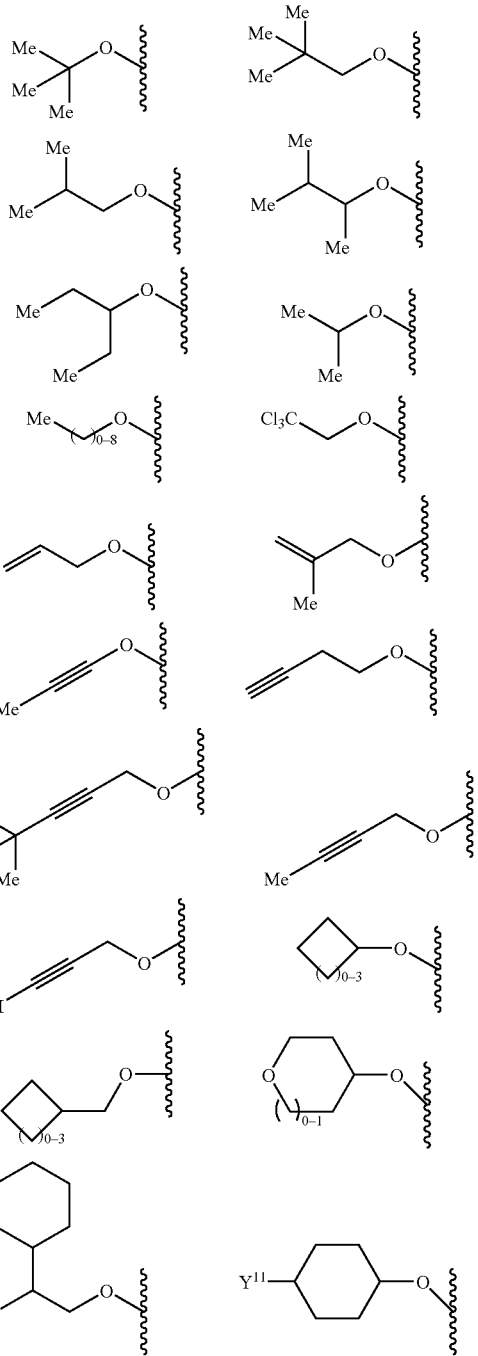

-continued
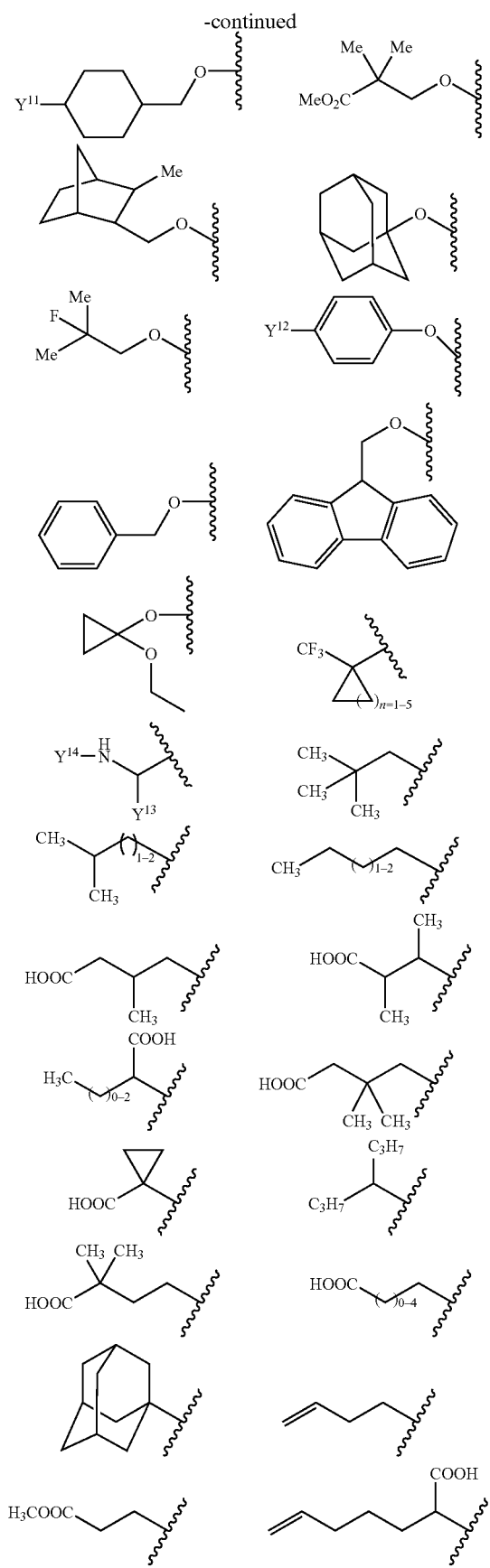
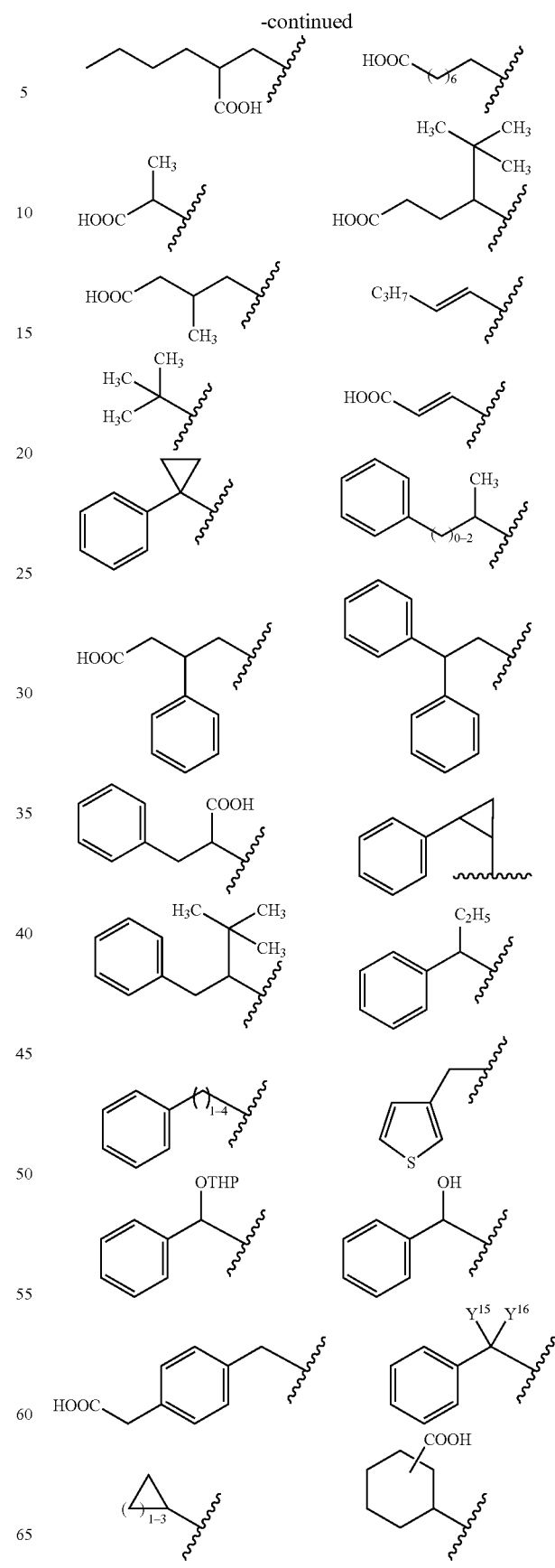

-continued
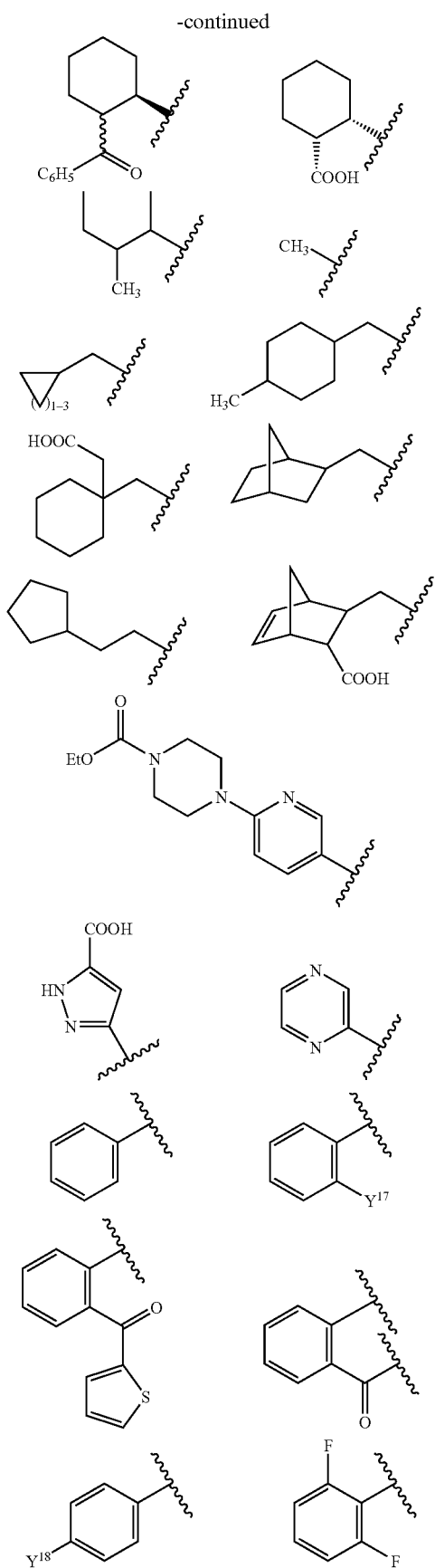
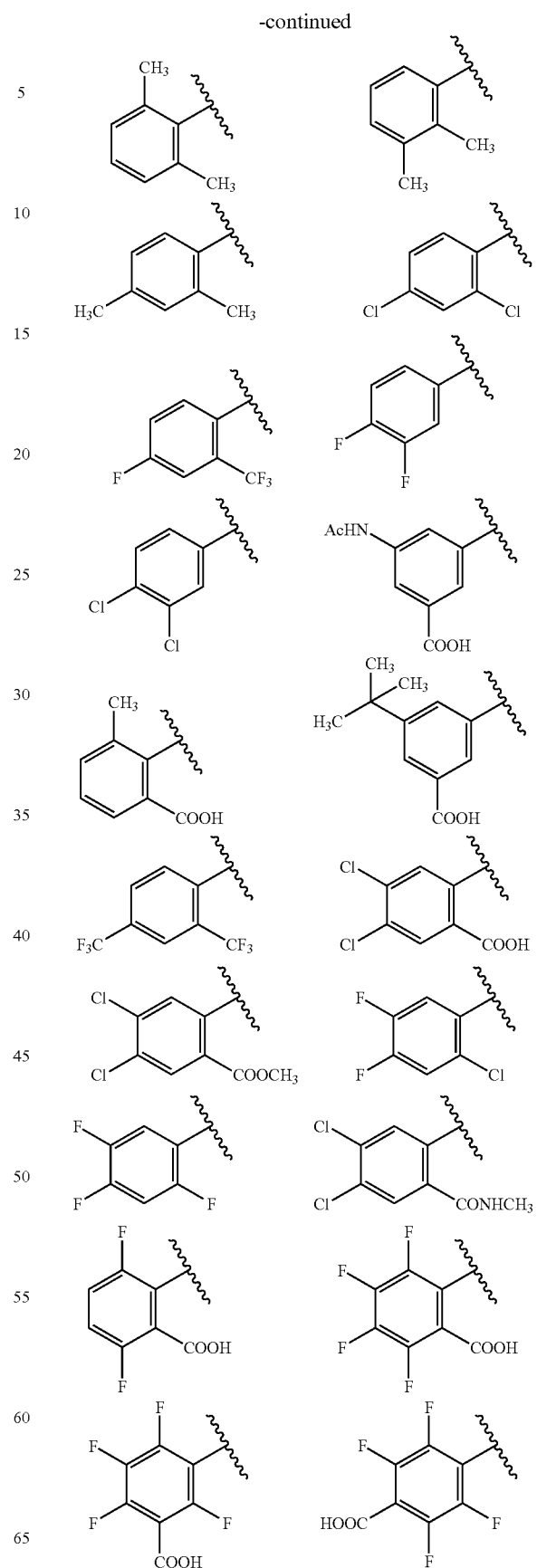

-continued
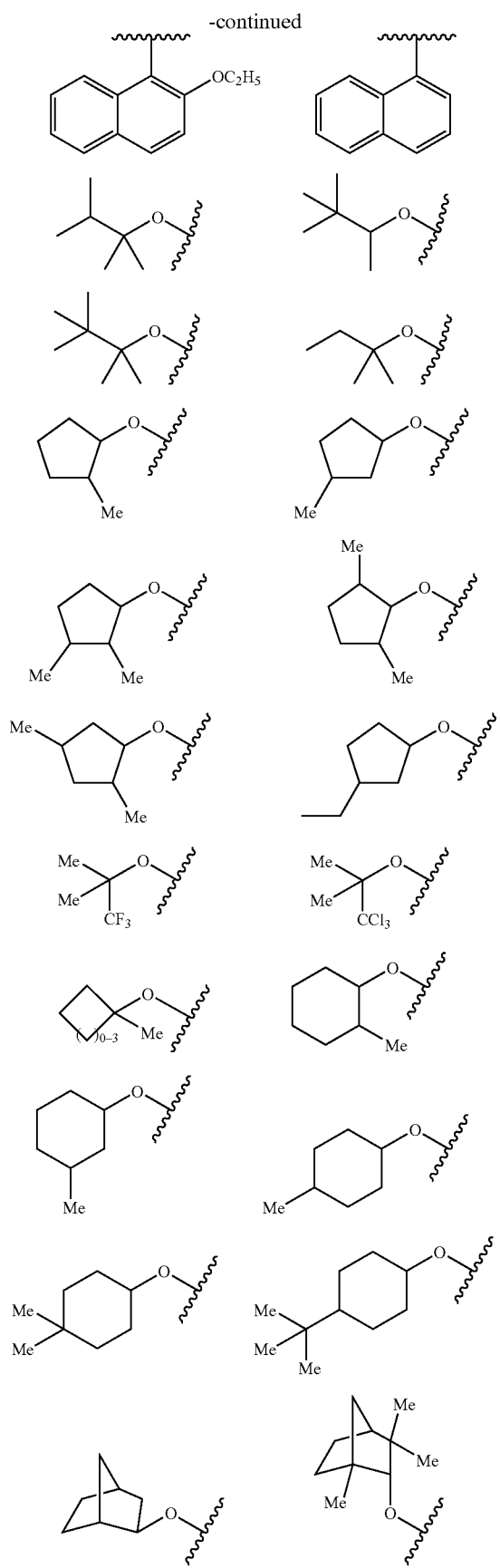
wherein:
Y[11] is selected from H, COOH, COOEt, OMe, Ph, OPh, NHMe, NHAC, NHPh, CH(Me)$_2$, 1-triazolyl, 1-imidazolyl, and NHCH$_2$COOH;
Y[12] is selected from H, COOH, COOMe, OMe, F, Cl, or Br;
Y[13] is selected from the following moieties:
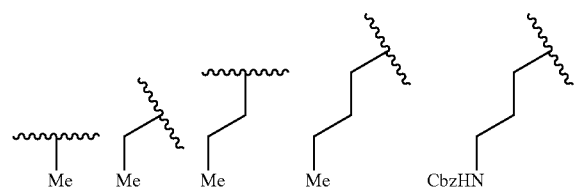

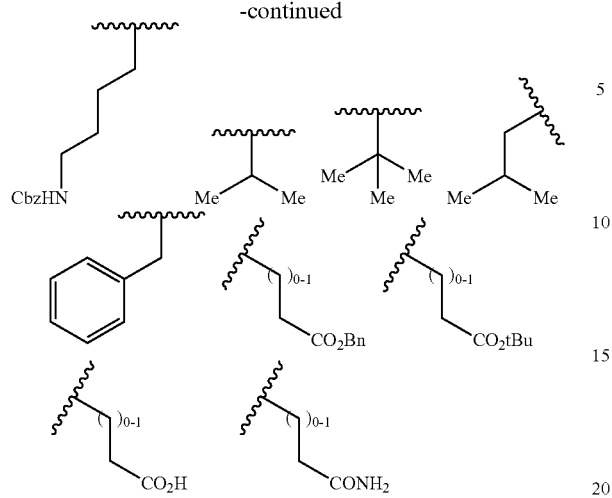
$Y^{14}$ is selected from MeSO$_2$, Ac, Boc, iBoc, Cbz, or Alloc;
$Y^{15}$ and $Y^{16}$ are independently selected from alkyl, aryl, heteroalkyl, and heteroaryl;
$Y^{17}$ is CF$_3$, NO$_2$, CONH$_2$, OH, COOCH$_3$, OCH$_3$, OC$_6$H$_5$, C$_6$H$_5$, COC$_6$H$_5$, NH$_2$, or COOH; and
$Y^{18}$ is COOCH$_3$, NO$_2$, N(CH$_3$)$_2$, F, OCH$_3$, CH$_2$COOH, COOH, SO$_2$NH$_2$, or NHCOCH$_3$.
Y may be more preferably represented by:
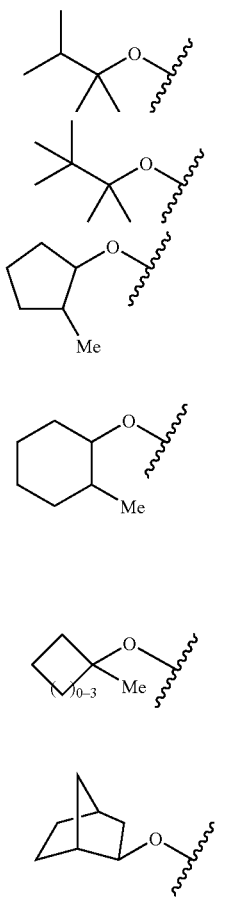
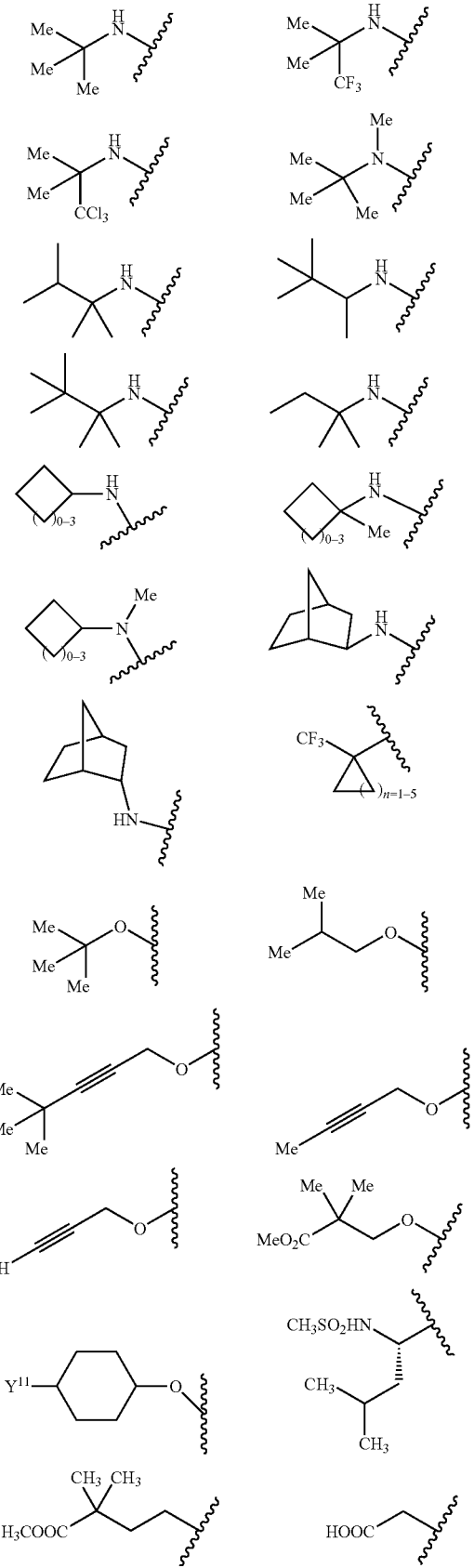

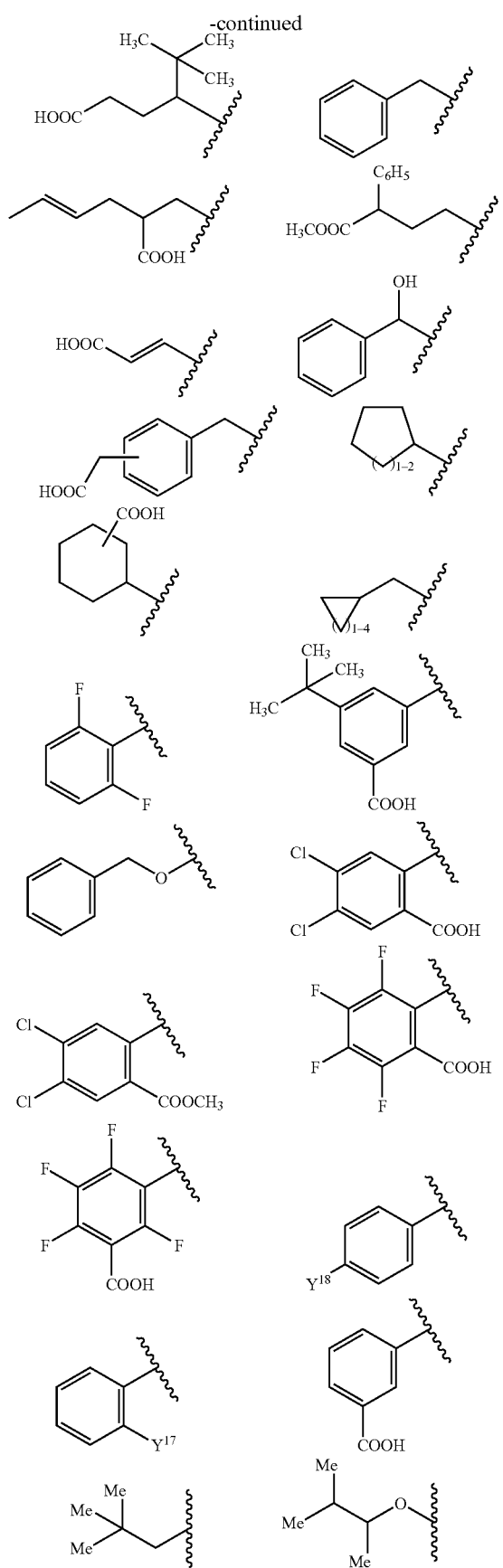
wherein:
$Y^{17}$=CF$_3$, NO$_2$, CONH$_2$, OH, NH$_2$, or COOH;
$Y^{18}$=F, COOH,
Still more preferred moieties for Y are:

-continued

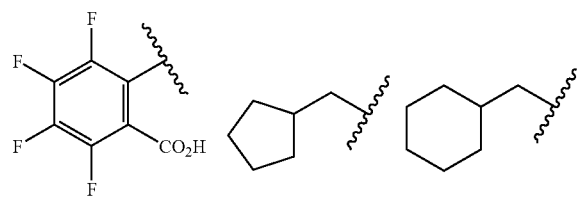

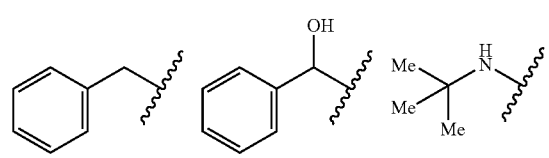

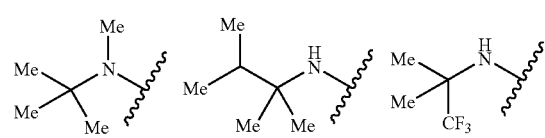

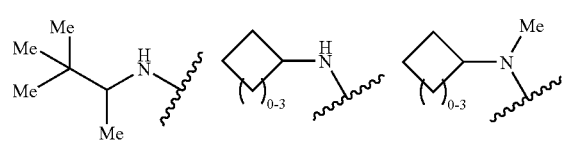

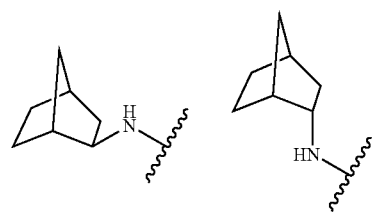

As shown in Formula I, the unit:

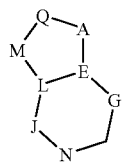

represents a cyclic ring structure, which may be a five-membered or six-membered ring structure. When that cyclic ring represents a five-membered ring, it is a requirement of this invention that that five-membered cyclic ring does not contain a carbonyl group as part of the cyclic ring structure. Preferably, that five-membered ring is of the structure:

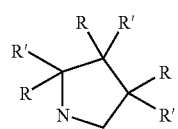

wherein R and R' are defined above. Preferred representations for that five-membered cyclic ring structure is:

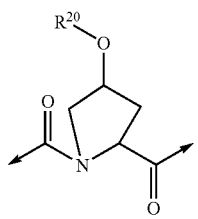

where $R^{20}$ is selected from the following moieties:

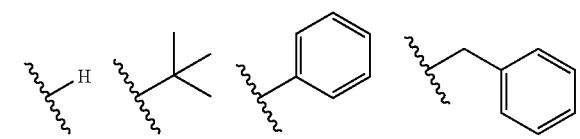

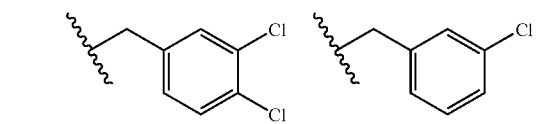

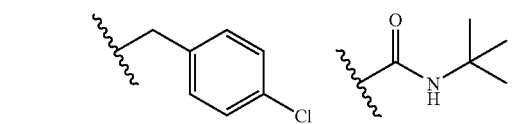

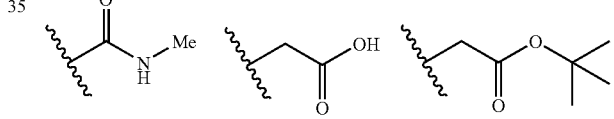

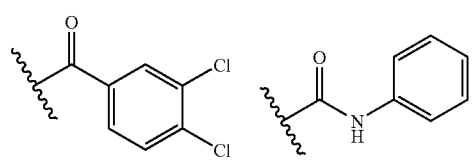

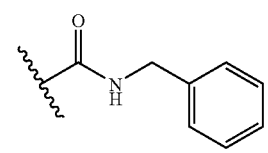

Furthermore, that five-membered ring, along with its adjacent two exocyclic carbonyls, may be represented as follows:

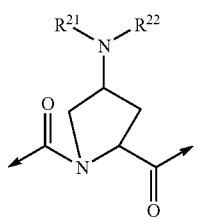

in which case, $R^{21}$ and $R^{22}$ may be the same or different and are independently selected from the following moieties:
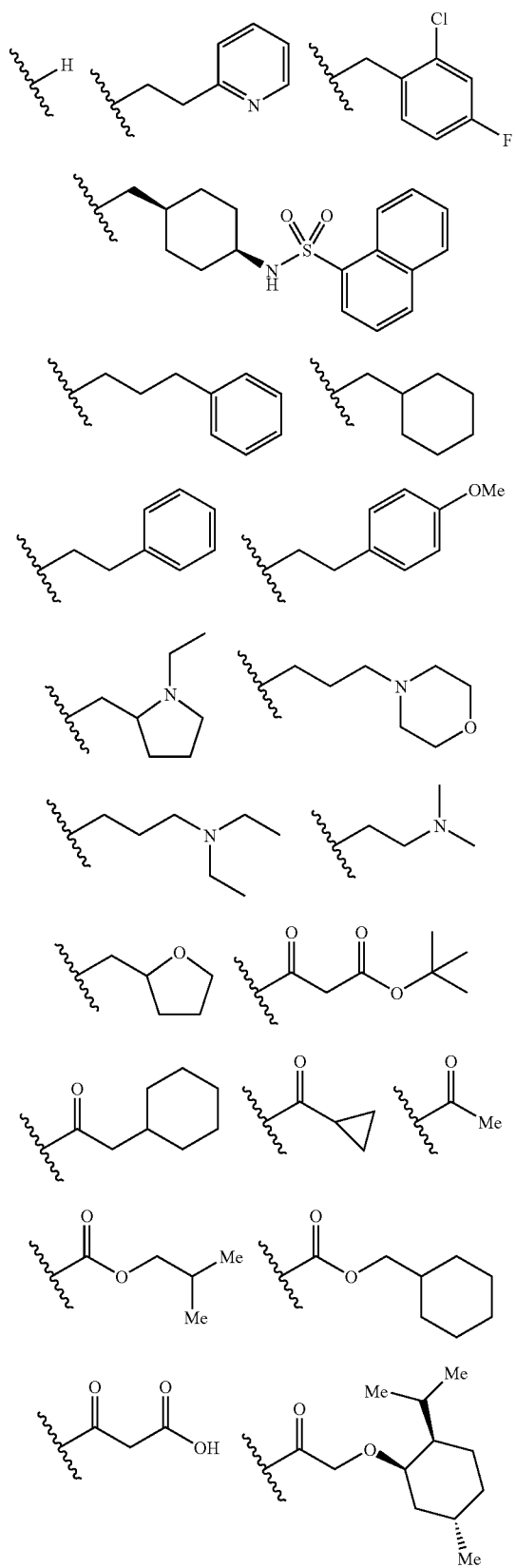
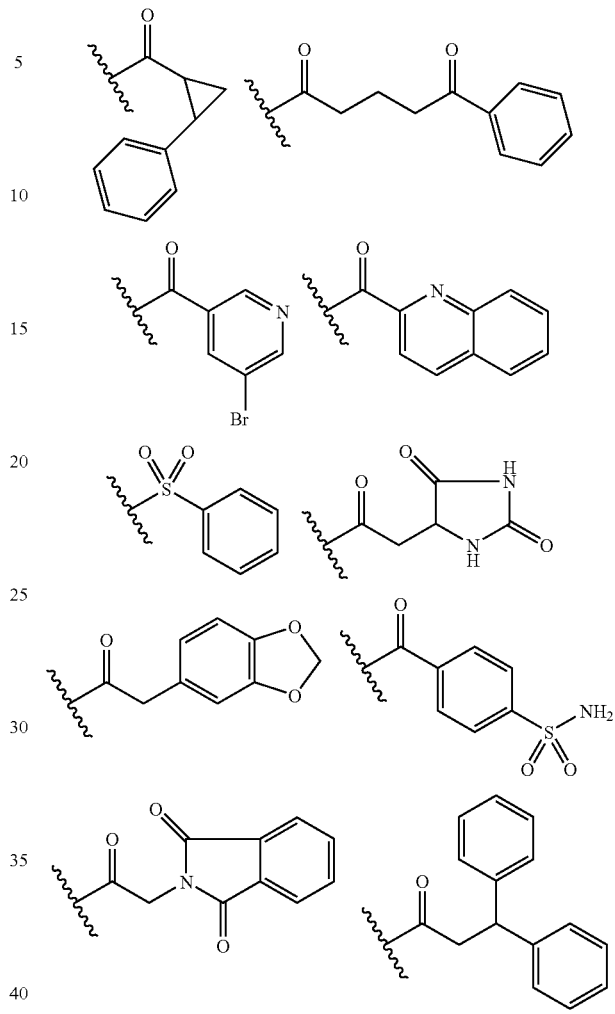
Some preferred illustrations for the five-membered ring structure:
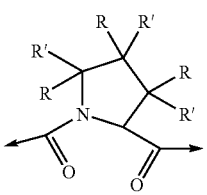
are as follows:
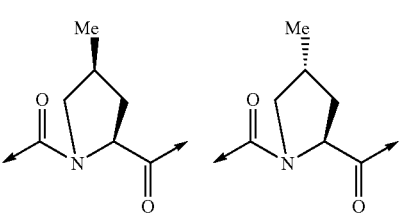

-continued
Additionally, the unit:
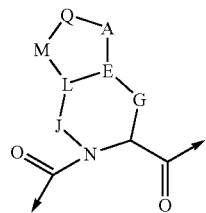
in Formula I may be represented by the following structures b and c:
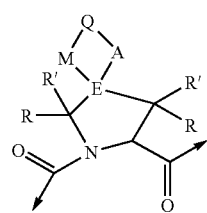
b
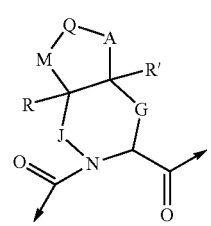
c
Preferred definitions for b are:
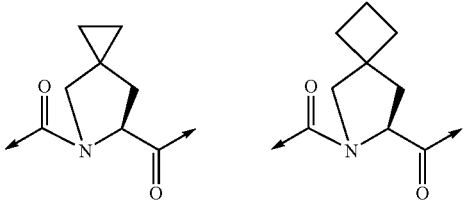
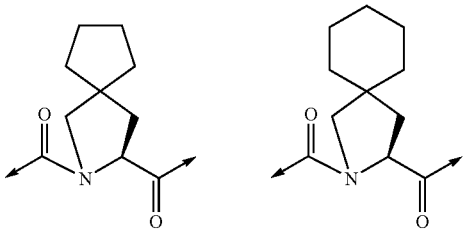
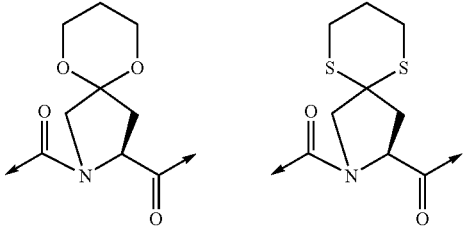

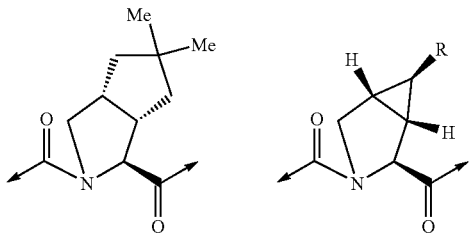
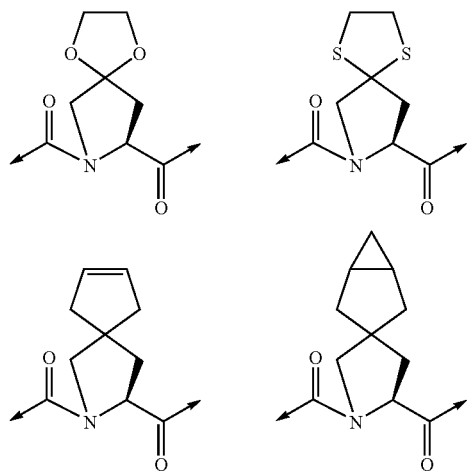
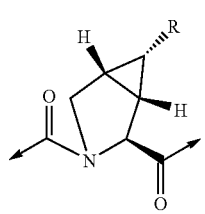
In c, G and J are independently selected from the group consisting of $(CH_2)_p$, $(CHR)_p$, $(CHR-CHR')_p$, and $(CRR')_p$; A and M are independently selected from the group consisting of O, S, $SO_2$, NR, $(CH_2)_p$, $(CHR)_p$, $(CHR-CHR')_p$, and $(CRR')_p$; and Q is $CH_2$, CHR, CRR', NH, NR, O, S, $SO_2$, NR, $(CH_2)$ p, $(CHR)_p$, and $(CRR')_p$. Preferred definitions for c are:
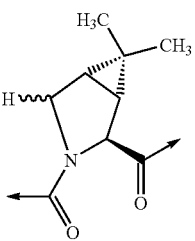
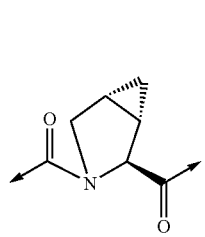
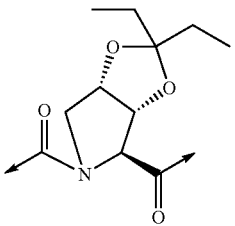
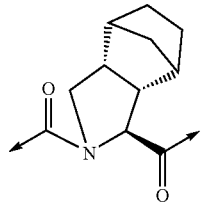
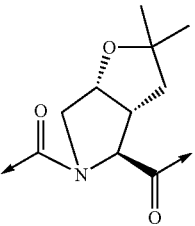

-continued
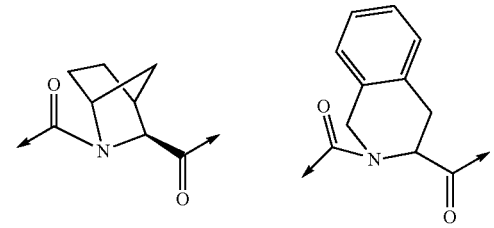 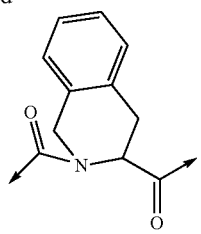
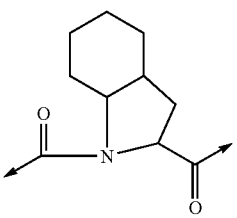 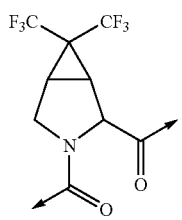
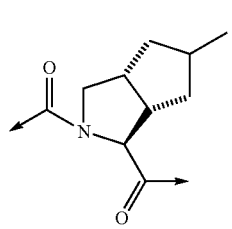 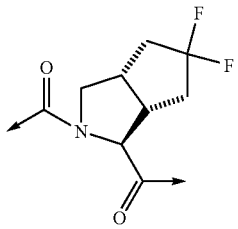
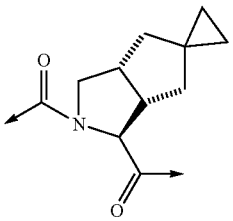 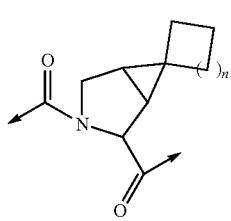
where n = 0-4
When the cyclic ring structure is depicted as:
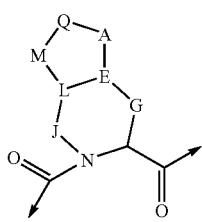
its most preferred illustrations are as follows:
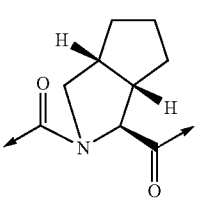 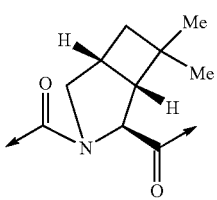
-continued
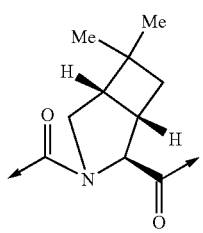 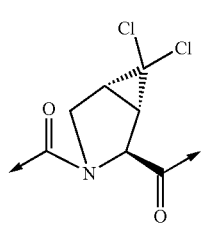
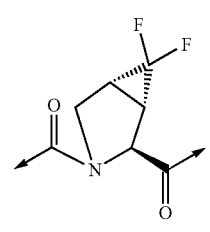 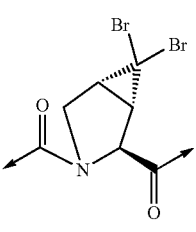
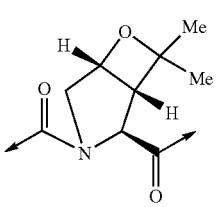 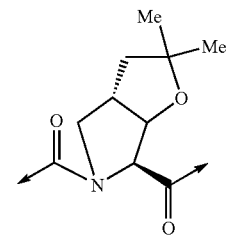
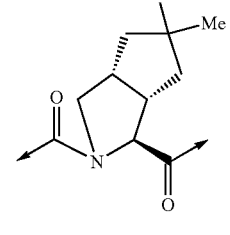 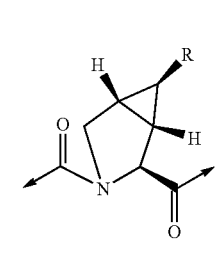
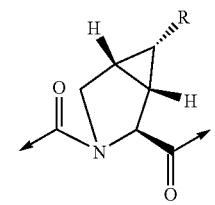 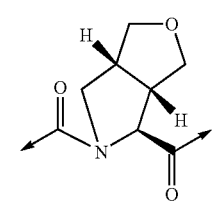
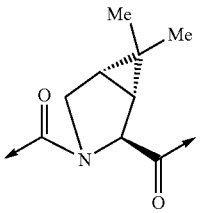 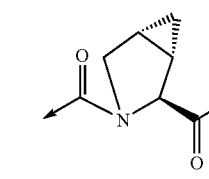
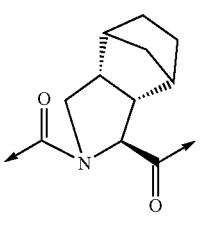 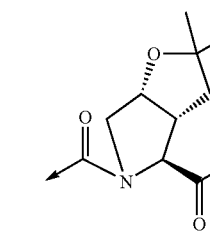

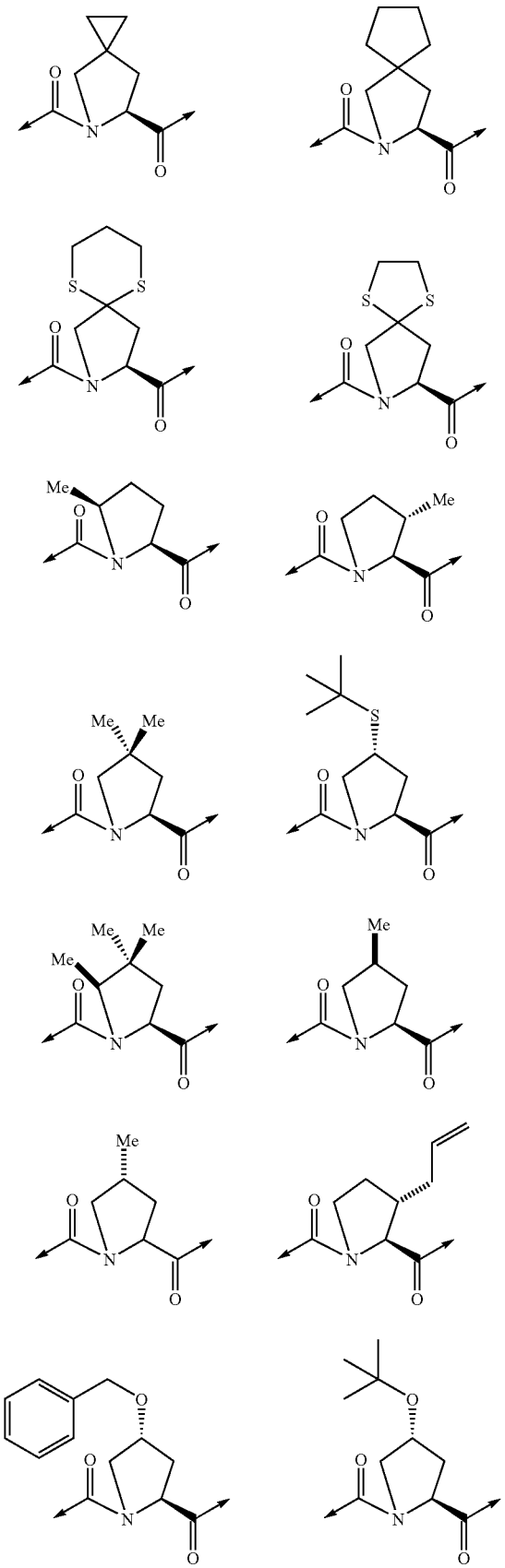
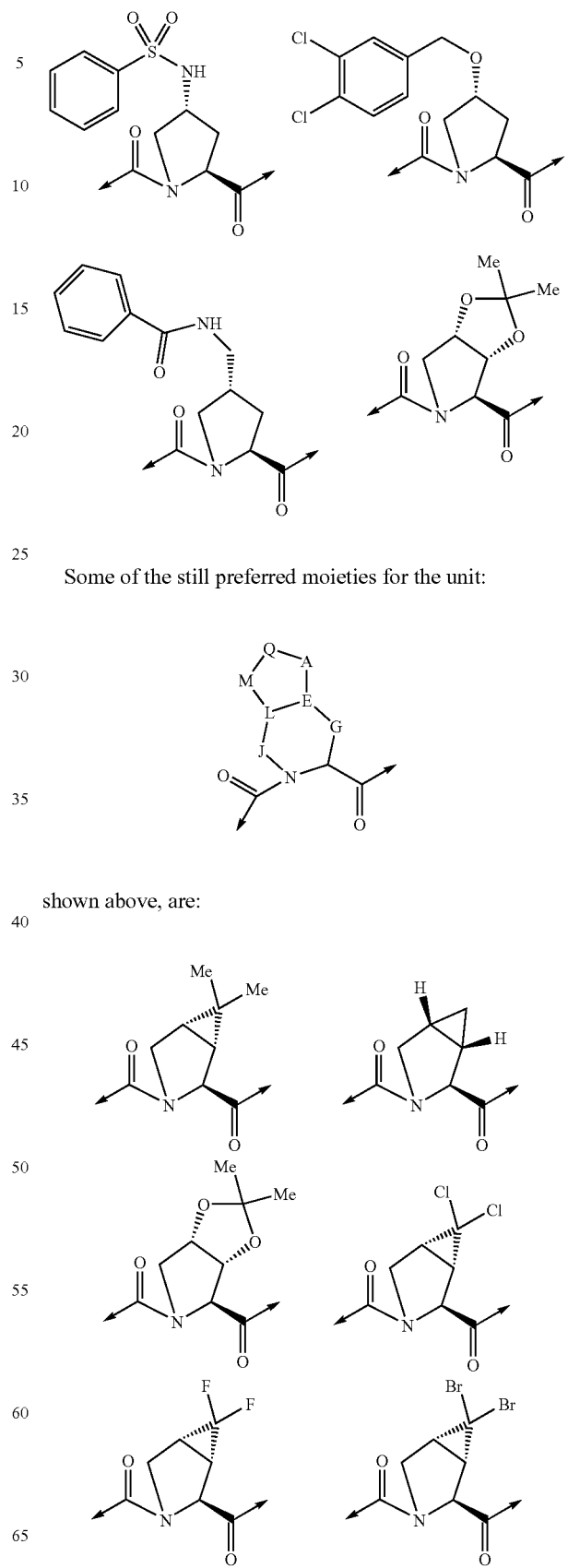
Some of the still preferred moieties for the unit:
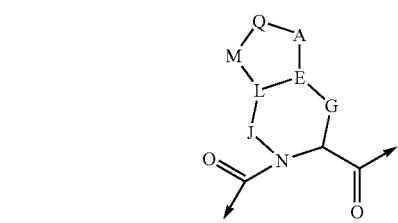
shown above, are:
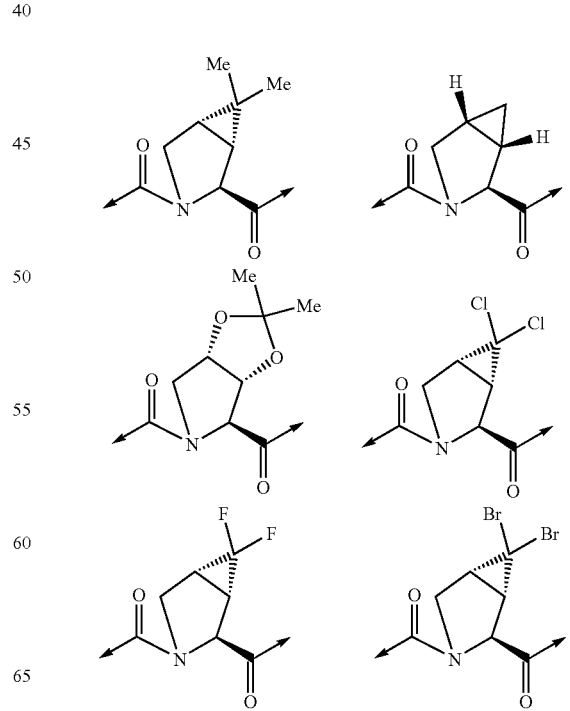

-continued

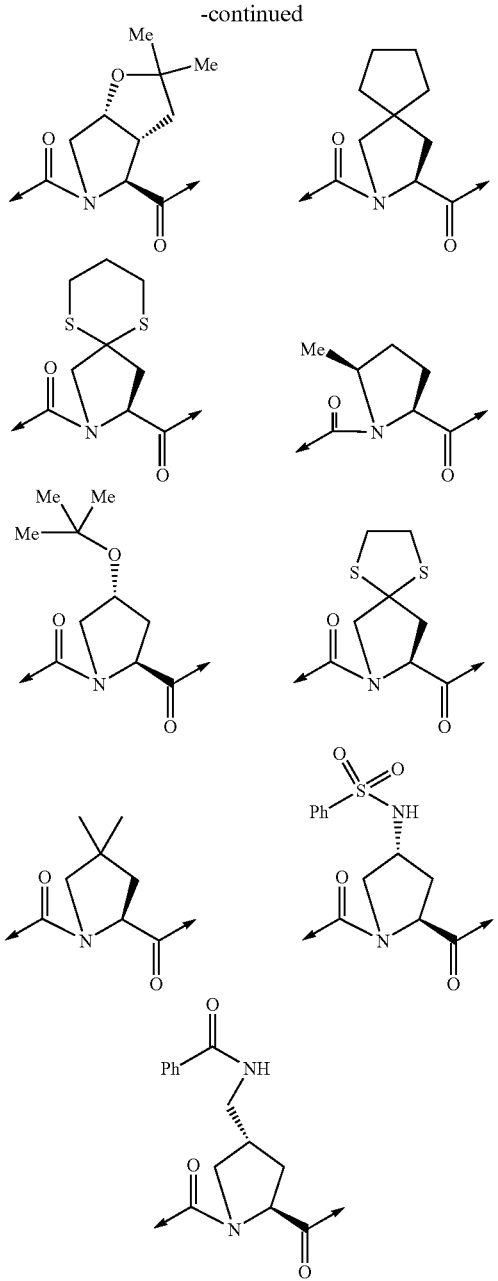

Unless defined otherwise, all technical and scientific terms used herein have the same meaning as is commonly understood by one of skill in the art to which this invention belongs. Thus, for example, the term alkyl (including the alkyl portions of alkoxy) refers to a monovalent group derived from a straight or branched chain saturated hydrocarbon by the removal of a single atom having from 1 to 8 carbon atoms, preferably from 1 to 6;

aryl—represents a carbocyclic group having from 6 to 14 carbon atoms and having at least one benzenoid ring, with all available substitutable aromatic carbon atoms of the carbocyclic group being intended as possible points of attachment. Preferred aryl groups include phenyl, 1-naphthyl, 2-naphthyl and indanyl, and especially phenyl and substituted phenyl;

aralkyl—represents a moiety containing an aryl group linked vial a lower alkyl;

alkylaryl—represents a moiety containing a lower alkyl linked via an aryl group;

cycloalkyl—represents a saturated carbocyclic ring having from 3 to 8 carbon atoms, preferably 5 or 6, optionally substituted.

heterocyclic—represents, in addition to the heteroaryl groups defined below, saturated and unsaturated cyclic organic groups having at least one O, S and/or N atom interrupting a carbocyclic ring structure that consists of one ring or two fused rings, wherein each ring is 5-, 6- or 7-membered and may or may not have double bonds that lack delocalized pi electrons, which ring structure has from 2 to 8, preferably from 3 to 6 carbon atoms, e.g., 2- or 3-piperidinyl, 2- or 3-piperazinyl, 2- or 3-morpholinyl, or 2- or 3-thiomorpholinyl;

halogen—represents fluorine, chlorine, bromine and iodine;

heteroaryl—represents a cyclic organic group having at least one O, S and/or N atom interrupting a carbocyclic ring structure and having a sufficient number of delocalized pi electrons to provide aromatic character, with the aromatic heterocyclyl group having from 2 to 14, preferably 4 or 5 carbon atoms, e.g., 2-, 3- or 4-pyridyl, 2- or 3-furyl, 2- or 3-thienyl, 2-, 4- or 5-thiazolyl, 2- or 4-imidazolyl, 2-, 4- or 5-pyrimidinyl, 2-pyrazinyl, or 3- or 4-pyridazinyl, etc. Preferred heteroaryl groups are 2-, 3- and 4-pyridyl; such heteroaryl groups may also be optionally substituted. Additionally, unless otherwise specifically defined, as stated above, the term "substituted or unsubstituted" or "optionally substituted" refers to the subject moiety being optionally and chemically-suitably substituted with a moiety belonging to $R^{12}$ or $R^{13}$. As used herein, "prodrug" means compounds that are drug precursors which, following administration to a patient, release the drug in vivo via some chemical or physiological process (e.g., a prodrug on being brought to the physiological pH or through enzyme action is converted to the desired drug form).

Also included in the invention are tautomers, rotamers, enantiomers and other optical isomers, as well as prodrugs, of compounds of Formula I, as well as pharmaceutically acceptable salts, solvates and derivatives thereof.

A further feature of the invention is pharmaceutical compositions containing as active ingredient a compound of Formula I (or its salt, solvate or isomers) together with a pharmaceutically acceptable carrier or excipient.

The invention also provides methods for preparing compounds of Formula I, as well as methods for treating diseases such as, for example, HCV, AIDS (Acquired Immune Deficiency Syndrome), and related disorders. The methods for treating comprise administering to a patient suffering from said disease or diseases a therapeutically effective amount of a compound of Formula I, or pharmaceutical compositions comprising a compound of Formula I.

Also disclosed is the use of a compound of Formula I for the manufacture of a medicament for treating HCV, AIDS, and related disorders.

Also disclosed is a method of treatment of a hepatitis C virus associated disorder, comprising administering an effective amount of one or more of the inventive compounds.

Also disclosed is a method of modulating the activity of hepatitis C virus (HCV) protease, comprising contacting HCV protease with one or more inventive compounds.

Also disclosed is a method of treating, preventing, or ameliorating one or more symptoms of hepatitis C, comprising administering an effective amount of one or more of the inventive compounds. The HCV protease is the NS3 or NS4a protease. The inventive compounds inhibit such protease. They also modulate the processing of hepatitis C virus (HCV) polypeptide.

DETAILED DESCRIPTION OF PREFERRED EMBODIMENTS

In one embodiment, the present invention discloses compounds of Formula I as inhibitors of HCV protease, especially the HCV NS3/NS4a serine protease, or a pharmaceutically acceptable derivative thereof, where the various definitions are given above.

Representative compounds of the invention which exhibit excellent HCV protease inhibitory activity are listed below in Tables 1 to 5 along with their activity (ranges of Ki* values in nanomolar, nM). Several compounds as well as additional compounds are additionally disclosed in the Claims.

TABLE 1

Compounds and HCV protease continuous assay results

| Compound from Example No. | Ki* Range |
|---|---|
| 1 | C |
| 2 | C |
| 3 | C |
| 4 | C |
| 5 | C |
| 6 | C |
| 7 | C |
| 8 | C |
| 9 | C |
| 10 | C |
| 11 | C |
| 12 | C |
| 13 | C |
| 14 | C |
| 15 | C |
| 16 | C |
| 17 | C |
| 18 | C |
| 19 | C |
| 20 | C |
| 21 | C |
| 22 | C |
| 23 | C |
| 24 | C |
| 25 | C |
| 26 | C |
| 27 | C |
| 28 | C |
| 29 | C |
| 30 | C |
| 31 | C |
| 32 | C |
| 33 | C |
| 34 | C |
| 35 | C |
| 36 | C |
| 37 | C |
| 38 | C |
| 39 | C |
| 40 | C |
| 41 | C |
| 42 | C |
| 43 | C |
| 44 | C |
| 45 | C |
| 46 | C |
| 47 | C |
| 48 | C |
| 49 | C |
| 50 | C |
| 51 | C |
| 52 | C |
| 53 | C |

TABLE 1-continued

Compounds and HCV protease continuous assay results

| Compound from Example No. | Ki* Range |
|---|---|
| 54 | C |
| 55 | C |
| 56 | C |
| 57 | C |
| 58 | C |
| 59 | C |
| 60 | C |
| 61 | C |
| 62 | C |
| 63 | C |
| 64 | C |
| 65 | C |
| 66 | C |
| 67 | C |
| 68 | B |
| 69 | C |
| 70 | C |
| 71 | B |
| 72 | C |
| 73 | B |
| 74 | C |
| 75 | C |
| 76 | A |
| 77 | B |
| 78 | A |
| 79 | C |
| 80 | A |
| 81 | C |
| 82 | A |
| 83 | B |
| 84 | C |
| 85 | C |
| 86 | B |
| 87 | B |
| 88 | A |
| 89 | B |
| 90 | C |
| 91 | C |
| 92 | C |
| 93 | C |
| 94 | C |
| 95 | C |
| 96 | C |
| 97 | C |
| 98 | B |
| 99 | B |
| 100 | A |
| 101 | A |
| 102 | C |
| 103 | C |
| 104 | C |
| 105 | C |
| 106 | C |
| 107 | B |
| 108 | A |
| 109 | A |
| 110 | A |
| 111 | A |
| 112 | A |
| 113 | B |
| 114 | A |
| 115 | B |
| 116 | A |
| 117 | A |
| 118 | A |
| 119 | A |
| 120 | A |
| 121 | B |
| 122 | B |
| 123 | A |
| 124 | B |
| 125 | B |
| 126 | B |
| 127 | A |
| 128 | A |

TABLE 1-continued

Compounds and HCV protease continuous assay results

| Compound from Example No. | Ki* Range |
|---|---|
| 129 | A |
| 130 | B |
| 131 | A |
| 132 | A |
| 133 | A |
| 134 | B |
| 135 | A |
| 136 | A |
| 137 | A |
| 138 | A |
| 139 | A |
| 140 | B |
| 141 | A |
| 142 | A |
| 143 | B |
| 144 | B |
| 145 | C |
| 146 | A |
| 147 | A |
| 148 | B |
| 149 | A |
| 150 | A |
| 151 | A |
| 152 | A |
| 153 | A |
| 154 | A |
| 155 | B |
| 156 | B |
| 157 | B |
| 158 | C |
| 159 | B |
| 160 | A |
| 161 | A |
| 162 | A |
| 163 | C |
| 164 | A |
| 165 | C |
| 166 | B |
| 167 | A |
| 168 | C |
| 169 | B |
| 170 | B |
| 171 | A |
| 172 | A |
| 173 | A |
| 174 | A |
| 175 | A |
| 176 | B |
| 177 | B |
| 178 | A |
| 179 | A |
| 180 | B |
| 181 | A |
| 182 | B |
| 183 | A |
| 184 | A |
| 185 | A |
| 186 | A |
| 187 | A |
| 188 | A |
| 189 | B |
| 190 | B |
| 191 | B |
| 192 | A |
| 193 | A |
| 194 | B |
| 195 | A |
| 196 | B |
| 197 | A |
| 198 | A |
| 199 | A |
| 200 | A |
| 201 | B |
| 202 | A |
| 203 | B |
| 204 | B |
| 205 | B |
| 206 | B |
| 207 | B |
| 208 | A |
| 209 | A |
| 210 | A |
| 211 | A |
| 212 | A |
| 213 | B |
| 214 | B |
| 215 | B |
| 216 | B |
| 217 | C |
| 218 | A |
| 219 | A |
| 220 | A |
| 221 | A |
| 222 | A |
| 223 | B |
| 224 | C |
| 225 | C |
| 226 | A |
| 227 | A |
| 228 | C |
| 229 | A |
| 230 | A |
| 231 | A |
| 232 | C |
| 233 | C |
| 234 | C |
| 235 | C |
| 236 | B |
| 237 | C |
| 238 | A |
| 239 | C |
| 240 | A |
| 241 | C |
| 242 | B |
| 243 | C |
| 244 | B |
| 245 | C |
| 246 | B |
| 247 | A |
| 248 | A |
| 249 | C |
| 250 | C |
| 251 | B |
| 252 | C |
| 253 | C |
| 254 | B |
| 255 | B |
| 256 | A |
| 257 | C |
| 258 | A |
| 259 | A |
| 260 | C |
| 261 | C |
| 262 | A |
| 263 | B |
| 264 | B |
| 265 | C |
| 266 | B |
| 267 | A |
| 268 | C |
| 269 | A |
| 270 | C |
| 271 | A |
| 272 | C |
| 273 | C |
| 274 | C |
| 275 | C |
| 276 | A |
| 277 | B |
| 278 | A |

TABLE 1-continued

Compounds and HCV protease continuous assay results

| Compound from Example No. | Ki* Range |
|---|---|
| 279 | B |
| 280 | A |
| 281 | C |
| 282 | C |
| 283 | C |
| 284 | C |
| 285 | C |
| 286 | C |
| 287 | C |
| 288 | B |
| 289 | B |
| 290 | C |
| 291 | C |
| 292 | C |
| 293 | C |
| 294 | C |
| 295 | C |
| 296 | B |
| 297 | C |
| 298 | C |
| 299 | B |
| 300 | B |
| 301 | C |
| 302 | C |
| 303 | B |
| 304 | C |
| 305 | C |
| 306 | C |
| 307 | B |
| 308 | B |
| 309 | C |
| 310 | C |
| 311 | C |
| 312 | C |
| 313 | B |
| 314 | A |
| 315 | B |
| 316 | B |
| 317 | A |
| 318 | A |
| 319 | A |
| 320 | A |
| 321 | C |
| 322 | C |
| 323 | C |
| 324 | C |
| 325 | A |
| 326 | A |
| 327 | C |
| 328 | B |
| 329 | B |
| 330 | A |
| 331 | A |
| 332 | A |
| 333 | B |
| 334 | B |
| 335 | B |
| 336 | A |
| 337 | A |
| 338 | C |
| 339 | A |
| 340 | C |
| 341 | C |
| 342 | C |
| 343 | A |
| 344 | C |
| 345 | C |
| 346 | C |
| 347 | B |
| 348 | B |
| 349 | C |
| 350 | C |
| 351 | C |
| 352 | C |
| 353 | C |
| 354 | C |
| 355 | C |
| 356 | A |
| 357 | A |
| 358 | C |
| 359 | A |
| 360 | B |
| 361 | B |
| 362 | C |

HCV continuous assay Ki* range:

Category A=1-100 nM; Category B=101-1,000 nM; Category C>1000 nM.

Some of the types of the inventive compounds and methods of synthesizing the various types of the inventive compounds of Formula I are listed below, then schematically described, followed by the illustrative Examples.

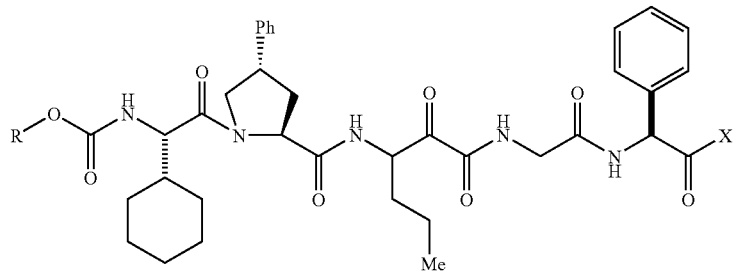

(R = t-butyl, X = NH$_2$)
(R = Isobutyl, X = NH$_2$)
(R = t-butyl, X = OH)
(R = Trichloroethyl, X = OH)

-continued
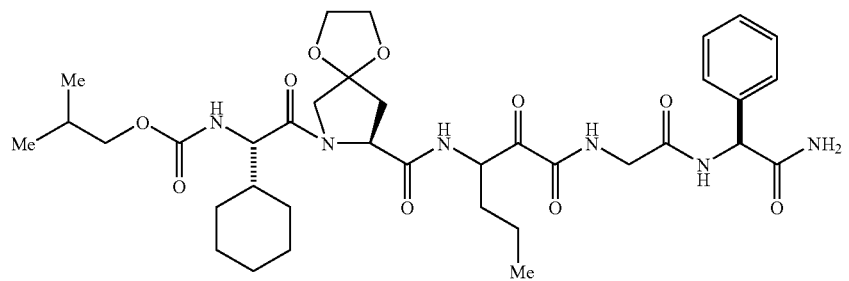
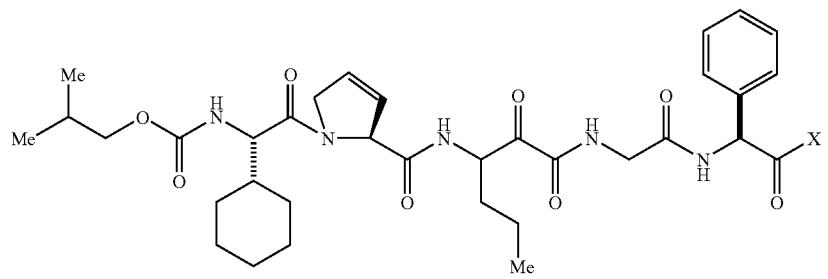
(X = O^tBu)
(X = OH)
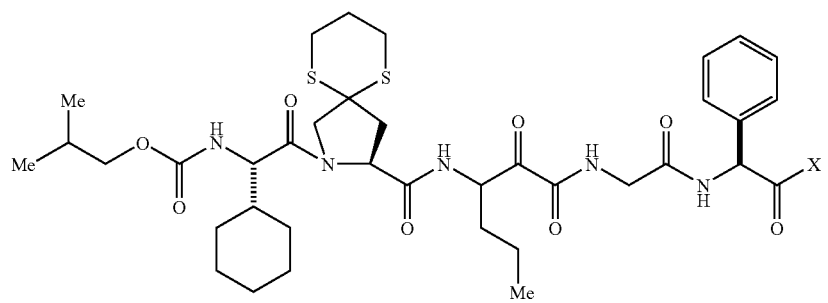
(X = OH)
(X = O^tBu)
(X = NH_2)
(X = NHMe)
(X = NMe_2)
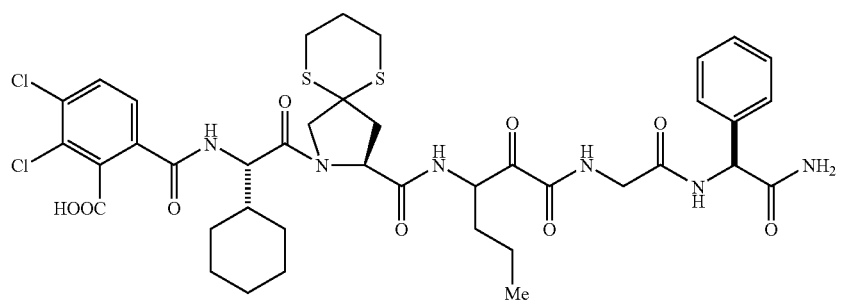
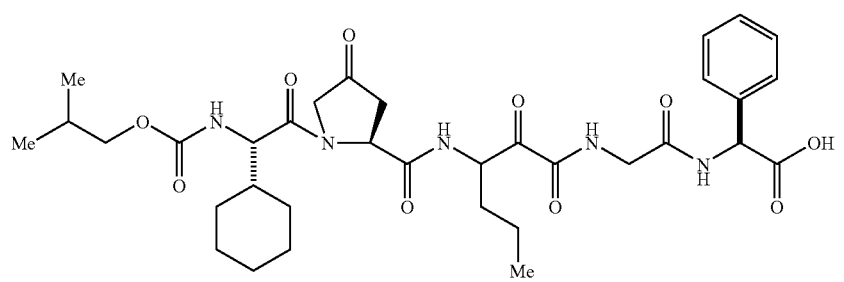

-continued
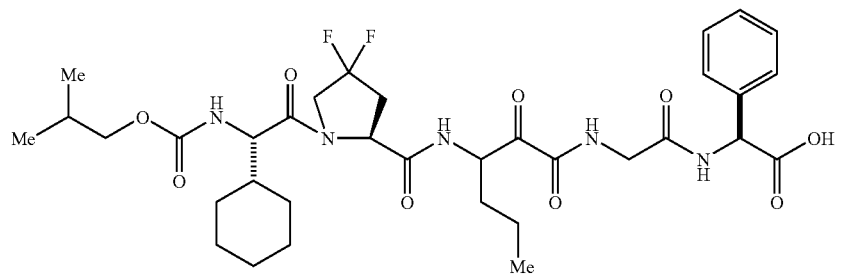
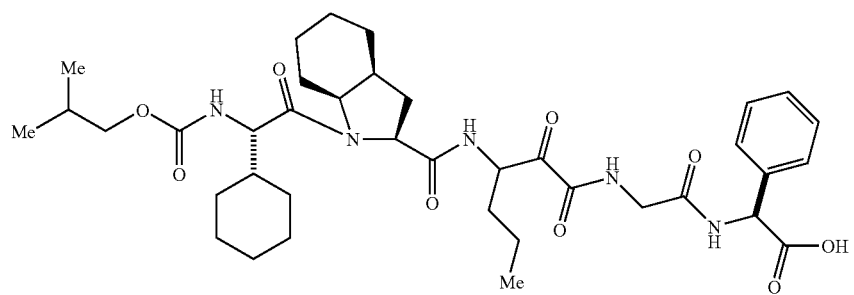
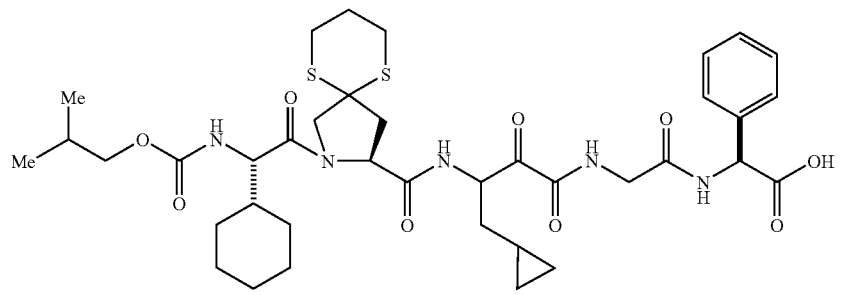
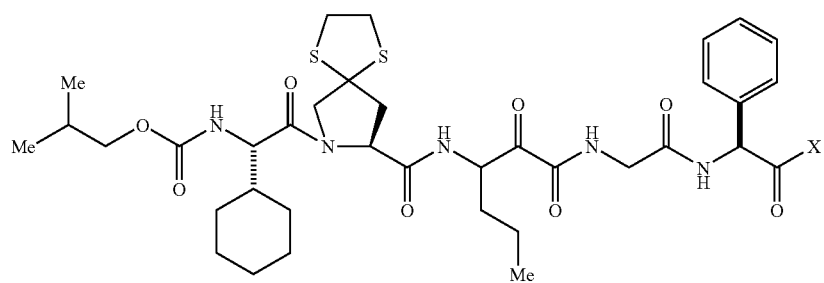
(X = NH₂)
(X = NMe₂)
(X = NHMe)
(X = OH)
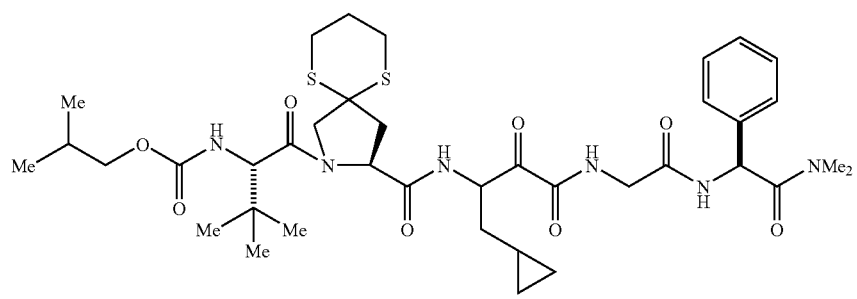

-continued
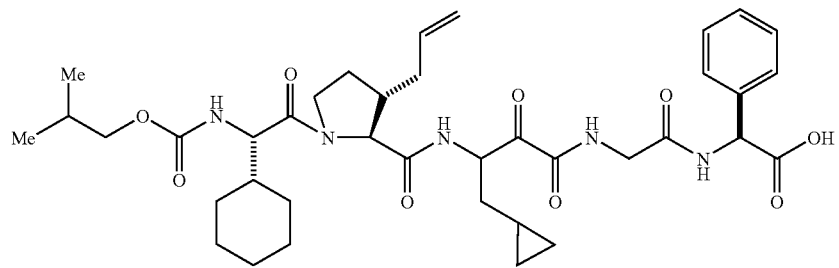
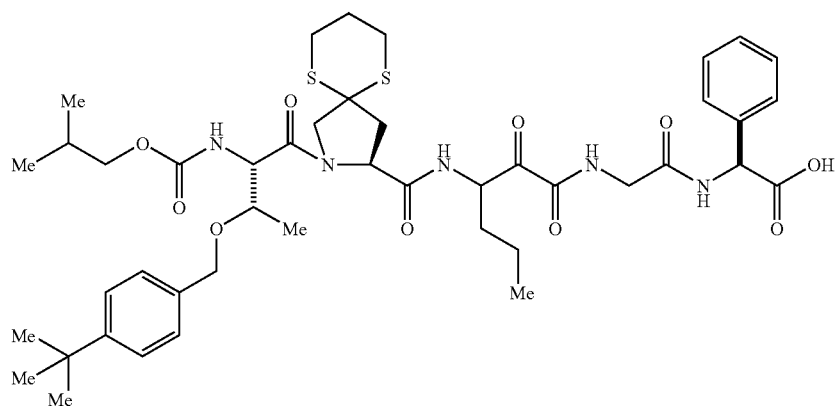
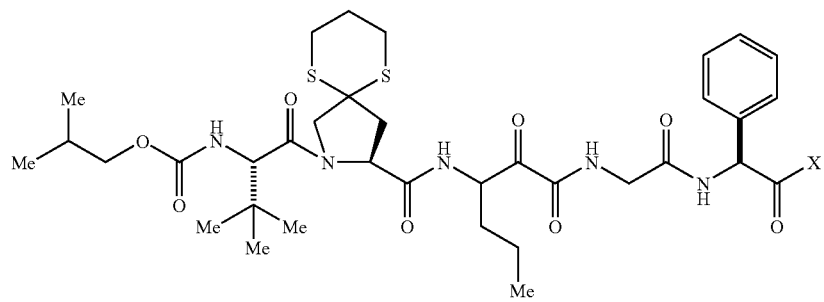
(X = O$^t$Bu)
(X = OH)
(X = NH$_2$)
(X = NMe$_2$)
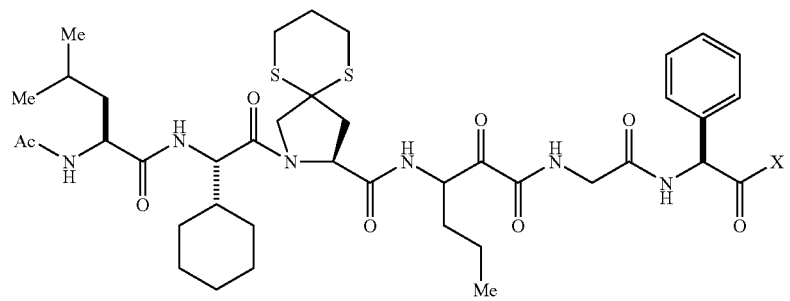
(X = O$^t$Bu)
(X = OH)
(X = NH$_2$)
(X = NMe$_2$)
(X = NMeOMe)

-continued
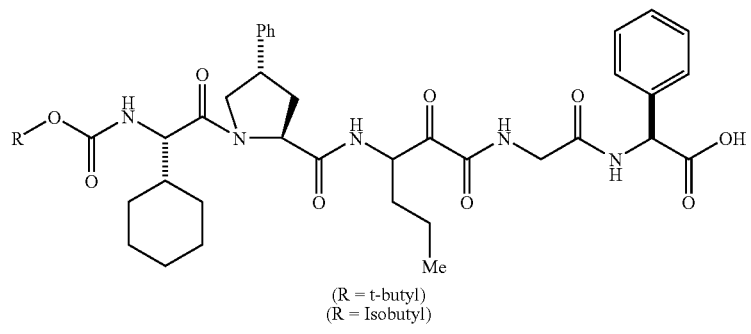
(R = t-butyl)
(R = Isobutyl)
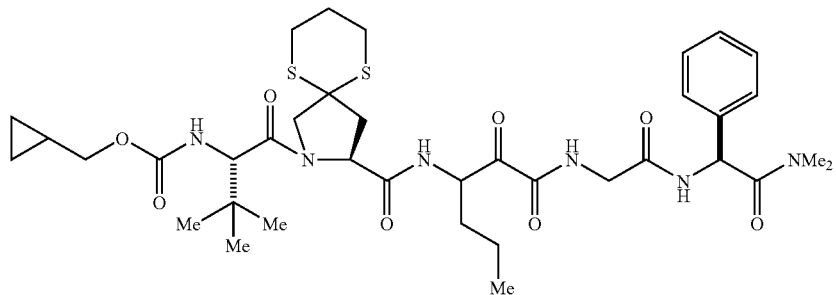
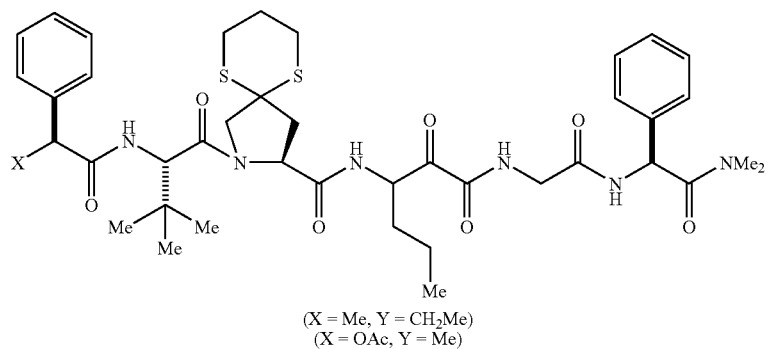
(X = Me, Y = CH₂Me)
(X = OAc, Y = Me)
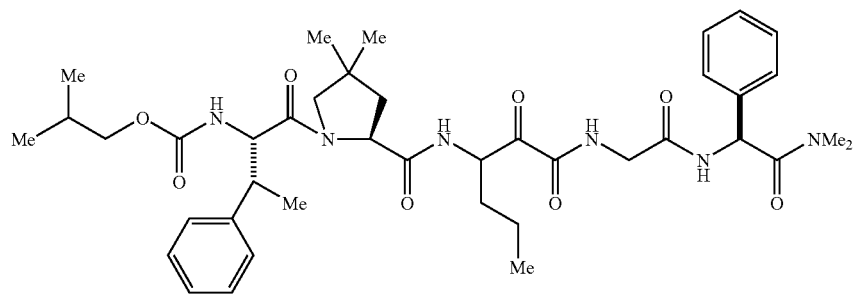
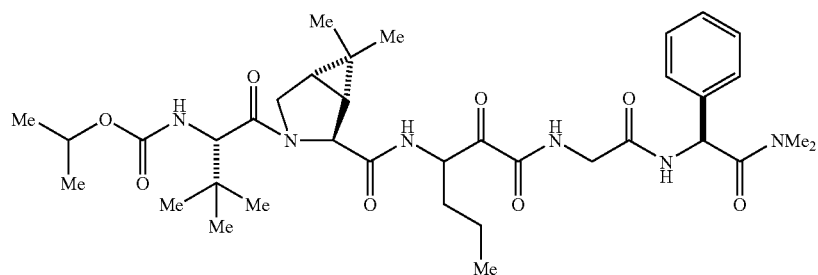

-continued
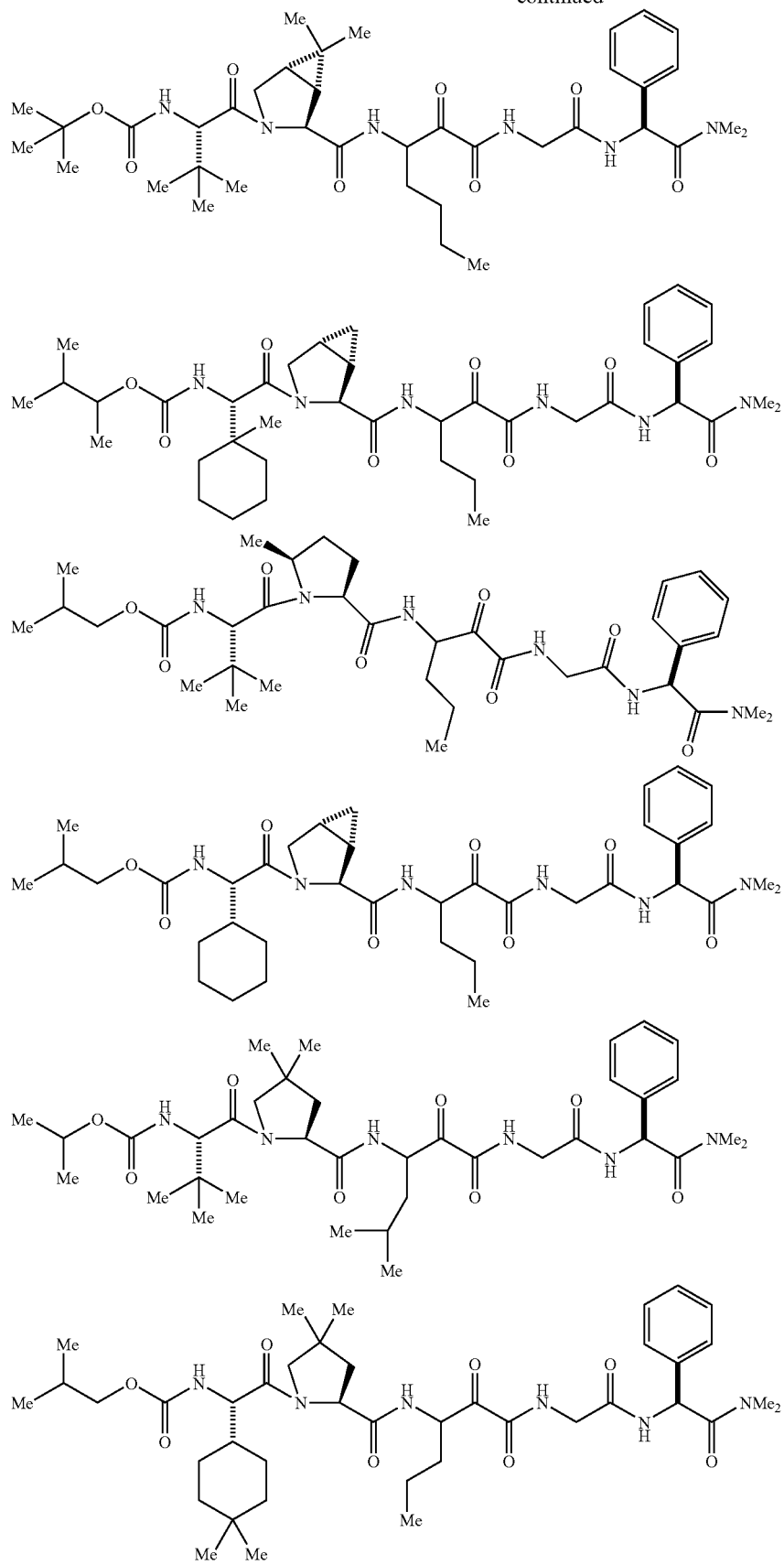

-continued
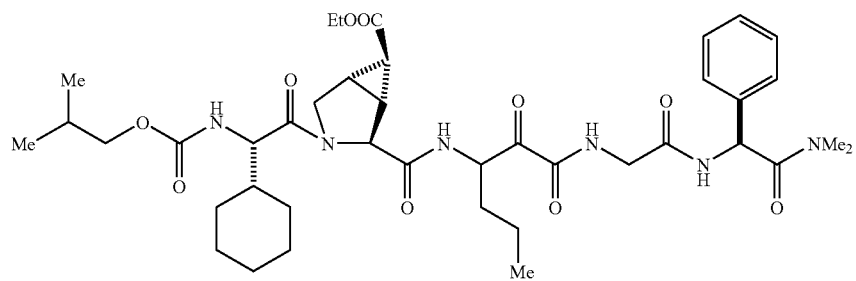
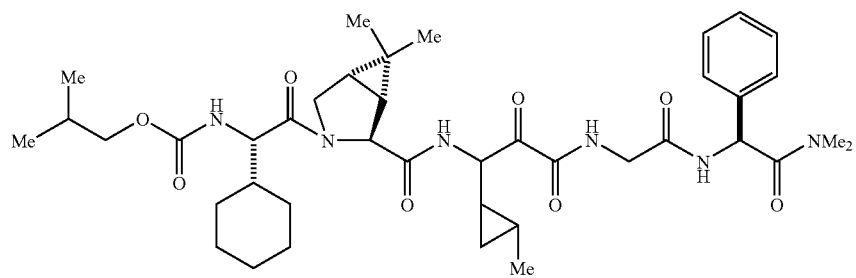
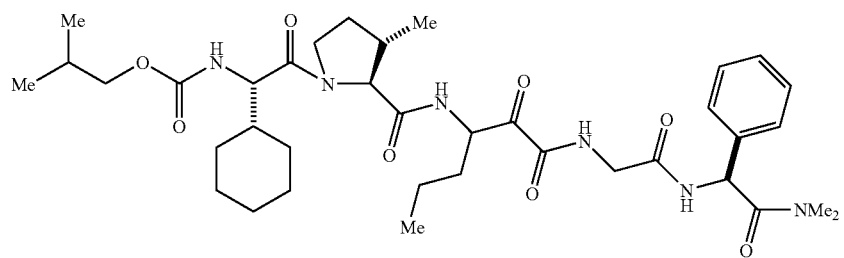
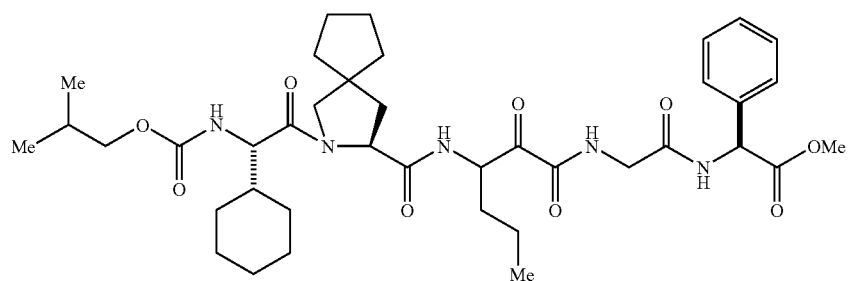
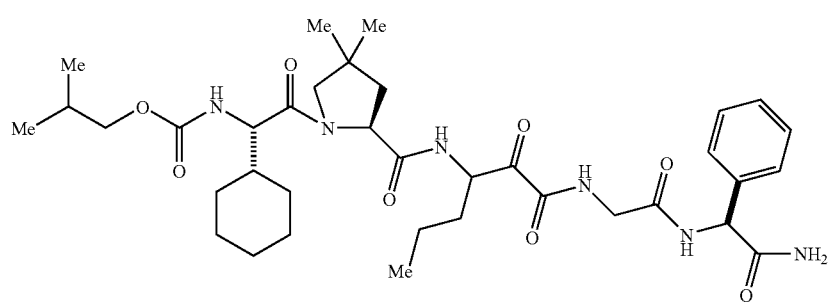

-continued
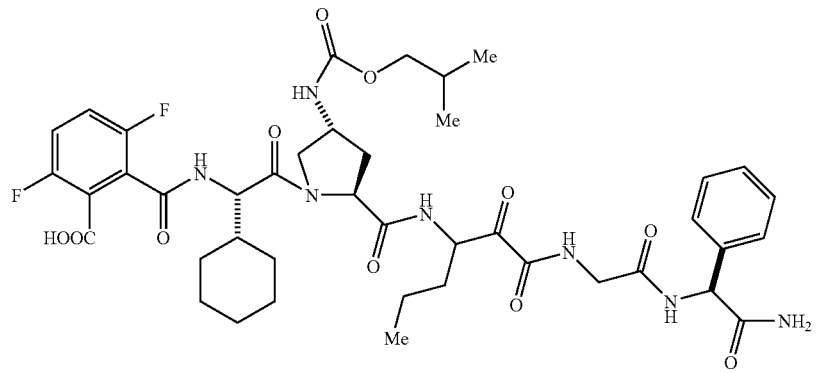
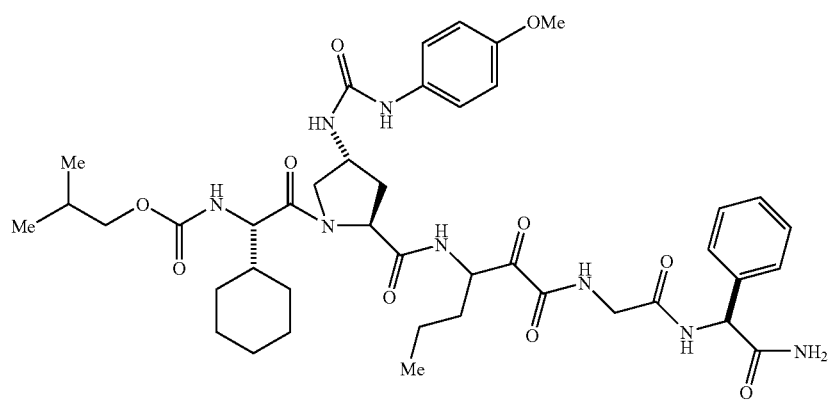
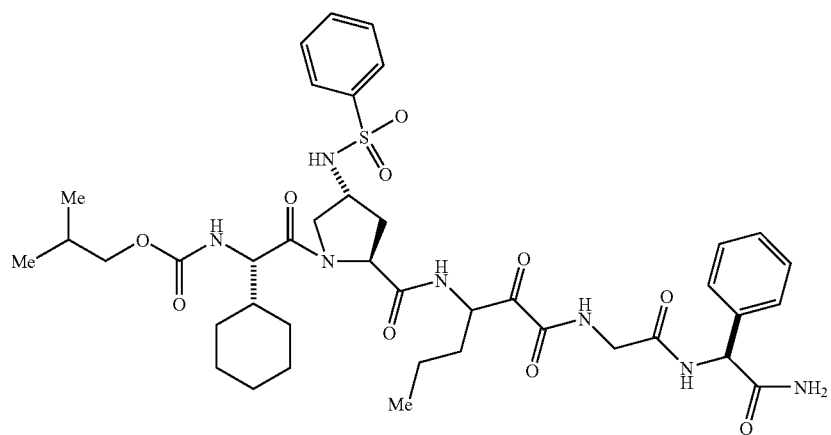
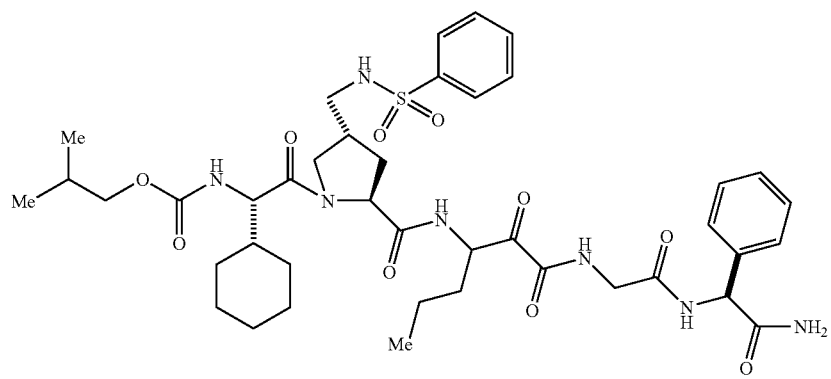

-continued
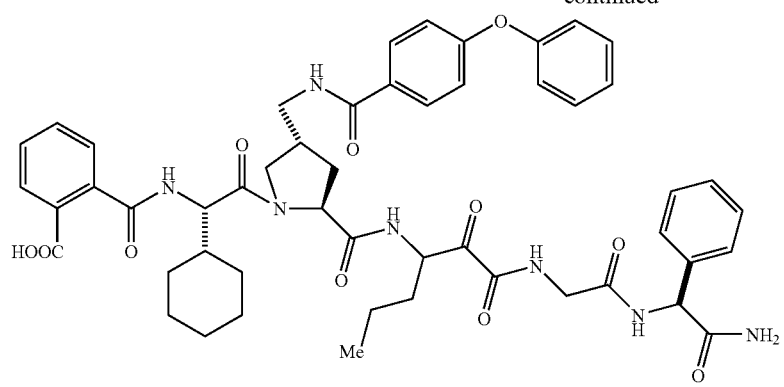
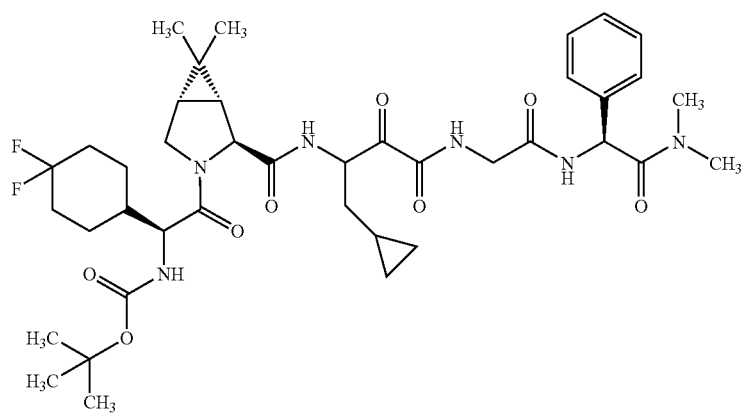
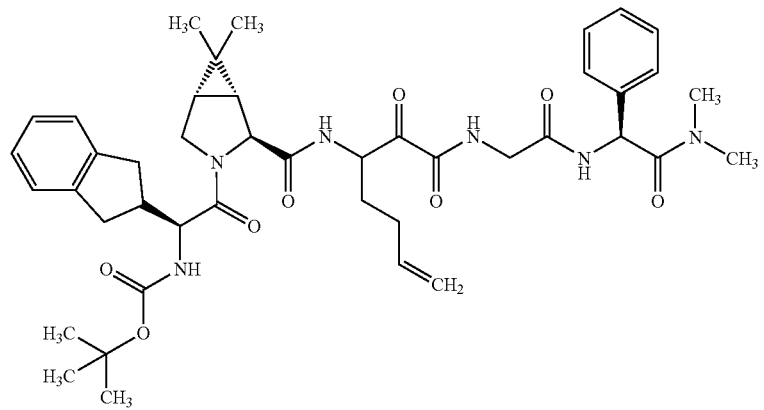
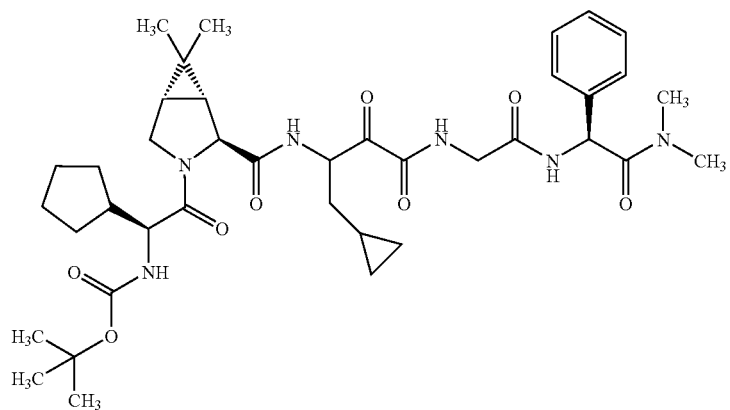

-continued
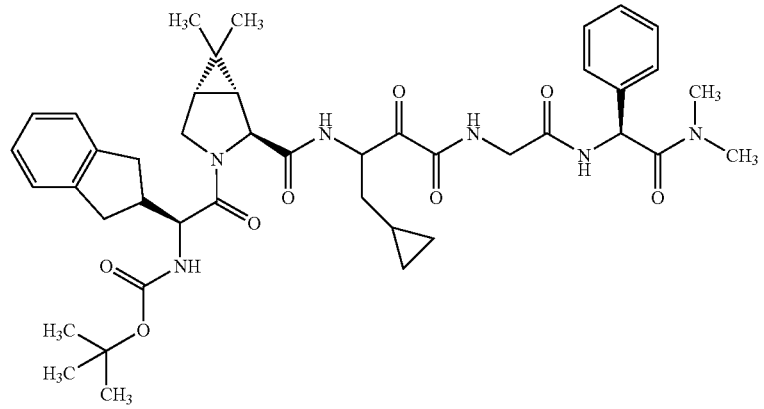
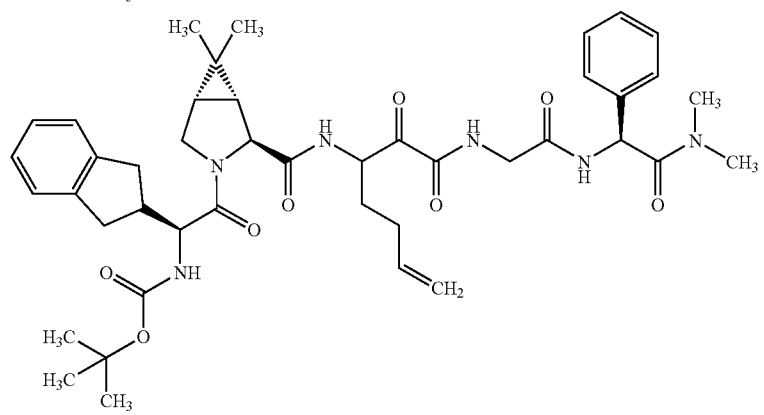
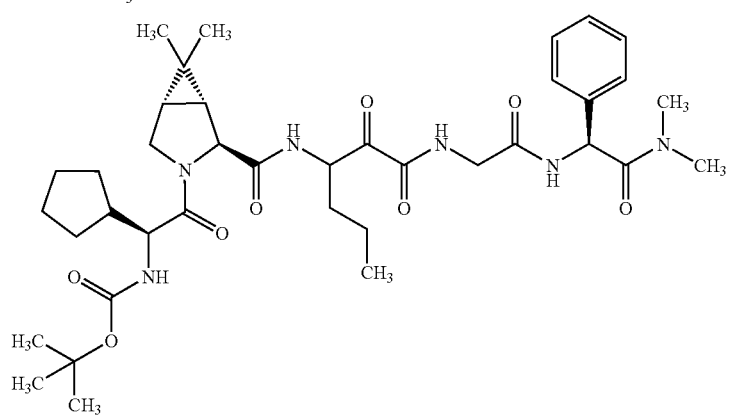
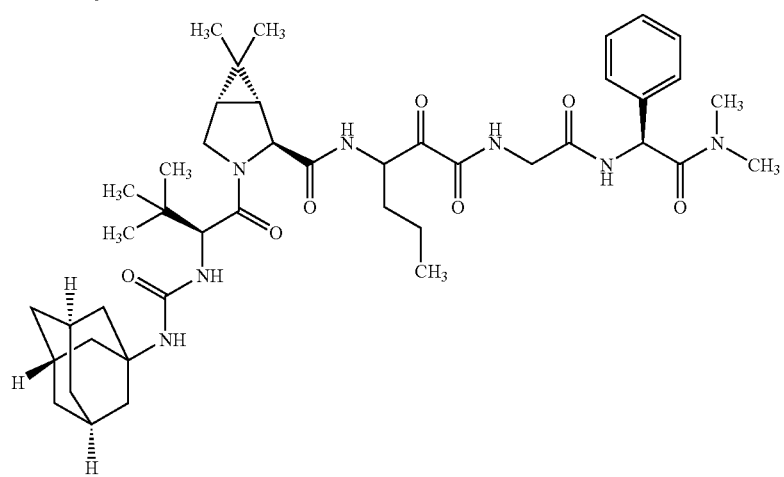

-continued
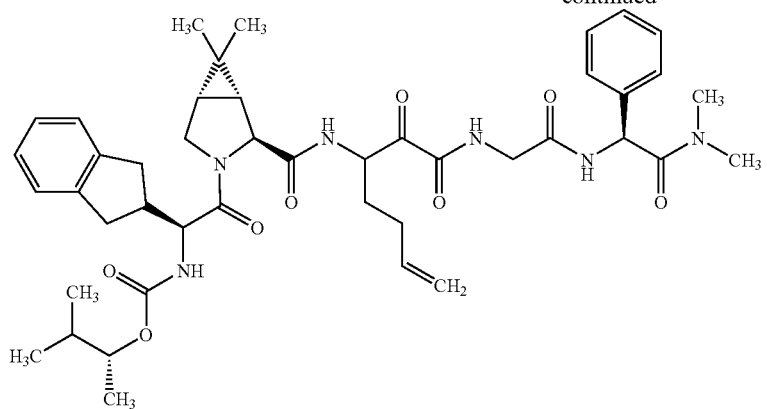
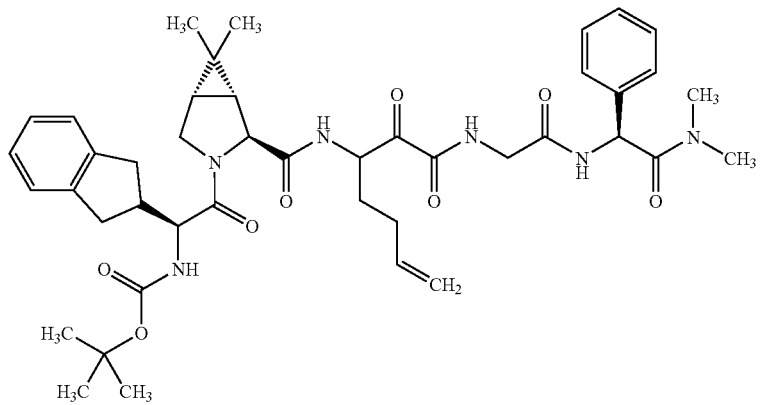
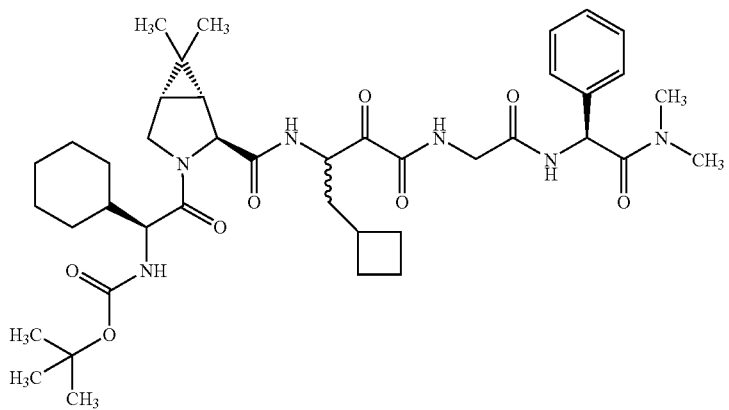
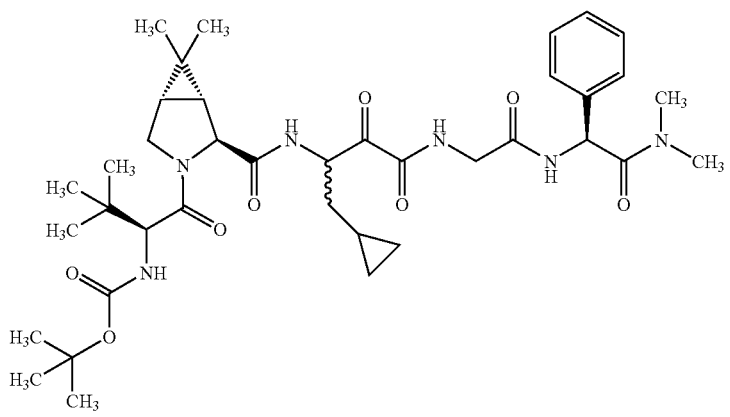

-continued
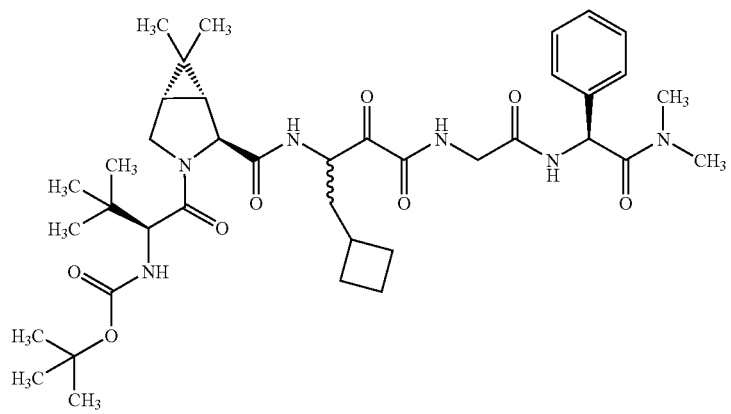
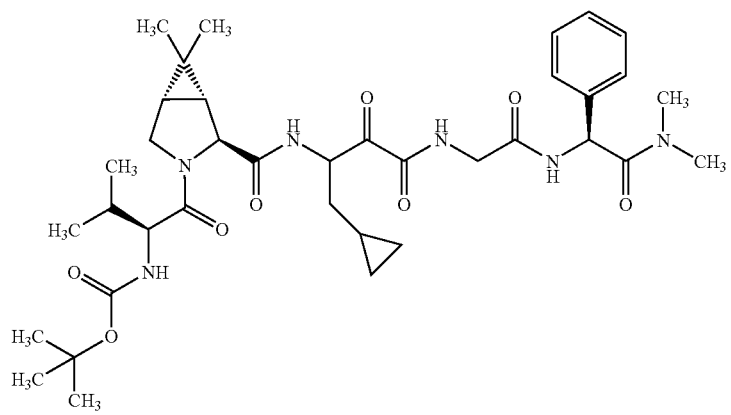
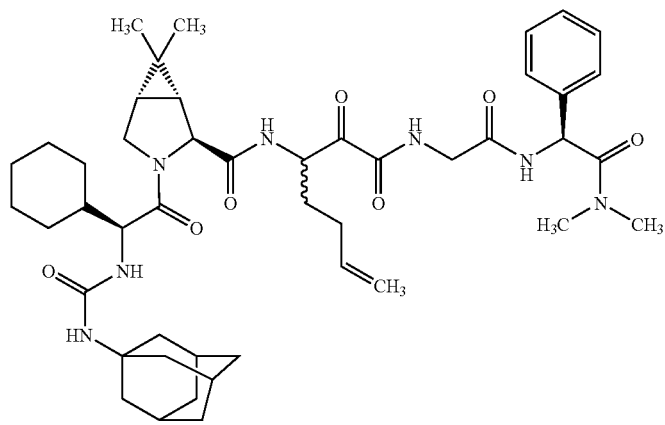
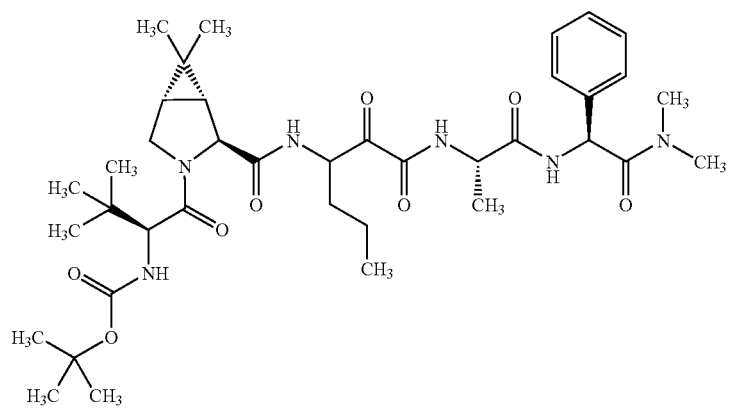

-continued
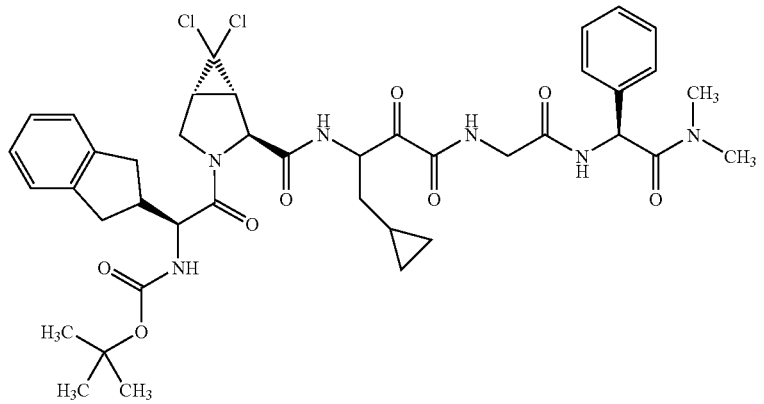
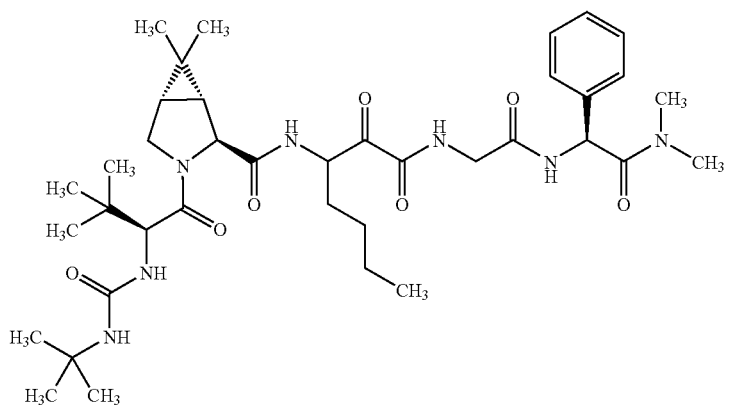
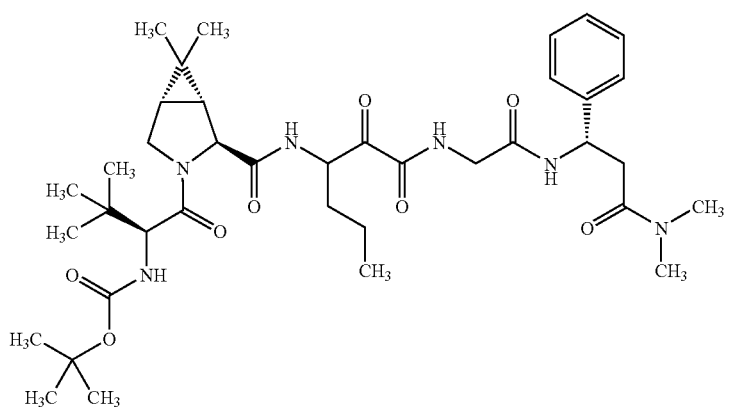
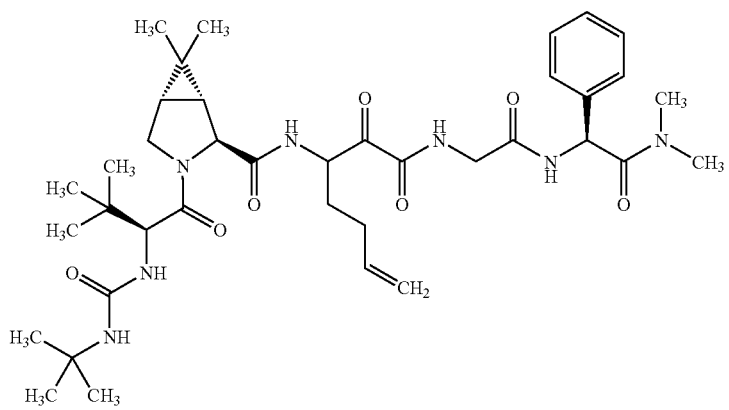

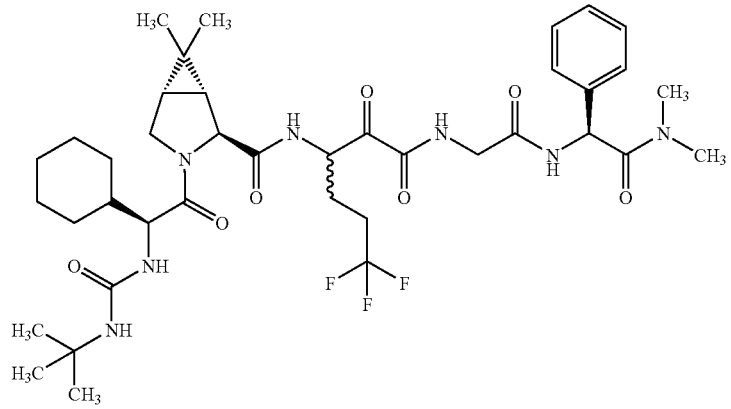
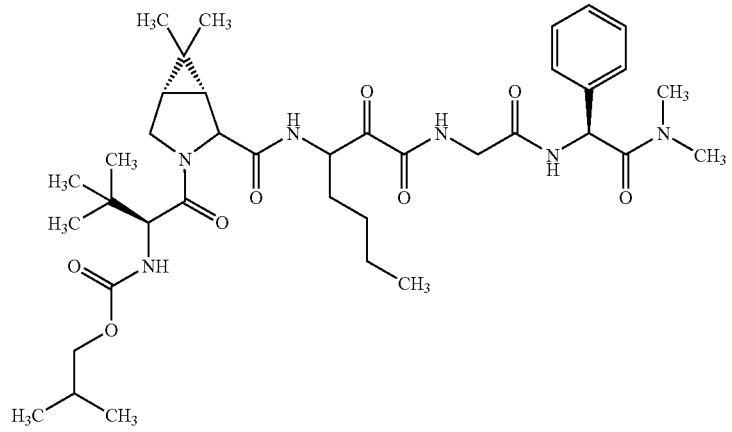
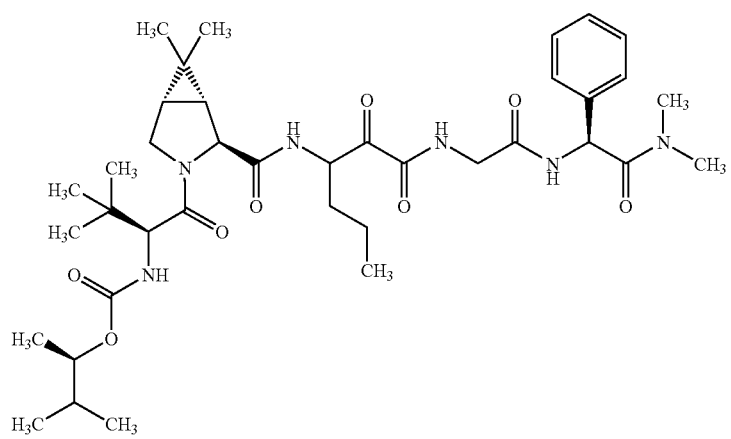

-continued
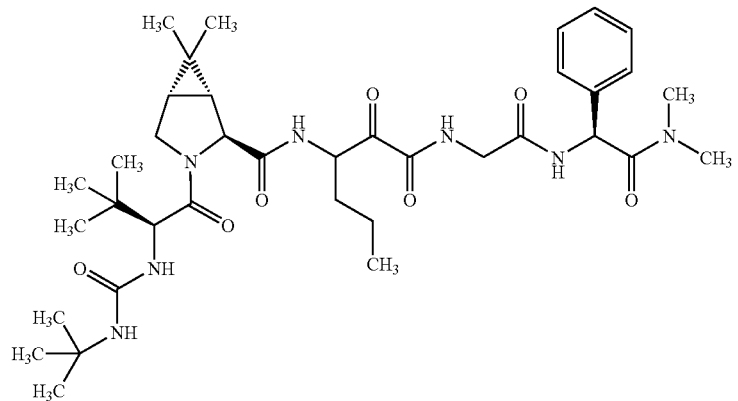
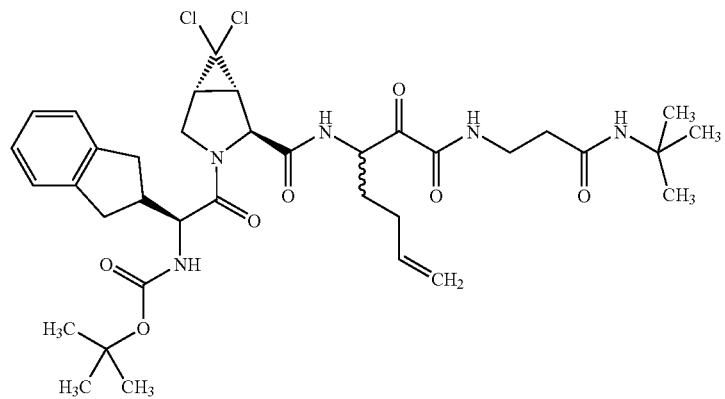
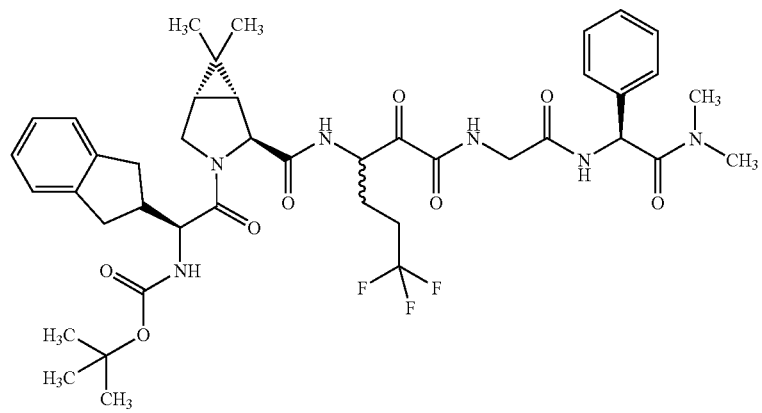
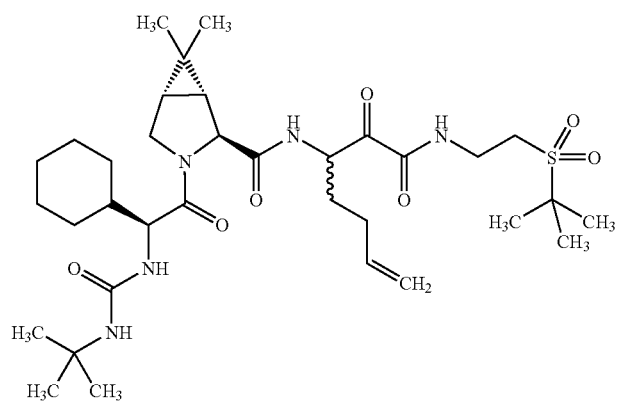

-continued
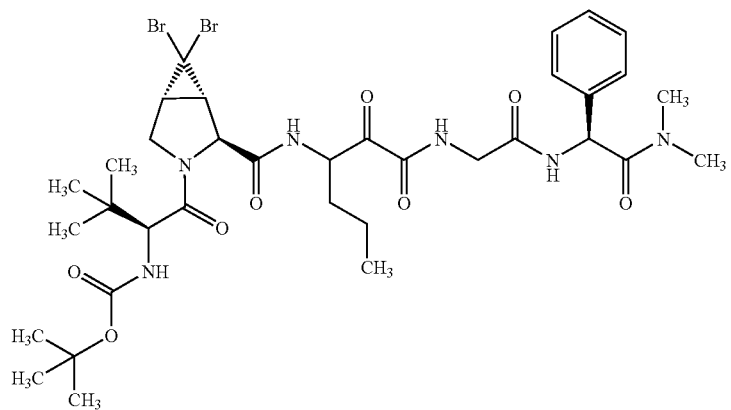
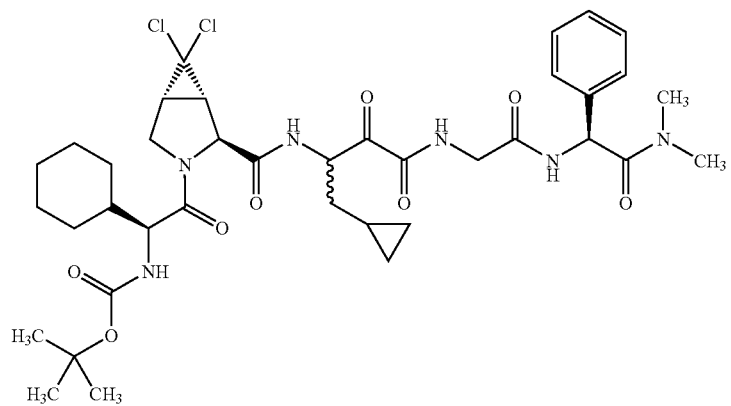
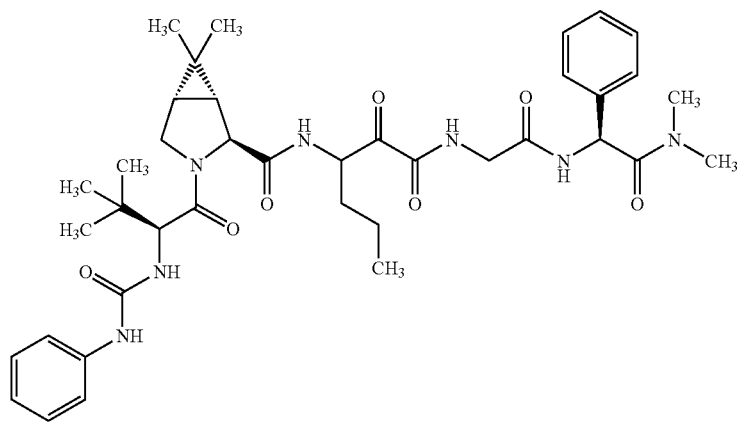
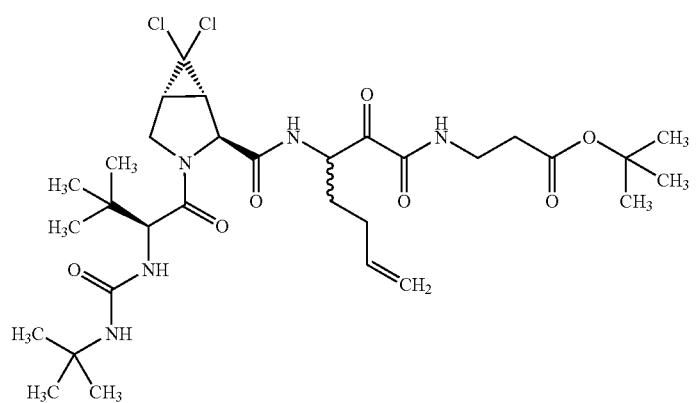

-continued
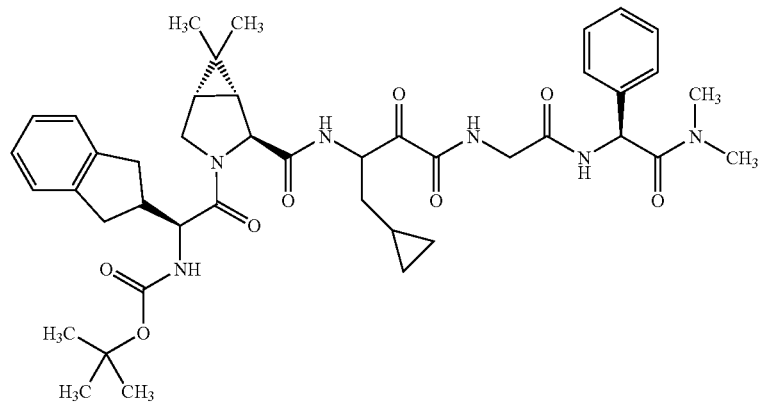
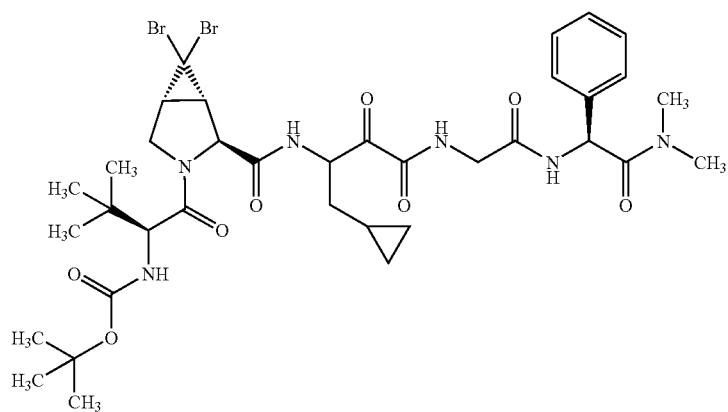
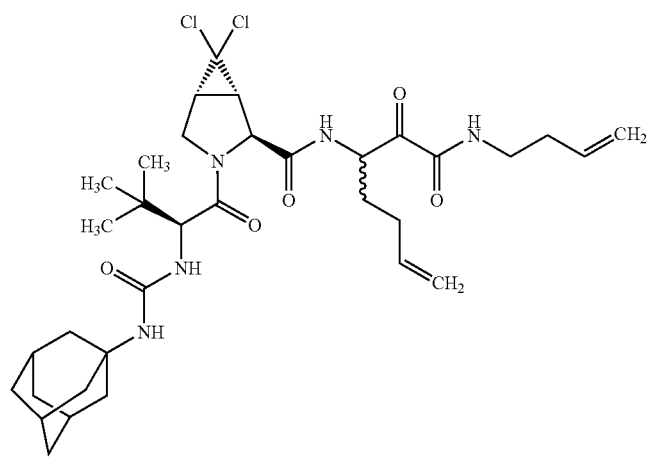
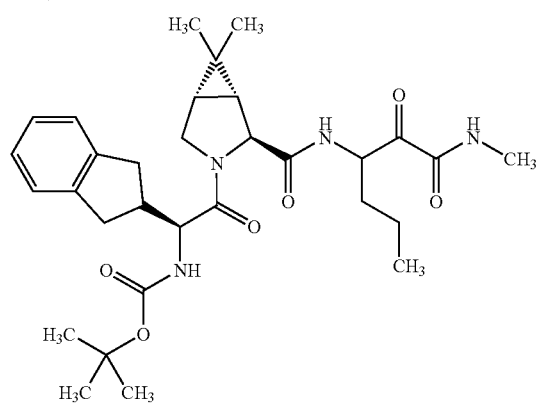

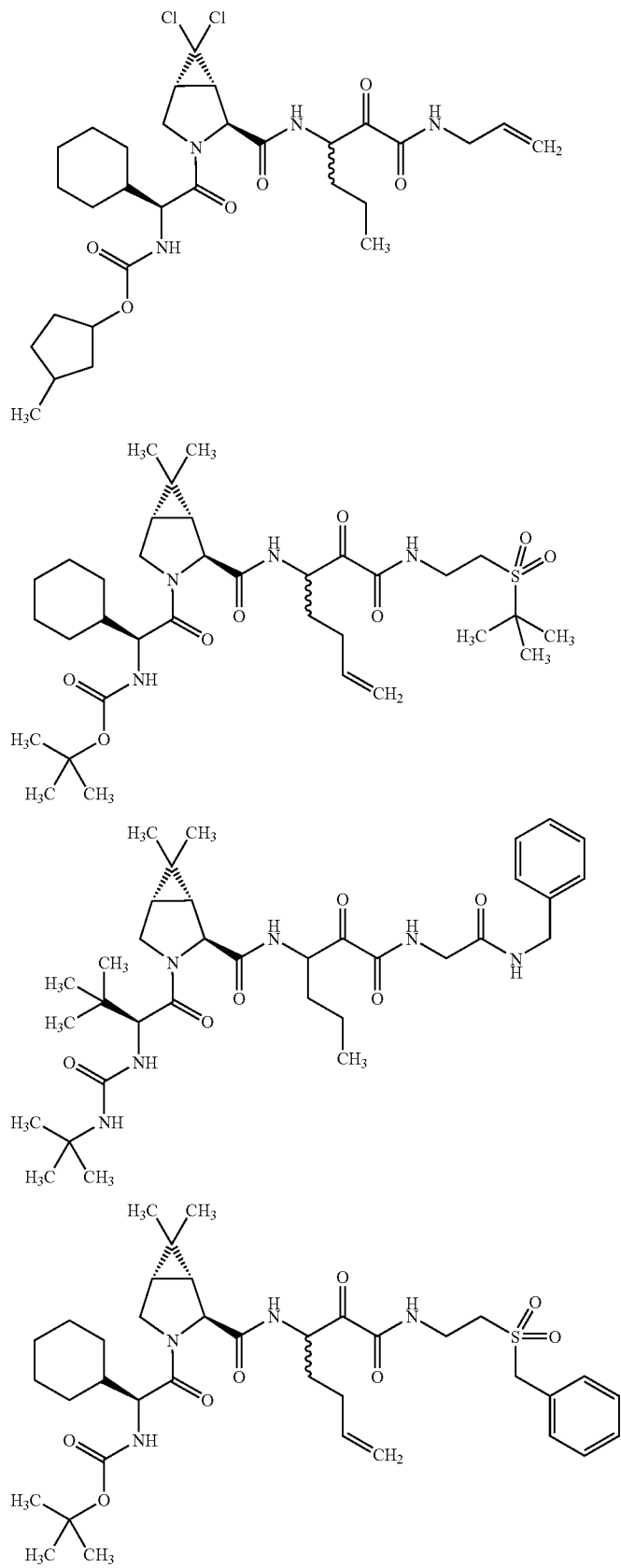

-continued
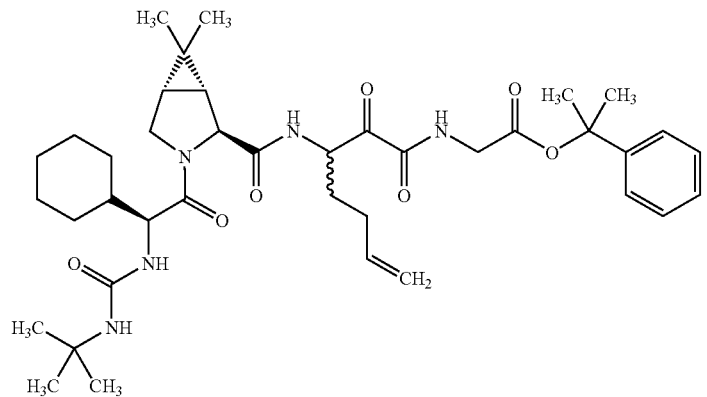
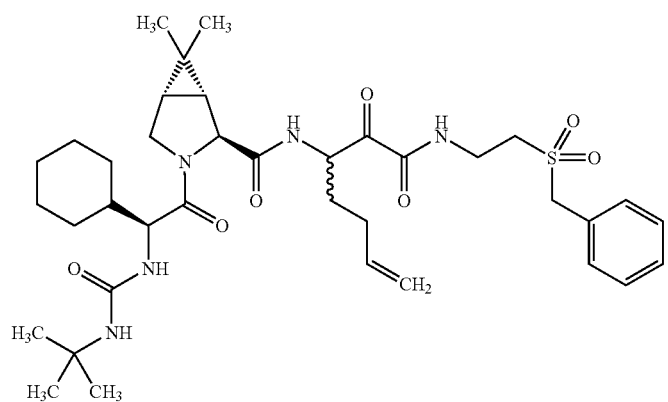
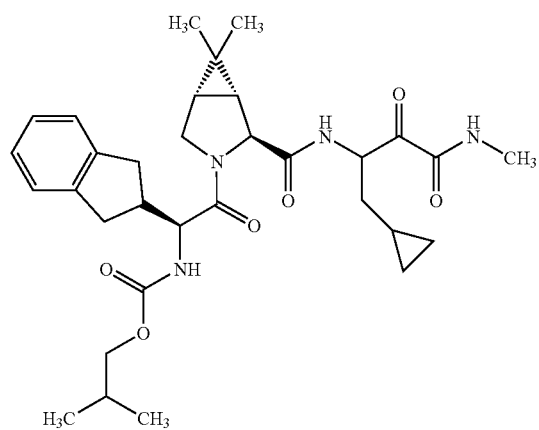
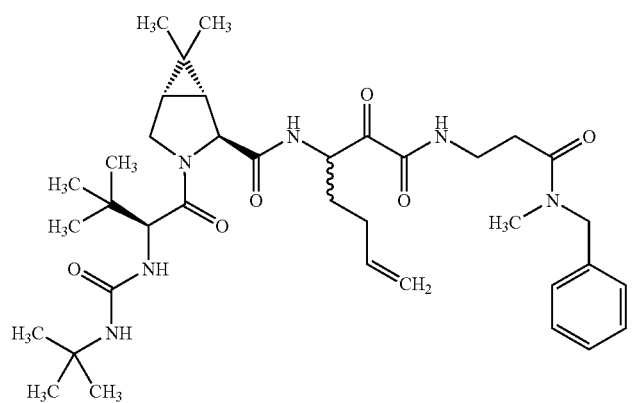

-continued
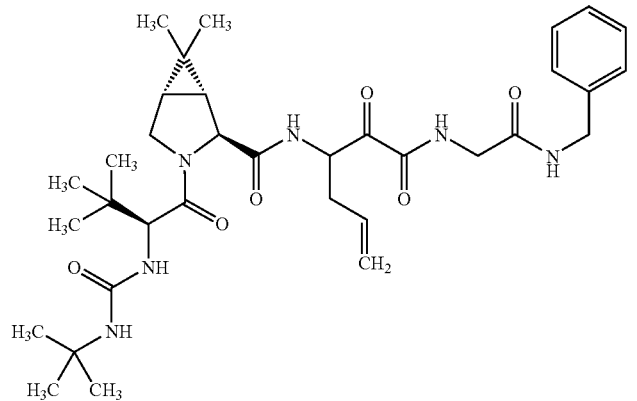
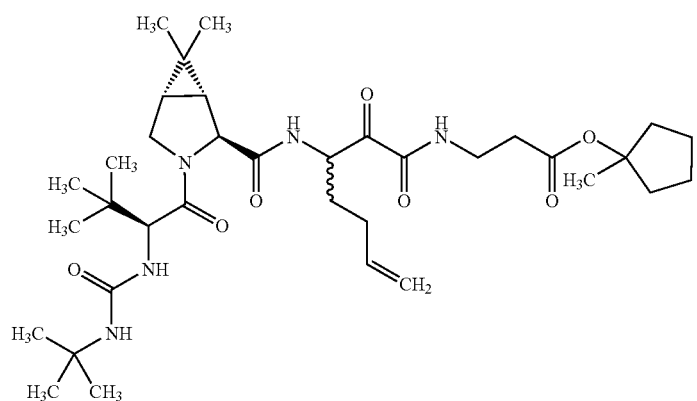
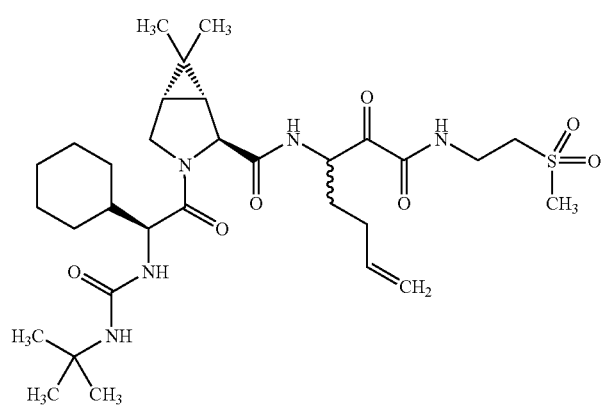
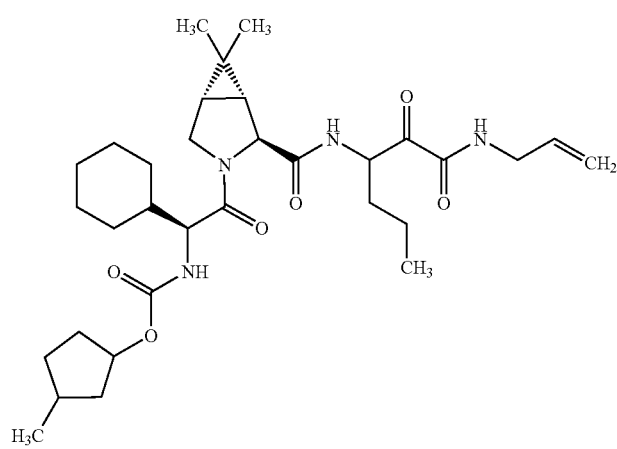

-continued
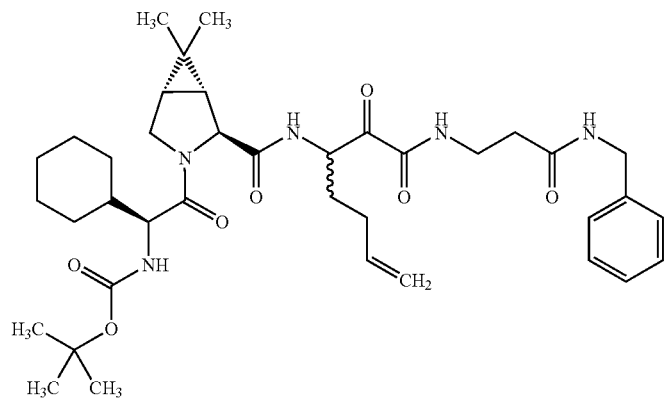
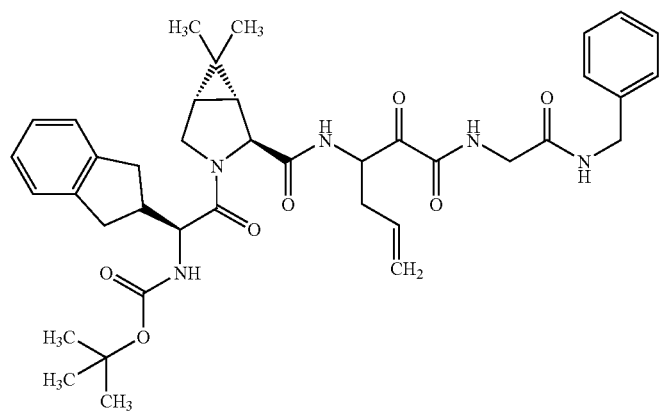
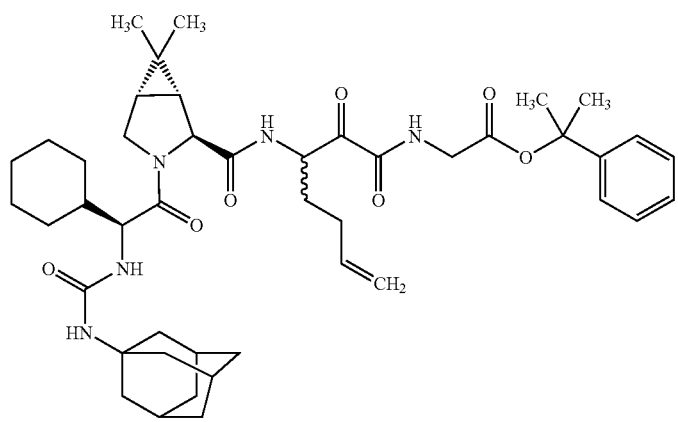
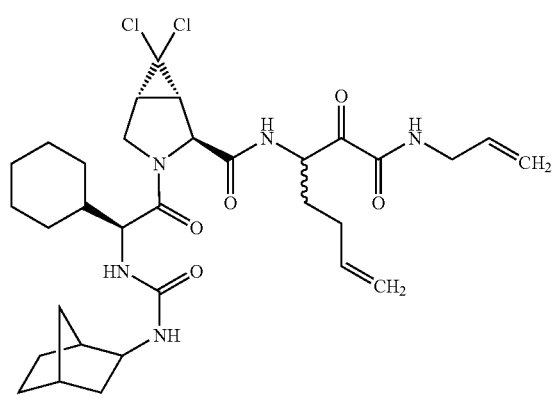

-continued
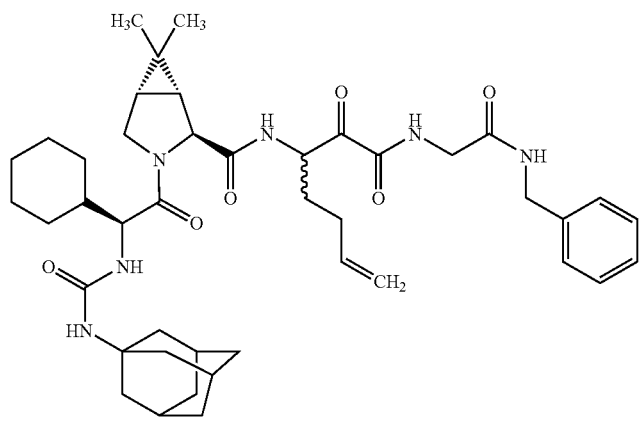
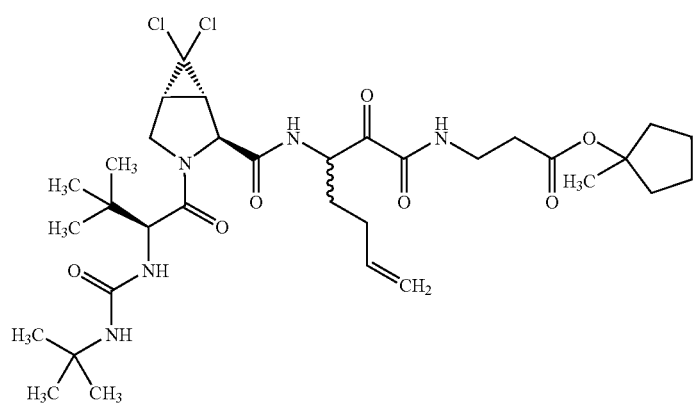
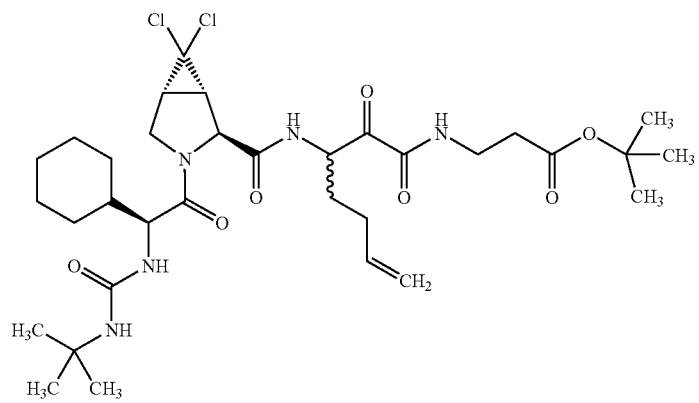
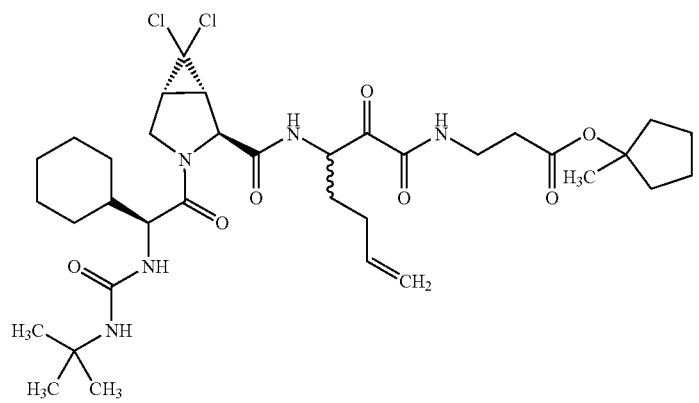

-continued
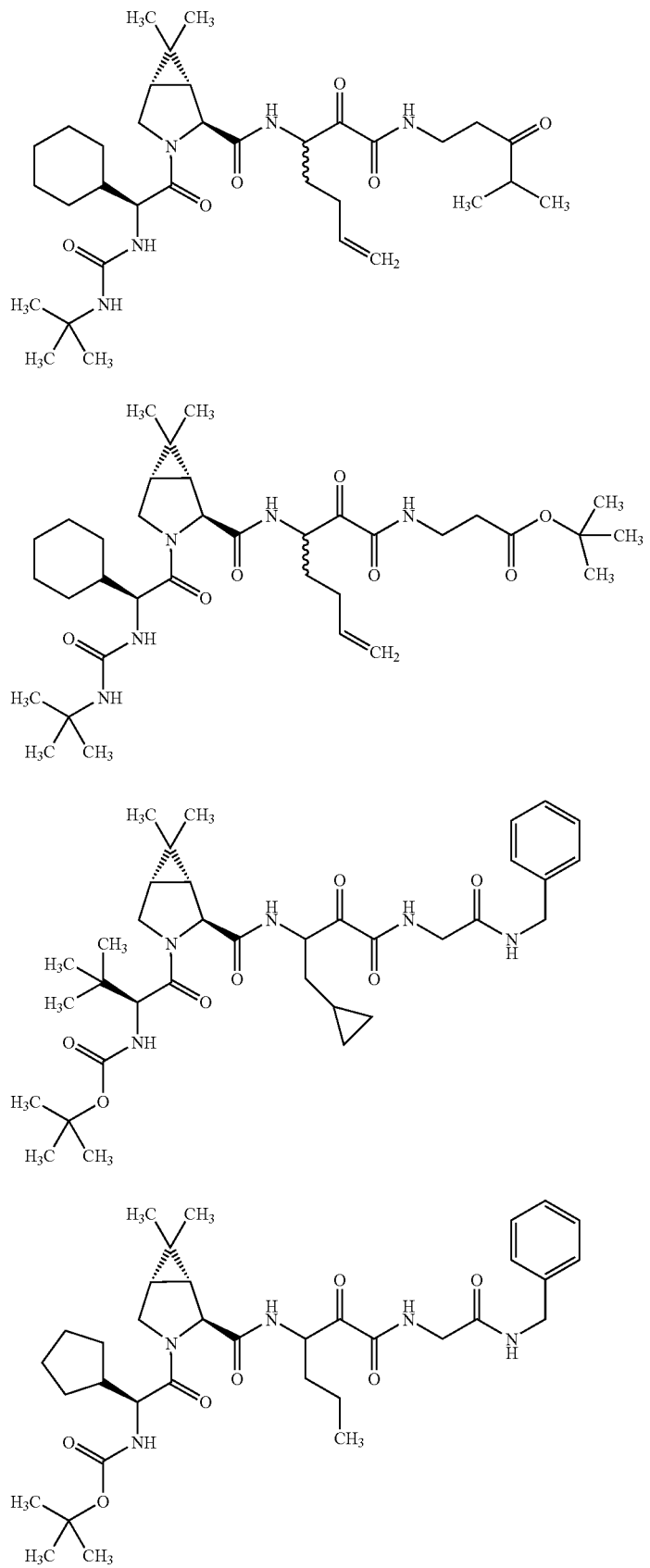

-continued
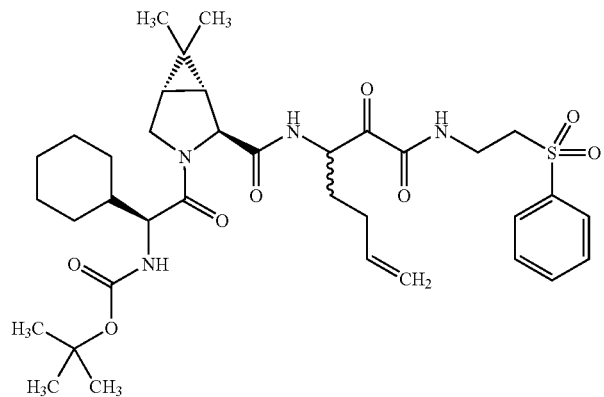
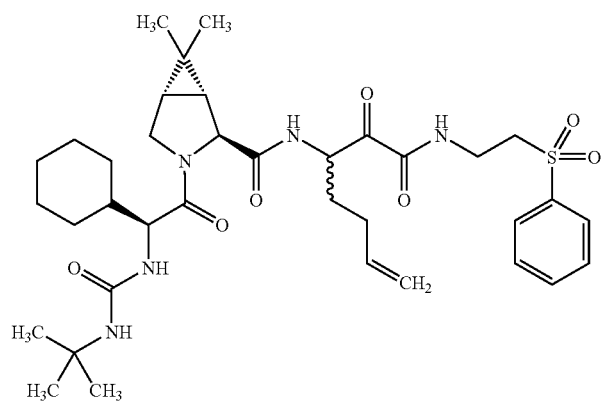
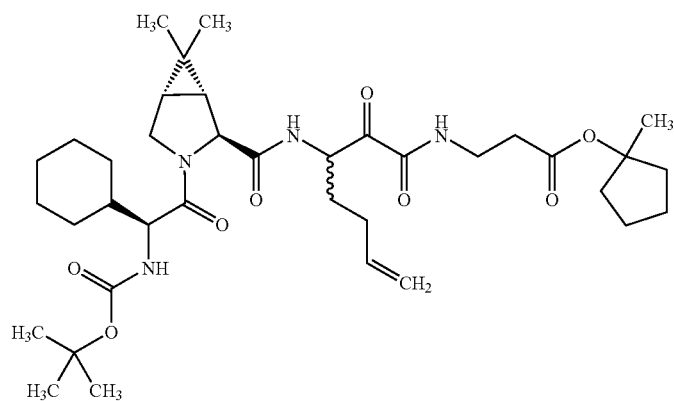
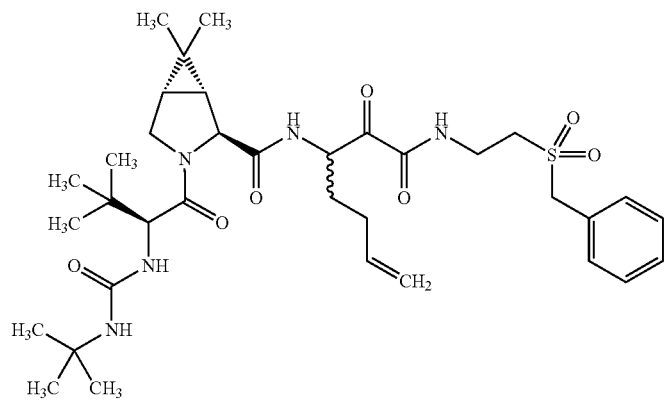

-continued
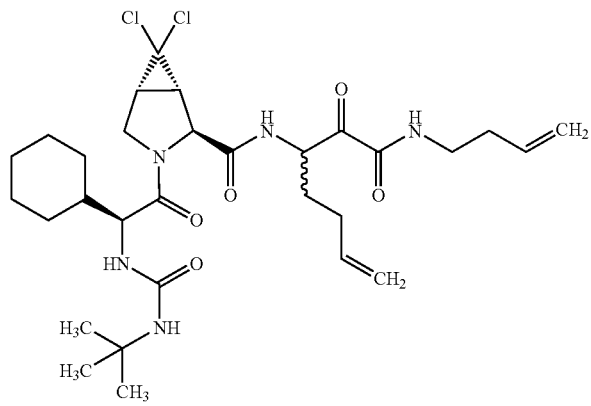
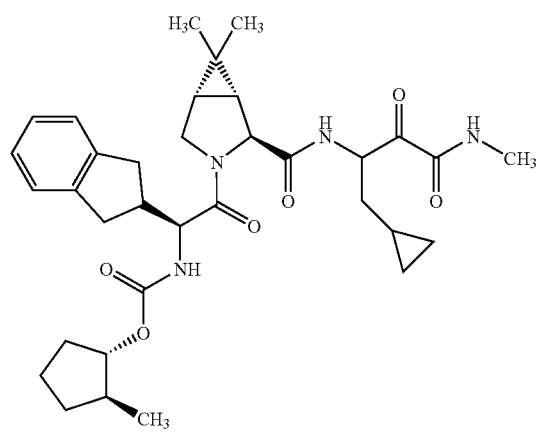
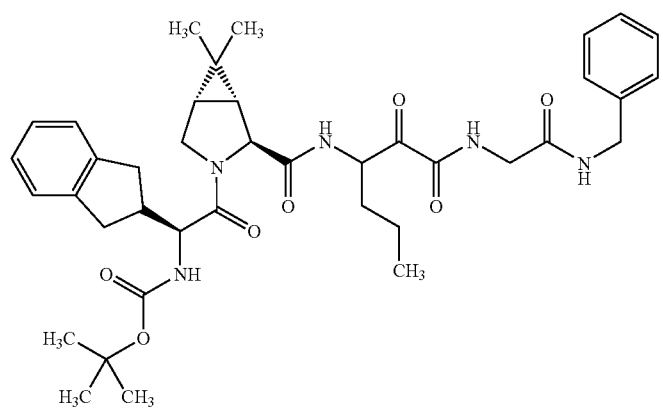
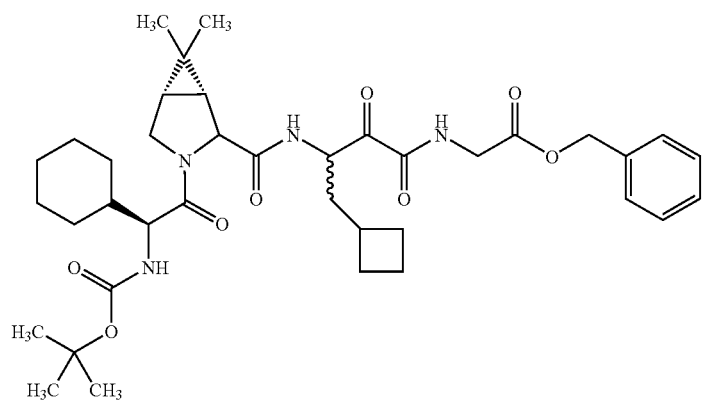

-continued
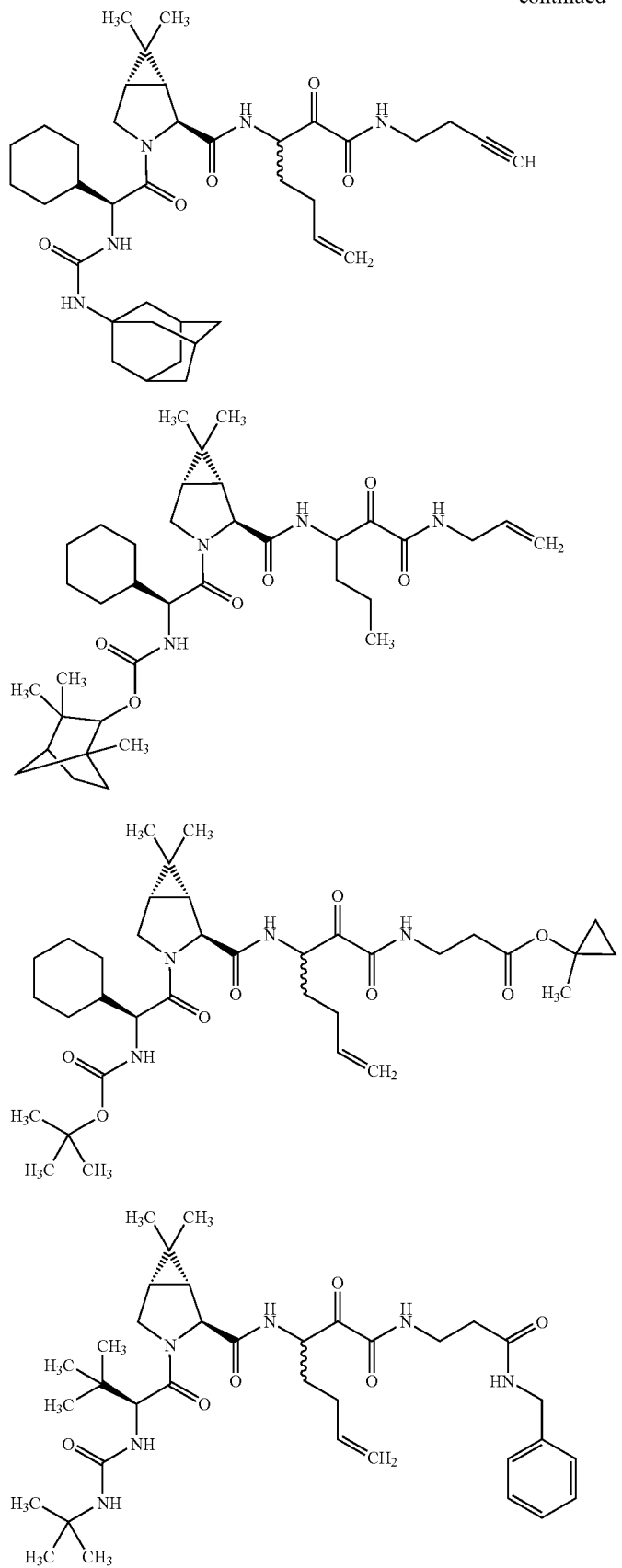

-continued
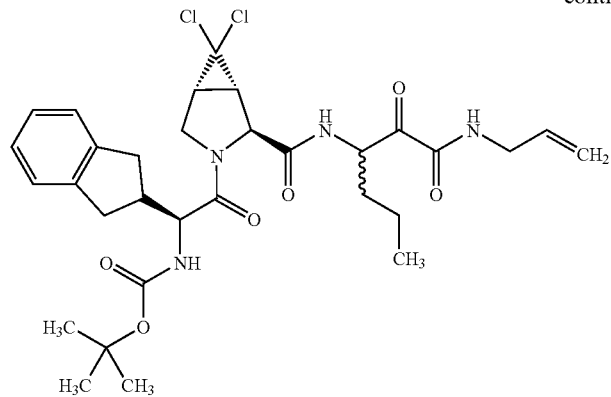
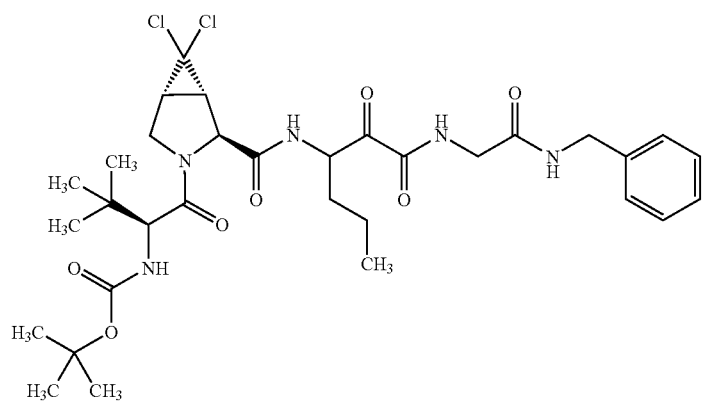
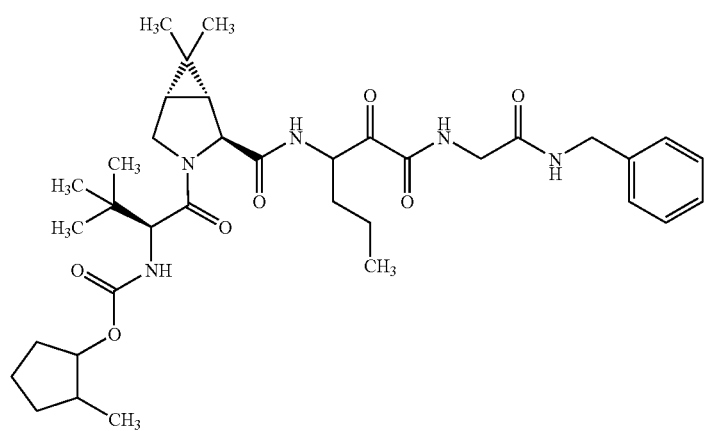
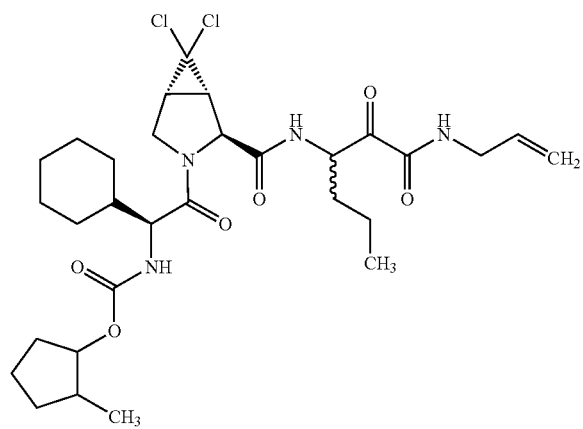

-continued
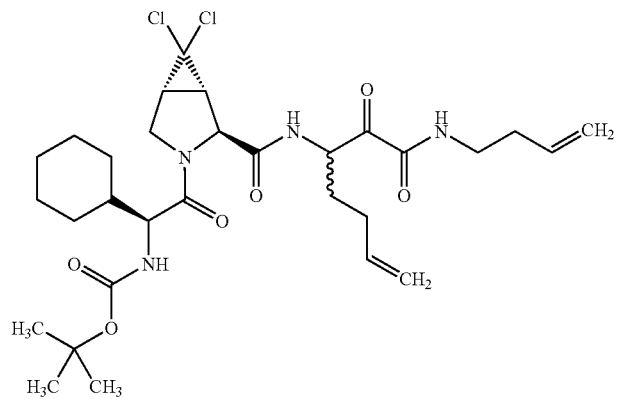
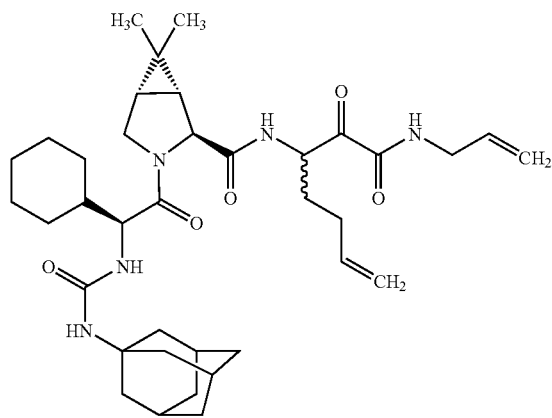
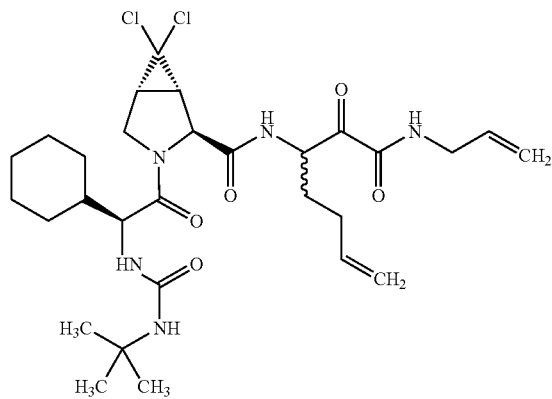
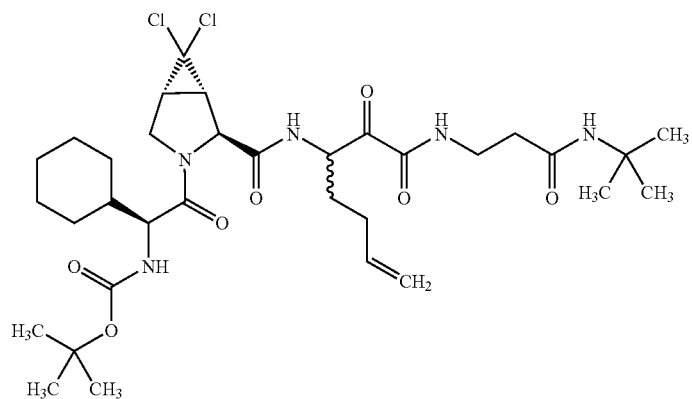

-continued
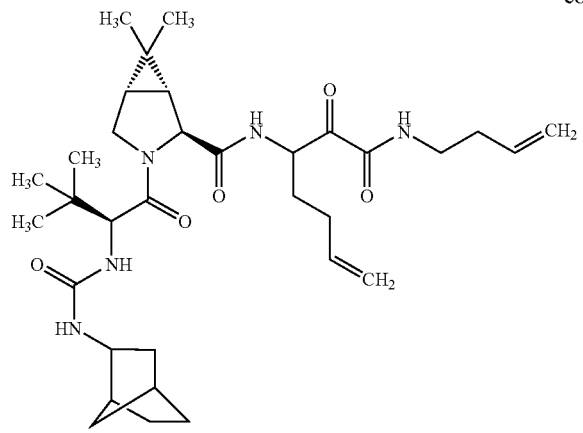
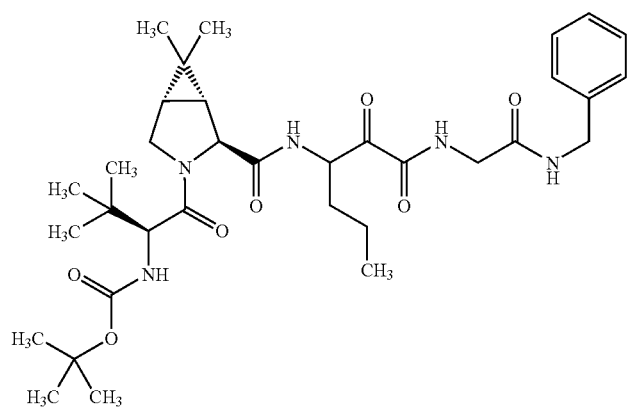
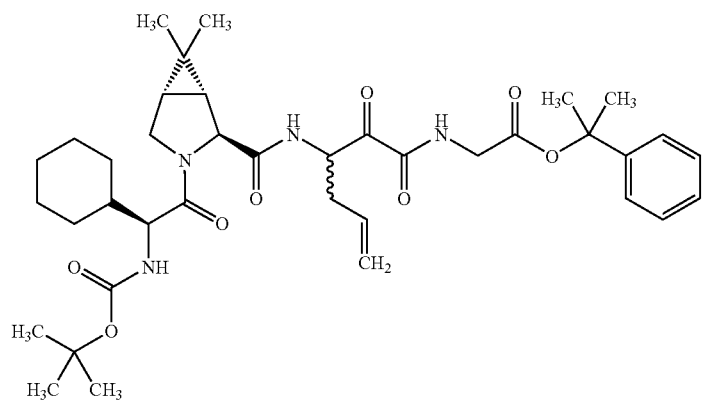
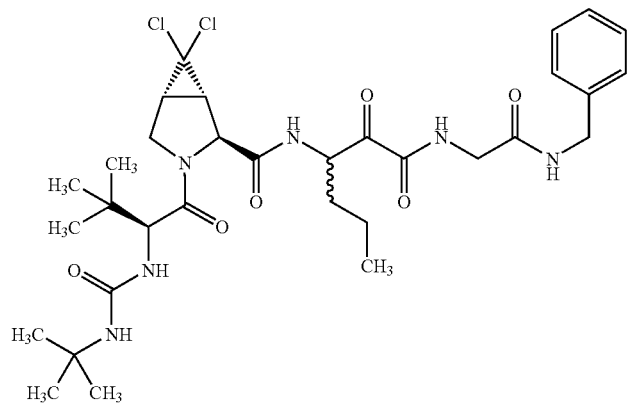

-continued
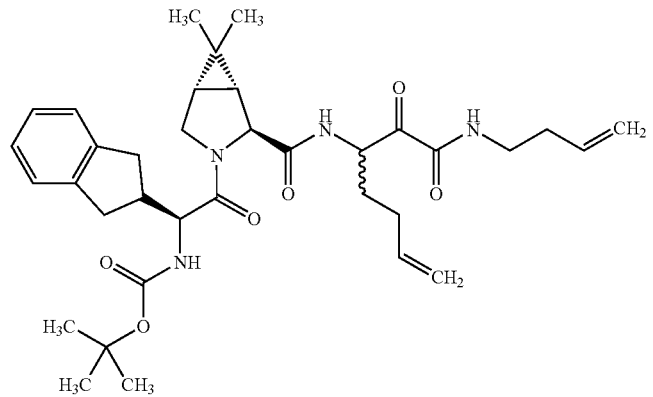
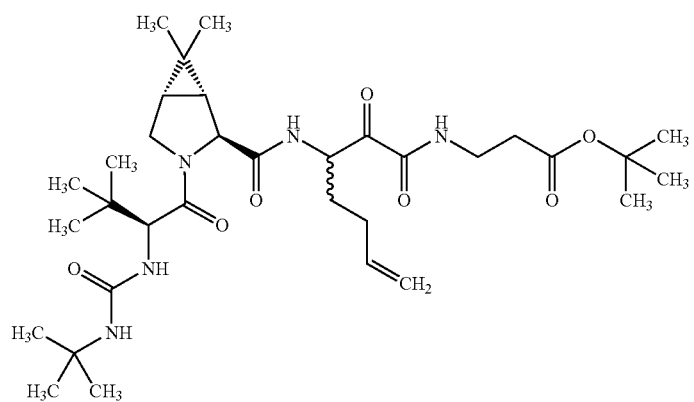
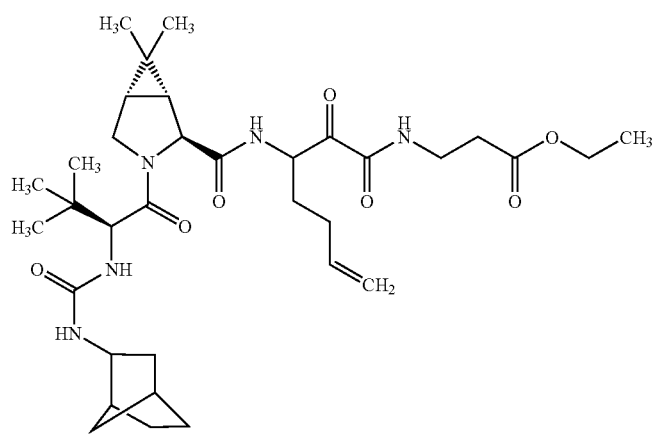
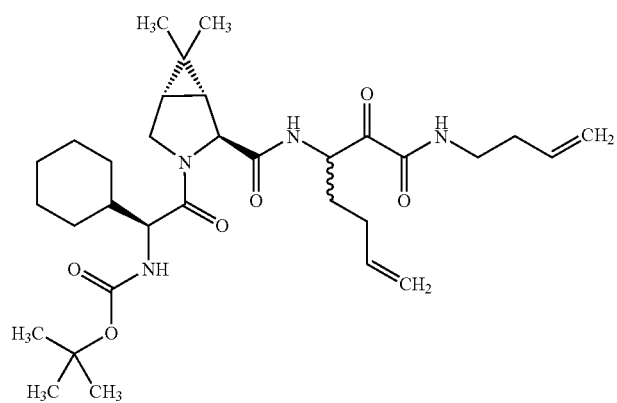

-continued
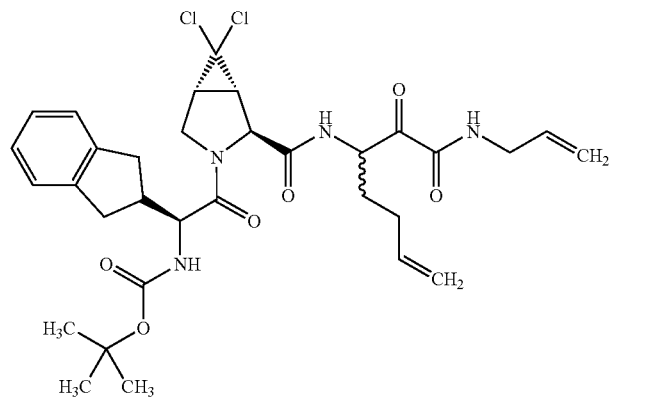
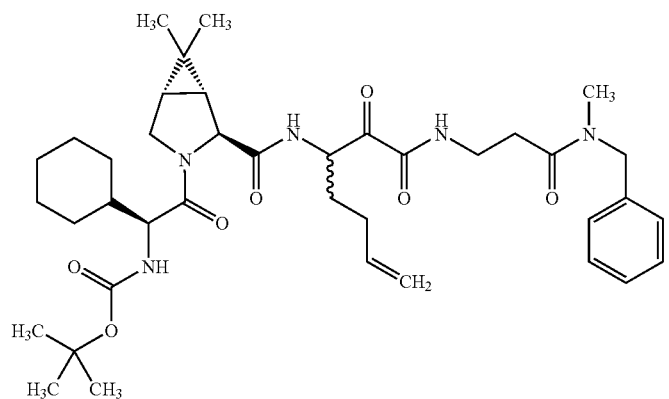
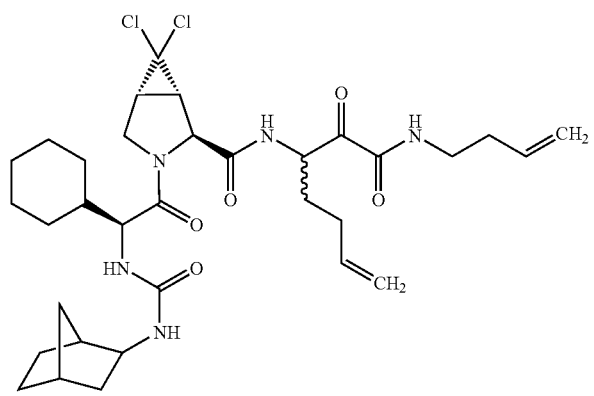
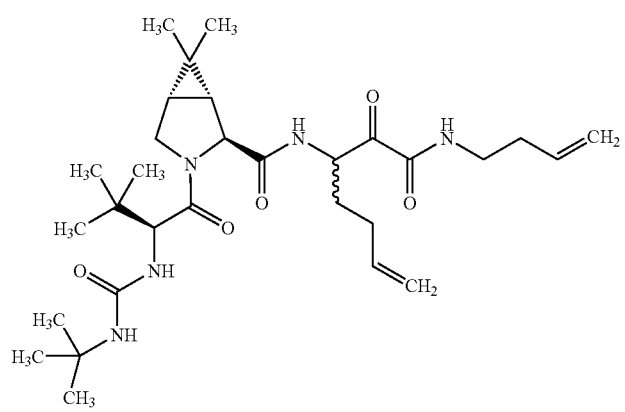

-continued
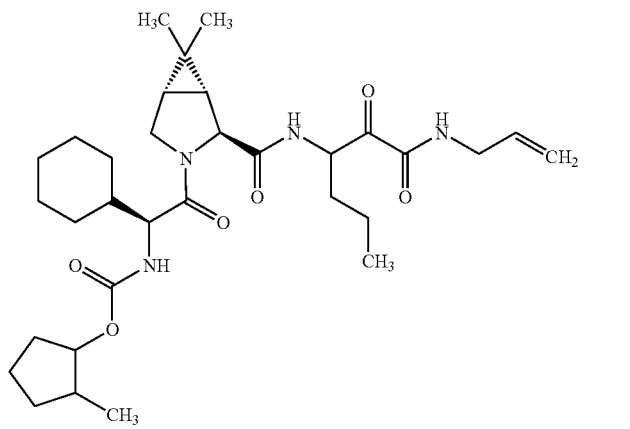
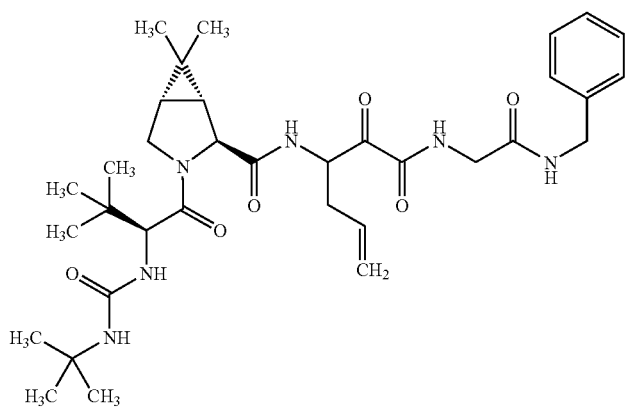
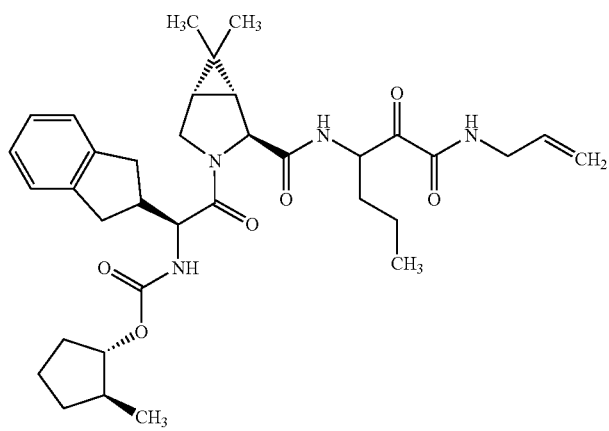
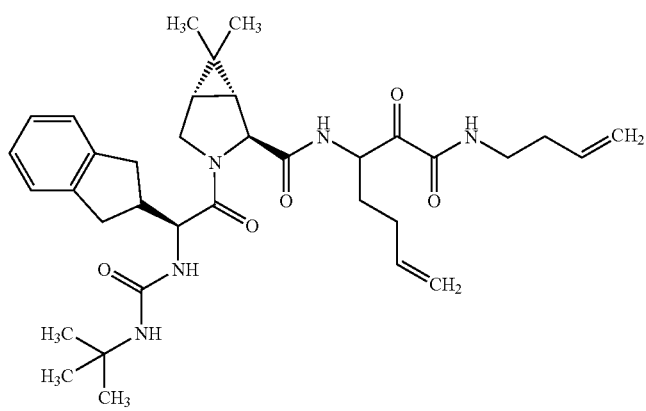

-continued
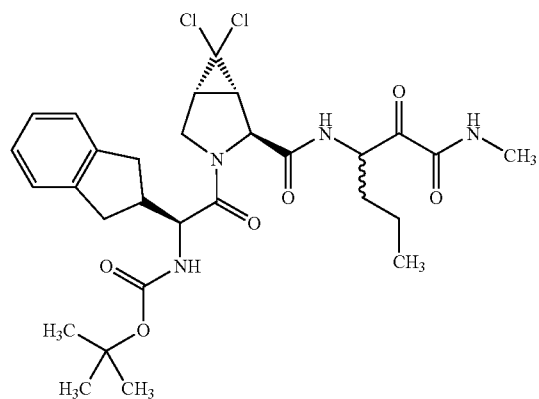
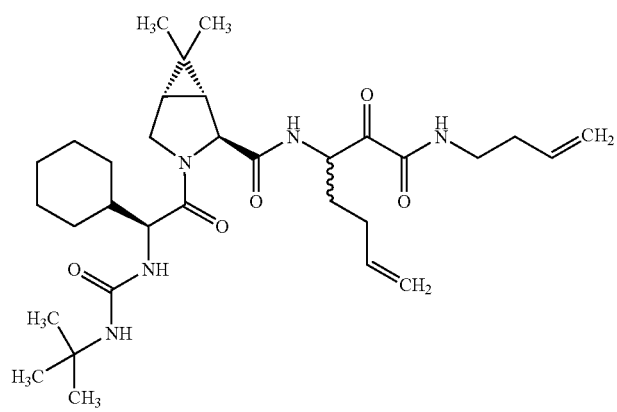
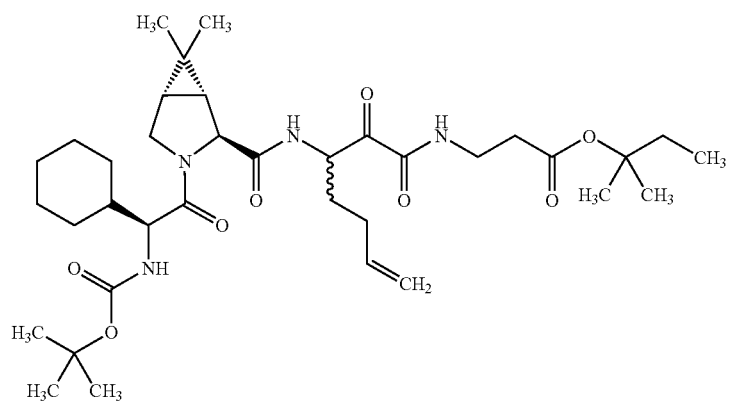
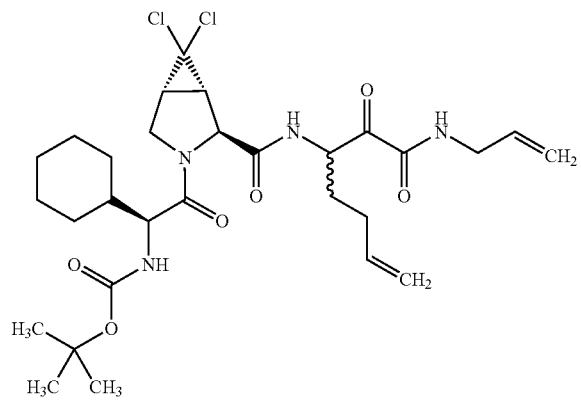

-continued
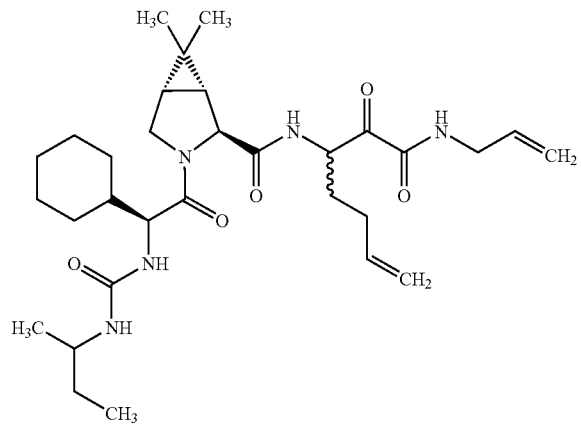
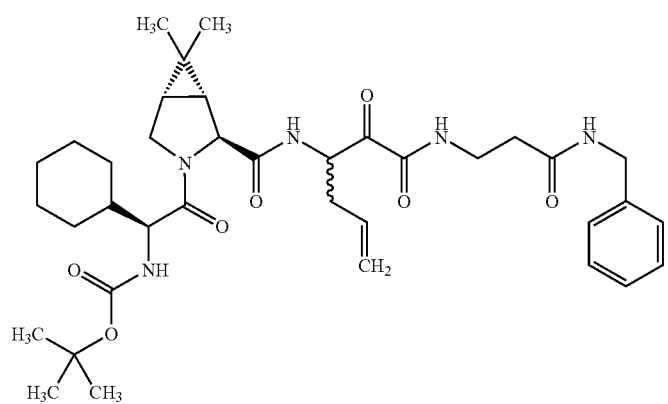
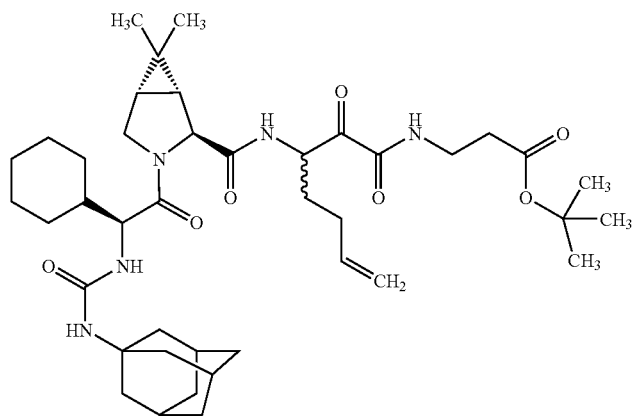
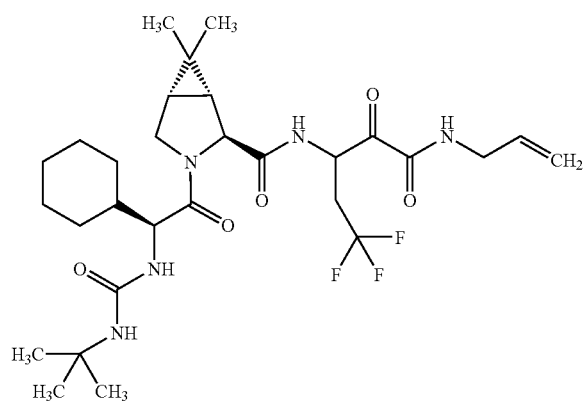

-continued
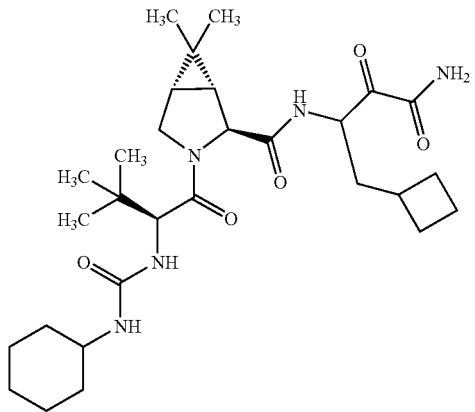
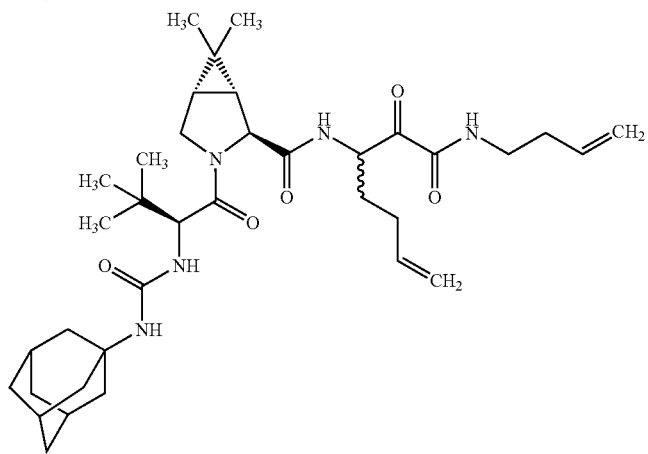
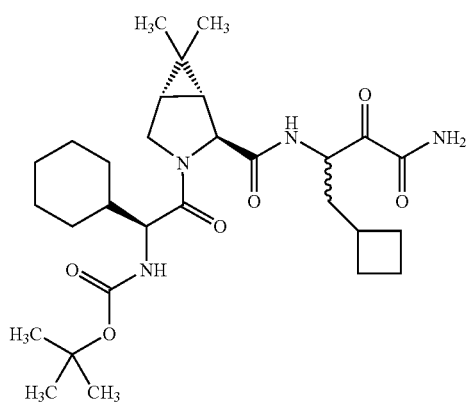
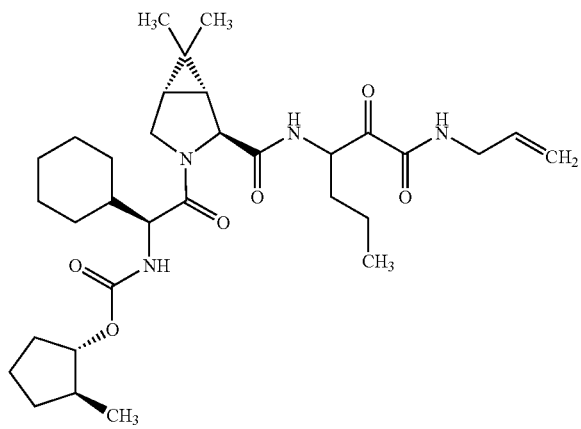

-continued
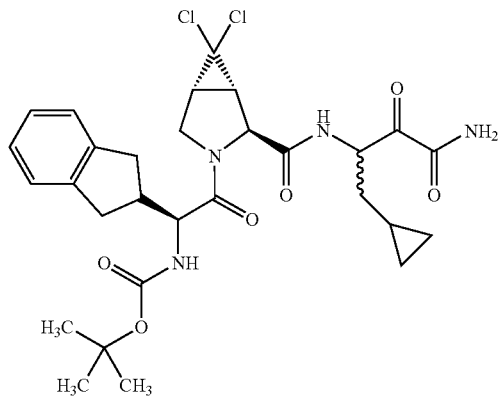
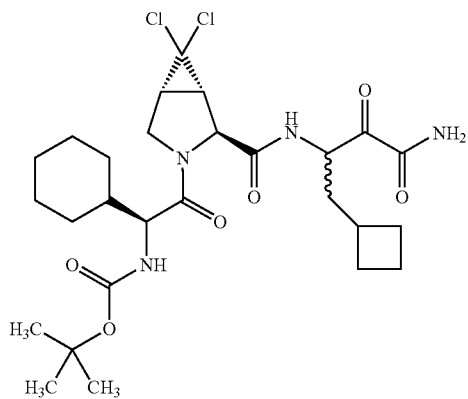
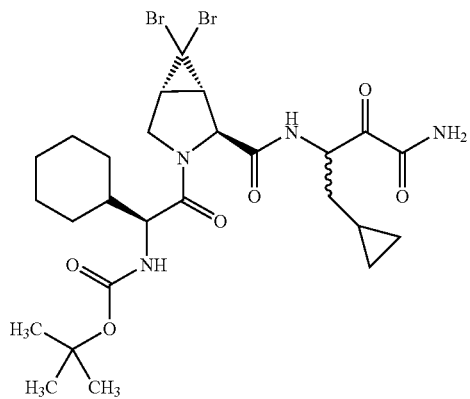
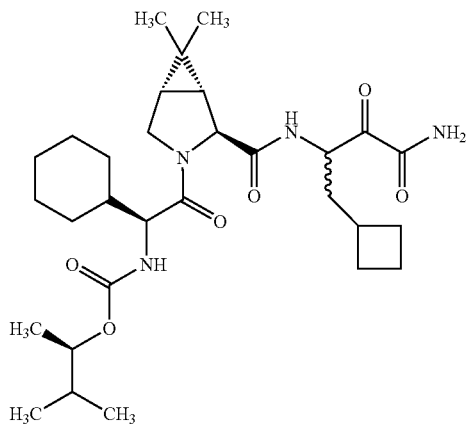
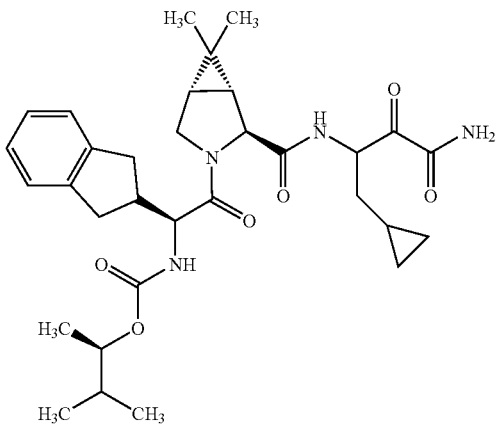
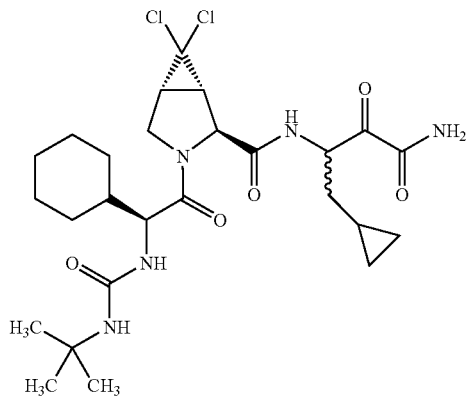
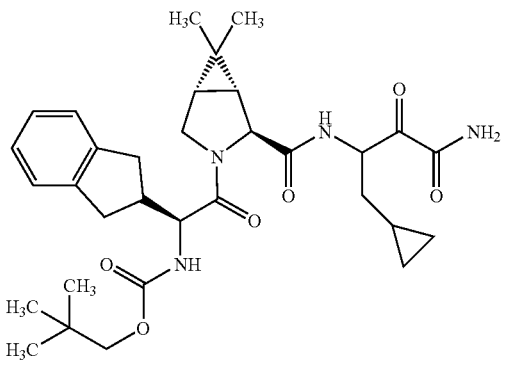

115
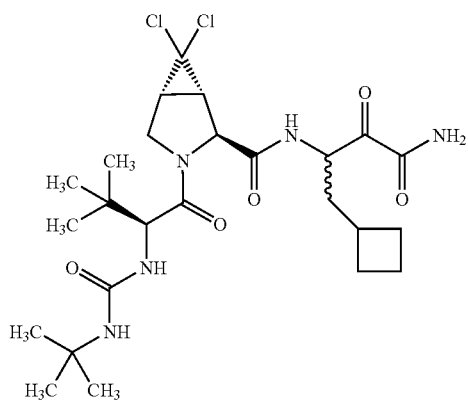
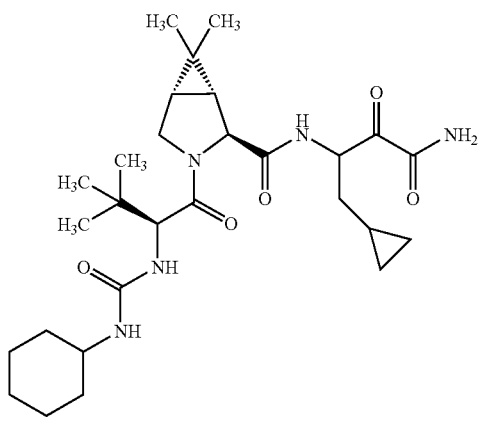
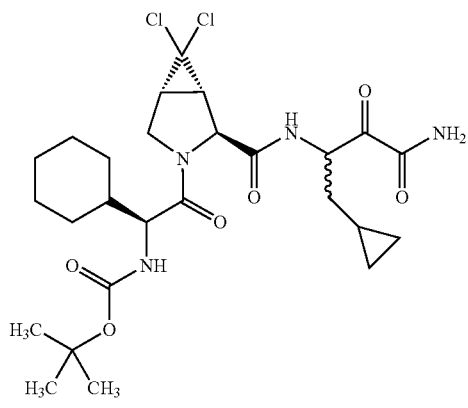
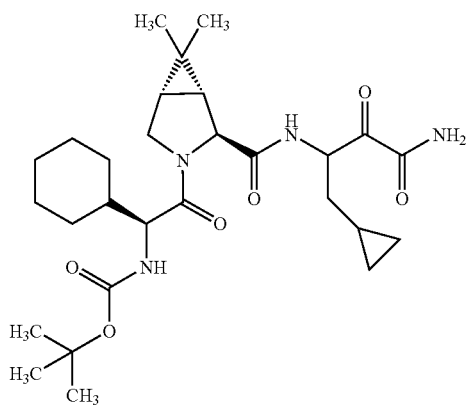
116
-continued
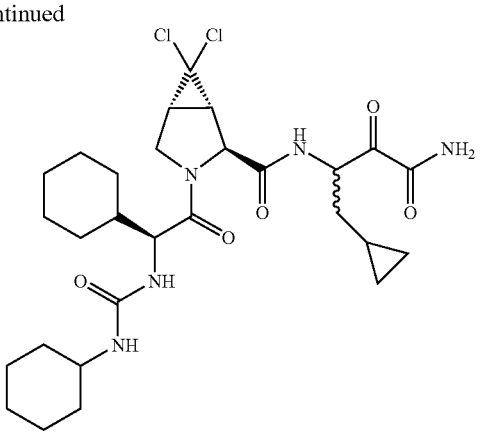
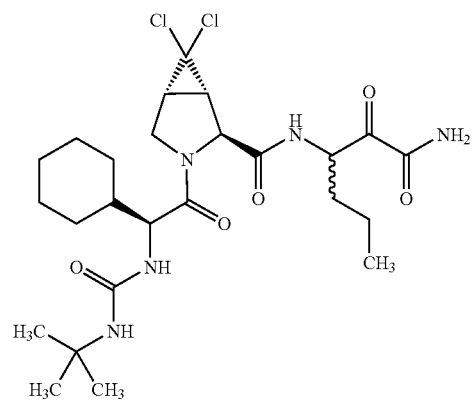
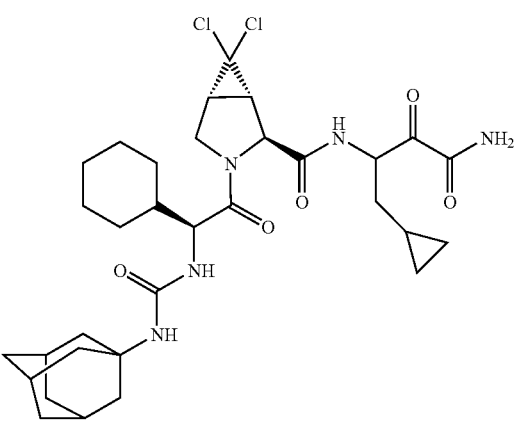

117 118
-continued
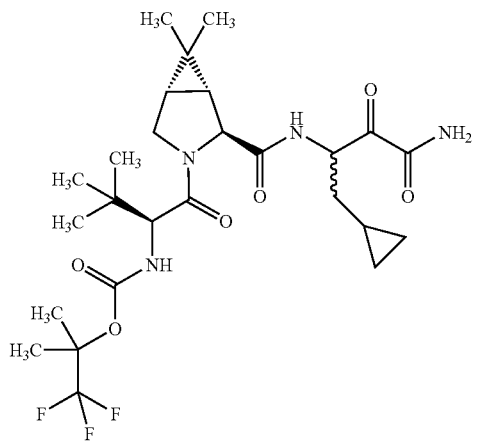
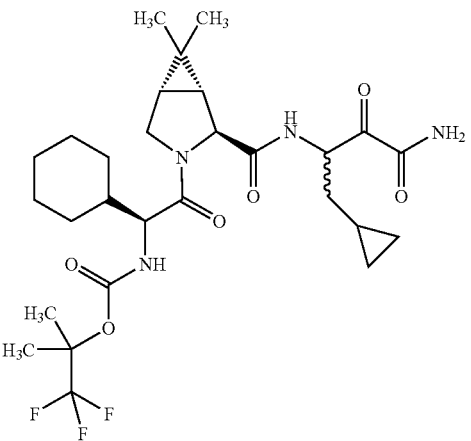
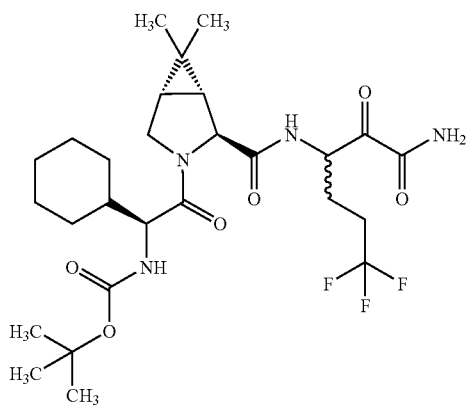
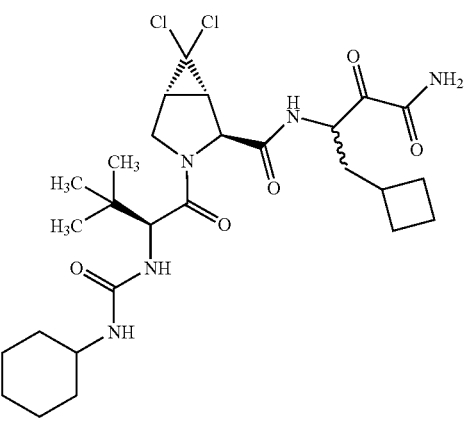
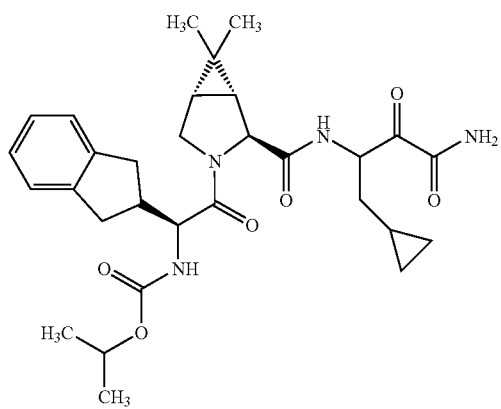
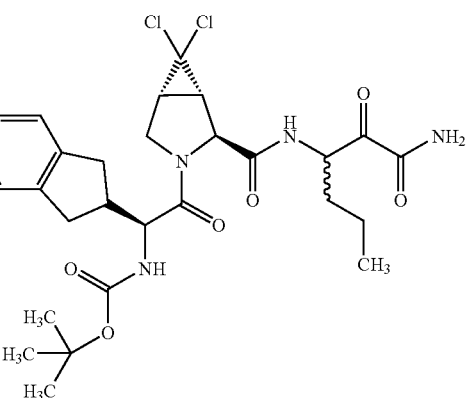
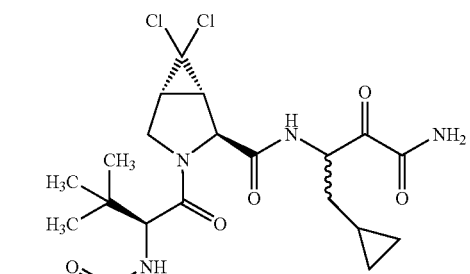
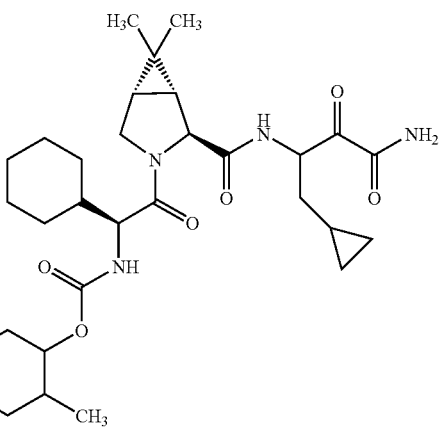

-continued
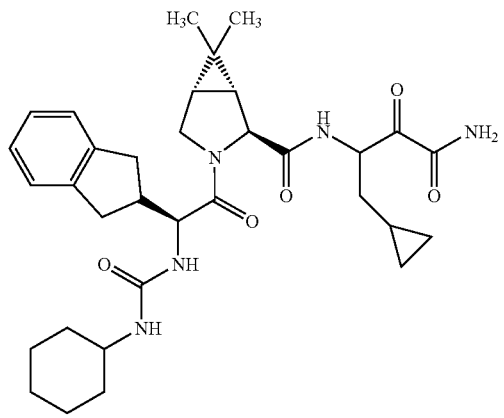
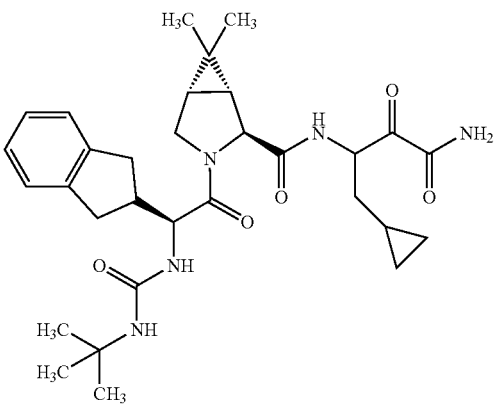
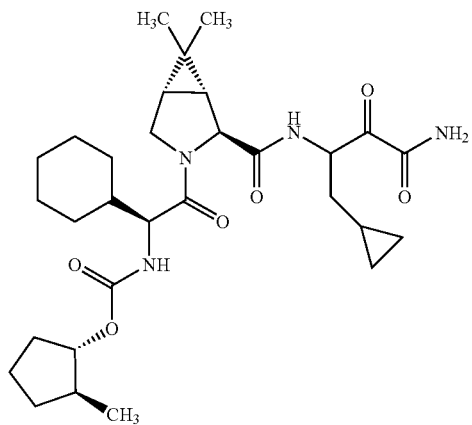
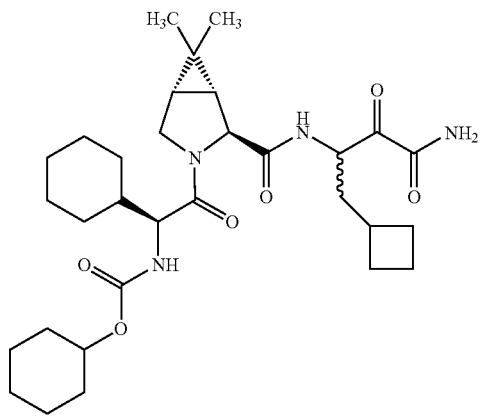
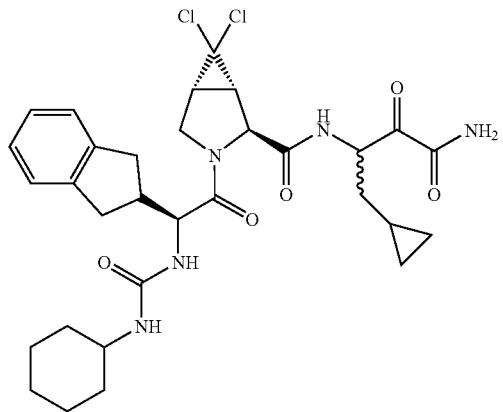
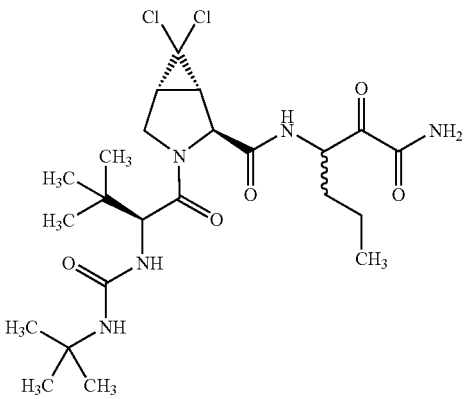
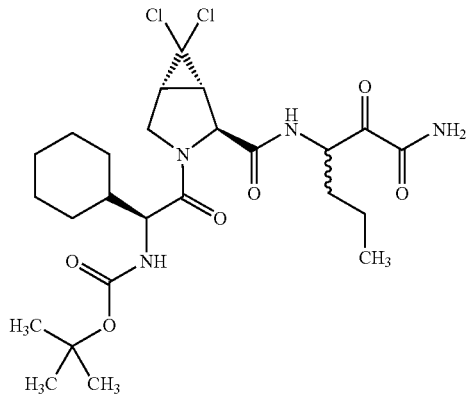
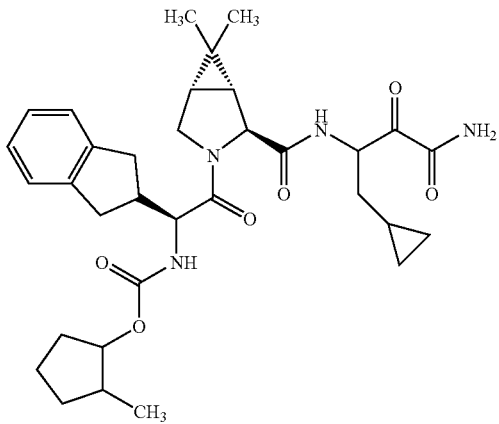

121
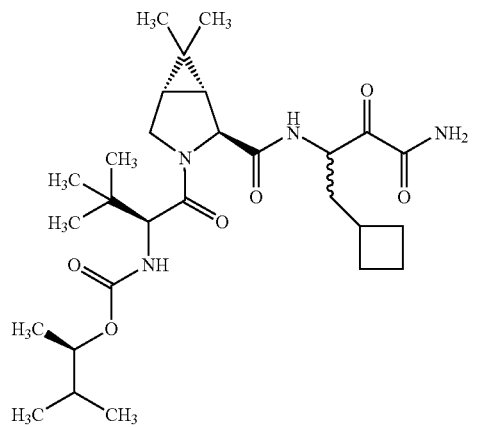
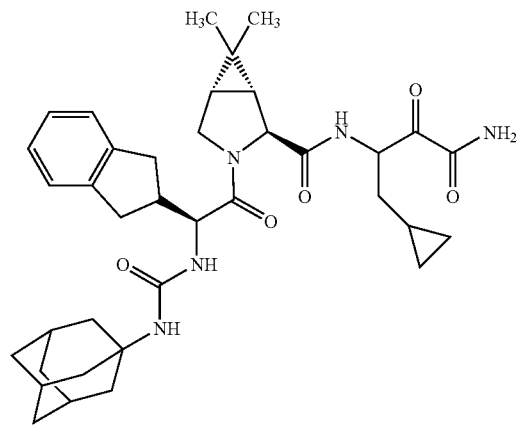
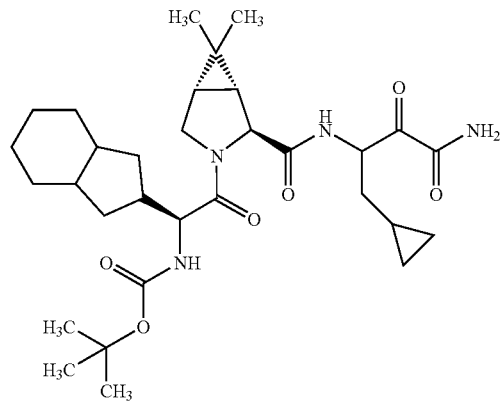
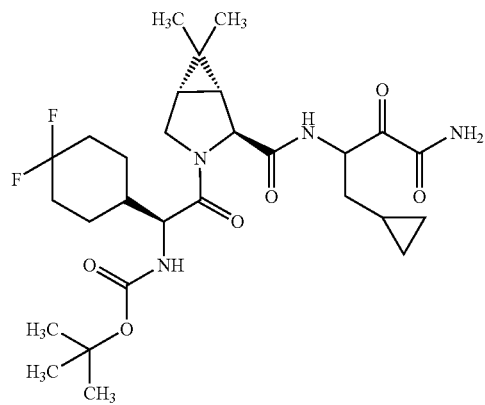
122
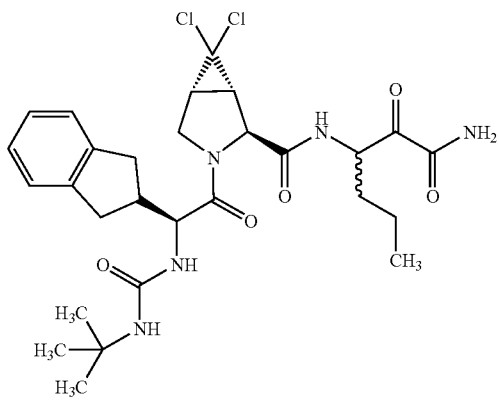
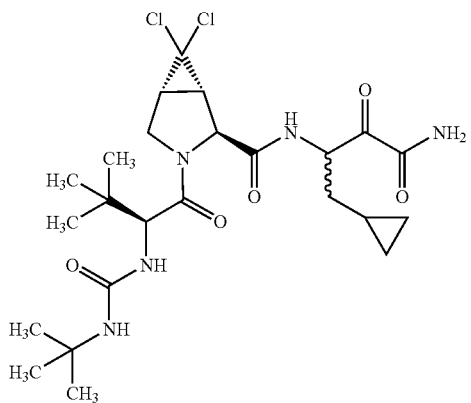
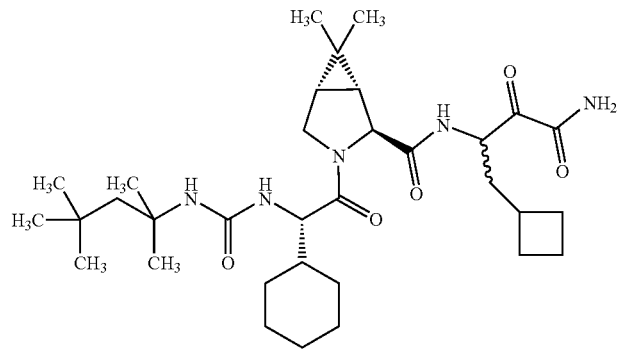
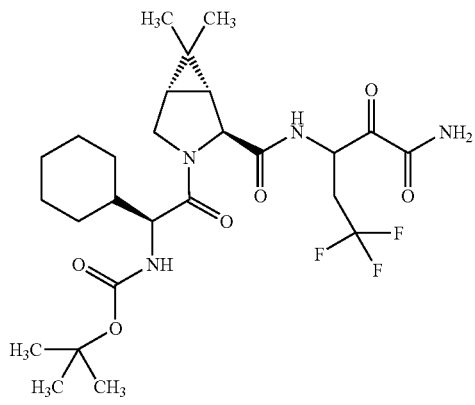

-continued
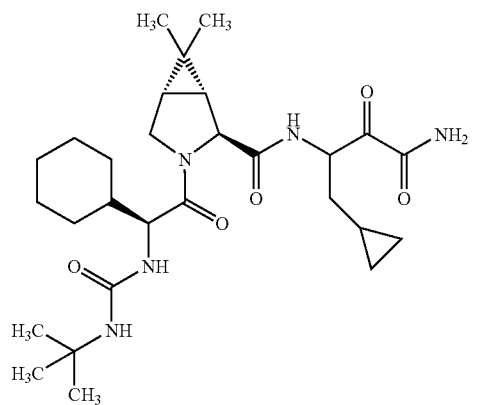
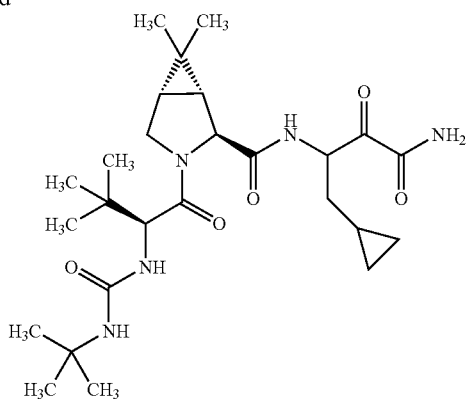
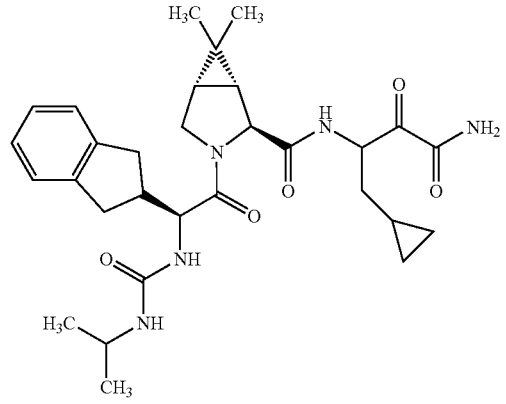
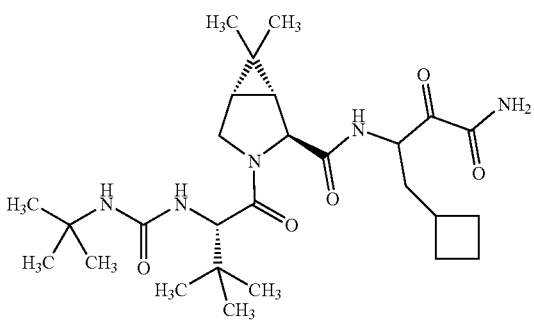
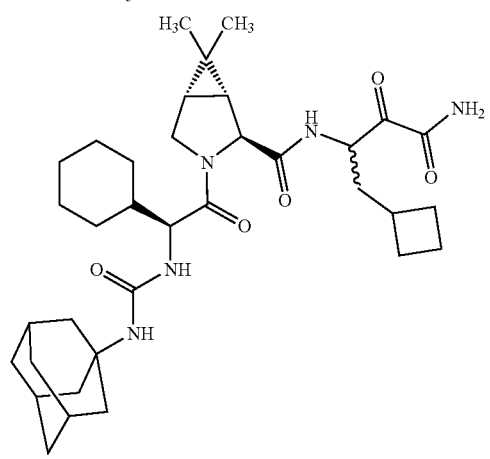
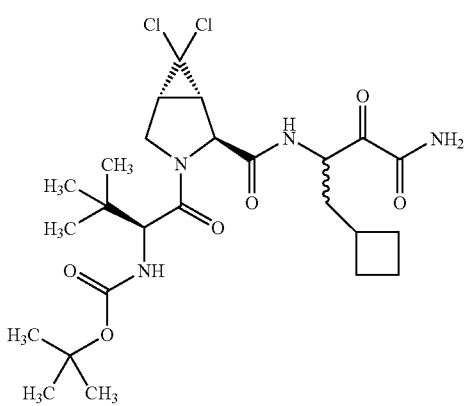
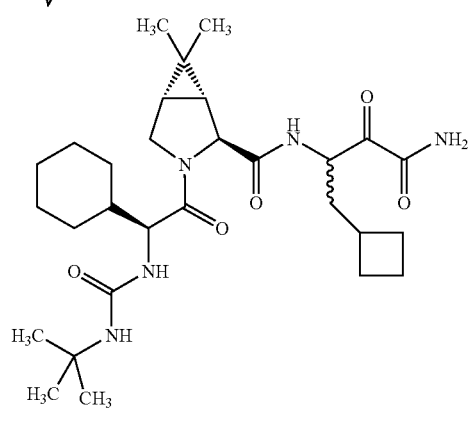
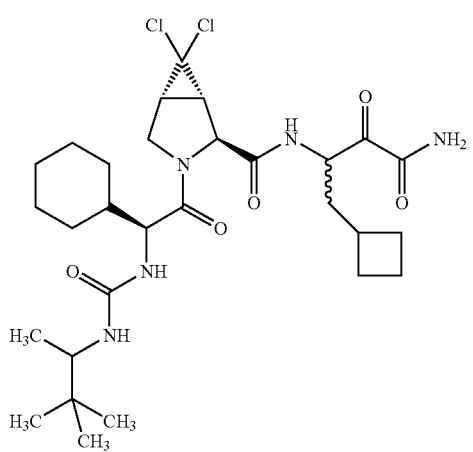

-continued
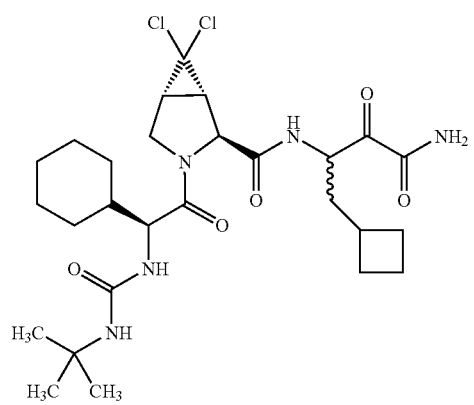
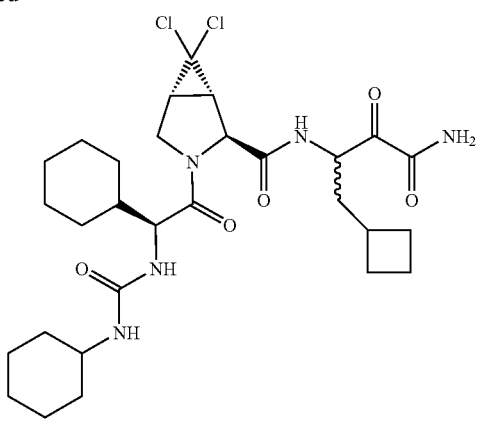
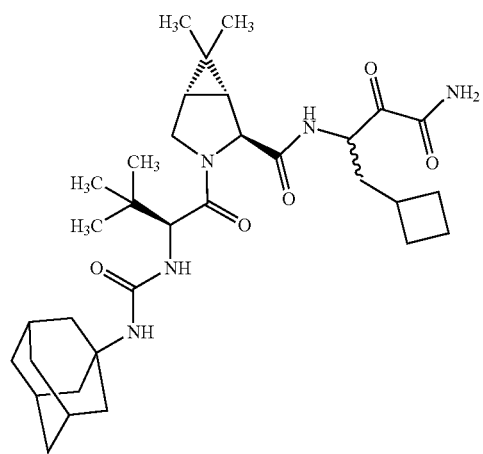
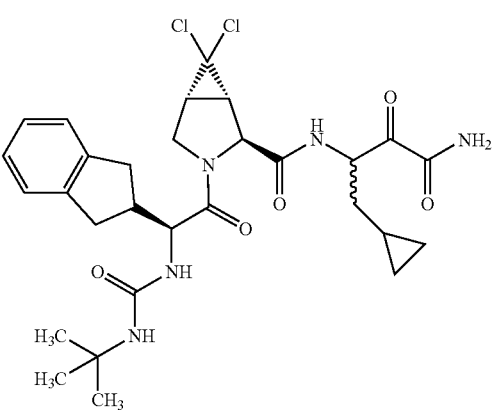
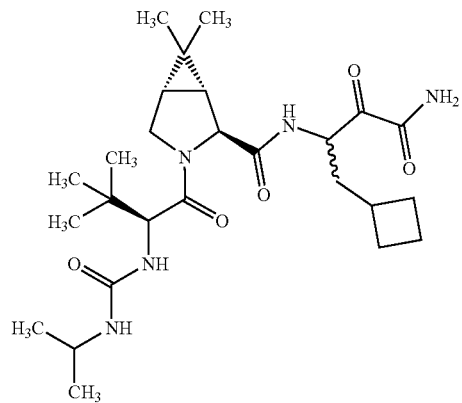
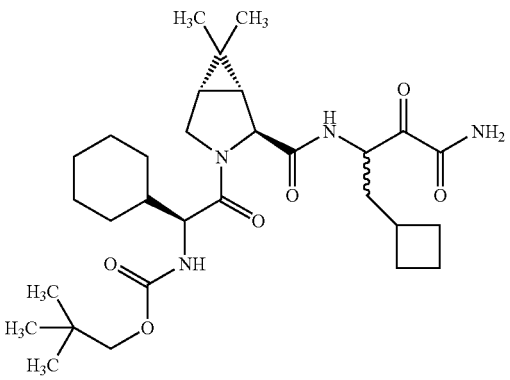
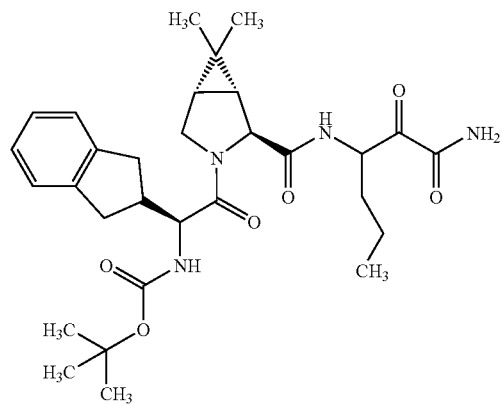

-continued
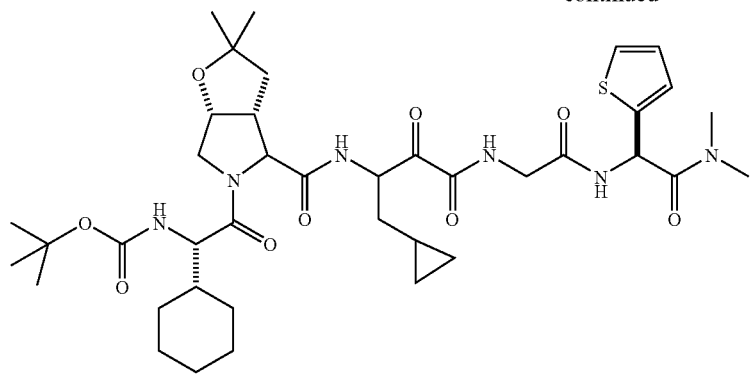
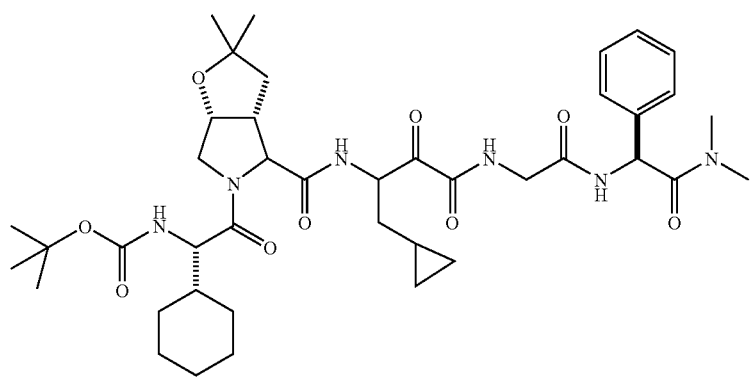
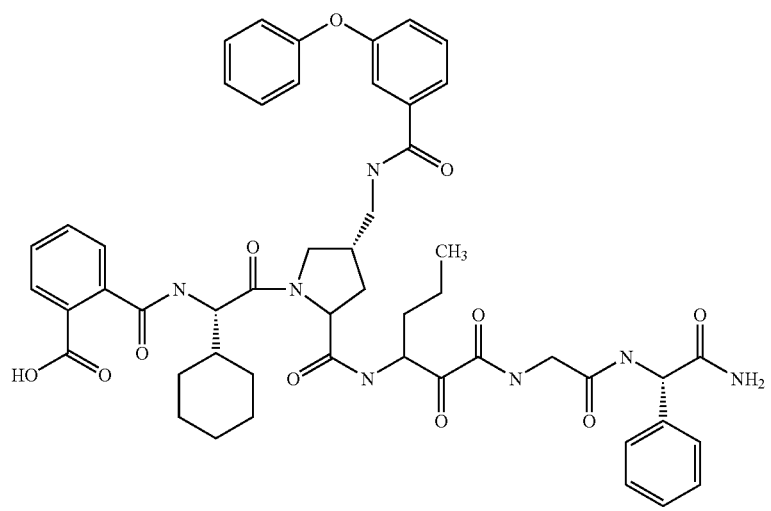

-continued
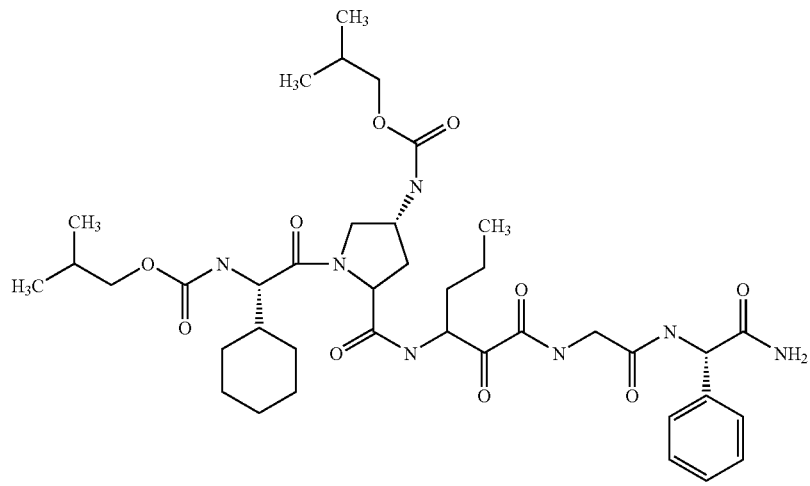
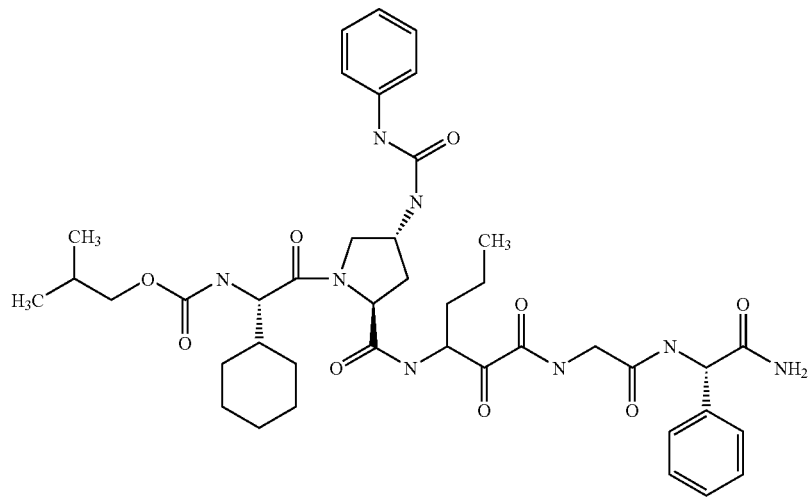
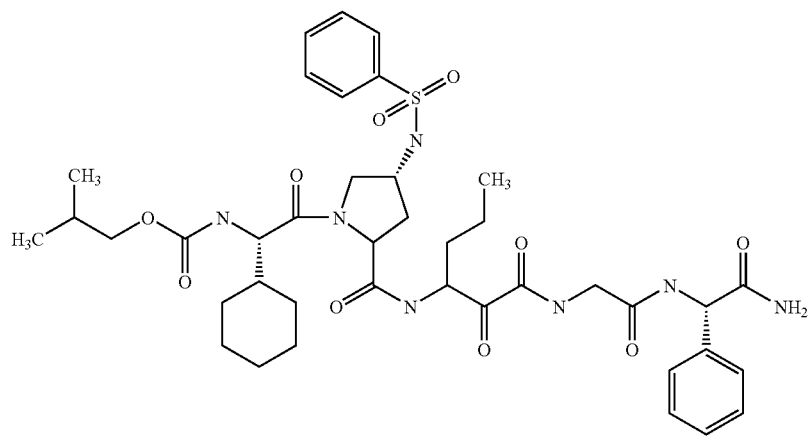

-continued
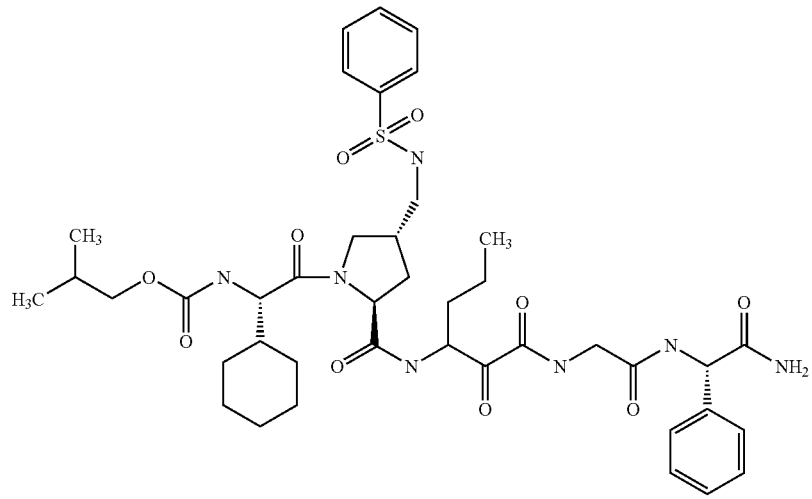
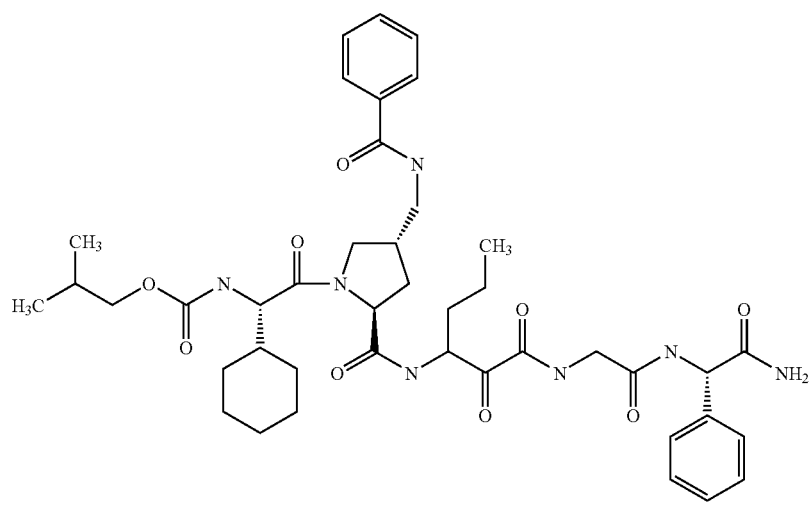
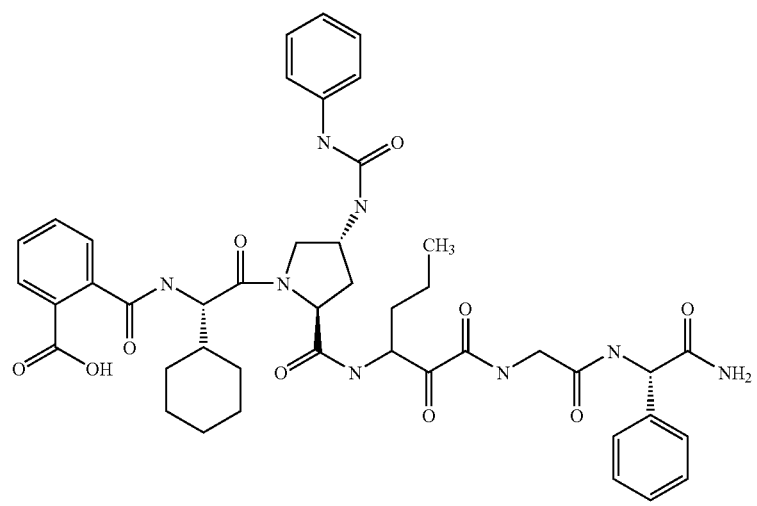

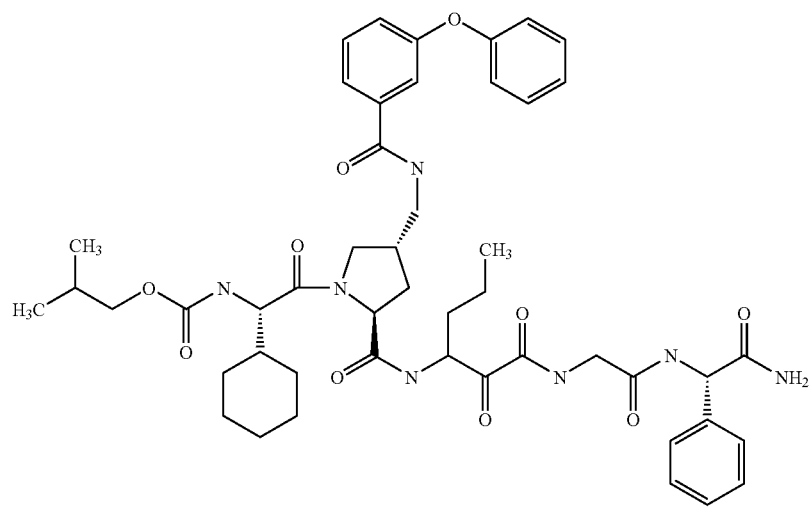
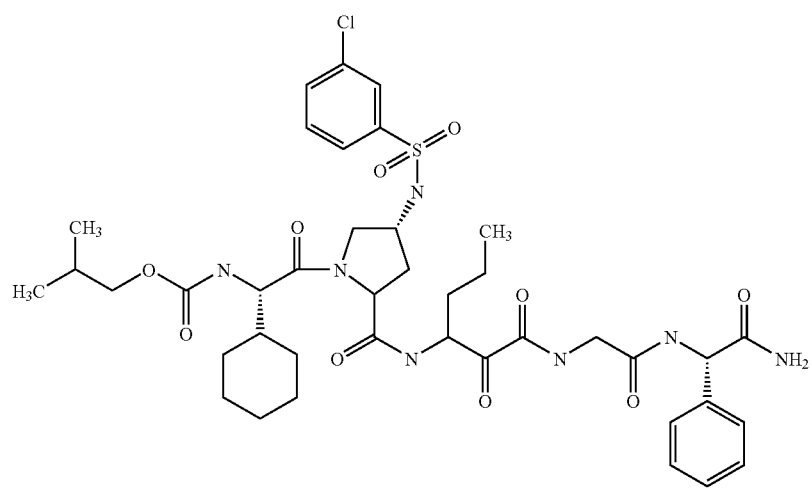
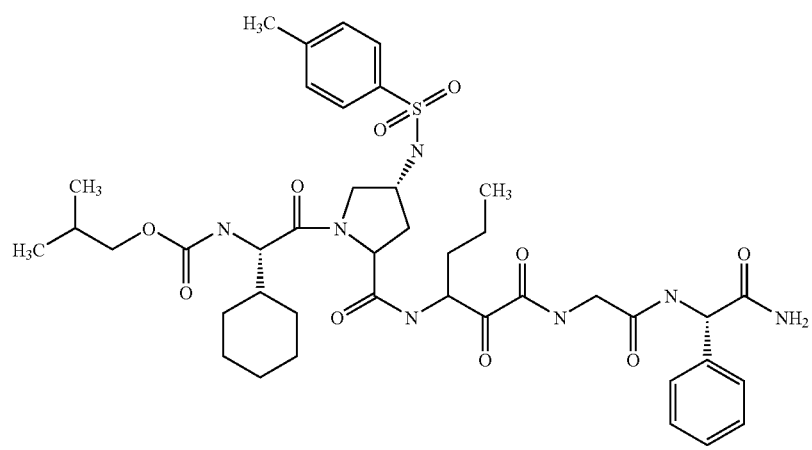

-continued
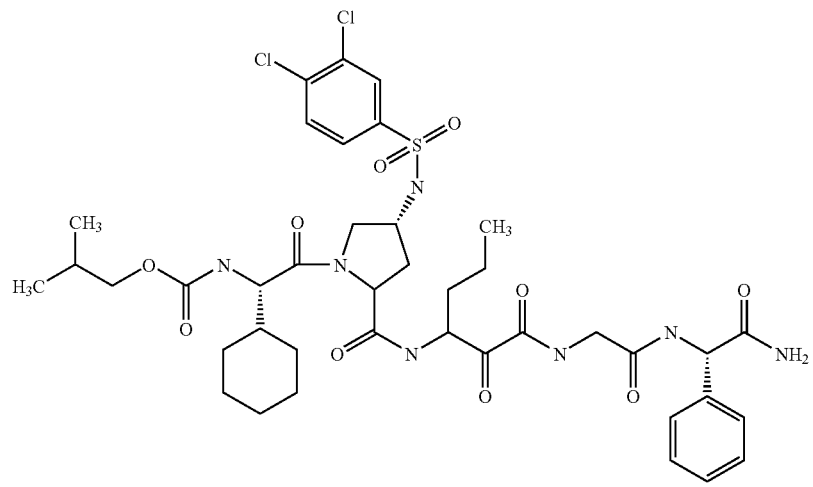
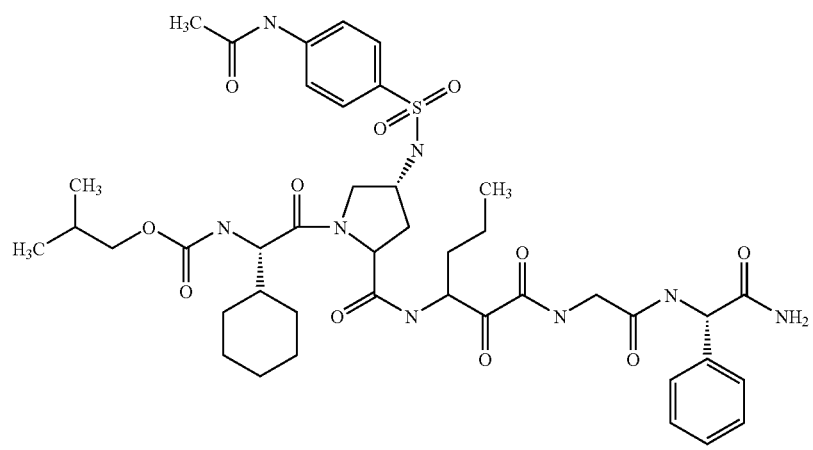
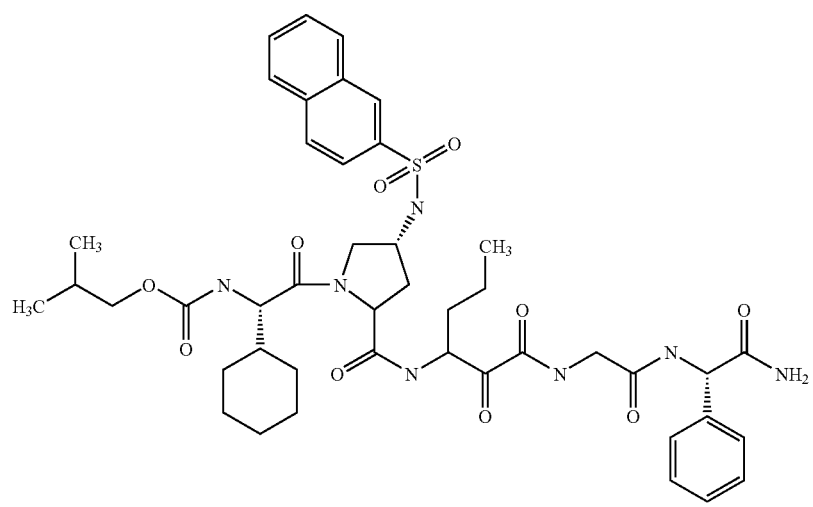

-continued
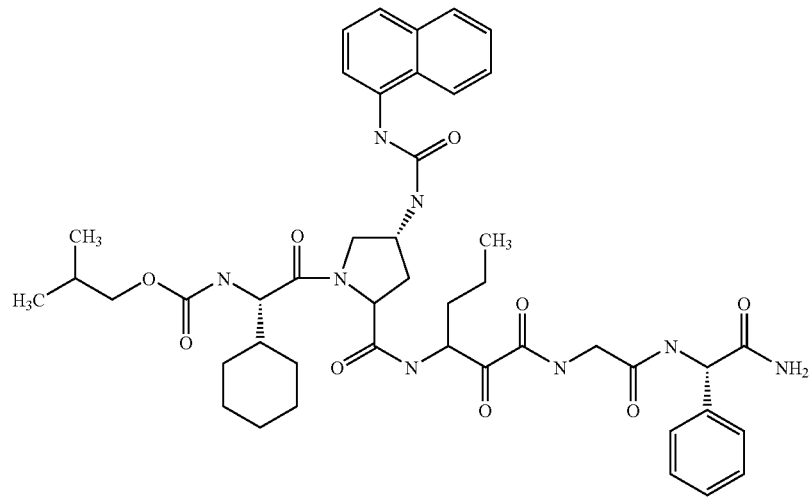
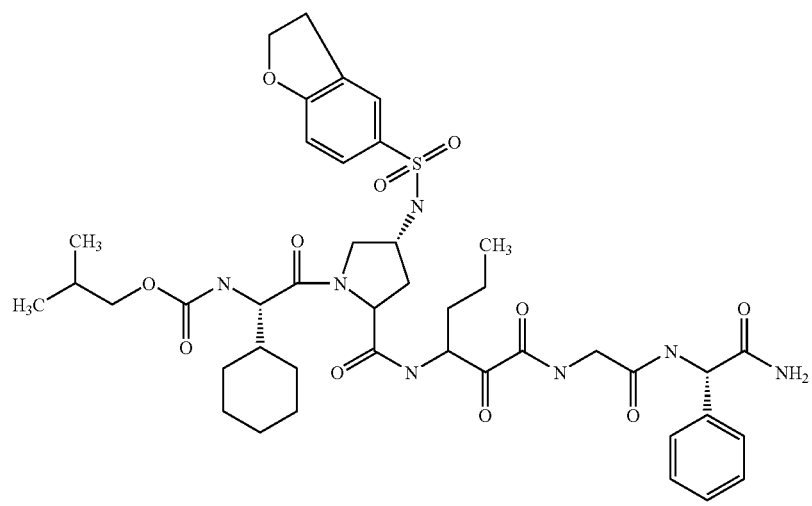
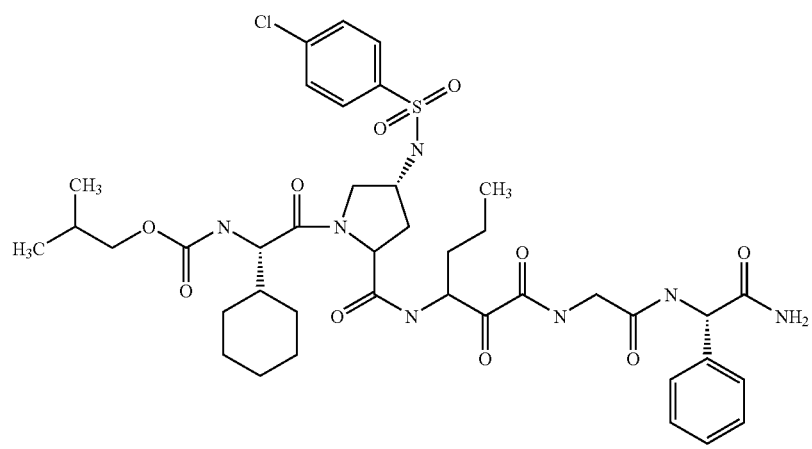

-continued
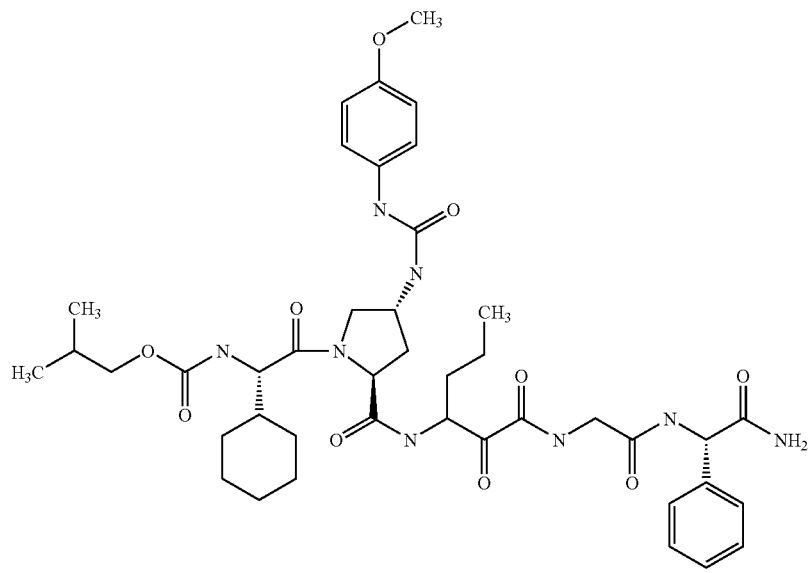
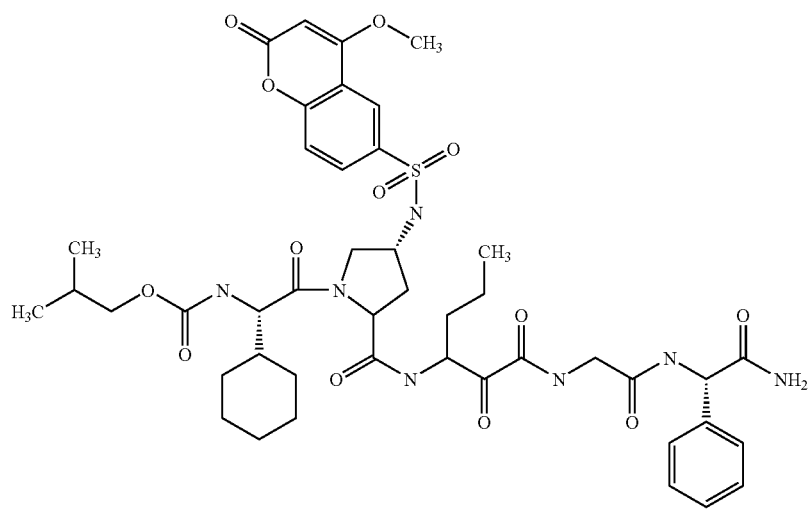
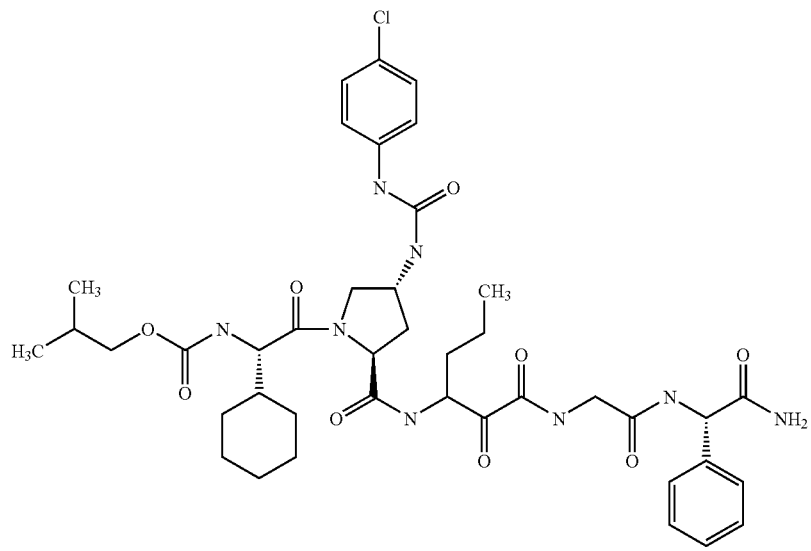

-continued
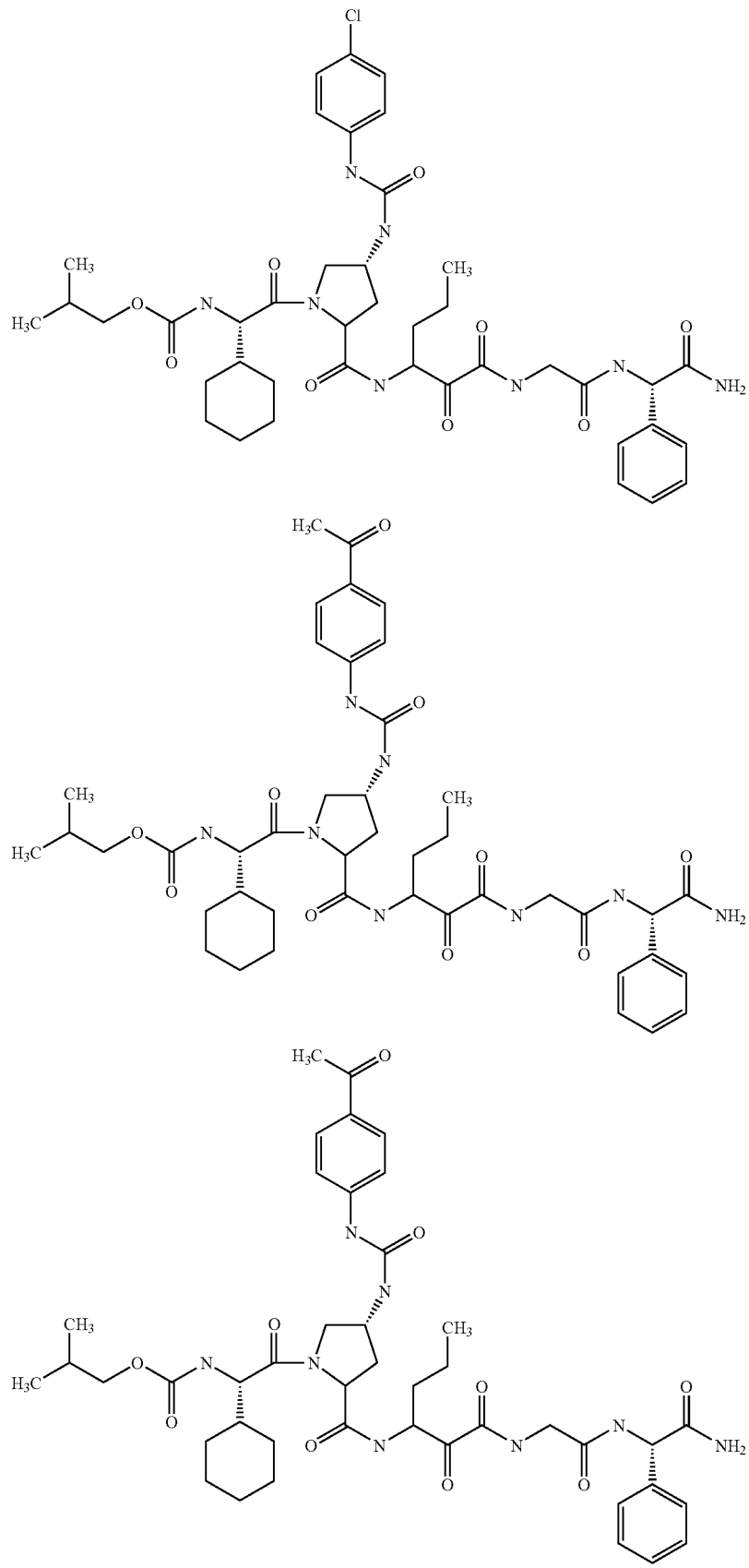

-continued
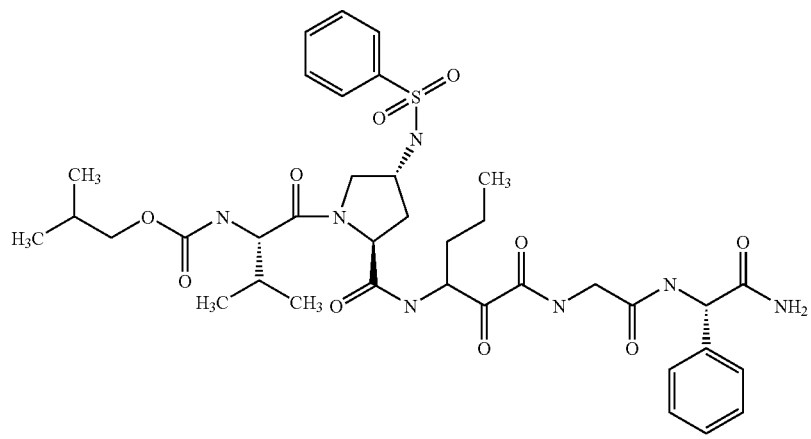
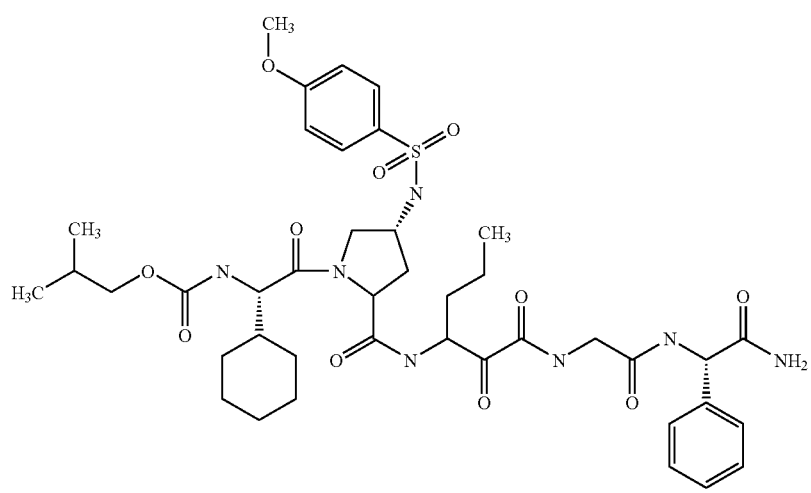
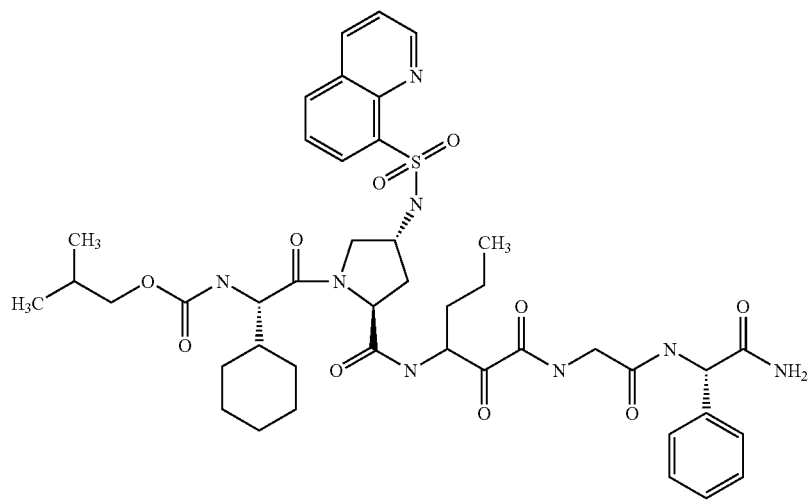

-continued
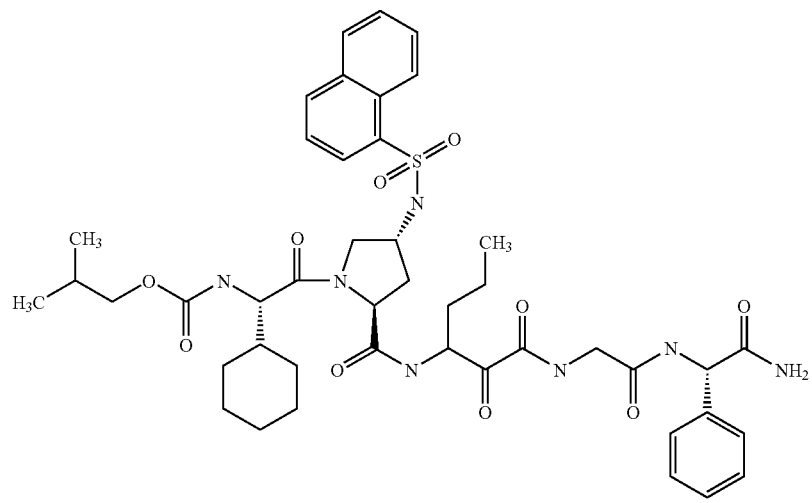
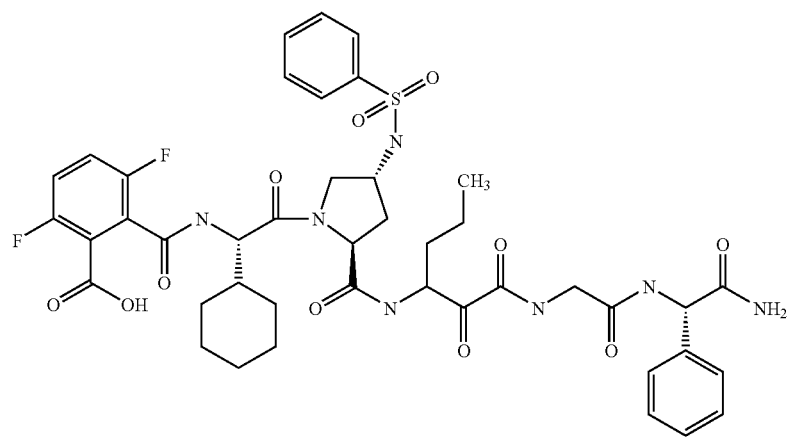
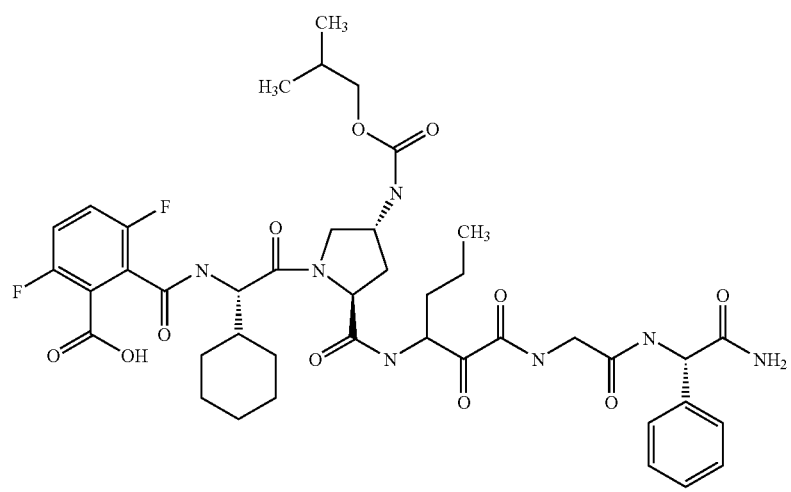

-continued
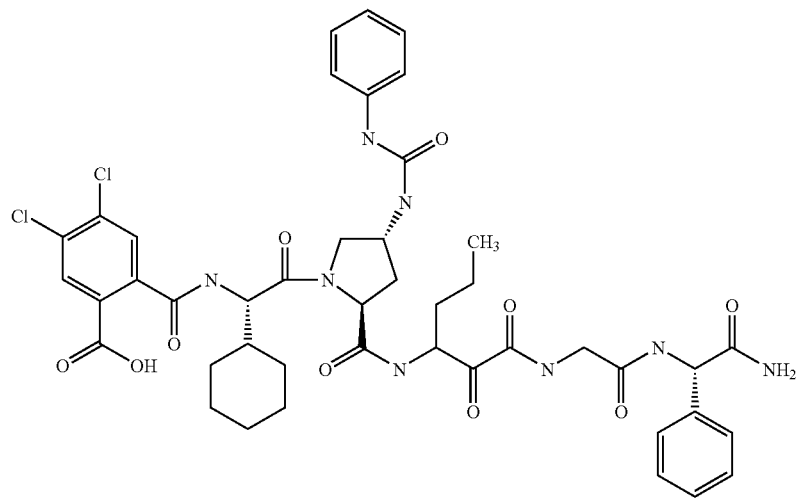
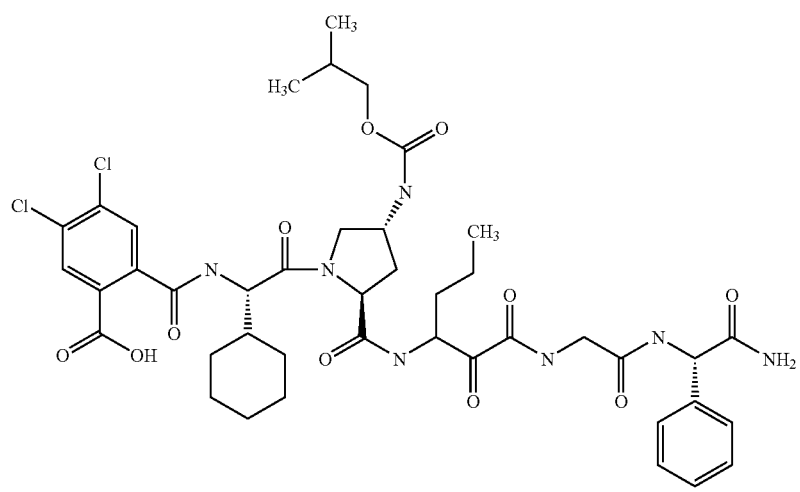
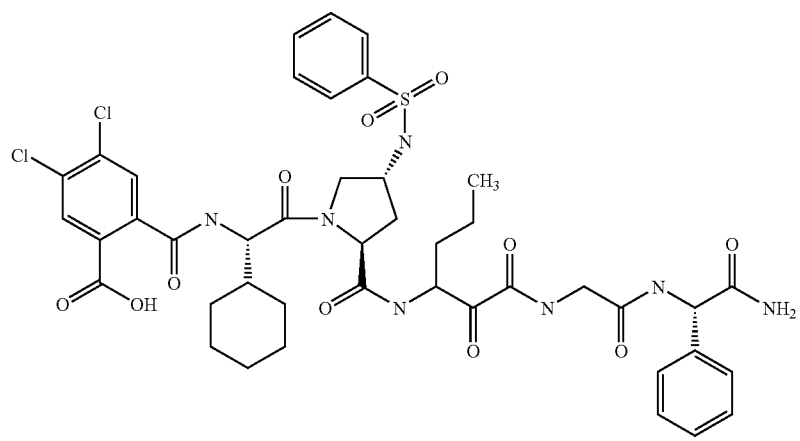

-continued
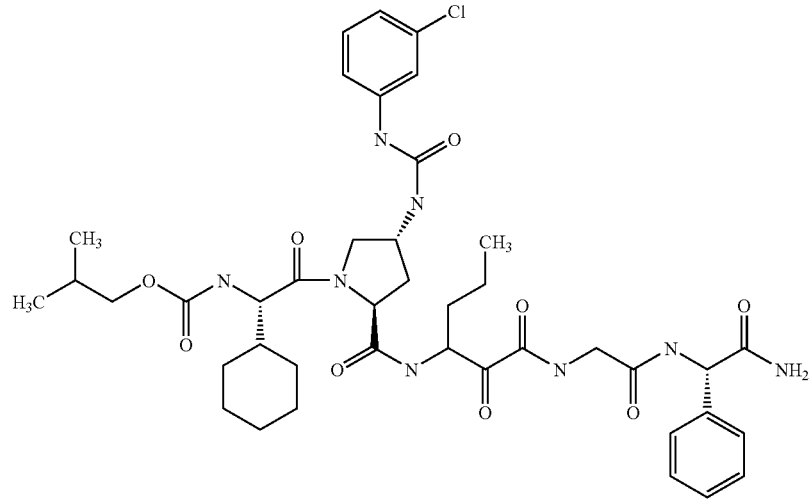
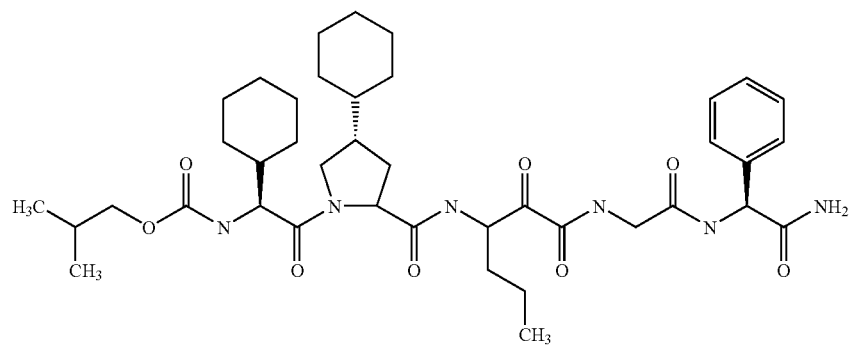
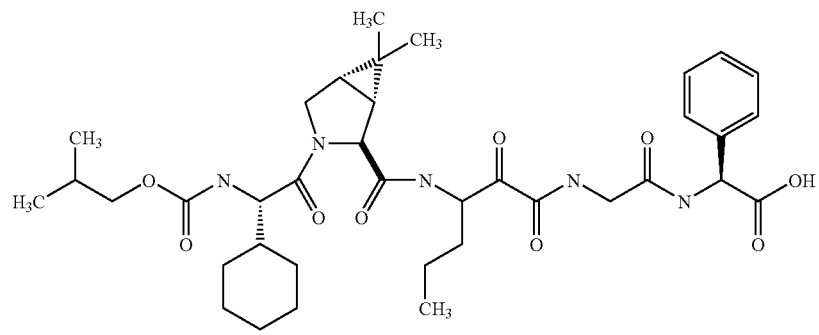
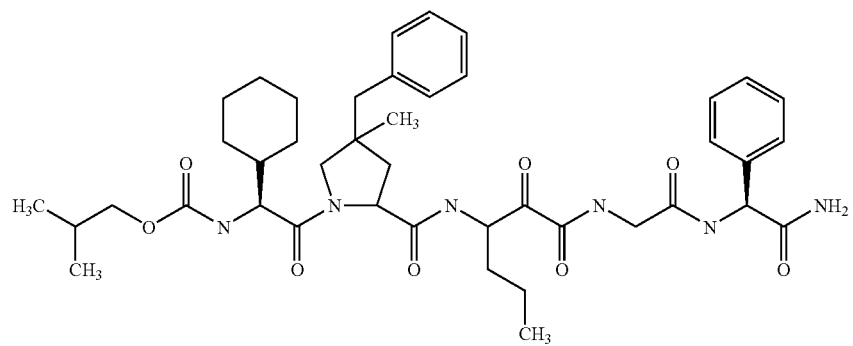

-continued
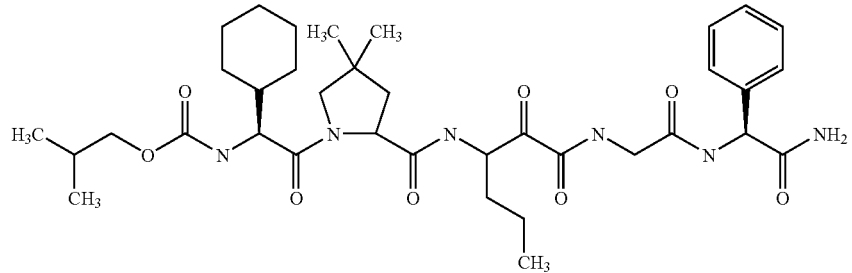
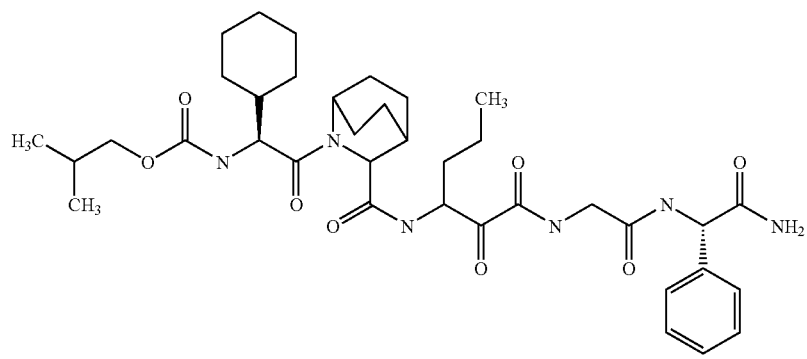
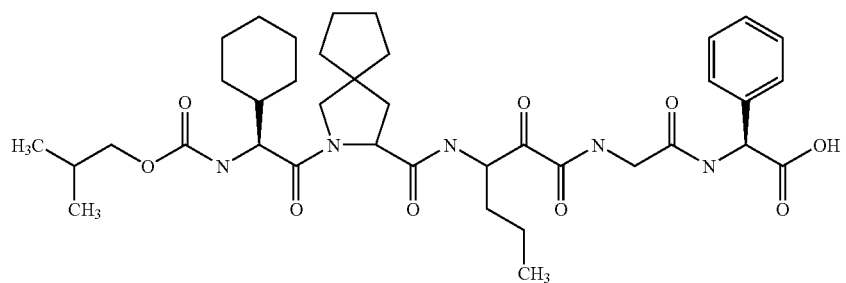
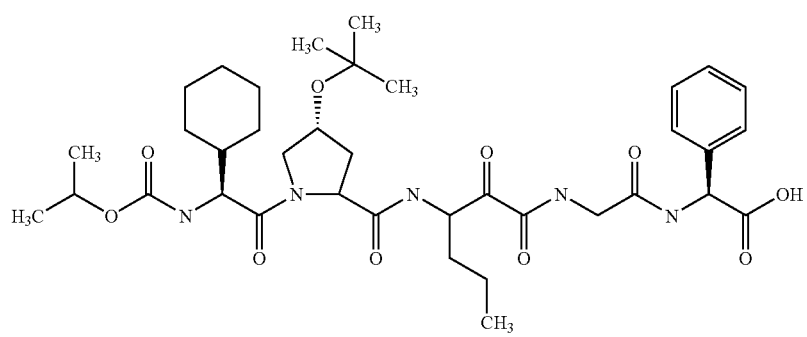
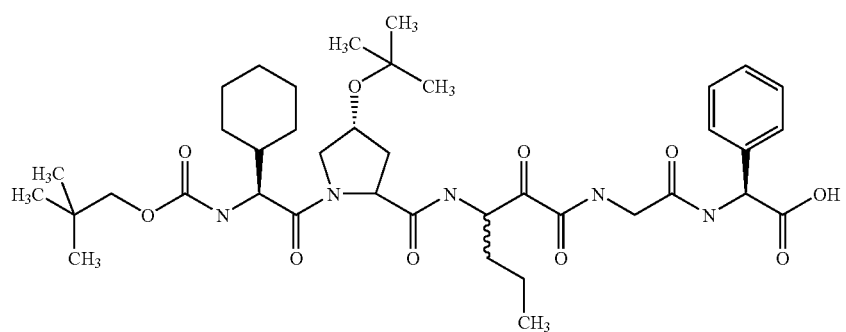

-continued
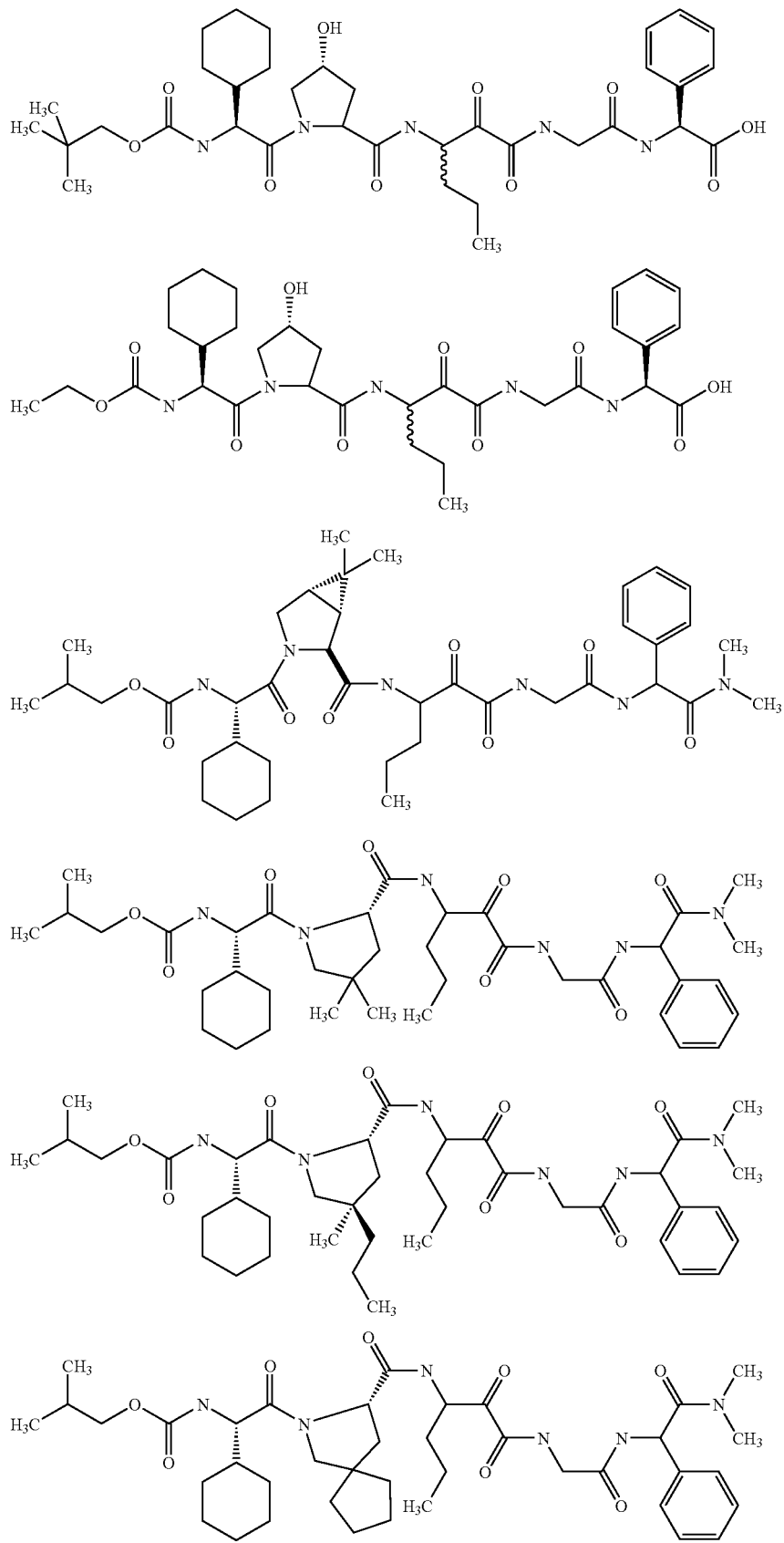

-continued
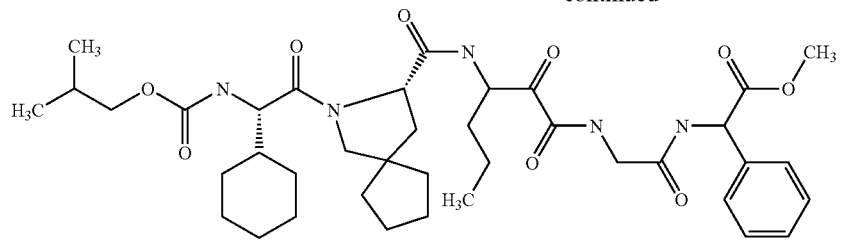
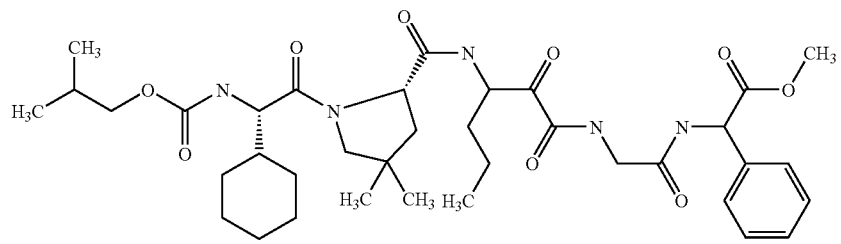
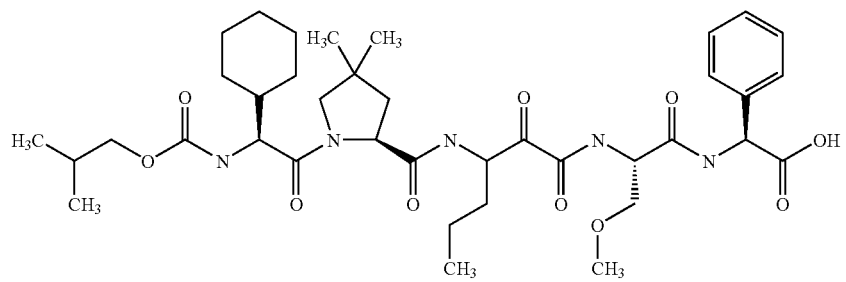
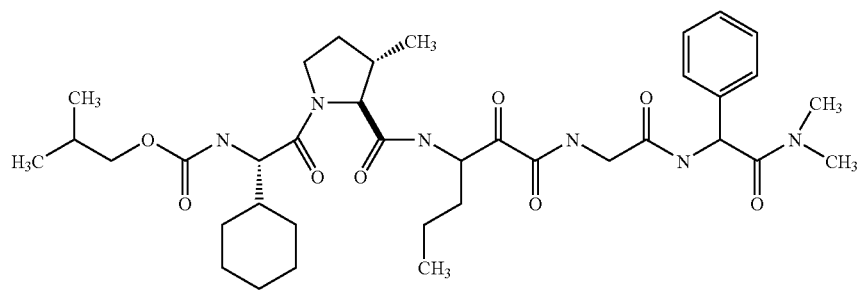
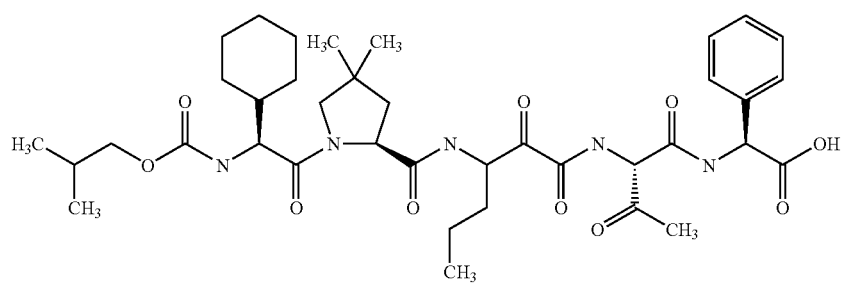
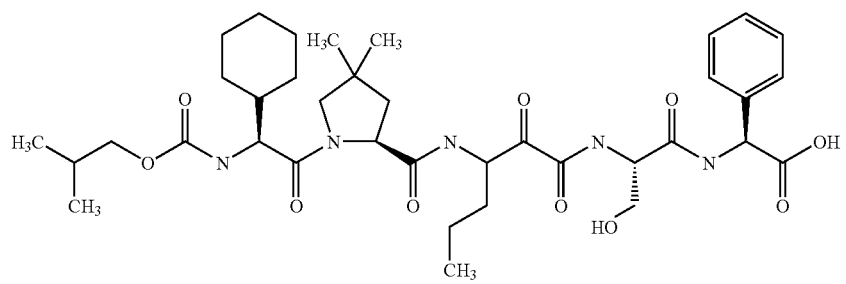

-continued
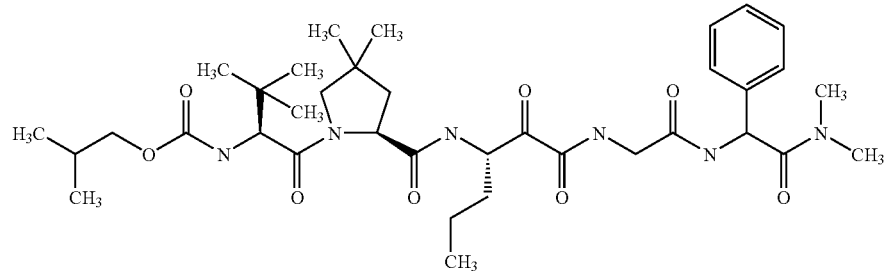
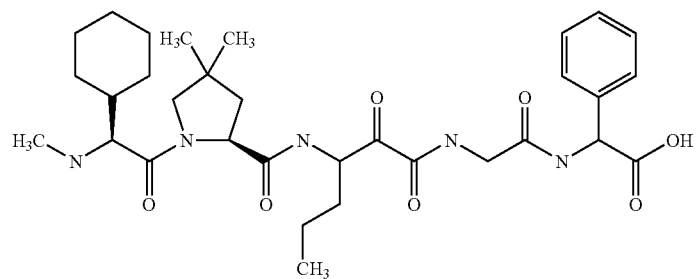
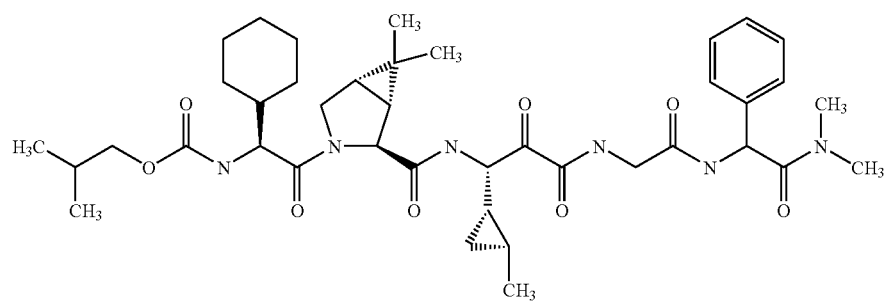
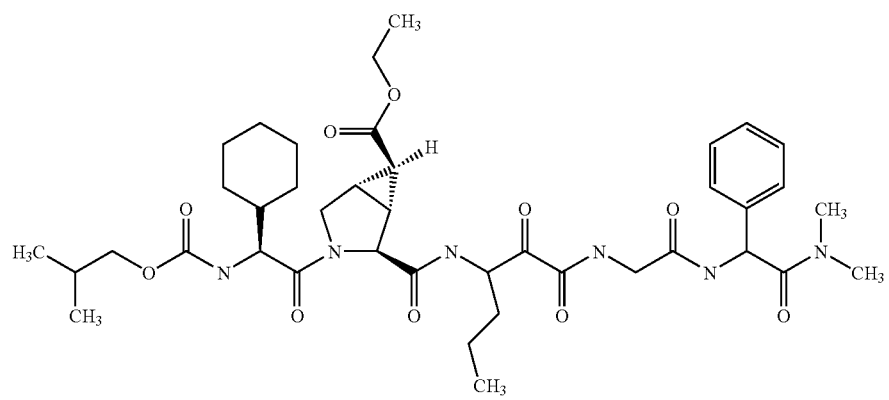
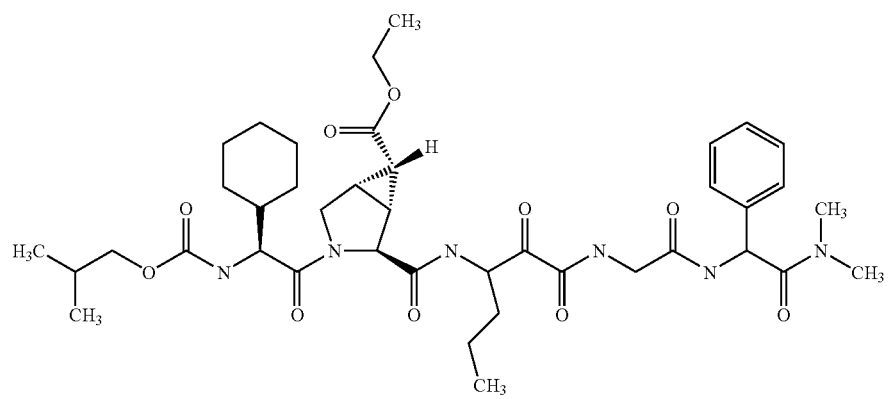

-continued
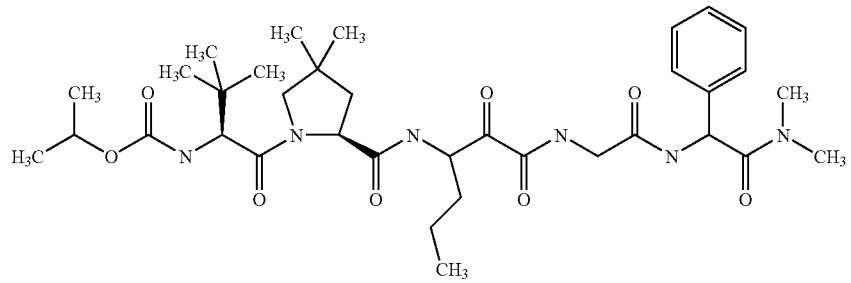
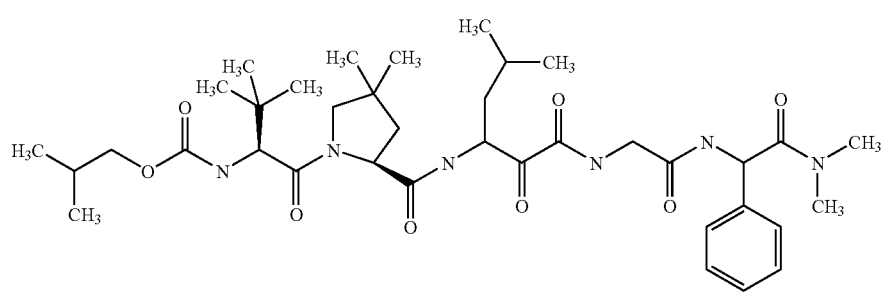
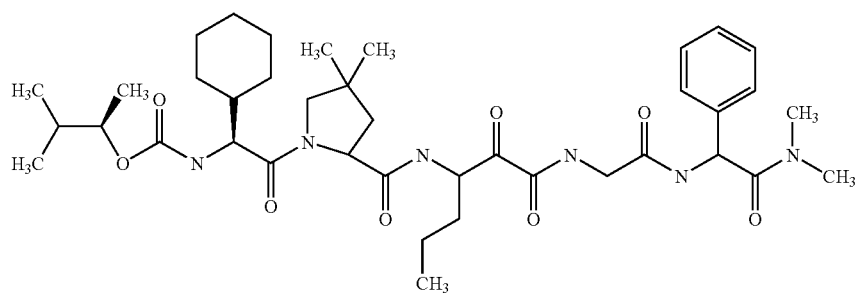
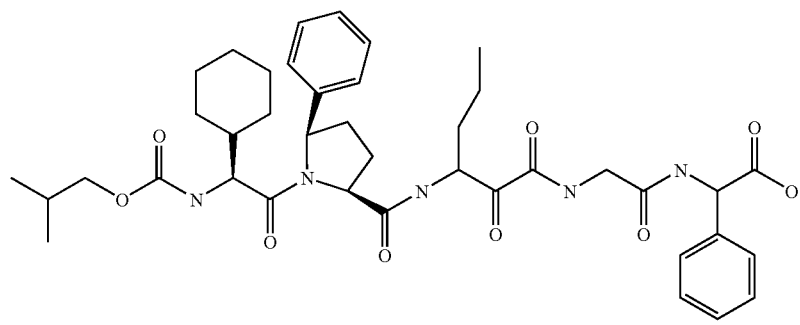
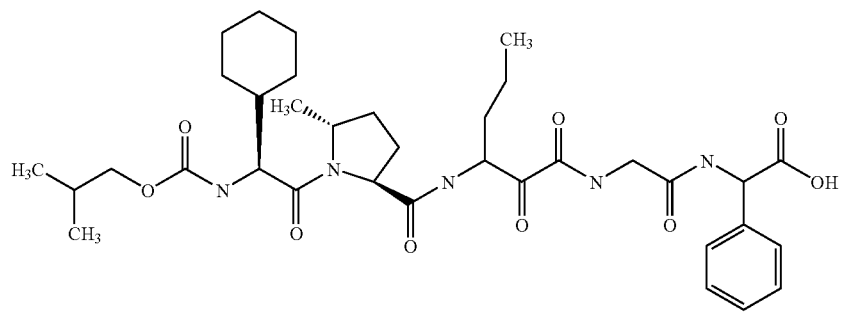

-continued
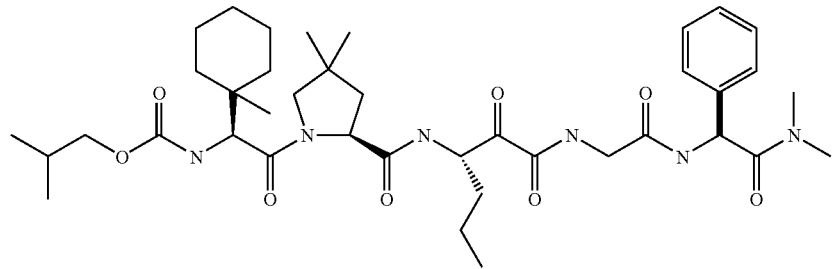
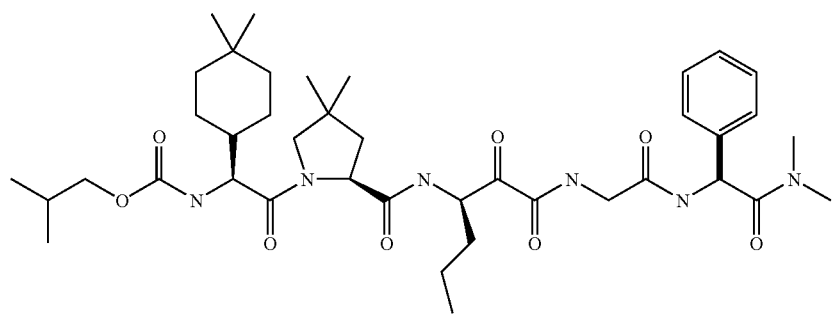
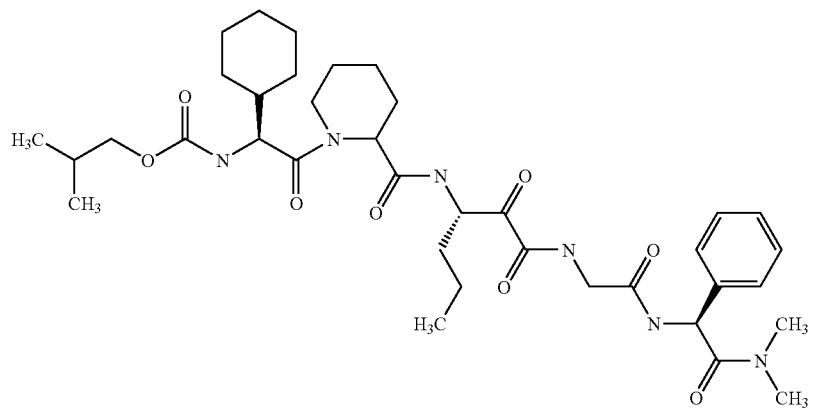
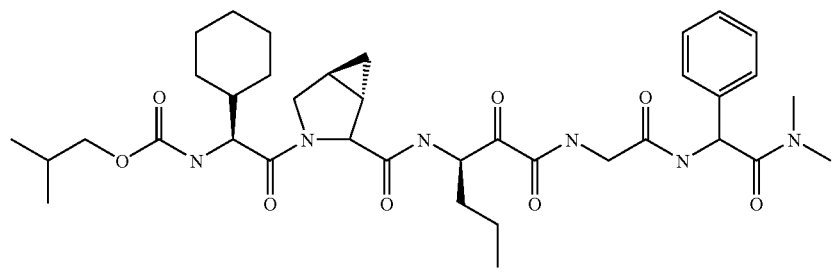
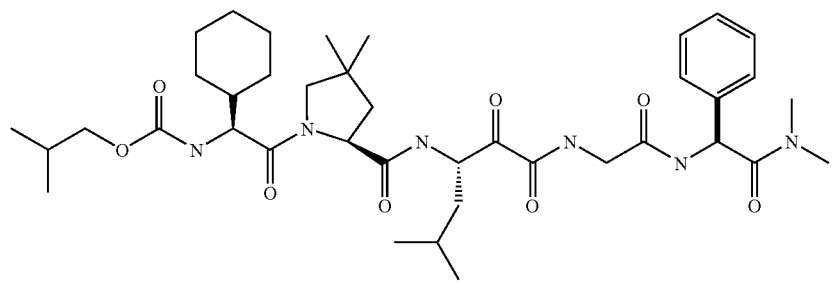

-continued
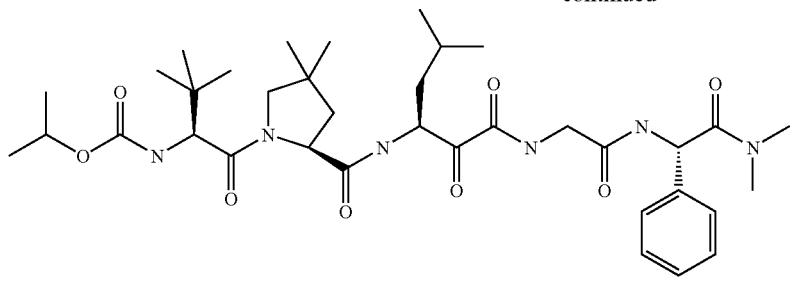
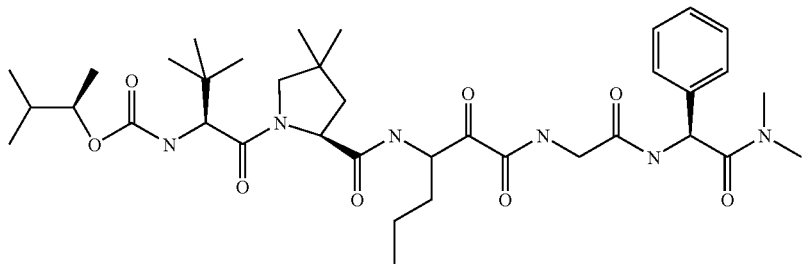
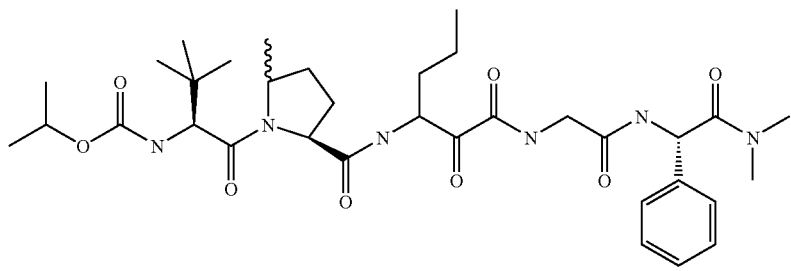
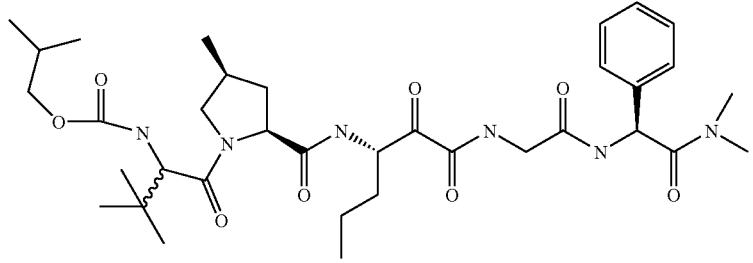
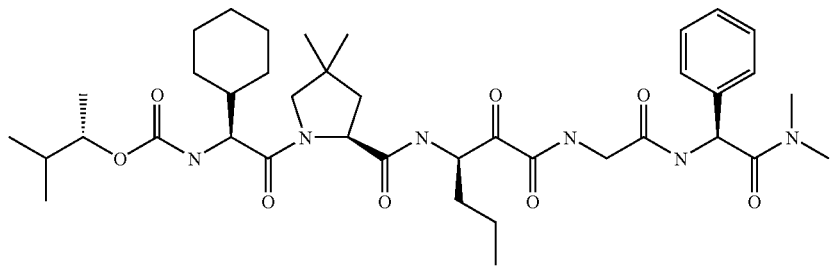
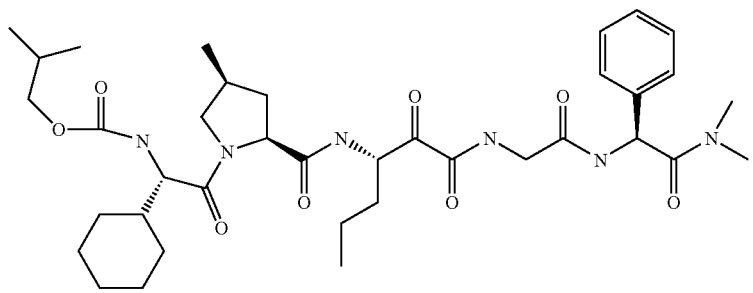

-continued
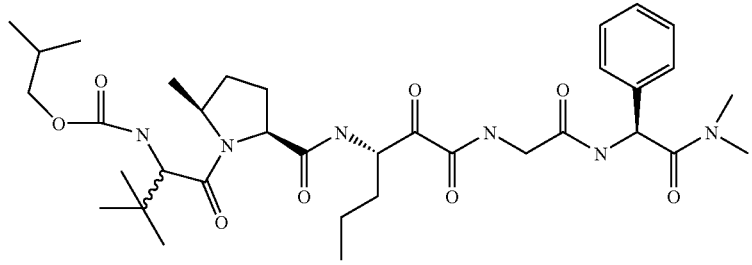
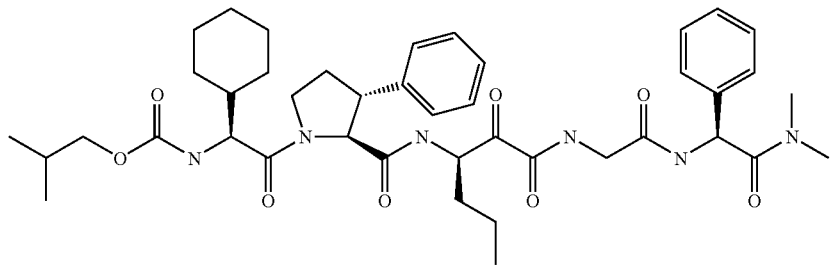
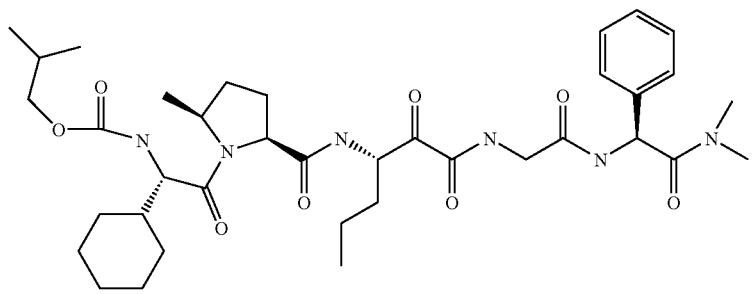
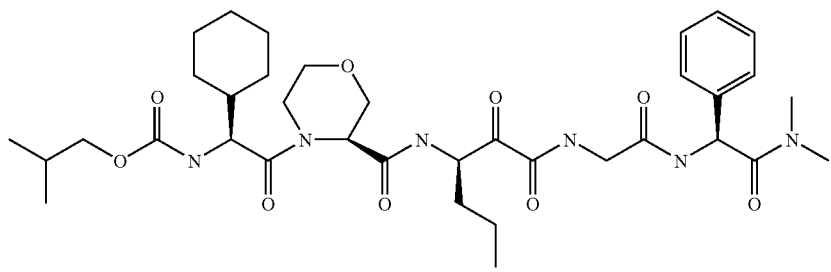
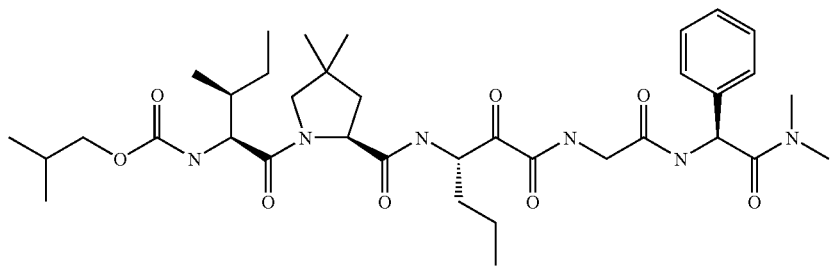
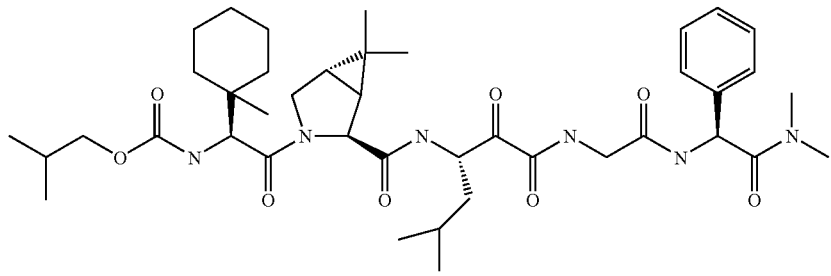

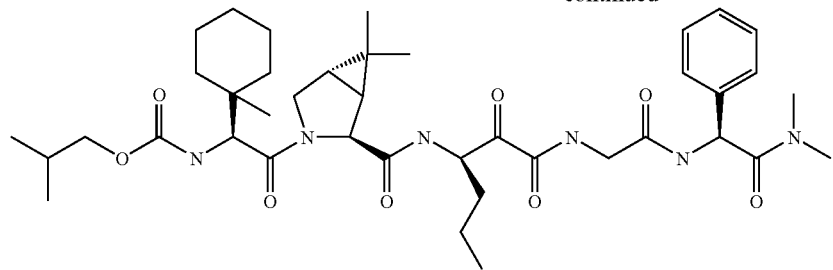
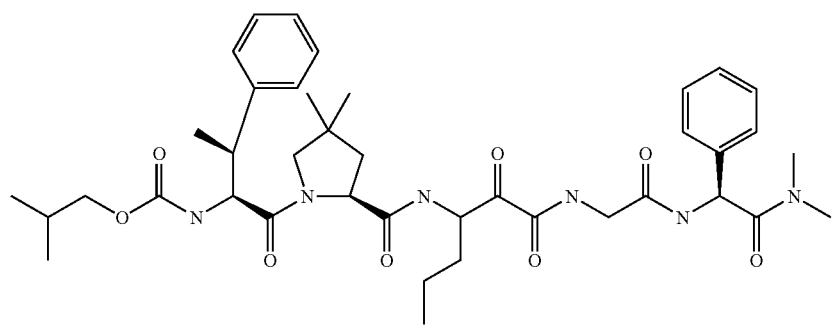
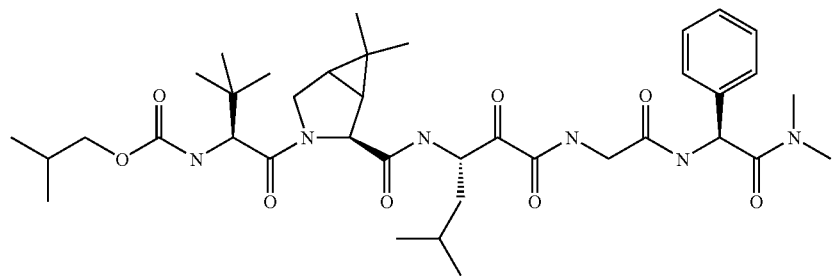
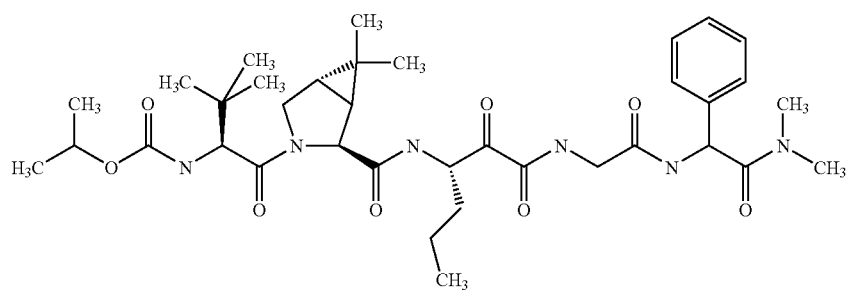
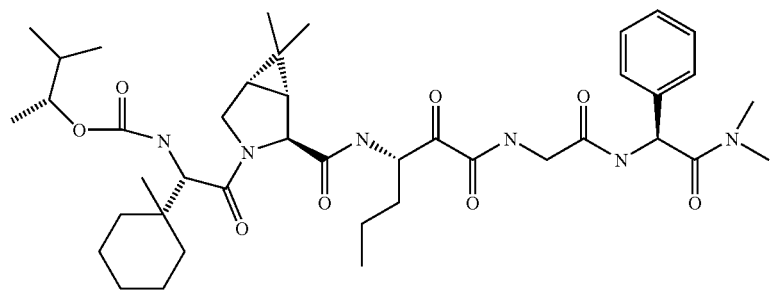

-continued
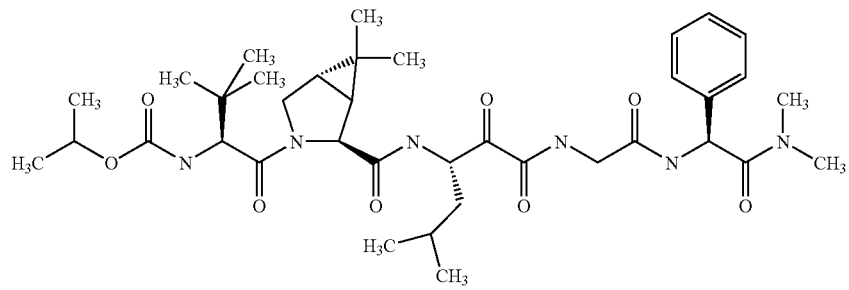
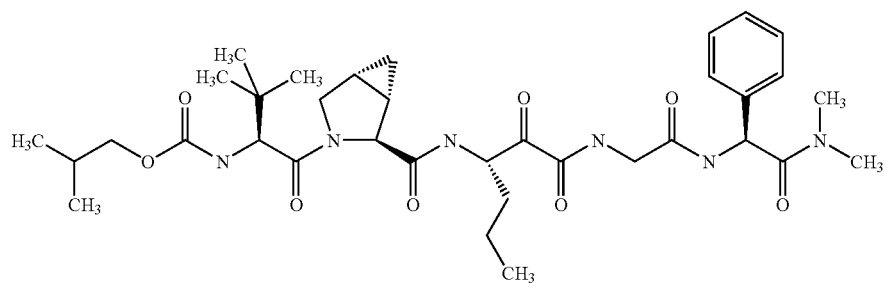
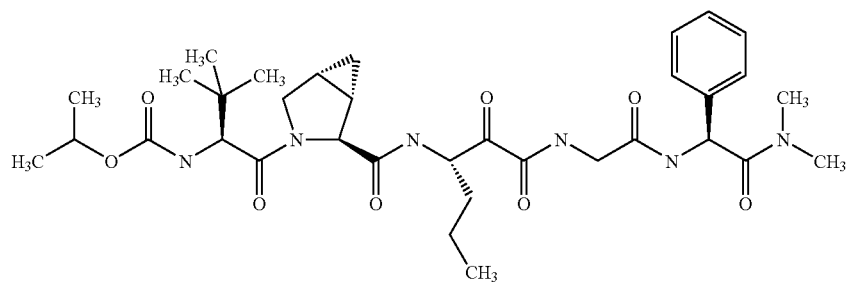
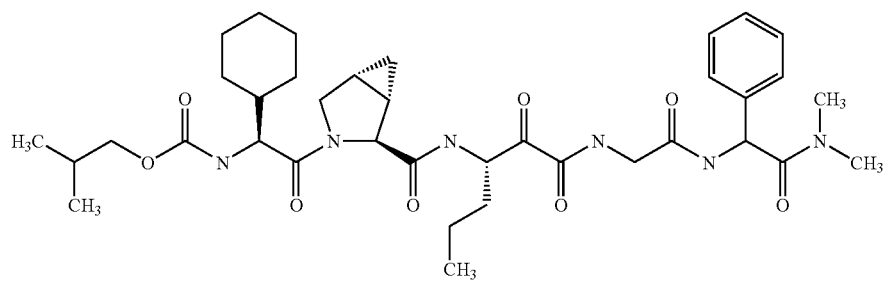
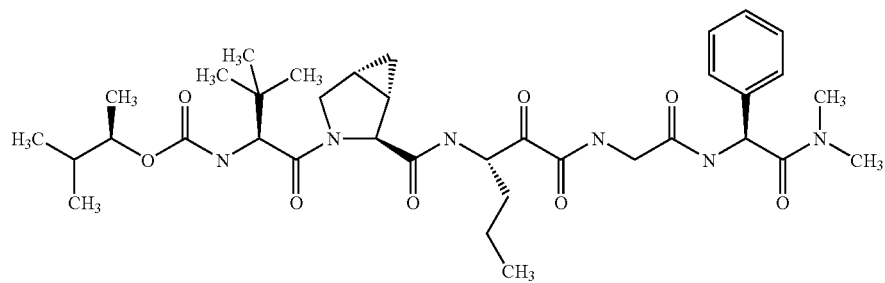

-continued

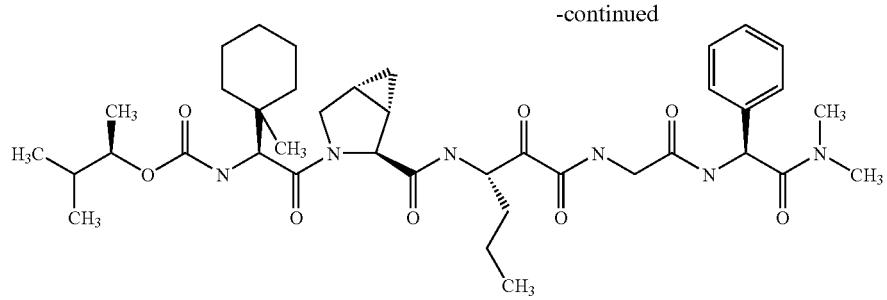

Depending upon their structure, the compounds of the invention may form pharmaceutically acceptable salts with organic or inorganic acids, or organic or inorganic bases. Examples of suitable acids for such salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. For formation of salts with bases, suitable bases are, for example, NaOH, KOH, NH$_4$OH, tetraalkylammonium hydroxide, and the like.

In another embodiment, this invention provides pharmaceutical compositions comprising the inventive peptides as an active ingredient. The pharmaceutical compositions generally additionally comprise a pharmaceutically acceptable carrier diluent, excipient or carrier (collectively referred to herein as carrier materials). Because of their HCV inhibitory activity, such pharmaceutical compositions possess utility in treating hepatitis C and related disorders.

In yet another embodiment, the present invention discloses methods for preparing pharmaceutical compositions comprising the inventive compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like.

Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. HCV inhibitory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparation s include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally, intravenously or subcutaneously.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day.

The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gel—refers to the active ingredients dispersed or solubilized in a hydrophillic semi-solid matrix.

Powder for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrant—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and, sodium carboxymethylcellulose; microcrystalline delluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binder—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant-refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glident—material that prevents caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses the use of the pharmaceutical compositions disclosed above for treatment of diseases such as, for example, hepatitis C and the like. The method comprises administering a therapeutically effective amount of the inventive pharmaceutical composition to a patient having such a disease or diseases and in need of such a treatment.

In yet another embodiment, the compounds of the invention may be used for the treatment of HCV in humans in monotherapy mode or in a combination therapy (e.g., dual combination, triple combination etc.) mode such as, for example, in combination with antiviral and/or immunomodulatory agents. Examples of such antiviral and/or immunomodulatory agents include Ribavirin (from Schering-Plough Corporation, Madison, N.J.) and Levovirin™ (from ICN Pharmaceuticals, Costa Mesa, Calif.), VP50406™ (from Viropharma, Incorporated, Exton, Pa.), ISIS14803™ (from ISIS Pharmaceuticals, Carlsbad, Calif.), Heptazyme™ (from Ribozyme Pharmaceuticals, Boulder, Colo.), VX497™ (from Vertex Pharmaceuticals, Cambridge, Mass.), Thymosin™ (from SciClone Pharmaceuticals, San Mateo, Calif.), Maxamine™ (Maxim Pharmaceuticals, San Diego, Calif.), mycophenolate mofetil (from Hoffman-LaRoche, Nutley, N.J.), interferon (such as, for example, interferon-alpha, PEG-interferon alpha conjugates) and the like. "PEG-interferon alpha conjugates" are interferon alpha molecules covalently attached to a PEG molecule. Illustrative PEG-interferon alpha conjugates include interferon alpha-2a (Roferon™, from Hoffman La-Roche, Nutley, N.J.) in the form of pegylated interferon alpha-2a (e.g., as sold under the trade name Pegasys™), 10 interferon alpha-2b (Intron™, from Schering-Plough Corporation) in the form of pegylated interferon alpha-2b (e.g., as sold under the trade name PEG- Intron™), interferon alpha-2c (BeroforAlpha™, from Boehringer Ingelheim, Ingelheim, Germany) or consensus interferon as defined by determination of a consensus sequence of naturally occurring interferon alphas (Infergen™, from Amgen, Thousand Oaks, Calif.).

As stated earlier, the invention includes tautomers, rotamers, enantiomers and other stereoisomers of the inventive compounds also. Thus, as one skilled in the art appreciates, some of the inventive compounds may exist in suitable isomeric forms. Such variations are contemplated to be within the scope of the invention.

Another embodiment of the invention discloses a method of making the compounds disclosed herein. The compounds may be prepared by several techniques known in the art. Representative illustrative procedures are outlined in the following reaction schemes. It is to be understood that while the following illustrative schemes describe the preparation of a few representative inventive compounds, suitable substitution of any of both the natural and unnatural amino acids will result in the formation of the desired compounds based on such substitution. Such variations are contemplated to be within the scope of the invention.

Abbreviations which are used in the descriptions of the schemes, preparations and the examples that follow are:
THF: Tetrahydrofuran
DMF: N,N-Dimethylformamide
EtOAc: Ethyl acetate
AcOH: Acetic acid
HOOBt: 3-Hydroxy-1,2,3-benzotriazin-4($^3$H)-one.
EDCl: 1-(3-dimethylaminopropyl)-3-ethylcarbodiimide hydrochloride
NMM: N-Methylmorpholine
ADDP: 1,1'-(Azodicarbobyl)dipiperidine
DEAD: Diethylazodicarboxylate
MeOH: Methanol
EtOH: Ethanol
Et$_2$O: Diethyl ether
DMSO: Dimethylsulfoxide
HOBt: N-Hydroxybenzotriazole
PyBrOP: Bromo-tris-pyrrolidinophosphonium hexafluorophosphate
DCM: Dichloromethane
DCC: 1,3-Dicyclohexylcarbodiimide
TEMPO: 2,2,6,6-Tetramethyl-1-piperidinyloxy
Phg: Phenylglycine
Chg: Cyclohexylglycine
Bn: Benzyl
Bzl: Benzyl
Et: Ethyl
Ph: Phenyl
iBoc: isobutoxycarbonyl
iPr: isopropyl
$^t$Bu or Bu$^t$: tert-Butyl
Boc: tert-Butyloxycarbonyl
Cbz: Benzyloxycarbonyl
Cp: Cylcopentyldienyl
Ts: p-toluenesulfonyl
Me: Methyl
HATU: O-(7-azabenzotriazol-1-yl)-1,1,3,3-tetramethyluronium hexafluorophosphate
DMAP: 4-N,N-Dimethylaminopyridine
Bop: Benzotriazol-1-yl-oxy-tris(dimethylamino)hexafluorophosphate General Preparative Schemes:
The following schemes describe the methods of synthesis of intermediate building blocks:

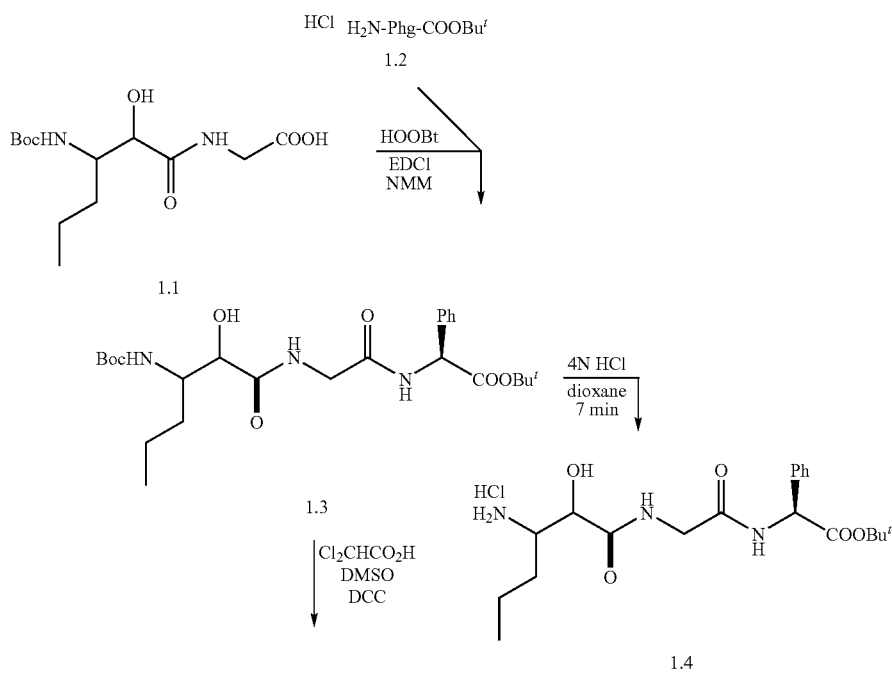

SCHEME 1

-continued
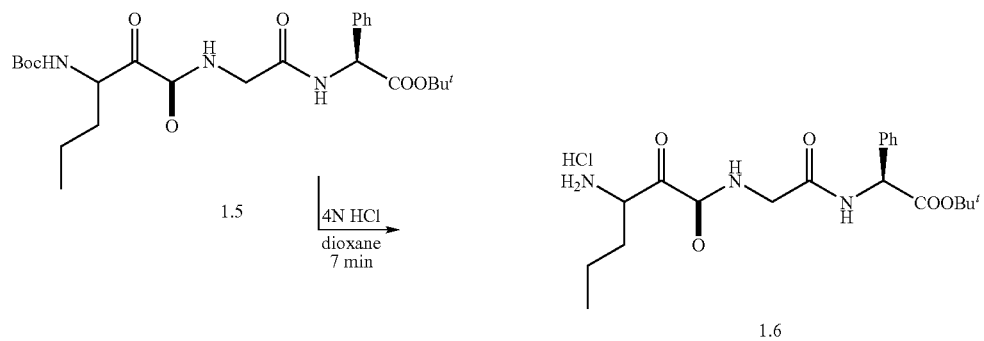
SCHEME 2
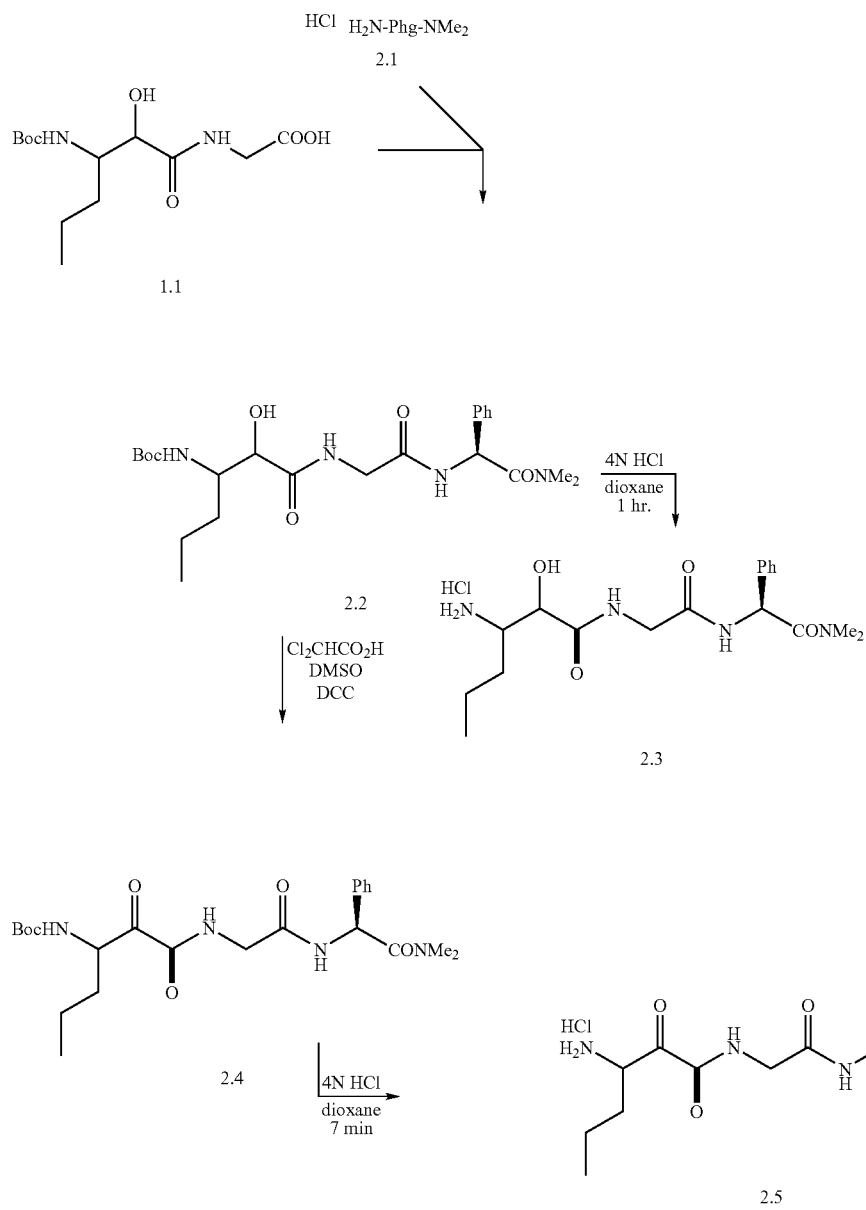

SCHEME 3
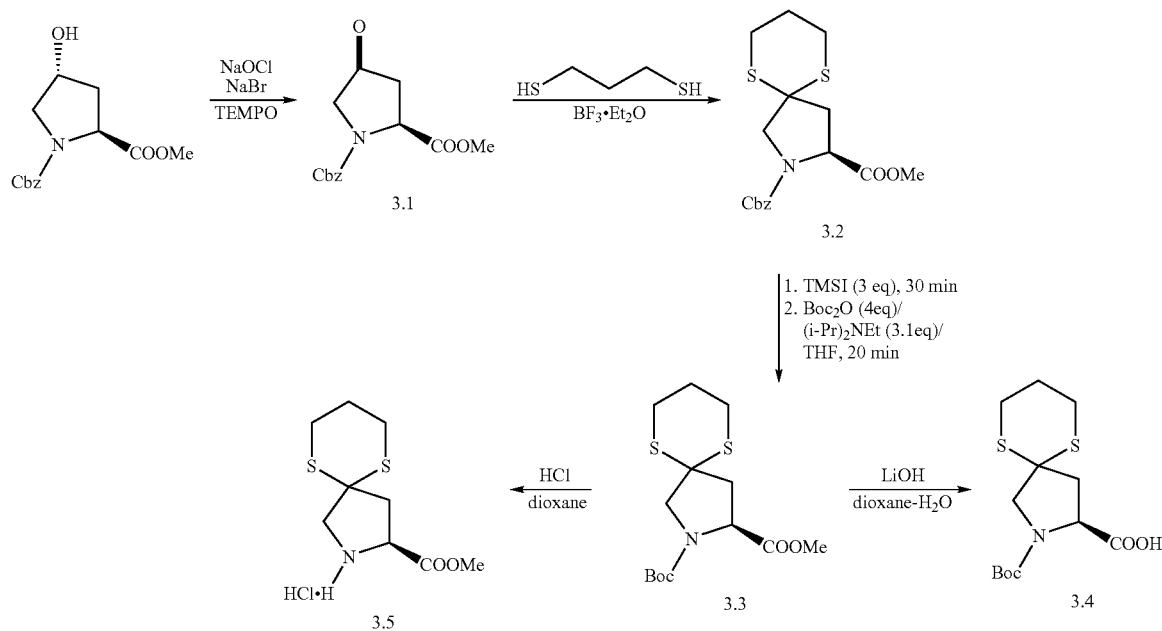
SCHEME 4
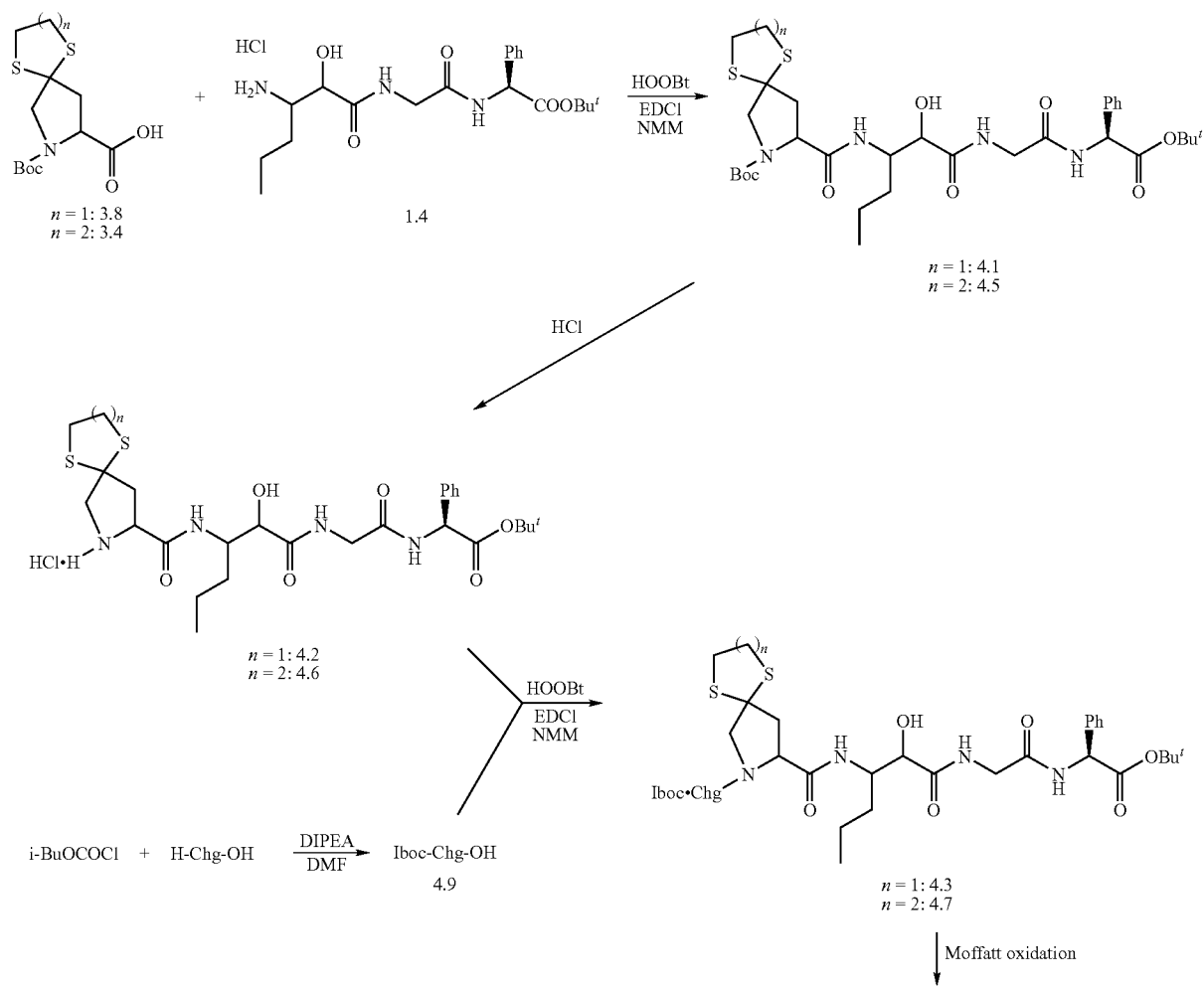

-continued
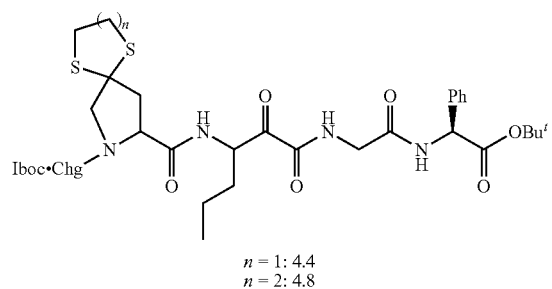
n = 1: 4.4
n = 2: 4.8
SCHEME 5
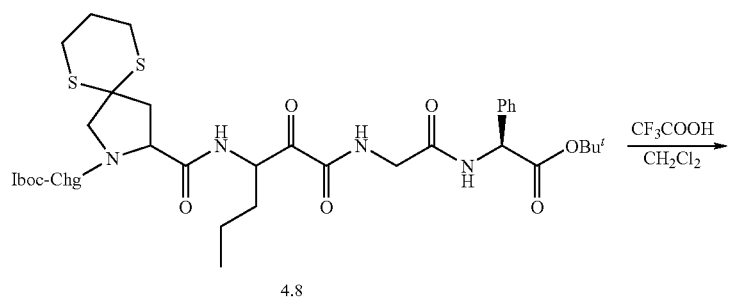
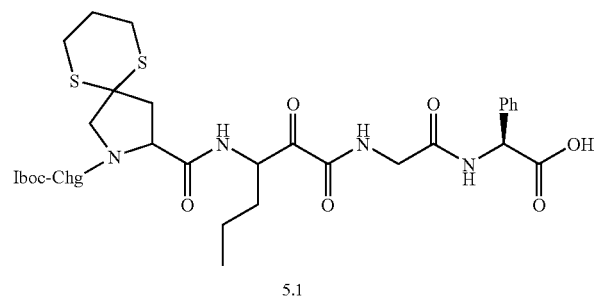
5.1
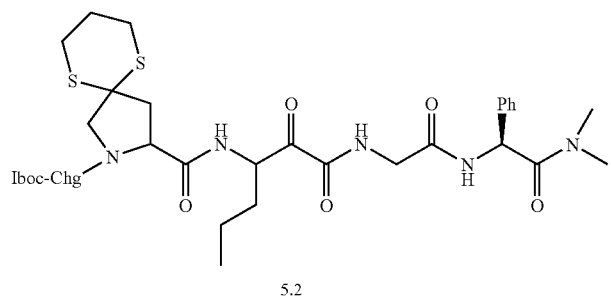
5.2
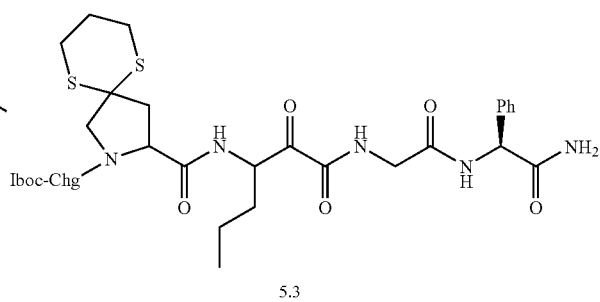
5.3

SCHEME 6
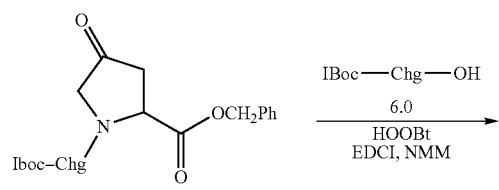
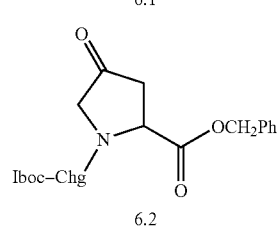
SCHEME 7
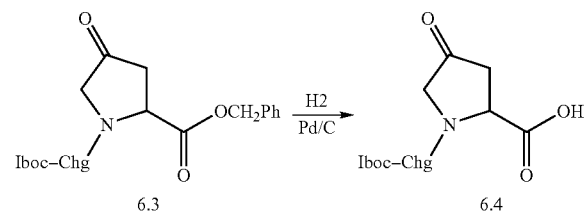
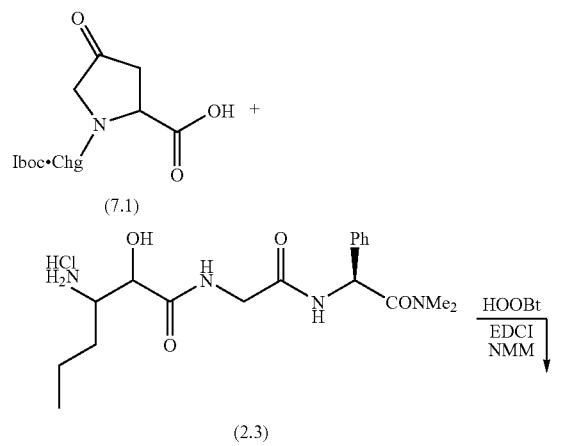
Moffatt oxidation
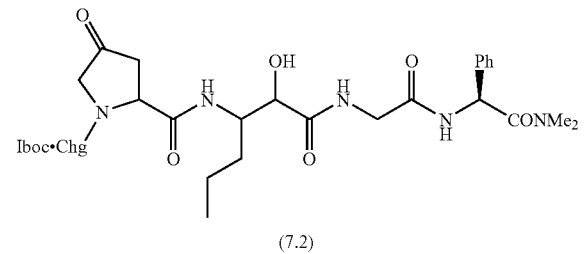
SCHEME 8
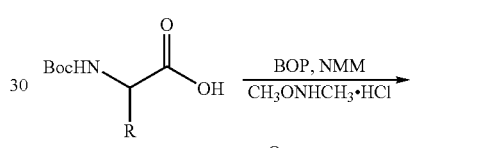
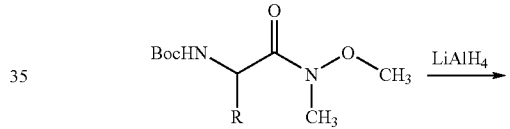
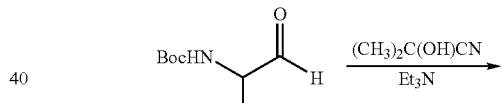
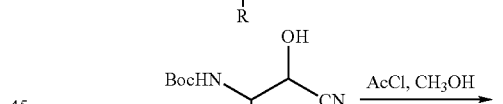
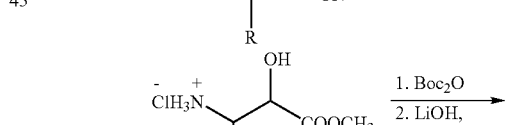
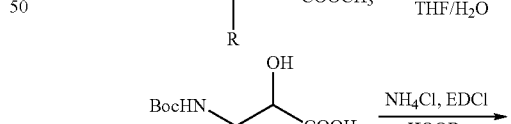
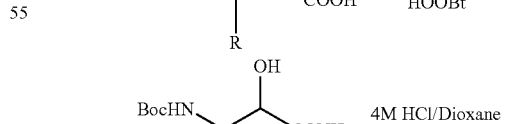
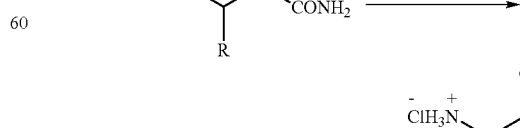

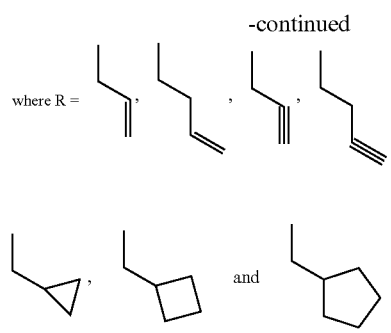
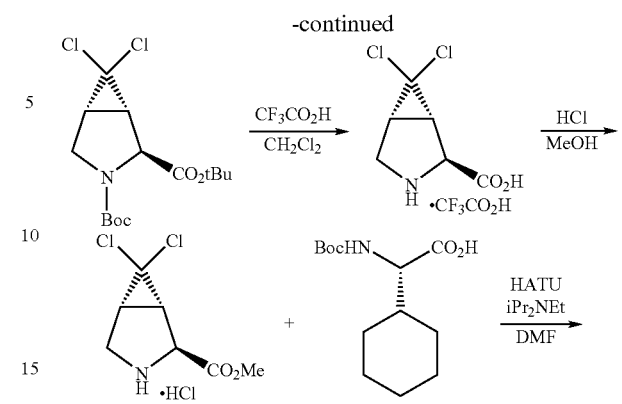
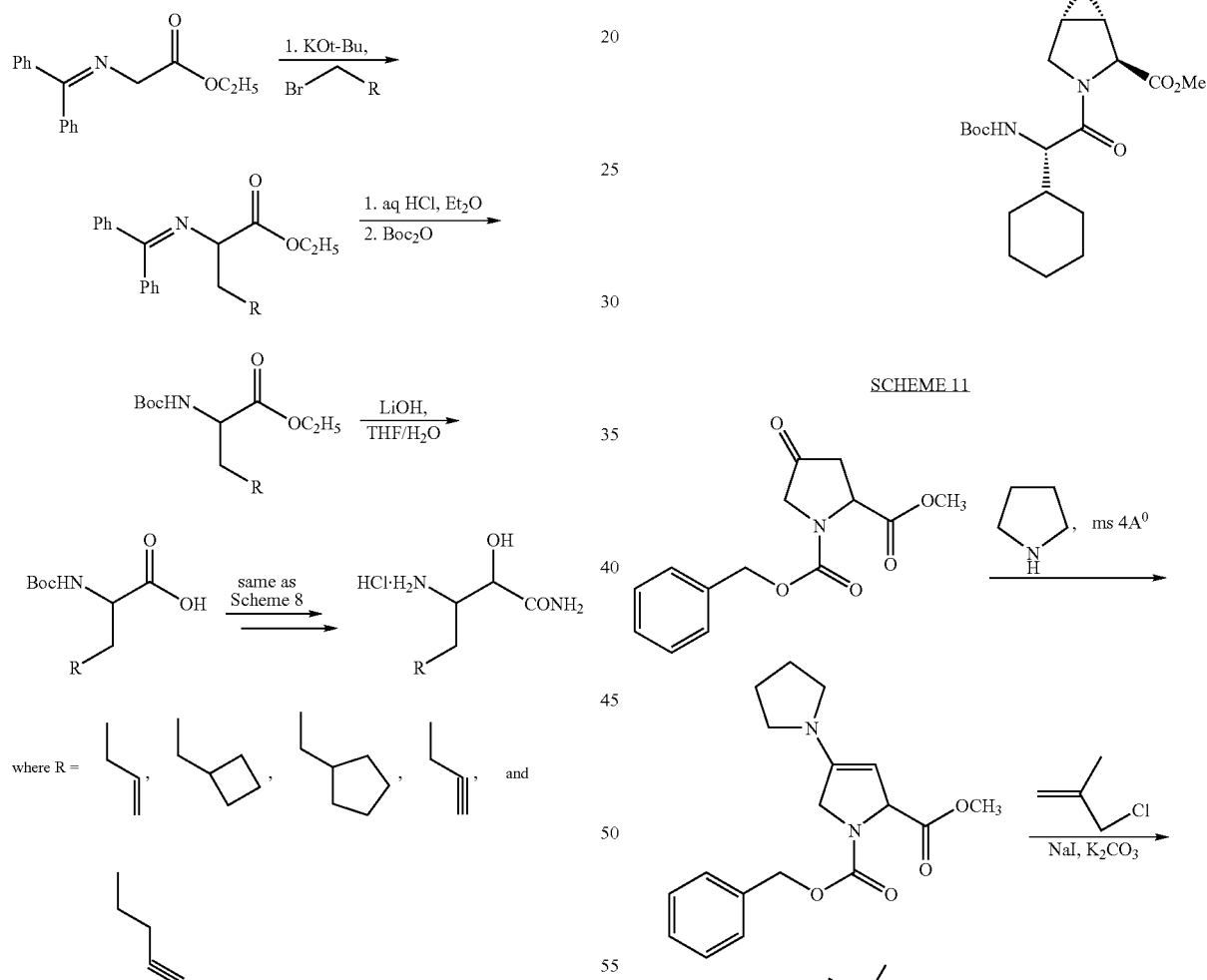
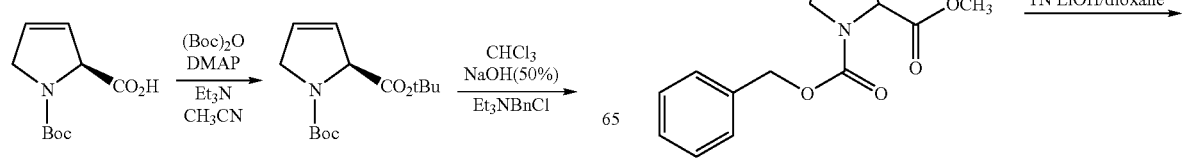

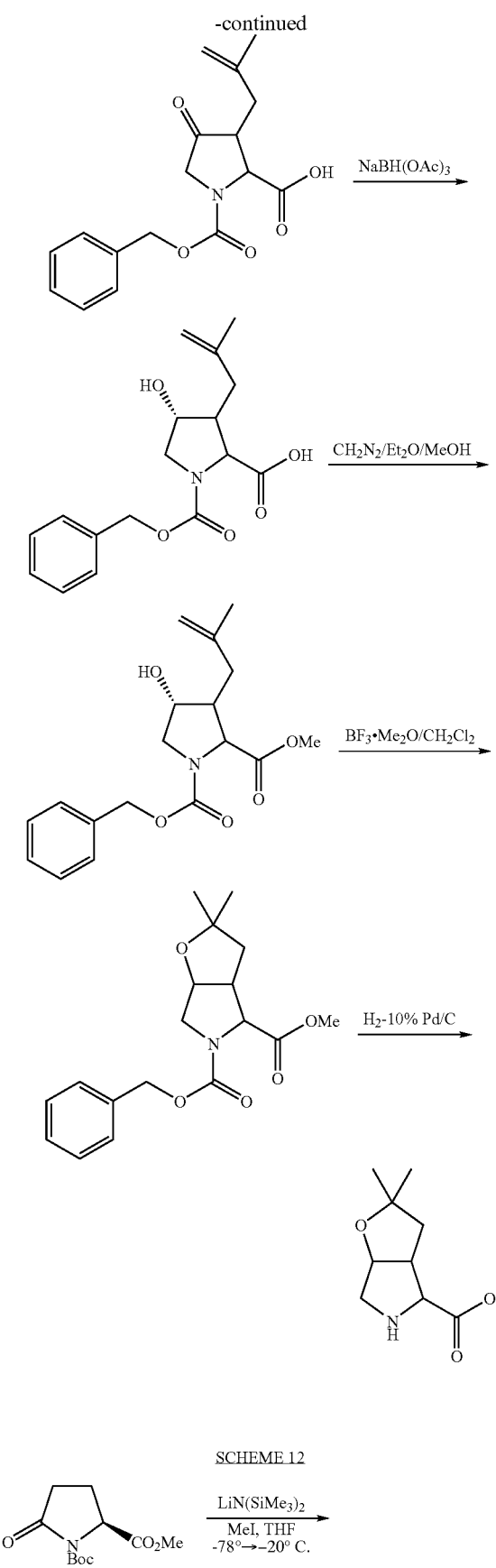
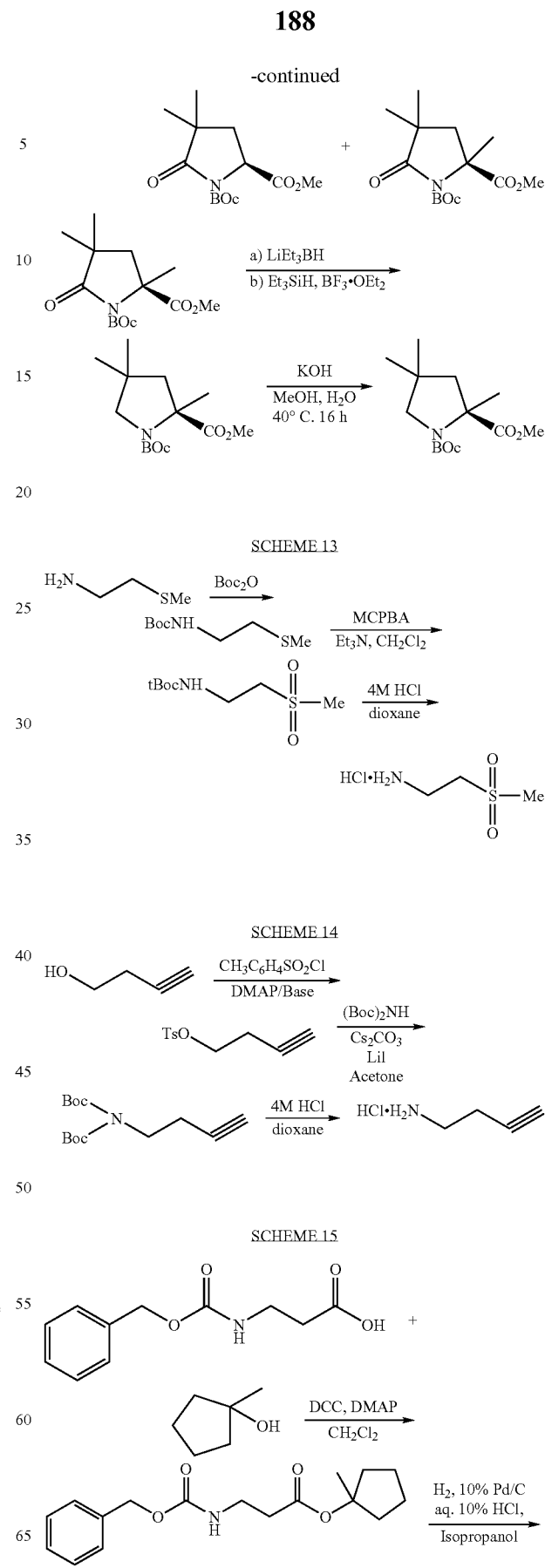

189
-continued
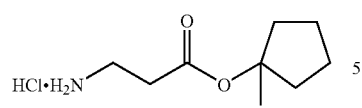
SCHEME 16
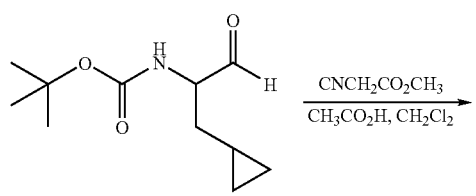
CNCH₂CO₂CH₃
CH₃CO₂H, CH₂Cl₂
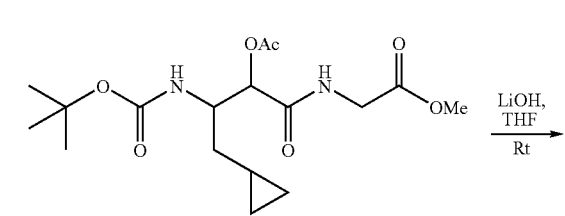
LiOH,
THF
Rt
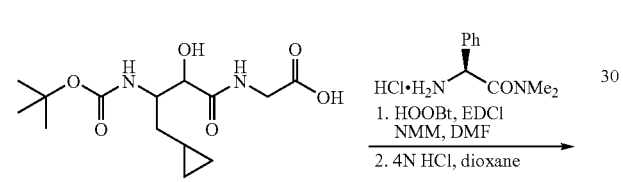
1. HOOBt, EDCl
NMM, DMF
2. 4N HCl, dioxane
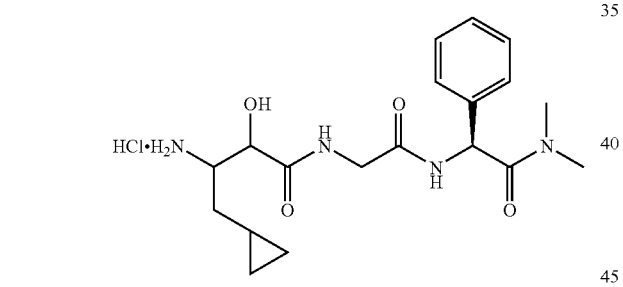
SCHEME 17
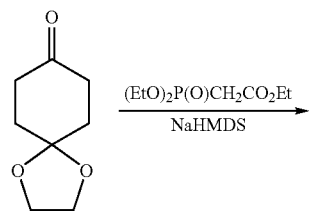
(EtO)₂P(O)CH₂CO₂Et
NaHMDS
190
-continued
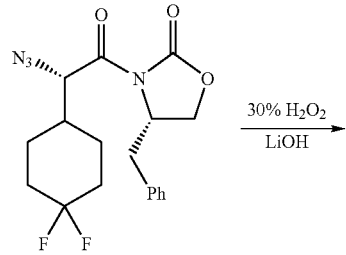
1) Me₃CCOCl, Et₃N
2) (S)-4-benzyl-2-oxazolidinone
   n-BuLi
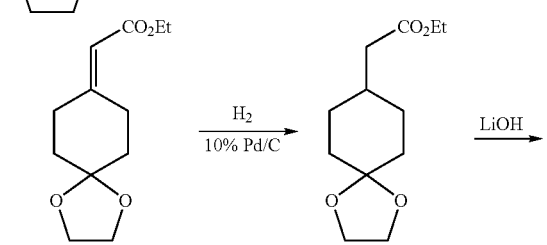
KHMDS
trisyl azide
HCO₂H
DAST
30% H₂O₂
LiOH
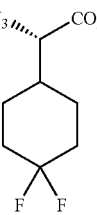 CH₂N₂ 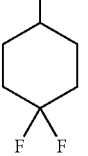 H₂, 10% Pd/C
HCO₂H

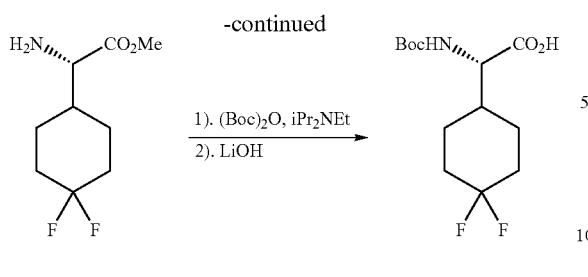

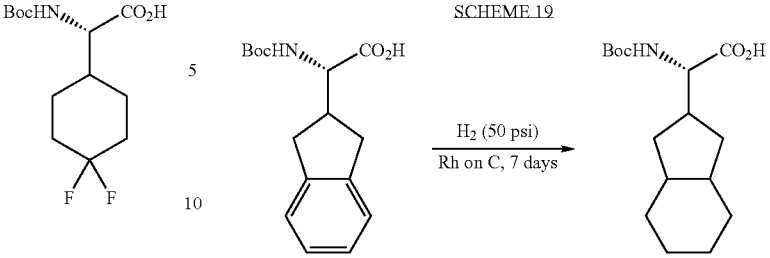

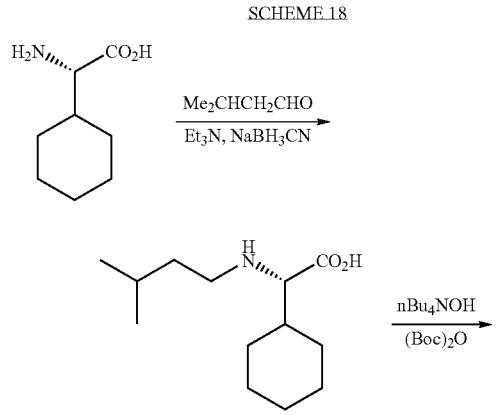

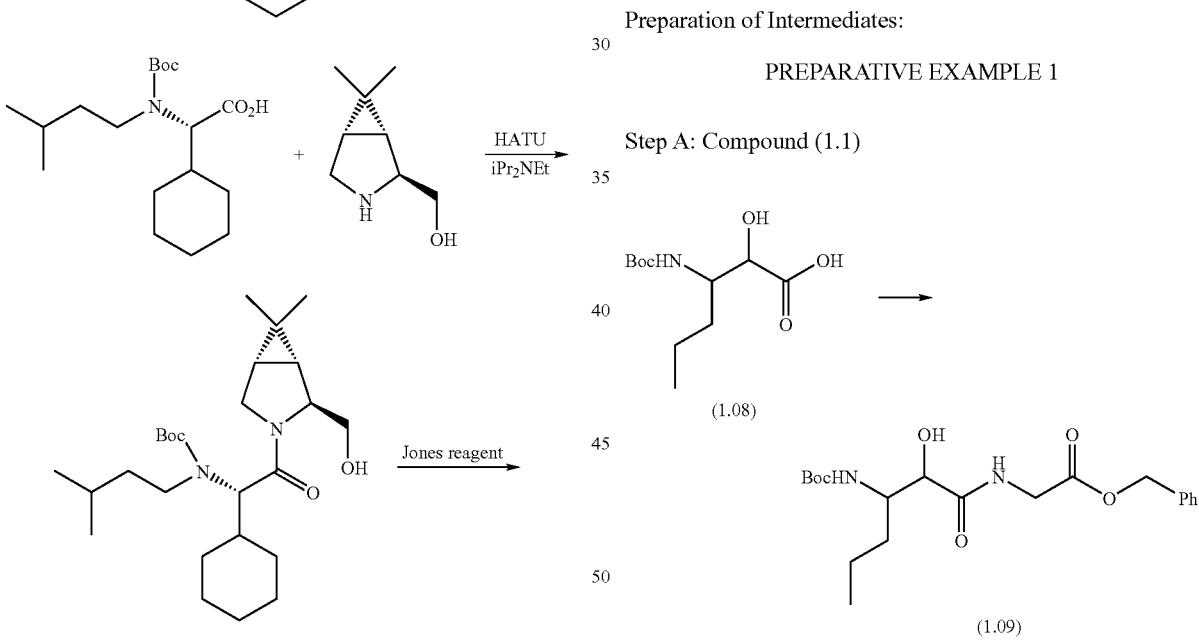

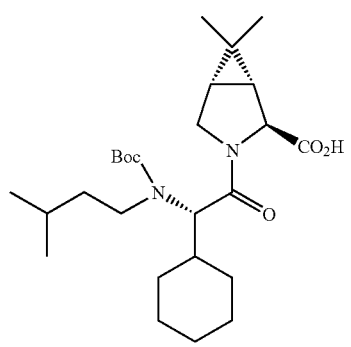

Preparation of Intermediates:

PREPARATIVE EXAMPLE 1

Step A: Compound (1.1)

To a stirred solution of Compound (1.08)(3.00 g, 12.0 mmol (S. L. Harbeson et al. *J. Med. Chem.* 37 No. 18 (1994) 2918-2929) in DMF (15 mL) and $CH_2Cl_2$ (15 mL) at −20° C. was added HOOBt (1.97 g, 12.0 mmol), N-methyl morpholine (4.0 mL, 36.0 mmol) and EDCl (2.79 g, 14.5 mmol) and stirred for 10 minutes, followed by addition of $HCl.H_2N$-Gly-OBn (2.56 g, 13.0 mmol). The resulting solution was stirred at −20° C. for 2 hrs, kept refrigerated overnight and then concentrated to dryness, followed by dilution with EtOAc (150 mL). The EtOAc solution was then washed twice with saturated $NaHCO_3$, $H_2O$, 5% $H3PO_4$, brine, dried over $Na_2SO_4$, filtered and concentrated to dryness to give the Compound (1.09) (4.5 g, 94%). LRMS m/z $MH^+$=395.1.

Step B: Compound (1.1)

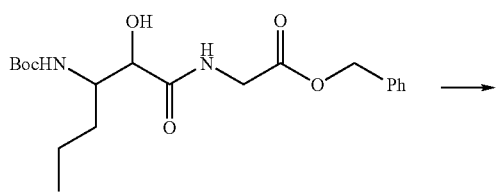

(1.09)

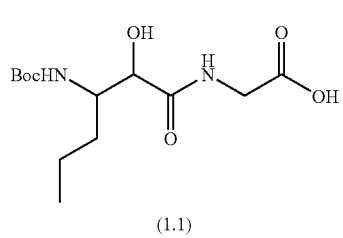

(1.1)

A solution of Compound (1.09) (7.00 g, 17.8 mmol) in absolute ethanol (300 mL) was stirred at room temperature under a hydrogen atmosphere in the presence of Pd—C (300 mg, 10%). The reaction progress was monitored by tlc. After 2 h, the mixture was filtered through a celite pad and the resulting solution was concentrated in vacuo to give Compound (1.1) (5.40 g, quantitative). LRMS m/z MH$^+$=305.1.

PREPARATIVE EXAMPLE 2

Step A Compound (1.3)

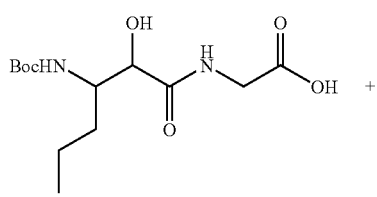

(1.1)

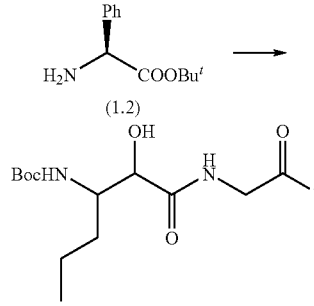

(1.2)

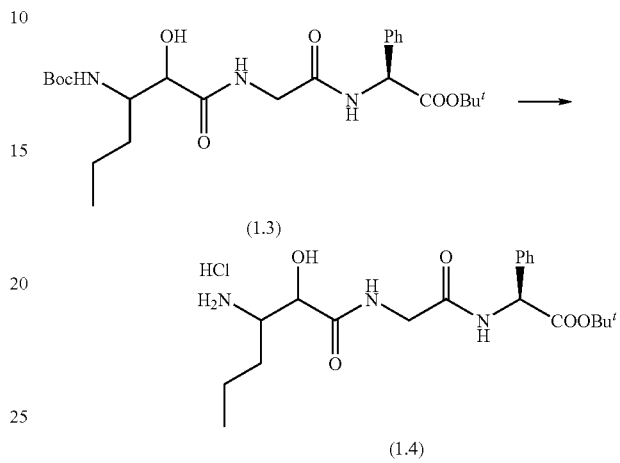

(1.3)

A mixture of Compound (1.1) from Preparative Example 1, Step B above (1 eq.), Compound (1.2) (from Novabiochem, Catalog No. 04-12-5147) (1.03 eq.), HOOBt (1.03 eq.), N-methylmorpholine (2.2 eq.), and dimethylformamide (70 mL/g) was stirred at −20° C. EDCl (1.04 eq.) was added and the reaction stirred for 48 hr. The reaction mixture was poured into 5% aqueous KH$_2$PO$_4$ and extracted with ethyl acetate (2×). The combined organics were washed with cold 5% aqueous K$_2$CO$_3$, then 5% aqueous KH$_2$PO$_4$, then brine, and the organic layer was dried over anhydrous MgSO$_4$. The mixture was filtered, then evaporated and the filtrate dried under vacuum, the residue was triturated with Et$_2$O-hexane, and filtered to leave the title compound (1.3)(86% yield), C$_{25}$H$_{39}$N$_3$O$_7$ (493.60), mass spec. (FAB) M+1=494.3.

Step B Compound (1.4)

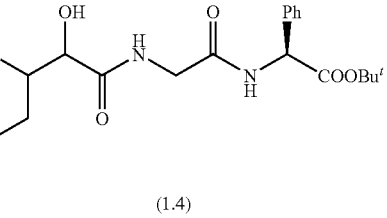

(1.3)

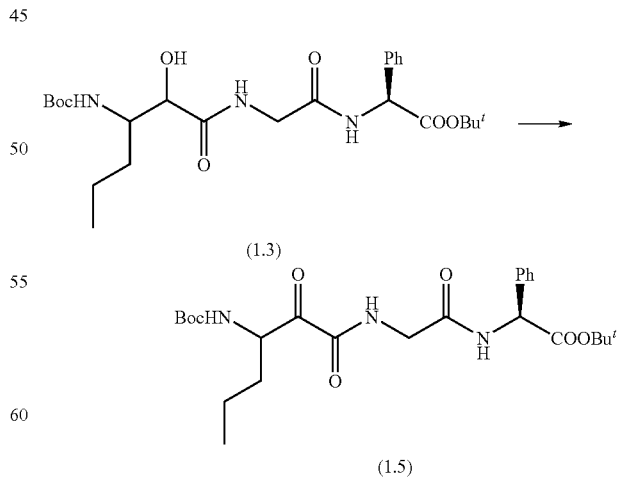

(1.4)

Compound (1.3) from Preparative Example 2, Step A (3.0 g) was treated with 4 N HCl/dioxane (36 mL) and stirred at room temperature for 7 min. The mixture was poured into 1.5 L cold (5° C.) hexane and stirred, then allowed to set cold for 0.5 hr. The mixture was suction-filtered in a dry atmosphere, and the collected solid was further dried to afford the title compound (1.4) (2.3 g, 88% yield), C$_{20}$H$_{31}$N$_3$O$_5$HCl, H$^1$ NMR (DMSO-d$_6$/NaOD) δ 7.38 (m, 5H), 5.25 (m, 1H), 4.3-4.1 (m, 1H), 3.8 (m, 2H), 3.4-3.3 (m, obscured by D20), 1.7-1.1 (m, 4H), 1.35 (s, 9H), 0.83 (m, $^3$H).

PREPARATIVE EXAMPLE 3

Compound (1.5)

Compound (1.3) from Preparative Example 2, Step A, was treated in essentially the same manner as in Preparative Example 7, Step A below to afford Compound (1.5).

PREPARATIVE EXAMPLE 4

Compound (1.6)

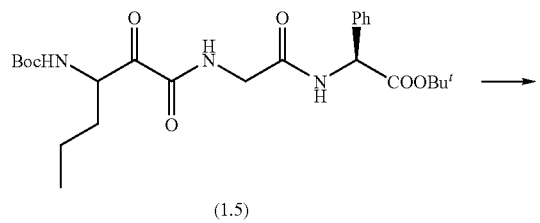

(1.5)

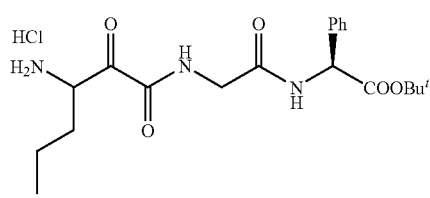

(1.6)

Compound (1.5) from Preparative Example 3, was treated in essentially the same manner as in Preparative Example 2, Step B, to afford Compound (1.6).

PREPARATIVE EXAMPLE 5

Step A Compound (2.09)

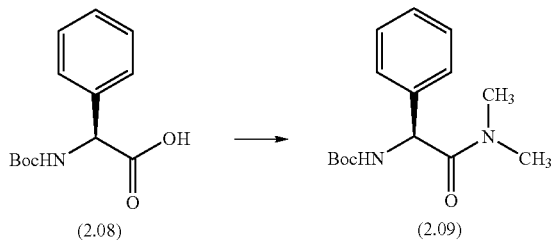

To a solution of dimethylamine hydrochloride (1.61 g, 19.7 mmol), N-Boc-phenylglycine, Compound (2.08)(4.50 g, 17.9 mmol, Bachem Co. # A-2225), HOOBt (3.07 g, 18.8 mmol) and EDCl (4.12 g, 21.5 mmol) in anhydrous DMF (200 mL) and $CH_2Cl_2$ (150 mL) at −20° C. was added NMM (5.90 mL, 53.7 mmol). After being stirred at this temperature for 30 min, the reaction mixture was kept in a freezer overnight (18 h). It was then allowed to warm to rt, and EtOAc (450 mL), brine (100 mL) and 5% $H_3PO_4$ (100 mL) were added. After the layers were separated, the organic layer washed with 5% $H_3PO_4$ (100 mL), saturated aqueous sodium bicarbonate solution (2×150 mL), water (150 mL), and brine (150 mL), dried ($MgSO_4$), filtered and concentrated in vacuo to afford Compound (2.09) (4.86 g) as a white solid, which was used without further purification.

Step B Compound (2.1)

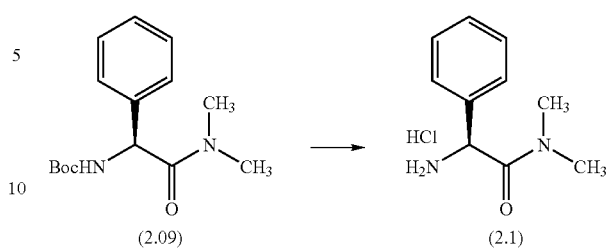

Compound (2.09) from Preparative Example 5, Step A (4.70 g, crude) was dissolved in 4 N HCl (60 mL, 240 mmol) and the resulting solution was stirred at room temperature. The progress of the reaction was monitored by TLC. After 4 h, the solution was concentrated in vacuo to yield Compound (2.1) as a white solid which was used in the next reaction without further purification. LRMS m/z $MH^+=179.0$.

PREPARATIVE EXAMPLE 6

Step A Compound (2.2)

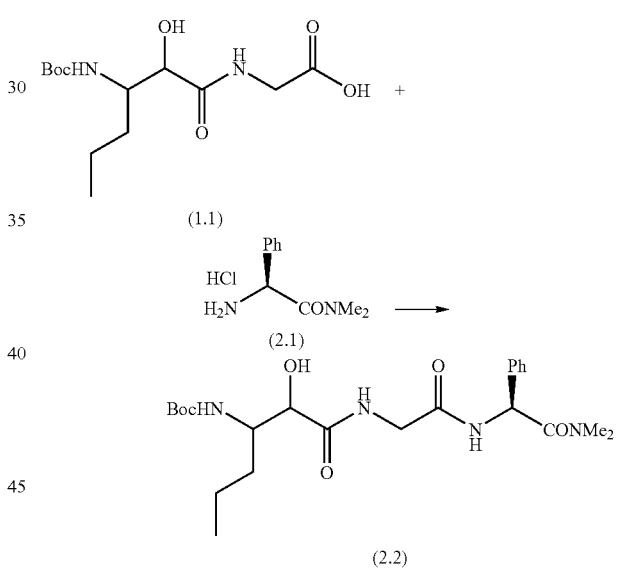

In essentially the same manner as Preparative Example 2, Step A. substituting phenylglycine N,N-dimethylamide hydrochloride in place of phenylglycine t-butyl ester hydrochloride, Compound (2.2) was prepared mass spec. (FAB) M+1=465.3.

Step B Compound (2.3)

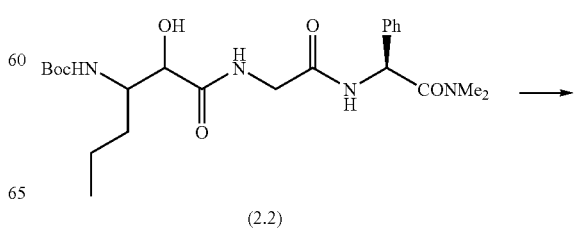

(2.2)

Step B Compound (2.5)

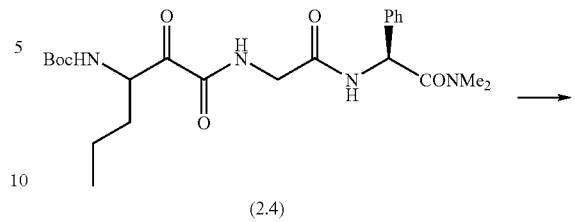

(2.4)

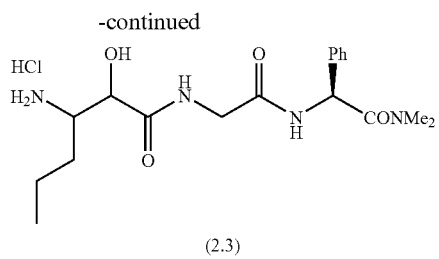

(2.3)

Compound (2.2) from Step A (1.85 g) was reacted with 4 N HCl/dioxane (50 mL) at room temperature for 1 hr. The mixture was evaporated under vacuum in a 20° C. water bath, triturated under isopropyl ether, filtered, and dried to afford Compound (2.3) (1.57 g, 98% yield), $C_{18}H_{28}N_4O_4 \cdot HCl$, mass spec. (FAB) M+1=365.3

(2.5)

In essentially the same manner as Preparative Example 2, Step B, Compound (2.5) was prepared.

PREPARATIVE EXAMPLE 7

Step A Compound (2.4)

PREPARATIVE EXAMPLE 8

Step A Compound (3.1)

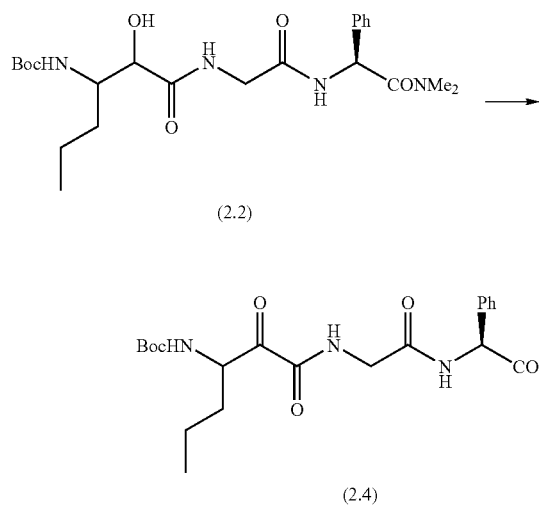

(2.2)

(2.4)

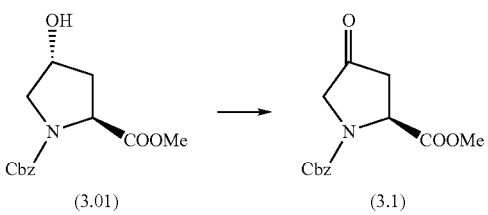

(3.01)  (3.1)

A solution of Compound (2.2) from Preparative Example 5, Step A (2.0 g) in dichloromethane (60 mL) was treated with dimethylsulfoxide (3.0 mL) and 2,2-dichloroacetic acid (0.70 mL). The stirred mixture was cooled to 5° C. and then added 1 M dicyclohexylcarbodiimide/dichloromethane solution (8.5 mL). The cold bath was removed and the mixture stirred for 22 hr. Then added 2-propanol (0.5 mL), and stirred for an additional 1 hr. The mixture was filtered then washed with ice-cold 0.1 N NaOH (50 mL), then ice-cold 0.1 N HCl (50 mL), then 5% aqueous $KH_2PO_4$, then saturated brine. The organic solution was dried over anhydrous magnesium sulfate, then filtered. The filtrate was evaporated, and chromatographed on silica gel, eluting with ethyl acetate to afford Compound (2.3) (1.87 g, 94% yield), $C_{23}H_{34}N_4O_6$, mass spec. (FAB) M+1=463.3.

In a flask were combined N-Cbz-hydroxyproline methyl ester (available from Bachem Biosciences, Incorporated, King of Prussia, Pa.), compound (3.01) (3.0 g), toluene (30 mL), and ethyl acetate (30 mL). The mixture was stirred vigorously, and then a solution of NaBr/water (1.28 g/5 mL) was added. To this was added 2,2,6,6-tetramethyl-1-piperidinyloxy free radical (TEMPO, 17 mg, from Aldrich Chemicals, Milwaukee, Wis.). The stirred mixture was cooled to 5° C. and then was added a prepared solution of oxidant [commercially available bleach, Clorox® (18 mL), $NaHCO_3$ (2.75 g) and water to make up 40 mL] dropwise over 0.5 hr. To this was added 2-propanol (0.2 mL). The organic layer was separated, and the aqueous layer extracted with ethyl acetate. The organic extracts were combined, washed with 2% sodium thiosulfate, then saturated brine. The organic solution was dried over anhydrous $MgSO_4$, filtered, and evaporated the filtrate under vacuum to leave a pale yellow gum suitable for subsequent reactions (2.9 g, 97% yield), $C_{14}H_{15}NO_5$ (277.28), mass spec. (FAB) M+1=278.1.

Step B Compound (3.2)

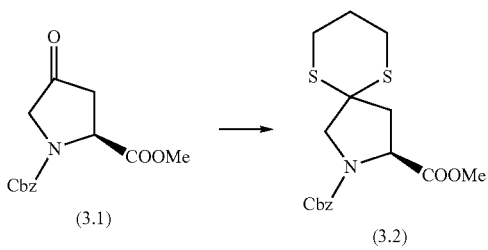

Compound (3.1) from Step A above (7.8 g) was dissolved in dichloromethane (100 mL), and cooled to 15° C. To this mixture was first added 1,3-propanedithidl (3.1 mL), followed by freshly distilled boron trifluoride etherate (3.7 mL). The mixture was stirred at room temperature for 18 h. While stirring vigorously, a solution of $K_2CO_3$/water (2 g/30 mL)was carefully added, followed by saturated $NaHCO_3$ (10 mL). The organic layer was separated from the aqueous layer (pH ~7.4), washed with water (10 mL), then brine. The organic solution was dried over anhydrous $MgSO_4$, filtered, and evaporated under vacuum. The residue was chromatographed on silica gel, eluting with toluene, then a with a gradient of hexane-$Et_2O$ (2:3 to 0:1) to afford a brown oil (7.0 g, 68% yield), $C_{17}H_{21}NO_4S2$ (367.48), mass spec. (FAB) M+1=368.1.

Step C Compound (3.3)

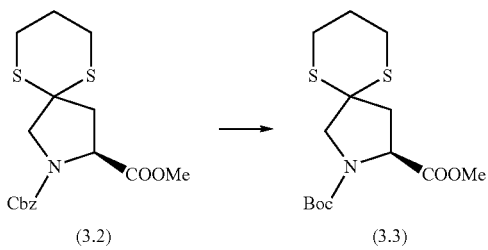

A solution of compound (3.2) from Step B above (45 g) in acetonitrile (800 mL) at 20° C. was treated with freshly distilled iodotrimethylsilane (53 mL) at once. The reaction was stirred for 30 min., then poured into a freshly prepared solution of di-t-butyldicarbonate (107 g), ethyl ether (150 mL), and diisopropylethylamine (66.5 mL). The mixture stirred for 30 min. more then washed with hexane (2×500 mL). Ethyl acetate (1000 mL) was added to the lower acetonitrile layer, and then the layer washed with 10% aqueous $KH_2PO_4$ (2×700 mL), and brine. The filtrate was evaporated under vacuum in a 25° C. water bath, taken up in fresh ethyl acetate (1000 mL), and washed successively with 0.1 N HCl, 0.1 N NaOH, 10% aqueous $KH_2PO_4$, and brine. The organic solution was dried over anhydrous $MgSO_4$, filtered, and evaporated under vacuum. The residue (66 g) was chromatographed on silica gel (2 kg), eluting with hexane (2 L), then $Et_2O$/hexane (55:45, 2 L), then $Et_2O$ (2 L) to afford an orange gum which slowly crystallized on standing (28 g, 69% yield), $C_{14}H_{23}NO_4S2$ (333.46), mass spec. (FAB) M+1=334.1.

Step D Compound (3.4)

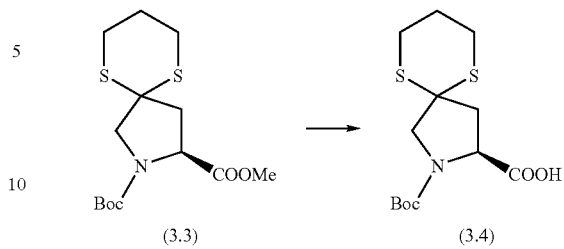

A solution of compound (3.3) from Step C above (11 g) in dioxane (150 mL) at 20° C. was treated with 1 N aqueous LiOH (47 mL) and stirred for 30 h. The mixture was concentrated under vacuum in a 30° C. water bath to half volume. The remainder was diluted with water (300 mL), extracted with $Et_2O$ (2×200 mL). The aqueous layer was acidified to pH ~4 with 12 N HCl (3-4 mL), extracted with ethyl acetate, and washed with brine. The organic solution was dried over anhydrous $MgSO_4$, filtered, and evaporated under vacuum to leave Compound (3.4) (8.1 g, 78%), $C_{13}H_{21}NO_4S2$ (319.44), mass spec. (FAB) M+1=320.1.

Step E Compound (3.5)

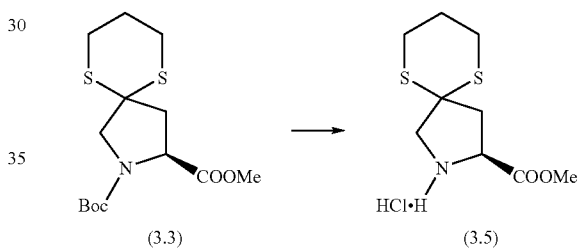

To a solution of compound (3.3) from Step C above (1 g) in dioxane (5 mL), was added 4 NHCl-dioxane solution (50 mL). The mixture was stirred vigorously for 1 hr. The mixture was evaporated under vacuum in a 25° C. water bath. The residue was triturated with $Et_2O$, and filtered to leave the title compound (0.76 g, 93% yield), $C_9H_{15}NO_2S2 \cdot HCl$ (269.81), mass spec. (FAB) M+1=234.0.

PREPARATIVE EXAMPLE 9

Step A Compound (3.6)

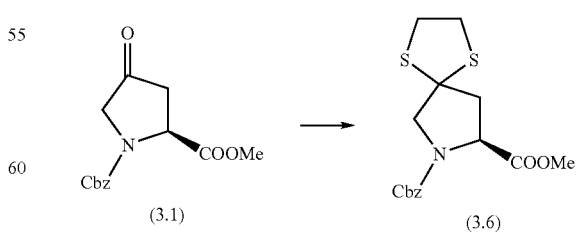

Following essentially the same procedure of Preparative Example 8, Step B, substituting ethane dithiol for propane dithiol, compound (3.6) was obtained.

Step B Compound (3.7).

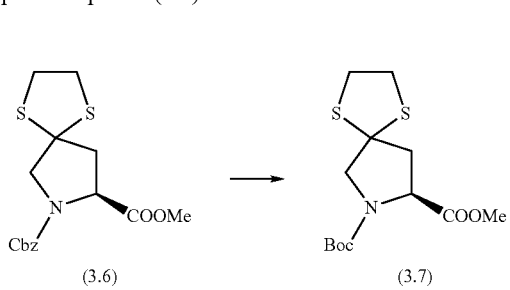

Following essentially the same procedure of Preparative Example 8, Step C, substituting compound (3.6) for compound (3.2), the product compound (3.7) was obtained.

Step C Compound (3.8)

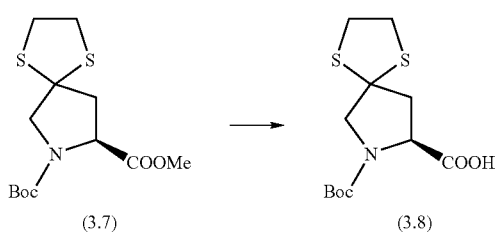

Following essentially the same procedure of Preparative Example 8, Step D, substituting compound (3.7) for compound (3.3) the product compound (3.8) was obtained.

Step D Compound (3.9)

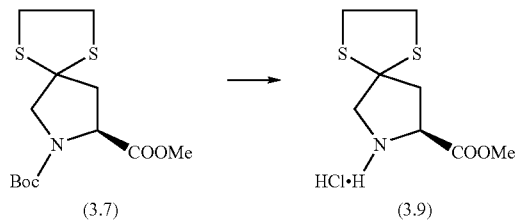

Following essentially the same procedure of Preparative Example 8, Step E, substituting compound (3.7) for compound (3.3) the product compound (3.9) was obtained.

PREPARATIVE EXAMPLE 10

Step A Compound (4.1)

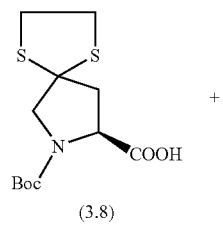

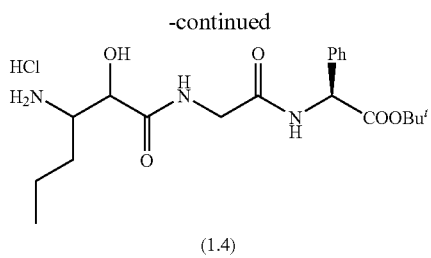

In essentially the same manner as Preparative Example 2, Step A, Compound (4.1) was prepared $C_{33}H_{48}N_4O_9S_2$ (708.89).

Step B Compound (4.2)

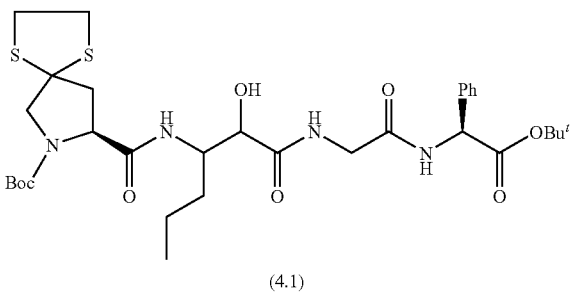

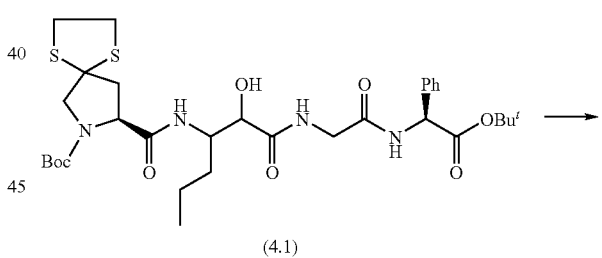

In essentially the same manner as Preparative Example 2, Step B, Compound (4.2) was prepared mass spec. (FAB) M+1=609.3.

Step C Compound (4.3)

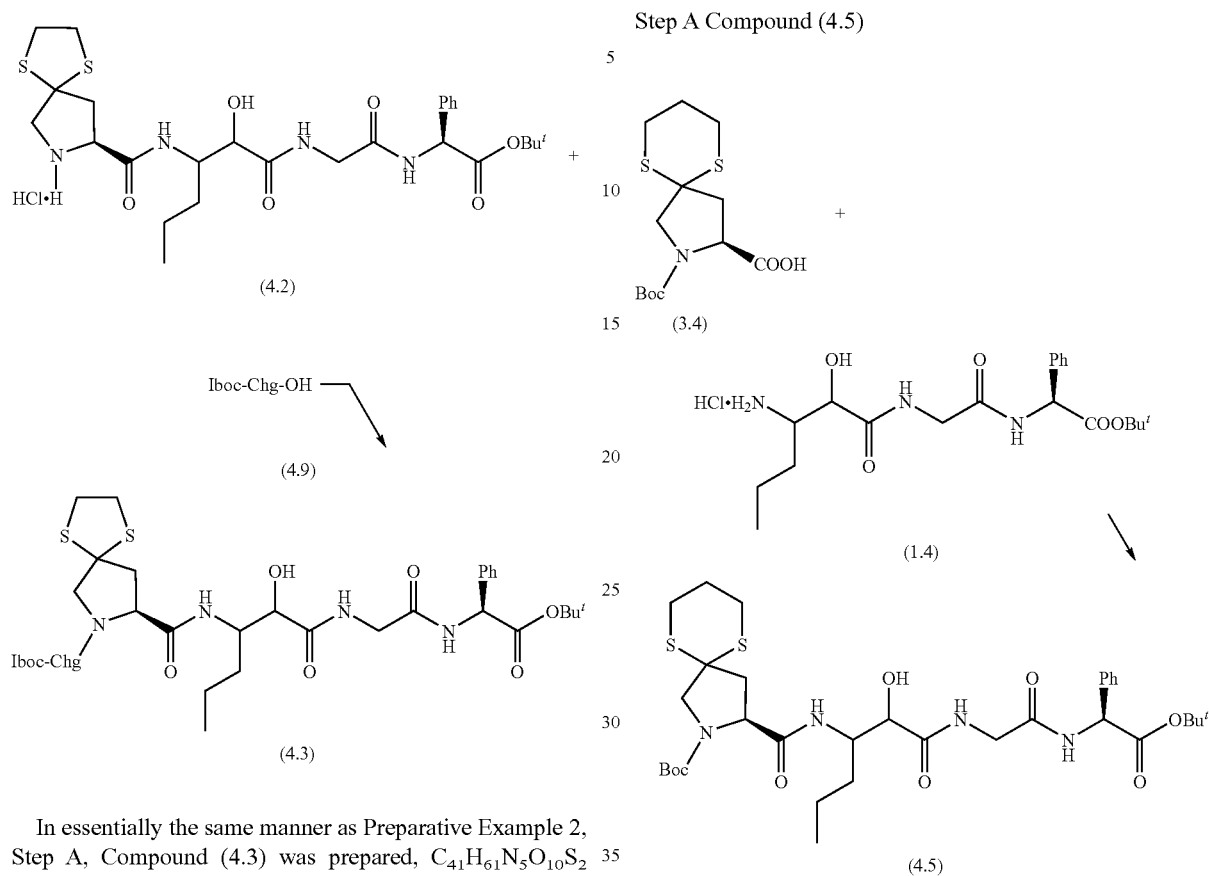

In essentially the same manner as Preparative Example 2, Step A, Compound (4.3) was prepared, $C_{41}H_{61}N_5O_{10}S_2$ (708.89), mass spec. (FAB) M+1=709.3.

Step D Compound (4.4)

In essentially the same manner as Preparative Example 7, Step A, Compound (4.4) was prepared.

PREPARATIVE EXAMPLE 11

Step A Compound (4.5)

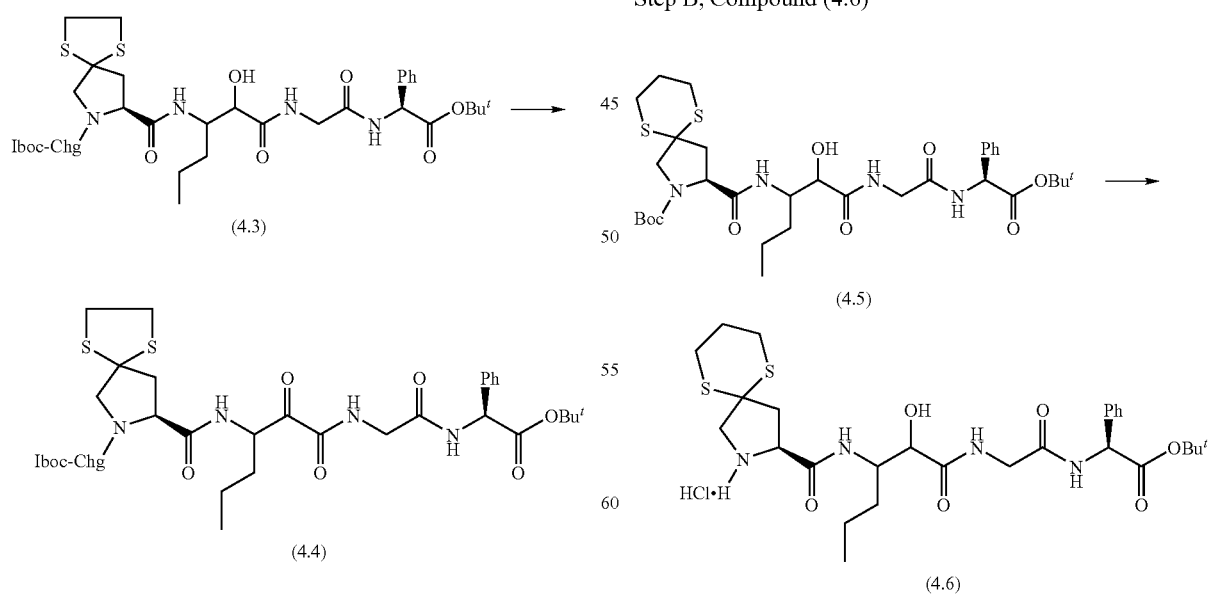

In essentially the same manner as Preparative Example 2, Step A, Compound (4.5) was prepared.

Step B, Compound (4.6)

In essentially the same manner as Preparative Example 2, Step B, Compound (4.6) was prepared.

Step C, Compound (4.7)

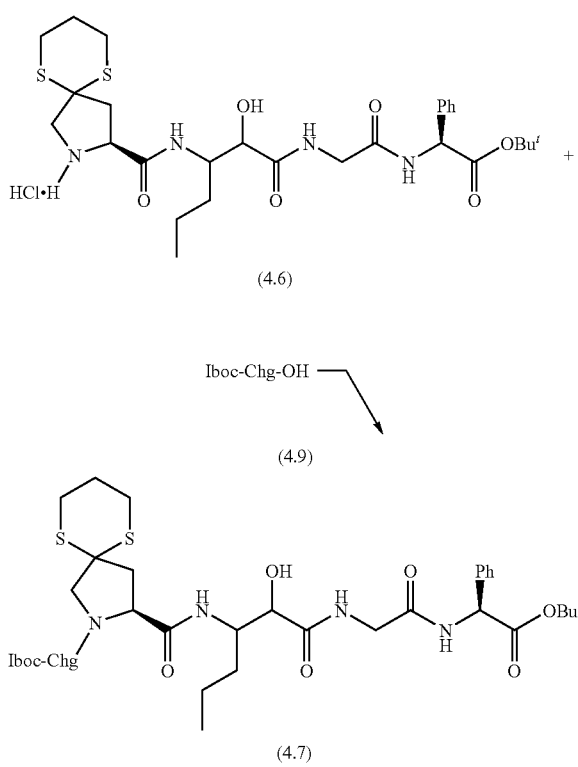

Compound (4.9) from Preparative Example 12, was reacted with Compound (4.6) from Step B above, in essentially the same manner as Preparative Example 2, Step A, to afford Compound (4.7).

Step D, Compound (4.8)

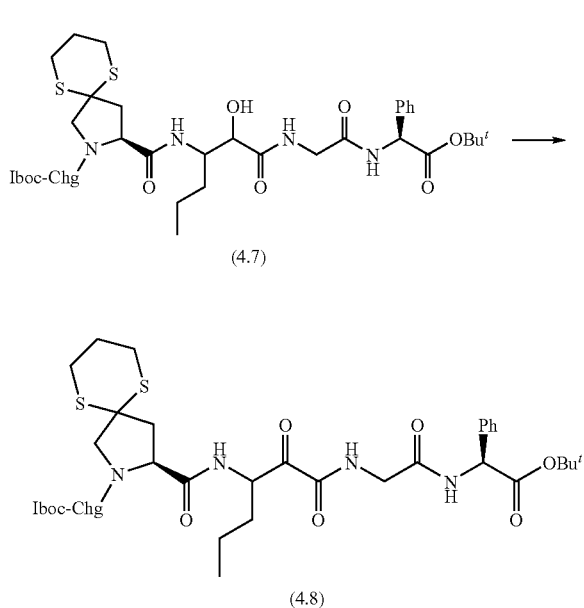

In essentially the same manner as Preparative Example 7, Step A, Compound (4.8) was prepared.

PREPARATIVE EXAMPLE 12

Compound (4.9)

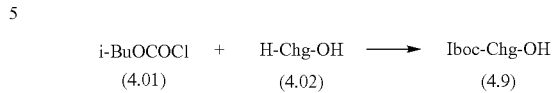

A solution of L-cyclohexylglycine (4.02) (1.0 eq.), dimethylformamide (20 mL/g), and diisopropylethylamine (1.1 eq.) at 5° C. is treated with isobutyl chloroformate (4.01) (1.1 eq.). The cold bath is removed and it is stirred for 6 hr. The reaction mixture is poured into 5% aqueous $KH_2PO_4$ and extracted with ethyl acetate (2×). The combined organics are washed with cold 5% aqueous $K_2CO_3$, then 5% aqueous $KH_2PO_4$, then brine, and the organics are dried over anhydrous $MgSO_4$. The mixture is filtered, the filtrate evaporated under vacuum, the residue chromatographed if necessary or else the residue triturated with $Et_2O$-hexane, and filtered to leave the title compound (4.9), $C_{13}H_{23}NO_4$ (257.33).

PREPARATIVE EXAMPLE 13

Compound (13.1)

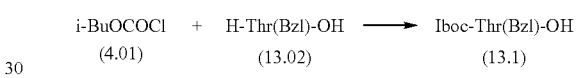

In essentially the same manner as Preparative Example 12, substituting L-O-benzylthreonine (13.02) (Wang et al, *J. Chem. Soc., Perkin Trans.* 1, (1997) No. 5, 621-624.) for L-cyclohexylglycine (4.02) Compound (13.1) is prepared $C_{16}H_{23}NO_5$ (309.36), mass spec. (FAB) M+1=310.2.

PREPARATIVE EXAMPLE 14

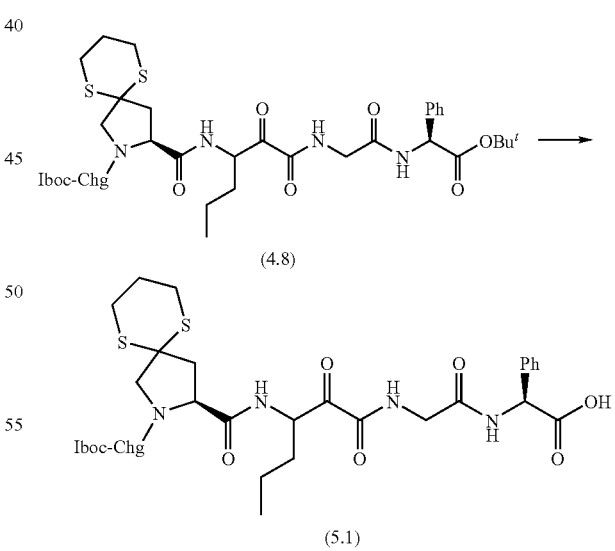

Compound (4.8) from Preparative Example 11, Step D (1.0 g) was reacted with a solution of anhydrous trifluoroacetic acid-dichloromethane (1:1, 50 mL) for 2 hr. The solution was diluted with xylene (100 mL) and evaporated under vacuum. The residue was triturated with $Et_2O$, and filtered to leave the title compound (5.1) (0.9 g), $C_{37}H_{53}N_5O_9S_2$ (775.98), mass spec. (FAB) M+1=776.5.

Step B Compound (5.2)

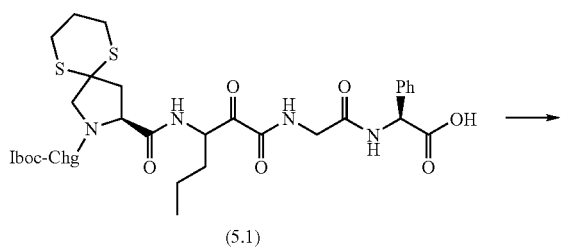

(5.1)

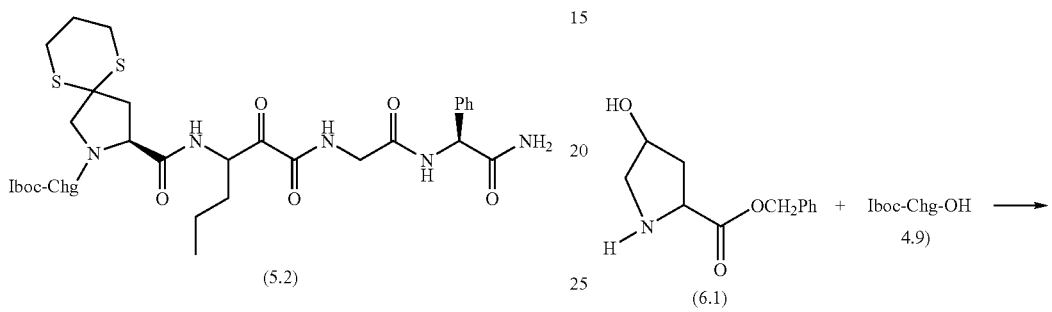

In essentially the same manner as Preparative Example 2, Step A, Compound (5.1) was reacted with ammonia (0.5 M 1,4-dioxane solution), to obtain the title compound (5.2) $C_{37}H_{54}N_6O_8S_2$ (774.99), mass spec. (FAB) M+1=775.4.

PREPARATIVE EXAMPLE 15

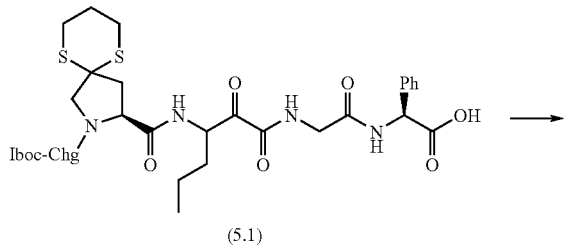

(5.1)

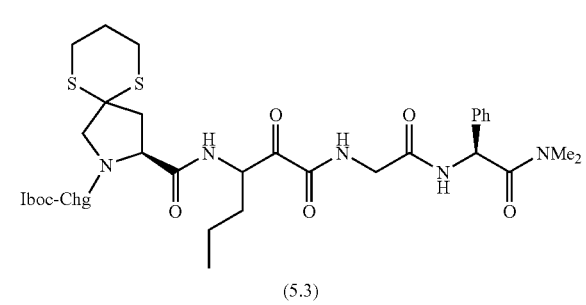

(5.3)

A mixture of Compound (5.1) from Preparative Example 14, Step A (0.15 g), N,N-dimethylamine (0.12 mL of 2 M THF solution), dimethylformamide (10 mL), and PyBrOP coupling reagent (0.11 g) was cooled to 5° C., then diisopropylethylamine (DIEA or DIPEA, 0.12 mL) was added. The mixture was stirred cold for 1 min., then stirred at room temperature for 6 hr. The reaction mixture was poured into cold 5% aqueous H3PO4 (50 mL) and extracted with ethyl acetate (2×). The combined organics were washed with cold 5% aqueous $K_2CO_3$, then 5% aqueous $KH_2PO_4$, then brine. The organic solution was dried over anhydrous $MgSO_4$, filtered, and evaporated under vacuum. The residue was chromatographed on silica gel, eluting with MeOH—$CH_2Cl_2$ to afford the title compound (5.3), $C_{39}H_{58}N_6O_8S_2$ (803.05), mass spec. (FAB) M+1=803.5.

PREPARATIVE EXAMPLE 16

Step A Compound (6.2)

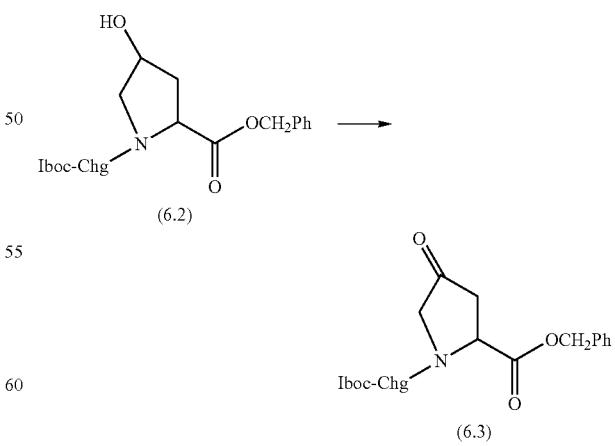

In essentially the same manner as Preparative Example 2, Step A, Compound (6.1) hydroxyproline benzyl ester hydrochloride was reacted with Compound (4.9) from Preparative Example 12, to obtain the title compound (6.2), $C_{25}H_{36}N_2O_6$ (460.56), mass spec. (FAB) M+1=461.2.

Step B Compound (6.3)

In essentially the same manner as Preparative Example 8, Compound (6.3) was prepared, $C_{25}H_{34}N_2O_6$ (458.55), mass spec. (FAB) M+1=459.2.

Step C Compound (6.4)

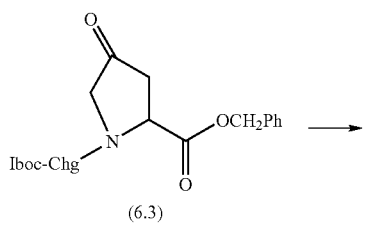

(6.3)

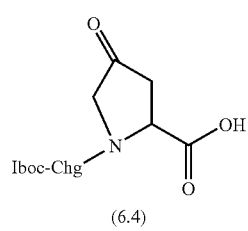

(6.4)

A mixture of Compound (6.3) from Step B (1 g), 10% Pd/C (0.05 g), and EtOH (100 mL) was stirred under 1 atm. H2 for 6 hr. The mixture was filtered, and evaporated to dryness under vacuum to leave the title compound (6.4) (0.77 g), $C_{18}H_{28}N_2O_6$ (368.42) mass spec. (FAB) M+1=369.2.

PREPARATIVE EXAMPLE 17

Step A Compound (7.1)

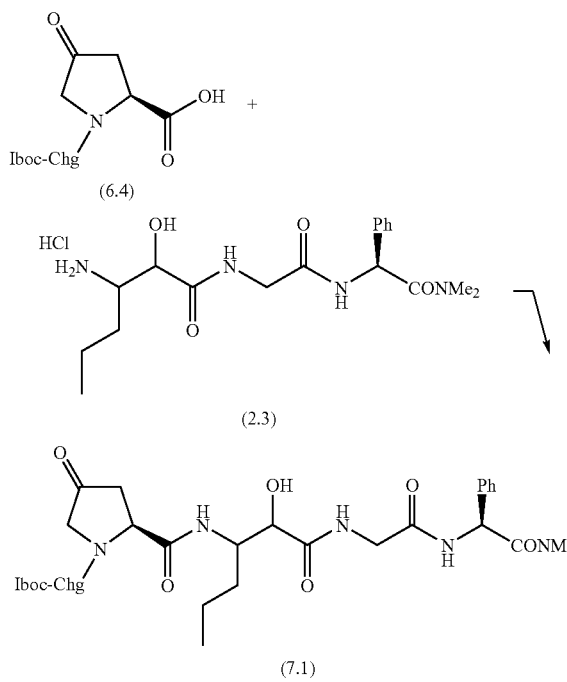

Compound (6.4) from Preparative Example 16, Step C, was reacted with Compound (2.3) from Preparative Example 6, Step B, in essentially the same manner as Preparative Example 2, Step A, to afford Compound (7.1), $C_{36}H_{54}N_6O_9$ (714.85), mass spec. (FAB) M+1=715.9.

Step B Compound (7.2)

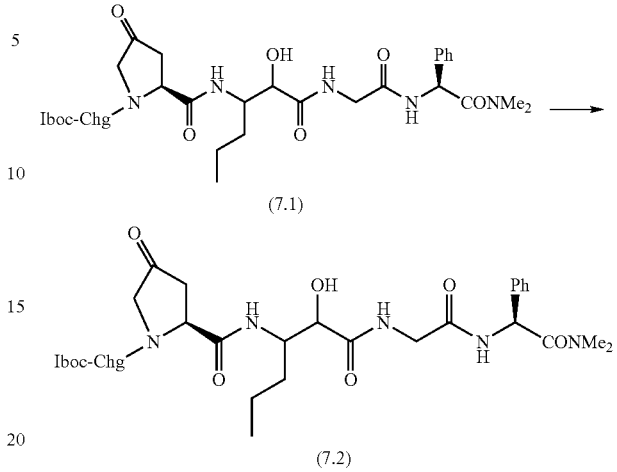

Compound (7.1) was reacted in essentially the same manner as Preparative Example 7, Step A, to afford Compound (7.2), $C_{36}H_{52}N_6O_9$ (712.83), mass spec. (FAB) M+1=713.5.

Step C Compound (7.3)

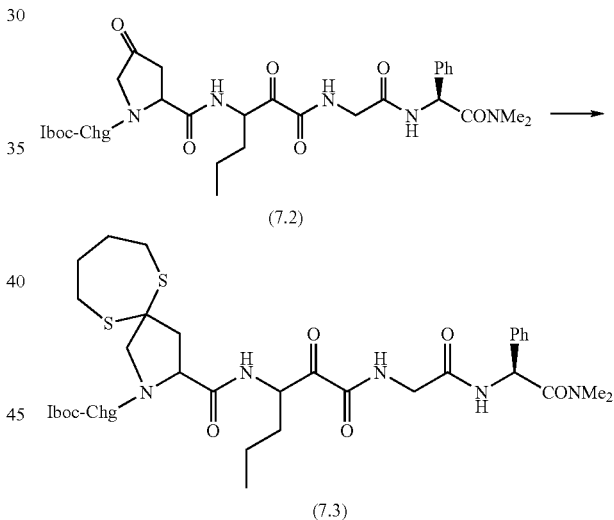

Compound (7.2) from Step B above, was reacted in essentially the same manner as Preparative Example 8, Step B, with 1,4-butanedithiol, to obtain the title compound (7.3), $C_{40}H_{60}N_6O_8S_2$ (817.07), mass spec. (FAB) M+1=817.5.

Using the above-noted and herein-described procedures, the compounds in the attached Tables 2 through 6 were prepared. As a general note to all the Tables (1 through 6) that are attached hereto as well as to the Examples and Schemes in this specification, any open-ended nitrogen atom with unfulfilled valence in the chemical structures in the Examples and Tables refers to NH, or in 10, the case of a terminal nitrogen, —NH$_2$. Similarly, any open-ended oxygen atom with unfulfilled valence in the chemical structures in the Examples and Tables refers to —OH and any open-ended carbon atom with unfilled valence is appropriately filled with —H.

Solid Phase Synthesis:

General Procedure for Solid-phase Coupling Reactions.

The synthesis was done in a reaction vessel which was constructed from a polypropylene syringe cartridge fitted with a polypropylene frit at the bottom. The Fmoc-protected amino acids were coupled under standard solid-phase techniques. Each reaction vessel was loaded with 100 mg of the starting Fmoc-Sieber resin (approximately 0.03 mmol). The resin washed with 2 mL portions of DMF (2 times). The Fmoc protecting group was removed by treatment with 2 mL of a 20% v/v solution of piperidine in DMF for 20 min. The resin was washed with 2 mL portions of DMF (4 times). The coupling was done in DMF (2 mL), using 0.1 mmol of Fmoc-amino acid, 0.1 mmol of HATU [O-(7-azabenzotriazol-1-yl)-1,1,3,3-tetramethyluronium hexafluorophosphate] and 0.2 mmol of DIPEA (N,N-diisopropylethylamine). After shaking for 2 h, the reaction vessel was drained and the resin washed with 2 mL portions of DMF (4 times). The coupling cycle was repeated with the next Fmoc-amino acid or capping group.

General Procedure for Solid-phase Dess-Martin Oxidation.

The synthesis was conducted in a reaction vessel which was constructed from a polypropylene syringe cartridge fitted with a polypropylene frit at the bottom. Resin-bound hydroxy compound (approximately 0.03 mmol) was treated with a solution of 0.12 mmol of Dess-Martin periodinane and 0.12 mmol of t-BuOH in 2 mL of DCM for 4 h. The resin washed with 2 mL portions of a 20% v/v solution of iPrOH in DCM, THF, a 50% v/v solution of THF in water (4 times), THF (4 times) and DCM (4 times).

PREPARATIVE EXAMPLE 18

Preparation of N-Fmoc-2',3'-dimethoxyphenylglycine Compound (901)

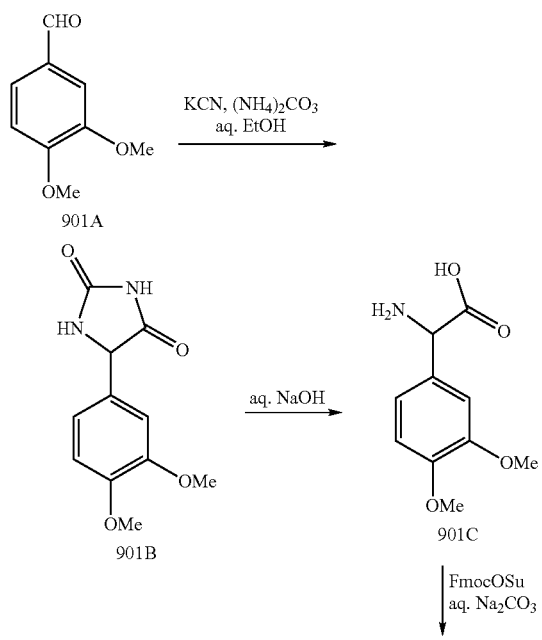

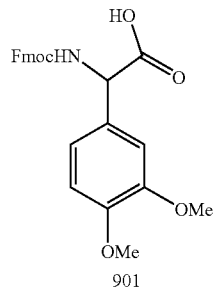

To a solution of potassium cyamide (1.465 g, 22.5 mmol) and ammonium carbonate (5.045 g, 52.5 mmol) in water (15 mL) was added a solution of 2,3-dimethoxybenzaldehye 901A (2.5 g, 15 mmol) in ethanol (15 mL). The reaction mixture was heated at 40° C. for 24 h. The volume of the solution was reduced to 10 mL by evaporating under reduced pressure. Concentrated hydrochloric acid (15 mL) was added and compound 901B was obtained as a white precipitate. Compound 901B was isolated by filtration (2.2 g, 9.3 mmol). Compound 901B was dissolved in 10% w/w aqueous sodium hydroxide solution (15 mL) and the resulting solution was heated under reflux for 24 h. Concentrated hydrochloric is acid was added and the pH was adjusted to neutral (pH 7). The resulting solution containing compound 901C was evaporated under reduced pressure. The residue was dissolved in 5% w/w aqueous sodium bicarbonate solution (150 mL). The solution was cooled to 0° C. in an ice bath and 1,4-dioxane (30 mL) and a solution of 9-fluorenylmethyl succinimidyl carbonate (2.7 g, 8 mmol) in 1,4-dioxane (30 mL) was added at 0° C. The reaction mixture was allowed to warm to room temperature and was stirred at room temperature for 24 h. 1,4-dioxane was evaporated under reduced pressure. The aqueous solution washed with diethyl ether. Concentrated hydrochloric acid was added and the pH was adjusted to acidic (pH 1). Ethyl acetate was added the organic layer washed with water and brine. The organic layer was dried over anhydrous sodium sulfate. The solvent was evaporated under reduced pressure to afford the desired compound 901 as a white foamy solid (3.44 g, 7.9 mmol). MS (LCMS-Electrospray) 434.1 MH+.

PREPARATIVE EXAMPLE 19

Compound (801)

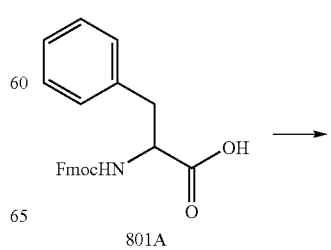

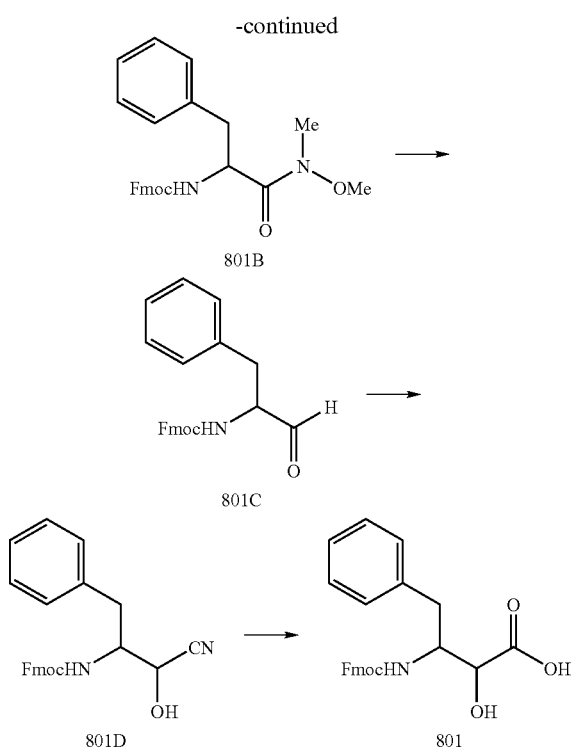

To a solution of N-Fmoc-phenylalanine 801A (5 g, 12.9 mmol) in anhydrous DCM (22 mL) cooled to −30° C. in a dry ice-acetone bath was added N-methylpyrrolidine (1.96 mL, 16.1 mmol) and methyl chloroformate (1.2 mL, 15.5 mmol) sequentially. The reaction mixture was stirred at −30° C. for 1 h and a solution of N,O-dimethylhydroxylamine hydrochloride (1.51 g, 15.5 mol) and N-methylpyrrolidine (1.96 mL, 16.1 mmol) in anhydrous DCM (8 mL) was added. The reaction mixture was allowed to warm to room temperature and was stirred at room temperature overnight. Toluene was added and the organic layer was washed with dilute hydrochloric acid, aqueous sodium bicarbonate solution and brine. The organic layer was dried over anhydrous sodium sulfate. The solvent was evaporated under reduced pressure to afforded compound 801B (4 g, 9.29 mmol).

To a solution of Red-Al (6.28 mL, 21.4 mmol) in anhydrous toluene (8 mL) cooled to −20° C. in a dry ice-acetone bath was added a solution of compound 801B (4 g, 9.29 mmol) in anhydrous toluene (12 mL). The reaction mixture was stirred at −20° C. for 1.5 h. The organic layer washed with dilute hydrochloric acid, aqueous sodium bicarbonate solution and brine. The organic layer was dried over anhydrous sodium sulfate. The solvent was evaporated under reduced pressure and the crude product 801C was used in the next reaction without further purification.

To a solution of compound 801C (approx. 9.29 mmol) in hexane (15 mL) was added a solution of potassium cyamide (24 mg, 0.37 mmol) and tetrabutylammonium iodide (34 mg, 0.092 mmol) in water (4 mL) and acetone cyanohydrin (1.27 mL, 13.9 mmol) sequentially. The reaction mixture was stirred at room temperature for 24 h. Ethyl acetate was added and the organic layer was washed with water and brine. The organic layer was dried over anhydrous sodium sulfate. The solvent was evaporated under reduced pressure to afford compound 801D (2.4 g, 6.03 mmol).

To a solution of compound 801 D (2.4 g, 6.03 mmol) in 1,4-dioxane (11 mL) was added concentrated hydrochloric acid (11 mL). The reaction mixture was heated at 80° C. for 3 h. Ethyl acetate (25 mL) and water (25 mL) was added. The organic layer washed with brine and dried over anhydrous sodium sulfate. The solvent was evaporated under reduced pressure to afford the desired compound 801 as a white foamy solid (2 g, 4.8 mmol). MS (LCMS-Electrospray) 418.1 MH$^+$.

Scheme 8

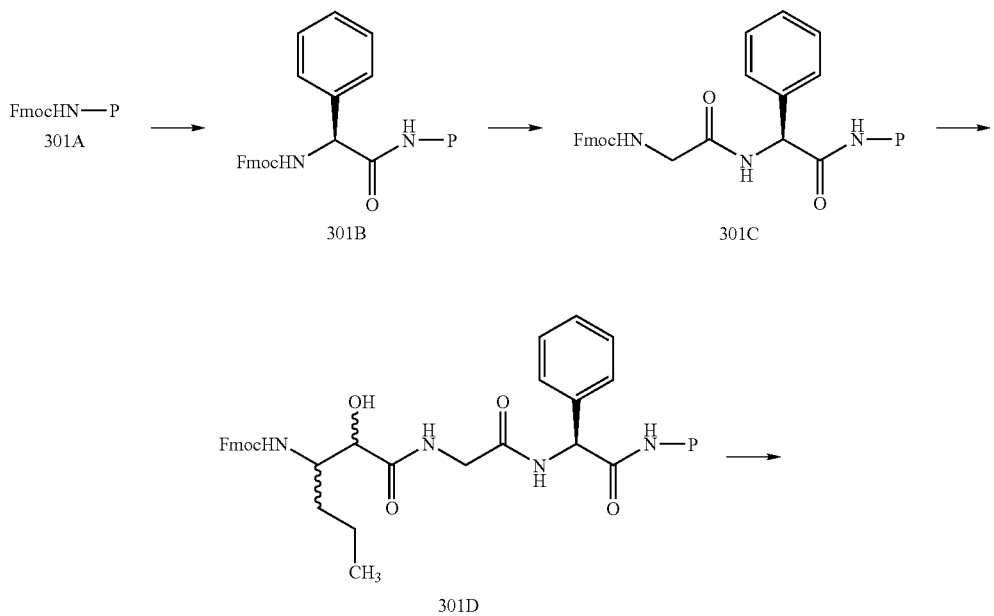

-continued
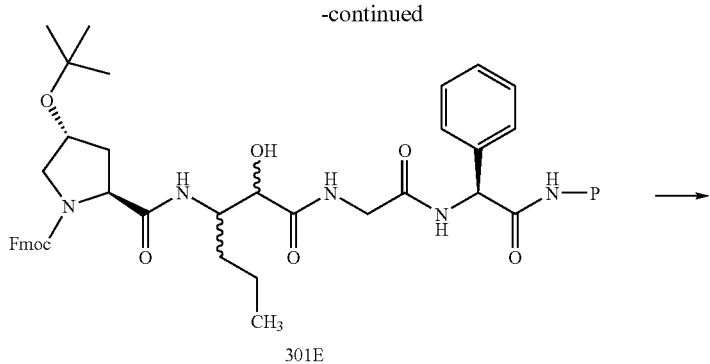
301E
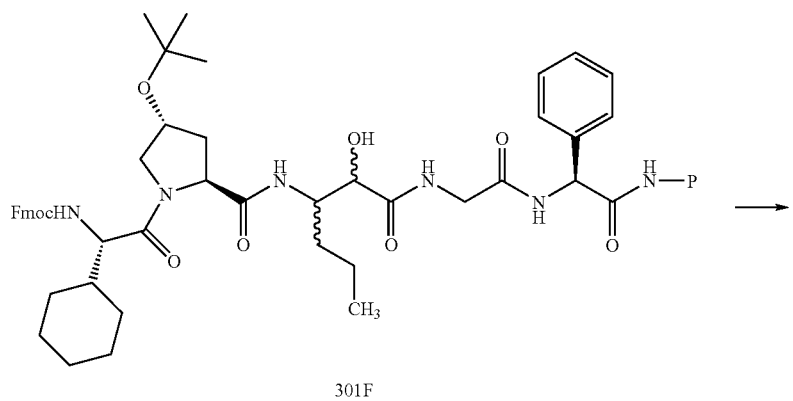
301F
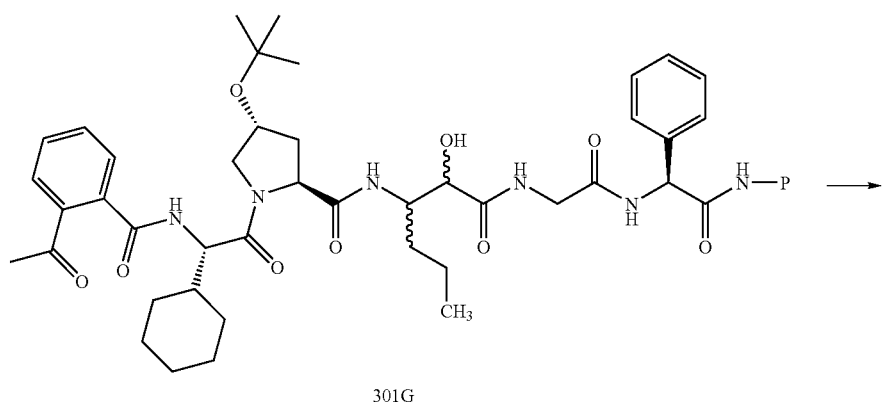
301G
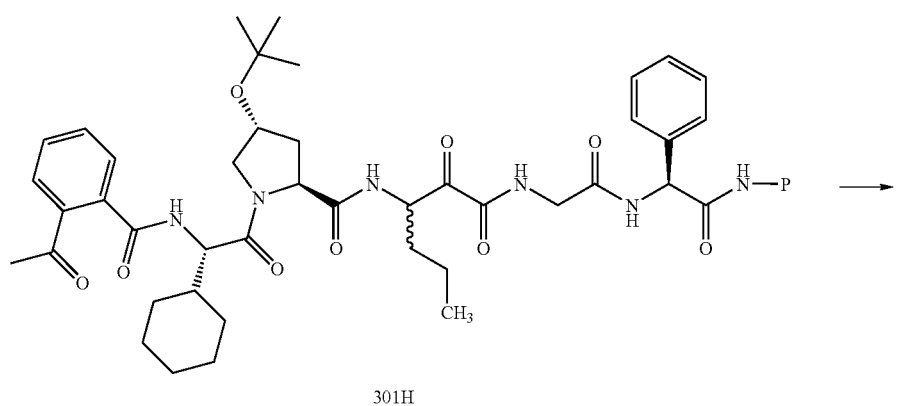
301H

EXAMPLE (301J)

Scheme 8 Compound (301J)

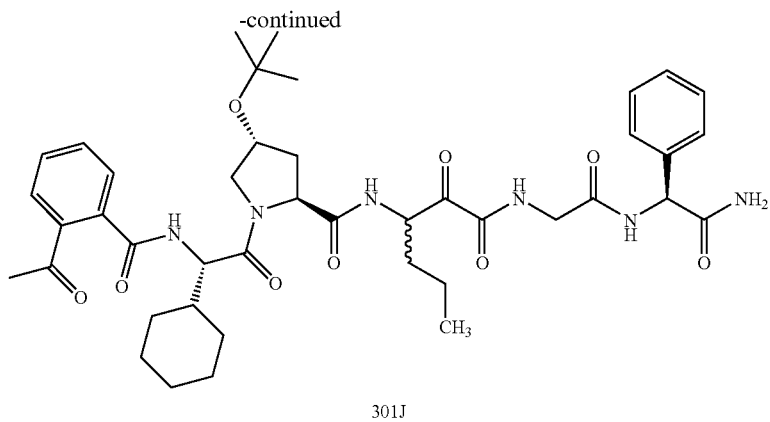

301J

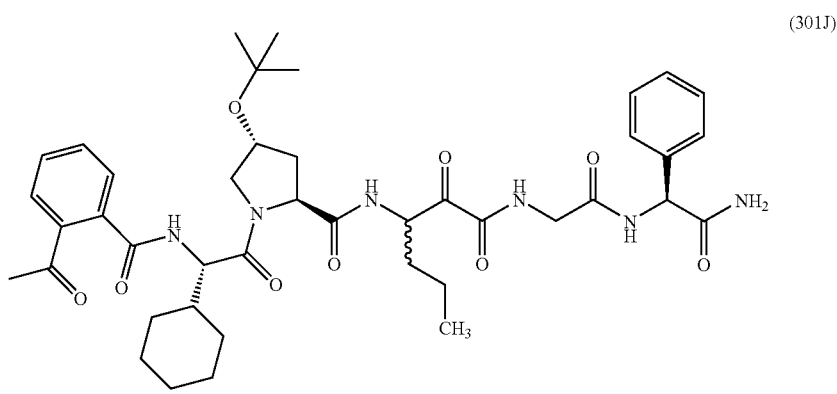

(301J)

Resin-bound compound 301B, 301C, 301D, 301E, 301F and 301G were prepared according to the general procedure for solid-phase coupling reactions started with 100 mg of Fmoc-Sieber resin (0.03 mmol). Resin-bound compound 301G was oxidized to resin-bound compound 301H according to the general procedure for solid-phase Dess-Martin oxidation. The resin-bound compound 301H was treated with 4 mL of a 2% v/v solution of TFA in DCM for 5 min. The filtrate was added to 1 mL of AcOH and the solution was concentrated by vacuum centrifugation to provide compound 301J (0.0069 g, 29% yield). MS (LCMS-Electrospray) 771.2 MH+.

Using the solid phase synthesis techniques detailed above, and the following moieties for the various functionalities in the compound of Formula I, the compounds in Table 3 were prepared:

—W—:

Y—W—:

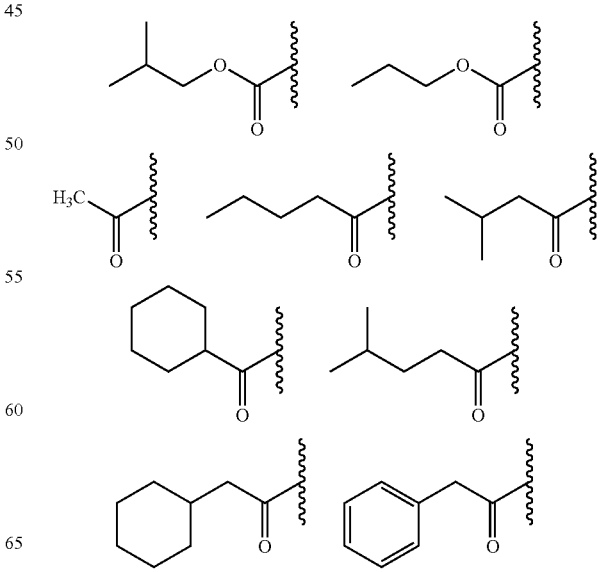

-continued
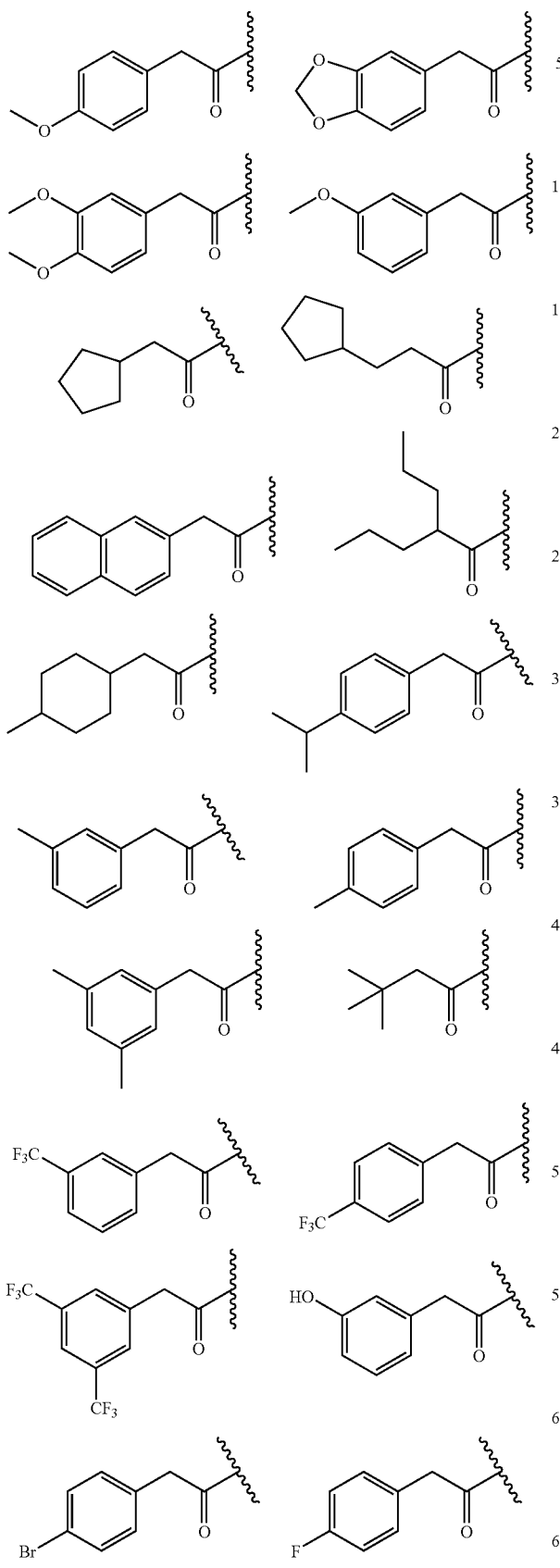
-continued
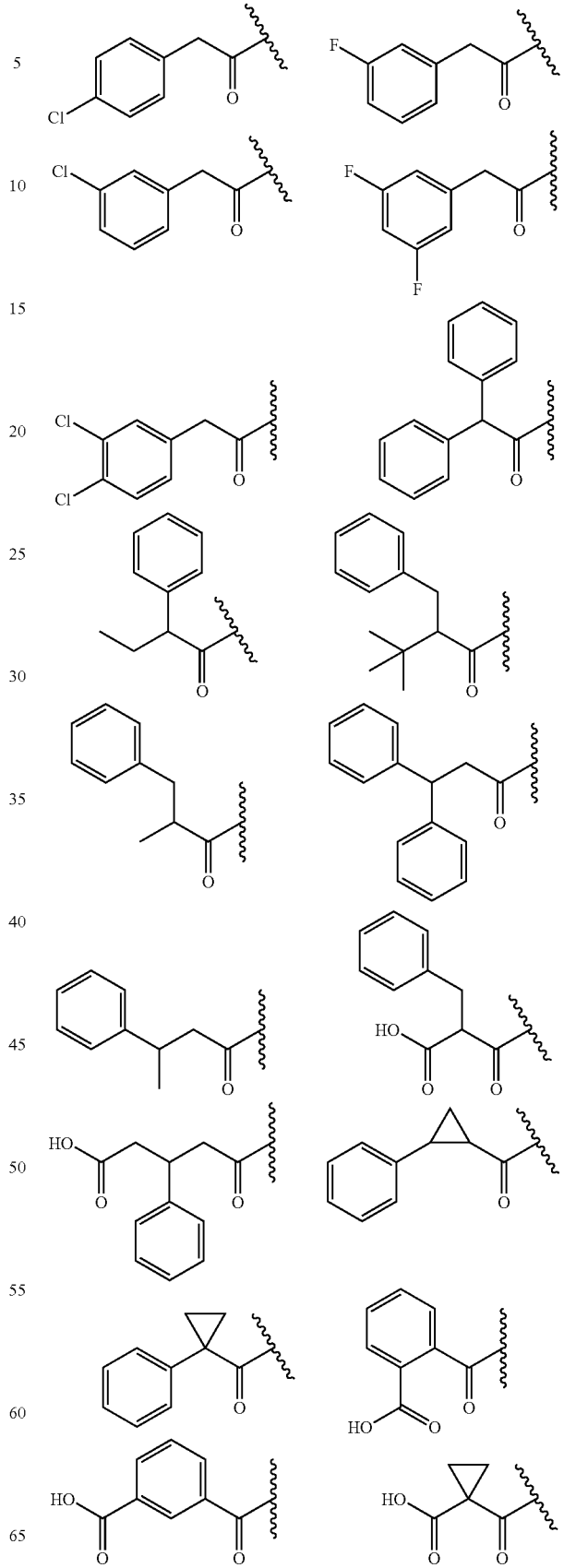

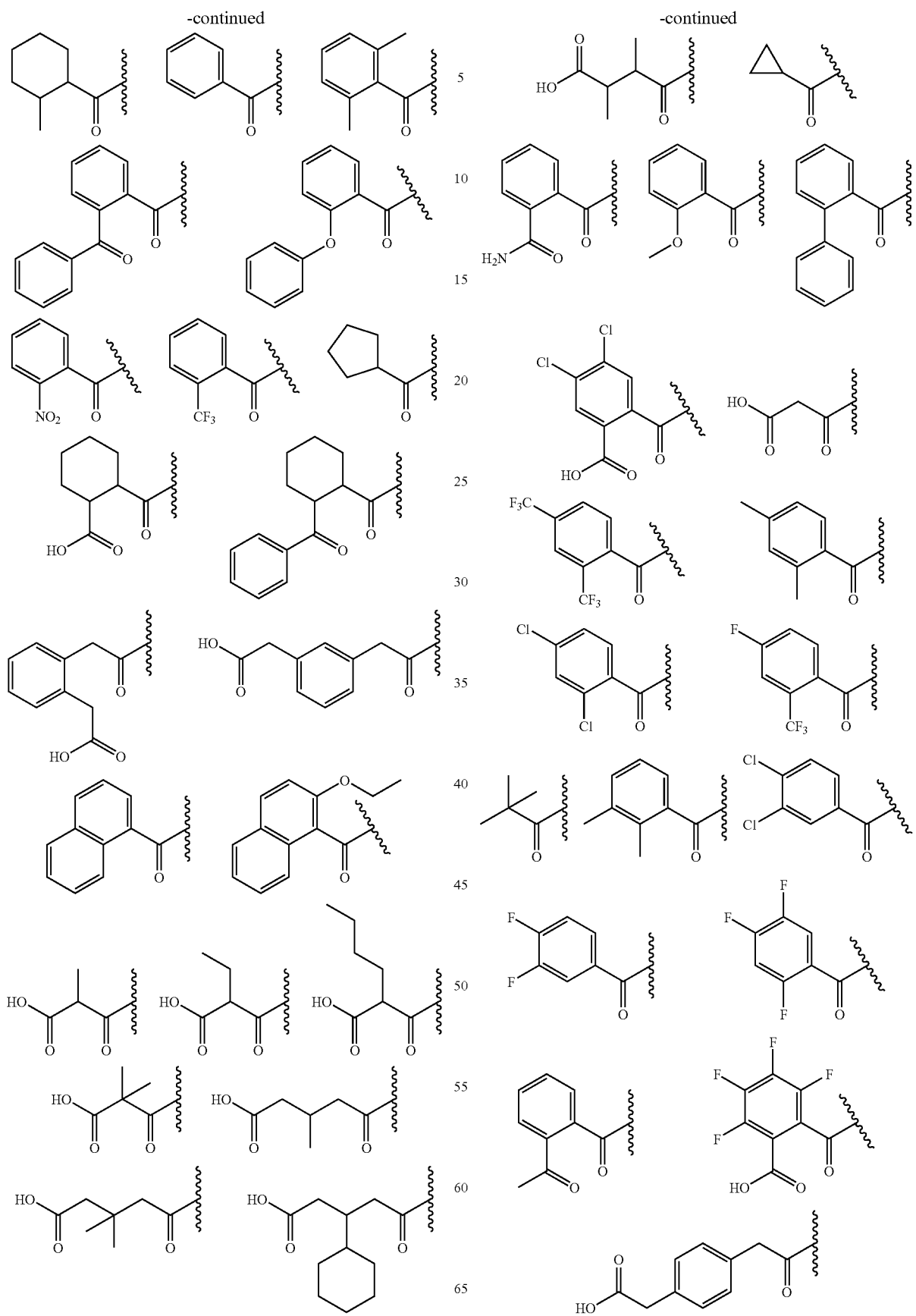

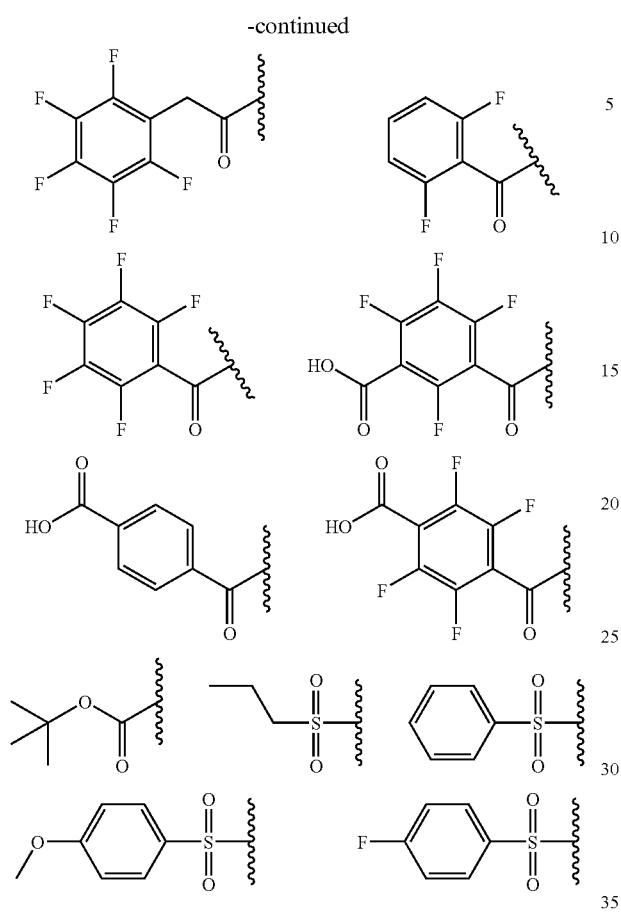
—R⁴:
—Z—:
—R³:
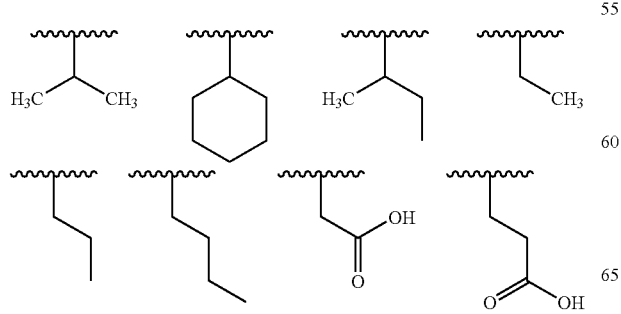
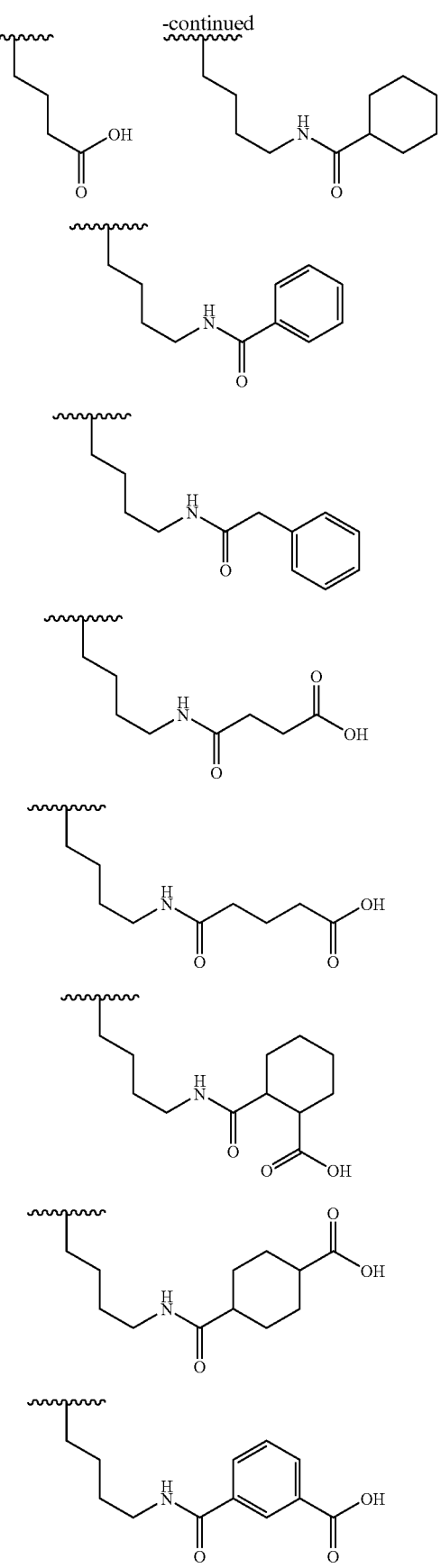

225
-continued
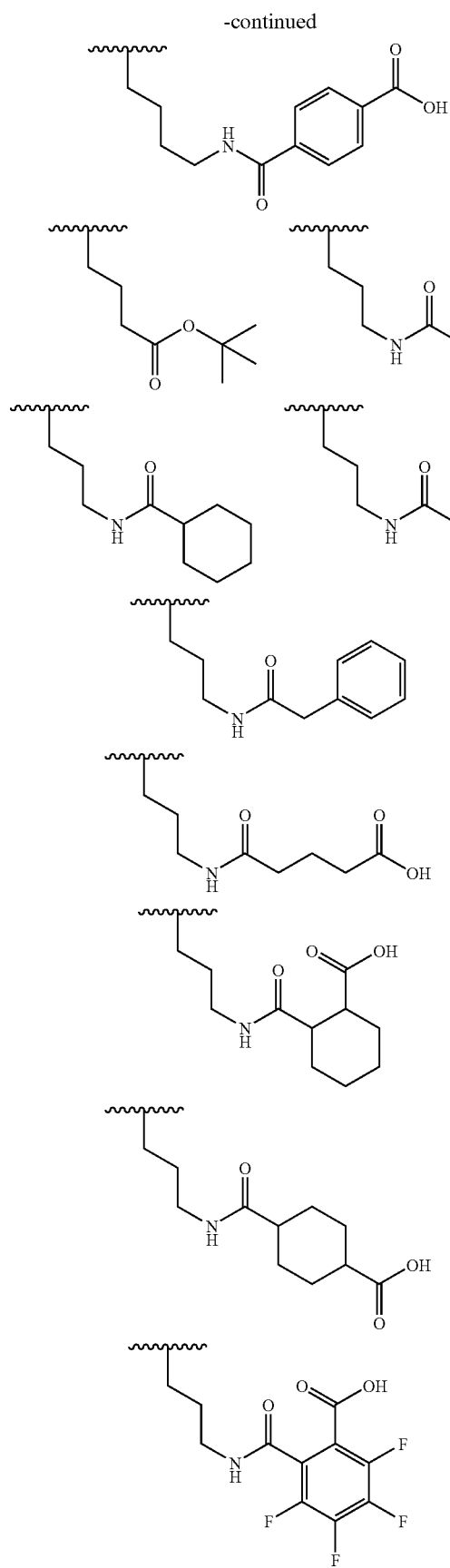
226
-continued
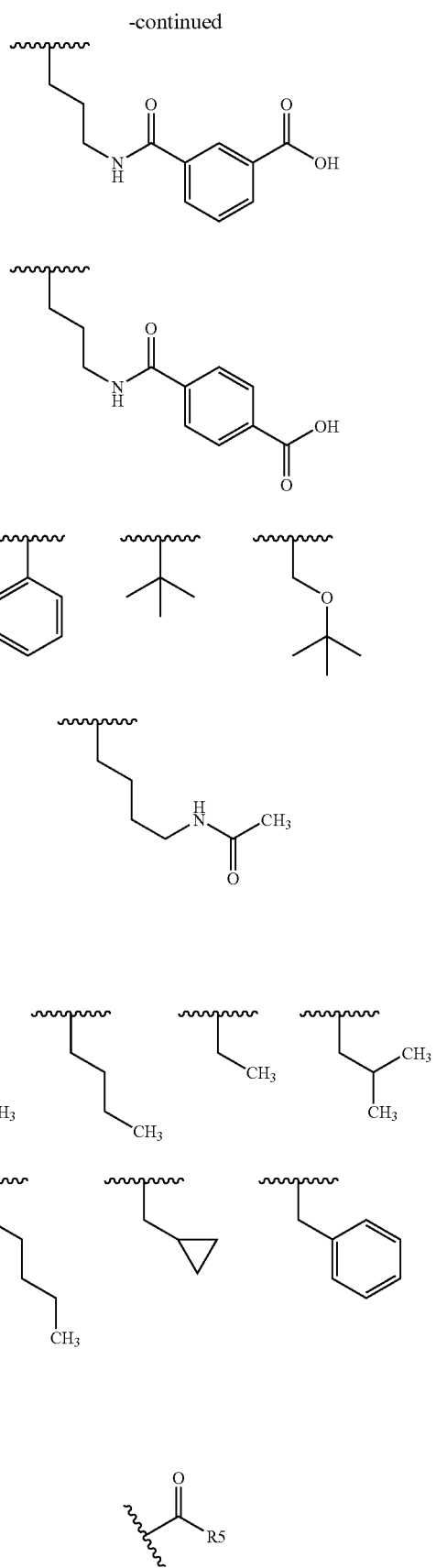

—R⁵:
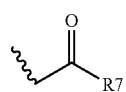
—R⁷:
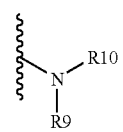
—R⁹:
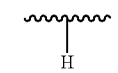
—R¹⁰:
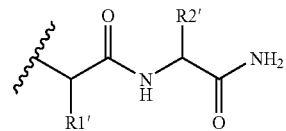
—R¹':
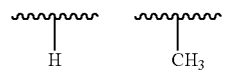
—R²':
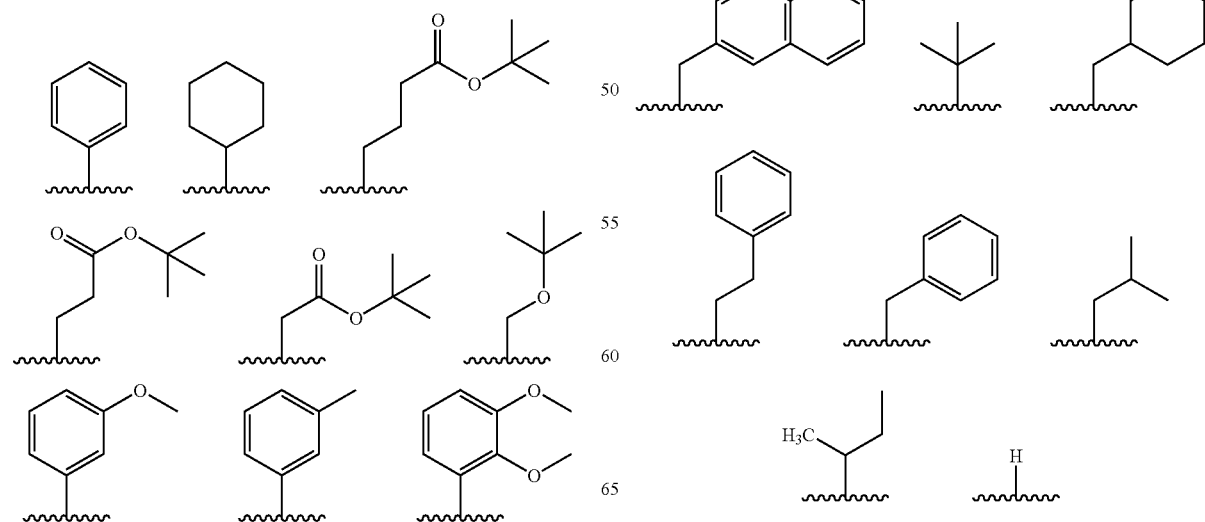
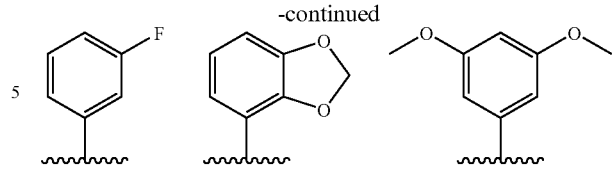
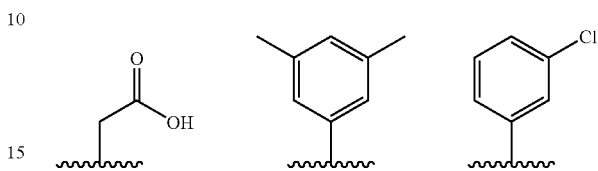
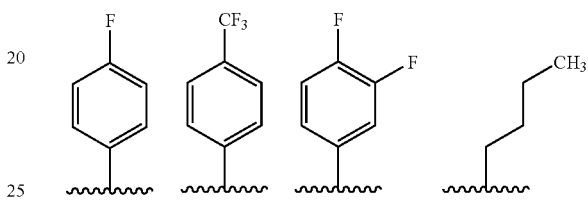
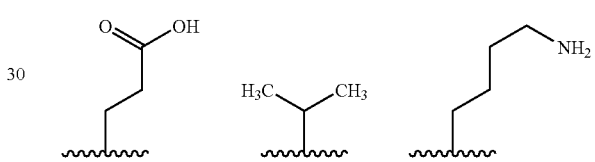
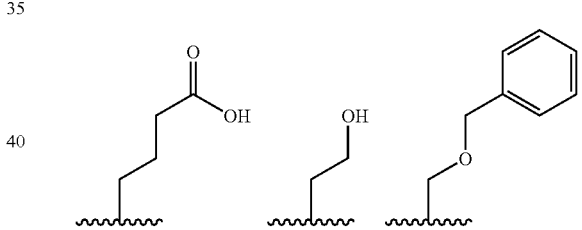
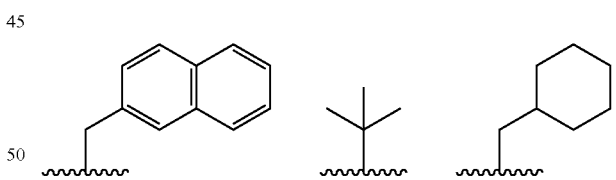
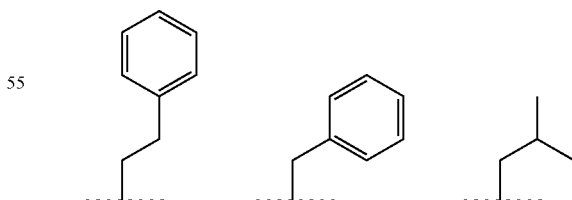
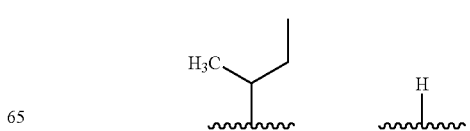

TABLE 3
Compounds prepared by Solid Phase Synthesis
| STRUCTURE | Ki* CLASS |
|---|---|
| 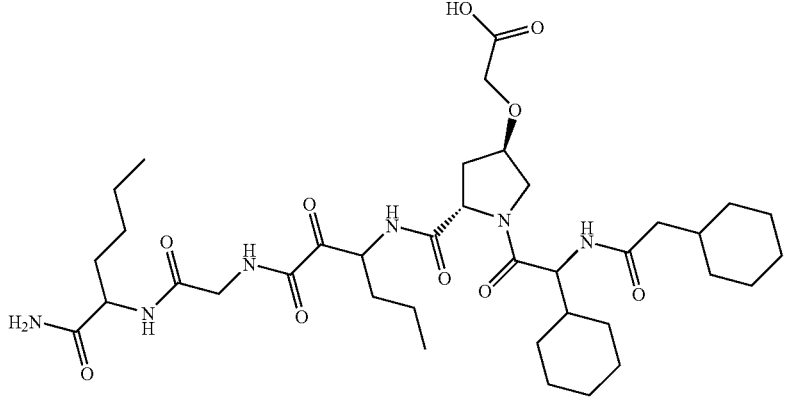 | C |
| 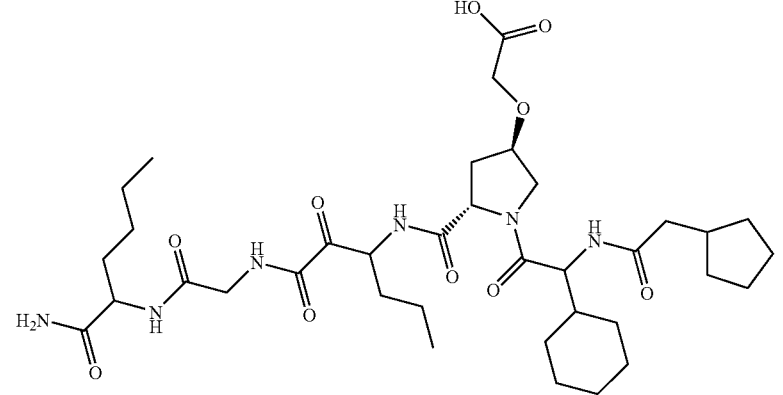 | C |
| 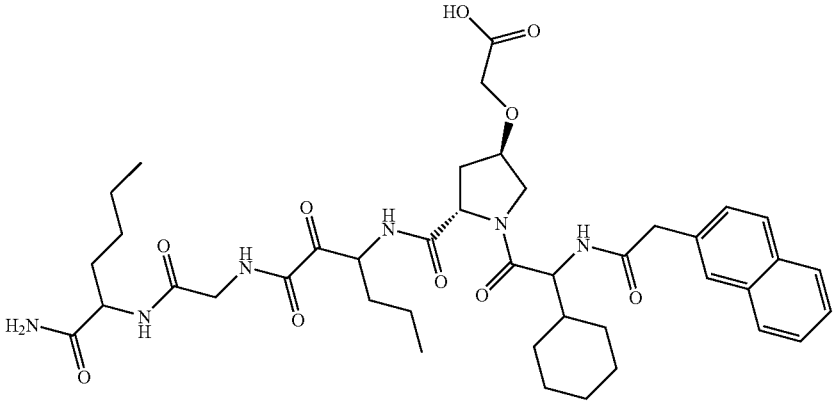 | C |

TABLE 3-continued
Compounds prepared by Solid Phase Synthesis
| STRUCTURE | Ki* CLASS |
|---|---|
| 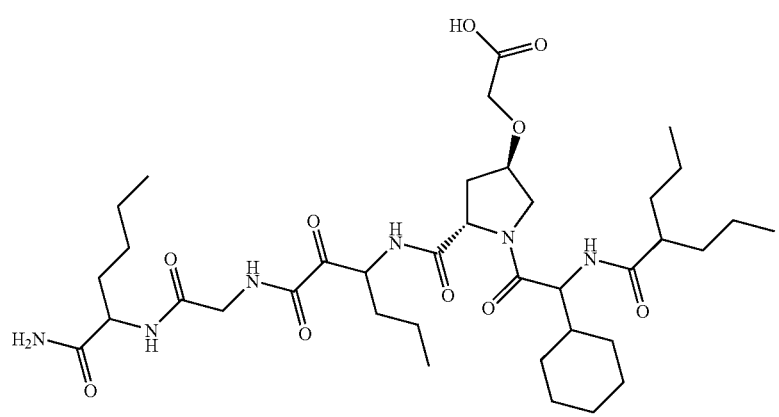 | C |
| 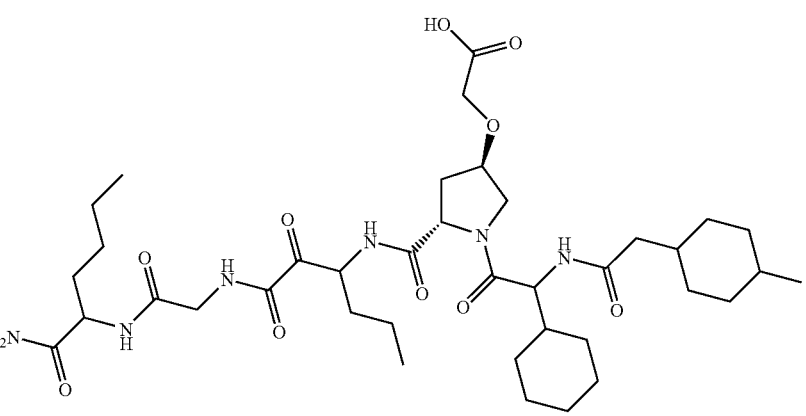 | C |
| 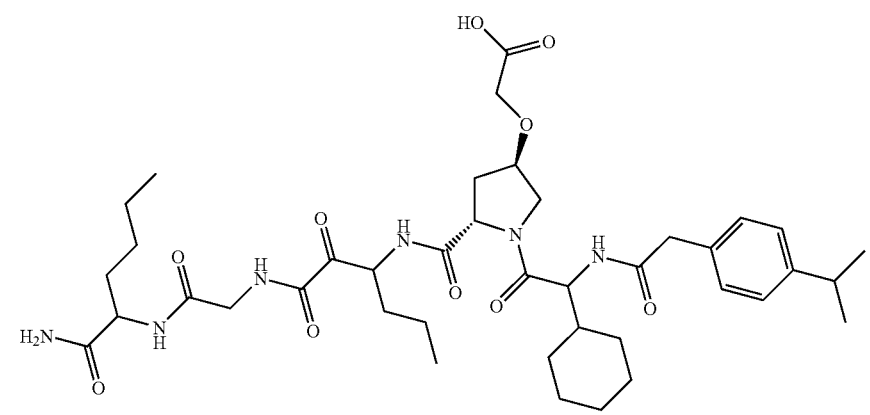 | C |

TABLE 3-continued

Compounds prepared by Solid Phase Synthesis

| STRUCTURE | Ki* CLASS |
|---|---|
| | C |
| | C |
| | C |

TABLE 3-continued

Compounds prepared by Solid Phase Synthesis

| STRUCTURE | Ki* CLASS |
|---|---|
| | B |
| | B |
| | C |
| | B |

TABLE 3-continued
Compounds prepared by Solid Phase Synthesis
| STRUCTURE | Ki* CLASS |
|---|---|
| 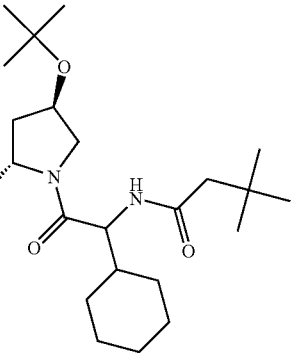 | C |
| 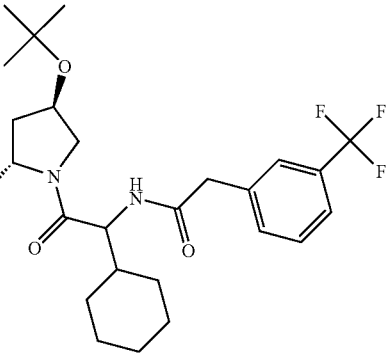 | B |
| 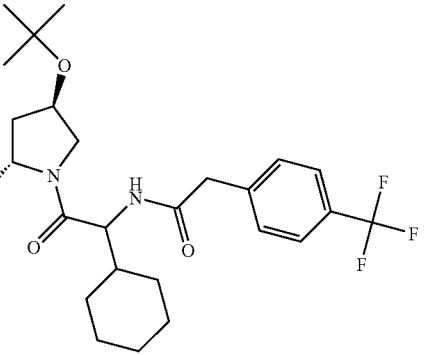 | B |
| 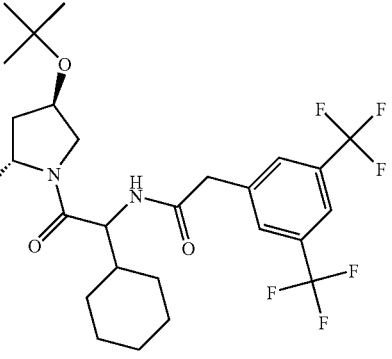 | C |

TABLE 3-continued

Compounds prepared by Solid Phase Synthesis

| STRUCTURE | Ki* CLASS |
|---|---|
| | C |
| | C |
| | C |

TABLE 3-continued

Compounds prepared by Solid Phase Synthesis

| STRUCTURE | Ki* CLASS |
|---|---|
| | C |
| | C |
| | C |

TABLE 3-continued

Compounds prepared by Solid Phase Synthesis

| STRUCTURE | Ki* CLASS |
|---|---|
| | C |
| | C |
| | C |

TABLE 3-continued
Compounds prepared by Solid Phase Synthesis
| STRUCTURE | Ki* CLASS |
|---|---|
| 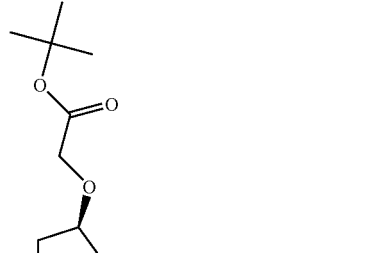 | C |
| 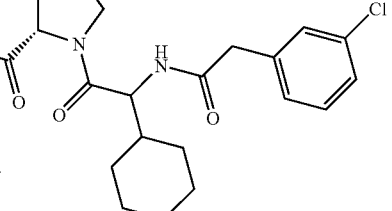 | C |
| 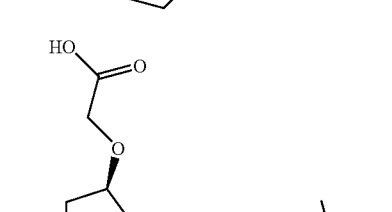 | C |
|  | C |

TABLE 3-continued

Compounds prepared by Solid Phase Synthesis

| STRUCTURE | Ki* CLASS |
|---|---|
| | C |
| | C |
| | C |
| | C |

TABLE 3-continued

Compounds prepared by Solid Phase Synthesis

| STRUCTURE | Ki* CLASS |
|---|---|
| | C |
| | C |
| | C |
| | C |

TABLE 3-continued
Compounds prepared by Solid Phase Synthesis
| STRUCTURE | Ki* CLASS |
|---|---|
| 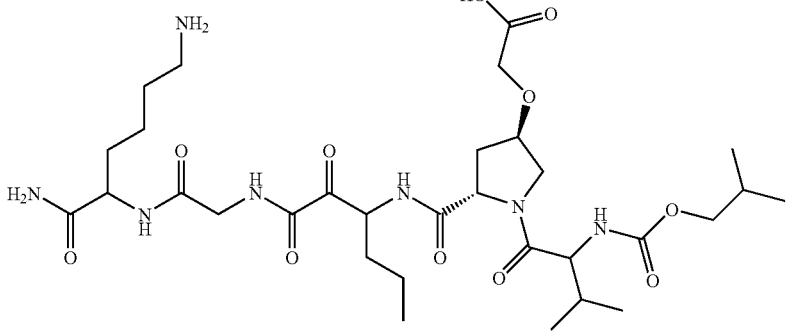 | C |
| 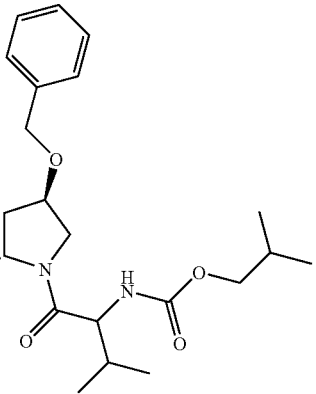 | C |
| 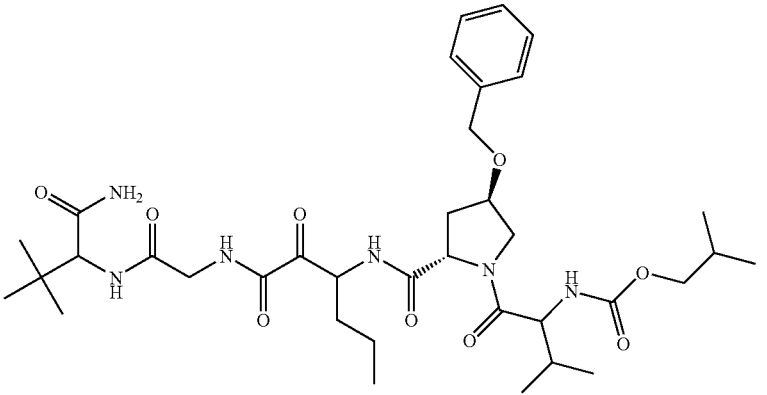 | C |
| 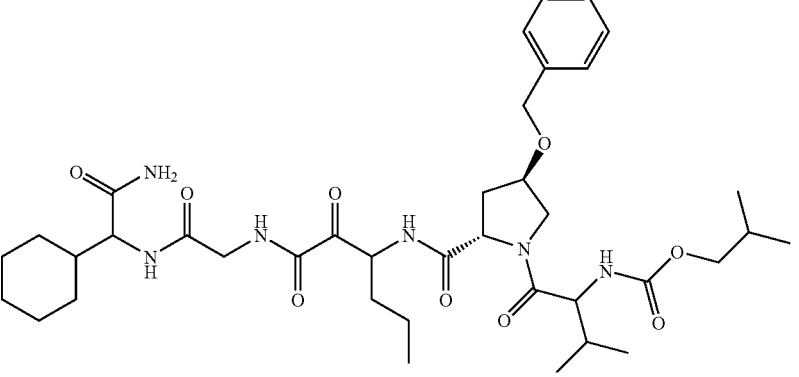 | B |

TABLE 3-continued
Compounds prepared by Solid Phase Synthesis
| STRUCTURE | Ki* CLASS |
|---|---|
| 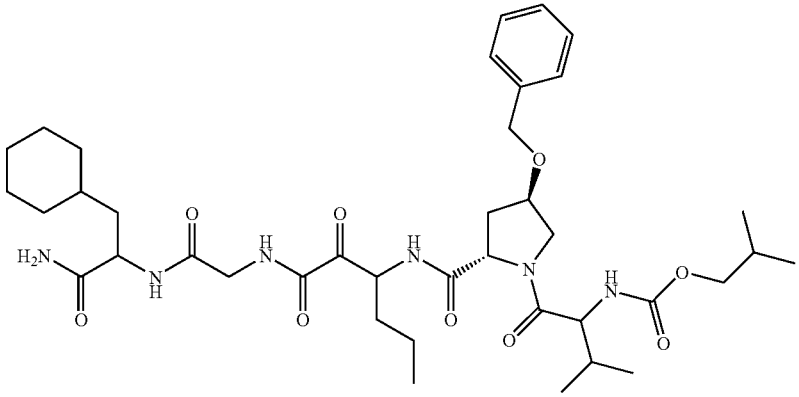 | C |
| 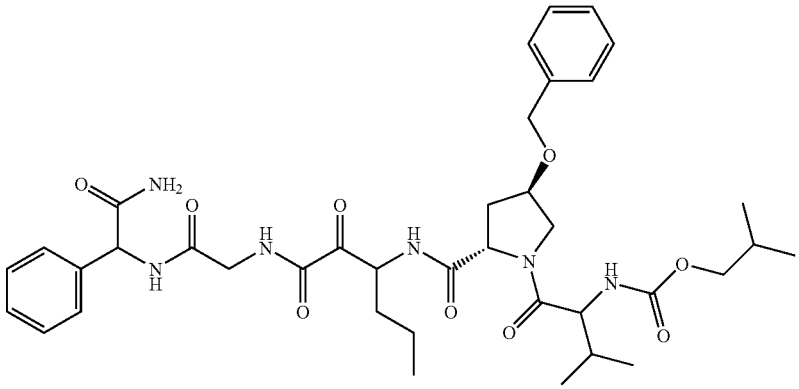 | B |
| 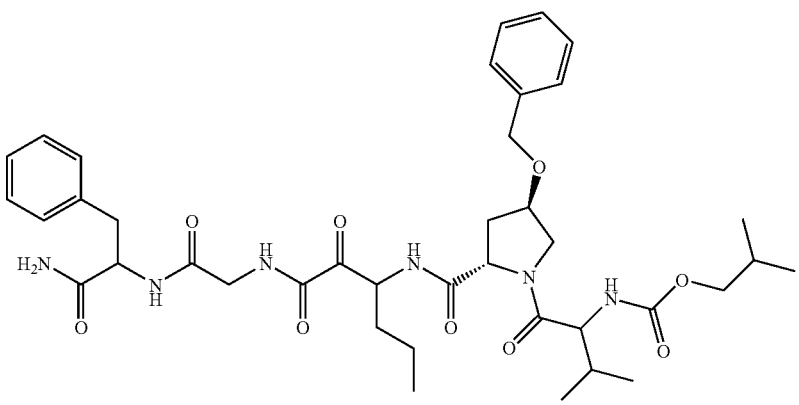 | C |

TABLE 3-continued
Compounds prepared by Solid Phase Synthesis
| STRUCTURE | Ki* CLASS |
|---|---|
| 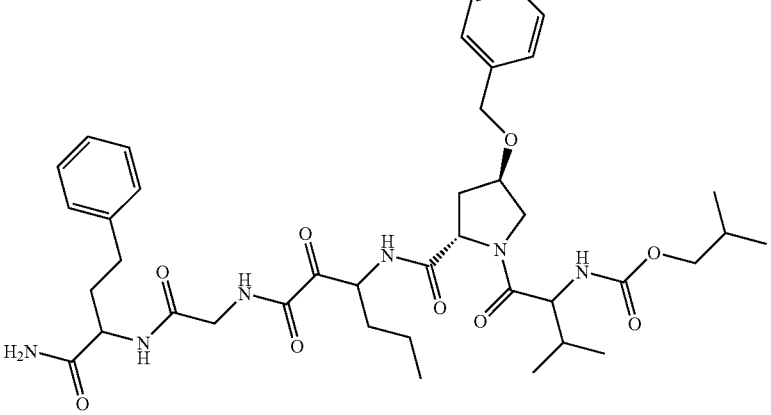 | C |
| 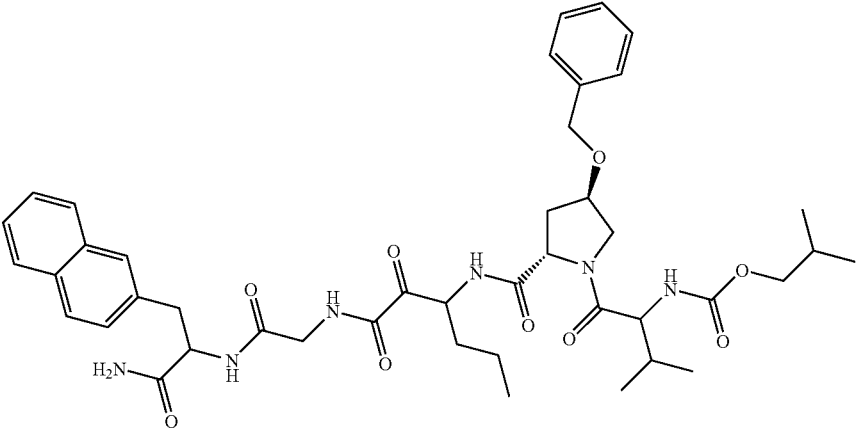 | C |
| 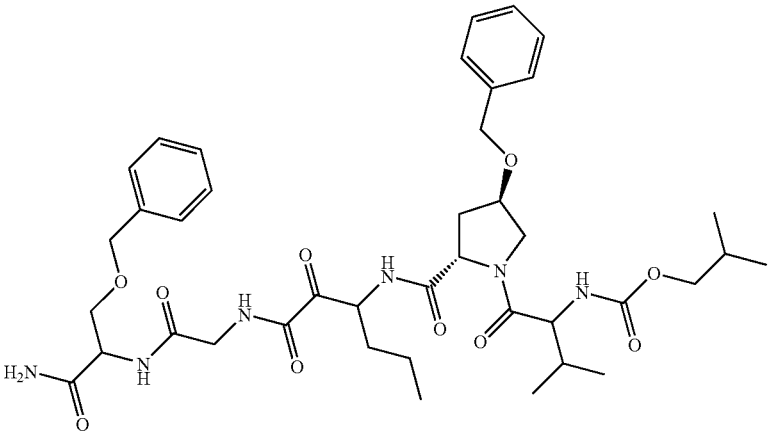 | C |

TABLE 3-continued
Compounds prepared by Solid Phase Synthesis
| STRUCTURE | Ki* CLASS |
|---|---|
| 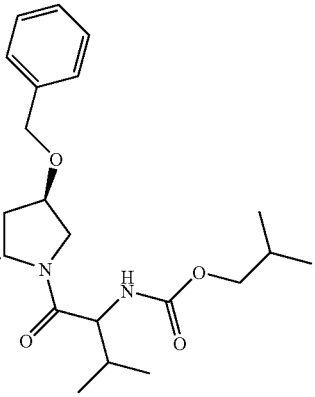 | C |
| 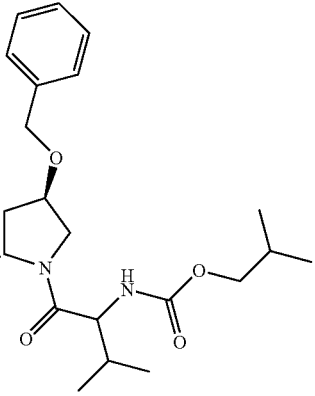 | C |
| 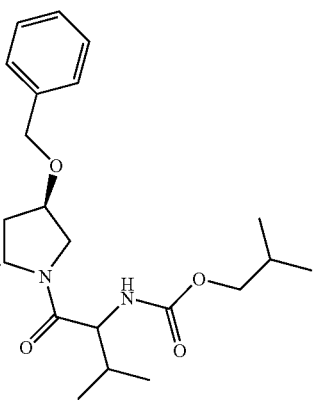 | C |
| 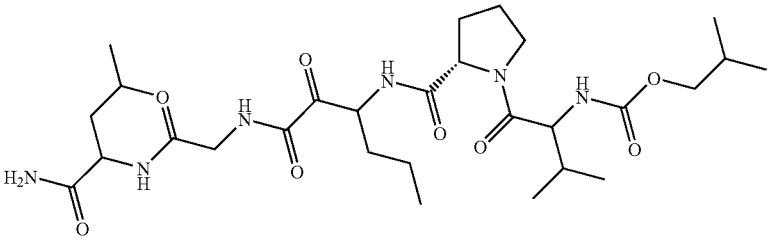 | C |

TABLE 3-continued

Compounds prepared by Solid Phase Synthesis

| STRUCTURE | Ki* CLASS |
|---|---|
| | C |
| | C |
| | C |
| | C |
| | C |

TABLE 3-continued
Compounds prepared by Solid Phase Synthesis
| STRUCTURE | Ki* CLASS |
|---|---|
| 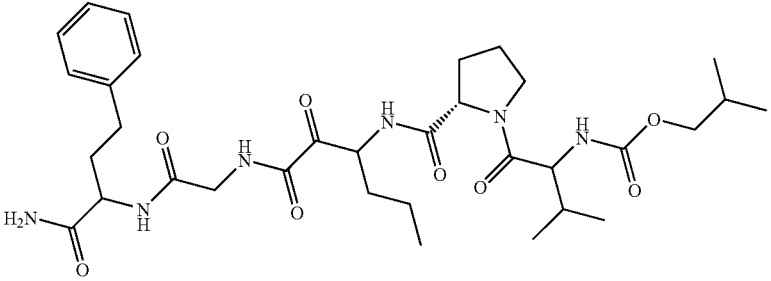 | C |
| 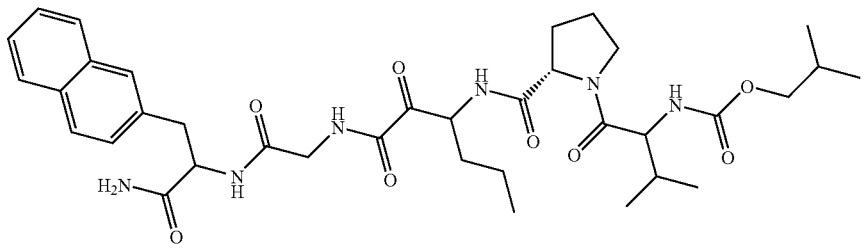 | C |
| 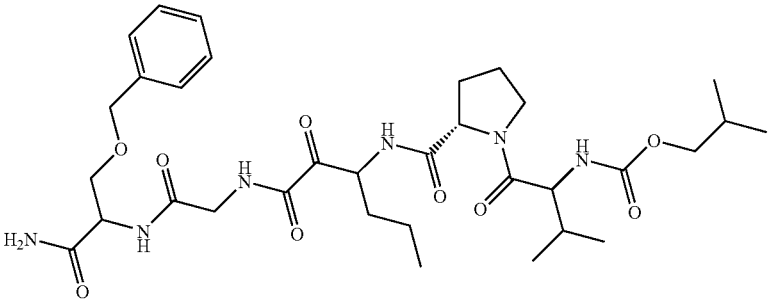 | C |
| 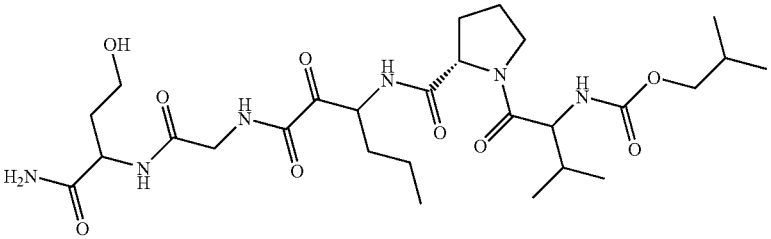 | C |
| 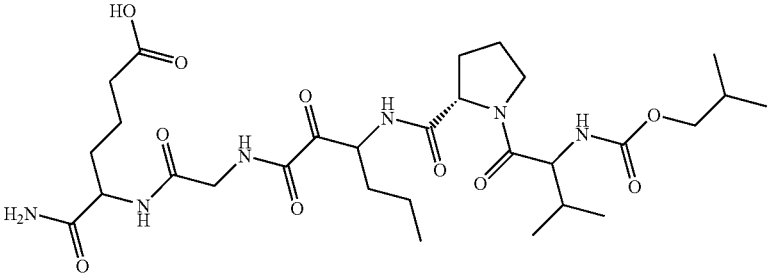 | C |

TABLE 3-continued

Compounds prepared by Solid Phase Synthesis

| STRUCTURE | Ki* CLASS |
|---|---|
| 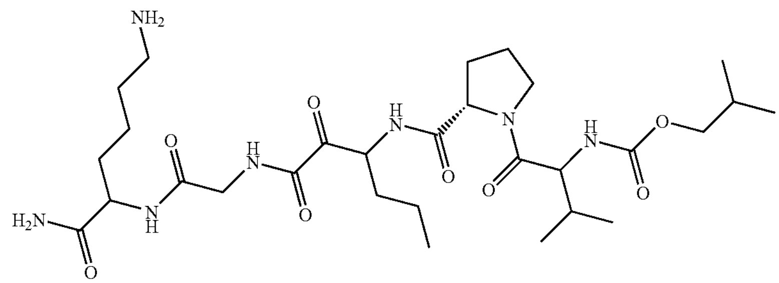 | C |
| | B |
| | B |

TABLE 3-continued

Compounds prepared by Solid Phase Synthesis

| STRUCTURE | Ki* CLASS |
|---|---|
| | B |
| | C |
| | C |

TABLE 3-continued

Compounds prepared by Solid Phase Synthesis

| STRUCTURE | Ki* CLASS |
|---|---|
| | C |
| | C |
| | C |

TABLE 3-continued

Compounds prepared by Solid Phase Synthesis

| STRUCTURE | Ki* CLASS |
|---|---|
| | C |
| | C |
| | C |

TABLE 3-continued

Compounds prepared by Solid Phase Synthesis

| STRUCTURE | Ki* CLASS |
|---|---|
| 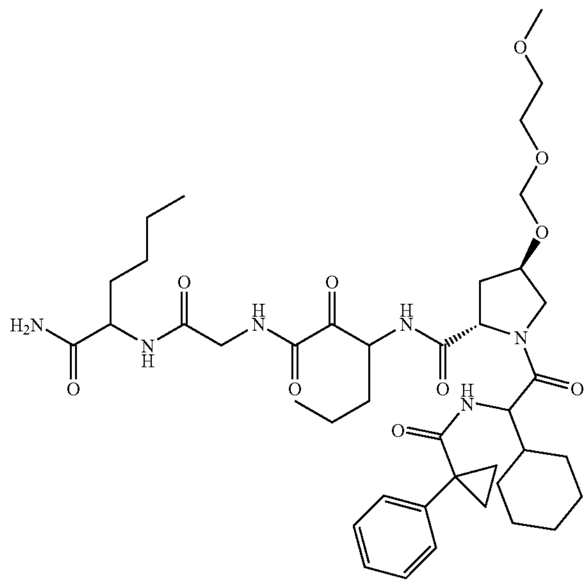 | C |
| 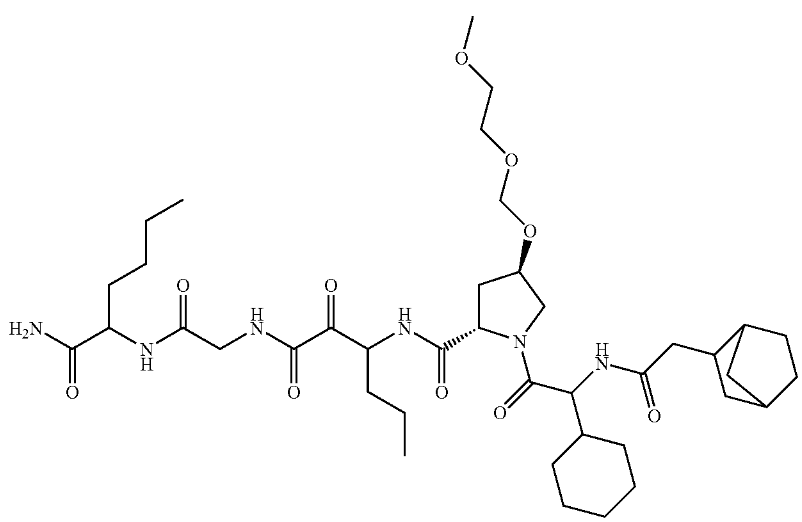 | B |

TABLE 3-continued
Compounds prepared by Solid Phase Synthesis
| STRUCTURE | Ki* CLASS |
|---|---|
| 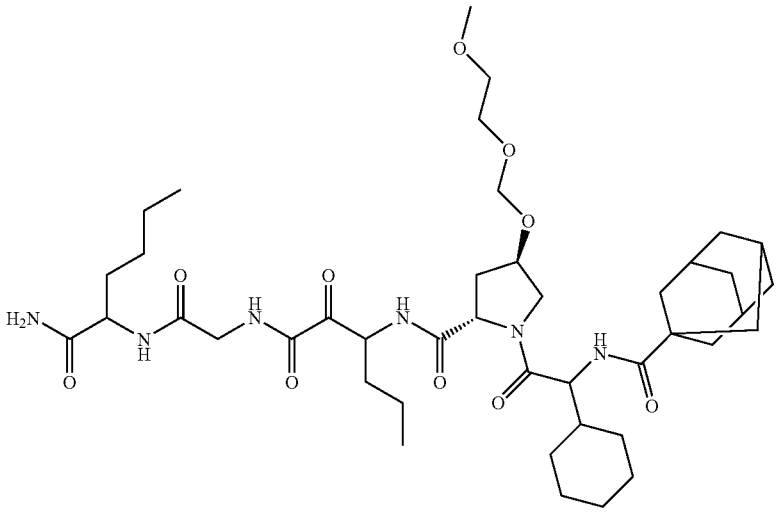 | C |
| 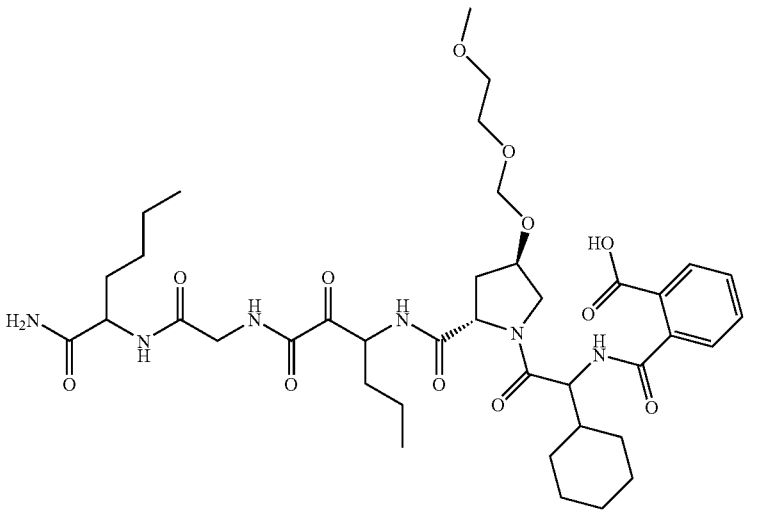 | B |
| 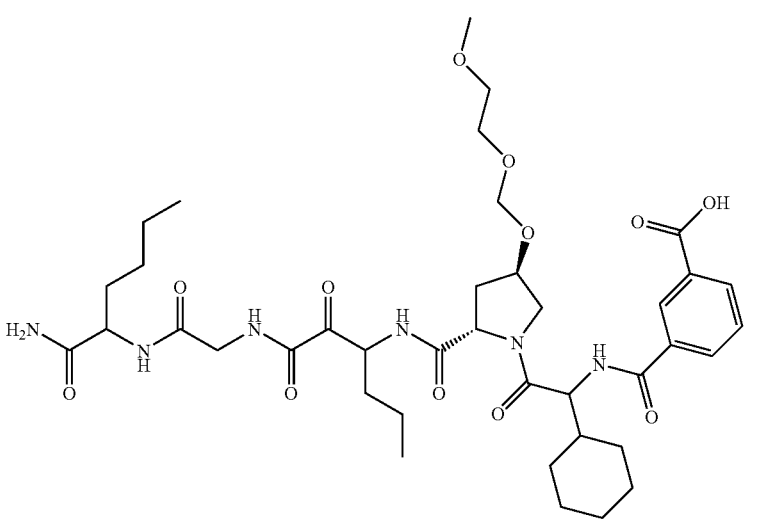 | C |

TABLE 3-continued
Compounds prepared by Solid Phase Synthesis
| STRUCTURE | Ki* CLASS |
|---|---|
| 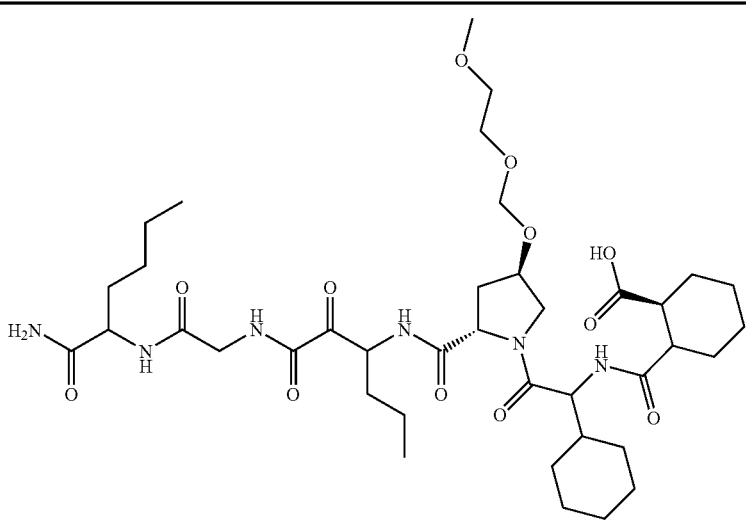 | B |
| 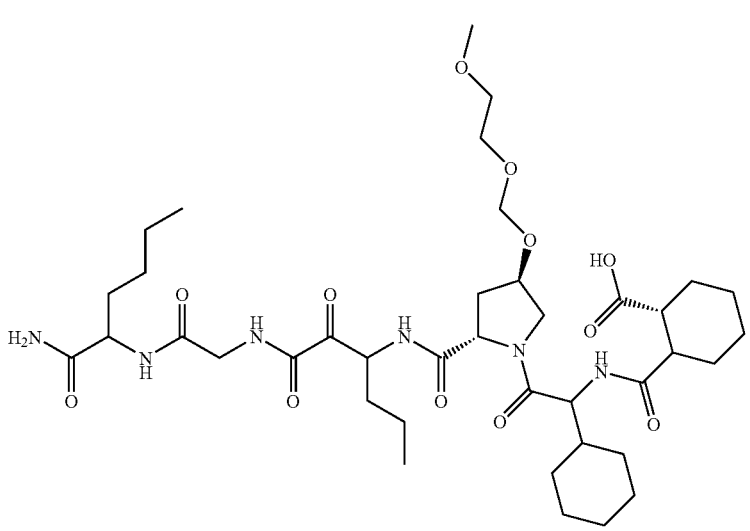 | B |
| 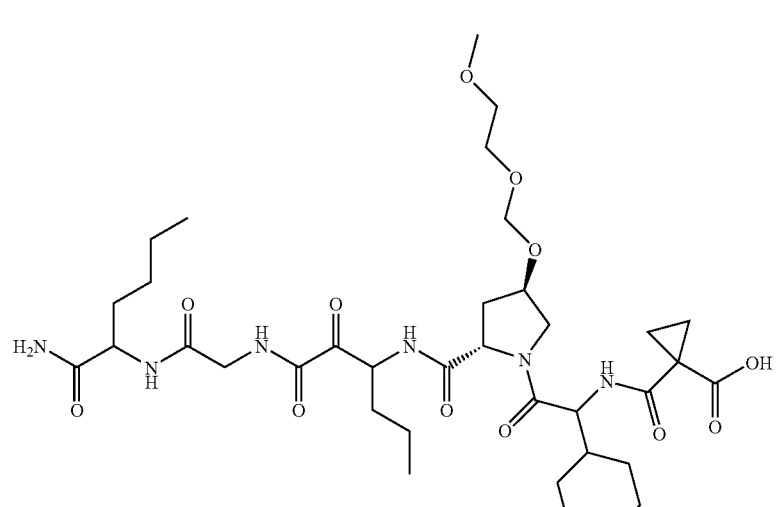 | C |

TABLE 3-continued

Compounds prepared by Solid Phase Synthesis

| STRUCTURE | Ki* CLASS |
|---|---|
|  | A |
|  | A |
|  | A |

TABLE 3-continued

Compounds prepared by Solid Phase Synthesis

| STRUCTURE | Ki* CLASS |
|---|---|
| | B |
| 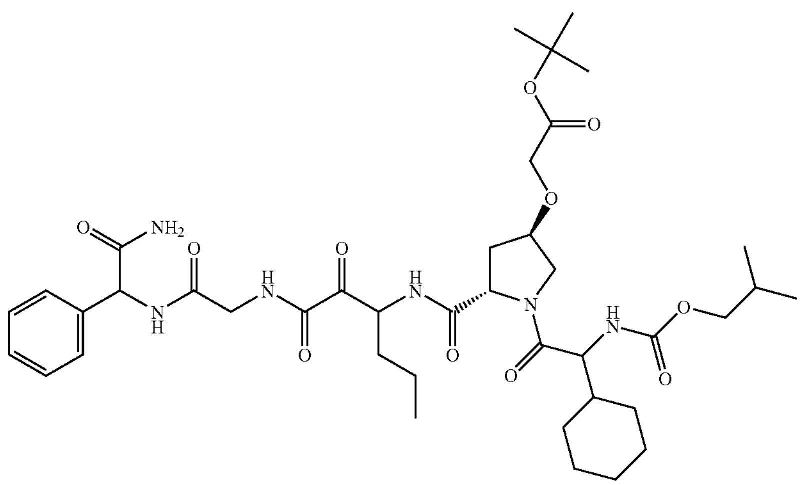 | A |
| | B |

TABLE 3-continued
Compounds prepared by Solid Phase Synthesis
| STRUCTURE | Ki* CLASS |
|---|---|
| 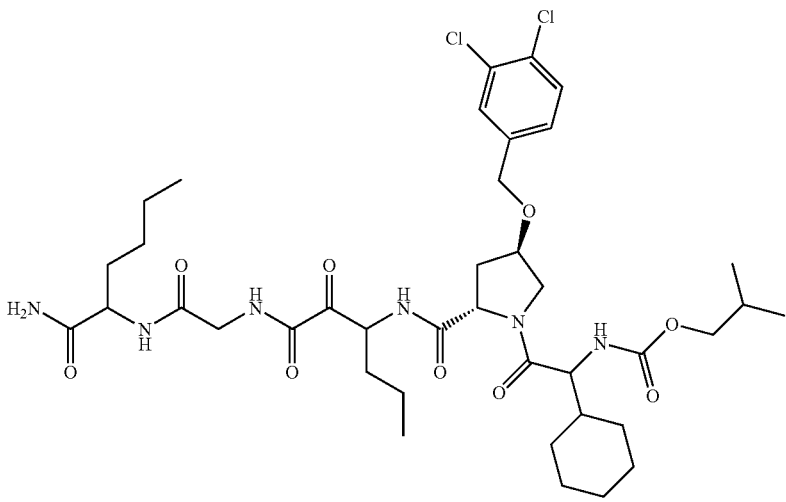 | B |
| 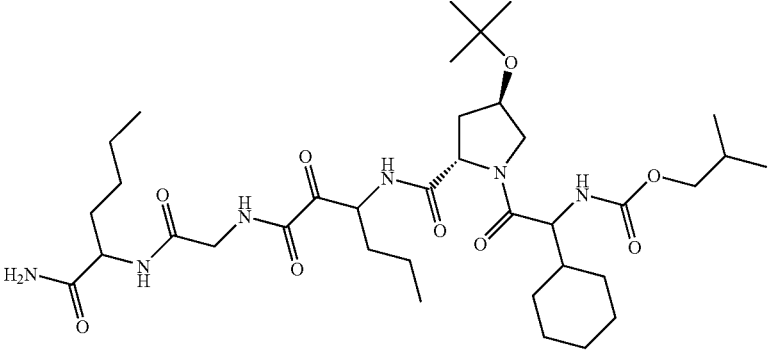 | B |
| 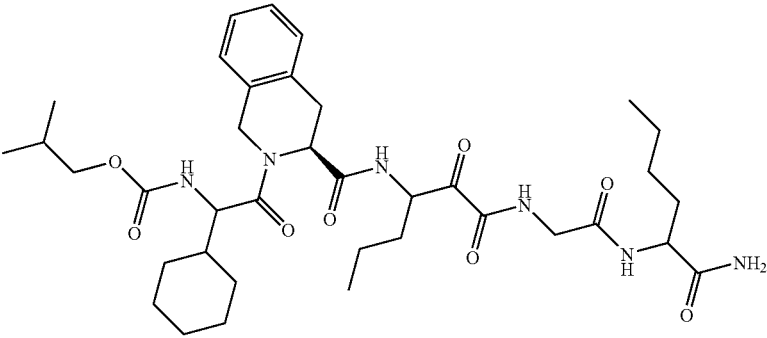 | C |

TABLE 3-continued
Compounds prepared by Solid Phase Synthesis
| STRUCTURE | Ki* CLASS |
|---|---|
| 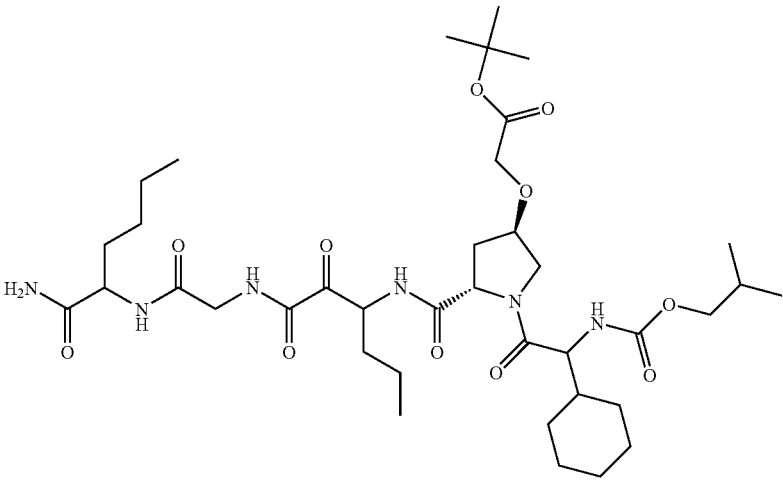 | B |
| 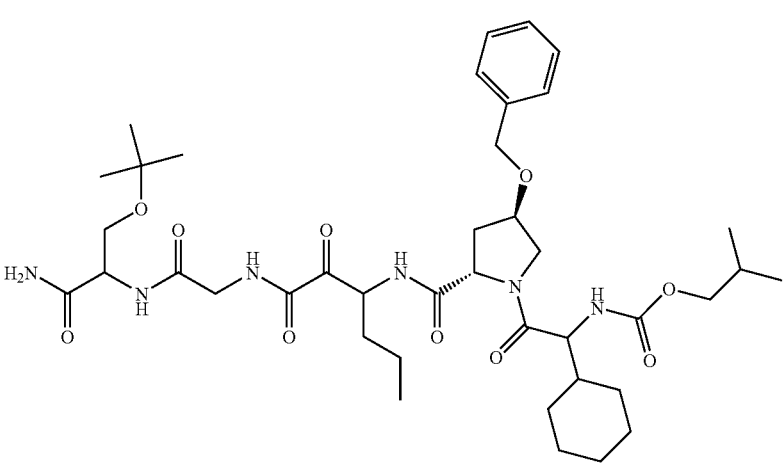 | B |
| 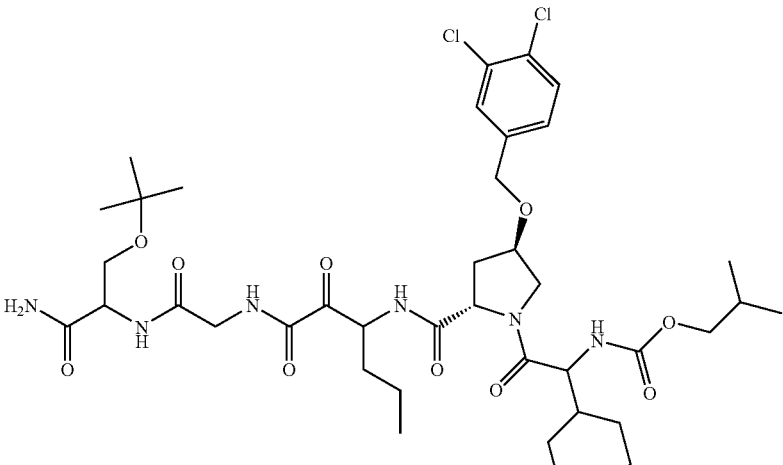 | B |

TABLE 3-continued

Compounds prepared by Solid Phase Synthesis

| STRUCTURE | Ki* CLASS |
|---|---|
| | B |
| 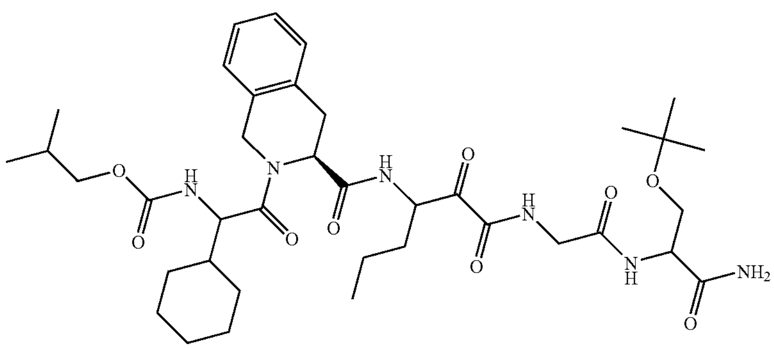 | C |
| | B |

TABLE 3-continued
Compounds prepared by Solid Phase Synthesis
| STRUCTURE | Ki* CLASS |
|---|---|
| 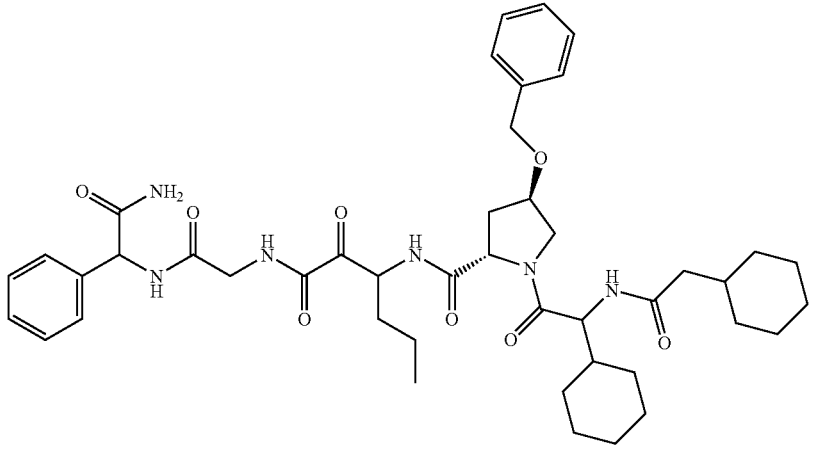 | B |
| 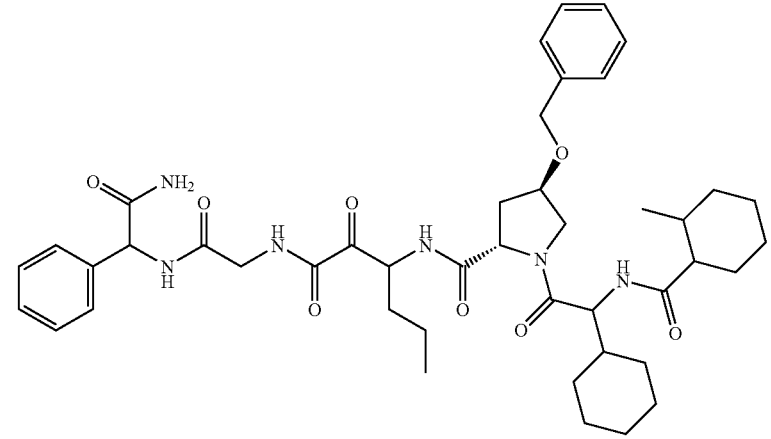 | B |
| 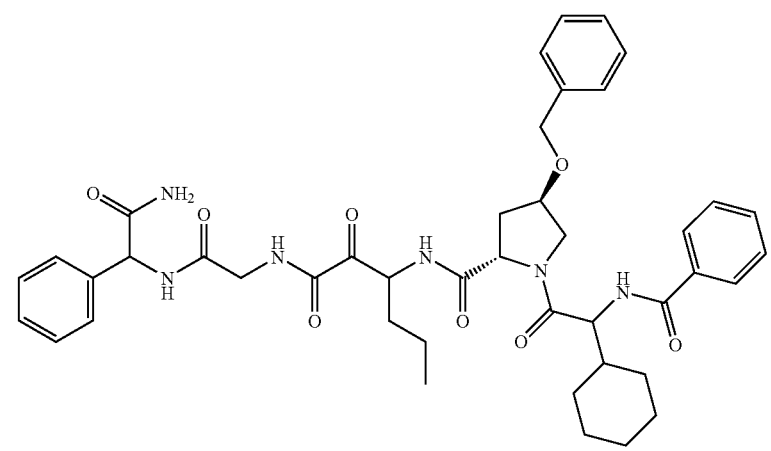 | B |

TABLE 3-continued

Compounds prepared by Solid Phase Synthesis

| STRUCTURE | Ki* CLASS |
|---|---|
| | B |
| | B |
| 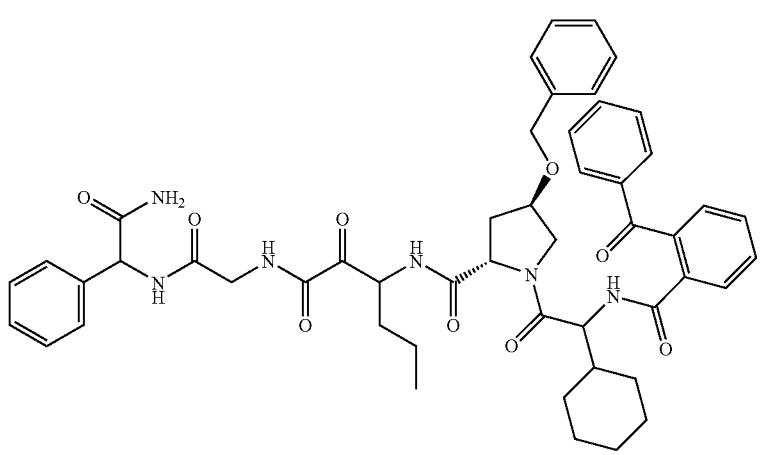 | C |

TABLE 3-continued
Compounds prepared by Solid Phase Synthesis
| STRUCTURE | Ki* CLASS |
|---|---|
| 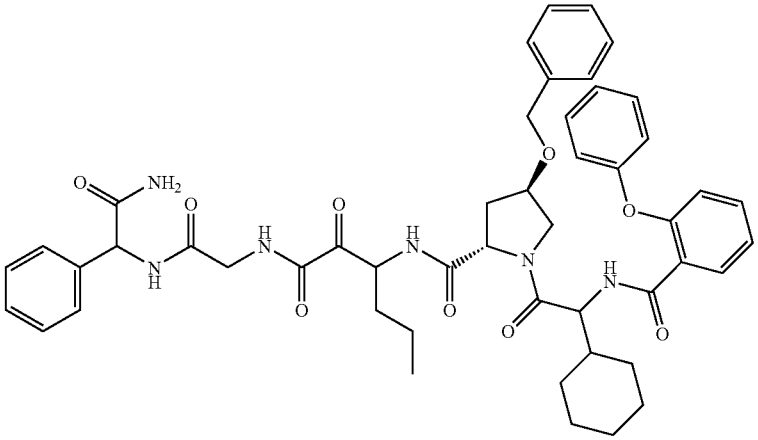 | C |
| 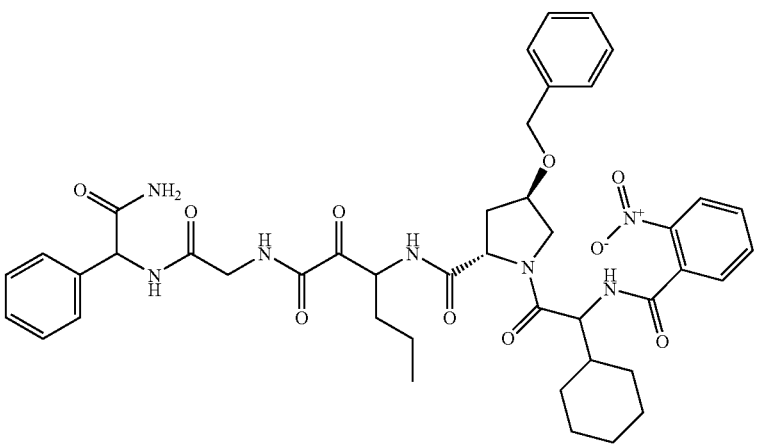 | A |
| 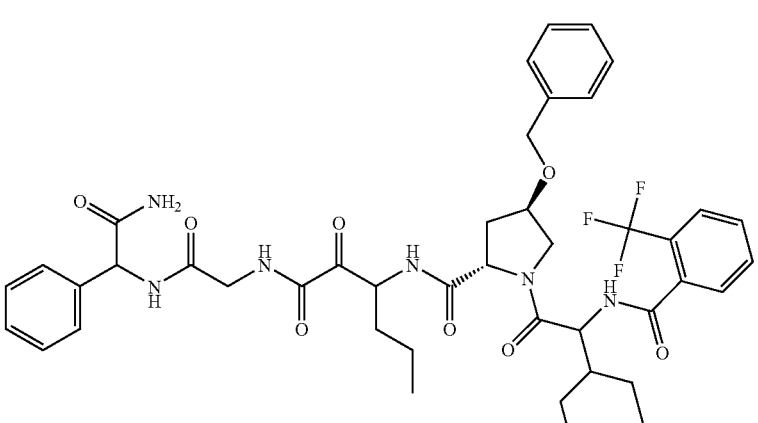 | B |

TABLE 3-continued
Compounds prepared by Solid Phase Synthesis
| STRUCTURE | Ki* CLASS |
|---|---|
| 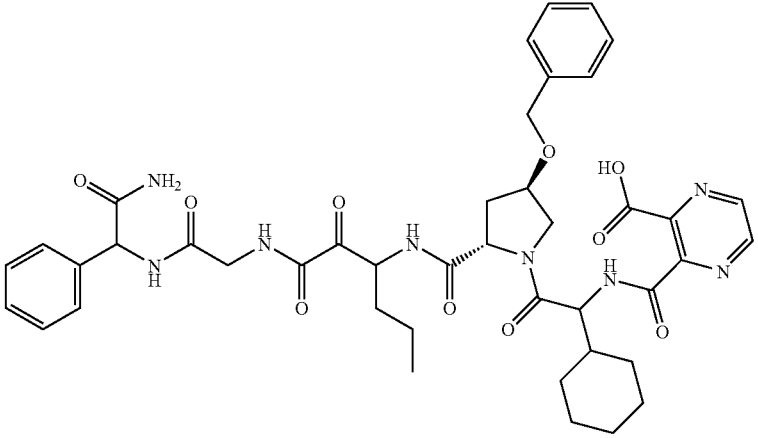 | B |
| 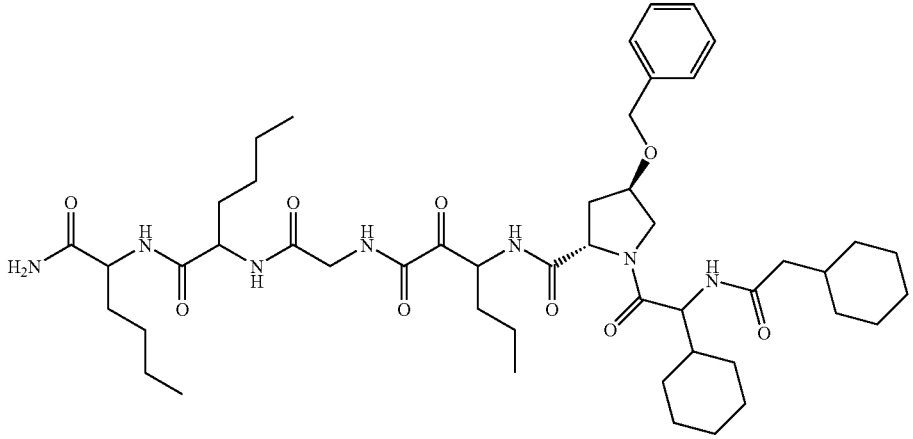 | B |
| 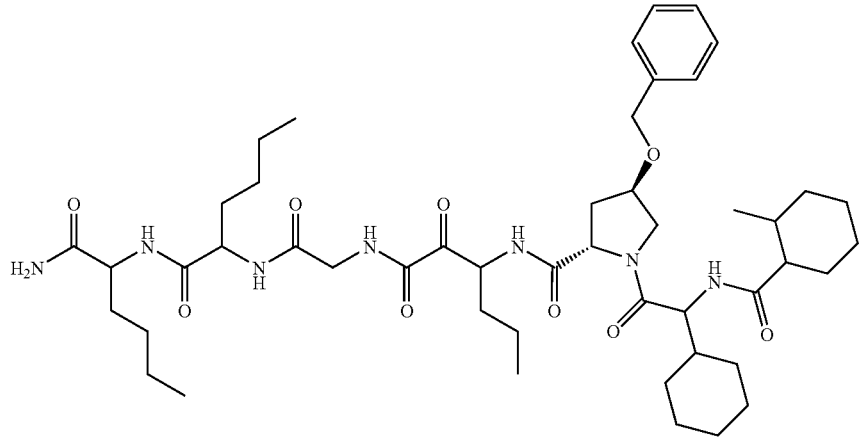 | B |

TABLE 3-continued

Compounds prepared by Solid Phase Synthesis

| STRUCTURE | Ki* CLASS |
|---|---|
| | B |
| | B |
| | B |

TABLE 3-continued
Compounds prepared by Solid Phase Synthesis
| STRUCTURE | Ki* CLASS |
|---|---|
| 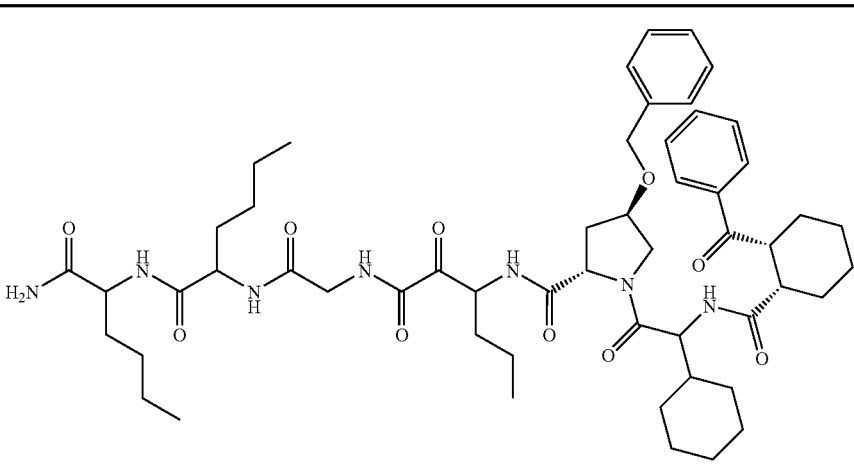 | C |
| 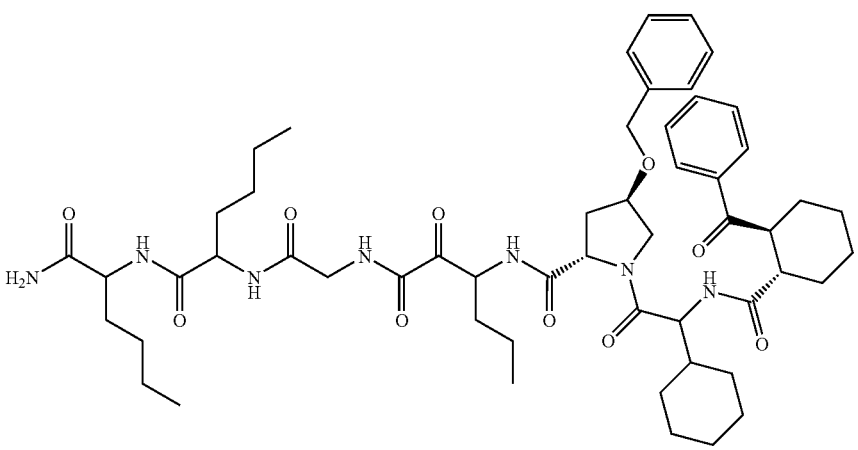 | B |
| 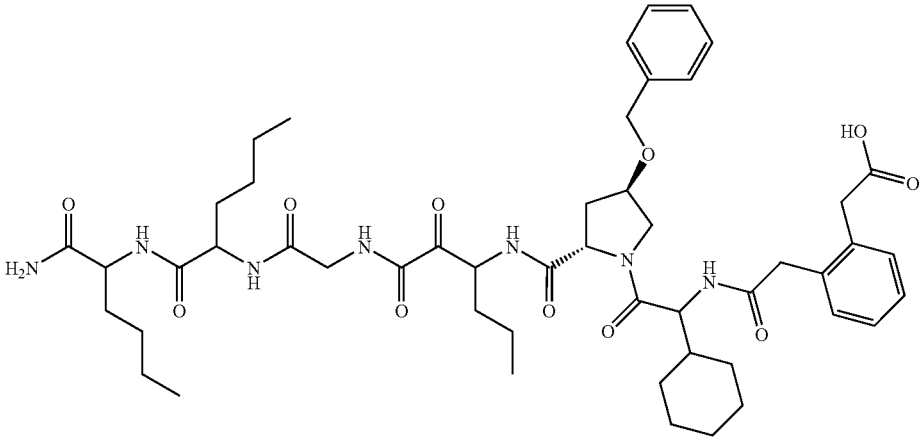 | B |

TABLE 3-continued

Compounds prepared by Solid Phase Synthesis

| STRUCTURE | Ki* CLASS |
|---|---|
| | B |
| | B |
| | B |

TABLE 3-continued
Compounds prepared by Solid Phase Synthesis
| STRUCTURE | Ki* CLASS |
|---|---|
| 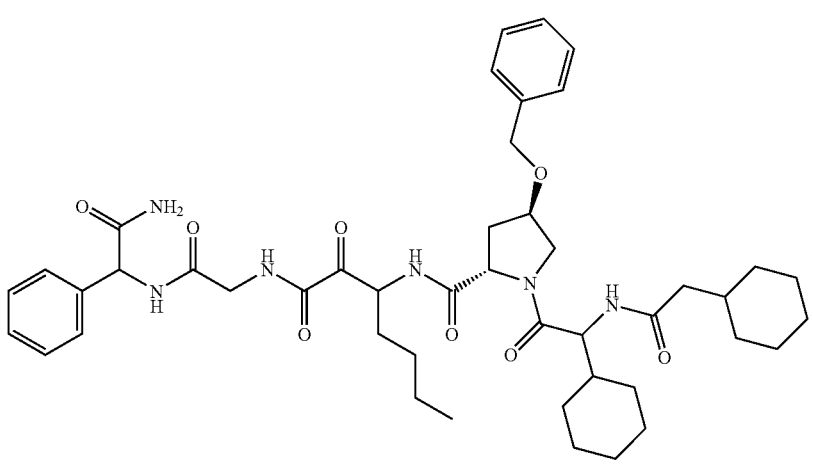 | A |
| 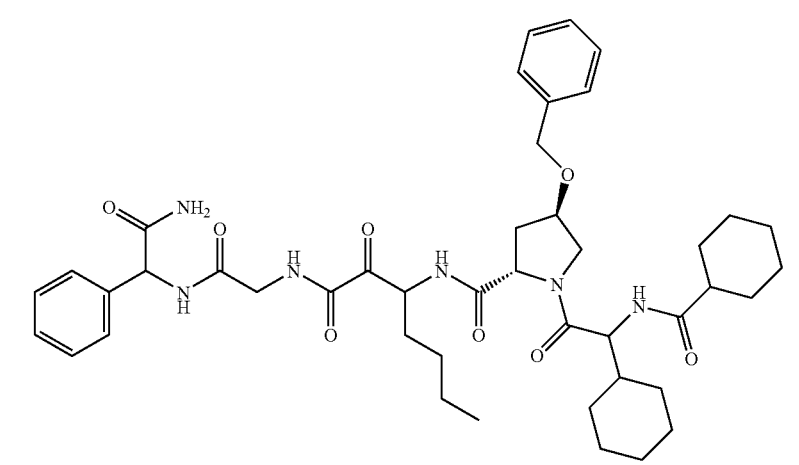 | B |
| 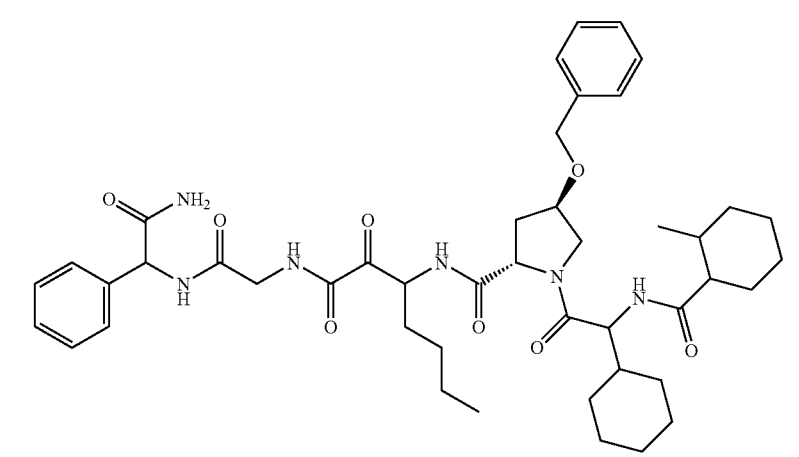 | B |

TABLE 3-continued
Compounds prepared by Solid Phase Synthesis
| STRUCTURE | Ki* CLASS |
|---|---|
| 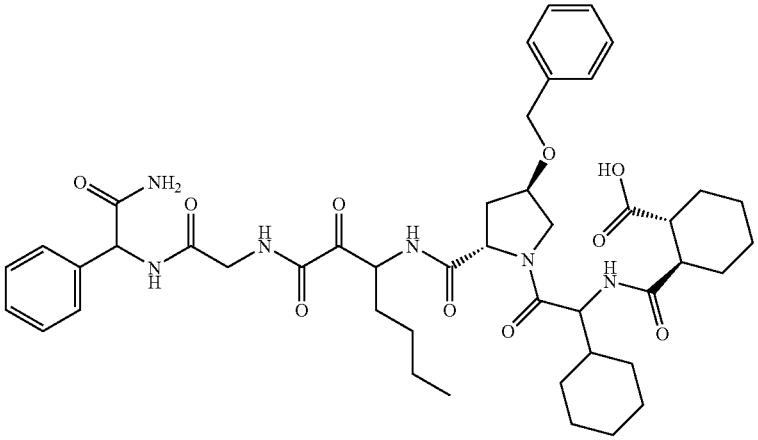 | B |
| 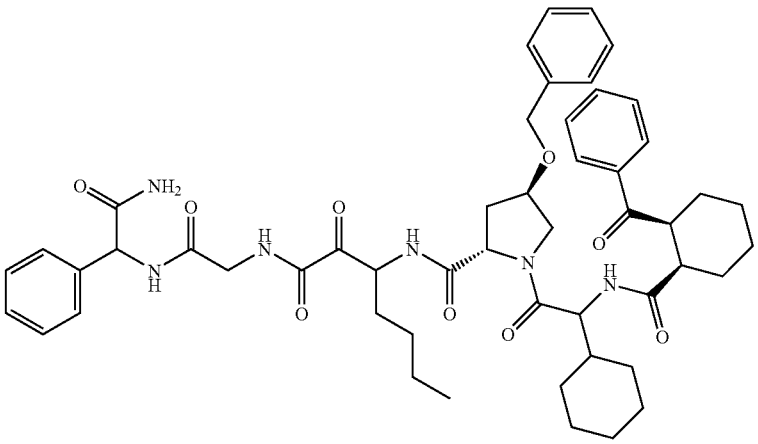 | B |
| 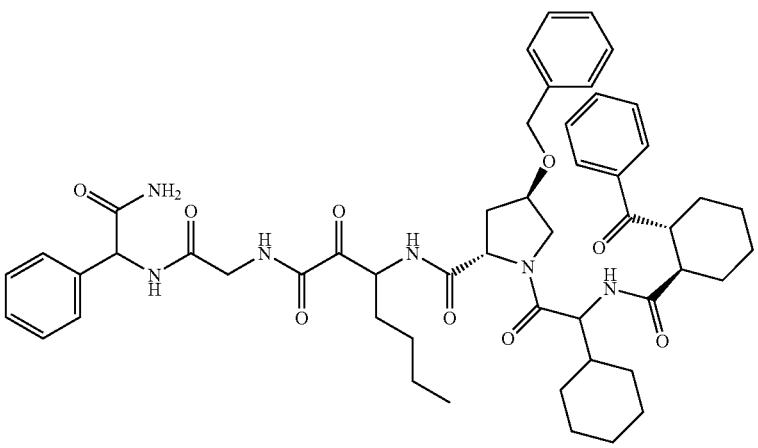 | C |

TABLE 3-continued

Compounds prepared by Solid Phase Synthesis

| STRUCTURE | Ki* CLASS |
|---|---|
|  | B |
|  | B |
|  | B |

TABLE 3-continued
Compounds prepared by Solid Phase Synthesis
| STRUCTURE | Ki* CLASS |
|---|---|
| 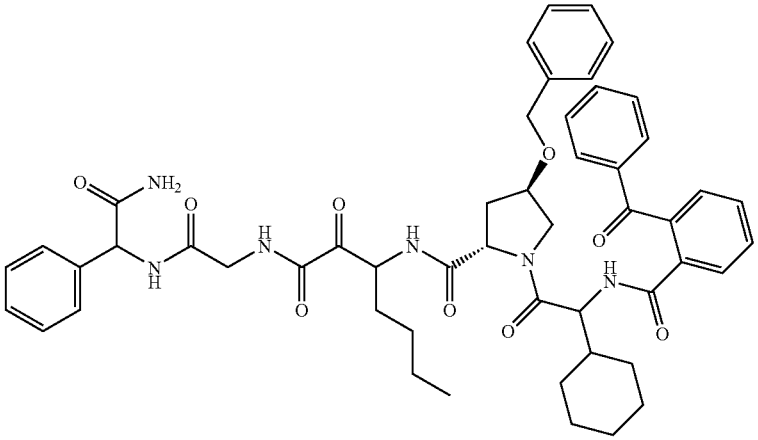 | B |
| 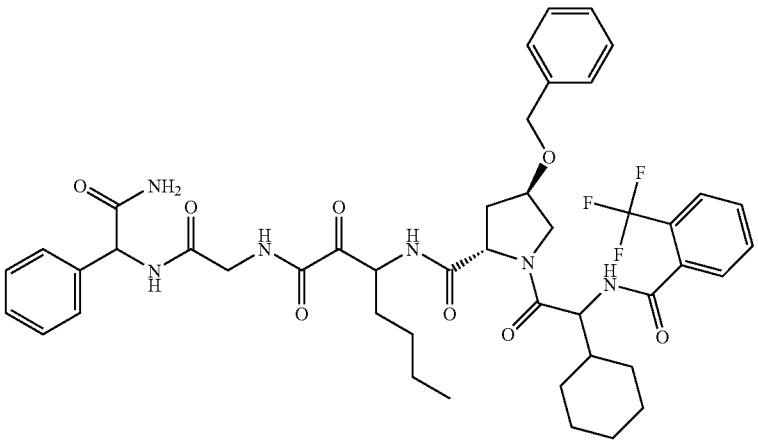 | B |
| 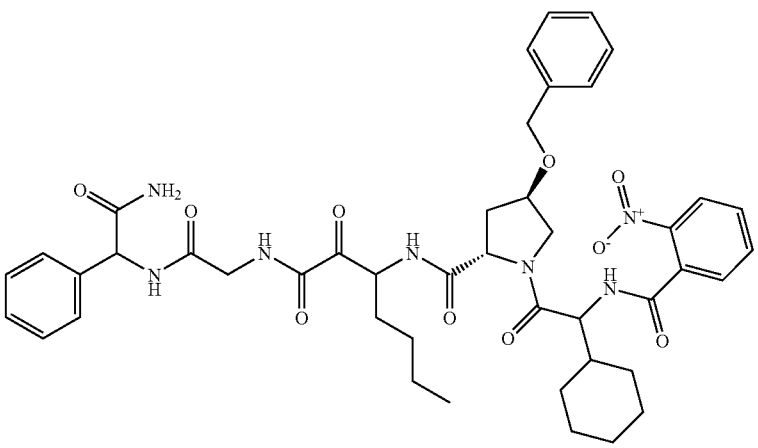 | B |

TABLE 3-continued
Compounds prepared by Solid Phase Synthesis
| STRUCTURE | Ki* CLASS |
|---|---|
| 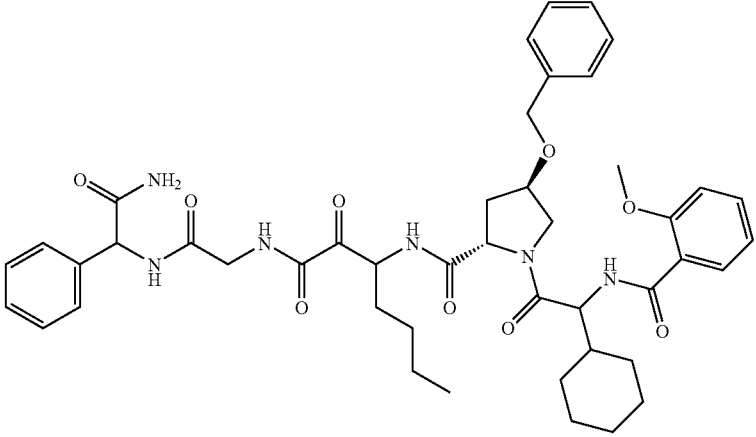 | C |
| 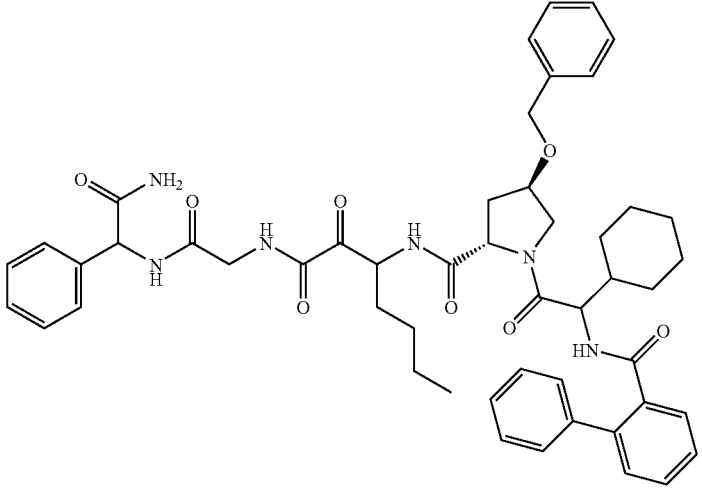 | C |
| 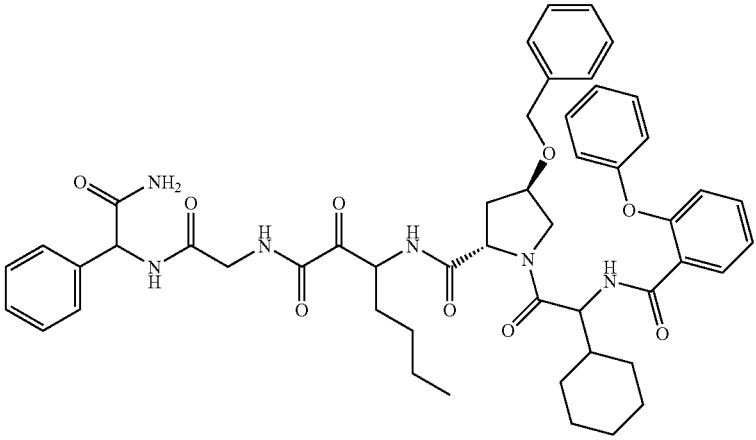 | C |

TABLE 3-continued
Compounds prepared by Solid Phase Synthesis
| STRUCTURE | Ki* CLASS |
|---|---|
| 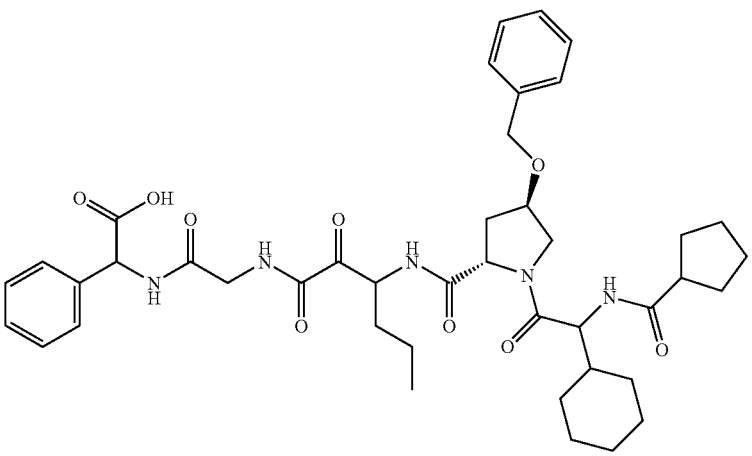 | A |
| 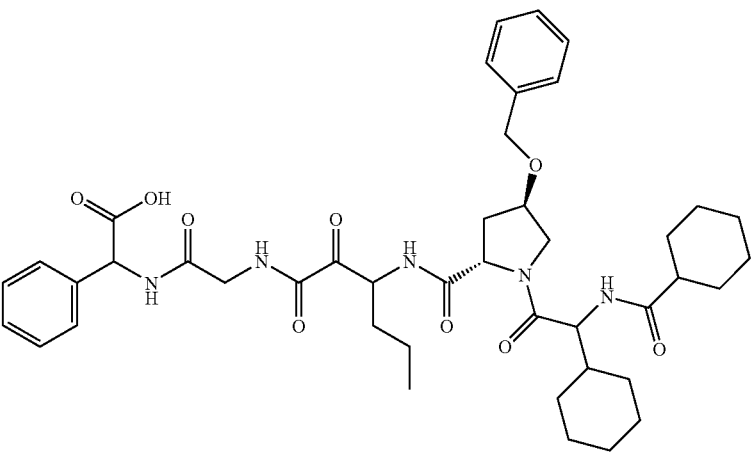 | B |
| 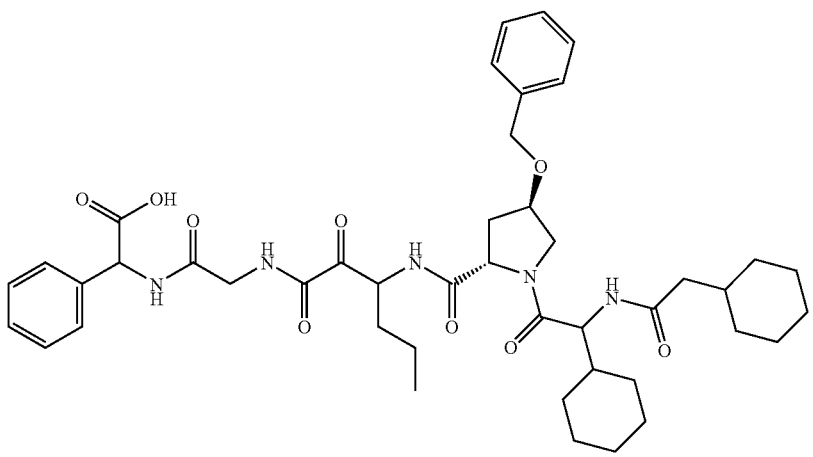 | A |

TABLE 3-continued

Compounds prepared by Solid Phase Synthesis

| STRUCTURE | Ki* CLASS |
|---|---|
| | A |
| | B |
| | A |

TABLE 3-continued

Compounds prepared by Solid Phase Synthesis

| STRUCTURE | Ki* CLASS |
|---|---|
| | A |
| | A |
| | A |

TABLE 3-continued

Compounds prepared by Solid Phase Synthesis

| STRUCTURE | Ki* CLASS |
|---|---|
| | B |
| | B |
| 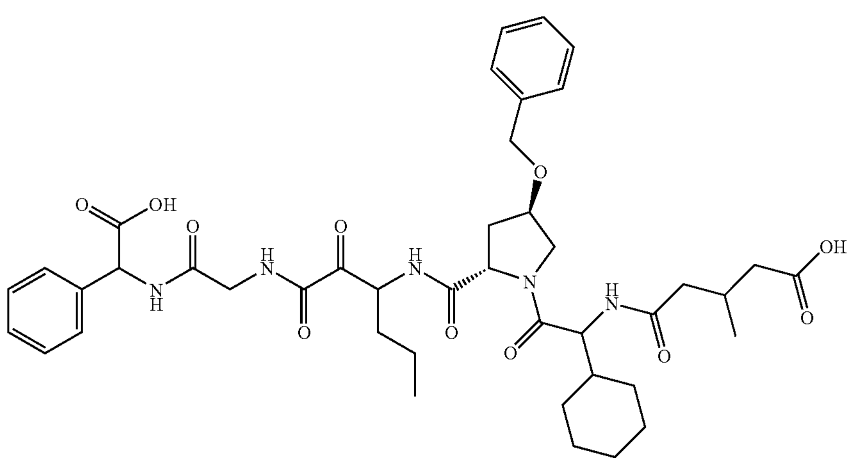 | A |

TABLE 3-continued
Compounds prepared by Solid Phase Synthesis
| STRUCTURE | Ki* CLASS |
|---|---|
| 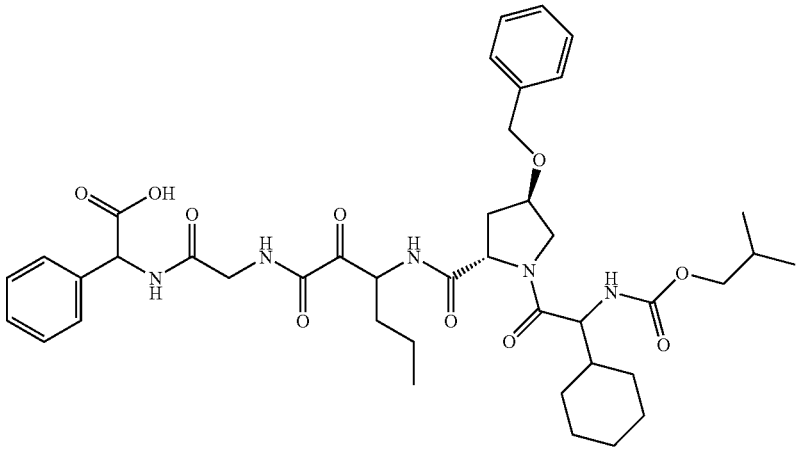 | A |
| 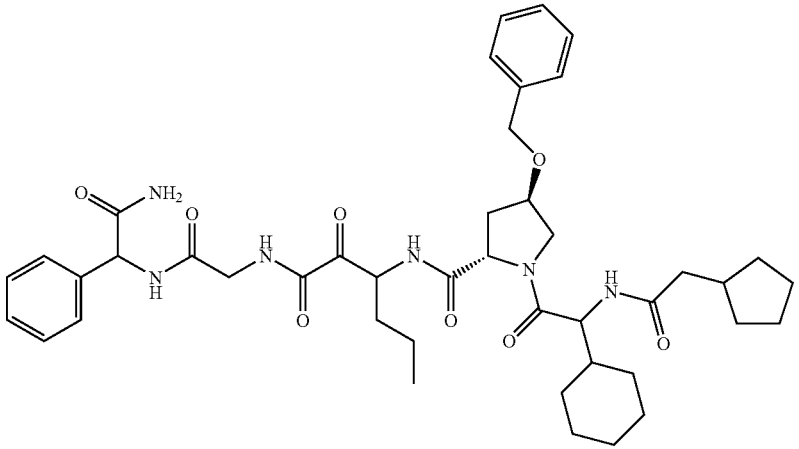 | B |
| 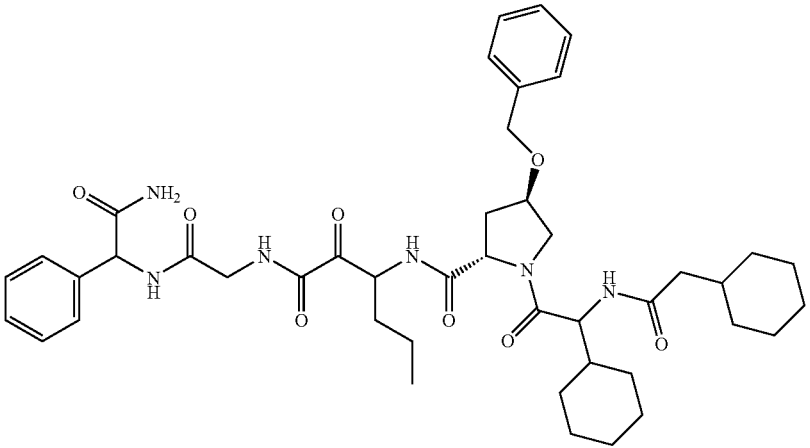 | B |

TABLE 3-continued
Compounds prepared by Solid Phase Synthesis
| STRUCTURE | Ki* CLASS |
|---|---|
| 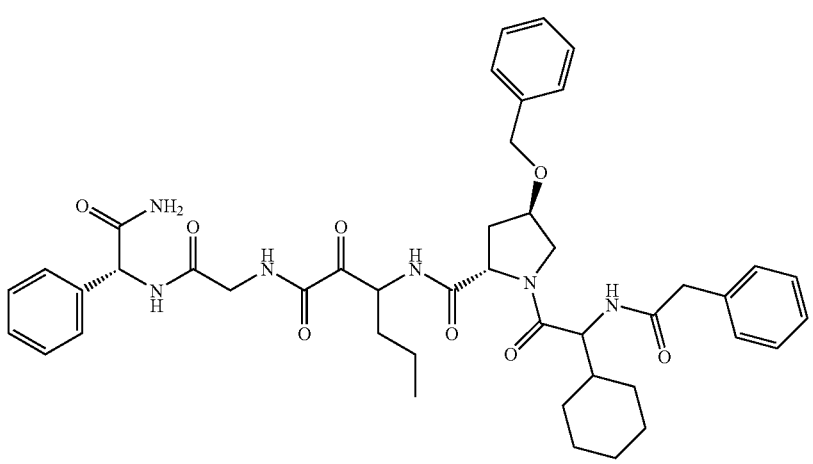 | C |
| 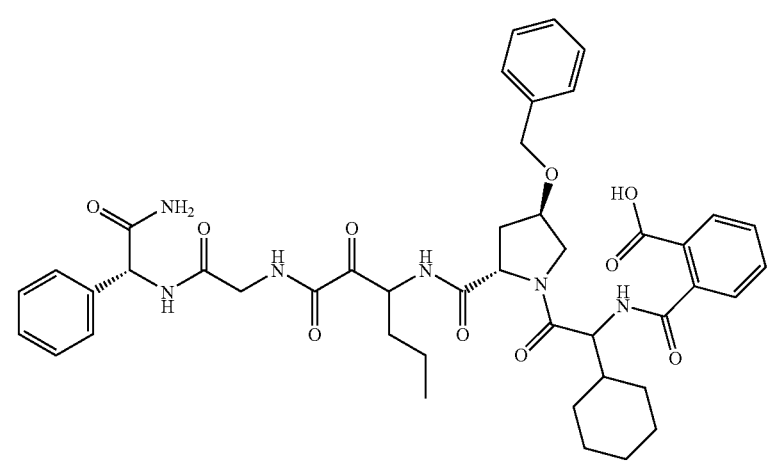 | B |
| 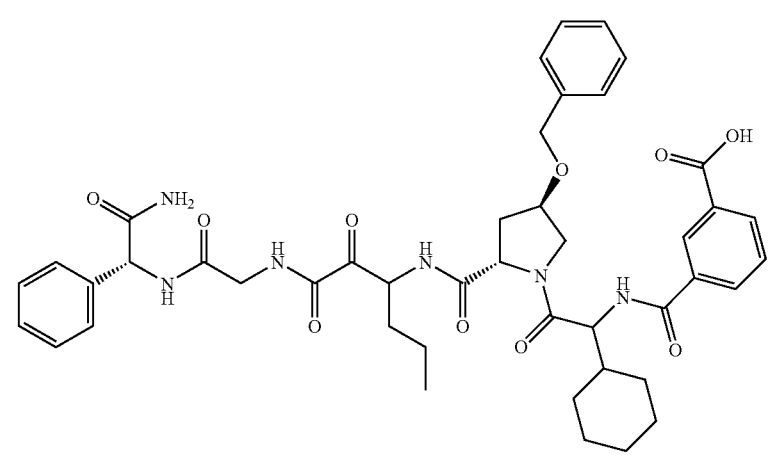 | B |

TABLE 3-continued

Compounds prepared by Solid Phase Synthesis

| STRUCTURE | Ki* CLASS |
|---|---|
| | B |
| | B |
| 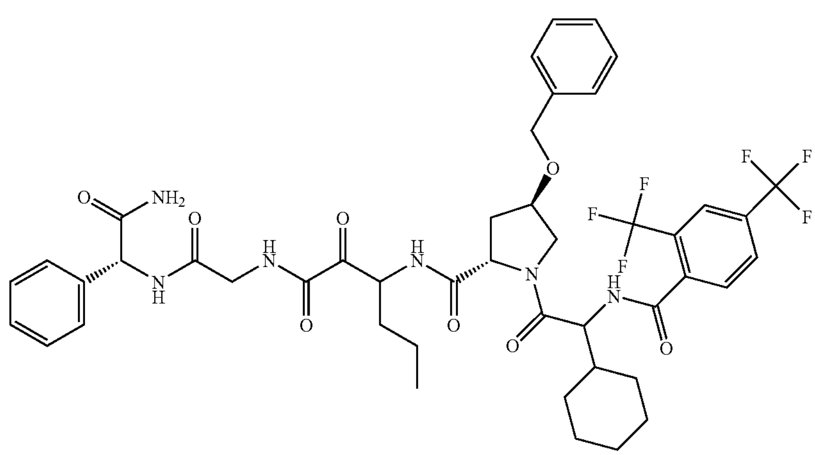 | C |

TABLE 3-continued
Compounds prepared by Solid Phase Synthesis
| STRUCTURE | Ki* CLASS |
|---|---|
| 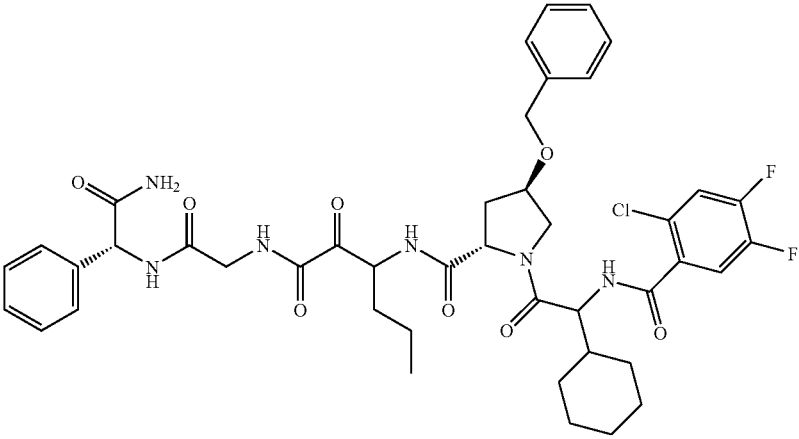 | C |
| 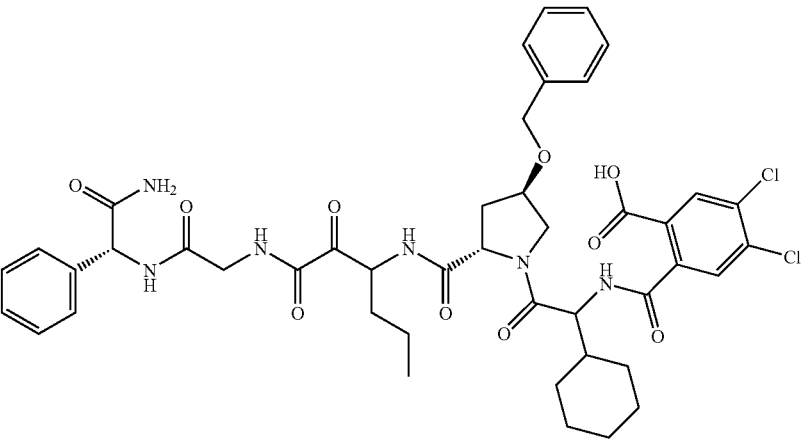 | C |
| 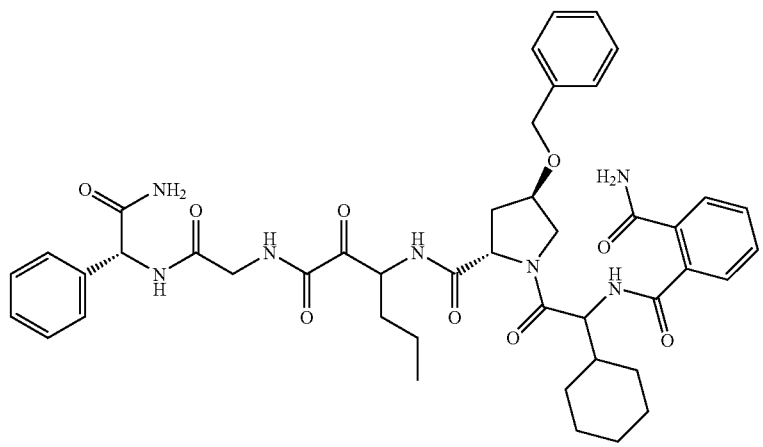 | C |

TABLE 3-continued
Compounds prepared by Solid Phase Synthesis
| STRUCTURE | Ki* CLASS |
|---|---|
| 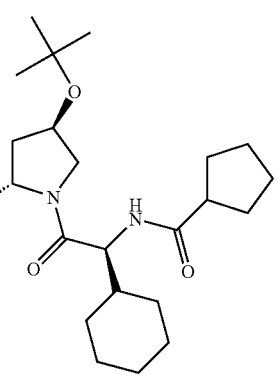 | B |
| 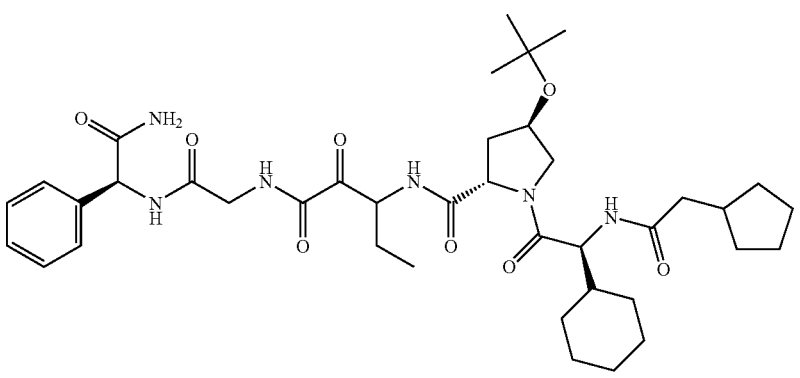 | B |
| 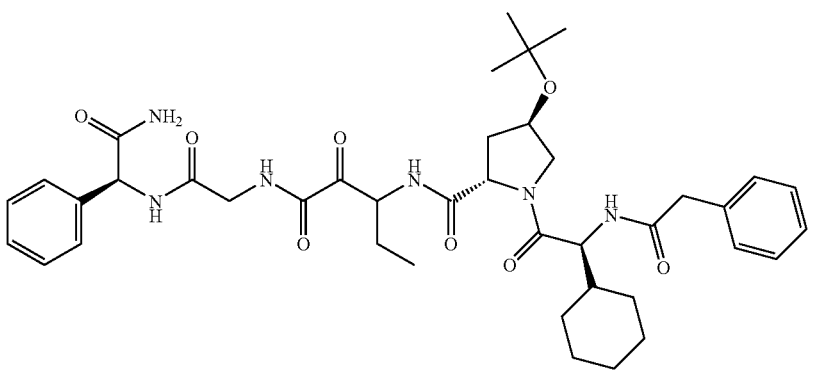 | B |
| 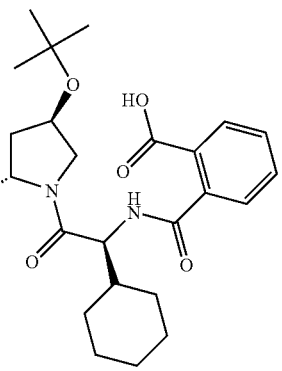 | B |

TABLE 3-continued
Compounds prepared by Solid Phase Synthesis
| STRUCTURE | Ki* CLASS |
|---|---|
| 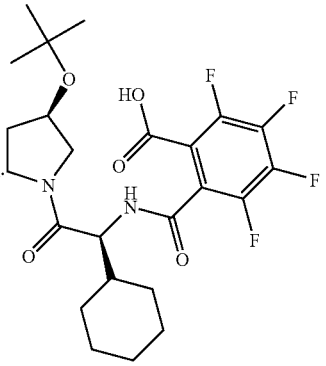 | A |
| 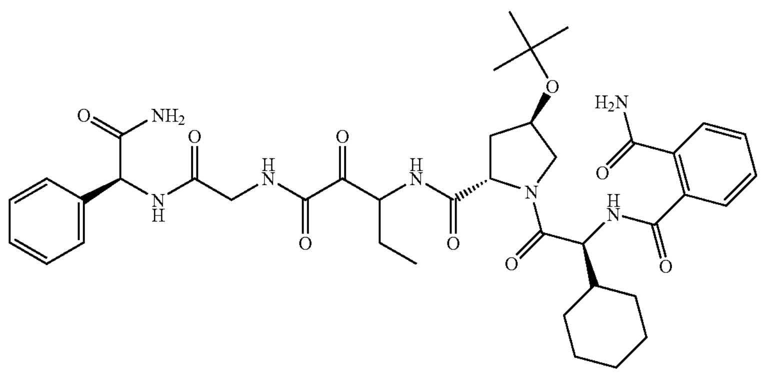 | B |
|  | C |
| 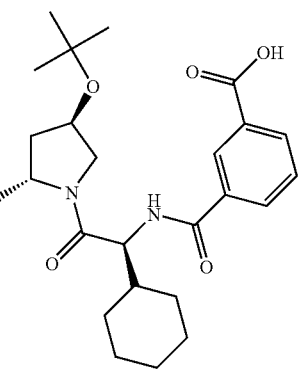 | C |

US 7,592,316 B2
331                                                                                                              332
TABLE 3-continued
Compounds prepared by Solid Phase Synthesis
| STRUCTURE | Ki* CLASS |
|---|---|
| 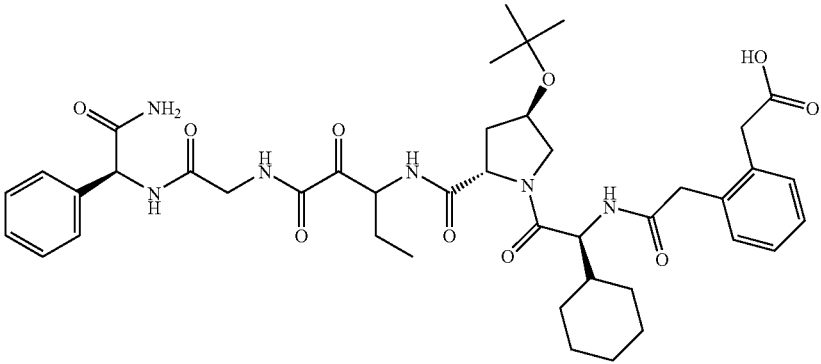 | B |
| 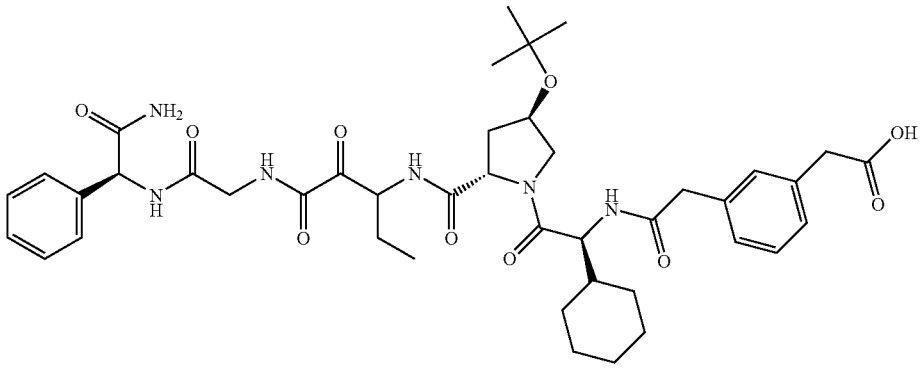 | B |
| 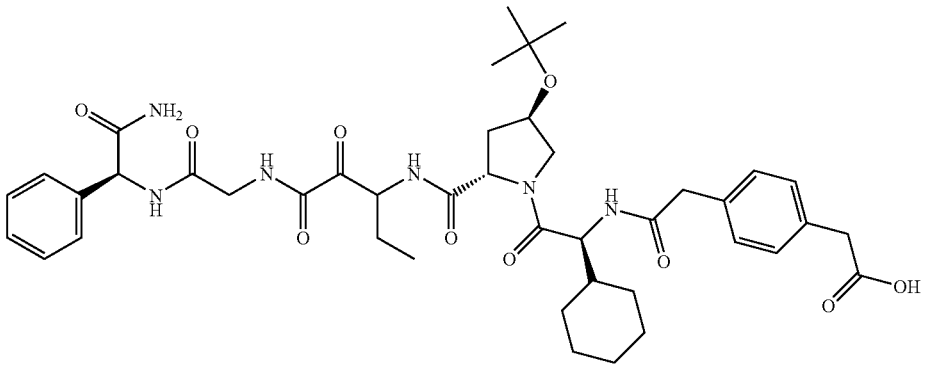 | B |
| 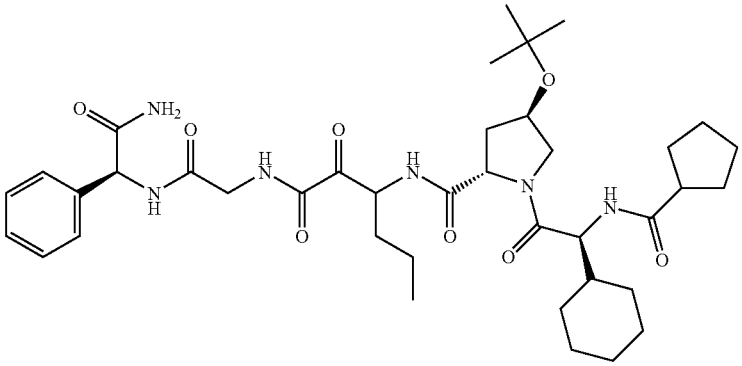 | B |

TABLE 3-continued
Compounds prepared by Solid Phase Synthesis
| STRUCTURE | Ki* CLASS |
|---|---|
| 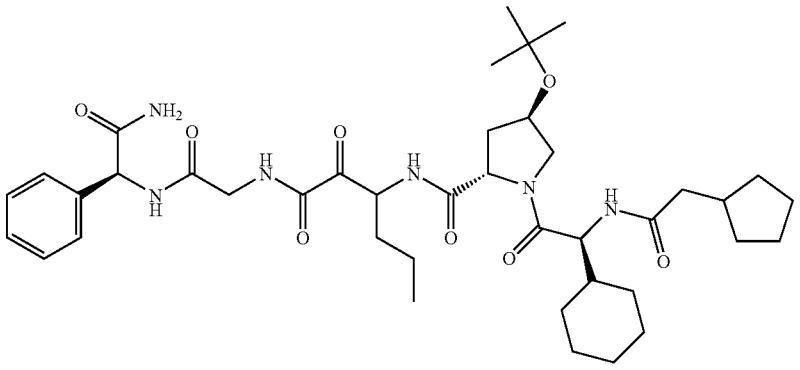 | A |
| 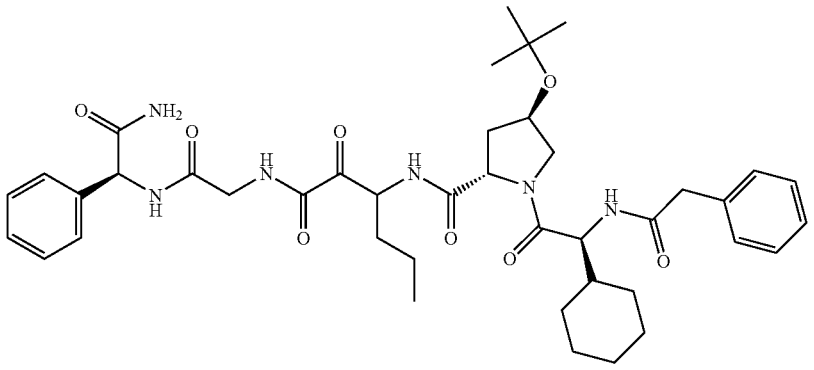 | A |
| 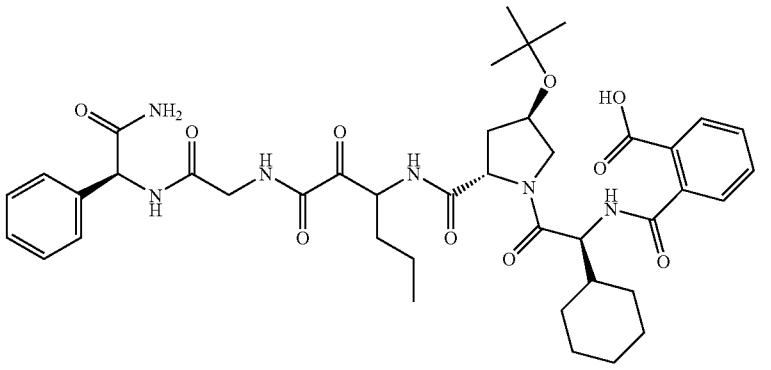 | A |
| 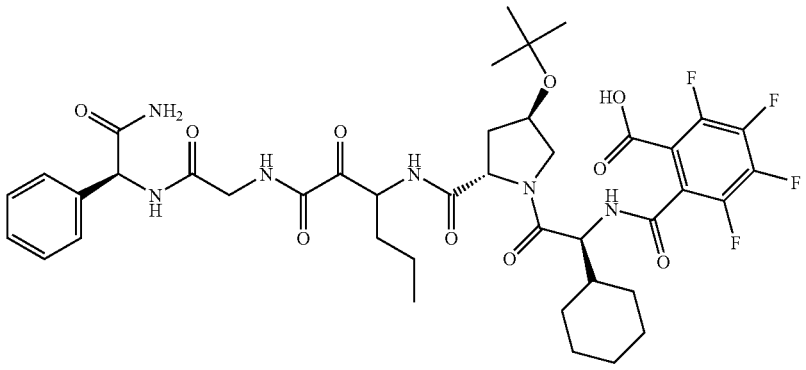 | A |

TABLE 3-continued
Compounds prepared by Solid Phase Synthesis
| STRUCTURE | Ki* CLASS |
|---|---|
|  | B |
| 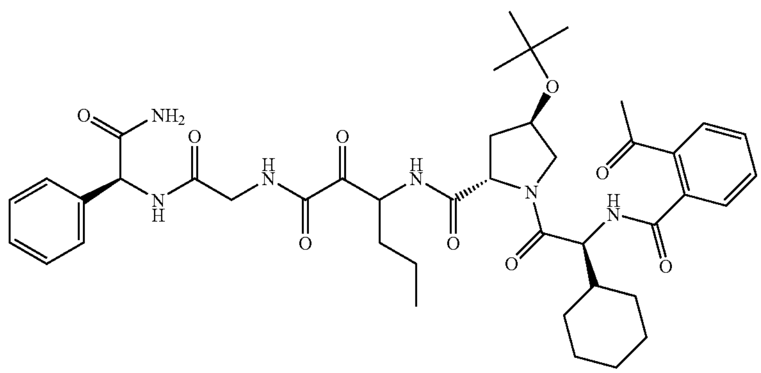 | C |
|  | B |
| 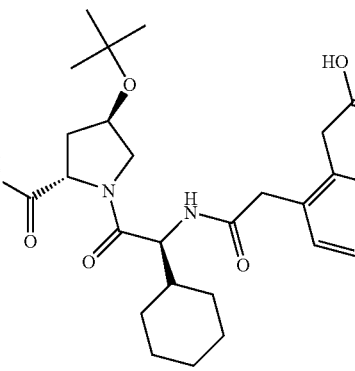 | A |

TABLE 3-continued

Compounds prepared by Solid Phase Synthesis

| STRUCTURE | Ki* CLASS |
|---|---|
| | C |
| 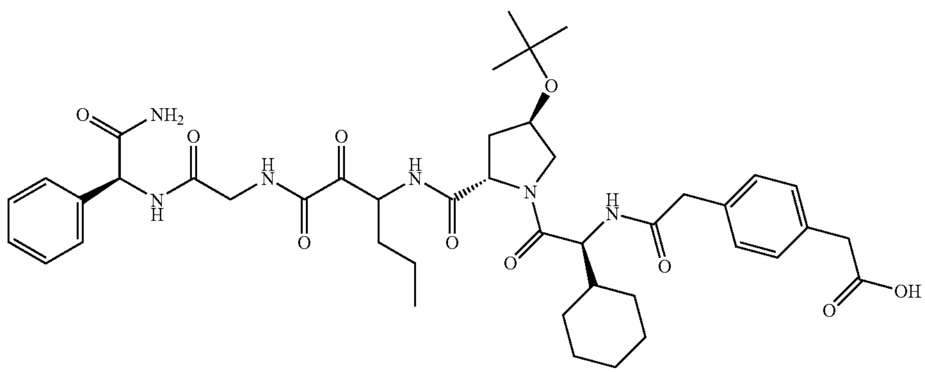 | A |
| | C |
| | C |

TABLE 3-continued

Compounds prepared by Solid Phase Synthesis

| STRUCTURE | Ki* CLASS |
|---|---|
| | C |
| | C |
| | C |
| | C |

TABLE 3-continued

Compounds prepared by Solid Phase Synthesis

| STRUCTURE | Ki* CLASS |
|---|---|
| | C |
| | C |
| | C |

TABLE 3-continued

Compounds prepared by Solid Phase Synthesis

| STRUCTURE | Ki* CLASS |
|---|---|
| | C |
| | C |
| | C |

TABLE 3-continued

Compounds prepared by Solid Phase Synthesis

| STRUCTURE | Ki* CLASS |
| --- | --- |
| | B |
| | B |
| | B |
| | B |
| 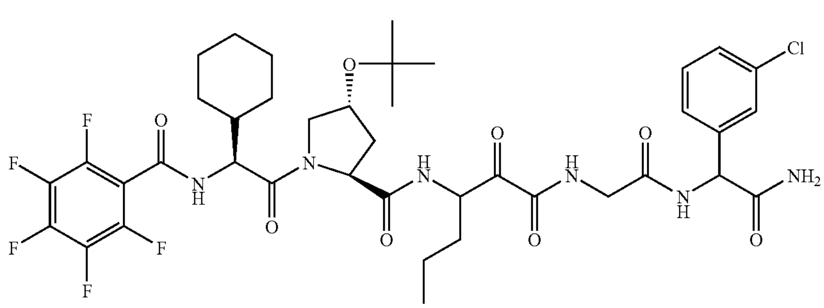 | C |

TABLE 3-continued
Compounds prepared by Solid Phase Synthesis
| STRUCTURE | Ki* CLASS |
|---|---|
| 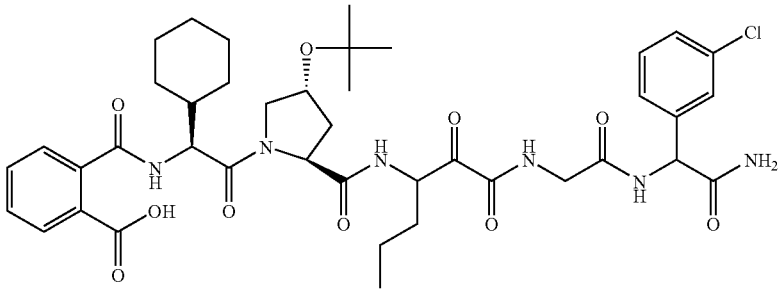 | B |
| 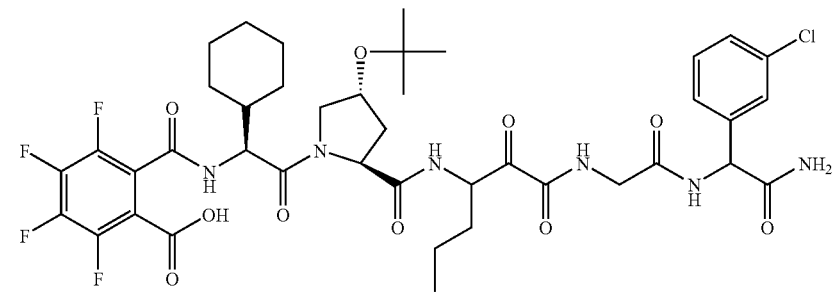 | A |
| 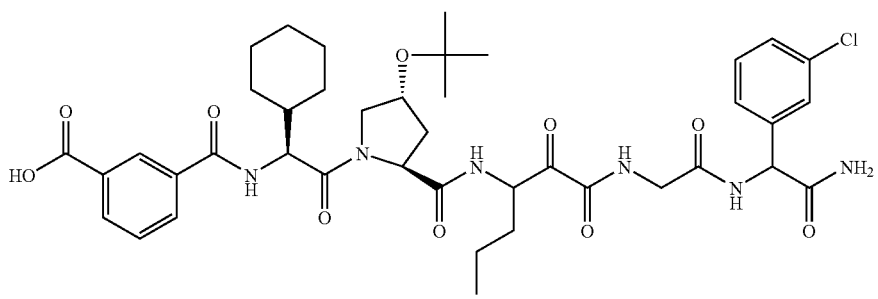 | B |
| 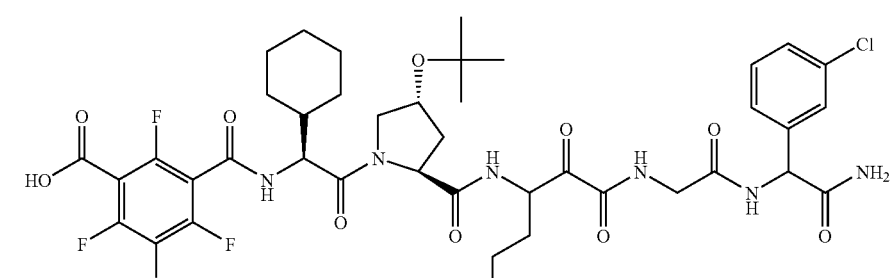 | B |
| 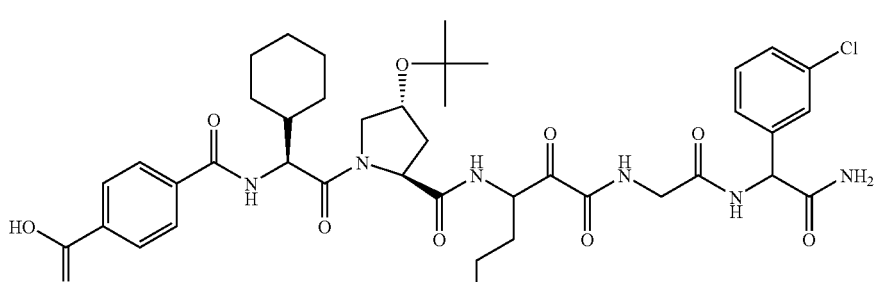 | B |

TABLE 3-continued

Compounds prepared by Solid Phase Synthesis

| STRUCTURE | Ki* CLASS |
|---|---|
| | B |
| | B |
| | B |
| | B |
| | B |

TABLE 3-continued
Compounds prepared by Solid Phase Synthesis
| STRUCTURE | Ki* CLASS |
|---|---|
| 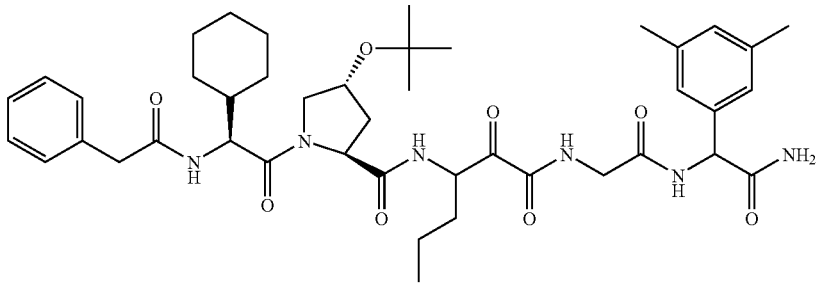 | B |
| 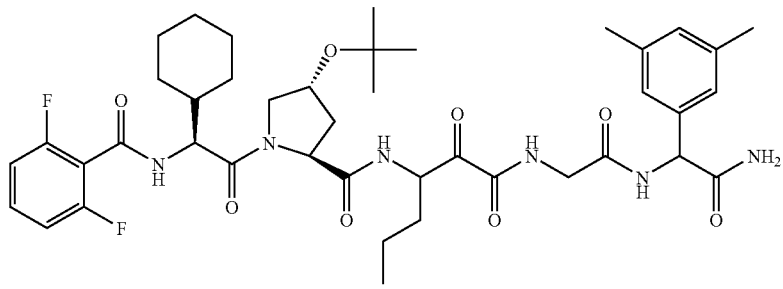 | B |
| 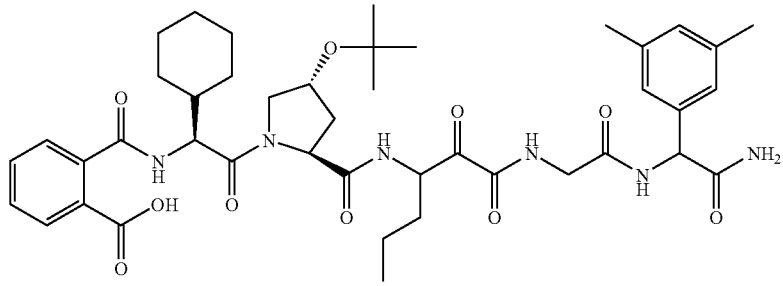 | B |
| 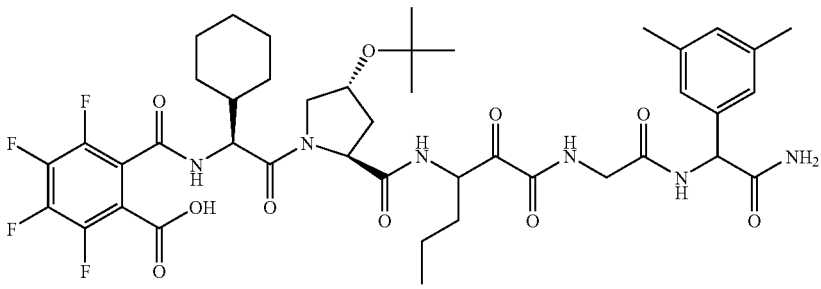 | A |
| 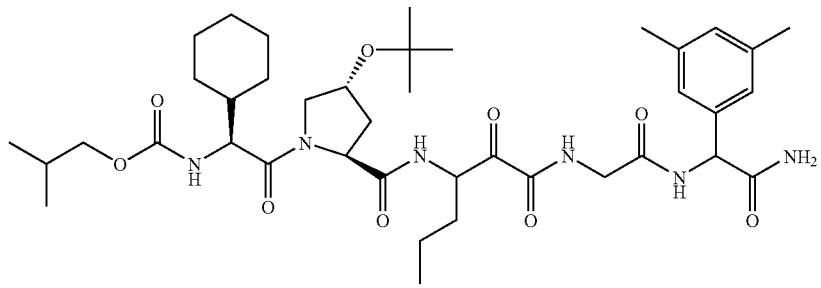 | B |

TABLE 3-continued
Compounds prepared by Solid Phase Synthesis
| STRUCTURE | Ki* CLASS |
|---|---|
| 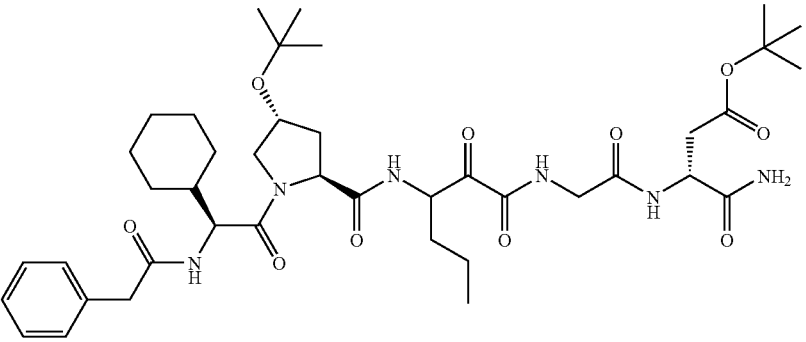 | C |
| 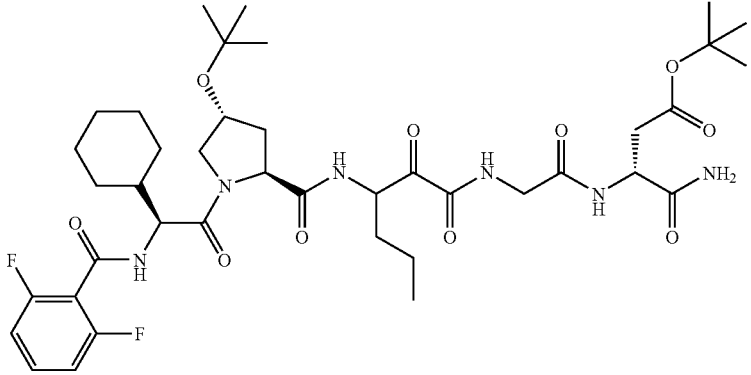 | C |
| 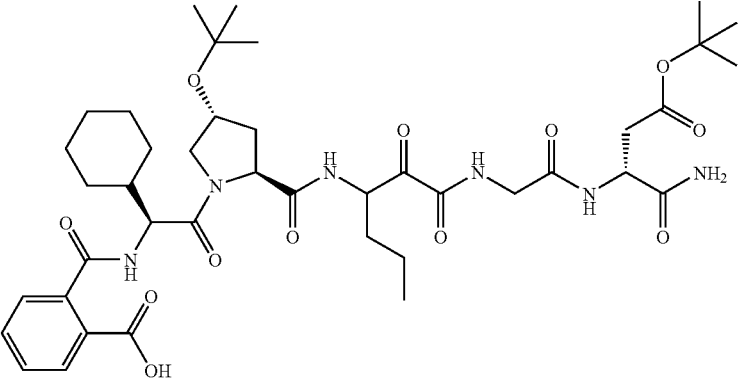 | C |
| 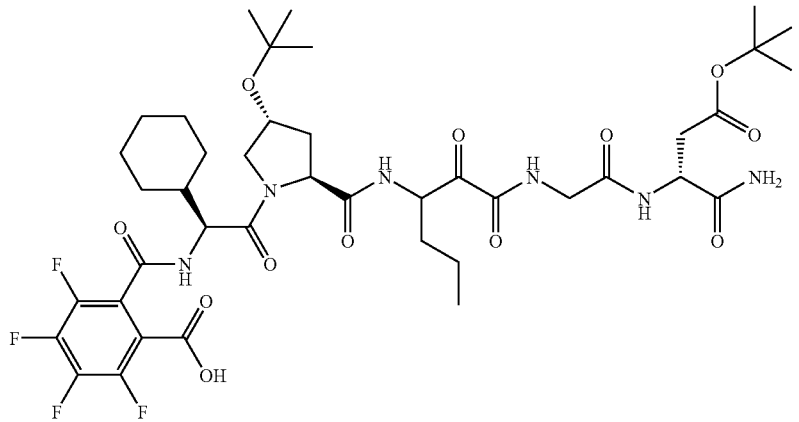 | C |

TABLE 3-continued

Compounds prepared by Solid Phase Synthesis

| STRUCTURE | Ki* CLASS |
|---|---|
| | C |
| | B |
| | C |
| | C |
| | B |

TABLE 3-continued
Compounds prepared by Solid Phase Synthesis
| STRUCTURE | Ki* CLASS |
|---|---|
| 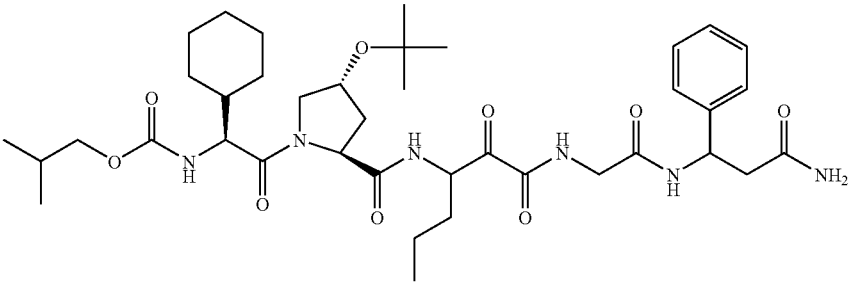 | C |
| 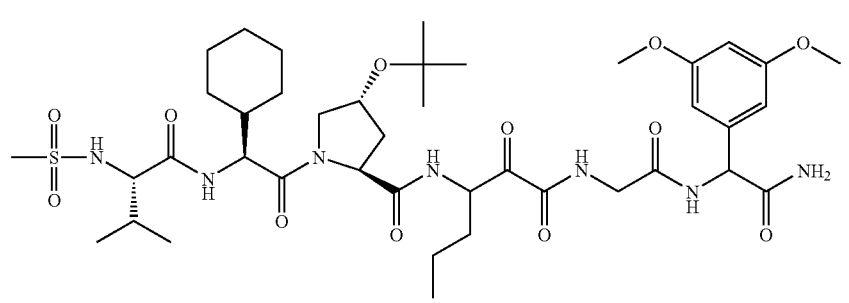 | B |
| 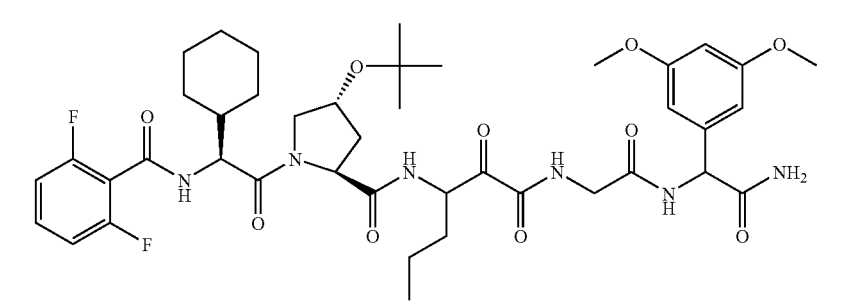 | B |
| 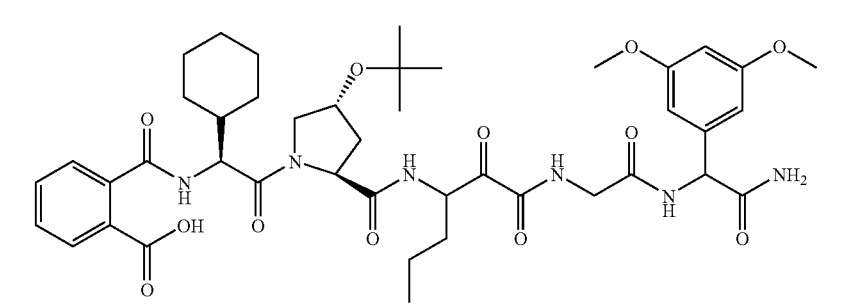 | B |
| 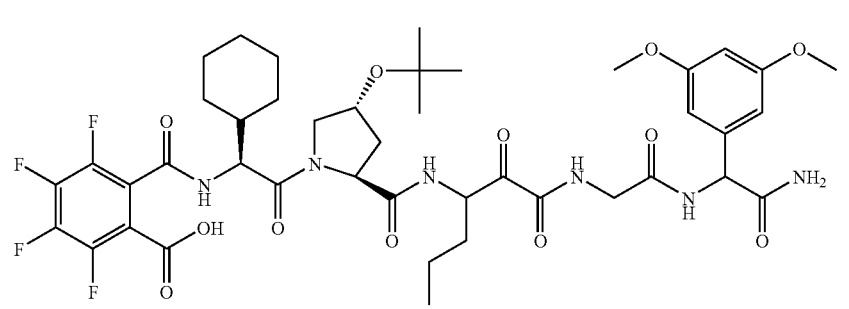 | B |

TABLE 3-continued

Compounds prepared by Solid Phase Synthesis

| STRUCTURE | Ki* CLASS |
|---|---|
| | B |
| | B |
| | B |
| | B |
| | B |

TABLE 3-continued

Compounds prepared by Solid Phase Synthesis

| STRUCTURE | Ki* CLASS |
|---|---|
| | B |
| | B |
| | B |
| | B |
| | B |

TABLE 3-continued

Compounds prepared by Solid Phase Synthesis

| STRUCTURE | Ki* CLASS |
|---|---|
| | B |
| | B |
| | B |
| | B |
| | B |

TABLE 3-continued

Compounds prepared by Solid Phase Synthesis

| STRUCTURE | Ki* CLASS |
|---|---|
| | B |
| | B |
| | B |
| | B |

TABLE 3-continued

Compounds prepared by Solid Phase Synthesis

| STRUCTURE | Ki* CLASS |
|---|---|
| | B |
| | B |
| 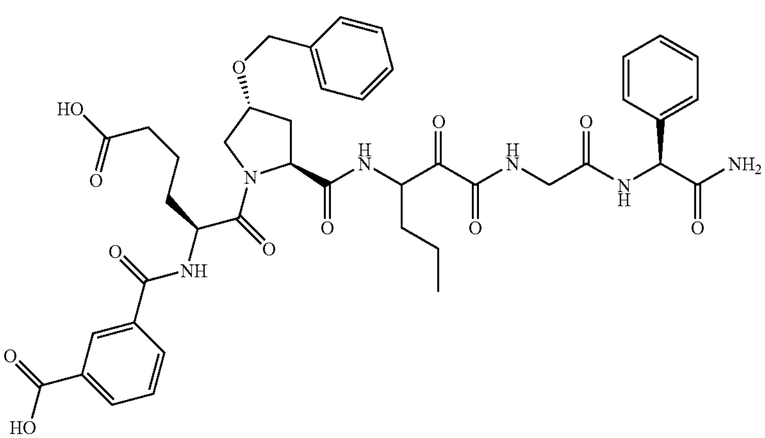 | C |

TABLE 3-continued
Compounds prepared by Solid Phase Synthesis
| STRUCTURE | Ki* CLASS |
|---|---|
| 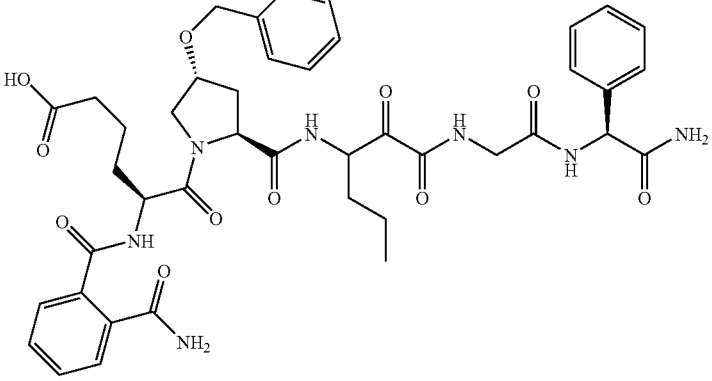 | B |
| 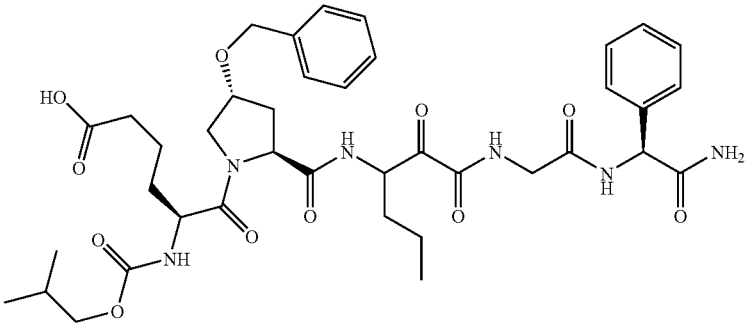 | B |
| 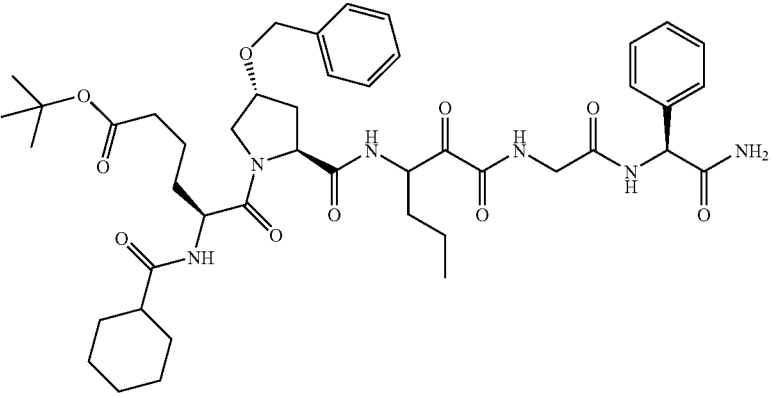 | C |
| 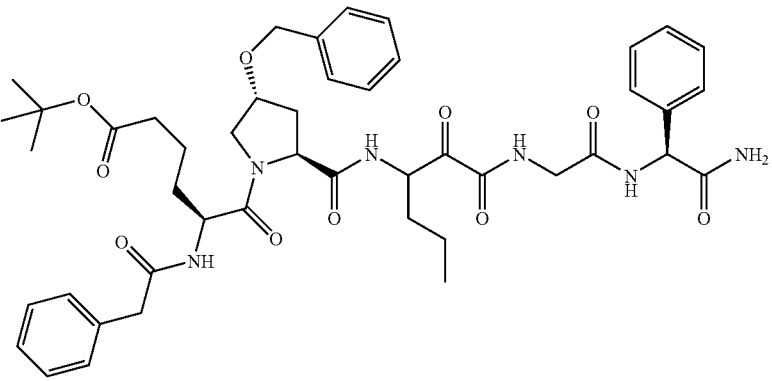 | C |

TABLE 3-continued

Compounds prepared by Solid Phase Synthesis

| STRUCTURE | Ki* CLASS |
|---|---|
| | C |
| | C |
| 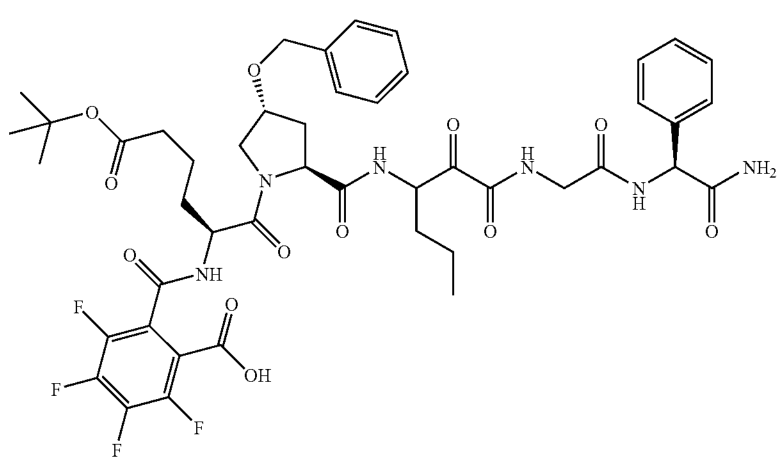 | B |

TABLE 3-continued

Compounds prepared by Solid Phase Synthesis

| STRUCTURE | Ki* CLASS |
|---|---|
| | C |
| | C |
| | C |
| | C |

TABLE 3-continued
Compounds prepared by Solid Phase Synthesis
| STRUCTURE | Ki* CLASS |
|---|---|
| 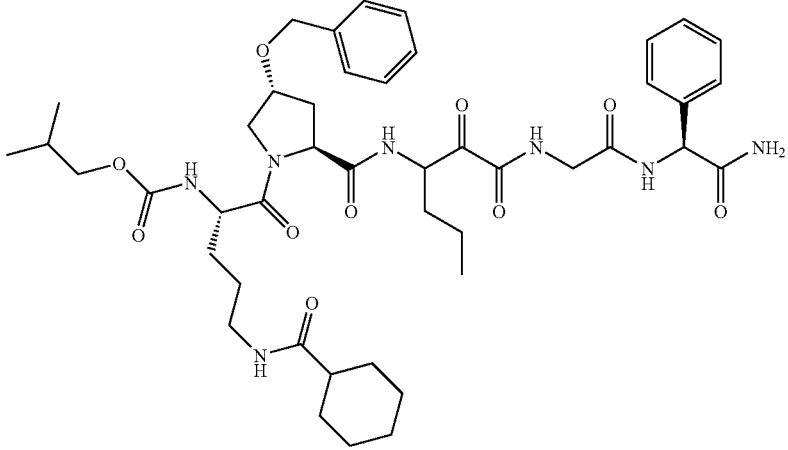 | C |
| 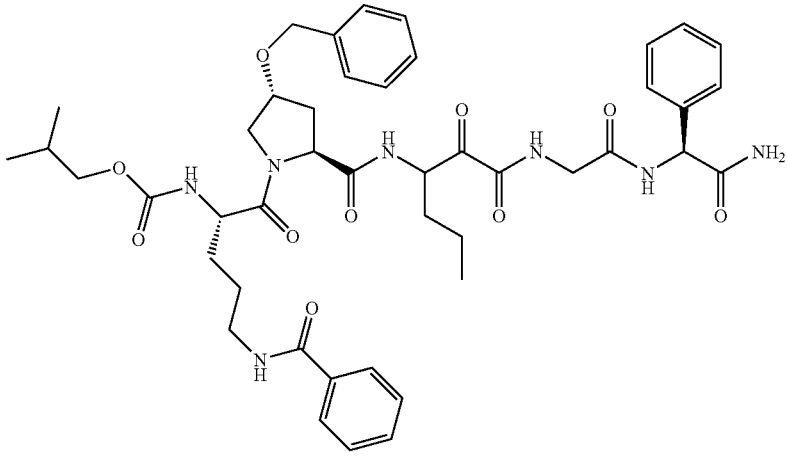 | C |
| 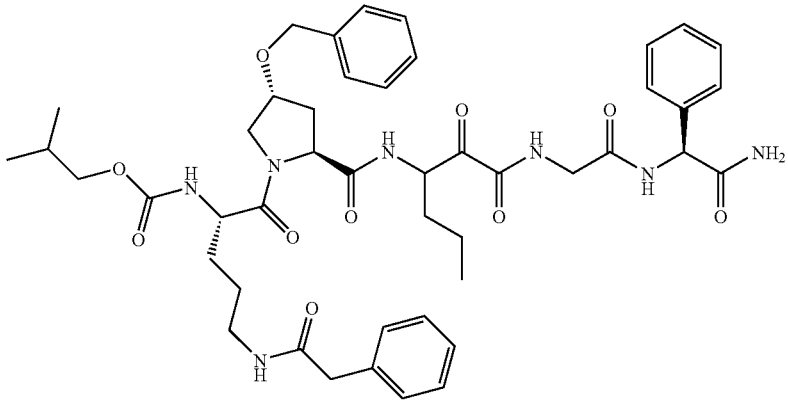 | C |

TABLE 3-continued

Compounds prepared by Solid Phase Synthesis

| STRUCTURE | Ki* CLASS |
|---|---|
| | C |
| | C |
| | C |

TABLE 3-continued

Compounds prepared by Solid Phase Synthesis

| STRUCTURE | Ki* CLASS |
|---|---|
| | C |
| | C |
| | C |

TABLE 3-continued

Compounds prepared by Solid Phase Synthesis

| STRUCTURE | Ki* CLASS |
|---|---|
| | B |
| | B |
| | B |

TABLE 3-continued
Compounds prepared by Solid Phase Synthesis
| STRUCTURE | Ki* CLASS |
|---|---|
| 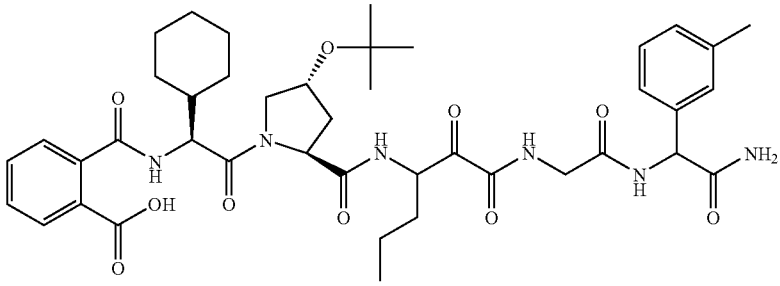 | B |
| 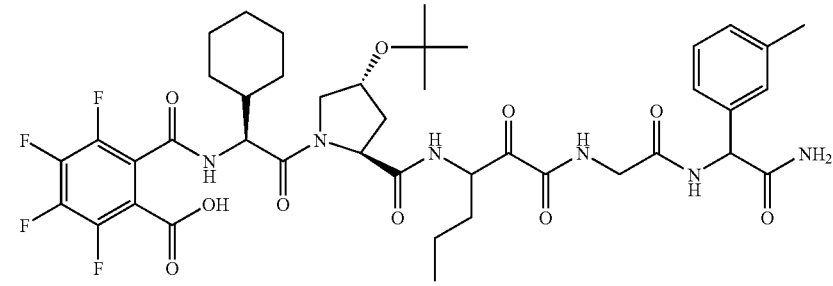 | B |
| 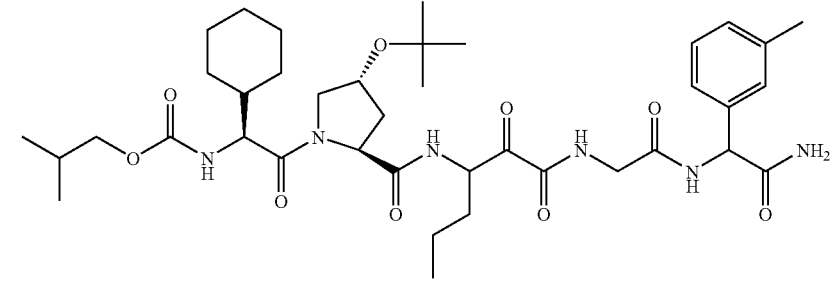 | B |
| 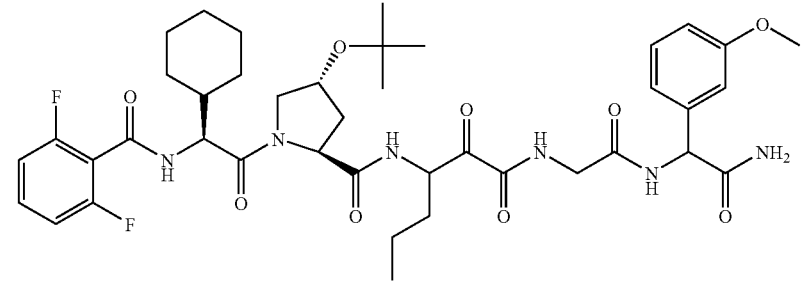 | B |
| 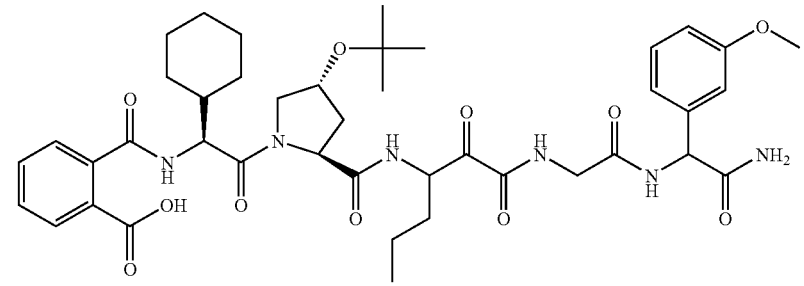 | B |

TABLE 3-continued
Compounds prepared by Solid Phase Synthesis
| STRUCTURE | Ki* CLASS |
|---|---|
| 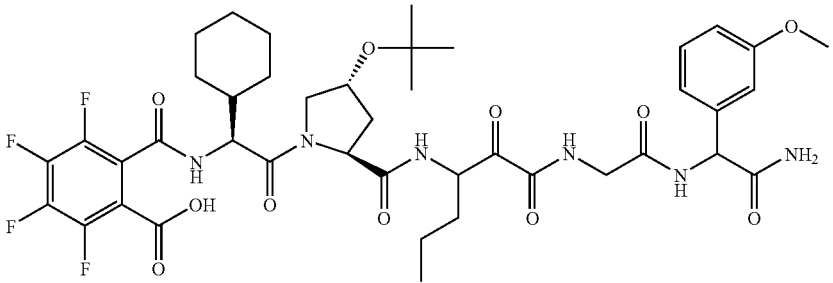 | B |
| 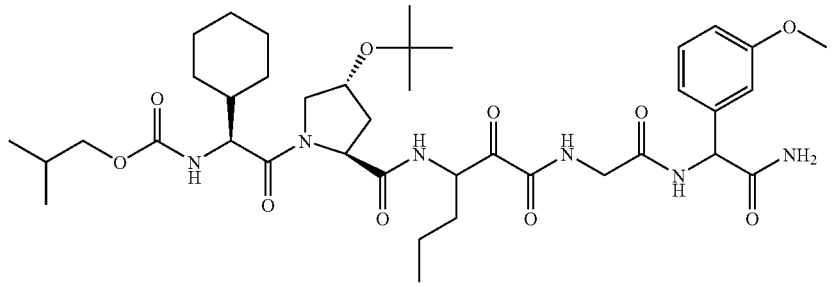 | B |
| 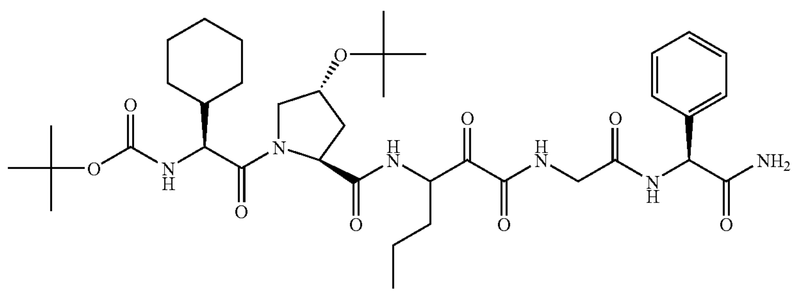 | C |
|  | B |
| 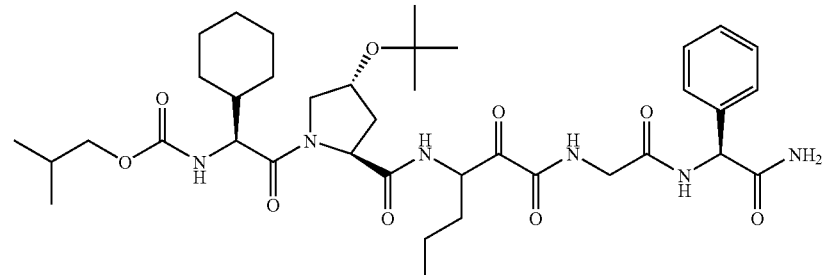 | B |

TABLE 3-continued

Compounds prepared by Solid Phase Synthesis

| STRUCTURE | Ki* CLASS |
| --- | --- |
| | C |
| | B |
| | C |
| | B |

TABLE 3-continued
Compounds prepared by Solid Phase Synthesis
| STRUCTURE | Ki* CLASS |
|---|---|
| 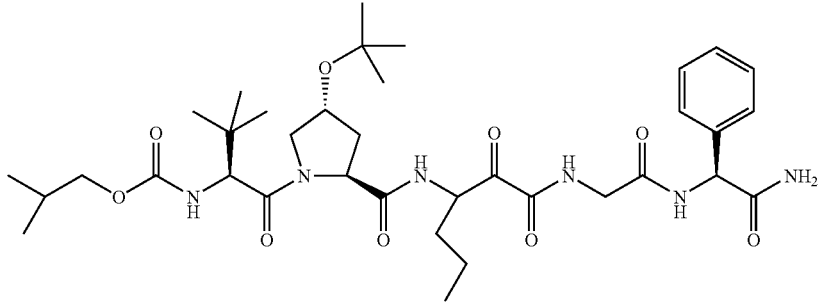 | B |
| 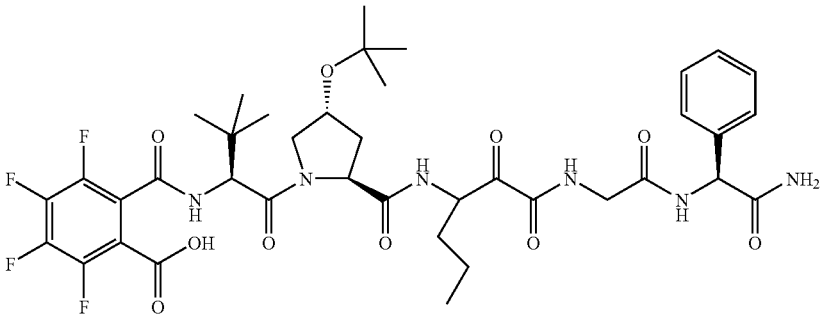 | B |
| 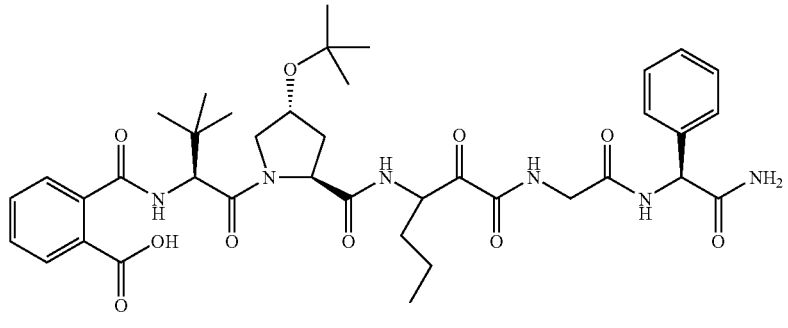 | B |
| 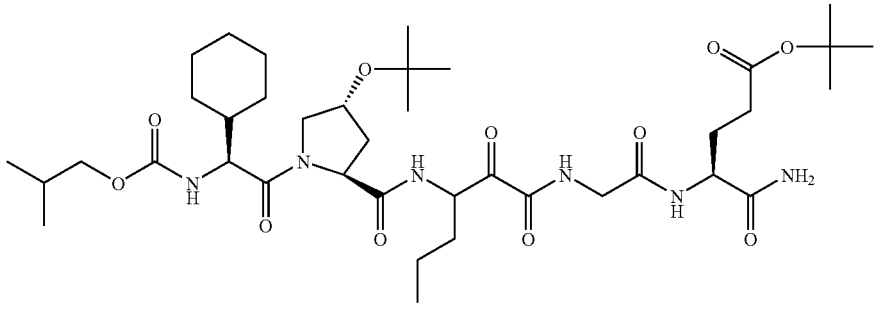 | C |

TABLE 3-continued
Compounds prepared by Solid Phase Synthesis
| STRUCTURE | Ki* CLASS |
|---|---|
| 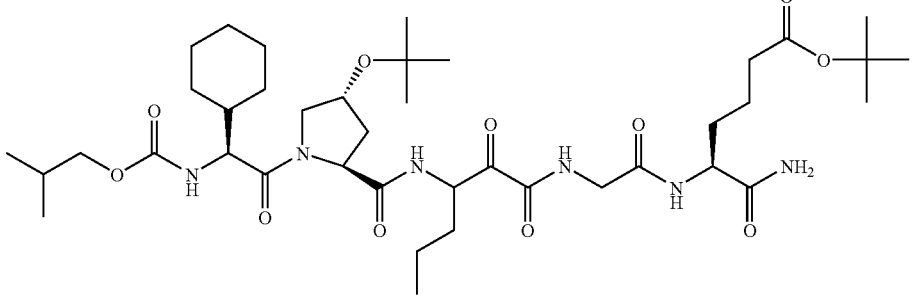 | C |
| 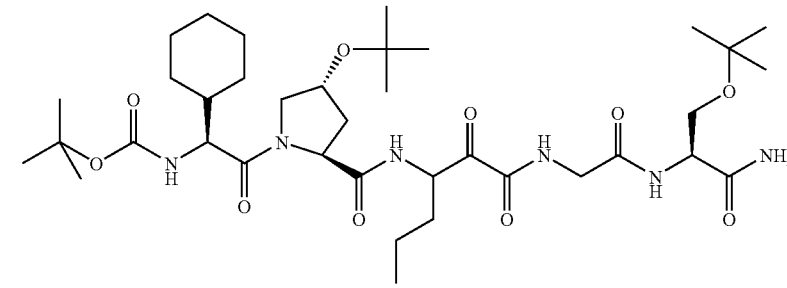 | C |
| 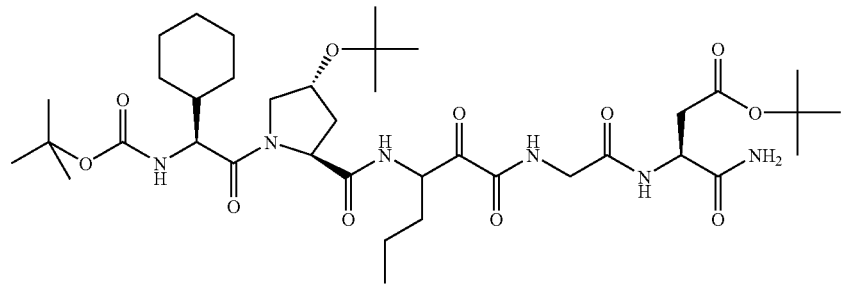 | C |
| 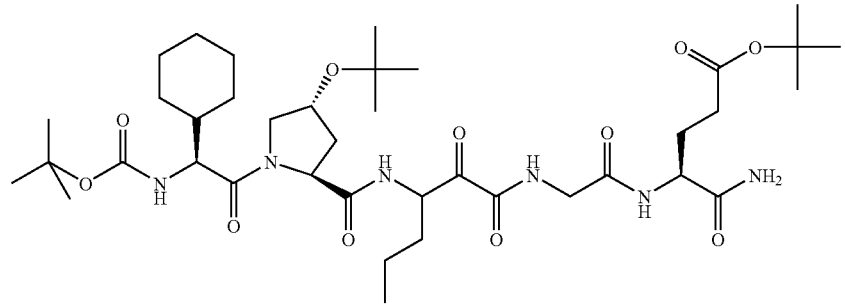 | C |
| 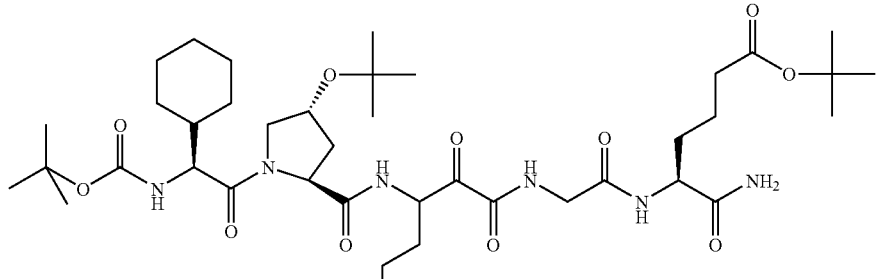 | C |

TABLE 3-continued
Compounds prepared by Solid Phase Synthesis
| STRUCTURE | Ki* CLASS |
|---|---|
| 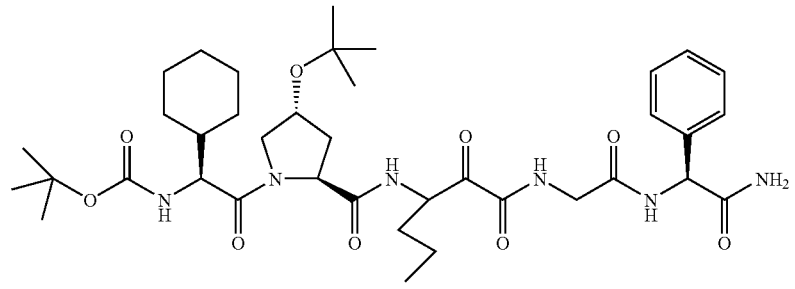 | B |
| 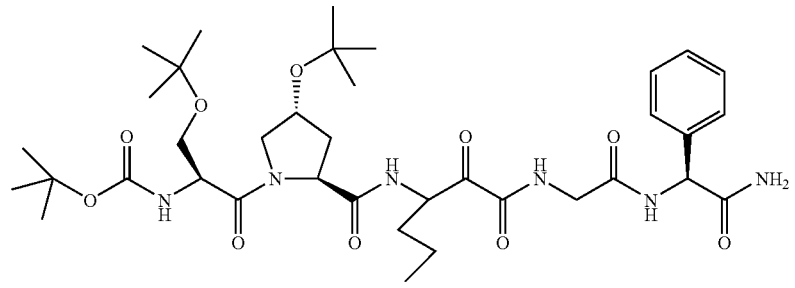 | C |
| 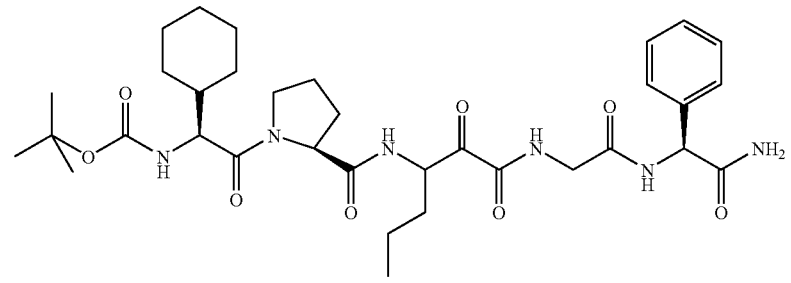 | C |
| 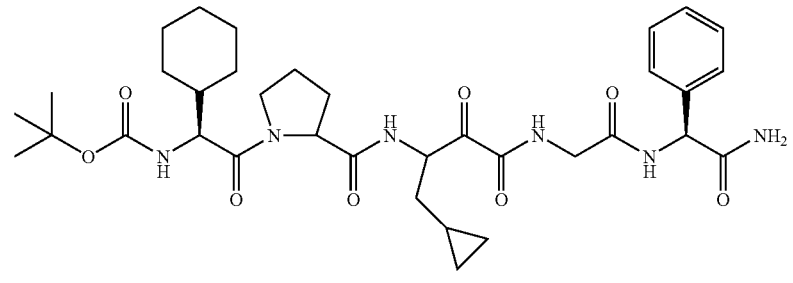 | C |
| 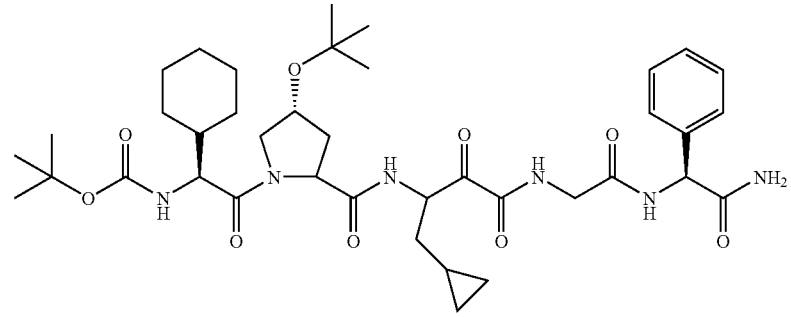 | B |

TABLE 3-continued

Compounds prepared by Solid Phase Synthesis

| STRUCTURE | Ki* CLASS |
|---|---|
| | C |
| 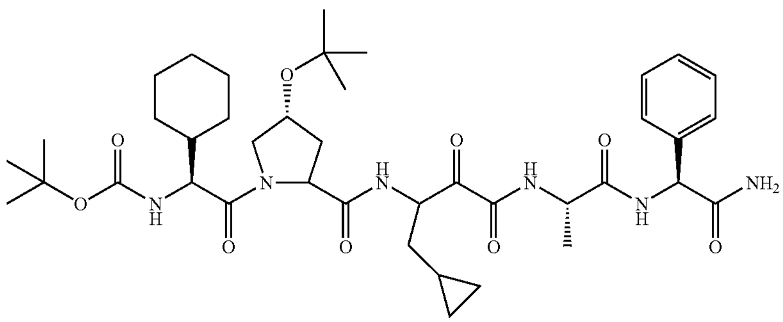 | B |
| | C |
| | C |
| | C |

TABLE 3-continued

Compounds prepared by Solid Phase Synthesis

| STRUCTURE | Ki* CLASS |
|---|---|
| | C |
| | B |
| | B |
| | C |

TABLE 3-continued

Compounds prepared by Solid Phase Synthesis

| STRUCTURE | Ki* CLASS |
|---|---|
|  | C |
|  | C |
|  | C |

Additional compounds that were prepared and their activity (Ki*) ranges are given in the attached Tables 4, 5 and 6. The procedure used to prepare the compounds in Tables 4, 5 and 6 is outlined below.

I) Synthesis of Intermediates for the Compounds in Tables 4, 5 and 6:

EXAMPLE I

Synthesis of 4,4-dimethyl proline methyl ester (H-Pro(4,4-diMe)-OMe)

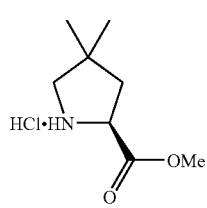

Step 1. Synthesis of tert-Butyl N-tert-butoxycarbonyl-4-methyl-L-pyroglutamate (Boc-PyroGlu(4-methyl)-OtBu):

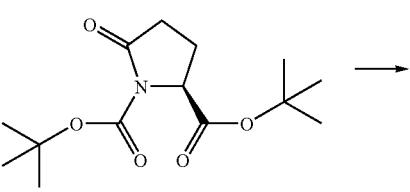

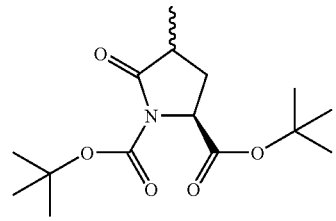

To a solution of tert-butyl N-tert-butoxycarbonyl-pyroglutamate (11.5 g, 40 mmol) in THF (200 mL) stirring at −78° C., was added a 1 M solution of lithium hexamethyldisilazide in THF (42 mL, 42 mmol) dropwise over 5 minutes. After 30 minutes, methyliodide (3.11 mL, 50 mmol) was added. After an additional 2 hours at −78° C., the cooling bath was removed and 50% saturated aqueous ammonium chloride (200 mL) was added. The solution was stirred for 20 minutes, then extracted with ether (3×200 mL). The combined organic layers were washed with brine (200 mL), dried (Na₂SO₄), filtered and concentrated. The residue was chromatographed with 1:1 ethylacetate/hexanes to give Boc-PyroGlu(4-methyl)-OtBu (10.6 grams, 35.4 mmol, 88%) as a mixture of isomers (2:1 cis to trans).

Step 2. Synthesis of tert-Butyl N-tert-butoxycarbonyl-4,4-dimethyl-L-pyroglutamate (Boc-PyroGlu(4,4-dimethyl)-OtBu):

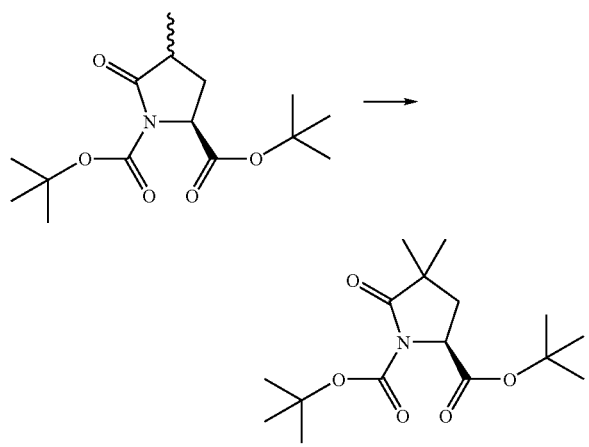

To a solution of tert-butyl N-tert-butoxycarbonyl-4-methyl-L-pyroglutamate (1.2 g, 4.0 mmol) in tetrahydrofuran (20 mL) stirring at −78° C., was added a 1 M solution of lithium hexamethyldisilazide in tetrahydrofuran (4.4 mL, 4.4 mmol) dropwise over 5 minutes. After 30 minutes, methyliodide (0.33 mL, 5.2 mmol) was added. After an additional 3 hours at −78° C., the cooling bath was removed and 50% saturated aqueous ammonium chloride (40 mL) was added. The solution was stirred for 20 minutes, then extracted with ether (2×50 mL). The combined organic layers were washed with water (2×25 mL), saturated sodium bicarbonate (2×25 mL), brine (50 mL), dried (Na₂SO₄), filtered and concentrated to give Boc-PyroGlu(4,4-dimethyl)-OtBu (0.673 g, 54%).

Step 3. Synthesis of tert-butyl N-tert-butoxycarbonyl-4,4-dimethylproline (Boc-Pro(4, 4-dimethyl)-OtBu):

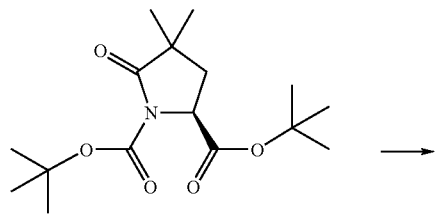

-continued

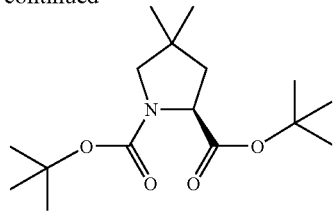

Modification of known procedure: Pedregal, C.; Ezquerra, J.; Escribano, A.; Carreno, M. C.; Garcia Ruano, J. L. *Tetrahedron Letters* 1994, 35(13), 2053-2056).

To a solution of tert-butyl N-tert-butoxycarbonyl-4,4-dimethylpyroglutamate (2.0 mmol) in tetrahydrofuran (5 mL) stirring at −78° C., was added a 1 M solution of lithium triethylborohydride in tetrahydrofuran (2.4 mL, 2.4 mmol) dropwise over 5 minutes. After 30 minutes, the cooling bath was removed and saturated aqueous sodium bicarbonate (5 mL) was added. The reaction mixture was immersed in an ice/water bath and 30% aqueous hydrogen peroxide (10 drops) was added. The solution was stirred for 20 minutes at 0° C., then the reaction mixture was concentrated in vacuo to remove the tetrahydrofuran. The aqueous solution was diluted with water (10 mL) and extracted with dichloromethane (3×40 mL). The organic layers were dried (Na₂SO₄), filtered and concentrated. The residue was dissolved in dichloromethane (20 mL) and triethylsilane (310 μL, 2.0 mmol), then cooled to −78° C. and boron trifluoride diethyletherate (270 μL, 2.13 mmol) was added dropwise. Stirring was continued for 30 minutes, at which time additional triethylsilane (310 μL, 2.0 mmol) and boron trifluoride diethyletherate (270 μL, 2.13 mmol) were added. After stirring at −78° C. for an additional two hours, the cooling bath was removed and saturated aqueous sodium bicarbonate (4 mL) was added. After 5 minutes the mixture was extracted with dichloromethane (3×40 mL). The organic layers were dried (Na₂SO₄), filtered and concentrated to give Boc-Pro(4,4-dimethyl)-OtBu.

Step 4. Synthesis of 4,4-dimethylproline (H-Pro(4,4-dimethyl)-OH):

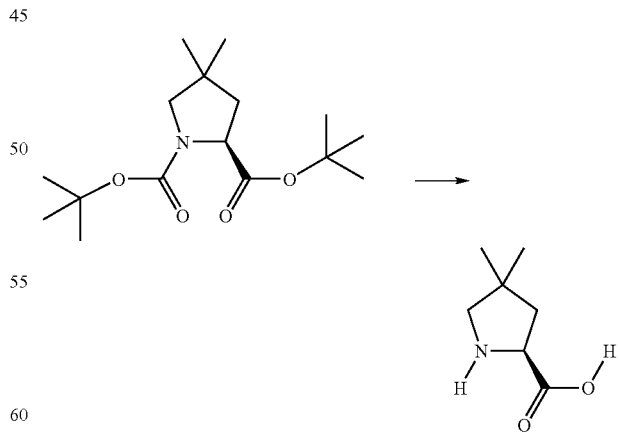

A solution of tert-butyl N-tert-butoxycarbonyl-4,4-dimethylproline in dichloromethane (5 mL) and trifluoroacetic (5 mL) was stirred at room temperature for five hours. The solution was concentrated, dried under high vacuum and taken to the next step without further purification.

Step 5. Synthesis of N-tert-butoxycarbonyl 4,4-dimethylproline (Boc-Pro(4,4-dimethyl)-OH):

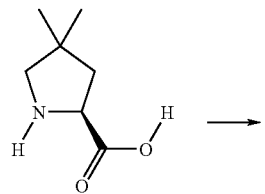

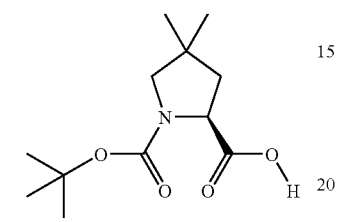

To a solution of 4,4-dimethylproline trifluoroacetic salt (1.5 mmol) in dioxane (7 mL), acetonitrile (12 mL) and diisopropylethylamine (700 µL, 4 mmol) was added a solution of di-tert-butyl-dicarbonate (475 mg, 2.18 mmol) in acetonitrile (5 mL). After stirring for 12 hours at room temperature the solution was concentrated in vacuo, dissolved in saturated aqueous sodium bicarbonate (50 mL) and washed with diethyl ether (3×40 mL). The aqueous layer was acidified to pH=3 with citric acid, then extracted with dichloromethane (3×40 mL). The combined organic layers were dried over sodium sulfate filtered and concentrated.

Step 6. Synthesis of 4,4-dimethylproline methylester hydrochloride salt (HCl.H-Pro(4,4-dimethyl)-OMe):

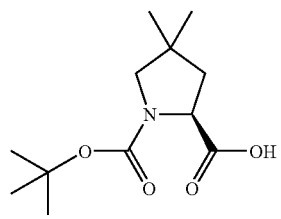

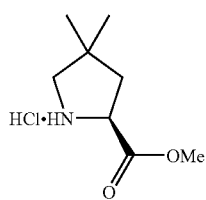

To a solution of Boc-Pro(4,4-diMe)-OH (0.5 g, 2.06 mmol) in anhydrous methanol (8 ml) was added dropwise thionylchloride (448 l, 6.18 mmol) and the reaction was stirred for six hours at room temperature. The reaction mixture was concentrated to an amorphous solid (377 mg, 95%).

EXAMPLE II

General Procedure for the synthesis of N-tertbutoxycarbonyl-4-alkyl-4-methyl proline

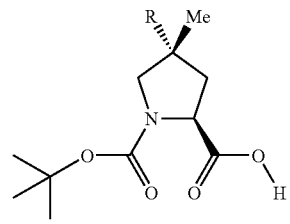

Compounds where R group is allyl and benzyl were synthesized following steps 1-4 below:

Step 1. Synthesis of tert-Butyl N-tert-butoxycarbonyl-4-alkyl-4-methyl-L-pyroglutamate:

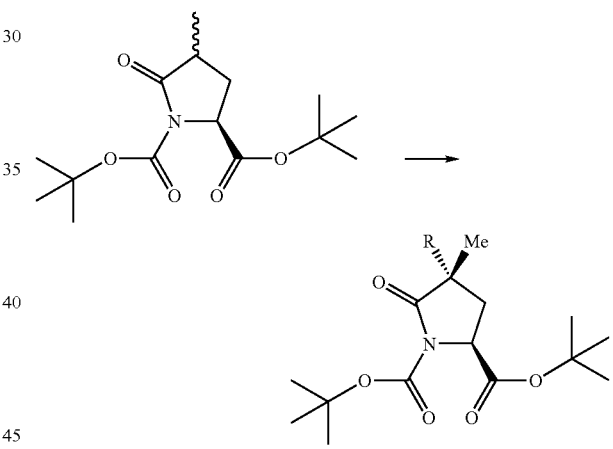

To a solution of tert-butyl N-tert-butoxycarbonyl-4-methyl-L-pyroglutamate (10.2 g, mmol) (see Example I, step 1) in tetrahydrofuran (170 mL) stirring at −78° C., was added a 1 M solution of lithium hexamethyldisilazide in tetrahydrofuran (37.5 mL, 37.5 mmol) dropwise over 5 minutes. After 40 minutes, alkyl halide (61.4 mmol) was added. After an additional 3 hours at −78° C., the cooling bath was removed and 50% saturated aqueous ammonium chloride (200 mL) was added. The solution was stirred for 20 minutes, then extracted with ether (2×200 mL). The combined organic layers were diluted with hexanes (150 mL) and washed with saturated sodium bicarbonate (100 mL), water (2×100 mL) and brine (100 mL), dried ($Na_2SO_4$), filtered and concentrated. The residue was flash chromatographed using 20% ethylacetate in hexanes to give the pure tert-Butyl N-tert-butoxycarbonyl-4-alkyl-4-methyl-L-pyroglutamate.

Step 2. Synthesis of tert-butyl N-tert-butoxycarbonyl-4-alkyl-4-methylproline:

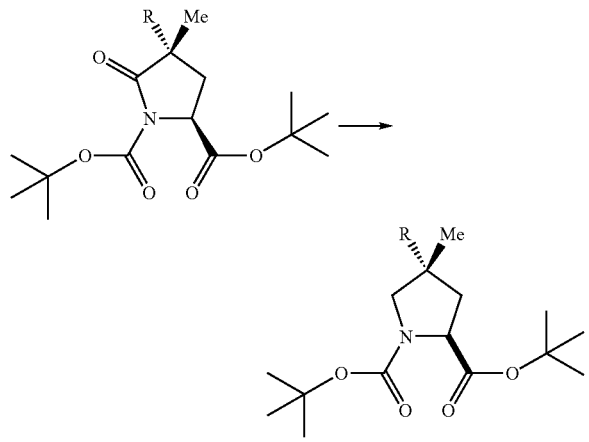

Modification of known procedure: Pedregal, C.; Ezquerra, J.; Escribano, A.; Carreno, M. C.; Garcia Ruano, J. L. *Tetrahedron Letters* (1994) 35(13), 2053-2056).

To a solution of tert-butyl N-tert-butoxycarbonyl-4-alkyl-4-methylpyroglutamate (16.6 mmol) in tetrahydrofuran (40 mL) stirring at −78° C., was added a 1 M solution of lithium triethylborohydride in tetrahydrofuran (20 mL, 20 mmol) dropwise over 10 minutes. After 120 minutes, the cooling bath was allowed to warm to −25° C. at which point saturated aqueous sodium bicarbonate (40 mL) was added. The reaction mixture was immersed in an ice/water bath and 30% aqueous hydrogen peroxide (4 mL) was added. The solution was stirred for 10 minutes at 0° C., then the reaction mixture was concentrated in vacuo to remove the tetrahydrofuran. The aqueous solution was diluted with water (300 mL) and extracted with dichloromethane (3×200 mL). The organic layers were dried (sodium sulfate), filtered and concentrated. The residue was dissolved in dichloromethane (100 mL) and triethylsilane (2.6 mL, mmol), then cooled to −78° C. and boron trifluoride diethyletherate (2.2 mL, mmol) was added dropwise. Stirring was continued for 1 hour, at which time additional triethylsilane (2.6 mL, mmol) and boron trifluoride diethyletherate (2.2 mL, mmol) were added. After stirring at −78° C. for an additional 4 hours, the cooling bath was removed and saturated aqueous sodium bicarbonate (30 mL) and water (150 mL) were added. After 5 minutes the mixture was extracted with dichloromethane (3×200 mL). The organic layers were dried (Na$_2$SO$_4$), filtered and concentrated.

Step 3. Synthesis 4-alkyl-4-methylproline:

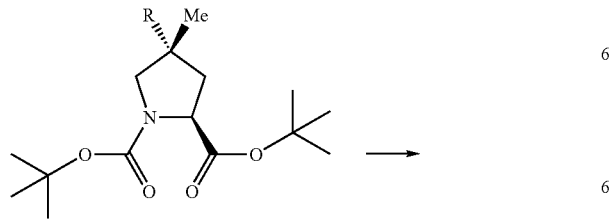

-continued

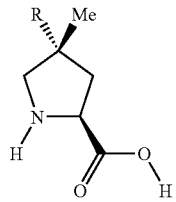

A solution of tert-butyl N-tert-butoxycarbonyl-4-alkyl-4-methylproline in dichloromethane (5 mL) and trifluoroacetic (5 mL) was stirred at room temperature for 5 hours. Toluene was added and the solution was concentrated and then dried under high vacuum.

Step 4. Synthesis of N-tert-butoxycarbonyl 4-alkyl-4-methylproline:

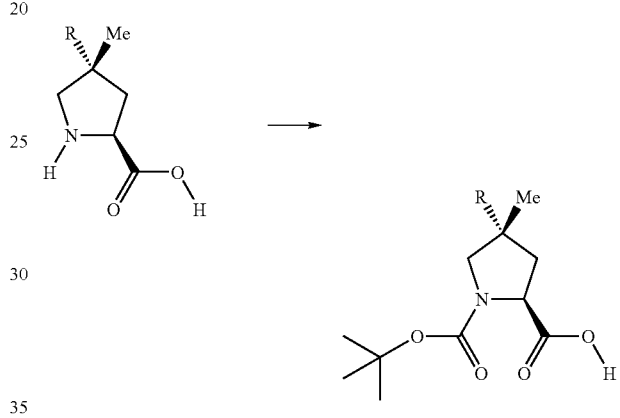

To a solution of 4-alkyl-4-methylproline trifluoroacetic salt (1.5 mmol) in dioxane (7 mL), acetonitrile (12 mL) and diisopropylethylamine (700 μL, 4 mmol) was added a solution of di-tert-butyl-dicarbonate (475 mg, 2.18 mmol) in acetonitrile (5 mL). After stirring for 12 hours at room temperature the solution was concentrated in vacuo, dissolved in saturated aqueous sodium bicarbonate (50 mL) and washed with diethyl ether (3×40 mL). The aqueous layer was acidified to pH=3 with 1 N hydrochloric acid, then extracted with dichloromethane (3×40 mL). The combined organic layers were dried (Na$_2$SO$_4$), filtered and concentrated. The residue was purified by flash chromatography using 1:1 ethylacetate/hexanes with 1% acetic acid.

EXAMPLE III

Synthesis of N-tert-butoxycarbonyl 4-propyl-4-methylproline

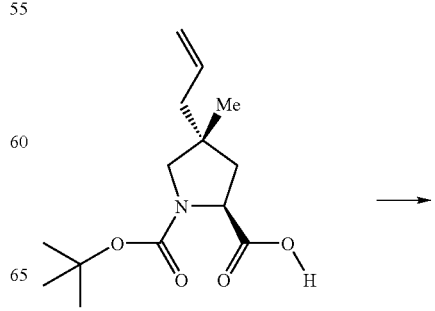

-continued

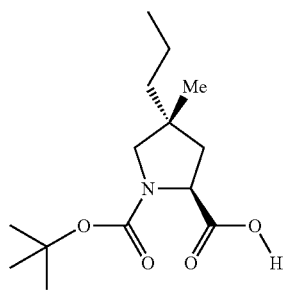

A solution of N-tertbutoxycarbonyl-4-allyl-4-methylproline (400 mg, 1.48 mmol) (see Example II Step 4) and 10% Pd on carbon (400 mg) in methanol (20 mL) was hydrogenated at 50 psi for 4 hours. The mixture was filtered and concentrated.

EXAMPLE IV

Synthesis of Boc-4-cyclohexylproline

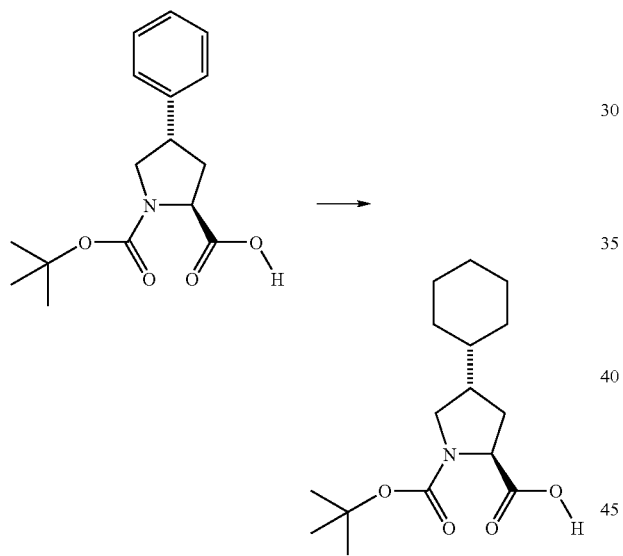

A solution of the commercially available Boc-4-phenylproline (750 mg) and 5% Rh on carbon (750 mg) in methanol (15 mL) was hydrogenated at 50 psi for 24 hours. The mixture was filtered and concentrated to give 730 mg of product.

EXAMPLE V

Preparation of Fluorenylmethoxycarbonyl-Pro(4-spirocyclopentane)-carboxylic acid

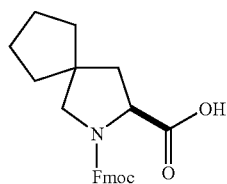

Step 1. Synthesis of Boc-pyroglutamic(4-allyl)-tert-butylester:

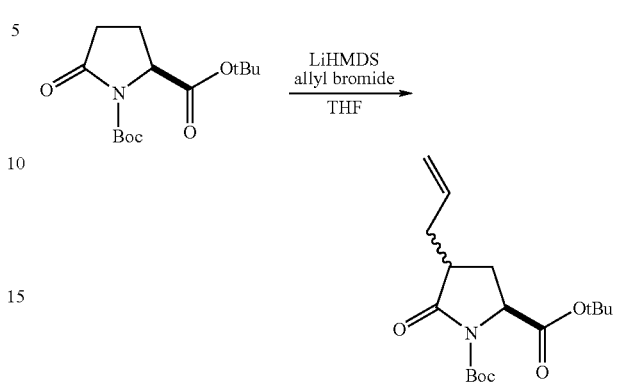

To a cooled (−78° C.) solution of the commercially available N-Boc-tert-butyl pyroglutamate (10 g, 35.1 mmol) in THF (175 ml) was added lithium hexamethyldisilazide (36.8 mL, 36.8 mmol) over five minutes. Stirring continued for thirty minutes. A solution of allyl bromide (6.1 ml, 70.2 mmol) in THF (39 mL) was added dropwise to the first solution. After two hours at −78° C., the reaction was quenched by the slow addition of saturated ammonium chloride (50 mL) solution. The reaction mixture was then diluted with ethylacetate and the layers were separated. The organic layer dried over sodium sulfate and concentrated. Flash column chromatography carried out in 2:8 ethylacetate:hexanes afforded the product (6 g, 53%). NMR δ ppm (CDCl$_3$): 5.7 (m, 1H), 5.1 (dd, 2H), 4.4 (m, 1H), 2.6 (m, 2H), 2.4 (m, 1H), 1.8-2.2 (m, 1H), 1.45 (s, 9H), 1.4 (s, 9H).

Step 2. Synthesis of N-Boc-pyroglutamic(4,4-diallyl)-tert-butylester:

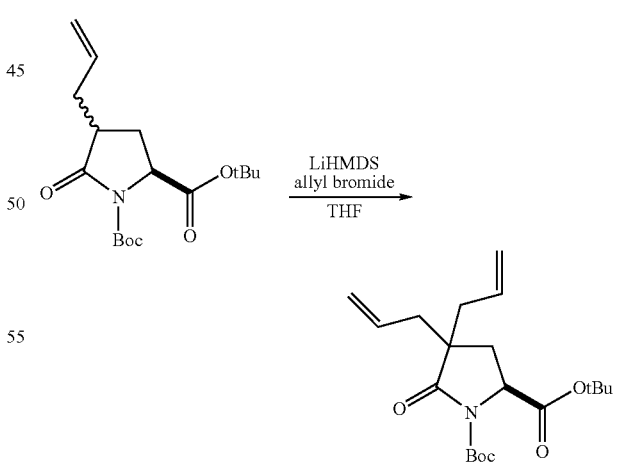

N-Boc-pyroglutamic(4-allyl)-tert-butylester obtained in the Step 1 above (2.68 g, 8.24 mmol) was subjected to a second alkylation with allyl bromide under similar conditions. Flash chromatography in 15:85 ethylacetate:hexanes provided 2.13 g product (71%) as a clear oil.

Step 3. Synthesis of Boc-Pro(4,4-diallyl)-tert-butylester:

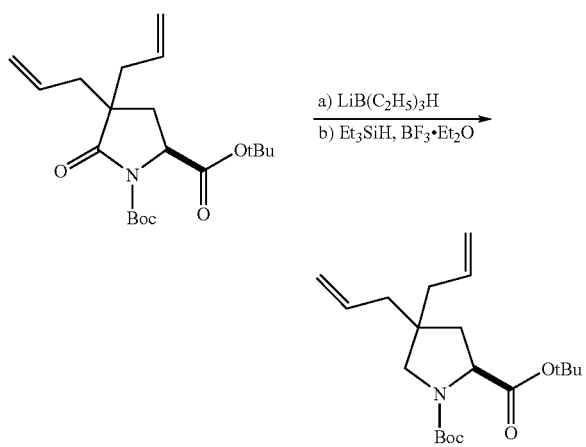

Part a: To a cooled (−78° C.) solution of Boc-PyroGlu(4,4-diallyl)-tert-butylester (2.13 g, 5.83 mmol) in tetrahydrofuran (14 ml) was added lithium triethylborohydride (1 M in tetrahydrofuran, 7.29 ml, 7.29 mmol) over five minutes. After two hours at −78° C., the reaction was warmed-up to 0° C. and quenched by the slow addition of saturated sodium bicarbonate solution (20 ml) and 30% hydrogen peroxide (20 drops). Stirring continued for 20 minutes. The tetrahydrofuran was removed under reduced pressure and the remaining thick white residue was diluted with water (80 ml) and extracted three times with dichloromethane. The organic layer was dried, filtered and concentrated and taken to the next step without further purification.

Part b): To the product obtained in part (a) in dichloromethane (14 ml) was added triethylsilane (931 μl, 5.83 mmol) followed by boron trifluoride diethyl etherate (776 μl, 6.12 mmol). After thirty minutes more triethylsilane (931 μl, 5.83 mmol) and boron trifluoride diethyl etherate etherate (776 μl, 6.12 mmol) were added and the reaction was stirred at −78° C. for three hours at which time the reaction was quenched by the slow addition of saturated sodium bicarbonate solution and water. The reaction mixture was extracted with dichloromethane and the organic layer was dried, filtered and concentrated. Flash column chromatography in 15% ethylacetate in hexanes afforded 1.07 colorless oil (57%). NMR δ ppm (CDCl$_3$): 5.7-5.8 (m, 2H), 5.1 (m, 4H), 4.1-4.2 (2 dd's, 1H rotamers), 3.5-3.3 (dd, 1H) and 3.2 (dd, 1H) rotamers, 2.2-2.0 (m, 5H), 1.7(m, 1H), 1.46 (s, 9H), 1.43 (s, 9H).

Step 4. Synthesis of Boc-Pro(4-spirocyclopentene)-tert-butylester:

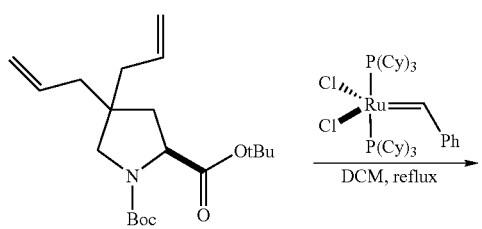

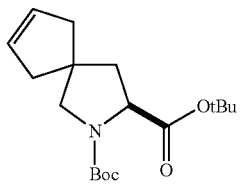

To Boc-Pro(4,4-diallyl)-tert-butylester (1.07 g, 3.31 mmol) in dichloromethane (66 ml) was added 5% Bis(tricyclohexylphosphin)benzylidene ruthenium IV dichloride (Grubbs catalyst) and the mixture was heated at reflux for 1.5 hours. The reaction mixture was concentrated and the remaining residue was purified by flash column chromatography in 15% ethylacetate in hexanes. A yellow oil was obtained (0.57 g, 53%). NMR δ ppm (CDCl$_3$): 5.56 (bs, 2H), 4.2 and 4.1 (t, 1H, rotamers), 3.2-3.5 (m, 2H), 2.2-2.5 (m, 5H), 1.9 (dd, 1H) 1.47 and 1.46 (2 s's, 9H, rotamers), 1.45 and 1.44 (2 s's, 9H, rotamers).

Step 5. Synthesis of Boc-Pro(4-spirocyclopentane)-tert-butylester:

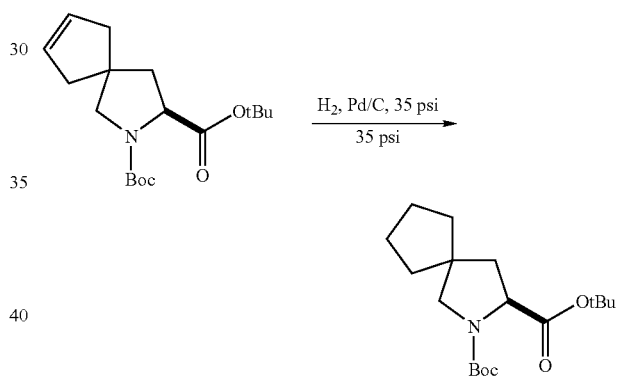

A solution of Boc-Pro(4-spirocyclopentene)-tert-butylester (1.12 g) in methanol (18 ml), water (4 ml) and acetic acid (4 ml) was placed in the Parr shaker and was hydrogenated for three hours at 35 psi in the presence of 10% palladium on carbon (300 mg). The catalyst was filtered off and the filtrate was concentrated to a colorless oil (1.26 g). NMR δ ppm (CDCl$_3$): 4.1 and 4.2 (t, 1H, rotamers), 3.4 (d, 1H), 3.2 (d, 1H), 2.1 (m, 1H), 1.9 (m, 1H), 1.6-1.7 (m, 10H), 1.5 (3 s's, 18H, rotamers).

Step 6. Synthesis of Fmoc-Pro(4-spirocyclopentane)-carboxylic acid:

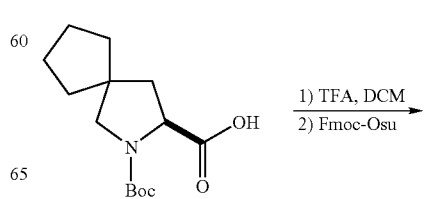

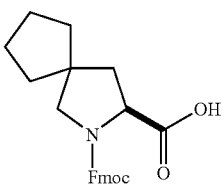

The Boc-Pro(4-spirocyclopentane)-tert-butylester (1.26, 3.9 mmol) was treated with dichloromethane (10 ml) and trifluoroacetic acid (15 ml) for three hours. The reaction mixture was concentrated and the yellow oil obtained was dissolved in water (6 ml). Fluorenylmethyl succinyl carbonate (1.45 g, 4.3 mmol) dissolved in dioxane (6 ml) was added portionwise followed by the addition of potassium carbonate (2.16 g, 15.6 mmol). The reaction was stirred for 18 hours and concentrated. The remaining residue was diluted with the saturated sodium bicarbonate solution (10 mL) and washed with diethylether (3×10 ml). The aqueous layer was then acidified to pH ~1 with 1 N sodium bisulfate solution and extracted with ethylacetate. The organic layer was dried over sodium sulfate, filtered and concentrated to a beige foam (1.3 g, 100%).

EXAMPLE VI

Synthesis of Boc-Pro(4t-NH(Fmoc))-OH

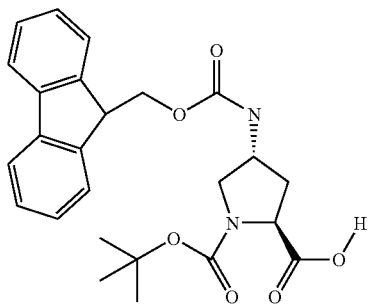

Step 1. Synthesis of N$^\alpha$-tert-butoxycarbonyl-cis-4-chloro-L-proline benzyl ester:

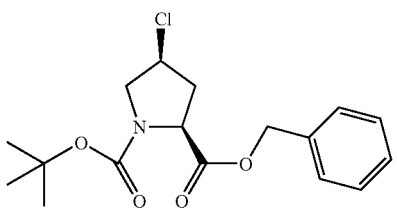

A mixture of the commercially available N-tert-butoxycarbonyl-trans-4-hydroxy-proline (8.79 g, 38 mmol), potassium carbonate (13.0 g, 94 mmol), benzyl bromide (4.5 ml, 38 mmol) and dimethylformamide (150 mL) was stirred for 18 h. Addition of ethyl acetate (100 mL) was followed by filtration. The white cloudy filtrate was clarified by the addition of 1 M HCl (100 mL). The layers were separated and the aqueous layer was extracted with additional ethyl acetate (2×100 mL). The combined organic layers were washed with water (2×50 mL), dried (sodium sulfate), filtered and concentrated. Toluene was added to the crude benzyl ester, and the solution was filtered and reconcentrated. Dichloromethane (70 mL) and carbon tetrachloride (70 mL) was added, followed by triphenylphosphine (21.11 g, 80 mmol). The reaction mixture was stirred for 10 h, quenched with ethanol (7 mL) and stirred for 5 more h. The solution was concentrated to approx. 100 ml, then dichloromethane (40 mL) was added, followed by the addition of ether (200 mL) while stirring. The solution was cooled for 4 h, filtered and concentrated to give a yellow-brown oil which was purified by flash chromatography using ether/hexane/dichloromethane 2:2:1 to give the title compound (9.13 g, 26.9 mmol, 71%) as a white solid.

Step 2. Synthesis of N$^\alpha$-tert-butoxycarbonyl-trans-4-azido-L-proline benzyl ester:

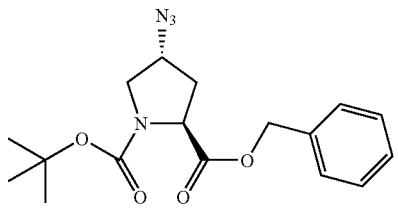

A solution of N$^\alpha$-tert-butoxycarbonyl-cis-4-chloro-L-proline benzyl ester (9.0 g, 26.5 mmol) and sodium azide (7.36 g, 113 mmol) in dimethylformamide (270 mL) was heated at 75° C. for 2 days. Water (100 mL) was added and the reaction mixture was extracted with ethyl acetate (3×100 mL). The combined organic layers were washed with water (3×50 mL), dried (sodium sulfate), filtered and concentrated. The oil was purified by flash chromatography using ethyl acetate/hexanes 1:1 to give the title compound (8.59 g, 24.8 mmol, 94%).

Step 3. Synthesis of Boc-Pro(4t-NH(Fmoc))-OH:

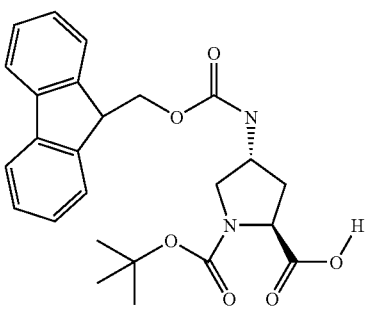

A mixture of N-α-t-butoxycarbonyl-trans-4-azido-L-proline benzyl ester (8.59 g, 24.8 mmol) and 10% palladium on carbon (900 mg) in ethanol (500 mL) was hydrogenated at 50 psi for 14 h using a Parr hydrogenation apparatus. The mixture was filtered, concentrated, dissolved in methanol (60 mL), refiltered and concentrated to give a colorless oil. The oil was dissolved in water (53 mL) containing sodium carbonate (5.31 g, 50.1 mmol) and a solution of fluorenylmethyl succinyl carbonate (8.37 g, 29.8 mmol) in dioxane (60 mL) was added over 40 min. The reaction mixture was stirred at room temperature for 17 h, then concentrated to remove the dioxane and diluted with water (200 mL). The solution washed with ether (3×100 mL). The pH of the aqueous solution was adjusted to 2 by the addition of citric acid (caution! foaming!) and water (100 mL). The mixture was extracted with dichloromethane (400 mL, 100 mL, 100 mL) and the combined organic layers were dried (sodium sulfate), filtered and concentrated to give the title compound.

EXAMPLE VII

Synthesis of N-t-butoxycarbonyl-4-trans-(N-fluorenylmethyloxycarbonyl aminomethyl)-L-proline (Boc-Pro(4t-MeNHFmoc)-OH)

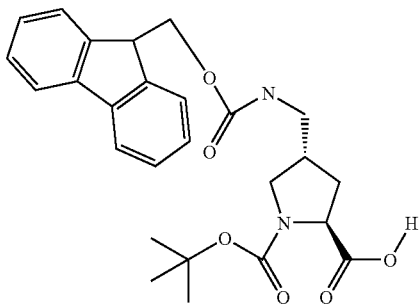

Step 1, Synthesis tert-butoxycarbonyl cis-4-hydroxy-L-proline benzyl ester (Boc-Pro(4-cis-OH)-OBn):

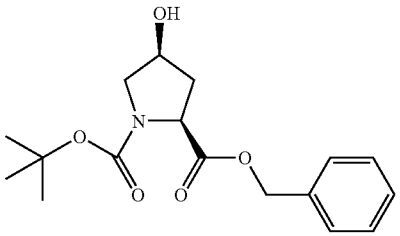

To a mixture of cis-hydroxy-L-proline (5 g, 38.1 mmol) in benzene (45 mL) and benzyl alcohol (45 mL) was added p-toluenesulfonic acid monohydrate (7.6 g, 40.0 mmol). The reaction mixture was heated at 125° C. for 20 h while water (2 ml) was removed using a Dean-Stark trap. The solution was filtered while still hot, and then ether (150 ml) was added. The solution was allowed to cool for three h at room temperature, then three h at 4° C. The resulting solid was collected, washed with ether (100 mL) and dried in vacuo for 1 h to give 13.5 grams of white solid. The solid was dissolved in dioxane (40 mL) and diisopropylethylamine (7.6 mL), and then di-tert-butyl-dicarbonate (10 g, 45.8 mmol) was added over 5 min while using an ice bath to maintain a constant reaction temperature. After 10 h at room temperature the reaction mixture was poured into cold water (200 mL) and extracted with ethyl acetate (3×200 mL). The combined organic layers were washed with water (3×100 mL) and saturated aqueous sodium chloride (50 mL), dried (sodium sulfate), filtered and concentrated. The crude product was purified by flash chromatography using 40-60% ethyl acetate in hexanes to give the title compound (10.04 g, 31.24 mmol, 82%).

Step 2. Synthesis of N-t-butoxycarbonyl cis-4-mesyloxy-L-proline benzyl ester (Boc-Pro(4-cis-OMs)-OBn):

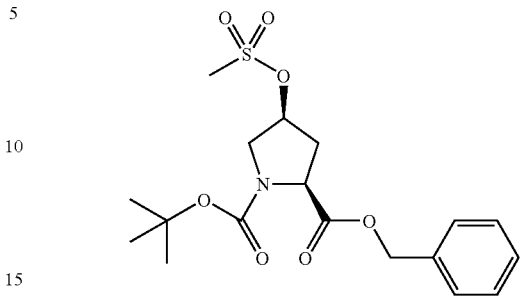

To a solution of Boc-Pro(4-cis-OH)-OBn (8.45 g, 26.3 mmol) in pyridine (65 mL) at 0° C., was added methanesulfonyl chloride (3.4 mL, 44 mmol) dropwise over 7 min. The reaction mixture was allowed to warm to room temperature over 2 h, then stirred overnight. A solution of 10% water in pyridine (20 mL) was added over 15 min and the reaction mixture was concentrated. The residue was dissolved in water and extracted with ethyl acetate (2×200 mL). The combined organic layers were washed with water (2×50 mL) saturated aqueous sodium bicarbonate (50 mL) and saturated aqueous sodium chloride (50 mL), dried (sodium sulfate), filtered and concentrated. The resulting residue was dissolved in toluene (100 mL) and concentrated to remove traces of pyridine. The residue was dried in vacuo for 30 min to afford the title compound (10.7 g, 102%), then used in the next step without purification.

Step 3. N-t-butoxycarbonyl-trans-4R-cyano-L-proline benzylester (Boc-Pro(4-trans-CN)-OBn):

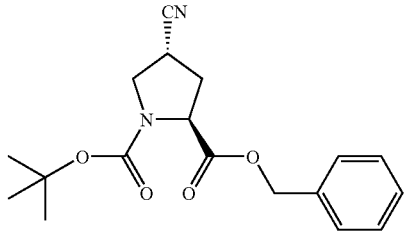

A solution of Boc-Pro(4-cis-OMs)-OBn (10.7 g, 26.3 mmol) and tetrabutylammonium cyamide (15.0 g, 56 mmol) in dimethylformamide (100 mL) was heated in an oil bath at 55° C. for 28 h. After cooling, water (150 mL) was added and the mixture was extracted with ethyl acetate (3×200 mL). The combined organic layers were washed with water (3×100 mL) and saturated aqueous sodium chloride (100 mL), dried (sodium sulfate), filtered and concentrated. The resulting residue was purified by flash chromatography (1:1 ether/hexanes) and then recrystallized from ethyl acetate/hexanes to provide the title compound (2.40 g, 7.26 mmol, 28%).

415

Step 4. N-t-butoxycarbonyl-4-trans-(N-fluorenylmethyloxycarbonyl aminomethyl)-L-proline (Boc-Pro(4t-MeNHFmoc)-OH):

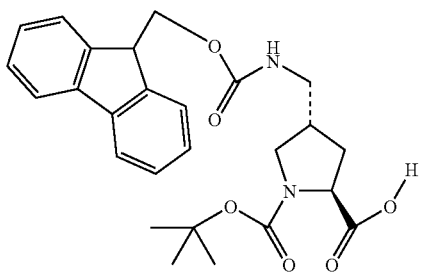

A mixture of the compound of Step 3 above (2.31 g, 7 mmol), water (10 mL), methanol (85 mL) and 10% palladium on carbon (700 mg) was hydrogenated at 50 psi for 11 h using a Parr hydrogenation apparatus. The mixture was filtered and concentrated. Water (15 mL) and sodium carbonate (1.5 g, 14.2 mmol) was added to the residue. A solution of fluorenylmethyl succinyl carbonate (2.36 g, 7.0 mmol) in dioxane (17 mL) was added over 5 min and stirring was continued for 28 h at room temperature. The reaction was concentrated in vacuo to a 15 mL volume, and water (100 mL) was added. The solution washed with ether (3×75 mL). The pH of the aqueous solution was adjusted to 2 by the addition of citric acid (approx. 20 g, caution! foaming!) and water (100 mL). The mixture was extracted with dichloromethane (4×100 mL), and the combined organic layers were dried (sodium sulfate), filtered and concentrated. The crude product contained a major impurity which necessitated a three step purification. The crude product was dissolved in dichloromethane (50 mL) and trifluoroacetic acid (50 mL) and stirred for 5 h before being concentrated. The residue was purified by preparatory reverse-phase HPLC. The pure 4-(N-fluorenylmethyloxycarbonyl aminomethyl)proline trifluoroacetate salt (1.887 g, 3.93 mmol) was dissolved in dioxane (10 mL), acetonitrile (20 mL) and diisopropylethylamine (1.4 mL, 8 mmol). To the reaction mixture was added a solution of di-tert-butyldicarbonate (1.1 g, 5 mmol) in dioxane (5 mL). After stirring for 18 h, the pH of the solution was adjusted to 2 by the addition of citric acid (caution: foaming!) and water (100 mL). The mixture was extracted with ethyl acetate (3×150 mL) and the combined organic layers were washed with saturated aqueous sodium chloride (100 mL), dried (sodium sulfate), filtered and concentrated. The crude product was dissolved in saturated aqueous sodium bicarbonate (100 mL) and washed with ether (3×75 mL). The aqueous layer was adjusted to pH=3 by the addition of citric acid, then extracted with dichloromethane (4×100 mL). The combined organic layers were dried (sodium sulfate), filtered and concentrated to the title compound (1.373 g, 2.94 mmol, 42%).

EXAMPLE VIII

Synthesis of 3,4-isoproylideneprolinol

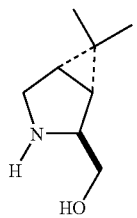

416

Step 1. Cyclopropanation Reaction (*Tetrahedron Lett.* 1993, 34(16), 2691 and 2695):

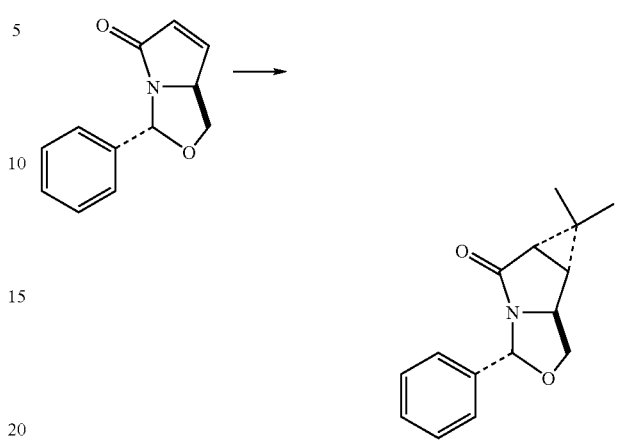

To a stirring solution of isopropyltriphenyl-phosphonium iodide (4.14 g, 9.58 mmol) in tetrahydrofuran (60 mL) at 0° C., was added n-butyllithium (1.6 M in hexanes, 5.64 mL, 9.02 mmol) over 5 min. After 30 min, a solution of enamide ((5R,7S)-5-phenyl-5,6,7,7a-tetrahydro-6-oxapyrrolizin-3-one) (1.206 grams, 6.0 mmol) (see *J. Org. Chem.* 1999, 64(2), 547 for the synthesis of the enamide starting material) in tetrahydrofuran (40 mL) was added over 10 min. After an additional 10 min, the cooling bath was removed and the reaction mixture was stirred at room temperature for 4 hours. The reaction was poured into water (400 mL) and extracted with diethyl ether (400 mL) and ethylacetate (2×400 mL). The combined organic extracts were dried with sodium sulfate, filtered and concentrated to give the desired crude product. The residue was purified by flash chromatography eluting with 3:5:2 ethylacetate/hexanes/methylene chloride to give pure cyclopropanated product (750 mg, 3.08 mmol, 51%).

Step 2. Synthesis of 3,4-isopropylideneprolinol P[3,4-(diMecyclopropyl)]-alcohol) (*J. Org. Chem.* (1999) 64(2), 330):

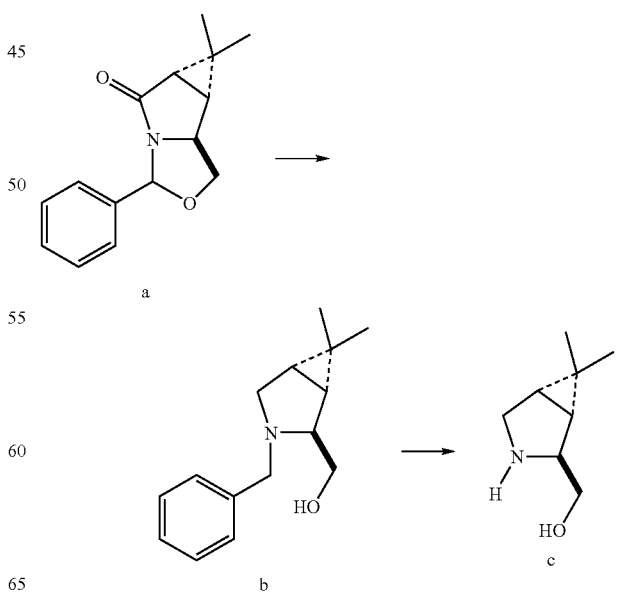

A mixture of the product obtained in step 1 above (1.23 grams, 5.06 mmol) and lithium aluminum hydride (1.0 M in THF, 15 mL, 15 mmol) was heated at reflux for 5 hours. After cooling to 0° C., the remaining aluminum hydride was carefully quenched by the dropwise addition of saturated aqueous sodium sulfate (1.5 mL) over 15 min. The mixture was diluted with ethylacetate (40 mL) and then filtered through celite. The filtrate was dried with sodium sulfate, filtered and concentrated to give crude N-benzyl aminoalcohol (1.25 grams), which was carried on to the next step without further purification. A solution of crude N-benzyl aminoalcohol (1.25 grams, 5.06 mmol) in 1:1 acetic acid/ethylacetate (30 mL) with 10% Pd/C (1 gram) was hydrogenated at 50 psi for 16 hours using a Parr hydrogenation apparatus. The reaction mixture was filtered to remove the carbon-based catalyst and the filtrate was concentrated. The residue was dissolved in water (30 mL) and the pH was adjusted to 13 with 50% NaOH. The mixture was extracted with ether (3×60 mL). The combined extract was dried with sodium sulfate, filtered and concentrated to give crude aminoalcohol (485 mg, 3.43 mmol). This material was taken to the next step without further purification.

EXAMPLE IX

Synthesis of iBoc-G(Chx)-Pro(3,4-isopropylidene)-carboxylic acid

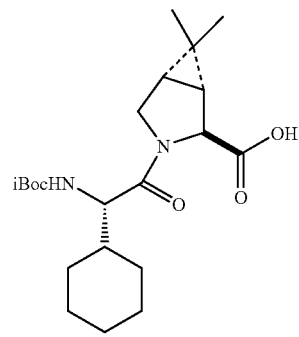

Step 1. Synthesis of isobutyloxycarbonyl-cyclohexylglycine (iBoc-G(Chx)-OH):

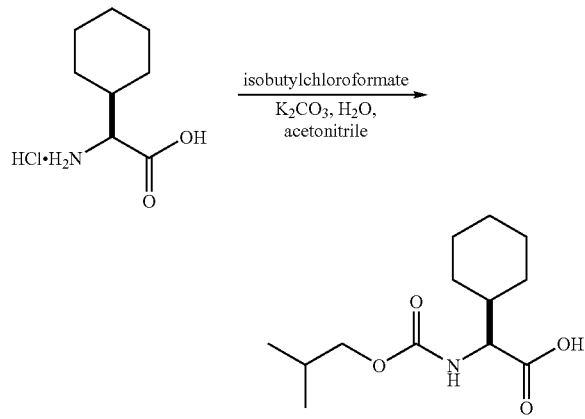

To a solution of the commercially available cyclohexylglycine hydrochloride (15 g, 77.4 mmol) in acetonitrile (320 ml) and water (320 ml) was added potassium carbonate. Isobutylchloroformate (11.1 ml, 85.1 mmol) was added to the clear solution over 15 minutes and the reaction was stirred for 17 hours. The acetonitrile was removed under reduced pressure and the remaining aqueous layer was extracted twice with ether (100 ml). The aqueous layer was then acidified to pH 1 with 6N hydrochloric acid and extracted with dichloromethane (3×300 ml). The organic layer was dried over sodium sulfate, filtered and concentrated to yield 18.64 g (94%) product as a white solid.

Step 2. Synthesis of isobutyloxycarbonyl-cyclohexylglycyl-3,4-isopropylideneproline (iBoc-G(Chx)-P[3,4-(diMe-cyclopropyl)]-OH):

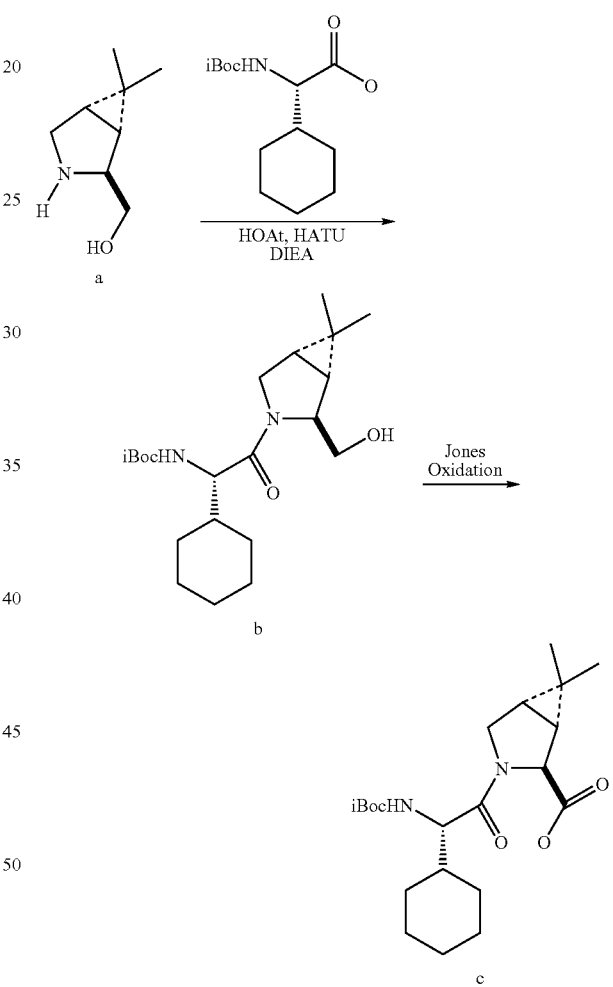

a) Coupling Step

To a solution of iBoc-G(Chx)-OH (890 mg, 3.45 mmol) in acetonitrile (20 mL) was added HATU (1.33 g, 3.5 mmol), HOAt (476 mg, 3.5 grams) and then diisopropylethylamine (2.5 mL, 14 mmol). After a 2 minutes, 3,4-isopropylideneprolinol (485 mg, 3.43 mmol) was added and the reaction mixture was stirred overnight. Addition of saturated aqueous sodium bicarbonate was followed by extraction with ether and ethylacetate. The combined organic layers were dried, filtered and concentrated. The residue was purified by flash chromatography eluting with 1:1 ethylacetate/hexanes to give pure dipeptide alcohol iBoc-G(Chx)-3,4-isopropylideneprolinol (870 mg, 2.3 mmol, 67%)

b) Jones Oxidation Step

To a solution of dipeptide alcohol iBoc-G(Chx)-3,4-isopropylideneprolinol (100 mg, 0.26 mmol) in acetone (2 mL) stirring at 0° C. was added Jones reagent (300 μL) dropwise over 5 min. [Jones Reagent: Prepared from chromium trioxide (13.4 g) and concentrated sulfuric acid (11.5 mL) diluted with water to a total volume of 50 mL.] After stirring at 0° C. for 3 hours, isopropanol (500 μL) was added and stirring continued for an additional 10 minutes. The reaction mixture was diluted with water (20 mL) and extracted with ethylacetate (3×70 mL). The combined organic layers were dried, filtered and concentrated to give the dipeptide iBoc-G(Chx)-3,4-isopropylideneproline (100 mg, 0.25 mmol, 96%).

EXAMPLE X

Synthesis of N-Cbz-3,4-methanoproline

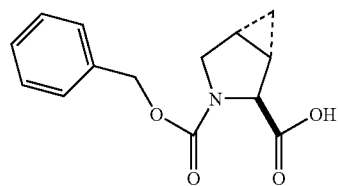

Step 1. Synthesis of N-benzyl-3,4-methanoprolinol:

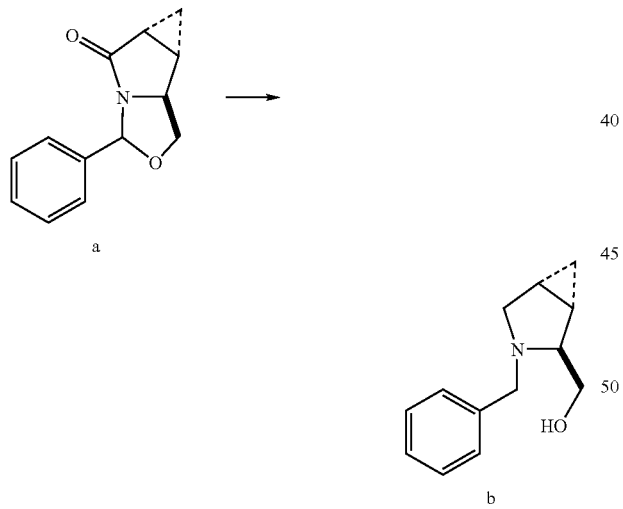

A mixture of the benzylidene starting material (J. Org. Chem. 1999, 64(2), 547) (4.6 grams, 21.4 mmol) and lithium aluminum hydride (1.0 M in THF, 64 mL, 64 mmol) was heated at reflux for 5 hours. After cooling to 0° C., the remaining aluminum hydride was carefully quenched by the dropwise addition of saturated aqueous sodium sulfate (5 mL) over 15 min. The mixture was diluted with ethylacetate (200 mL) and then filtered through celite. The filtrate was dried with sodium sulfate, filtered and concentrated to give crude N-benzyl aminoalcohol (3.45 grams), which was carried on to the next step without further purification.

Step 2. Synthesis of N-benzyloxycarbonyl-3,4-methanoprolinol (CBz-P(3,4-CH$_2$)-ol):

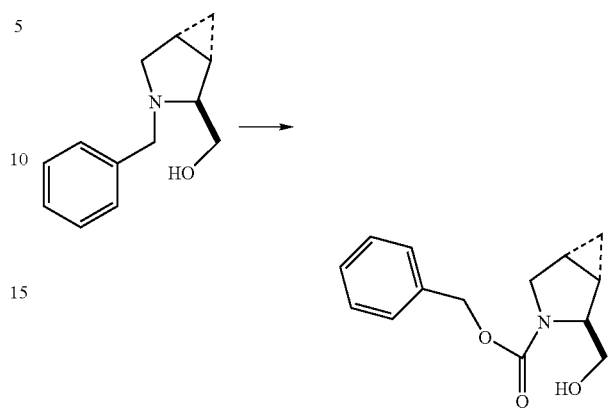

A solution of crude N-benzyl aminoalcohol (3 grams, 14.76 mmol) in methanol (120 mL) and concentrated HCl (1.5 mL) with 10% Pd/C (300 mg) was hydrogenated at 50 psi for 16 hours. The reaction mixture was filtered to remove the carbon-based catalyst and the filtrate was concentrated. The residue was dissolved in water/dioxane (100 mL) and diisopropylethylamine (3.2 mL) was added. Benzyl chloroformate (2.76 mL, 16.2 mmol) was added and the reaction was stirred overnight. The reaction mixture was concentrated, dissolved in 1 M HCl (100 mL) and extracted with ethylacetate (3×200 mL). The combined organic layers were dried with magnesium sulfate, filtered and concentrated. The residue was purified by flash chromatography using 1:3 ethylacetate/hexanes to give the N-Cbz-3,4-methanoprolinol (2.4 g)

Step 3. Synthesis of N-benzyloxycarbonyl-3,4-methanoproline (CBz-P(3,4-CH2)-OH):

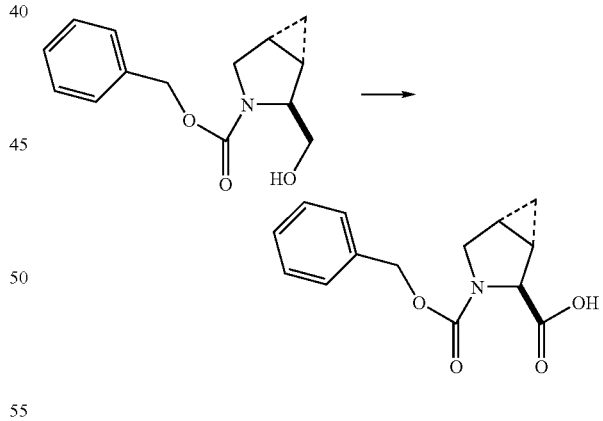

To a solution of N-Cbz-3,4-methanoprolinol (2.2 g, 8.90 mmol) in acetone (68 mL) stirring at 0° C., was added Jones reagent (6.6 mL) dropwise over 5 min. [Jones Reagent: Prepared from chromium trioxide (13.4 g) and concentrated sulfuric acid (11.5 mL) diluted with water to a total volume of 50 mL.] After stirring at 0° C. for 3 hours, isopropanol (11 mL) was added and stirring continued for an additional 10 minutes. The reaction mixture was diluted with water (400 mL) and extracted with ethylacetate (3×500 mL). The combined organic layers were dried over magnesium sulfate, filtered and concentrated to give N-Cbz-3,4-methanoproline (2.25 g, 96%)

EXAMPLE XI

Synthesis of Boc-(6S-carboethoxymethano)proline

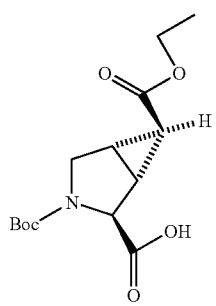

The synthesis of the title compound was carried out according to the published procedure: Marinozzi, M.; Nataini, B.; Ni, M. H.; Costantino, G.; Pellicciari R. IL Farmaco (1995) 50 (5), 327-331.

EXAMPLE XII

Synthesis of Boc-3-morpholine carboxylic acid

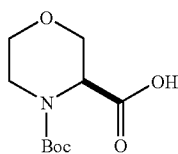

The synthesis of the title compound was carried out according to the published procedure: Kogami Y., Okawa, K. *Bull. Chem. Soc. Jpn.* (1987) 60, 2963-2965.

EXAMPLE XIII

Synthesis of N-tert-butoxycarbonyl 2-aza-3S-hydroxycarbonyl-[2,2,2]-bicyclooctane

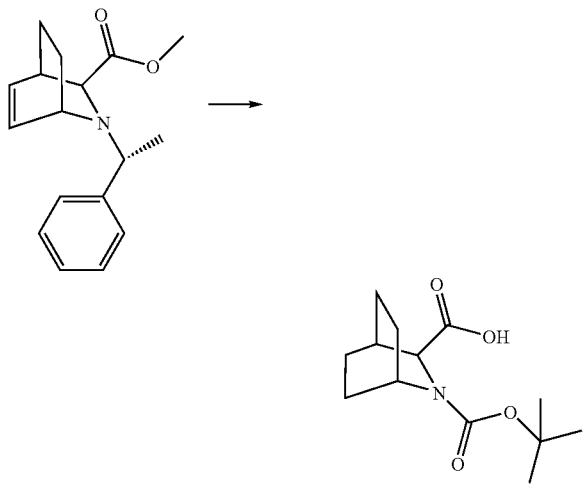

A solution of crude 2-aza-2-(1-phenylethyl)-3S-methoxycarbonyl-[2,2,2]-bicyclooct-5-ene (10 mmol) (Tetrahedron (1992) 48(44) 9707-9718) and 10% Pd on carbon (1 g) in methanol (30 mL) was acidified with 12N HCl then hydrogenated at 50 psi for 16 hours using a Parr hydrogenation apparatus. The reaction mixture was filtered to remove the carbon-based catalyst and the filtrate was concentrated. The residue was dissolved in concentrated HCl and stirred overnight. The solution was concentrated and redissolved in acetonitrile (50 mL). Diisopropylethylamine (3.5 mL) and di-tert-butyldicarbonate (1 g) were added. The reaction mixture was stirred for 24 hours and then concentrated. The residue was dissolved in $CH_2Cl_2$ and 5% aqueous sulfuric acid. The reaction mixture was extracted with $CH_2Cl_2$ and the combined organic layers were concentrated. The residue was dissolved in 10% saturated sodium bicarbonate, washed with diethyl ether (2×) and acidified with 5% aqueous sulfuric acid. The aqueous layer was extracted with ethylacetate (2×). The combined ethylacetate layers were dried filtered and concentrated to give N-tert-butoxycarbonyl 2-aza-3S-hydroxycarbonyl-[2,2,2]-bicyclooctane (650 mg).

EXAMPLE XIV

Synthesis of isobutyloxycarbonyl-cyclohexylglycyl-4,4-dimethyl proline (iBoc-G(Chx)-P(4,4-dimethyl)-OH)

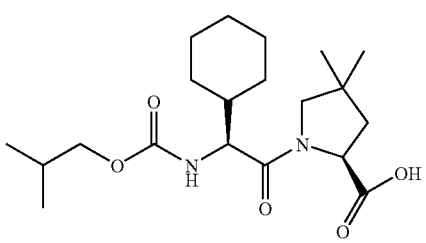

Step I. Synthesis of iBoc-G(Chx)-P(4,4-dimethyl)-OMe:

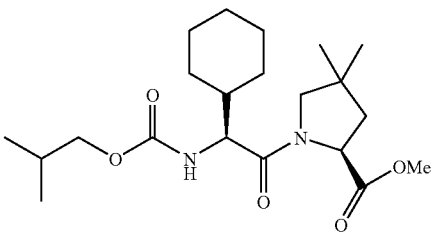

To a solution of iBoc-G(Chx)-OH (Example IX, Step 1.) (377 mg, 1.95 mmol) in acetonitrile (7 mL) was added successively HCl.HN-Pro(4,4-dimethyl)-OMe (Example I, step 6)(377 mg, 1.95 mmol), N-hydroxybenzotriazole (239 mg, 1.75 mmol), TBTU (845 mg, 2.63 mmol) and diisopropylethylamine (1.35 mL, 7.8 mmol). The reaction mixture was stirred at room temperature for 18 hours. The reaction mixture was concentrated and the remaining residue was dissolved in ethylacetate. The organic layer washed twice with 10 ml portions of saturated sodium bicarbonate solution, 1 N hydrochloric solution, and brine. The organic layer was dried over sodium sulfate, filtered and concentrated to a white solid (612 mg, 79%).

Step 2. Synthesis of iBoc-G(Chx)-P(4,4-dimethyl)-OH:

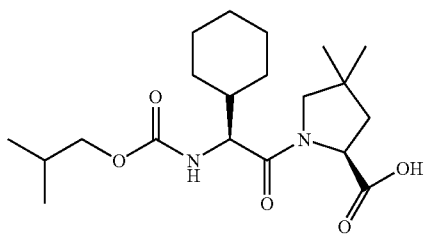

The methyl ester obtained in Step 1 above (612 mg, 1.54 mmol) in methanol (6 ml) was saponified in the presence of 2M lithium hydroxide (1.16 ml) for three hours. The methanol was removed under reduced pressure and the remaining residue was diluted with ethylacetate and acidified to pH=2 with 1 N hydrochloric acid. The layers were separated and the organic layer washed with water and brine, dried over sodium sulfate, filtered and concentrated.

EXAMPLE XV

Synthesis of L-phenylglycine dimethylamide

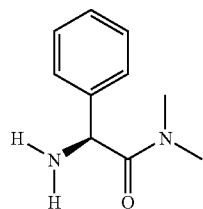

Step 1. Synthesis of N-benzyloxycabonyl-L-phenylglycine dimethylamide (CBz-Phg-NMe2):

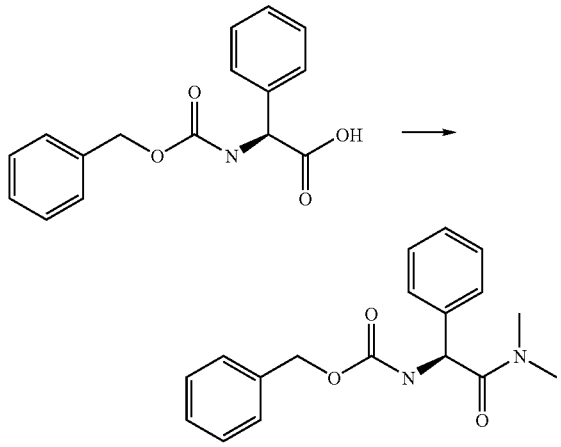

N-benzyloxycarbonyl-L-phenylglycine (25 g, 88 mmols) was dissolved in THF (800 mL) and cooled to −10° C. N-methylmorpholine (9.7 mL, 88 mmols) and isobutylchloroformate (11.4 mL, 88.0 mmols) were added and the mixture allowed to stir for 1 minute. Dimethylamine (100 mL, 2M in THF) was added and the reaction was allowed to warm to room temperature. The mixture was filtered and the filtrate concentrated in vacuo to afford N-benzyloxycabonyl-L-phenylglycine dimethylamide (32.5 g) as a yellow oil.

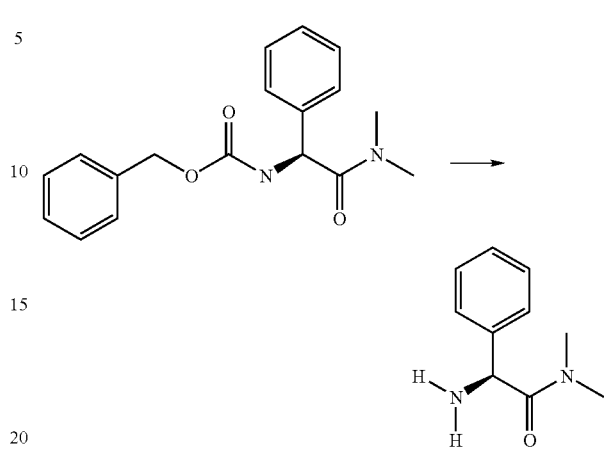

Step 2. Synthesis of L-phenylglycine dimethylamide (H-Phq-NMe2):

The N-benzyloxycarbonyl-L-phenylglycine dimethylamide (32.5 g) obtained above was dissolved in methanol (750 ml) and 10% palladium on activated carbon (3.3 g) was added. This mixture was hydrogenated on a Parr apparatus under 35 psi hydrogen for 2 hours. The reaction mixture was filtered and the solvent removed in vacuo and the residue recrystallized from methanol-hexanes to afford phenylglycine dimethylamide (26 g) as an off white solid. The ee of this material was determined to be >99% by HPLC analysis of the 2,3,4,6-tetra-O-acetylglucopyranosylthioisocyanate derivative.

EXAMPLE XVI

Synthesis of (1-methylcyclohexyl) glycine

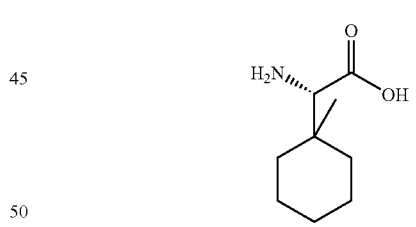

Step 1,1-methyl-1-hydroxymethylcyclohexane:

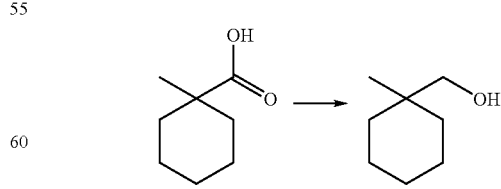

To a solution of 1-methyl-1-hydroxycarbonylcyclohexane (10 g, 70 mmol) in tetrahydrofuran (300 mL) at 0° C. was added 1 M diborane in tetrahydrofuran (200 mL, 200 mmol) over 90 minutes. The cooling bath was removed and the reaction mixture was stirred at room temperature for two days. The remaining borane was quenched by the slow addition of saturated sodium bisulfate (10 mL) over 90 min with cooling. Additional saturated sodium bisulfate (200 mL) was added and after 20 min of stirring the aqueous layer was removed. The organic layer washed with water and saturated sodium chloride, dried, filtered and concentrated. The residue was purified by flash chromatography using 20% diethylether in hexanes to give 1-methyl-1-hydroxymethylcyclohexane (6.17 g, 48 mmol, 69%).

Step 2. 1-methylcyclohexylcarboxaldehyde:

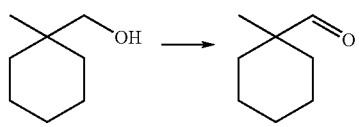

To a solution of 1-methyl-1-hydroxymethylcyclohexane (6.17 g, 48 mmol) and triethylamine (20.1 mL, 144 mmol) in dichloromethane (150 mL) at 0° C., was added a solution of pyridine sulfur trioxide complex (22.9 g, 144 mmol) in dimethylsulfoxide (150 mL) over 15 min. The cooling bath was allowed to warm to room temperature over two hours, at which time the reaction mixture was poured into brine with ice (400 mL). The layers were separated and the aqueous layer was extracted with dichloromethane (200 mL). The combined organic layers were diluted with hexanes (600 mL) and washed with 1 M HCl (2×150 mL), saturated sodium chloride (2×100 mL), dried, filtered and concentrated. The residue was purified by flash chromatography to give 1-methylcyclohexylcarboxaldehyde (1.77 g, 13.8 mmol, 29%).

Step 3. Synthesis of N-formyl-N-glycosyl-1-methylcyclohexyl-tert-butylamide:

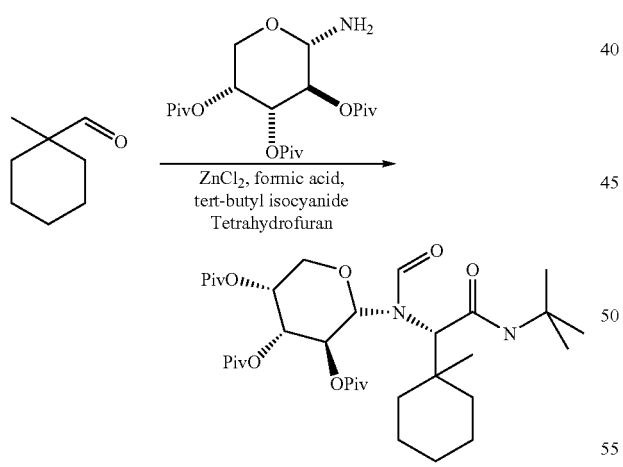

The synthesis of the 2,3,4-tri-O-pivaloyl- -D-arabinosylamine was carried out according to the published procedure (Kunz. H.; Pfrengle, W.; Ruck, K.; Wilfried, S. *Synthesis* (1991) 1039-1042).

To a solution of 1-methylcyclohexylcarboxaldehyde (1.17 g, 8.34 mmol), 2,3,4-tri-O-pivaloyl-1-D-arabinosylamine (8.3 g, 20.7 mmol), formic acid (850 μL, 22.2 mmol) and tert-butylisocyamide (2.4 mL, 21.2 mmol) in tetrahydrofuran (170 mL) at −30° C. was added 0.5M zinc chloride in tetrahydrofuran (41 mL, 20.57 mmol). The solution was stirred at −20° C. for 3 days, then concentrated. The residue was diluted with CH$_2$Cl$_2$ (500 mL), washed with saturated sodium bicarbonate (2×500 mL), water (500 mL). The organic layer was dried, filtered and concentrated to give a clear oil. Flash chromatography (20% ethylacetate in hexanes) provided pure product (4.3 g, 6.6 mmol, 33%)

Step 4. Synthesis of (1-methylcyclohexyl)glycine:

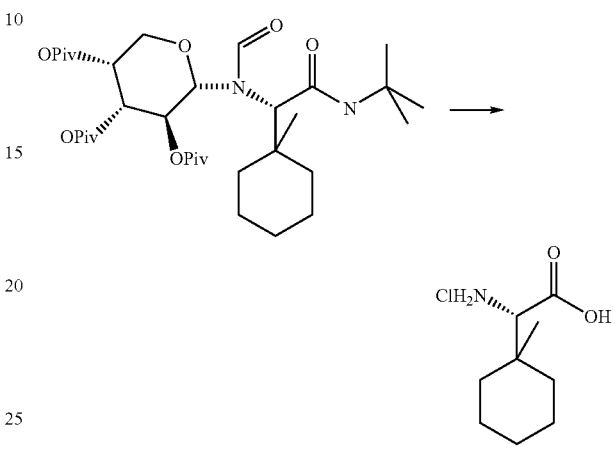

A solution of the product obtained in step 3 above (4.3 g, 6.6 mmol) in dichloromethane (30 mL) and saturated anhydrous methanolic HCl (30 mL) was stirred overnight. The solution was concentrated and the residue was dissolved in water (100 mL) and washed with pentane (2×100 mL). The aqueous layer was concentrated and the residue was dissolved in 6N HCl (50 mL) and heated at reflux for 30 hours. The solution was concentrated to give the crude (1-methylcyclohexyl)glycine hydrochloride (790 mg, 3.82 mmol, 58%).

EXAMPLE XVII

Synthesis of (4,4-dimethylcyclohexyl)glycine

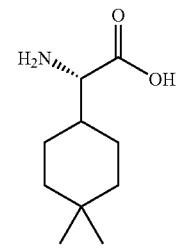

Step 1. Synthesis of 4,4-dimethylcyclohexanone:

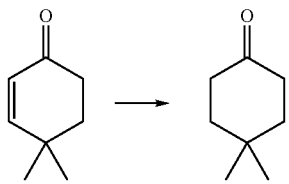

A mixture of 4,4-dimethylcyclohex-2-en-1-one (12 mL, 91.2 mmol) and Degussa type 10% Pd on carbon (2 g) was hydrogenated at 40 psi for 18 hours. The mixture was filtered and concentrated ($^1$H NMR showed a mixture of ketone and alcohol in a 5:3 ratio). The mixture was dissolved in acetone (400 mL) and cooled to 0° C. Jones reagent (40 mL) was added over 30 min and the cooling bath was removed. After 2 days the excess acetone was evaporated and the resulting residue was dissolved in water and diethylether. The ether layer was washed with water until colorless, dried, filtered and concentrated to give 4,4-dimethylcyclohexanone (7.4 g, 58.6 mmol, 64%).

Step 2. Synthesis of the methyl enol ether of 4,4-dimethylcyclohexylcarboxaldehyde:

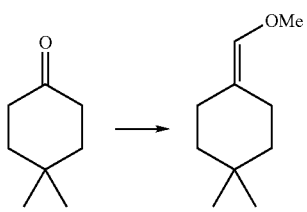

To a solution of methoxymethyl triphenylphosphonium chloride (8.6 g) in tetrahydrofuran (125 mL) at 0° C. was added n-butyllithium (1.6M in hexanes, 14.3 mL) over 10 min. After 30 min the reaction mixture was cooled to –78° C. and a solution of 4,4-dimethylcyclohexanone (2.45 g, 19.1 mmol) in tetrahydrofuran (50 mL) was added over 20 min. After 1 hour the cooling bath was remove and the reaction was warmed slowly to 0° C. The reaction was diluted with saturated ammonium chloride (50 mL), ethylacetate (100 mL) and hexanes (100 mL). The organic layer washed with water and brine, dried filtered and concentrated. The residue was stirred with hexanes (70 mL) for 10 min and filtered. The filtrate was concentrated and chromatographed using 25% ethylacetate in hexanes to give the title compound (1.925 g, 12.5 mmol, 65%).

Step 3: 4,4-dimethylcyclohexylcarboxaldehyde:

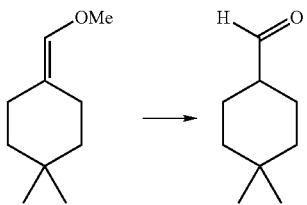

A solution of the methyl enol ether of 4,4-dimethylcyclohexylcarboxaldehyde (1.925 g, 12.5 mmol) (Step 11 above), tetrahydrofuran (100 mL) and 6M HCl (20 mL) was stirred at room temperature for 4 hours. The reaction mixture was diluted with hexanes, diethylether, brine and water. The organic layer was dried, filtered and concentrated to give 4,4-dimethylcyclohexylcarboxaldehyde (1.0 g, 7.1 mmol, 57%).

Step 4. Synthesis of N-formyl-N-glycosyl-4,4-dimethylcyclohexyl-tert-butylamide:

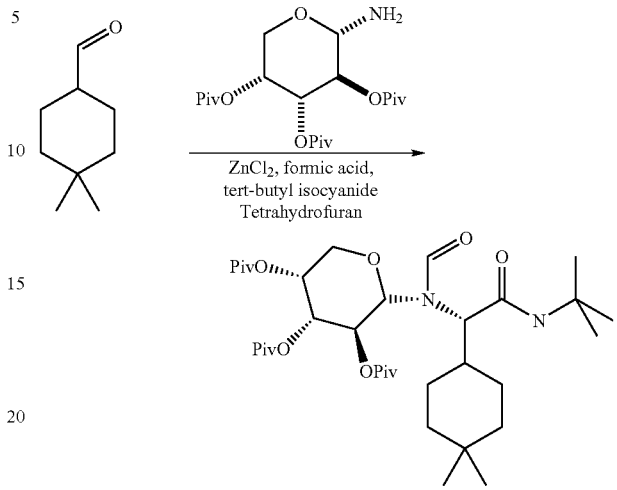

To a solution of 4,4-dimethylcyclohexylcarboxaldehyde (1.17 g, 8.34 mmol), 2,3,4-tri-O-pivaloyl-α-D-arabinosylamine (3.43 g, 8.55 mmol), formic acid (350 µL, 9.17 mmol) and tert-butylisocyamide (990 µL, 8.76 mmol) in THF (70 mL) at –30° C. was added 0.5M zinc chloride in tetrahydrofuran (17 mL, 8.5 mmol). The solution was stirred at –20° C. for 2 days, then concentrated. The residue was diluted with dichloromethane (200 mL), washed with saturated sodium bicarbonate (2×200 mL), water (200 mL). The organic layer was dried, filtered and concentrated to give a clear oil. Flash chromatography (20% ethylacetate in hexanes) provided pure product (2.1 g, 3.3 mmol, 39%)

Step 5. Synthesis of (4,4-dimethylcyclohexyl)glycine:

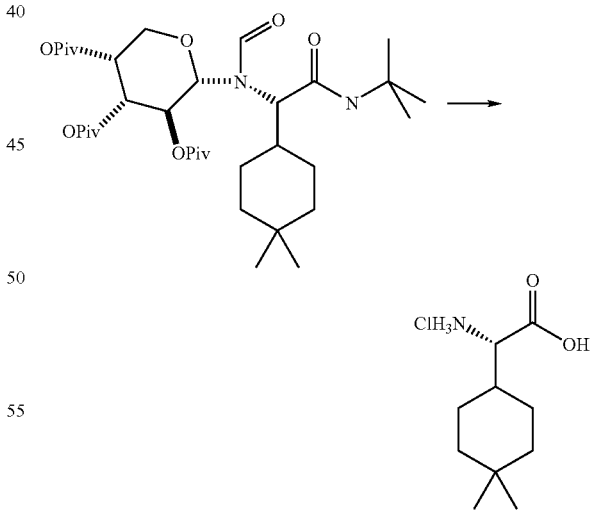

A solution of the Ugi product obtained in step 4 above (2.1 g, 3.3 mmol) in dichloromethane (20 mL) and saturated anhydrous methanolic HCl (20 mL) was stirred overnight. The solution was concentrated and the residue was dissolved in water (100 mL) and washed with pentane (2×100 mL). The aqueous layer was concentrated and the residue was dissolved in 6N HCl (40 mL) and heated at reflux for 30 hours. The solution was concentrated to give the crude (1-methylcyclohexyl)glycine hydrochloride (300 mg, 1.36 mmol, 41%).

EXAMPLE XVIII

Synthesis of Boc-nVal-(CHOH)-Gly-OH

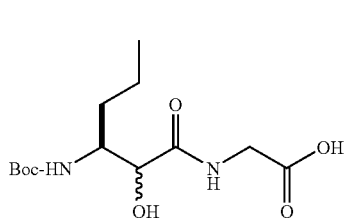

Step 1. Preparation of Boc-norvalinol:

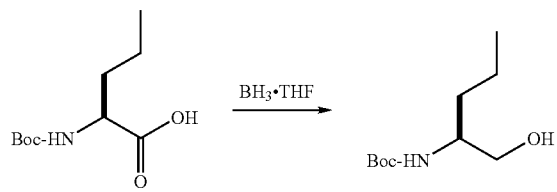

To a solution of Boc-norvaline (25.0 g, 0.115 mol) in tetrahydrofuran (461 mL), cooled to 0° C., was added borane/tetrahydrofuran complex (461 mL of a 1.0M solution in tetrahydrofuran) dropwise. After 1 h at 0° C., the solution was warmed to room temperature over a period of 1.5 h. TLC indicated that the reaction was complete. Methanol was added to quench the reaction. The solution was concentrated to yield the title compound (22.56 g, 96%) as a foamy syrup. TLC of the products indicated satisfactory purity. $R_f$=0.34 (40% ethyl acetate/hexanes).

Step 2. Preparation Boc-norvalinal:

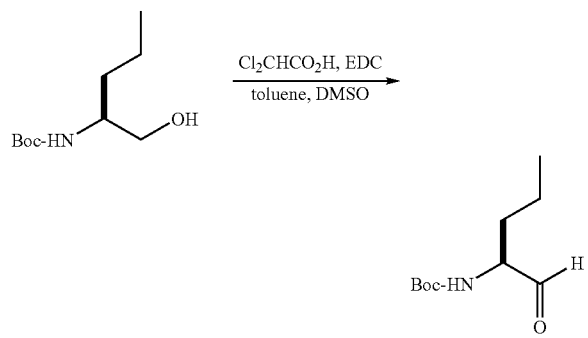

To Boc-norvalinol (7.77 g, 38 mmol), in anhydrous dimethylsulfoxide (153 mL) and toluene (153 mL) was added EDC (73.32 g, 382 mmol). After the solution was cooled to 0° C., dichloroacetic acid (15.8 mL, 191 mmol) was added dropwise. After addition was complete, the reaction was stirred for 15 min. The solution was allowed to warm to room temperature over a period of 2 h. The reaction mixture was concentrated to remove the toluene, then dissolved in ethyl acetate. The solution washed successively with 1 N sodium bisulfate, saturated sodium bicarbonate and brine, dried over sodium sulfate, filtered and concentrated to afford crude Boc-norvalinal which was used directly in the next step. TLC $R_f$=0.84 (40% ethyl acetate/hexanes).

Step 3. Synthesis of Boc-nVal-(CHOH)-Gly-OEt:

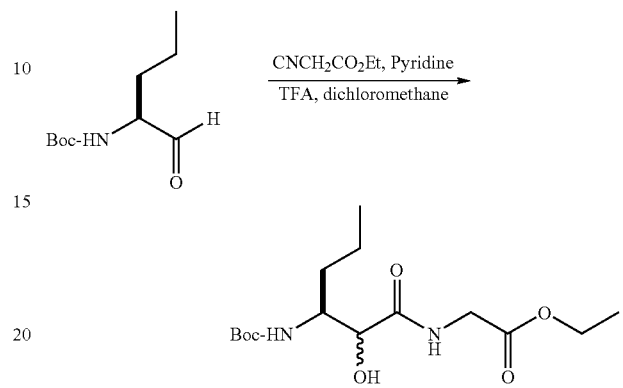

To a solution of the crude Boc-norvalinal (4.18 g, 20.77 mmol) in dichloromethane (83 mL) was added ethylisocyanoacetate (2.72 ml, 24.93 mmol) and pyridine (6.72 ml, 83.09 mmol). After the solution was cooled to 0° C., trifluoroacetic acid (4.15 ml, 41.54 mmol) was added dropwise. After stirring for 1 h, the solution was stirred at room temperature for 18 hours while allowing the solvent from the reaction mixture in an uncovered vessel to evaporate under ambient conditions. The reaction mixture was concentrated, then dissolved in ethyl acetate. The solution washed successively with 1 N sodium bisulfate, saturated sodium bicarbonate and brine, dried over sodium sulfate, filtered and then concentrated. The residue was purified by flash chromatography eluting with 20% to 40% ethylacetate/hexanes to afford 2.8 g of the title compound as a yellow syrup. Low resolution mass spectroscopy confirmed the presence of the desired product (MH$^+$ 333).

Step 4. Synthesis of Boc-nVal-(CHOH)-Gly-OH:

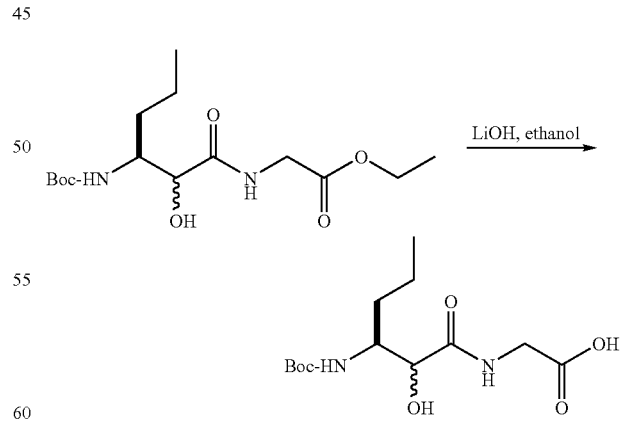

The product obtained (Boc-nVal-(CHOH)-Gly-OEt) (1.52 g, 4.70 mmol) dissolved in ethanol (23 ml) was saponified with 1 N lithium hydroxide (18.81 ml) for two hours at room temperature. The reaction mixture was acidified to pH≈2 with Dowex® 50 WX8 ion exchange resin, stirred for 20 minutes and then filtered. The resin washed well with ethanol and water and the combined filtrates were concentrated to a white foam (0.48 g, 33%).

EXAMPLE XVIV

Synthesis of (2R,3S,4S,5S)-tert-Butyl N-CBz-3-amino-2-hydroxy-4,5 methylene-hexanoate

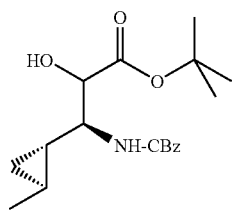

Step 1:

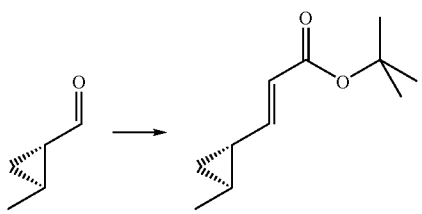

To a solution of tert-Butyl diethylphosphonoacetate (4.7 mL, 20 mmol) dissolved in THF (50 mL) at −78° C. was added 1.6M n-butyl lithium in hexanes (12.4 mL). After 30 minutes (1S,2S)-2-methylcyclopropylcarboxaldehyde (1 g, 12 mmol) (Barrett, A. G. M.; Doubleday, W. W.; Kasdorf, K.; Tustin, G. J., *J. Org. Chem.* (1996) 61, 3280) in diethyl ether (100 mL) was added over 10 min. The reaction was warmed to 0° C. for 2 hours and to 6° C. for 12 hours. The reaction was quenched with saturated ammonium chloride (20 mL) and the organic layer was separated, washed with 50 mL brine and dried over sodium sulfate, filtered and concentrated to afford 3.5 g of a clear oil. Flash chromatography (20% ethylacetate in hexanes) afforded pure unsaturated tert-butylester (1.4 g).

Step 2:

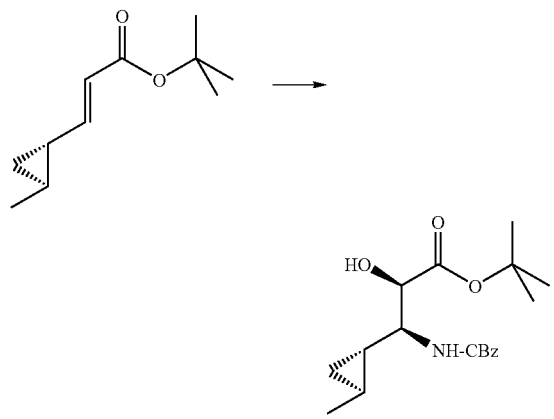

To a solution of benzyl carbamate (3.55 g, 23.5 mmols) in n-propanol (24 mL) was added a solution of sodium hydroxide (900 mg, 22.7 mmol)in water (48 mL), followed by tert-butylhypochlorite (2.57 mL, 22.7 mmol). After 15 minutes the reaction was cooled to 0° C. and (DHQ)₂PHAL (350 mg, 0.45 mmol) was added in n-propanol (24 mL), followed by unsaturated tert-butyl ester (1.4 g) from above in n-propanol (48 mL). Finally potassium osmate (110 mg, 0.30 mmol) in water (2 mL) was added and the solution very rapidly developed a dark green color which persisted for 4 hours. After 6 hours saturated sodium sulfate (50 mL) was added and the mixture extracted with ethyl acetate (2×50 mL). The combined organic layers were washed with brine (30 mL), dried over sodium sulfate, filtered and concentrated. Flash chromatography with 20% ethylacetate in hexanes afforded the desired cBz protected amino tert-butylester as a white solid (316 mg).

Step 3:

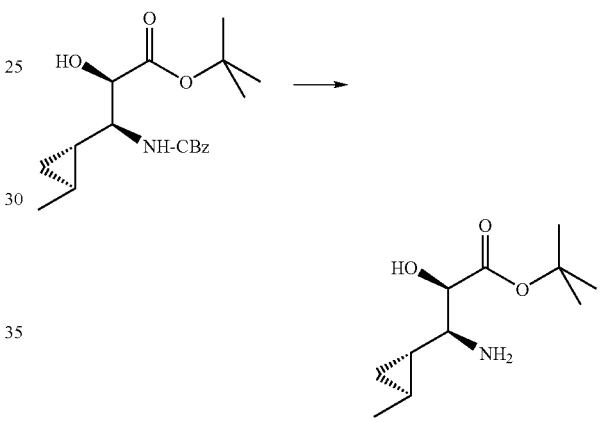

A mixture of CBz protected amino tert-butylester (316 mg, 0.9 mmol) and 32 mg 10% palladium on carbon in 9 mL methanol was hydrogenated for 8 hours. The mixture was filtered and concentrated to afford the free amine as a clear oil (195 mg).

EXAMPLE XX

Synthesis of 1R,2-dimethylPropyl chloroformate

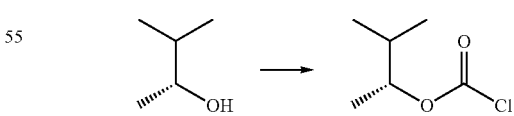

To the commercially available 2R-hydroxy-3-methylbutane (410 mg, 4.65 mmol) was added a solution of 20% phosgene in toluene (1 mL, 2 mmol). The solution was stirred for 6 hours to generate the chloroformate (2 mmol) which was reacted directly and immediately with the desired amine. The S-isomer was synthesized by the same procedure.

II) Representative Solution Phase Synthesis of HCV Inhibitors

EXAMPLE XXI

Solution Phase Synthesis of iBoc-G(Chx)-Pro(4,4-dimethyl)-Leu-(CO)-Gly-Phg-dimethylamide

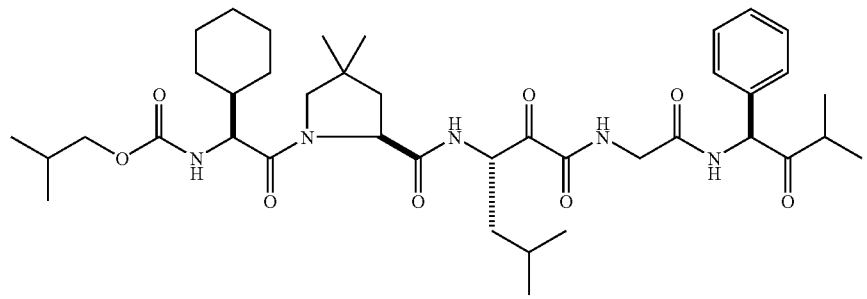

Step 1. Synthesis of tert-butyloxycarbonyl-leucinal (Boc-Leu-CHO):

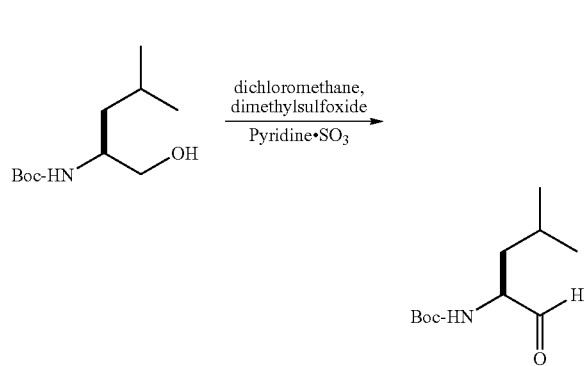

To a solution of the commercially available (Advanced Chem Tech) Boc-L-leucinol (0.78 g, 3.6 mmol) in anhydrous dichloromethane (17.5 ml) was added triethyl amine (2 ml, 14.36 mmol) and the mixture was cooled to 0° C. Dimethyl sulfoxide (17.5 ml) was added followed by sulfur trioxide pyridine complex (2.3 g, 14.36 mmol) and the reaction was stirred for two hours. TLC in 1:1 ethylacetate:hexanes confirmed the completion of the reaction. The reaction mixture was concentrated and the remaining residue diluted with ethylacetate. The ethylacetate layer washed with 1 M hydrochloric acid (2×75 ml) followed by saturated sodium bicarbonate solution (2×75 ml) and brine (75 ml). The organic layer was dried (sodium sulfate), filtered and concentrated to yield 775 mg of product.

Step 2. Synthesis of Boc-2-hydroxy-3-amino-5-methyl hexanoyl-glycine ethyl ester (Boc-Leu-(CHOH)-Gly-OEt):

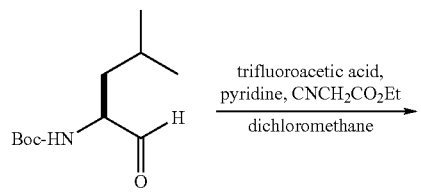

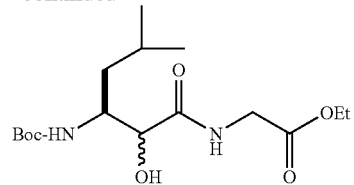

To a solution of Boc-Leucine aldehyde (0.77 g, 3.59 mmol) in anhydrous dichloromethane (24 ml) was added anhydrous pyridine (1.16 ml, 14.36 mmol) and ethylisocyanoacetate (0.4 ml, 4.66 mmol). The reaction mixture was cooled to 0° C. and trifluoroacetic acid (0.55 ml, 7/18 mmol) was added over two minutes. The reaction mixture was capped and stirred at 4° C. for four days, and at room temperature for one day. The reaction mixture was diluted with dichloromethane (350 ml) and washed twice each with 75 ml portions of 1 M hydrochloric acid, saturated sodium bicarbonate and brine. The organic layer was dried, filtered and concentrated. The residue obtained was subjected to flash chromatography in a 2"×6" silica gel column using 10% ethylacetate in hexanes (800 ml) followed by 1:1 ethylacetate in hexanes (800 ml). The fractions corresponding to the product were pooled and concentrated to yield 980 mg (79%) product.

Step 3. Synthesis of Boc-Leu-(CHOH)-Gly-OH:

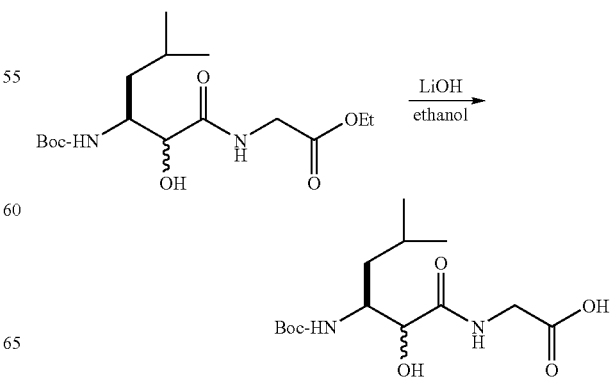

To a solution of Boc-Leu-(CHOH)-Gly-Oet (0.98 g, 2.83 mmol) in ethanol (11.3 ml) was added 2M lithium hydroxide (4.25 ml) and the reaction was stirred for five hours at room temperature. The ethanol was removed under reduced pressure and the aqueous layer was diluted with ethylacetate. The organic layer washed with 1 M hydrochloric acid followed by brine, dried, filtered and concentrated to yield 775 mg (86%) product as a white solid.

Step 4. Synthesis of Boc-Leu-(CHOH)-Gly-Phg-dimethylamide:

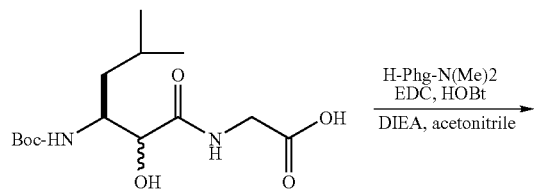

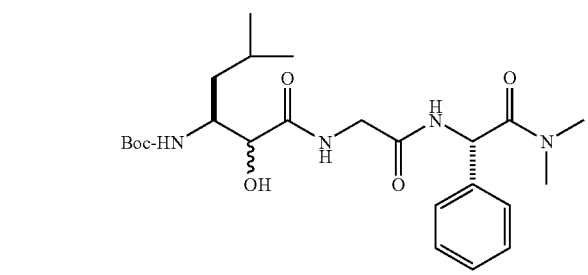

To a solution of Boc-Leu-(CHOH)-Gly-OH (0.37 g, 1.18 mmol) in acetonitrile (23 ml) was added successively phenylglycine dimethylamide (obtained in Example XV, Step 2), EDC (0.34 g, 1.76 mmol), N-hydroxybenzotriazole (HOBt) (0.18 g, 1.18 mmol) and diisopropylethylamine (DIEA) (0.82 ml, 4.7 mmol) and the reaction was stirred for 18 hours at room temperature. The reaction mixture was concentrated and the remaining residue was diluted with ethylacetate and washed successively with two 75 ml portions of 1 M hydrochloric acid, saturated sodium bicarbonate and brine. The organic layer was then dried filtered and concentrated. The crude product was subjected to flash chromatography in a 2"×6" silica gel column using 4:1 ethylacetate:hexanes (700 ml) followed by ethylacetate (1000 ml) and 10% methanol in dichloromethane (600 ml). The fractions corresponding to the product were pooled and concentrated to yield 445 mg (80%) white solid.

Step 5. Synthesis of H-Leu-(CHOH)-Gly-Phg-dimethylamide trifluoroacetate salt:

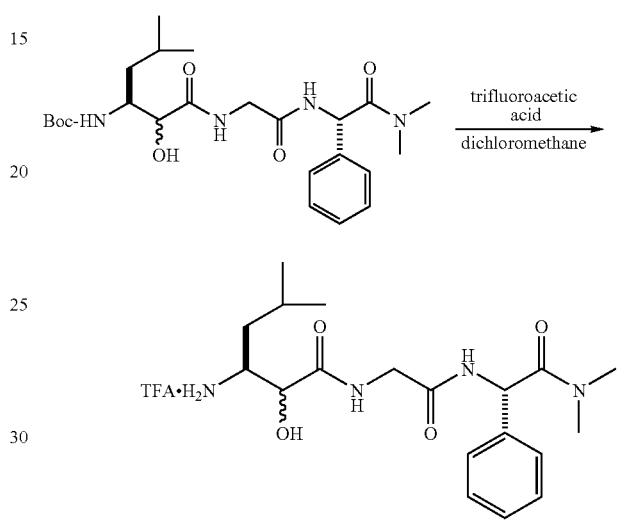

To a solution Boc-Leu-(CHOH)-Gly-Phg-dimethylamide (70 mg, 0.146 mmol) in dichloromethane (1 ml) was added trifluoroacetic acid (1 ml) and the reaction was stirred at room temperature for 1 hour. The reaction mixture was concentrated and taken to the next step without further purification.

Step 6. Synthesis of iBoc-G(Chx)-Pro(4,4-dimethyl)-Leu-(CHOH)-Gly-Phg-dimethylamide:

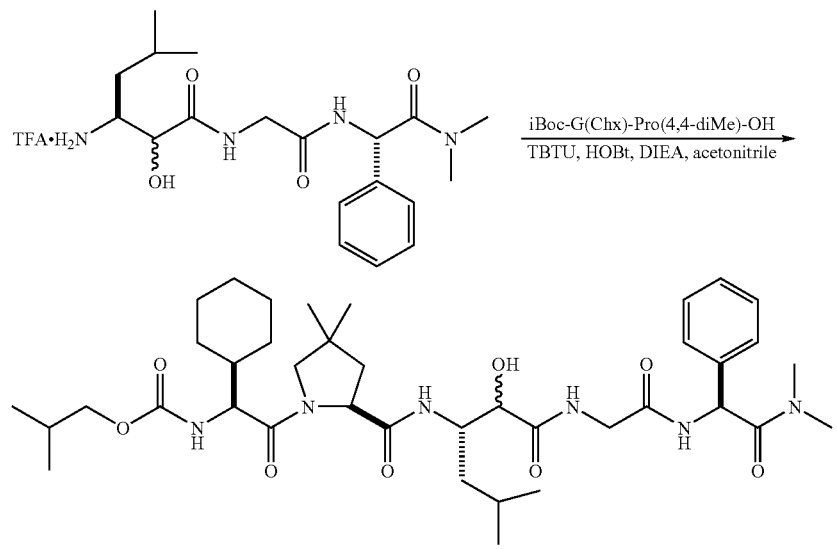

To a solution of iBoc-G(Chx)-P(4,4-diMe)-OH (Example XIV, step 2)(53 mg, 0.148 mmol) in acetonitrile (3 ml) was added successively TFA-2HN-Leu(CHOH)-Gly-Phg-NMe2 (61 mg, 0.148 mmol), N-Hydroxybenzotriazole (HOBt) (23 mg, 0.148 mmol), TBTU (71.5 mg, 0.222 mmol and diisopropylethyl amine (103 l, 0.593 mmol). The reaction was stirred at room temperature for 18 hours and concentrated. The remaining residue was dissolved in ethylacetate and washed with 1 M hydrochloric acid (2×5 ml), saturated sodium bicarbonate solution (2×5 ml), and brine (2×5 ml). The organic layer was dried, filtered and concentrated. The product (100 mg) was taken to the next step without further purification.

Step 7. Synthesis of iBoc-G(Chx)-Pro(4,4-dimethyl)-Leu-(CO)-Gly-Phg-dimethylamide:

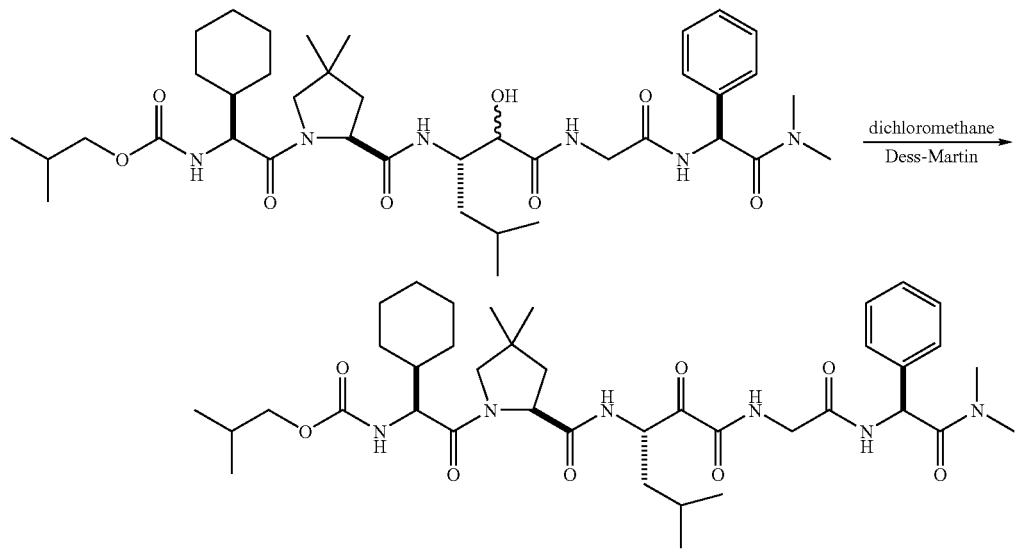

To a solution of iBoc-G(Chx)-Pro(4,4-dimethyl)-Leu-(CHOH)-Gly-Phg-dimethylamide (30 mg, 0.04 mmol) in dichloromethane (1 ml) was added the commercially available Dess-Martin reagent (Omega Chemical Company Inc.) (67.8 mg, 0.16 mmol) and the reaction was stirred at room temperature for 90 minutes. The reaction mixture was concentrated and the remaining residue was stirred in 5% sodium thiosulfate. It was then diluted with dichloromethane and the layers were separated. The organic layer washed with sodium thiosulfate (4×3 ml), followed by water and brine. The organic layer was dried over sodium sulfate, filtered and concentrated. The crude product was dissolved in hexanes and isopropyl alcohol and was subjected to HPLC purification using a normal phase Kromasil 5 silica column (Phenomenex, 250×21.20 mm, 100 angstrom pore size, 5 μm gel particles) eluting with a 30 minutes gradient consisting of 0 to 25% isopropyl alcohol in hexanes (25 ml/minutes). The fractions corresponding to the product were pooled and concentrated. Lyophilization from water yielded 6.7 mg white powder. Low resolution mass spectra confirmed the desired mass (MH$^+$=741.4).

III) Solid Phase Synthesis:

Solid-phase synthesis is useful for the production of small amounts of certain compounds of the present invention. As with the conventional solid-phase synthesis of peptides, reactors for the solid-phase synthesis of peptidyl ketoamides are comprised of a reactor vessel with at least one surface permeable to solvent and dissolved reagents, but not permeable to synthesis resin of the selected mesh size. Such reactors include glass solid phase reaction vessels with a sintered glass frit, polypropylene tubes or columns with frits, or reactor Kans™ made by Irori Inc., San Diego Calif. The type of reactor chosen depends on volume of solid-phase resin needed, and different reactor types might be used at different stages of a synthesis. The following procedures will be referenced in the subsequent examples:

Procedure A: Coupling reaction: To the resin suspended in N-methylpyrrolidine (NMP) (10-15 mL/gram resin) was added Fmoc-amino acid (2 eq), HOAt (2 eq), HATU (2 eq) and diisopropylethylamine (4 eq). The mixture was let to react for 4-48 hours. The reactants were drained and the resin washed successively with dimethylformamide, dichloromethane, methanol, dichloromethane and diethylether (use 10-15 mL solvent/gram resin). The resin was then dried in vacuo.

Procedure B: Fmoc deprotection: The Fmoc-protected resin was treated with 20% piperidine in dimethylformamide (10 mL reagent/g resin) for 30 minutes. The reagents were drained and the resin washed successively with dimethylformamide, dichloromethane, methanol, dichloromethane and diethyl ether (10 mL solvent/gram resin).

Procedure C: Boc deprotection: The Boc-protected resin was treated with a 1:1 mixture of dichloromethane and trifluoroacetic acid for 20-60 minutes (10 mL solvent/gram resin). The reagents were drained and the resin washed successively with dichloromethane, dimethylformamide, 5% diisopropylethylamine in dimethylformamide, dimethylformamide, dichloromethane and dimethylformamide (10 mL solvent/gram resin).

Procedure D: Semicarbazone hydrolysis: The resin was suspended in the cleavage cocktail (10 mL/g resin) consisting of trifluoroacetic acid:pyruvic acid:dichloromethane:water 9:2:2:1 for 2 hours. The reactants were drained and the procedure was repeated three more times. The resin washed successively with dichloromethane, water and dichloromethane and dried under vacuum.

Procedure E: HF cleavage: The dried peptide-nVal(CO)-G-O-PAM resin (50 mg) was placed in an HF vessel containing a small stir bar. Anisole (10% of total volume) was added as a scavenger. In the presence of glutamic acid and cysteine amino acids, thioanisole (10%) and 1,2-ethanedithiol (0.2%) were also added. The HF vessel was then hooked up to the HF apparatus (Immuno Dynamics) and the system was flushed with nitrogen for five minutes. It was then cooled down to −70° C. with a dry ice/isopropanol bath. After 20 minutes, HF was distilled to the desired volume (10 mL HF/g resin). The reaction was let to proceed for one and a half hour at 0° C. Work up consisted of removing all the HF using nitrogen. Dichloromethane was then added to the resin and the mixture was stirred for five minutes. This was followed by the addition of 20% acetic acid in water (4 mL). After stirring for 20 minutes, the resin was filtered using a fritted funnel and the dichloromethane was removed under reduced pressure. The remaining residue and the mixture washed with hexanes (2×) to remove scavengers. Meanwhile, the resin was soaked in 1 mL methanol. The aqueous layer (20% HOAC) was added back to the resin and the mixture was agitated for five minutes and then filtered. The methanol was removed under reduced pressure and the aqueous layer was lyophilized. The peptide was then dissolved in 10-25% methanol (containing 0.1% trifluoroacetic acid) and purified by reverse phase HPLC.

EXAMPLE XXII

Representative Solid Phase Synthesis of Hen C Inhibitors: (iBoc-G(Chx)-P(4t-NHSO2Ph)-nV-(CO)-G-G(Ph)-NH2)

hydroxide (59.52 g, 1.0 mol). The reaction was slowly warmed to room temperature. After two hours the precipitated product was filtered on a glass funnel and washed with several portions of chilled ethanol. The potassium salt of isocyanoacetic acid thus obtained was dried in vacuo to a golden-brown solid (99.92 g, 91.8%).

b) Synthesis of Allyl Isocyanoacetate:

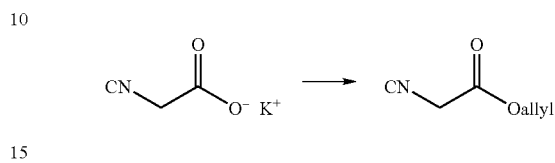

To the product of part a (99.92 g, 0.81 mol) dissolved in acetonitrile (810 ml) was added allyl bromide (92 ml, 1.05 mol). After heating at reflux for four hours a dark brown solution was obtained. The reaction mixture was concentrated and the remaining residue was dissolved in ether (1.5 L) and washed three times with water (500 ml). The organic layer was dried, filtered and concentrated to a dark brown syrup. The crude was purified by vacuum distillation at 7 mm Hg (98 C) to a clear oil (78.92 g, 78%). NMR 5 ppm (CDCl$_3$): 5.9 (m, 1 H), 5.3 (m, 2H), 4.7 (d, 2H), 4.25 (s, 2H).

B) Synthesis of 9-fluorenylmethoxycarbonyl-norvalinal (Steps a-c Below):

a) Synthesis of 9-fluorenylmethoxycarbonyl-L-norvaline methyl ester (Fmoc-nVal-OMe):

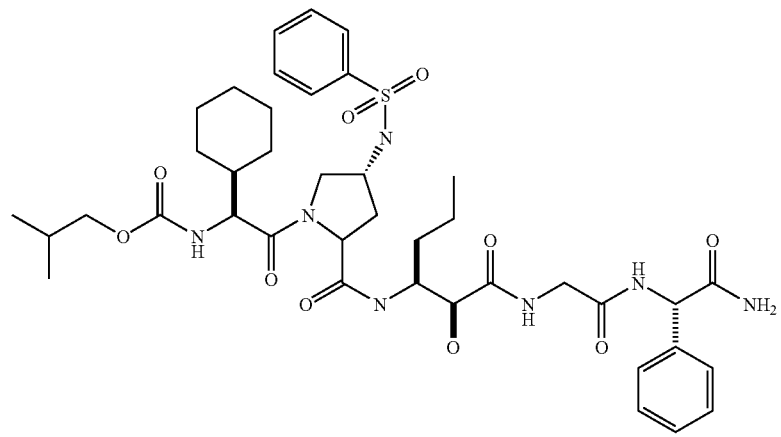

Step 1. Synthesis of Fmoc-nV-(dpsc)-Gly-OH:

A) Synthesis of allyl isocyanoacetate (Steps a-b Below):
  a) Synthesis of Isocyanoacetic Acid Potassium Salt:

Ethyl isocyanoacetate (96.6 ml, 0.88 mol) was added dropwise to a chilled solution of ethanol (1.5 L) and potassium

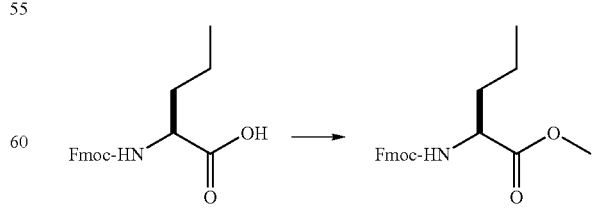

To a chilled solution of the commercially available Fmoc-norvaline (25 g, 73.75 mmol) in anhydrous methanol (469 ml) was added thionyl chloride (53.76 ml, 737.5 mmol) over one hour. TLC in ethylacetate taken an hour later confirmed the completion of the reaction (R$_f$=0.85). The reaction mixture was concentrated and the remaining residue was dissolved in ethylacetate. The organic layer was washed with several 200 ml portions of saturated sodium bicarbonate followed by brine. The organic layer was dried, filtered and concentrated to afford Fmoc-norVal-OMe) as a white solid (26.03 g) in quantitative yield. NMR δ ppm (CD$_3$OD): 7.7 (m, 2H), 7.6 (m, 2H), 7.4 (m, 2H), 7.3 (m, 2H), 4.3 (m, 2H), 4.1 (m, 2H), 3.7 (s, $^3$H), 1.7 (m, 1H), 1.6 (m, 1H), 1.4 (m, 2H), 0.95 (t, 3H).

b) Synthesis of 9-fluorenylmethoxycarbonyl-norvalinol (Fmoc-nValinol):

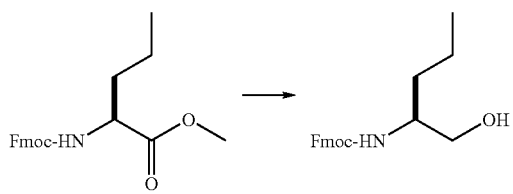

To Fmoc-nVal-OMe (26.03 g, 73.75 mmol) in tetrahydrofuran (123 ml) and methanol (246 ml) was added calcium chloride (16.37 g, 147.49 mmol). The reaction mixture was cooled to 0° C. and sodium borohydride (11.16 g, 294.98 mmol) was added in several batches. To the thick paste obtained, methanol (500 ml) was added and the reaction was let to stir at room temperature for 90 minutes. TLC in 2:3 ethylacetate:hexanes confirmed the completion of the reaction (R$_f$=0.25). The reaction was quenched with the slow addition of water (100 ml) at 0° C. The methanol was removed under reduced pressure and the remaining aqueous phase was diluted with ethylacetate. The organic layer washed with water (3×500 ml), saturated sodium bicarbonate (3×500 ml) and brine (500 ml). The organic layer was dried over sodium sulfate, filtered and concentrated to a white solid (21.70 g, 90.5%). NMR δ ppm (CD$_3$OD): 7.8 (m, 2H), 7.7 (m, 2H), 7.4 (m, 2H), 7.3 (m, 2H), 4.3-4.5 (m, 2H), 4.2 (m, 1H), 3.6 (s, 1H), 3.5 (s, 2H), 1.5 (m, 1H), 1.3-1.4 (m, $^3$H), 0.99 (m, $^3$H).

c) Synthesis of 9-fluorenylmethoxycarbonyl-norvalinal (Fmoc-nVal-CHO):

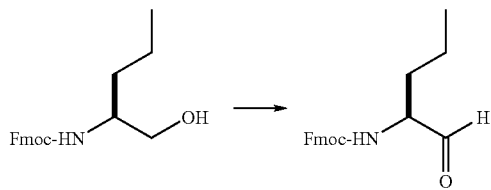

To a solution of Fmoc-norValinol (21.70 g, 66.77 mmol) in dichloromethane (668 ml) was added triethylamine (37.23 ml, 267 mmol) and the solution was cooled to 0° C. A suspension of pyridine sulfur trioxide complex (42.51 g, 267 mmol) in dimethylsulfoxide (96 ml) was added to the chilled solution. After one hour, TLC in 2:3 ethylacetate:hexanes confirmed the completion of the reaction. The dichloromethane was removed under reduced pressure and the remaining residue was dissolved in ethylacetate and washed with water (2×50 ml), 1 N saturated sodium bisulfate (2×50 ml), saturated sodium bicarbonate (2×50 ml) and brine (50 ml). The organic layer was concentrated to yield a white solid. Theoretical yield (21.57 g) was assumed and the reaction was taken to the next step without further purification.

C) Synthesis of diphenylmethyl semicarbazide (dpsc) trifluoroacetate Salt (Steps a-b Below):

a) Synthesis of Boc-semicarbazid-4-yl diphenylmethane

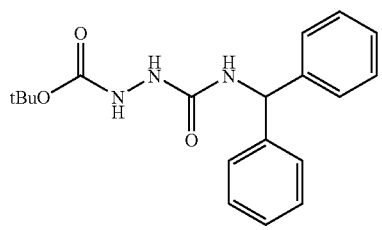

To a solution of carbonyldiimidazole (16.2 g, 0.10 mole) in dimethylformamide (225 ml) was added a solution of t-butyl carbazate (13.2 g, 0.100 mol) in dimethylformamide (225 ml) dropwise over 30 minutes. Diphenylmethylamine (18.3 g, 0.10 mol) was added next over 30 minutes. The reaction was allowed to stir at room temperature for one hour. Water (10 mL) was added and the mixture was concentrated to about 150 mL under reduced pressure. This solution was poured into water (500 mL) and extracted with ethyl acetate (400 mL). The ethylacetate phase washed two times each with 75 mL 1N HCl, water, saturated sodium bicarbonate solution and sodium chloride, and dried with magnesium sulfate. The mixture was filtered and the solution was concentrated to give 29.5 g (85% yield) of a white foam. This material could be purified by recrystallization from ethyl acetate/hexane, but was pure enough to use directly in the next step: mp 142-143° C. $^1$H NMR (CDCl$_3$) δ 1.45 (s, 9H), 6.10 (dd, 2H), 6.42 (s, 1H), 6.67 (bs, 1H), 7.21-7.31 (m, 10H). Anal calculated for C$_{19}$H$_{23}$N$_3$O$_3$: C, 66.84; H, 6.79; N, 12.31. Found: C, 66.46; H, 6.75; N, 12.90.

b) Synthesis of diphenylmethyl semicarbazide (dpsc) trifluoroacetate Salt

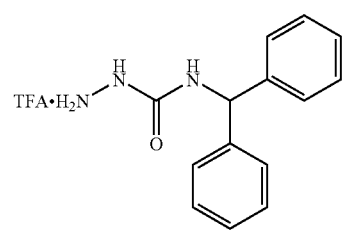

A solution of Boc-semicarbazid-4-yl diphenylmethane (3.43 g, 10 mmol) in dichloromethane (12.5 mL) was treated with 12.5 mL of trifluoroacetic acid at room temperature and stirred for 30 min. The solution was added dropwise to 75 mL of ether and the resulting solid (2.7 g, 80%) was collected by filtration. mp 182-184° C. $^1$H NMR (CD$_3$OD) δ 6.05 (s, 1H), 7.21-7.35 (m, 10H). $^{13}$C NMR (CD$_3$OD) δ 57.6, 118.3 (q, CF$_3$), 126.7, 127.9, 141.6, 156.9, 160.9 (q, CF$_3$CO$_2$H).

D) Synthesis of Fmoc-nVal-(CHOH)-Gly-Oallyl:

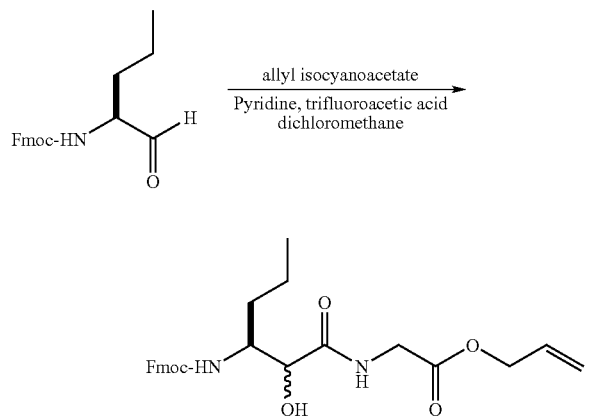

To a solution of Fmoc-nVal-CHO (Step 1B) (5.47 g, 16.90 mmol) in dichloromethane (170 ml) was added allyl isocyanoacetate (Step 1A) (2.46 ml, is 20.28 mmol) and pyridine (5.47 ml, 67.61 mmol). The reaction mixture was cooled to 0° C. and trifluoroacetic acid (3.38 ml, 33.80 mmol) was added dropwise. The reaction was stirred at 0° C. for 1 h, and then at room temperature for 48 hours. TLC taken in ethylacetate confirmed the completion of the reaction. The reaction mixture was concentrated and subjected to flash chromatography using 20% to 70% ethylacetate in hexanes. Fractions containing the desired product were pooled and concentrated to a white foam (6.88 g, 87.3%). TLC in 50:50 ethylacetate shows one spot ($R_f$=0.37). NMR δ ppm (CD$_3$OD): 7.8 (m, 2H), 7.65 (m, 2H), 7.4 (m, 2H), 7.3 (m, 2H), 5.9 (m, 1H), 5.1-5.4 (m, 2H), 4.55-4.65 (m, 2H), 4.3-4.4 (m, 2H), 4.15-4.25 (m, 1H), 4.01 (s, 1H), 3.9-4.0 (m, $^3$H), 1.5-1.6 (m, 2H), 1.35-1.45 (m, 3H), 0.9 (m, 3H).

E) Synthesis of Fmoc-nVal-(CO)-Gly-Oallyl:

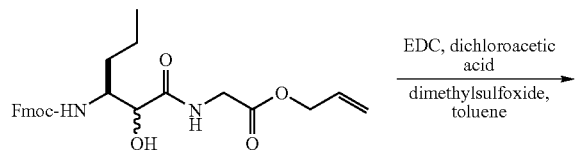

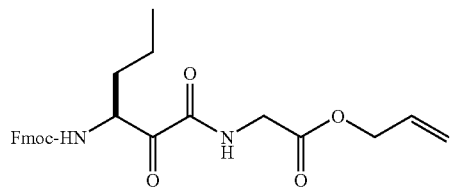

to a solution of Fmoc-nVal-(CHOH)-Gly-Oallyl (Step D) (5.01 g, 10.77 mmol) in dimethylsulfoxide (100 ml) and toluene (100 ml) was added EDC (20.6 g, 107.7 mmol). The reaction mixture was cooled to 0° C. and dichloroacetic acid (4.44 ml, 53.83 mmol) was added dropwise. The reaction was stirred for 15 minutes at 0° C. and 1 h at room temperature. After cooling back to 0 C, water (70 ml) was added and the toluene was removed under reduced pressure. The remaining residue was diluted with ethylacetate and washed several times with a saturated sodium bicarbonate solution followed by 1 N sodium bisulfate and brine. The organic layer was dried over sodium sulfate, filtered and concentrated. The theoretical yield of 4.99 g was assumed and the reaction was taken to the next step without further purification. TLC in 50:50 ethylacetate shows one spot ($R_f$=0.73).

F) Synthesis of Fmoc-nVal-(dpsc)-Gly-Oallyl:

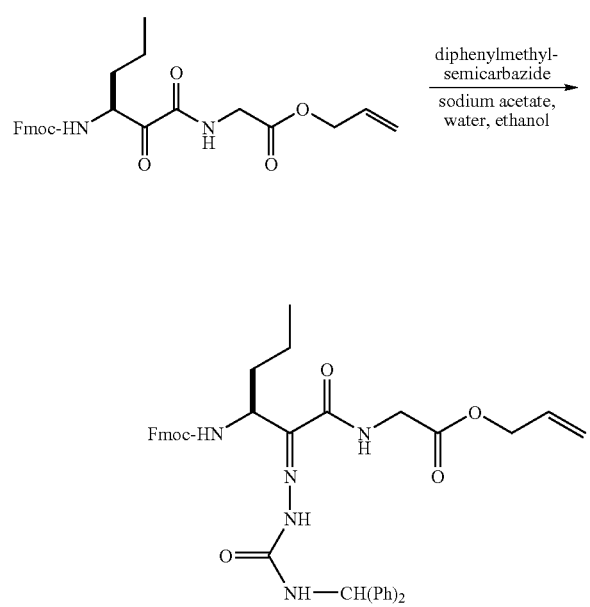

To a solution of Fmoc-nVal-(CO)-Gly-Oallyl (Step E) (4.99 g, 10.75 mmol) in ethanol (130 ml) and water (42 ml) was added diphenylmethyl semicarbazide (dpsc) trifluoroacetate salt (Step 1C) (7.6 g, 21.5 mmol) and sodium acetate .3H$_2$O (1.76 g, 12.9 mmol), successively. The reaction mixture was heated at reflux for 90 minutes. The completion of reaction was confirmed by TLC taken in 1:1 ethylacetate:hexane. Ethanol was removed under reduced pressure and the remaining residue was dissolved in ethylacetate and washed with 1 N sodium bisulfate (2×10 ml), saturated sodium bicarbonate (2×10 ml), followed by brine (10 ml). The organic layer was dried, filtered and concentrated. The resulting residue was purified by flash chromatography in 20% to 50% ethylacetate in hexanes to give a white solid (5.76 g, 78%). TLC in 50:50 ethylacetate:hexanes showed two spots (cis and trans isomers) with $R_f$=0.42 and 0.5.

G) Synthesis of Fmoc-nVal-(dpsc)-Gly-OH:

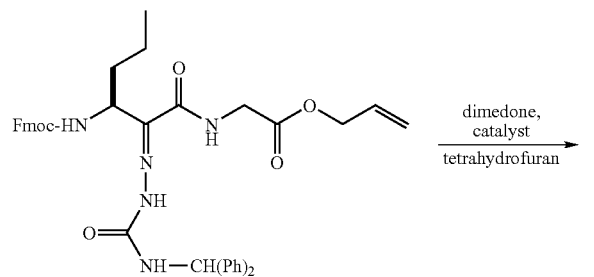

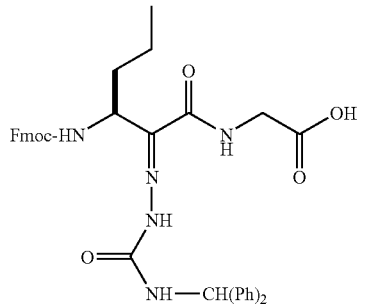

To a solution of Fmoc-nVal-(dpsc)-Gly-Oallyl (Step 1G) (4.53 g, 6.59 mmol) in tetrahydrofuran (300 ml) was added dimedone (4.62 g, 32.97 mmol) followed by tetrakis(triphenylphosphine) palladium(0) catalyst (0.76 g, 0.66 mmol). The completion of the reaction was confirmed by TLC after 90 minutes using 9:1 dichloromethane:methanol. The reaction mixture was concentrated and the remaining residue was dissolved in ethylacetate and washed three times with 50 ml portions of 0.1 M potassium biphosphate. The organic layer was then treated with 50 ml sodium bisulfite and the two phase system was stirred for 15 minutes. The phases were separated and the procedure was repeated twice more. The organic layer was dried and concentrated and subjected to flash chromatography with 20% to 100% ethylacetate in hexanes. This was followed with 9:1 dichloromethane:methanol solution. The fractions corresponding to the pure product were pooled and concentrated to obtain a white solid (3.99 g, 94%). TLC in 9:1 dichloromethane:methanol showed two spots (cis and trans isomers). NMR δ ppm (CD$_3$OD): 7.75 (m, 2H), 7.6 (m, 3H), 7.2-7.4 (m, 14H), 6.1-6.2 (m, 1H), 4.25-4.4 (m, 2H), 4.1-4.2 (m, 2H), 3.85 (s, 2H), 1.6-1.8 (m, 2H), 1.3-1.5 (m, 2H), 0.95 (t, 3H).

Step 2. Synthesis H-Phg-MBHA resin:

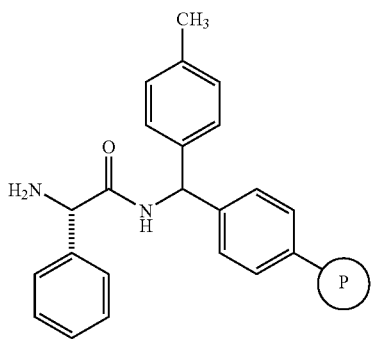

The commercially available MBHA resin (2.6 g, 1.12 mmol/g, 2.91 mmol) was transferred to a 250 mL fritted solid phase reaction vessel equipped with a nitrogen inlet. It was then washed thoroughly with 30 ml portions of dichloromethane, methanol, dimethylformamide and dichloromethane and coupled over 18 hours to the commercially available Fmoc-Phg-OH (2.17 g, 5.82 mmol) according Procedure A with 99.82% efficiency. The resin was then subjected to Fmoc deprotection according to procedure B. A qualitative ninhydrin assay on a small aliquot gave dark blue resin and solution, indicating a successful reaction.

Step 3. Synthesis of H-nVal(dpsc)-Gly-Phg-MBHA resin:

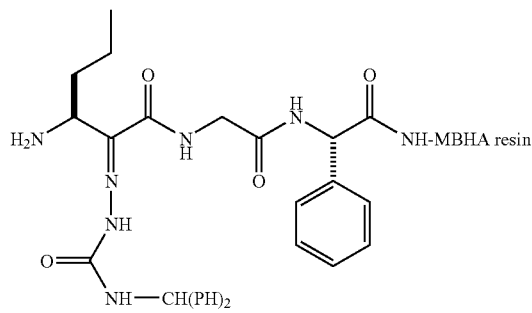

The resin obtained in step 11 (2.6 g, 0.8 mmol/g, 2.91 mmol) was reacted with Fmoc-nVal-(dpsc)-Gly-Oallyl (Step 1G) (5.82 mmol, 3.77 g) according to Procedure A. After 18 hours, quantitative ninhydrin analysis indicated 99.91% coupling efficiency. The resin was subjected to Fmoc deprotection according to procedure B. A qualitative ninhydrin assay on a small aliquot gave dark blue resin and solution, indicating a successful reaction.

Step 4. Synthesis of Boc-Pro(4t-NHFmoc)-nVal(dpsc)-Gly-Phg-MBHA resin:

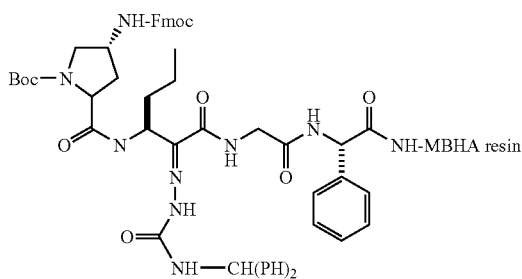

The compound H-nVal(dpsc)-Gly-Phg-MBHA resin (Step 3 above) (600 mg, 0.8 mmol/g, 0.67 mmol) was transferred to a fritted polypropylene tube and was coupled to Boc-Pro(4t-NHFmoc)-OH (Example VI, Step 3) (610 mg, 1.34 mmol) according to procedure A. After 18 hours, quantitative ninhydrin analysis indicated 99.96% coupling efficiency.

Step 5. Synthesis of Boc-Pro(4t-NH₂)-nVal(dpsc)-Gly-Phq-MBHA resin:

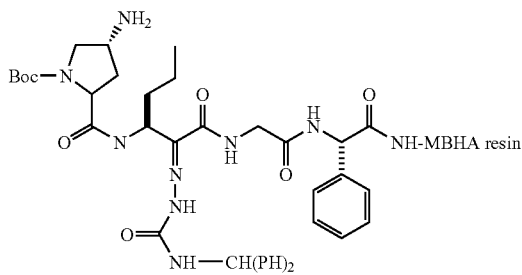

The resin from the previous step (Boc-Pro(4t-NHFmoc)-nVal(dpsc)-Gly-Phg-MBHA resin) was subjected to Fmoc deprotection according to procedure B. A qualitative ninhydrin assay on a small aliquot gave dark blue resin and solution, indicating a successful reaction.

Step 6. Synthesis of Boc-Pro(4t-NHSO₂Bn)-nVal(dpsc)-Gly-Phq-MBHA resin:

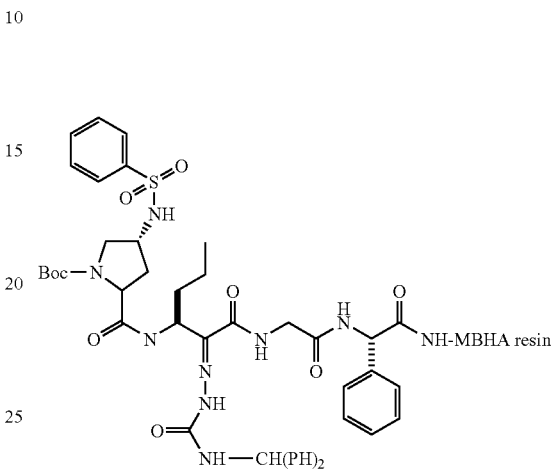

To the resin obtained from the previous step (Boc-Pro(4t-NH₂)-nVal(dpsc)-Gly-Phg-MBHA resin) (0.2 g, 0.22 mmol) suspended in NMP (2 ml) was added 2,4,6-collidine (0.24 ml, 1.79 mmol) and benzenesulfonyl chloride and the reaction was shaken for 18 hours. The solvent was drained and the resin washed thoroughly with 2 ml portions of dichloromethane, methanol, dimethylformamide and dichloromethane. Qualitative ninhydrin analysis showed colorless beads and solution indicating a successful reaction.

Step 7. Synthesis of Fmoc-G(Chx)-Pro(4t-NHSO₂Bn)-nVal(dpsc)-Gly-Phq-MBHA resin:

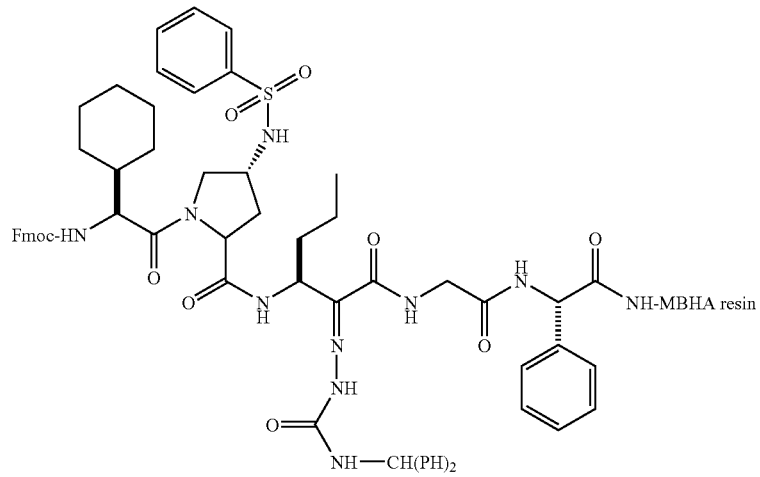

The resin obtained in the previous step (Boc-Pro(4t-NHSO$_2$Bn)-nVal(dpsc)-Gly-Phg-MBHA resin) was subjected to the Boc deprotection procedure according to Procedure C. Fmoc-G(Chx) (0.17 g, 0.45 mmol) was then coupled according to procedure A. After 18 hours qualitative ninhydrin analysis showed colorless beads and the quantitative ninhydrin analysis indicated 99.79% coupling efficiency.

Step 8. Synthesis of iBoc-G(Chx)-Pro(4t-NHSO2Bn)-nVal(dpsc)-Gly-Phq-MBHA resin:

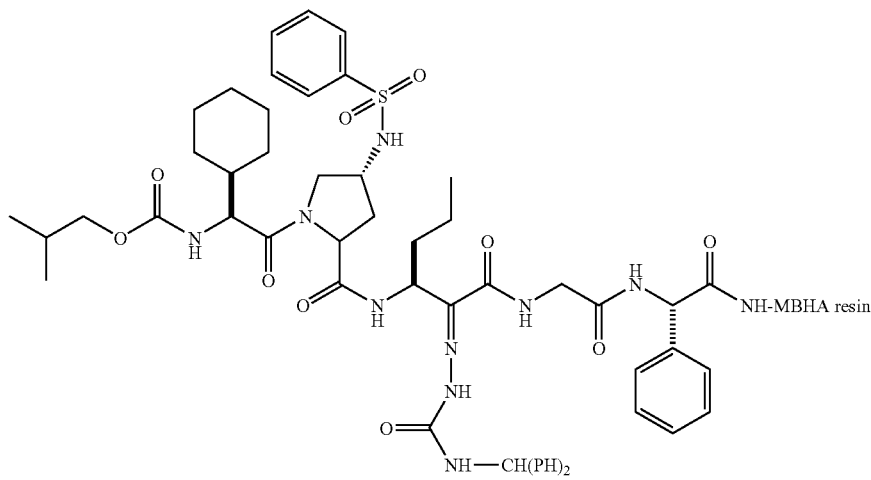

The resin obtained in the previous step (Fmoc-G(Chx)-Pro(4t-NHSO2Bn)-nVal(dpsc)-Gly-Phg-MBHA resin) was subjected to Fmoc deprotection according to procedure B. A ninhydrin assay on a small aliquot gave dark blue resin and solution, indicating a successful reaction. To the resin (0.2 g, 0.22 mmol) suspended in 2 ml NMP was added isobutylchloroformate (0.12 ml, 0.90 mmol) followed by diisopropylethylamine (0.31 ml, 1.79 mmol), and the reaction mixture was shaken for 18 hours at room temperature. Qualitative ninhydrin analysis showed colorless beads and solution indicating a successful reaction.

Step 9. Synthesis of iBoc-G(Chx)-Pro(4t-NHSO2Bn)-nVal(CO)-Gly-Phg-MBHA resin:

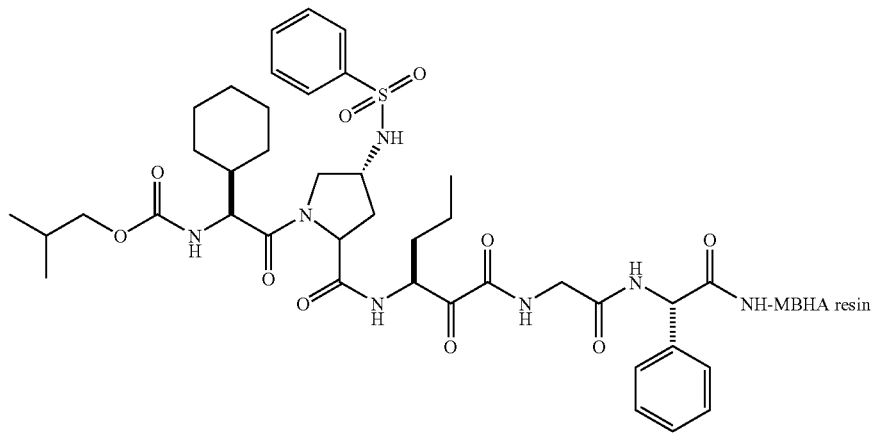

The compound of the previous step (iBoc-G(Chx)-Pro(4t-NHSO$_2$Bn)-nVal(dpsc)-Gly-Phg-MBHA resin) (200 mg) was subjected to semicarbazone hydrolysis Procedure D.

Step 10. Synthesis of Synthesis of iBoc-G(Chx)-Pro(4t-NHSO2Bn)-nVal(CO)-Gly-Phg-NH₂:

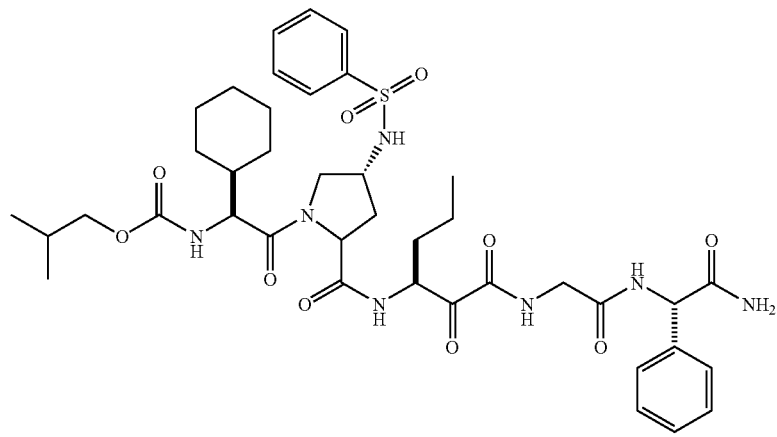

The resin of the previous step (iBoc-G(Chx)-NHSO₂Bn)-nVal(CO)-Gly-Phg-MBHA resin) (100 mg) was subjected to HF cleavage condition (Procedure E) to yield the desired crude product. The material was purified by HPLC using a 2.2×25 cm reverse phase column, containing a C-18 resin comprised of 10 micron size gel particles with a 300 angstrom pore size, eluting with a gradient using 20-50% acetonitrile in water. Analytical HPLC using a 4.6×250 mm reverse phase column, containing a C-18 resin comprised of 5 micron size gel particles with a 300 angstrom pore size, eluting with 25-75% acetonitrile (containing 0.1% trifluoroacetic acid) showed one peak at 13.5 minutes. Low resolution mass spectrum confirmed the desired mass (MH⁺ 826.4).

IV. Additional Compounds Prepared by Solution Phase Synthesis:

Representative procedures to prepare additional inventive compounds are shown below, and the compounds prepared by such procedures are listed in Tables 5 and 6.

EXAMPLE XXIII

Preparation of a Compound of Formula XXIII

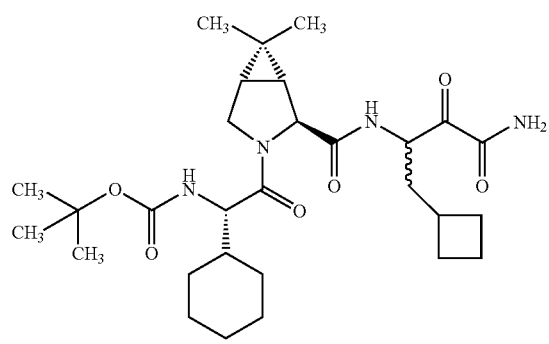

XXIII

Step 1.

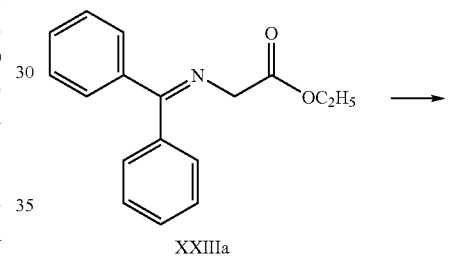

XXIIIa

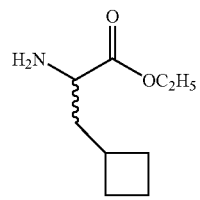

XXIIIb

A stirred solution of ketimime XXIIIa (50 g, 187.1 mmol) under N₂ in dry THF (400 mL) was cooled to −78° C. and treated with 1 M solution of K-tBuO (220 mL, 1.15 equiv.) in THF. The reaction mixture was warmed to 0° C. and stirred for 1 h and treated with bromomethyl cyclobutane (28 mL, 249 mmol). The reaction mixture was stirred at room temperature for 48 h and concentrated in vacuo. The residue was dissolved in Et₂O (300 mL) and treated with aq. HCl (2 M, 300 mL) The resulting solution was stirred at room temperature for 5 h and extracted with Et₂O (1 L). The aqueous layer was made basic to pH ~12-14 with NaOH (50% aq.) and extracted with CH₂Cl₂ (3×300 mL). The combined organic layers were dried (MgSO₄), filtered, and concentrated to give pure amine (XXIIIb, 18 g) as a colorless oil.

Step 2.

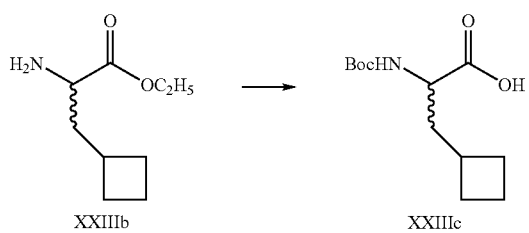

A solution of amine XXIIIb (18 g, 105.2 mmol) at 0° C. in CH$_2$Cl$_2$ (350 mL) was treated with di-tert-butyldicarbonate (23 g, 105.4 mmol) and stirred at rt. for 12 h. After the completion of the reaction (TLC), the reaction mixture was concentrated in vacuo and the residue was dissolved in THF/H$_2$O (200 ml, 1:1) and treated with LiOH.H$_2$O (6.5 g, 158.5 mmol) and stirred at room temperature for 3 h. The reaction mixture was concentrated and the basic aqueous layer was extracted with Et$_2$O. The aqueous layer was acidified with conc. HCl to pH-1-2 and extracted with CH$_2$Cl$_2$. The combined organic layers were dried (MgSO$_4$), filtered, and concentrated in vacuo to yield XXIIIc as a colorless viscous oil which was used for next step without any further purification.

Step 3.

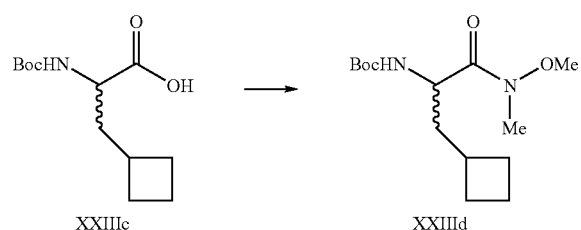

A solution of acid XXIIIc (15.0 g, 62 mmol) in CH$_2$Cl$_2$ (250 mL) was treated with BOP reagent (41.1 g, 93 mmol), N-methyl morpholine (27 mL), N,O-dimethyl hydroxylamine hydrochloride (9.07 g, 93 mmol) and stirred overnight at rt. The reaction mixture was diluted with 1 N aq. HCl (250 mL), and the layers were separated and the aqueous layer was extracted with CH$_2$Cl$_2$ (3×300 ml). The combined organic layers were dried (MgSO$_4$), filtered and concentrated in vacuo and purified by chromatography (SiO$_2$, EtOAc/Hex 2:3) to yield the amide XXIIId (15.0 g) as a colorless solid.

Step 4.

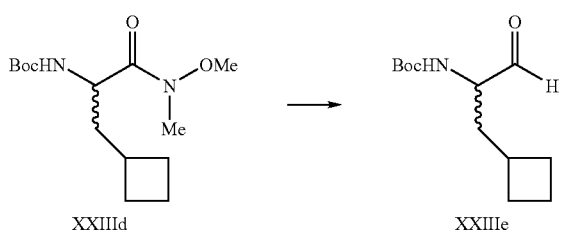

A solution of amide XXIIId (15 g, 52.1 mmol) in dry THF (200 mL) was treated dropwisely with a solution of LiAlH$_4$ (1M, 93 mL, 93 mmol) at 0° C. The reaction mixture was stirred at room temperature for 1 h and carefully quenched at 0° C. with a solution of KHSO$_4$ (10% aq.) and stirred for 0.5 h. The reaction mixture was diluted with aq. HCl (1 M, 150 mL) and extracted with CH$_2$Cl$_2$ (3×200 mL), The combined organic layers were washed with aq. HCl (1 M), saturated NaHCO$_3$, brine, and dried (MgSO$_4$). The mixture was filtered and concentrated in vacuo to yield XXIIIe as a viscous colorless oil (14 g).

Step 5.

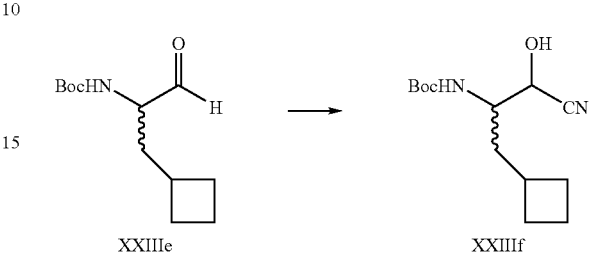

A solution of the aldehyde XXIIIe (14 g, 61.6 mmol) in CH$_2$Cl$_2$ (50 mL), was treated with Et$_3$N (10.73 mL, 74.4 mmol), and acetone cyanohydrin (10.86 g, 127.57 mmol) and stirred at room temperature for 24 hrs. The reaction mixture was concentrated in vacuo and diluted with aq. HCl (1 M, 200 mL) and extracted into CH$_2$Cl$_2$ (3×200 mL). The combined organic layer were washed with H$_2$O, brine, dried (MgSO$_4$), filtered, concentrated in vacuo and purified by chromatography (SiO$_2$, EtOAc/Hex 1:4) to yield XXIIIf (10.3 g) as a colorless liquid Step 6.

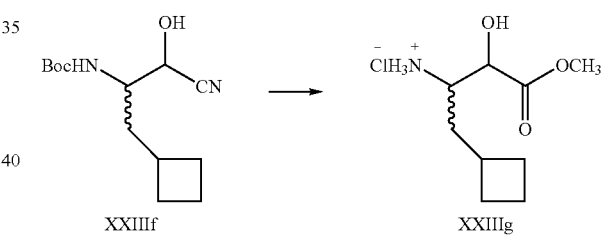

Methanol saturated with HCl*, prepared by bubbling HCl gas to CH$_3$OH (700 ml) at 0° C., was treated with cyanohydrin XXIIIf and heated to reflux for 24 h. The reaction was concentrated in vacuo to yield XXIIIg, which was used in the next step without purification.

*Alternatively 6M HCl prepared by addition of AcCl to dry methanol can also be used.

Step 7.

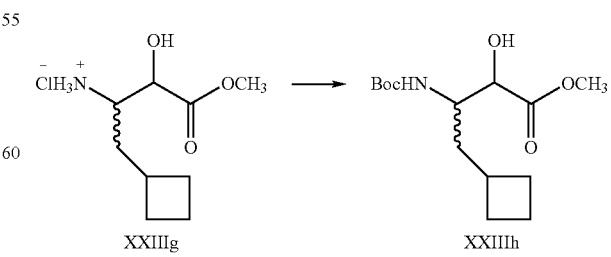

A solution of the amine hydrochloride XXIIIg in CH$_2$Cl$_2$ (200 mL) was treated with Et$_3$N (45.0 mL, 315 mmol) and Boc₂O (45.7 g, 209 mmol) at −78° C. The reaction mixture was then stirred at room temperature overnight and diluted with HCl (2 M, 200 mL) and extracted into CH₂Cl₂. The combined organic layer were dried (MgSO₄) filtered, concentrated in vacuo and purified by chromatography (EtOAc/Hex 1:4) to yield hydroxy ester XXIIIh.

Step 8.

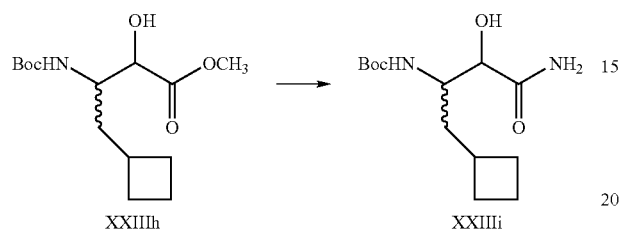

A solution of methyl ester XXIIIh (3 g, 10.5 mmol) in THF/H₂O (1:1) was treated with LiOH.H₂O (645 mg, 15.75 mmol) and stirred at rt. for 2 h. The reaction mixture was acidfied with aq HCl (1 M, 15 mL) and concentrated in vacuo. The residue was dried in vacuum.

A solution of the acid in CH₂Cl₂ (50 mL) and DMF (25 mL) was treated with NH₄Cl (2.94 g, 55.5 mmol), EDCl (3.15 g, 16.5 mmol), HOOBt (2.69 g, 16.5 mmol), and NMM (4.4 g, 44 mmol). The reaction mixture was stirred at room temperature for 3 d. The solvents were removed under vacuo and the residue was diluted with aq. HCl (250 mL) and extracted with CH₂Cl₂. The combined organic layers were washed with aq. Sat'd. NaHCO₃, dried (MgSO₄) filtered concentrated in vacuo to obtain XXIIIi, which was used as it is in the following steps. (Alternatively XXIIIi can also be obtained directly by the reaction of XXIIIf (4.5 g, 17.7 mmol) with aq. H₂O₂ (10 mL), LiOH.H₂O (820 mg, 20.8 mmol) at 0° C. in 50 mL of CH₃OH for 0.5 h.)

Step 9.

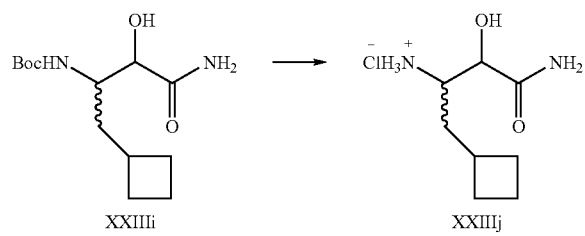

A solution of XXIIIi obtained in the previous step was dissolved in 4 N HCl in dioxane and stirred at rt. for 2 h. The reaction mixture was concentrated in vacuo to give XXIIIj as a solid, which was used without further purification.

Step 10.

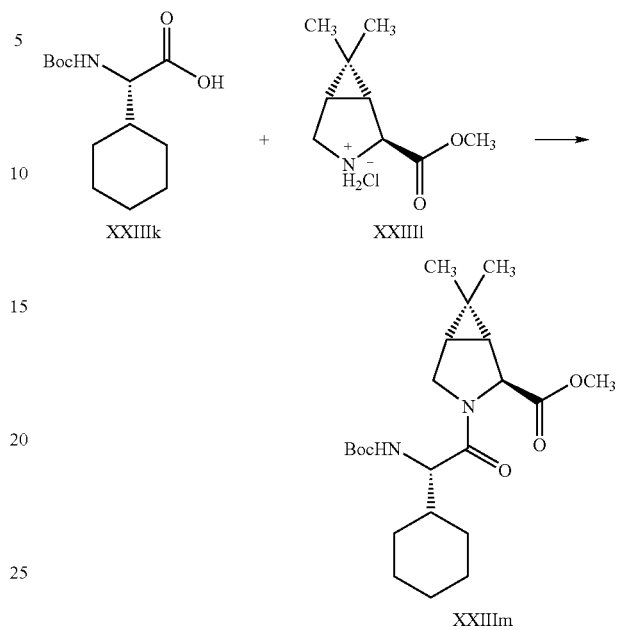

The amino ester XXIIII was prepared following the method of R. Zhang and J. S. Madalengoitia (*J. Org. Chem.* 1999, 64, 330), with the exeception that the Boc group was cleved by the reaction of the Boc-protected amino acid with methanolic HCl.

A solution of commercial amino acid Boc-Chg-OH, XXIIIk (Senn chemicals, 6.64 g, 24.1 mmol) and amine hydrochloride XXIIII (4.5 g, 22 mmol) in CH₂Cl₂ (100 mL) at, 0° C. was treated with BOP reagent and stirred at rt. for 15 h. The reaction mixture was concentrated in vacuo, then it was diluted with aq. 1 M HCl and extracted into EtOAc (3×200 mL). The combined organic layers were washed with sat'd. NaHCO₃ (200 mL), dried (MgSO₄), filtered and concentrated in vacuo, and chromatographed (SiO₂, EtOAc/Hex 3:7) to obtain XXIIIm (6.0 g) as a colorless solid.

Step 11.

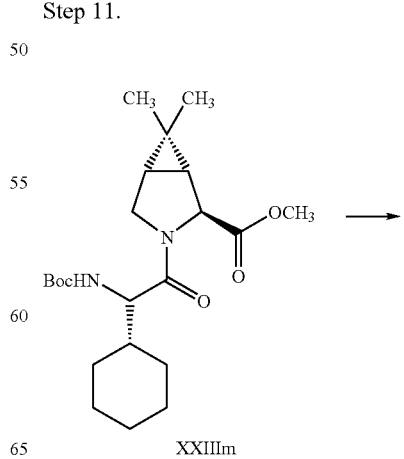

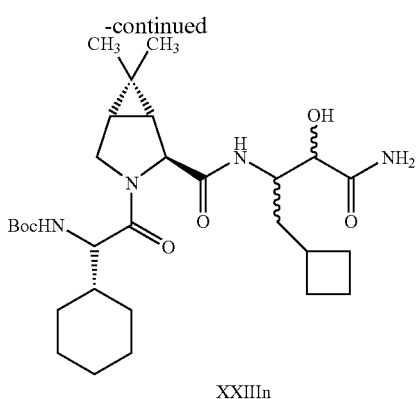

XXIIIn

A solution of methyl ester XXIIIm (4.0 g, 9.79 mmol) in THF/H₂O (1:1) was treated with LiOH.H₂O (401 mg, 9.79 mmol) and stirred at rt. for 3 h. The reaction mixture was acidified with aq. HCl and concentrated in vacuo to obtain the free acid.

A solution of acid (1.5 g, 3.74 mmol) in DMF/CH₂Cl₂ (1:1 50 mL) was treated with amine XXIIIj (772 mg, 3.74 mmol), EDCl (1.07 g, 5.61 mmol), HOOBt (959 mg, 5.61 mmol) and NMM (2.15 mL, 14.96 mmol) at −10° C. The reaction mixture was stirred at 0° C. for 48 h and concentrated in vacuo. The residue was diluted with aq. 1 M HCl and extracted with CH₂Cl₂, The combined organic layers were extracted with aq. NaHCO₃, aq. HCl, brine, dried (MgSO₄), filtered and concentrated in vacuo to obtain XXIIIn (2.08 g) as a tan colored solid.

Step 12.

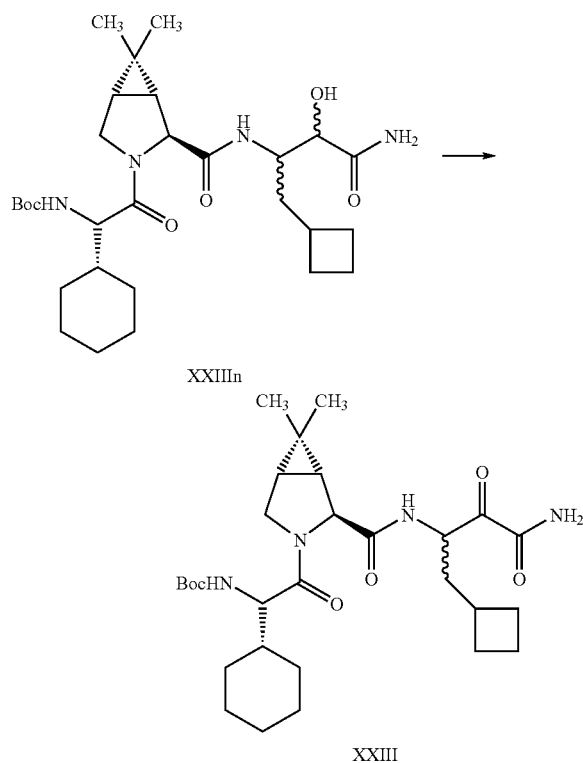

A solution of amide XXIIIn (2.08 g, 3.79 mmol) in toluene and DMSO (1:1 mL) at 0° C. was treated with EDCl (7.24 g, 37.9 mmol) and dichloroacetic acid (2.42 g, 19.9 mmol) and stirred at rt. for 4 h. The reaction mixture was diluted with CH₂Cl₂, washed with sat'd. NaHCO₃, and brine. The organic layer were dried (MgSO₄) filtered, concentrated, in vacuo and purified by chromatography (SiO₂, Acetone/Hexanes 3:7) to yield XXIII as a colorless solid.

EXAMPLE XXIV

Preparation of a Compound of Formula XXIV

XXIV

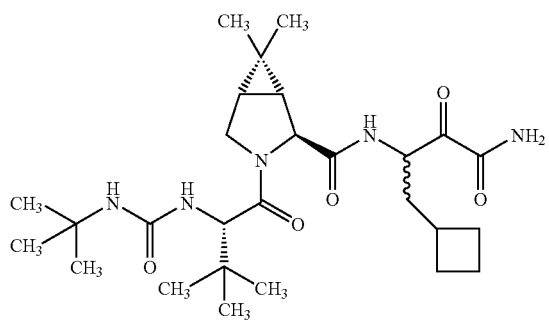

Step 1.

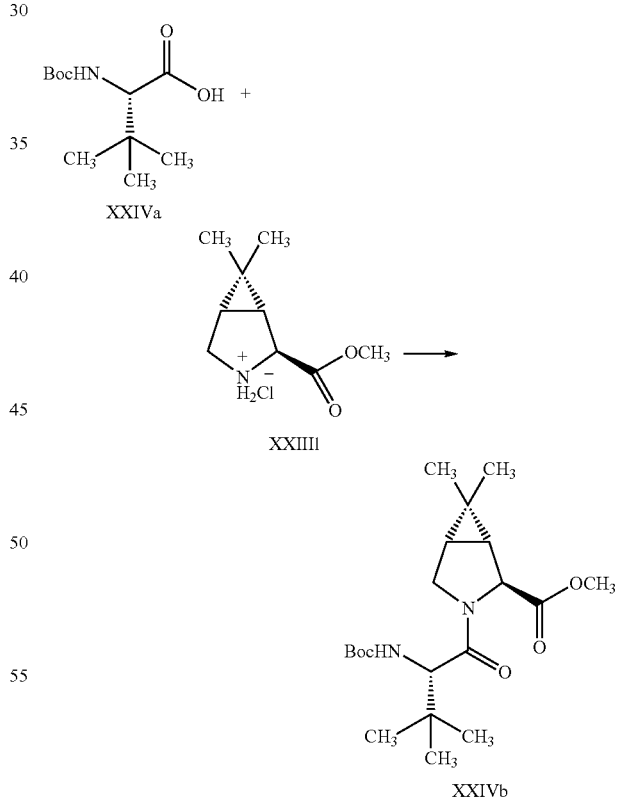

A solution of Boc-tert-Lue XXIVa (Fluka, 5.0 g 21.6 mmol) in dry CH₂Cl₂/DMF (50 mL, 1:1) was cooled to 0° C. and treated with the amine XXIIII (5.3 g, 25.7 mmol), NMM (6.5 g, 64.8 mmol) and BOP reagent (11.6 g, 25.7 mmol). The reaction was stirred at rt. for 24 h, diluted with aq. HCl (1 M) and extracted with CH₂Cl₂. The combined organic layers were washed with HCL (aq, 1 M), sat'd. NaHCO₃, brine, dried (MgSO₄), filtered and concentrated in vacuo and purified by chromatography (SiO₂, Acetone/Hexane 1:5) to yield XXIVb as a colorless solid.

Step 2.

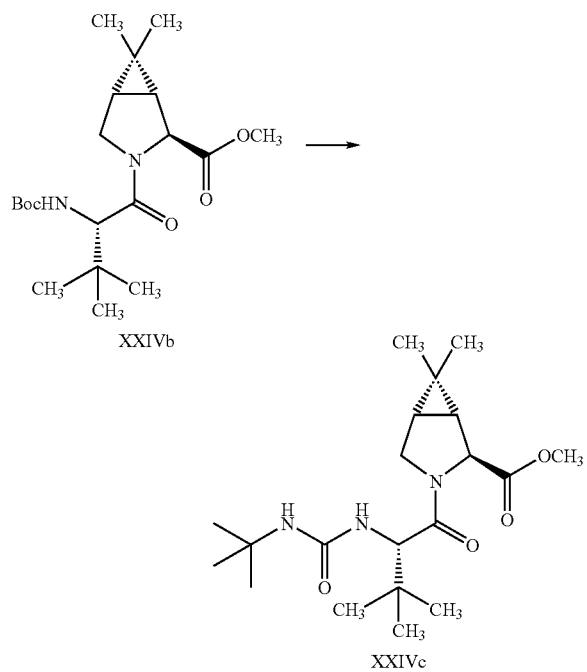

XXIVb

XXIVc

A solution of methyl ester XXIVb (4.0 g, 10.46 mmol) was dissolved in HCl (4 M soln. dioxane) and stirred at rt. for 3 h. The reaction mixture was concentrated in vacuo to obtain the amine hydrochloride salt used in the next step.

A solution of the amine hydrochloride salt (397 mg, 1.24 mmol) in CH₂Cl₂ (10 mL) was cooled to −78° C. and treated with tert-butyl isocyanate (250 mg, 2.5 mmol) and stirred at rt. overnight. The reaction mixture was concentrated in vacuo and the residue was diluted with aq. HCl (1M) and extracted with CH₂Cl₂. The combined organic layers were washed with aq. HCl (1M), sat'd. NaHCO₃ and brine. The organic layers were dried, filtered and concentrated in vacuo and the residue was purified by chromatography (SiO₂, acetone/Hex 1:4) to yield XXIVc as a colorless solid.

Step 3.

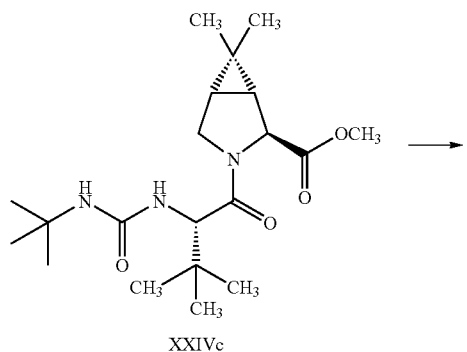

XXIVc

-continued

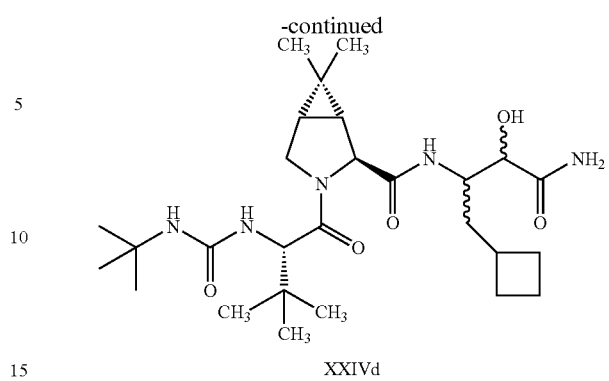

XXIVd

A solution of methyl ester XXIVc (381 mg, 1.0 mmol) in THF/H₂O (1:1, 5 mL) was treated with LiOH.H₂O (62 mg, 1.5 mmol) and stirred at rt. for 3 h. The reaction mixture was acidified with aq. HCl and concentrated in vacuo to obtain the free acid.

A solution of acid (254.9 mg, 0.69 mmol) in DMF/CH₂Cl₂ (1:1, 5.0 mL) was treated with amine XXIIIj (159 mg, 0.763 mmol), EDCl (199 mg, 1.04 mmol), HOOBt (169.5 mg, 1.04 mmol) and NMM (280 mg, 2.77 mmol) at −20° C. The reaction mixture was stirred at −20° C. for 48 h and concentrated in vacuo. The residue was diluted with aq. 1 M HCl and extracted with EtOAc, The combined organic layers were extracted with aq. NaHCO₃, aq. HCl, brine, dried (MgSO₄) filtered concentrated in vacuo to obtain XXIVd (470 mg) as a tan colored solid.

Step 4.

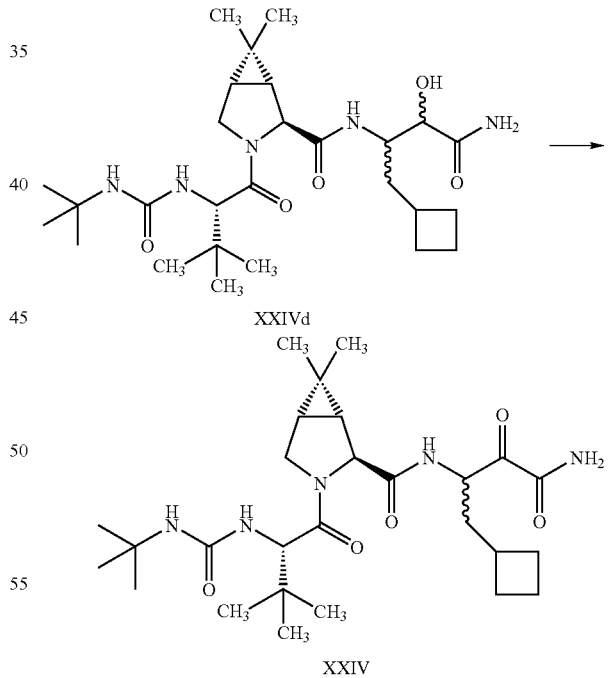

XXIVd

XXIV

A solution of amide XXIVd (470 mg, 0.9 mmol) in toluene and DMSO (1:1 mL) at 0° C. was treated with EDCl (1.72 g, 9.0 mmol) and dichloroacetic acid (0.37 mL, 4.5 mmol) and stirred at 0° C. for 4 h. The reaction mixture was diluted with CH₂Cl₂, and washed with satd. NaHCO₃, and brine. The organic layer was dried (MgSO₄), filtered, concentrated, in vacuo and purified by chromatography (SiO₂, Acetone/Hexanes 3:7) to yield XXIV as a colorless solid.

EXAMPLE XXV

Preparation of a Compound of Formula XXV

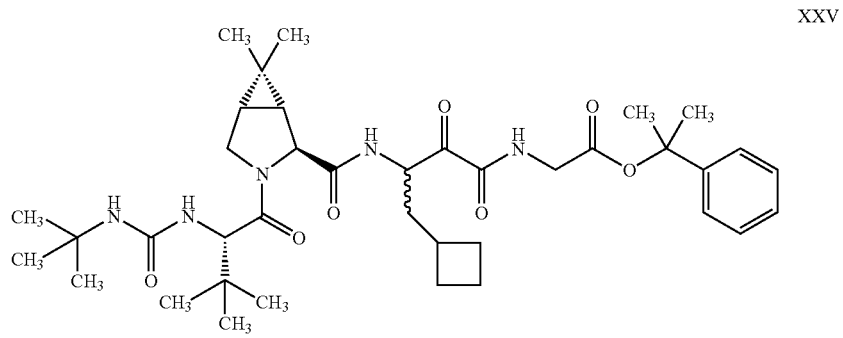

Step 1.

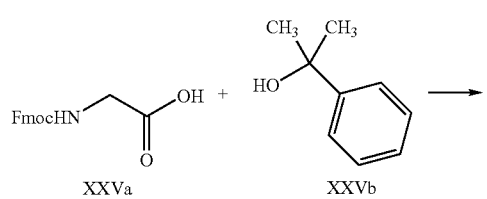

A solution of Fmoc-glycine (Bachem, 2.0 g, 6.87 mmol) in CH$_2$Cl$_2$ (20 mL) was treated with 2-phenyl-2-propanol (Aldrich, 3.36 g, 24.7 mmol), DCC (1 M soln CH$_2$Cl$_2$, 8.24 mL), DMAP (167 mg, 1.37 mmol) and stirred at rt. for 24 h. The reaction mixture was concentrated in vacuo and diluted with Et$_2$O (100 mL). The solid separating out was filtered and the filterate washed with satd. NaHCO$_3$. The organic layer was dried (MgSO$_4$), filtered, concentrated in vacuo, and purified by chromatography (SiO$_2$, EtOAc/Hex 1:5) to yield ester XXVc (1.1 g) as a colorless viscous liquid.

Step 2.

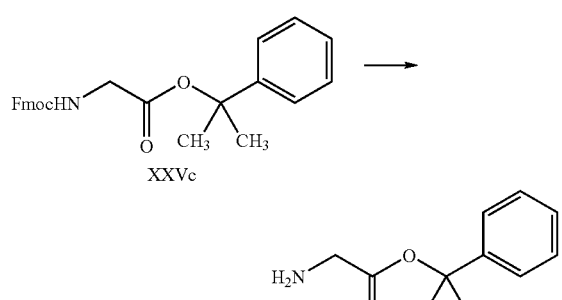

A solution of XXVc in CH$_2$Cl$_2$ (16.0 mL) was treated with piperidine (4.0 mL) and stirred at rt. for 0.5 h. The reaction mixture was concentrated in vacuo and purified by chromatography (SiO$_2$, Acetone/Hexanes 1:10 to 1:1) to yield the amine XXVd (420 mg) as a colorless liquid.

Step 3.

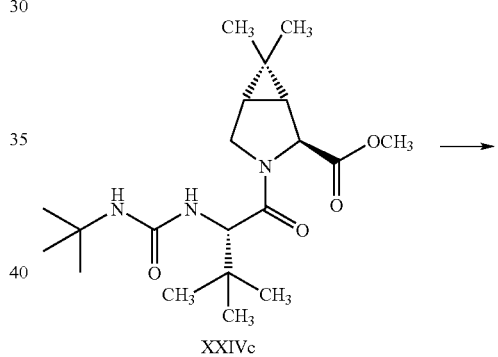

A solution of methyl ester XXIVc (381 mg, 1.0 mmol) in THF/H$_2$O (1:1, 5 mL) was treated with LiOH.H$_2$O (62 mg, 1.5 mmol) and stirred at rt. for 3 h. The reaction mixture was acidified with aq. HCl and concentrated in vacuo to obtain the free acid.

A solution of acid (2.0 g, 5.5 mmol) in DMF/CH₂Cl₂ (1:1, 40.0 mL) at −10° C. was treated with amine XXIIIg (1.51 g, 6.8 mmol), EDCl (1.57 g, 8.25 mmol), HOOBt (1.41 g, 8.25 mmol) and NMM (2.5 g, 24.7 mmol). The reaction mixture was stirred at 0° C. for 48 h and concentrated in vacuo. The residue was diluted with aq. 1M HCl (100 mL) and extracted with CH₂Cl₂ (3×100 mL). The combined organic layers were extracted with aq. NaHCO₃, aq. HCl, brine, dried (MgSO₄) filtered, concentrated in vacuo to obtain XXVe (3.17 g) as a tan colored solid used further without any purification.

Step 4.

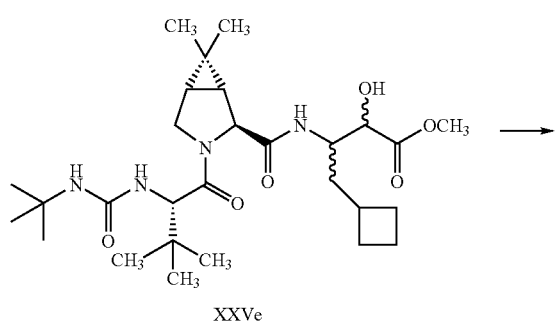

XXVe

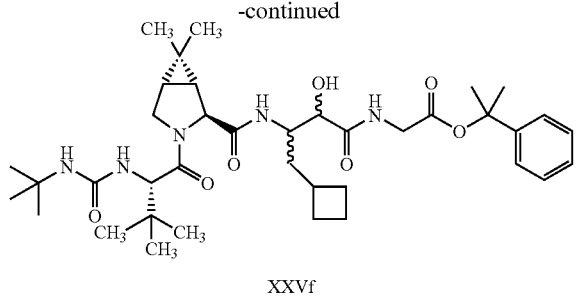

-continued

XXVf

A solution of methyl ester XXVe (2.5 g, 4.66 mmol) in THF/H₂O/CH₃OH (1:1:1, 60 mL) was treated with LiOH.H₂O (200 mg, 4.87 mmol) and stirred at rt. for 4 h. The reaction mixture was acidified with aq. HCl and concentrated in vacuo to obtain the free acid.

A solution of acid (200.0 mg, 0.38 mmol) in DMF/CH₂Cl₂ (1:1, 6.0 mL) at −10° C. was treated with amine XXVd (78 mg, 0.4 mmol), EDCl (105 mg, 0.55 mmol), HOOBt (95 mg, 0.55 mmol) and NMM (150 mg, 1.48 mmol). The reaction mixture was stirred at 0° C. for 48 h and concentrated in vacuo. The residue was diluted with aq. 1 M HCl (30 mL) and extracted with CH₂Cl₂ (3×30 mL). The combined organic layers were extracted with aq. NaHCO₃ (2×30 mL), aq. HCl, brine (30 mL), dried (MgSO₄) filtered, concentrated in vacuo to obtain XXVf (240 mg) as a tan colored solid.

Step 5.

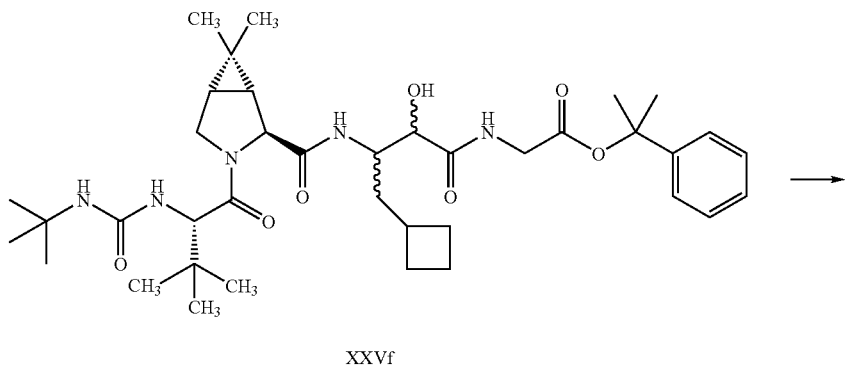

XXVf

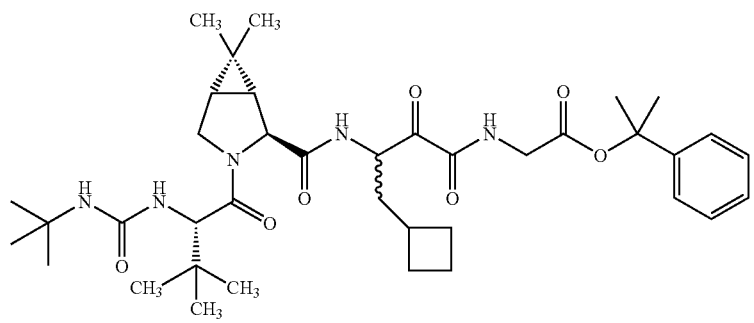

XXV

A solution of XXVf (240 mg, 0.28 mmol) in CH$_2$Cl$_2$ (10 mL) was treated with Dess-Martin reagent (Omega, 242 mg, 0.56 mmol) and stirred at rt. for 2 h. After the oxidation was complete (TLC, Acetone/Hex 1:4) the reaction mixture was diluted with satd. NaHCO$_3$ (20 mL) and Na$_2$S$_2$O$_3$ (10% aq soln, 20 mL). The reaction mixture was stirred for 30 min and extracted with CH$_2$Cl$_2$ (3×30 mL). The combined organic layers were extracted with satd. NaHCO$_3$, brine, dried (MgSO$_4$) filtered concentrated in vacuo and purified by chromatography (SiO$_2$, acetone/Hexanes 1:5) to yield XXV (122 mg) as a colorless solid.

EXAMPLE XXVI

Preparation of a Compound of Formula XXVI

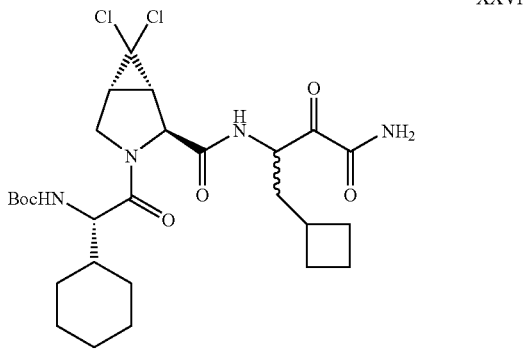

XXVI

Step 1:

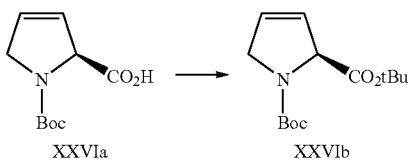

To a stirred solution of N-Boc-3,4-dehydroproline XXVIa (5.0 g, 23.5 mmol), di-tert-butyl dicarbonate (7.5 g, 34.4 mmol), and 4-N,N-dimethylaminopyridine (0.40 g, 3.33 mmol) in acetonitrile (100 mL) at room temperature was added triethylamine (5.0 mL, 35.6 mmol). The resulting solution was stirred at this temperature for 18 h before it was concentrated in vacuo. The dark brown residue was purified by flash column chromatography eluting with 10-25% EtOAc/hexane to give the product XXVIb as a pale yellow oil (5.29 g, 84%).

Step 2:

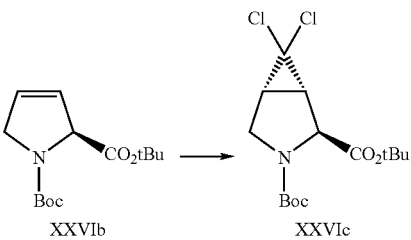

To a stirred solution of dehydroproline XXVIb (10.1 g, 37.4 mmol), benzyltriethylammonium chloride (1.60 g, 7.02 mmol) in chloroform (120 mL) at room temperature was added 50% aqueous sodium hydroxide (120 g). After vigorously stirred at this temperature for 24 h, the black mixture was diluted with CH$_2$Cl$_2$ (200 mL) and diethyl ether (600 mL). After the layers were separated, the aqueous solution was extracted with CH$_2$Cl$_2$/Et$_2$O (1:2, 3×600 mL). The organic solution was dried (MgSO$_4$) and concentrated. The residue was purified by flash column chromatography using 5-20% EtOAc/hexane to afford 9.34 g (71%) of XXVIc as an off-white solid.

Step 3:

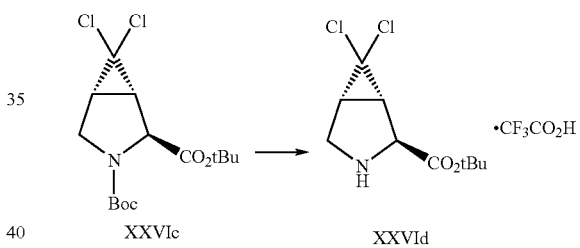

The solution of XXVIc (9.34 g, 26.5 mmol) in CH$_2$Cl$_2$ (25 mL) and CF$_3$CO$_2$H (50 mL) was stirred at room temperature for 4.5 h before it was concentrated in vacuo to give a brown residue which was used in Step 4 without further purification.

Step 4

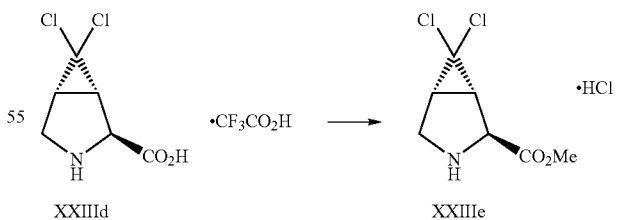

Commercial concentrated hydrochloric acid (4.5 mL) was added to a solution of the residue from Step 3 in methanol (70 mL) and the resulting mixture was warmed to 65° C. in an oil bath. After 18 h, the mixture was concentrated in vacuo to give a brown oil XXVIe, which was used in Step 5 without further purification.

Step 5:

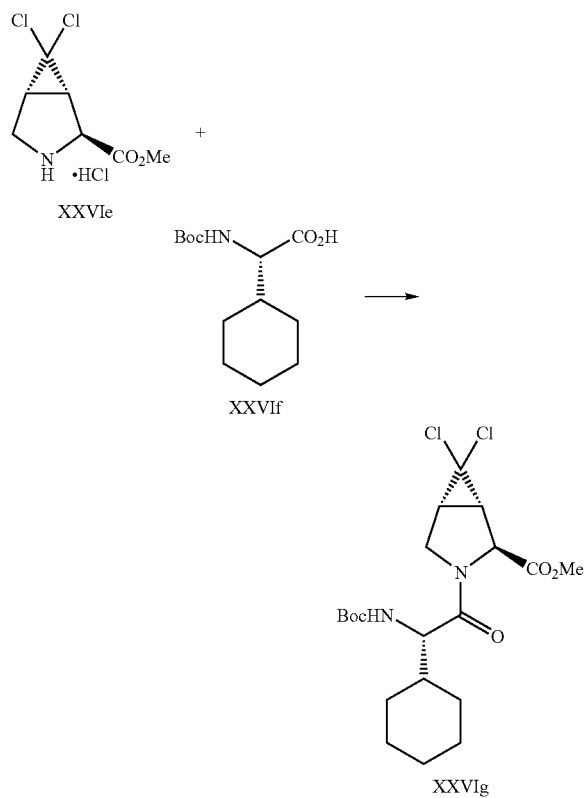

To a stirred solution of proline methyl ester XXVIe from Step 4, commercial N-Boc-cyclohexylglycine XXVIf (10.2 g, 40.0 mmol) and [O-(7-azabenzotriazol-1-yl)-1,1,3,3-tetramethyluronium hexafluorophosphate] (HATU) (16.0 g, 42.1 mmol) in DMF (200 mL) at 0° C. was added diisopropylethylamine (18.0 mL, 104 mmol). After allowed to warm to room temperature along with the ice bath over night (18 h), the reaction mixture was diluted with EtOAc (600 mL), 5% $H_3PO_4$ (150 mL) and brine (150 mL). The organic solution washed with 5% $H_3PO_4$ (150 mL), saturated $NaHCO_3$ (2×200 mL) before it was dried ($MgSO_4$), filtered and concentrated in vacuo. The residue was purified by flash column chromatography using 5-20% EtOAc/hexane to afford 3.84 g (32%, three steps) of XXVIg as an off-white solid.

Step 6:

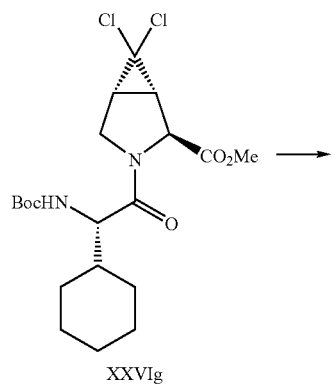

-continued

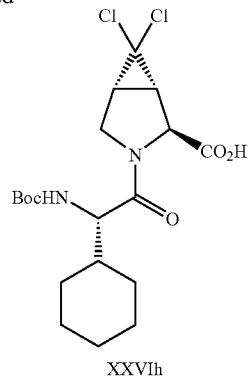

The solution of methyl ester XXVIg (5.87 g, 13.1 mmol) and LiOH (1.65 g, 39.3 mmol) in $THF/MeOH/H_2O$ (1:1:1, 90 mL) was stirred at room temperature for 4 h. Methanol and THF were removed under reduced pressure. The aqueous solution was acidified to PH~2 using 1 N aqueous HCl solution (50 mL) and saturated with solid sodium chloride before it was extracted with EtOAc (3×150 mL). The organic solutions were combined, dried ($MgSO_4$), filtered and concentrated in vacuo to give a white solid XXVIh (5.8 g, quantitative).

Step 7:

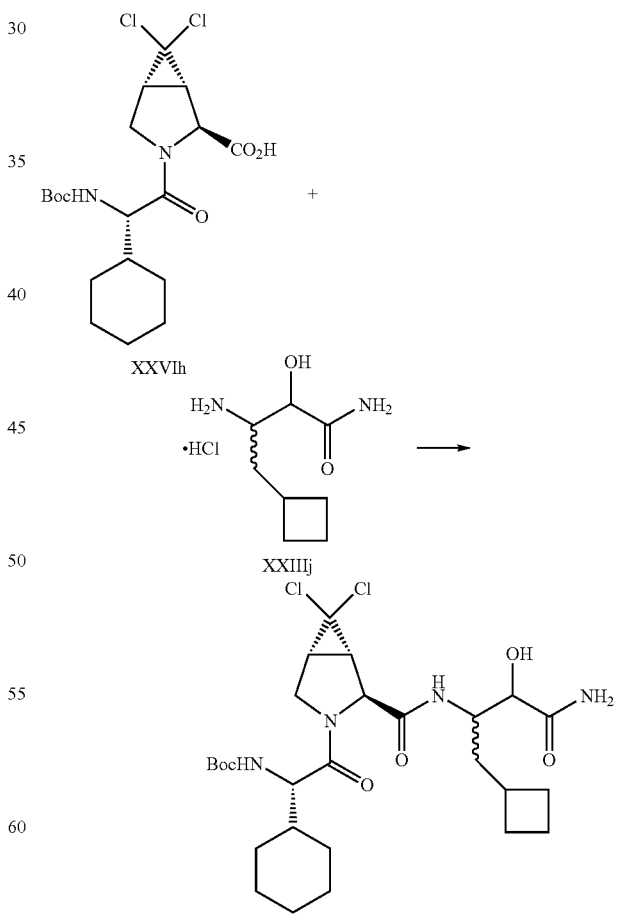

The desired product XXIIIi was prepared according to the procedure in Example XXIII, Step 11.

Step 8:
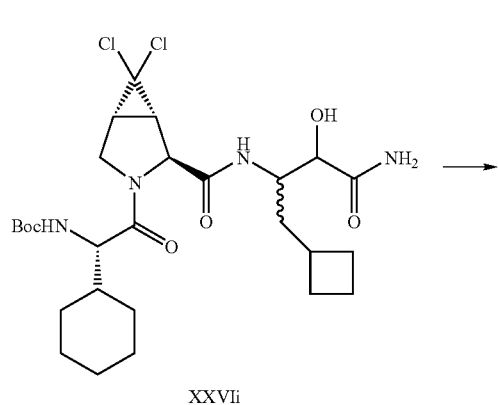
XXVIi
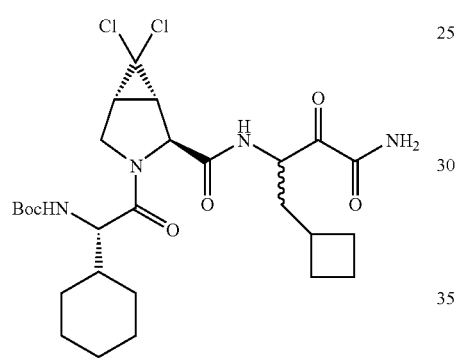
XXVI
The desired product XXVI was prepared according to the procedure in Example XXIII, Step 12.
EXAMPLE XXVII
Preparation of Compound of Formula XXVII
XXVII
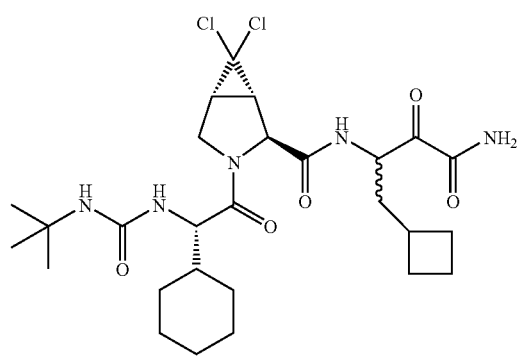
Step 1
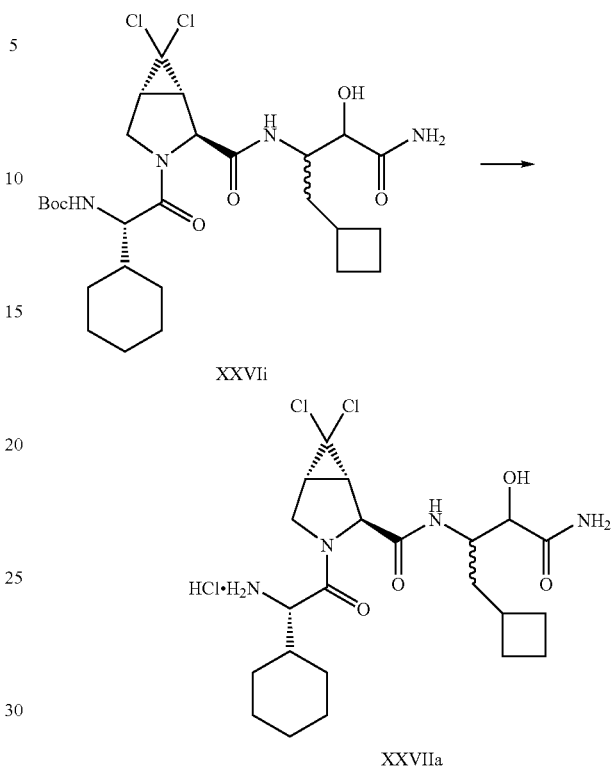
The desired product XXVIIa was prepared according to the procedure in Example XXIII, Step 9.
Step 2
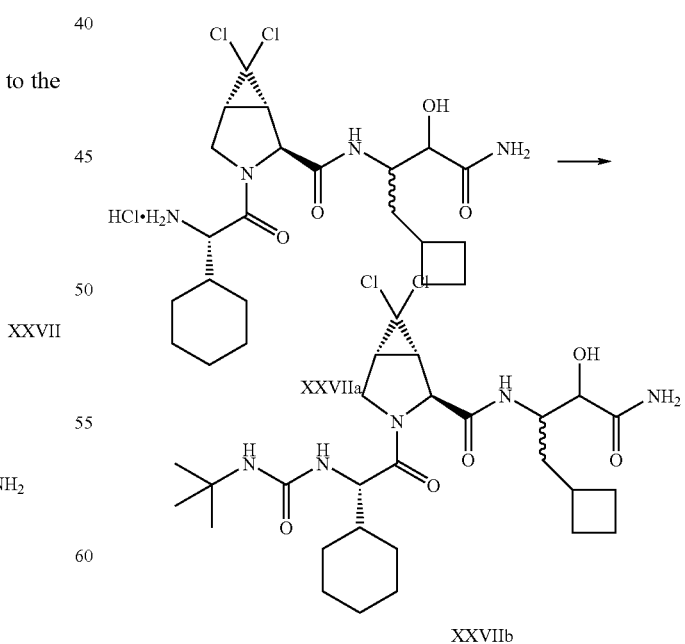
The desired product XXVIIb was prepared according to the procedure in Example XXIV, Step 2.

Step 3

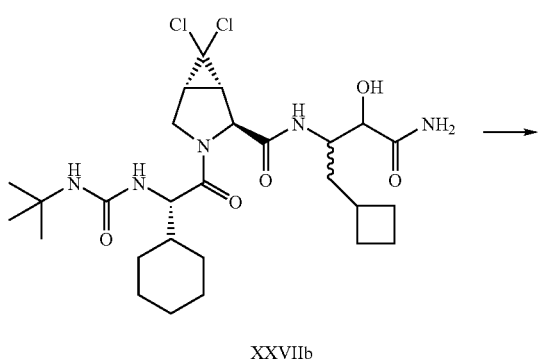

XXVIIb

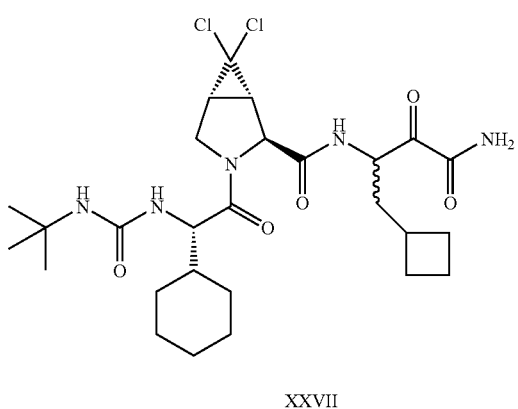

XXVII

The desired product XXVII was prepared according to the procedure in Example XXIII, Step 12.

EXAMPLE XXVIII

Preparation of a Compound of Formula XXVIII

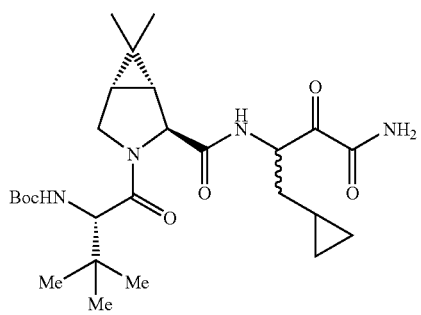

XXVIII

Step 1:

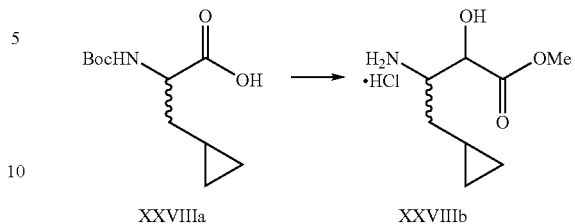

XXVIIIa          XXVIIIb

The intermediate XXVIIIb was prepared according to the procedure in Example XXIII, Steps 3-6.

Step 2:

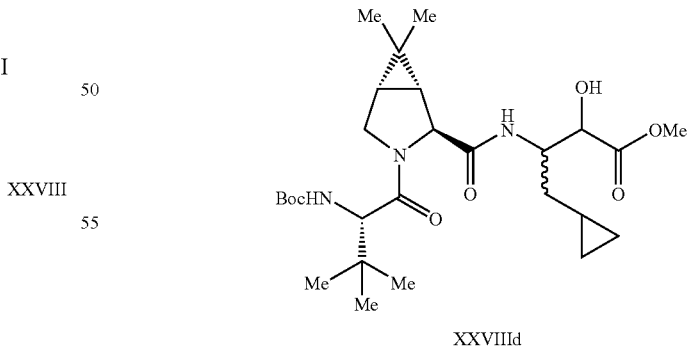

XXVIIIc

XXVIIIb

XXVIIId

The acid from Example XXIV, Step 2 (XXVIIIc) (0.7 g) was reacted with product from Step 1 above (0.436 g), HATU (0.934 g) and DIPEA (1.64 mL) in the manner previously described in Example IX, Step 2a to afford 0.66 g of the desired product XXVIIId.

Step 3:

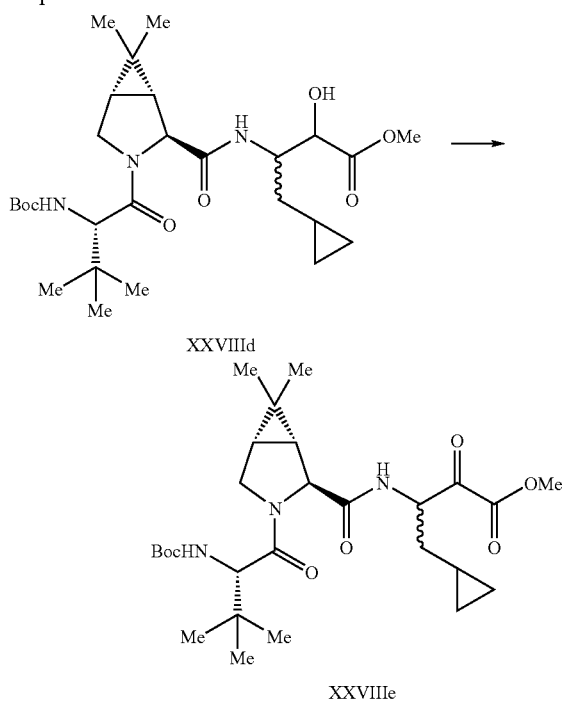

XXVIIId

XXVIIIe

The product of Step 2 (0.5 g) was reacted with Dess-Martin reagent (1 g) in the manner previously described in Example XX, Step 7. Purification by flash column chromatography (40% EtOAc, Hexane, silica) furnished 0.35 g of product XXVIIIe. Mass spectrum (LCMS) 522 (M+H$^+$).

Step 4:

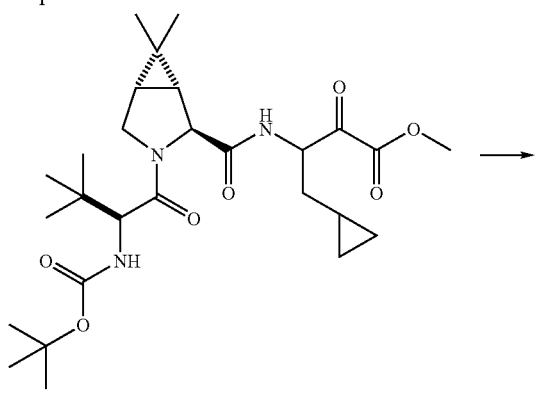

XXVIIIe

The product of Step 4 (0.3 g) was added a 1/1 H$_2$O/MeOH solution (20 mL) and NaHCO$_3$ solid (242 mg, 5 equiv.). After being stirred for 18 hours at room temperature, the reaction was diluted with EtOAc and layers were separated. The aqueous layer was acidified to pH 2 with HCl 1.0 N and extracted with EtOAc. The EtOAc layer washed with brine then dried over MgSO$_4$, filtered and concentrated in vacuo to afford product XXVIIIf as a white powder (0.26 g). Mass spectrum (LCMS) 508 (M+H$^+$).

Step 5:

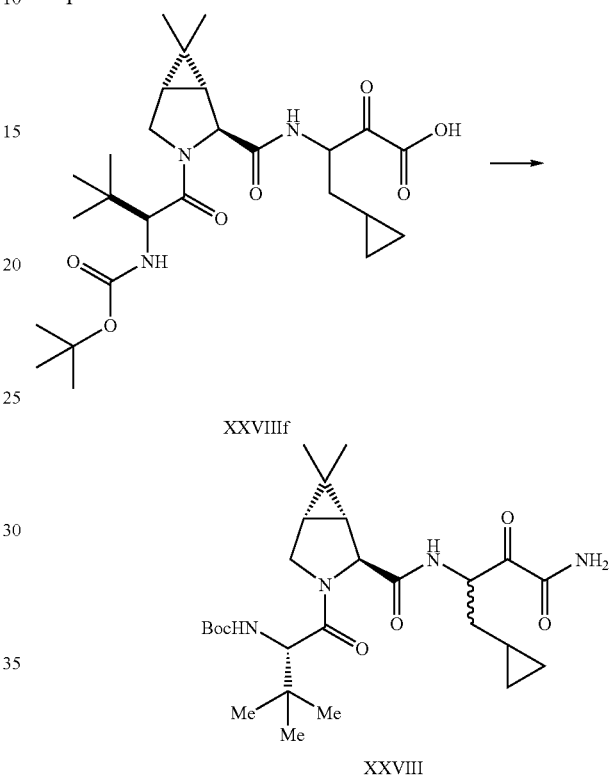

XXVIIIf

XXVIII

The product of Step 5 (0.15 g) was dissolved in CH$_2$Cl$_2$ and reacted with HATU (0.137 g), NH$_4$Cl (0.08 g, 5 equiv.) and DIPEA (0.53 mL). After 2 hours at room temperature, the reaction was diluted with EtOAc, washed with a 10% citric acid solution, then a saturated NaHCO$_3$ solution. The EtOAc layer washed with brine then dried over MgSO$_4$, filtered and concentrated in vacuo to afford a crude mixture. Purification by flash column chromatography (30% Acetone, Hexane, silica) furnished the desired product XXVIII (0.096 g). Mass spectrum (LCMS) 507 (M+H$^+$).

EXAMPLE XXIX

Preparation of a Compound of Formula XXIX

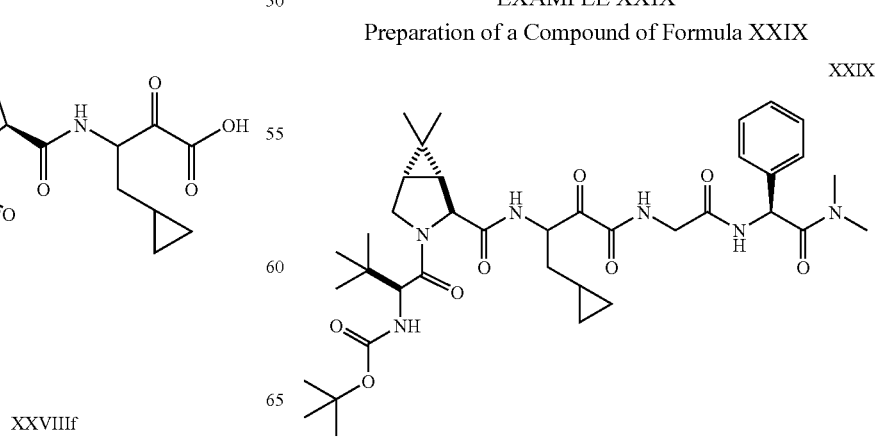

XXIX

Step 1:

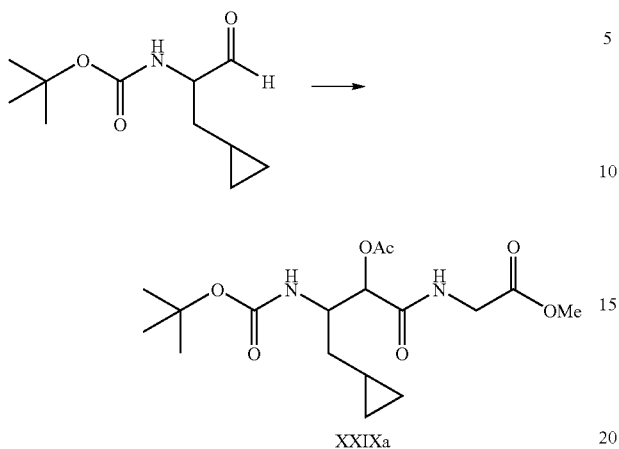

To a 0° C. solution of the starting aldehyde (4.0 g) in CH$_2$Cl$_2$ (75 mL) was added acetic acid (2.0 equiv., 2.15 mL) followed by methylisocyanoacetate (1.1 equiv., 1.9 mL). The reaction was then gradually warmed-up to room temperature. After 18 hours (overnight), the reaction was diluted with EtOAc and washed with a saturated NaHCO$_3$ solution. The EtOAc layer washed with brine then dried over MgSO$_4$, filtered and concentrated in vacuo to afford a crude mixture. Purification by flash column chromatography (30 to 40% EtOAc, Hexane, silica) furnished the product XXIXa (4.5 g).

Step 2:

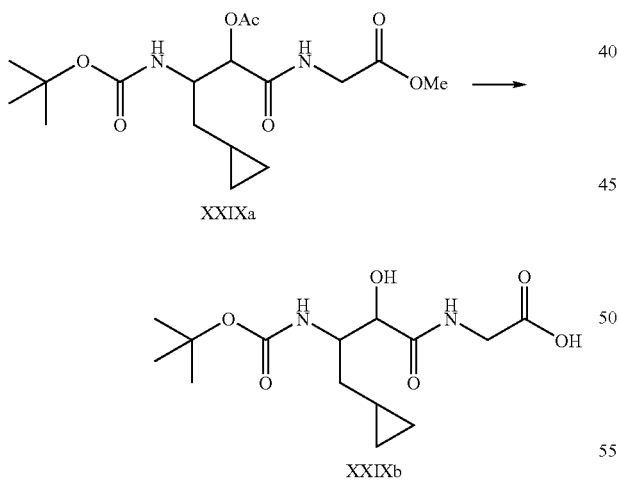

To a 0° C. solution of XXIXa (4.4 g) in THF (100 mL) was added 26 mL (2.2 equiv.) of a 1.0 N LiOH solution. The reaction was stirred at this temperature for 2 hours then warmed-up to room temperature. After 2 hours, reaction mixture was acidified to pH 2 with a 1.0 N HCl solution. EtOAc was added and layers were separated. The EtOAc layer washed with brine then dried over MgSO$_4$, filtered and concentrated in vacuo to afford product XXIXb (3.7 g).

Step 3:

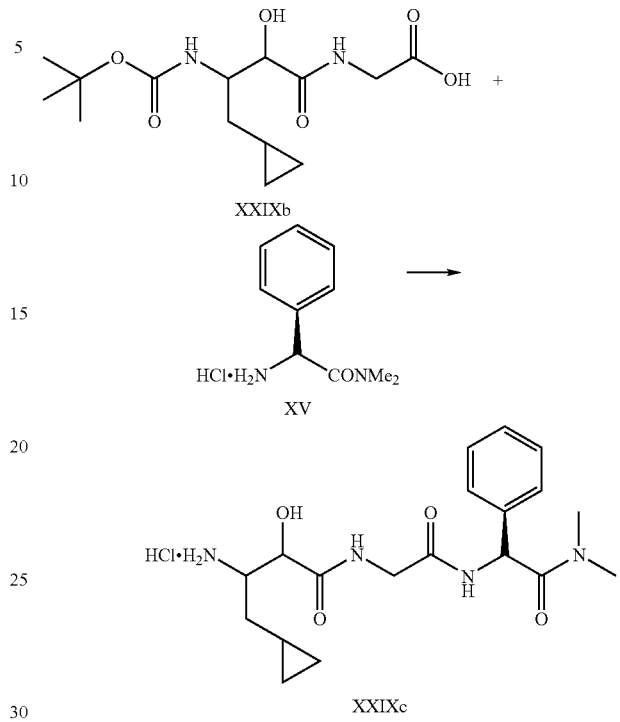

The acid XXIXb was reacted with the amine from Example XV in the manner previously described in Example XXI, Step 4. The resulting intermediate was then treated with HCl in the manner previously described in Example XXIII, Step 9 to afford product XXIXc.

Step 4:

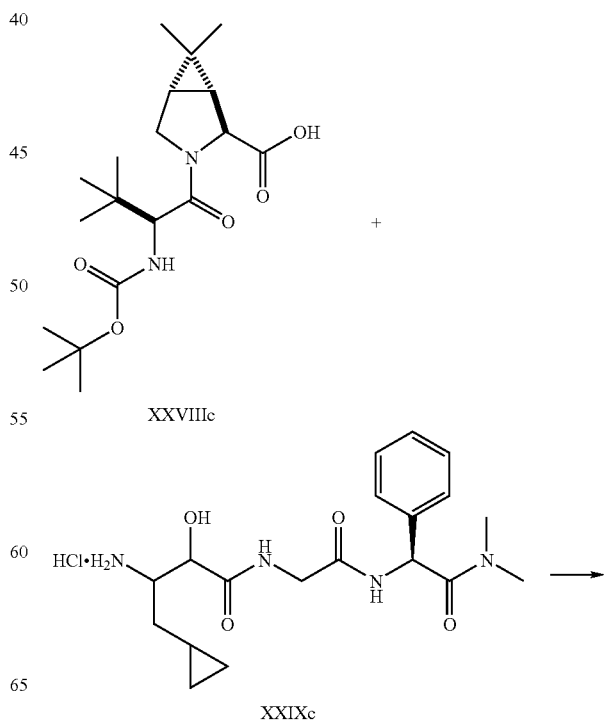

-continued

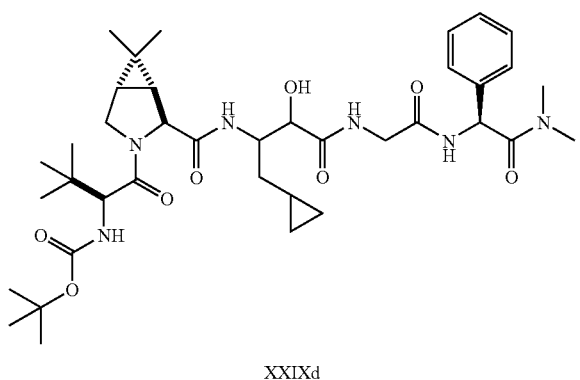

XXIXd

The acid XXVIIIc (2.43 g) was dissolved in CH₂Cl₂ and was reacted with amine XXIXc (2.47 g), HATU (2.5 g) and DIPEA (5.8 mL) in the manner previously described in Example IX, Step 2a to afford, after purification by flash column chromatography (4% MeOH, CH₂Cl₂, silica), the desired product XXIXd (4.35 g). Mass spectrum (LCMS) 727 (M+H⁺).

Step 5:

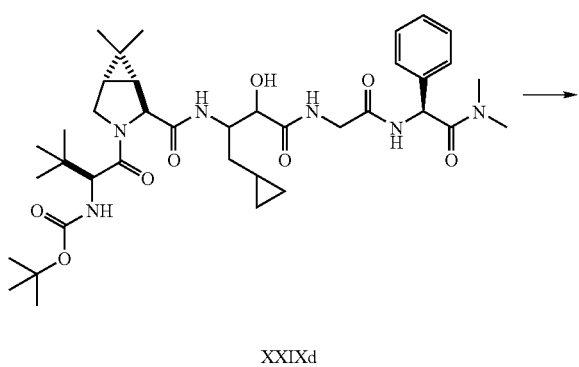

XXIXd

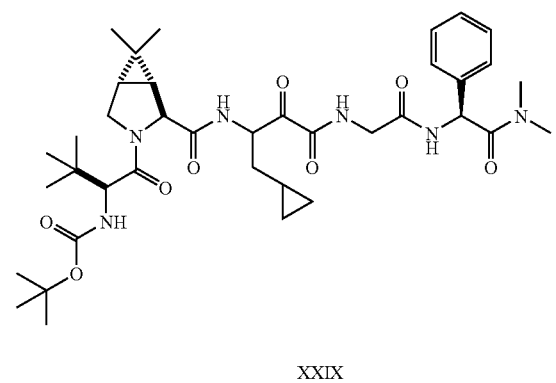

XXIX

The product of Step 4 (4.2 g) was reacted with Dess-Martin reagent (6.4 g) in the manner previously described in preparative Example XX, Step 7. Purification by flash column chromatography (100% EtOAc, silica) furnished 3 g of the final product XXIX. Mass spectrum (LCMS) 725 (M+H⁺).

EXAMPLE XXX

Preparation of a Compound of Formula XXX

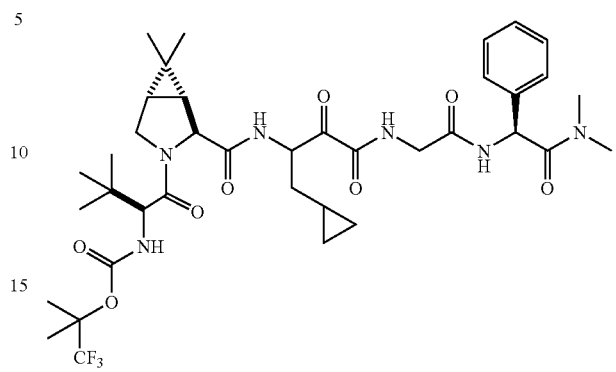

XXX

Step 1:

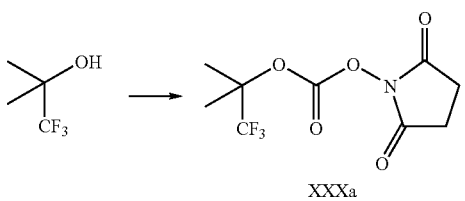

XXXa

The alcohol 2-(trifluoromethyl)propan-2-ol (1.28 g) was reacted with N,N-disucciminidyl carbonate (3.84 g) and Et₃N (4.2 mL) in dry CH₃CN (50 mL) for 18 hours. The mixture was diluted with EtOAc (200 mL) and filtered. The filtrate was washed with NaHCO₃, brine then dried over MgSO₄, filtered and concentrated in vacuo to afford a crude mixture. Purification by flash column chromatography (50% EtOAc, Hexane, silica) furnished the desired product XXXa (0.3 g).

Step 2:

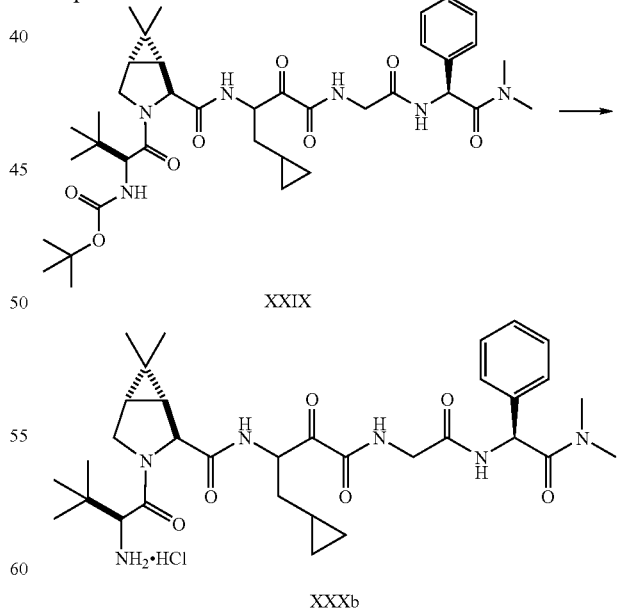

The product from Example XXIX (0.3 g) was treated with 100 mL of 4.0 N HCl in dioxane. After 1 h, 200 mL of Et₂O were added and the resulting precipitate was filtered off and dried under vacuo to afford the product XXXb (0.27 g) as a white powder. Mass spectrum (LCMS) 625 (M−HCl+H⁺).

Step 3:

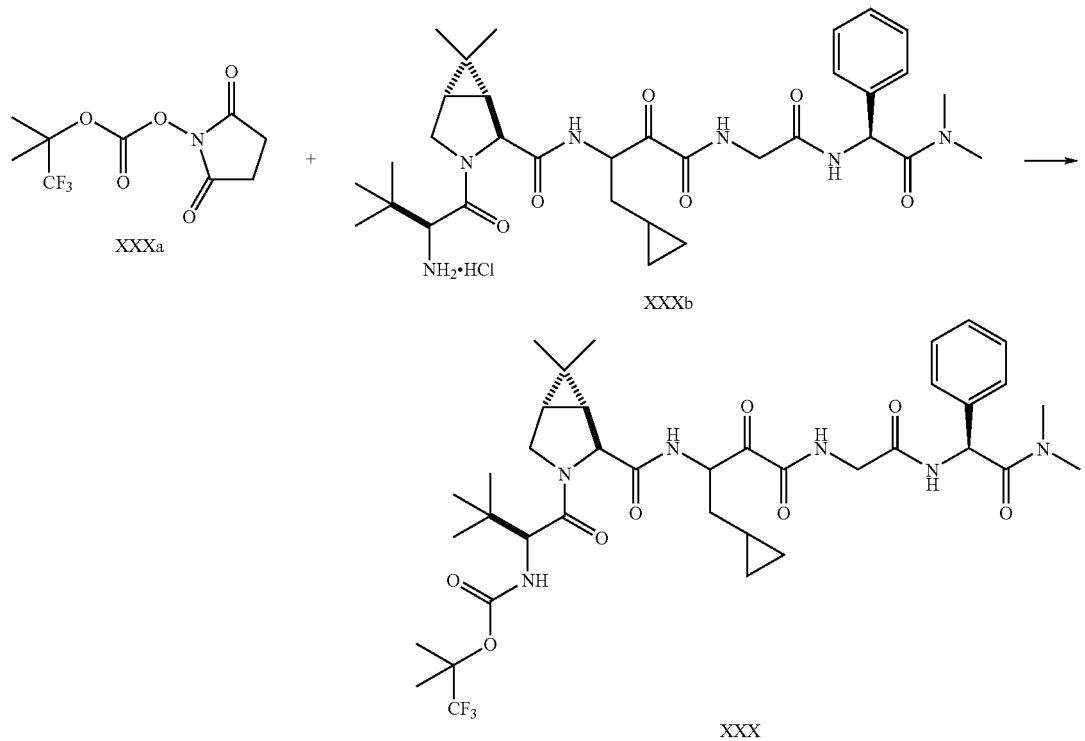

To a room temperature solution of XXXb (0.05 g) in CH$_2$Cl$_2$ (5 mL) was added DIPEA (0.040 mL) XXXa (1.5 equiv., 0.030 g), followed by 1 crystal of DMAP. After 30 minutes, reaction was diluted with EtOAc (20 mL) and washed with HCl 1.5 N then NaHCO$_3$ then brine. EtOAc layer was dried over MgSO$_4$, filtered and concentrated in vacuo to afford a crude mixture. Purification by preparative chromatography (40% Acetone, Hexane, silica) furnished the desired product XXX (0.044 g). Mass spectrum (LCMS) 779 (M+H$^+$).

EXAMPLE XXXI

Preparation of a Compound of Formula XXXI

XXXI

Step 1:

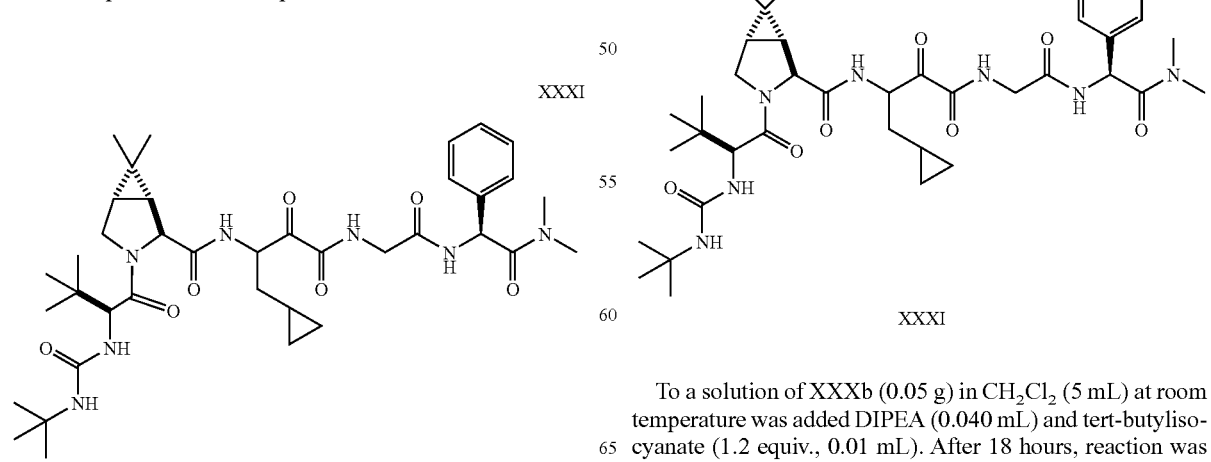

To a solution of XXXb (0.05 g) in CH$_2$Cl$_2$ (5 mL) at room temperature was added DIPEA (0.040 mL) and tert-butylisocyanate (1.2 equiv., 0.01 mL). After 18 hours, reaction was diluted with EtOAc (20 mL) and washed with HCl 1.5 N, NaHCO$_3$ and brine. EtOAc layer was dried over MgSO$_4$, filtered and concentrated in vacuo to afford a crude mixture. Purification by preparative chromatography (100% EtOAc, silica) furnished the final product XXXI (0.021 g). Mass spectrum (LCMS) 724 (M+H⁺).

EXAMPLE XXXII

Preparation of a Compound of Formula XXXII

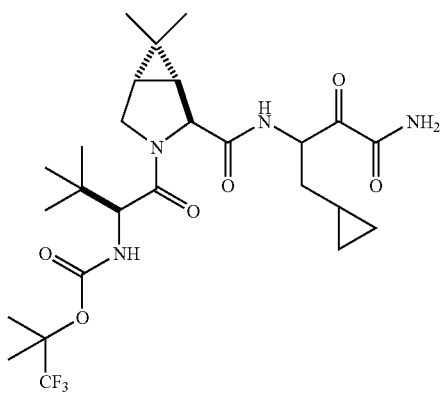

XXXII

Step 1:

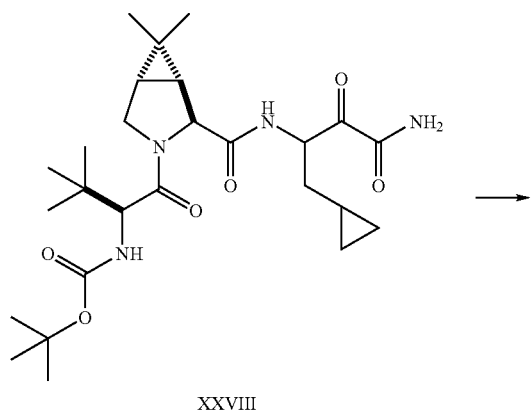

XXVIII

The product from Example XXVIII was treated in the manner previously described in preparative Example XXX, Step 2 to afford product XXXIIa. Mass spectrum (LCMS) 407 (M−HCl+H⁺).

Step 2:

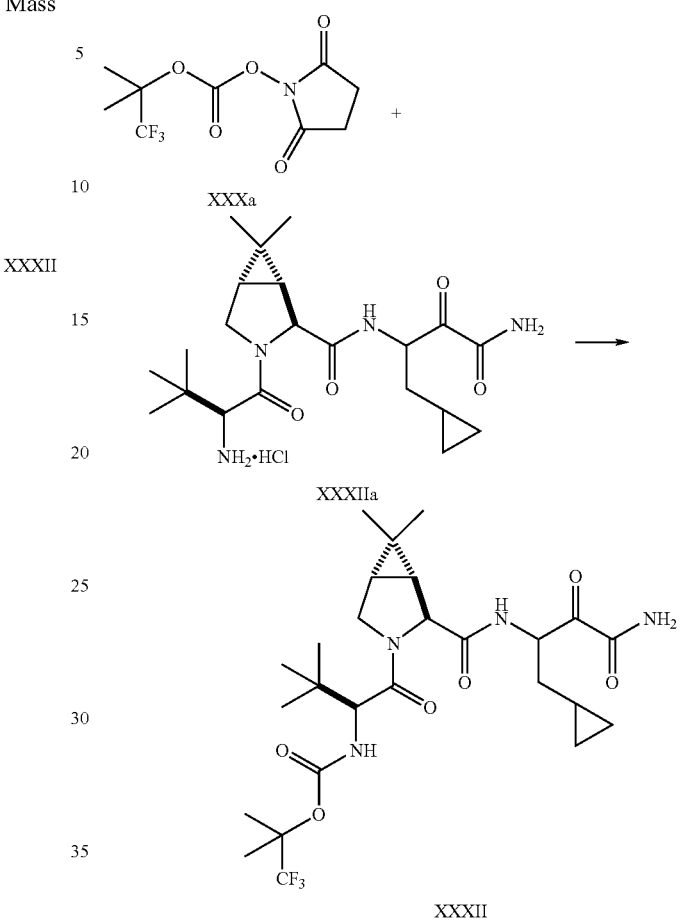

The amine XXXIIa was reacted with XXXa in the manner previously described in preparative Example XXX, Step 3 to afford the desired product XXXII. Mass spectrum (LCMS) 508 (M+H⁺).

EXAMPLE XXXIII

Preparation of a Compound of Formula XXXIII

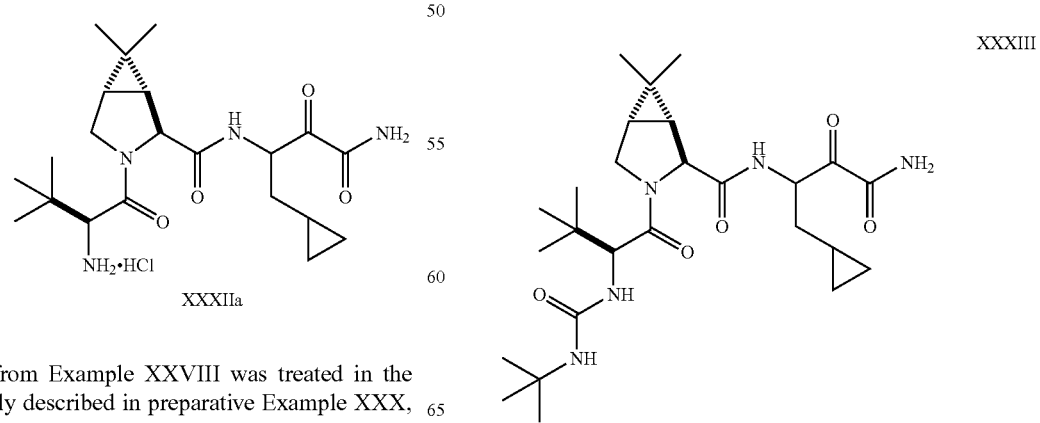

XXXIII

483

Step 1:

[Structure XXXIIa shown, with NH₂·HCl]

→

[Structure XXXIII shown]

The amine XXXIIa was reacted with tert-butylisocyanate in the manner previously described in Example XXXI, Step 1, to afford the product XXXIII. Mass spectrum (LCMS) 561 (M+H⁺).

EXAMPLE XXXIV

Preparation of a Compound of Formula XXXIV

[Structure XXXIV shown]

484

Step 1:

[Reaction scheme: ester + pyrrolidine, ms 4A°]

[Product structure shown]

To the mixture of ester (6.0 g) and molecular sieve (5.2 g) in anhydrous methylene chloride (35 mL) was added pyrrolidine (5.7 mL, 66.36 mmol.). The resulting brown slurry was stirred at room temperature under $N_2$ for 24 h, filtered and washed with anhydrous $CH_3CN$. The combined filtrate was concentrated to yield the desired product.

Step 2:

[Reaction scheme with methallyl chloride, NaI, $K_2CO_3$]

[Product structure shown]

To a solution of the product from proceeding step in $CH_3CN$ (35 mL) was added anhydrous $K_2CO_3$, methallyl chloride (2.77 g, 30.5 mmol.), NaI (1.07 g, 6.7 mmol.). The resulting slurry was stirred at ambient temperature under $N_2$ for 24 h. 50 mL of ice-cold water was added followed by 2N $KHSO_4$ solution until pH was 1. EtOAc (100 mL) was added and the mixture was stirred for 0.75 h. Combined organic layer was collected and washed with brine, dried over MgSO₄, and evaporated to yield the desired product.

Step 3:

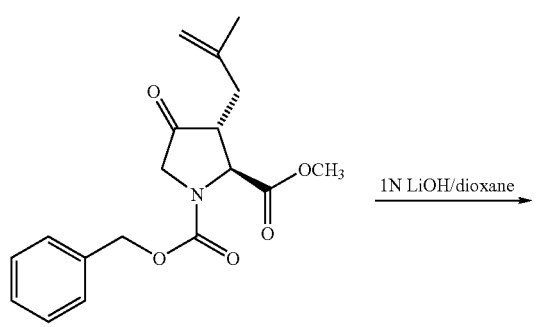

1N LiOH/dioxane

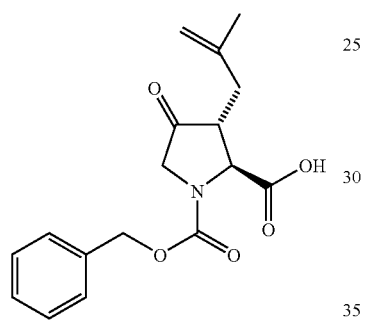

The product from preceding step (2.7 g, 8.16 mmol.) was dissolved in dioxane (20 mL) and treated with freshly prepared 1 N LiOH (9 mL). The reaction mixture was stirred at ambient temperature under N₂ for 20 h. The reaction mixture was taken in EtOAc and washed with H₂O. The combined aqueous phase was cooled to 0° C. and acidifed to pH 1.65 using 1 N HCl. The turbid mixture was extracted with EtOAc (2×100 mL). Combined organic layer washed with brine, dried over MgSO₄, concentrated to give the desired acid (3.40 g).

Step 4:

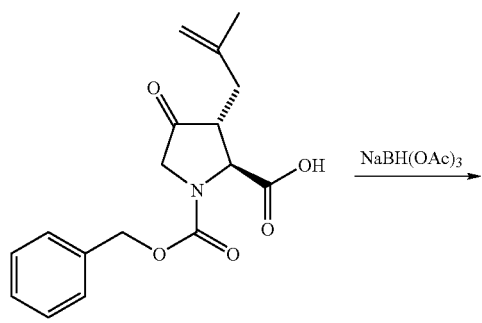

NaBH(OAc)₃

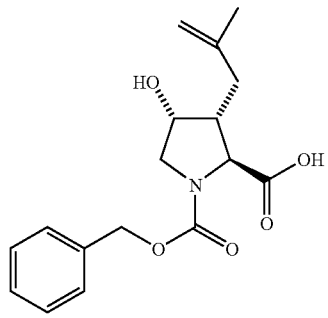

To a suspension of NaBH(OAc)₃ (3.93 g, 18.5 mmol.) in CH₂Cl₂ (55 mL) was added a solution of product from preceding step in anhydrous CH₂Cl₂ (20 mL) and acetic acid (2 mL). The slurry was stirred at ambient temperature for 20 h. Ice cold water (100 mL) was added to the slurry and stirred for 1/2 hr. Organic layer was separated, filtered, dried and evaporated to yield the desired product.

Step 5:

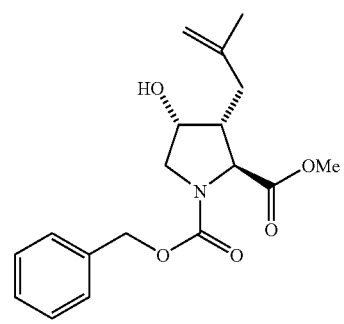

CH₂N₂/Et₂O/MeOH

To a solution of the product from preceding step (1.9 g) in MeOH (40 mL) was treated with excess of CH₂N₂/Et₂O solution and stirred for overnight. The reaction mixture was concentrated to dryness to yield a crude residue. The residue was chromatographed on silica gel, eluting with a gradient of EtOAc/hexane to afford 1.07 g of the pure desired product.

Step 6:

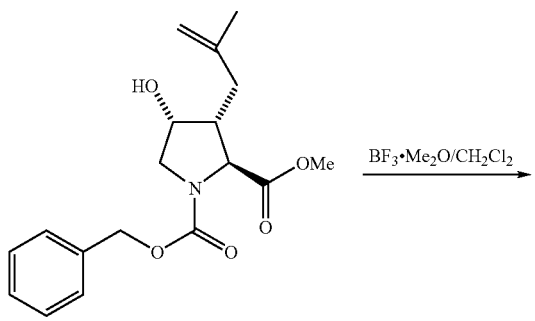

To a solution of product from preceding step (1.36 g) in anhydrous CH$_2$Cl$_2$ (40 mL) was treated with BF$_3$.Me$_2$O (0.7 mL). The reaction mixture was stirred at ambient temperature for 20 h and quenched with sat. NaHCO$_3$ (30 mL) ad stirred for ½ hr. Organic layer was separated and combined organic layer washed with brine, dried over MgSO$_4$, concentrated to give crude residue. The residue was chromotagraphed on silica gel eluting with a gradient of EtOAc/hexane to afford 0.88 g of the desired compound.

Step 7:

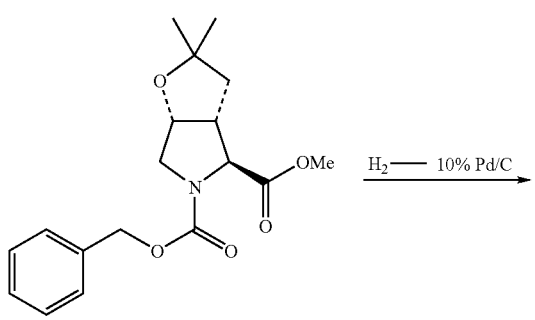

To a solution of the product (0.92 g) from preceding step in MeOH (30 mL) was added 10% Pd/C (0.16 g) at room temperature and hydrogenated at ambient temperature under 1 atm. Pressure. The reaction mixture was stirred for 4 h and concentrated to dryness to yield the desired compound.

Step 8:

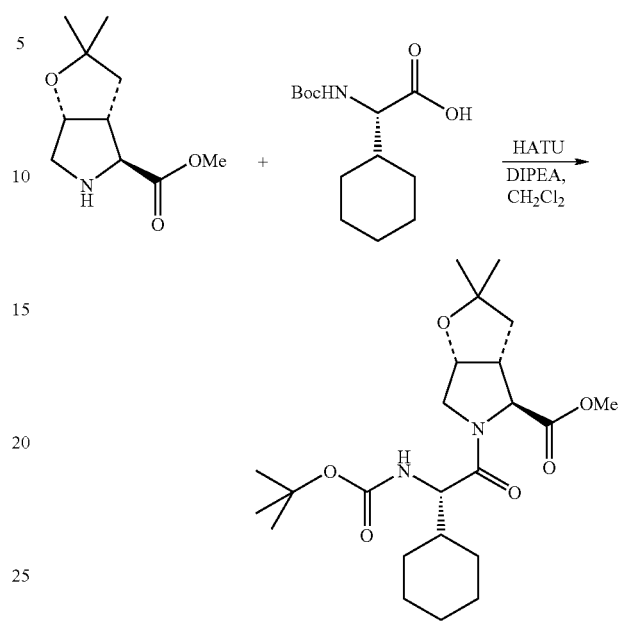

The desired product was prepared according to the procedure in Example XXIII, Step 10.

Step 9:

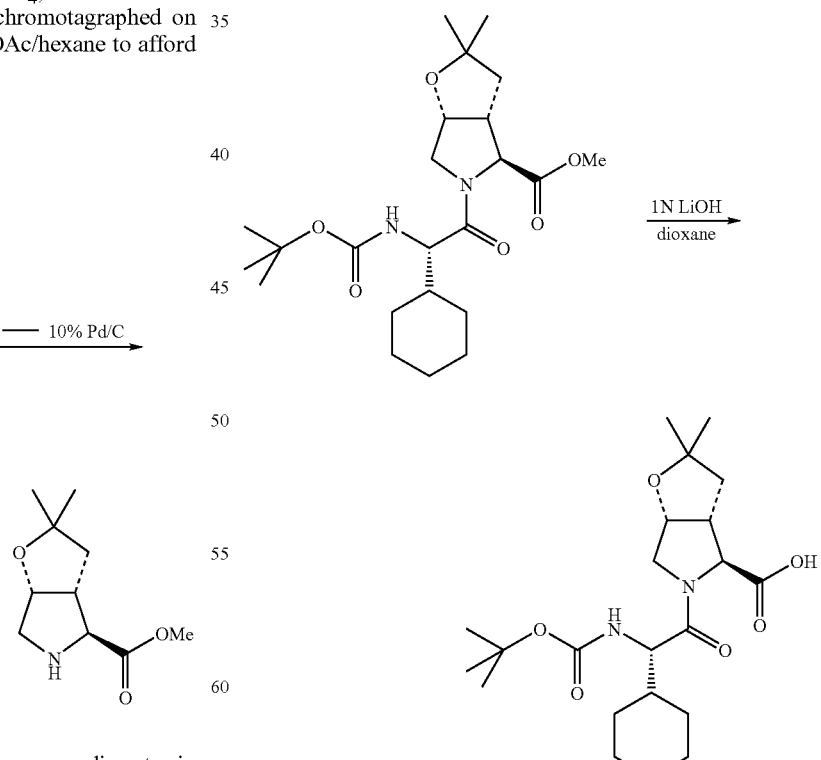

The desired acid product was prepared according to the procedure in Example XXIV, Step 3.

Step 10:

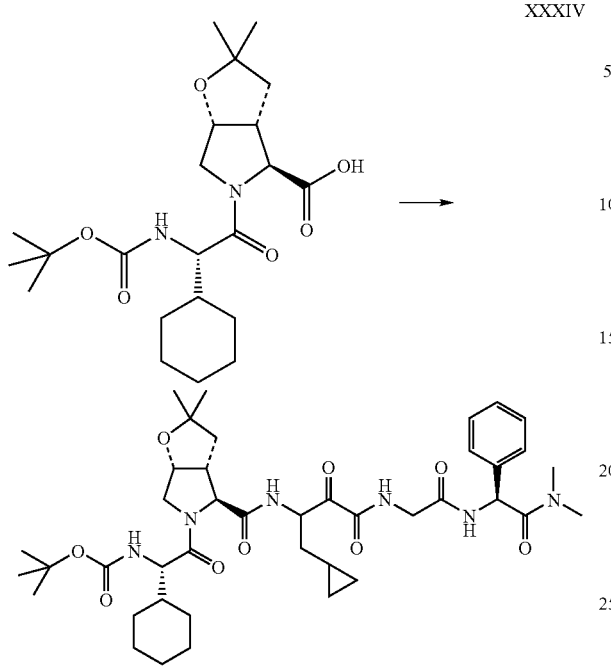

The desired product XXXIV was prepared according to the procedure in Example XXIX, Steps 4-5.

EXAMPLE XXXV

Preparation of a Compound of Formula XXXV

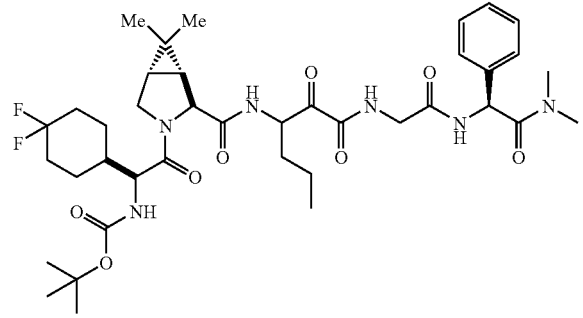

Step 1:

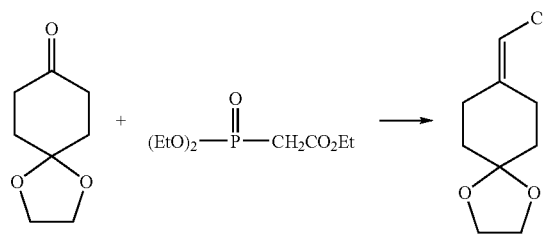

A solution of triethyl phosphonate (44.8 g) in THF (30 mL) at 0° C. was treated with a 1 M solution (200 mL) of sodium bis(trimethylsilylamide) in THF. The resulting mixture was stirred at RT for 0.5 hour, and then cooled to 0° C. A solution of 1,4-cyclohexanedione ethylene ketal (15.6 g) in THF (50 mL) was added dropwise, and the resulting solution was stirred at RT for 18 hours. The reaction mixture was then cooled to 0° C., treated with cold aqueous citric acid, and the mixture was extracted with EtOAc. The extract washed with saturated aqueous $NaHCO_3$, then brine; then dried over anhydrous $Na_2SO_4$, filtered, and the filtrate evaporated. The residue was chromatographed on silica gel, eluting with a gradient of $CH_2Cl_2$/EtOAc to afford the title compound (21 g), 92% yield. Mass spectrum (FAB) 227.3 ($M+H^+$).

Step 2:

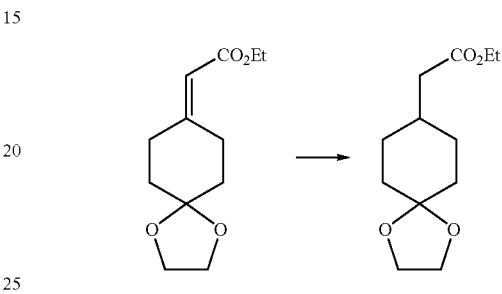

The product of the preceding step (20 g) was dissolved in EtOH (150 mL) and treated with 10% Pd/C under 1 atm of hydrogen for 3 days. The mixture was filtered and the filtrate evaporated to afford the title compound (20.3 g), 100% yield. Mass spectrum (FAB) 229.2 ($M+H^+$).

Step 3:

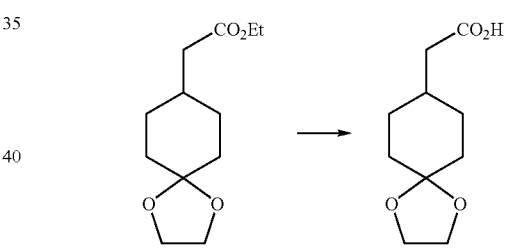

The product of the preceding step (20 g) was dissolved in MeOH (150 mL) and treated with a solution of LiOH (3.6 g) in water (50 mL). The mixture was stirred for 18 hours, and concentrated under vacuum. The residue was dissolved in cold water (100 mL), the solution was acidified to pH 2-3 with 5N HCl, and the resulting mixture was extracted with EtOAc. The extract was dried over anhydrous $Na_2SO_4$, filtered, and the filtrate evaporated to afford the title compound (17.1 g), 97% yield. Mass spectrum (FAB) 201.2 ($M+H^+$).

Step 4:

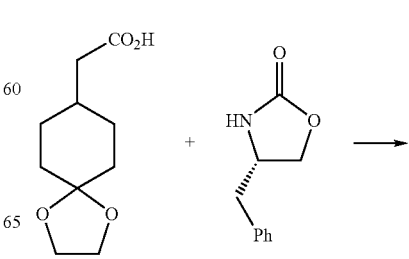

-continued

Step 6:

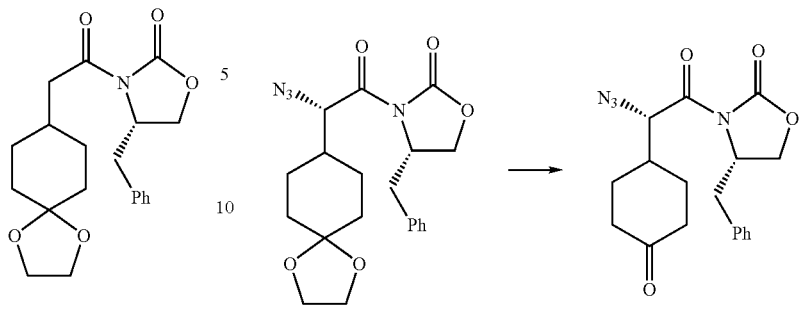

1. The product of the preceding step (3.0 g) was dissolved in Et₂O (150 mL), treated with Et₃N (2.1 mL), and the solution cooled to −78° C. Pivaloyl chloride (1.85 mL) was added dropwise, and after 0.25 hour additional stirring, the reaction was allowed to warm to 0° C. over 0.75 hour, and then cooled again to −78° C. to afford a solution of mixed anhydride for reaction in part 2.

2. A solution of (S)-4-benzyl-2-oxazolidinone (2.66 g) in THF (22 mL) was cooled to −78° C., and a 1.6 M solution (9.38 mL) of n-butyllithium in hexane was added dropwise. After an additional 0.33 hour stirring at this temperature, the solution was transferred via canula to the cold solution of part 1. The mixture was stirred is at −78° C., then warmed to 0° C., and stirred at this temperature for 0.5 hour. The organic layer was separated, the aqueous layer was extracted with Et₂O, the combined organics were washed with brine, dried over anhydrous Na₂SO₄, filtered, and the filtrate evaporated. The residue was chromatographed on silica gel, eluting with a gradient of hexane/EtOAc (9:1) to afford the title compound (5.0 g), 93% yield. Mass spectrum (FAB) 360.4 (M+H⁺).

Step 5:

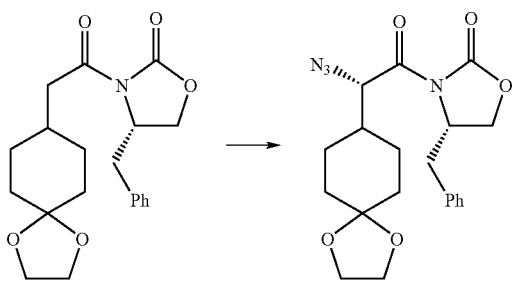

The product of the preceding step (2.7 g) was dissolved in THF (25 mL), cooled to −78° C., transferred by canula to a solution of 0.5 M potassium bis(trimethylsilyl)amide/toluene (16.5 mL) in THF (25 mL) at −78° C., and the resulting solution was stirred at −78° C. for 0.75 hour. To this solution was added via canula a solution of trisyl azide (3.01 g) in THF (25 mL) pre-cooled to −78° C. After 1.5 minutes, the reaction was quenched with acetic acid (1.99 mL), the reaction was warmed to RT, and then stirred for 16 hours. The reaction was diluted with EtOAc (300 mL), and washed with 5% aqueous NaCl. The aqueous phase was extracted with EtOAc, the combined organic phases were washed with saturated aqueous NaHCO₃, then brine; then dried over anhydrous Na₂SO₄, filtered, and the filtrate evaporated. The residue was chromatographed on silica gel, eluting with EtOAc/hexane (1:3) to afford the title compound (2.65 g), 88% yield.

The product of the preceding step (11.4 g) was dissolved in 95% formic acid (70 mL) and heated at 70° C. for 0.5 hour while stirring. The solution was evaporated under vacuum, and the residue was taken up in EtOAc. The solution washed with saturated aqueous NaHCO₃, then brine; then dried over anhydrous Na₂SO₄, filtered, and the filtrate evaporated. The residue was chromatographed on silica gel to afford the title compound (8.2 g).

Step 7:

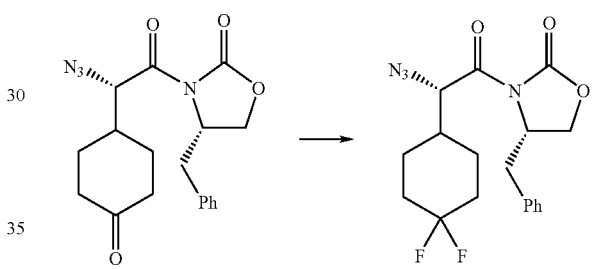

The product of the preceding step (8.2 g) was dissolved in CH₂Cl₂ (16 mL) and treated with diethylaminosulfur trifluoride (DAST, 7.00 mL) at RT for 3 hours. The reaction was poured over ice/water (200 cc), and extracted with CH₂Cl₂. The extract washed with saturated aqueous NaHCO₃, then brine; then dried over anhydrous Na₂SO₄, filtered, and the filtrate evaporated. The residue was chromatographed on silica gel, eluting with EtOAc/hexane (15:85) to afford the title compound (4.5 g), 52% yield.

Step 8:

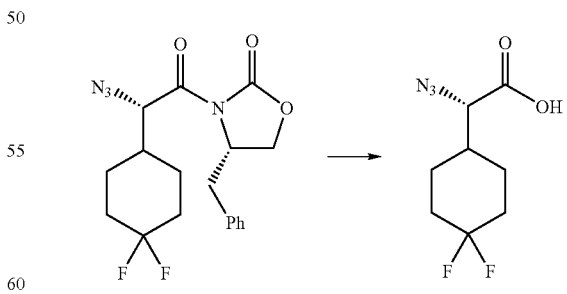

The product of the preceding step (3.7 g) was dissolved in a mixture of THF (150 mL) and water (48 mL), cooled to 0° C., treated with 30% H₂O₂ (3.95 mL), and then with LiOH·H₂O (0.86 g). The mixture was stirred for 1 hour at 0° C., then quenched with a solution of Na₂SO₃ (5.6 g) in water (30 mL), followed by a solution of 0.5 N NaHCO₃ (100 mL).

The mixture was concentrated under vacuum to 1/2 volume, diluted with water (to 500 mL), and extracted with CH$_2$Cl$_2$ (4×200 mL). The aqueous phase was acidified to pH 1-2 with 5N HCl, and extracted with EtOAc (4×200 mL). The extract washed brine; then dried over anhydrous Na$_2$SO$_4$, filtered, and the filtrate evaporated to afford the title compound (1.95 g), 91% yield, which was used directly in the next step.

Step 9:

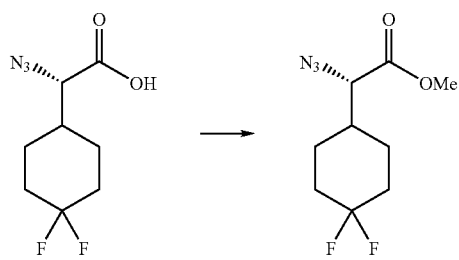

The product of the preceding example (2.6 g) was dissolved in Et$_2$O (50 mL) and treated dropwise with a solution of CH$_2$N2 in Et$_2$O until the solution remained yellow. The solution was stirred for 18 hours, then evaporated under vacuum to afford the title compound (2.8), which was used directly in the next step.

Step 10:

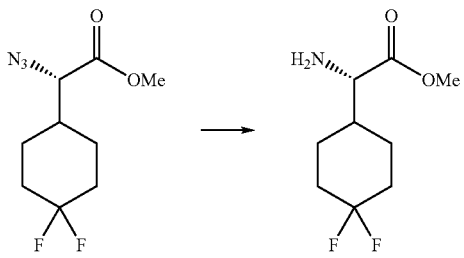

The product of the preceding step (1.95 g) was dissolved in MeOH (150 mL), treated with formic acid (1.7 mL), then treated with 10% Pd/C (3.3 g, Degussa type E101) under 1 atm of hydrogen for 1.5 hours. The mixture was is filtered and the filtrate evaporated to afford the title compound (2.1 g) as the formic acid salt, which was used directly in the next step.

Step 11:

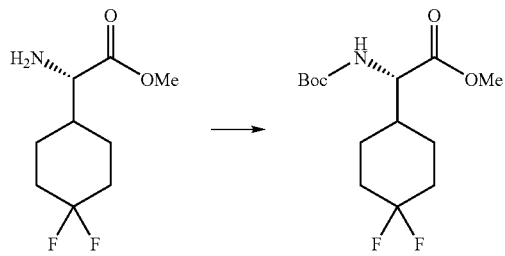

The product of the preceding step (2.1 g) was dissolved in 1,4-dioxane (100 mL) and di-tert-butyl dicarbonate (1.9 g) was added, followed by diisopropylethylamine (2.9 mL). The solution was stirred for 18 hours, and concentrated under vacuum. The residue was treated with aqueous 5% KH$_2$PO$_4$ and the mixture extracted with EtOAc. The extract washed with brine; then dried over anhydrous MgSO$_4$, filtered, and the filtrate evaporated. The residue was chromatographed on silica gel, eluting with a gradient of CH$_2$Cl$_2$/Et$_2$O to afford the title compound (2.5 g), 99% yield. Mass spectrum (FAB) 307.9 (M+H$^+$).

Step 12:

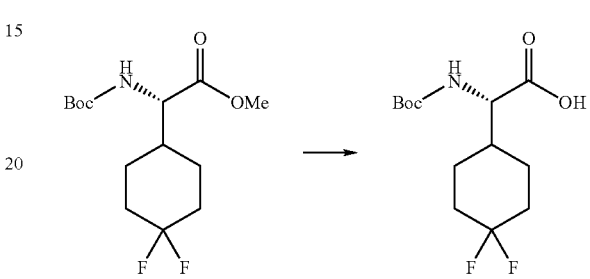

The product of the preceding step (2.5 g) was dissolved in 1,4-dioxane (35 mL), treated with aqueous 1 M LiOH (17 mL), and stirred for 2 hours. The mixture was quenched with ice/water (125 cc), the mixture was acidified to pH 3-4 with 3N HCl, and extracted with EtOAc. The extract was dried over anhydrous MgSO$_4$, filtered, and the filtrate evaporated to afford the title compound (2.3 g), 96% yield. Mass spectrum (FAB) 294.0 (M+H$^+$).

Step 13:

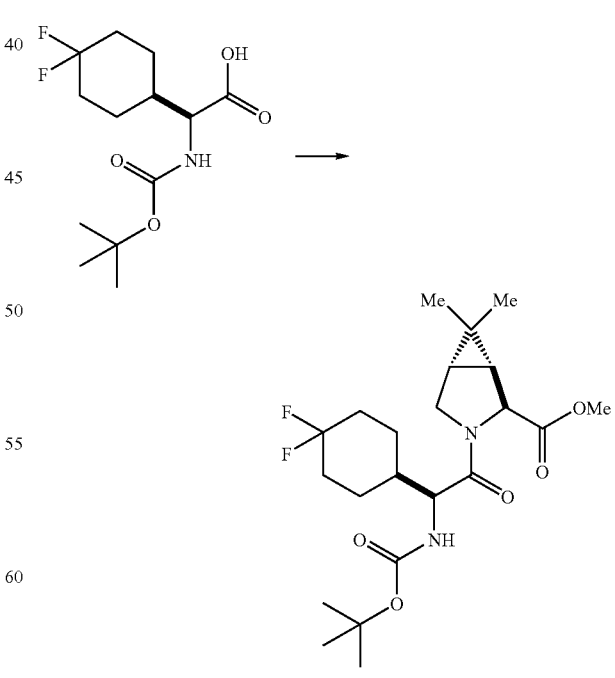

The desired product was prepared according to the procedure in Example XXIII, Step 10.

Step 14:

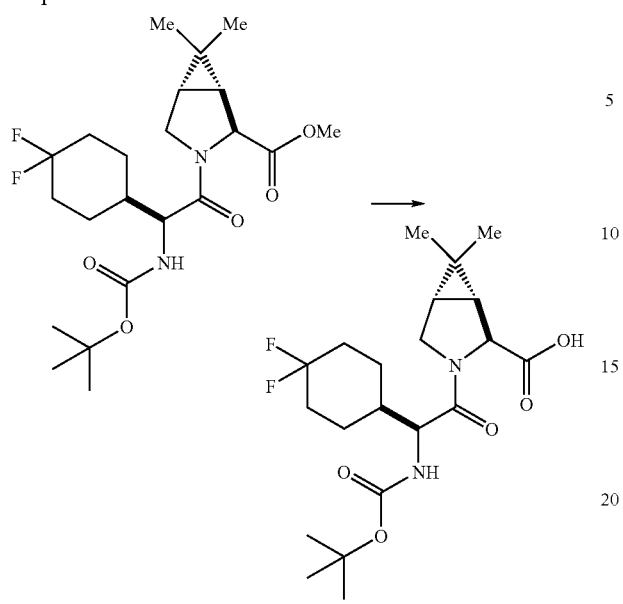

The desired acid product was prepared according to the procedure in Example XXIV, Step 3.

Step 15:

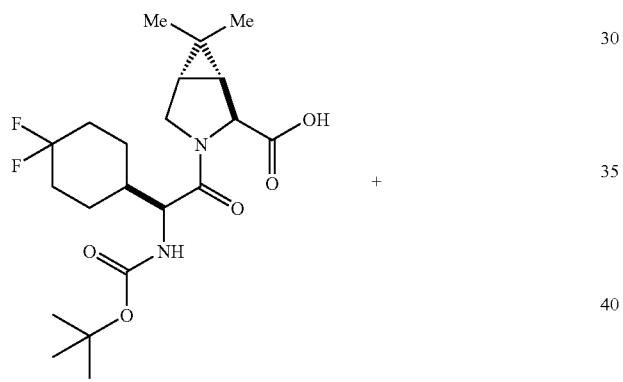

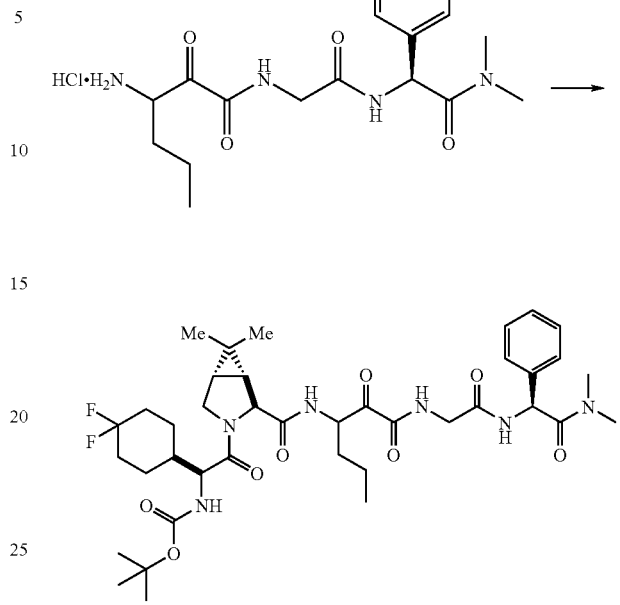

XXXV

The desired acid product was prepared according to the procedure in Example XXIX, Step 4.

EXAMPLE XXXVI

Preparation of Compounds of Formulas XXXVI and XXXVIII

Compounds of formulas XXXVI and XXXVIII were prepared according to the scheme below and utilizing preparative Examples 11 through 15 discussed above.

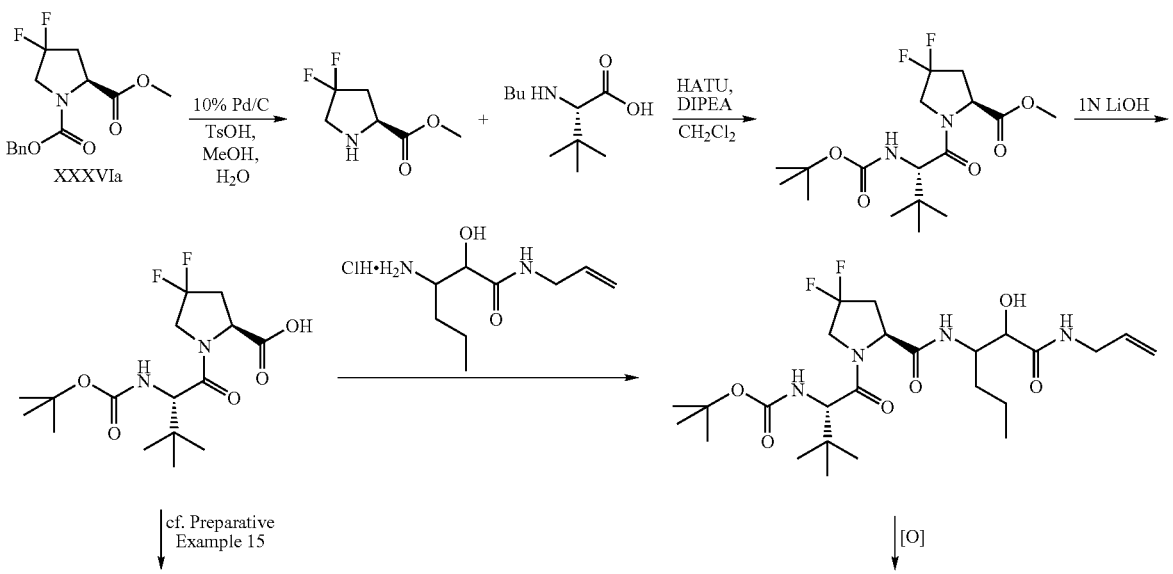

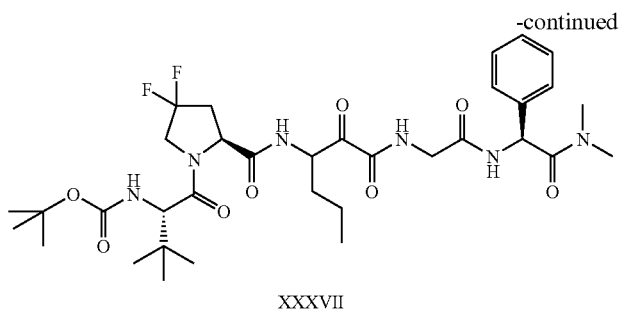

XXXVII

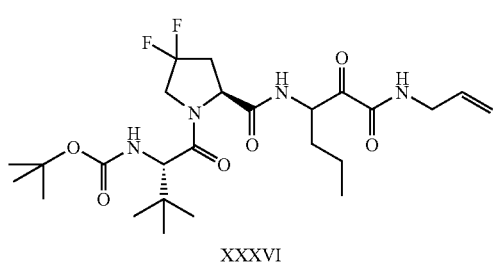

XXXVI

The compound of formula XXXVIb was prepared from a compound of formula XXXVIa as follows by known procedures:

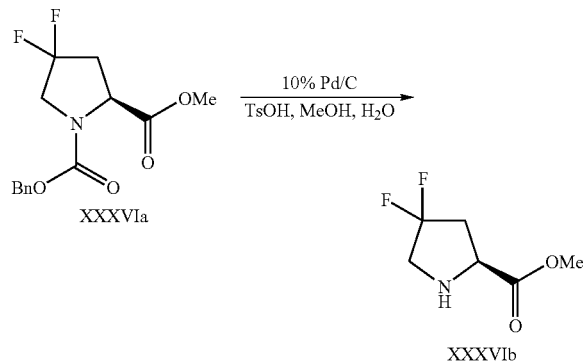

To a solution of Compound XXXVIa (6.58 g, 22 mmol) in 100 mL of MeOH was added 10% Pd/C (0.8 g) and p-toluene sulfonic acid (4.2 g). The reaction mixture was subjected to hydrogenation at room temperature overnight. The reaction mixture was filtered through celite and washed with excess MeOH. The combined filtrate was concentrated in-vacuo to provide the title compound XXXVIb as a gummy. Conversion of XXXVIb to XXXVI and XXXVII followed the route as shown in the scheme above and according to preparative examples 11-15.

EXAMPLE XXXVIII

Preparation of a Compound of Formula XXXVIII

A compound of the formula XXXVIII was prepared utilizing the following scheme and following preparative Examples 11 through 15 discussed earlier.

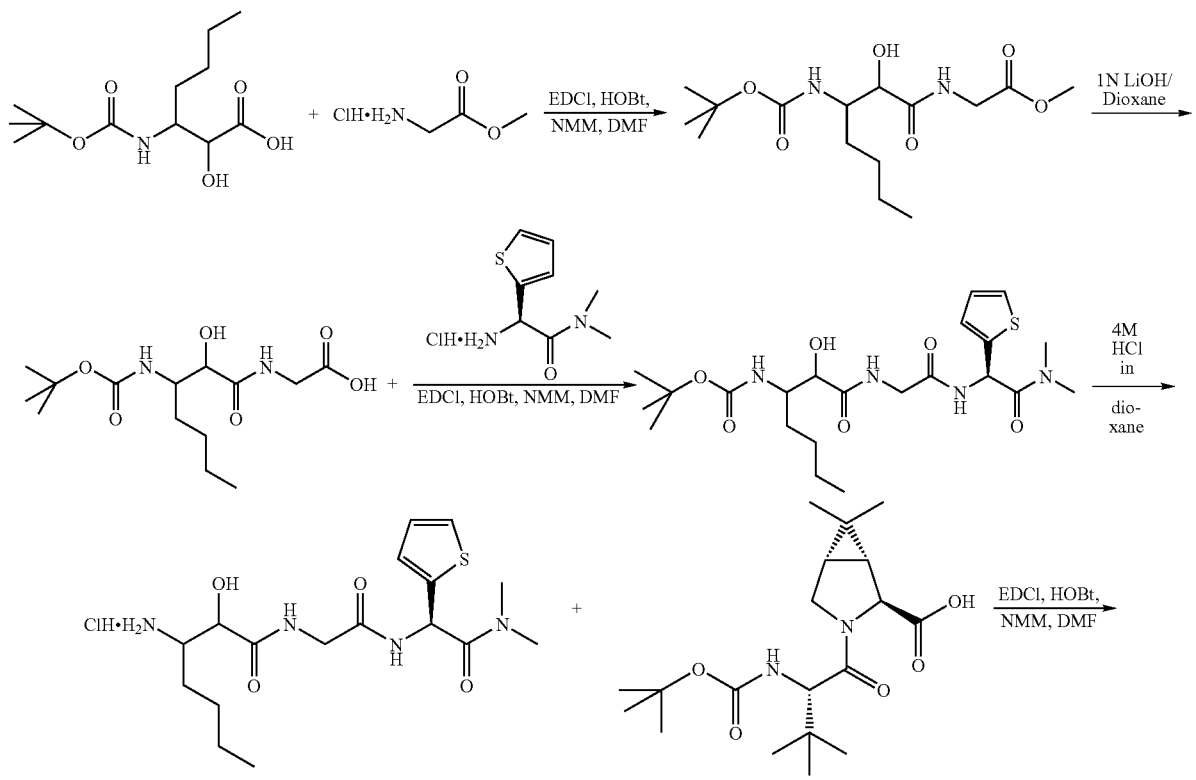

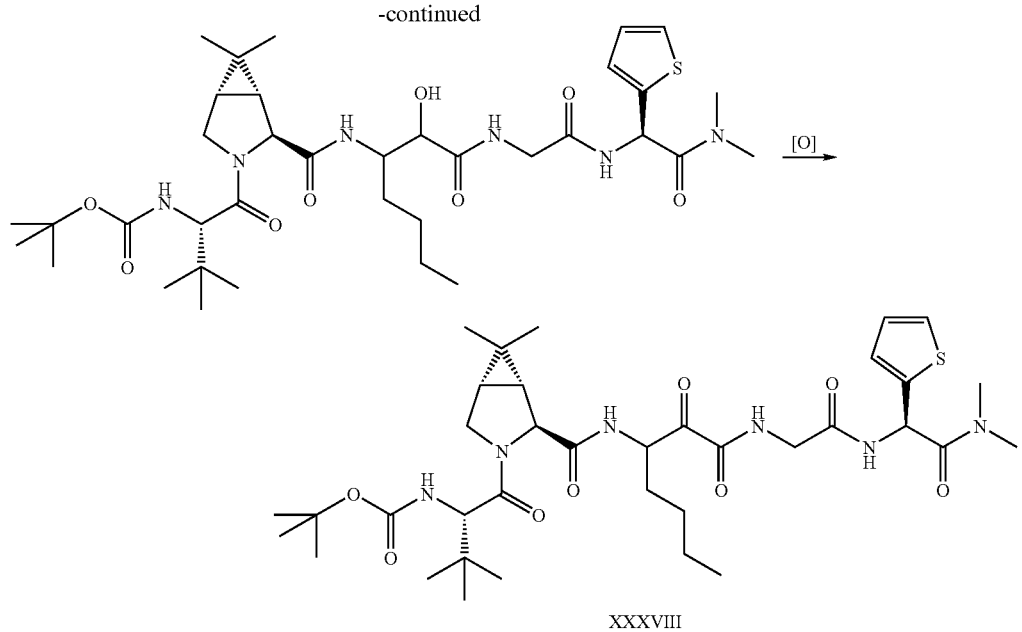

XXXVIII

EXAMPLE XXXIX

Synthesis of the Compound of Formula XXXIX

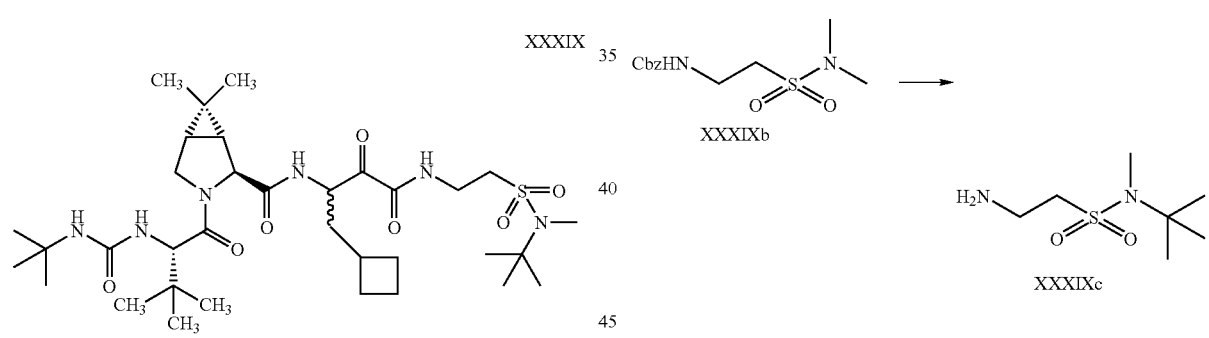

Step 1:

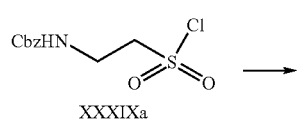

XXXIXa

A solution of the sulfonyl chloride XXXIXa prepared by the procedure of H. Mcklwain (*J. Chem. Soc* 1941, 75) was added dropwise to a mixture of 1.1. equiv of t-butylmethylamine and triethylamine at −78° C. and stirred at rt for 2 h. The reaction mixture was concentrated in vacuo and purified by chromatography (SiO$_2$, Hex/Acetone 4:1) to yield sulfonamide XXXIXb as a colorless oil.

Step 2:

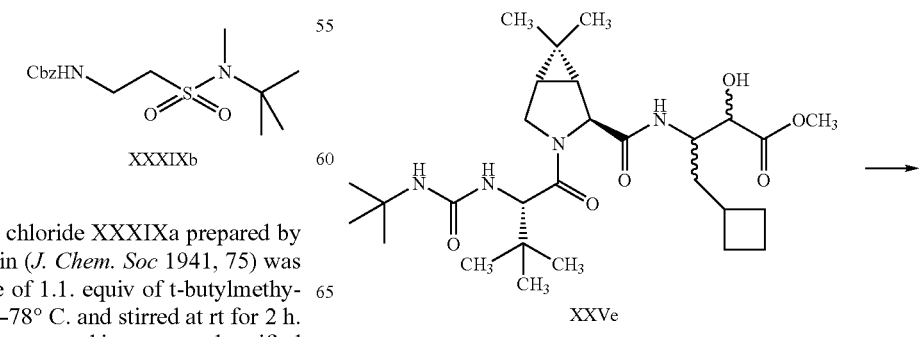

A solution of the Cbz-protected amine XXXIXb was dissolved in methanol and treated with 5 mol % of Pd/C (5% w/w) and hydrogenated at 60 psi. The reaction mixture was filtered through a plug of celite and concentrated in vacuo to obtain the free amine XXXIXc which solidified on standing.

Step 3:

-continued

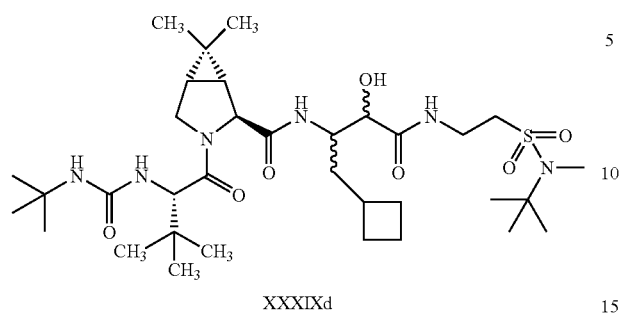

XXXIXd

The hydroxy sulfonamide XXXIXd was synthesized similar to the procedure for the synthesis of XXVF except replacing the amine XXVD with XXXIXc. The crude reaction mixture directly used for the next reaction.

Step 4:

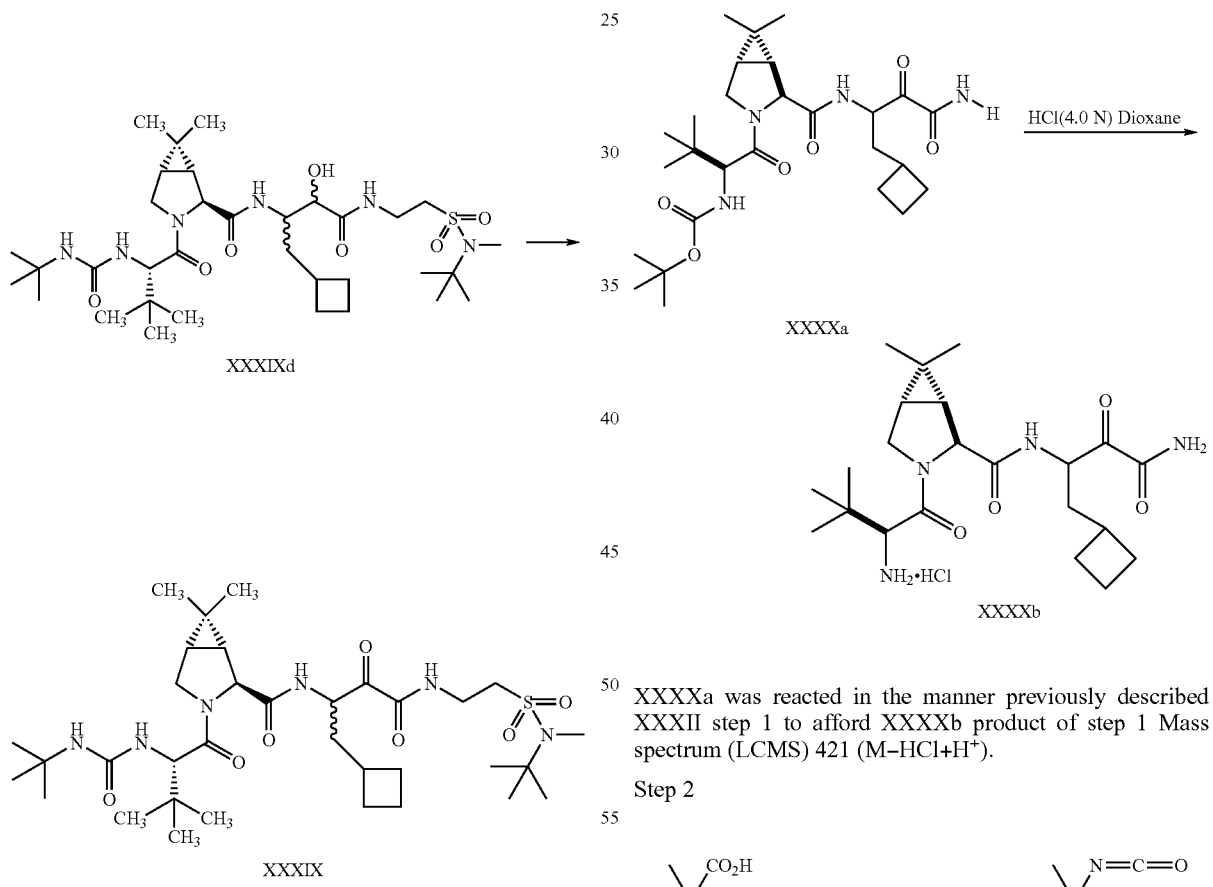

XXXIXd

XXXIX

The hydroxy amine XXXIXd was oxidized to compound XXXIX using the Dess Martin reagent following the procedure for the synthesis of XXV (step 5). The crude mixture was purified by chromatography ($SiO_2$, Acetone/Hexane 3:7) to obtain XXXIX as a colorless solid.

EXAMPLE XXXX

Preparation of Compound of Formula XXXX

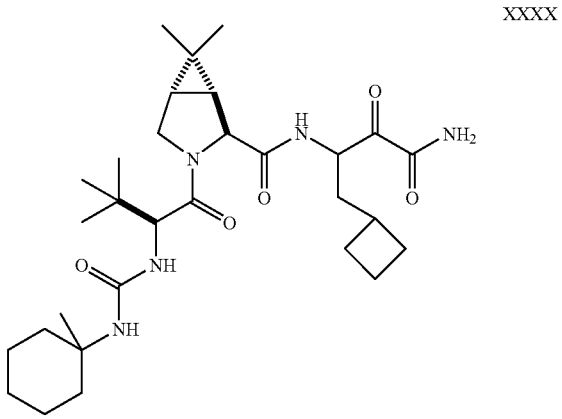

XXXX

Step 1

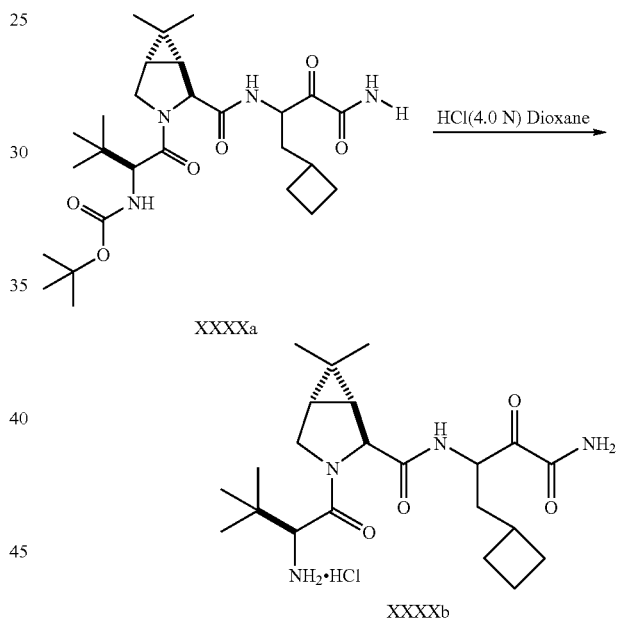

XXXXa was reacted in the manner previously described XXXII step 1 to afford XXXXb product of step 1 Mass spectrum (LCMS) 421 (M–HCl+$H^+$).

Step 2

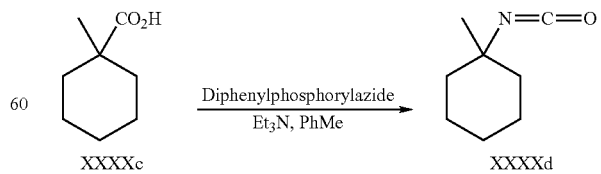

XXXXc          XXXXd $Et_3N$ (1.4 mL) and Diphenylphosphorylazide (2.2 mL) were added to a solution of carboxylic acid XXXXc in toluene (13 mL). Reaction was stirred at RT for 30 min then refluxed overnight. After 18 h, reaction is cooled to RT and XXXXd product of step2, which was used directly 0as a 0.7 M solution in Toluene.

Step 3

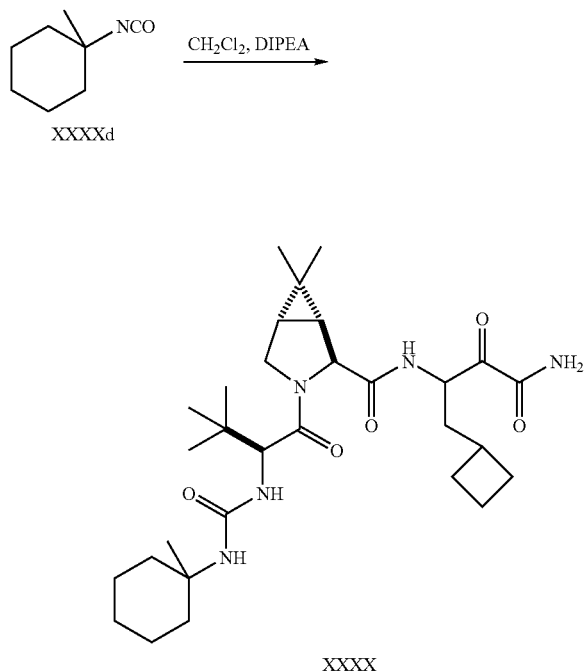

XXXXb, Product of step 1 of preparative example XXXX was reacted with XXXXd product of step 2 of preparative example XXXX in the manner previously described in example XXXIII to afford XXXX. Mass spectrum (LCMS) 560 (M+H$^+$).

EXAMPLE XXXXI

Preparation of Compound of Formula XXXXI

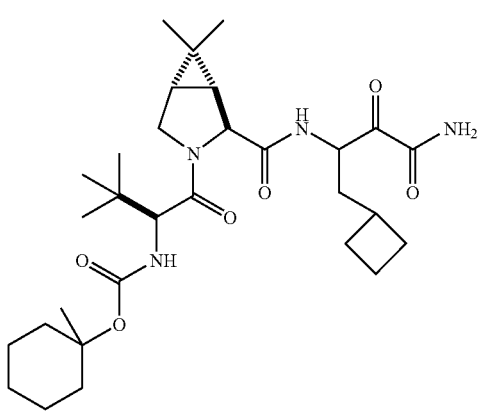

Step 4

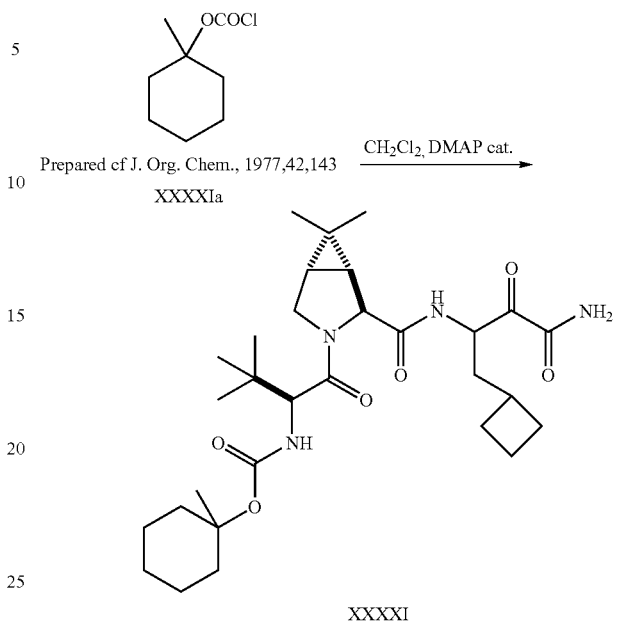

XXXXb, product of step 1 of preparative example XXXX was reacted with chloroformate XXXXIa prepared as *J. Org. Chem.*, 1977,42,143 in the manner previously preparative example 12 compound 4.1 described to afford XXXXI. Mass spectrum (LCMS) 561 (M+H$^+$).

EXAMPLE XXXXII

Preparation of Compound of Formula XXXXII

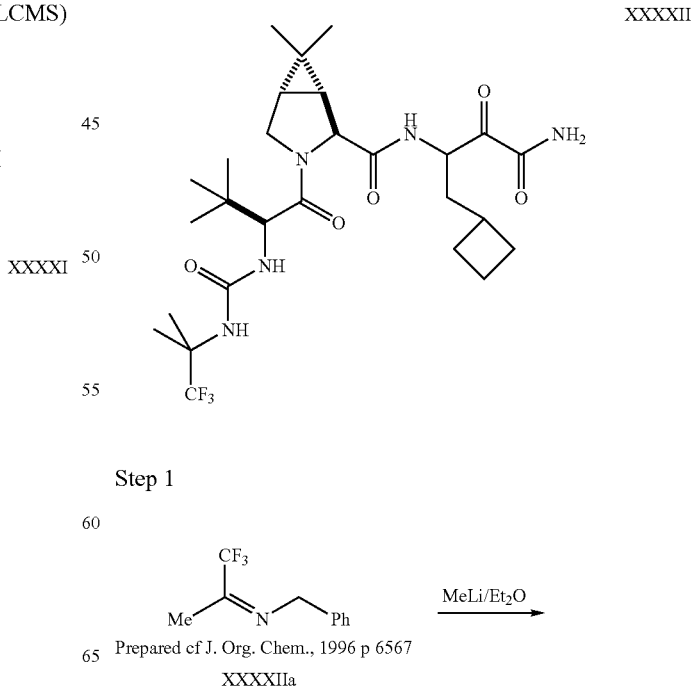

Step 1

Prepared cf J. Org. Chem., 1996 p 6567

XXXXIIa

Step 4

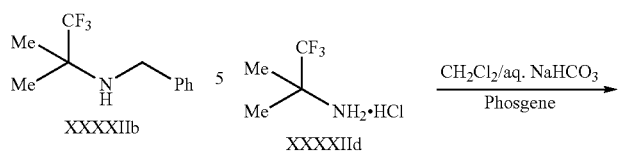

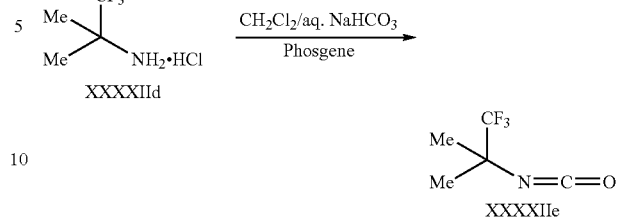

To a stirred and cooled (ice bath) solution of XXXXIId the product from step C (0.1 g) in CH$_2$Cl$_2$ (6 ml) was added saturated NaHCO$_3$ solution (4 ml) followed by phosgene (0.64 ml). The reaction mixture was stirred at 0° C. for 30 min and at room temperature for 1 hr. The organic phase was separated, dried over anhydrous MgSO$_4$ and concentrated to dryness in vacuum to provide the desired isocyanate XXXXIIe (0.0611 g).

Step 5

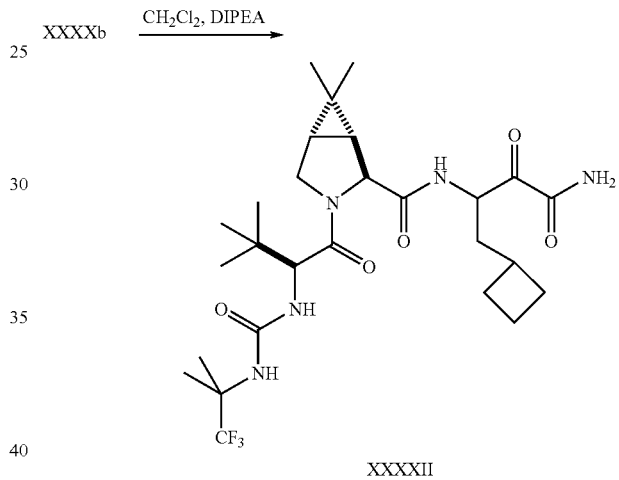

XXXXIIe, product of step 5 was reacted with XXXXb of preparative example XXXX in the manner previously in example XXXIII described to afford XXXXII. Mass spectrum (LCMS) 574 (M+H$^+$).

EXAMPLE XXXXIII

Preparation of Compound of Formula XXXXIII

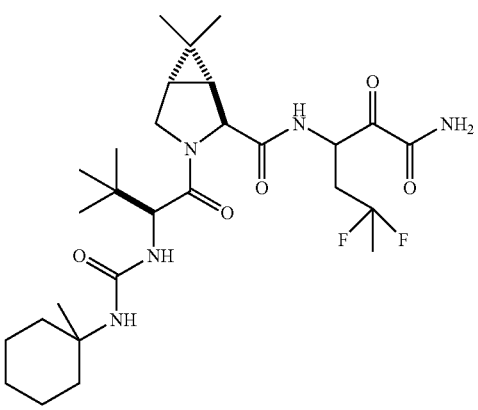

-continued

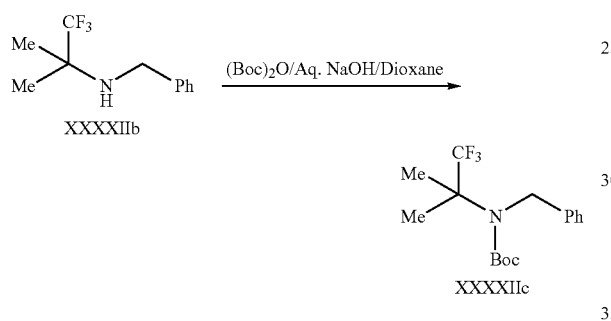

To a stirred and cooled (acetone/dry ice bath) solution of the starting imine XXXXII a (3.679 g) in diethyl ether (50 ml) was added 1.6M methyl lithium in diethyl ether (12.6 ml). The reaction mixture was allowed to warm up to room temperature over 2 hrs. Saturated NaHCO$_3$ was added and after stirring for ~30 min the organic phase was separated. It was then washed with brine, dried over anhydrous Na$_2$SO$_4$ and concentrated to dryness under vacuum. The crude product was subjected to chromatography over silica gel (2% ethyl acetate in n-hexane) to provide the desired product XXXXIIb (0.3 g).

Step 2

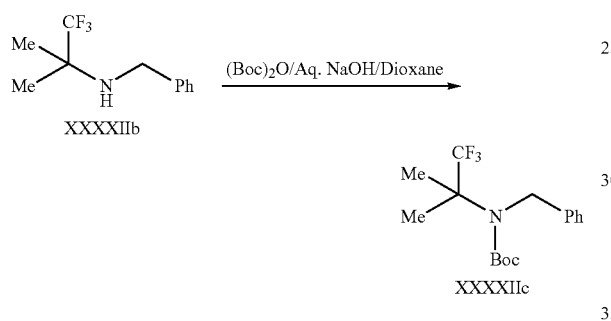

To a stirred and cooled (ice bath) solution of XXXXIIb the product from step 1 (0.3 g) was added 1.0N NaOH (1.38 ml) followed by (Boc)$_2$O. The reaction mixture was stirred at room temperature for ~20 hrs after which it was distributed between ethyl acetate (50 ml) and water (10 ml). The ethyl acetate phase was separated, washed with brine and dried over anhydrous Na$_2$SO$_4$. Evaporation under vacuum to dryness provided the desired NBoc derivative XXXXIIc (0.660 g), which was used without further purification in the following step.

Step 3

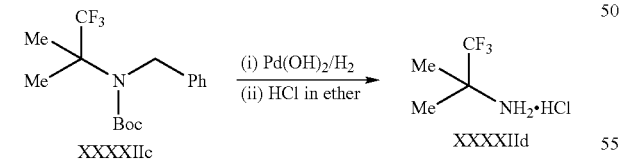

A solution of the XXXXIIc product from step 2 in methanol (10 ml) was hydrogenated in the presence of Pd(OH)$_2$ until thin layer chromatography showed the absence of the starting material. Pd(OH)$_2$ was removed by filtration and washed with methanol. The combined filtrate and washings were concentrated to dryness under vacuum to provide a solid which was dissolved in methanol and treated with 1.0N HCl in diethyl ether. After ~2 hr the reaction mixture was evaporated to dryness under vacuum to provide XXXXIId the desired amine hydrochloride as a white solid (0.2 g).

Step 1

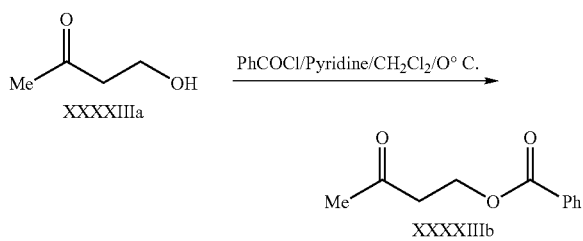

To a cooled solution (ice bath) of 4-hydroxy-2-butanone (8.81 g) XXXXIIIa in CH$_2$Cl$_2$ (100 ml) was added with stirring, benzoyl chloride (14.76 g) followed by pyridine (16.15 ml) and DMAP (0.01 g). The reaction mixture was stirred at room temperature overnight then diluted with ethyl acetate (~200 ml). The solution was washed with aqueous CuSO$_4$, aqueous NH$_4$Cl and brine. The organic phase was then dried over anhydrous MgSO$_4$ and evaporated to dryness. The product was purified by column chromatography over silica gel (5%-15% ethyl acetate in n-hexane) to provide XXXXIIIb (16.3 g; 84.9%).

Step 2

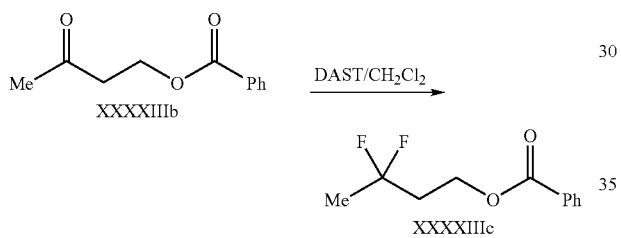

To a solution of XXXXIIIb, the product from step 1 (16.3 g) in CH$_2$Cl$_2$ (150 ml), was added DAST (26.1 ml) and the reaction mixture stirred at room temperature for ~72 hrs. The mixture was then added dropwise to a cold saturated solution of Na$_2$CO$_3$ (150 ml). The mixture was diluted with ethyl acetate (~200 ml) and after stirring for ~30 min the organic phase was separated; washed with brine and dried over anhydrous MgSO$_4$. Concentration in-vacuo and purification by chromatography over silica gel (4% ethyl acetate in n-hexane) provided XXXXIIIc (14.6 g; 80.4%).

Step 3

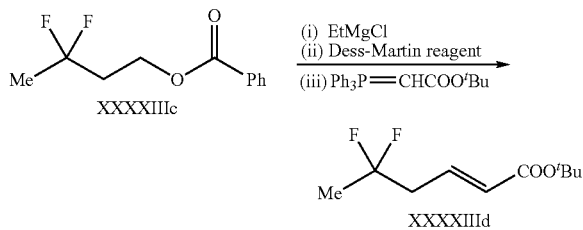

To a solution of XXXXIIIc the product from step 2 (4 g) in dry diethyl ether (150 ml) was added with cooling (ice bath) EtMgCl (28 ml). The reaction mixture was stirred in the cooling bath for ~6 hrs after which it was poured into saturated aqueous NH$_4$Cl with ice cooling. The organic layer was separated, washed with brine, dried over anhydrous MgSO$_4$ and concentrated to dryness in vacuum. The residue was dissolved in CH$_2$Cl$_2$ (100 ml) and treated with Dess-Martin reagent (15.8 g). After stirring at room temperature for 1 hr Ph$_3$P=CHCOOtBu (10.54 g) was added. Stirring was continued for ~20 hrs. Ethyl acetate (~200 ml) was added followed by a mixture of saturated Na$_2$S$_2$O$_3$ and saturated NaHCO$_3$ (200 ml; 1/1) and stirred for ~10 min. The organic layer was separated and washed successively with saturated NaHCO3 and brine. The washed organic phase was dried over anhydrous MgSO$_4$ and evaporated to dryness under vacuum to provide the desired crude product.

The above reaction was repeated using the product from step 2 (10.6 g). The final crude products from the two reactions were combined and subjected to purification by chromatography on silica gel (10% CH$_2$Cl$_2$ in n-hexane) to provide XXXXIIId (7.93 g; 57%).

Step 4

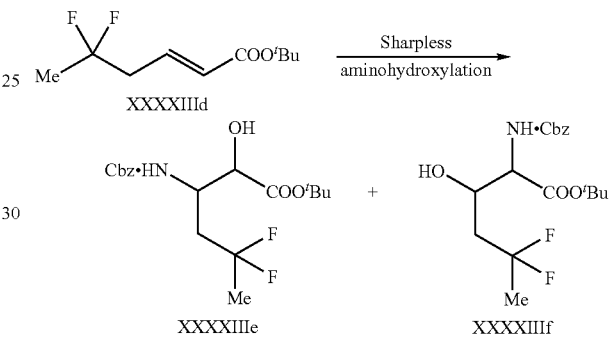

Benzyl carbamate (8.92 g) was dissolved in n-propyl alcohol (79 ml). To the resulting solution was added with stirring a freshly prepared solution of NaOH (2.33 g) in water (145 ml), followed by tert-butylhypochlorite (6.57 ml). To the resulting mixture (DHQ)$_2$PHAL (0.742 g) dissolved in n-propyl alcohol (66 ml) was added followed by XXXXIIId (19.05 mmol). The osmium catalyst, K$_2$OsO$_2$(OH)$_2$ was then added and the reaction mixture stirred at room temperature for 1 hr.

The above reaction was repeated using XXXXIIId (19.36 mmol). The two reactions were combined followed by dilution with ethyl acetate (500 ml). The mixture was shaken with water (100 ml), the organic phase separated and washed with water, brine and finally dried over anhydrous MgSO$_4$. Evaporation under vacuum provided the crude product which was chromatographed over silica gel (10%-20% ethyl acetate in n-hexane) to provide pure desired product (3 g) as a mixture of XXXXIIIe and XXXXIIIf Step 5

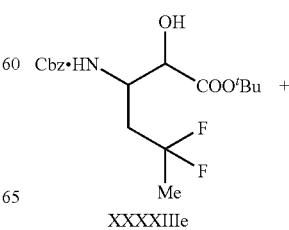

Step 7

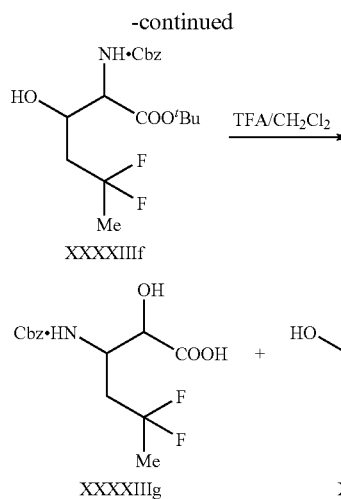

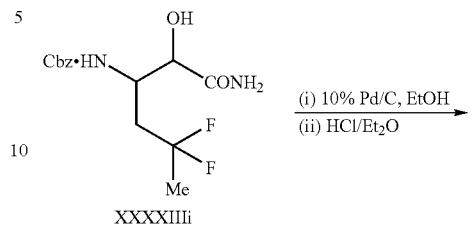

A stirred solution of XXXXIIIf and XXXXIIIe the product from step 4 in CH$_2$Cl$_2$ (50 ml) was treated with trifluoroacetic acid (50 ml). After 4 hrs the reaction mixture was concentrated to dryness under vacuum. The residue was dissolved in 10% aqueous Na$_2$CO$_3$ the solution washed with diethyl ether and the aqueous phase acidified with 2M H$_2$SO$_4$ to pH ~1.5. Extraction of the acidic solution with ethyl acetate followed by drying over anhydrous MgSO$_4$ and evaporation under vacuum provided the desired product as a mixture of XXXXIIIg and XXXXIIIh (2.6 g).

Step 6

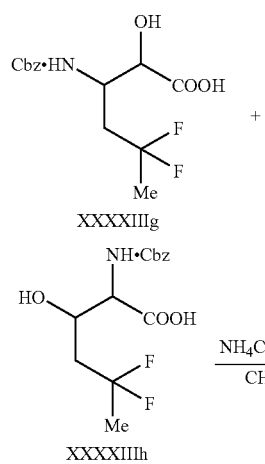

To a solution of the product from step 5 (1 g) in CH$_2$Cl$_2$ (50 ml) was added HATU (1.43 g), NH$_4$Cl (0.842 g) and DMSO (5.59 ml). The reaction mixture was stirred at room temperature for ~20 hrs, diluted with ethyl acetate and washed with saturated NaHCO$_3$ and brine. The organic phase was then dried over anhydrous MgSO$_4$ and concentrated to dryness under vacuum to provide the crude product. Chromatography on silica gel (10% n-hexane in ethyl acetate) provided in one of the fractions the pure desired product XXXXIIIi (0.205 g).

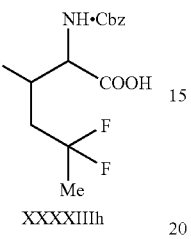

To a solution of XXXXIIIi the product from step 6 (0.205 g) in ethanol (15 ml) was added 10% Pd/C catalyst. The resulting suspension was hydrogenated until thin layer chromatography indicated complete consumption of the starting material (~3 hrs). The catalyst was removed by filtration and washed with ethanol. The combined filtrate and washings were evaporated under vacuum to dryness to provide the desired product XXXXIIIj (0.164 g).

Step 8

XXXXIIIj ⟶

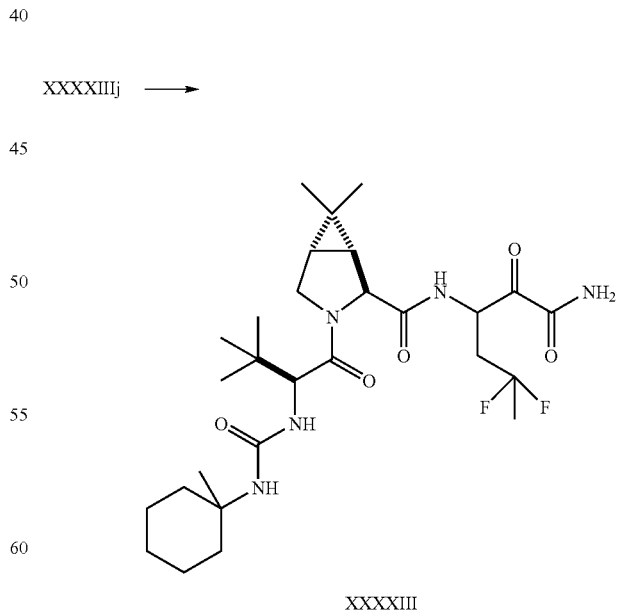

XXXXIIIj was converted to XXXIII following the procedure similar to example XXVIII and XXXIII

EXAMPLE XXXXIV

Preparation of Compound of Formula XXXXIV

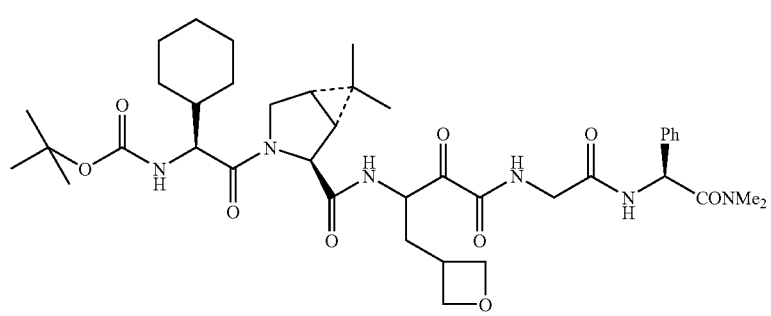

XXXXIV

Step 1

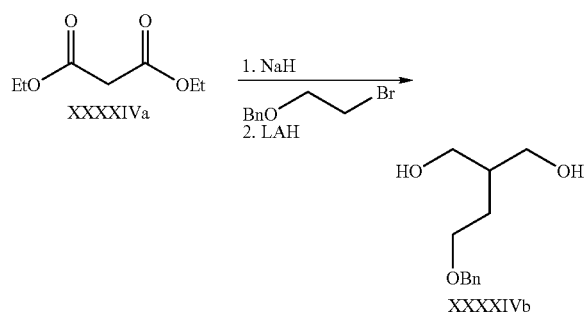

Ethyl malonate XXXXIVa (5.4 ml; 36 mmol) was added to a suspension of NaH (1.44 g of a 60% dispersion in mineral oil; 0.9 eq.) in anhydrous tetrahydrofuran (THF; 60 ml) at 0° C., under an atmosphere of nitrogen and the mixture was stirred at room temperature for 30 min. Benzyl 2-bromoethylether (8.5 ml; 40 mmol) was added before refluxing the reaction for a period of 24 h. After cooling, the reaction was partitioned between EtOAc and dilute HCl (approx. 1M). The organic layer was separated, dried (MgSO$_4$) and concentrated to yield a residue.

The aforementioned residue was dissolved in anhydrous THF (100 ml) and a solution of lithium aluminum hydride (LAH; 66 ml of a 1.0M solution) was added under an atmosphere of nitrogen and the resulting mixture was stirred at room temp. for a period of 4 h. and EtOAc followed by dilute HCl was added. The organic layer was separated, washed with brine, dried (MgSO$_4$) and concentrated. The crude reaction product was purified by silica gel column chromatography using EtOAc:Hexane (70:30) as eluent to provide the desired diol XXXXIVb (3.59 g) as a colourless oil.

Step 2

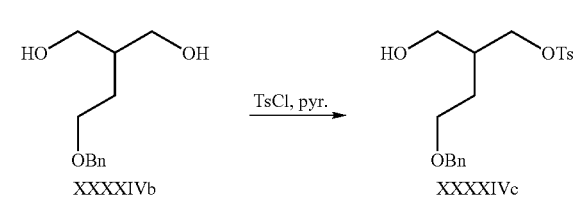

p-Toluene sulfonylchloride (1.12 g; 5.9 mmol) was added to the diol XXXXIVb (1.00 g; 4.9 mmol) in a mixture of dichloromethane (15 ml) and pyridine (1.18 ml; 14.6 mmol) and the resulting mixture was stirred at room temperature overnight (approx 16 h.). The reaction mixture was partitioned between EtOAc and dilute aqueous HCl. The organic phase was separated, washed with sat. aq. Sodium bicarbonate, dried (MgSO4) and concentrated under reduced pressure. The residue was purified by silica gel column chromatography using EtOAc:hexane (30:70) as eluent to provide 1) the ditosylate (0.291 g), followed by ii) the desired mono-tosylate XXXXIVc (1.02 g) and iii) recovered diol (0.27 g).

Step 3

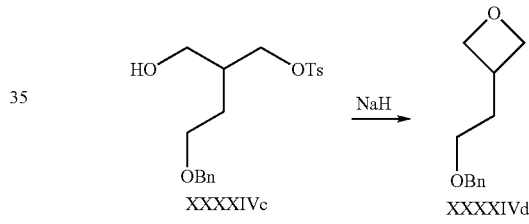

The mono-tosylate XXXXIVC (1.0 g; 2.8 mmol) in anhydrous dimethylformamide (DMF; 3 ml) was added to a suspension of NaH (0.333 g of a 60% dispersion in mineral oil; 8.3 mmol) in DMF (13 ml) and the resulting mixture was stirred at room temperature for a period of 3 h. The reaction mixture was partitioned between EtOAc and water. The organic phase was separated, washed with brine, dried (MgSO4) and concentrated to provide a residue which was purified by silica gel column chromatography using EtOAc:hexane (1:5) as eluent to provide the desired oxetane XXXX-IVd (0.37 g) as a colourless oil.

Step 4

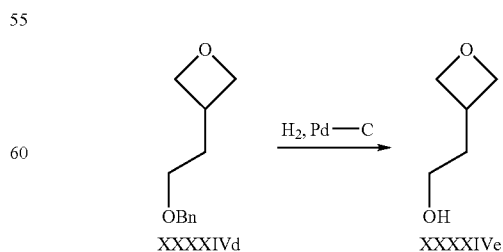

A suspension of 10% Pd—C (0.10 g) and the benzylether XXXXIVd (0.33 g) in methanol (10 ml) was placed under an atmosphere of hydrogen (balloon) for a period of 1 h. The reaction mixture was filtered through a pad of celite and the solid washed thoroughly with methanol. The combined filtrate was concentrated under reduced pressure to provide the alcohol XXXXIVe (0.17 g) as a colourless oil used in subsequent procedures without purification.

Step 5

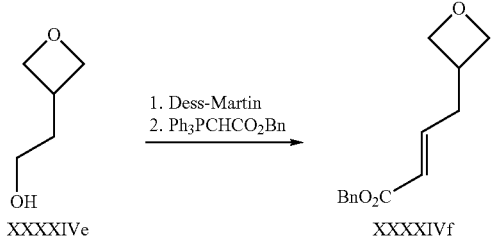

The Dess-Martin periodinane (0.658 g; 0.16 mmol) was added to a solution of the alcohol XXXXIVe (0.144 g; 1.4 mmol) in dichloromethane (5 ml) and stirred at room temperature for a period of 1 h., before adding the phosphorane (0.637 g; 0.16 mmol). The resulting reaction mixture was stirred for a period of approx. 16 h., then partitioned between EtOAc and water. The organic phase was separated, dried (MgSO$_4$) and concentrated under reduced pressure. The residue was purified by silica gel column chromatography using EtOAc:hexane; 1:5 to provide the ester XXXXIVf (0.131 g) as a colourless oil.

Step 6

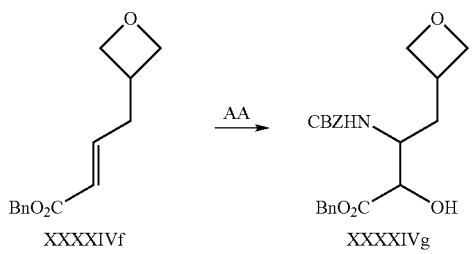

Benzyl carbamate (0.657 g; 4.3 mmol) was dissolved in n-propanol (6 ml). Aqueous sodium hydroxide (0.171 g; 4.3 mmol, in 11 ml of water) was added followed by tert-butyl hypochlorite (0.49 ml; approx 4.3 mmol) and a solution of (DHQ)$_2$PHAL (0.056 g) in n-propanol (5 ml). The resulting mixture was placed in a water bath and stirred for 5 min. before adding the olefin XXXXIVf (0.326 g; 1.4 mmol) followed by potassium osmate dihydrate (0.021 g). The resulting reaction mixture was stirred for 3 h., and added to EtOAc. The aqueous layer was separated and washed with EtOAc. The combined organic phases were washed with brine, dried (MgSO$_4$) and concentrated under reduced pressure. The residue was purified by silica gel column chromatography using EtOAc; hexane (7:3) as eluent to give the alpha-hydroxy ester XXXXIVg (0.367 g), containing approx. 20% of the undesired beta-hydroxy ester.

Step 7

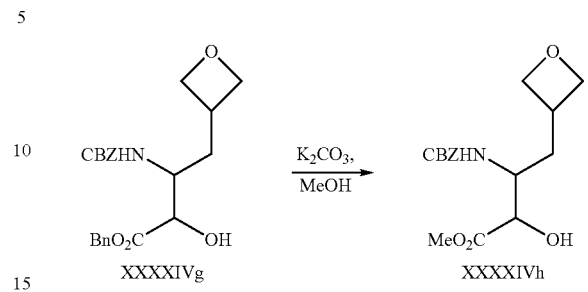

Potassium carbonate (0.100 g) was added to a methanol (30 ml) solution of approx. 2 g of the benzyl ester XXXXIVg (contaminated with a small quantity of benzyl carbamate). The resulting mixture was stirred at room temperature for 2 h., then partitioned between EtOAc and water. The organic phase was separated, washed with brine, dried and concentrated under reduced pressure. The residue was purified by silica gel column chromatography using EtOAc:hexanes (7:3) to provide the ester XXXXIVh (1.02 g).

Step 8

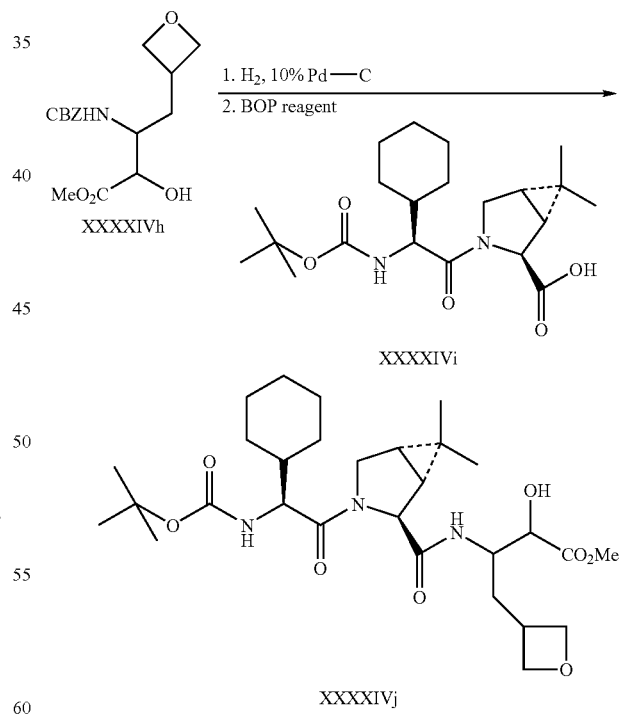

A suspension of 10% Pd—C (0.030 g) and the benzyl carbamate XXXXIVh (0.090 g) in methanol (5 ml) was placed under an atmosphere of hydrogen (balloon) for a period of 1 h. The reaction was filtered through a pad of celite and the solid was washed thoroughly with methanol. The combined filtrate was concentrated under reduced pressure to yield the intermediate amine (0.050 g) which was used immediately.

BOP reagent (0.131 g; 0.31 mmol) followed by triethylamine (0.130 ml; 0.93 mmol) were added to a mixture of the amine (0.050 g; 0.28 mmol) and the carboxylic acid XXXXIVI (0.121 g; 0.31 mmol) in dichloromethane (3 ml) and the resulting mixture was stirred for a period of 4 h. and partitioned between dil. aq. HCl (approx. 1 M) and EtOAc. The organic phase was separated, washed with sat. aq. Sodium bicarbonate, dried (MgSO₄) and concentrated under reduced pressure. The residue was purified by silica gel column chromatography using EtOAc as eluent to provide the methyl ester XXXXIVj (0.107 g) as a white solid.

Step 9

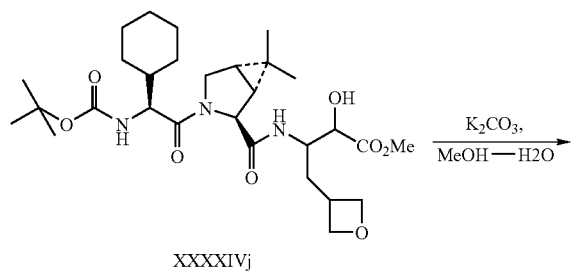

XXXXIVj

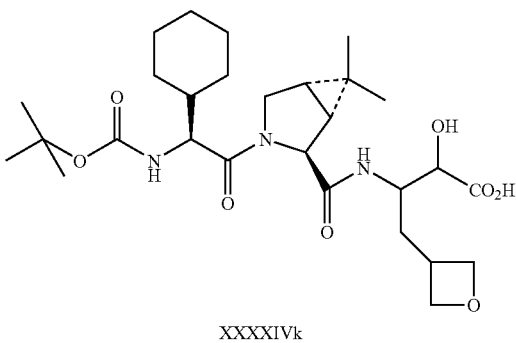

XXXXIVk

Potassium carbonate (0.054 g; 0.39 mmol) was added to the ester XXXXIVj (0.107 g; 0.19 mmol) in a mixture of methanol (3 ml) and water (1 ml) and the resulting reaction was stirred for a period of 16 h. and partitioned between EtOAc and water. The organic phase was separated, washed with brine, dried and concentrated to yield the acid XXXXIVk (0.099 g).

Step 10

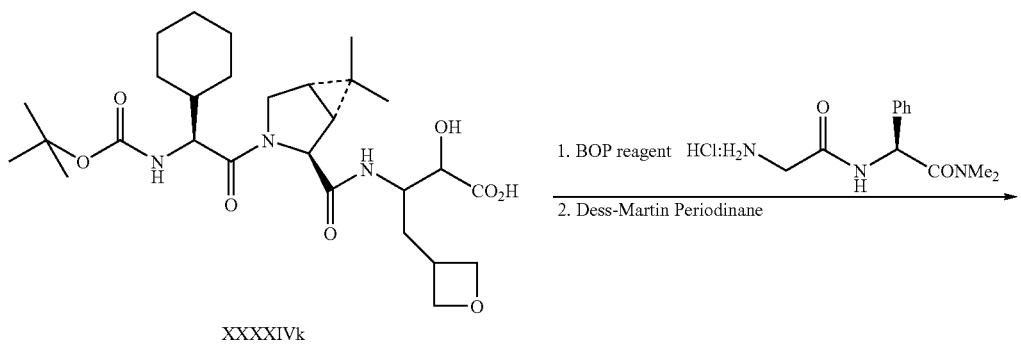

XXXXIVk

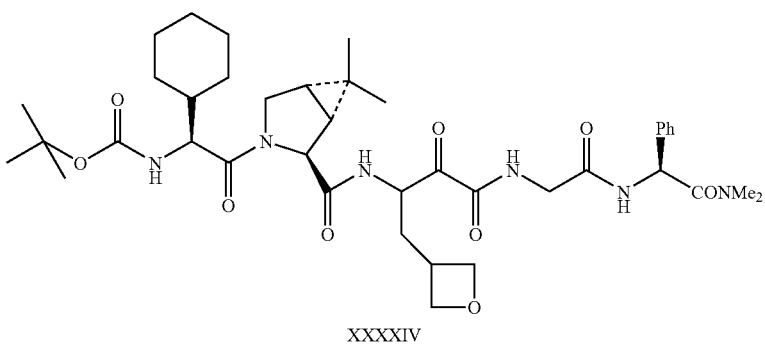

XXXXIV

Triethylamine (0.035 ml; 0.25 mmol) was added to a mixture of the carboxylic acid XXXXIVk (0.041 g; 0.08 mmol), the hydrochloride salt (0.023 g; 0.08 mmol) and BOP reagent (0.037 g; 0.08 mmol) in dichloromethane (3 ml) and the resulting mixture was stirred at room temperature for a period of 4 h. The reaction was partitioned between EtOAc and dilute aq. HCl (1 M). The organic phase was separated, washed with sat. aq. sodium bicarbonate, water, dried and concentrated under reduced pressure.

The residue from the aforegoing procedure was dissolved in dichloromethane (3 ml) and Dess-Martin periodinane (0.065 g; 0.15 mmol) was added and the mixture stirred at room temperature for 2 h. The reaction was partioned between 5% aq. sodium sulfite, sat. aq. sodium bicarbonate, water, dried and concentrated under reduced pressure. The residue was purified by silica gel column chromatography using $CH_2Cl_2$; MeOH; 20:1 as eluent to provide the alpha-keto amide XXXXIV (0.021 g). FABMS: $MH^+$, 767.4.

EXAMPLE XXXXVI

Preparation of Compound of Formula XXXXVI

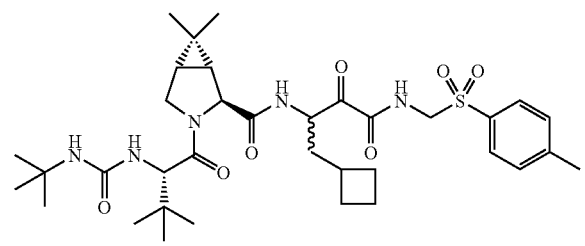

XXXXVI

Step 1

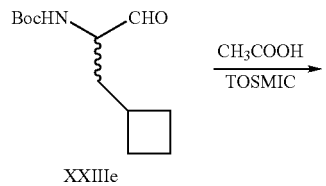

XXIIIe

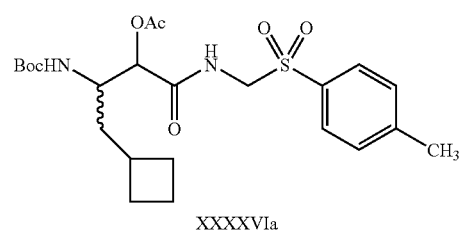

XXXXVIa

A solution of aldehyde XXIIIe (0.626 g, 2.75 mmol), TOSMIC (1.63 g, 8.27 mmol) and $CH_3COOH$ (0.48 mL, 8.27 mmol) in dry $CH_2Cl_2$ (15 mL) was stirred at rt. for 36 h. The reaction mixture was concentrated in vacuo and purified by chromatography ($SiO_2$, EtOAc/Hex 2:3) to yield 0.90 g (68%) of XXXXVIa as a colorless solid MS (ES) m/z, relative intensity 965 [$(2M+1)^+$, 30], 483 [$(M+1)^+$, 53], 427 (60), 383 (100), 365 (71), 272 (64).

Step 2

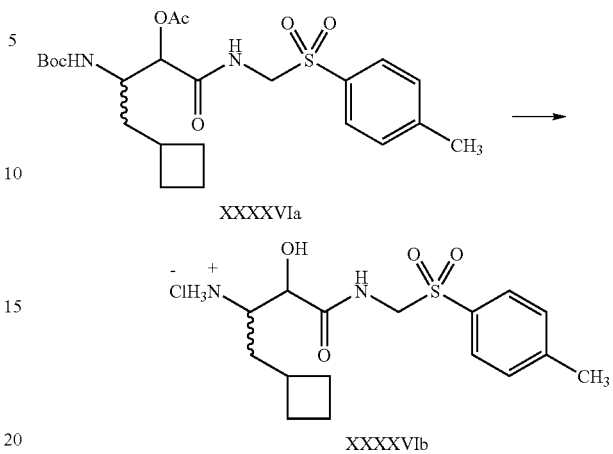

A solution of XXXXVIa (0.9 g, 1.86 mmol) in HCl (30 mL, 6 M in $CH_3OH$, prepared by addition of acetyl chloride to $CH_3OH$ at 0° C.) was stirred at rt. overnight. The reaction mixture was concentrated in vacuo and used as it is in the following step MS (ES) m/z, relative intensity 681 [$(2M+1)^+$, 26], 341 [$(M+1)^+$, 100], 180 (40)

Step 3

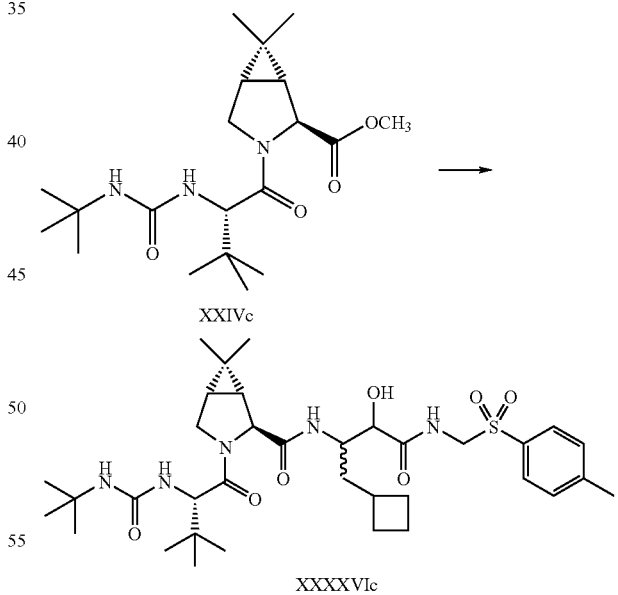

The synthesis of XXXXVIc was accomplished using XXIVc (134 mg, 0.36 mmol), and amine XXXXVIb (120 mg, 0.32 mmol) following the procedure reported for example XXIV from step 3 to yield product XXXXVIc which was used for further oxidation without purification MS (ES) m/z, relative intensity 690 [$(M+1)^+$, 100], 591 (27), 537 (18), 513 (27), 478 (63), 438 (18), 414 (60), 268 (27)

Step 4

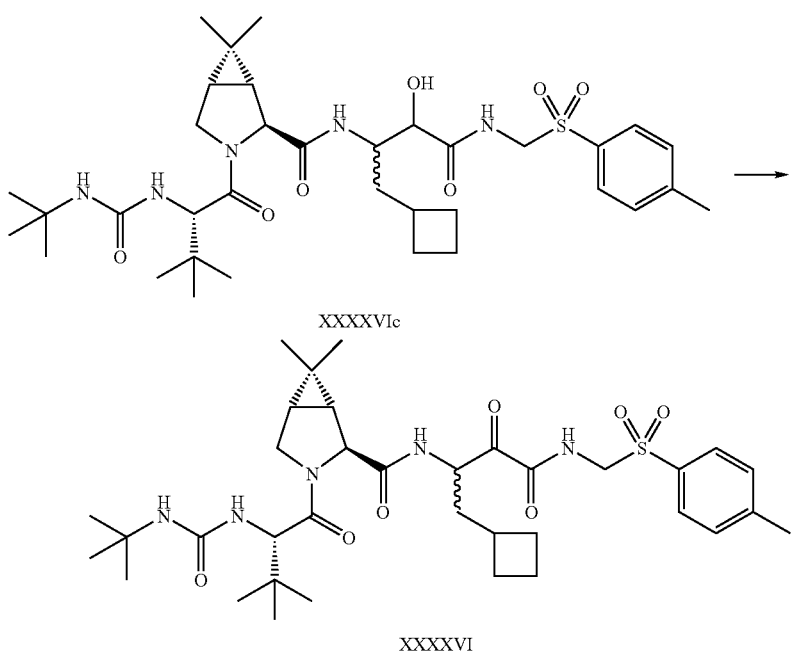

The synthesis of XXXXVI was accomplished by the oxidation of using alcohol XXXXVIc (219 mg, 0.32 mmol), EDCl (609 mg, 3.2 mmol), and Gl$_2$CHCOOH (131 L, 1.59 mmol) following the procedure reported in example XXIV, step 4 which purified by chromatography (SiO$_2$, Acetone/Hexanes 3:7) to yield product XXXXVI (117 mg, 53% over 2 steps) as a colorless solid.

MS (ES) m/z, relative intensity 688 [(M+1)$^+$, 32], 589 (81), 476 (100)

Synthesis of Intermediates

EXAMPLE XXXXVII

Preparation of Intermediate of Formula XXXXVII

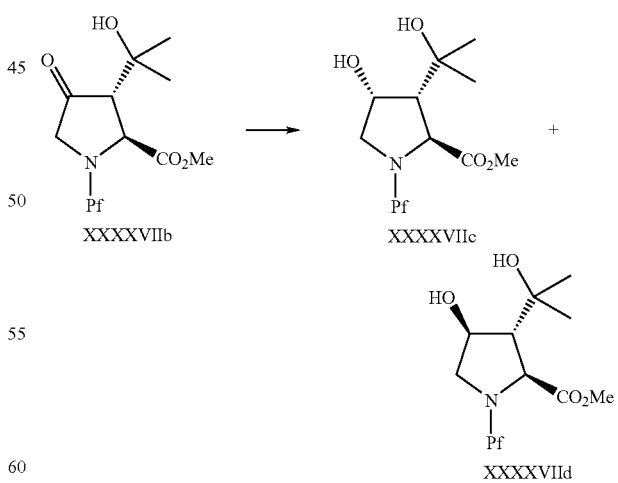

Step 1

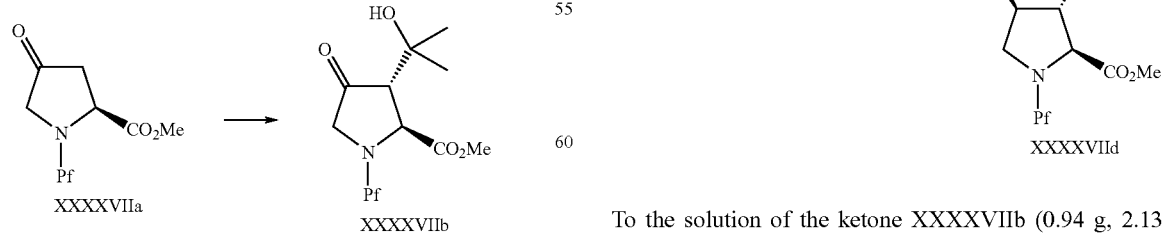

To the solution of ketone XXXXVIIa (4.93 g, 12.8 mmol) in anhydrous THF (100 mL) at −78 C was added a solution of lithium hexamethyldisilylazide (LIHMDS) (17.0 mL, 17.0 mmol). The resulting solution was stirred at that temperature for 1 h before a solution of acetone (1.51 mL, 20.5 mmol) and BF$_3$.Et$_2$O (2.60 mL, 20.5 mmol) in THF (15 mL) was added. After stirred for another 4 h, 5% H$_3$PO$_4$ (20 mL) was added followed by saturated ammonium chloride solution (200 mL) and diethyl ether (200 mL). The layers were separated and aqueous layer was extracted with diethyl ether (2×200 mL). The combined organic solution was dried (MgSO$_4$), filtered and concentrated in vacuo. The crude product Was purified by flash chromatography with 20-50% EtOAc/hexane to give 1.84 g of XXXXVIIb (33%) and 3.26 g starting material XXXXVIIa Step 2

To the solution of the ketone XXXXVIIb (0.94 g, 2.13 mmol) in anhydrous THF (20 mL) at −78 C was added a solution of LiAlH$_4$ in THF (2.6 mL, 2.6 mmol) and the reaction mixture was stirred for 40 min before KHSO$_4$ solution (1.0 M, 16 mL) was added. The mixture was allowed to warm to rt and to it was added EtOAc (100 mL) and water (50 mL). After the layers were separated and aqueous layer was extracted with EtOAc (2×50 mL). The combined organic solution was dried (MgSO$_4$), filtered and concentrated in vacuo. The crude product was purified by flash chromatography with 30-100% EtOAc/hexane to give 0.49 g of XXXXVIIc (52%) and 0.18 g (19%) XXXXVIId.

Step 3

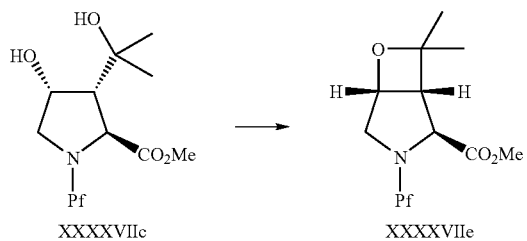

XXXXVIIc → XXXXVIIe

The solution of XXXXVIIc (103 mg, 0.232 mmol), triphenylphosphine (120 mg, 0.456 mmol) and diethyl azodicarboxylate (0.055 mL, 0.349 mmol) in anhydrous CH$_2$Cl$_2$ (5 mL) was stirred at rt for 18 h. After concentrated in vacuo, the mixture was purified by flash column chromatography using 10-30% EtOAc/hexane to give 24 mg (24%) of XXXXVIIe.

Step 4

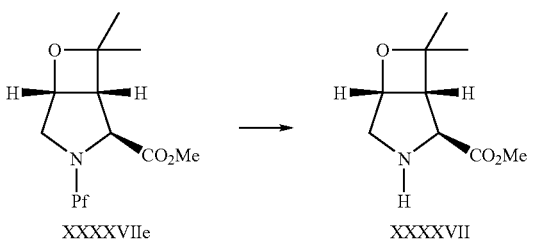

XXXXVIIe → XXXXVII

The solution of XXXXVIIe in EtOH was hydrogenated at rt in the 10% Pd—C catalyst to XXXXVII.

A number of inhibitors described in table-6 using the intermediates XXXXVII were synthesized following the procedures outlined for preparative examples XXIII, XXIV, XXVIII, XXIX, and XXXX

EXAMPLE XXXXVIII

Preparation of Intermediate of Formula XXXXVIII

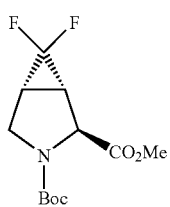

XXXXVIII

Step 1

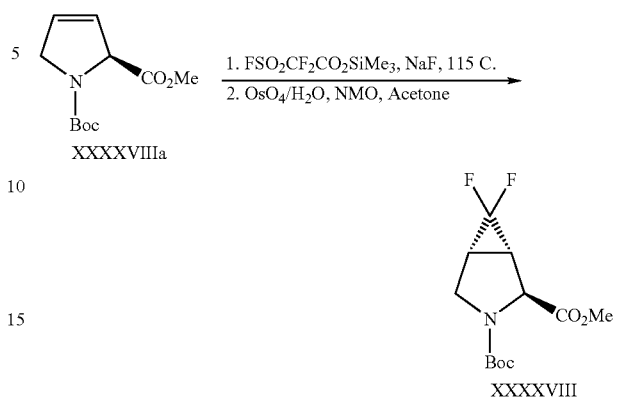

XXXXVIIIa → XXXXVIII

To 5 g (22 mmol) of N-Boc-dehydroprolinemethylester XXXXVIIIa was added 25 mg of NaF and 2 g of Toluene. At 110 C, was added via syringe-pump 1.6 equiv (35 mmol, 8.75 g) of TMSfluorosulfonyldifluoroacetate (TFDA) in 1 h. After 2 h, reaction is cooled down to RT. To the mixture is added NMO(6.8 g, 50 mmol), Acetone (50 mL), H2O (25 mL) and OsO4 (0.015 M in H2O, 1 mol %, 0.44 mmol, 28 mL). Reaction is stirred overnight at RT then diluted with EtOAc and washed with H$_2$O and Brine. Organic layer was dried over MgSO$_4$, filtered and concentrated to dryness. Purification by flash column chromatography (10 EtOAc, Hexane, silica) furnished Product XXXXVIII (0.76 g).

A number of inhibitors described in table-6 using the intermediate XXXXVIII were synthesized following the procedures outlined for preparative examples XXIII, XXIV, XXVIII, XXIX, and XXXX

EXAMPLE IL

Preparation of Intermediate of Formula IL

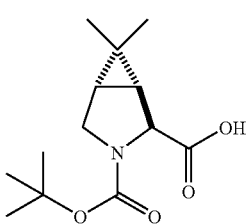

IL

Step 1.(1R,3S)-2,2-DIMETHYL-3-(2-OXOPROPYL)CYCLOPROPANEACETIC ACID.

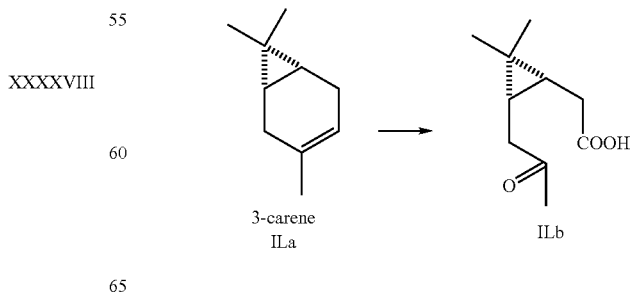

3-carene ILa → ILb

A mixture of 0.55 L tert-butanol, 1.1 L water, 100 mL 3-carene ILa (Aldrich Chemical Co.), and 490 g NaIO4, was treated with 2.2 g ruthenium chloride hydrate. The vigorously stirred mixture was alternately heated and cooled for 2 hr. to maintain a temperature of 35-40° C. The vigorously stirred mixture was alternately heated and cooled for another 1 hr. to maintain a temperature of 40-50° C. The vigorously stirred mixture was then heated for another ½ hr. to maintain a temperature of 50-55° C. The mixture was then cooled to 30° C., filtered on a Buchner funnel, and the precipitates were washed with 700 mL of iso-propyl ether. The aqueous portion of the filtrate was extracted with 900 mL of EtOAc-hexane (2:1), and the extract was combined with the ethereal portion of the filtrate. The combined organics were washed with 300 mL of 20% aqueous NaCl, then extracted with a solution of 36 g NaOH in 2.2 L water. The cooled aqueous extract was acidified with 100 mL of 12 N HCl and extracted with $Et_2O$ (3×800 mL). The extract washed with brine, dried over anhydrous $MgSO_4$, and evaporated in vacuo to leave the title compound ILb 98 g (88%) as a gum.

$H^1$NMR ($CDCl_3$) δ 2.39 (m, 2), 2.28 (m, 2), 2.19 (s, 3), 1.1.12 (s, 3), 0.90 (m, 2), 0.63 (s, 3).

Step 2. (1R,3S)-METHYL 2,2-DIMETHYL-3-(2-OXO-PROPYL)CYCLOPROPANEACETATE.

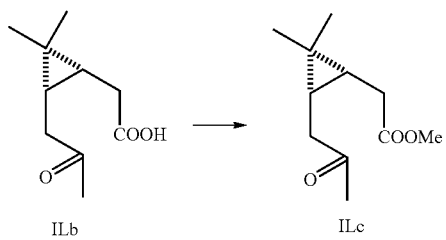

A solution of 98 g of ILb, the product of the preceding step and 0.55 L DMF was treated with 98 g $Cs_2CO_3$. The mixture was stirred for 10 minutes, 41.5 mL MeI was added, and the mixture was stirred at 40° C. for 1 hr. The mixture was cooled and filtered on a Buchner funnel. The filtrate was quenched with 2.5 L of 18% aqueous NaCl, the organic layer was separated, and the aqueous solution was extracted with $Et_2O$-hexane (1:1; 2×1 L). The combined organic layer and extracts were washed with water, dried over anhydrous $MgSO_4$, filtered, and evaporated in vacuo to leave the title compound ILc as 91 g (86%) thick oil. $H^1$NMR ($CDCl_3$) δ 3.67 (s, 3), 2.3 (m, 4), 2.17 (s, 3), 1.12 (s, 3), 0.97 (m, 2), 0.91 (s, 3).

Step 3. (1R,3S)-METHYL 3-(ACETOXYMETHYL)-2,2-DIMETHYLCYCLOPROPANEACETATE.

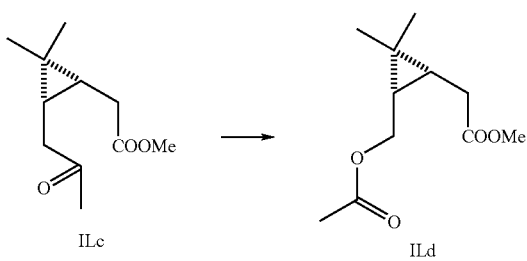

A solution of ILc 91 g of the product of the preceding step and 0.7 L 1,1,2-trichloroethane was treated with 165 g of 70% m-chloroperbenzoic acid. The mixture was stirred at ambient temperature for 1 hr, then heated with an oil bath to maintain a reaction temperature of 65-70° C. for 1 hr., and then heated at 75° C. for 1 hr. more. The mixture was cooled, filtered on a Buchner funnel, and the filter cake washed with fresh trichloroethane. The combined filtrate and washings were concentrated in vacuo to 0.5 L, and the residue was diluted with 2.5 L of hexane-$Et_2O$ (3:1). The organic solution washed repeatedly with a solution of 3.5% aqueous $K_2CO_3$-brine (3:1; 8×0.9 L), then with brine, then dried over anhydrous $MgSO_4$, filtered, and evaporated in vacuo to leave the title compound ILd as 98 g (100%) thick oil. $H^1$NMR ($CDCl_3$) δ 4.1-3.9 (m, 2), 3.68 (s, 3), 2.34 (d, 2), 2.04 (s, 3), 1.12 (s, 3), 1.04 (m, 2), 1.00 (s, 3).

Step 4. (1R,3S)-METHYL 3-(HYDROXYMETHYL)-2,2-DIMETHYLCYCLOPROPANEACETATE

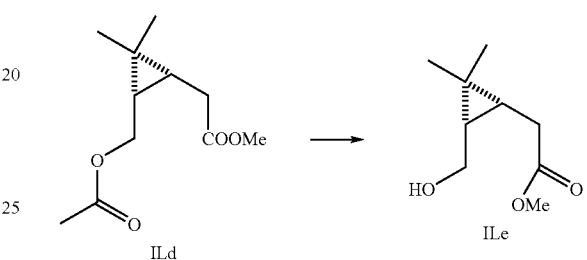

A solution of 98 g ILd of the product of the preceding step and 1 L methanol was treated with 19 g $K_2CO_3$, and the mixture was stirred at 30° C. for 1 hr. The mixture was concentrated in vacuo to remove 0.6 L methanol, the residue was quenched with cold 10% aqueous $KH_2PO_4$, and the mixture was extracted with EtOAc. The extract washed with brine, dried over anhydrous $MgSO_4$, filtered, and evaporated in vacuo to leave 70 g (89%) of the title compound ILe as a gum. $H^1$NMR ($CDCl_3$) δ 3.80 (q, 1), 3.73 (s, 3), 3.52 (m, 1), 2.68 (d of d, 1), 2.23 (d of d, 1), 1.09 (s, 3), 1.1-0.9 (m, 2), 0.98 (s, 3).

Step 5. (1S,6R)-7,7-DIMETHYL-3-OXABICYCLO[4.1.0]HEPTAN-4-ONE.

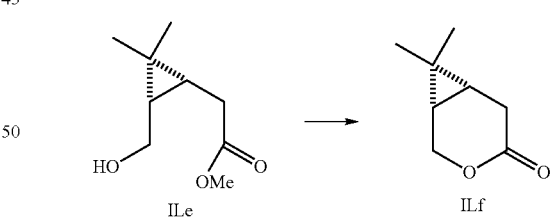

A solution of ILe 70 g of the product of the preceding step and 1.1 L xylenes was treated with 30.8 g DBU. The solution was heated to a gentle reflux for 18 hr. as methanol was removed from the distillate. The solution was cooled, washed with cold 1 N HCl, then with brine; dried over anhydrous $MgSO_4$, filtered, and evaporated in vacuo. The residue was chromatographed on 600 g silica gel using a gradient of $CH_2Cl_2$ to 1:10 EtOAc-$CH_2Cl_2$ to obtain the title compound ILf as 54 g (94%) oil. $H^1$NMR ($CDCl_3$) δ 4.71 (d of d, 1), 4.04 (d of d, 1), 2.75 (d of d, 1), 2.16 (d of d, 1), 1.16 (s, 3), 1.25 (m, 1), 1.12 (s, 3).

Step 6. (1S,6R,5E)-7,7-DIMETHYL-3-OXABICYCLO[4.1.0]HEPTANE-4,5-DIONE, 5-OXIME.

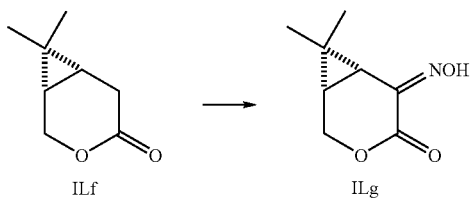

A solution of 42 g of the product of the preceding step ILf and 300 mL anhydrous toluene was treated with 102 mL of 90% tert-butylnitrite. The stirred mixture was alternately heated and cooled as needed as 45 g potassium tert-butoxide was added in 6 portions over 20 minutes at 30-35° C. Then 180 mL of anhydrous methanol was added, the temperature raised to 40° C., and stirring continued at 40° C. for 2.5 hr. The mixture was cooled, quenched with a cold solution of 1.1 L of 10% aqueous and 20 mL 12N HCl, then extracted with EtOAc-toluene (3:1). The extracts were washed with 5% aqueous NaHCO$_3$, then brine; dried over anhydrous MgSO$_4$, filtered, and evaporated in vacuo. The residue (25 g) was chromatographed on 150 g silica gel using a gradient of CH$_2$Cl$_2$ to 35:65 EtOAc-CH$_2$Cl$_2$ to obtain 15 g (29%)of the title compound ILg as an oil. H$^1$NMR (CDCl$_3$) δ 4.82 (d of d, 1), 4.55 (d of d, 1), 2.40 (d, 1), 1.49 (m, 1), 1.27 (s, 3), 1.18 (s, 3).

Step 7.

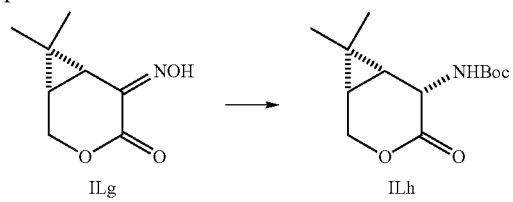

A solution of 18 g of the product of the preceding step ILg and 400 mL EtOAc was treated with 32 g di-tert-butyldicarbonate (Boc$_2$O), and 2.0 g of 10% Pd on carbon. The mixture was hydrogenated at 2.5 atm for 18 hr, filtered, and the filtrate evaporated to leave 36 g of the title compound mixed with Boc$_2$O, which was taken directly to the next step. A portion was chromatographed to obtain ILh as pure title compound: H$^1$NMR (DMSO-d$_6$) δ 7.28 (d, NH), 4.76-4.64 (m, 2), 4.44 (d, 1), 1.40 (s, 9), 1.24 (m, 1), 1.11 (m, 2), 1.07 (s, 3), 0.99 (s, 3).

Step 8. (1R,3S)-METHYL ALPHA(S)-[[(1,1-DI METHYL-ETHOXY)CARBONYL]AMINO]-3-(HYDROXYM-ETHYL)-2,2-DIMETHYLCYCLOPROPANEACETATE

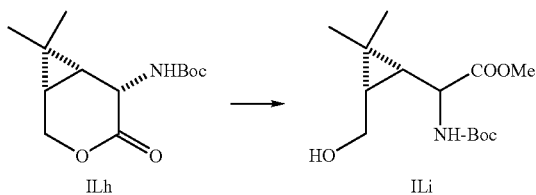

A solution of 35 g of ILh the product mixture of the preceding step and 350 mL anhydrous methanol was treated with 12 g of finely ground anhydrous K$_2$CO$_3$. The mixture was vigorously stirred for 2 hr., concentrated in vacuo with a 25° C. bath, and then quenched with 0.6 L of 10% aqueous KH$_2$PO$_4$. The solution was extracted with EtOAc-hexane (95:5; 2×200 mL), the extracts were washed with brine, dried over anhydrous MgSO$_4$, filtered, and the filtrate was evaporated in vacuo to leave ILi 22 g (70%) of the title compound as a gum mixture of the two epimers in an α-S/α-R ratio of 8:2, which did not have to be separated for the present purpose. A portion was chromatographed with Et$_2$O-hexane (60:40) to obtain pure α-S-epimer of the title compound: H$^1$NMR (CDCl$_3$) δ 5.2 (br s, 1), 4.05 (br s, 1), 3.81 (m, 1), 3.76 (s, 3), 3.65 (m, 1), 1.43 (s, 9), 1.14 (s, 3), 1.06 (s, 3), 1.05 (m, 1), 0.86 (m, 1). Optical rotation: $[\alpha]_D^{25}$ −62.9° (c=1, MeOH). Elemental analysis: theory C, 58.52; H, 8.77; N, 4.87; found C, 58.48; H, 8.75; N, 5.10.

Further elution provided the α-R-epimer of the title compound: H$^1$NMR (CDCl$_3$) δ 4.95 (br d, 1), 4.03 (m, 1), 3.82 (m, 1), 3.78 (s, 3), 3.71 (m, 1), 1.44 (s, 9), 1.13 (m, 1), 1.10 (s, 3), 1.08 (s, 3), 0.86 (m, 1). Optical rotation: $[\alpha]_D^{25}$ −32.8° (c=1, MeOH). Elemental analysis: theory C, 58.52; H, 8.77; N, 4.87; found C, 58.46; H, 8.69; N, 4.74.

Step 9. (1R,5S)-6,6-DIMETHYL-,3-AZABICYCLO[3.1.0]HEXANE-2(S),3-DICARBOXYLIC ACID 3-(1,1-DIM-ETHYLETHYL)2-METHYL ESTER

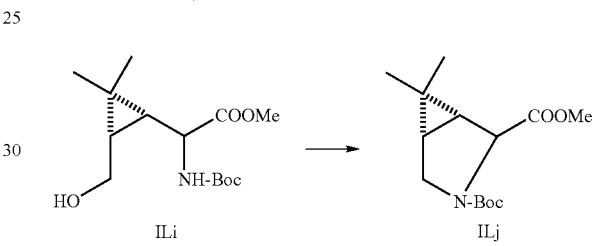

A solution of 21.6 g triphenylphosphine and 250 mL anhydrous THF was cooled to −10° C. and treated dropwise with 16.2 g diisopropylazodicarboxylate as the temperature of the reaction rose to +5° C. After 5 minutes additional stirring, the mixture was treated a solution of 19.7 g of ILi the product mixture of the preceding step in 35 mL THF. After 10 minutes additional stirring, the mixture was heated at reflux for 3 hr., cooled, and evaporated in vacuo. The residue was transferred to a separatory funnel with a total of 450 mL of methanol-water (1:1), and he 2 phase mixture was extracted with hexane (7×225 mL). The combined extracts were washed with 20 mL of methanol-water (1:1), then brine; dried over anhydrous Na$_2$SO$_4$, filtered, and the filtrate evaporated in vacuo. The residue was taken up in 400 mL hexane, suction-filtered through a pad of 30 g silica gel, and the silica pad was eluted with an additional 210 mL of EtOAc-hexane (1:9). The combined filtrates were evaporated in vacuo to leave 12.8 g (69%) of the title compound ILj as a gum mixture of 2 epimers, contaminated with a small amount of diisopropylhydrazinedicarboxylate, but suitable for the subsequent reactions.

The pure S-epimer of the preceding step was treated in the same fashion to afford the pure S-epimer of the title compound: H$^1$NMR (CDCl$_3$) δ 4.21 and 4.09 (s+s, 1), 3.75 (s, 3), 3.65 (m, 1), 3.41 (m, 1), 1.44 and 1.39 (s+s, 9), 1.38 (m, 2), 1.03 (s, 3), 0.98 and 0.97 (s+s, 3). Elemental analysis, theory C, 62.43; H, 8.61; N, 5.20; found C, 61.82; H, 8.67; N, 5.15.

The R-epimer of the preceding step was treated in the same fashion to afford the R-epimer of the title compound: H$^1$NMR (CDCl$_3$) δ 4.49 and 4.30 (d+d, 1), 3.62 (s, 3), 3.59 (m, 1), 3.42 (m, 1), 1.65 (m, 1), 1.45 and 1.39 (s+s, 9), 1.36 (m, 1), 1.10 (s, 3), 0.99 (s, 3).

Step 10.

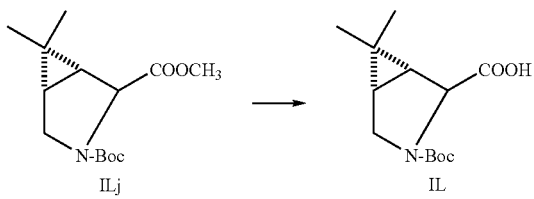

A solution of 14.5 g of the product mixture ILj of the preceding step and 270 mL 1,4-dioxane was treated with 135 mL of 1 M aqueous LiOH, and the mixture was heated at 80° C. for 4 hr. The mixture was cooled, concentrated in vacuo to half volume, diluted with 200 mL water, and extracted with hexane. The aqueous layer was chilled and treated with a solution of 9 ml of 12N HCl in 50 mL of 10% aqueous $KH_2PO_4$, and then extracted with EtOAc. The extract washed with brine, dried over anhydrous $Na_2SO_4$, filtered, and the filtrate evaporated in vacuo to leave the title compound IL as 10.8 g (78%) gum, >90% chemically and diasteriomerically pure by PMR, and suitable for subsequent synthesis: $H^1$NMR ($CDCl_3$) δ 4.20 and 4.11 (s+s, 1), 3.62 (m, 1), 3.44 (m, 1), 1.68 and 1.45 (d+unk, 1), 1.46 and 1.40 (s+s, 9), 1.45 (m buried under 1.46, 1), 1.07 (s+s, =2 Hz, 3), 0.99 and 0.95 (s+s, 3).

A number of inhibitors described in table-6 using the intermediates IL were synthesized following the procedures outlined for preparative examples XXIII, XXIV, XXVIII, XXIX, and XXXX

EXAMPLE L

Preparation of Intermediate of Formula L

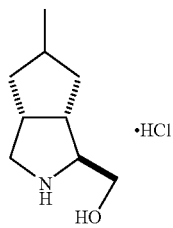

Step 1

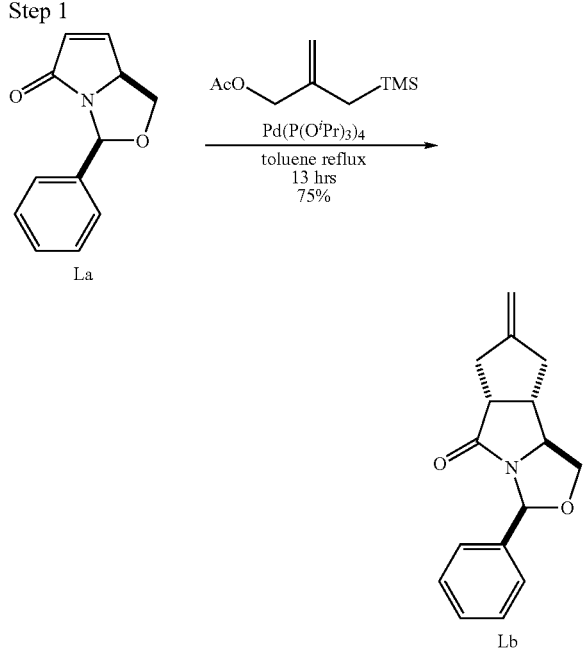

To a mixture of La (10.0 g, 50.0 mmole), 2-[(trimethylsilyl)methyl]-2-propanen-1-yl acetate (22.0 g, 118 mmole) and triisopropyl phosphite (18.6 g, 89.2 mmole) in toluene (50 ml) was added palladium (II) acetate (2.5 g, 11 mmole) with stirring at room temperature under an Ar atmosphere. It was heated to 120° C. (oil bath) for thirteen hours. Cooling down to room temperature followed by flash chromatography ($CH_2Cl_2$: Hexane=4:1) provided 9.55 gram of Lb (75%). [ ]$^{25}$=+132° ($CHCl_3$). HRMS (FAB) Calcd for $C_{16}H_{18}NO_2$ ($MH^+$): 256.1338; found: 256.1340.

Step 2

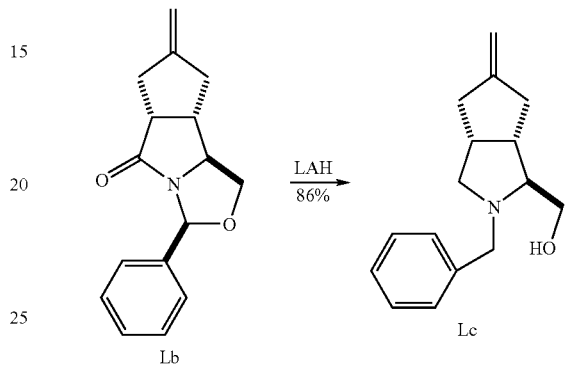

To a solution of Lb (2 g, 7.8 mmol) in anhydrous THF (50 ml) was added LAH (1.13 g, 28.9 mmol) in small portions at 0° C. The mixture then refluxed for six hours before cooled to 0° C. To the reaction were carefully added 2 ml of $H_2O$, 2 ml of 15% NaOH and 6 ml of $H_2O$. The solid was removed by filtration and the concentrated filtrate was chromatographed (2% MeOH in $CH_2Cl_2$) to give 1.33 gram of Lc (70%). HRMS (FAB) Calcd for $C_{16}H_{22}NO$ ($MH^+$): 244.1701; found: 244.1697.

Step 3

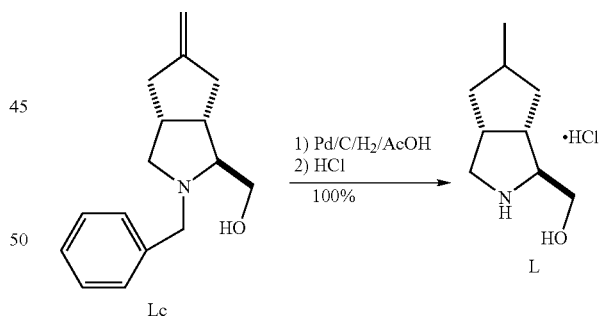

A mixture of compound Lc (1.33 g, 5.46 mmol) and 10% Pd on carbon (1.3 gram) in acetic acid (20 ml) was hydrogenated under 60 psi for three days. The catalyst was filtered off and the filtrate was concentrated in vacuum. The residue was dissolved in 20 ml of 4N HCl in dioxane and the solution was evaporated to dryness. Compound L was obtained in 1.04 gram (100%) as a 1:1 mixture of two epimers. HRMS (FAB) Calcd for $C_9H_{18}NO$ ($MH^+$): 156.1388; found: 156.1390. A number of inhibitors described in table-6 using the intermediates L were synthesized following the procedures outlined for preparative examples XXIII, XXIV, XXVIII, XXIX, and XXXX

EXAMPLE LI

Preparation of Intermediate of Formula LI

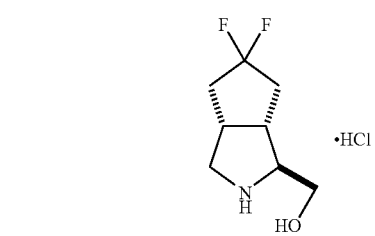

Step 1

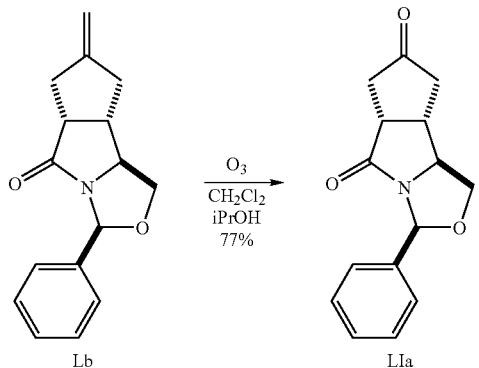

Compound Lb (2.6 g, 10.2 mmol) in a mixture of $CH_2Cl_2$ (30 ml) and $^i$PrOH (10 ml) was ozonized at −78° C. until a bluish color persisted (Ca. 40 minutes). Dimethyl sulfide (10 ml) was added and the solution was stirred at room temperature over night. The solvent was removed in vacuum and the residue was partitioned between water and EtOAc. The organic phase washed with brine, dried over $Na_2SO_4$ and concentrated. Flash chromatography (2% MeOH in $CH_2Cl_2$) provided 2.32 gram of LIa (77%). MS (MH+, FAB)=257.

Step 2

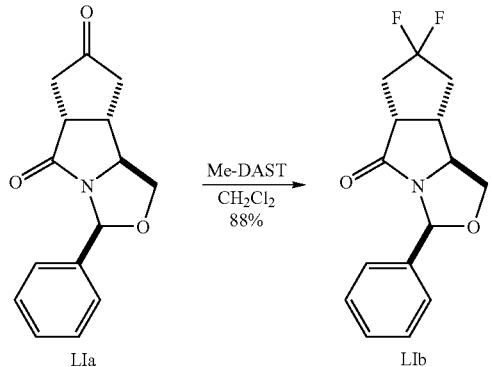

To a solution of LIa (0.86 g, 3.35 mmol) in dry $CH_2Cl_2$ (30 ml) was added dimethylaminosulfur trifluoride (methyl DAST, 2.23 g, 16.8 mmol) at room temperature. The solution was stirred at room temperature for two days. It was carefully added to a mixture of ice and saturated $NaHCO_3$ and extracted with EtOAc. The EtOAc solution washed with brine, dried over $Na_2SO_4$ and concentrated. The residue was chromatographed (0.8% of MeOH in $CH_2Cl_2$) to give LIb (0.82 g, 88%). HRMS (FAB) Calcd for $C_{15}H_{16}NO_2F_2$ (MH+): 280.1149; found: 280.1152.

Step 3

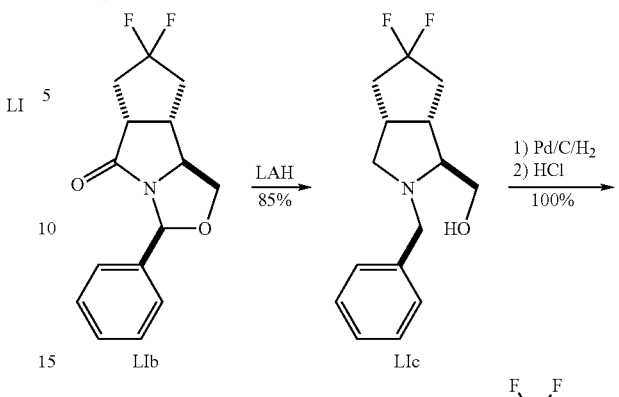

By following the same procedures as described for the preparation of L from Lb through L 0.44 gram of LIb provided 0.31 gram of LI (92% in two steps). HRMS (FAB) Calcd for $C_8H_{14}NOF_2$ (MH+): 178.1043; found: 178.1042.

A number of inhibitors described in table-6 using the intermediates LI were synthesized following the procedures outlined for preparative examples XXIII, XXIV, XXVIII, XXIX, and XXXX

EXAMPLE LII

Preparation of Intermediate of Formula LII

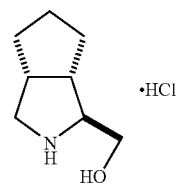

Step 1

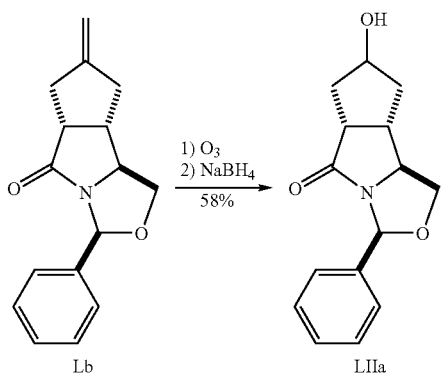

Compound Lb (3.74 g, 14.7 mmol) in $CH_2Cl_2$ (30 ml) was ozonized at −78° C. until a bluish color persisted (Ca. 60 minutes). It was purged with $N_2$ for 5 min, and was added to a cold solution of $NaBH_4$ (4.44 g, 117 mmol) in 50 ml of EtOH/H$_2$O (1:1). It was stirred for 12 hrs at RT then extracted twice with EtOAc. The combined organic layer washed with brine, dried over Na$_2$SO$_4$ and concentrated. The residue was chromatographed (2% MeOH in CH$_2$Cl$_2$) to give LIIa (2.19 g, 58%). HRMS (FAB) Calcd for C$_{15}$H$_{18}$NO$_3$ (MH+): 260.1287; found: 260.1283.

Step 2

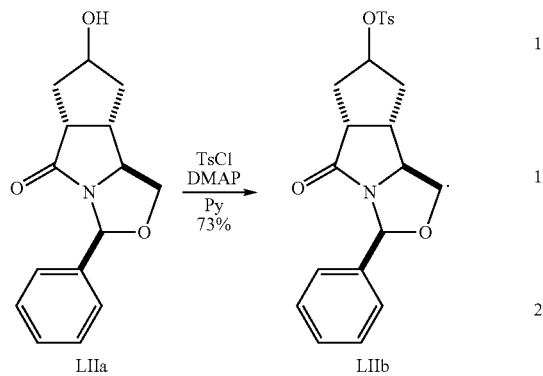

To a solution of LIIa (2.18 g, 8.40 mmol) in dry pyridine (50 ml) were added toluenesulfonyl chloride (3.2 g, 16.8 mmol) and N,N-dimethylaminopyridine (1.03 g, 8.40 mmol). It was stirred at RT for 3 days and concentrated in vacuum. The residue was partitioned between 3% citric acid and EtOAc. The organic layer was washed with 3% citric acid again, followed by brine. After removing the solvent the residue was chromatographed to provide LIIb (2.54 g, 73%). HRMS (FAB) Calcd for C$_{22}$H$_{24}$SNO$_5$ (MH$^+$): 414.1375; found: 414.1378.

Step 3

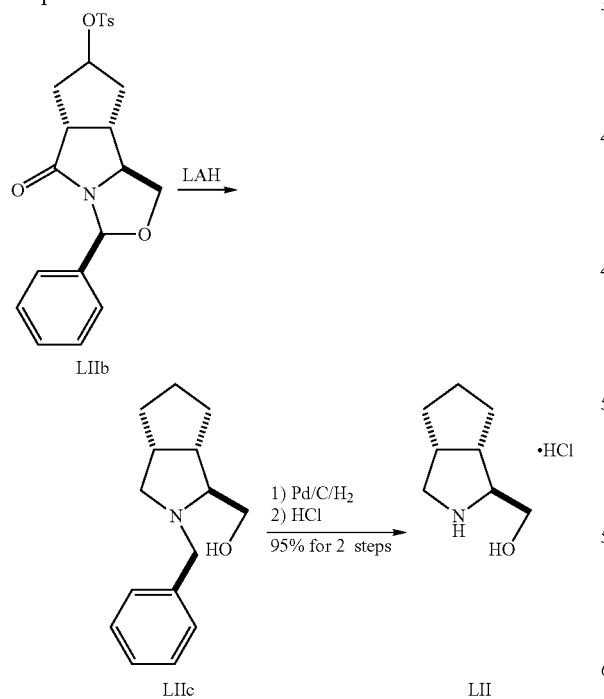

By following the same procedures as described for the preparation of L from Lb through L, 2.53 gram of LIIb provided 1.03 gram of LII (95% in two steps). HRMS (FAB) Calcd for C$_8$H$_{16}$NO (MH$^+$): 142.1232; found: 142.1233.

A number of inhibitors described in table-6 using the intermediates LII were synthesized following the procedures outlined for preparative examples XXIII, XXIV, XXVIII, XXIX, and XXXX

EXAMPLE LIII

Preparation of Intermediate of Formula LIII

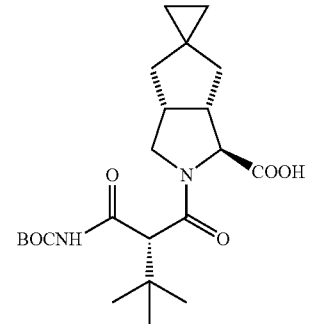

Step 1

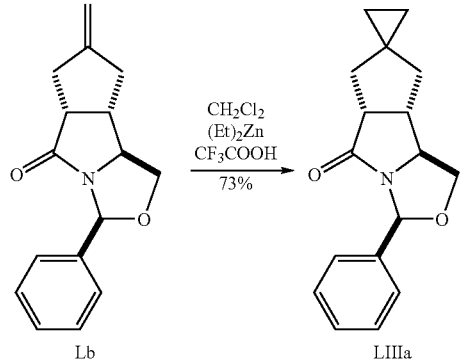

To 7.84 mmol of diethyl zinc (1 N in hexane) in dry CH$_2$Cl$_2$ (30 ml) was added trifluoroacetic acid (0.893 g, 7.84 mmol) dropwise at 0° C. Upon stirring for an additional 20 min diiodomethane (2.10 g, 7.84 mmol) was added, followed by Lb (1 g, 3.92 mmol) in 5 ml of CH$_2$Cl$_2$ in 20 min. The ice bath was removed and the mixture was stirred at RT for 14 hours. The reaction was quenched by saturated NH$_4$Cl and extracted with EtOAc. The EtOAc solution washed with saturated Na$_2$SO$_4$, followed by brine and concentrated in vacuum. The residue was chromatographed to provide LIIIa (4.61 g, 73%). HRMS (FAB) Calcd for C$_{17}$H$_{20}$NO$_2$ (MH$^+$): 270.1494; found: 270.1497.

Step 2

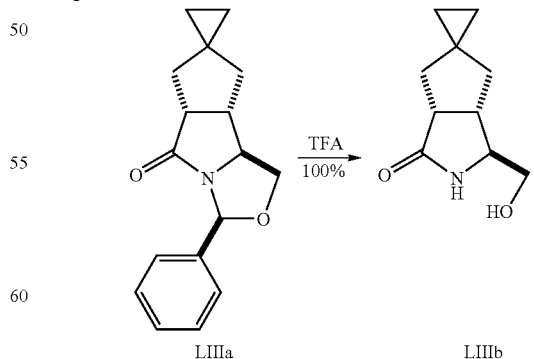

Trifluoroacetic acid (TFA, 10 ml) was added to a solution of LIIIa (4.6 g, 17.1 mmol) in THF (20 ml) and H$_2$O (20 ml) at RT. After stirring overnight the solvents were removed in vacuum. The residue was partitioned between saturated NaHCO$_3$ and EtOAc. The aqueous phase was back extracted with EtOAc five times. The combined organic phase was dried over Na$_2$SO$_4$ and concentrated. The residue was chromatographed to give LIIIb (3.1 g, 100%). HRMS (FAB) Calcd for C$_{10}$H$_{16}$NO$_2$ (MH$^+$): 182.1181; found: 180.1182.

Step 3

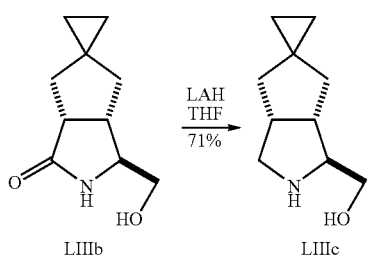

LAH (1.76 g, 46.3 mmol) was added to LIIIb in dry THF (50 ml) in small portions at 0° C. The mixture then refluxed for six hours before cooled to 0° C. To the reaction were carefully added 2 ml of H$_2$O, 2 ml of 15% NaOH and 6 ml of H$_2$O. The solid was removed by filtration and the concentrated filtrate was chromatographed (30% MeOH in CH$_2$Cl$_2$ with 1% NH$_4$OH) to give 0.39 gram of LIIIc (71%). HRMS (FAB) Calcd for C$_{10}$H$_{18}$NO (MH+): 168.1388; found: 168.1389.

Step 4

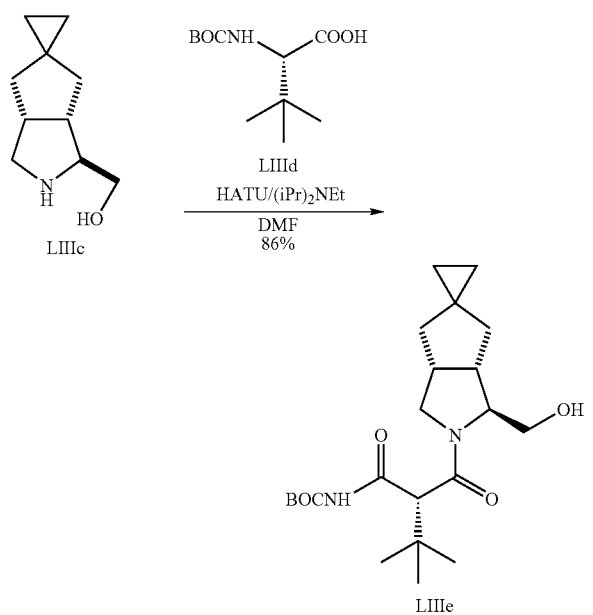

To a mixture of LIIIc (0.5 g, 2.99 mmol), LIIId (0.69 g, 2.99 mmol) and HATU (1.14 g, 3 mmol) in dry DMF (20 ml) was added N,N-diisopropylethylamine (1 ml, 5.89 mmol)) at 0° C. It was stirred at RT for 3 hrs. The reaction mixture was partitioned between H$_2$O and EtOAc. The organic layer was successively washed with 3% citric acid, saturated NaHSO$_4$ and brine, dried over Na$_2$SO$_4$ and concentrated. The product LIIIe (0.978 g, 86%) thus obtained was sufficiently pure for the next step. HRMS (FAB) Calcd for C$_{21}$H$_{37}$N$_2$O$_4$ (MH+): 381.2910; found: 381.2749.

Step 5

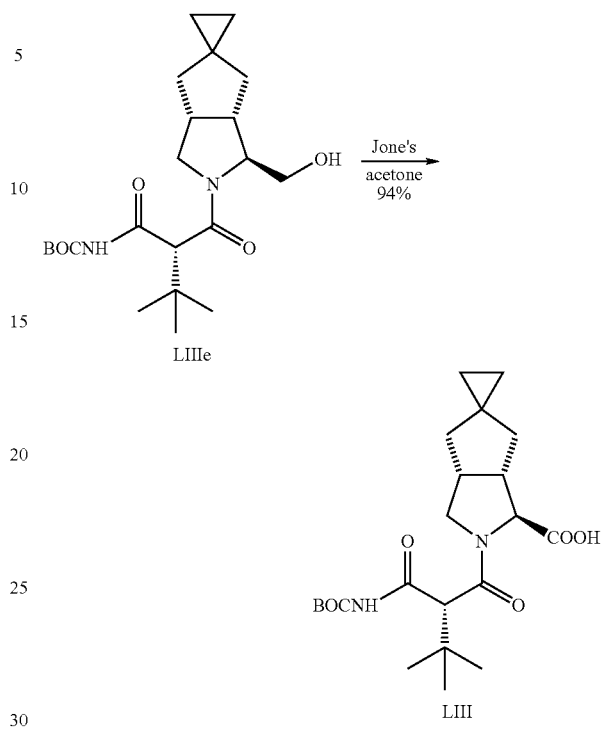

To a solution of LIIIe (0.49 g, 1.29 mmol) in acetone (20 ml) was added Jone's reagent (2 ml of 2.5 M solution, 5 mmol) at 0° C. It was stirred at 0° C. for 20 min, then at RT for 30 hrs. To this mixture were successively added EtOAc (50 ml), anhydrous Na$_2$SO$_4$ (3 g), celite (2 g) and $^i$PrOH (1 ml). It was stirred vigorously for 20 min. The solid was filtered off. The filtrate washed with 3% citric acid, dried over Na$_2$SO$_4$ and concentrated in vacuum. The residue was chromatographed (3% MeOH in CH$_2$Cl$_2$, 0.5% acetic acid) to provide LIII (0.48 g, 94%). HRMS (FAB) Calcd for C$_{21}$H$_{35}$N$_2$O$_5$ (MH$^+$): 395.2546; found: 395.2543.

A number of inhibitors described in table-6 using the intermediates LIII were synthesized following the procedures outlined for preparative examples XXIII, XXIV, XXVIII, XXIX, and XXXX

EXAMPLE LIV

Preparation of Intermediate of Formula LIV

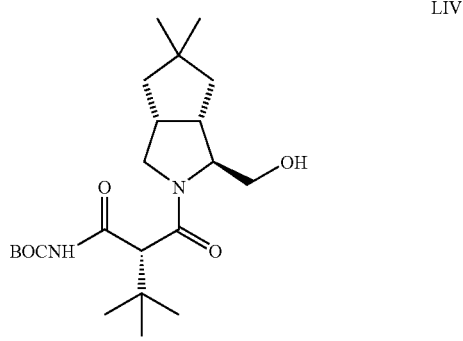

Step 1

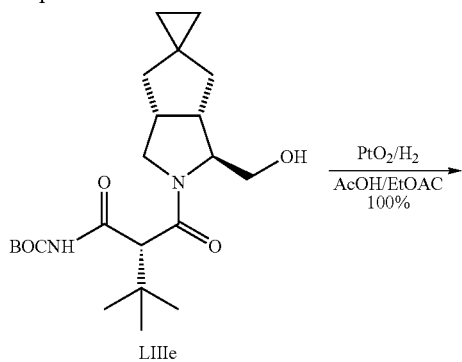

Compound LIIIe (0.41 g, 1.08 mmol) in a mixture of solvent of AcOH (10 ml) and EtOAc (20 ml) containing PtO$_2$ (1 g) was hydrogenated under 1 atm of H$_2$ for 3 hrs. The catalyst was removed by filtration and the filtrate was concentrated in vacuum to provide LIV (0.41 g, 100%). HRMS (FAB) Calcd for C$_{21}$H$_{39}$N$_2$O$_5$ (MH$^+$): 383.2910; found: 383.2906.

A number of inhibitors described in table-6 using the intermediates LIV were synthesized following the procedures outlined for preparative examples XXIII, XXIV, XXVIII, XXIX, and XXXX

EXAMPLE LV

Preparation of Intermediate of Formula LV

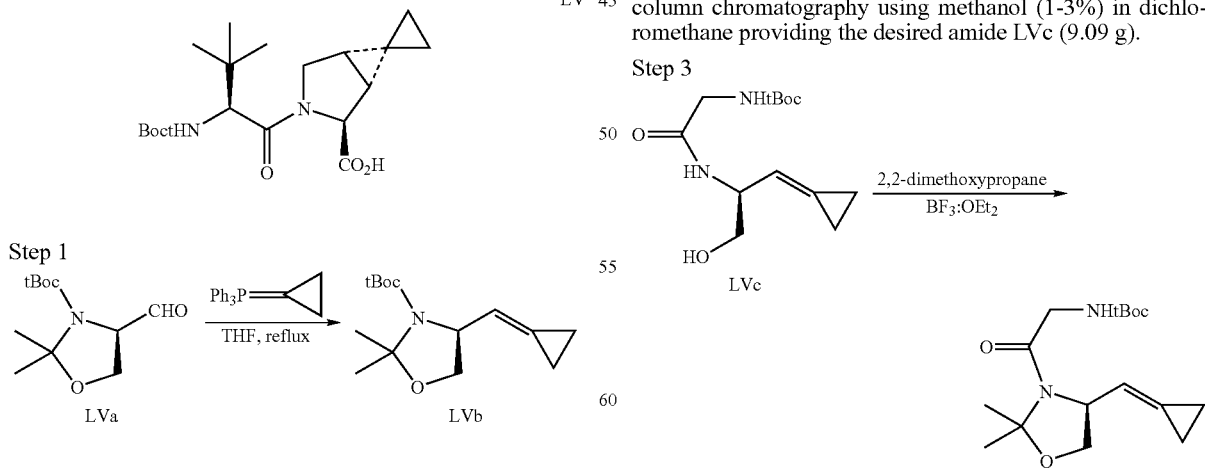

Step 1

Potassium bis(trimethylsilyl)amide (158 ml of a 0.5M solution in toluene; 79 mmol) was added to a stirred suspension of cyclopropyltriphenylphosphonium bromide (33.12 g; 86.4 mmol) in anhydrous tetrahydrofuran (130 ml) and the resulting orange mixture was stirred under an atmosphere of nitrogen at room temperature for a period of 1 h., before the addition of the aldehyde LVa (9.68 g; 42.2 mmol) in THF (8 ml). The reaction was then refluxed under an atmosphere of nitrogen for a period of 2 h. After cooling, methanol, diethyl ether and Rochelles salt were added. The organic phase was separated, washed with brine, dried and concentrated under reduced pressure. The crude reaction product was purified by silica gel column chromatography using EtOAc-hexane (1:99) to EtOAc-hexane (5:95) to provide the alkene LVb (8.47 g) as a yellow oil.

Step 2

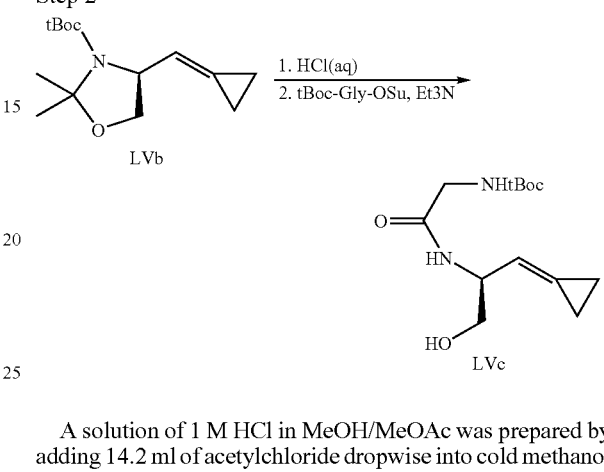

A solution of 1 M HCl in MeOH/MeOAc was prepared by adding 14.2 ml of acetylchloride dropwise into cold methanol and diluting the resulting solution to 200 ml at room temperature.

The carbamate LVb (9.49 g; 37.5 mmol) was dissolved in methanol (12 ml) and added to 1 M HCl in MeOH/MeOAc (150 ml) while cooled in an ice bath. The resulting mixture was maintained at this temperature for 1 h., then the ice bath was removed and stirring continued overnight at room temperature. The volatiles were removed under reduced pressure to yield a yellow oil which was used in the next step without purification.

The yellow oil is dissolved in a mixture of THF (30 ml) and MeOH (20 ml) and treated with triethylamine (15 ml; 108 mmol) until the solution was pH=9-10. After placing in an ice bath, the mixture was treated with N-Boc-Gly-OSu (11.22 g; 41 mmol). The icebath was withdrawn and the reaction stirred at room temp. for 1 h. The volatiles were removed under reduced pressure and the residue was purified by silica gel column chromatography using methanol (1-3%) in dichloromethane providing the desired amide LVc (9.09 g).

Step 3

The alcohol LVc (9.09 g; 33.6 mmol) was dissolved in acetone (118.5 ml) and treated with 2,2-dimethoxypropane (37.4 ml; 304 mmol) and BF$_3$:Et$_2$O (0.32 ml; 2.6 mmol) and the resulting mixture was stirred at room temperature for a period of 5.5 h The reaction solution was treated with a few drops of triethylamine and the volatiles were removed under reduced pressure. The residue was purified by silica gel column chromatography using 5-25% EtOAc in hexanes to provide the N,O-acetal LVd (8.85 g).

Step 4

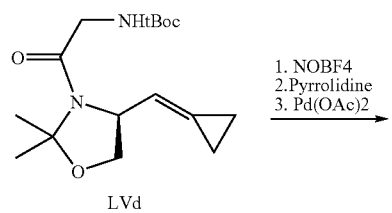

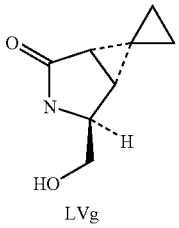

The carbamate LVd (8.81 g; 28.4 mmol) was dissolved in acetonitrile (45 ml) and the solution was cooled to −40 C under an atmosphere of nitrogen. Pyridine (6.9 ml; 85.3 mmol) followed by nitrosium tetrafluoroborate (6.63 g; 56.8 mmol) were added and the resulting reaction mixture maintained below 0 C until TLC indicated that no starting material remained (approx. 2.25 h.). Pyrrolidine (20 ml; 240 mmol) was added and the cooling bath was withdrawn and stirring was continued at room temperature for 1 h. and then the volatiles were removed under reduced pressure. The residue was quickly passed through a pad of silica gel to provide a yellow oil.

The yellow oil was dissolved in anhydrous benzene (220 ml) and palladium acetate (0.317 g; 1.41 mmol) was added before heating the resulting mixture to reflux, under an atmosphere of nitrogen for a period of 1.5 h. After cooling, the volatiles were removed under reduced pressure and the dark residue was purified by silica gel column chromatography using EtOAc-hexane (1:4) to provide the I) the trans-pyrrolidinone LVe (1.94 g) followed by ii) the cis-pyrrolidinone LVf (1.97 g).

Step 5

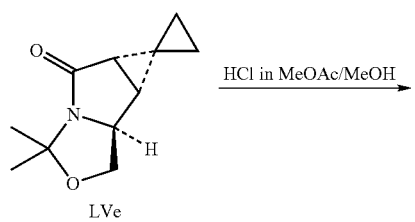

Freshly prepared 1 M HCl in MeOAc/MeOH (10 ml; as described above) was added to the N,O-acetal LVe and stirred at room temperature for 1 h. The solvent was removed under reduced pressure and the residue was purified by silica gel column chromatography using 0-4% MeOH in dichloromethane as eluent to provide the desired alcohol LVg (1.42 g), a yellow oil.

Step 6

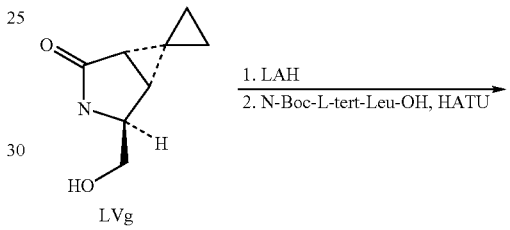

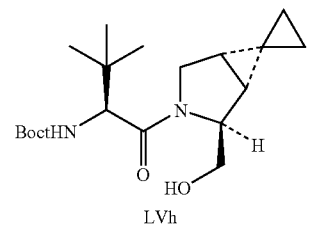

To a solution of the lactam LVg (1.29 g; 8.44 mmol) in anhydrous tetrahydrofuran (55 ml) was added lithium aluminum hydride (2.40 g; 63.2 mmol) and the resulting mixture was refluxed for 8 h. After cooling, water, followed by 15% aq. NaOH were added and the resulting mixture was filtered through celite and the solid was washed thoroughly with THF and MeOH. The solvent was removed under reduced pressure and the residue redissolved in dichloromethane, dried and concentrated under reduced pressure to provide the pyrrolidine, used without purification.

Hunigs base (4.5 ml; 25.8 mmol) was added to a mixture of N-Boc-L-tert-Leu-OH (1.76 g; 7.6 mmol), The crude pyrrolidine and HATU (2.89 g; 7.6 mmol) in anhydrous dichloromethane (50 ml) at −60 C, under an atmosphere of nitrogen. The resulting reaction was allowed to come to room temperature slowly, overnight. EtOAc was added and the yellow solution washed with dil.aq. HCl, sat. aq. sodium bicarbonate, water, brine. The organic layer was dried and concentrated under reduced pressure. The residue was purified by silica gel column chromatography using EtOAc:hexanes (1:3) to give the desired amide LVh (2.00 g).

Step 7

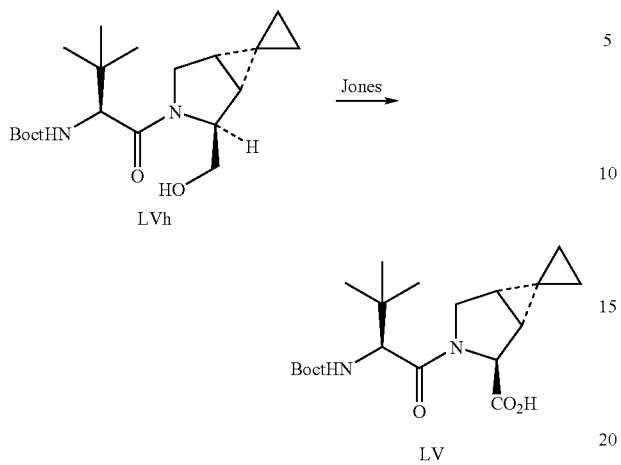

The alcohol LVh (2.00 g; 5.67 mmol) was dissolved in acetone (116 ml) and cooled in an ice bath for 10 min. This solution was then added to a cooled Jones reagent (14.2 ml; approx 2 mmol/ml) and the resulting mixture was stirred at 5 C for 0.5 h and the cooling bath was removed. The reaction was stirred for a further 2 h. at room temp., before adding to sodium sulfate (28.54 g), celite (15 g) in EtOAc (100 ml). Isopropanol (15 ml) was added after 1 min and then stirred for a further 10 min. and filtered. The filtrate was concentrated under reduced pressure, providing a brown oil which was dissolved in EtOAc. This solution washed with water, 3% aq. citric acid, brine, dried and concentrated to provide the desired carboxylic acid LV (1.64 g) as a white solid.

NOTE: Alternatively XXIVc-acid, XXVIg-acid, XXVIIc, could be synthesized following the procedure mentioned above in good yields. A number of inhibitors described in table6 using the intermediates LV were synthesized following the procedures outlined for preparative examples XXIII, XXIV, XXVIII, XXIX, and XXXX

EXAMPLE LVI

Preparation of Intermediate of Formula LVI

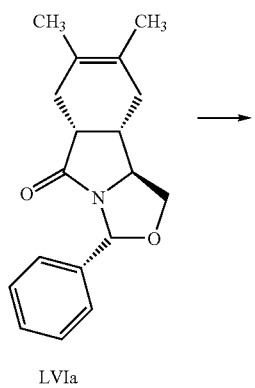

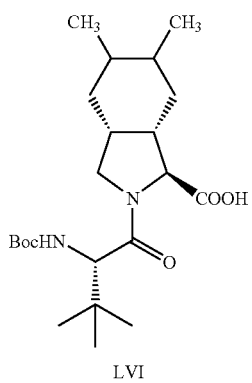

The synthesis of LVIa was accomplished following the procedure reported in Bailey, J, H.; Chemy, D, T.; Crapnell, K, M.; Moloney, M. G.; Shim, S. B.; Bamford, M. J.; Lamont, R. B. Tetrahedron (1997), 53, 11731. This was converted to LVI similar to the procedure for LIII (Step 2 to Step 5)

A number of inhibitors described in table-6 using the intermediates LVI were synthesized following the procedures outlined for preparative examples XXIII, XXIV, XXVIII, XXIX, and XXXX

EXAMPLE LVII

Preparation of Intermediate of Formula LVII

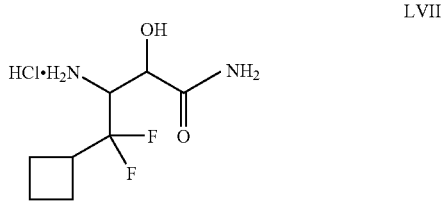

Step 1

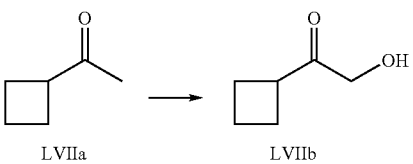

To the stirred solution of TFA (22.6 mL, 305 mmol), water (120 mL) and [bis(trifluoroacetoxy)iodo]benzene (131 g, 305 mmol) in acetonitrile (600 mL) was added cyclobutyl methyl ketone LVIIa (15.0 g, 153 mmol). The resulting solution was heated to reflux and stirred for 4 h. Acetonitrile was removed in vacuo. Water (120 mL) was added and the mixture was extracted with diethyl ether (2×500 mL). The combined organic solution was dried (MgSO$_4$), filtered and concentrated in vacuo. The crude product was purified by flash chromatography with 30% Et$_2$O/hexane to give 8.82 g of LVIIb (51%).

Step 2

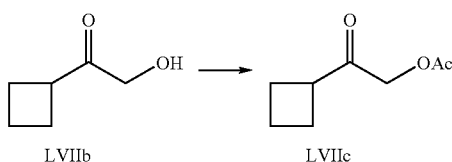

To the solution of LVIIb (1.4 g, 12.3 mmol), acetic anhydride (1.3 mL, 13.5 mmol) and triethyl amine (3.4 mL, 24.5 mmol) in $CH_2Cl_2$ (50 mL) was added DMAP (0.67 g, 5.5 mmol). The reaction mixture was stirred at rt for 4 h before 5% $H_3PO_4$ (50 mL) was added. After layers were separated, the aqueous layer was extracted with $CH_2Cl_2$ (2×50 mL). Combined organic solution was dried ($MgSO_4$), filtered and concentrated in vacuo to 2.0 g crude product LVIIc.

Step 3

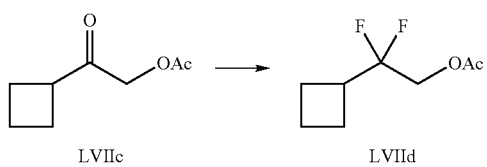

The mixture of LVIIc (1.9 g, 12.2 mmol) and DAST (Di-ethyl amino sulfur trifluoride, 3.0 mL, 22.3 mmol) was heated to 50 C and stirred for 2 h. The mixture was then slowly poured into ice water (50 mL), and extracted with diethyl ether (3×50 mL). The combined organic solution was dried ($MgSO_4$), filtered and concentrated in vacuo. The crude product was purified by flash chromatography with 1040% $Et_2O$/hexane to give 0.62 g of LVIId (29%) and 0.68 g starting material LVIIc.

Step 4

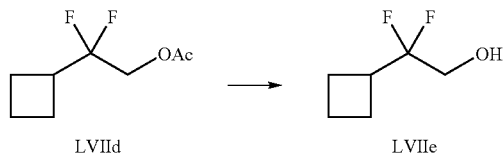

The mixture of LVIIId (3.10 g, 17.4 mmol) and lithium hydroxide (0.84 g, 34.8 mmol) in water (10 mL) was vigorously stirred at rt for 6 h before it was diluted with water (50 mL) and extracted with diethyl ether (3×60 mL). The combined organic solution was dried ($MgSO_4$), filtered and carefully concentrated in vacuo to is give LVIIe 2.68 g crude product.

Step 5

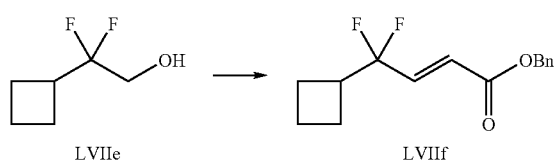

The solution of compound LVIIe and Dess-Martin reagent in $CH_2Cl_2$ was stirred at rt for 1 h before $Ph_3P$=$CHCO_2Bn$ was added and stirring was continued for another 20 h. Diethyl ether was added followed by saturated $NaS_2O_3$ and saturated $NaHCO_3$ solutions. After stirred for 15 min, the layers were separated. The organic solution washed with saturated $NaHCO_3$ and brine, dried ($MgSO_4$), filtered and concentrated in vacuo. The crude product was purified by flash chromatography to give the desired product LVIIf.

Step 6

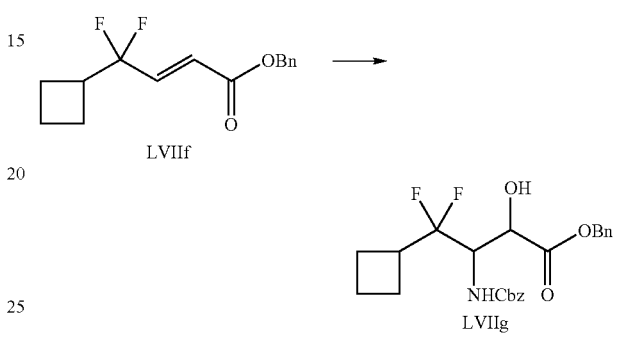

Compound LVIIg was prepared as described above (Step 4, Example XXXXIII) with appropriate amounts of reagents.

Step 7

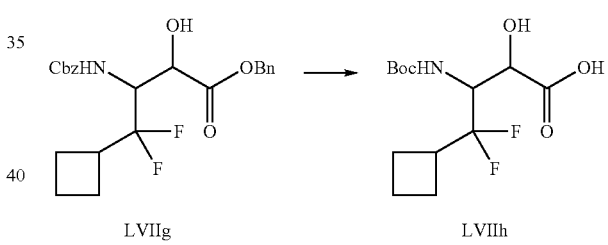

Catalytic hydrogenation of LVIIg over 10% Pd/C in MeOH followed by treatment with $Boc_2O$ in $NaHCO_3$/THF/water will afford LVIIh.

Step 8

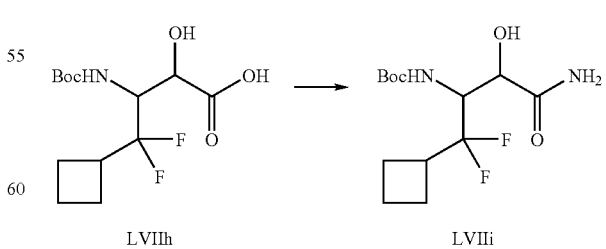

Conversion of LVIIh to compound LVIII will follow previously described procedures (Step 5, Example XXVIII).

Step 9

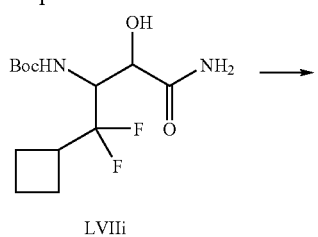

LVIIi

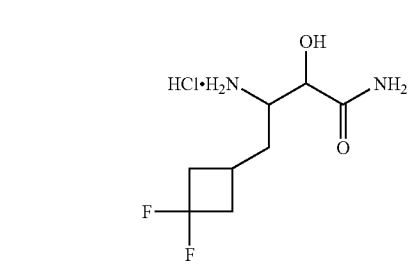

LVII

Conversion of LVIIi to compound LVII follows previously described procedures (Step 9, Example XXIII).

A number of inhibitors described in table-6 using the intermediates LVII were synthesized following the procedures outlined for preparative examples XXIII, XXIV, XXVIII, XXIX, and XXXX

EXAMPLE LVIII

Preparation of Intermediate of Formula LVIII

LVIII

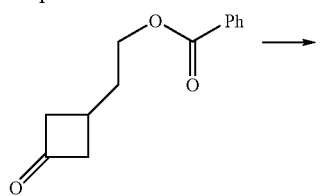

Step 1

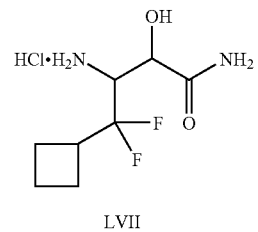

LVIIIa

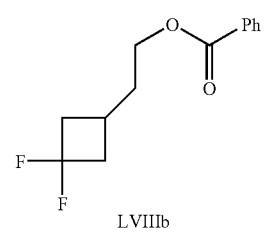

LVIIIb

To a solution of compound LVIIIa [for preparation of LVIIIa see J. Ramnauth and E. Lee-Ruff, *Can. J. Chem.*, 2001, 79, 114-120] (3 g) in dichloromethane (75 mL) was added DAST (Diethyl amino sulfur trifluoride, 9.1 mL) slowly and the reaction was stirred at room temperature overnight. The mixture was slowly poured into ice/saturated sodium bicarbonate solution (100/200 mL) with stirring. Added. 200 mL of dichloromethane and the organic layer was separated and washed with cold saturated sodium bicarbonate solution, brine, dried ($Na_2SO_4$) and concentrated. Purification by column chromatography (5/95 EtOAc/hexanes) afforded 2.59 g of LVIIIb.

Step 2

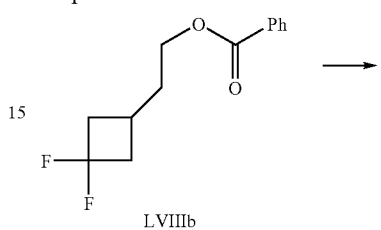

LVIIIb

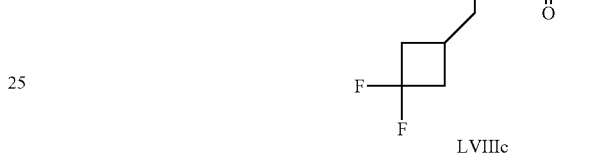

LVIIIc

Compound LVIIIb (3.42 g) was dissolved in THF/MeOH (1/1, 50 mL). To this was added a solution of potassium carbonate (1.97 g) in water (25 mL). The reaction mixture was stirred at room temperature for 4 hrs and then stored in the freezer (−10° C.) overnight. The reaction mixture was warmed to room temperature over 3 hrs when TLC indicated complete consumption of LVIIIb. Brine (100 mL) was added to the reaction mixture and was extracted with ethyl ether (3×100 mL). The ether layers were combined, dried ($Na_2SO_4$) and concentrated to afford a residue (2.77 g) which was processed further without purification.

The residue thus obtained was dissolved in $CH_2Cl_2$/DMSO (6/1, 140 mL). To this solution was added benzyl (triphenylphosphoranylidene)acetate (11.7 g) and then Dess-Martin's Periodinane (12.09 g, in three equal portions) carefully. The reaction mixture was stirred at room temperature for 4 hrs and quenched with cold sodium bicarbonate solution (200 mL) and diluted with $CH_2Cl_2$ (100 mL). The $CH_2Cl_2$ layer was separated and washed with 10% $Na_2S_2O_3$ solution (125 mL), $NaHCO_3$ solution (125 mL), water (125 mL), dried ($Na_2SO_4$) and concentrated. The residue was purified by column chromatography using 50/50 $CH_2Cl_2$/hexanes to afford the required compound, LVIIIc (2.25 g).

Step 3

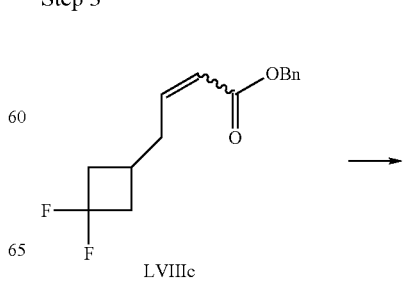

LVIIIc

-continued

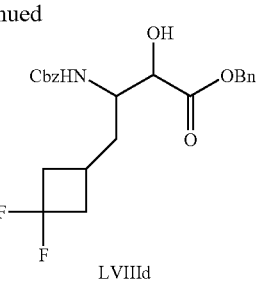
LVIIId

Compound LVIIId was prepared as described above (Step 4, Example XXXXIII) with appropriate amounts of reagents.

Step 4

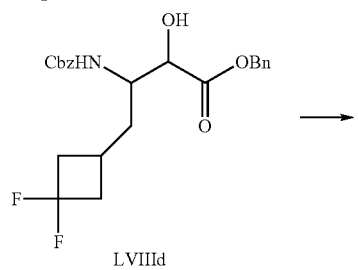
LVIIId

→

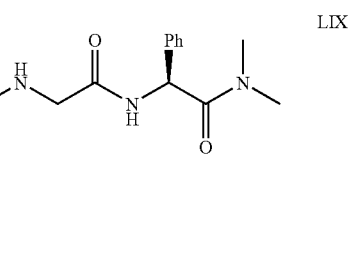
LVIIIe

Catalytic hydrogenation of LVIIId over 10% Pd/C in MeOH followed by treatment with Boc₂O in NaHCO₃/THF/water will afford LVIIIe.

Step 5

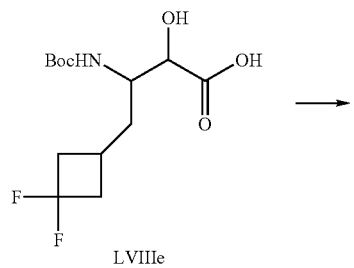
LVIIIe

→

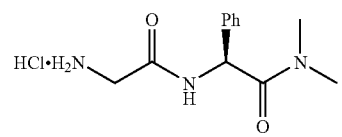
LVIIIf

Conversion of LVIIIe to compound LVIIIf will follow previously described procedures (Step 5, Example XXVIII).

Step 6

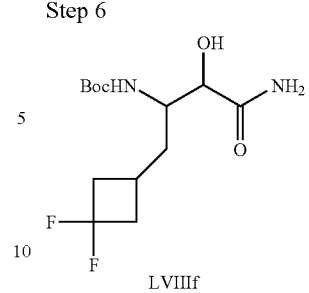
LVIIIf

→

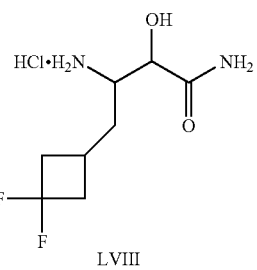
LVIII

Conversion of LVIIIF to compound LVIII will follow previously described procedures (Step 9, Example XXIII).

A number of inhibitors described in table-6 using the intermediates LVIII were synthesized following the procedures outlined for preparative examples XXIII, XXIV, XXVIII, XXIX, and XXXX

EXAMPLE LIX

Preparation of Intermediate of Formula LIX

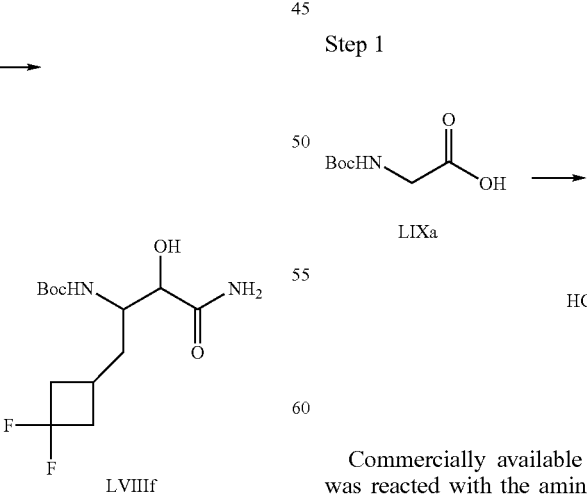

Step 1

BocHN—CH₂—C(=O)—OH

LIXa

→

HCl·H₂N—...—N(CH₃)₂

LIXb

Commercially available N-Boc protected glycine LIXa was reacted with the amine XV from Example XV in the manner previously described in Example XXI, Step 4. The resulting intermediate was then treated with HCl in the manner previously described in Example XXIII, Step 9 to afford product LIXb.

Step 2

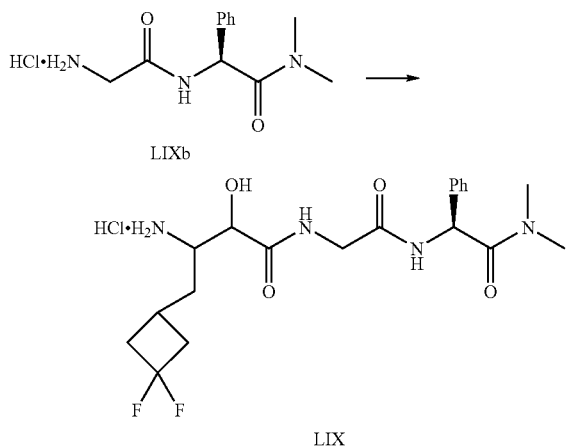

LIXb

LIX

Acid LVIIIe (from above) can be reacted with LIXb in the manner previously described in Example XXI, Step 4. The resulting intermediate can then be treated with HCl in the manner previously described in Example XXIII, Step 9 to afford product LIX.

A number of inhibitors described in table-6 using the intermediates LIX were synthesized following the procedures outlined for preparative examples XXIX, and XXXX

EXAMPLE LX

Preparation of Intermediate of Formula LX

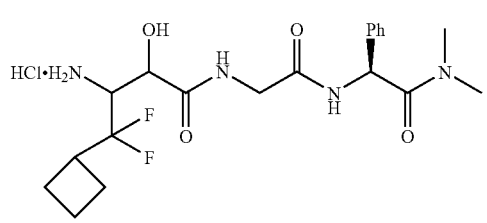

LX

Step 1

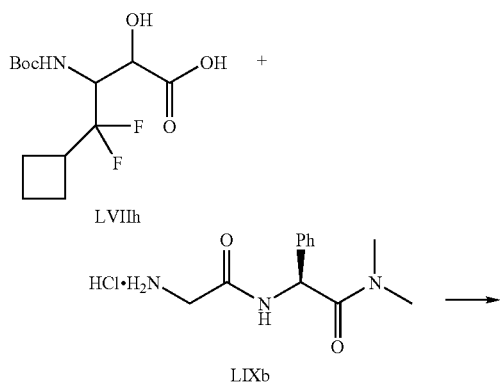

LVIIh

LIXb

-continued

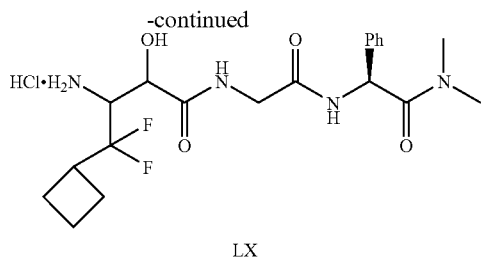

LX

Acid LVIIh (from above) was reacted with LIXb in the manner previously described in Example XXI, Step 4. The resulting intermediate was then treated with HCl in the manner previously described in Example XXIII, Step 9 to afford product LX.

A number of inhibitors described in table-6 using the intermediates LIX were synthesized following the procedures outlined for preparative examples XXIX, and XXXX

EXAMPLE LXI

Preparation of Intermediate of Formula LXI

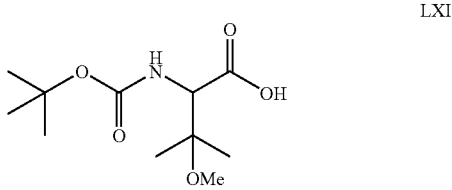

LXI

Step 1

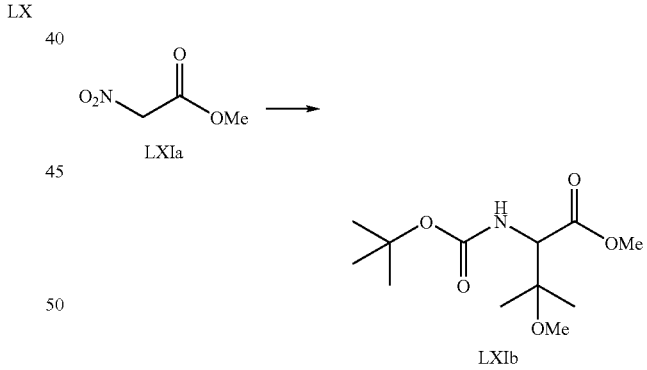

LXIa

LXIb

To a solution of methyl nitroacetate LXIa (3 g) in benzene (15 mL.) was added dimethoxy propane (6.2 mL) and acetic anhydride (4.87 mL). The mixture was refluxed overnight. The reaction mixture was concentrated; It was resubjected to the above conditions. The residue after concentration was taken in EtOAc (100 mL) and washed with cold saturated sodium bicarbonate solution (3×75 mL), brine: (100 mL), dried ($Na_2SO_4$) and concentrated.

The residue from above was taken in MeOH (150 mL). $Boc_2O$ (6 g) and 10% Pd/C (150 mg) were added and the mixture was hydrogenated using a balloon filled with hydrogen gas. After 24 hours, added some more 10% Pd/C and repeated the procedure. The reaction mixture was then filtered through celite, concentrated, and purified by column chromatography using 5/95 to 10/90 EtOAc/hexanes to afford 2.2 g of LXIb.

Step 2

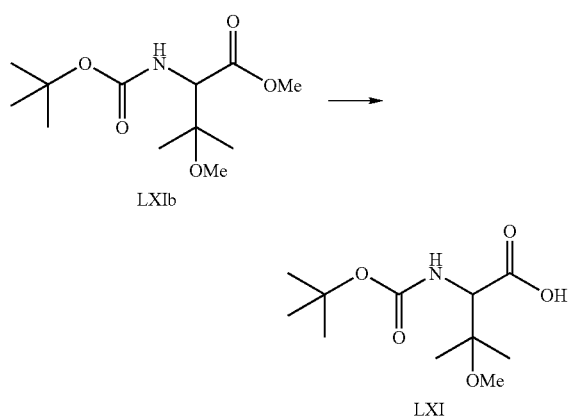

Compound LXIb was prepared from LXI in quantitative yield using procedures described above for the conversion of XXVIg to XXVIh (see Example XXVI).

A number of inhibitors described in table-6 using the intermediates LVIII were synthesized following the procedures outlined for preparative examples XXIII, XXIV, XXVIII, XXIX, and XXXX

EXAMPLE LXII

Preparation of Intermediate of Formula LXII

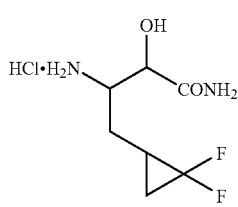

Step 1:

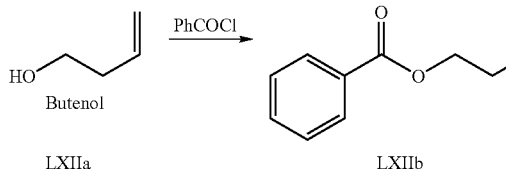

Butenol LXIIa was reacted in the manner previously described in preparative example XXXXIII step 1 to afford product LXIIb Step 2:

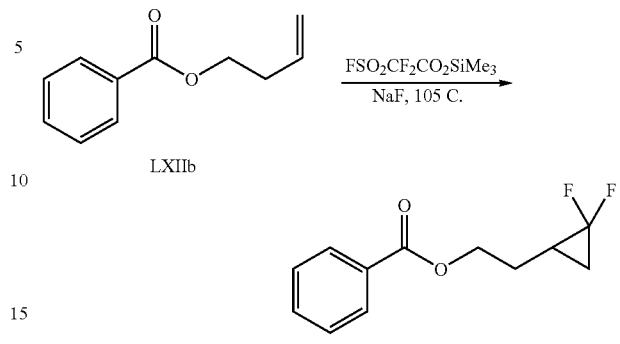

To 5.3 g (30 mmol) of LXIIb product of step 1 was added 25 mg of NaF. At 110° C., was added via syringe-pump 1.6 equiv (48 mmol, 12 g) of TMSfluorosulfonyldifluoroacetate (TFDA) in 2 h. After 2 h, reaction is cooled down to RT. Purification by flash column chromatography (3% EtOAc, Hexane, silica) furnished LXIIc, Product of step 2 (4.93 g).

Step 3:

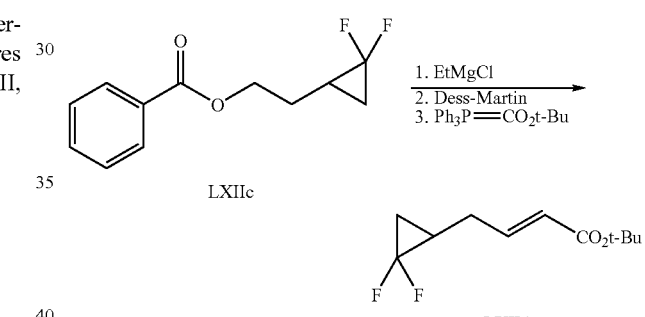

Product of step 2, LXIIc (1 g) was treated in the manner previously described in step3 of preparative XXXXIII to afford LXIId, Product of step 3 (0.89 g)

Step 4:

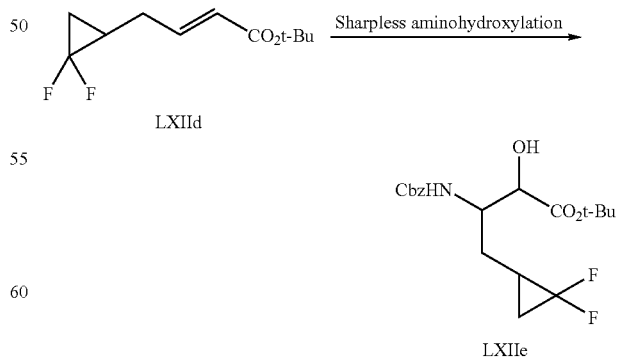

Product of step 3, LXIId (3.2 g) was treated in the manner previously described in step4 of preparative XXXXIII to afford Product LXIIe (1.4 g).

Step 5:

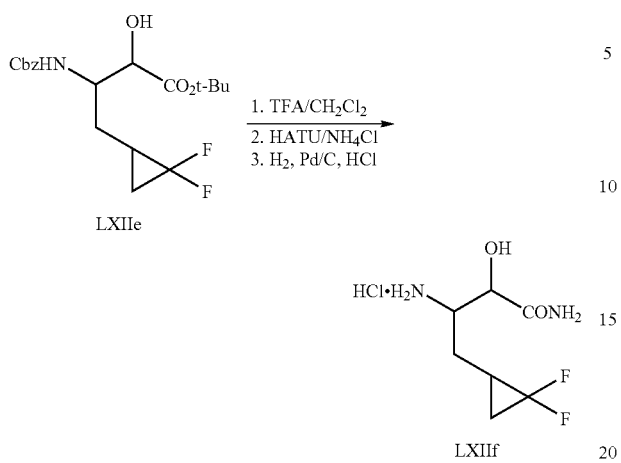

Product of step 4, LXIIe (0.54 g) was treated in the manner previously described in step5 then step6 and finally step7 of preparative example XXXXIII to afford Product LXIIf (0.24 g).

A number of inhibitors described in table-6 using the intermediate LXII were synthesized following the procedures outlined for preparative examples XXIII, XXIV, XXVIII, XXIX, and XXXX

EXAMPLE LXIII

Preparation of Intermediate of Formula LXIII

LXIII

Step 1:

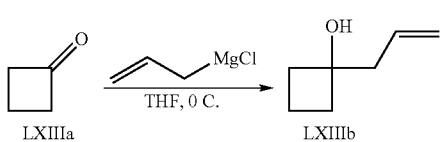

To a −78° C. solution of cyclobutanone (15 g, 214 mmol) in THF (100 mL) is added dropwise Allylmagnesiumchloride (2.0 M in THF, 1.1 equiv, 118 mL). After 1 hour, reaction is stopped by the addition of ice and HCl 1.0 N (100 mL). The mixture was diluted with ethyl acetate (~200 ml) and the organic phase was separated; washed with brine and dried over anhydrous $MgSO_4$. Concentration in-vacuo and purification by chromatography over silica gel (10% ethyl acetate in n-hexane) provided product LXIIIb (21 g).

Step 2:

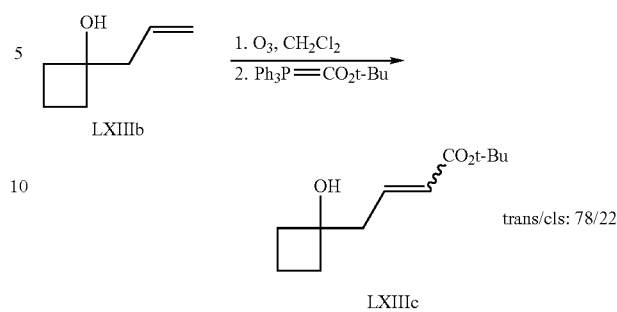

To a −78° C. solution of product of step 1, LXIIIb (11.2 g) in $CH_2Cl_2$ (200 mL) is bubbled Ozone until a persistent blue color was observed (after 1 hour). Ozone was stopped and $N_2$ was flushed into the reaction mixture for 10 minutes. $Me_2S$ (10 equiv., 7.3 mL) was added and reaction was gradually warmed-up to room temperature overnight.

After 18 hours, $Ph_3P$=$CHCOO^tBu$ (40 g) was added. Stirring was continued for ~24 hrs Evaporation under vacuum provided the crude product which was chromatographed over silica gel (10% ethyl acetate in n-hexane) to provide product LXIIIc as a mixture of isomers (6.65 g of trans isomer) and (1.9 g of cis olefin).

Step 3:

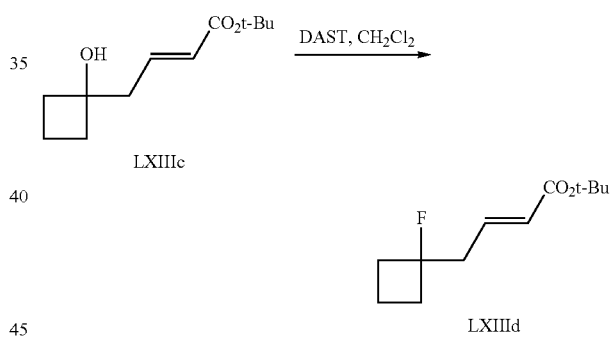

To a 0° C. solution of product of step2, LXIIIc (0.21 g) in $CH_2Cl_2$ (3 mL) is added DAST (1.1 equiv., 0.135 mL). After 15 minutes, reaction was stopped by the addition a cold saturated solution of $Na_2CO_3$ (150 ml). The mixture was diluted with ethyl acetate (~10 ml) and after stirring for ~30 min the organic phase was separated; washed with brine and dried over anhydrous $MgSO_4$. Concentration in-vacuum and purification by chromatography over silica gel (5% to 10% $CH_2Cl_2$ in n-hexane) provided LXIIId (0.1 g; 47%).

Step 4:

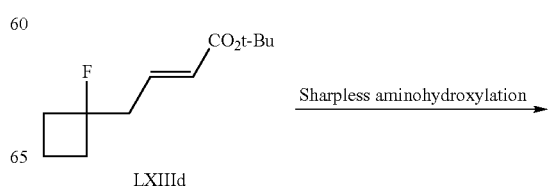

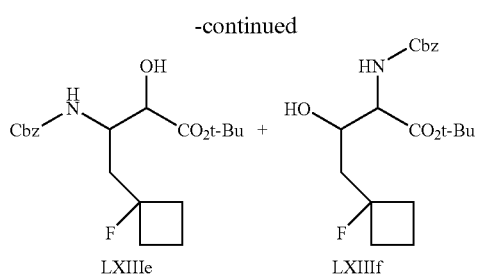

Product of step 3, LXIIId (3.5 g) was treated in the manner previously described in step4 of preparative XXXXIII to afford Products LXIIIe and LXIIIf as a mixture (3.25 g).

Step 5:

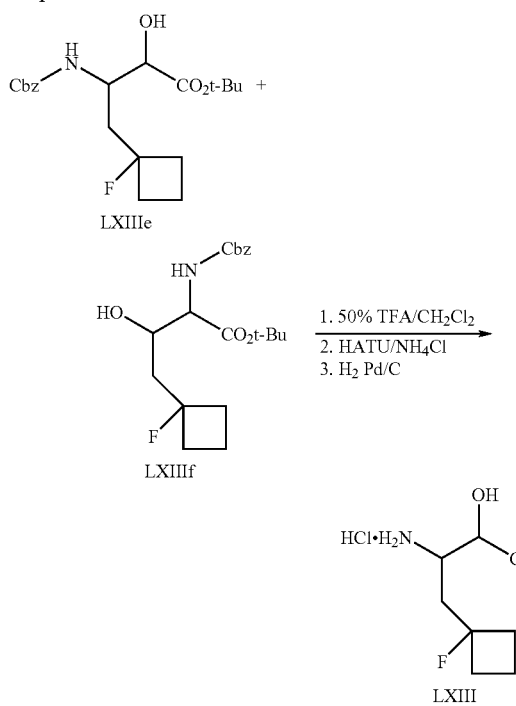

Products of step 4 (LXIIIe+LXIIIf) (2.3 g) was treated in the manner previously described in step5 then step6 and finally step7 of preparative example XXXXIII to afford Product LXIII (0.47 g).

A number of inhibitors described in table-6 using the intermediate LXII were synthesized following the procedures outlined for preparative examples XXIII, XXIV, XXVIII, XXIX, and XXXX

EXAMPLE LXIV

Preparation of Intermediate of Formula LXIV

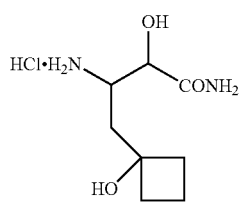

Step1:

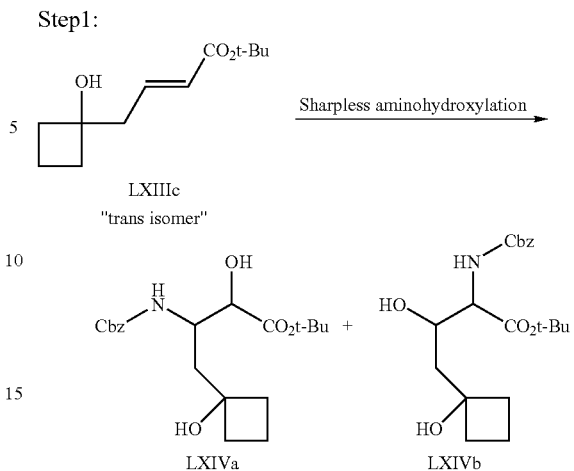

Product LXIIIc (1.36 g) was treated in the manner previously described in step4 of preparative example XXXXIII to afford Products IXIVa and LXIVb as a mixture (1.3 g).

Step 2:

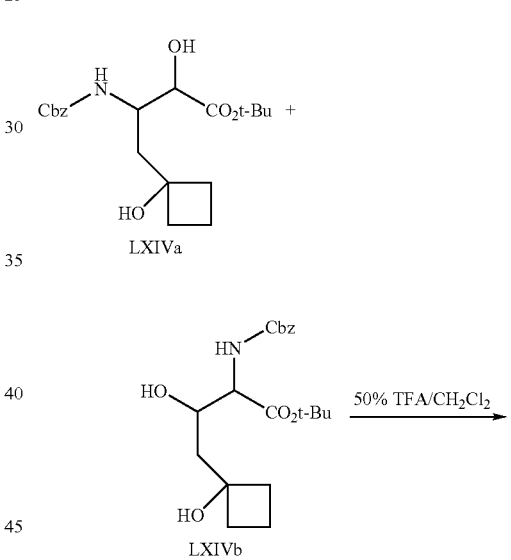

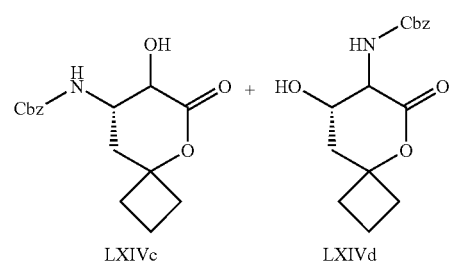

A stirred solution of Products of step 1 (LXIVa+LXIVb) (1.2 g) in $CH_2Cl_2$ (40 ml) was treated with trifluoroacetic acid (40 ml). After 45 minutes the reaction mixture was concentrated to dryness under vacuum. The residue was chromatographed over silica gel (2% MeOH in $CH_2Cl_2$) to provide products LXIVc and LXIVd as a mixture (0.97 g).

Step 3:

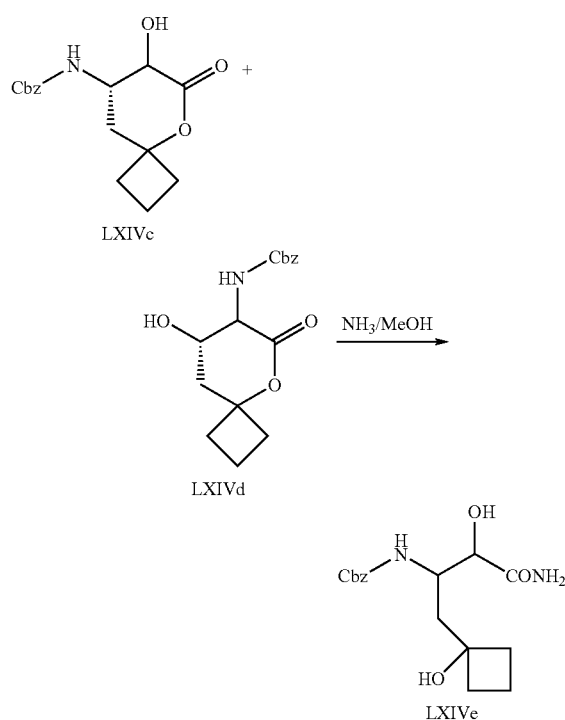

To products of step 2 (LXIVc+LXIVd) (0.4 g) was added 30 mL of NH$_3$ (2.0 M in MeOH). After 4 hours, the reaction mixture was concentrated to dryness under vacuum. The residue was preparative chromatography over silica gel (100% CH$_3$CN) to provide desired product LXIVe (0.3 g).

Step 4:

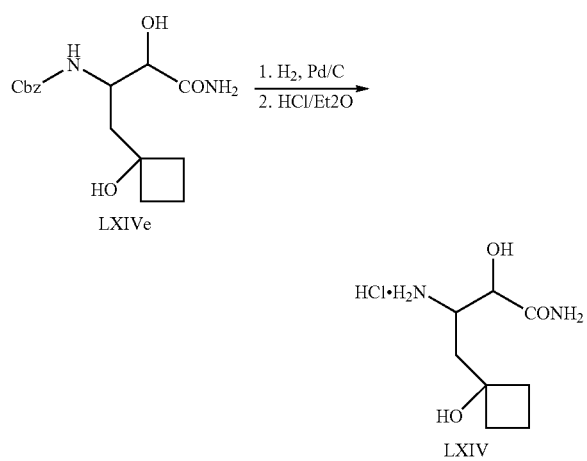

Product of step 3 LXIVe (0.054 g) was treated in the manner previously described in step7 of preparative example XXXXIII to afford Product LXIV (0.032 g)

A number of inhibitors described in table-6 using the intermediate LXII were synthesized following the procedures outlined for preparative examples XXIII, XXIV, XXVIII, XXIX, and XXXX

EXAMPLE LXV

Preparation of Intermediate of Formula LXV

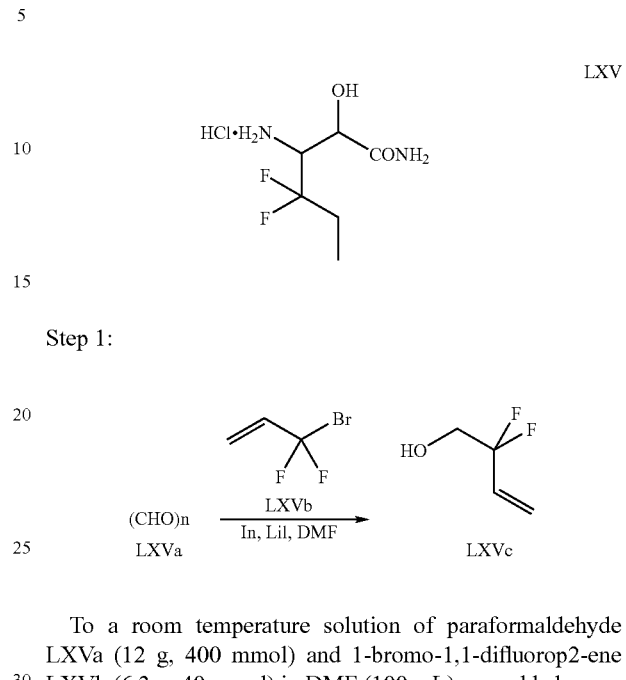

Step 1:

To a room temperature solution of paraformaldehyde LXVa (12 g, 400 mmol) and 1-bromo-1,1-difluorop2-ene LXVb (6.3 g, 40 mmol) in DMF (100 mL) was added In(0) (6.5 g, 57 mmol) and LiI (0.4 g, 3 mmol). The resulting slurry was stirred at RT for 48 h. After 48 h, reaction was filtered trough a pad of celite. The filtrate was diluted with EtOAc (250 mL) and washed with H$_2$O (3 times) then brine. The organic phase separated and finally dried over anhydrous MgSO$_4$. Evaporation under vacuum provided product LXVc; which was used as it is directly in the next step.

Step 2:

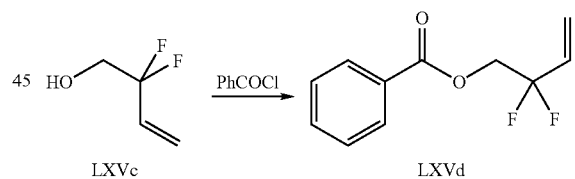

Product of step 1, LXVc (4 g, 37 mmol) was reacted in the manner previously described in preparative example XXXXIII step 1 to afford after purification by chromatography over silica gel (10% to 50% CH$_2$Cl$_2$ in n-hexane) product LXVd (4.3 g).

Step 3:

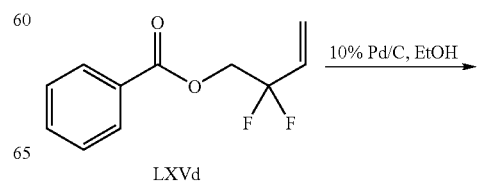

-continued

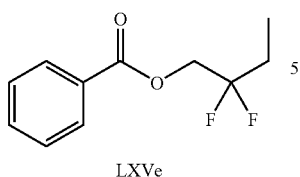

LXVe

To a solution of the product from step 2, LXVd (3.8 g) in ethanol (30 ml) was added 10% Pd/C catalyst (0.76 g). The resulting suspension was hydrogenated until NMR experiment indicated complete consumption of the starting material (~4 hrs). The catalyst was removed by filtration trough a pad of celite and washed with ethanol. The combined filtrate and washings were evaporated under vacuum to dryness to provide the desired product, LXVe (3.8 g).

Step 4:

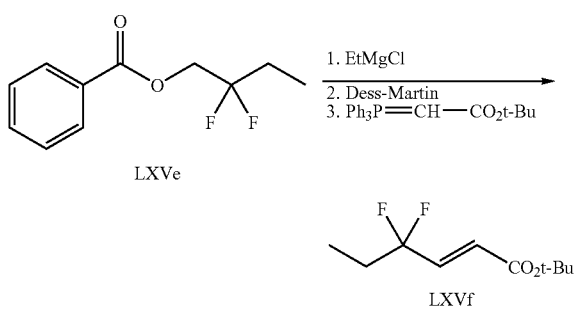

Product of step 3, LXVe (3.4 g) was treated in the manner previously described in step3 of XXXXIII to afford Product LXVf (2.5 g).

Step 5:

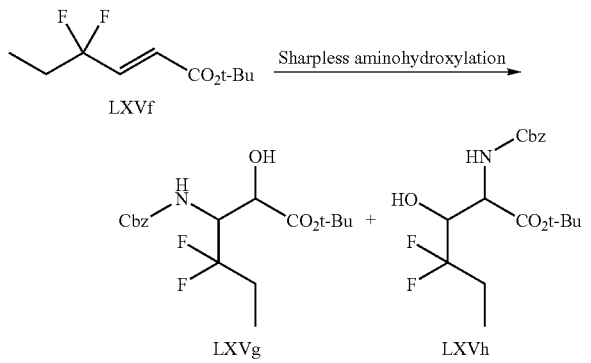

Product of step 4, LXVF (2 g) was treated in the manner previously described in step4 of preparative example XXXXIII to afford after purification by chromatography over silica gel (30% EtOAc in n-hexane) to give LXVg (0.27 g) and LXVh (0.26 g).

Step 6:

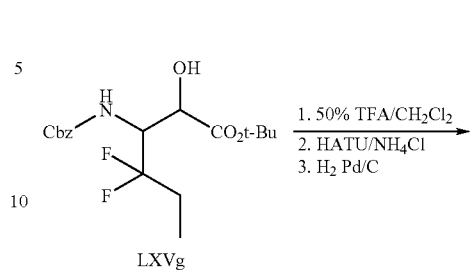

LXVg

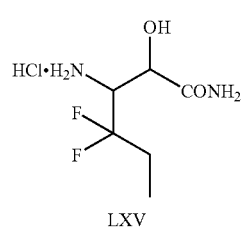

LXV

Product of step 5 LXVg (0.17 g) was treated in the manner previously described in step5 then step6 and finally step7 of preparative example XXXXIII to afford Product LXV (0.025 g).

A number of inhibitors described in table-6 using the intermediate LXV were synthesized following the procedures outlined for preparative examples XXIII, XXIV, XXVIII, XXIX, and XXXX Separation of diastereomers: The diastereomers arising from the α-center of ketoamide were separated using either chromatography ($SiO_2$) or HPLC(YMC diol column) with Hexane/$CH_2Cl_2$/Isopropanol/$CH_3CN$ 85|7.5/6.5/1 as the solvent, as is known to those skilled in the art.

Assay for HCV Protease Inhibitory Activity:

Spectrophotometric Assay Spectrophotometric assay for the HCV serine protease was performed on the inventive compounds by following the procedure described by R. Zhang et al, *Analytical Biochemistry*, 270 (1999) 268-275, the disclosure of which is incorporated herein by reference. The assay based on the proteolysis of chromogenic ester substrates is suitable for the continuous monitoring of HCV NS3 protease activity. The substrates were derived from the P side of the NS5A-NS5B junction sequence (Ac-DTEDWX(Nva), where X=A or chromophoric alcohols (3- or 4-nitrophenol, 7-hydroxy-4-methyl-coumarin, or 4-phenylazophenol). Presented below are the synthesis, characterization and application of these novel spectrophotometric ester substrates to high throughput screening and detailed kinetic evaluation of HCV NS3 protease inhibitors.

Materials and Methods:

Materials: Chemical reagents for assay related buffers were obtained from Sigma Chemical Company (St. Louis, Mo.). Reagents for peptide synthesis were from Aldrich Chemicals, Novabiochem (San Diego, Calif.), Applied Biosystems (Foster City, Calif.) and Perseptive Biosystems (Framingham, Mass.). Peptides were synthesized manually or on an automated ABI model 431A synthesizer (from Applied Biosystems). UVNIS Spectrometer model LAMBDA 12 was from Perkin Elmer (Norwalk, Conn.) and 96-well UV plates were obtained from Corning (Corning, N.Y.). The prewarming block was from USA Scientific (Ocala, Fla.) and the 96-well plate vortexer was from Labline Instruments (Melrose Park, Ill.). A Spectramax Plus microtiter plate reader with monochrometer was obtained from Molecular Devices (Sunnyvale, Calif.).

Enzyme Preparation Recombinant heterodimeric HCV NS3/NS4A protease (strain 1a) was prepared by using the procedures published previously (D. L. Sali et al, *Biochemistry*, 37 (1998) 3392-3401). Protein concentrations were determined by the Biorad dye method using recombinant HCV protease standards previously quantified by amino acid analysis. Prior to assay initiation, the enzyme storage buffer (50 mM sodium phosphate pH 8.0, 300 mM NaCl, 10% glycerol, 0.05% lauryl maltoside and 10 mM DTT) was exchanged for the assay buffer (25 mM MOPS pH 6.5, 300 mM NaCl, 10% glycerol, 0.05% lauryl maltoside, 5 µM EDTA and 5 µM DTT) utilizing a Biorad Bio-Spin P-6 prepacked column.

Substrate Synthesis and Purification: The synthesis of the substrates was done as reported by R. Zhang et al, (ibid.) and was initiated by anchoring Fmoc-Nva-OH to 2-chlorotrityl chloride resin using a standard protocol (K. Barlos et al, *Int. J. Pept. Protein Res.*, 37 (1991), 513-520). The peptides were subsequently assembled, using Fmoc chemistry, either manually or on an automatic ABI model 431 peptide synthesizer. The N-acetylated and fully protected peptide fragments were cleaved from the resin either by 10% acetic acid (HOAc) and 10% trifluoroethanol (TFE) in dichloromethane (DCM) for 30 min, or by 2% trifluoroacetic acid (TFA) in DCM for 10 min. The combined filtrate and DCM wash was evaporated azeotropically (or repeatedly extracted by aqueous $Na_2CO_3$ solution) to remove the acid used in cleavage. The DCM phase was dried over $Na_2SO_4$ and evaporated.

The ester substrates were assembled using standard acid-alcohol coupling procedures (K. Holmber et al, *Acta Chem. Scand.*, B33 (1979) 410-412). Peptide fragments were dissolved in anhydrous pyridine (30-60 mg/ml) to which 10 molar equivalents of chromophore and a catalytic amount (0.1 eq.) of para-toluenesulfonic acid (PTSA) were added. Dicyclohexylcarbodiimide (DCC, 3 eq.) was added to initiate the coupling reactions. Product formation was monitored by HPLC and found to be complete following 12-72 hour reaction at room temperature. Pyridine solvent was evaporated under vacuum and further removed by azeotropic evaporation with toluene. The peptide ester was deprotected with 95% TFA in DCM for two hours and extracted three times with anhydrous ethyl ether to remove excess chromophore. The deprotected substrate was purified by reversed phase HPLC on a C3 or C8 column With a 30% to 60% acetonitrile gradient (using six column volumes). The overall yield following HPLC purification was approximately 20-30%. The molecular mass was confirmed by electrospray ionization mass spectroscopy. The substrates were stored in dry powder form under desiccation.

Spectra of Substrates and Products: Spectra of substrates and the corresponding chromophore products were obtained in the pH 6.5 assay buffer. Extinction coefficients were determined at the optimal off-peak wavelength in 1-cm cuvettes (340 nm for 3-Np and HMC, 370 nm for PAP and 400 nm for 4-Np) using multiple dilutions. The optimal off-peak wavelength was defined as that wavelength yielding the maximum fractional difference in absorbance between substrate and product (product OD−substrate OD)/substrate OD).

Protease Assay: HCV protease assays were performed at 30° C. using a 200 µl reaction mix in a 96-well microtiter plate. Assay buffer conditions (25 mM MOPS pH 6.5, 300 mM NaCl, 10% glycerol, 0.05% lauryl maltoside, 5 µM EDTA and 5 µM DTT) were optimized for the NS3/NS4A heterodimer (D. L. Sall et al, ibid.)). Typically, 150 µl mixtures of buffer, substrate and inhibitor were placed in wells (final concentration of DMSO 4% v/v) and allowed to preincubate at 30° C. for approximately 3 minutes. Fifty µls of prewarmed protease (12 nM, 30° C.) in assay buffer, was then used to initiate the reaction (final volume 200 µl). The plates were monitored over the length of the assay (60 minutes) for change in absorbance at the appropriate wavelength (340 nm for 3-Np and HMC, 370 nm for PAP, and 400 nm for 4-Np) using a Spectromax Plus microtiter plate reader equipped with a monochrometer (acceptable results can be obtained with plate readers that utilize cutoff filters). Proteolytic cleavage of the ester linkage between the Nva and the chromophore was monitored at the appropriate wavelength against a no enzyme blank as a control for non-enzymatic hydrolysis. The evaluation of substrate kinetic parameters was performed over a 30-fold substrate concentration range (~6-200 µM). Initial velocities were determined using linear regression and kinetic constants were obtained by fitting the data to the Michaelis-Menten equation using non-linear regression analysis (Mac Curve Fit 1.1, K. Raner). Turnover numbers ($k_{cat}$) were calculated assuming the enzyme was fully active.

Evaluation of Inhibitors and Inactivators: The inhibition constants (Ki*) for the competitive inhibitors Ac-D-(D-Gla)-L-I-(Cha)-C—OH (27), Ac-DTEDVVA(Nva)-OH and Ac-DTEDWP(Nva)-OH were determined experimentally at fixed concentrations of enzyme and substrate by plotting vdvi vs. inhibitor concentration ($[I]_o$) according to the rearranged Michaelis-Menten equation for competitive inhibition kinetics: $v_o/v_i = 1 + [I]_o/(Ki^*(1+[S]_o/K_m))$, where $v_o$ is the uninhibited initial velocity, $v_i$ is the initial velocity in the presence of inhibitor at any given inhibitor concentration ($[I]_o$) and $[S]_o$ is the substrate concentration used. The resulting data were fitted using linear regression and the resulting slope, $1/(Ki^*(1+[S]o/K_m))$, was used to calculate the Ki* value.

The obtained Ki* values for the various compounds of the present invention are given in the afore-mentioned Tables wherein the compounds have been arranged in the order of ranges of Ki* values. From these test results, it would be apparent to the skilled artisan that the compounds of the invention have excellent utility as NS3-serine protease inhibitors.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

TABLE 2
| Ex. # | STRUCTURE | molecular weight |
|---|---|---|
| 1 | 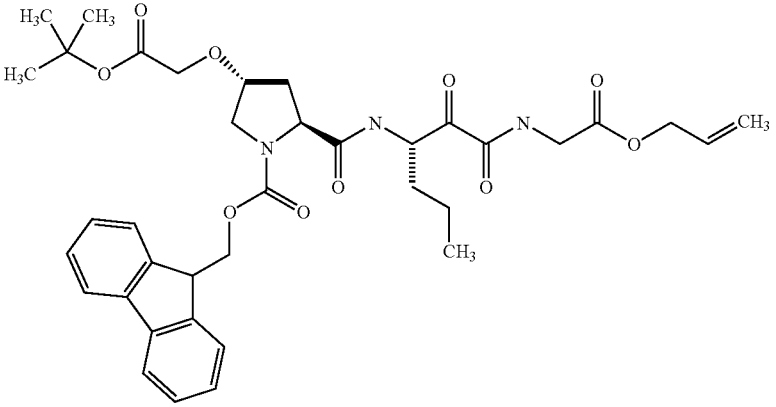 | 691.7853 |
| 2 | 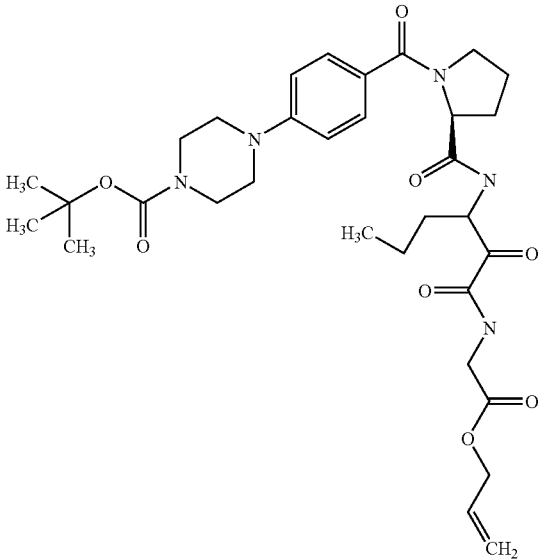 | 627.7441 |
| 3 | 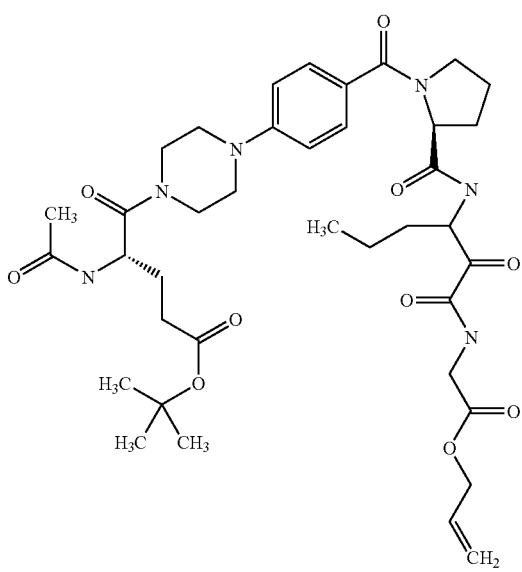 | 754.8883 |

TABLE 2-continued
| Ex. # | STRUCTURE | molecular weight |
|---|---|---|
| 4 | 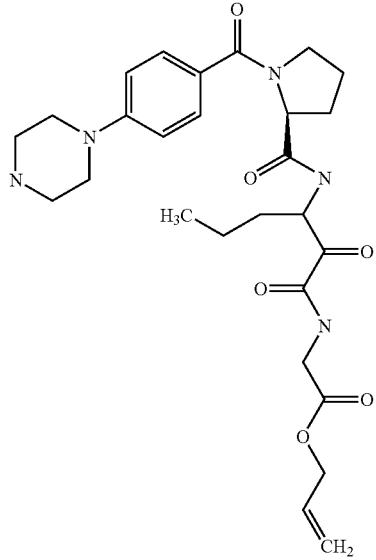 | 527.6259 |
| 5 | 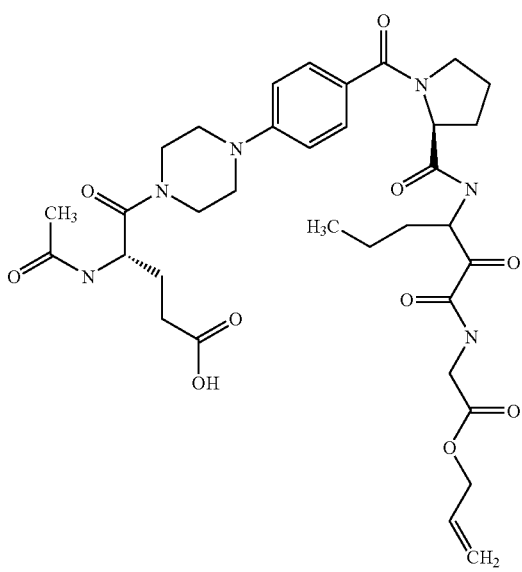 | 698.7799 |

TABLE 2-continued

| Ex. # | STRUCTURE | molecular weight |
|---|---|---|
| 6 | 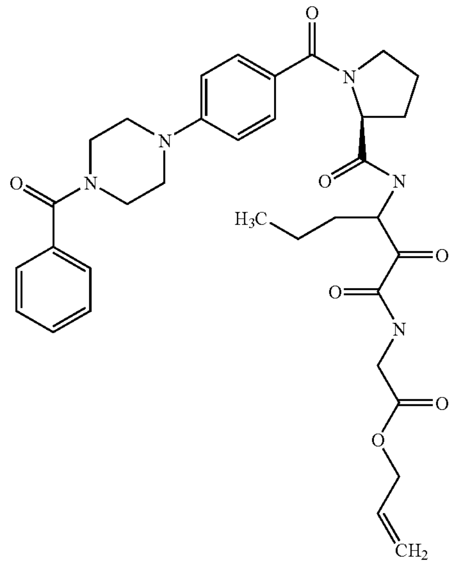 | 631.7352 |
| 7 | 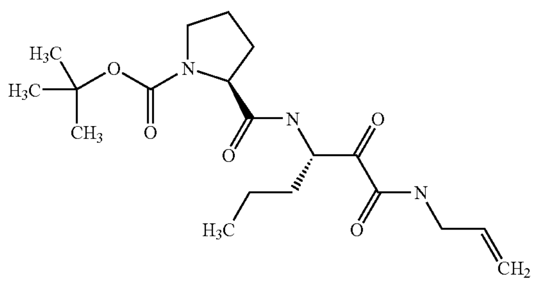 | 381.476 |
| 8 | 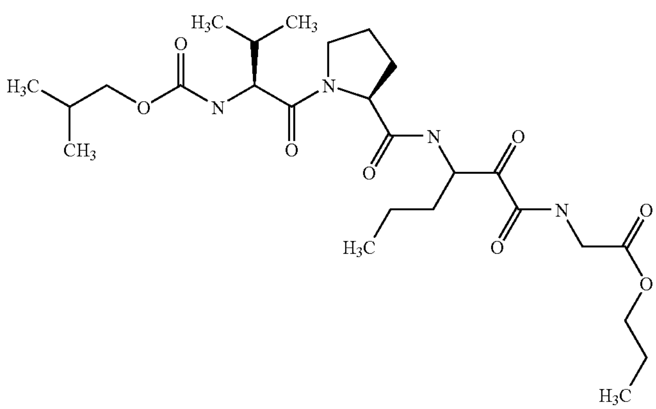 | 540.6626 |
| 9 | 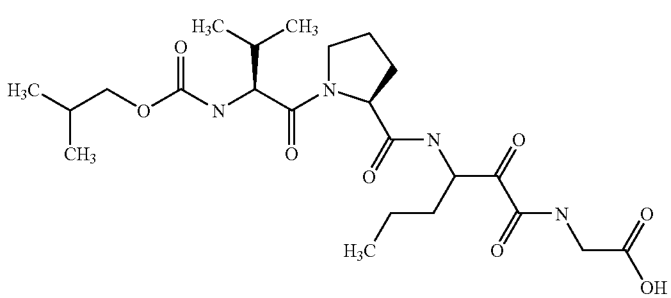 | 498.5813 |

TABLE 2-continued
| Ex. # | STRUCTURE | molecular weight |
|---|---|---|
| 10 | 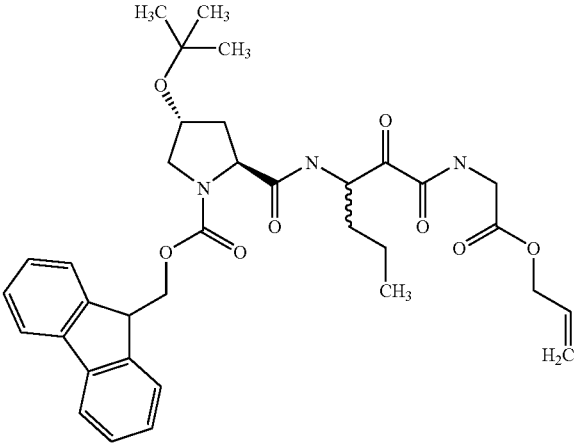 | 633.7482 |
| 11 | 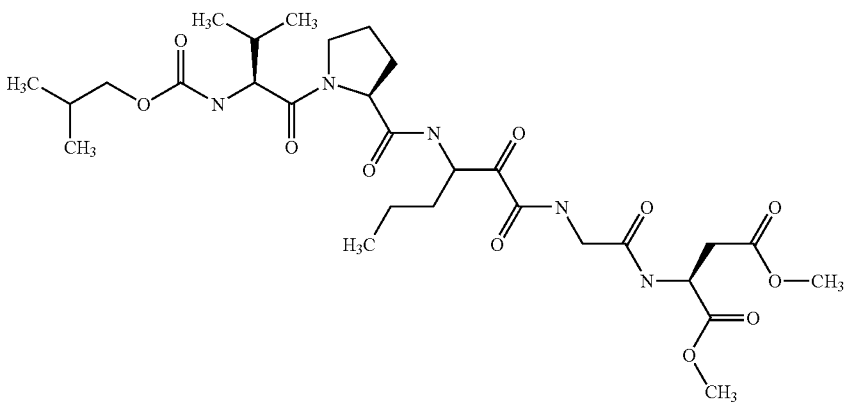 | 641.7249 |
| 12 | 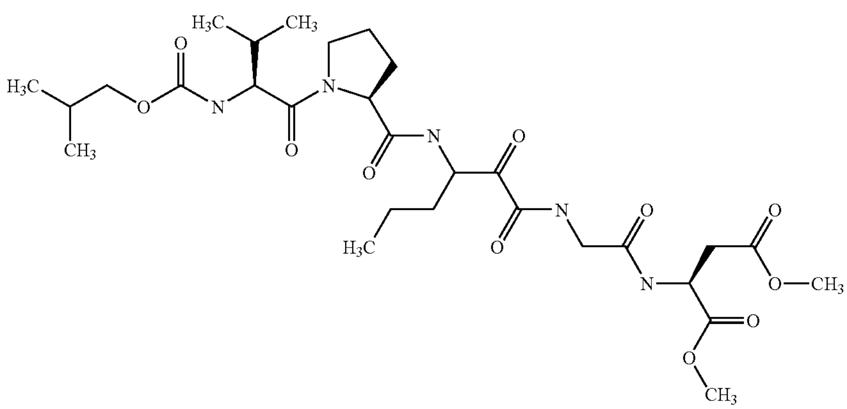 | 641.7249 |

TABLE 2-continued
| Ex. # | STRUCTURE | molecular weight |
|---|---|---|
| 13 | 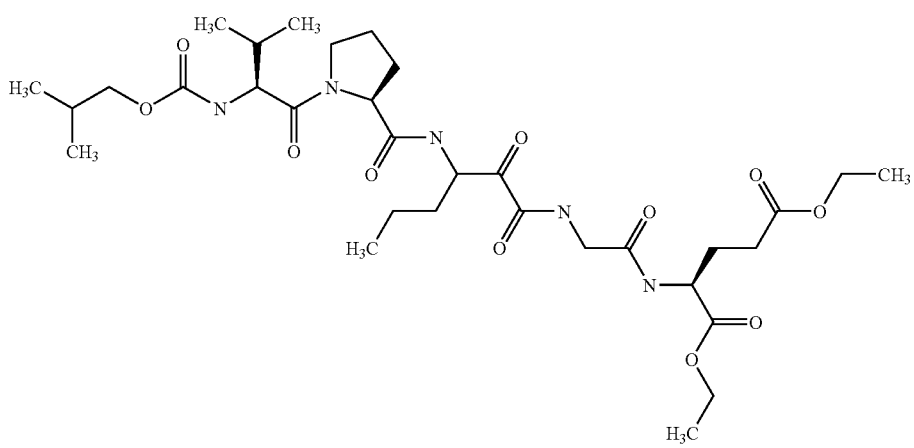 | 683.8061 |
| 14 | 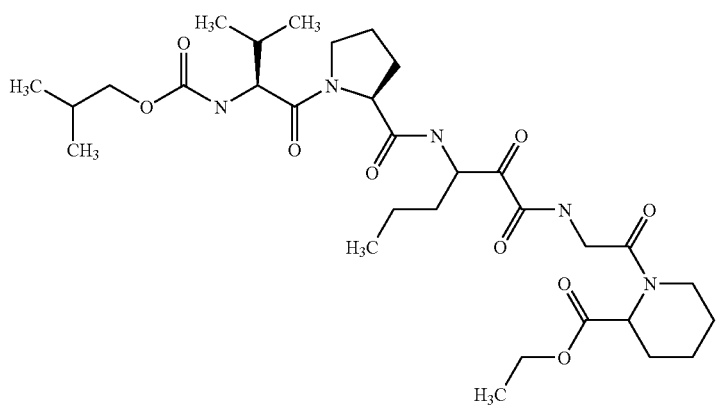 | 637.7802 |
| 15 | 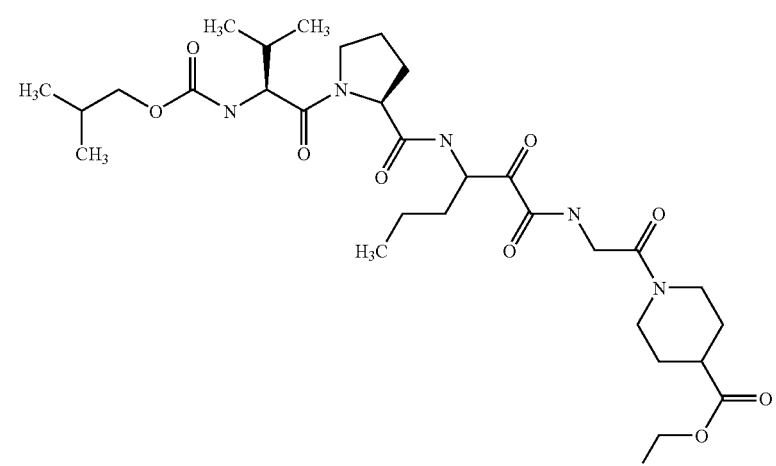 | 637.7802 |

TABLE 2-continued
| Ex. # | STRUCTURE | molecular weight |
|---|---|---|
| 16 | 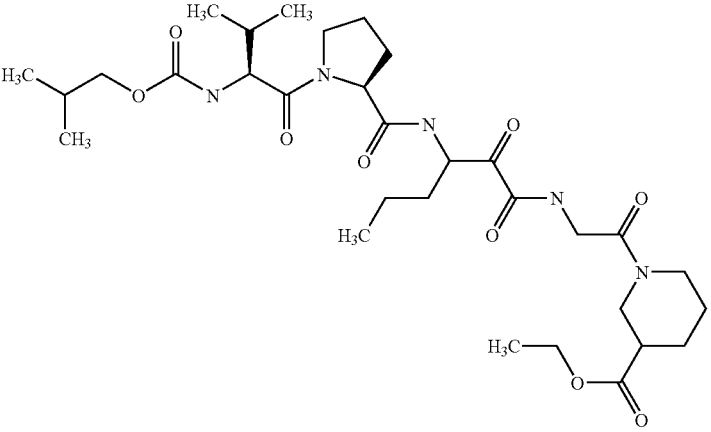 | 637.7802 |
| 17 | 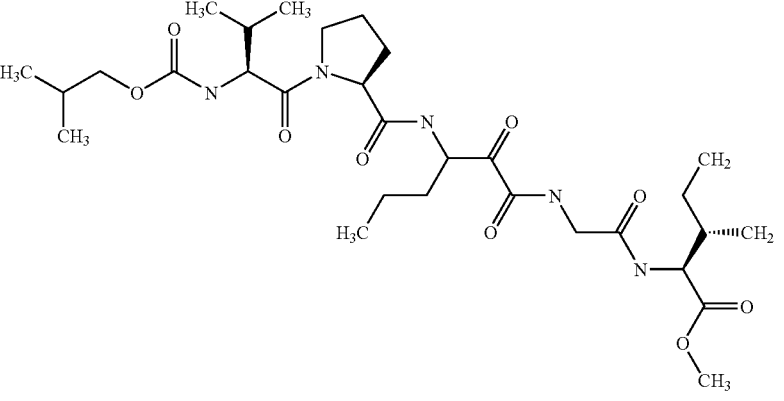 | 625.769 |
| 18 | 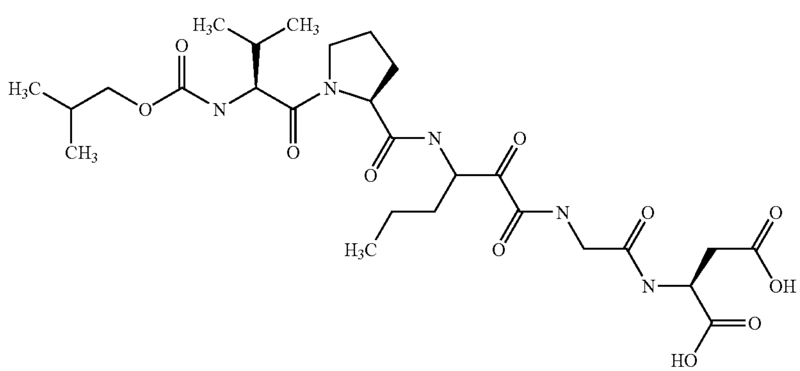 | 613.6707 |
| 19 | 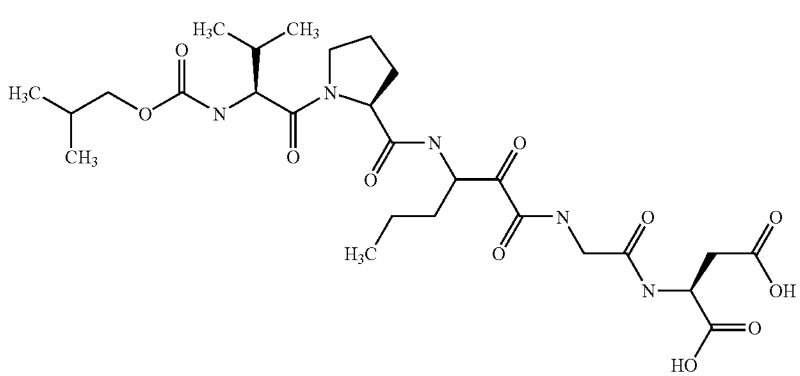 | 613.6707 |

TABLE 2-continued
| Ex. # | STRUCTURE | molecular weight |
|---|---|---|
| 20 | 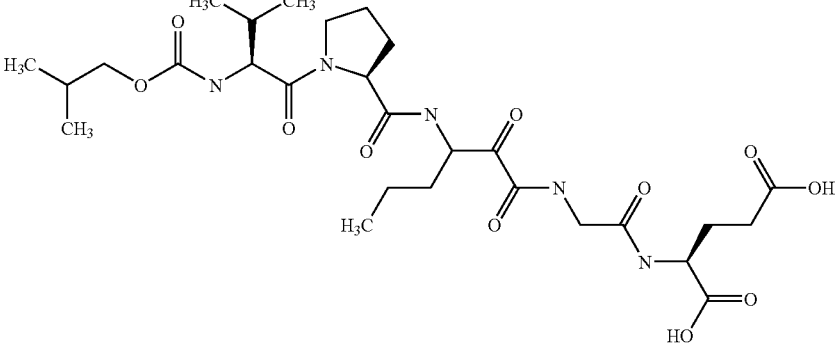 | 627.6978 |
| 21 | 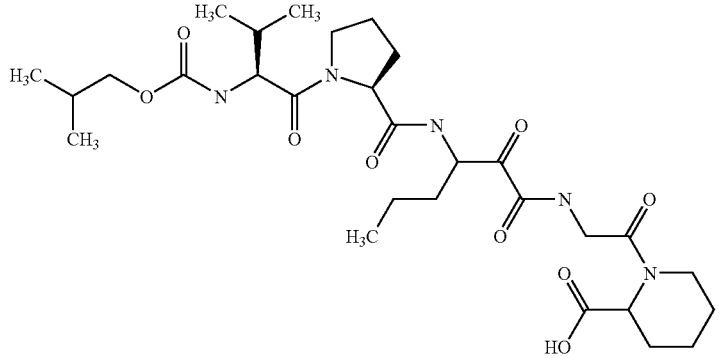 | 609.726 |
| 22 | 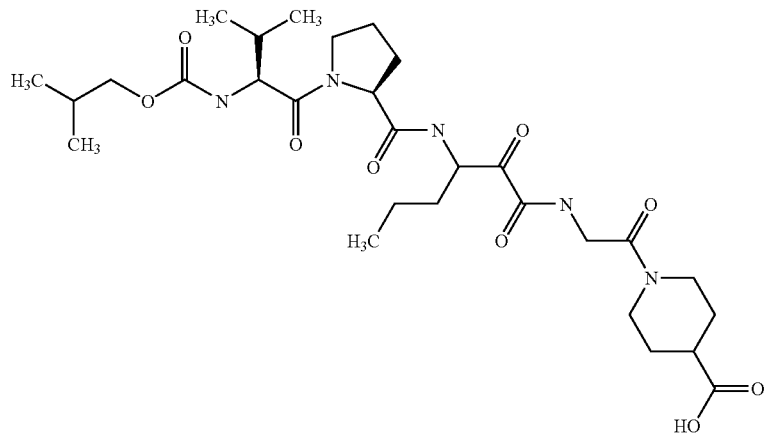 | 609.726 |
| 23 | 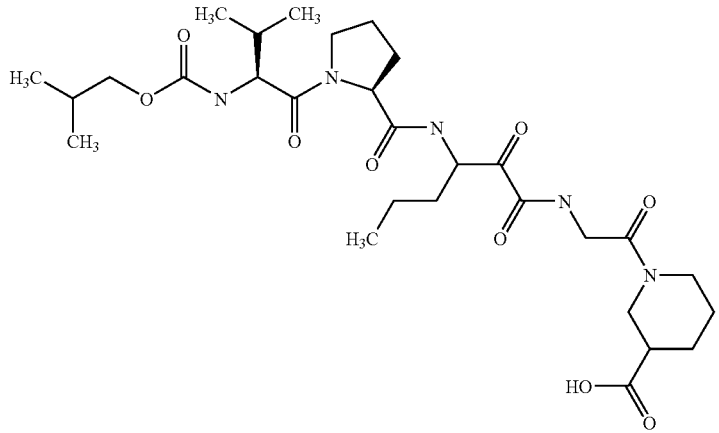 | 609.726 |

TABLE 2-continued

| Ex. # | STRUCTURE | molecular weight |
|---|---|---|
| 24 | 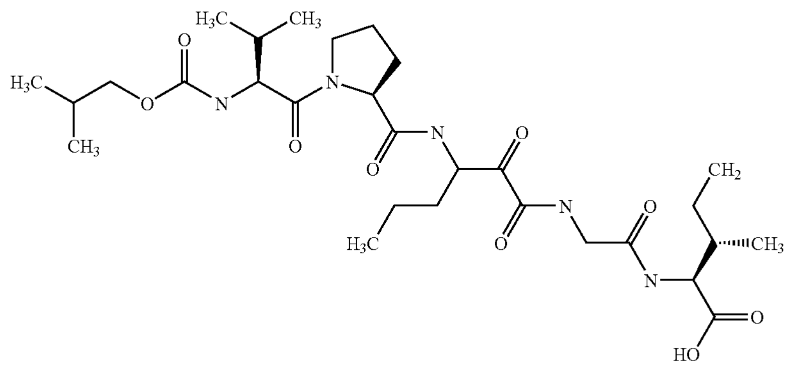 | 611.742 |
| 25 | 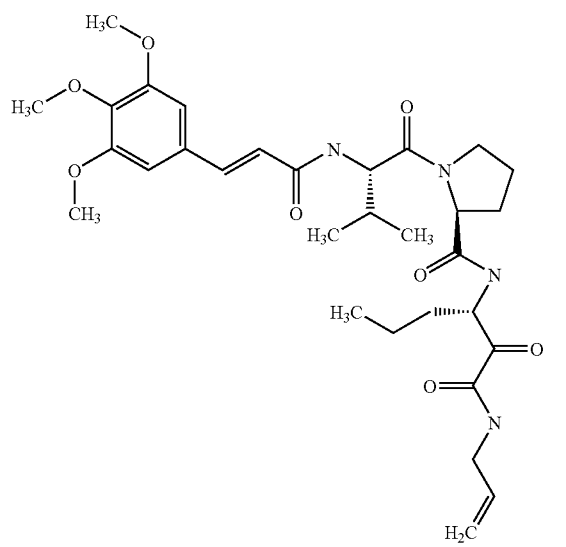 | 600.7183 |
| 26 | 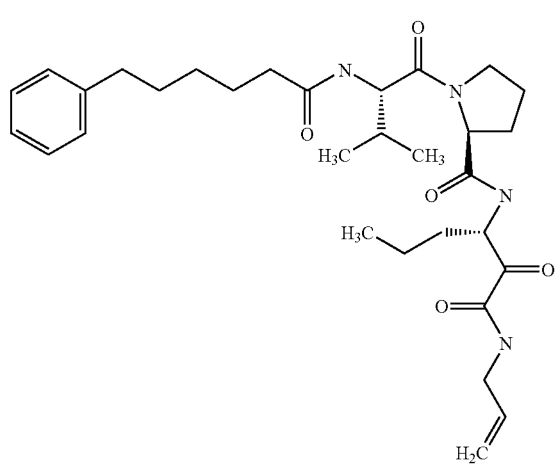 | 554.7361 |

TABLE 2-continued

| Ex. # | STRUCTURE | molecular weight |
|---|---|---|
| 27 | 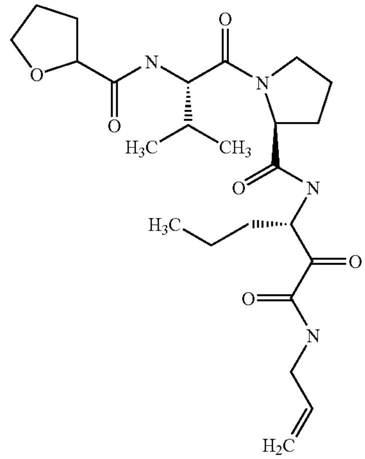 | 478.5937 |
| 28 | 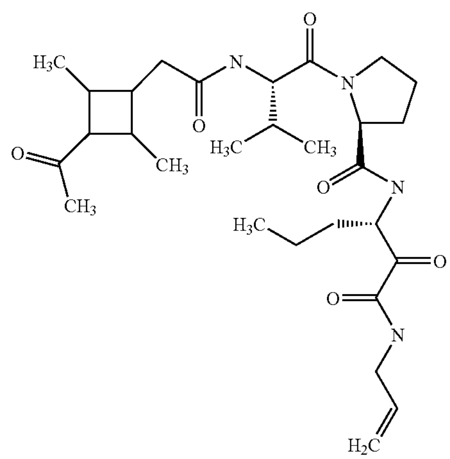 | 546.7132 |
| 29 | 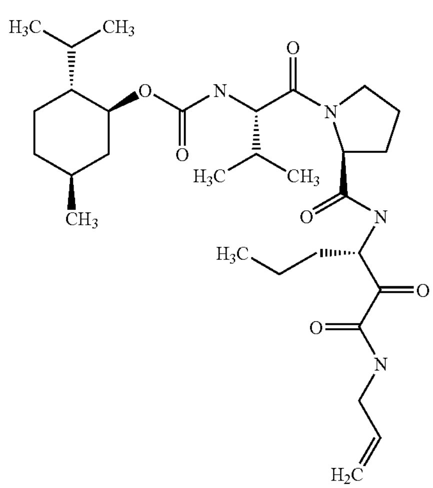 | 562.7562 |

TABLE 2-continued

| Ex. # | STRUCTURE | molecular weight |
|---|---|---|
| 30 | 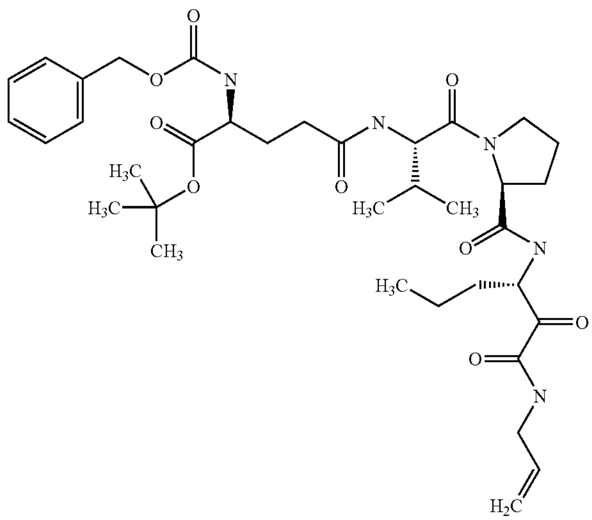 | 699.8519 |
| 31 | 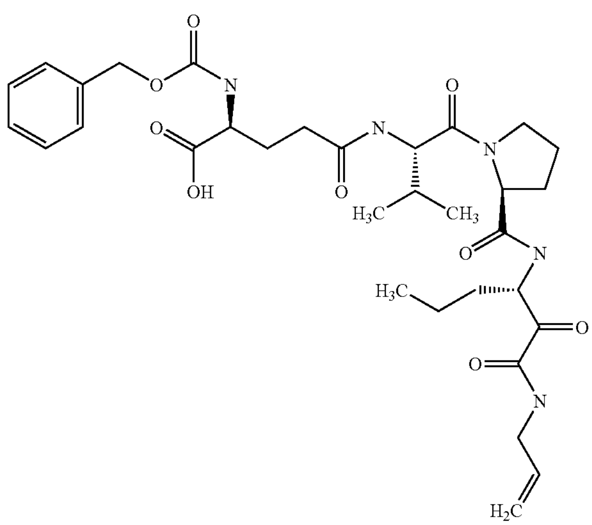 | 643.7435 |
| 32 | 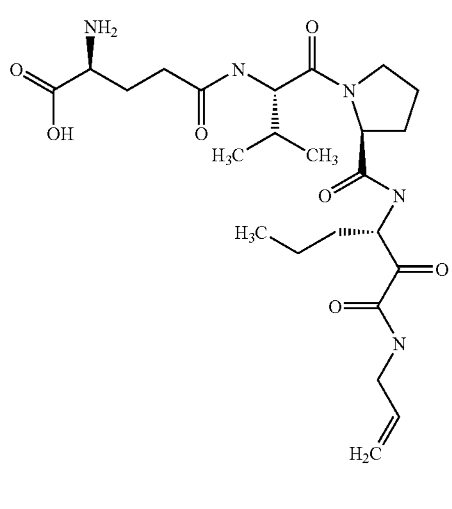 | 509.6077 |

TABLE 2-continued

| Ex. # | STRUCTURE | molecular weight |
|---|---|---|
| 33 | 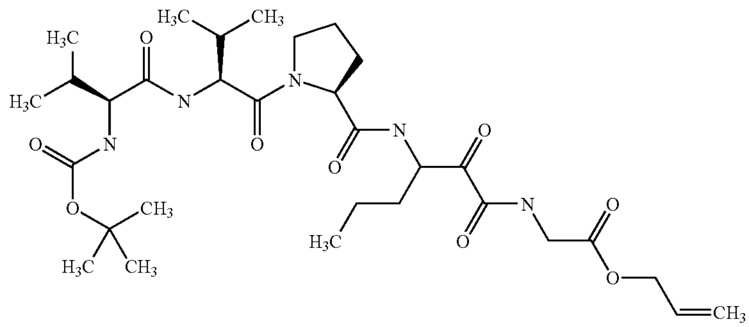 | 637.7802 |
| 34 | 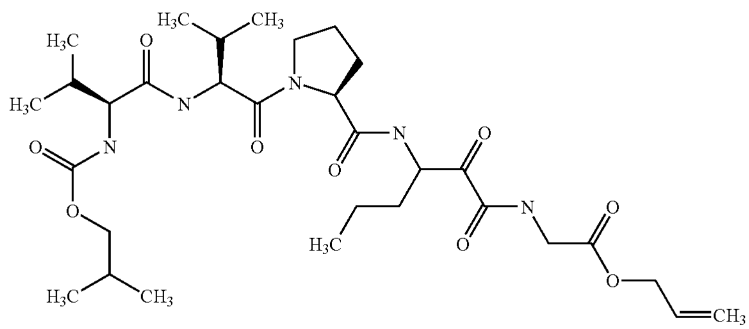 | 637.7802 |
| 35 | 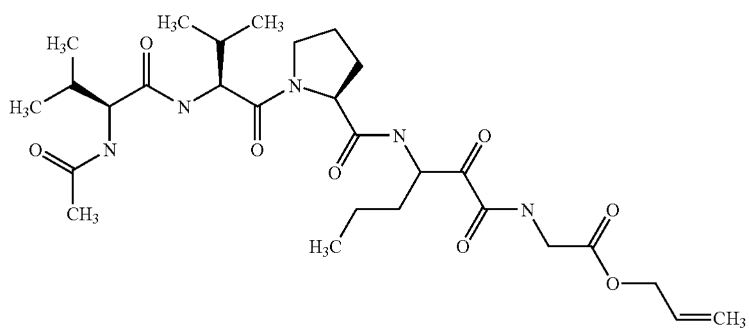 | 579.6995 |
| 36 | 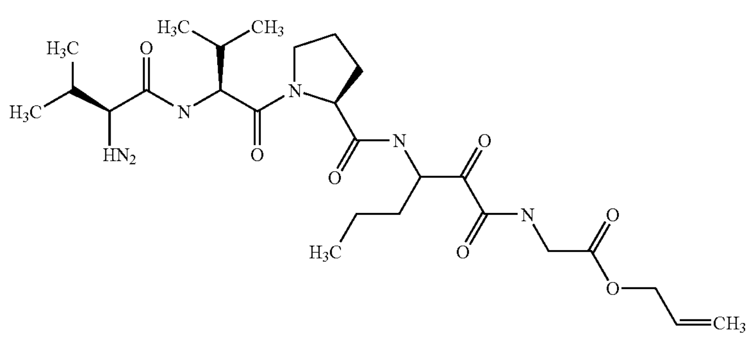 | 537.6619 |

TABLE 2-continued

| Ex. # | STRUCTURE | molecular weight |
|---|---|---|
| 37 | 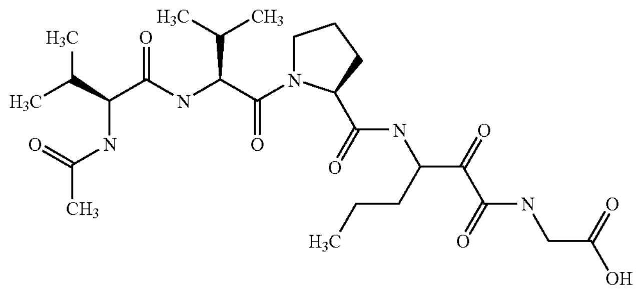 | 539.6342 |
| 38 | 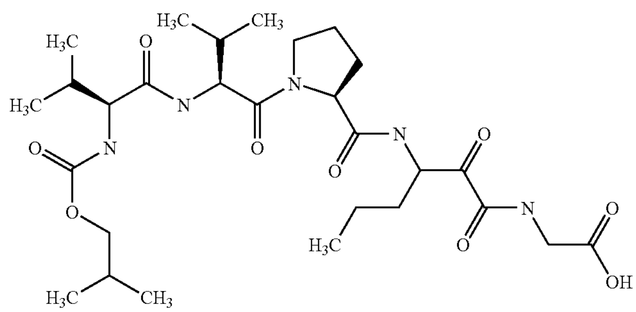 | 597.7149 |
| 39 | 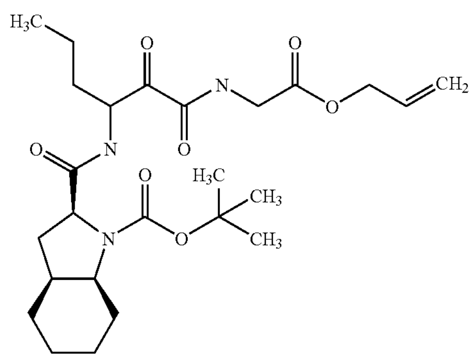 | 493.6055 |
| 40 | 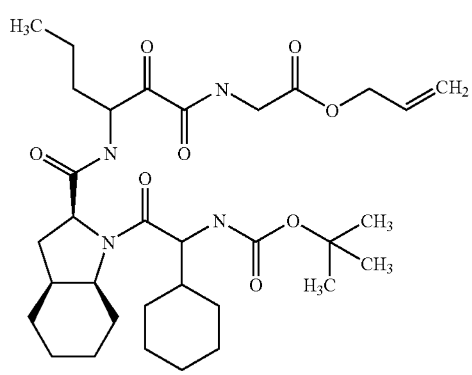 | 632.8044 |

TABLE 2-continued

| Ex. # | STRUCTURE | molecular weight |
|---|---|---|
| 41 | 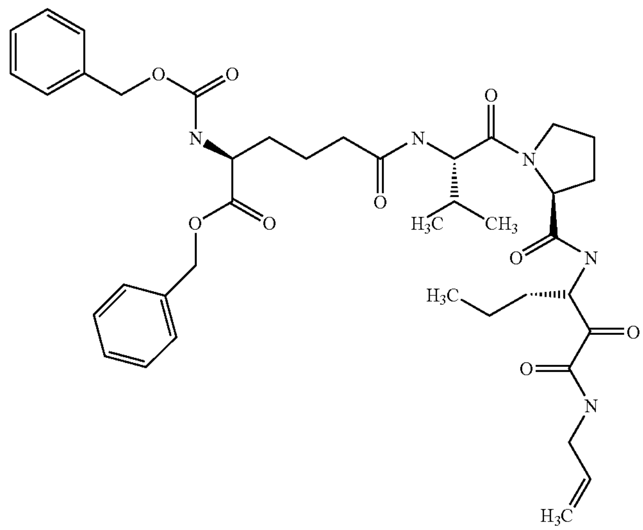 | 747.8965 |
| 42 | 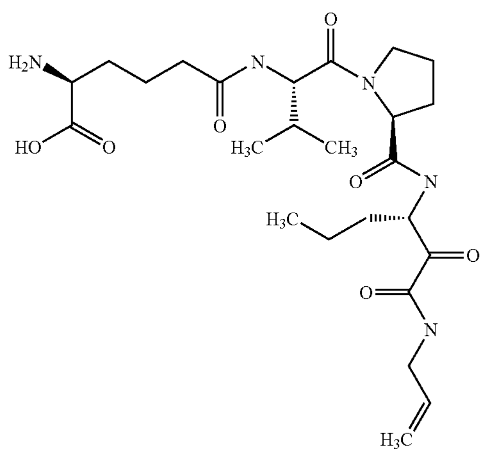 | 523.6348 |
| 43 | 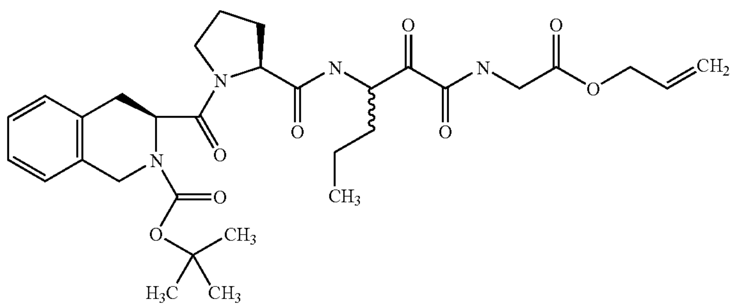 | 598.7024 |
| 44 | 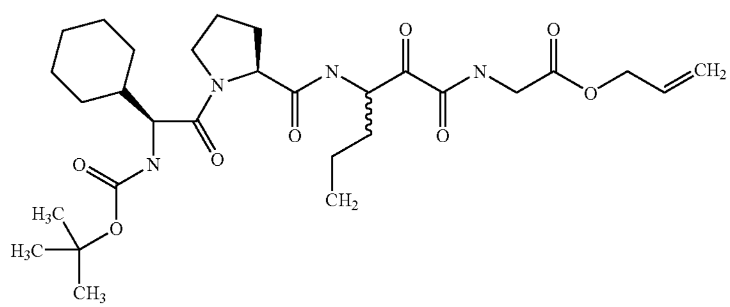 | 578.712 |

TABLE 2-continued

| Ex. # | STRUCTURE | molecular weight |
|---|---|---|
| 45 | 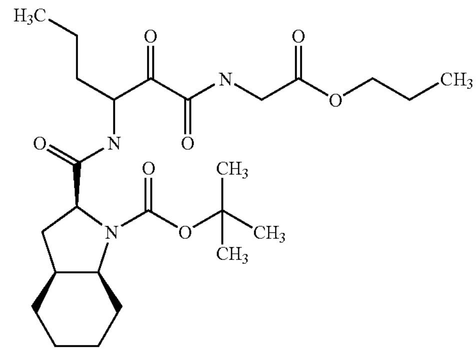 | 495.6214 |
| 46 | 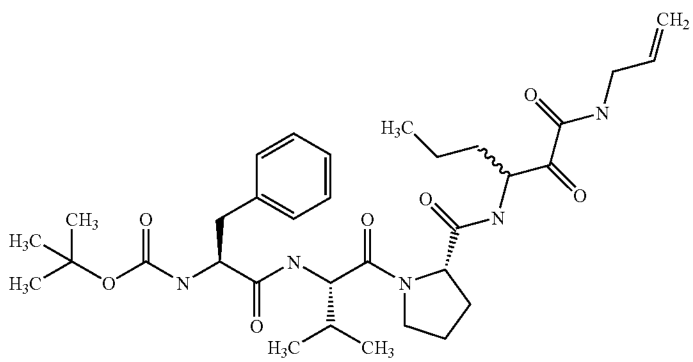 | 627.7878 |
| 47 | 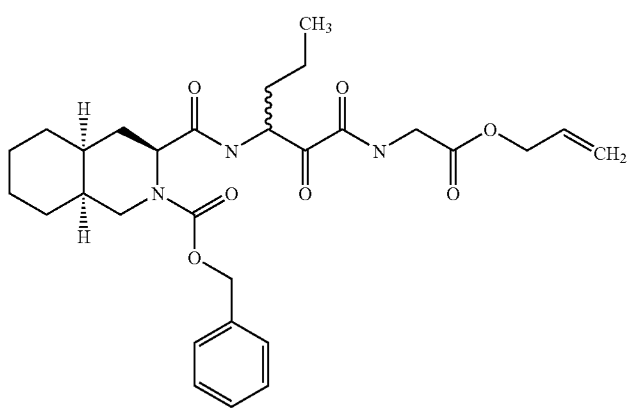 | 541.6501 |
| 48 | 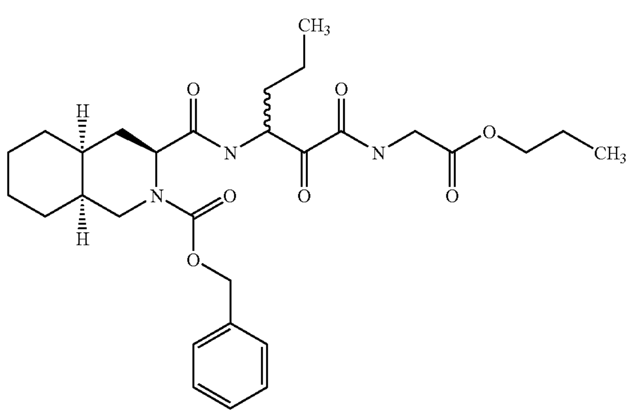 | 543.666 |

TABLE 2-continued

| Ex. # | STRUCTURE | molecular weight |
|---|---|---|
| 49 | 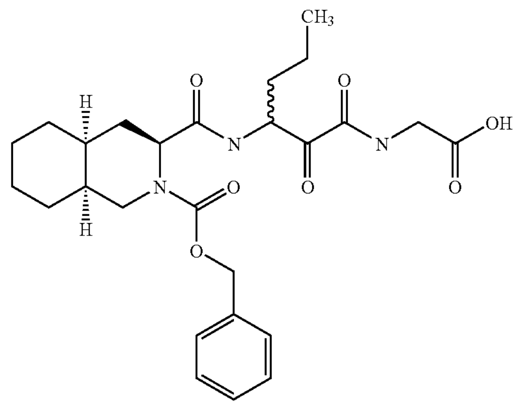 | 501.5847 |
| 50 | 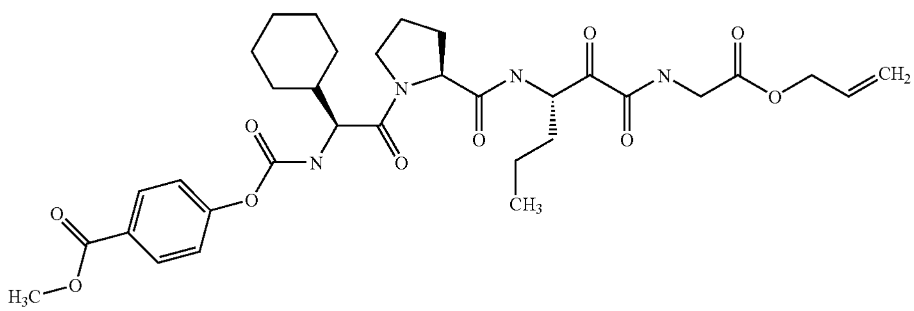 | 656.7394 |
| 51 | 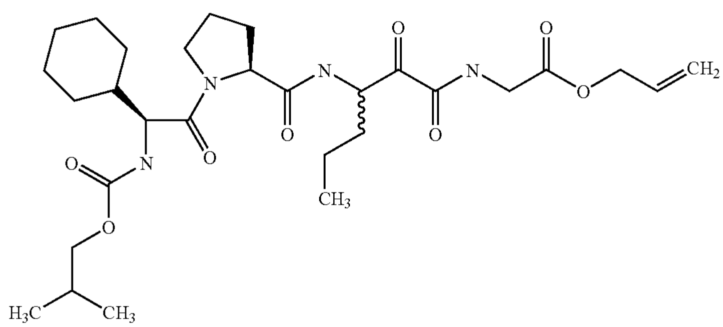 | 578.712 |
| 52 | 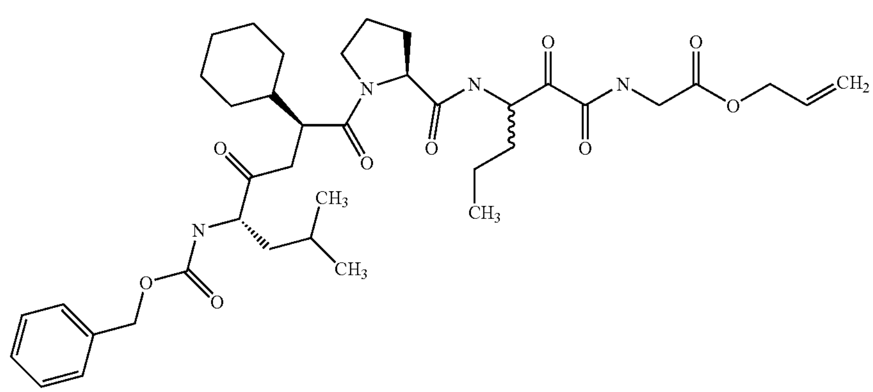 | 725.8901 |

TABLE 2-continued

| Ex. # | STRUCTURE | molecular weight |
|---|---|---|
| 53 | 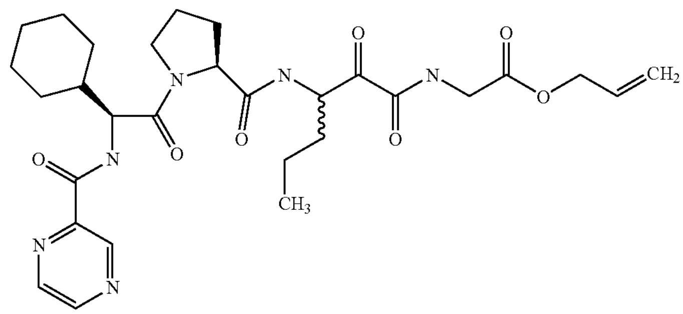 | 584.6782 |
| 54 | 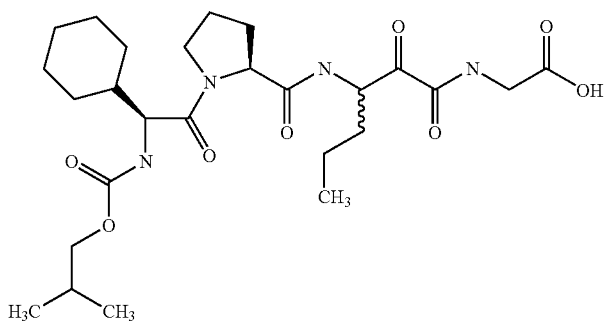 | 538.6467 |
| 55 | 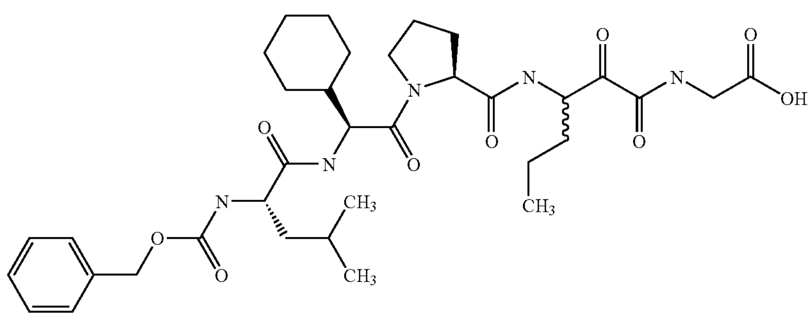 | 685.8248 |
| 56 | 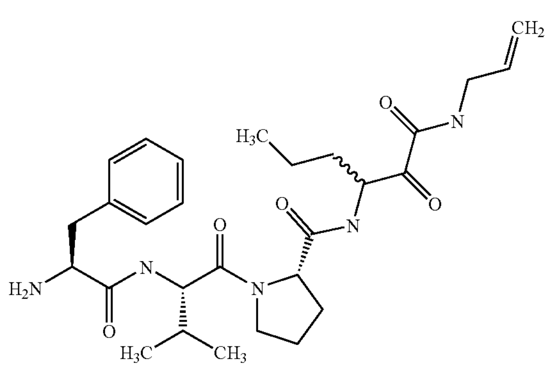 | 527.6695 |

TABLE 2-continued

| Ex. # | STRUCTURE | molecular weight |
|---|---|---|
| 57 | 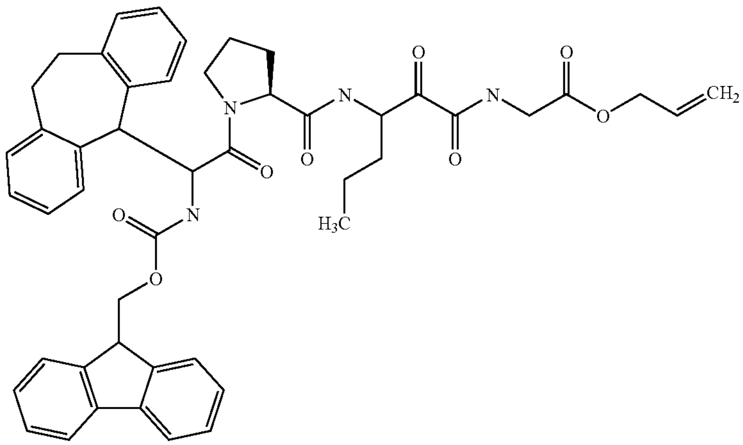 | 810.9557 |
| 58 | 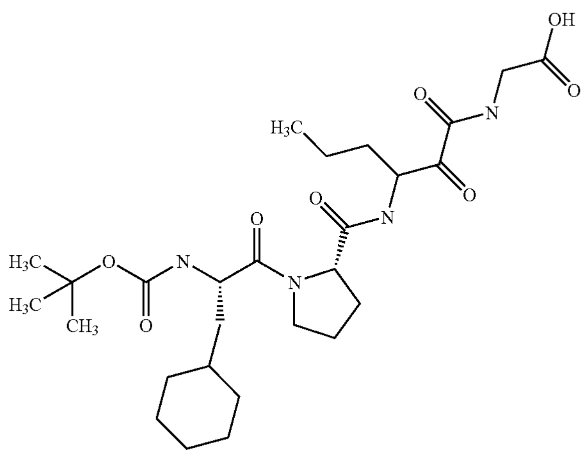 | 552.6737 |
| 59 | 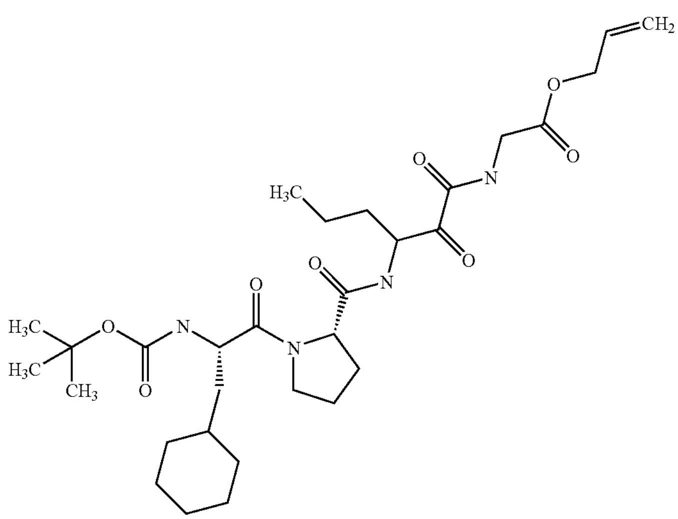 | 592.7391 |

TABLE 2-continued
| Ex. # | STRUCTURE | molecular weight |
|---|---|---|
| 60 | 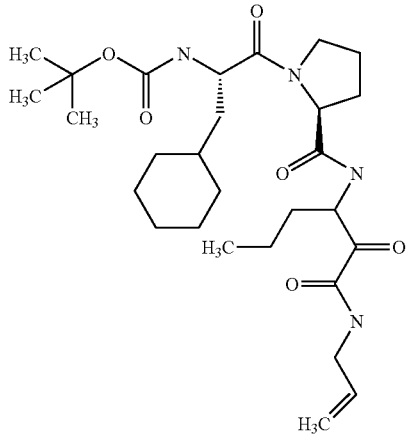 | 534.702 |
| 61 | 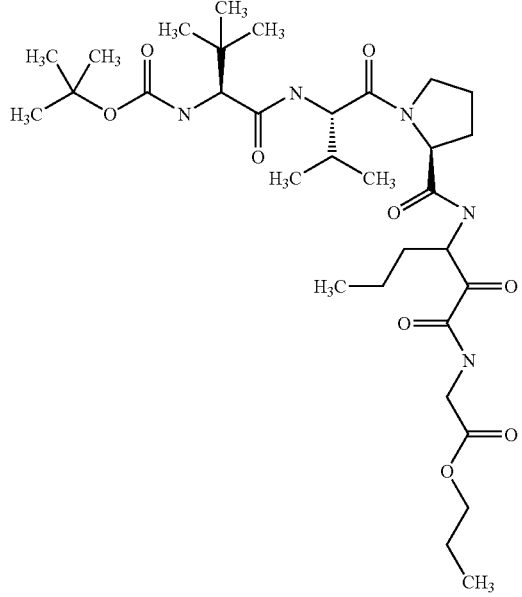 | 653.8232 |
| 62 | 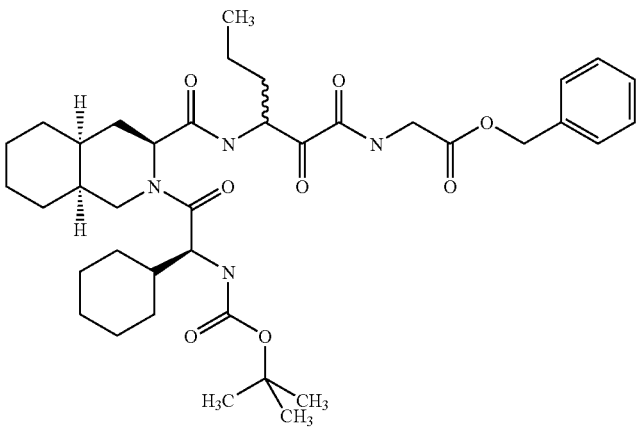 | 696.892 |

TABLE 2-continued

| Ex. # | STRUCTURE | molecular weight |
|---|---|---|
| 63 | 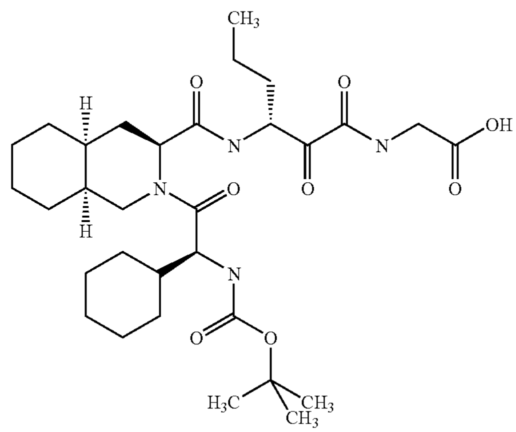 | 606.7662 |
| 64 | 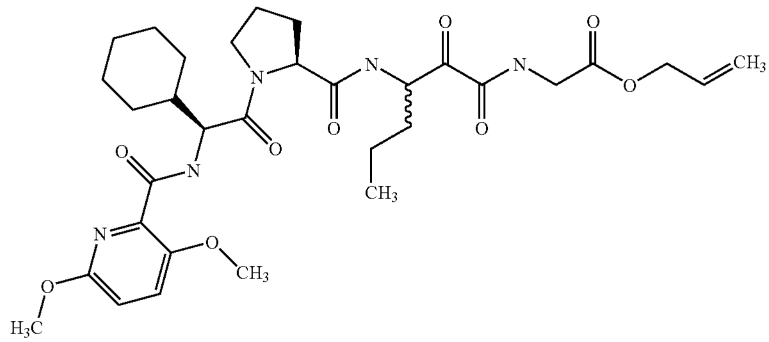 | 643.7435 |
| 65 | 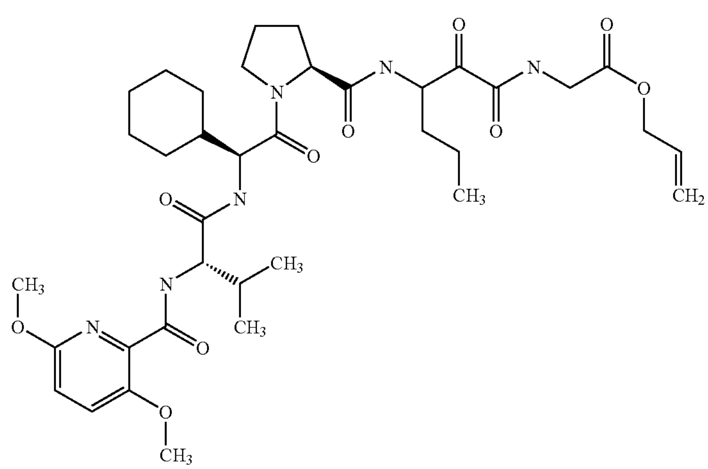 | 742.8771 |
| 66 | 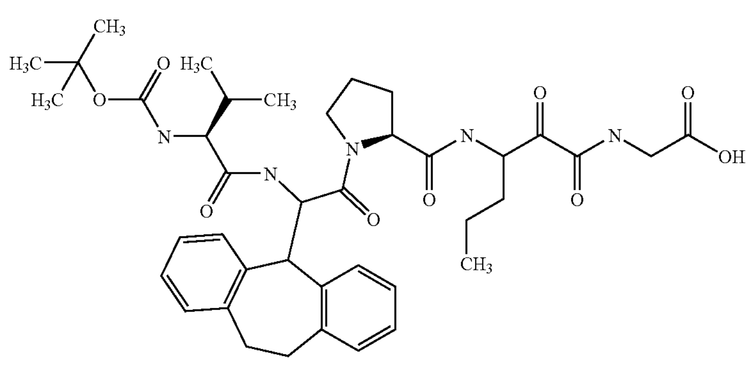 | 747.8965 |

TABLE 2-continued

| Ex. # | STRUCTURE | molecular weight |
|---|---|---|
| 67 | 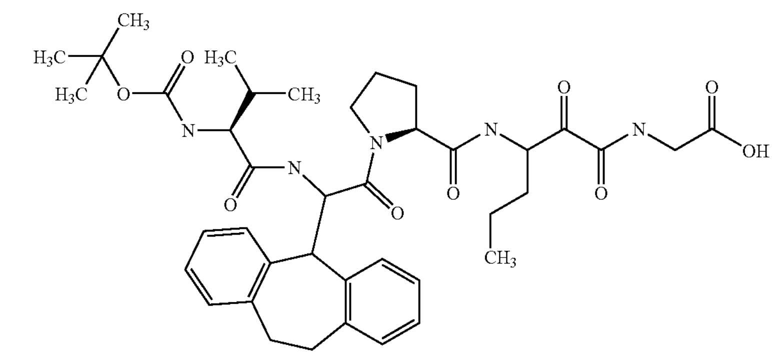 | 747.8965 |
| 68 | 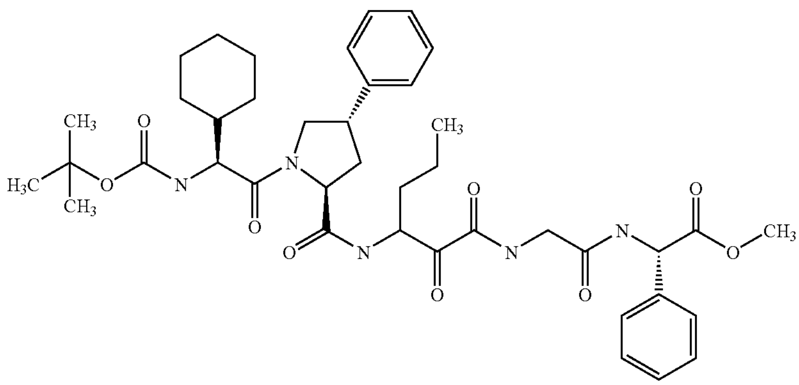 | 761.9236 |
| 69 | 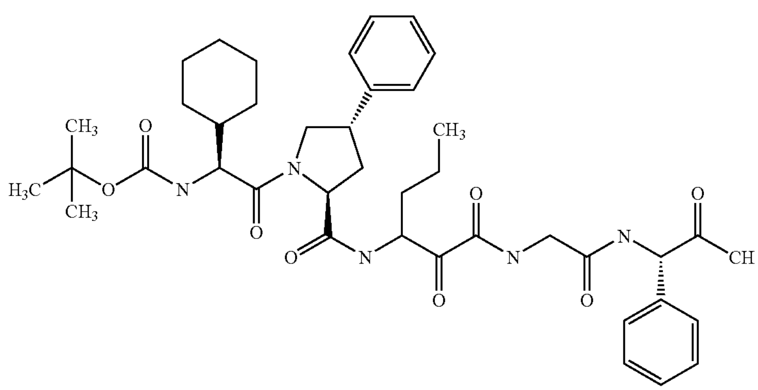 | 747.8965 |
| 70 | 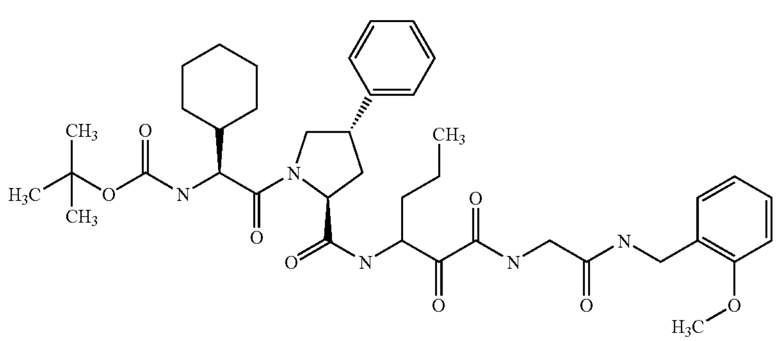 | 733.913 |

TABLE 2-continued

| Ex. # | STRUCTURE | molecular weight |
|---|---|---|
| 71 | 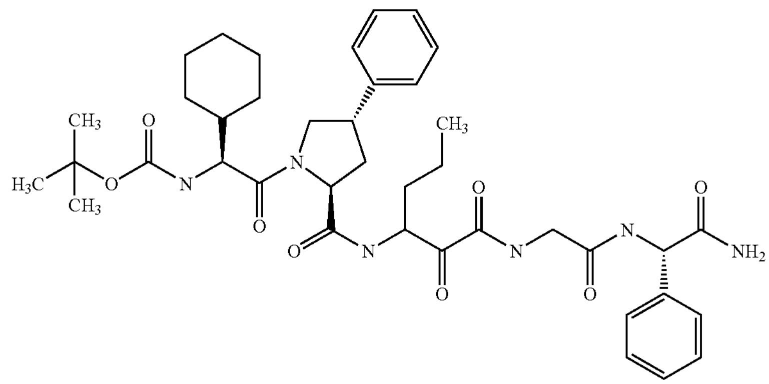 | 746.9118 |
| 72 | 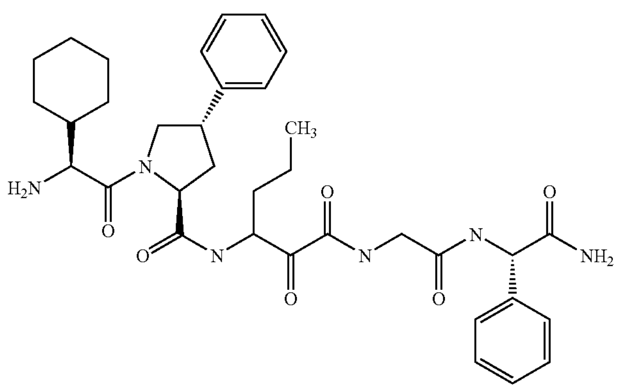 | 646.7935 |
| 73 | 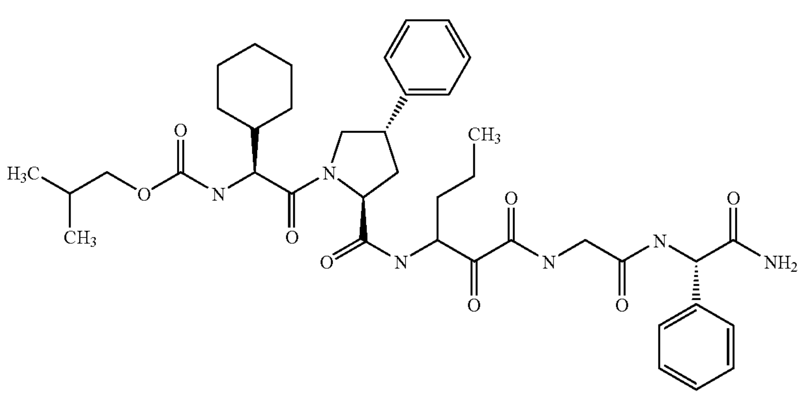 | 746.9118 |

TABLE 2-continued

| Ex. # | STRUCTURE | molecular weight |
|---|---|---|
| 74 | 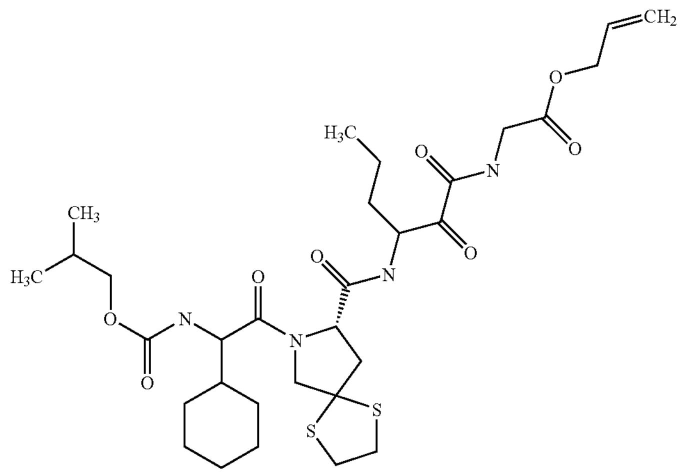 | 668.8782 |
| 75 | 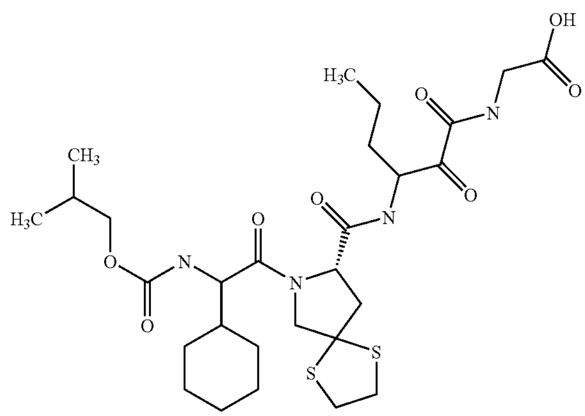 | 628.8129 |
| 76 | 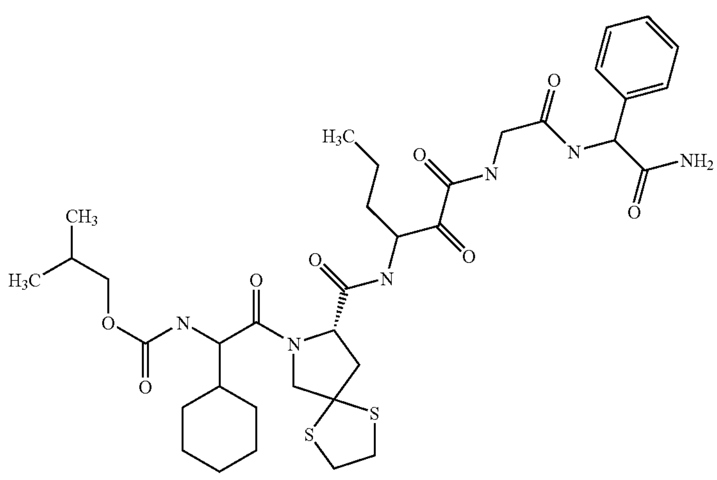 | 760.9792 |

TABLE 2-continued
| Ex. # | STRUCTURE | molecular weight |
|---|---|---|
| 77 | 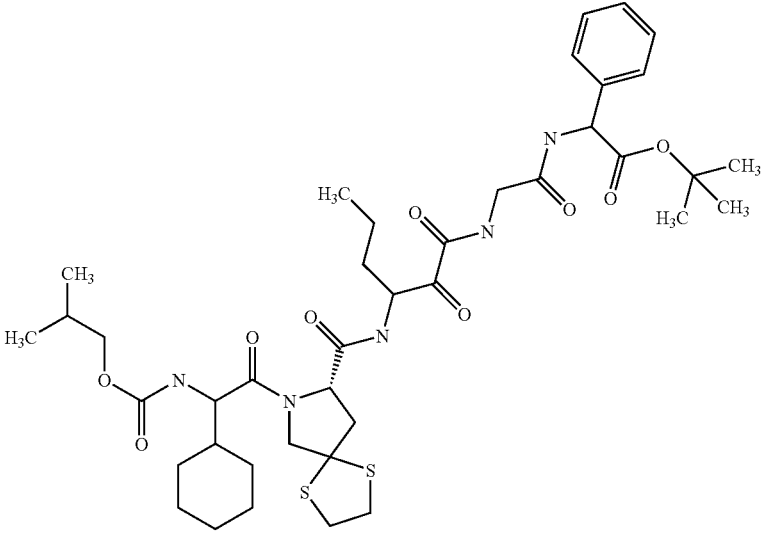 | 818.0723 |
| 78 | 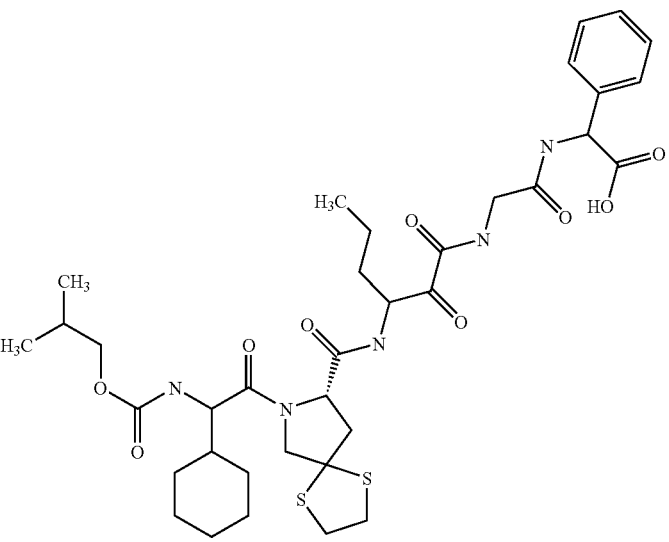 | 761.964 |
| 79 | 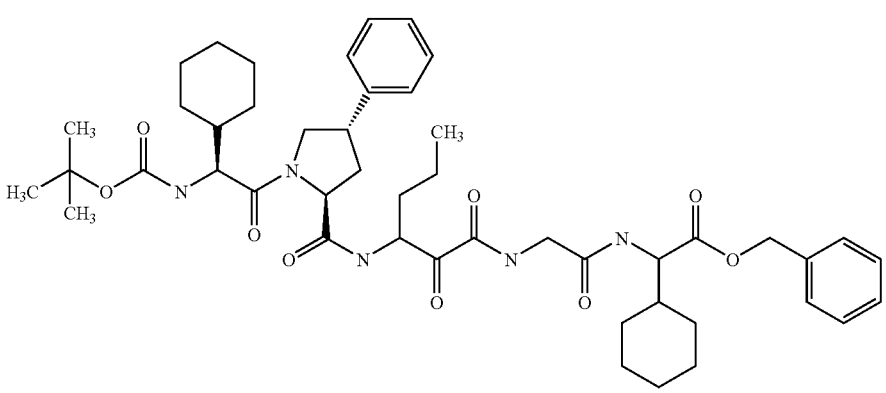 | 844.0702 |

TABLE 2-continued
| Ex. # | STRUCTURE | molecular weight |
|---|---|---|
| 80 | 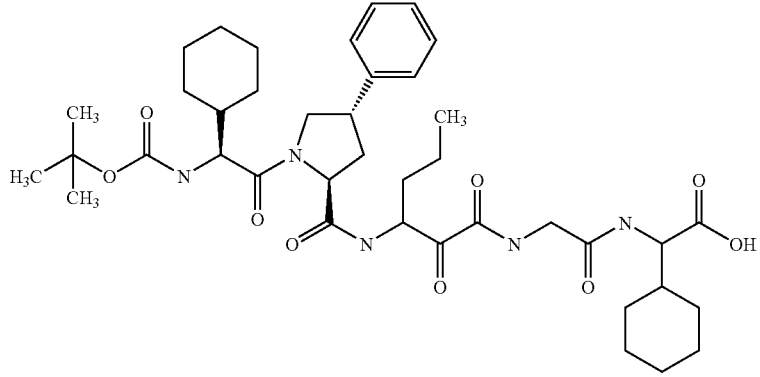 | 753.9443 |
| 81 | 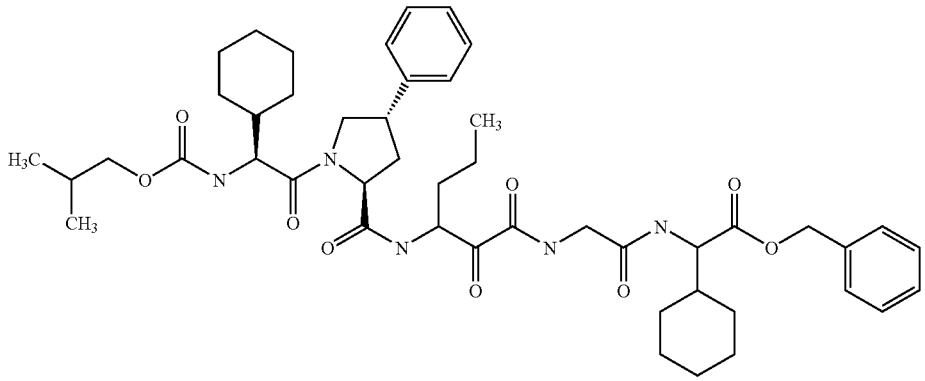 | 844.0702 |
| 82 | 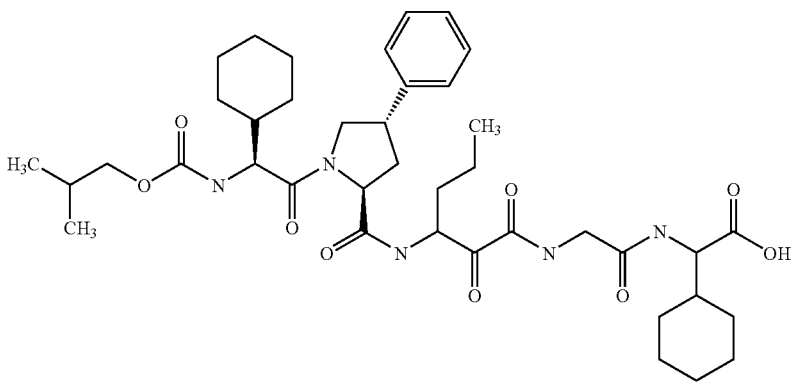 | 753.9443 |
| 83 | 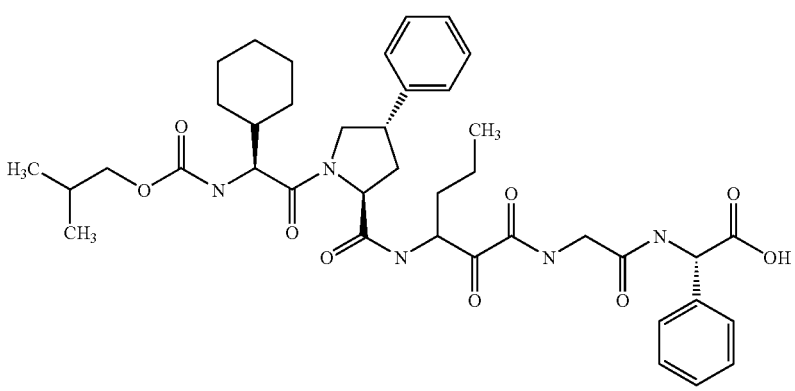 | 747.8965 |

TABLE 2-continued

| Ex. # | STRUCTURE | molecular weight |
|---|---|---|
| 84 | 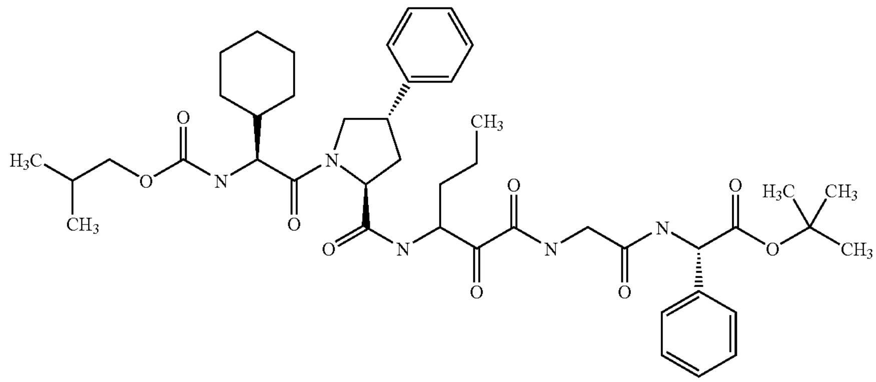 | 804.0049 |
| 85 | 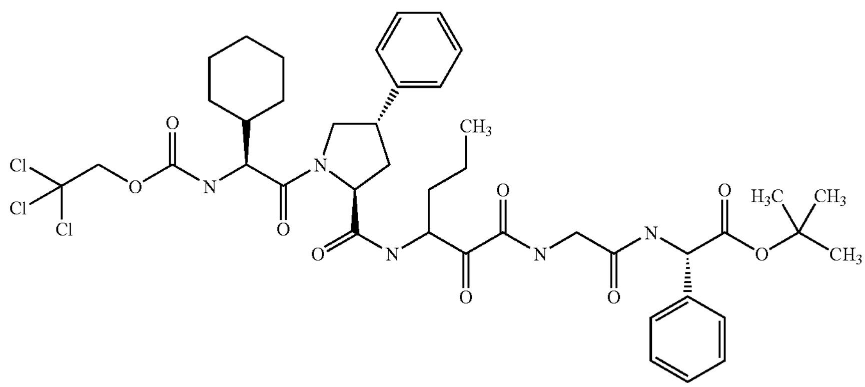 | 879.2858 |
| 86 | 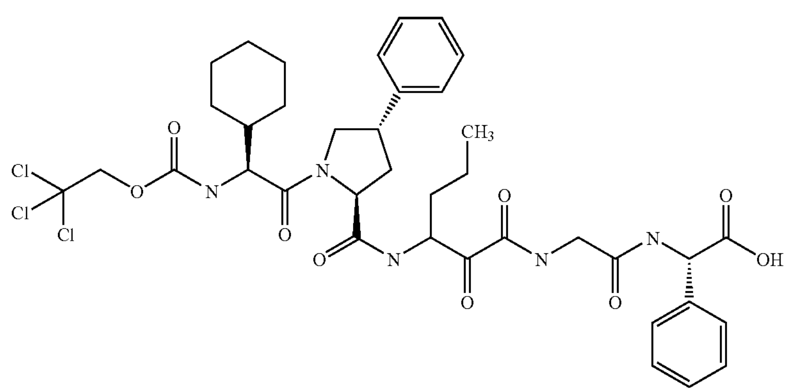 | 823.1774 |

TABLE 2-continued
| Ex. # | STRUCTURE | molecular weight |
|---|---|---|
| 87 | 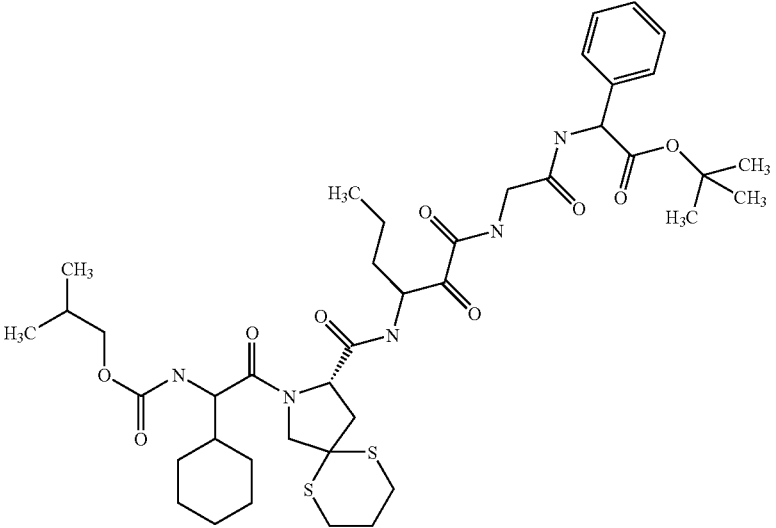 | 832.0994 |
| 88 | 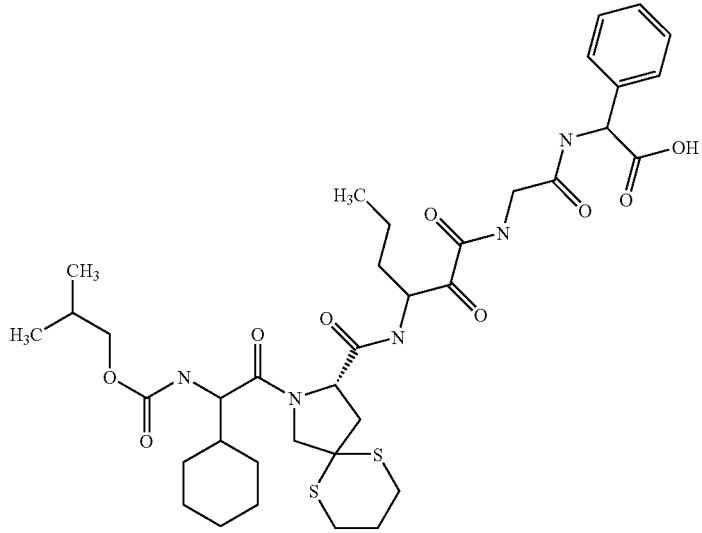 | 775.9911 |
| 89 | 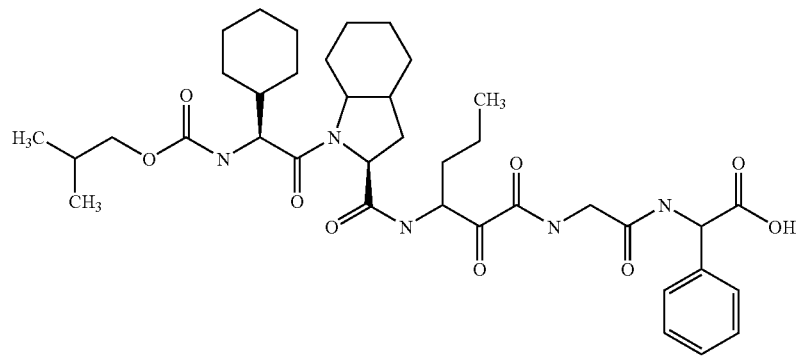 | 725.8901 |

TABLE 2-continued
| Ex. # | STRUCTURE | molecular weight |
|---|---|---|
| 90 | 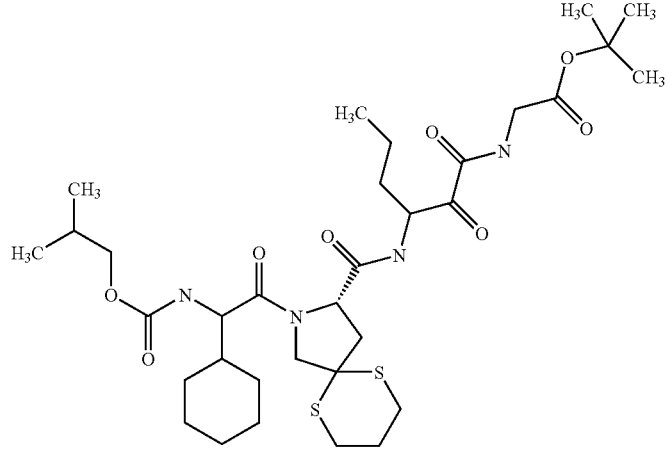 | 698.9483 |
| 91 | 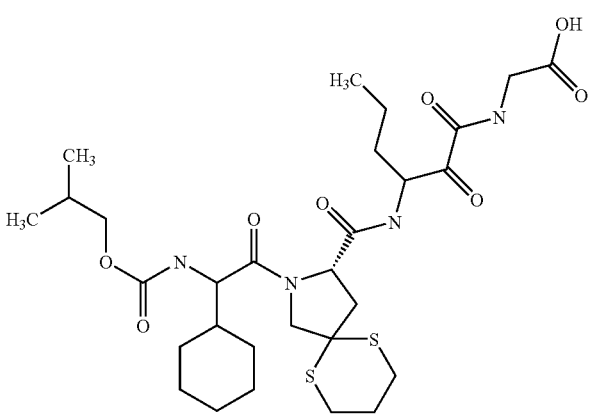 | 642.84 |
| 92 | 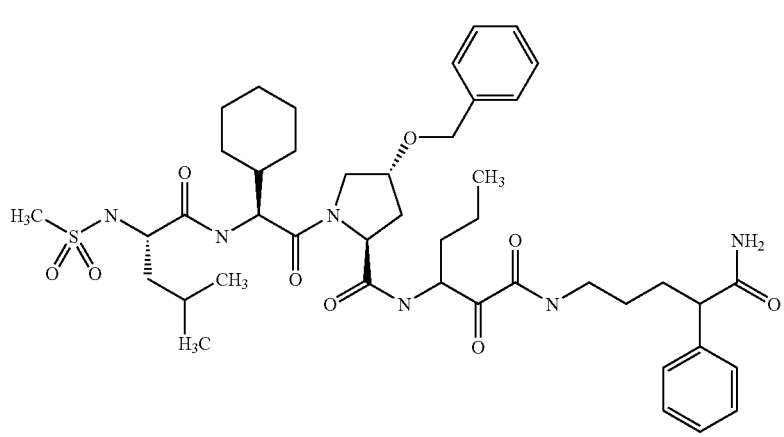 | 853.0995 |

TABLE 2-continued

| Ex. # | STRUCTURE | molecular weight |
|---|---|---|
| 93 | 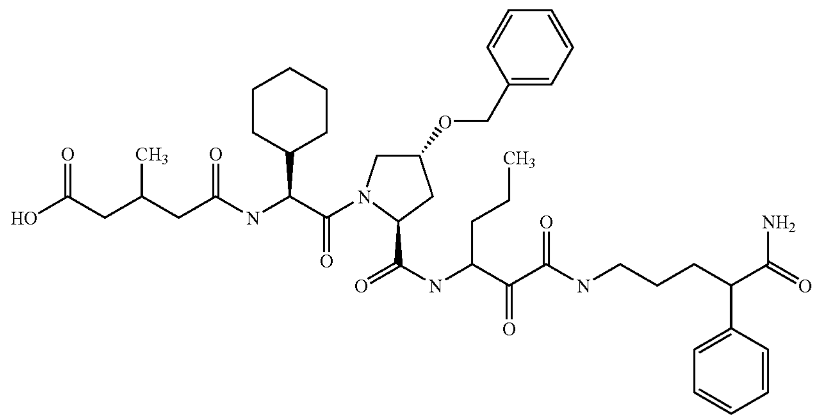 | 789.9778 |
| 94 | 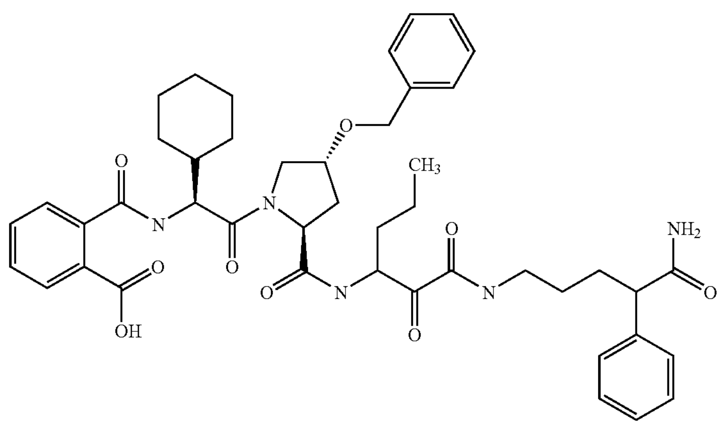 | 809.9682 |
| 95 | 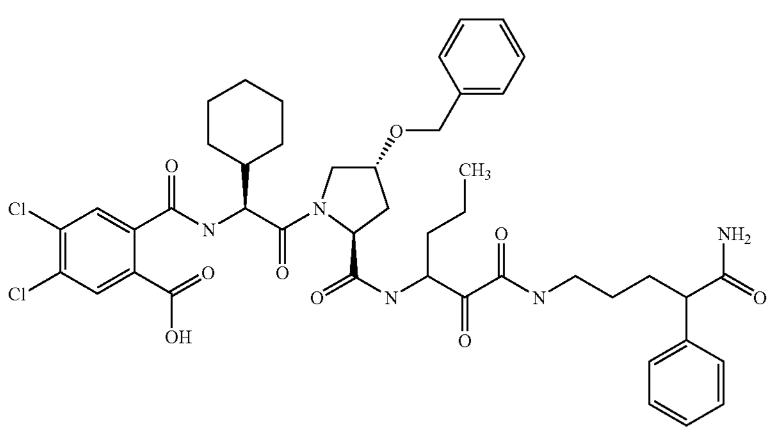 | 878.8583 |

TABLE 2-continued

| Ex. # | STRUCTURE | molecular weight |
|---|---|---|
| 96 | 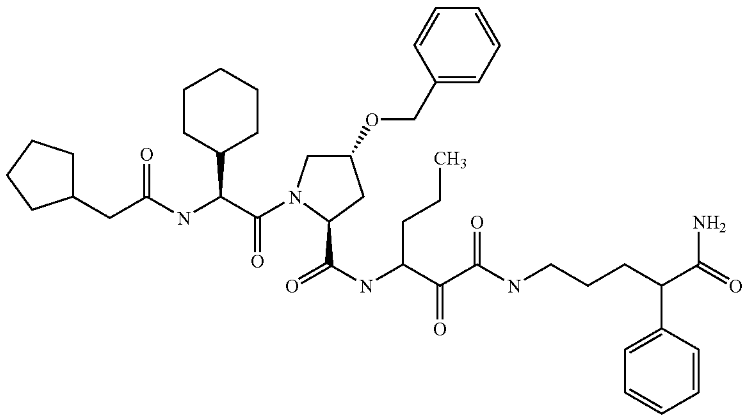 | 772.006 |
| 97 | 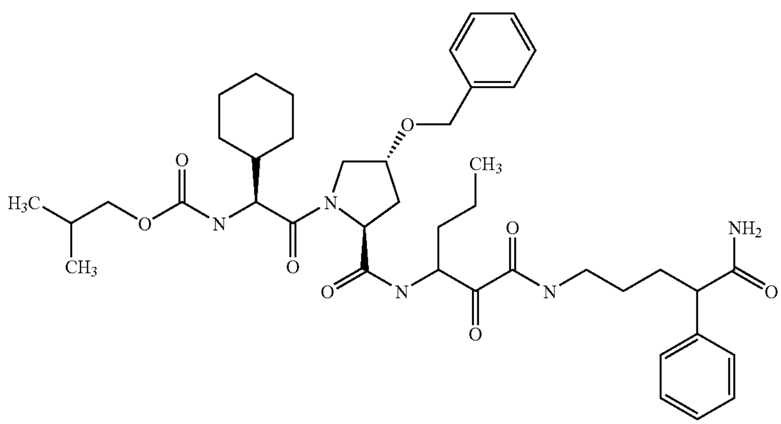 | 761.9672 |
| 98 | 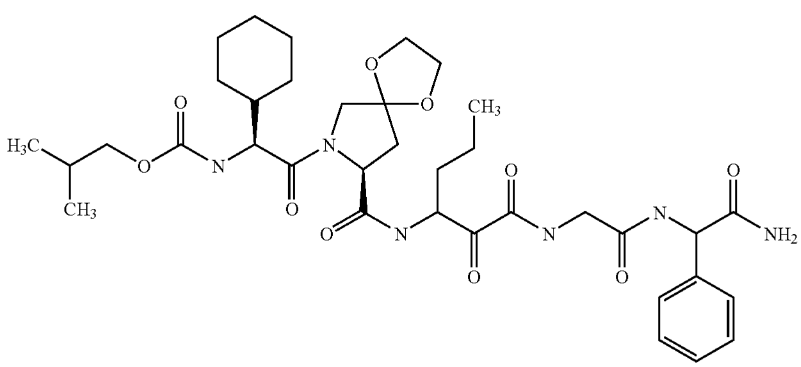 | 728.85 |

TABLE 2-continued

| Ex. # | STRUCTURE | molecular weight |
|---|---|---|
| 99 | 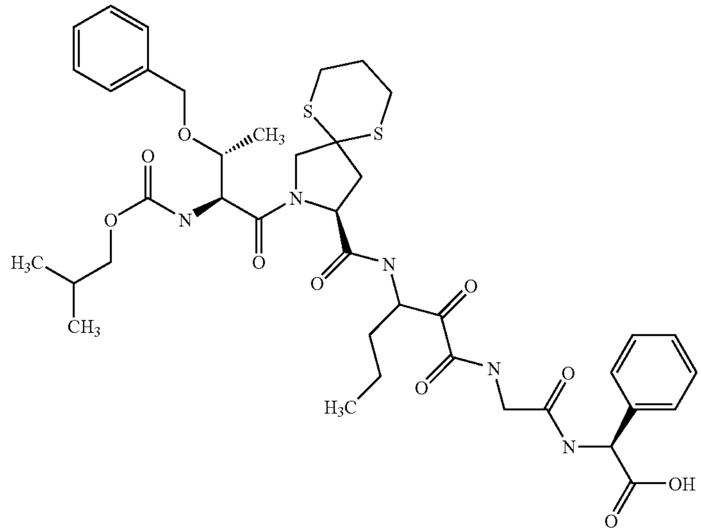 | 828.0239 |
| 100 | 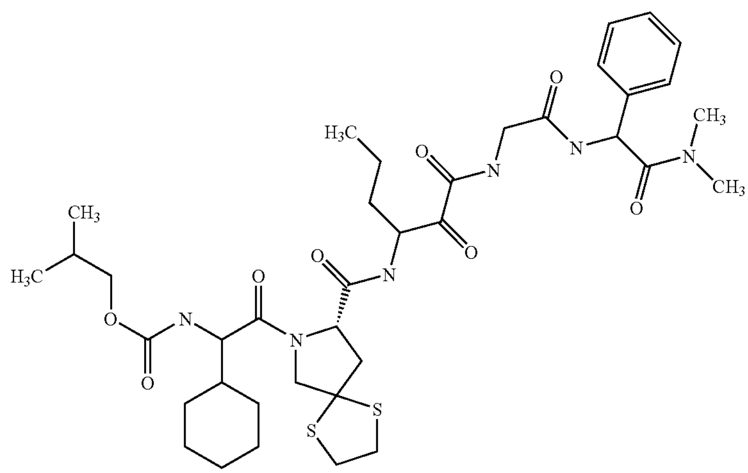 | 789.0334 |
| 101 | 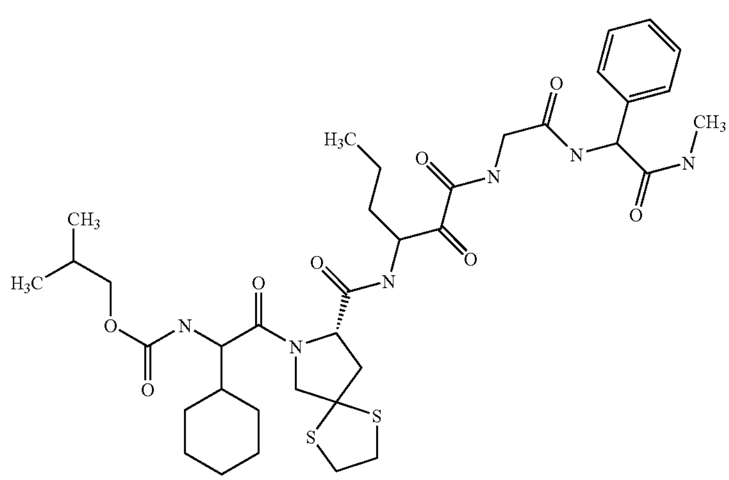 | 775.0063 |

TABLE 2-continued
| Ex. # | STRUCTURE | molecular weight |
|---|---|---|
| 102 | 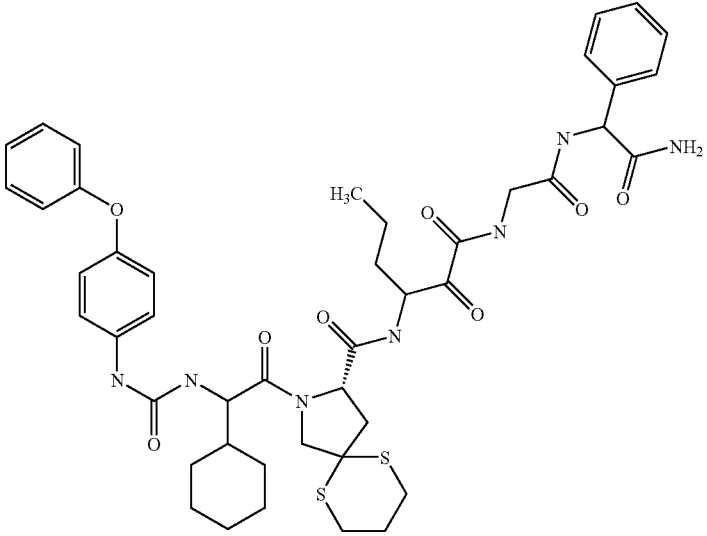 | 886.1102 |
| 103 | 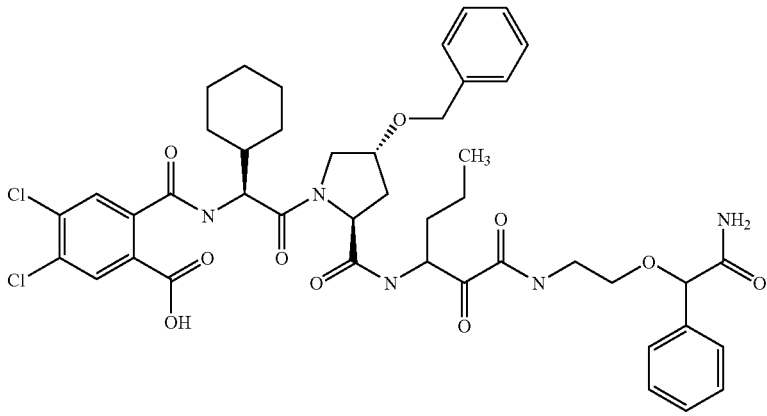 | 880.8306 |
| 104 | 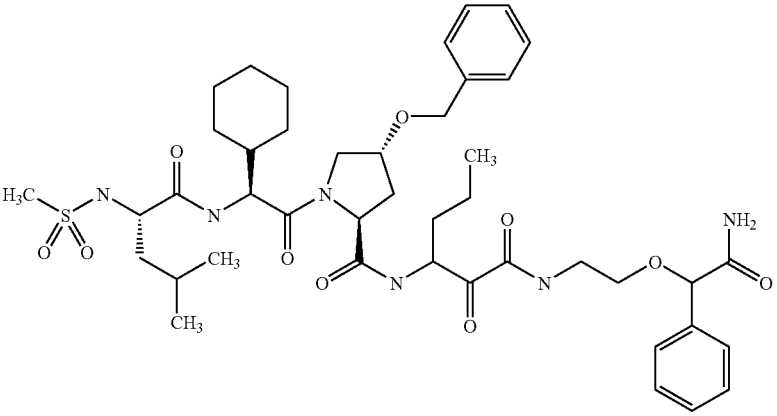 | 855.0718 |

TABLE 2-continued

| Ex. # | STRUCTURE | molecular weight |
|---|---|---|
| 105 | 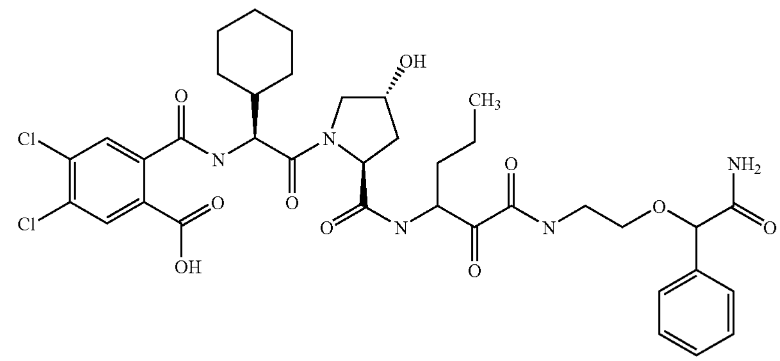 | 790.7047 |
| 106 | 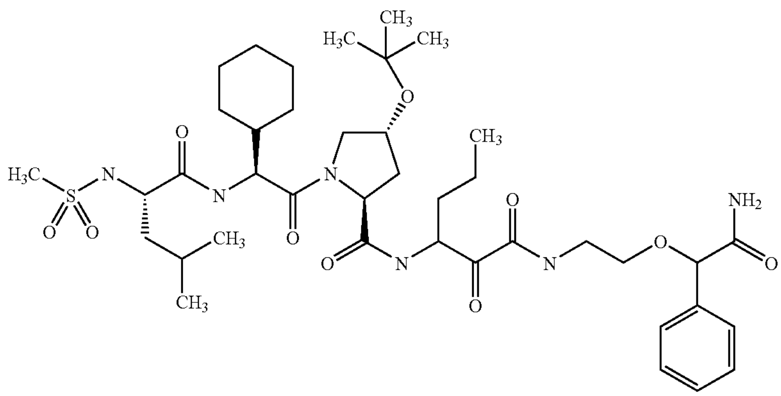 | 821.0543 |
| 107 | 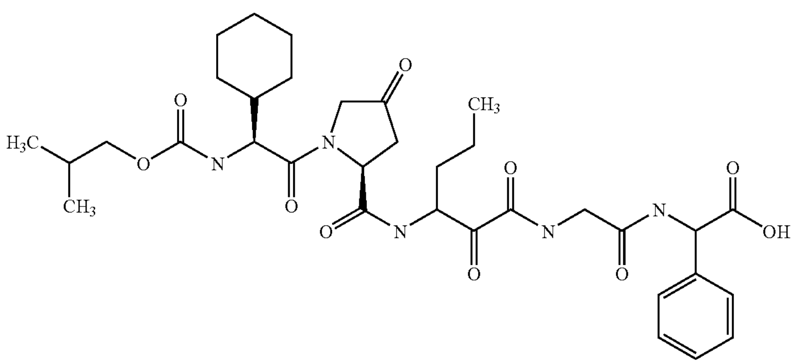 | 685.7812 |
| 108 | 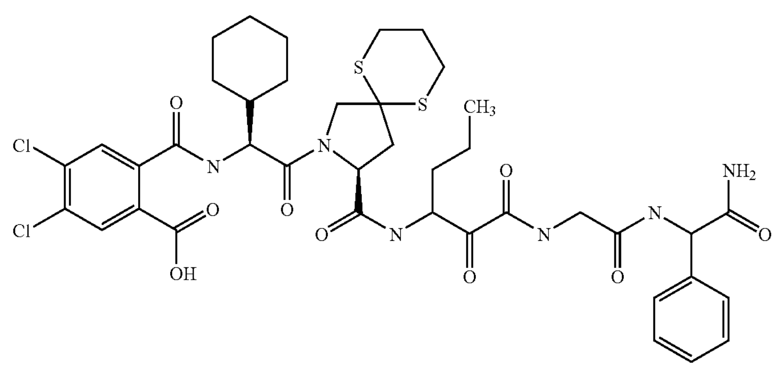 | 891.8973 |

TABLE 2-continued
| Ex. # | STRUCTURE | molecular weight |
|---|---|---|
| 109 | 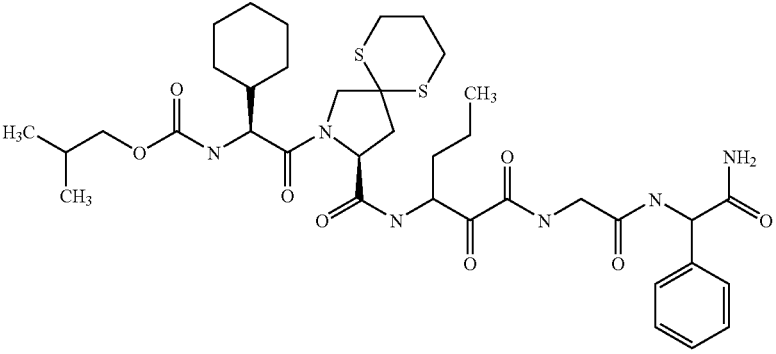 | 775.0063 |
| 110 | 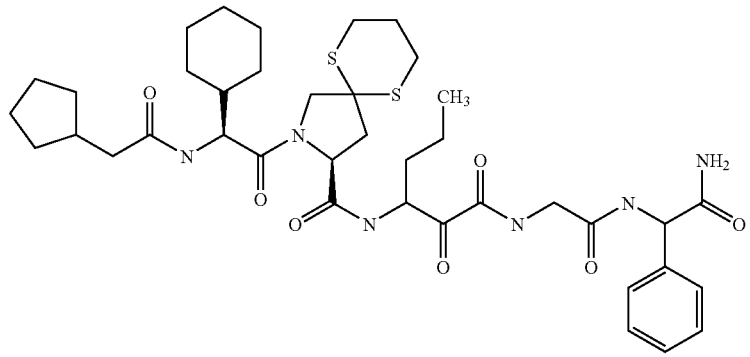 | 785.0452 |
| 111 | 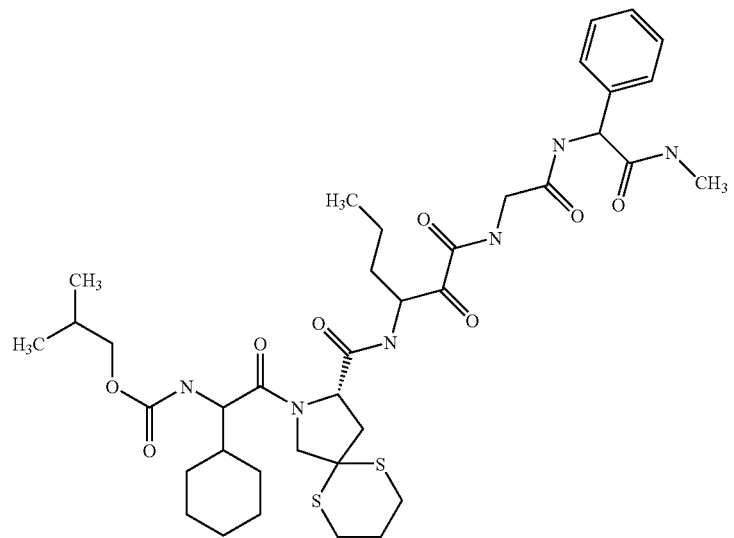 | 789.0334 |

TABLE 2-continued
| Ex. # | STRUCTURE | molecular weight |
|---|---|---|
| 112 | 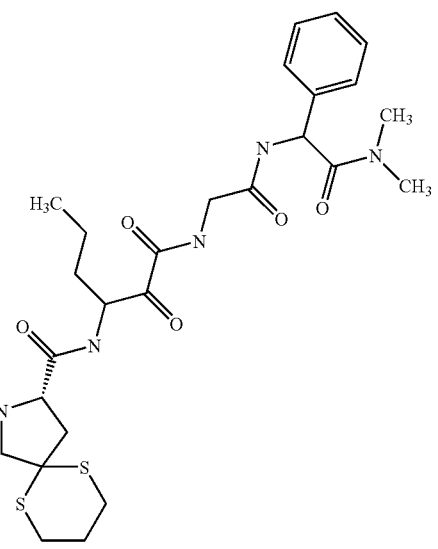 | 803.0605 |
| 113 | 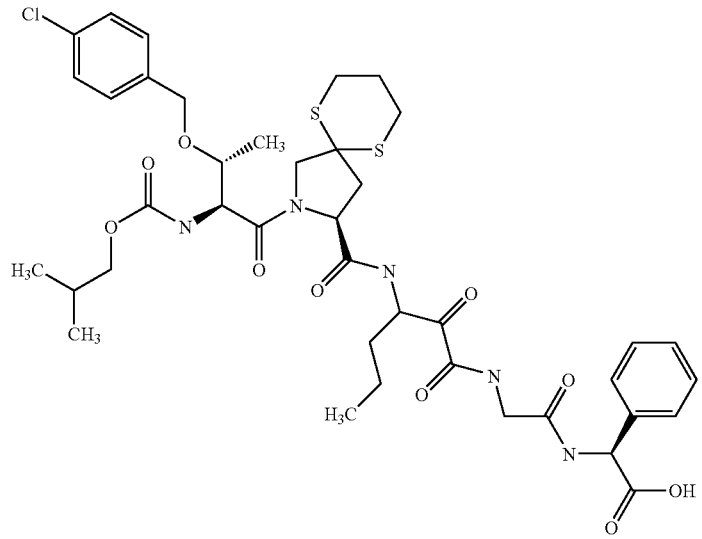 | 862.4689 |

TABLE 2-continued

| Ex. # | STRUCTURE | molecular weight |
|---|---|---|
| 114 | 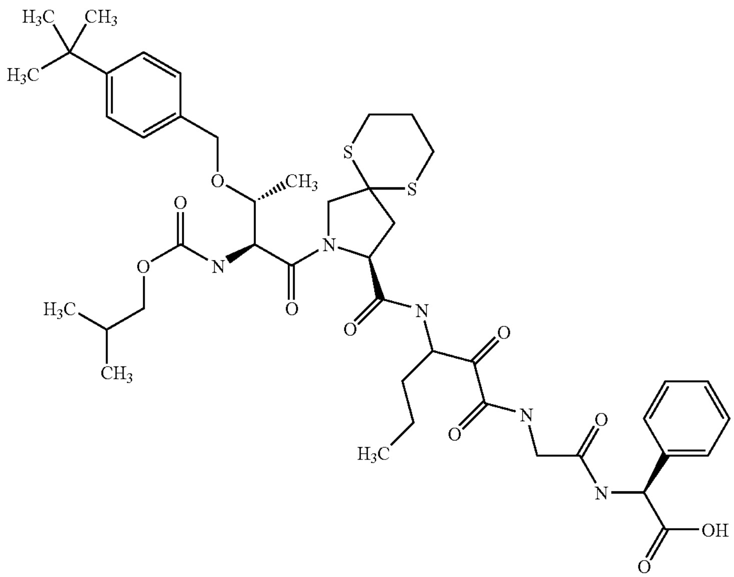 | 884.1323 |
| 115 | 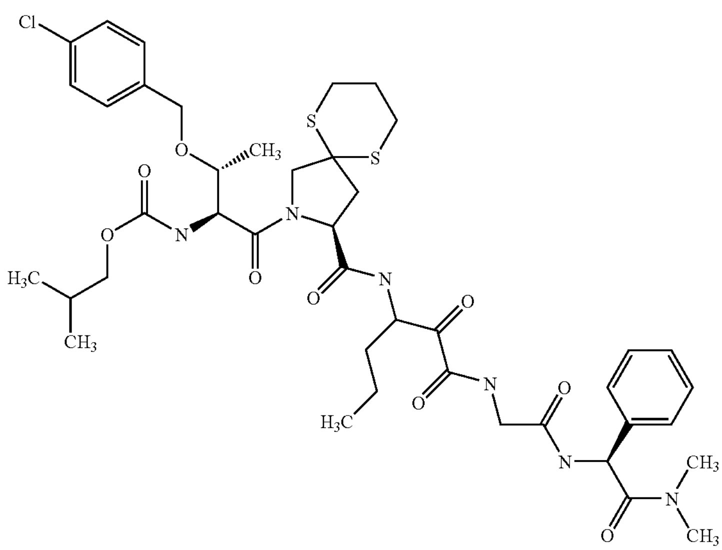 | 889.5384 |
| 116 | 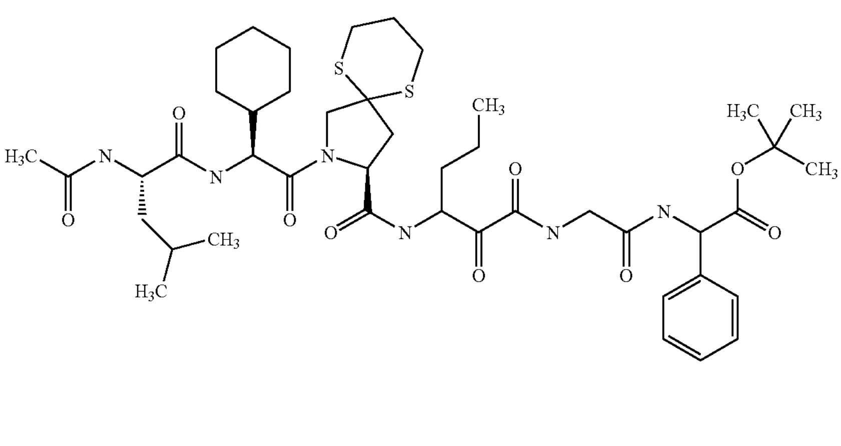 | 887.1794 |

TABLE 2-continued

| Ex. # | STRUCTURE | molecular weight |
|---|---|---|
| 117 | 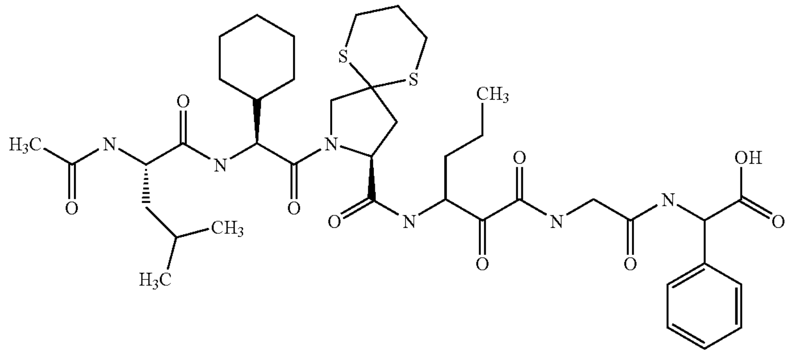 | 831.071 |
| 118 | 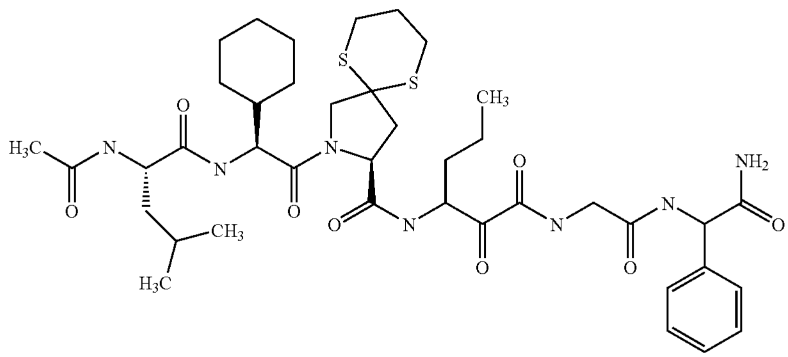 | 830.0863 |
| 119 | 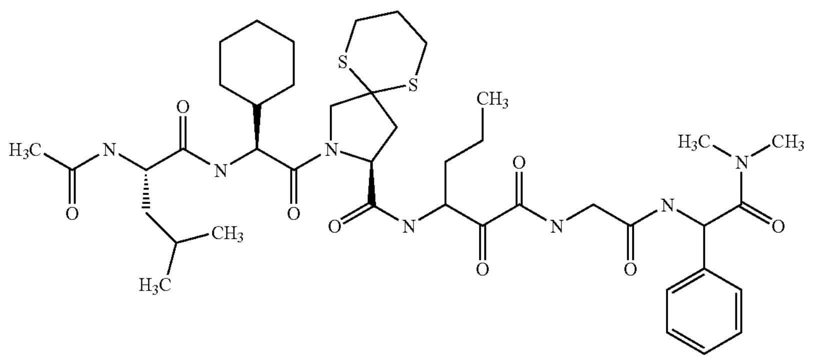 | 858.1405 |
| 120 | 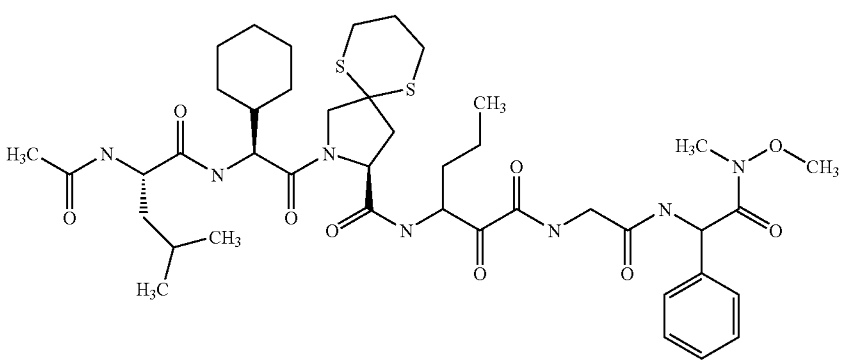 | 874.1399 |

TABLE 2-continued
| Ex. # | STRUCTURE | molecular weight |
|---|---|---|
| 121 | 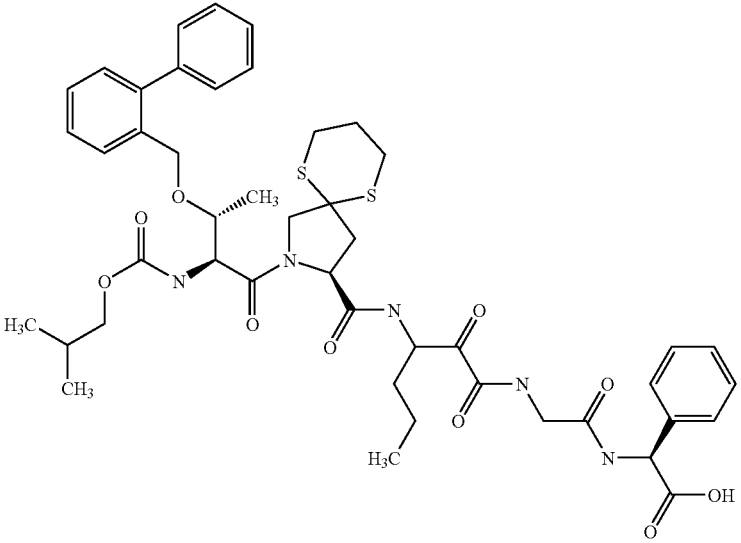 | 904.1227 |
| 122 | 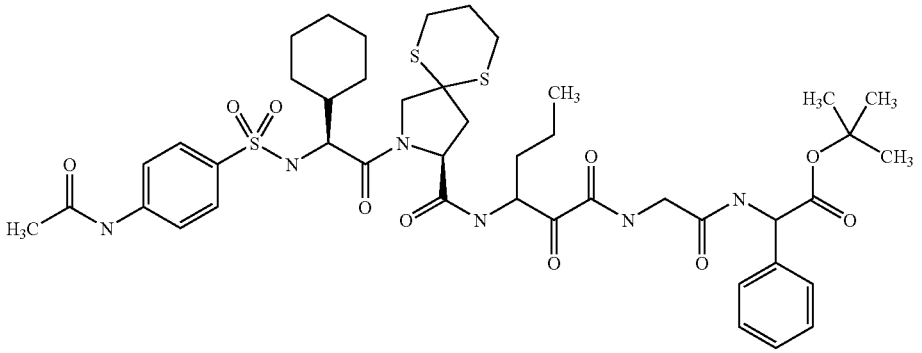 | 929.195 |
| 123 | 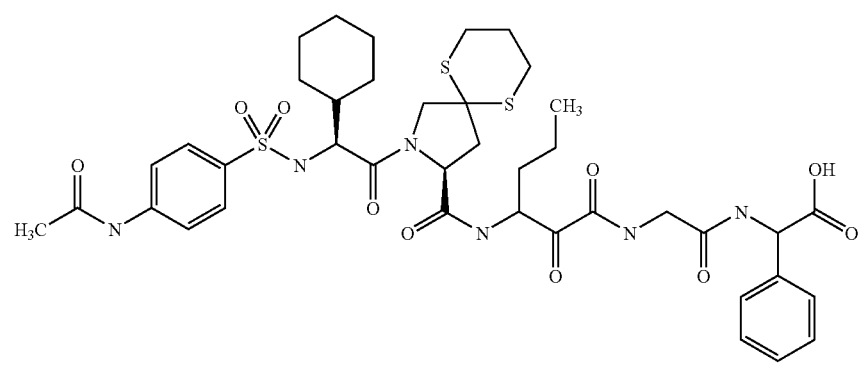 | 873.0867 |

TABLE 2-continued
| Ex. # | STRUCTURE | molecular weight |
|---|---|---|
| 124 | 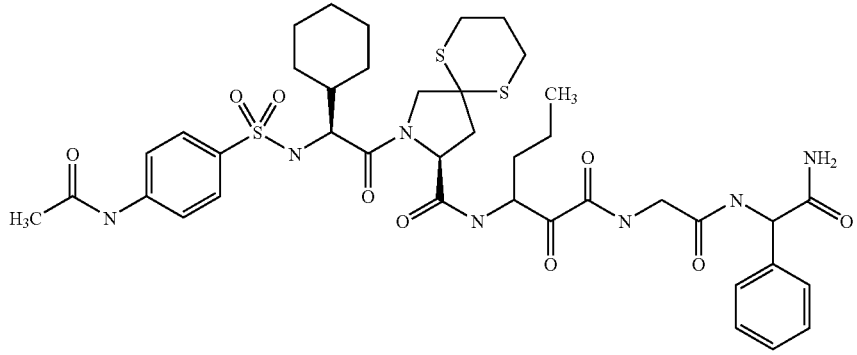 | 872.1019 |
| 125 | 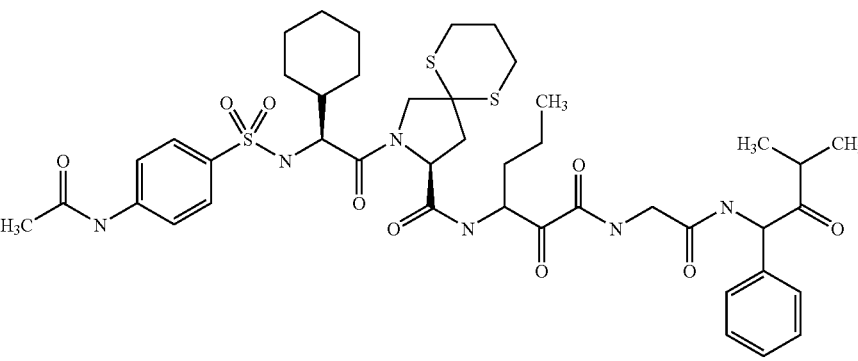 | 900.1561 |
| 126 | 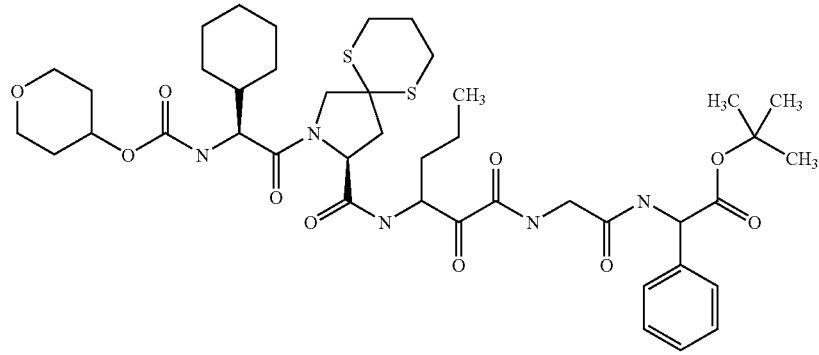 | 860.11 |
| 127 | 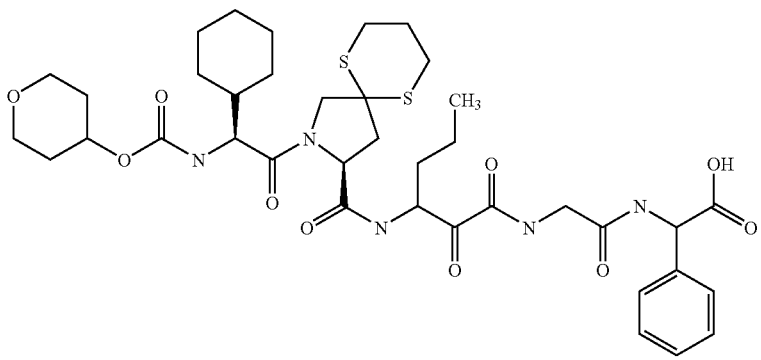 | 804.0016 |

TABLE 2-continued

| Ex. # | STRUCTURE | molecular weight |
|---|---|---|
| 128 | 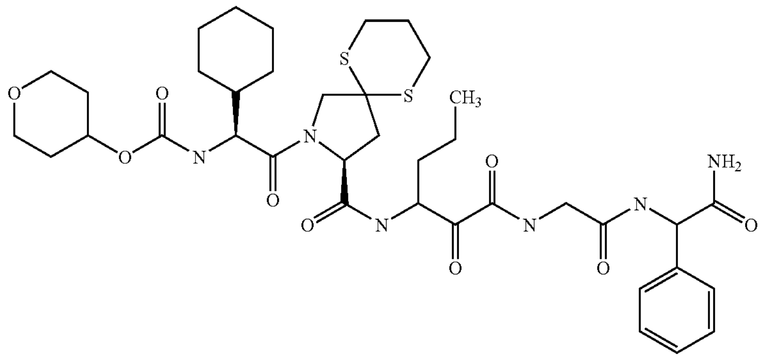 | 803.0169 |
| 129 | 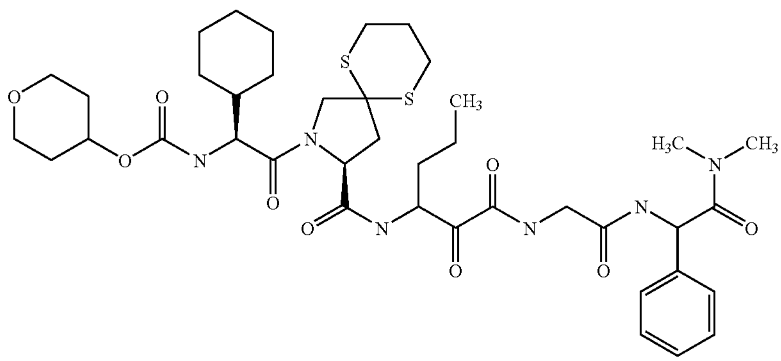 | 831.071 |
| 130 | 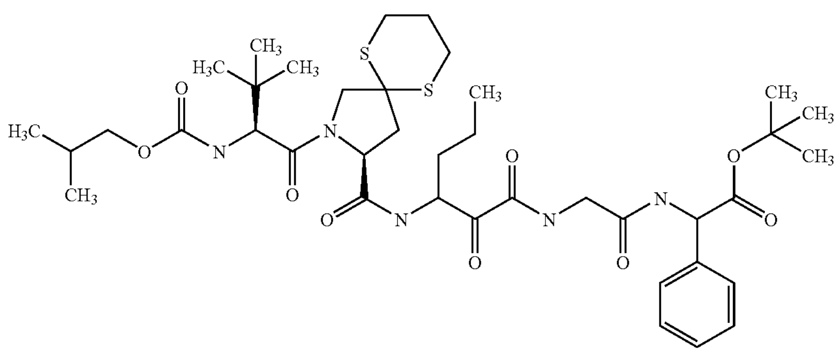 | 806.0612 |
| 131 | 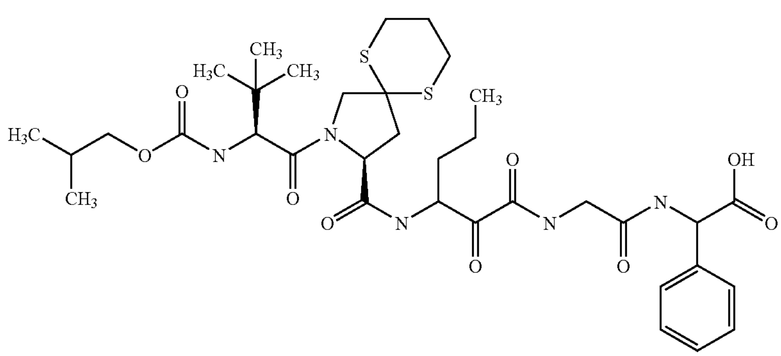 | 749.9528 |

TABLE 2-continued
| Ex. # | STRUCTURE | molecular weight |
|---|---|---|
| 132 | 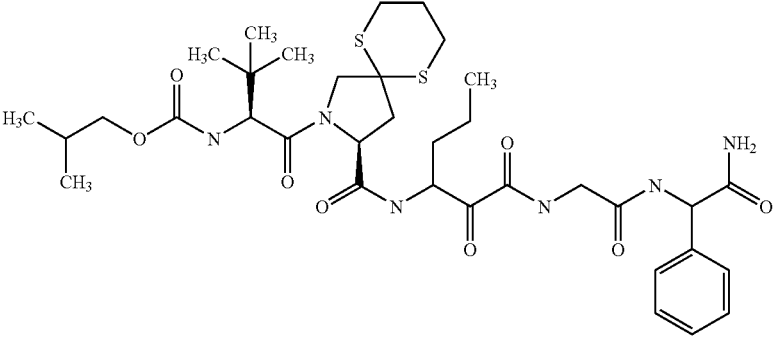 | 748.9681 |
| 133 | 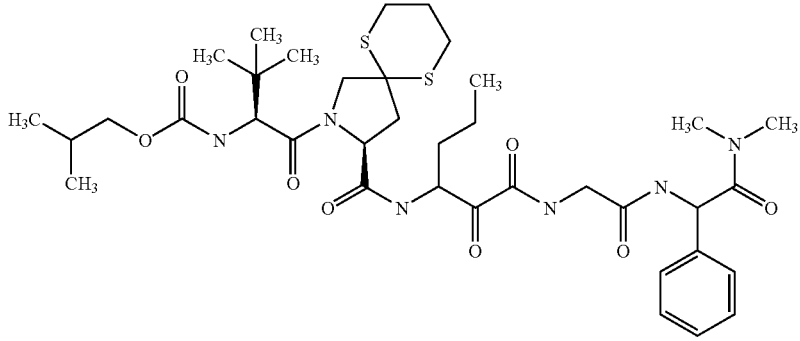 | 777.0223 |
| 134 | 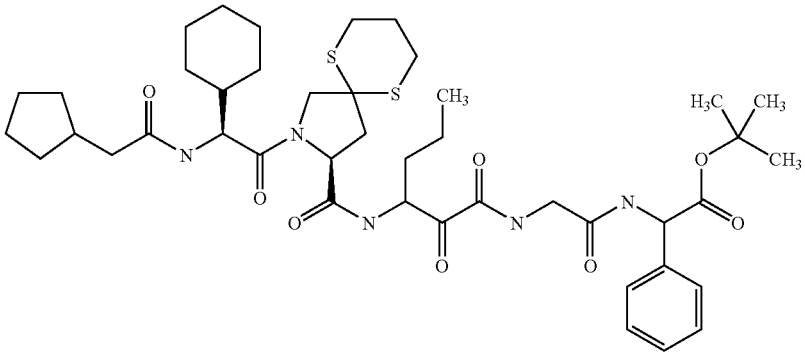 | 842.1382 |
| 135 | 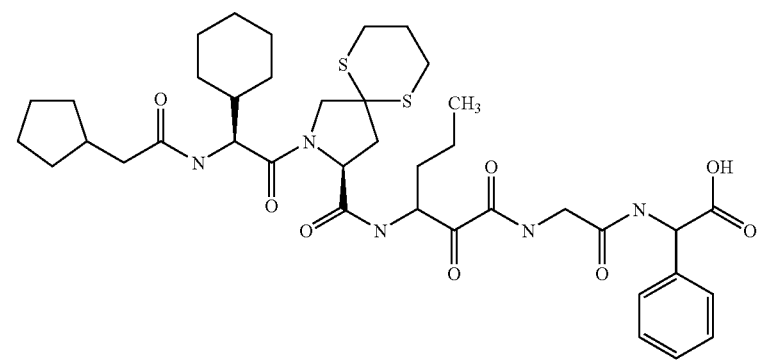 | 786.0299 |

TABLE 2-continued

| Ex. # | STRUCTURE | molecular weight |
|---|---|---|
| 136 | 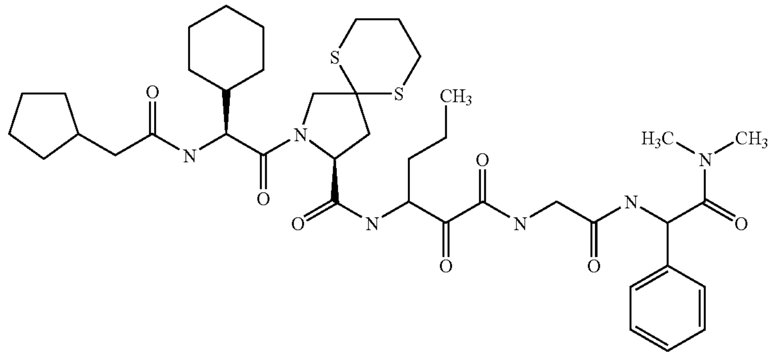 | 813.0994 |
| 137 | 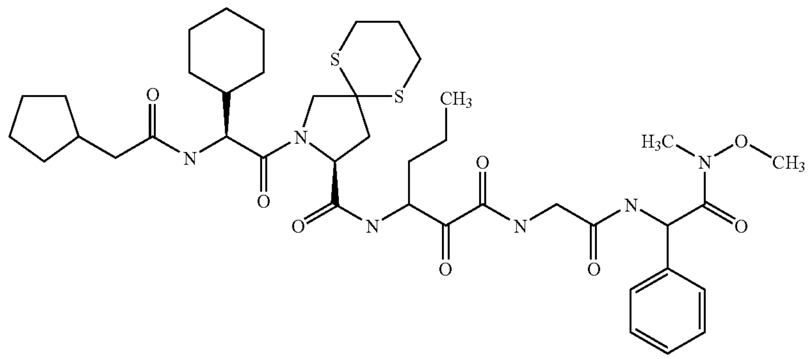 | 829.0988 |
| 138 | 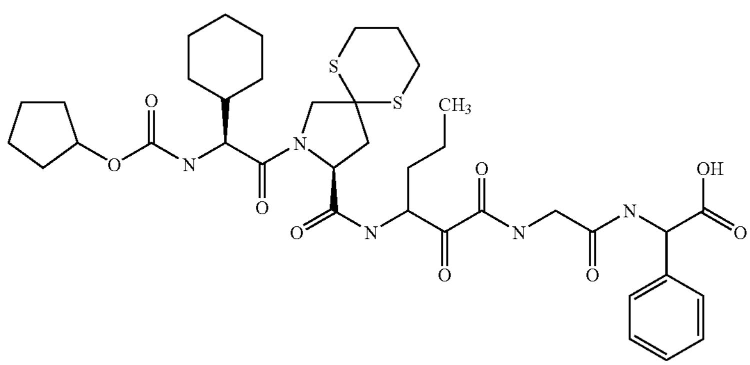 | 788.0022 |
| 139 | 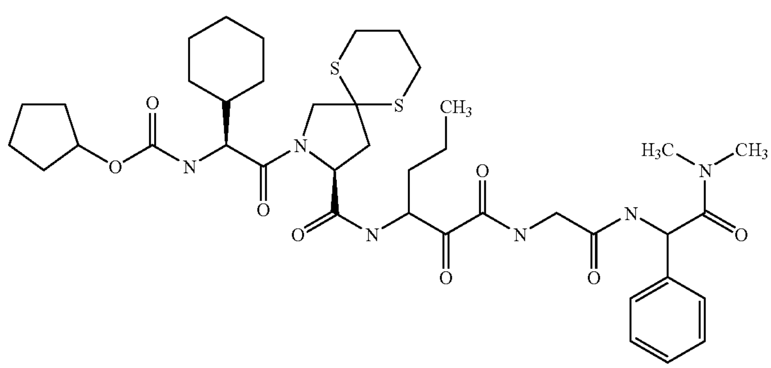 | 815.0717 |

TABLE 2-continued
| Ex. # | STRUCTURE | molecular weight |
| --- | --- | --- |
| 140 | 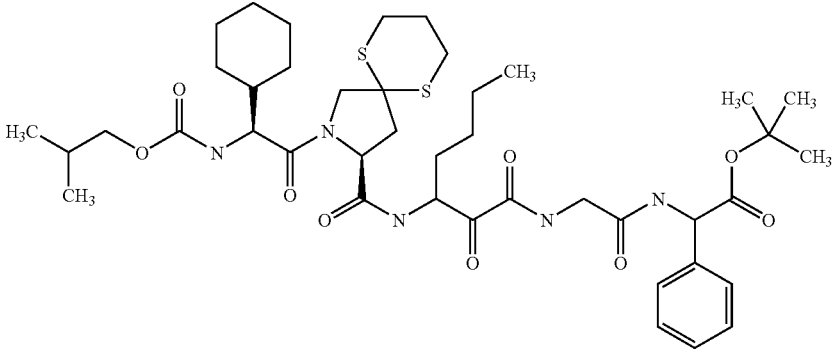 | 846.1265 |
| 141 | 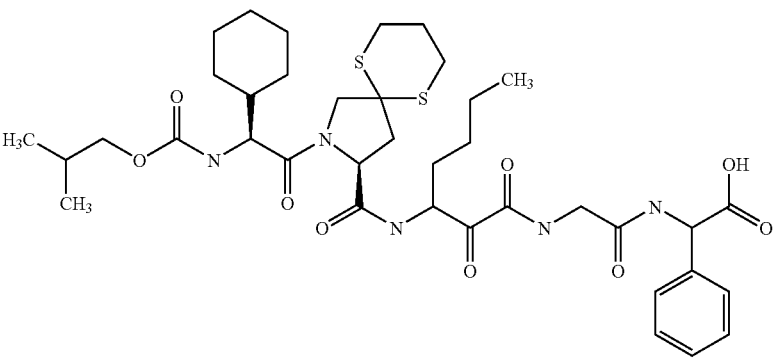 | 790.0181 |
| 142 | 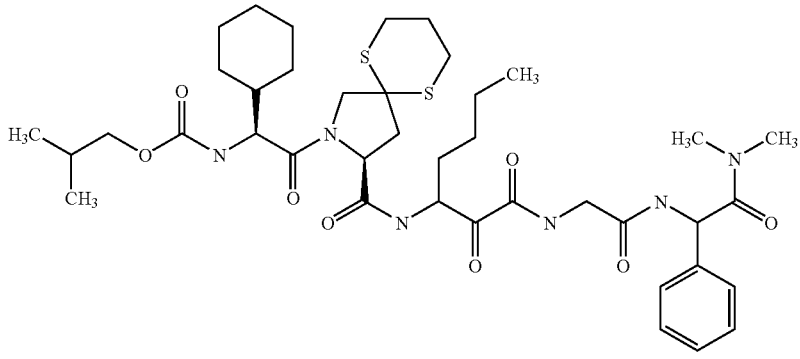 | 817.0876 |
| 143 | 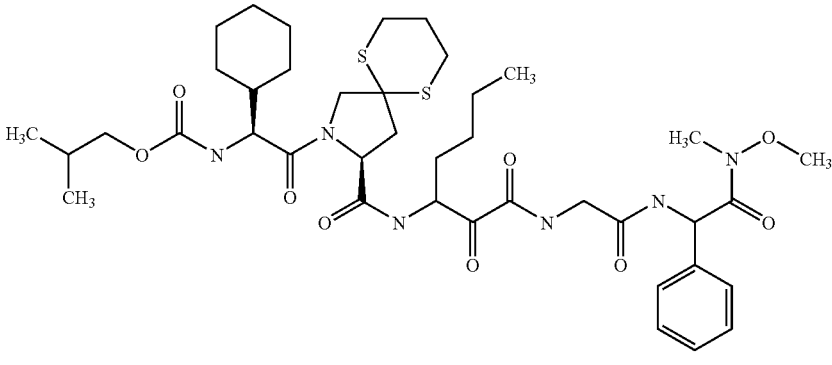 | 833.087 |

TABLE 2-continued

| Ex. # | STRUCTURE | molecular weight |
|---|---|---|
| 144 | 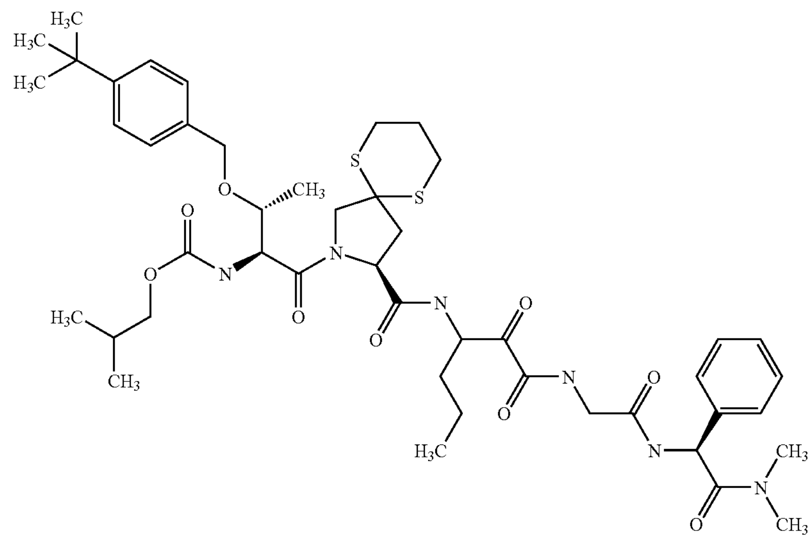 | 911.2017 |
| 145 | 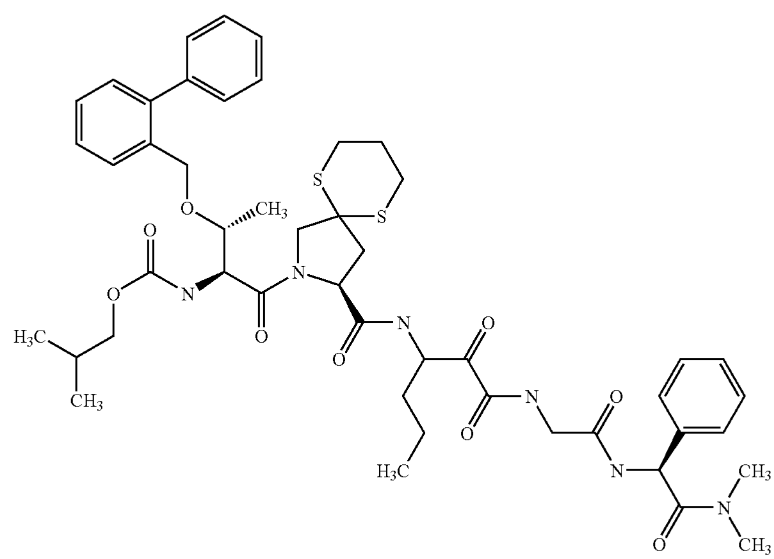 | 931.1921 |
| 146 | 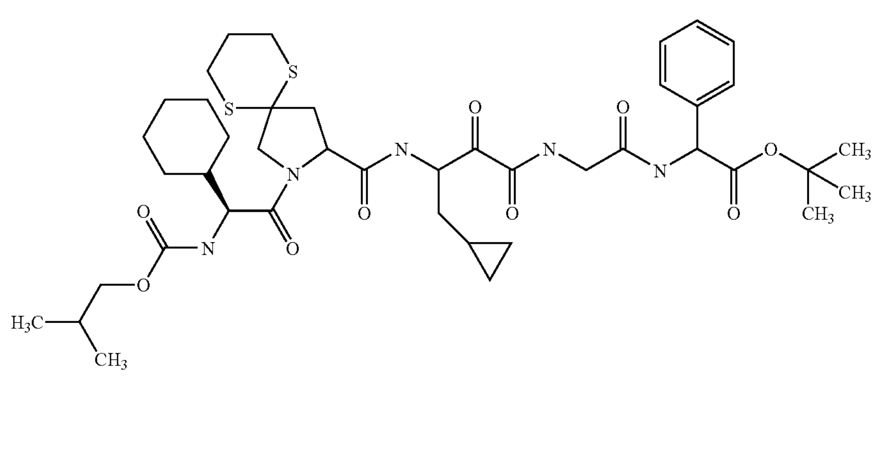 | 844.1106 |

TABLE 2-continued

| Ex. # | STRUCTURE | molecular weight |
|---|---|---|
| 147 | 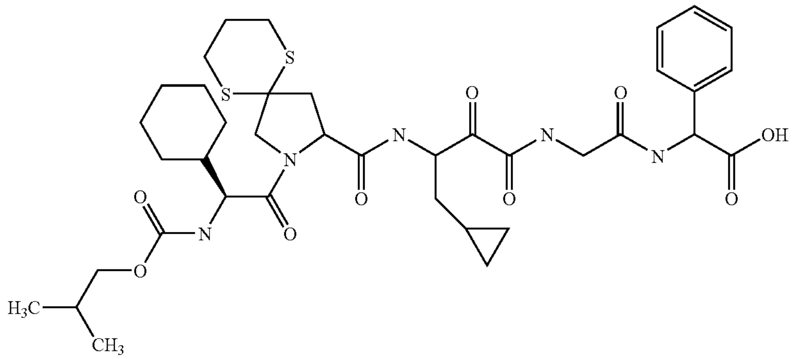 | 788.0022 |
| 148 | 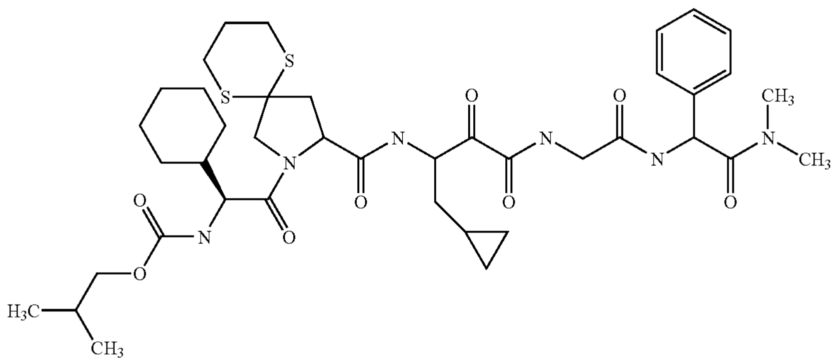 | 815.0717 |
| 149 | 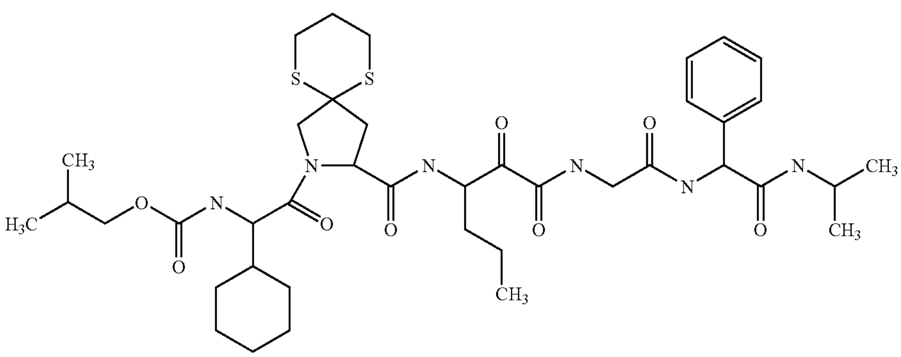 | 817.0876 |
| 150 | 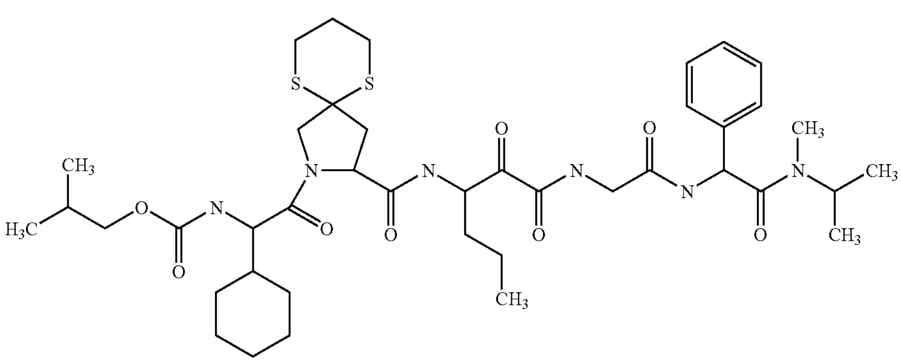 | 831.1147 |

TABLE 2-continued

| Ex. # | STRUCTURE | molecular weight |
|---|---|---|
| 151 | 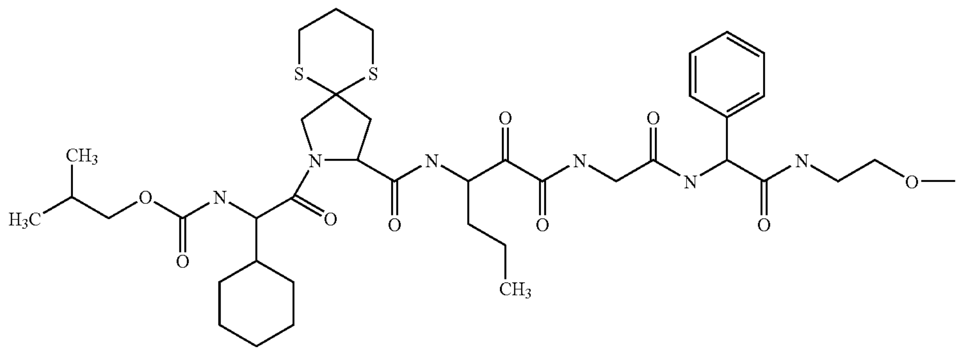 | 819.0599 |
| 152 | 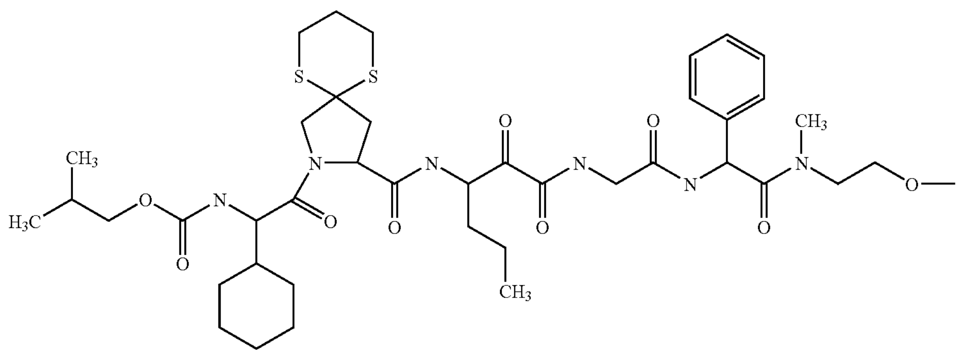 | 833.087 |
| 153 | 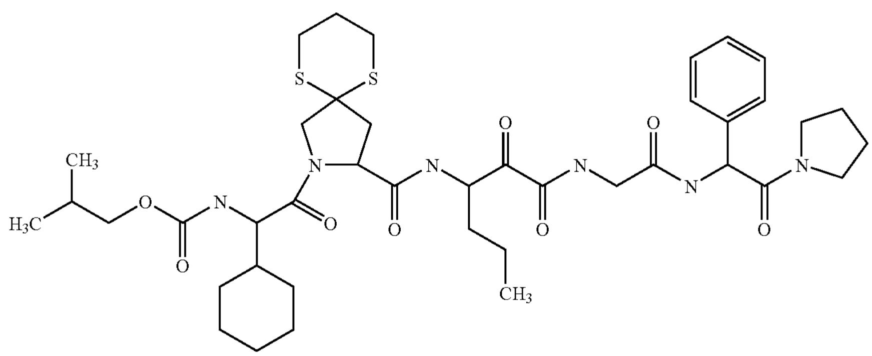 | 829.0988 |
| 154 | 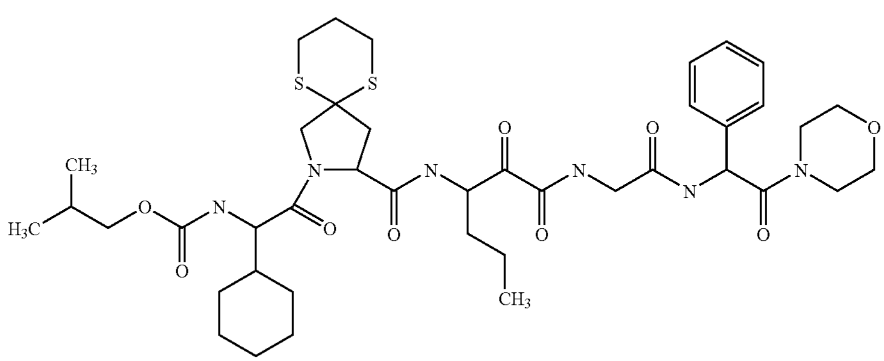 | 845.0981 |

TABLE 2-continued
| Ex. # | STRUCTURE | molecular weight |
|---|---|---|
| 155 | 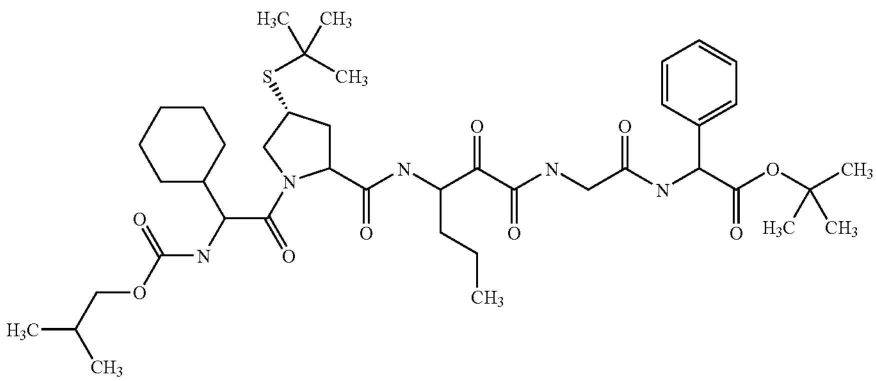 | 816.0784 |
| 156 | 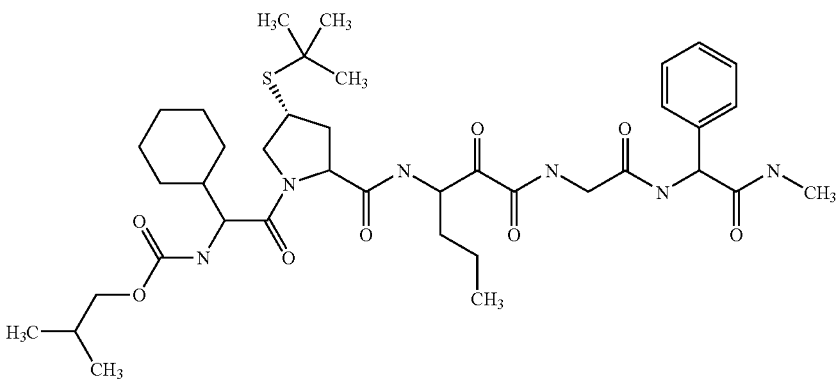 | 773.0125 |
| 157 | 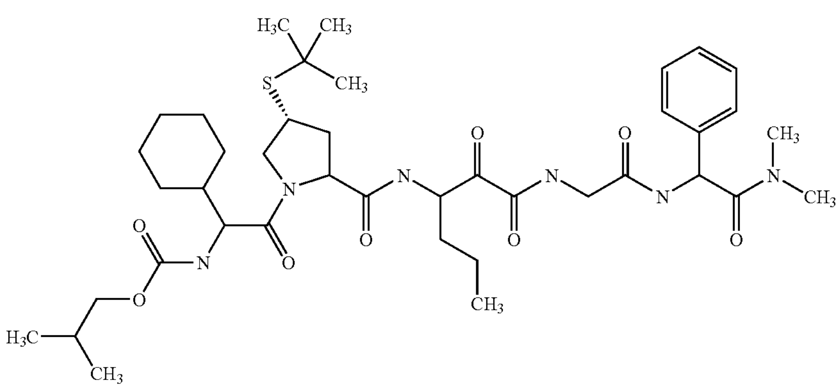 | 787.0396 |

TABLE 2-continued

| Ex. # | STRUCTURE | molecular weight |
|---|---|---|
| 158 | 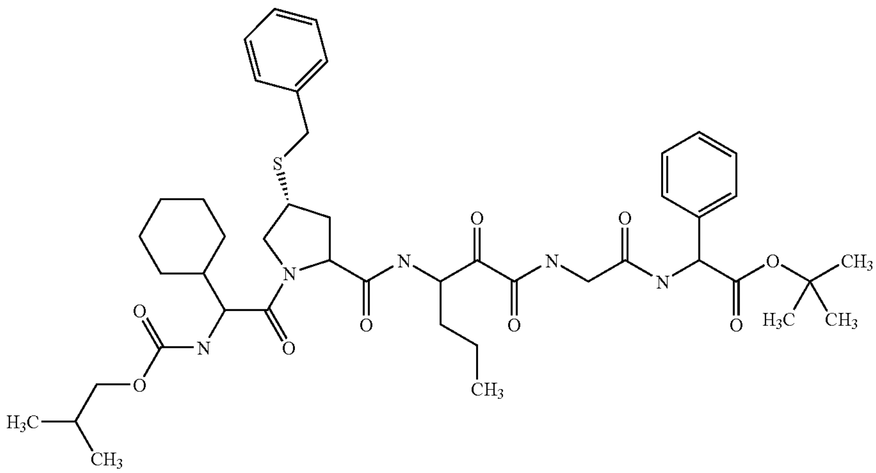 | 850.0959 |
| 159 | 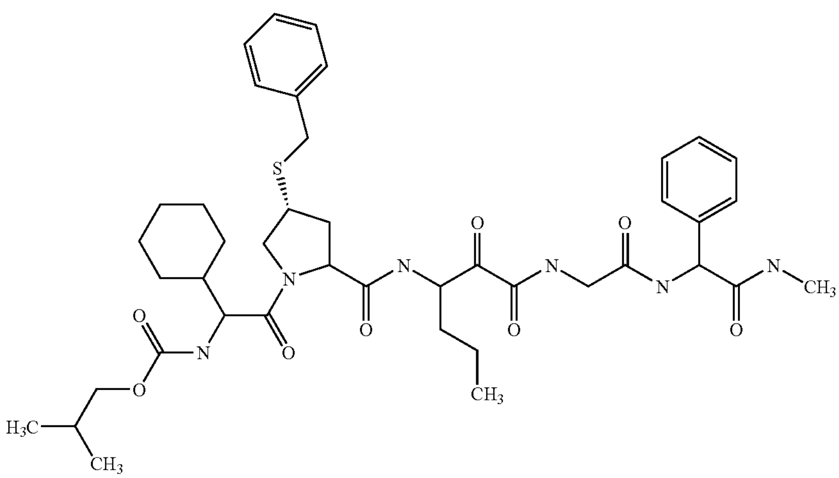 | 807.03 |
| 160 | 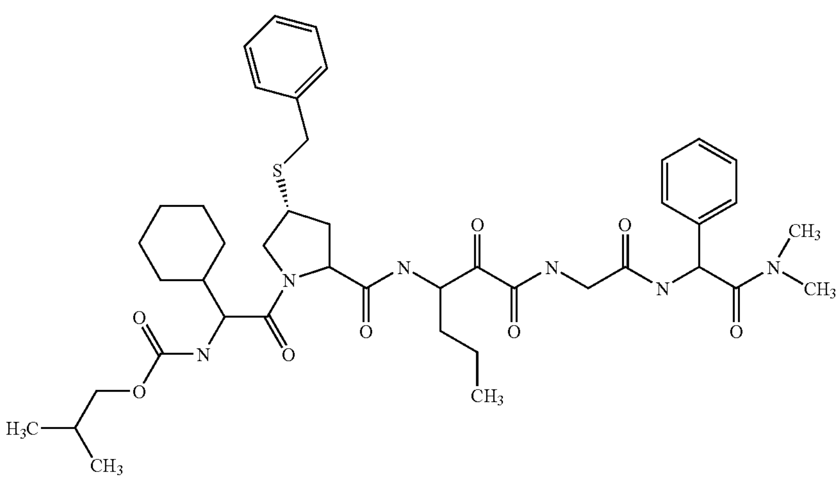 | 821.0571 |

TABLE 2-continued

| Ex. # | STRUCTURE | molecular weight |
|---|---|---|
| 161 | 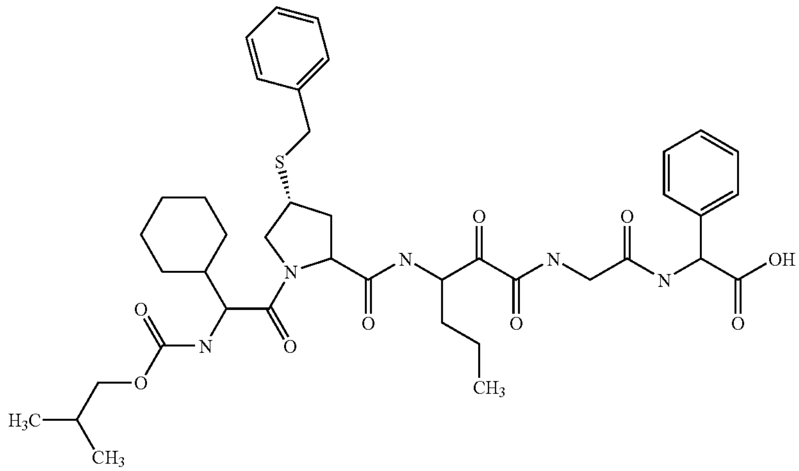 | 793.9876 |
| 162 | 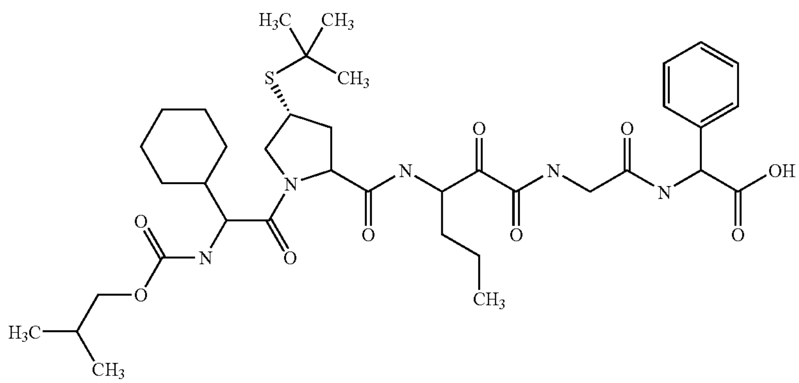 | 759.9701 |
| 163 | 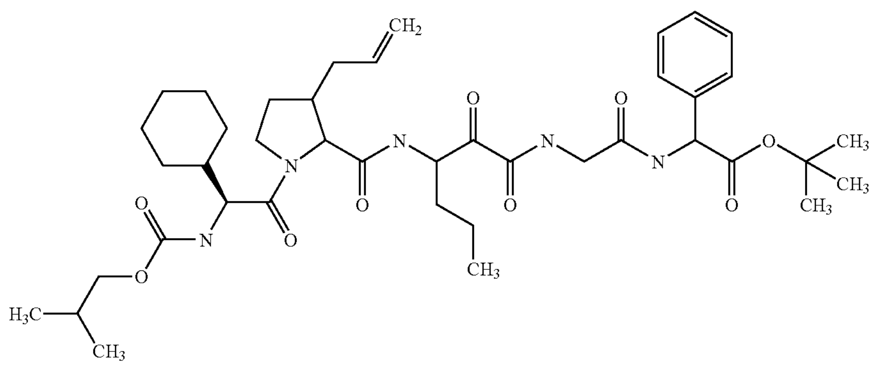 | 767.9714 |
| 164 | 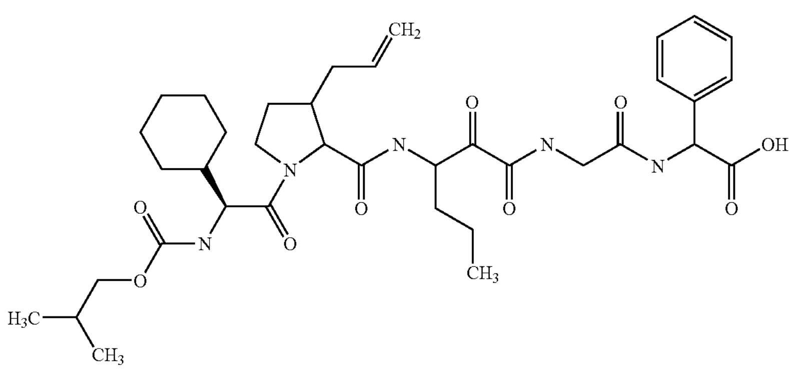 | 711.863 |

TABLE 2-continued

| Ex. # | STRUCTURE | molecular weight |
|---|---|---|
| 165 | 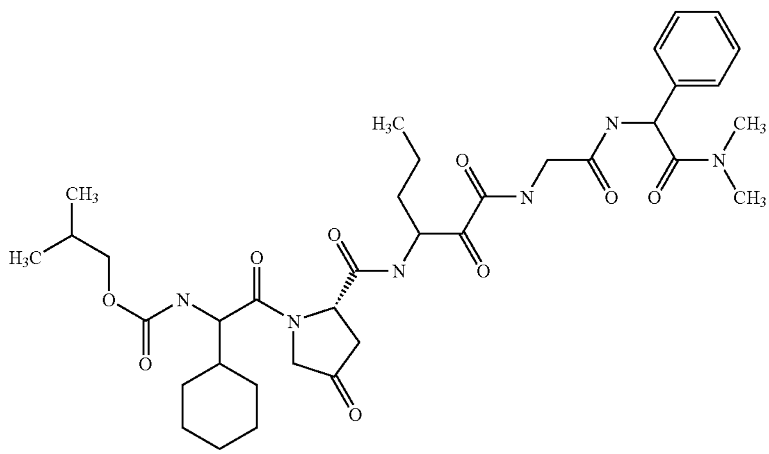 | 712.8506 |
| 166 | 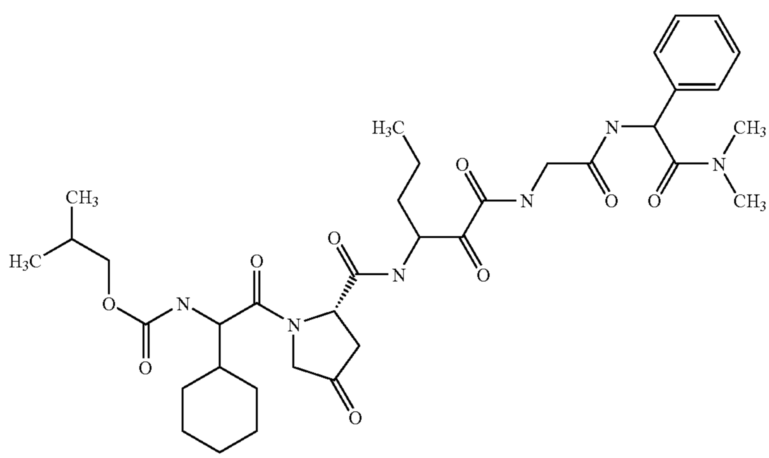 | 712.8506 |
| 167 | 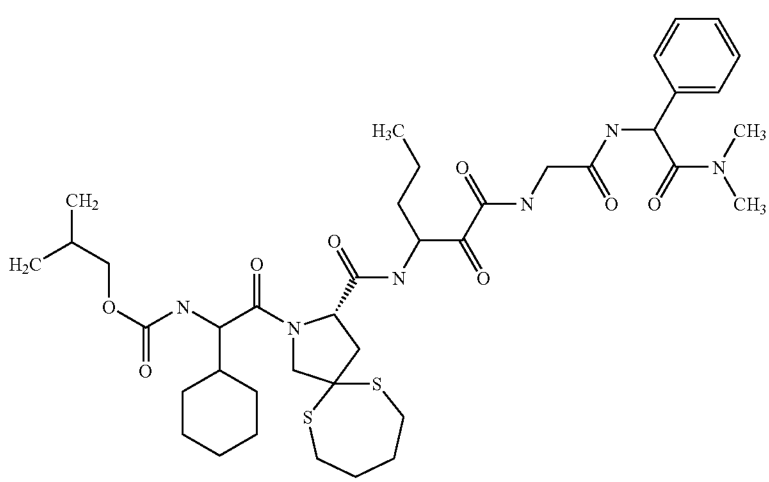 | 817.0876 |

TABLE 2-continued

| Ex. # | STRUCTURE | molecular weight |
|---|---|---|
| 168 | 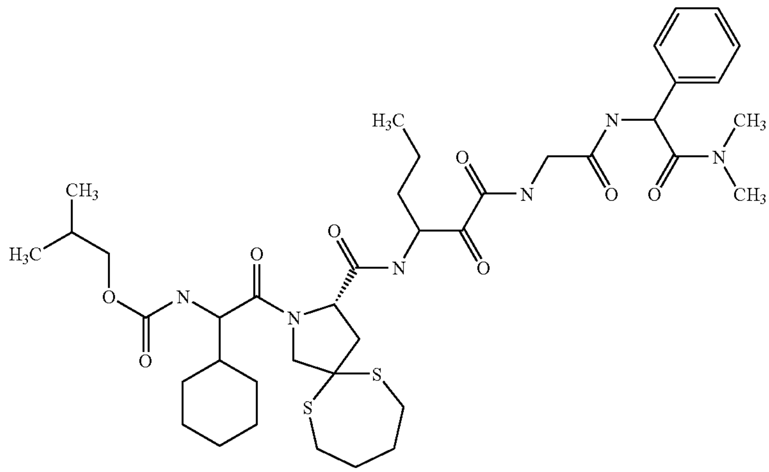 | 817.0876 |
| 169 | 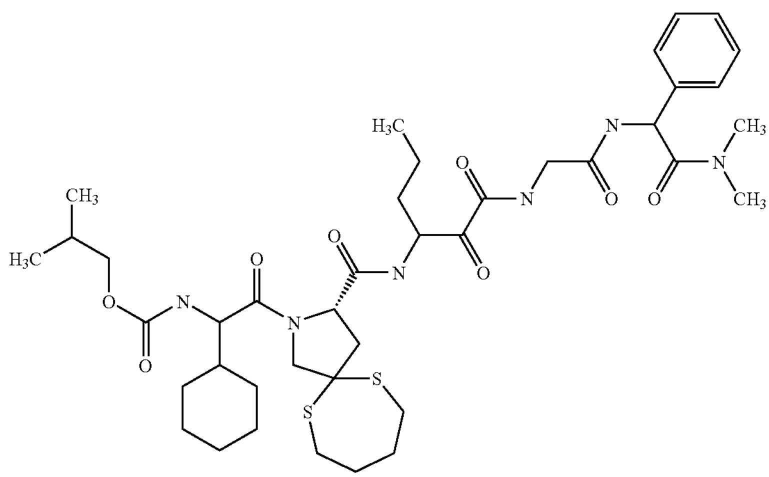 | 817.0876 |
| 170 | 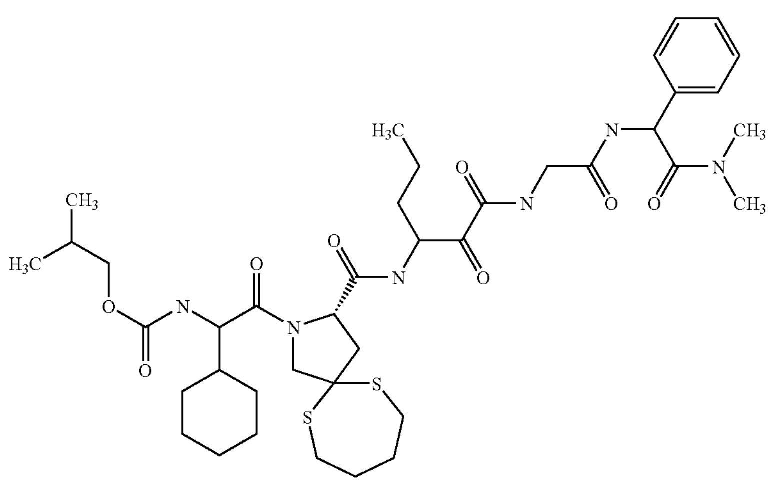 | 817.0876 |

TABLE 2-continued

| Ex. # | STRUCTURE | molecular weight |
|---|---|---|
| 171 | 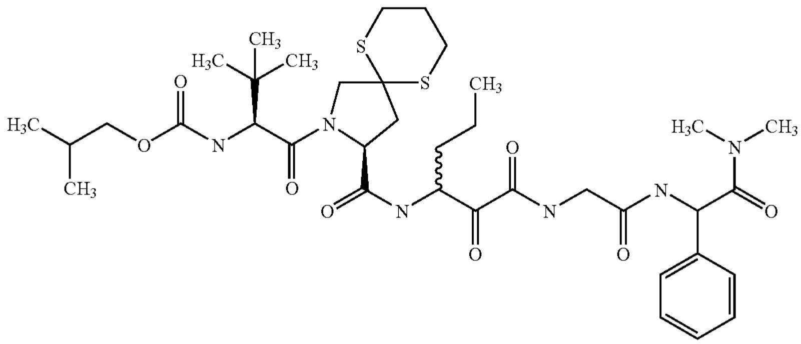 | 777.0223 |
| 172 | 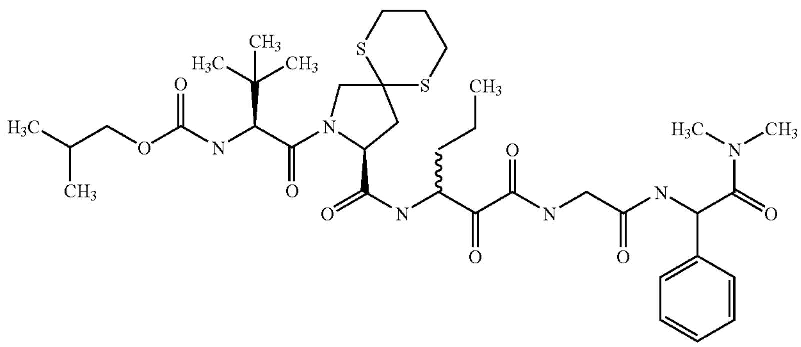 | 777.0223 |
| 173 | 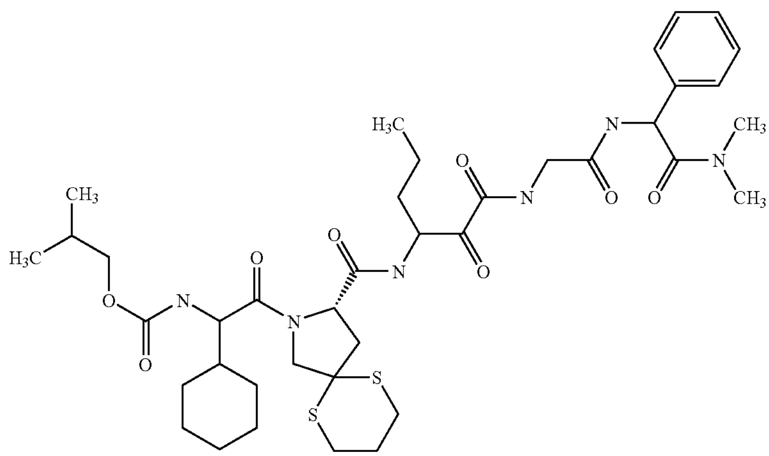 | 801.0882 |
| 174 | 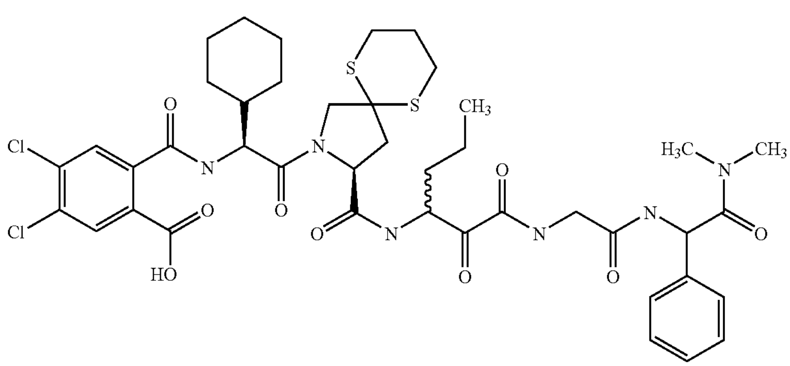 | 919.9515 |

TABLE 2-continued

| Ex. # | STRUCTURE | molecular weight |
|---|---|---|
| 175 | 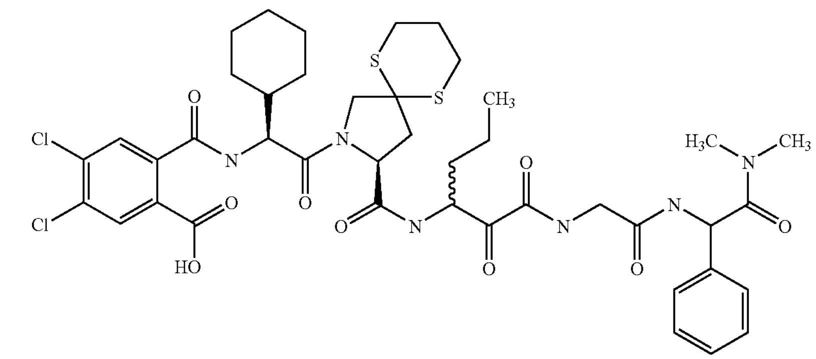 | 919.9515 |
| 176 | 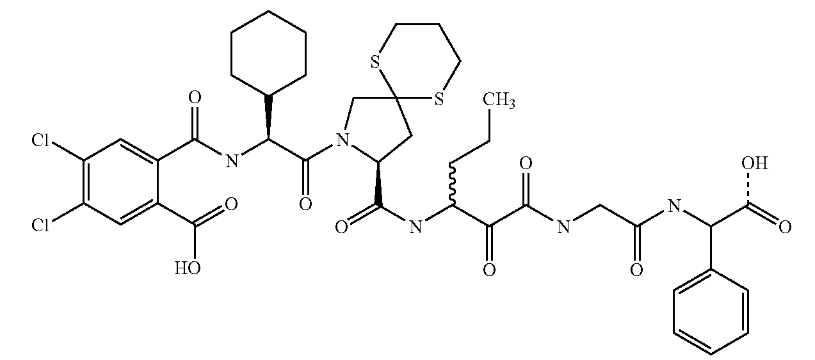 | 892.8821 |
| 177 | 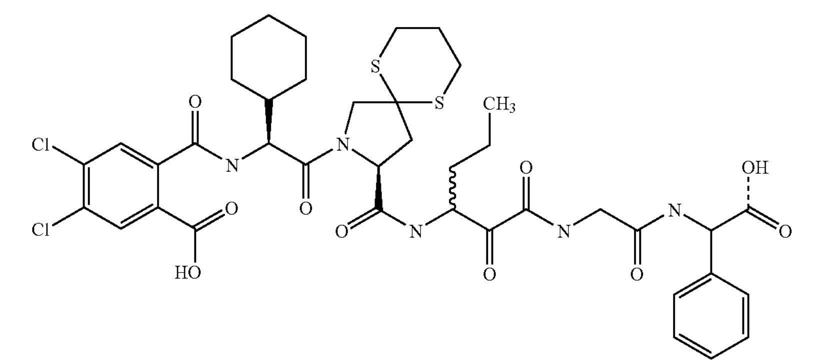 | 892.8821 |
| 178 | 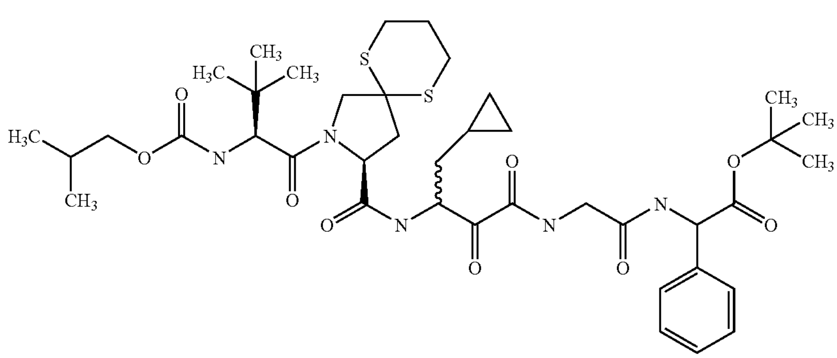 | 818.0723 |

| Ex. # | STRUCTURE | molecular weight |
|---|---|---|
| 179 | 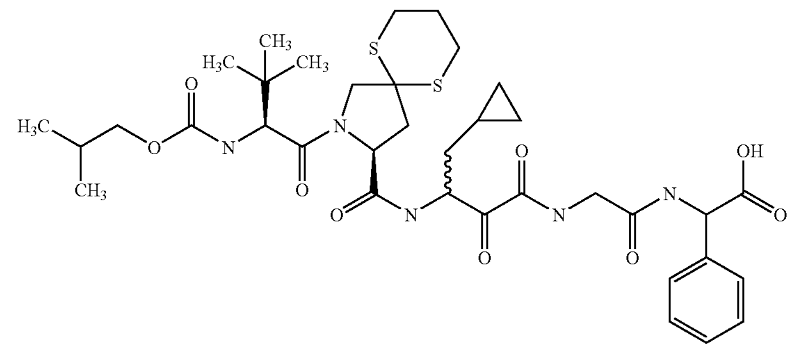 | 761.964 |
| 180 | 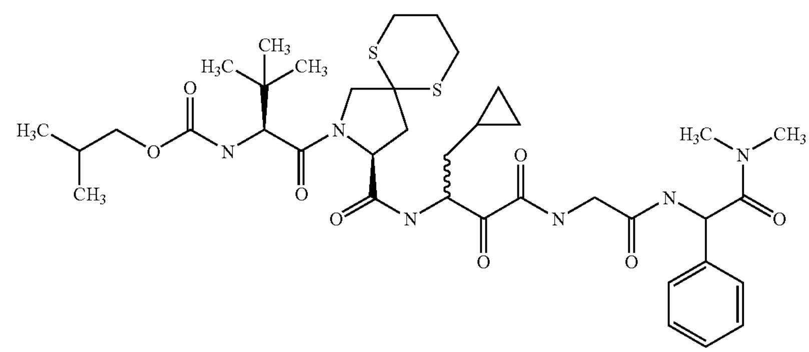 | 789.0334 |
| 181 | 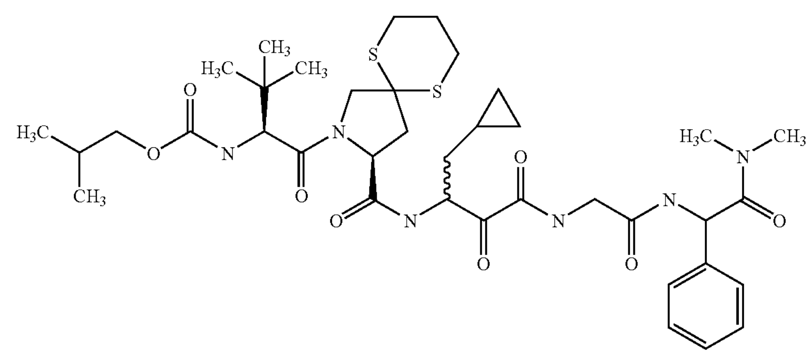 | 789.0334 |
| 182 | 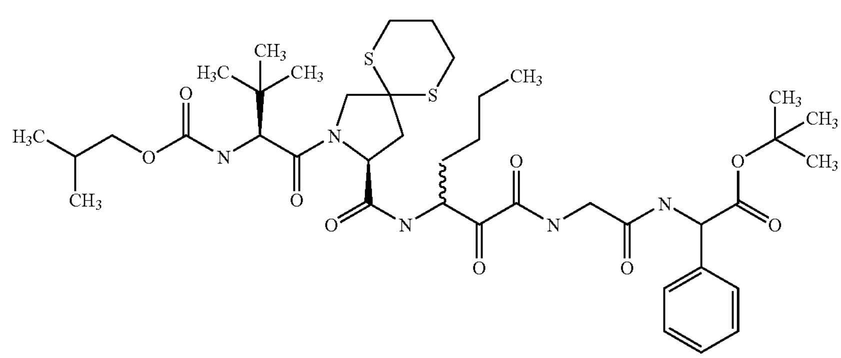 | 820.0883 |

TABLE 2-continued

| Ex. # | STRUCTURE | molecular weight |
|---|---|---|
| 183 | 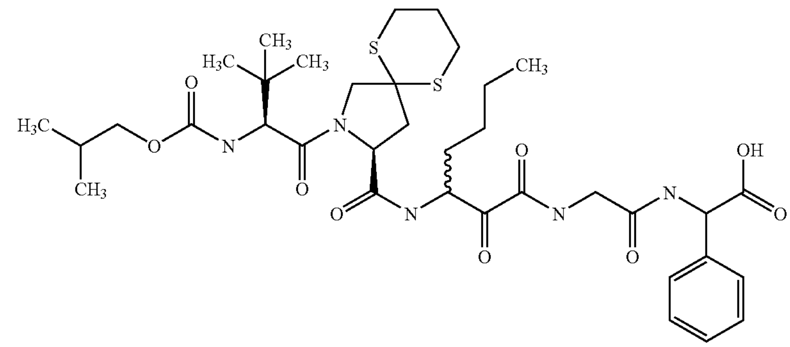 | 763.9799 |
| 184 | 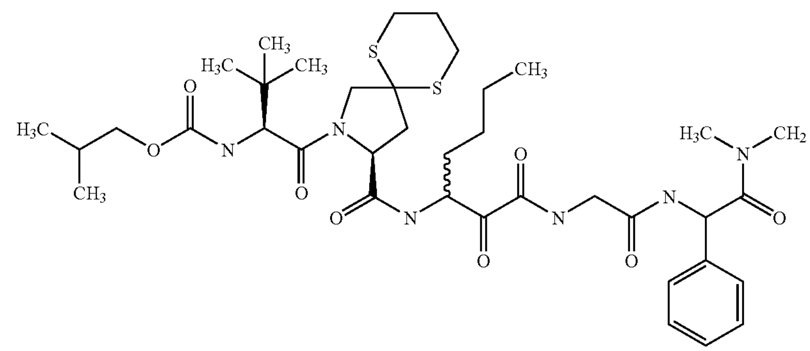 | 791.0494 |
| 185 | 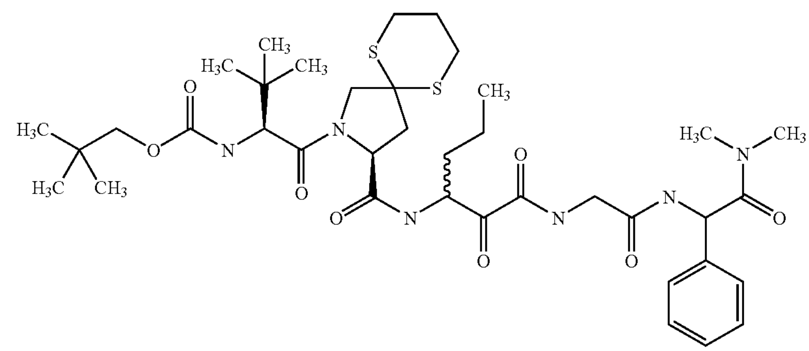 | 791.0494 |
| 186 | 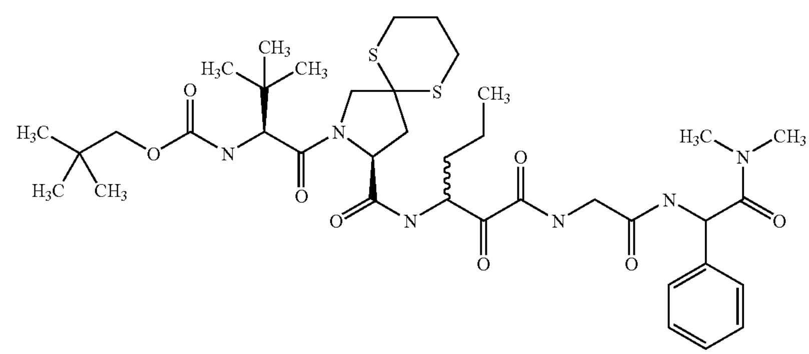 | 791.0494 |

TABLE 2-continued

| Ex. # | STRUCTURE | molecular weight |
|---|---|---|
| 187 | 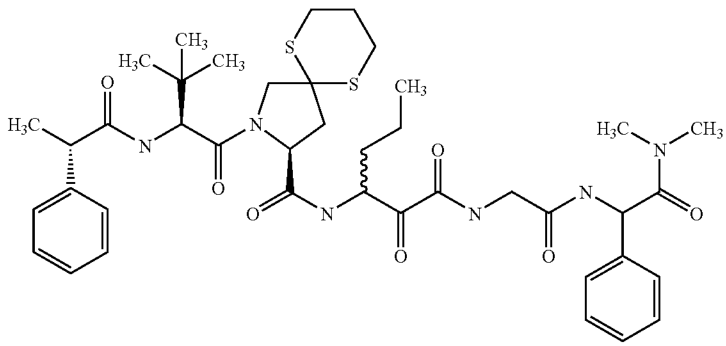 | 809.0674 |
| 188 | 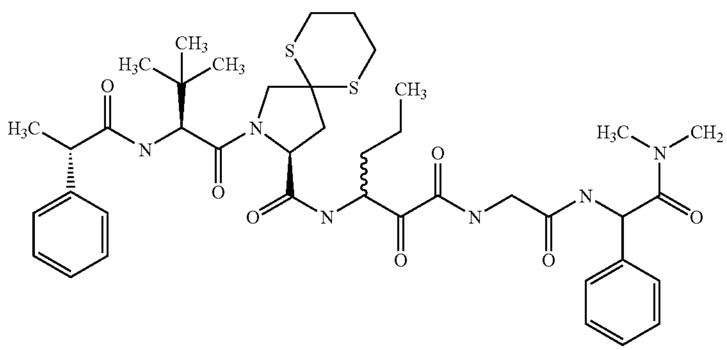 | 809.0674 |
| 189 | 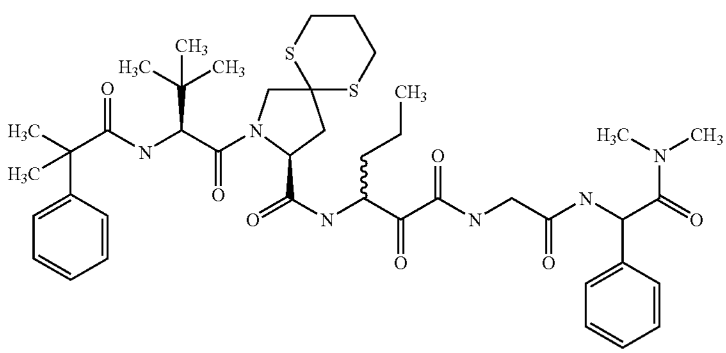 | 823.0945 |
| 190 | 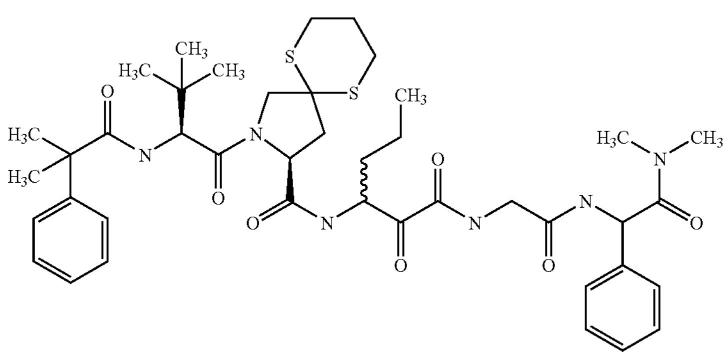 | 823.0945 |

TABLE 2-continued
| Ex. # | STRUCTURE | molecular weight |
|---|---|---|
| 191 | 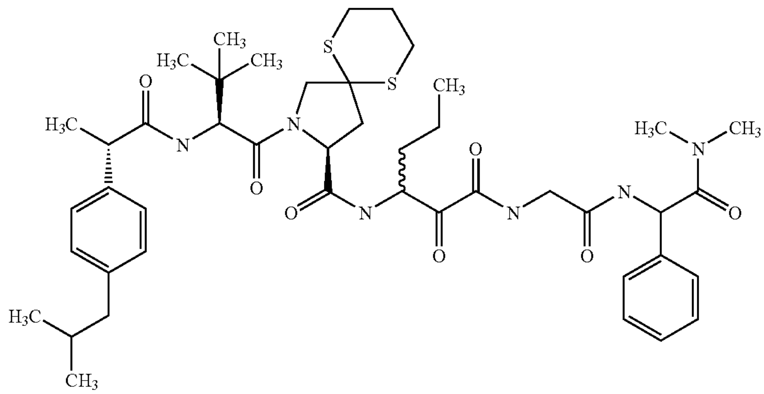 | 865.1758 |
| 192 | 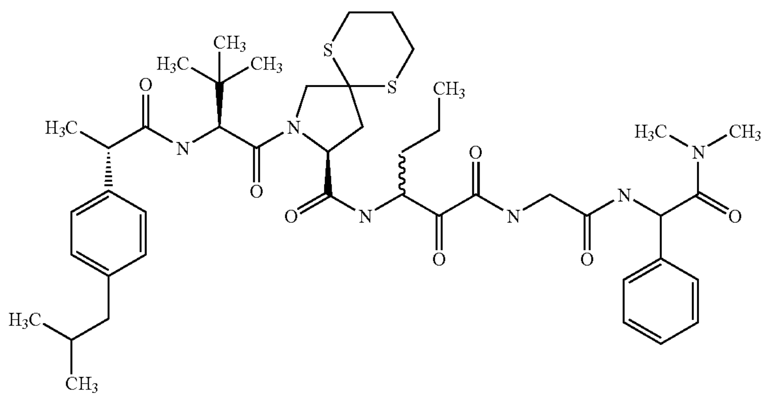 | 865.1758 |
| 193 | 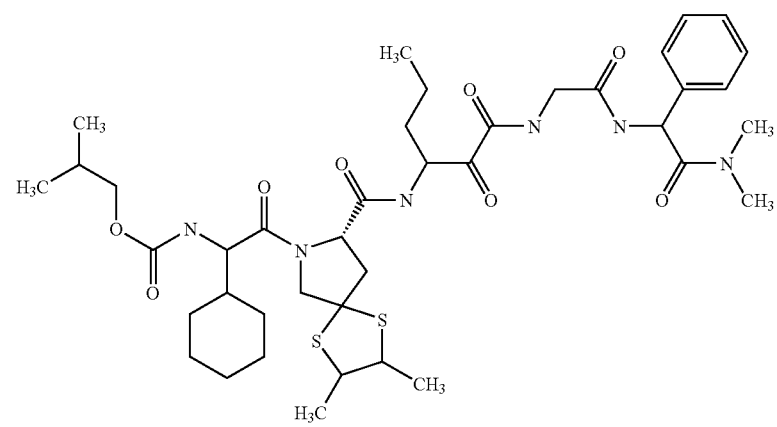 | 817.0876 |

TABLE 2-continued
| Ex. # | STRUCTURE | molecular weight |
|---|---|---|
| 194 | 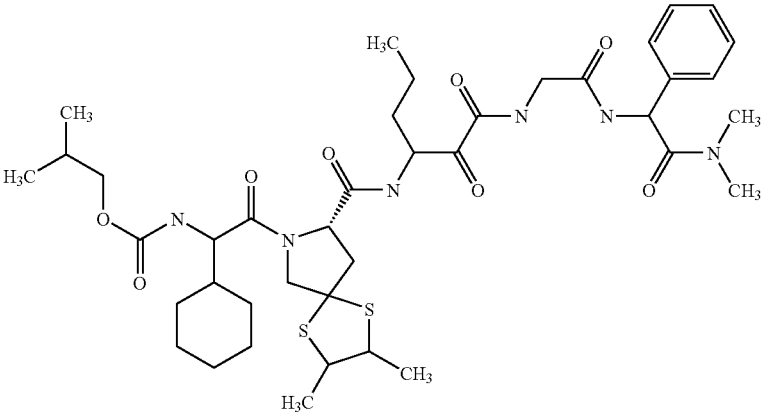 | 817.0876 |
| 195 | 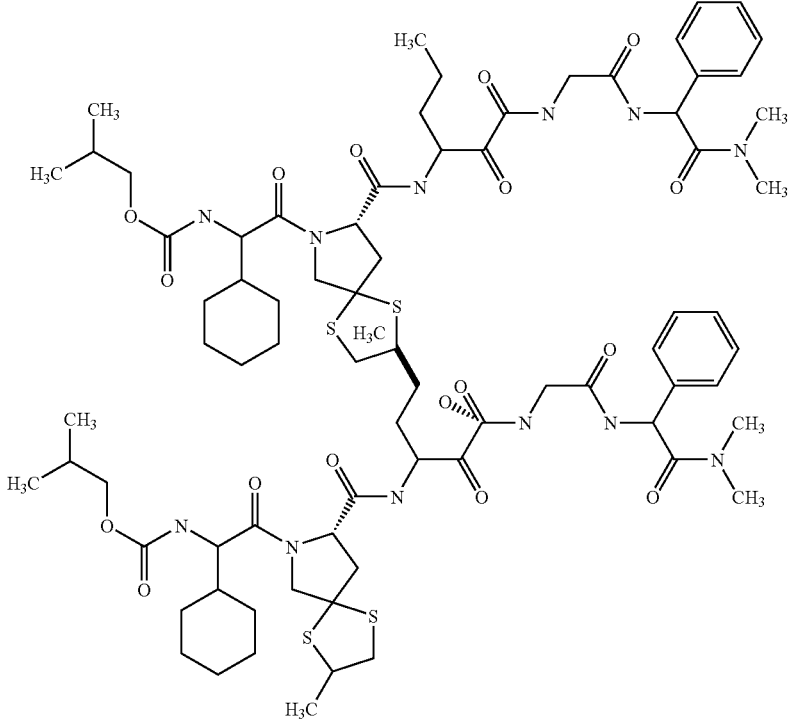 | 1606.121 |

TABLE 2-continued
| Ex. # | STRUCTURE | molecular weight |
|---|---|---|
| 196 | 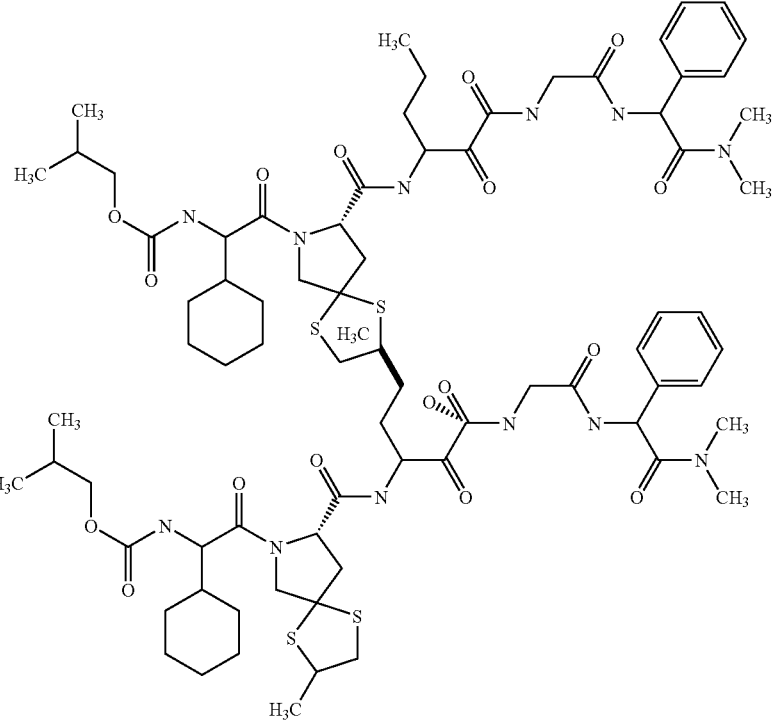 | 1606.121 |
| 197 | 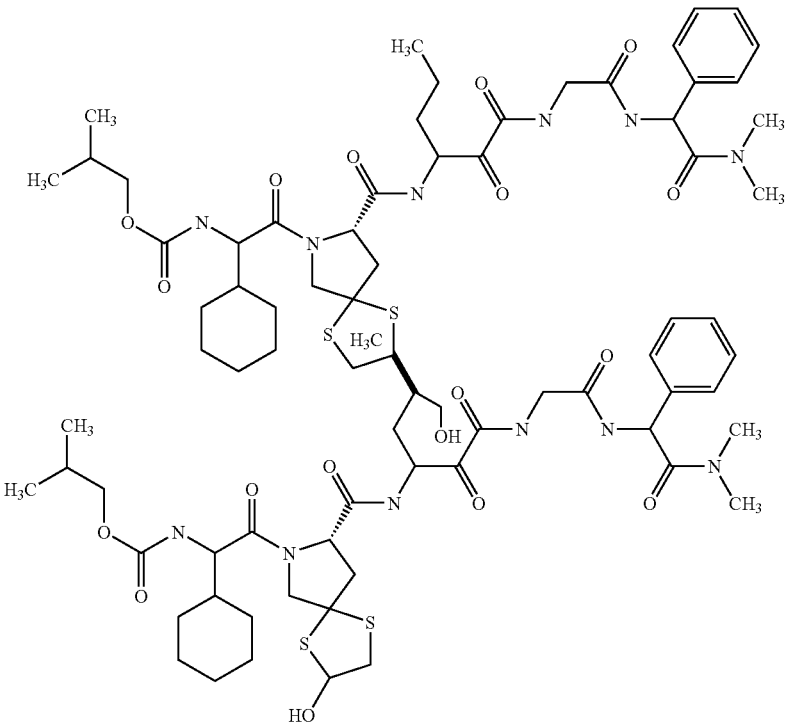 | 1638.12 |

TABLE 2-continued
| Ex. # | STRUCTURE | molecular weight |
|---|---|---|
| 198 | 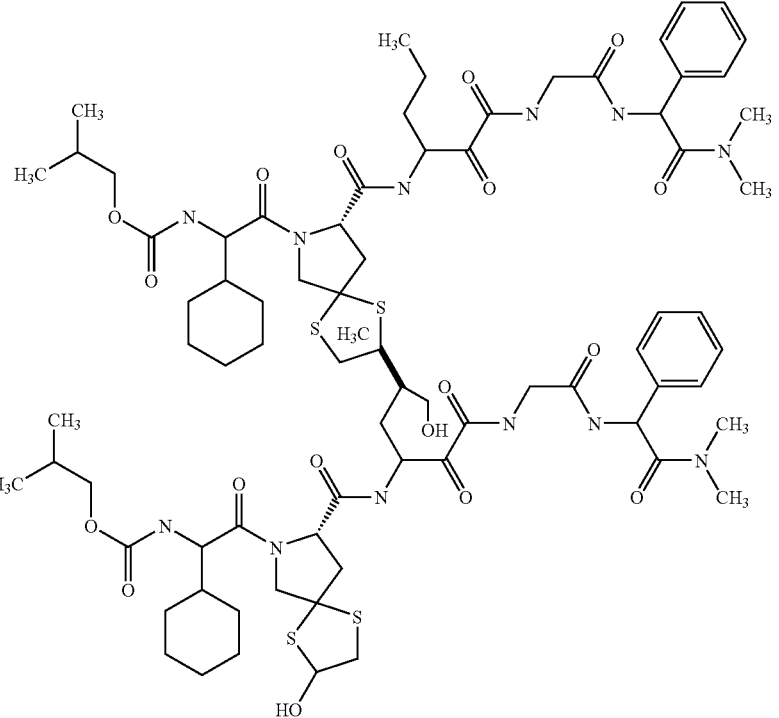 | 1638.12 |
| 199 | 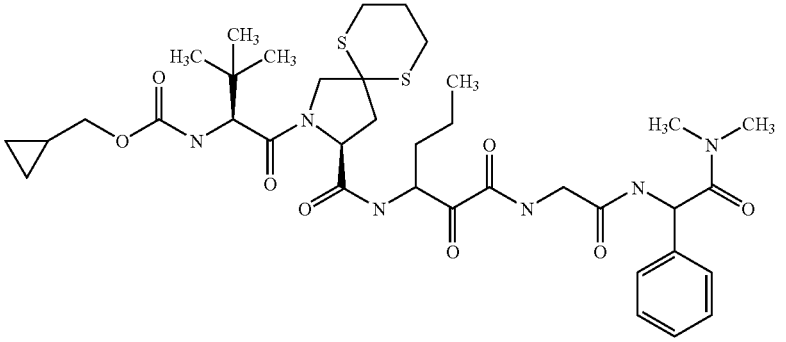 | 775.0063 |
| 200 | 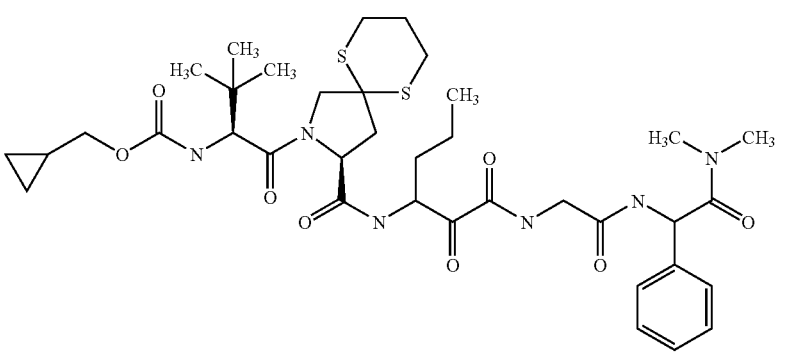 | 775.0063 |

TABLE 2-continued

| Ex. # | STRUCTURE | molecular weight |
|---|---|---|
| 201 | 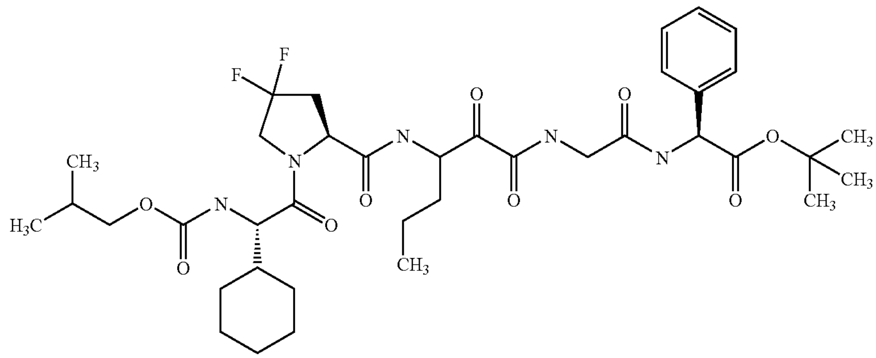 | 763.887 |
| 202 | 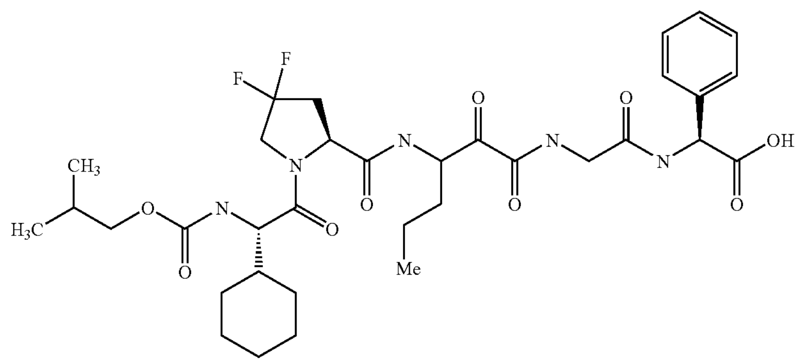 | 707.7786 |
| 203 | 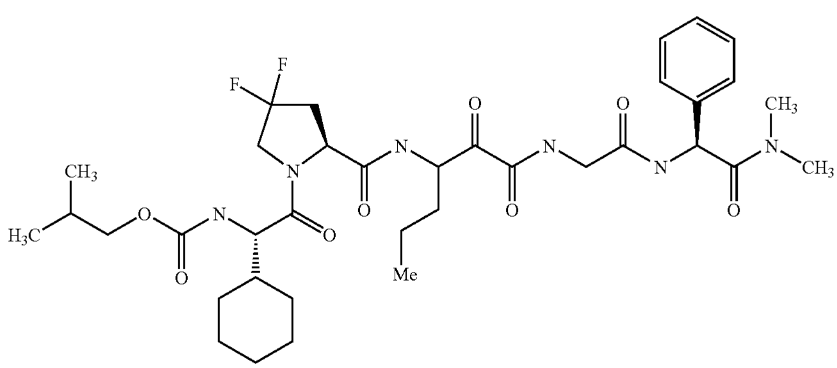 | 734.848 |
| 204 | 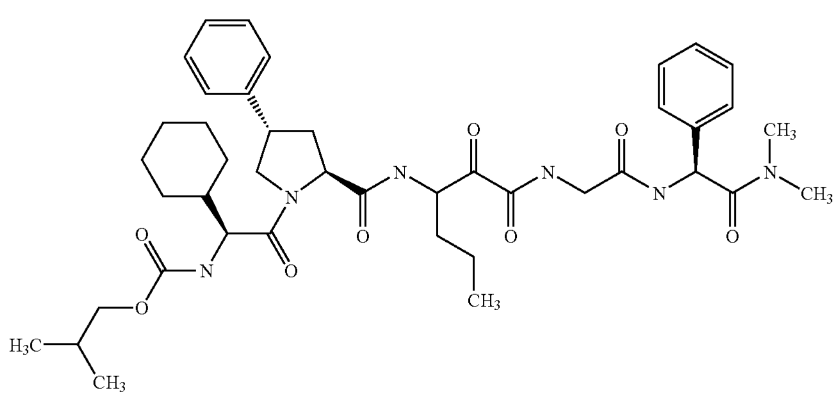 | 774.9659 |

TABLE 2-continued

| Ex. # | STRUCTURE | molecular weight |
|---|---|---|
| 205 | 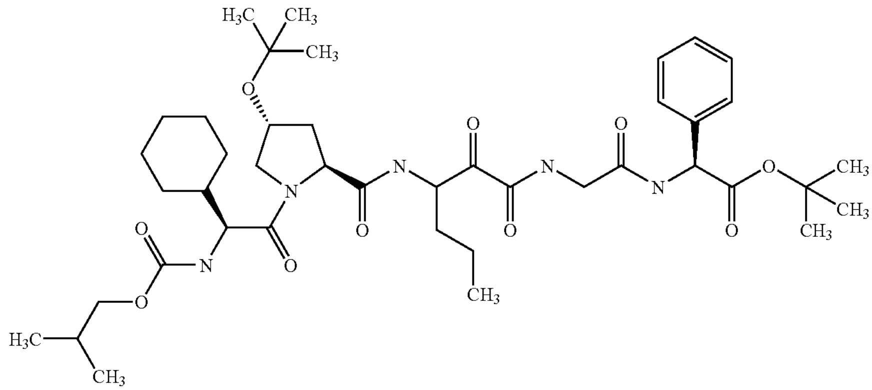 | 800.0139 |
| 206 | 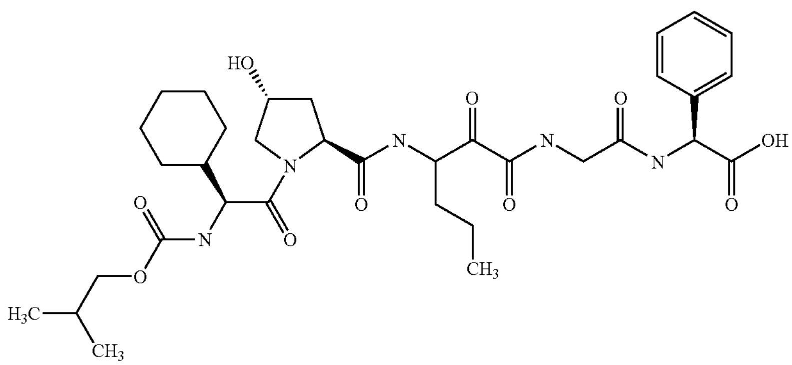 | 687.7971 |
| 207 | 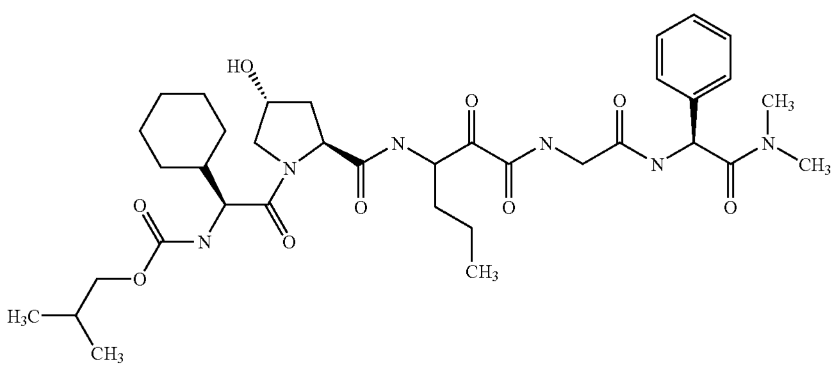 | 714.8666 |
| 208 | 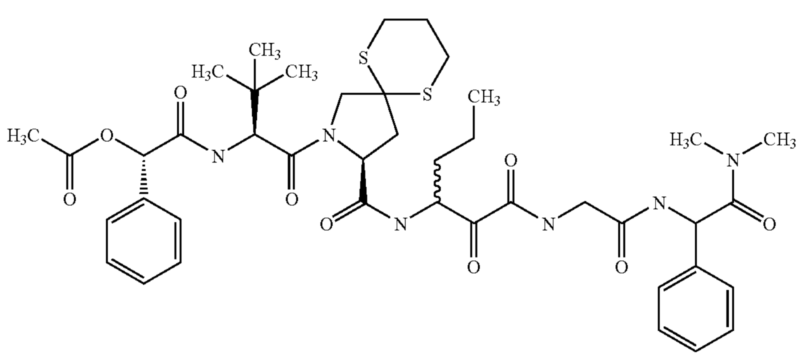 | 853.0774 |

TABLE 2-continued
| Ex. # | STRUCTURE | molecular weight |
| --- | --- | --- |
| 209 | 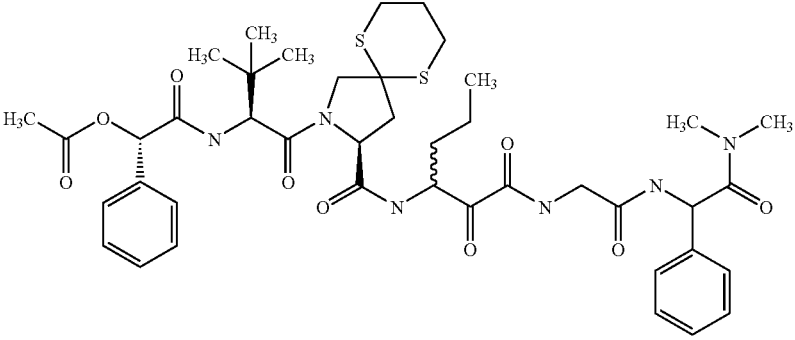 | 853.0774 |
| 210 | 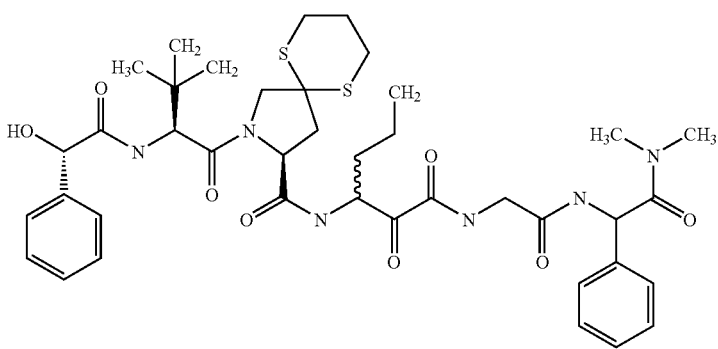 | 811.0398 |
| 211 | 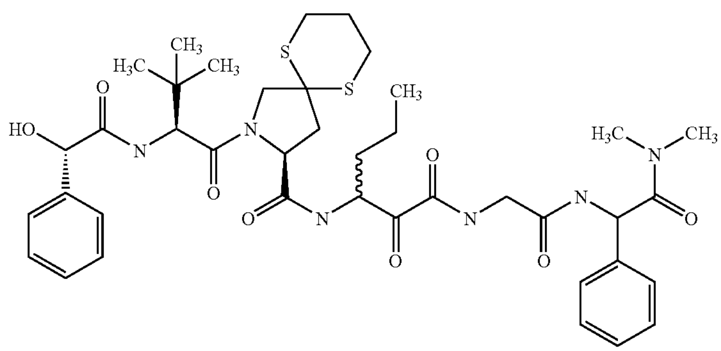 | 811.0398 |
| 212 | 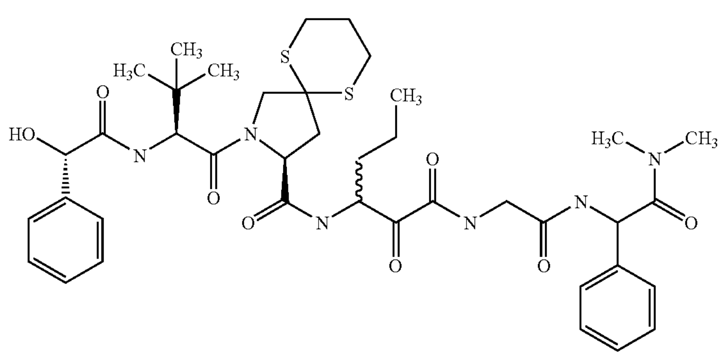 | 811.0398 |

TABLE 2-continued

| Ex. # | STRUCTURE | molecular weight |
|---|---|---|
| 213 | 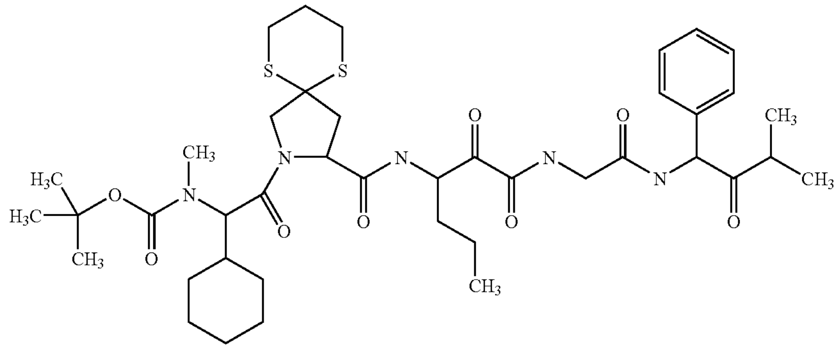 | 817.0876 |
| 214 | 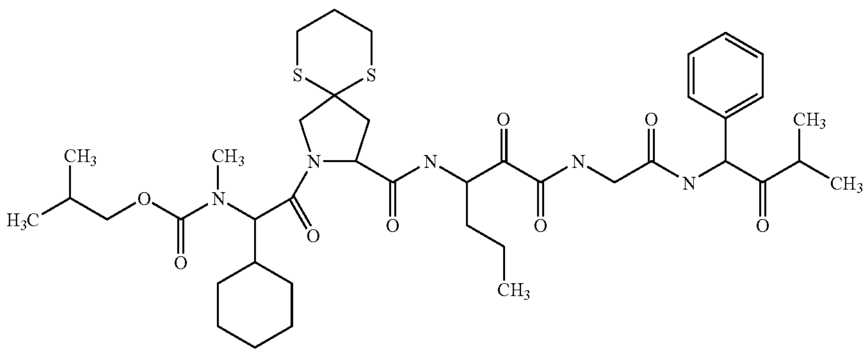 | 817.0876 |
| 215 | 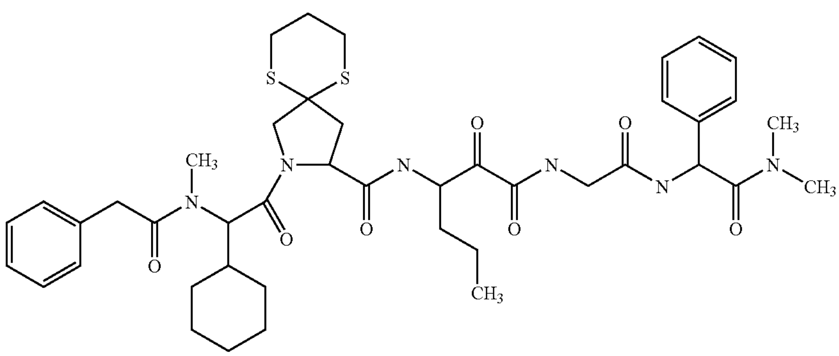 | 835.1057 |
| 216 | 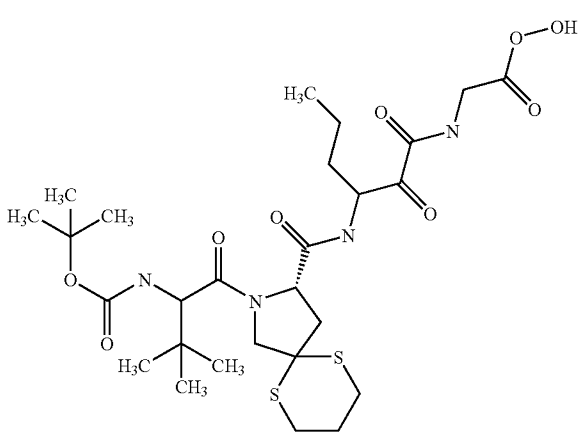 | 630.8288 |

TABLE 2-continued

| Ex. # | STRUCTURE | molecular weight |
|---|---|---|
| 217 | 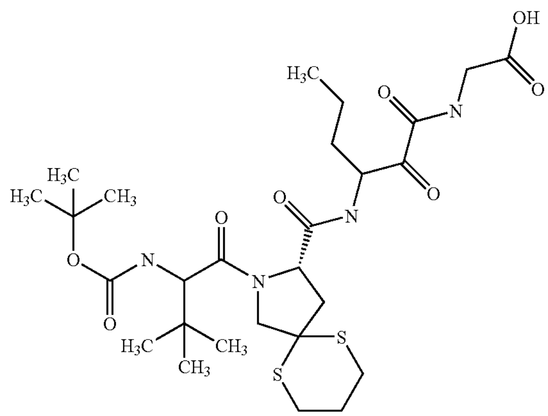 | 616.8018 |
| 218 | 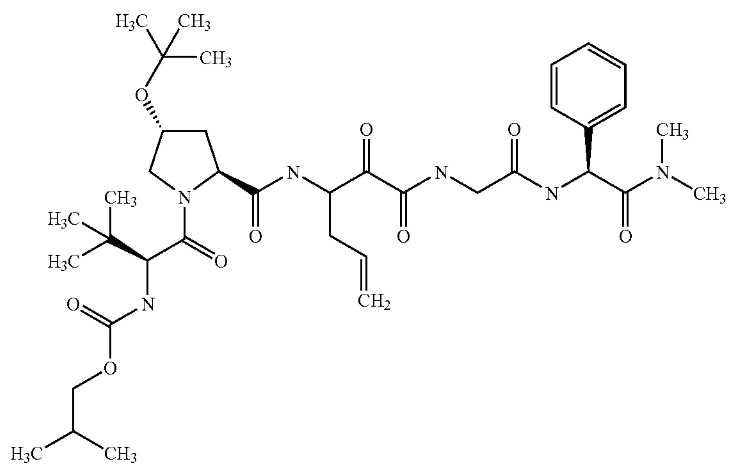 | 742.9208 |
| 219 | 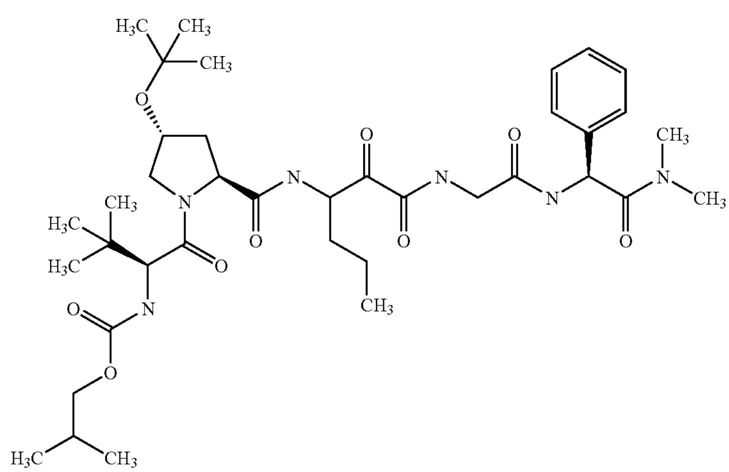 | 744.9367 |

TABLE 2-continued

| Ex. # | STRUCTURE | molecular weight |
|---|---|---|
| 220 | 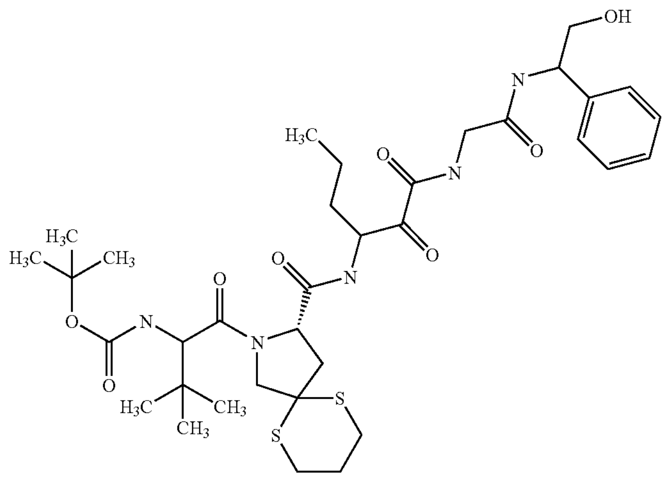 | 735.9694 |
| 221 | 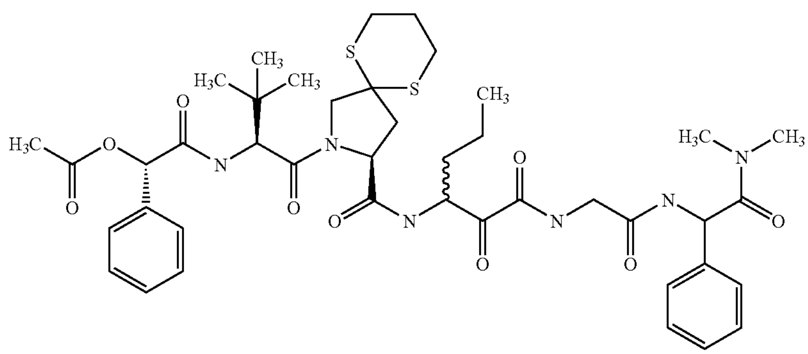 | 853.0774 |
| 222 | 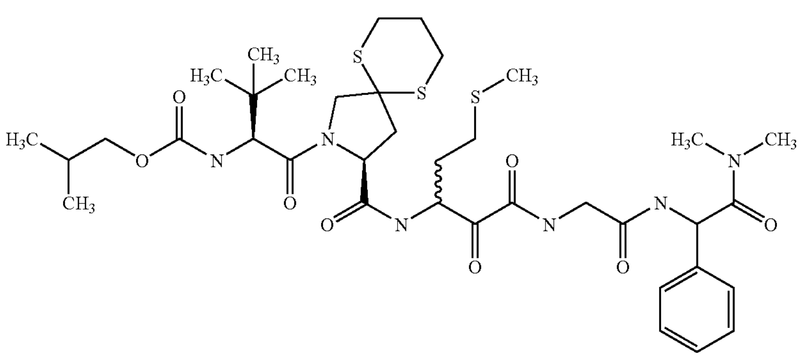 | 809.0862 |

TABLE 2-continued

| Ex. # | STRUCTURE | molecular weight |
|---|---|---|
| 223 | 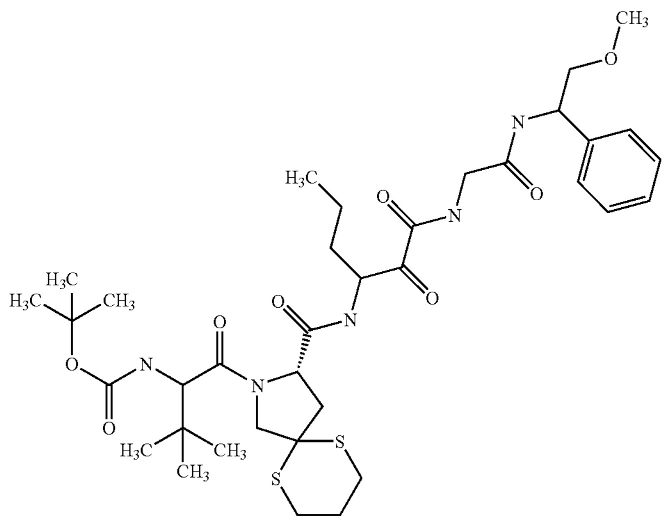 | 749.9965 |
| 224 | 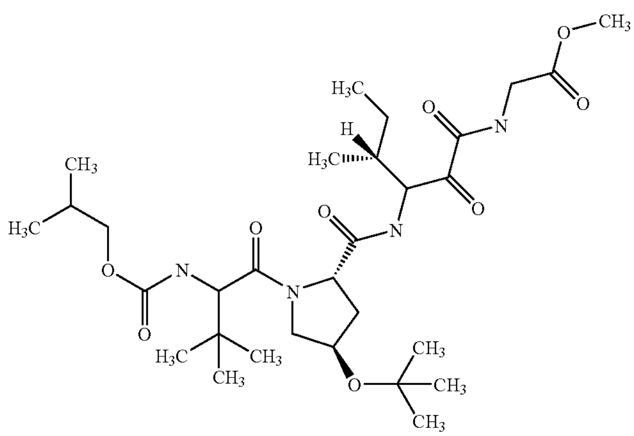 | 612.7703 |
| 225 | 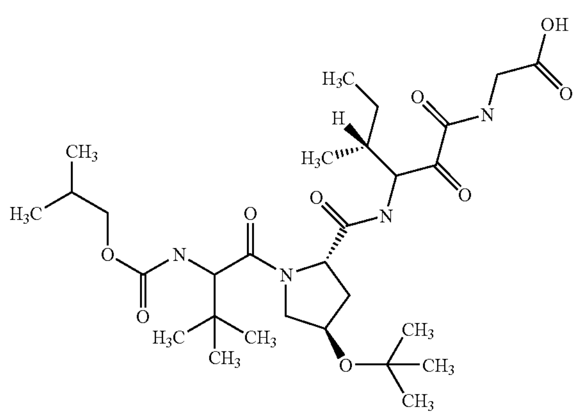 | 598.7432 |

TABLE 2-continued
| Ex. # | STRUCTURE | molecular weight |
|---|---|---|
| 226 | 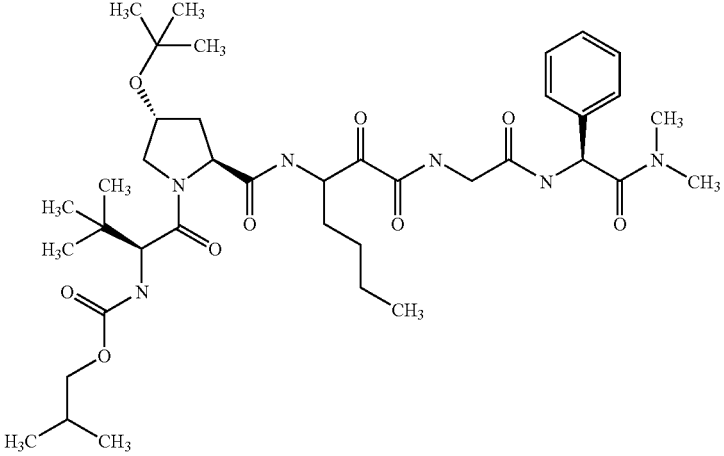 | 758.9638 |
| 227 | 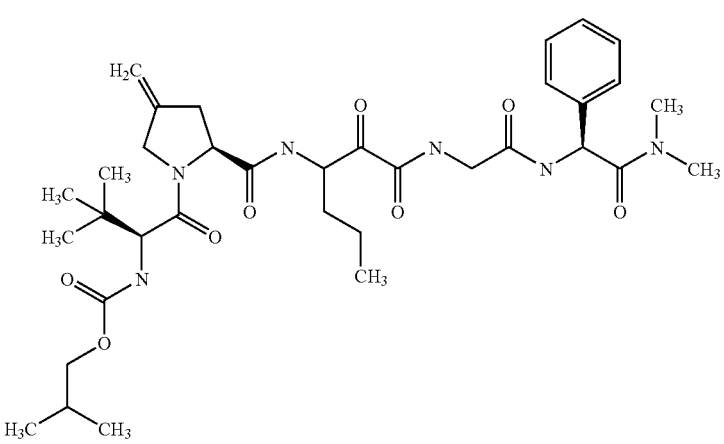 | 684.8401 |
| 228 | 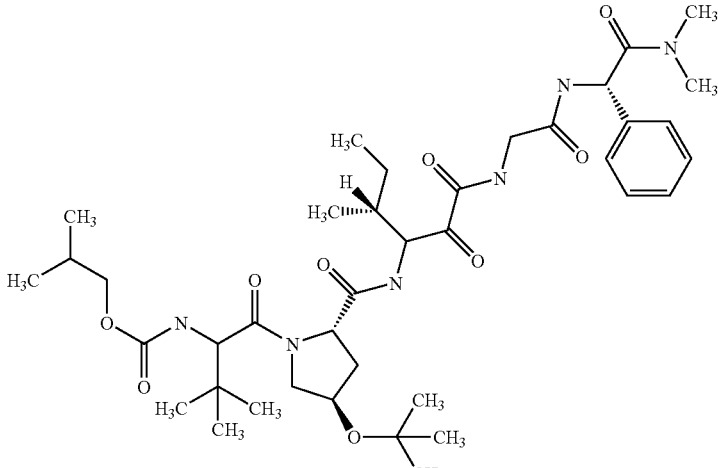 | 758.9638 |

TABLE 2-continued
| Ex. # | STRUCTURE | molecular weight |
|---|---|---|
| 229 | 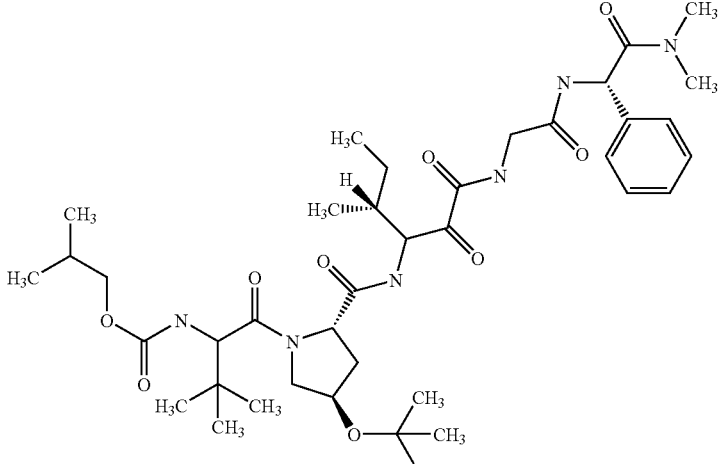 | 758.9638 |
| 230 | 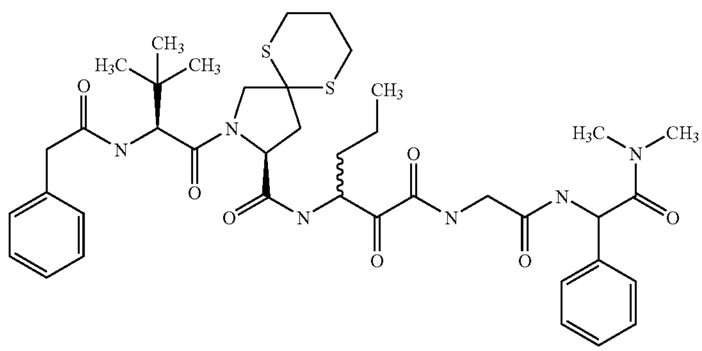 | 795.0404 |
| 231 | 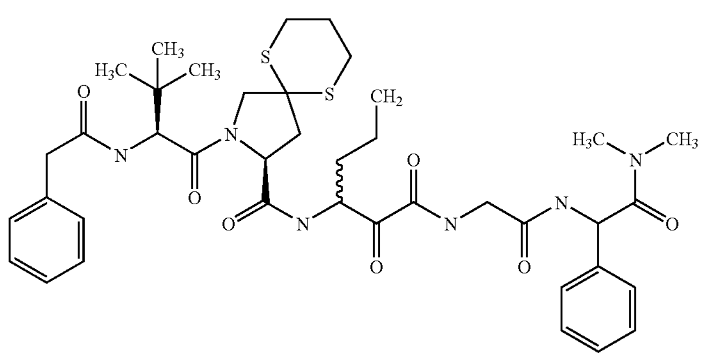 | 795.0404 |

TABLE 2-continued
| Ex. # | STRUCTURE | molecular weight |
|---|---|---|
| 232 | 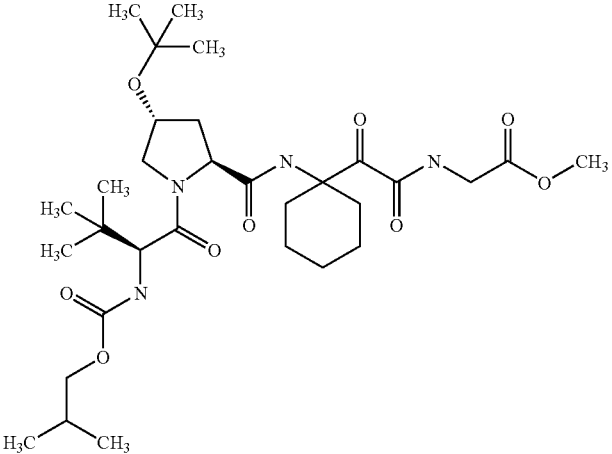 | 624.7815 |
| 233 | 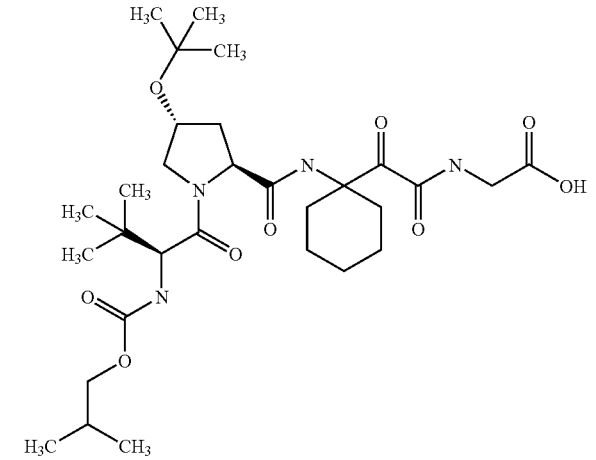 | 610.7544 |
| 234 | 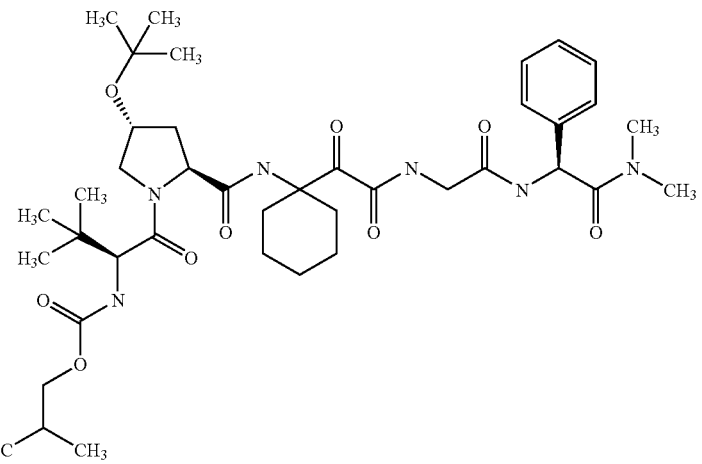 | 770.9749 |

TABLE 2-continued

| Ex. # | STRUCTURE | molecular weight |
|---|---|---|
| 235 | 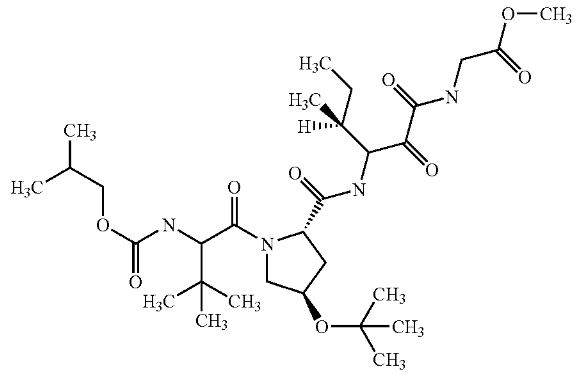 | 612.7703 |
| 236 | 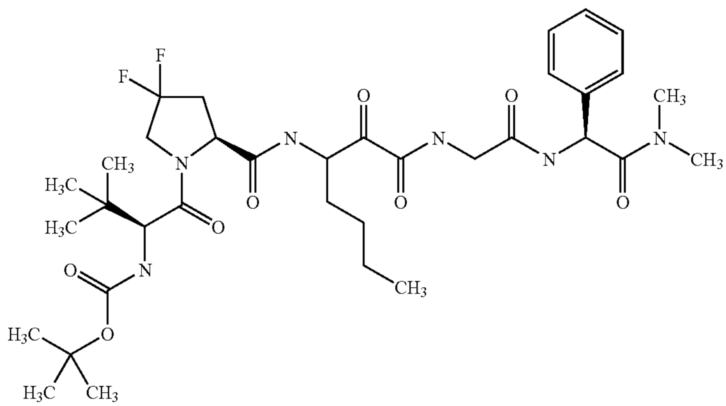 | 722.8369 |
| 237 | 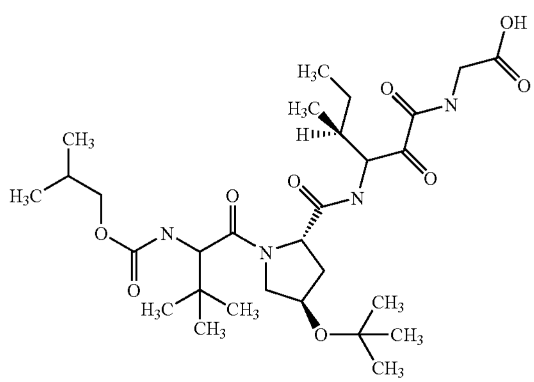 | 598.7432 |
| 238 | 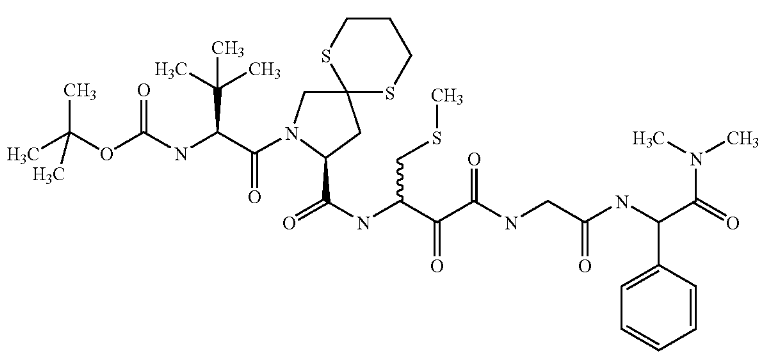 | 795.0592 |

TABLE 2-continued

| Ex. # | STRUCTURE | molecular weight |
|---|---|---|
| 239 | 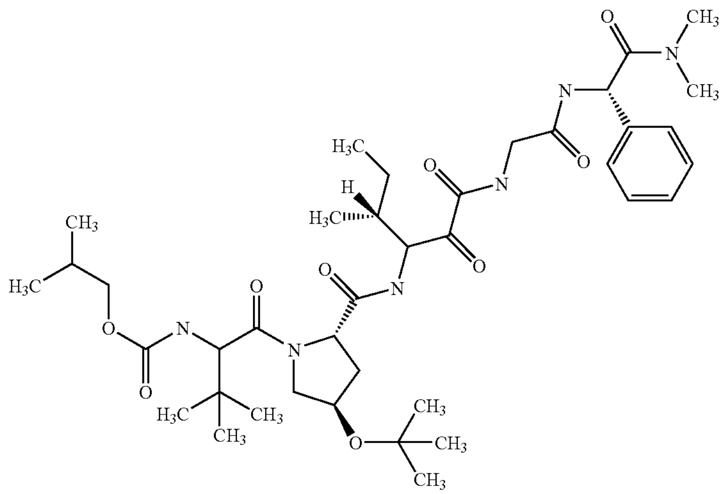 | 758.9638 |
| 240 | 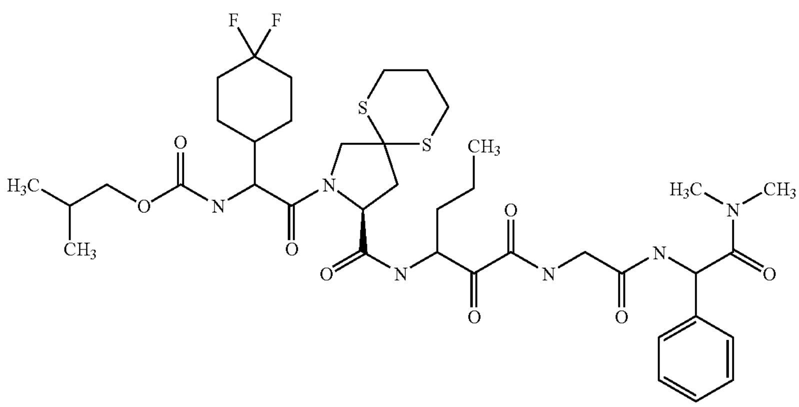 | 839.0414 |
| 241 | 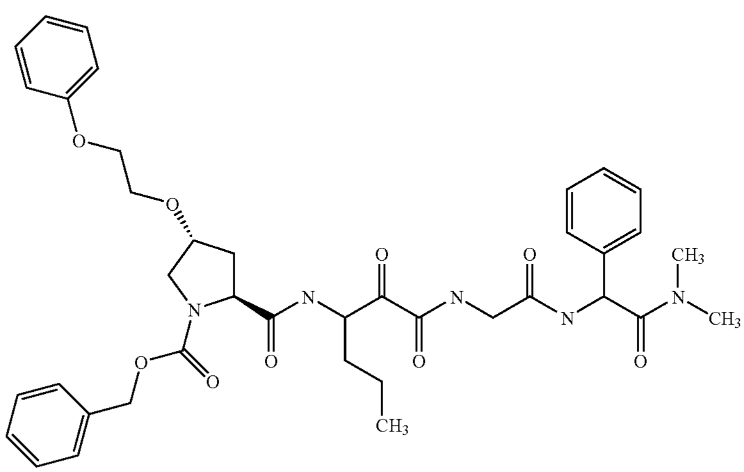 | 729.8375 |

TABLE 2-continued
| Ex. # | STRUCTURE | molecular weight |
|---|---|---|
| 242 | 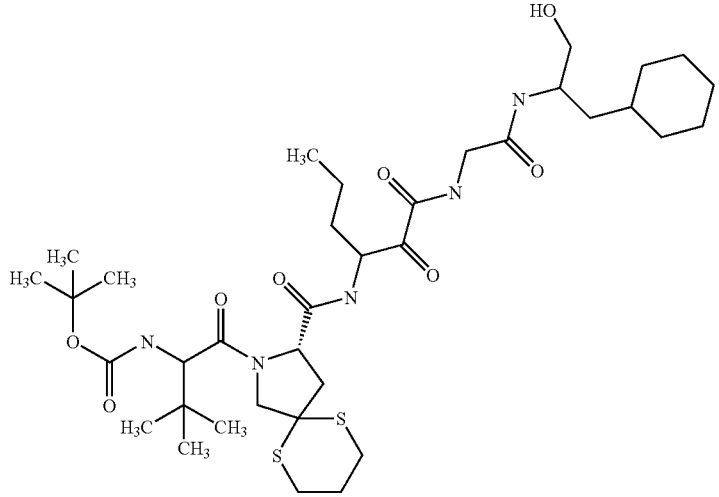 | 756.0443 |
| 243 | 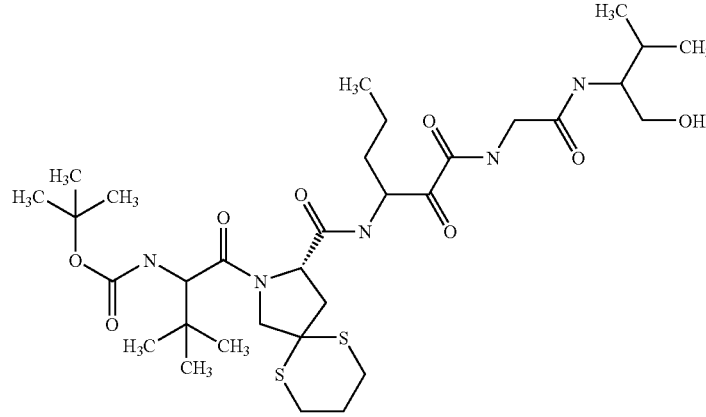 | 701.9518 |
| 244 | 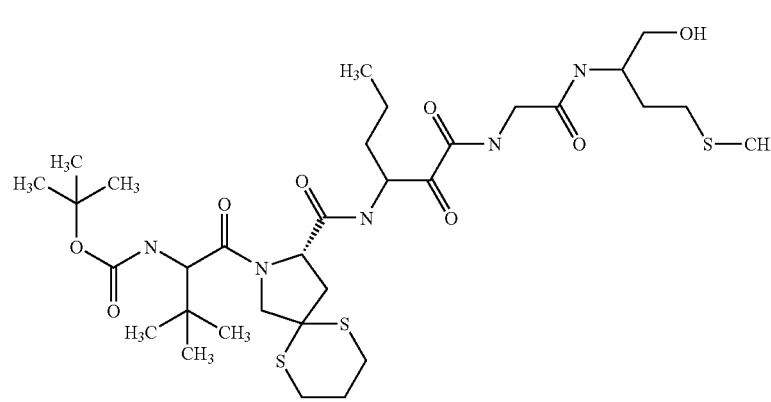 | 734.0159 |

TABLE 2-continued

| Ex. # | STRUCTURE | molecular weight |
|---|---|---|
| 245 | 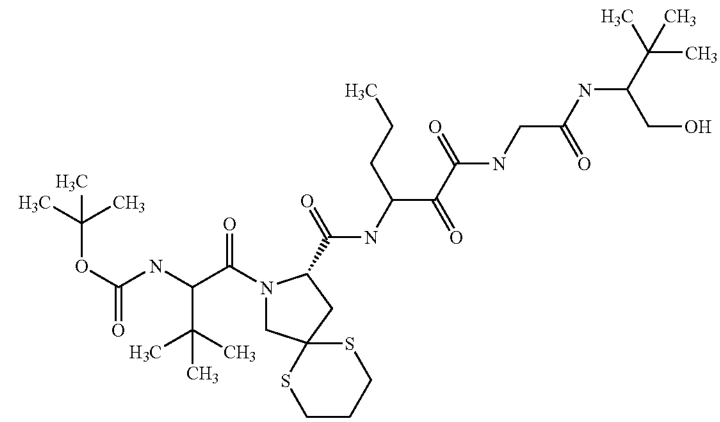 | 715.9789 |
| 246 | 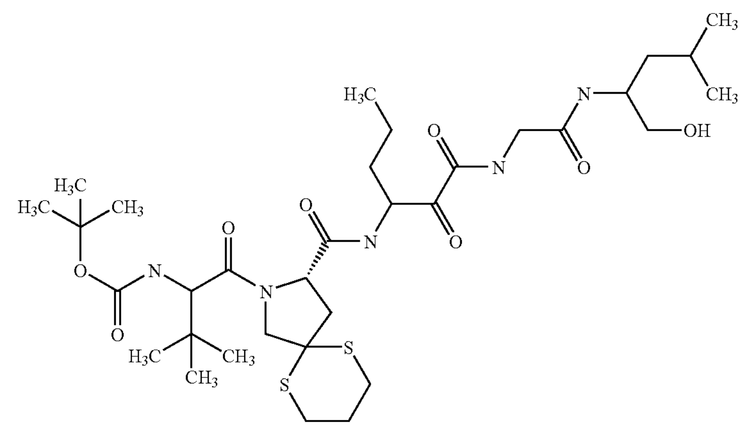 | 715.9789 |
| 247 | 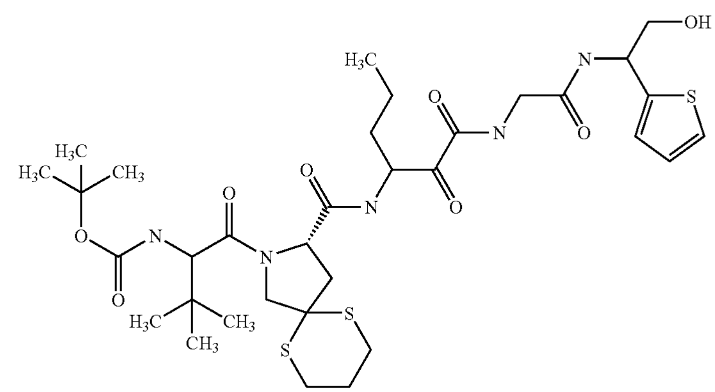 | 741.9951 |
| 248 | 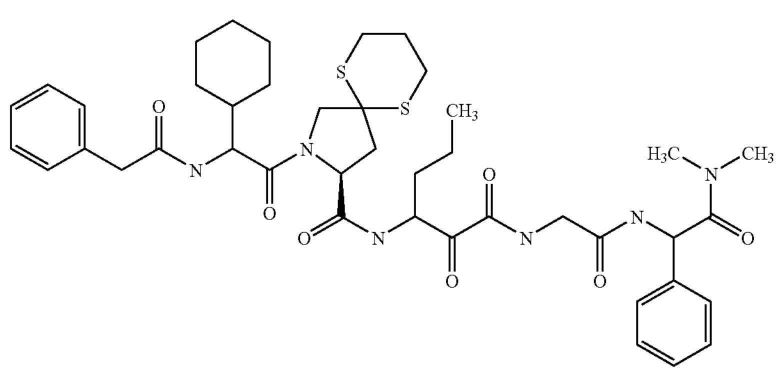 | 821.0786 |

TABLE 2-continued

| Ex. # | STRUCTURE | molecular weight |
|---|---|---|
| 249 | 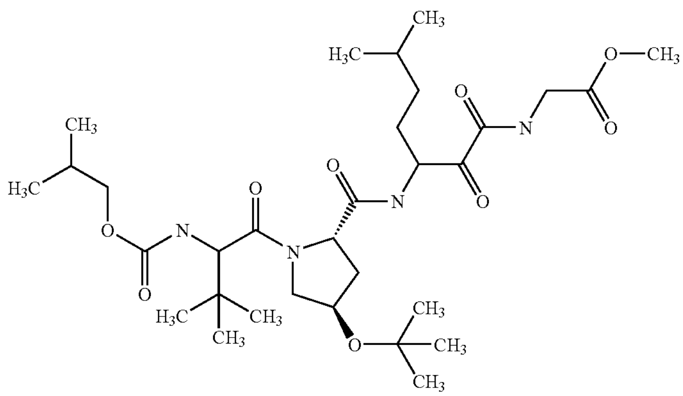 | 626.7974 |
| 250 | 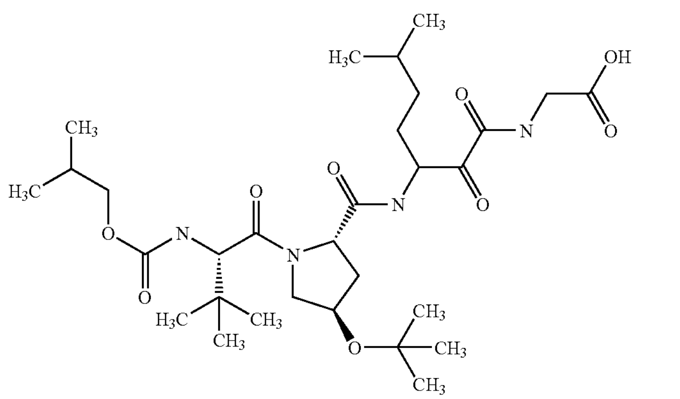 | 612.7703 |
| 251 | 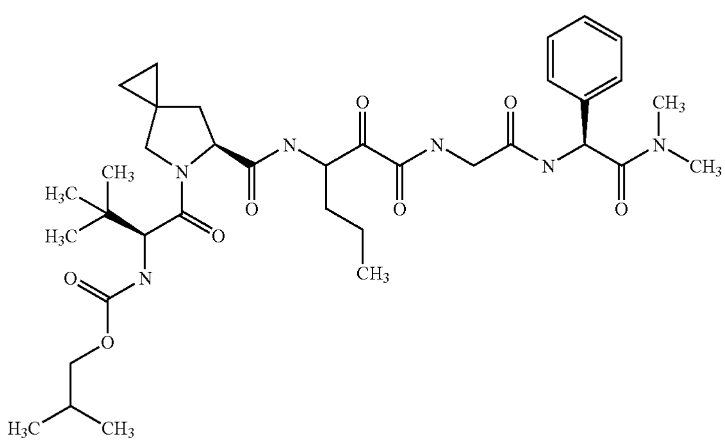 | 698.8672 |

TABLE 2-continued
| Ex. # | STRUCTURE | molecular weight |
|---|---|---|
| 252 | 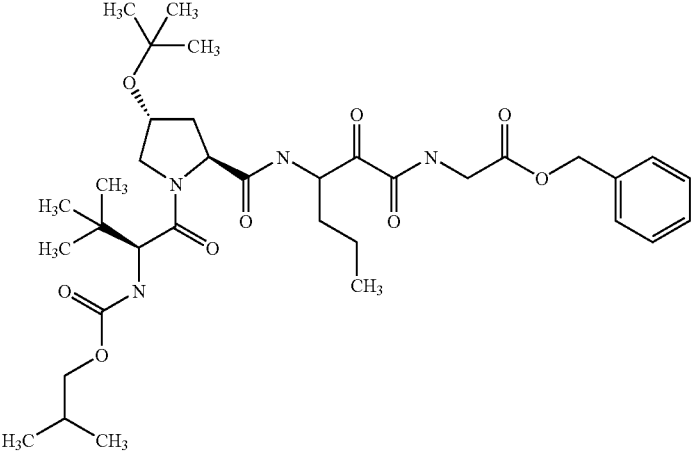 | 674.842 |
| 253 | 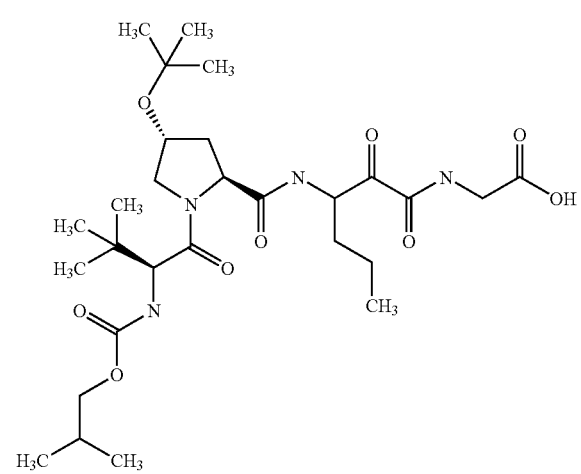 | 584.7162 |
| 254 | 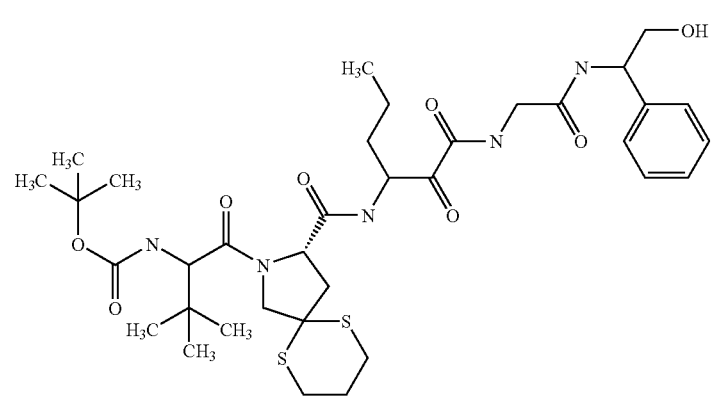 | 735.9694 |

TABLE 2-continued

| Ex. # | STRUCTURE | molecular weight |
|---|---|---|
| 254 | 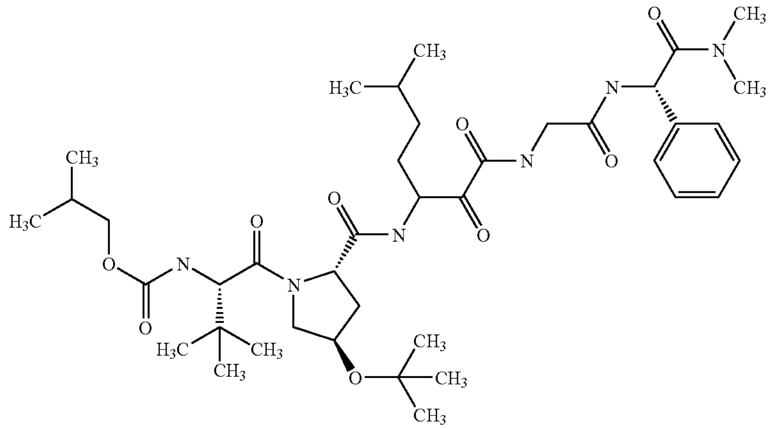 | 772.9909 |
| 256 | 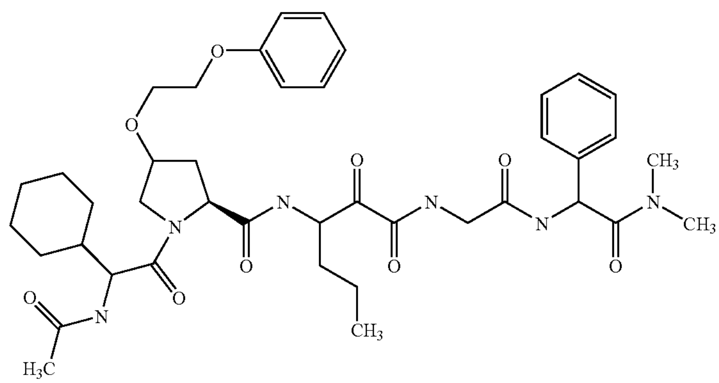 | 776.9383 |
| 257 | 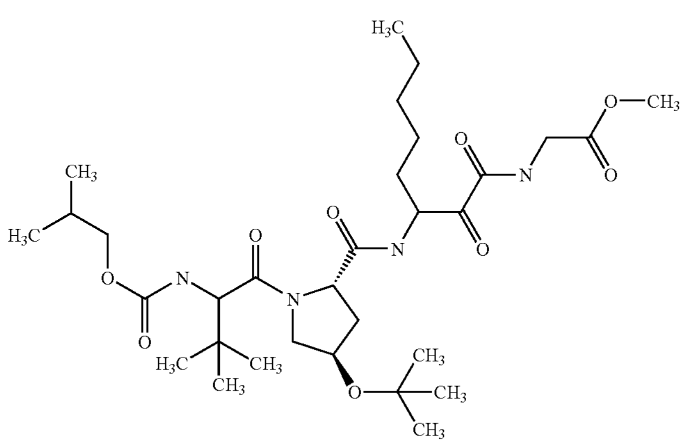 | 626.7974 |

TABLE 2-continued
| Ex. # | STRUCTURE | molecular weight |
|---|---|---|
| 258 | 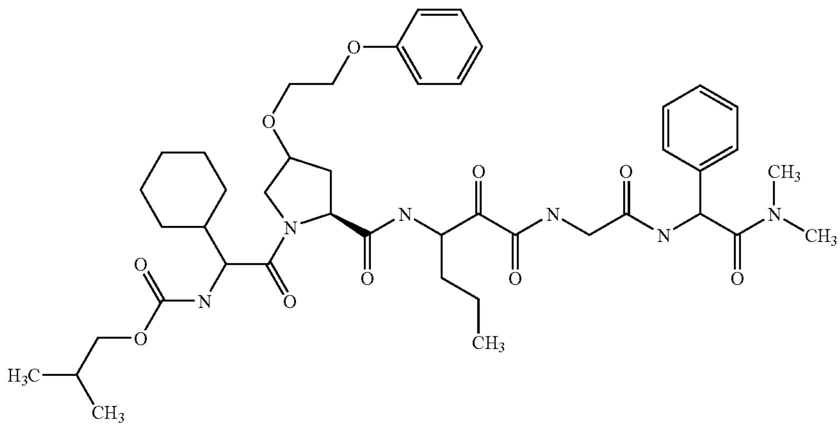 | 835.0189 |
| 259 | 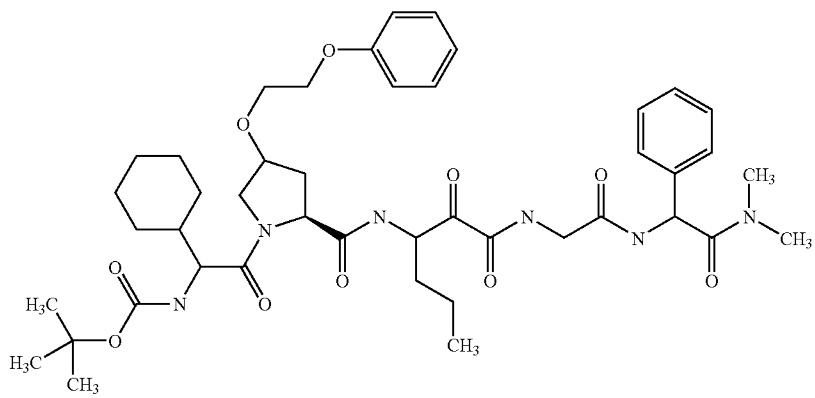 | 835.0189 |
| 260 | 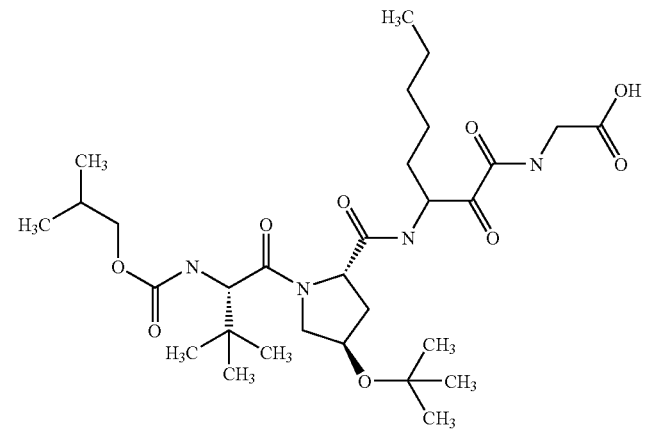 | 612.7703 |
| 261 | 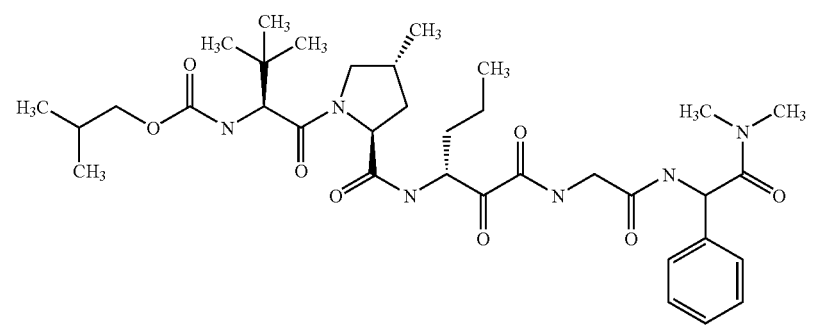 | 686.856 |

TABLE 2-continued

| Ex. # | STRUCTURE | molecular weight |
|---|---|---|
| 262 | 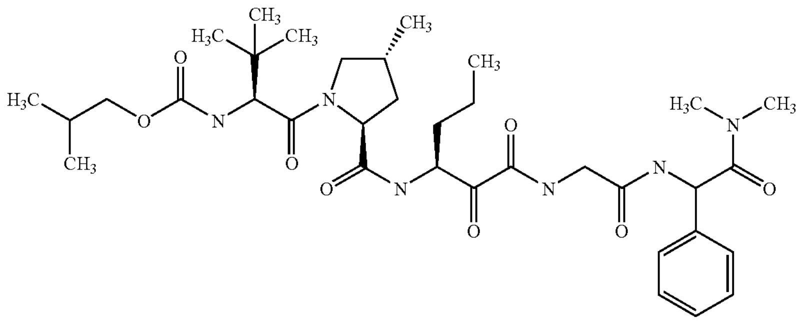 | 686.856 |
| 263 | 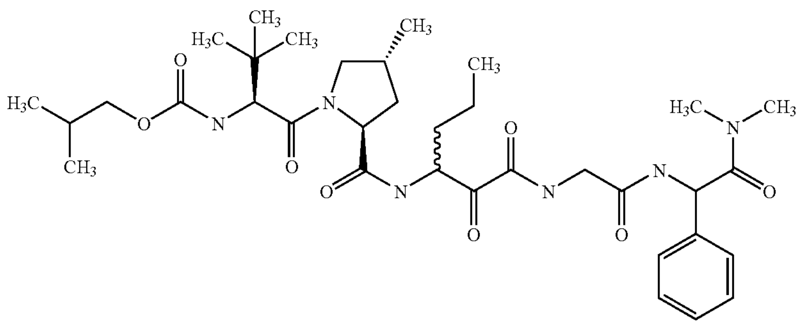 | 686.856 |
| 264 | 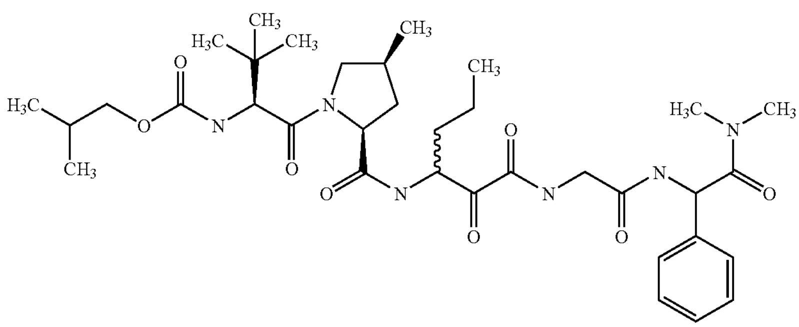 | 686.856 |
| 265 | 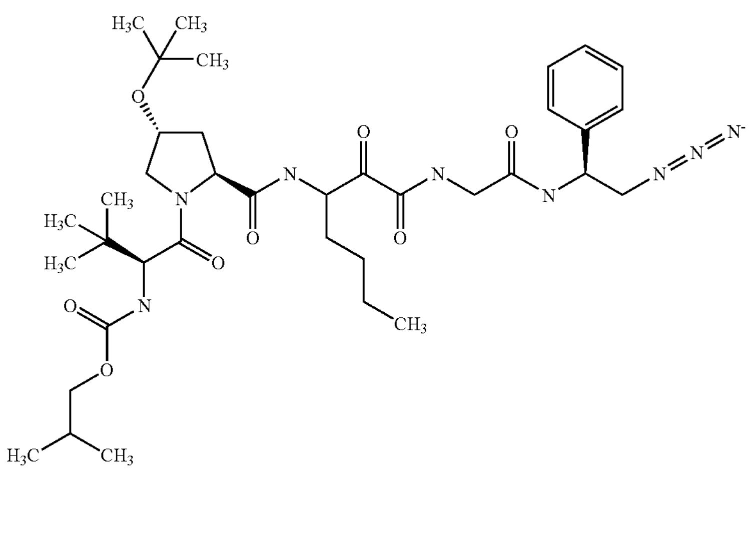 | 742.9236 |

TABLE 2-continued

| Ex. # | STRUCTURE | molecular weight |
|---|---|---|
| 266 | 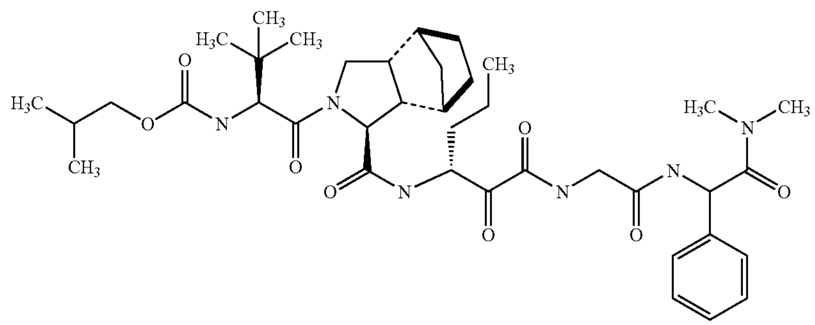 | 738.9325 |
| 267 | 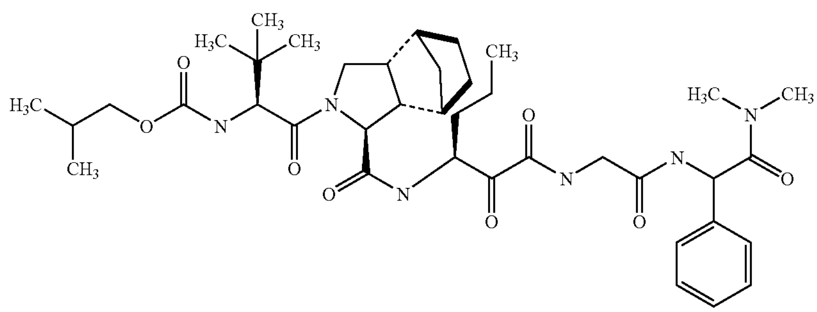 | 738.9325 |
| 268 | 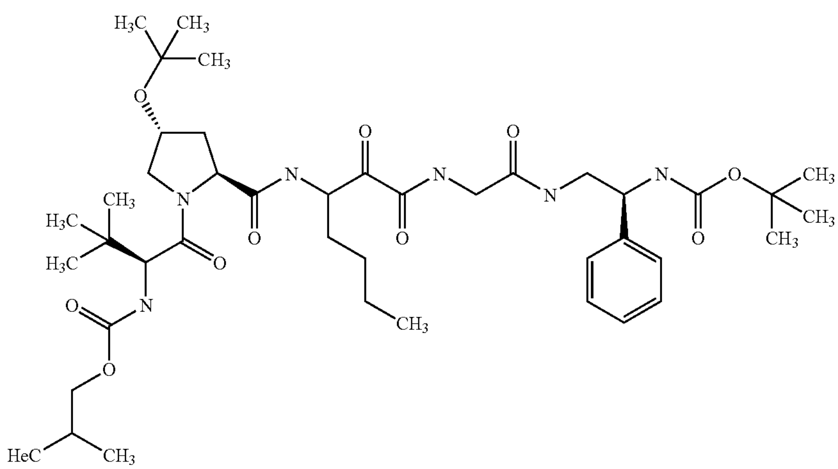 | 817.0444 |
| 269 | 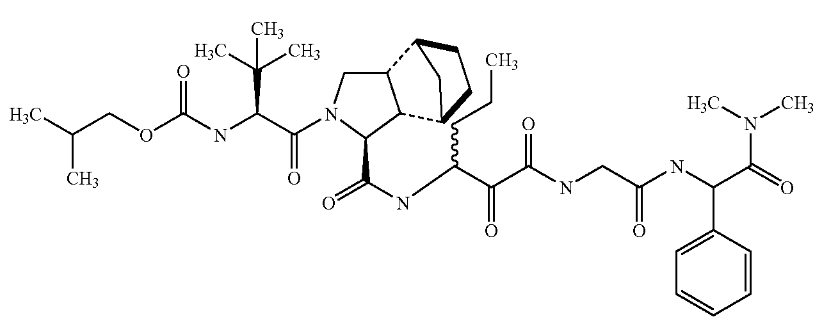 | 738.9325 |

TABLE 2-continued
| Ex. # | STRUCTURE | molecular weight |
|---|---|---|
| 270 | 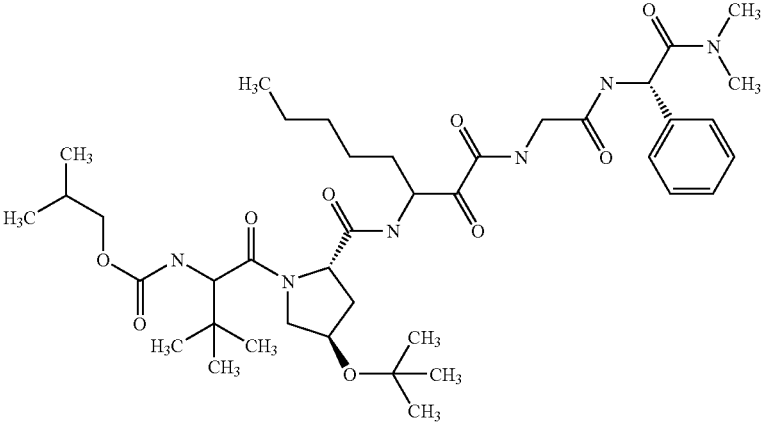 | 772.9909 |
| 271 | 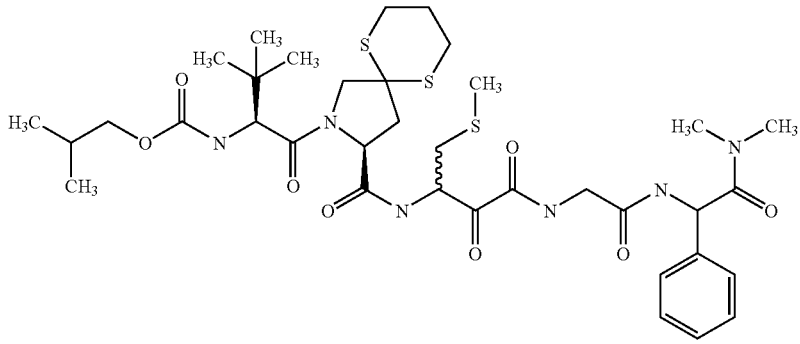 | 795.0592 |
| 272 | 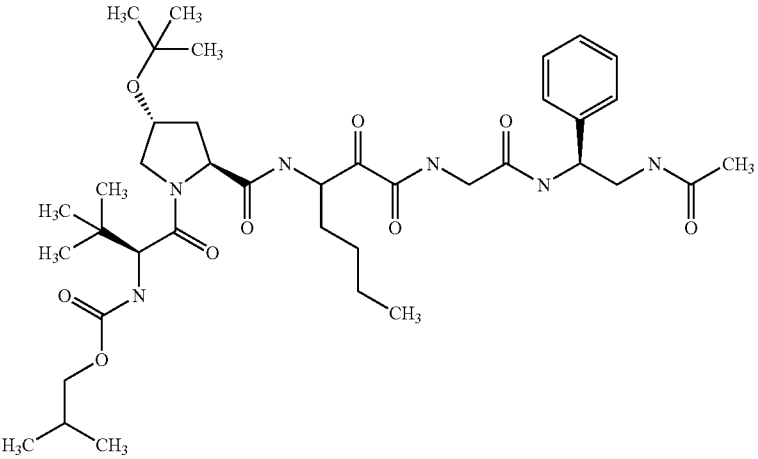 | 758.9638 |

TABLE 2-continued
| Ex. # | STRUCTURE | molecular weight |
|---|---|---|
| 273 | 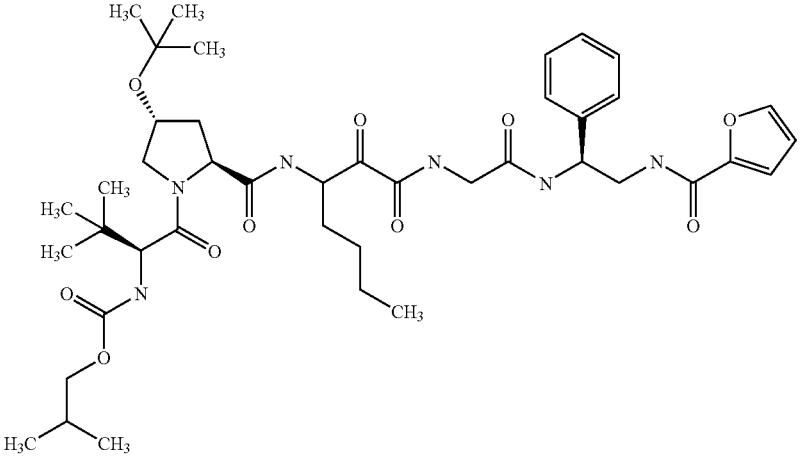 | 810.9966 |
| 274 | 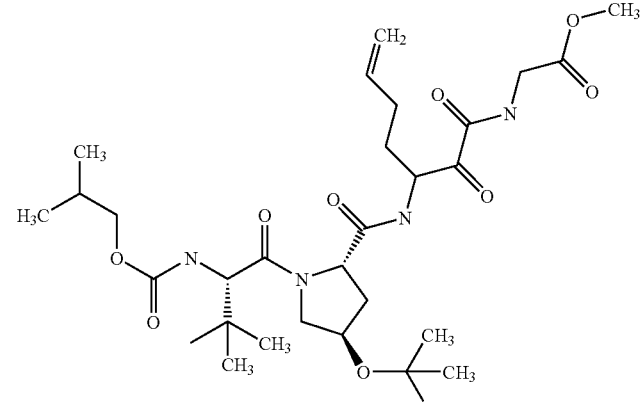 | 610.7544 |
| 275 | 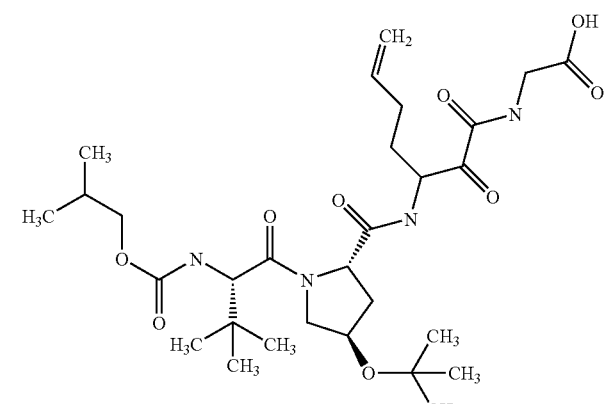 | 596.7273 |

TABLE 2-continued
| Ex. # | STRUCTURE | molecular weight |
|---|---|---|
| 276 | 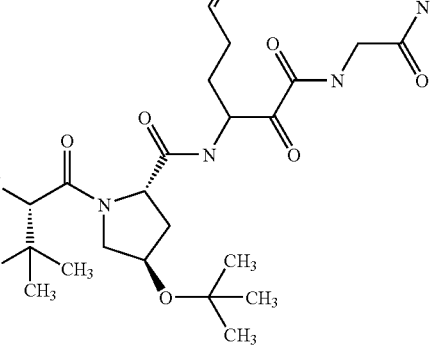 | 756.9479 |
| 277 | 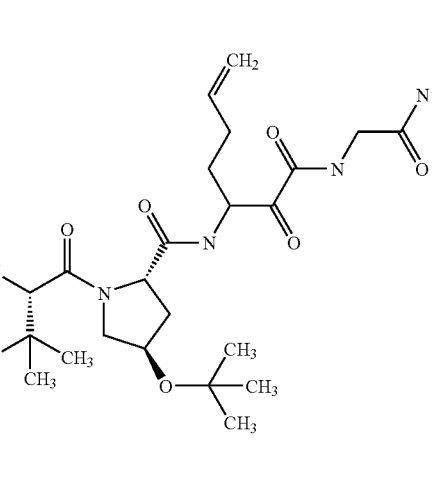 | 756.9479 |
| 278 | 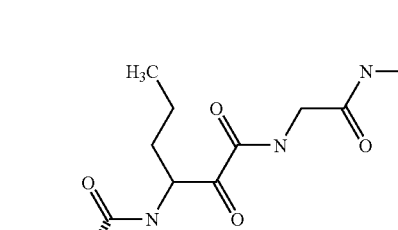 | 744.9799 |

TABLE 2-continued
| Ex. # | STRUCTURE | molecular weight |
|---|---|---|
| 279 | 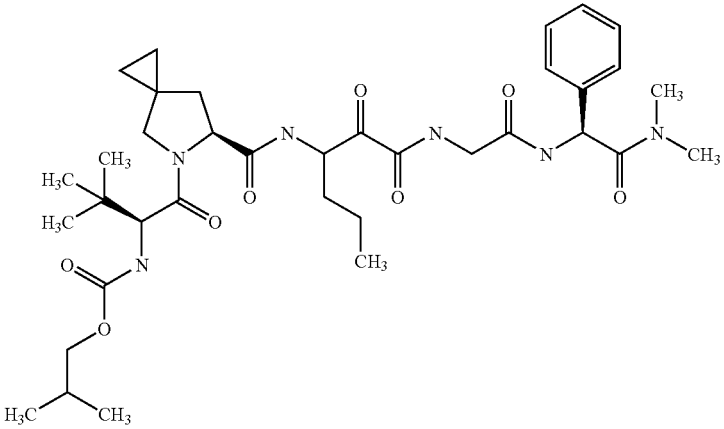 | 698.8672 |
| 280 | 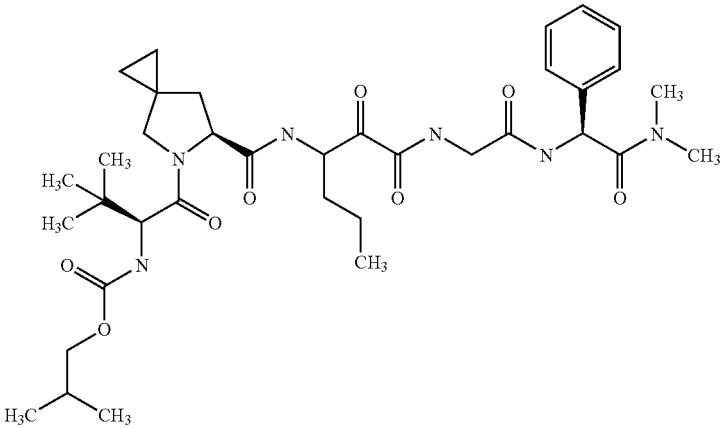 | 698.8672 |
| 281 | 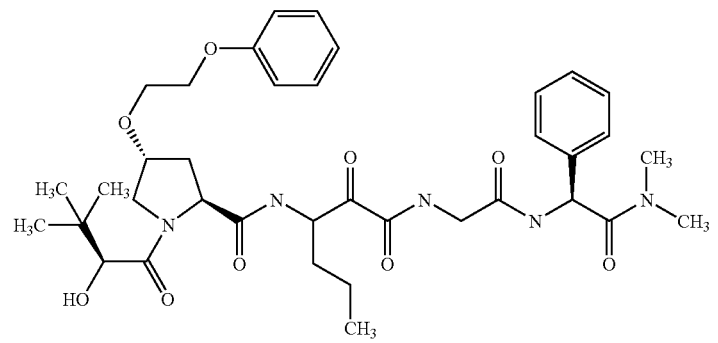 | 709.8471 |

TABLE 2-continued
| Ex. # | STRUCTURE | molecular weight |
|---|---|---|
| 282 | 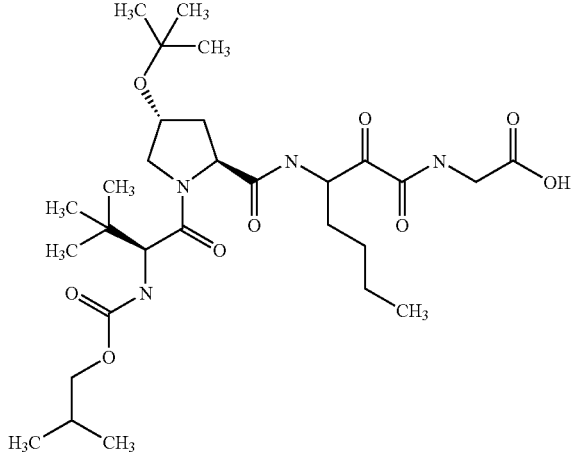 | 598.7432 |
| 283 | 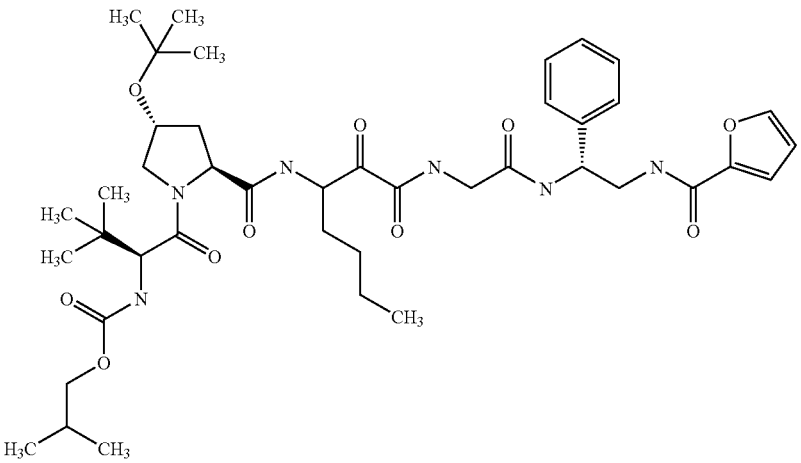 | 810.9966 |
| 284 | 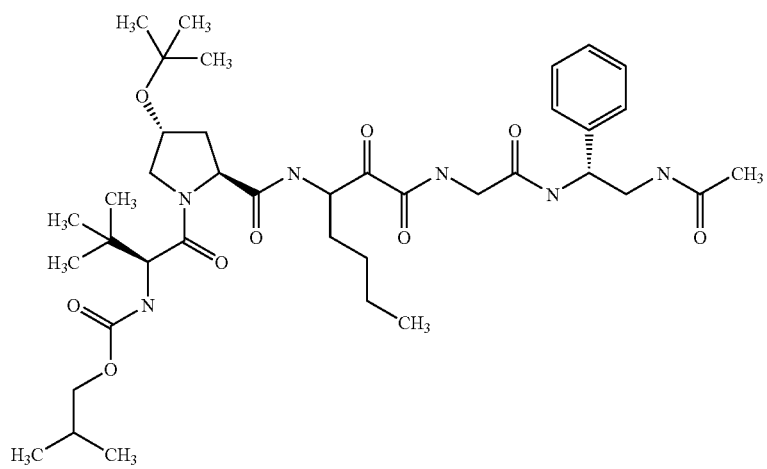 | 758.9638 |

TABLE 2-continued
| Ex. # | STRUCTURE | molecular weight |
|---|---|---|
| 285 | 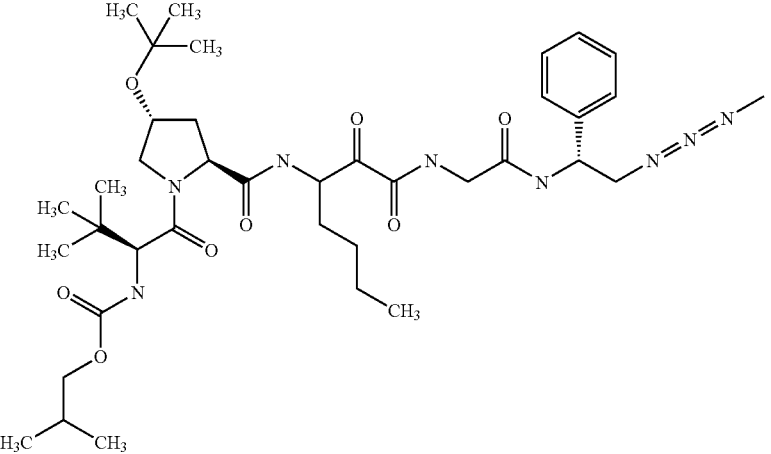 | 742.9236 |
| 286 | 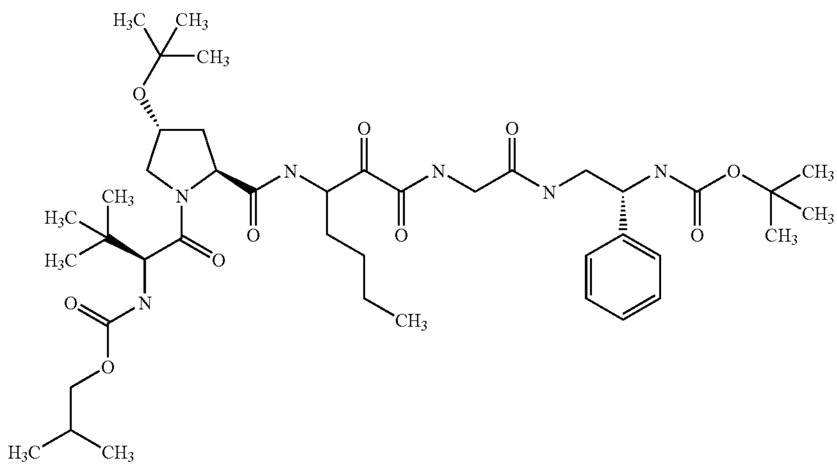 | 817.0444 |
| 287 | 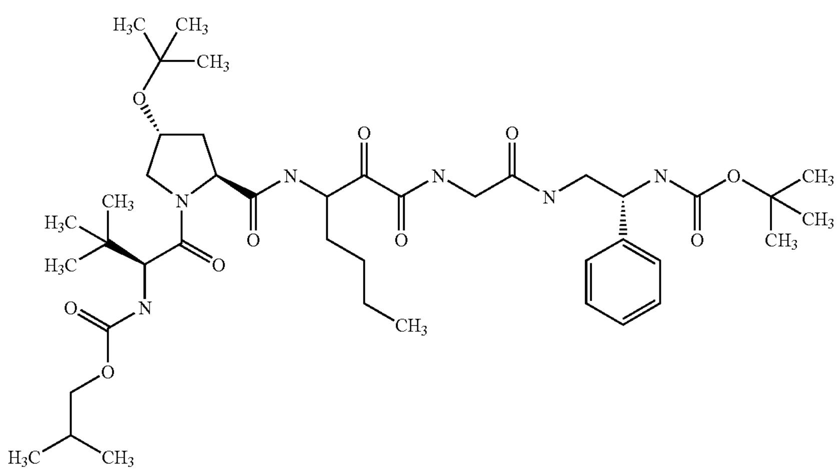 | 817.0444 |

TABLE 2-continued

| Ex. # | STRUCTURE | molecular weight |
|---|---|---|
| 288 | 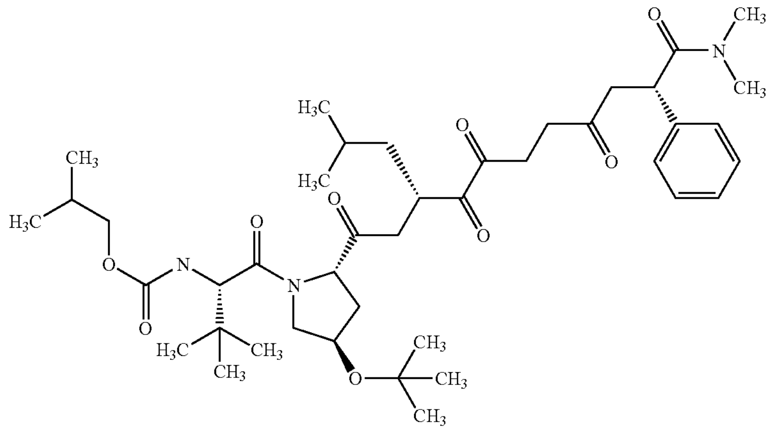 | 759.9526 |
| 289 | 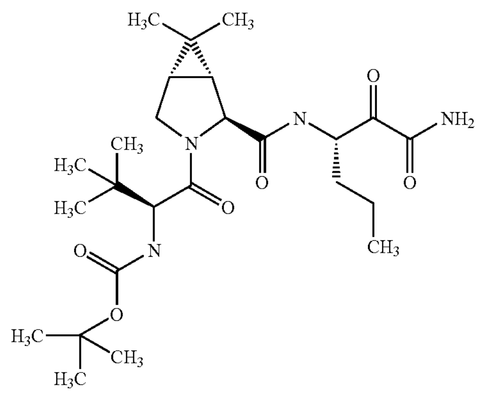 | 494.6367 |
| 290 | 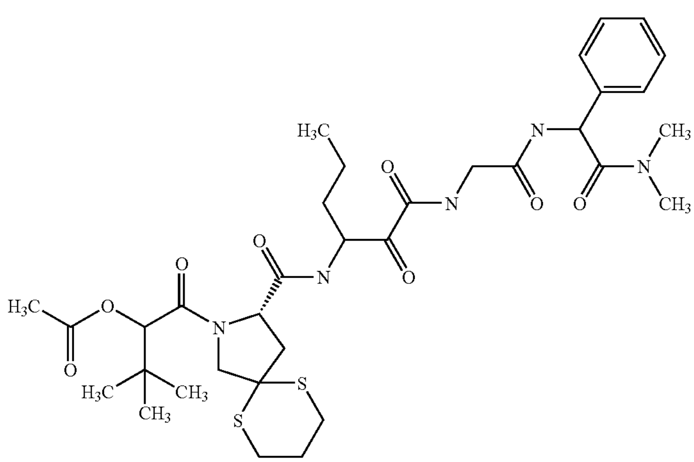 | 719.9263 |

TABLE 2-continued
| Ex. # | STRUCTURE | molecular weight |
|---|---|---|
| 291 | 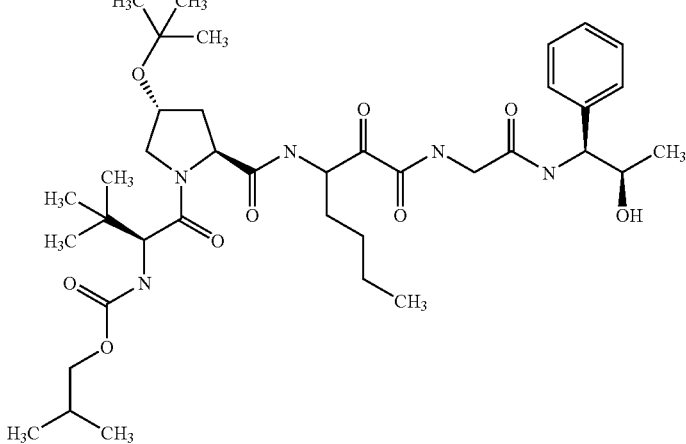 | 731.938 |
| 292 | 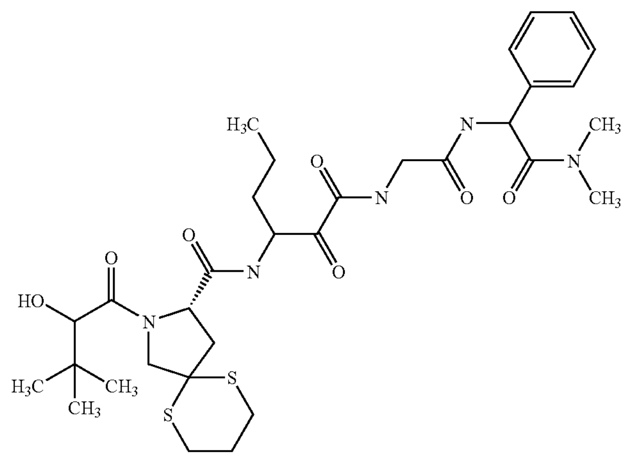 | 677.8887 |
| 293 | 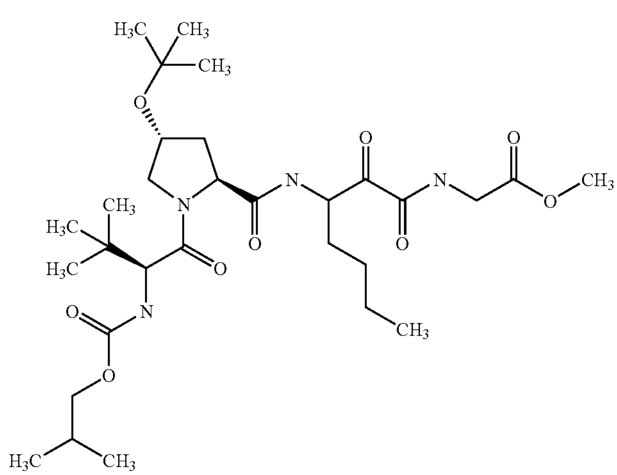 | 612.7703 |

TABLE 2-continued
| Ex. # | STRUCTURE | molecular weight |
|---|---|---|
| 294 | 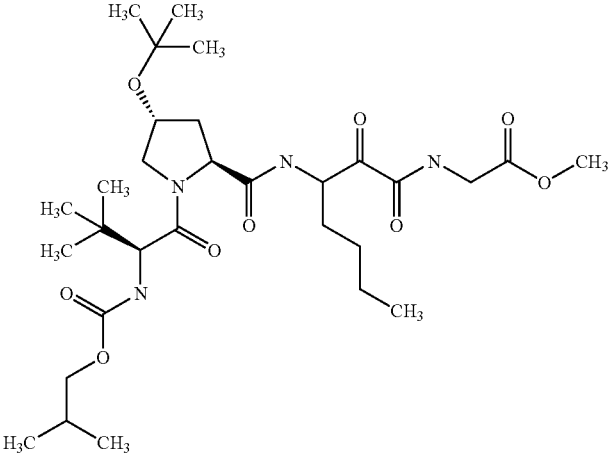 | 612.7703 |
| 295 | 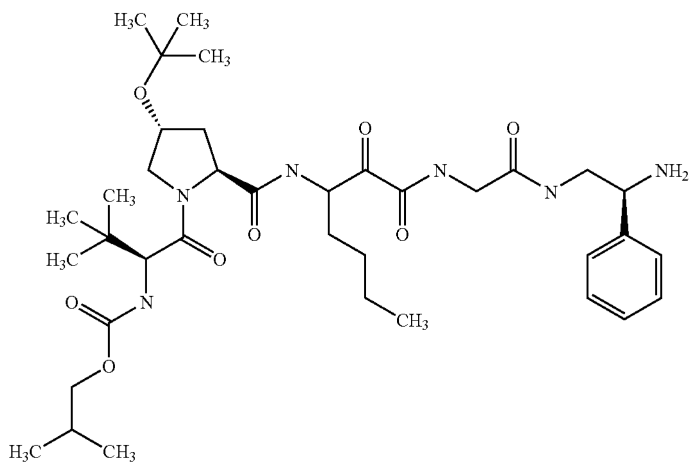 | 716.9261 |
| 296 | 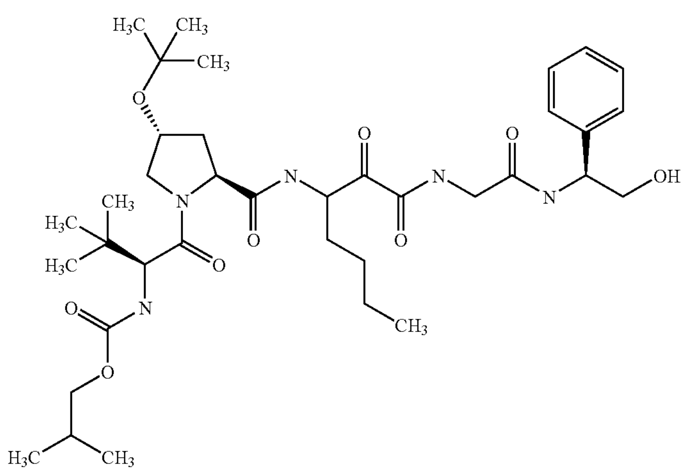 | 717.9109 |

TABLE 2-continued

| Ex. # | STRUCTURE | molecular weight |
|---|---|---|
| 297 | 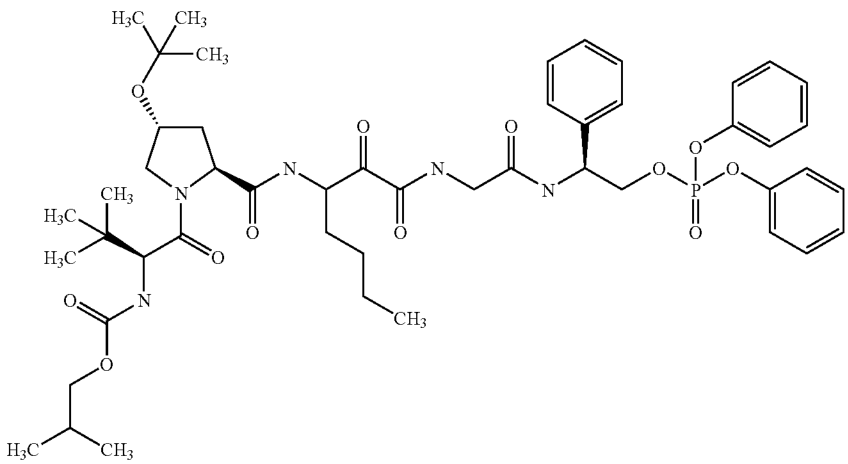 | 950.0884 |
| 298 | 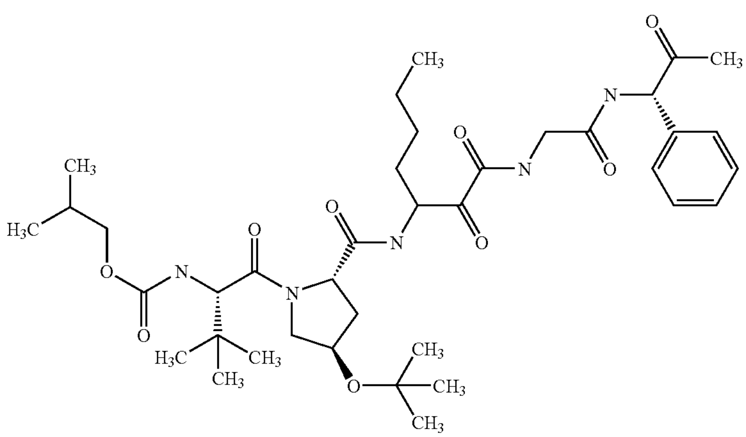 | 729.9221 |
| 299 | 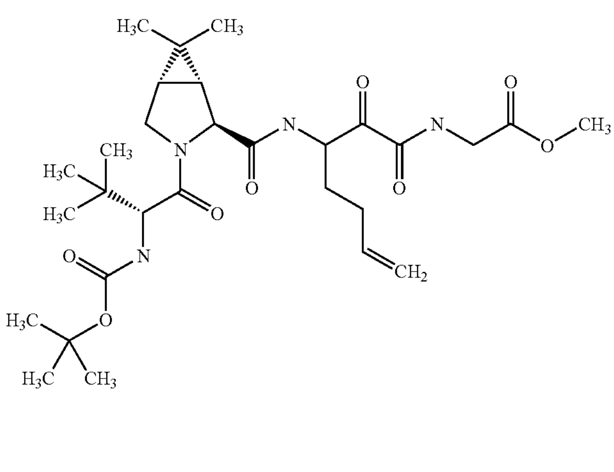 | 578.712 |

TABLE 2-continued

| Ex. # | STRUCTURE | molecular weight |
| --- | --- | --- |
| 300 | 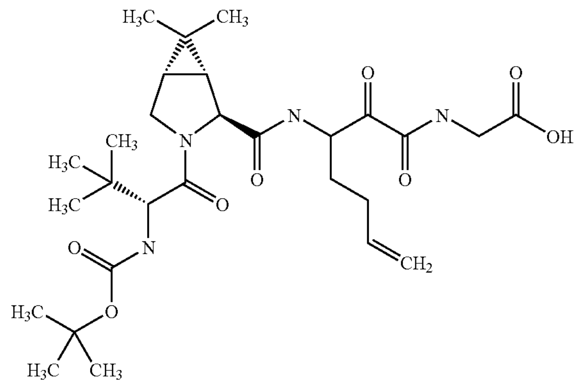 | 564.6849 |
| 301 | 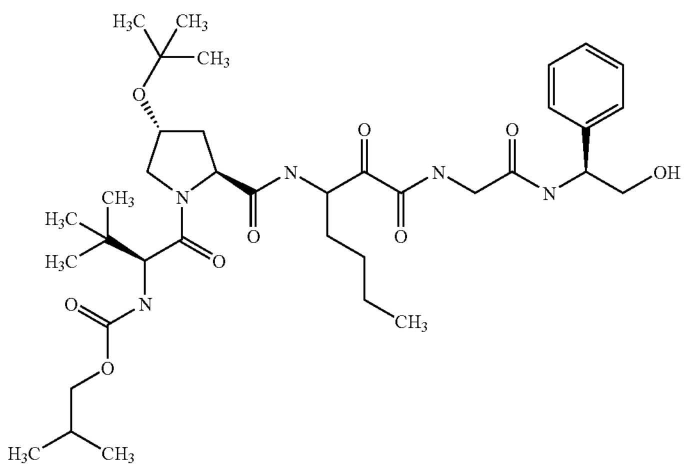 | 703.8838 |
| 302 | 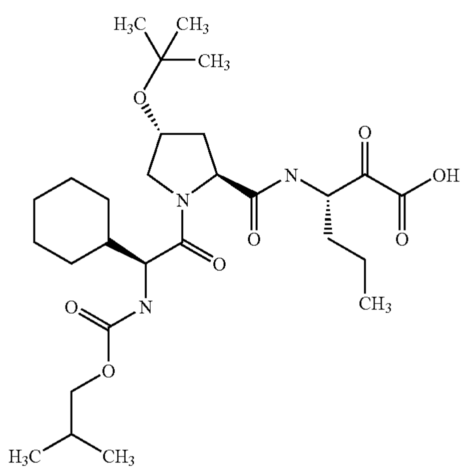 | 553.7021 |

TABLE 2-continued
| Ex. # | STRUCTURE | molecular weight |
|---|---|---|
| 303 | 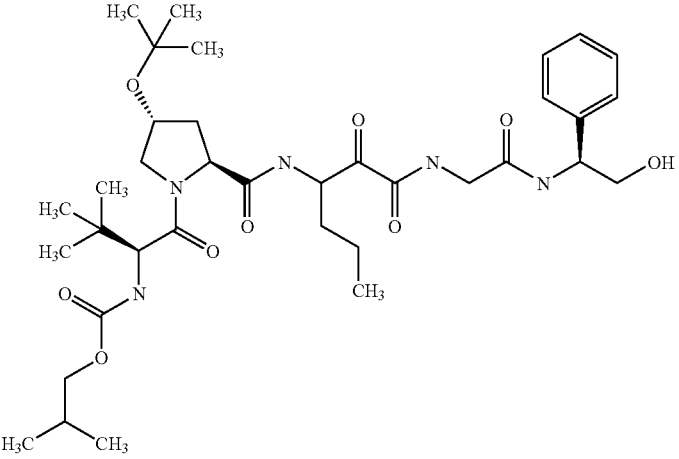 | 703.8838 |
| 304 | 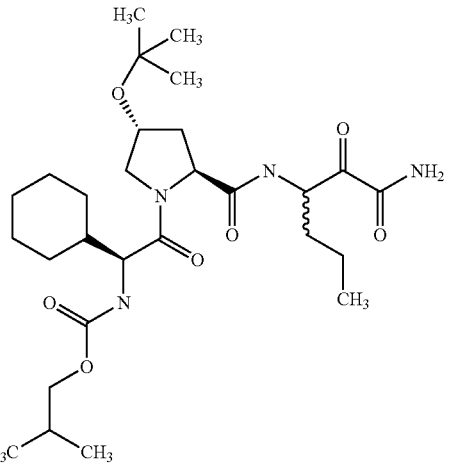 | 552.7173 |
| 305 | 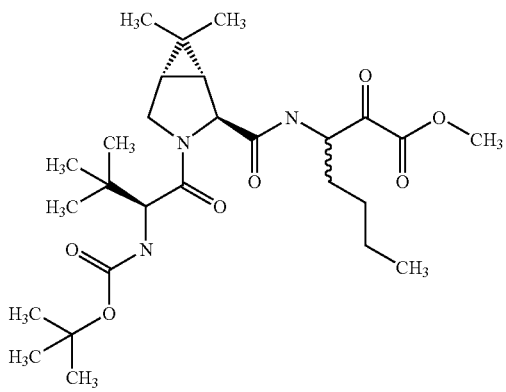 | 523.6756 |

TABLE 2-continued

| Ex. # | STRUCTURE | molecular weight |
|---|---|---|
| 306 | 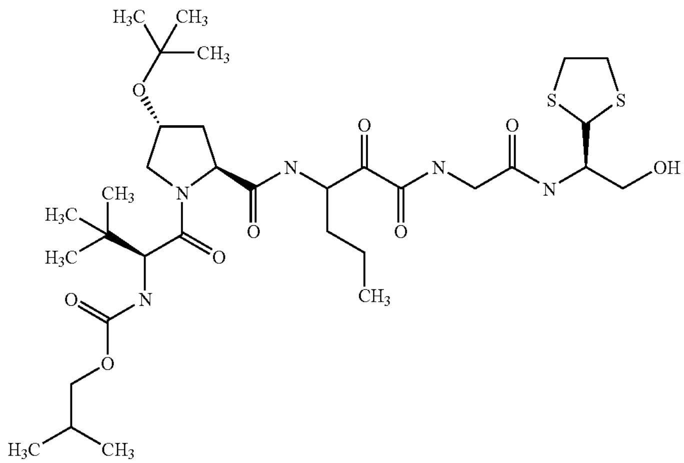 | 731.9783 |
| 307 | 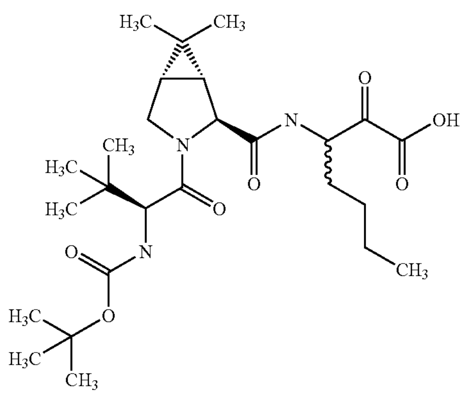 | 509.6485 |
| 308 | 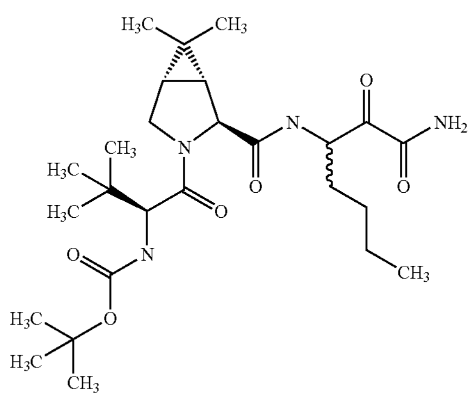 | 508.6638 |

TABLE 2-continued

| Ex. # | STRUCTURE | molecular weight |
|---|---|---|
| 309 | 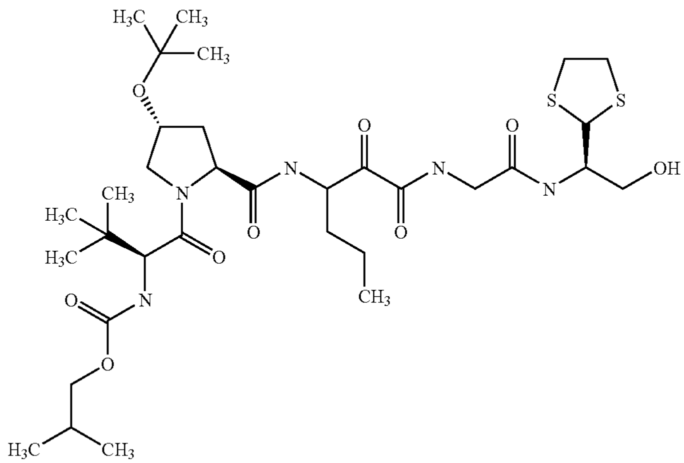 | 731.9783 |
| 310 | 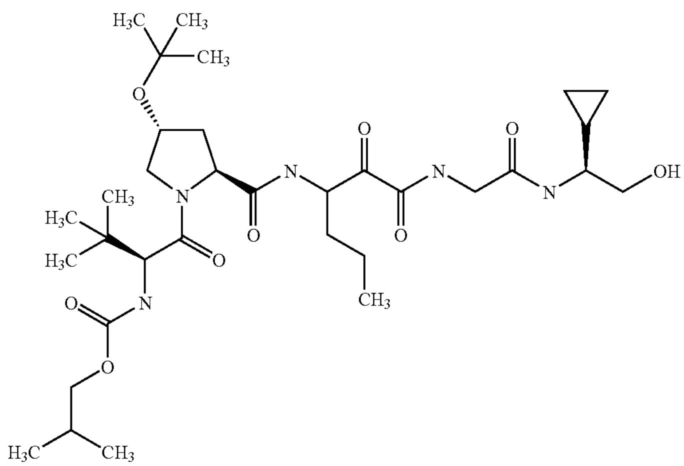 | 667.8503 |
| 311 | 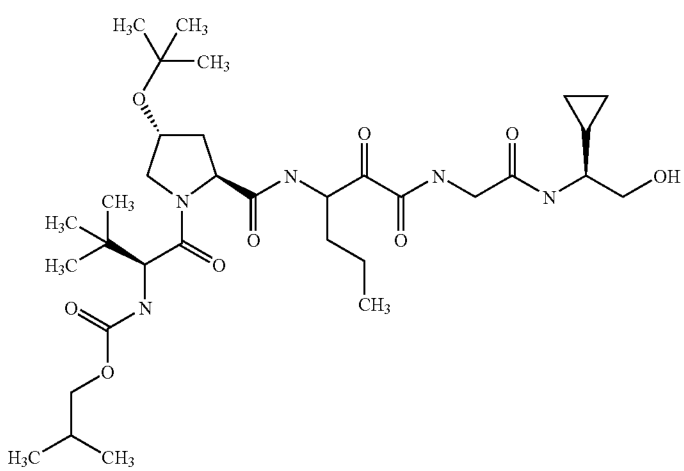 | 667.8503 |

TABLE 2-continued
| Ex. # | STRUCTURE | molecular weight |
|---|---|---|
| 312 | 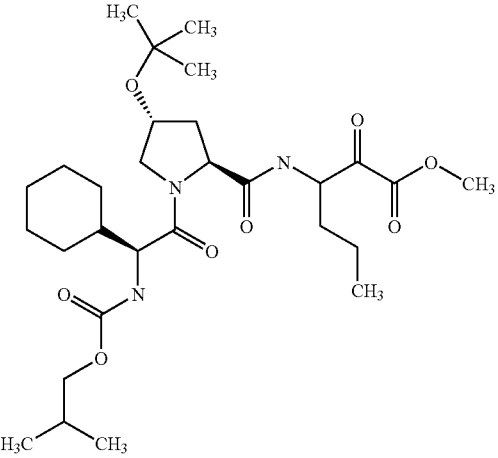 | 567.7292 |
| 313 | 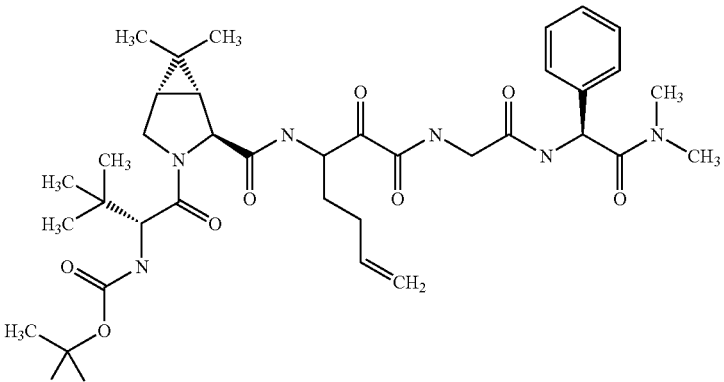 | 724.9054 |
| 314 | 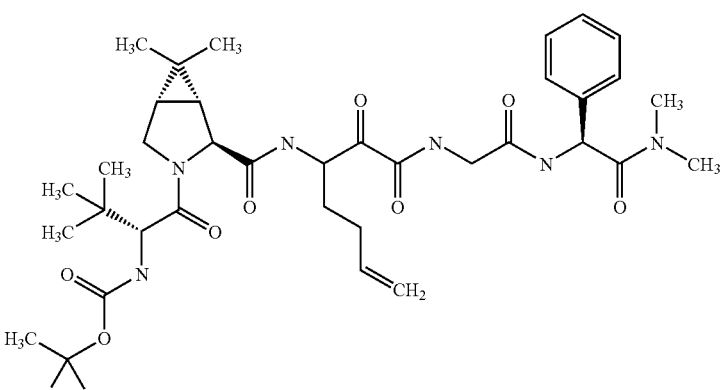 | 724.9054 |

TABLE 2-continued
| Ex. # | STRUCTURE | molecular weight |
|---|---|---|
| 315 | 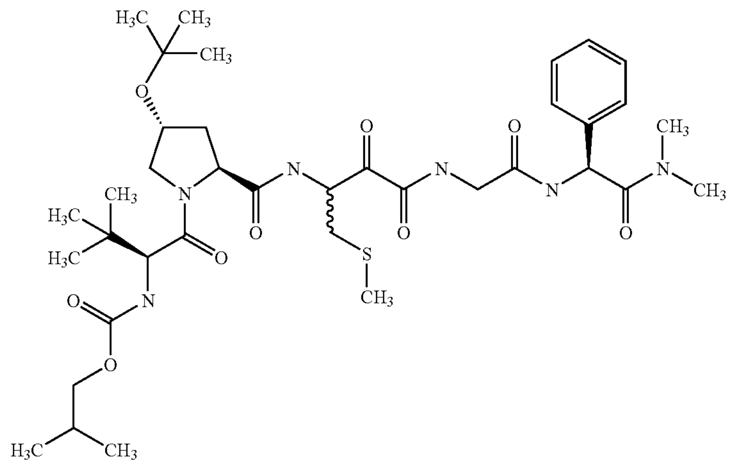 | 762.9736 |
| 316 | 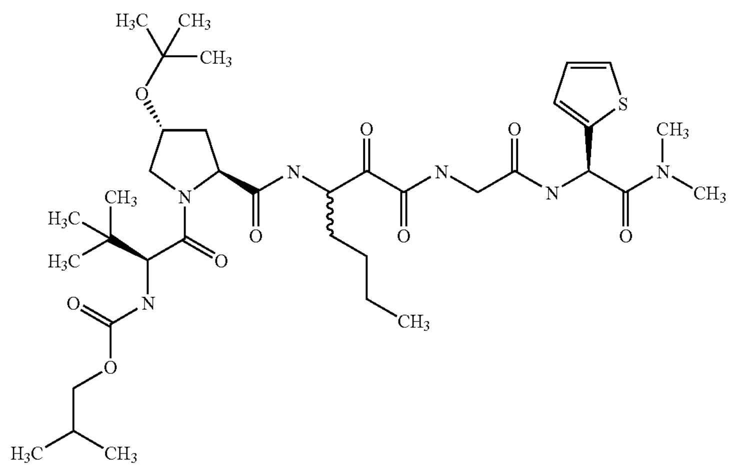 | 764.9896 |
| 317 | 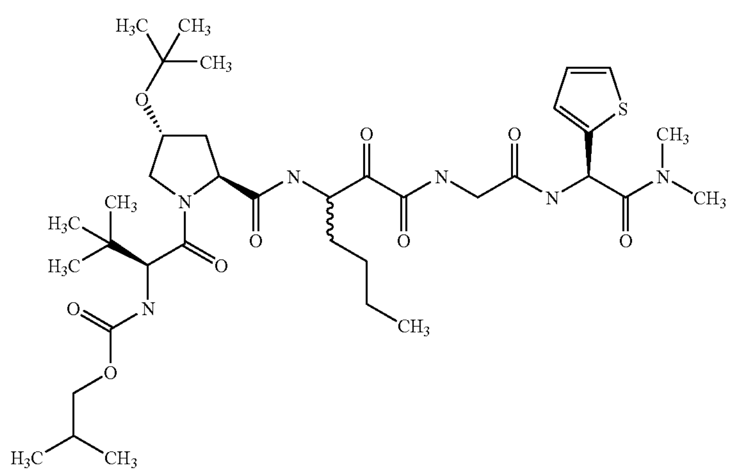 | 764.9896 |

TABLE 2-continued
| Ex. # | STRUCTURE | molecular weight |
|---|---|---|
| 318 | 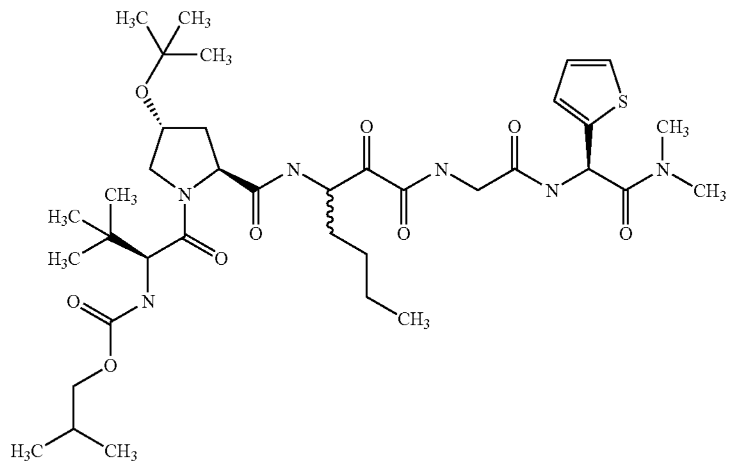 | 764.9896 |
| 319 | 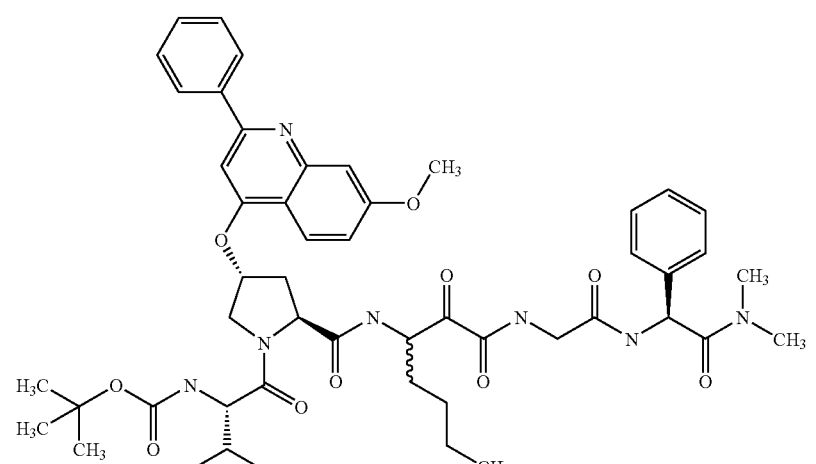 | 908.0734 |
| 320 | 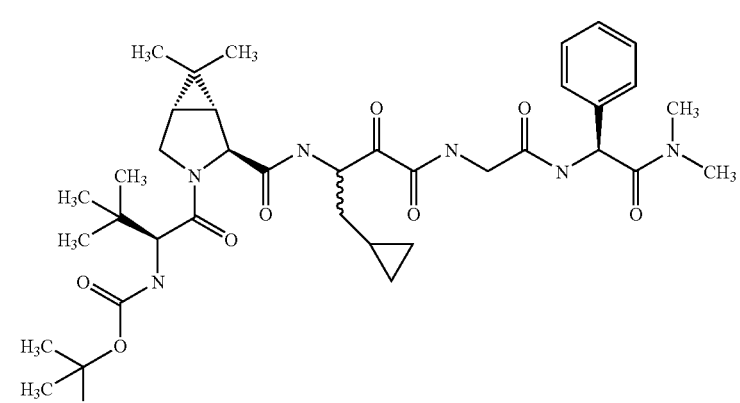 | 724.9054 |

TABLE 2-continued
| Ex. # | STRUCTURE | molecular weight |
|---|---|---|
| 321 | 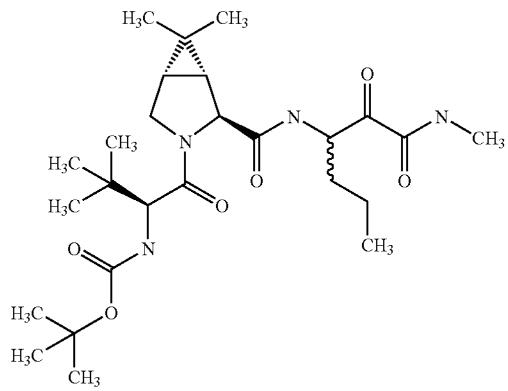 | 508.6638 |
| 322 | 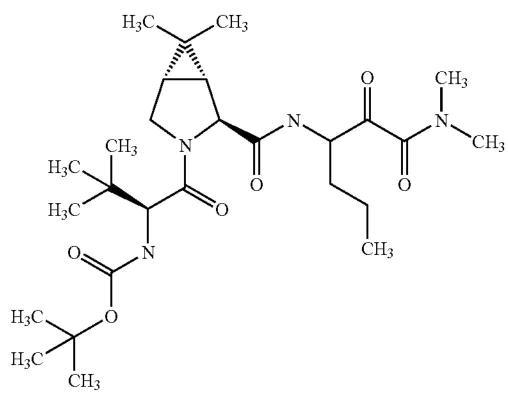 | 522.6909 |
| 323 | 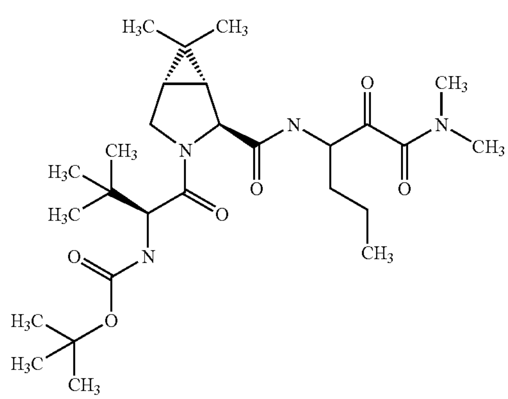 | 522.6909 |

TABLE 2-continued
| Ex. # | STRUCTURE | molecular weight |
|---|---|---|
| 324 | 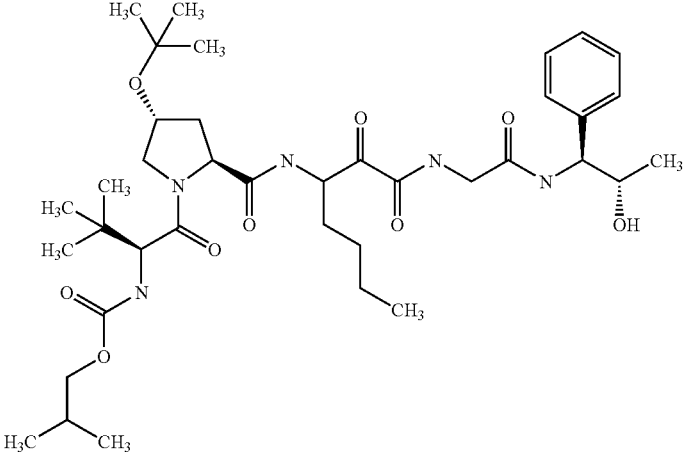 | 731.938 |
| 325 | 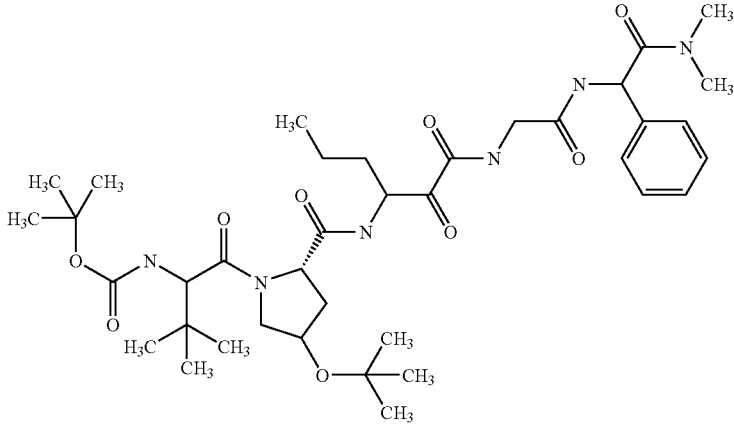 | 744.9367 |
| 326 | 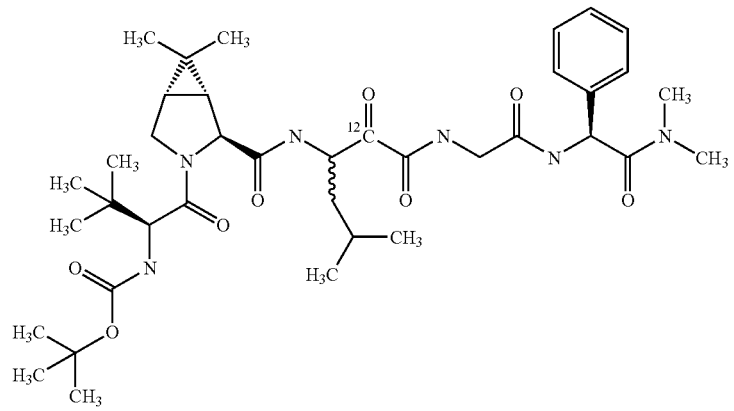 | 727.9102 |

TABLE 2-continued
| Ex. # | STRUCTURE | molecular weight |
| --- | --- | --- |
| 327 | 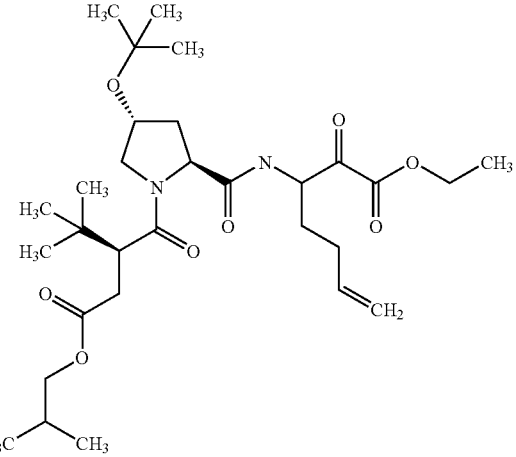 | 567.7292 |
| 328 | 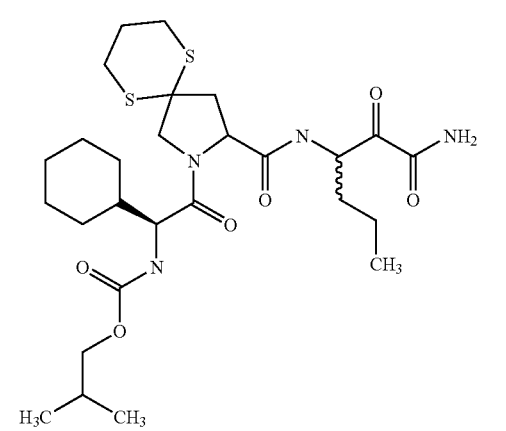 | 584.8029 |
| 329 | 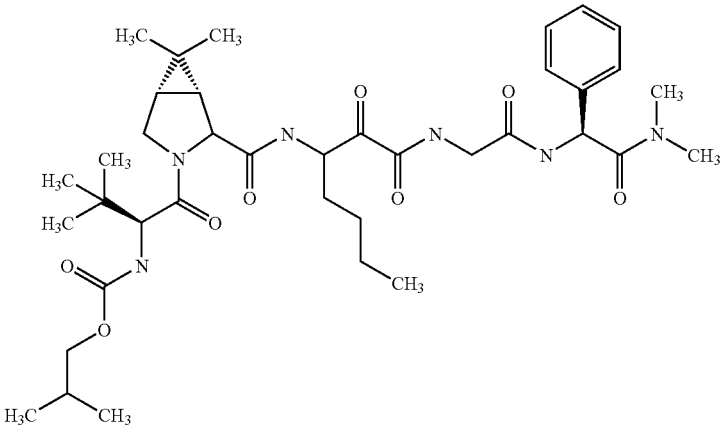 | 726.9214 |

TABLE 2-continued

| Ex. # | STRUCTURE | molecular weight |
|---|---|---|
| 330 | 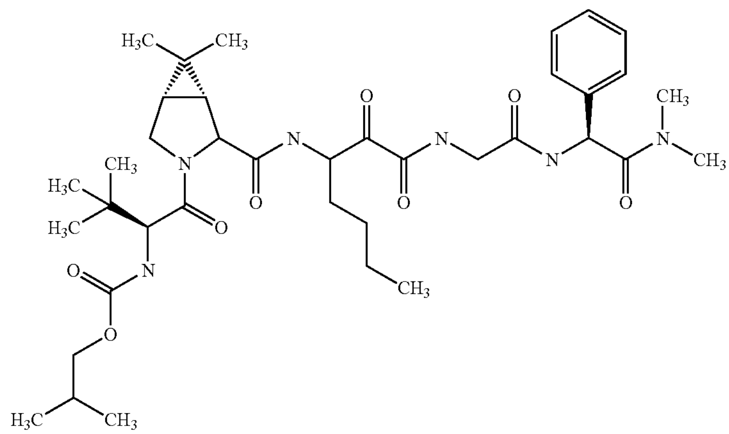 | 726.9214 |
| 331 | 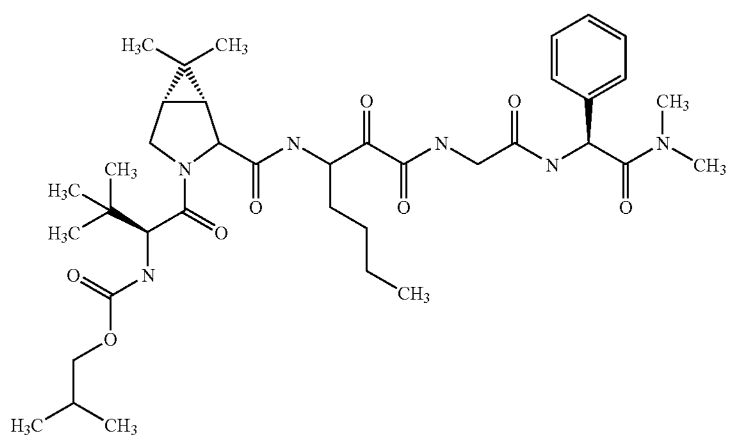 | 726.9214 |
| 332 | 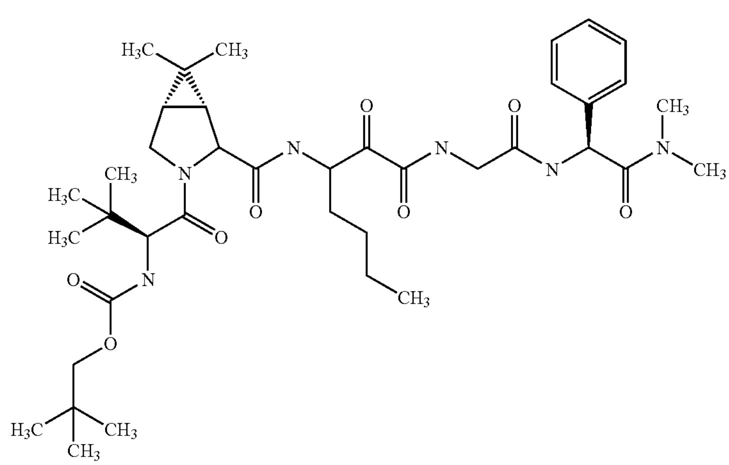 | 740.9484 |

TABLE 2-continued

| Ex. # | STRUCTURE | molecular weight |
|---|---|---|
| 333 | 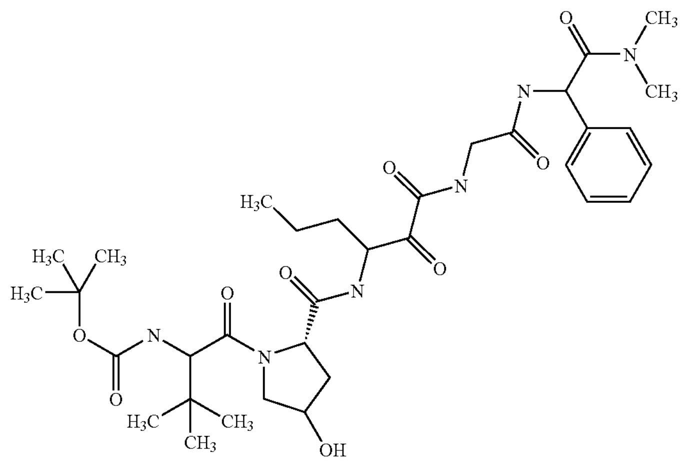 | 688.8284 |
| 334 | 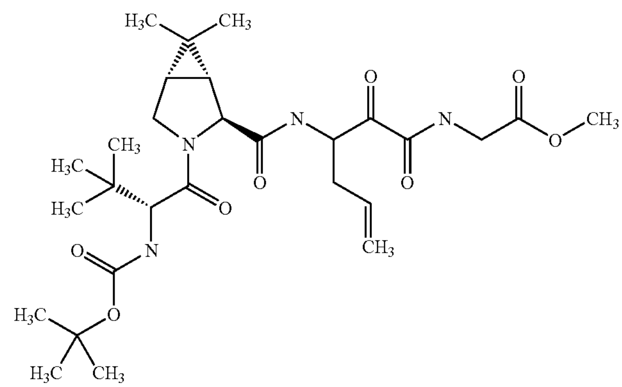 | 564.6849 |
| 335 | 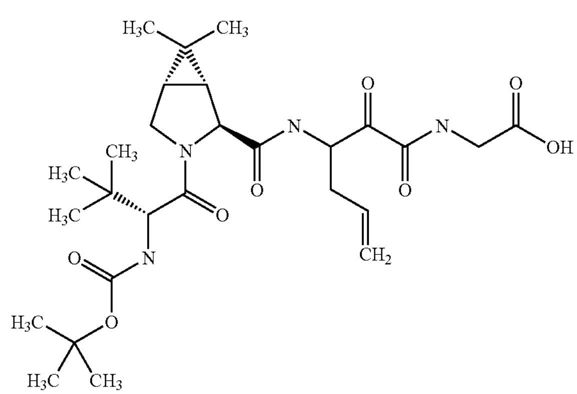 | 550.6578 |

TABLE 2-continued

| Ex. # | STRUCTURE | molecular weight |
|---|---|---|
| 336 | 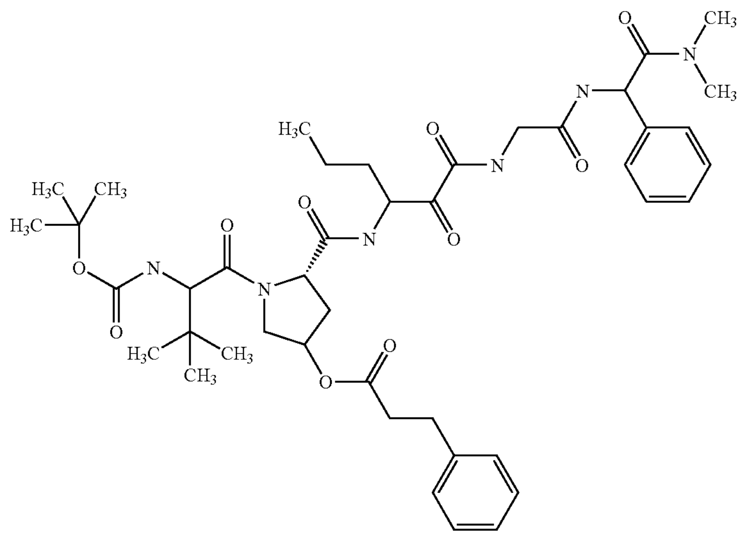 | 820.9918 |
| 337 | 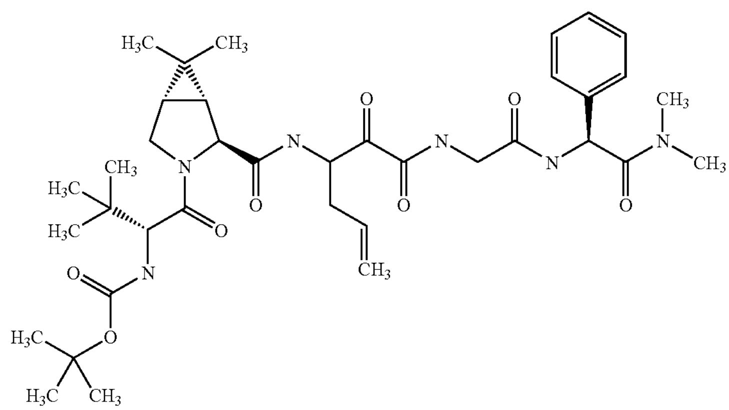 | 710.8784 |
| 338 | 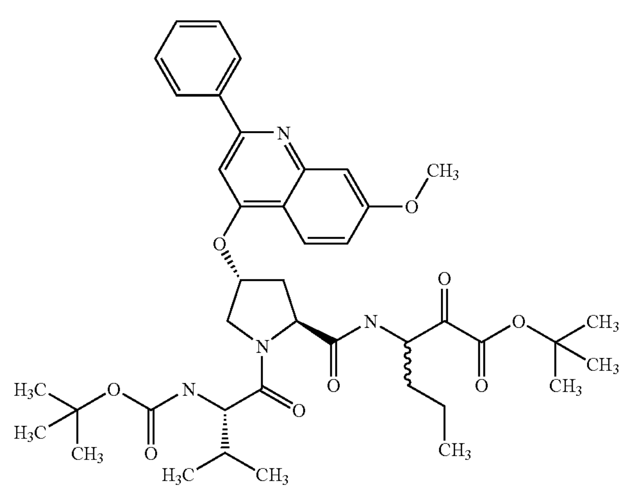 | 746.9089 |

TABLE 2-continued
| Ex. # | STRUCTURE | molecular weight |
|---|---|---|
| 339 | 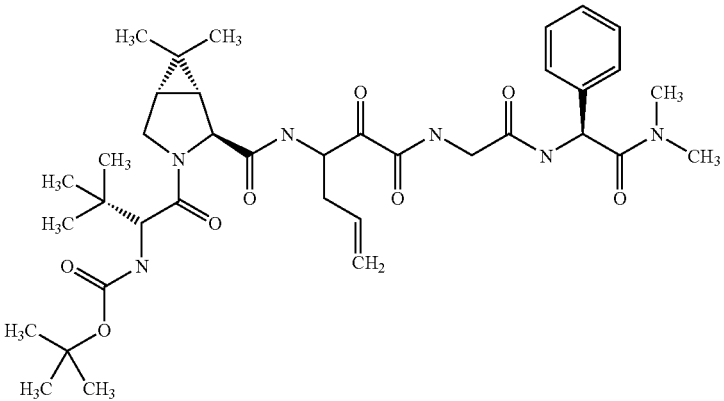 | 710.8784 |
| 340 | 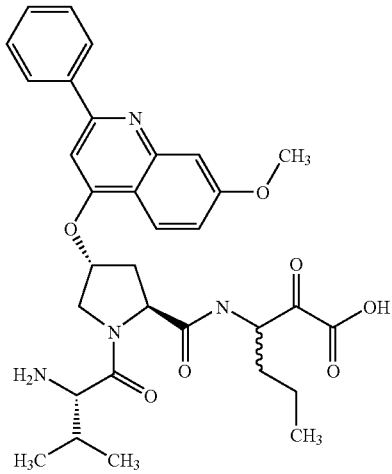 | 590.6823 |
| 341 | 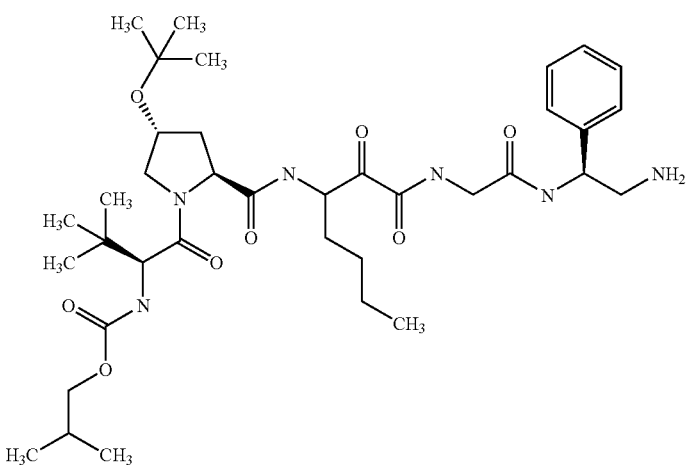 | 716.9261 |

TABLE 2-continued
| Ex. # | STRUCTURE | molecular weight |
|---|---|---|
| 342 | 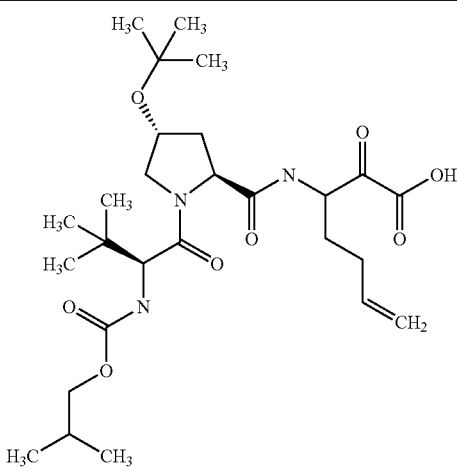 | 539.675 |
| 343 | 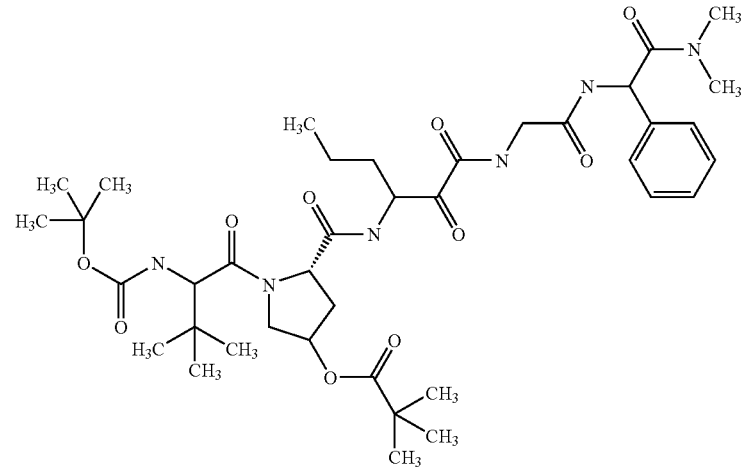 | 772.9473 |
| 344 | 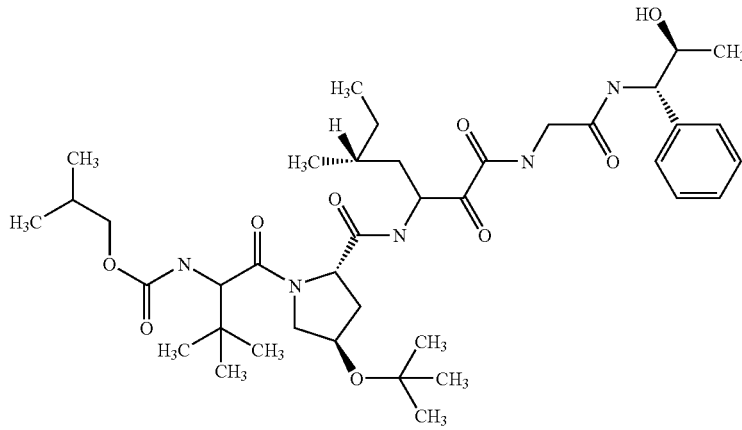 | 731.938 |

TABLE 2-continued
| Ex. # | STRUCTURE | molecular weight |
|---|---|---|
| 345 | 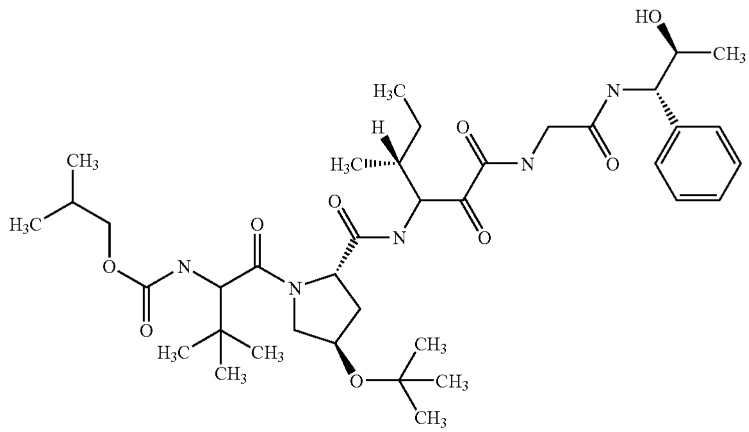 | 731.938 |
| 346 | 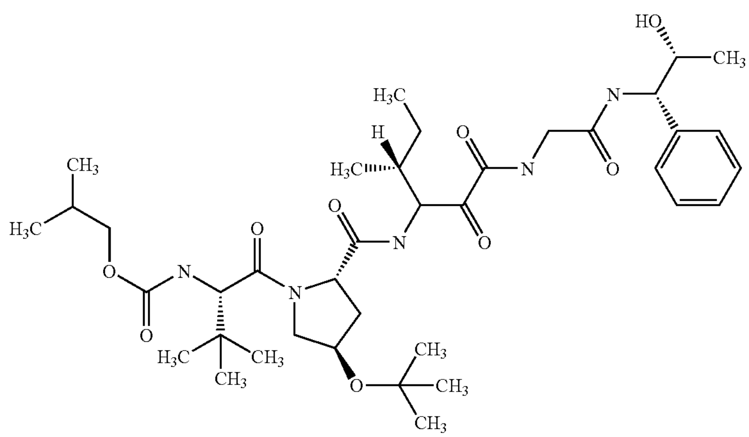 | 731.938 |
| 347 | 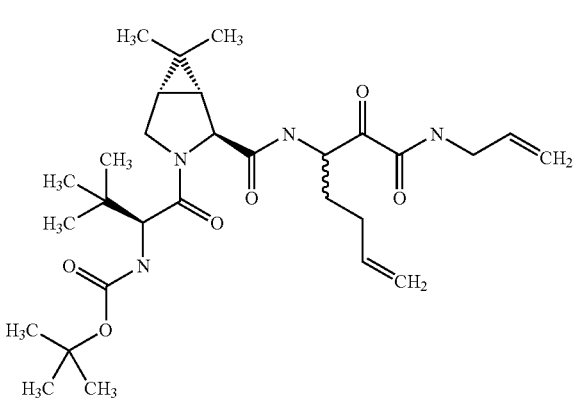 | 546.7132 |

TABLE 2-continued
| Ex. # | STRUCTURE | molecular weight |
|---|---|---|
| 348 | 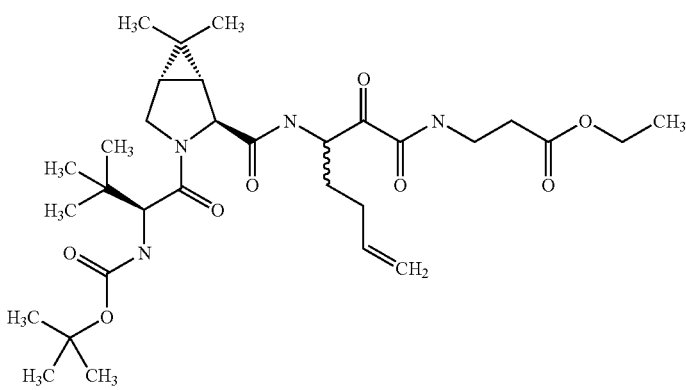 | 606.7662 |
| 349 | 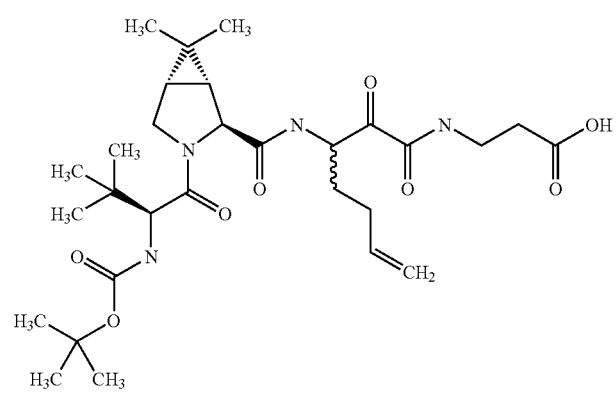 | 578.712 |
| 350 | 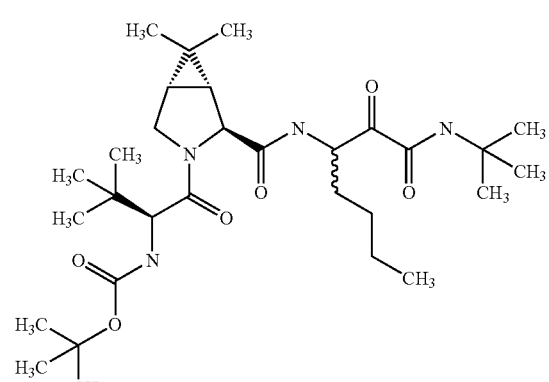 | 564.7722 |
| 351 | 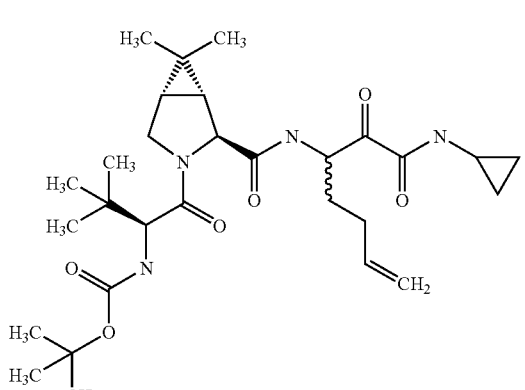 | 548.7291 |

TABLE 2-continued
| Ex. # | STRUCTURE | molecular weight |
|---|---|---|
| 352 | 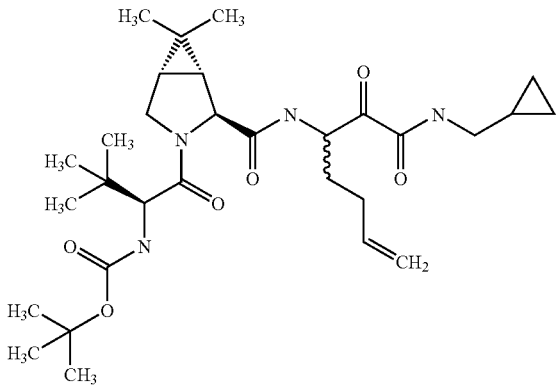 | 562.7562 |
| 353 | 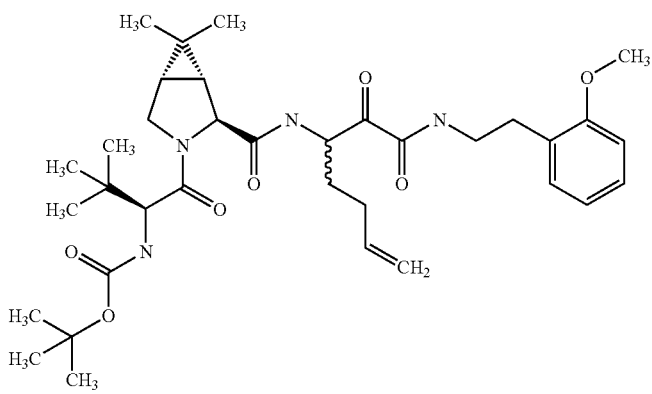 | 642.8432 |
| 354 | 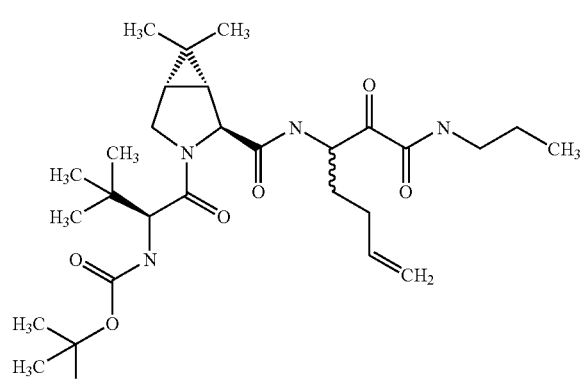 | 536.718 |
| 355 | 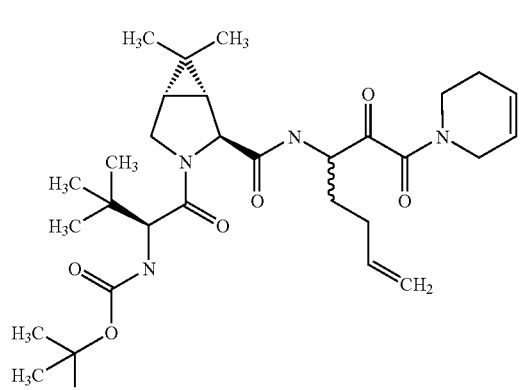 | 574.7673 |

TABLE 2-continued

| Ex. # | STRUCTURE | molecular weight |
|---|---|---|
| 356 | 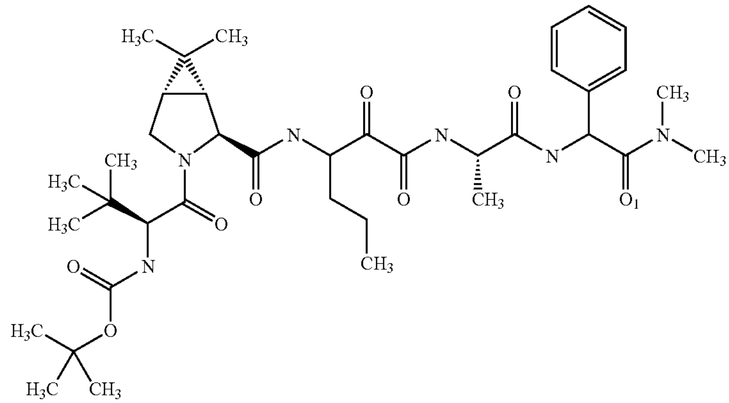 | 726.9214 |
| 357 | 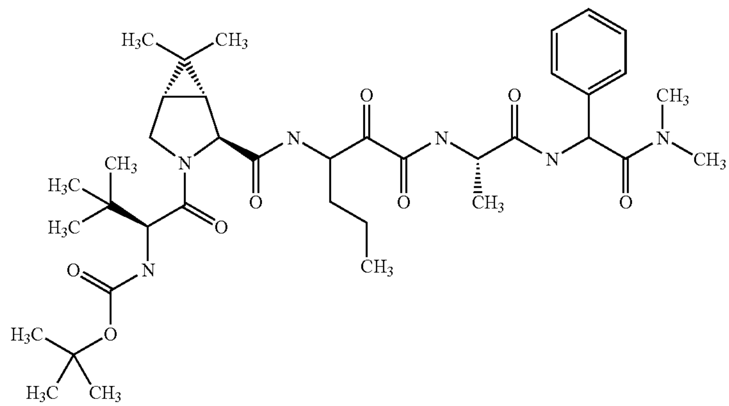 | 726.9214 |
| 358 | 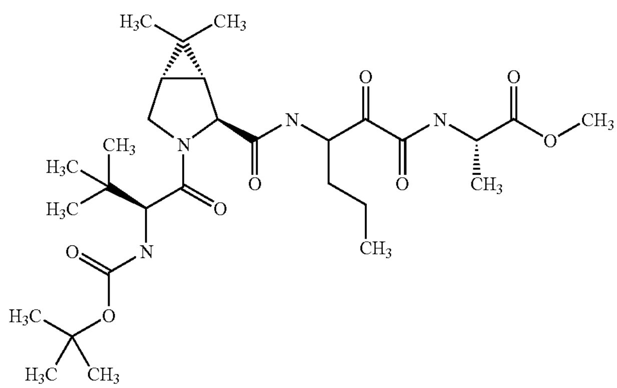 | 580.7279 |
| 359 | 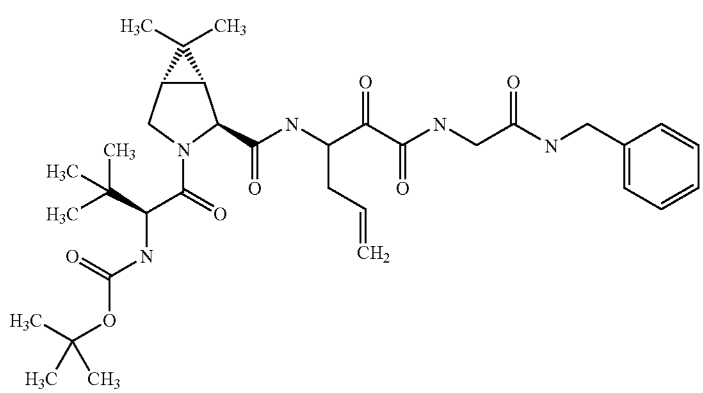 | 639.799 |

TABLE 2-continued
| Ex. # | STRUCTURE | molecular weight |
|---|---|---|
| 360 | 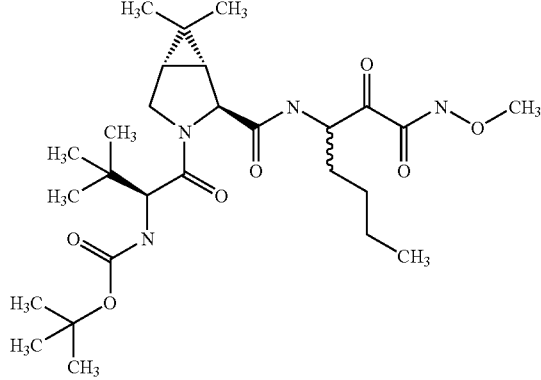 | 538.6902 |
| 361 | 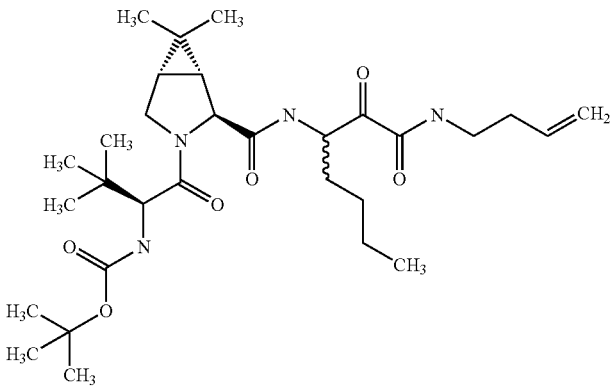 | 562.7562 |
| 362 | 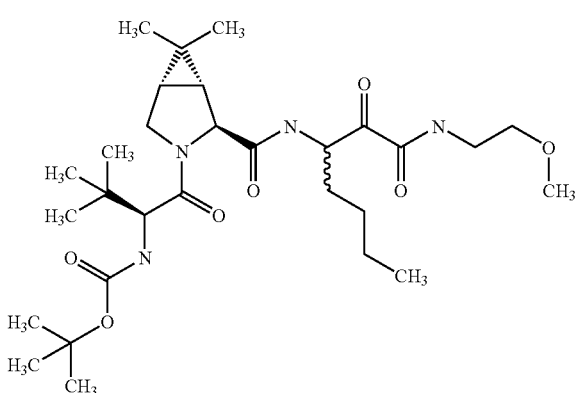 | 566.7444 |

TABLE 4
| STRUCTURE | NAME | Ki* Range |
|---|---|---|
| 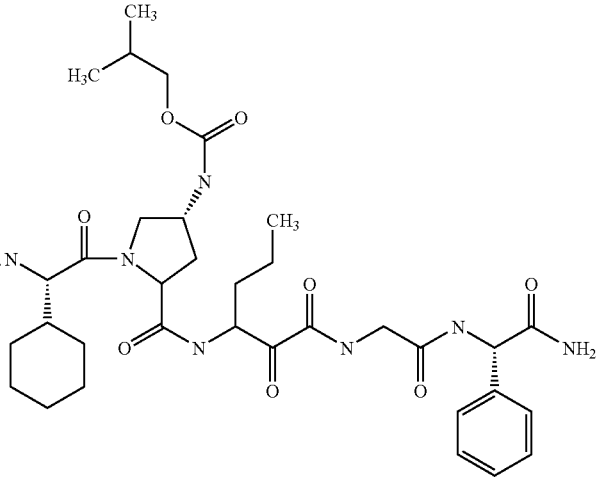 | iBoc-G(Chx)-P(4t-NHiBoc)-nV-(CO)-G-G(Ph)-Am | A |
| 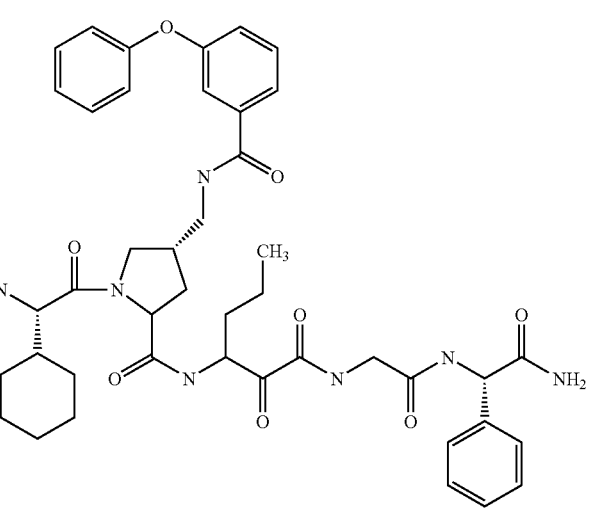 | (2-CO2)PhCO-G(Chx)-P(4t-MeNHCOPh(3-OPh)-nV-(CO)-G-G(Ph)-Am | A |
| 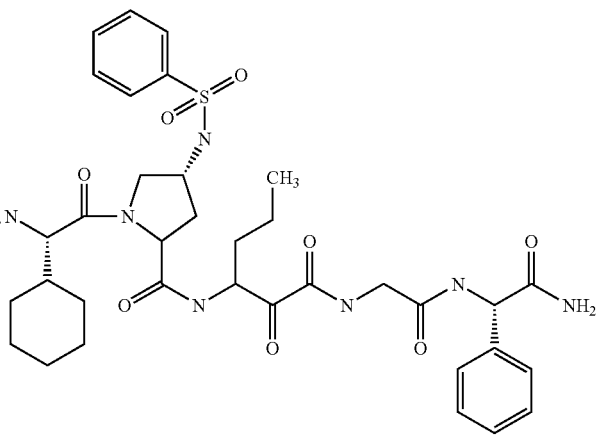 | iBoc-G(Chx)-P(4t-NHSO2Ph)-nV-(CO)-G-G(Ph)-Am | A |

TABLE 4-continued

| STRUCTURE | NAME | Ki* Range |
|---|---|---|
| 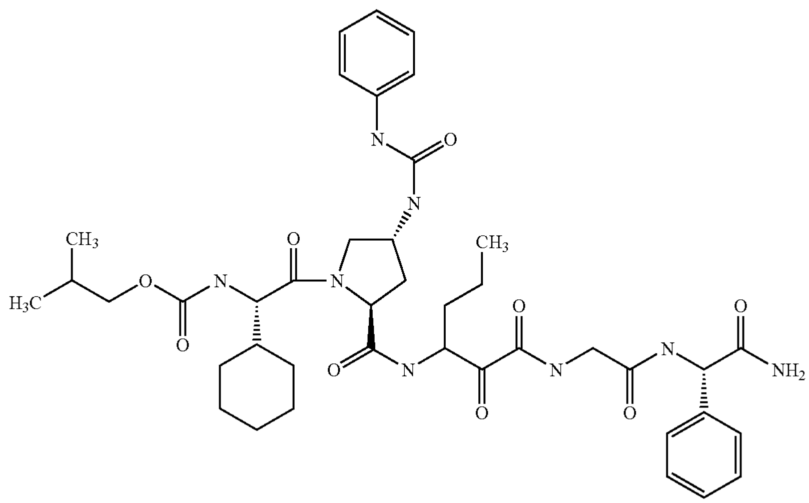 | iBoc-G(Chx)-P(4t-UreaPh)-nV-(CO)-G-G(Ph)-Am | A |
| 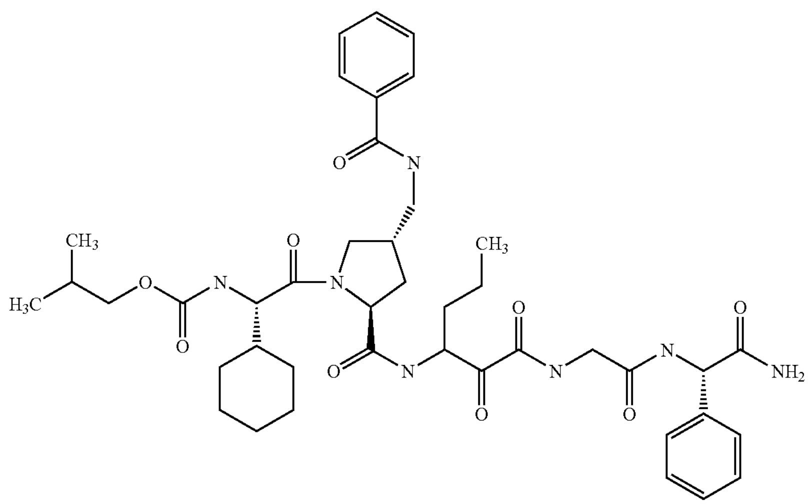 | iBoc-G(Chx)-P(4t-MeNHCOPh)-nV-(CO)-G-G(Ph)-Am | A |
| 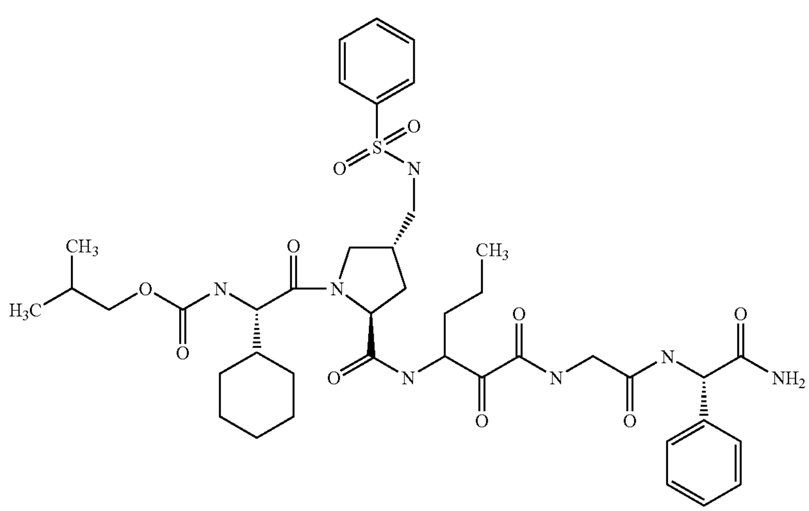 | iBoc-G(Chx)-P(4t-MeNHSO2Ph)~n[V]-(CO)-G-G(Ph)-Am | A |

TABLE 4-continued
| STRUCTURE | NAME | Ki* Range |
|---|---|---|
| 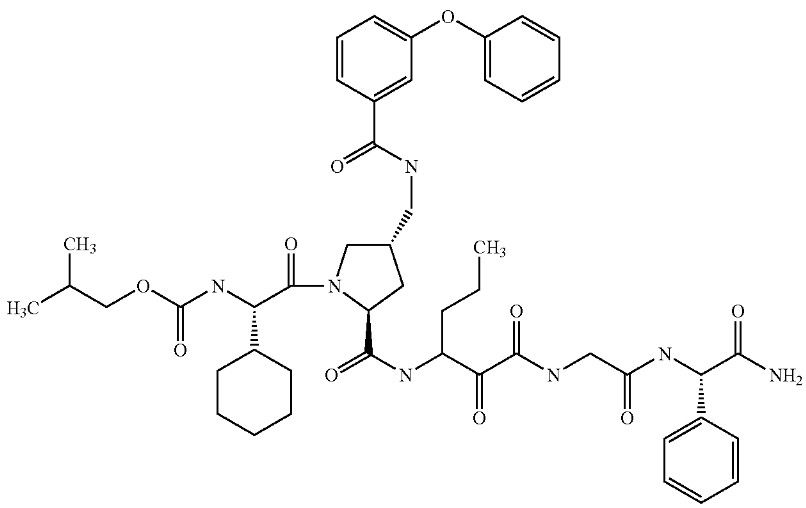 | iBoc-G(Chx)-P(4t-MeNHCOPh(3-OPh))-nV-(CO)-G-G(Ph)-Am | B |
| 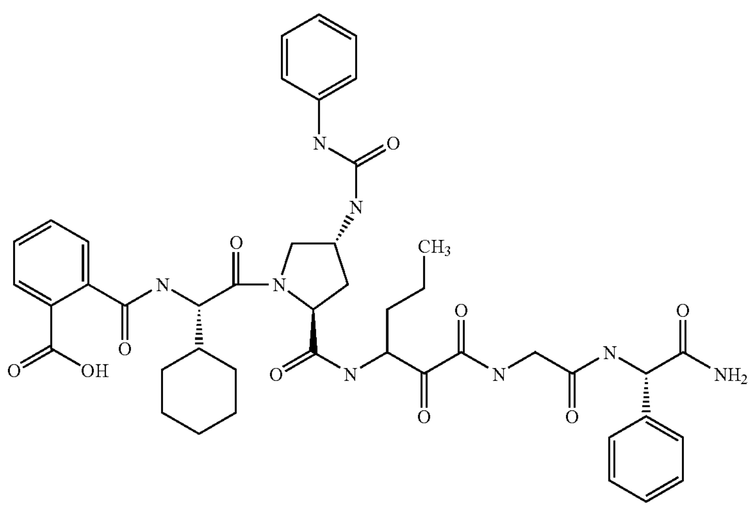 | (2-CO2)PhCO-G(chx)-P(4t-UreaPh)-nV-(CO)-G-G(ph)-Am | C |
| 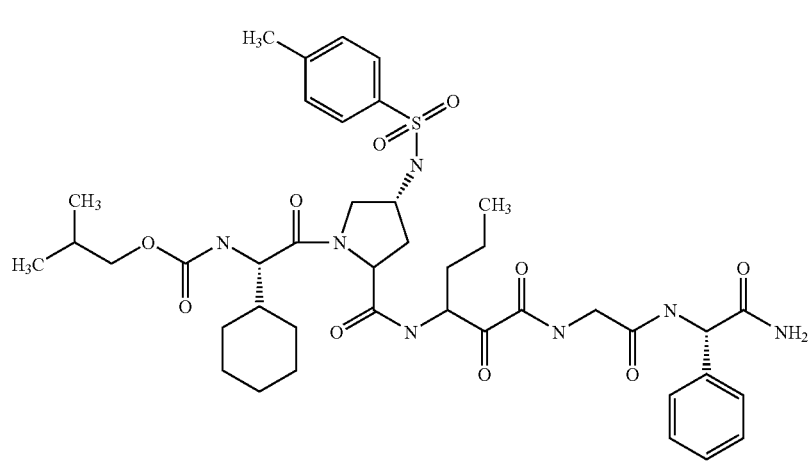 | iBoc-G(Chx)-P(4t-NHSO2-(4Me)Ph)-nV(CO)-G-G(Ph)-Am | B |

TABLE 4-continued
| STRUCTURE | NAME | Ki* Range |
|---|---|---|
| 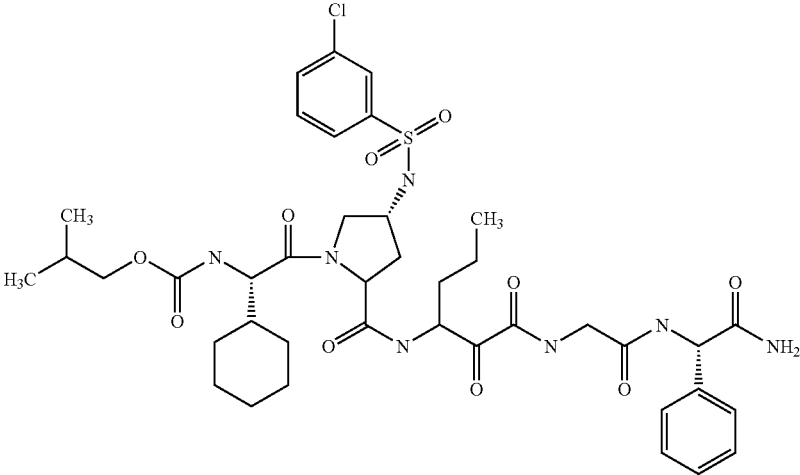 | iBoc-G(Chx)-P(4t-NHSO2-(3Cl)Ph)-nV(CO)-G-G(Ph)-Am | B |
| 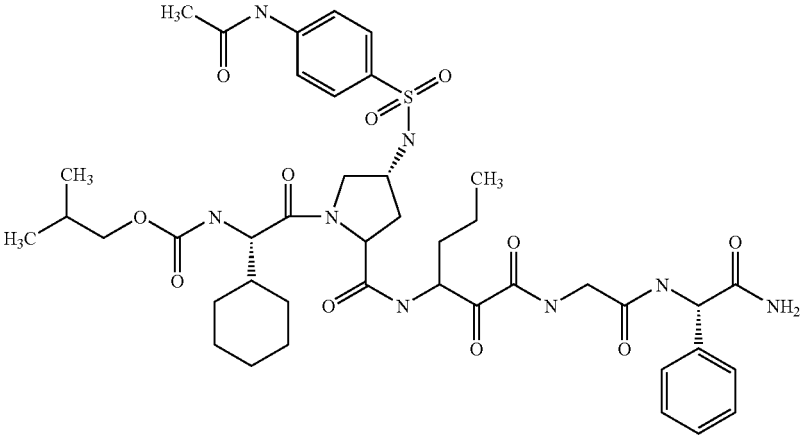 | iBoc-G(Chx)-P(4t-NHSO2-(4-NHAc)Ph)-nV-(CO)-G-G(Ph)-Am | A |
| 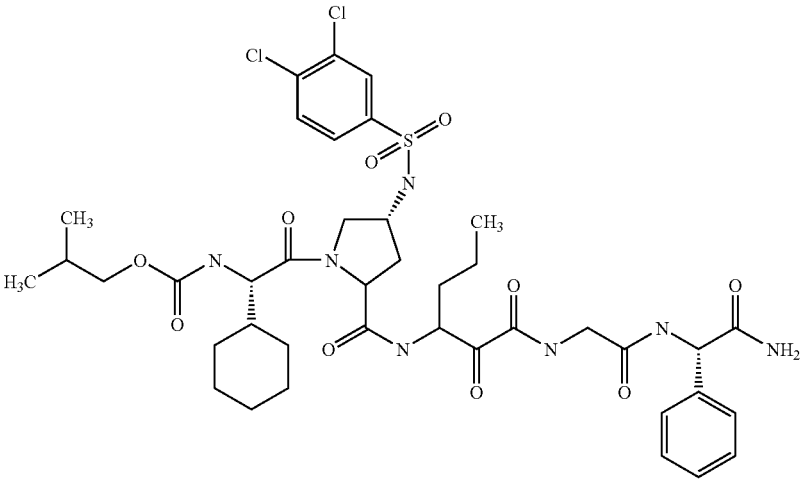 | iBoc-G(Chx)-P(4t-NHSO2-(3,4-diCl)Ph)-nV-(CO)-G-G(Ph)-Am | B |

TABLE 4-continued

| STRUCTURE | NAME | Ki* Range |
|---|---|---|
| 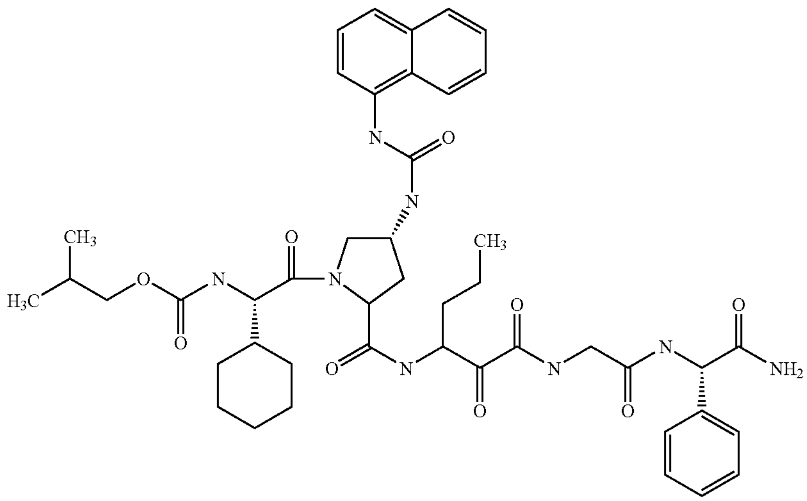 | iBoc-G(Chx)-P(4t-Urea-1-Np)-nV-(CO)-G-G(Ph)-Am | B |
| 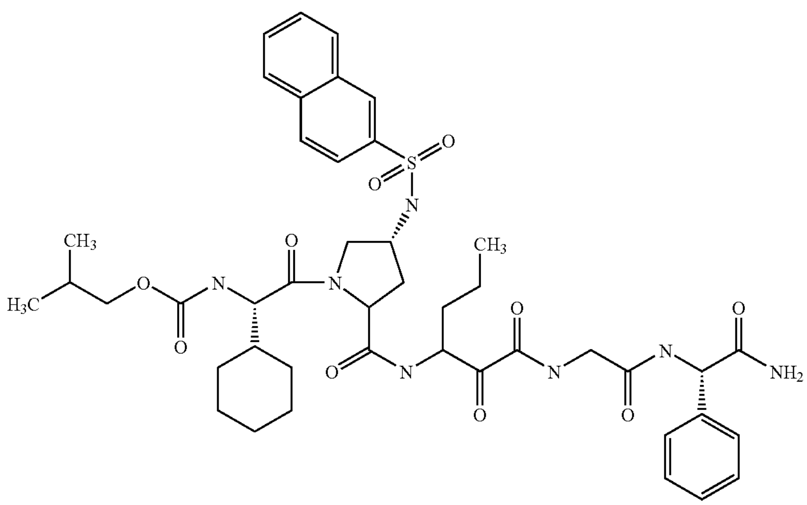 | iBoc-G(Chx)-P(4t-NHSO2-2-Np)-nV-(CO)-G-G(Ph)-Am | B |
| 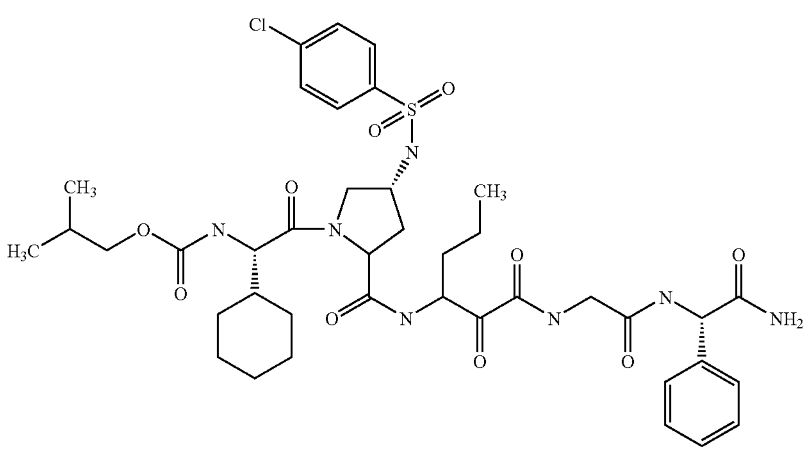 | iBoc-G(Chx)-P(4t-NHSO2-(4Cl)Ph)-nV-(CO)-G-G(Ph)-Am | B |

TABLE 4-continued
| STRUCTURE | NAME | Ki* Range |
|---|---|---|
| 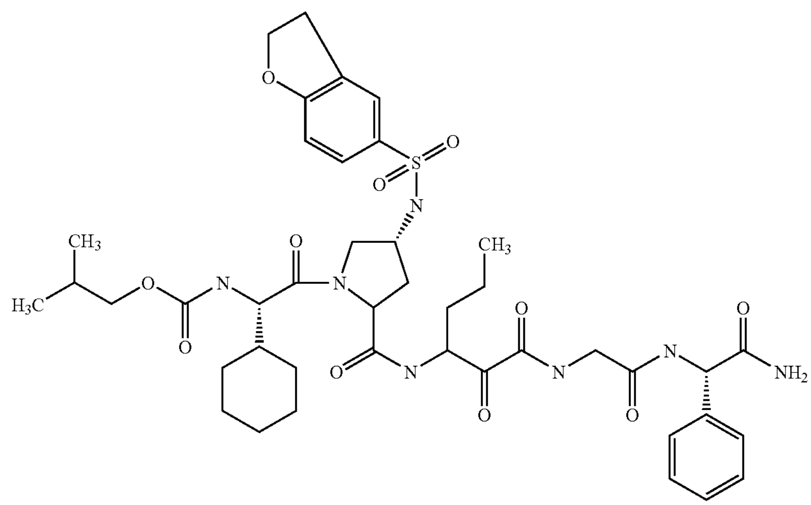 | iBoc-G(Chx)-P(4t-NHSO2-5(2,3-dihydrobenzofuran))-nV-(CO)-G-G(Ph)-Am | B |
|  | iBoc-G(Chx)-P(4t-NHSO2-6(4-OMe)Coumarin)-nV-(CO)-G-G(Ph)-Am | B |
| 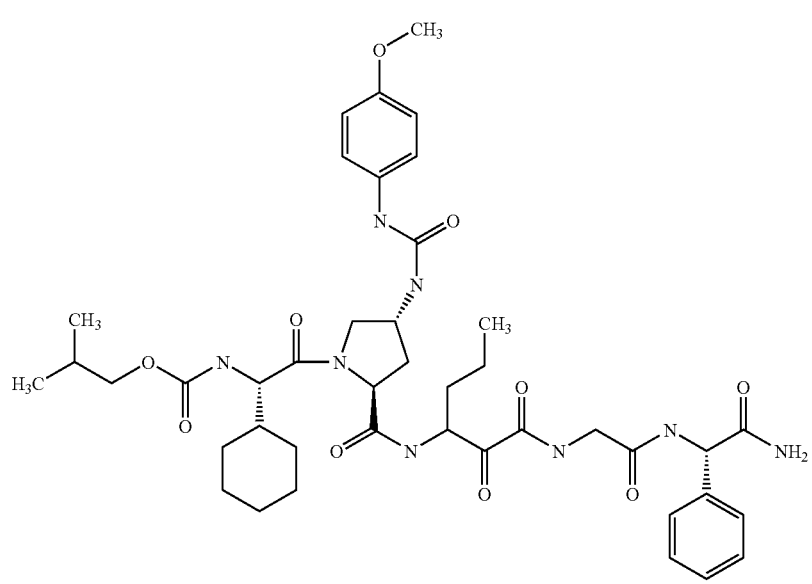 | iBoc-G(Chx)-P(4t-Urea-Ph(4-OMe))-nV-(CO)-G-G(Ph)-Am | A |

TABLE 4-continued
| STRUCTURE | NAME | Ki* Range |
|---|---|---|
| 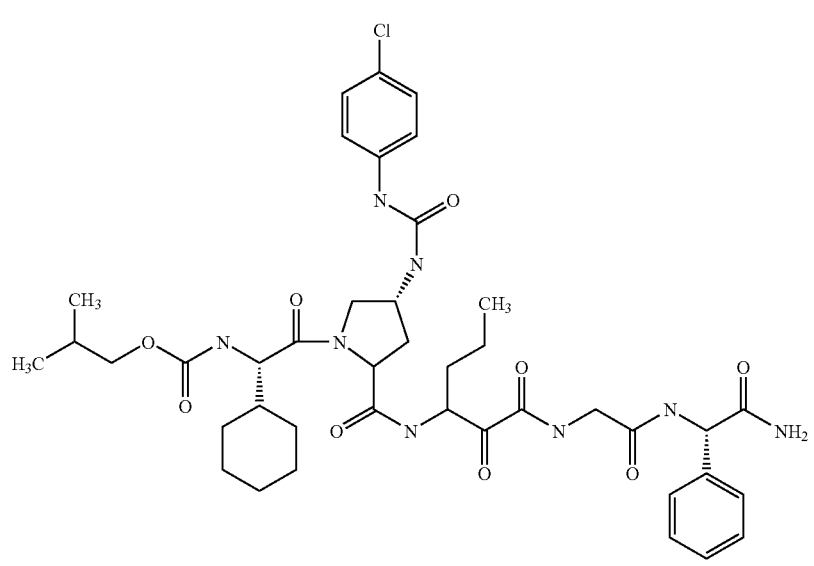 | iBoc-G(Chx)-P(4t-Urea-Ph(4-Cl))-nV-(CO)-G-G(Ph)-Am | B |
| 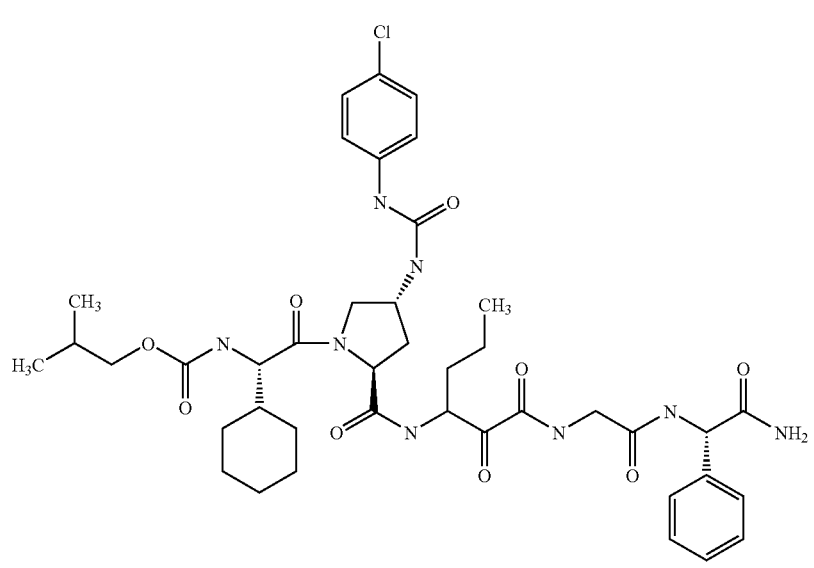 | iBoc-G(Chx)-P(4t-Urea-Ph(4-Cl))-nV-(CO)-G-G(Ph)-Am | C |

TABLE 4-continued
| STRUCTURE | NAME | Ki* Range |
|---|---|---|
| 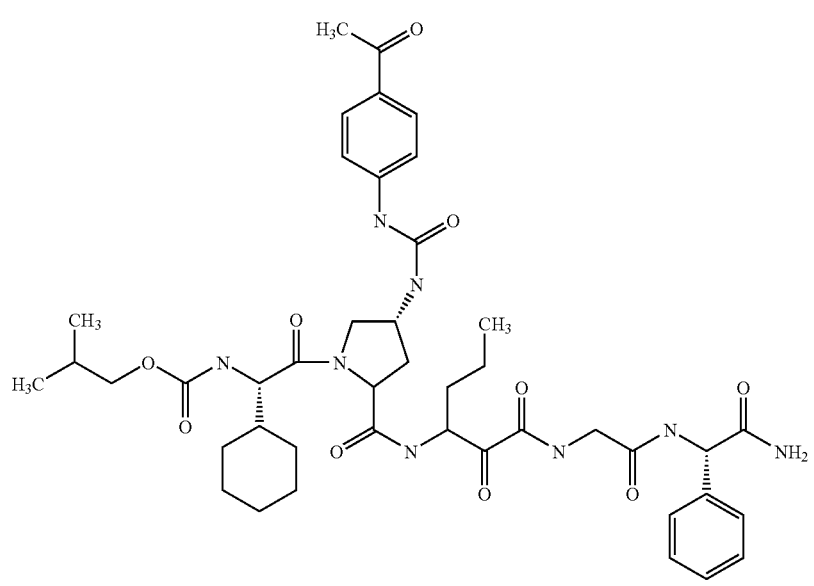 | iBoc-G(Chx)-P(4t-Urea-Ph(4-Ac))-nV-(CO)-G-G(Ph)-Am | B |
| 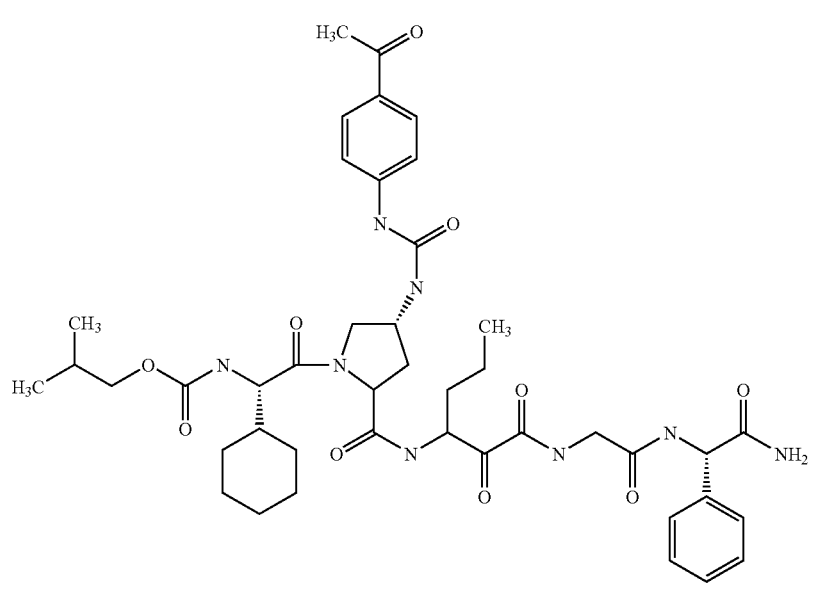 | iBoc-G(Chx)-P(4t-Urea-Ph(4-Ac))-nV-(CO)-G-G(Ph)-Am | B |

TABLE 4-continued

| STRUCTURE | NAME | Ki* Range |
|---|---|---|
| 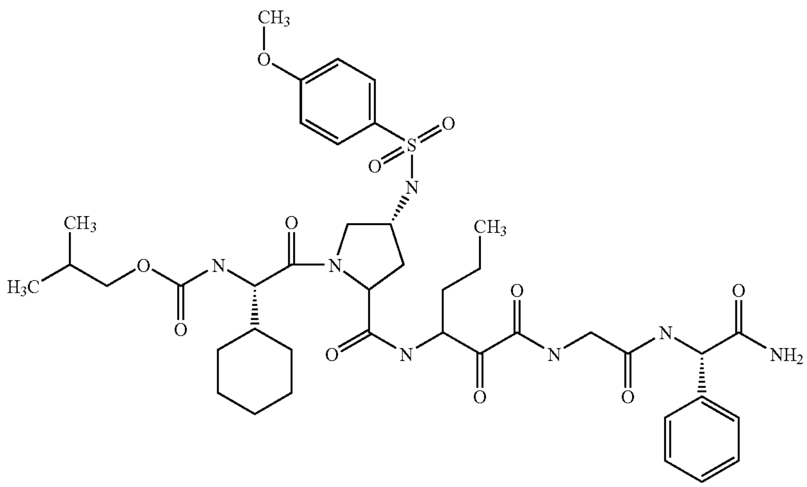 | iBoc-G(Chx)-P(4t-NHSO2-Ph(4-OMe))-nV-(CO)-G-G(Ph)-Am | B |
| 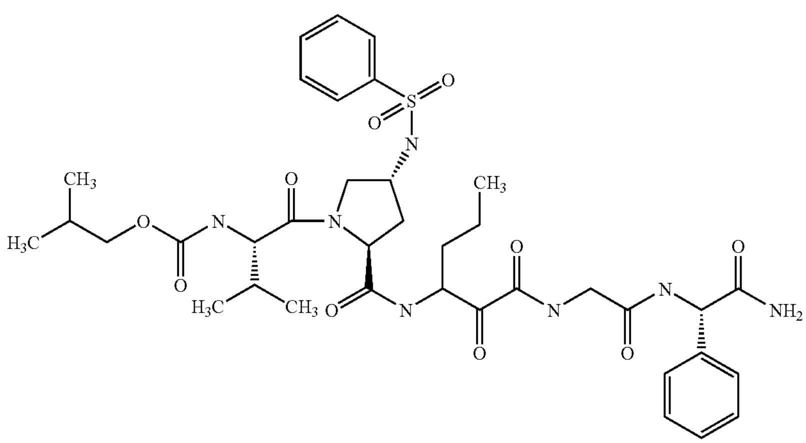 | iBoc-V-P(4t-NHSO2-Ph)-nV-(CO)-G-G(Ph)-Am | B |
| 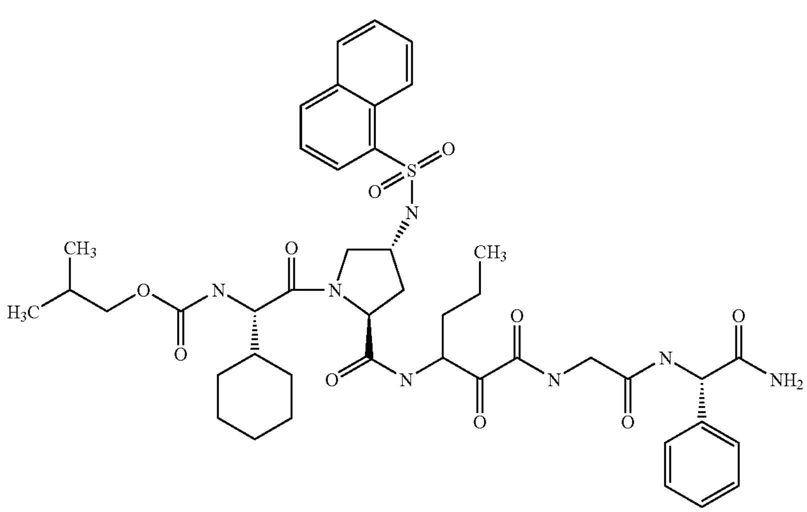 | iBoc-G(Chx)-P(4t-NHSO2-1Np)-nV-(CO)-G-G(Ph)-Am | B |

TABLE 4-continued

| STRUCTURE | NAME | Ki* Range |
|---|---|---|
| 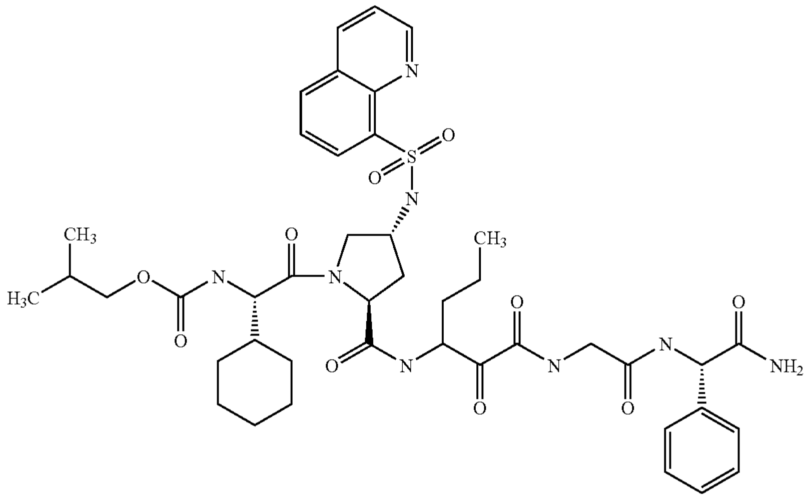 | iBoc-G(Chx)-P(4t-NHSO2-8-Quinoline)-nV-(CO)-G-G(Ph)-Am | B |
| 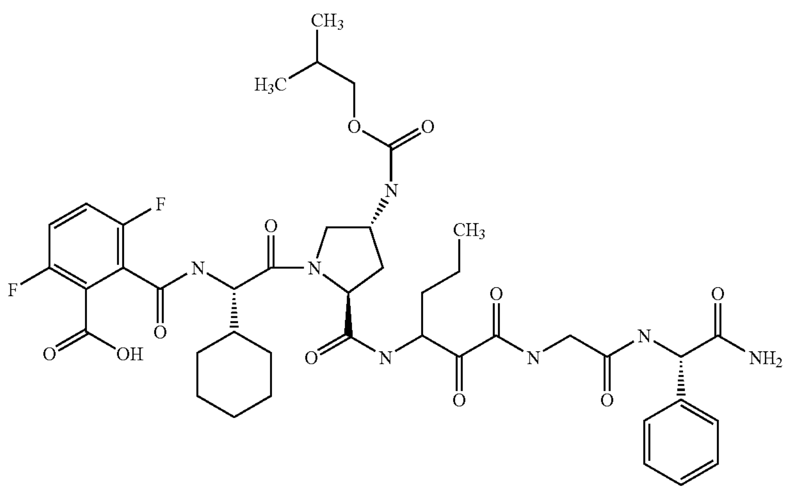 | (2,5-diF-6-CO2)PhCO-G(Chx)-P(4t-NH-iBoc)-nV-(CO)-G-G(Ph)-Am | A |
| 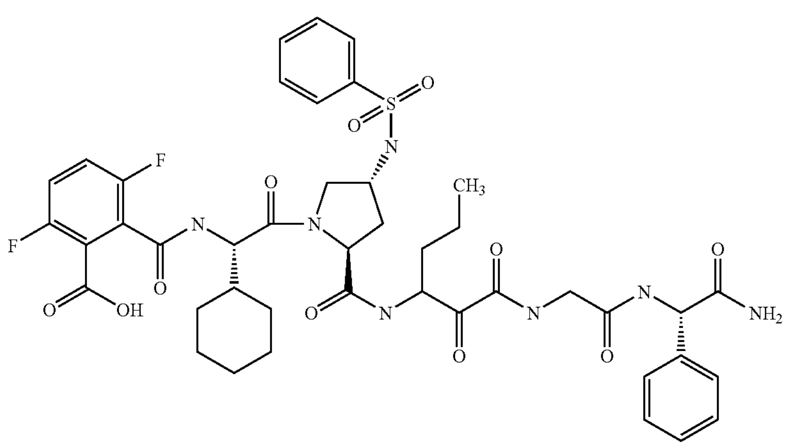 | (2,5-diF-6-CO2)PhCO-G(Chx)-P(4t-NHSO2-Ph)-nV-(CO)-G-G(Ph)-Am | A |

TABLE 4-continued
| STRUCTURE | NAME | Ki* Range |
|---|---|---|
| 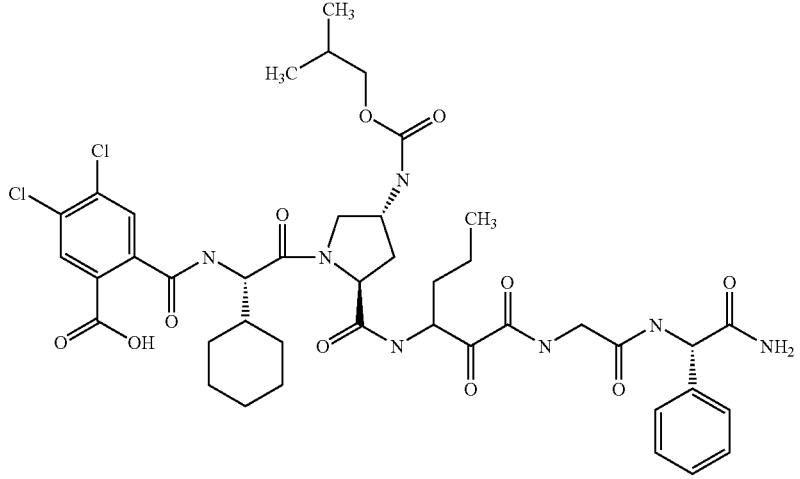 | (3,4-diCl-6-CO2)PhCO-G(Chx)-P(4t-NH-iBoc)-nV-(CO)-G-G(Ph)-Am | A |
| 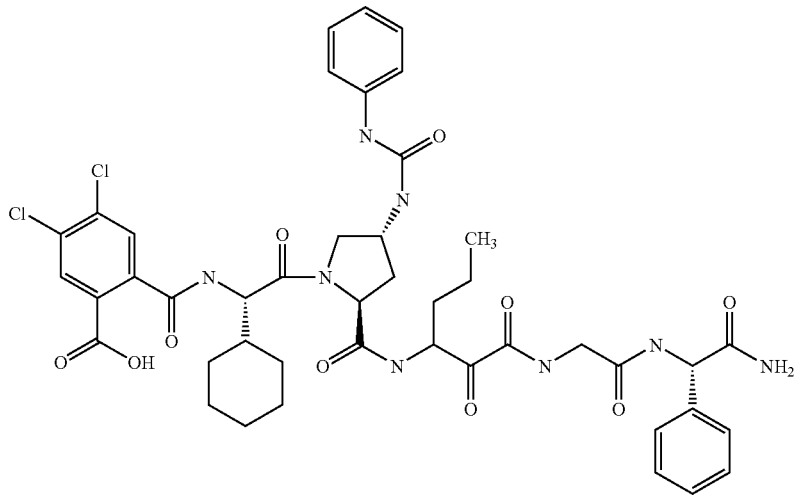 | (3,4-diCl-6-CO2)PhCO-G(Chx)-P(4t-UreaPh)-nV(CO)-G-G(Ph)-Am | A |
| 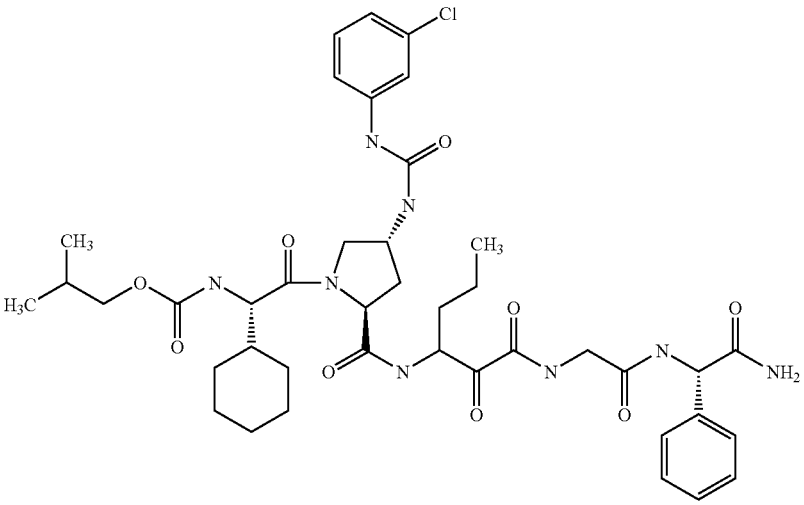 | iBoc-G(Chx)-P(4t-Urea-(3-Cl)Ph)-nV-(CO)-G-G(Ph)-Am | B |

TABLE 4-continued
| STRUCTURE | NAME | Ki* Range |
|---|---|---|
| 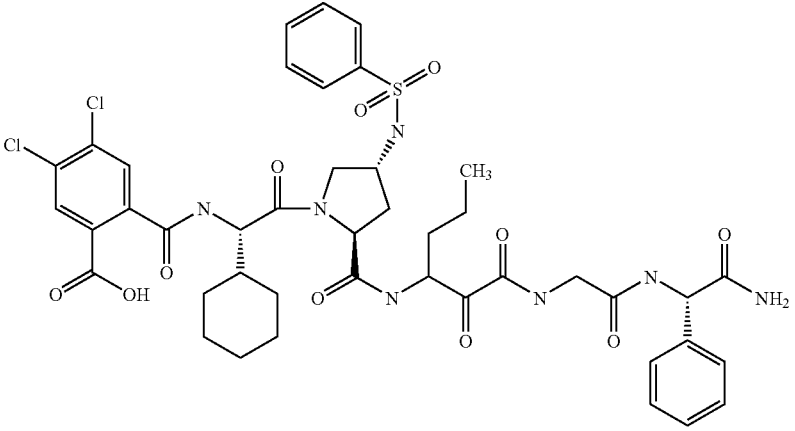 | (3,4-diCl-6-CO2)PhCO-G(Chx)-P(4t-NHSO2-Ph)-nV-(CO)-G-G(Ph)-Am | A |
| 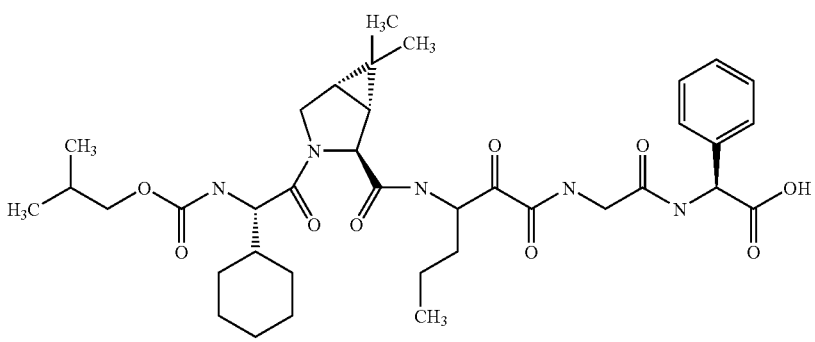 | iBoc-G(Chx)-P(3,4 iPr)-nV-(CO)-G-G(Ph)-OH | A |
| 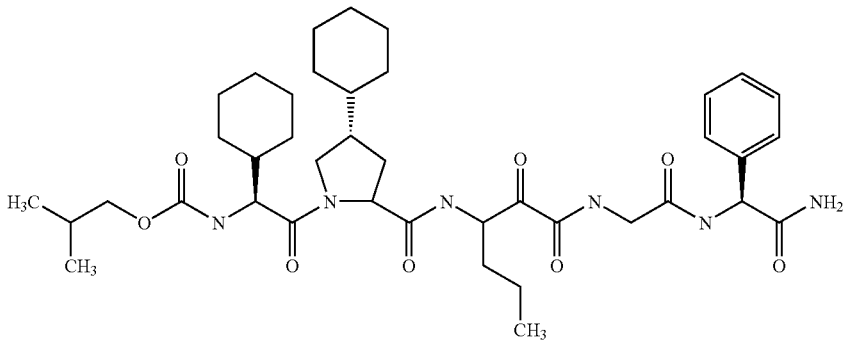 | iBoc-G(Chx)-P(4t-Chx)-nV-(CO)-G-G(Ph)-Am | B |
| 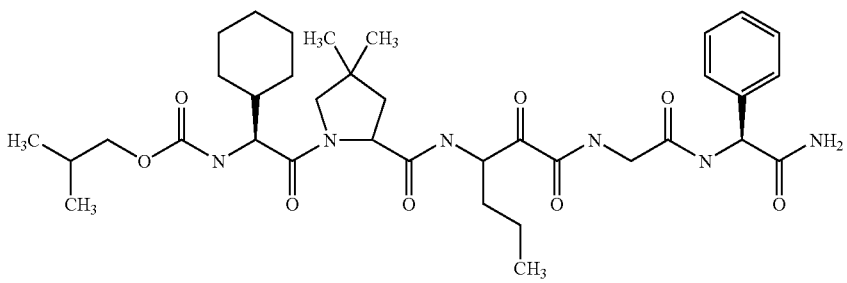 | iBoc-G(Chx)-P(4-diMe)-nV-(CO)-G-G(Ph)-Am | A |

TABLE 4-continued

| STRUCTURE | NAME | Ki* Range |
|---|---|---|
| 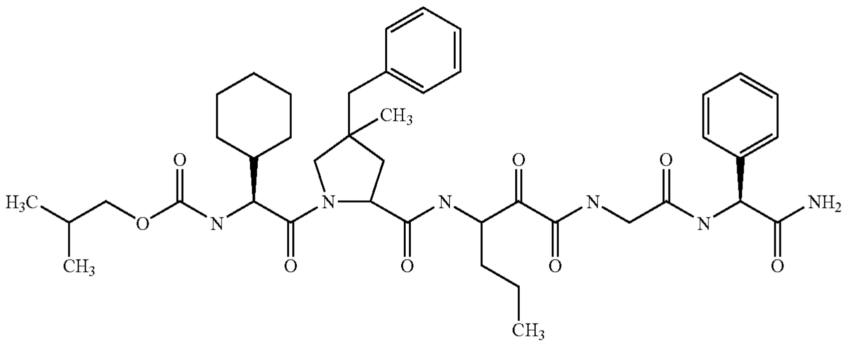 | iBoc-G(Chx)-P(4-Bn,4-Me)-nV-(CO)-G-G(Ph)-Am | B |
| 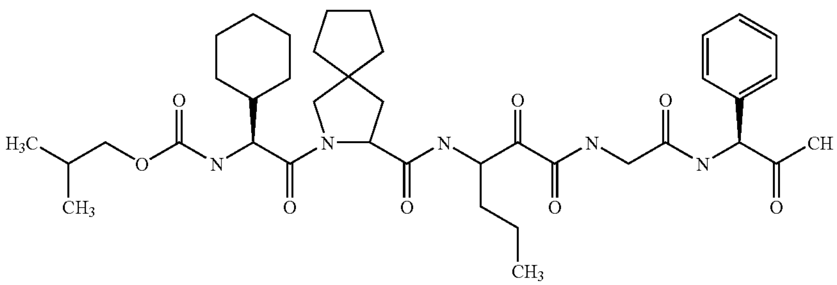 | iBoc-G(Chx)-P(4-spirocyclopentane)-nV-(CO)-G-G(Ph)-OH | A |
| 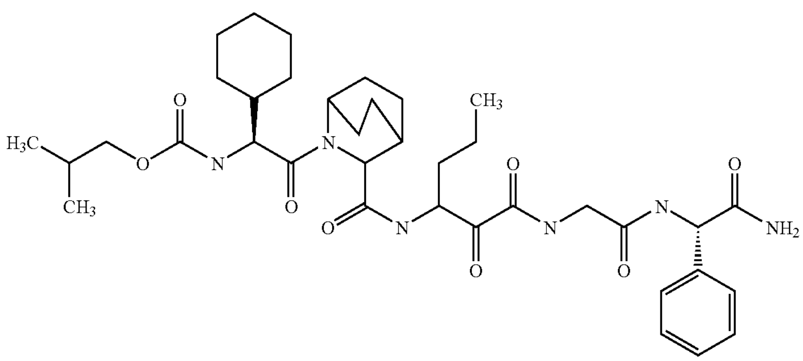 | iBoc-G(Chx)-2-Azabicyclo[2.2.2]octane-3-CO-nV-(CO)-G-G(Ph)-Am | B |
| 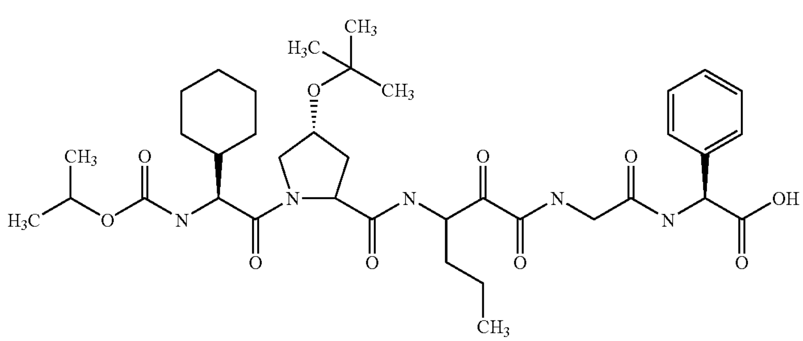 | iPrOCO-G(Chx)-P(4-OtBu)-nV-(CO)-G-G(Ph)-OH | A |

TABLE 4-continued

| STRUCTURE | NAME | Ki* Range |
|---|---|---|
| 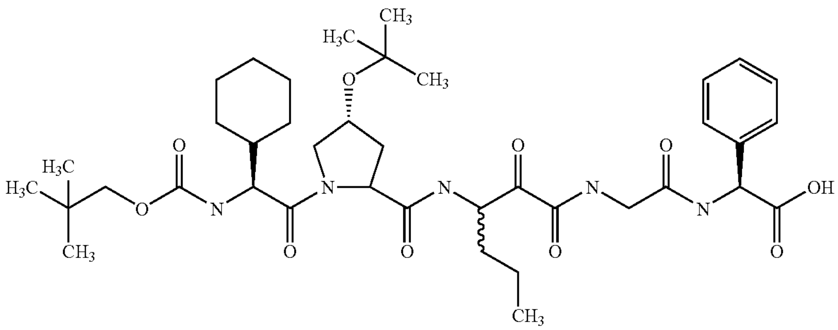 | Neopentoxy(CO)-G(Chx)-P(4-OtBu)-nV-(CO)-G-G(Ph)-OH | B |
| 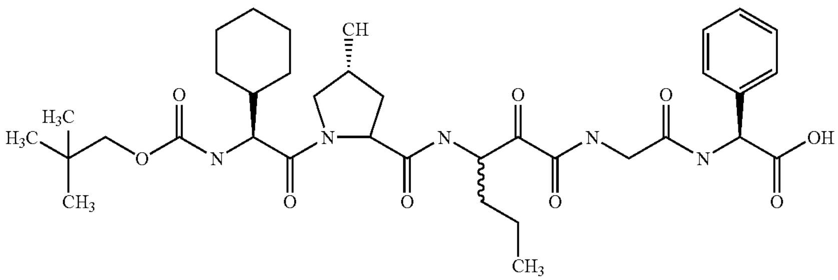 | Neopentoxy(CO)-G(Chx)-P(OH)-nV-(CO)-G-G(Ph)-OH | B |
| 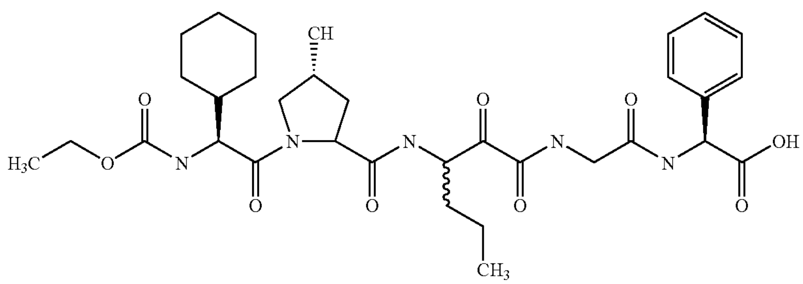 | Ethoxy(CO)-G(Chx)-P(OH)-nV-(CO)-G-G(Ph)-OH | B |
| 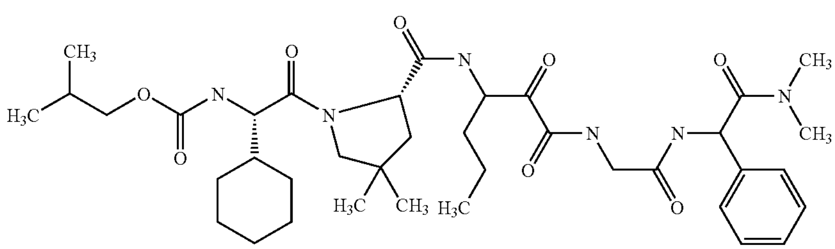 | iBoc-G(Chx)-P(4,4 diMe)-nV-(CO)-G-G(Ph)-N(Me)2 | A |
| 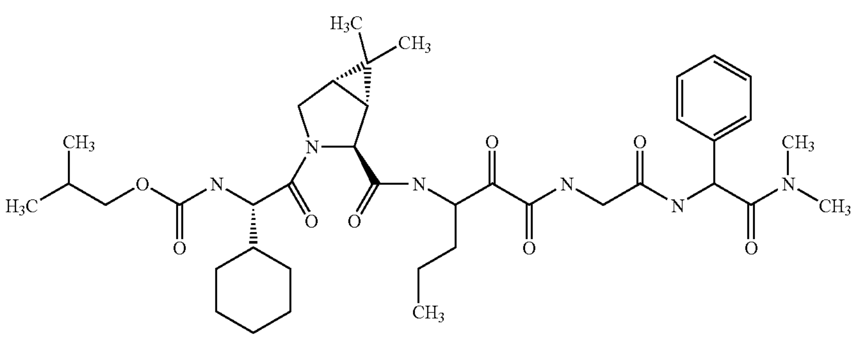 | iBoc-G(Chx)-P(3,4-iPr)-nV-(CO)-G-G(Ph)-N(Me)2 | A |

TABLE 4-continued
| STRUCTURE | NAME | Ki* Range |
|---|---|---|
| 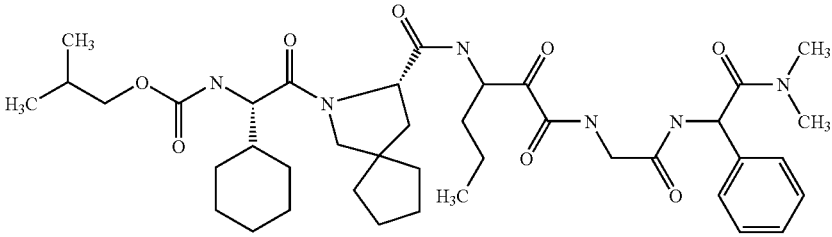 | iBoc-G(Chx)-P(4-spirocyclopentane)-nV-(CO)-G-G(Ph)-N(Me)2 | A |
| 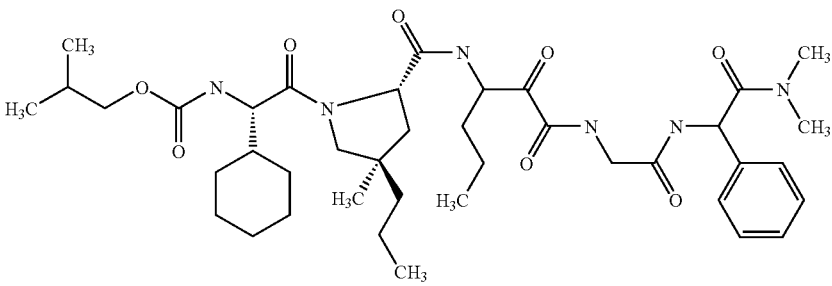 | iBoc-G(Chx)-P(4c-Me,4t-Pr)-nV-(CO)-G-G(Ph)-N(Me)2 | A |
| 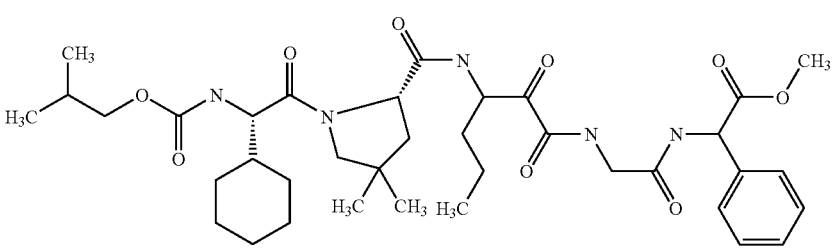 | iBoc-G(Chx)-P(4,4-diMe)-nV-(CO)-G-G(Ph)-OMe | A |
| 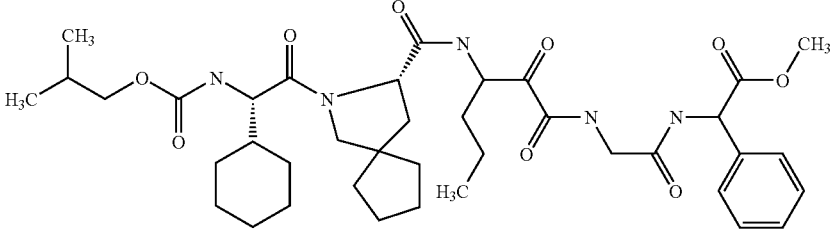 | iBoc-G(Chx)-P(4-spirocyclopentane)-nV-(CO)-G-G(Ph)-OMe | A |
| 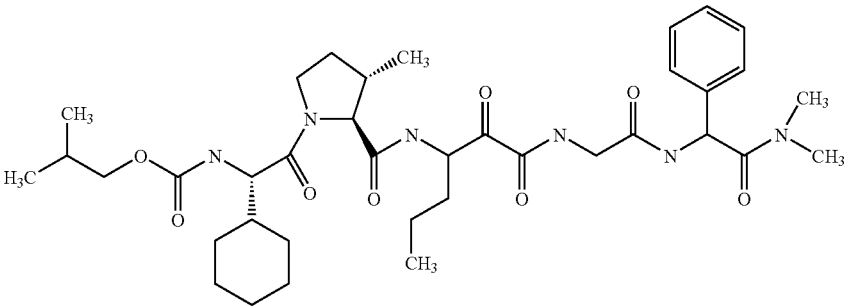 | iBoc-G(Chx)-P(3t-Me)-nV-(CO)-G-G(Ph)-N(Me)2 | A |

TABLE 4-continued

| STRUCTURE | NAME | Ki* Range |
|---|---|---|
| 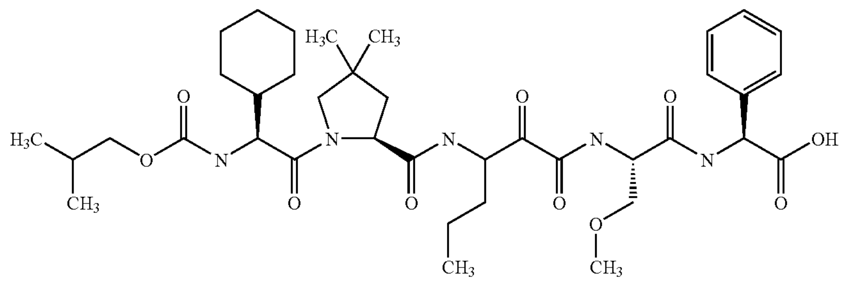 | iBoc-G(Chx)-P(4,4-diMe)-nV-(CO)-S(Me)-G(Ph)-OH | A |
| 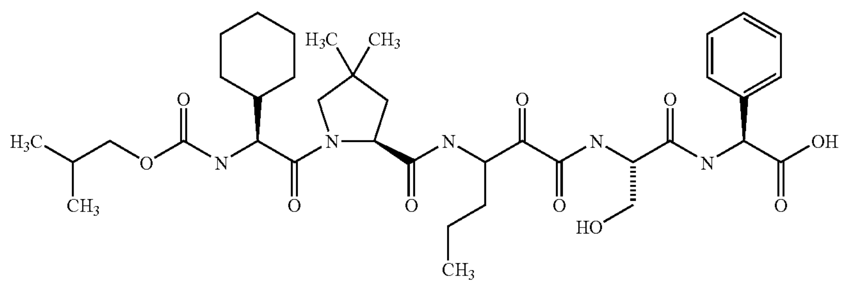 | iBoc-G(Chx)-P(4,4-diMe)-nV-(CO)-S-G(Ph)-OH | B |
| 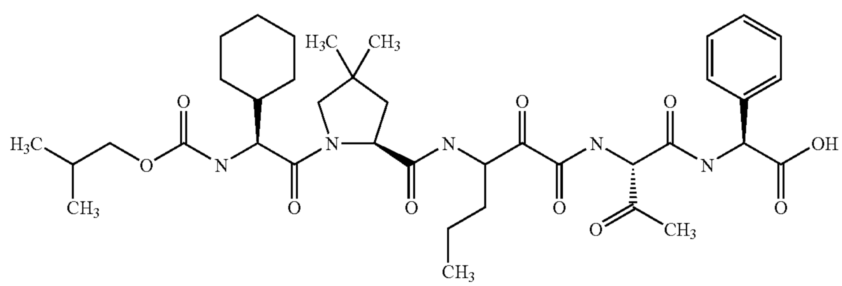 | iBoc-G(Chx)-P(4,4-diMe)-nV-(CO)-G(Ac)-G(Ph)-OH | C |
| 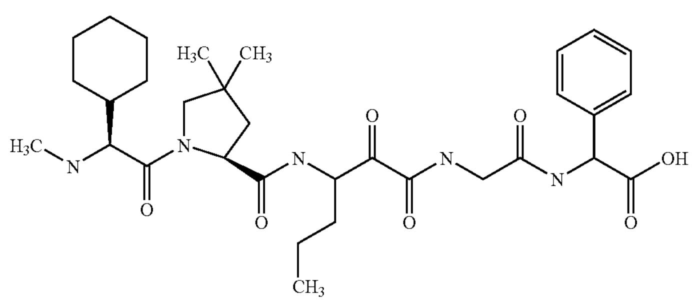 | N-Me-G(Chx)-P(4,4-diMe)-nV-(CO)-G-G(Ph)-CO2H | C |
| 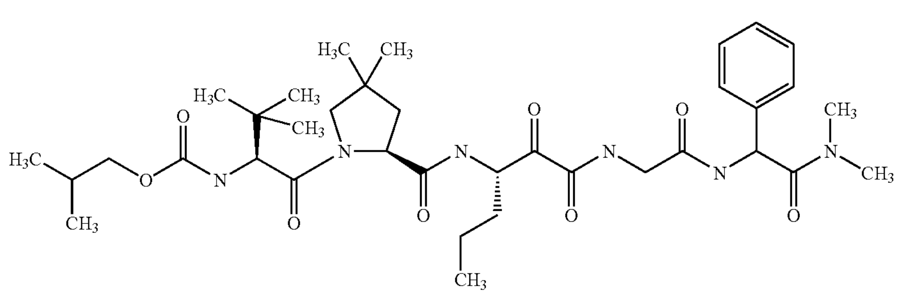 | iBoc-G(tBu)P(4,4-diMe)-nV-(CO)-G-G(Ph)-N(Me)2 | A |

TABLE 4-continued
| STRUCTURE | NAME | Ki* Range |
|---|---|---|
| 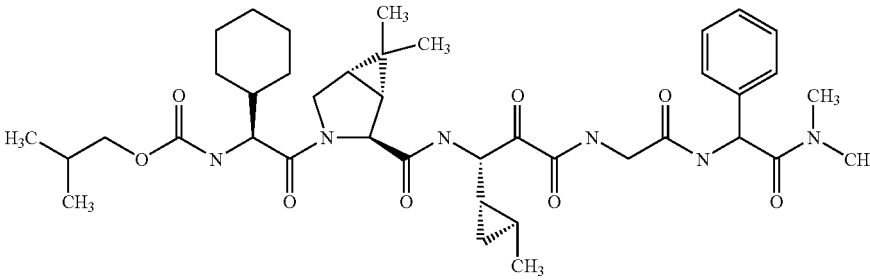 | iBoc-G(Chx)-P(3,4-(diMe-cyclopropyl))-G((S,S)-Me-cyclopropyl)-(CO)-G-G(Ph)-N(Me) | A |
| 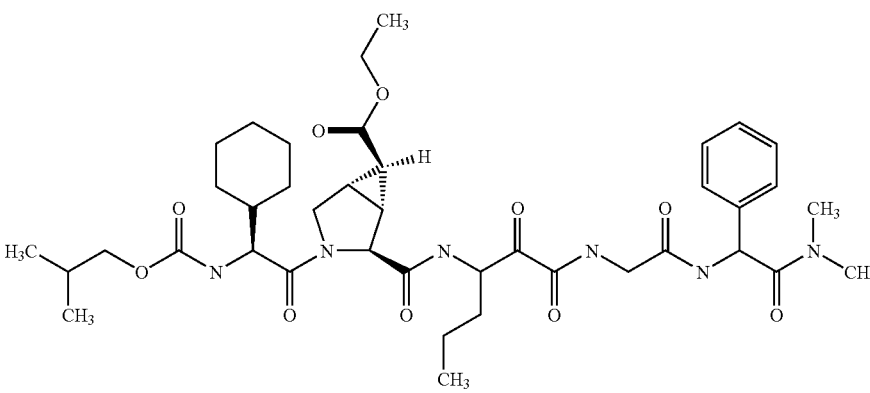 | iBoc-G(Chx)-P(6S-CEM)-nV-(CO)-G-G(Ph)-N(Me)2 | A |
| 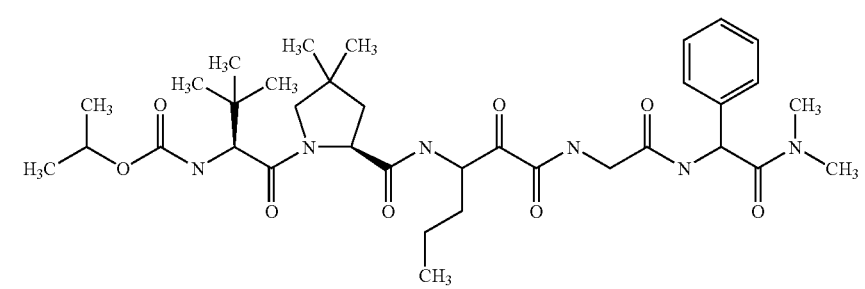 | iPoc-G(tBu)-P(4,4-diMe)-nV-(CO)-G-G(Ph)-N(Me)2 | A |
| 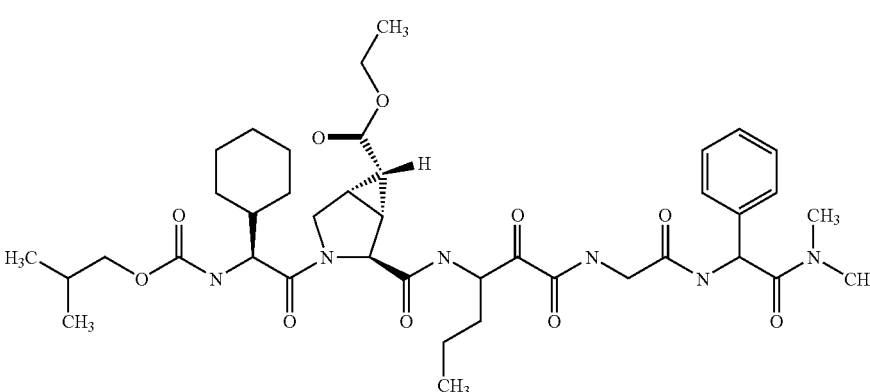 | iBoc-G(Chx)-P(6R-CEM)-nV-(CO)-G-G(Ph)-N(Me)2 | A |

TABLE 4-continued

| STRUCTURE | NAME | Ki* Range |
|---|---|---|
| 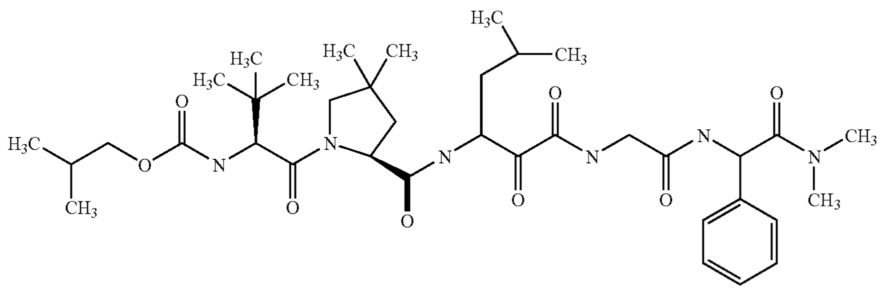 | iBoc-G(tBu)-P(4,4-diMe)-L-(CO)-G-G(Ph)-N(Me)2 | A |
| 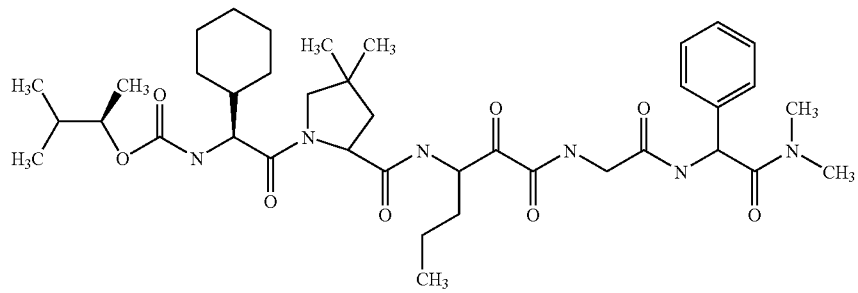 | ((R)-1-Me-iBoc)-G(Chx)-P(4,4-diMe)-nV-(CO)-G-G(Ph)-N(Me)2 | A |
| 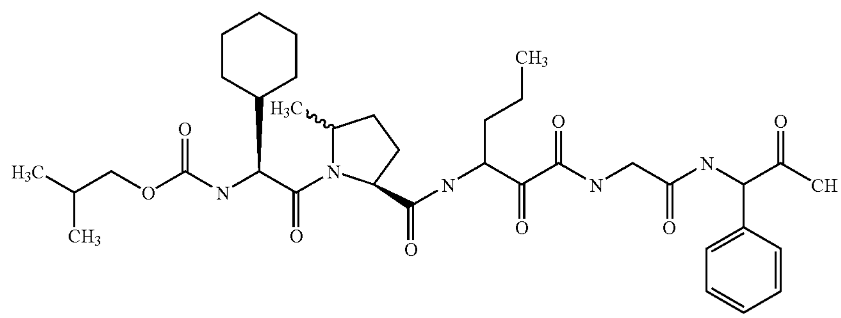 | iBoc-G(Chx)-P(5-c/t-Me)-nV-(CO)-G-G(Ph)-CO2H | A |
| 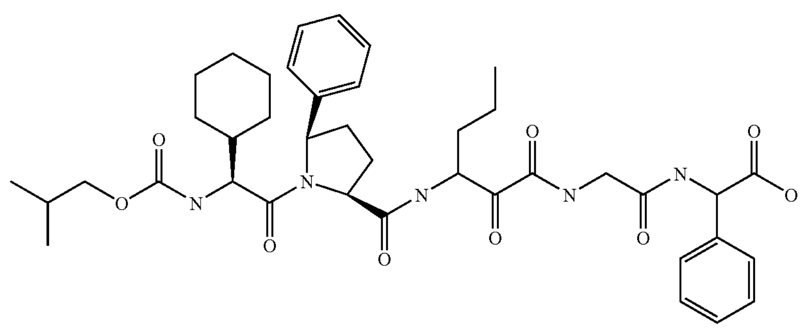 | iBoc-G(Chx)-P(5-cis-Ph)-nV-(CO)-G-G(Ph)-CO2H | B |
| 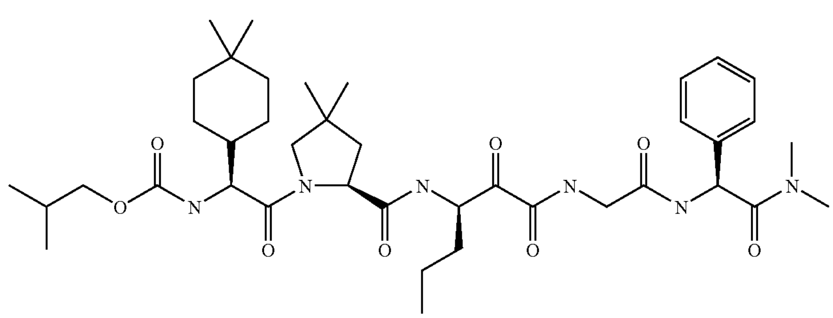 | iBoc-G(4,4-diMeChx)-P(4,4-diMe)-nV-(CO)-G-G(Ph)-N(Me)2 | A |

TABLE 4-continued

| STRUCTURE | NAME | Ki* Range |
|---|---|---|
| 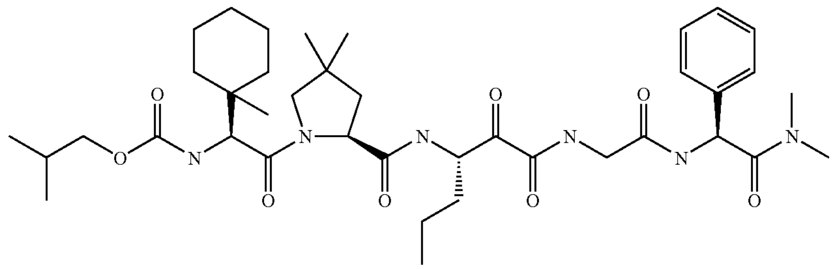 | iBoc-G(1-MeChx)-P(4,4-diMe)-nV-(CO)-G-G(Ph)-N(Me)2 | A |
| 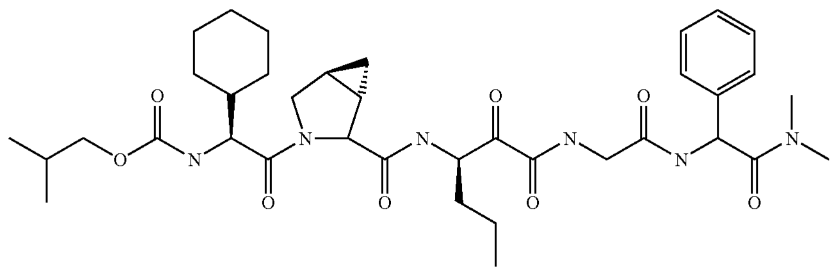 | iBoc-G(Chx)-P(3,4-CH2)-nV-(CO)-G-G(Ph)-N(Me)2 | A |
| 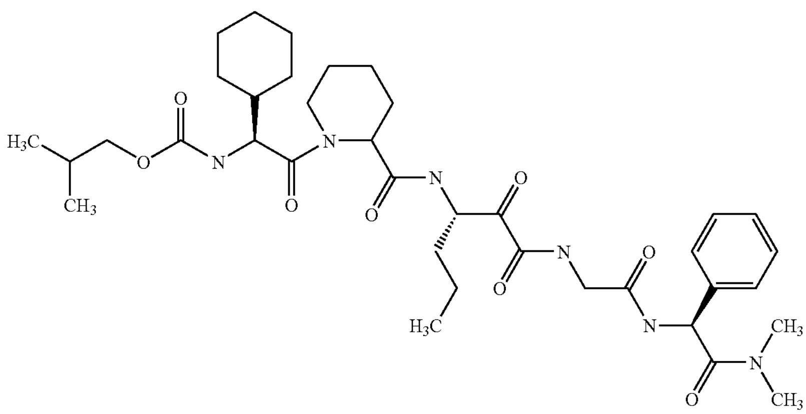 | iBoc-Chg-Pip-nV-(CO)-G-G(Ph)-N(Me)2 | C |
| 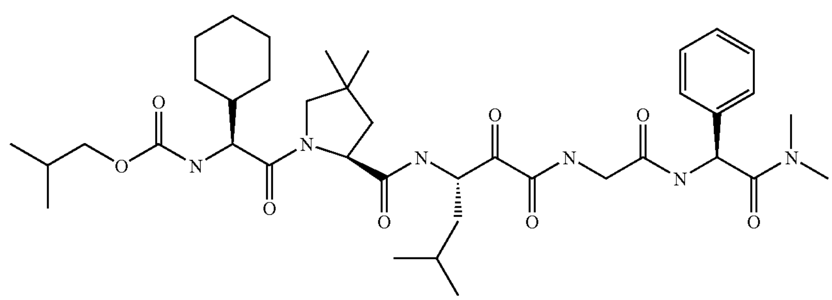 | iBoc-G(Chx)-P(4,4-diMe)-L-(CO)-G-G(Ph)-N(Me)2 | A |
| 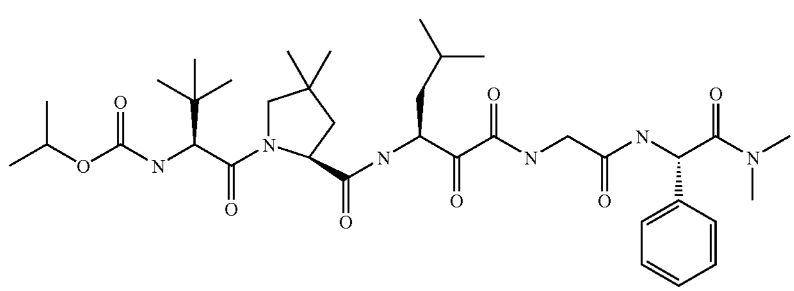 | iPoc-G(tBu)-P(4,4-diMe)-L-(CO)-G-G(Ph)-N(Me)2 | A |

TABLE 4-continued

| STRUCTURE | NAME | Ki* Range |
|---|---|---|
| 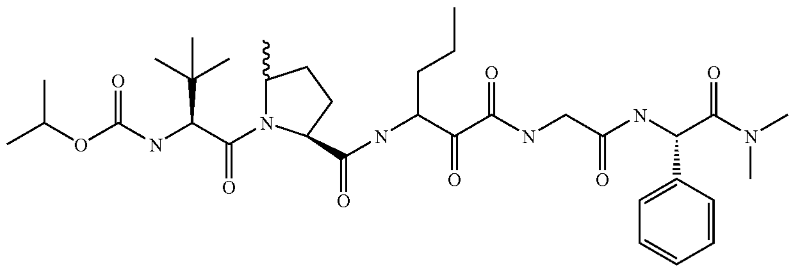 | iPoc-G(tBu)-P(5-c/t-Me)-nV-(CO)-G-G(Ph)-N(Me)2 | A |
| 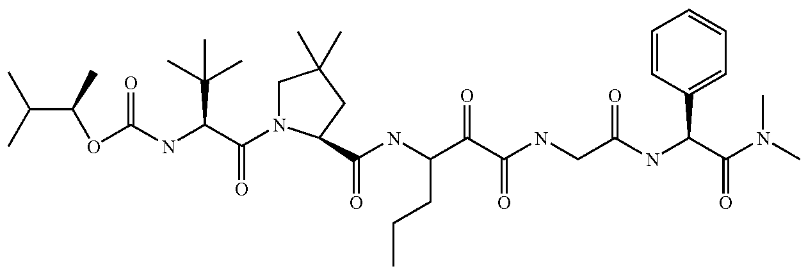 | ((R)-1-Me-iBoc)-G(tBu)-P(4,4-diMe)-nV-(CO)-G-G(Ph)-N(Me)2 | A |
| 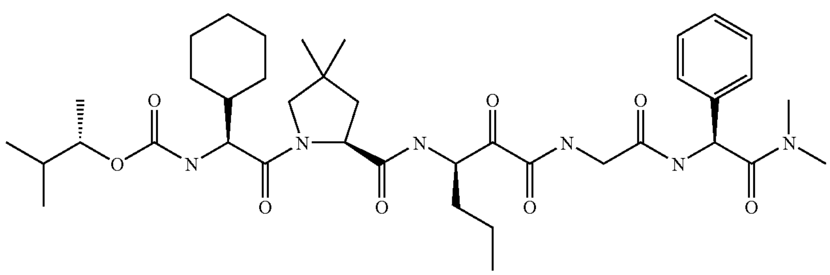 | (S)-1-MeiBoc-G(Chx)-P(4,4-diMe)-nV-(CO)-G-G(Ph)-N(Me)2 | A |
| 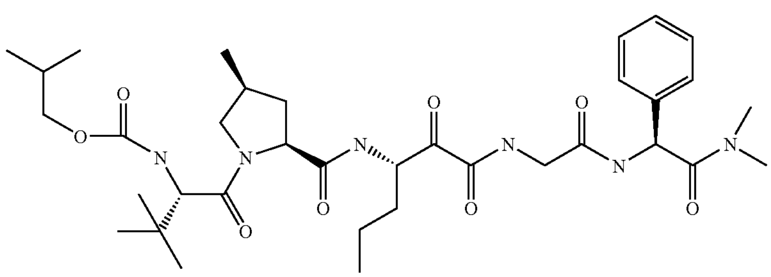 | iBoc-G(tBu)-P(4-cis-Me)-nV-(CO)-G-G(Ph)-N(Me)2 | A |
| 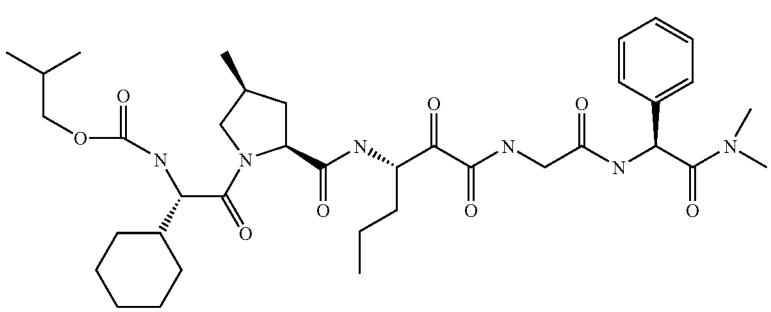 | iBoc-G(Chx)-P(4-cis-Me)-nV-(CO)-G-G(Ph)-N(Me)2 | A |

TABLE 4-continued

| STRUCTURE | NAME | Ki* Range |
|---|---|---|
| 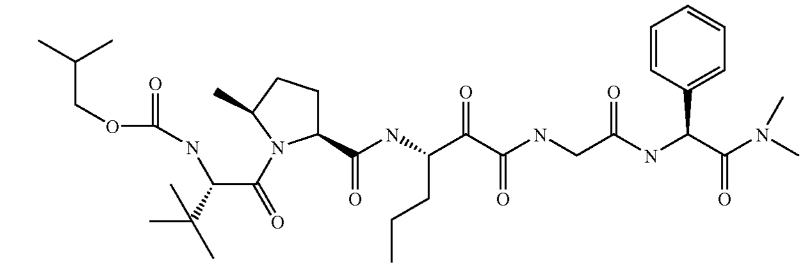 | iBoc-G(tBu)-P(5-cis-Me)-nV-(CO)-G-G(Ph)-N(Me)2 | A |
| 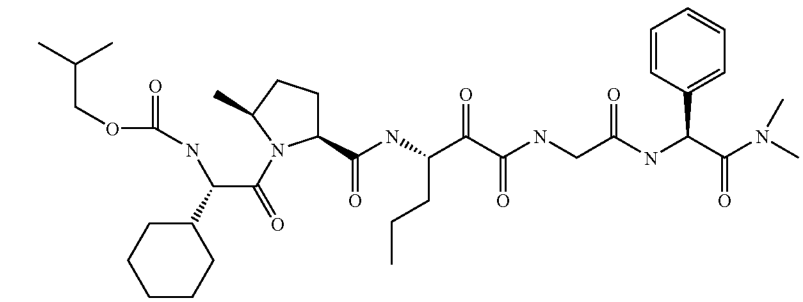 | iBoc-G(Chx)-P(5-cis-Me)-nV-(CO)-G-G(Ph)-N(Me)2 | A |
| 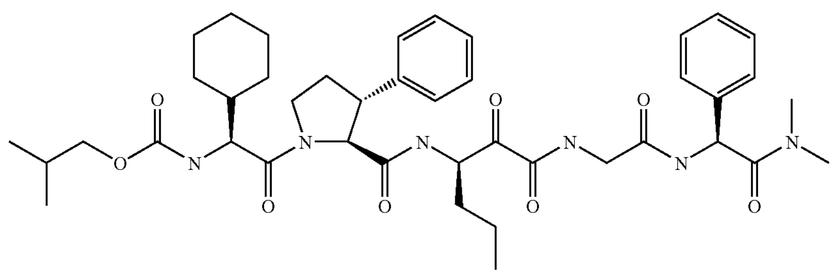 | iBoc-G(Chx)-P(t-3Ph)-nV-(CO)-G-G(Ph)-N(Me)2 | B |
| | iBoc-allo(Ile)-P(4,4-diMe)-nV-(CO)-G-G(Ph)-N(Me)2 | A |
| 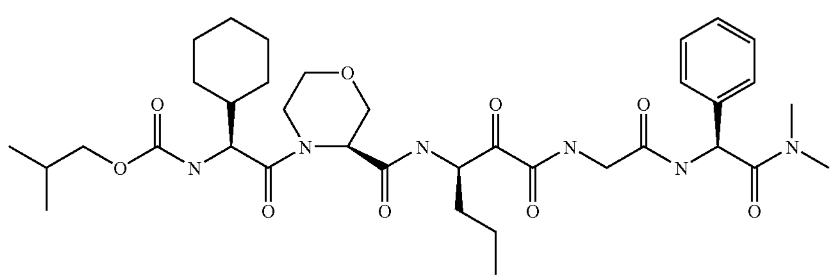 | iBoc-G(Chx)-Pip(4-morpholino)-nV-(CO)-G-G(Ph)-N(Me)2 | B |

TABLE 4-continued

| STRUCTURE | NAME | Ki* Range |
|---|---|---|
| 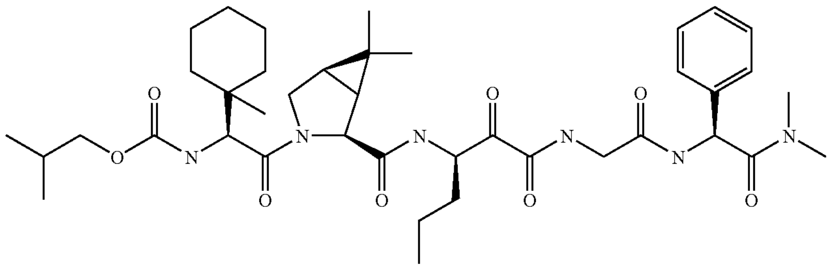 | iBoc-G(1-MeChx)-P[3,4-(diMe-cyclopropyl)]-nV-(CO)-G-G(Ph)-N(Me)2 | A |
| 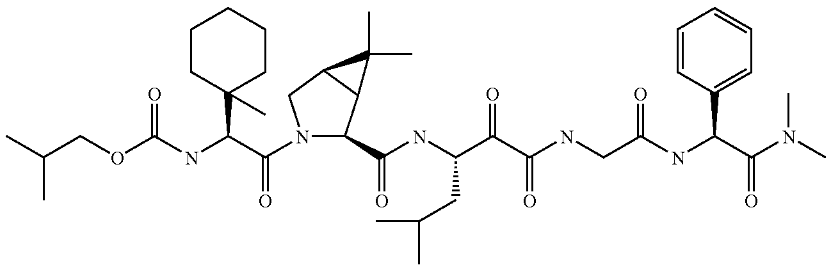 | iBoc-G(1-MeChx)-P[3,4-(diMe-cyclopropyl)]-L-(CO)-G-G(Ph)-N(Me)2 | A |
| 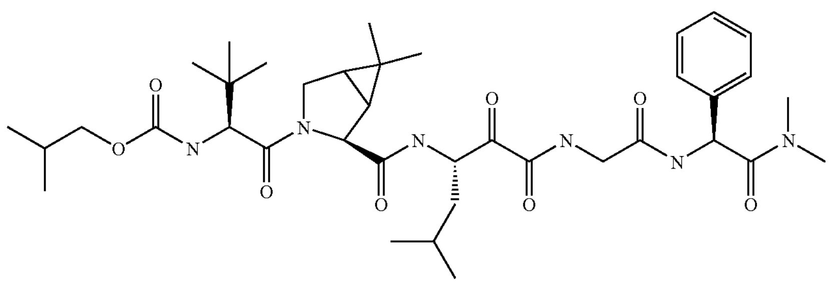 | iBoc-G(tBu)-P[3,4-(diMe-cyclopropyl)]-L-(CO)-G-G(Ph)-N(Me)2 | A |
| 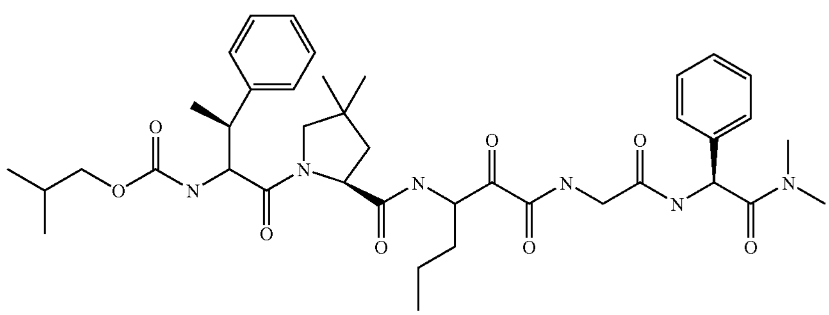 | iBoc-erythro-D,L-F(beta-Me)-P(4,4-diMe)-nV-(CO)-G-G(Ph)-N(Me)2 | A |
| 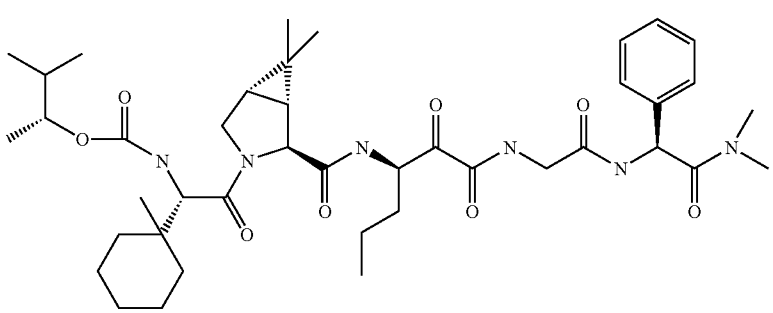 | ((R)-1-Me)iBoc-G(1-MeChx)-P[3,4-(diMe-cyclorpropyl)]-nV-(CO)-G-G(Ph)-N(Me)2 | A |

TABLE 4-continued

| STRUCTURE | NAME | Ki* Range |
|---|---|---|
| 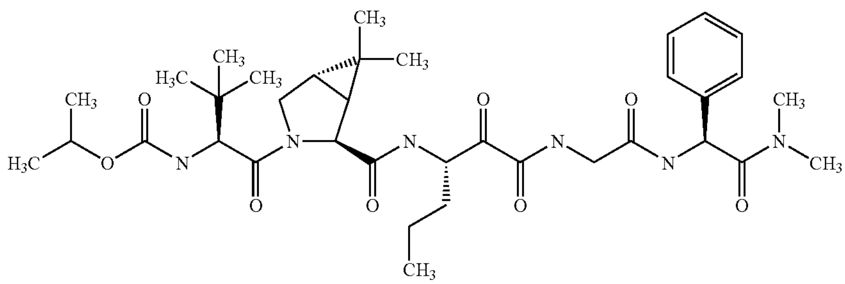 | iPoc-G(tBu)-P[3,4-(diMe-cyclopropyl)]-nV-(CO)-G-G(Ph)-N(Me)2 | A |
| 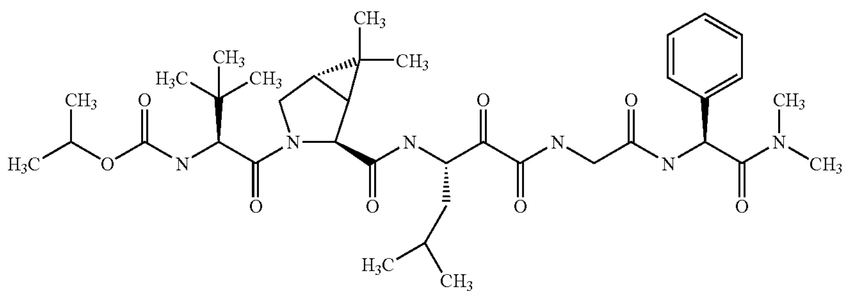 | iPoc-G(tBu)-P[3,4-(diMe-cyclopropyl)]-L-(CO)-G-G(Ph)-N(Me)2 | A |
| 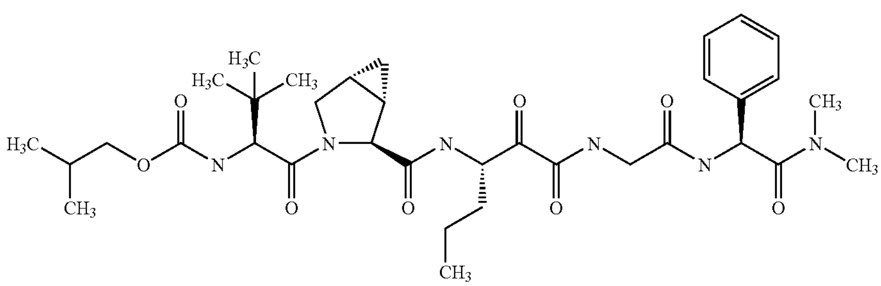 | iBoc-G(tBu)-P(3,4-CH2)-nV-(CO)-G-G(Ph)-N(Me)2 | A |
| 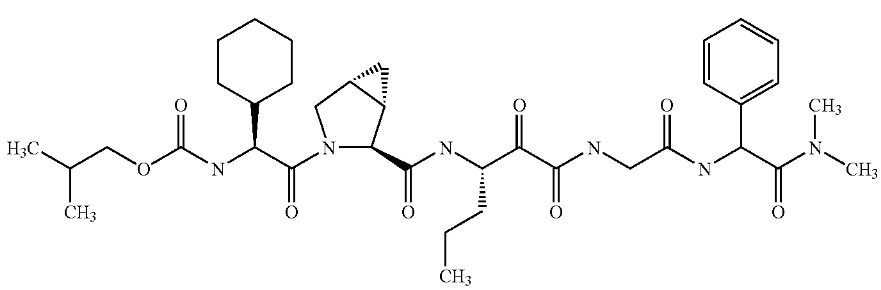 | iBoc-G(Chx)-P(3,4-CH2)-nV-(CO)-G-G(Ph)-N(Me)2 | A |
| 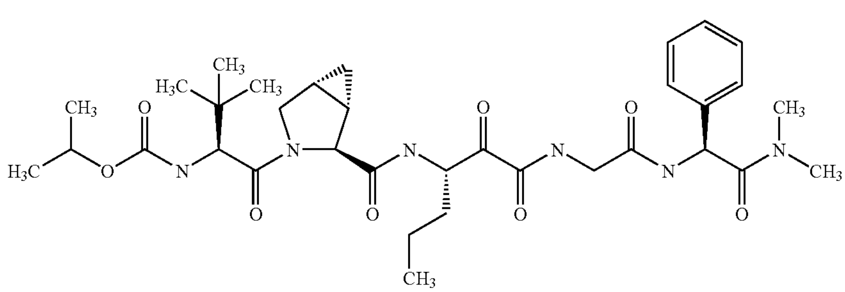 | iPoc-G(tBu)-P(3,4-CH2)-nV-(CO)-G-G(Ph)-N(Me)2 | A |

TABLE 4-continued

| STRUCTURE | NAME | Ki* Range |
|---|---|---|
| 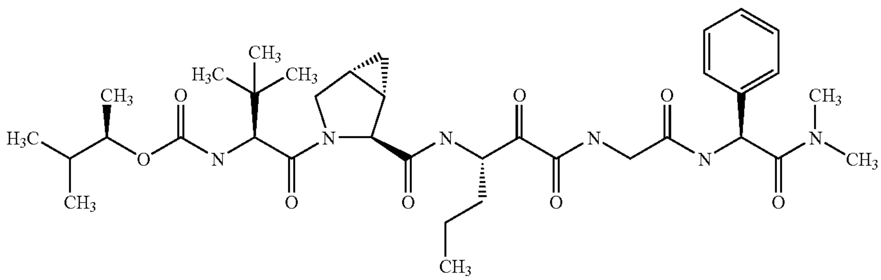 | ((R)-1-Me)iBoc-G(tBu)-P(3,4-CH2)-nV-(CO)-G-G(Ph)-N(Me)2 | A |
| 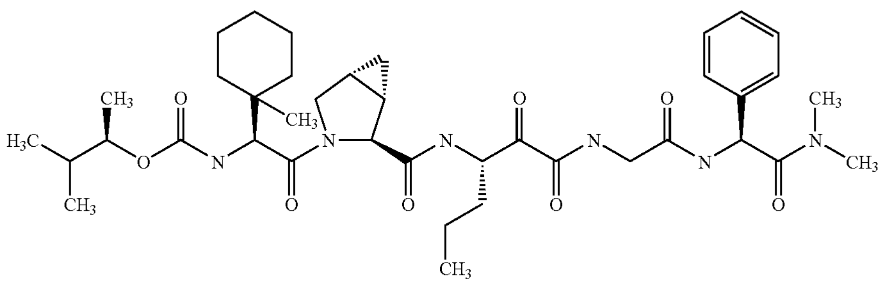 | ((R)-1-Me)iBoc-G(1-MeChx)-P(3,4-CH2)-nV-(CO)-G-G(Ph)-N(Me)2 | A |

TABLE 5

| STRUCTURE | MW | Ki* Range |
|---|---|---|
| 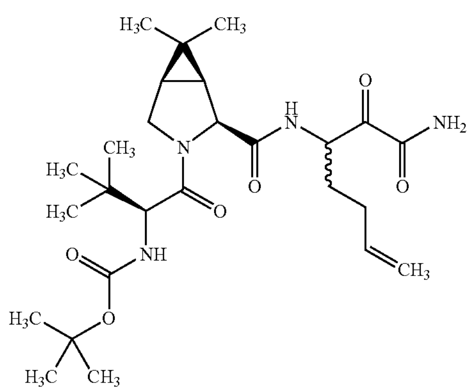 | 507 | B |
| 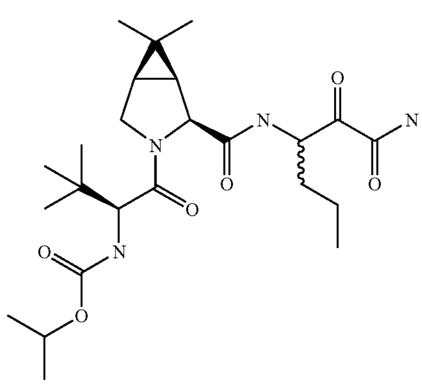 | 481 | B |

TABLE 5-continued

| STRUCTURE | MW | Ki* Range |
|---|---|---|
| 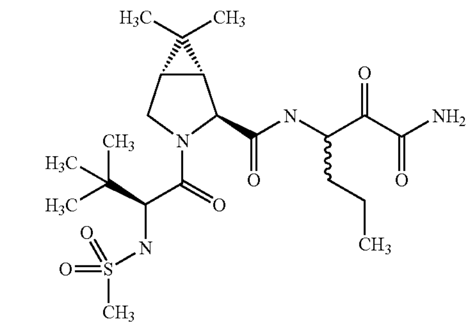 | 473 | C |
| 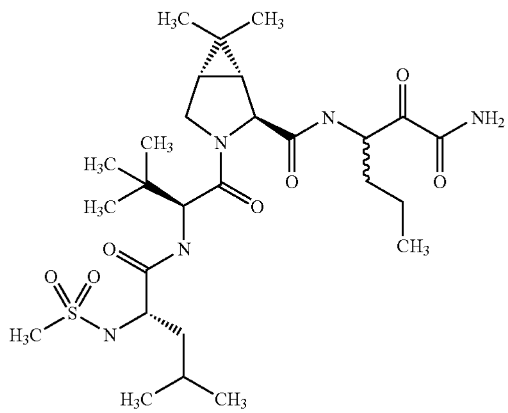 | 586 | B |
| 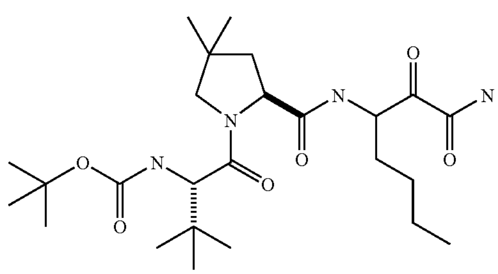 | 497 | C |
| 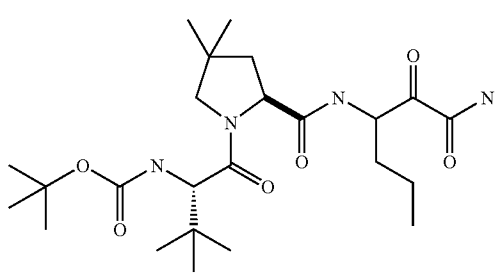 | 483 | C |
| 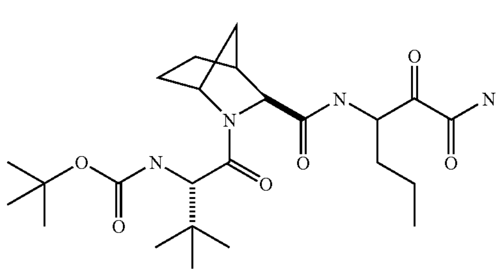 | 481 | C |

TABLE 5-continued

| STRUCTURE | MW | Ki* Range |
|---|---|---|
| 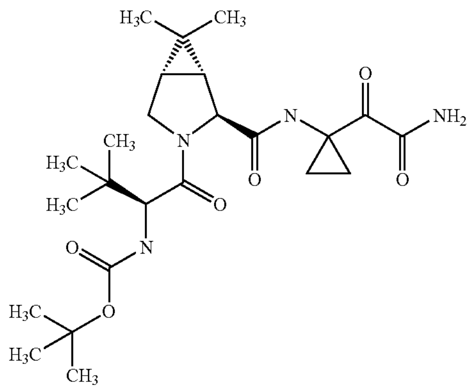 | 479 | B |
| 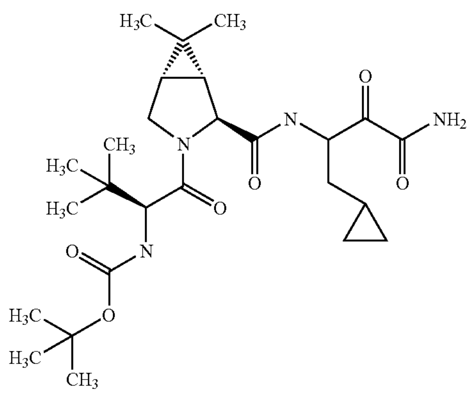 | 507 | A |
| 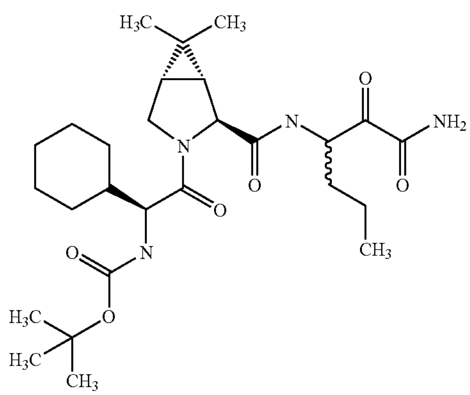 | 521 | A |
| 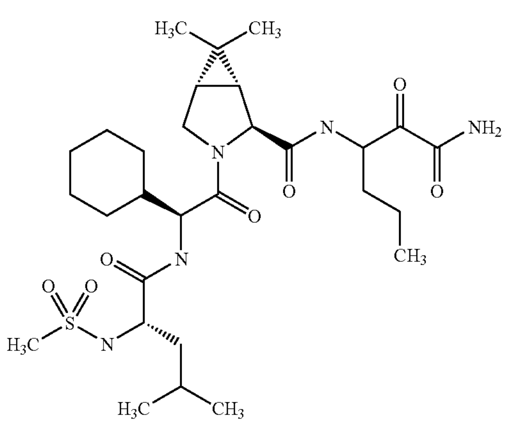 | 612 | A |

TABLE 5-continued

| STRUCTURE | MW | Ki* Range |
|---|---|---|
| 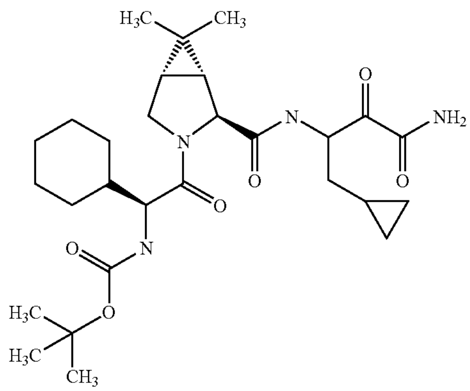 | 533 | A |
| 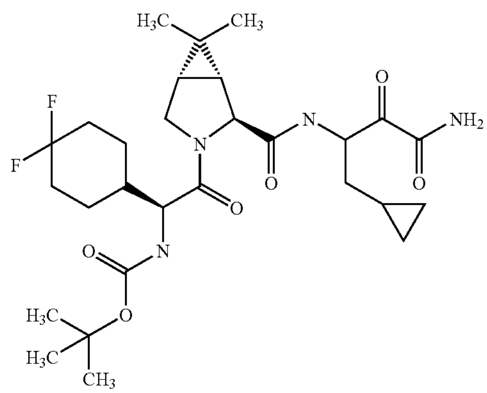 | 569 | A |
| 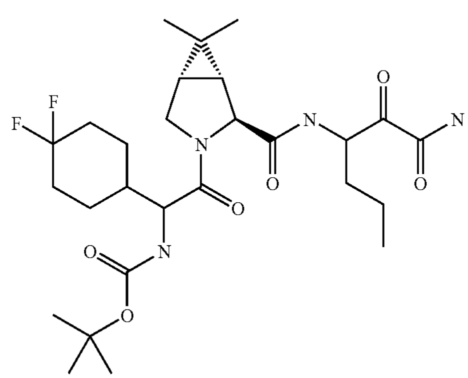 | 557 | B |
| 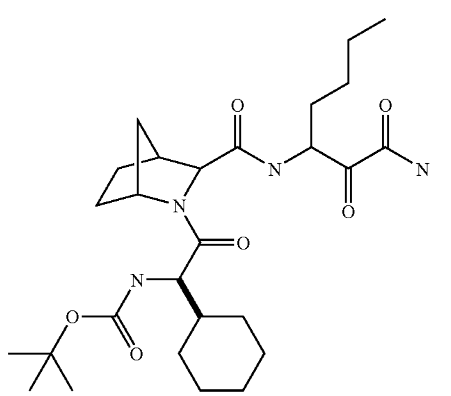 | 521 | C |

TABLE 5-continued
| STRUCTURE | MW | Ki* Range |
|---|---|---|
| 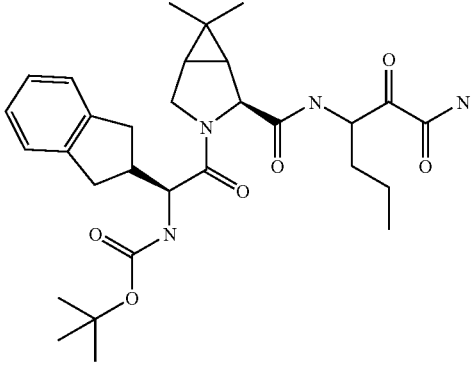 | 555 | A |
| 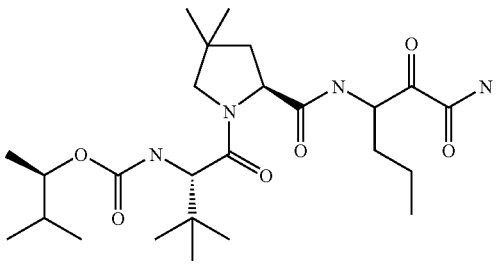 | 497 | C |
| 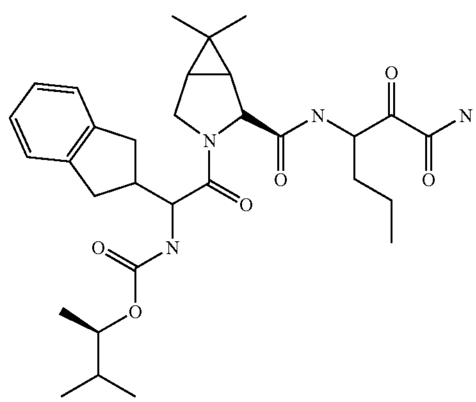 | 569 | B |
| 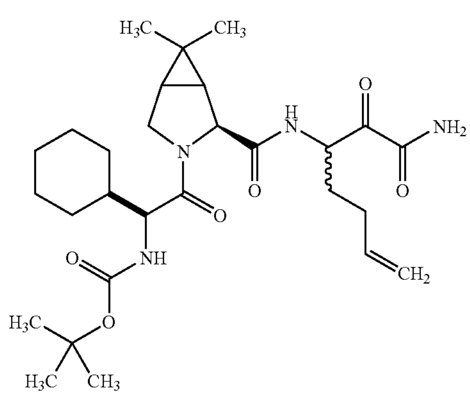 | 533 | B |

TABLE 5-continued
| STRUCTURE | MW | Ki* Range |
|---|---|---|
| 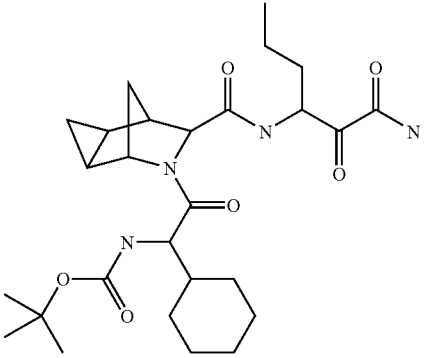 | 519 | C |
| 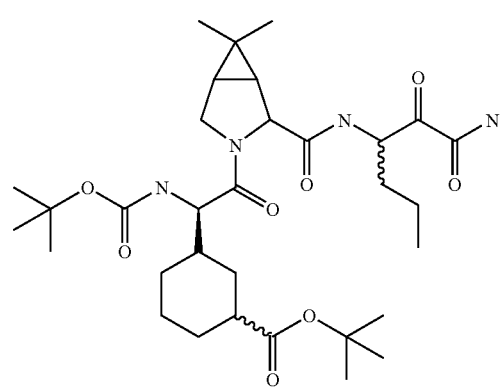 | 621 | B |
| 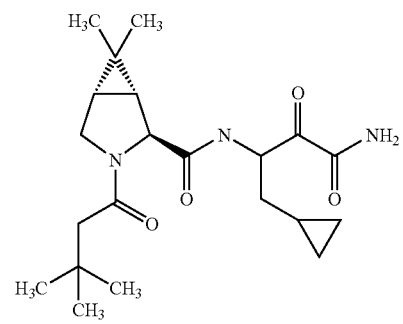 | 392 | C |
| 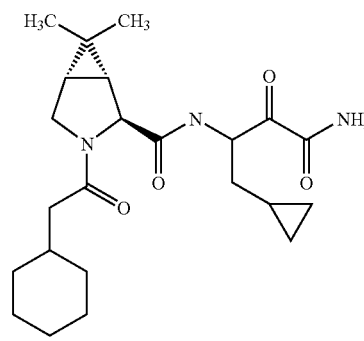 | 418 | C |

TABLE 5-continued

| STRUCTURE | MW | Ki* Range |
|---|---|---|
| 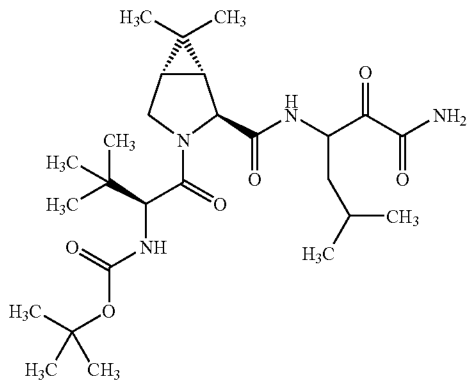 | 509 | B |
| 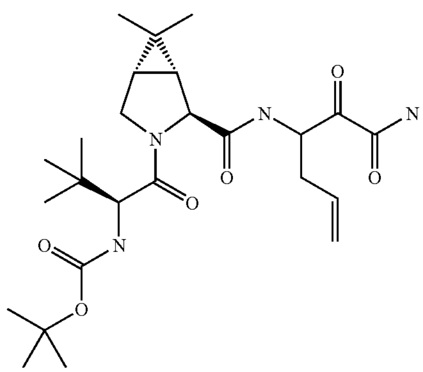 | 493 | C |
| 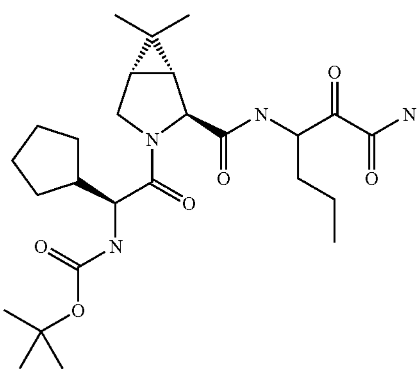 | 507 | B |
| 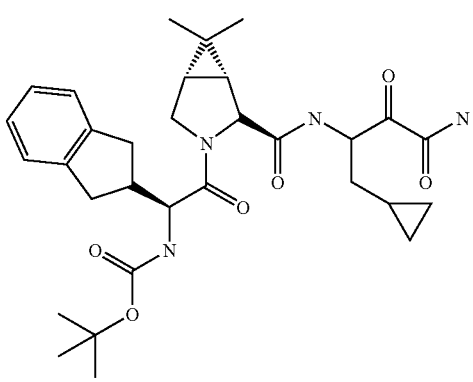 | 567 | A |

TABLE 5-continued
| STRUCTURE | MW | Ki* Range |
|---|---|---|
| 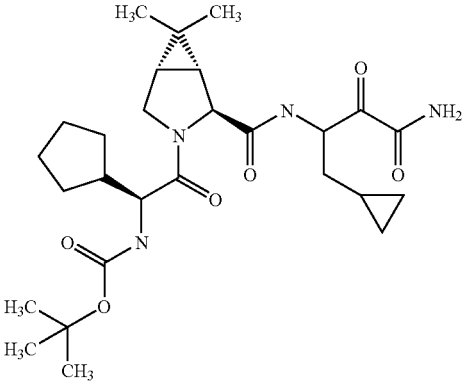 | 519 | A |
| 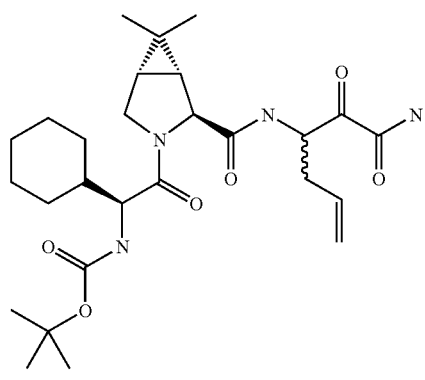 | 519 | B |
| 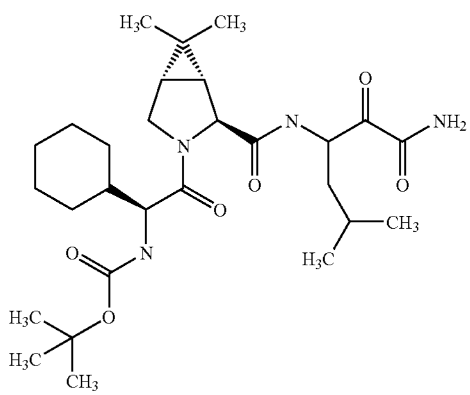 | 535 | B |
| 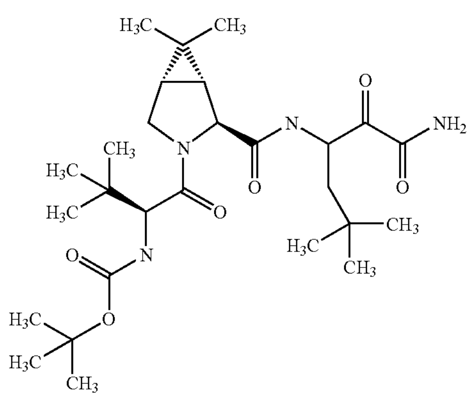 | 523 | C |

TABLE 5-continued

| STRUCTURE | MW | Ki* Range |
|---|---|---|
| 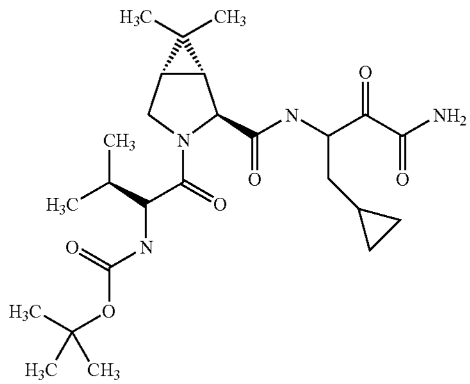 | 493 | B |
| 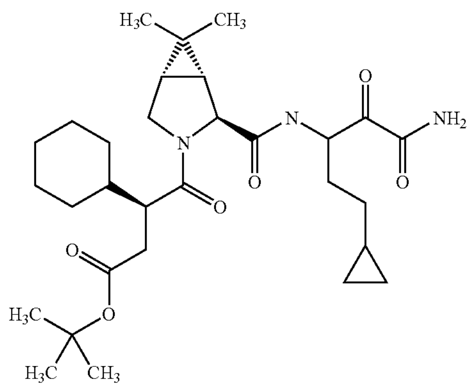 | 547 | B |
| 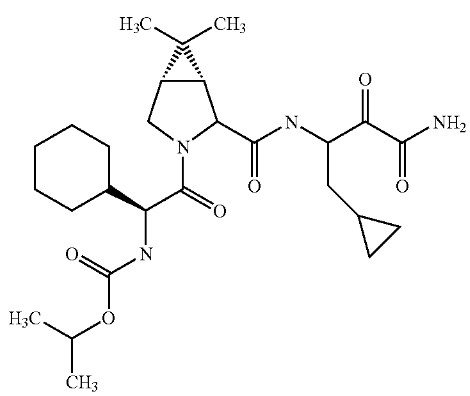 | 519 | A |
| 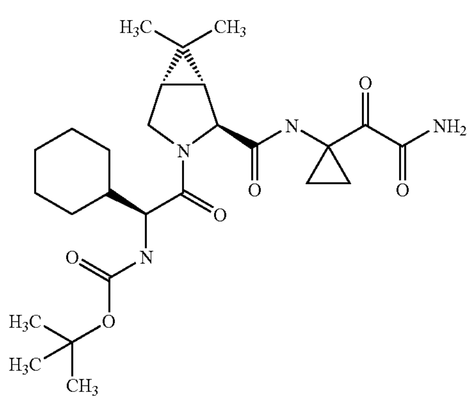 | 505 | C |

TABLE 5-continued

| STRUCTURE | MW | Ki* Range |
|---|---|---|
| 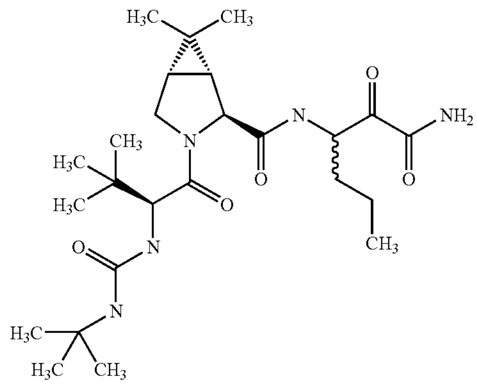 | 494 | B |
| 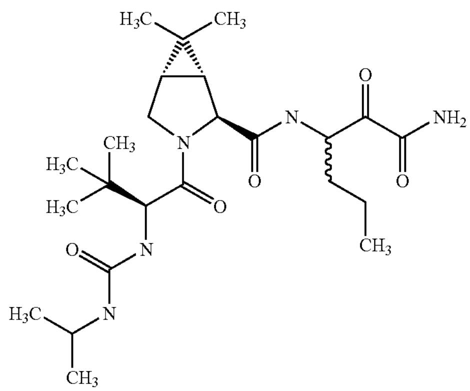 | 480 | B |
| 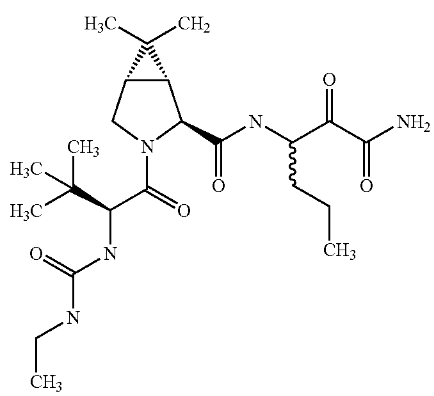 | 466 | C |
| 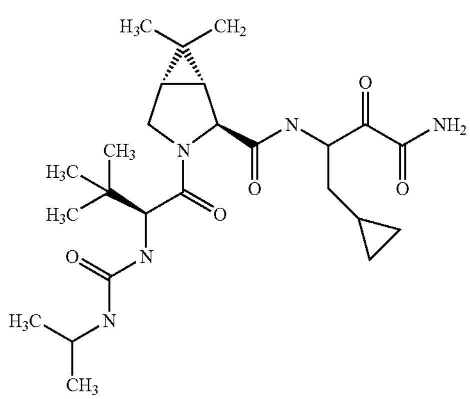 | 493 | B |

TABLE 5-continued

| STRUCTURE | MW | Ki* Range |
|---|---|---|
| 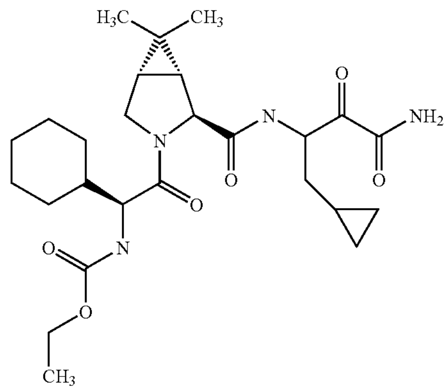 | 505 | B |
| 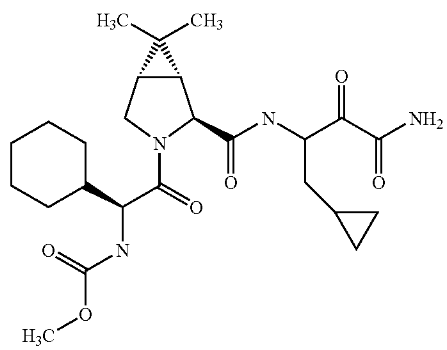 | 491 | B |
| 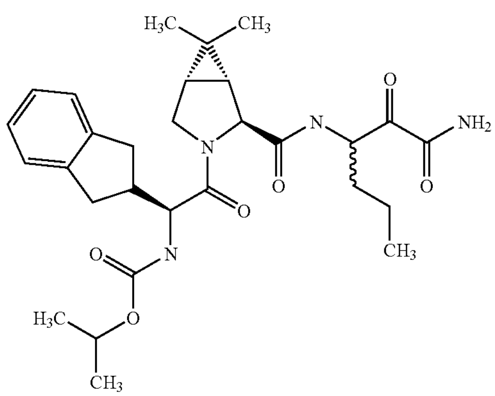 | 541 | B |
| 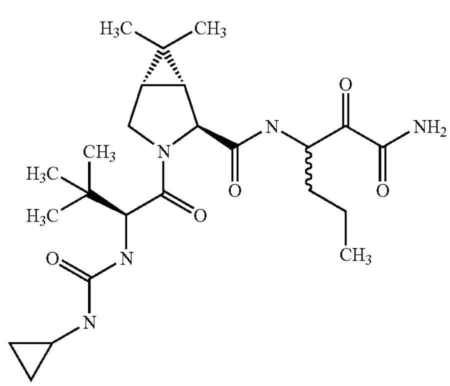 | 478 | C |

TABLE 5-continued

| STRUCTURE | MW | Ki* Range |
|---|---|---|
| 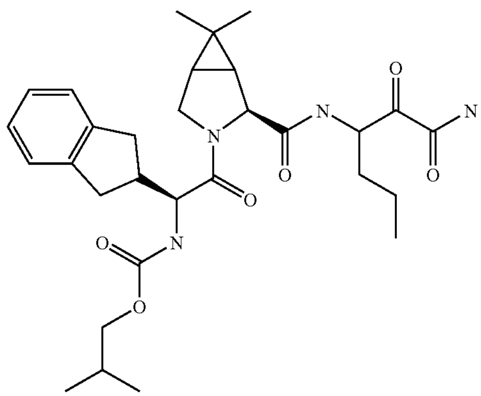 | 555 | B |
| 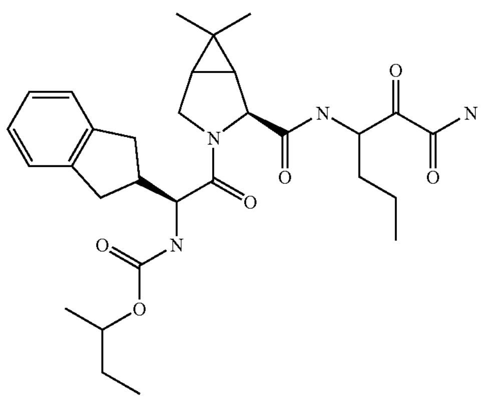 | 554 | B |
| 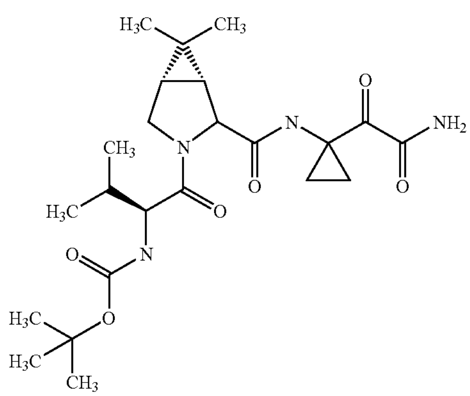 | 465 | C |
| 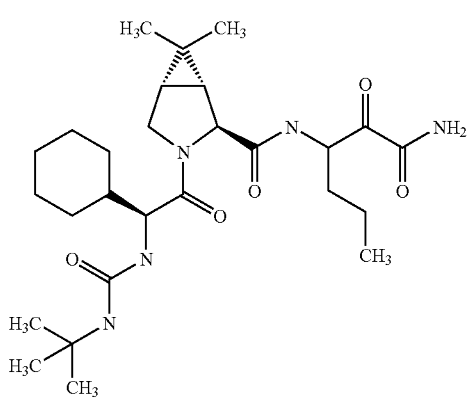 | 520 | A |

TABLE 5-continued

| STRUCTURE | MW | Ki* Range |
|---|---|---|
| 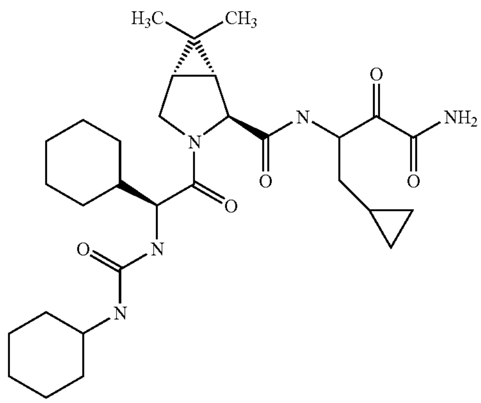 | 558 | A |
| 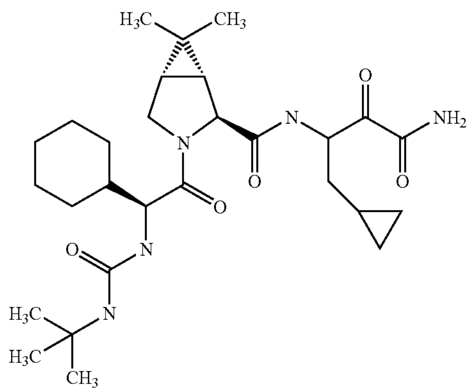 | 532 | A |
| | 547 | B |
| | 547 | B |

TABLE 5-continued

| STRUCTURE | MW | Ki* Range |
|---|---|---|
| 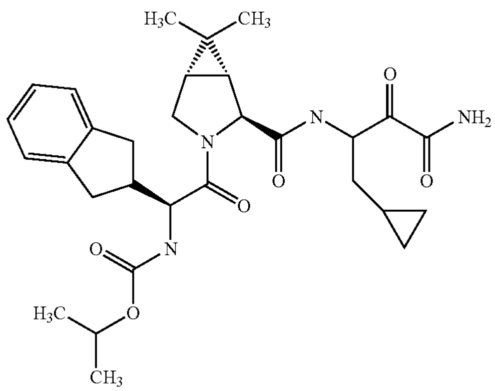 | 553 | A |
| 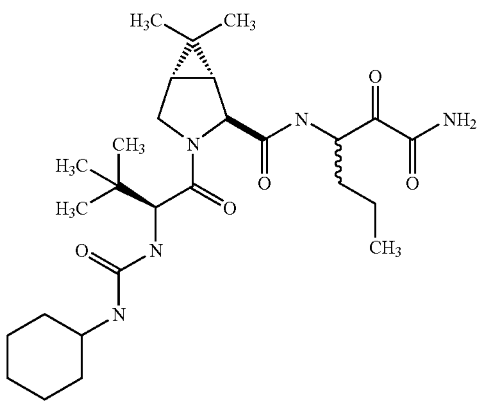 | 520 | B |
| 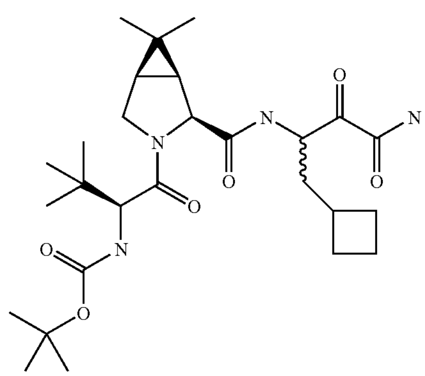 | 521 | A |
| 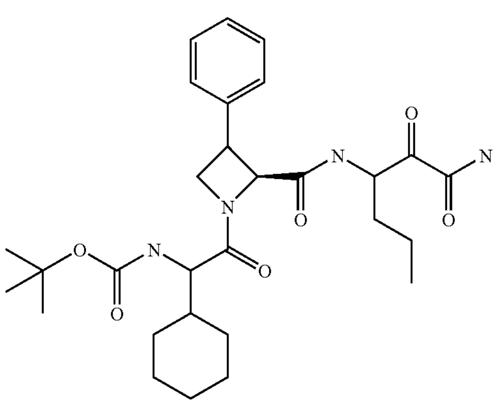 | 543 | C |

TABLE 5-continued

| STRUCTURE | MW | Ki* Range |
|---|---|---|
| 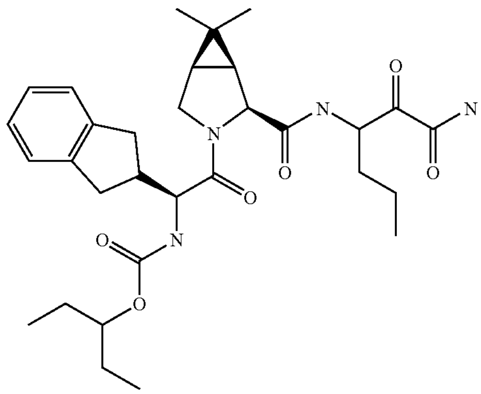 | 569 | B |
| 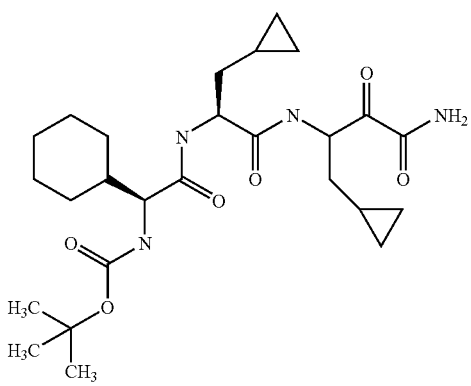 | 507 | B |
| 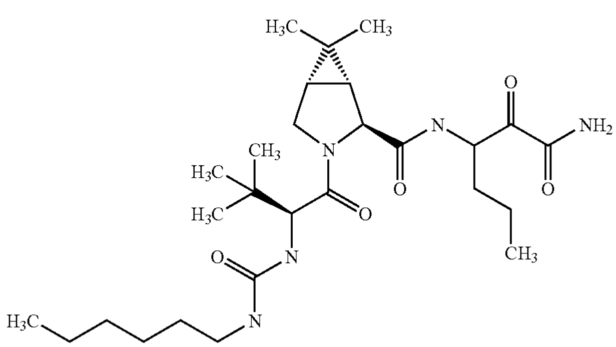 | 522 | B |
| 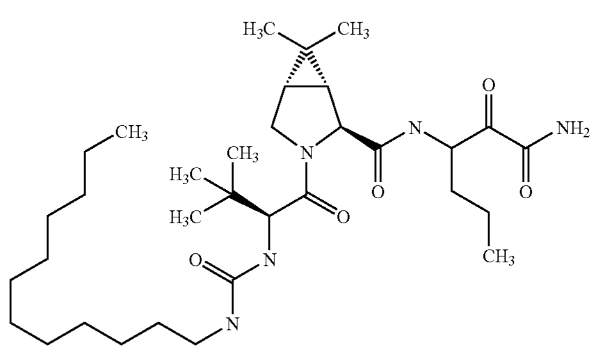 | 606 | C |

TABLE 5-continued

| STRUCTURE | MW | Ki* Range |
|---|---|---|
| 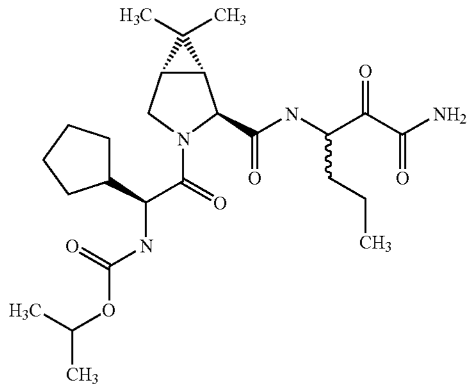 | 493 | B |
| 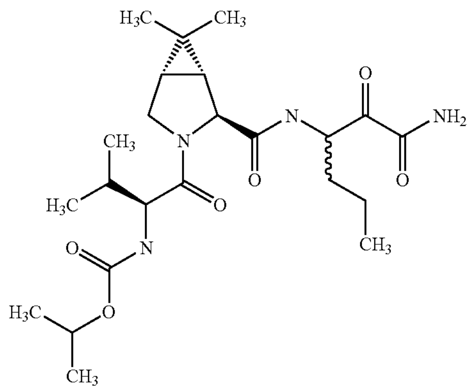 | 467 | C |
| 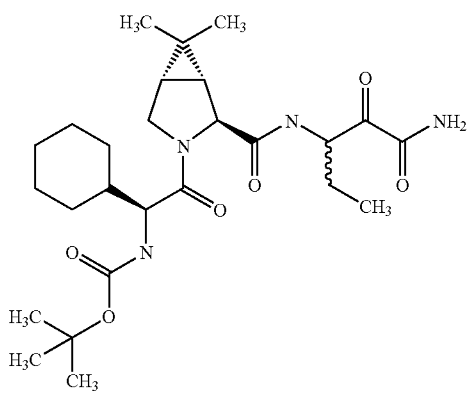 | 507 | B |
| 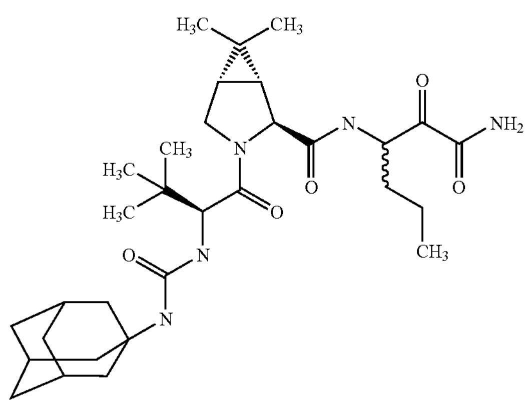 | 572 | A |

TABLE 5-continued
| STRUCTURE | MW | Ki* Range |
|---|---|---|
| 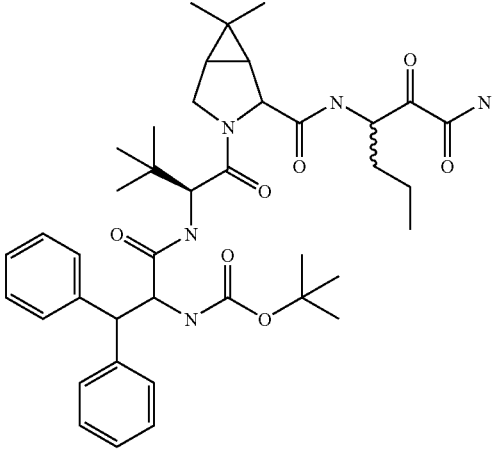 | 718 | C |
| 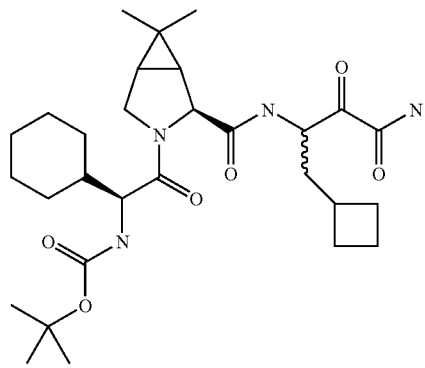 | 547 | A |
| 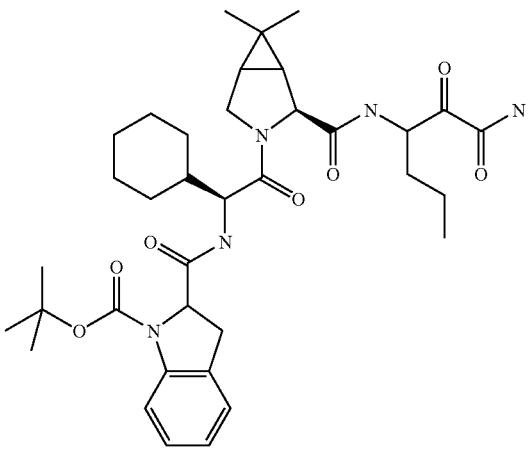 | 666 | B |

TABLE 5-continued

| STRUCTURE | MW | Ki* Range |
|---|---|---|
| | 540 | C |
| 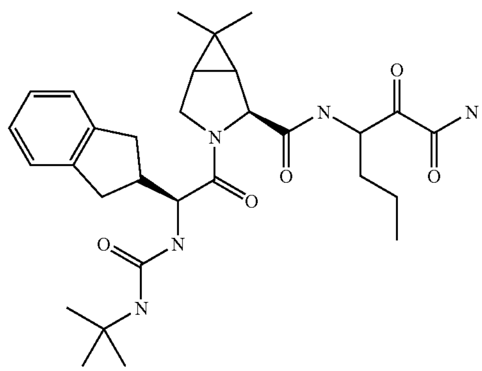 | 554 | B |
| | 540 | B |
| 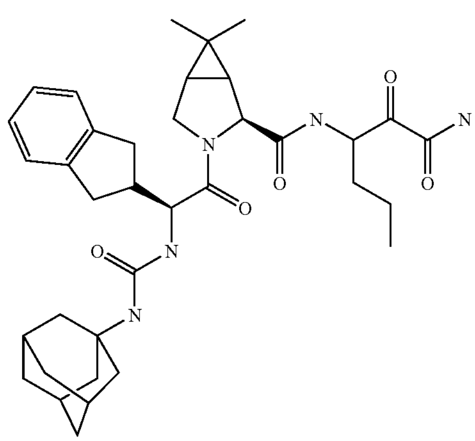 | 632 | B |

TABLE 5-continued

| STRUCTURE | MW | Ki* Range |
|---|---|---|
| 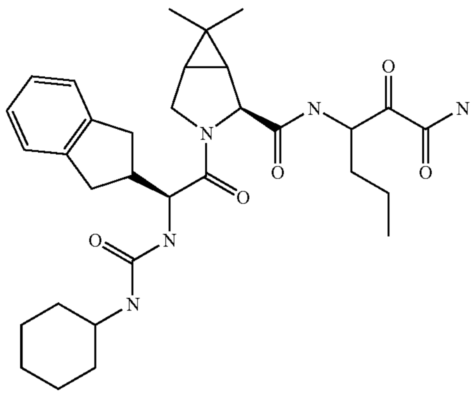 | 580 | B |
| 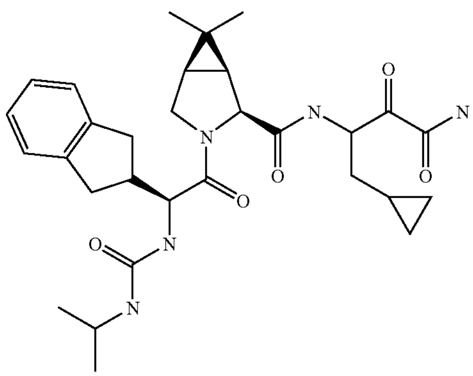 | 552 | A |
| 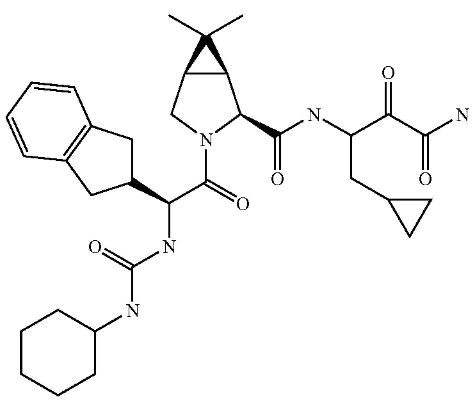 | 592 | A |
| 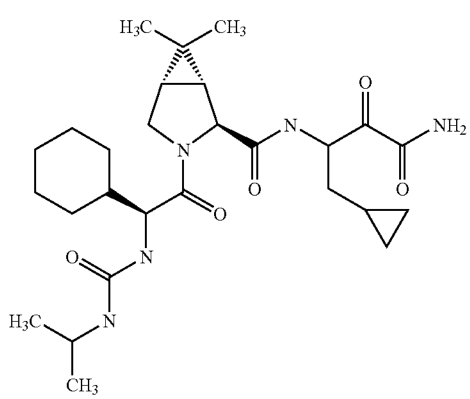 | 518 | A |

TABLE 5-continued
| STRUCTURE | MW | Ki* Range |
|---|---|---|
| 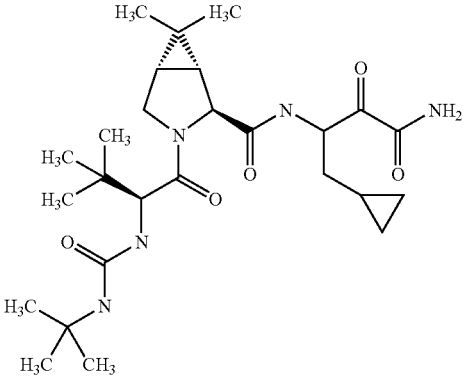 | 506 | A |
| 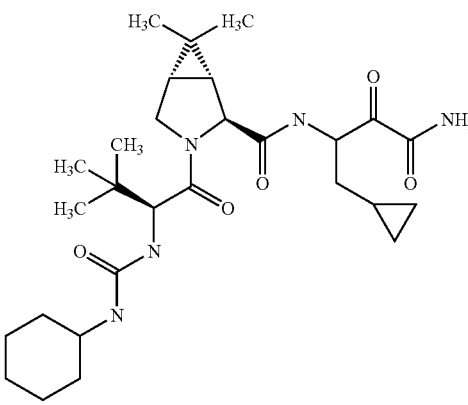 | 532 | A |
| 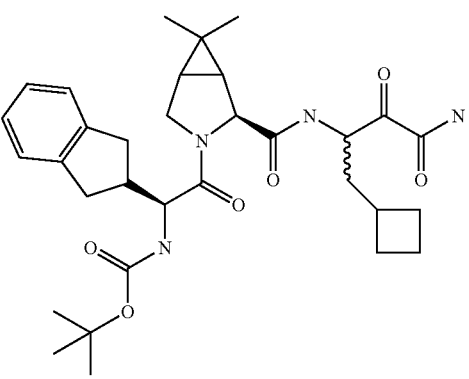 | 581 | B |

TABLE 5-continued
| STRUCTURE | MW | Ki* Range |
|---|---|---|
| 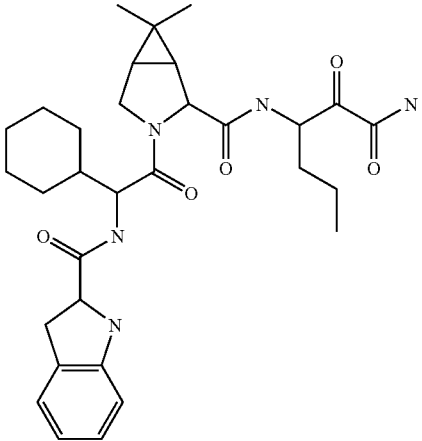 | 566 | C |
| 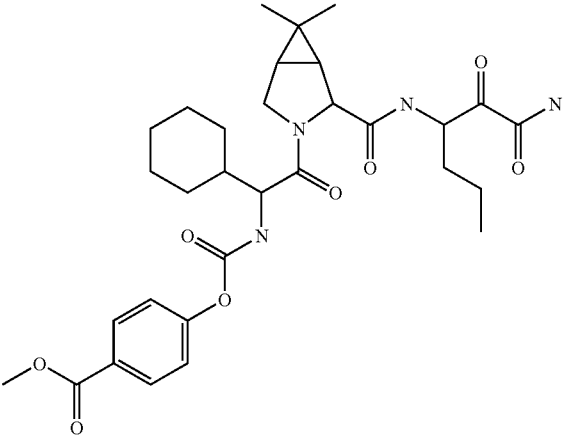 | 599 | B |
| 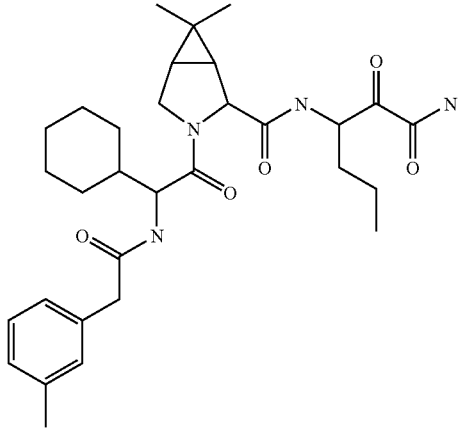 | 553 | B |

TABLE 5-continued

| STRUCTURE | MW | Ki* Range |
|---|---|---|
| 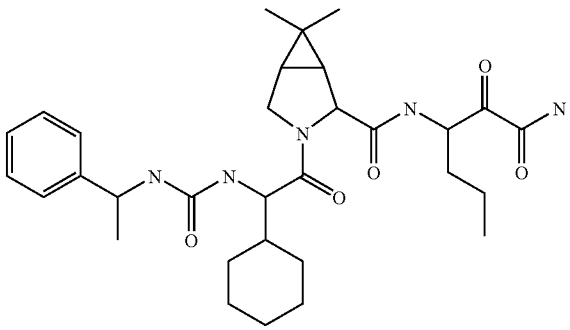 | 568 | B |
|  | 566 | A |
|  | 566 | A |
| 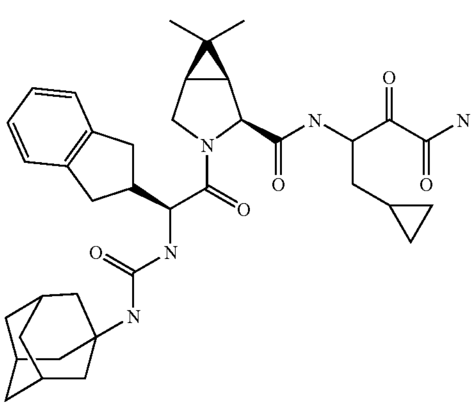 | 644 | A |

TABLE 5-continued

| STRUCTURE | MW | Ki* Range |
|---|---|---|
| 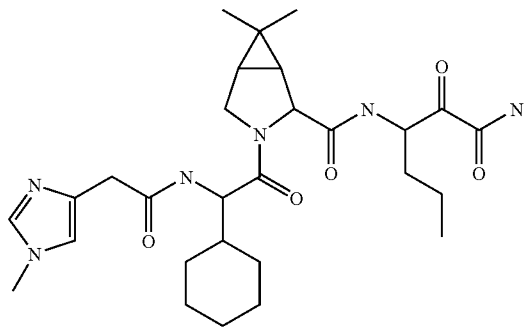 | 543 | C |
| 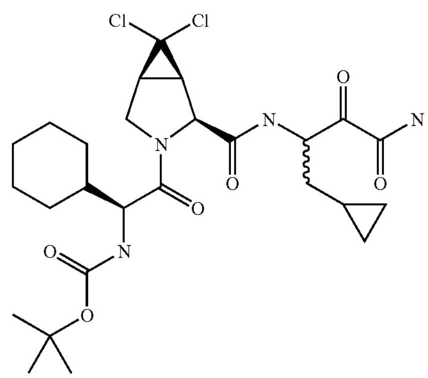 | 574 | A |
| 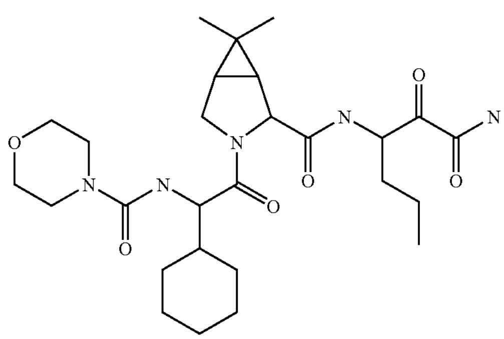 | 534 | C |
| 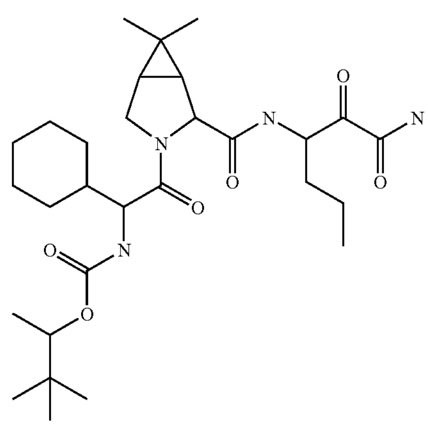 | 549 | B |

TABLE 5-continued

| STRUCTURE | MW | Ki* Range |
|---|---|---|
| 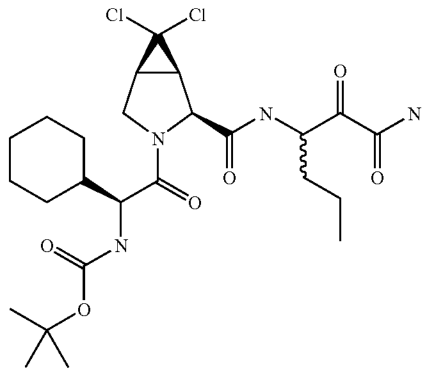 | 562 | A |
| 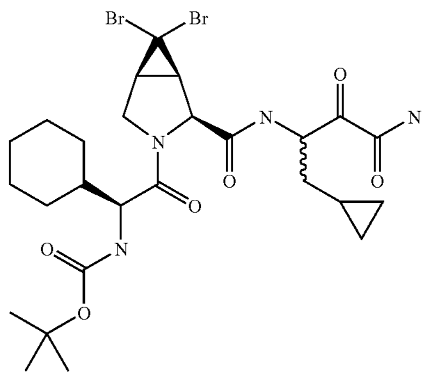 | 662 | A |
| 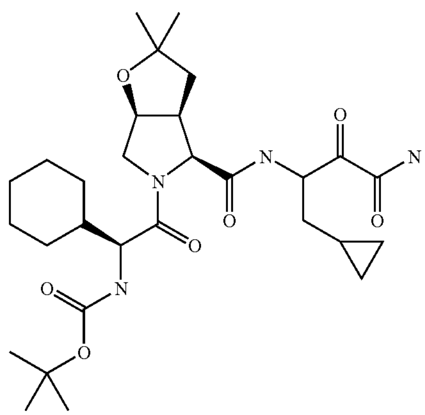 | 563 | B |
| 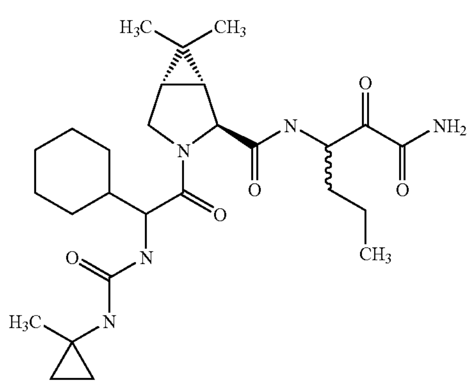 | 518 | B |

TABLE 5-continued

| STRUCTURE | MW | Ki* Range |
|---|---|---|
| 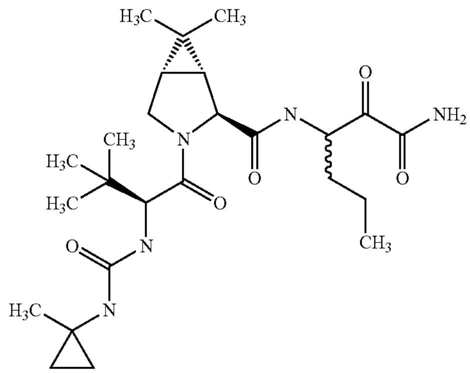 | 492 | B |
| 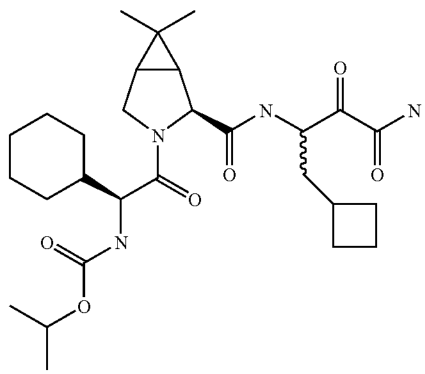 | 533 | A |
| 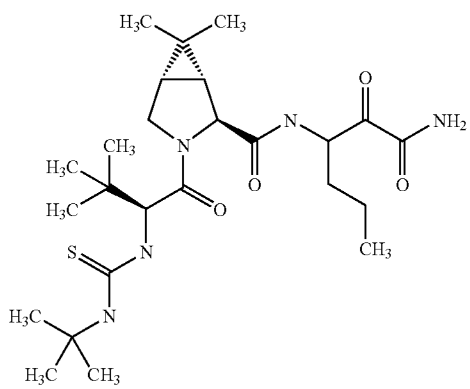 | 510 | C |
| 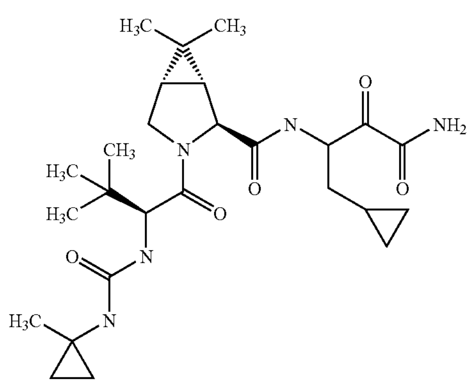 | 504 | A |

TABLE 5-continued

| STRUCTURE | MW | Ki* Range |
|---|---|---|
| 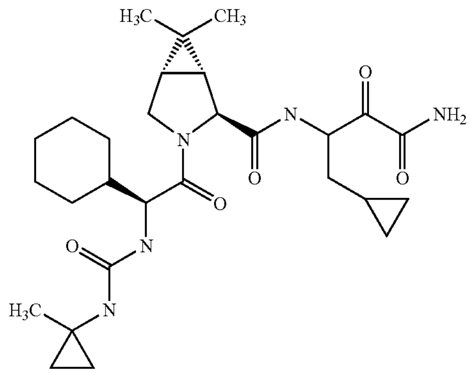 | 530 | B |
| 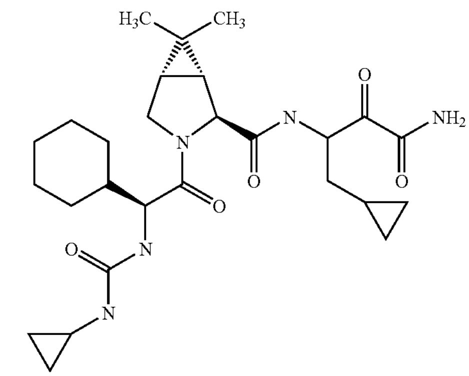 | 516 | B |
| 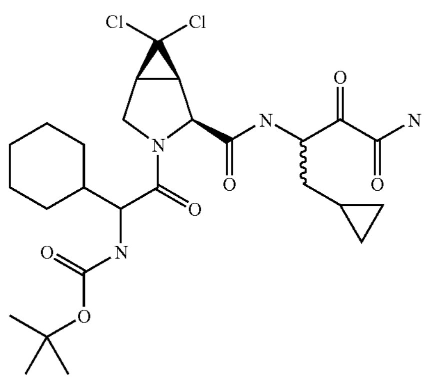 | 574 | B |
| 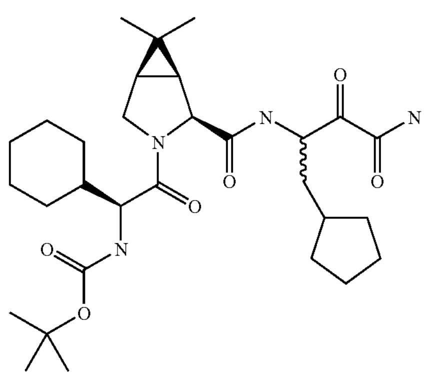 | 561 | B |

TABLE 5-continued

| STRUCTURE | MW | Ki* Range |
|---|---|---|
| 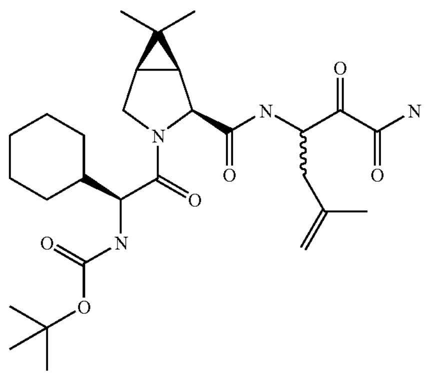 | 533 | B |
| 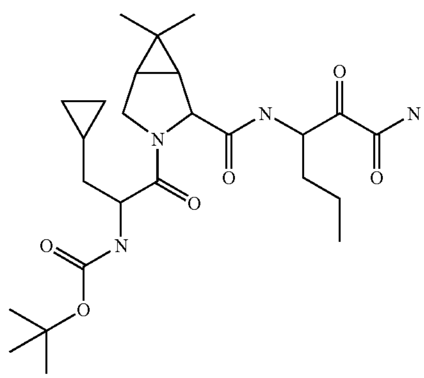 | 493 | C |
| 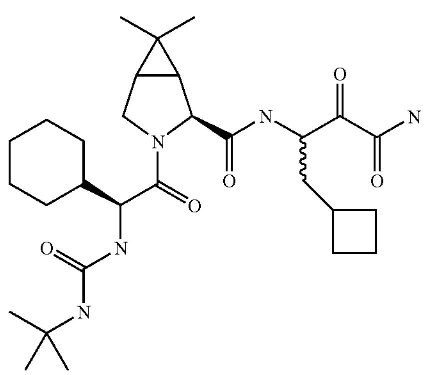 | 546 | A |
| 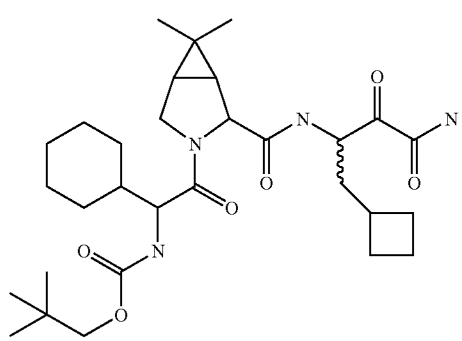 | 561 | A |

TABLE 5-continued

| STRUCTURE | MW | Ki* Range |
|---|---|---|
| 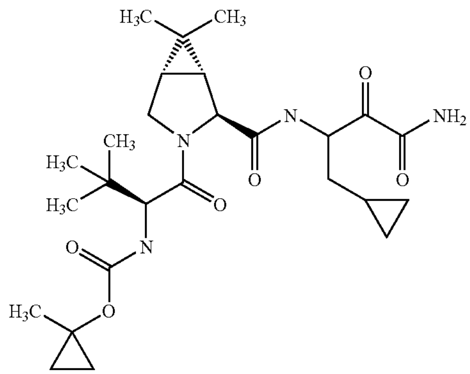 | 505 | B |
| 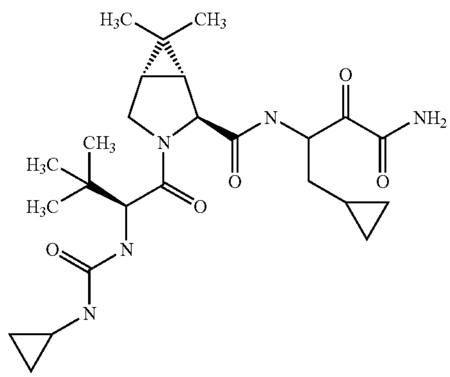 | 490 | B |
| 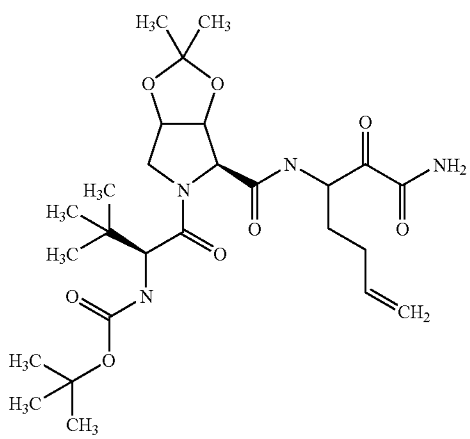 | 539 | C |
| 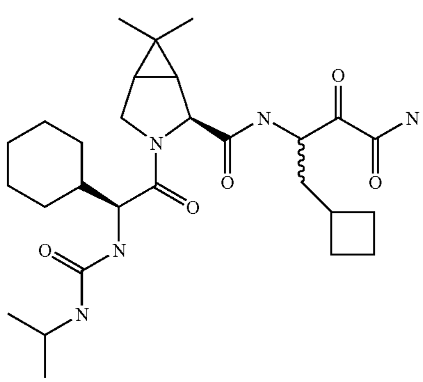 | 532 | A |

TABLE 5-continued

| STRUCTURE | MW | Ki* Range |
|---|---|---|
| 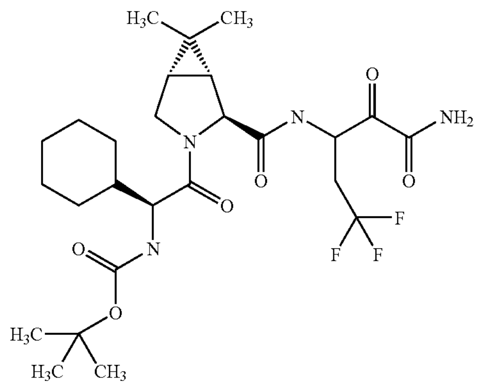 | 561 | A |
| 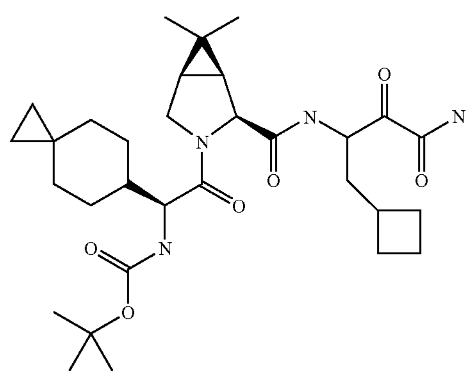 | 573 | A |
| 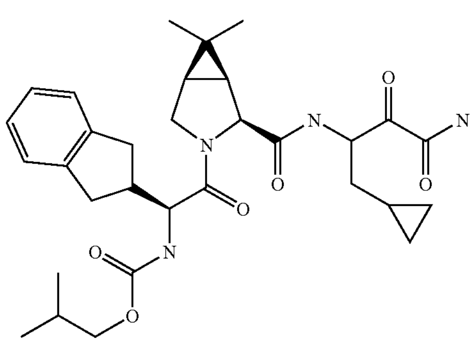 | 567 | A |
| 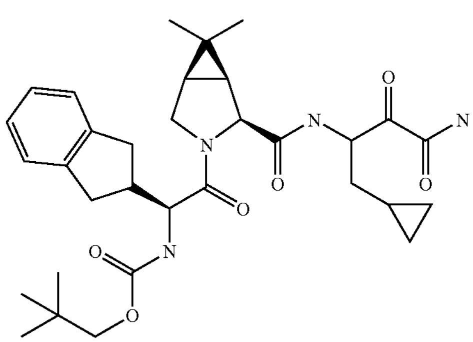 | 581 | A |

TABLE 5-continued
| STRUCTURE | MW | Ki* Range |
|---|---|---|
| 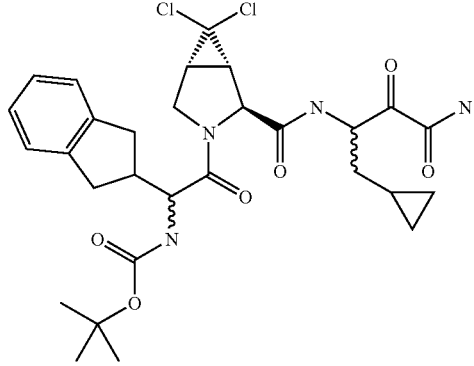 | 608 | A |
| 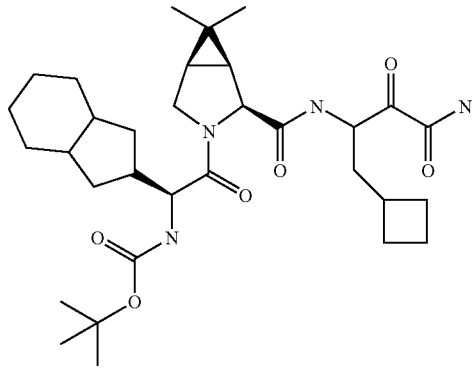 | 587 | B |
| 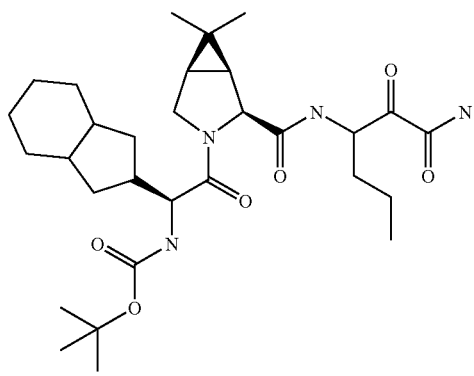 | 561 | B |
| 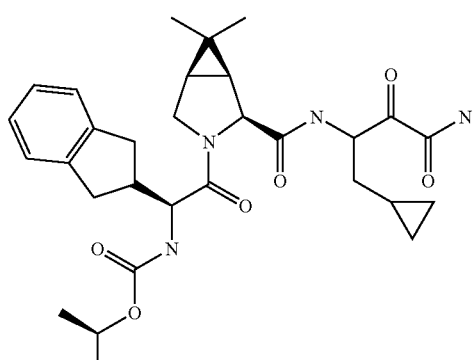 | 581 | A |

TABLE 5-continued

| STRUCTURE | MW | Ki* Range |
|---|---|---|
| 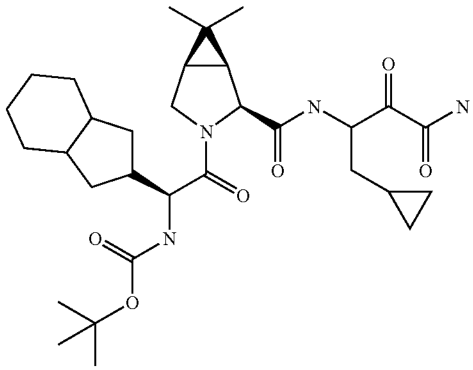 | 573 | A |
| 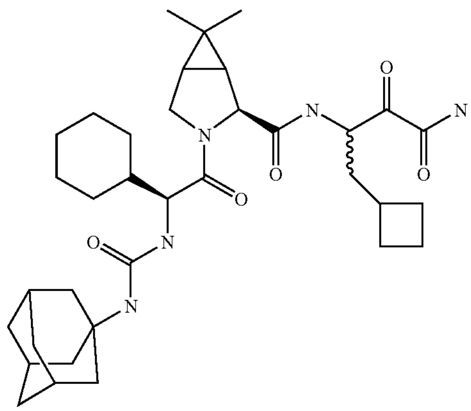 | 624 | A |
| 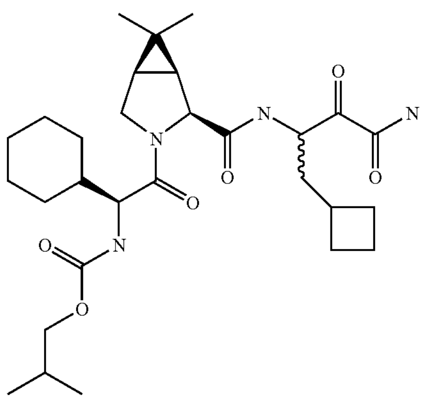 | 547 | A |
| 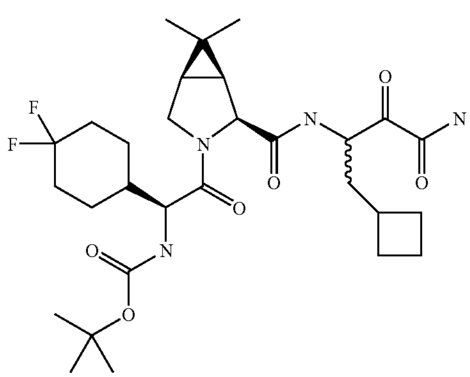 | 583 | A |

TABLE 5-continued

| STRUCTURE | MW | Ki* Range |
|---|---|---|
| 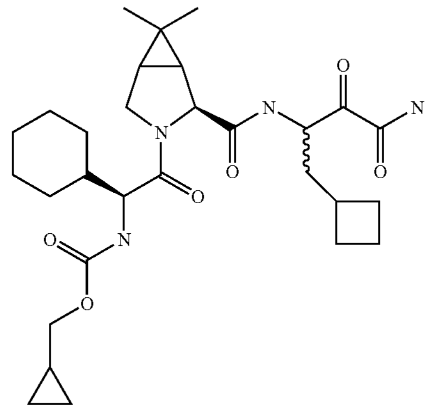 | 545 | B |
| 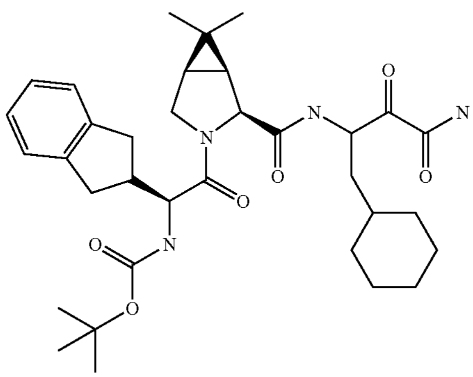 | 609 | C |
| 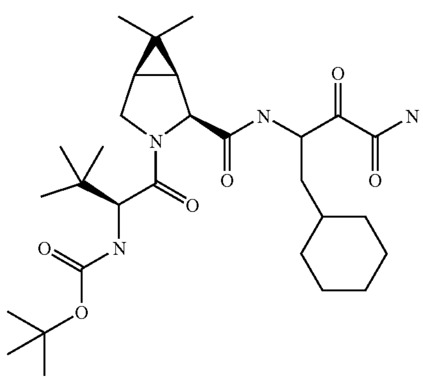 | 549 | C |
| 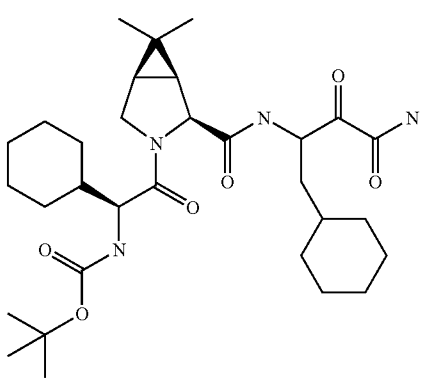 | 575 | C |

TABLE 5-continued

| STRUCTURE | MW | Ki* Range |
|---|---|---|
| 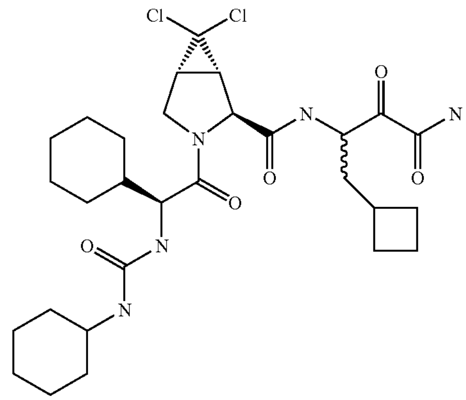 | 613 | A |
| 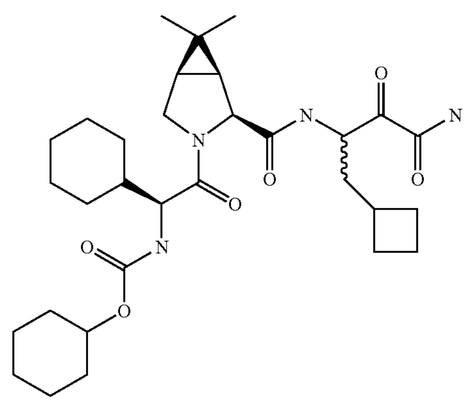 | 573 | A |
| 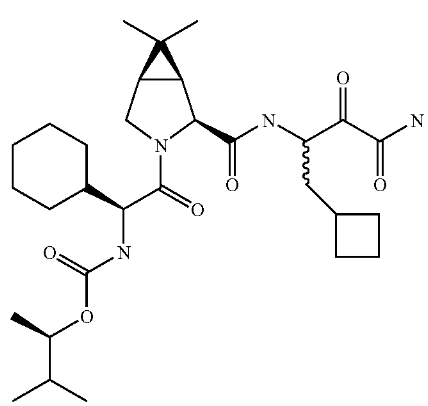 | 561 | A |
| 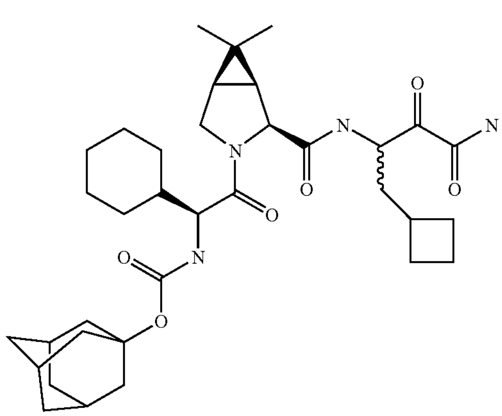 | 625 | A |

TABLE 5-continued
| STRUCTURE | MW | Ki* Range |
|---|---|---|
| 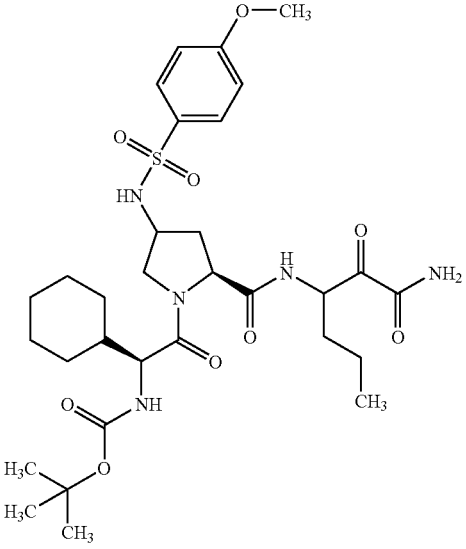 | 666 | C |
| 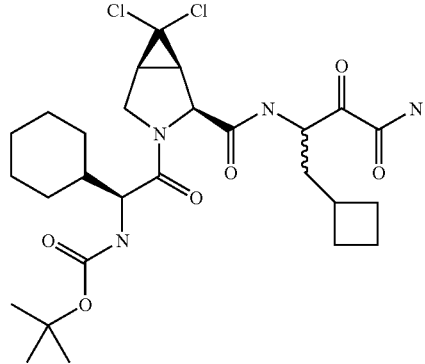 | 588 | A |
| 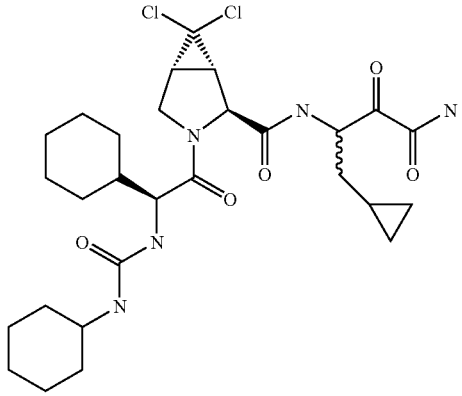 | 599 | A |

TABLE 5-continued

| STRUCTURE | MW | Ki* Range |
|---|---|---|
| 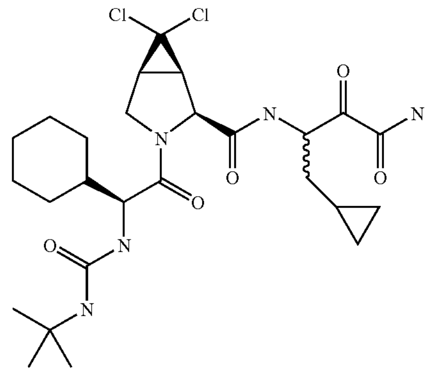 | 573 | A |
| 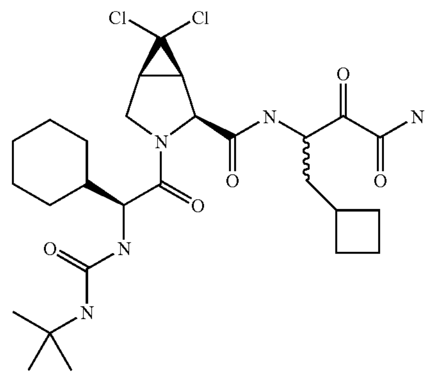 | 587 | A |
| 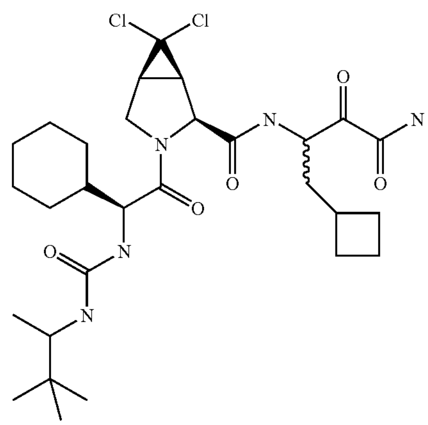 | 615 | A |
| 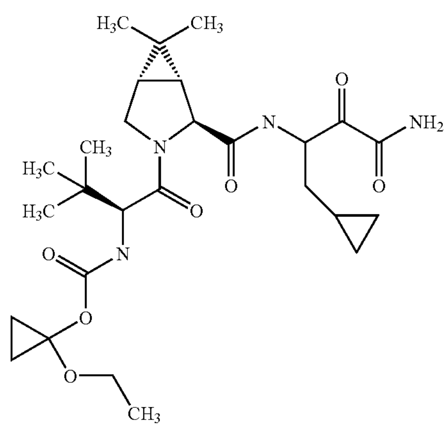 | 535 | B |

TABLE 5-continued

| STRUCTURE | MW | Ki* Range |
|---|---|---|
| 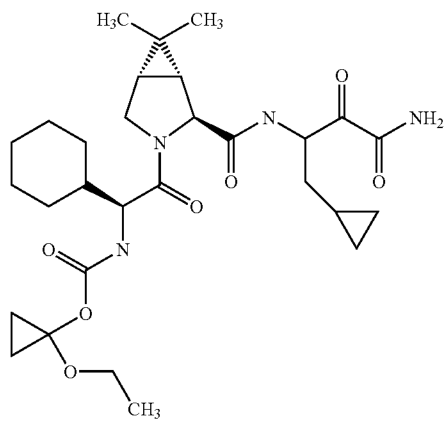 | 561 | A |
| 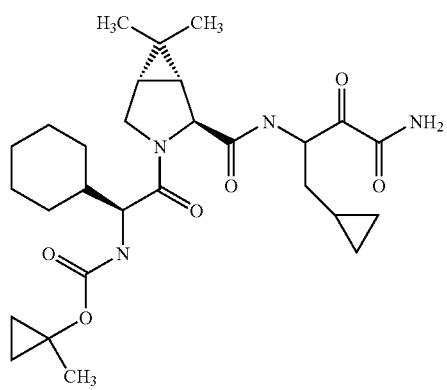 | 531 | A |
| 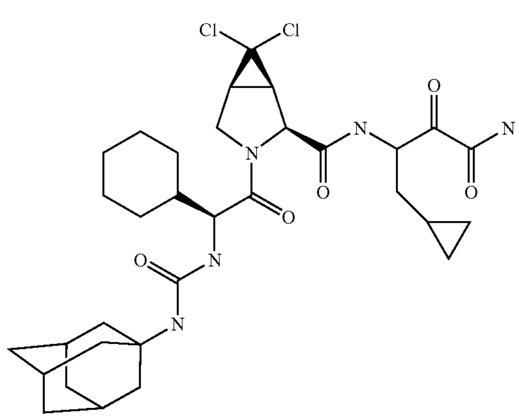 | 651 | A |

TABLE 5-continued

| STRUCTURE | MW | Ki* Range |
|---|---|---|
| 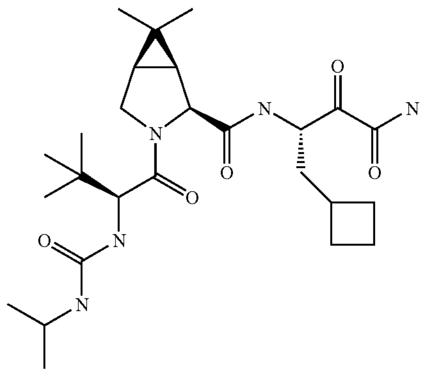 | 506 | A |
| 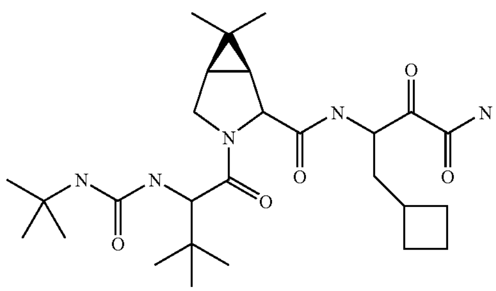 | 520 | A |
| 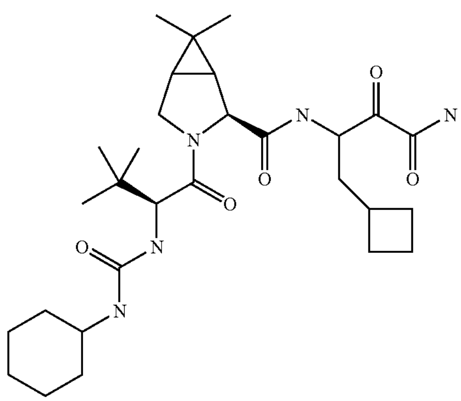 | 546 | A |
| 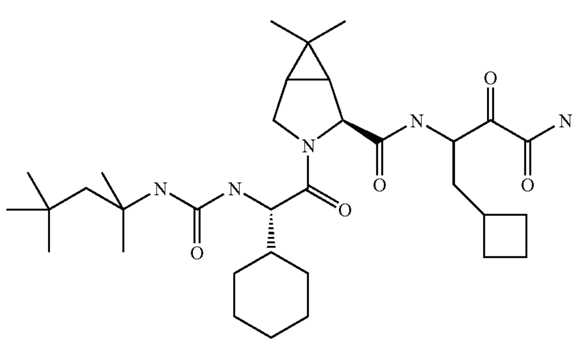 | 602 | A |

TABLE 5-continued
| STRUCTURE | MW | Ki* Range |
|---|---|---|
| 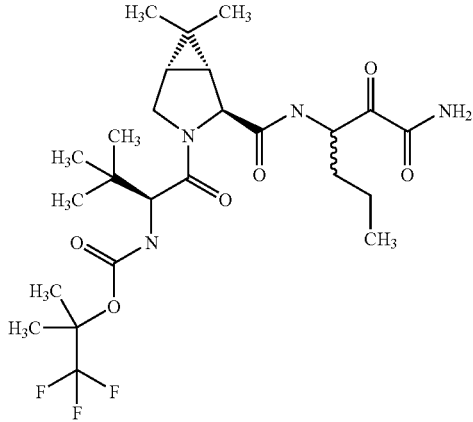 | 549 | B |
| 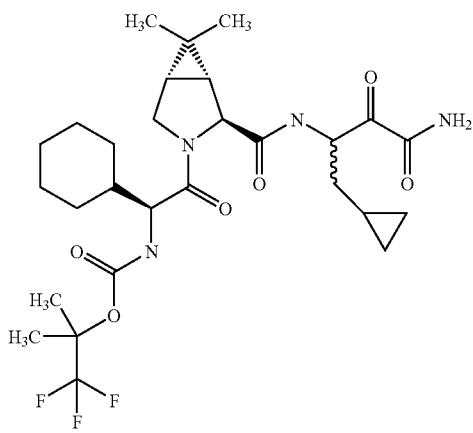 | 587 | A |
| 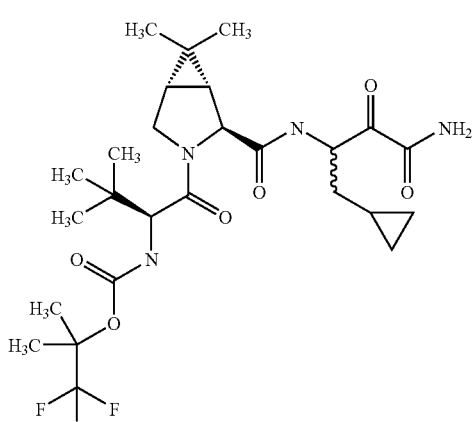 | 561 | A |

TABLE 5-continued

| STRUCTURE | MW | Ki* Range |
|---|---|---|
| 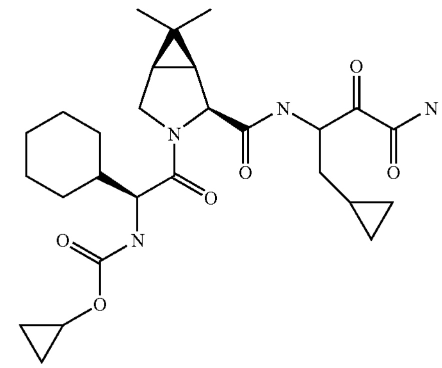 | 517 | B |
| 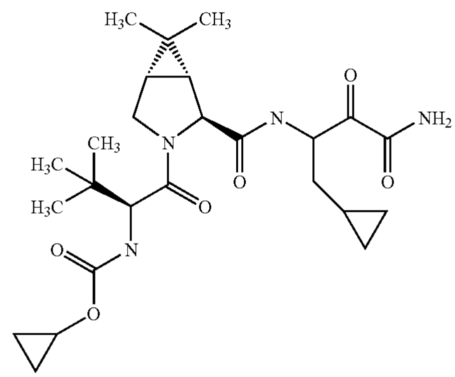 | 491 | B |
| 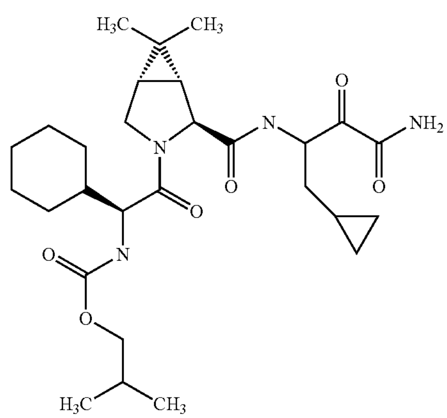 | 533 | B |
| 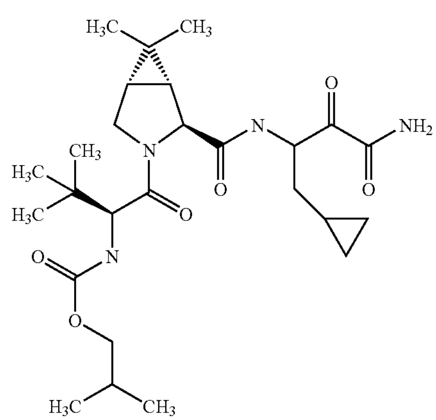 | 507 | A |

TABLE 5-continued

| STRUCTURE | MW | Ki* Range |
|---|---|---|
| 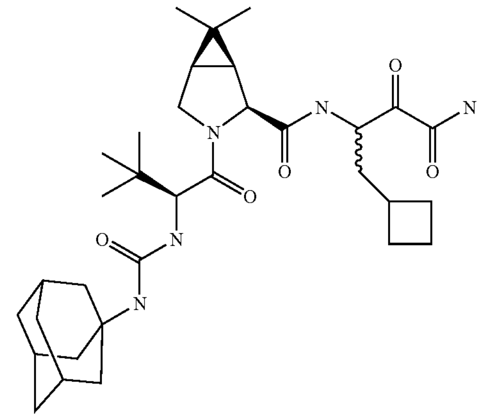 | 598 | A |
| 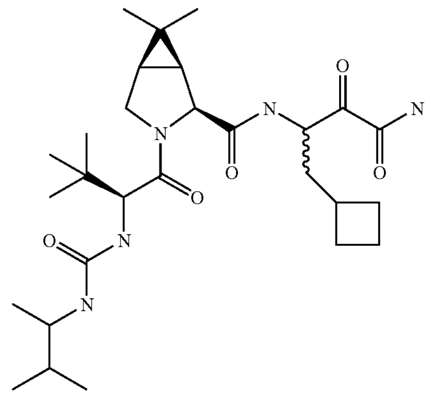 | 535 | A |
| 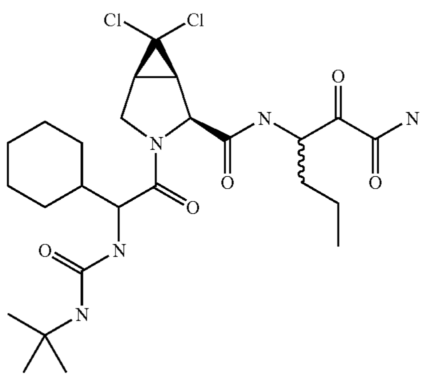 | 561 | A |
| 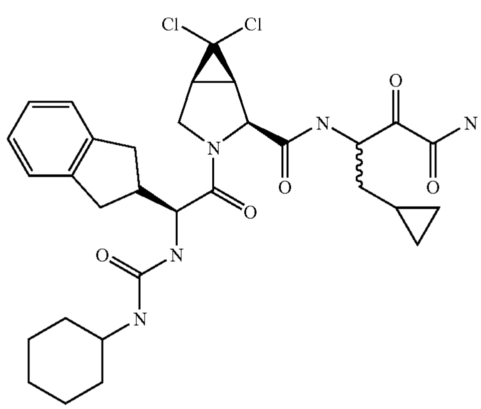 | 633 | A |

TABLE 5-continued

| STRUCTURE | MW | Ki* Range |
|---|---|---|
| 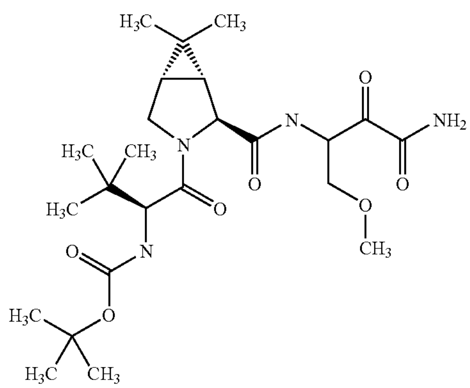 | 497 | C |
| 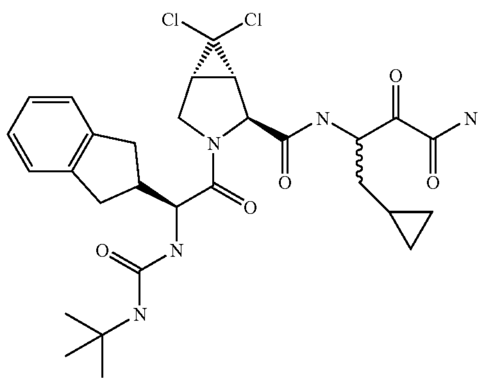 | 607 | A |
| 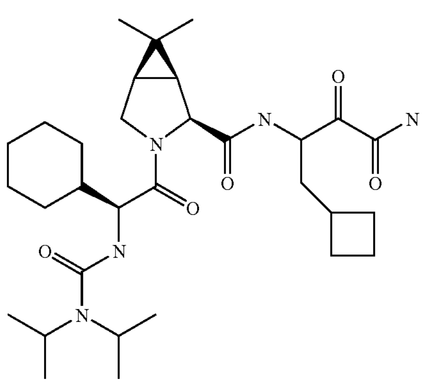 | 574 | B |
| 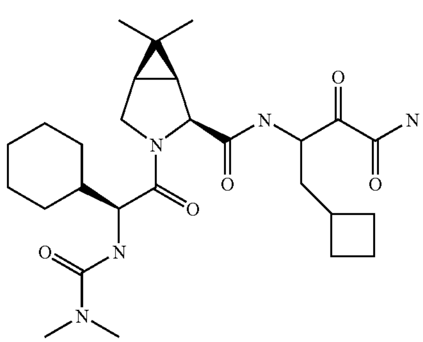 | 518 | B |

TABLE 5-continued

| STRUCTURE | MW | Ki* Range |
|---|---|---|
| 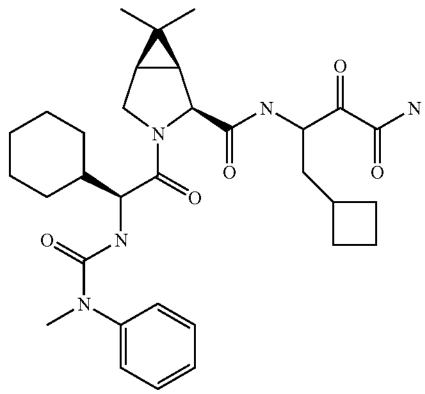 | 580 | C |
| 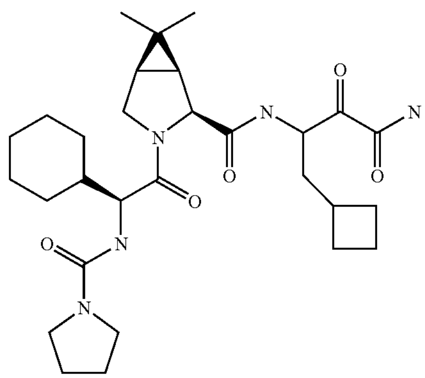 | 544 | B |
| 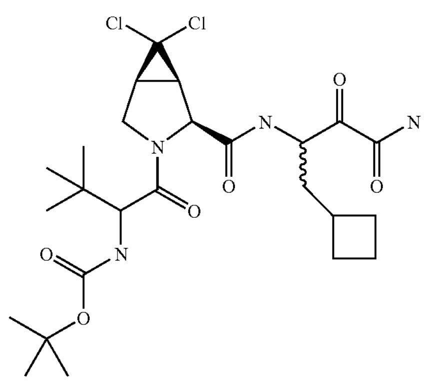 | 562 | A |
| 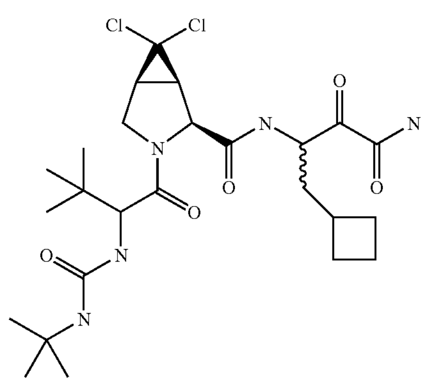 | 561 | A |

TABLE 5-continued
| STRUCTURE | MW | Ki* Range |
|---|---|---|
| 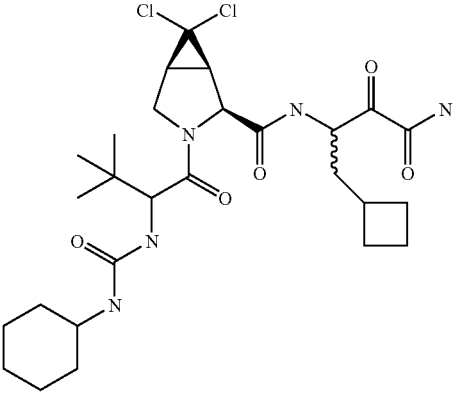 | 587 | A |
| 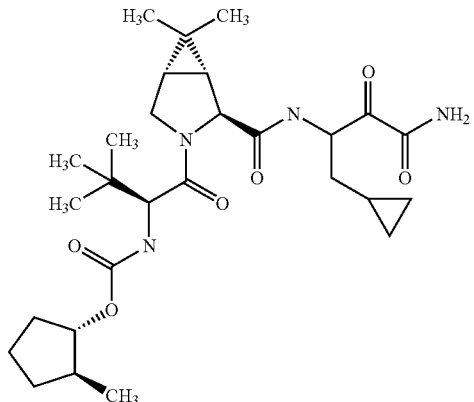 | 533 | A |
| 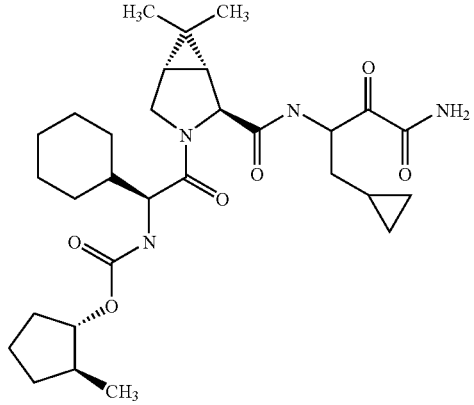 | 559 | A |

TABLE 5-continued
| STRUCTURE | MW | Ki* Range |
|---|---|---|
| 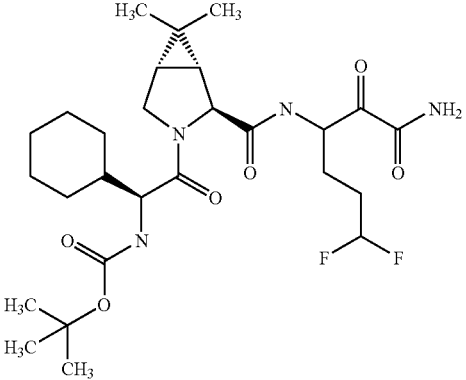 | 557 | C |
| 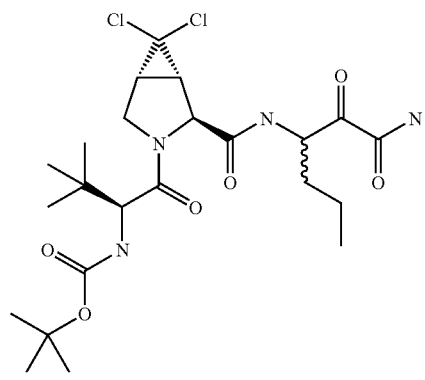 | 535 | A |
| 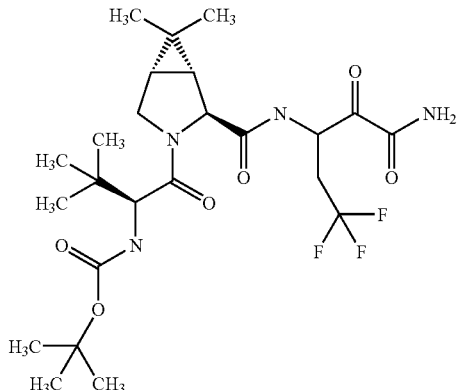 | 535 | B |
| 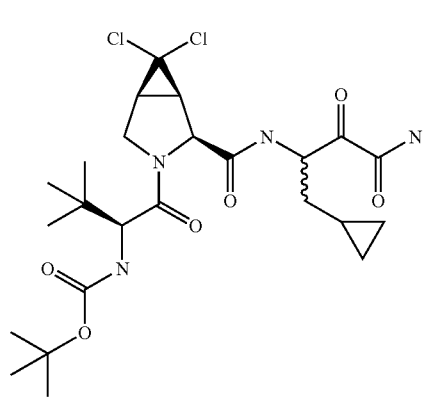 | 547 | A |

TABLE 5-continued

| STRUCTURE | MW | Ki* Range |
|---|---|---|
| | 546 | A |
| | 546 | B |
| 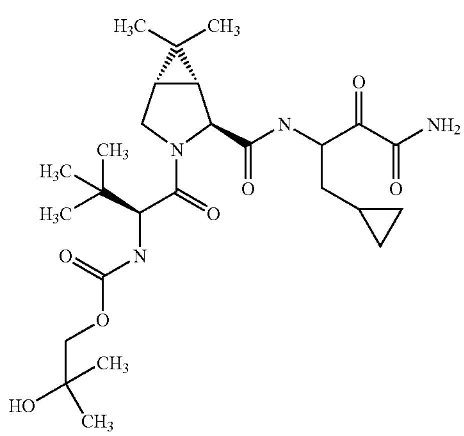 | 523 | B |

TABLE 5-continued
| STRUCTURE | MW | Ki* Range |
|---|---|---|
| 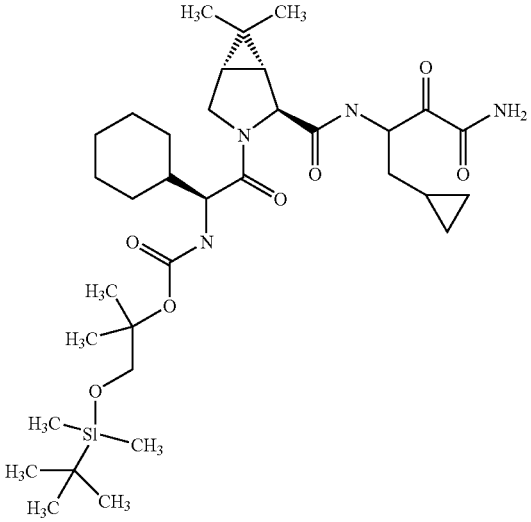 | 663 | C |
| 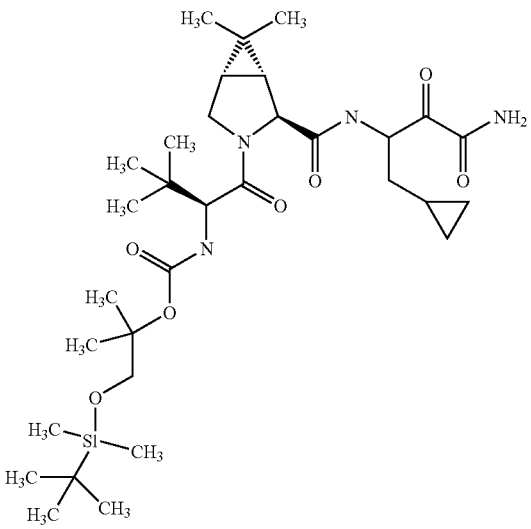 | 637 | C |
| 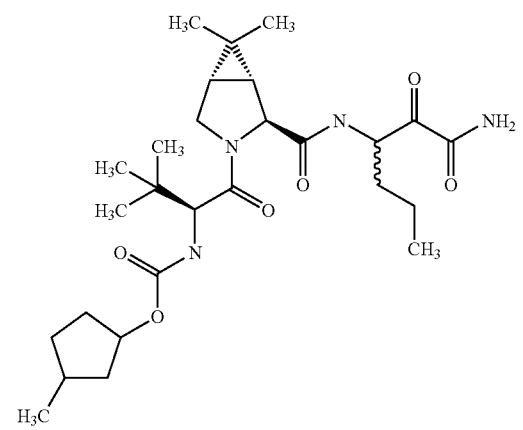 | 521 | B |

TABLE 5-continued
| STRUCTURE | MW | Ki* Range |
|---|---|---|
| 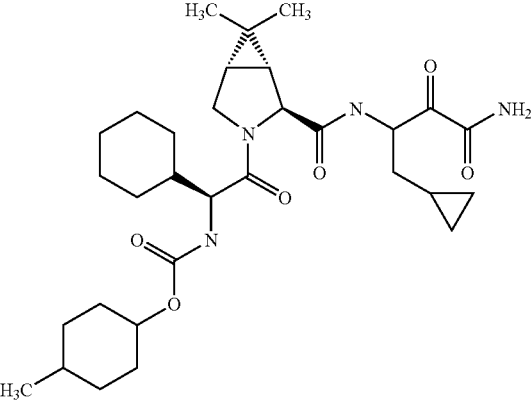 | 573 | B |
| 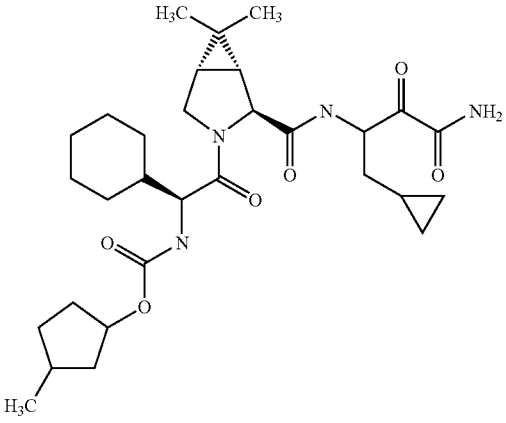 | 559 | A |
| 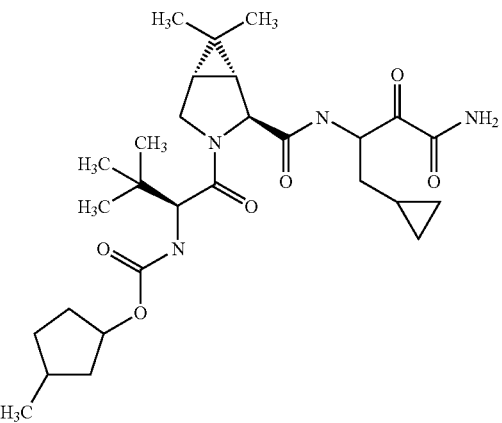 | 533 | A |

TABLE 5-continued
| STRUCTURE | MW | Ki* Range |
|---|---|---|
| 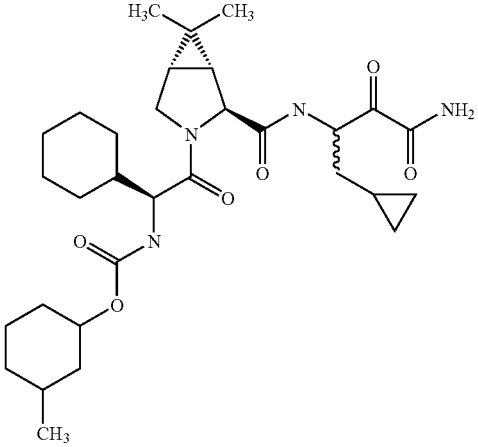 | 573 | B |
| 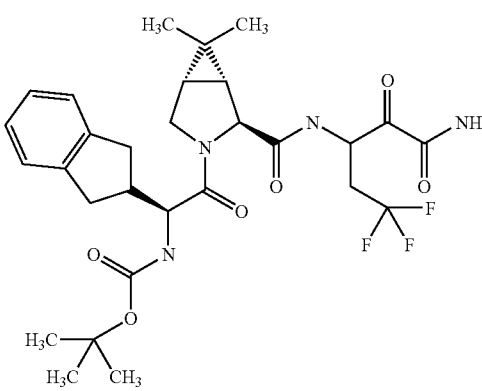 | 595 | B |
| 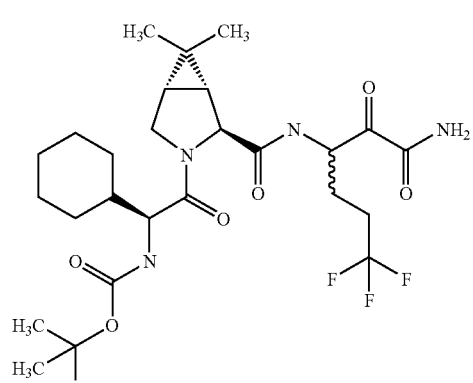 | 575 | A |

TABLE 5-continued

| STRUCTURE | MW | Ki* Range |
|---|---|---|
| 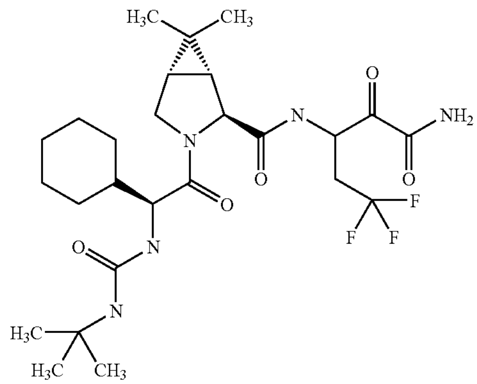 | 560 | B |
| 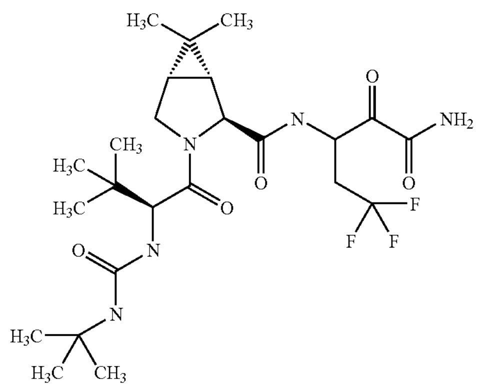 | 534 | C |
| | 727 | A |
| | 727 | A |

TABLE 5-continued
| STRUCTURE | MW | Ki* Range |
|---|---|---|
| 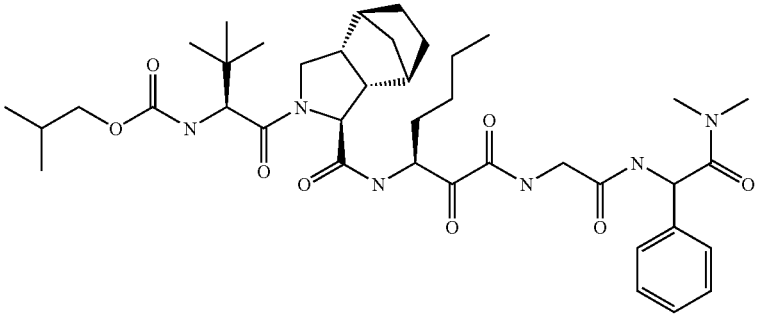 | 753 | C |
| 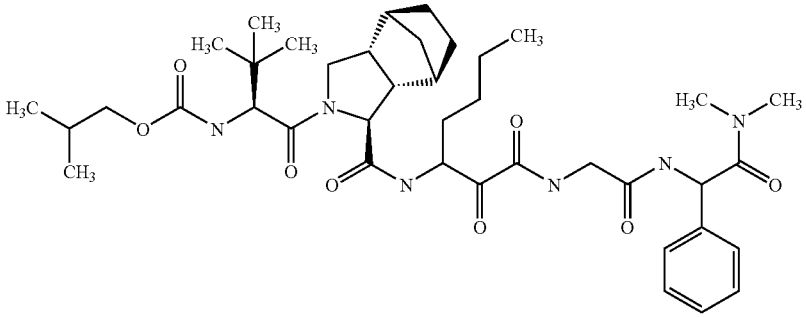 | 753 | B |
| 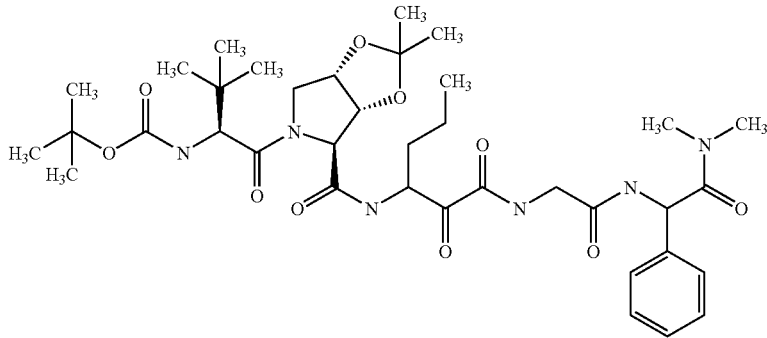 | 745 | A |
| 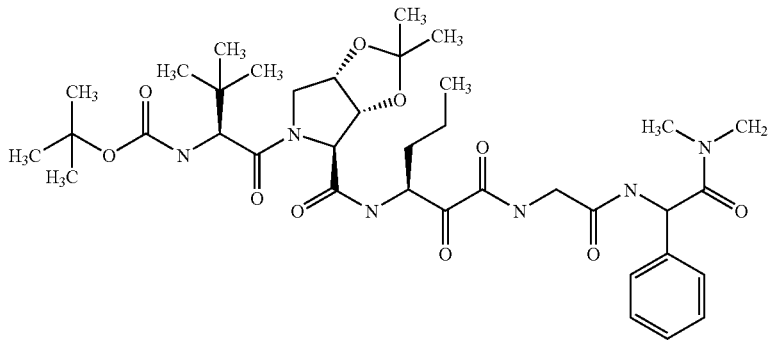 | 745 | A |

TABLE 5-continued

| STRUCTURE | MW | Ki* Range |
|---|---|---|
| | 759 | B |
| | 759 | B |
| | 669 | B |
| | 669 | A |

TABLE 5-continued

| STRUCTURE | MW | Ki* Range |
|---|---|---|
| 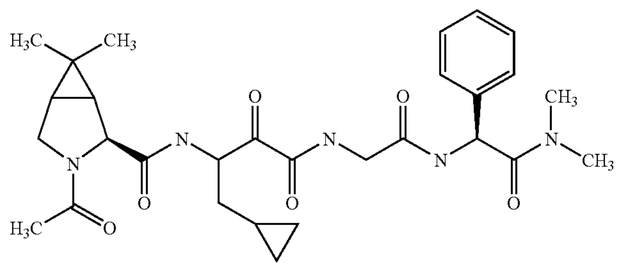 | 554 | C |
| 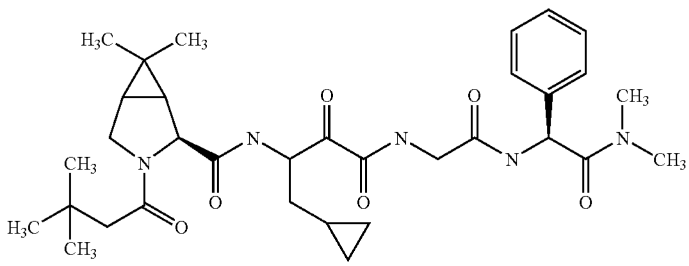 | 610 | B |
| 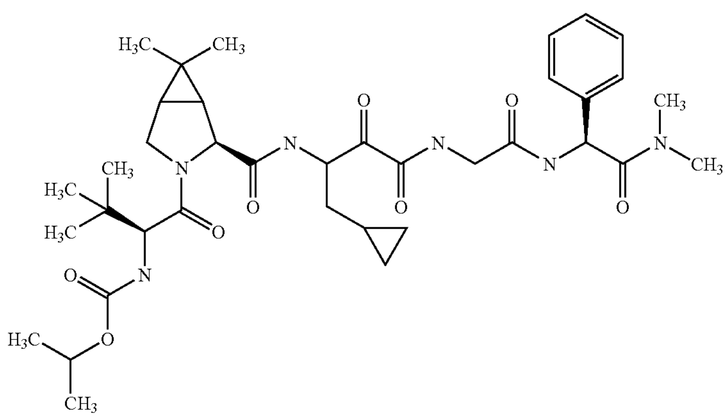 | 711 | A |
| 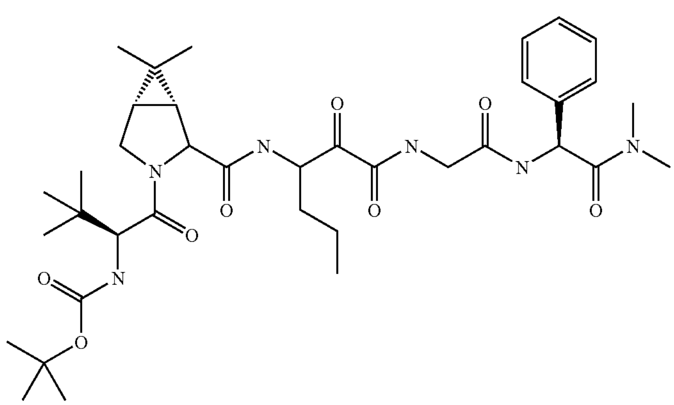 | 713 | A |

TABLE 5-continued

| STRUCTURE | MW | Ki* Range |
|---|---|---|
| 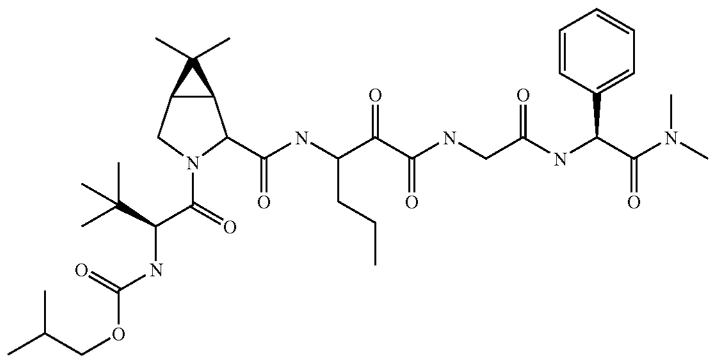 | 713 | A |
| 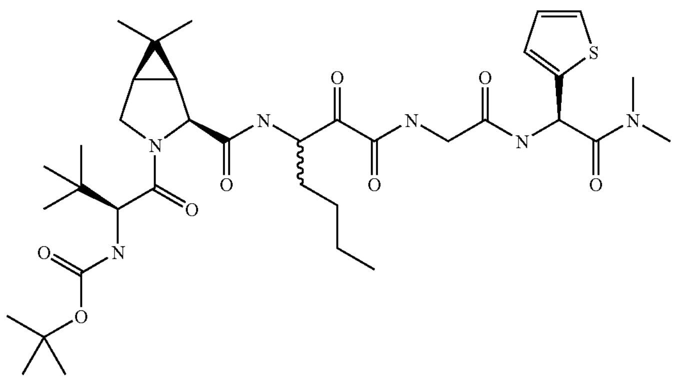 | 732 | A |
| | 733 | A |
| | 733 | A |

TABLE 5-continued

| STRUCTURE | MW | Ki* Range |
|---|---|---|
| 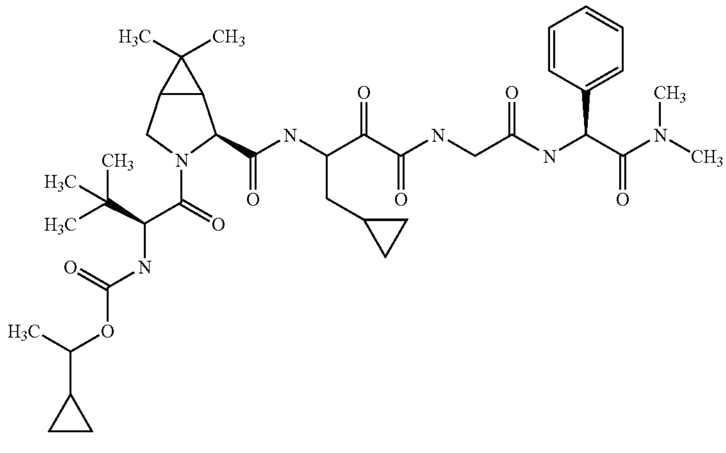 | 737 | A |
| 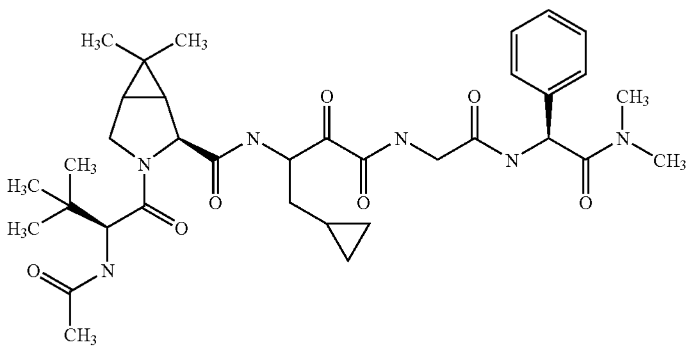 | 667 | A |
| 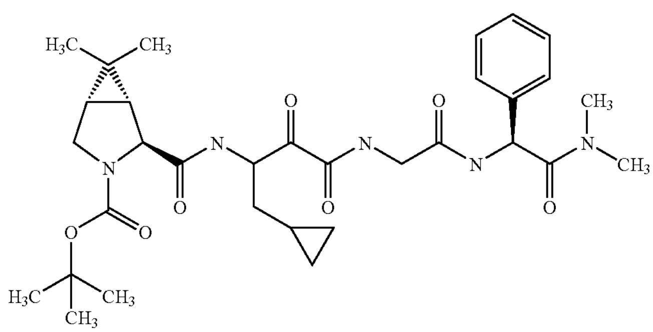 | 612 | C |
| 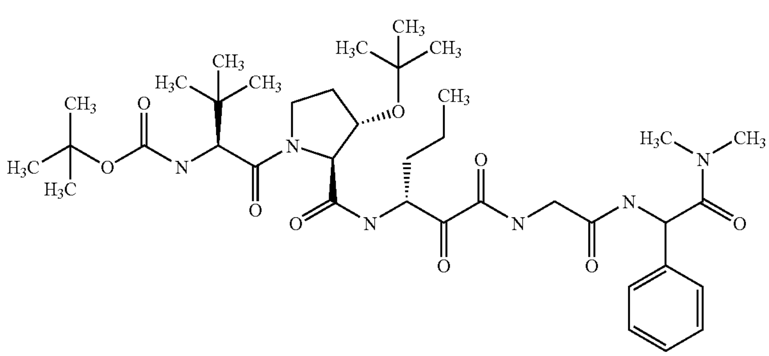 | 745 | C |

TABLE 5-continued
| STRUCTURE | MW | Ki* Range |
|---|---|---|
| 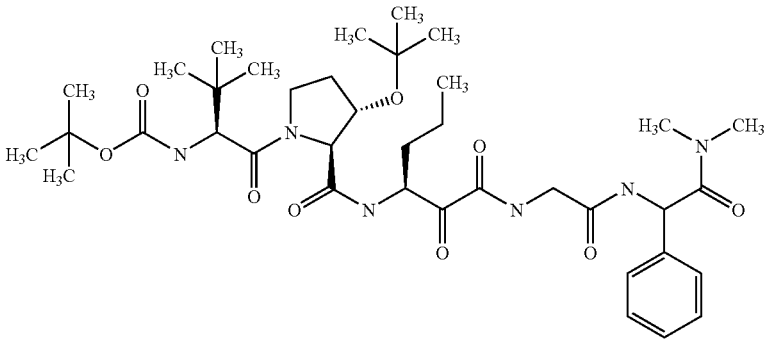 | 745 | C |
| 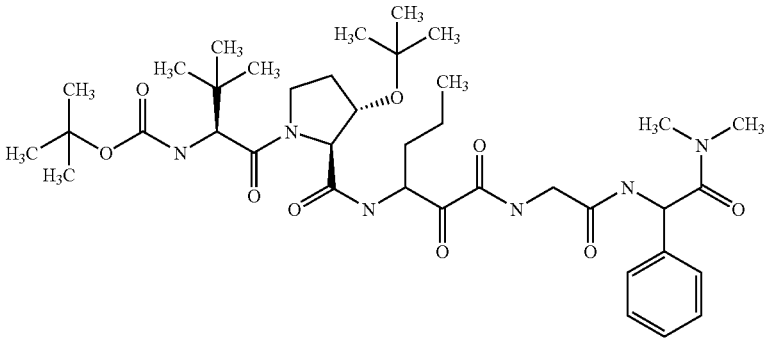 | 745 | C |
| 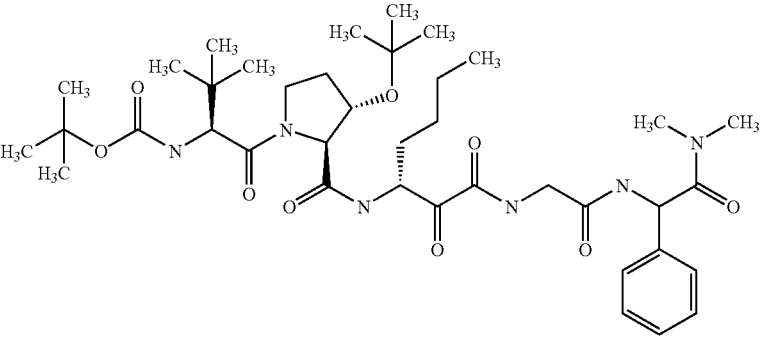 | 759 | C |
| 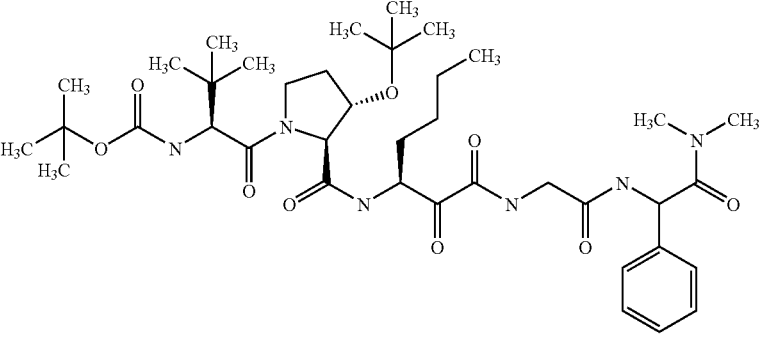 | 759 | C |

TABLE 5-continued

| STRUCTURE | MW | Ki* Range |
|---|---|---|
| 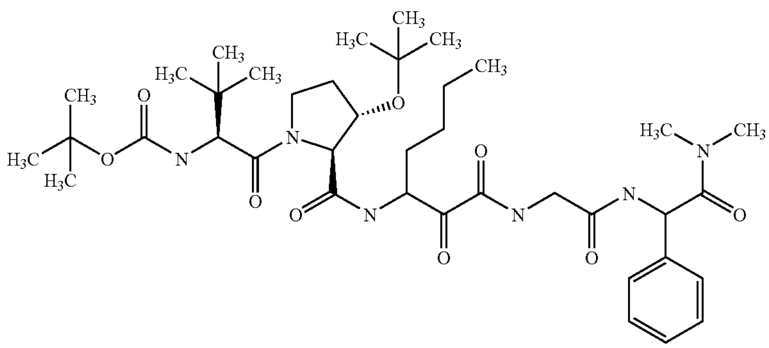 | 759 | C |
| 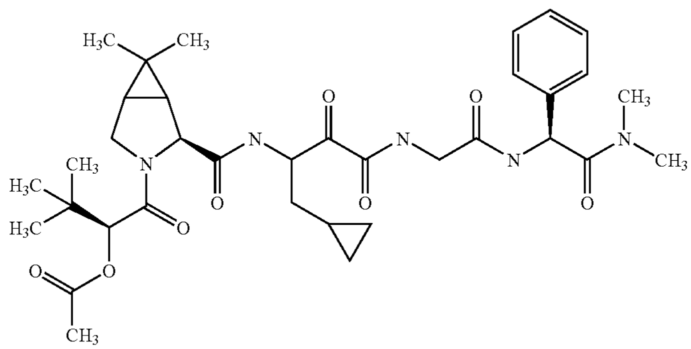 | 668 | C |
| 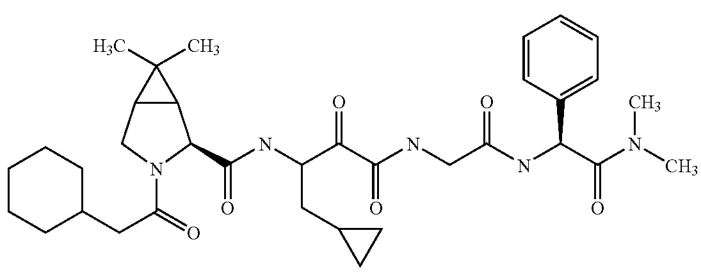 | 636 | B |
| 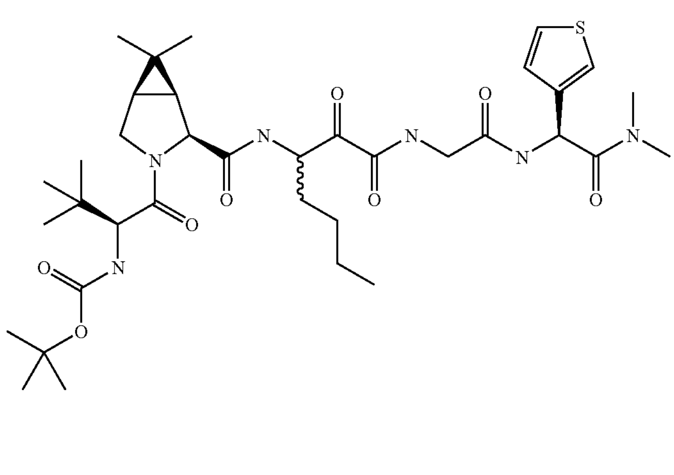 | 733 | A |

TABLE 5-continued

| STRUCTURE | MW | Ki* Range |
|---|---|---|
| 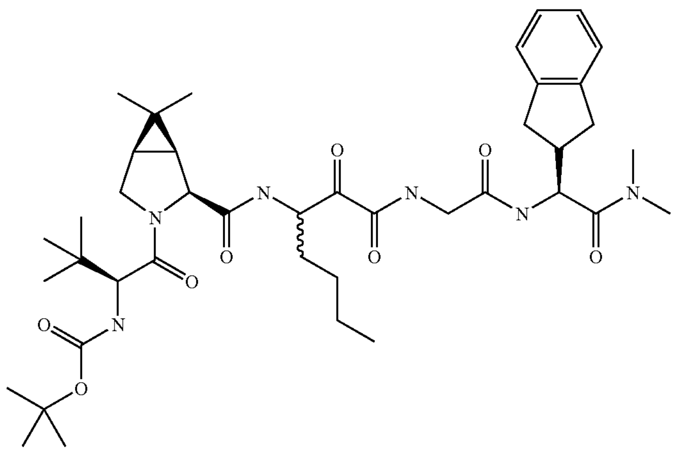 | 767 | B |
| 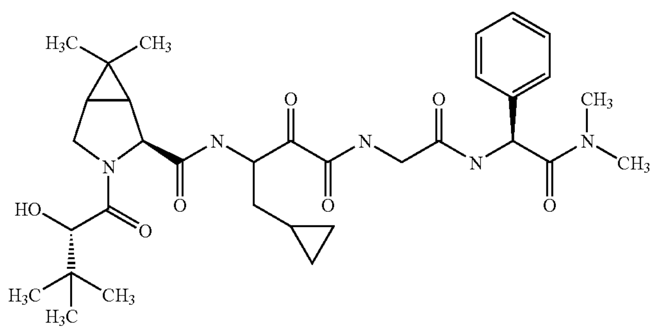 | 626 | B |
| | 715 | C |
| | 715 | A |

TABLE 5-continued

| STRUCTURE | MW | Ki* Range |
|---|---|---|
| 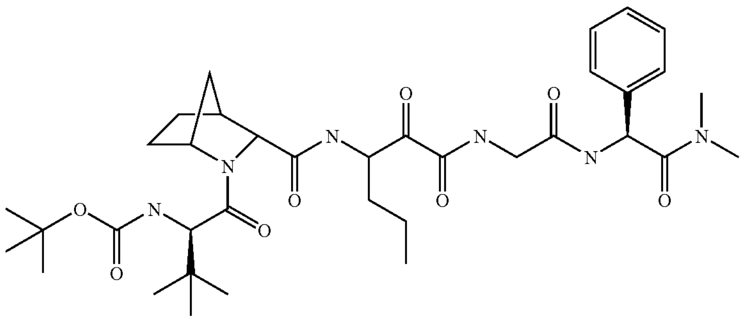 | 699 | B |
| 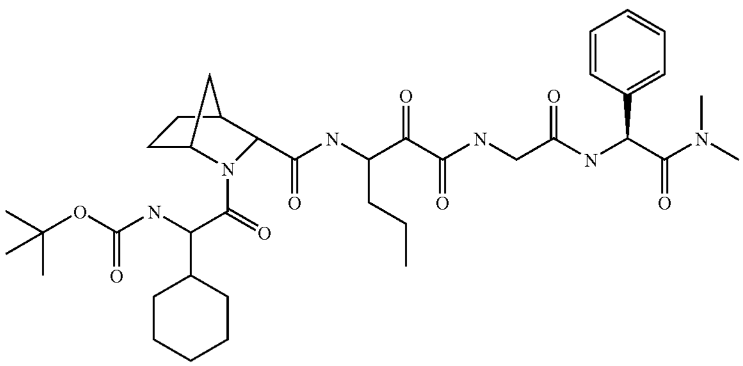 | 725 | A |
| 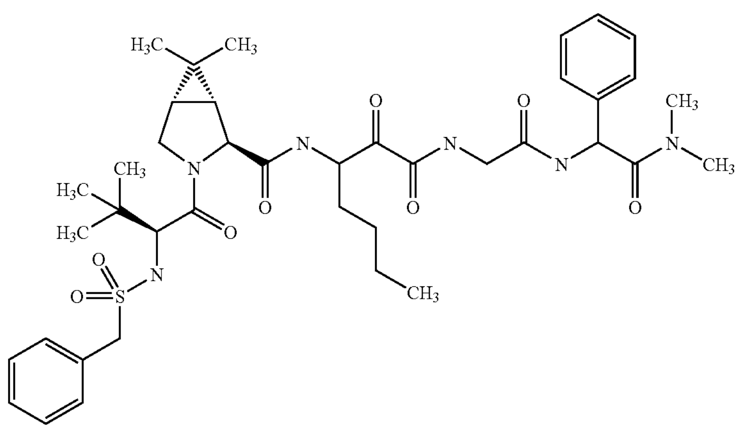 | 781 | B |
| 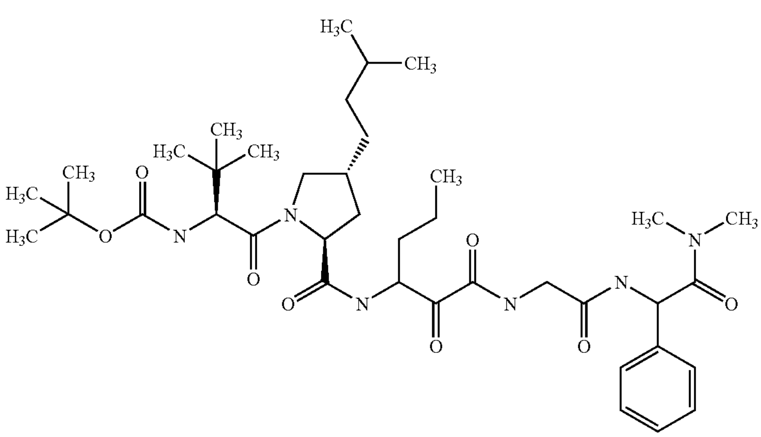 | 743 | B |

TABLE 5-continued
| STRUCTURE | MW | Ki* Range |
|---|---|---|
| 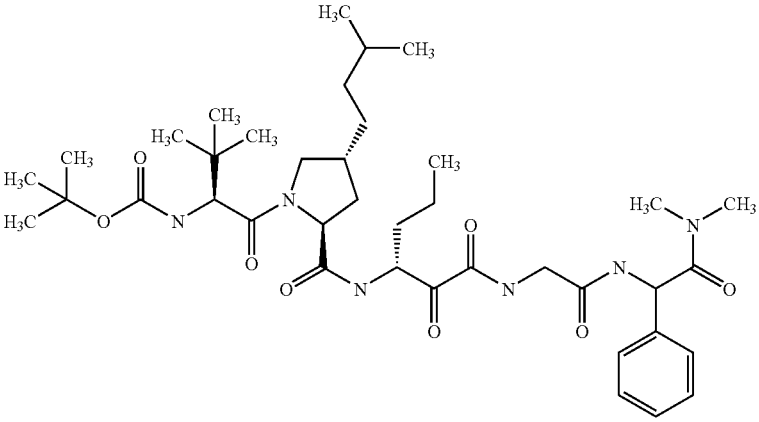 | 743 | C |
| 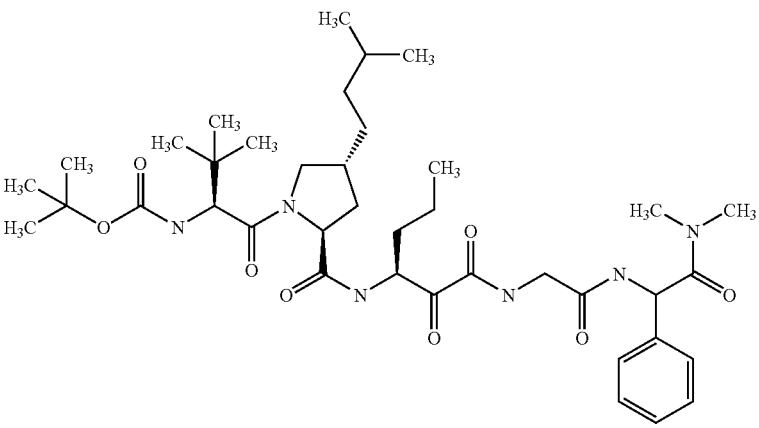 | 743 | A |
| 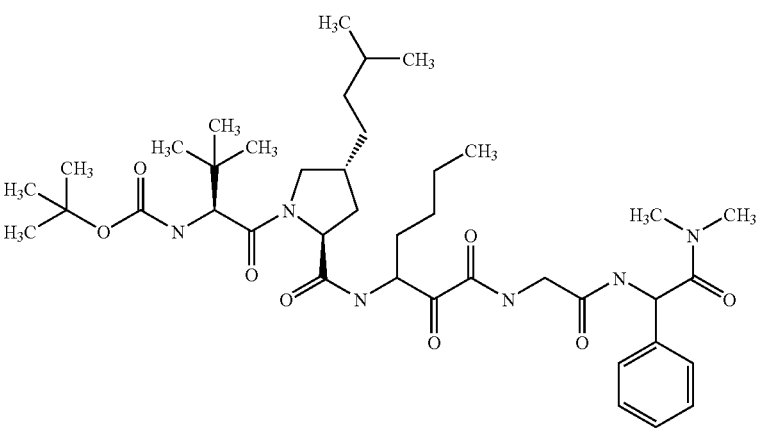 | 757 | B |

TABLE 5-continued
| STRUCTURE | MW | Ki* Range |
|---|---|---|
| 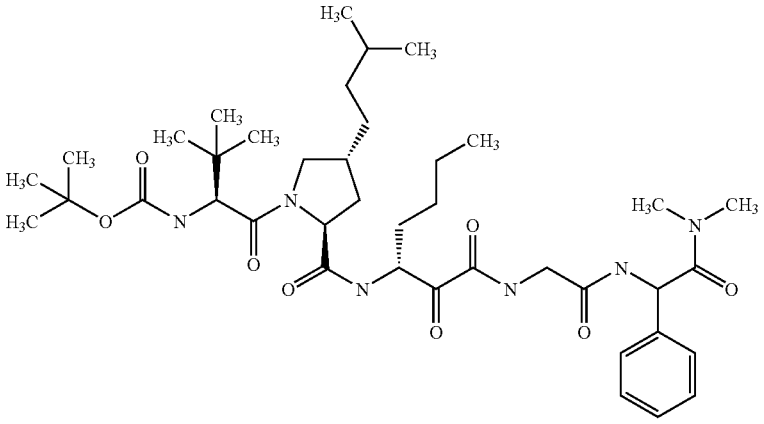 | 757 | C |
| 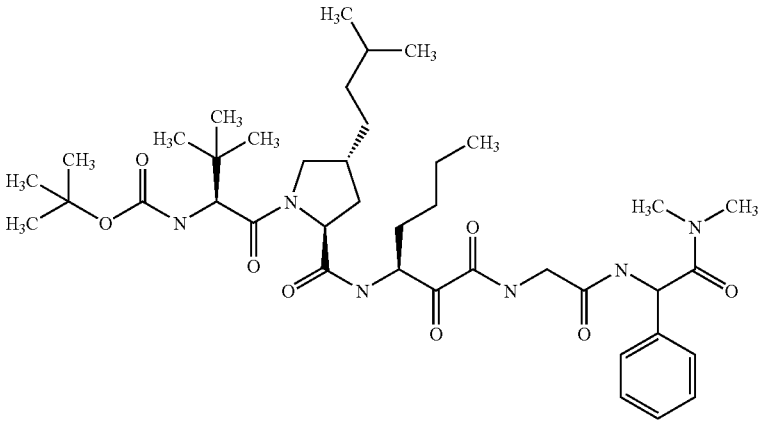 | 757 | B |
| 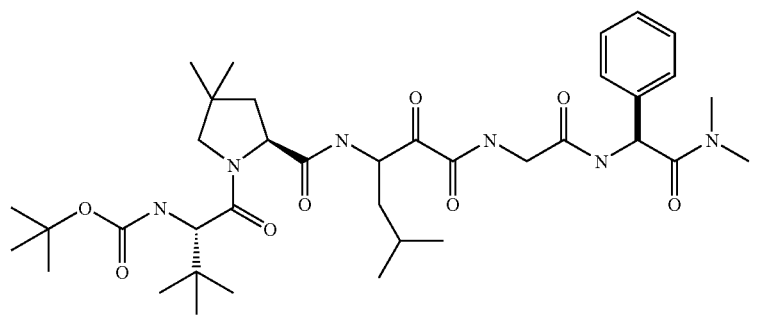 | 715 | A |
| 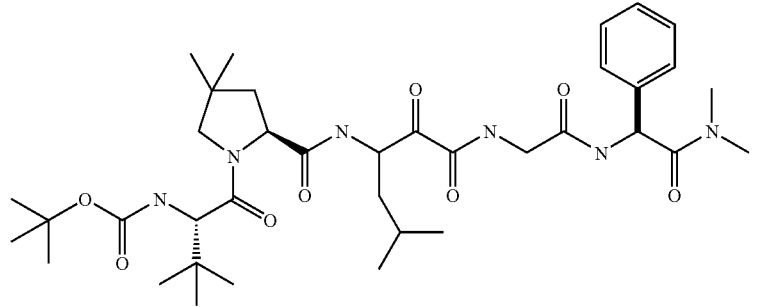 | 715 | A |

TABLE 5-continued
| STRUCTURE | MW | Ki* Range |
|---|---|---|
| 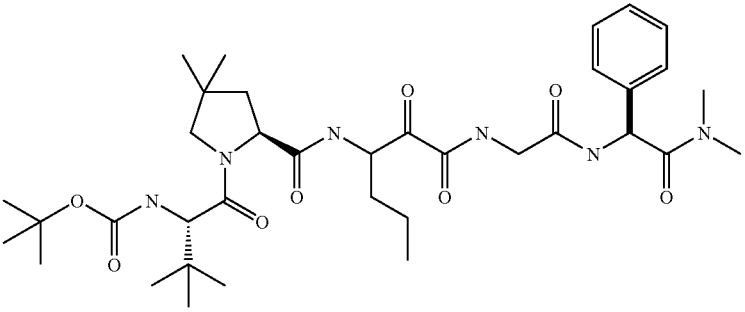 | 701 | A |
| 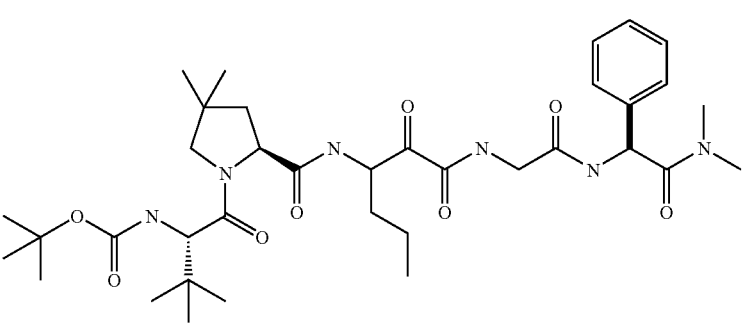 | 701 | A |
| 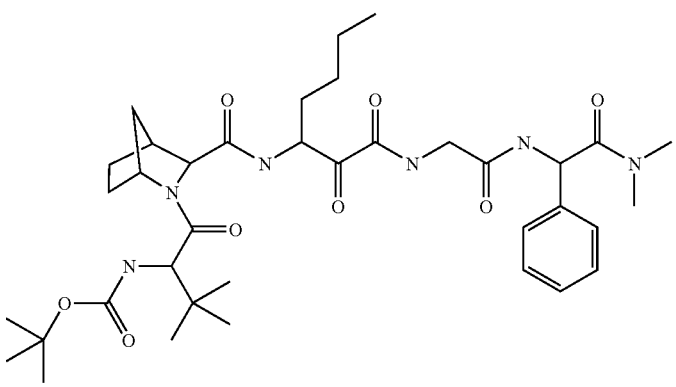 | 713 | A |
| 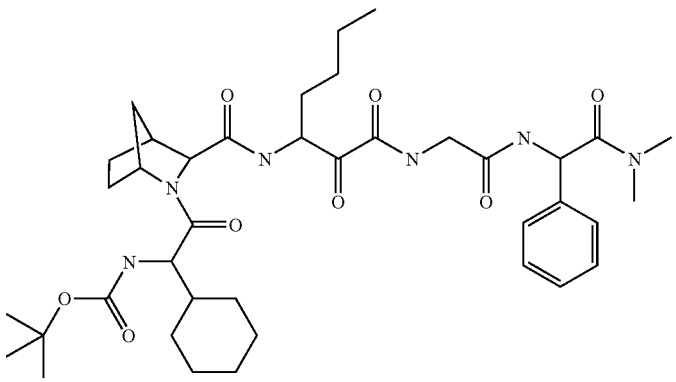 | 739 | A |

TABLE 5-continued

| STRUCTURE | MW | Ki* Range |
|---|---|---|
| 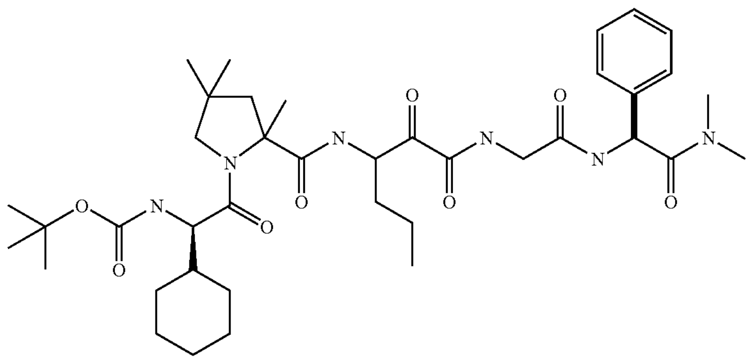 | 741 | C |
| 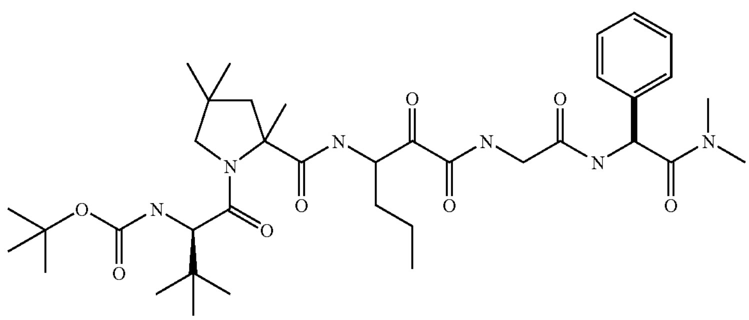 | 715 | C |
| 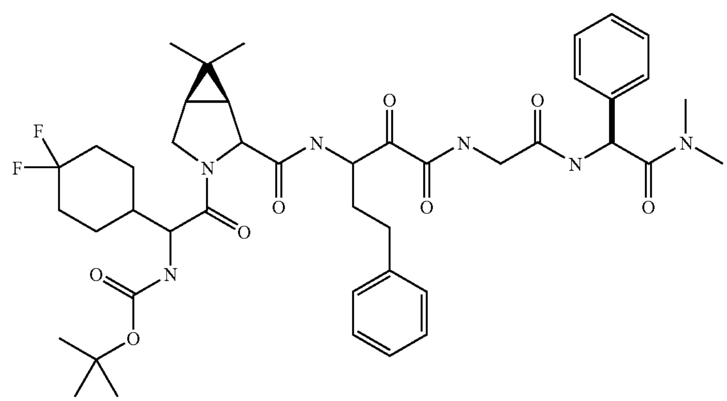 | 837 | B |
| 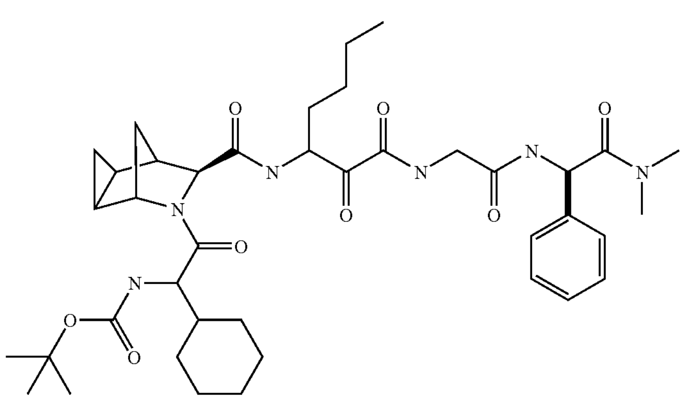 | 751 | A |

TABLE 5-continued

| STRUCTURE | MW | Ki* Range |
|-----------|-----|-----------|
| 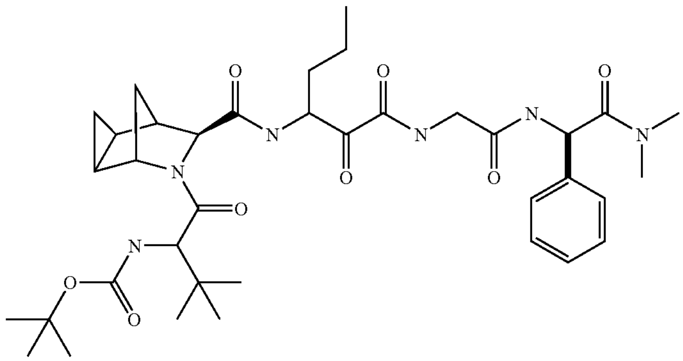 | 725 | C |
| 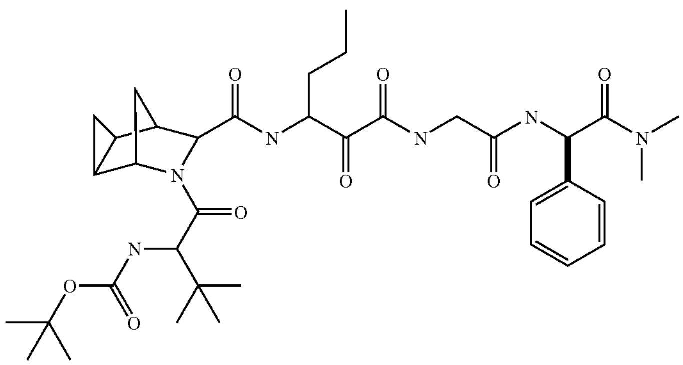 | 711 | C |
| 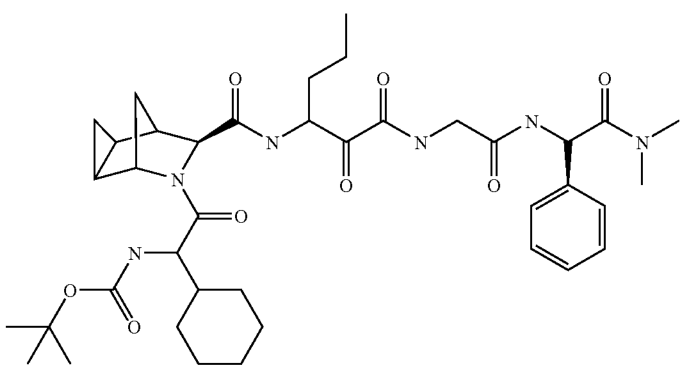 | 737 | A |
| 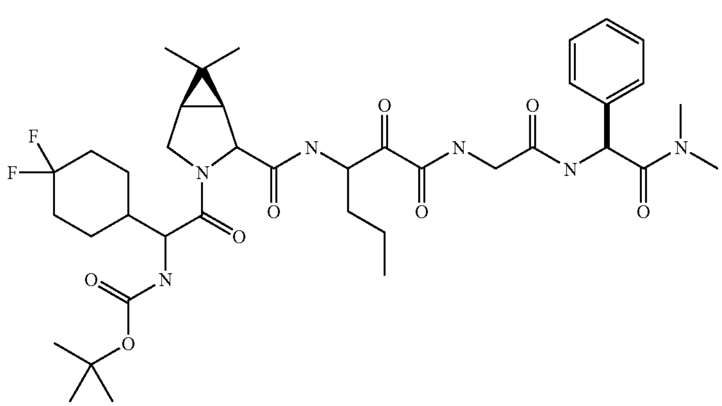 | 775 | A |

TABLE 5-continued

| STRUCTURE | MW | Ki* Range |
|---|---|---|
| | 729 | A |
| | 729 | A |
| 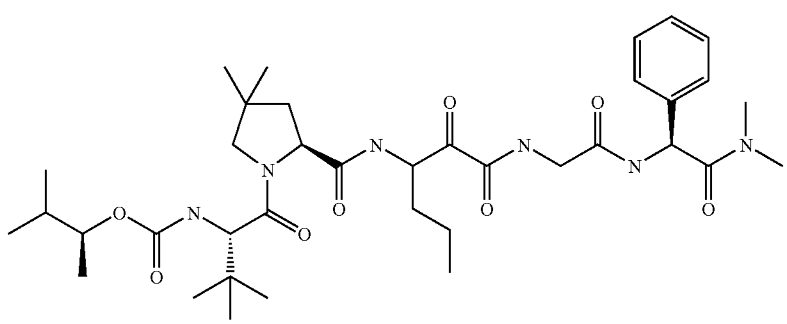 | 715 | A |
| 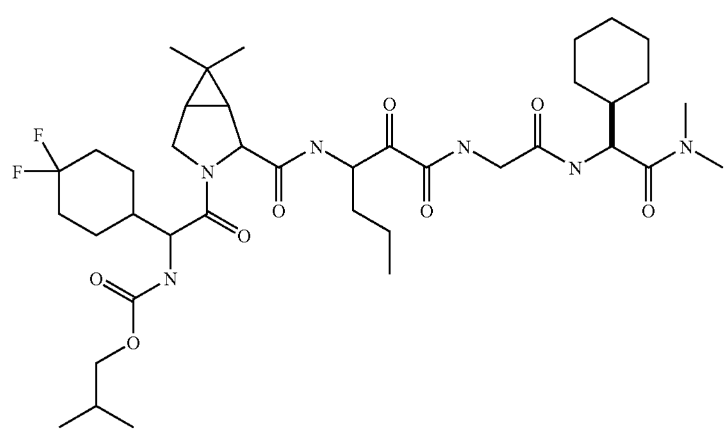 | 775 | A |

TABLE 5-continued
| STRUCTURE | MW | Ki* Range |
|---|---|---|
| 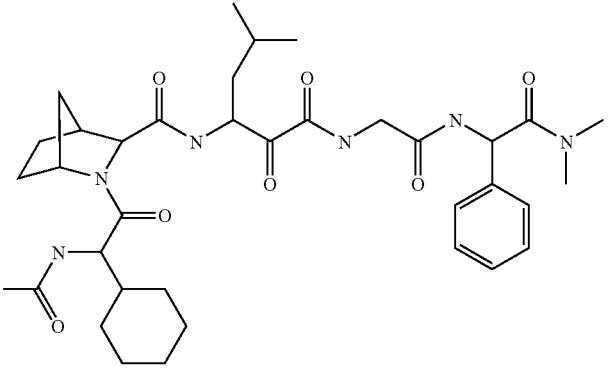 | 739 | A |
| 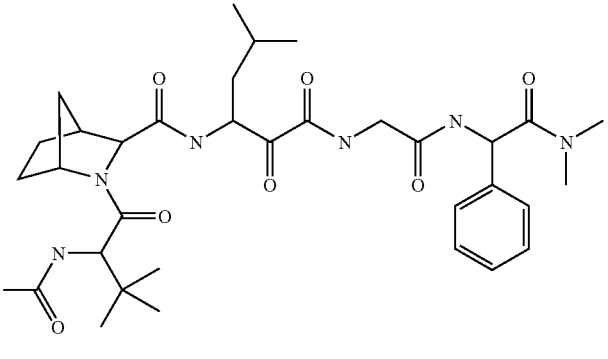 | 713 | A |
| 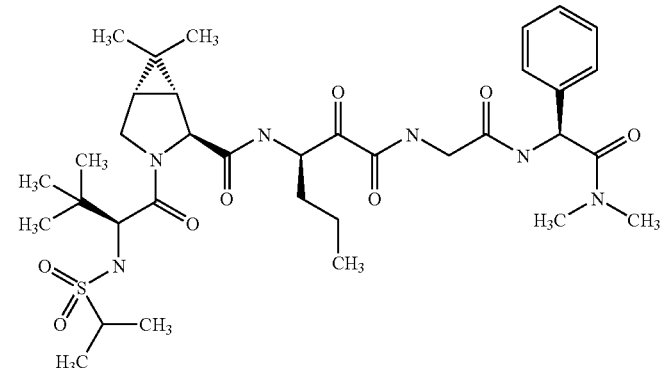 | 719 | A |
| 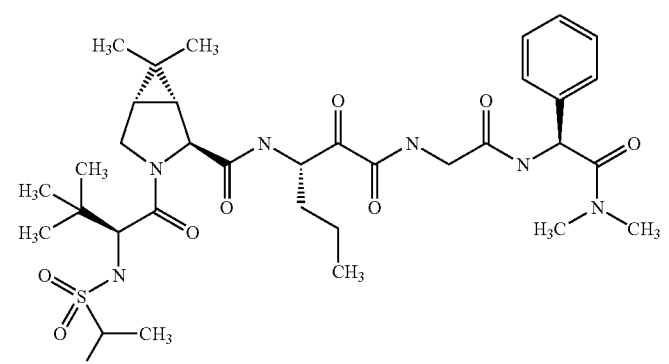 | 719 | A |

TABLE 5-continued

| STRUCTURE | MW | Ki* Range |
|---|---|---|
| 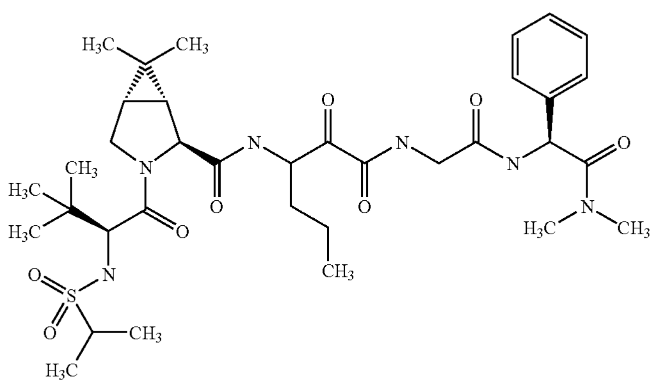 | 719 | A |
| 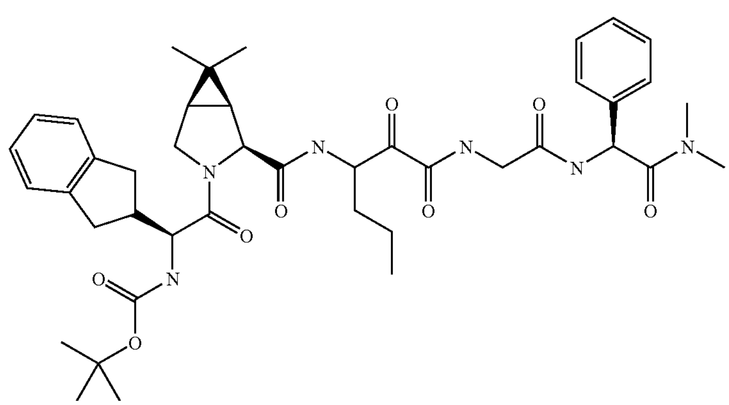 | 773 | A |
| 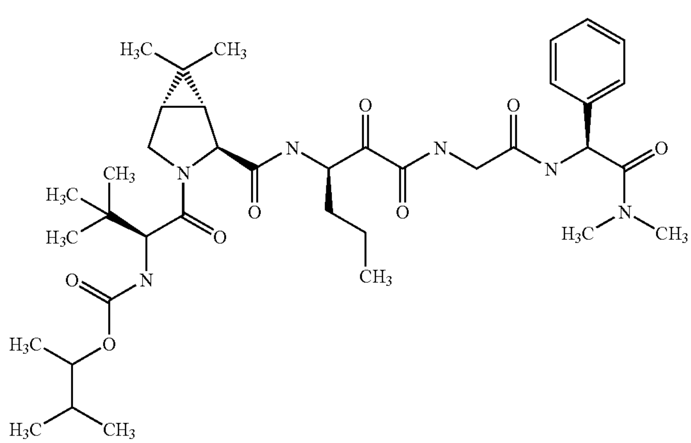 | 727 | A |

TABLE 5-continued

| STRUCTURE | MW | Ki* Range |
|---|---|---|
| | 727 | A |
| | 727 | A |
| 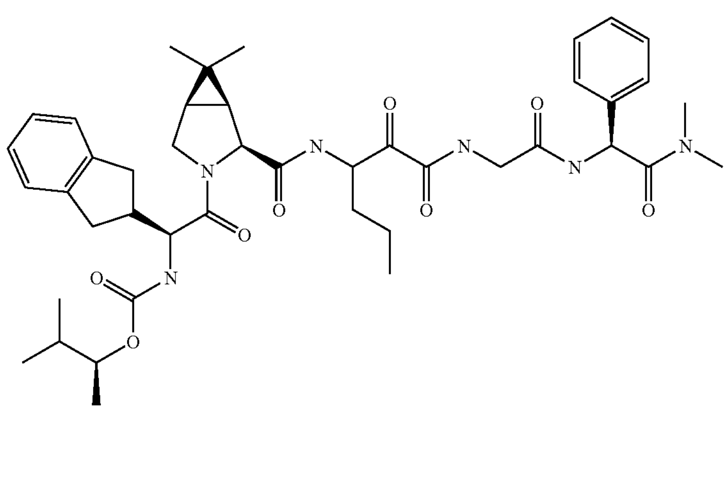 | 787 | A |

TABLE 5-continued

| STRUCTURE | MW | Ki* Range |
|---|---|---|
| 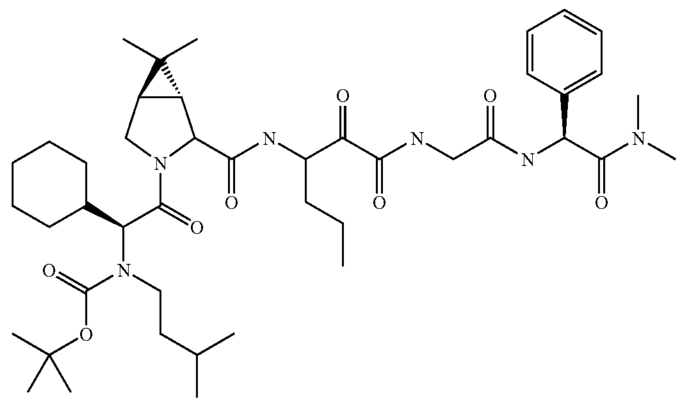 | 809 | C |
| 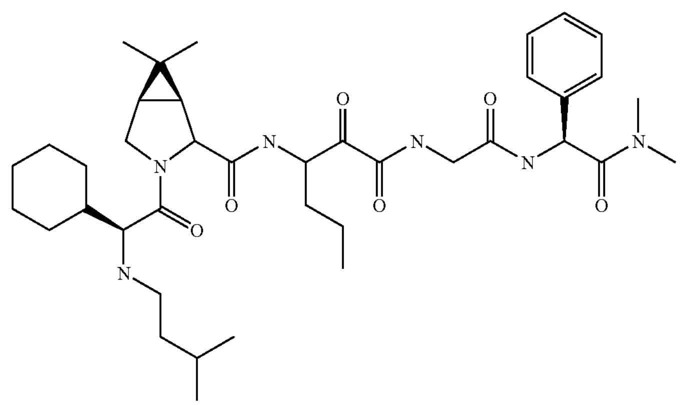 | 709 | A |
| 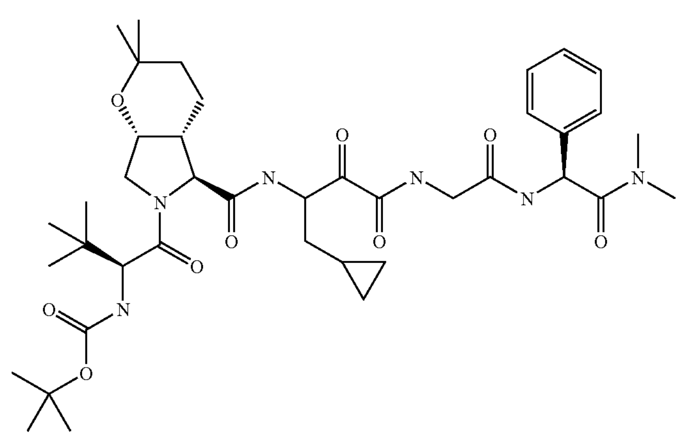 | 769 | B |

TABLE 5-continued
| STRUCTURE | MW | Ki* Range |
|---|---|---|
| 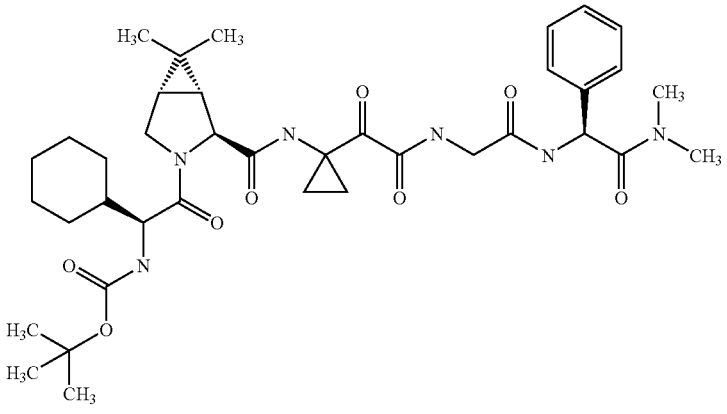 | 723 | C |
| 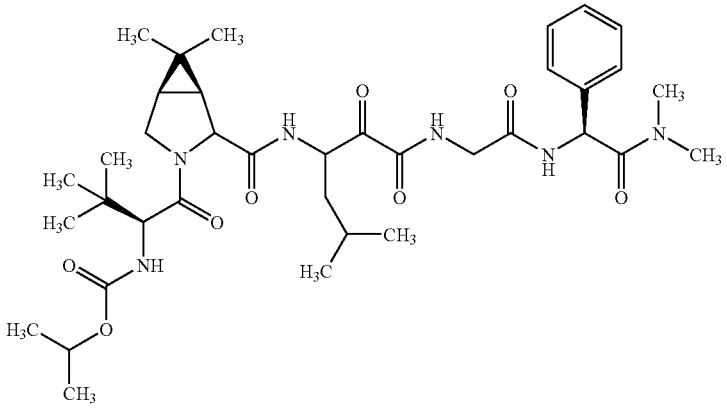 | 713 | A |
| 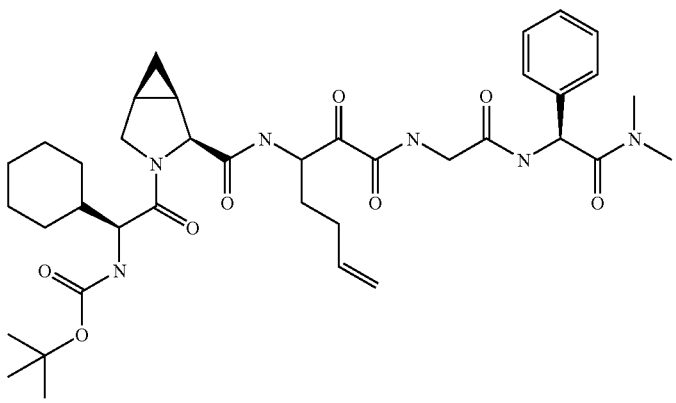 | 723 | A |

TABLE 5-continued

| STRUCTURE | MW | Ki* Range |
|---|---|---|
| 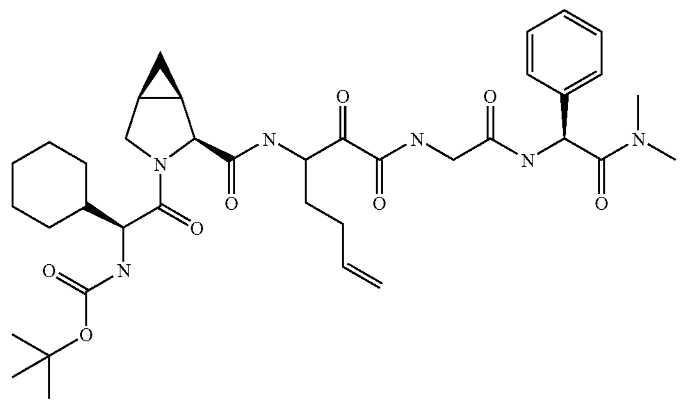 | 723 | B |
| 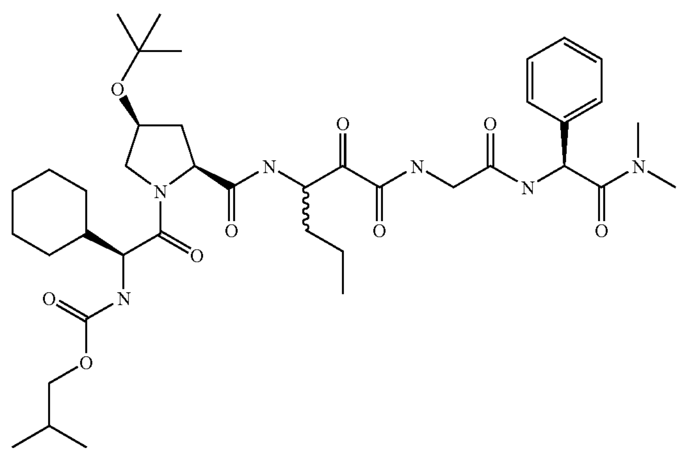 | 771 | C |
| 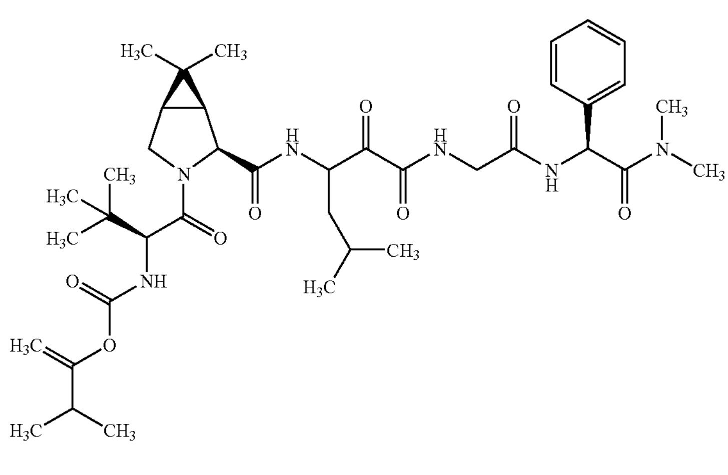 | 741 | A |

TABLE 5-continued

| STRUCTURE | MW | Ki* Range |
|---|---|---|
| 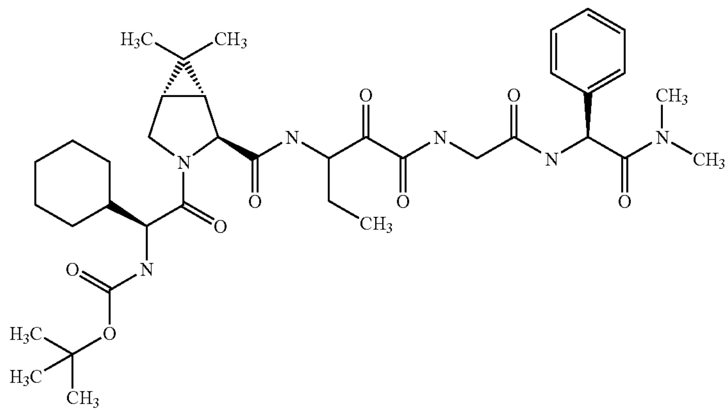 | 725 | A |
| 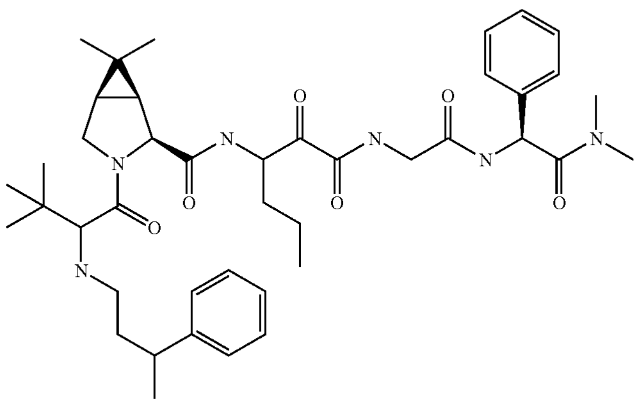 | 745 | A |
| 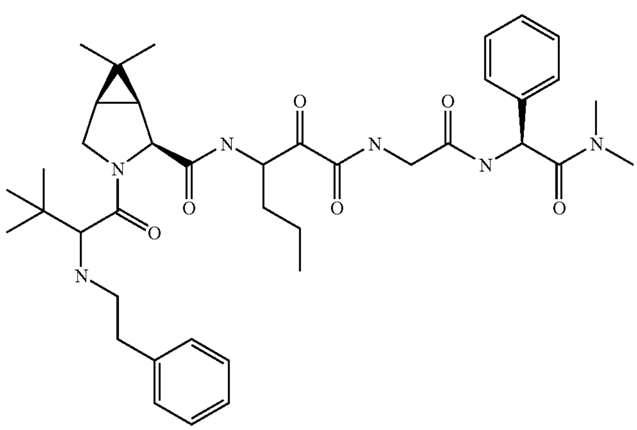 | 716 | A |

TABLE 5-continued

| STRUCTURE | MW | Ki* Range |
|---|---|---|
| 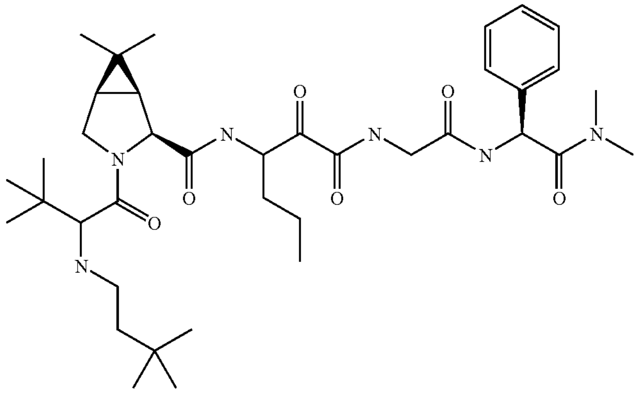 | 733 | A |
| 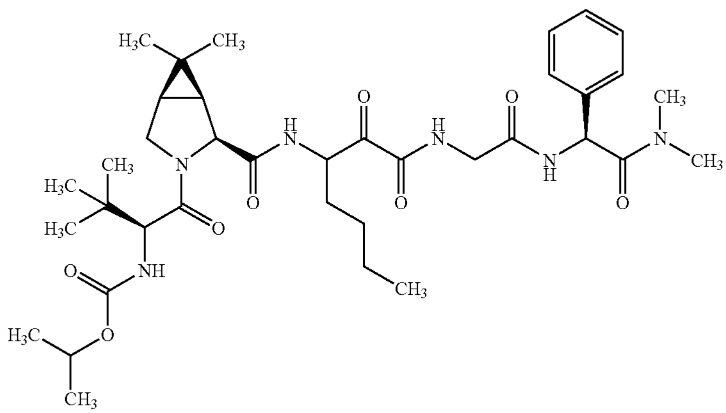 | 713 | A |
| 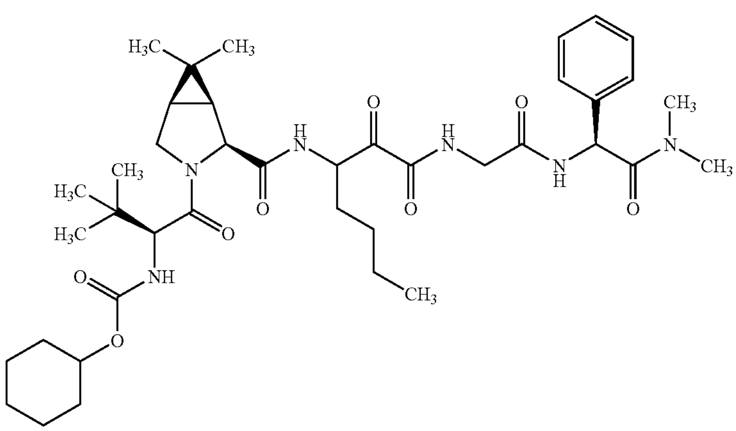 | 753 | A |

TABLE 5-continued

| STRUCTURE | MW | Ki* Range |
|---|---|---|
| 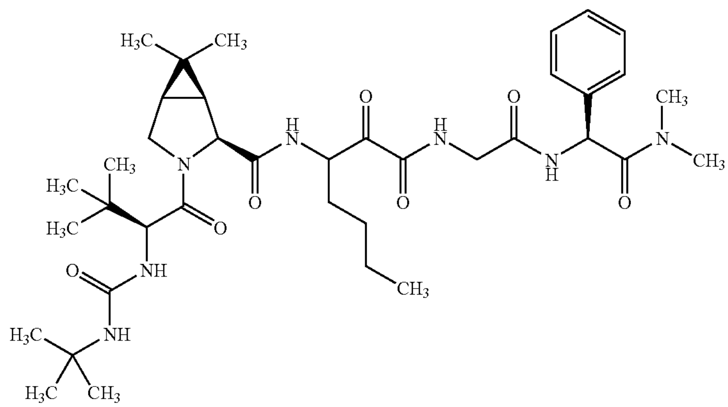 | 726 | A |
| 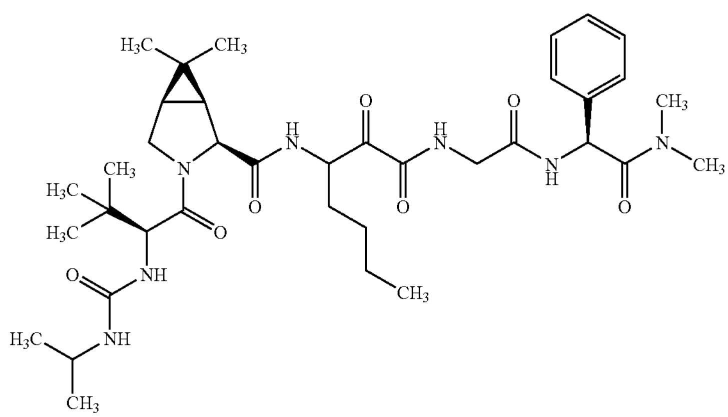 | 712 | A |
| 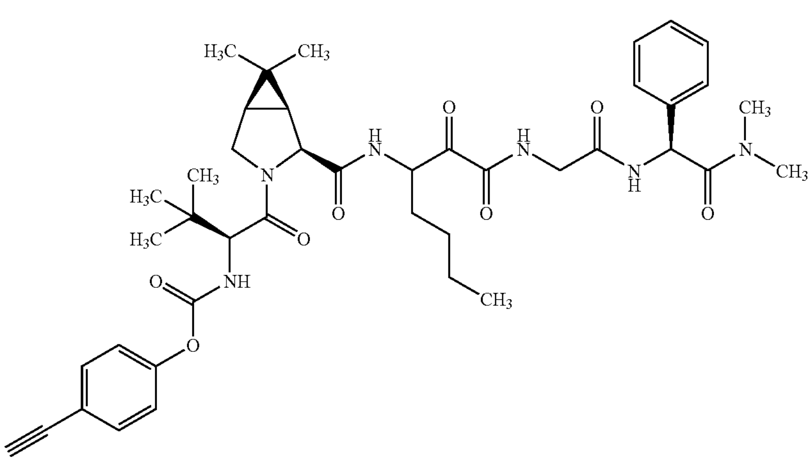 | 771 | B |

TABLE 5-continued

| STRUCTURE | MW | Ki* Range |
|---|---|---|
| 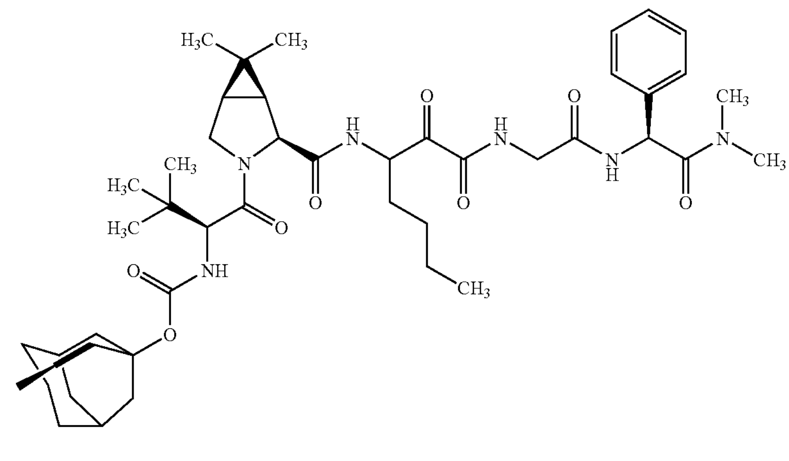 | 804 | A |
| 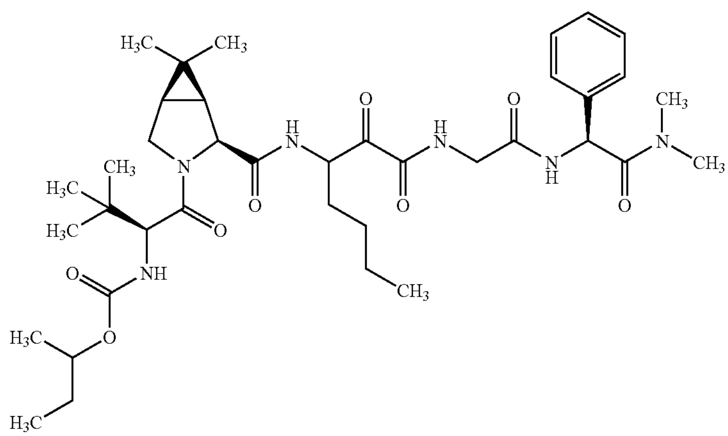 | 726 | A |
| 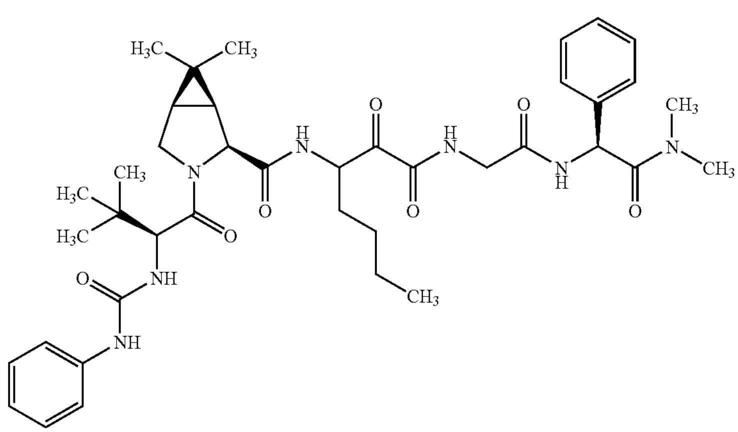 | 746 | A |

TABLE 5-continued

| STRUCTURE | MW | Ki* Range |
|---|---|---|
| 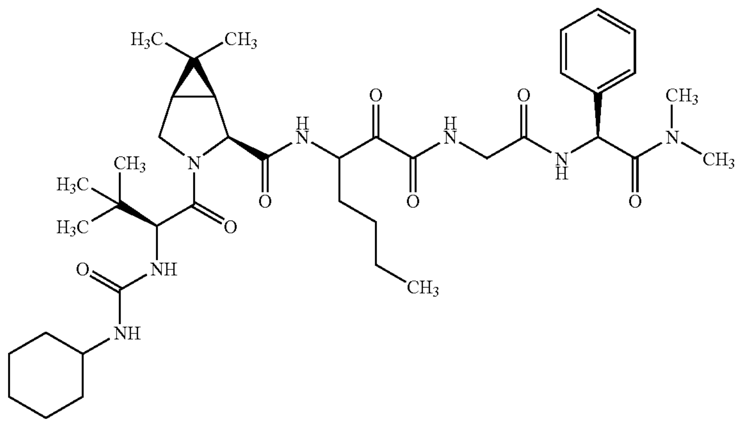 | 752 | A |
| 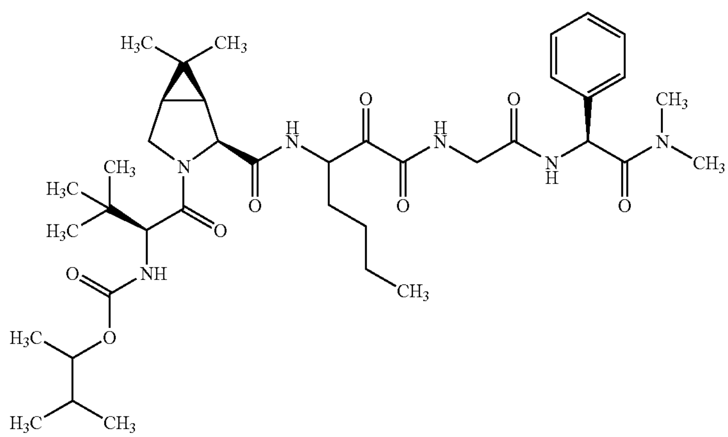 | 741 | A |
| 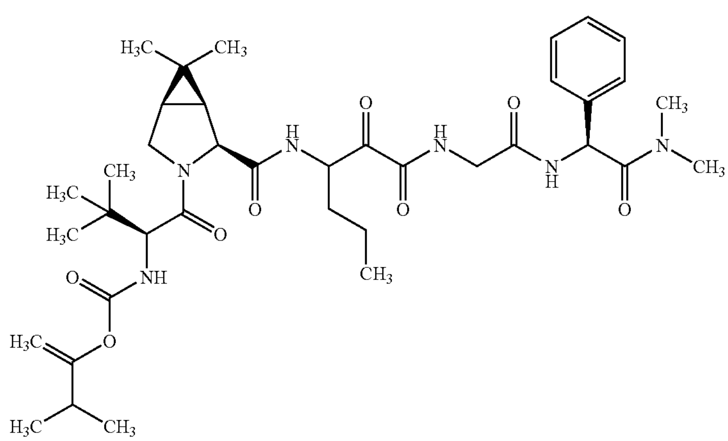 | 727 | A |

TABLE 5-continued

| STRUCTURE | MW | Ki* Range |
|---|---|---|
| 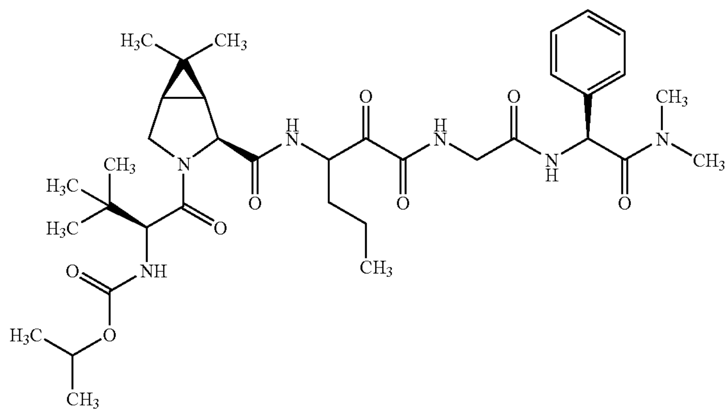 | 699 | A |
| 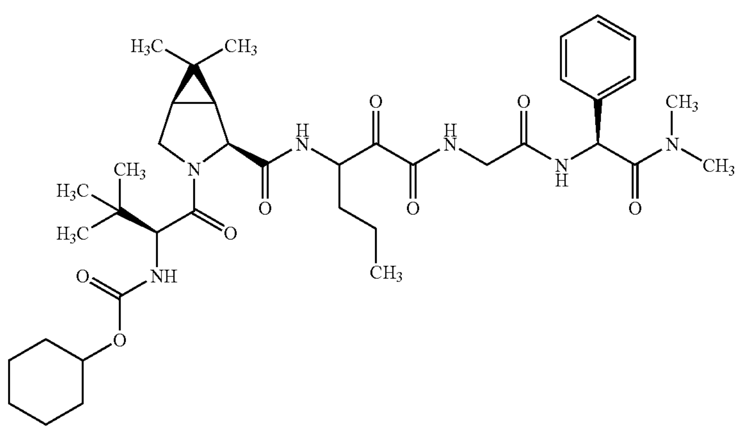 | 739 | A |
| 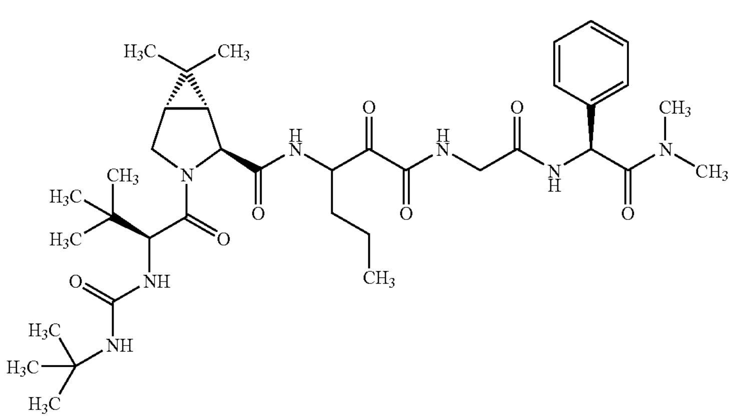 | 712 | A |

TABLE 5-continued

| STRUCTURE | MW | Ki* Range |
|---|---|---|
| 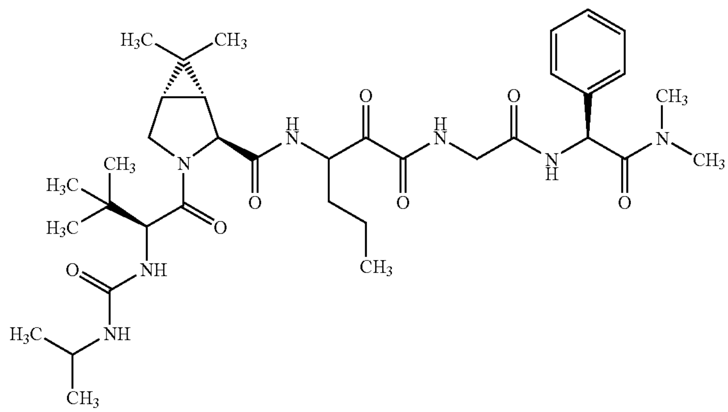 | 698 | A |
| 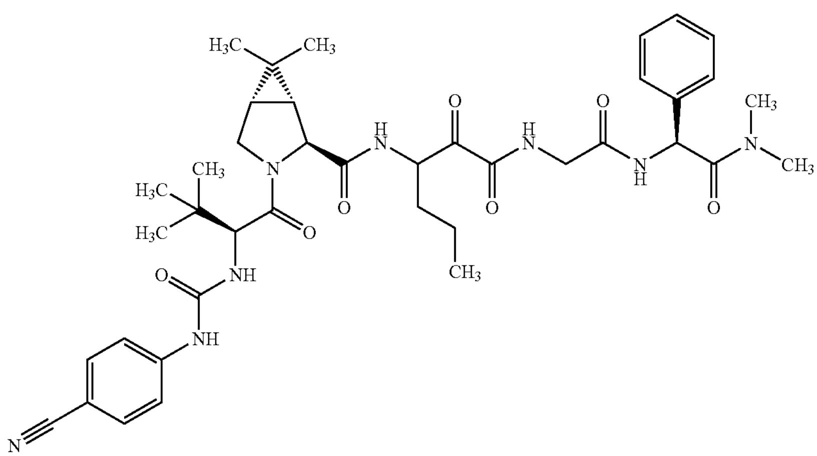 | 757 | B |
| 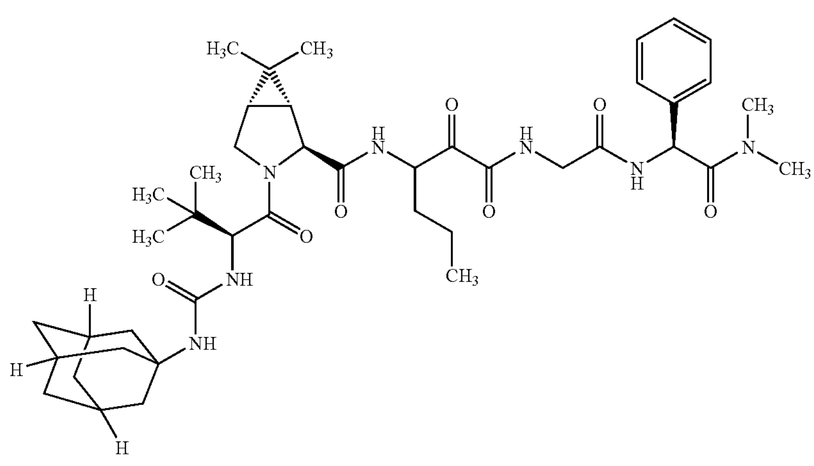 | 790 | A |

TABLE 5-continued

| STRUCTURE | MW | Ki* Range |
|---|---|---|
| 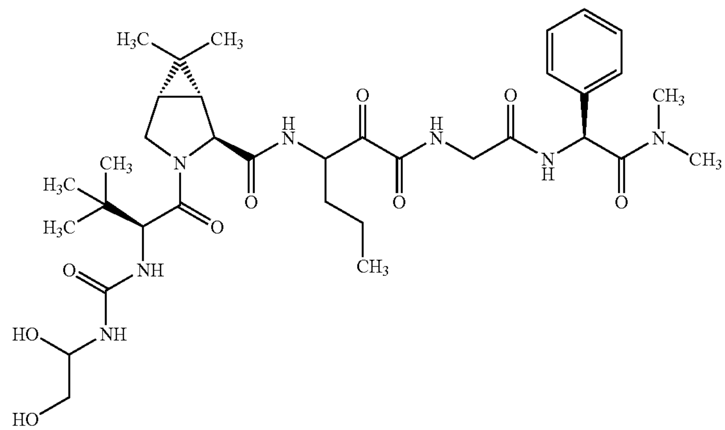 | 712 | A |
| 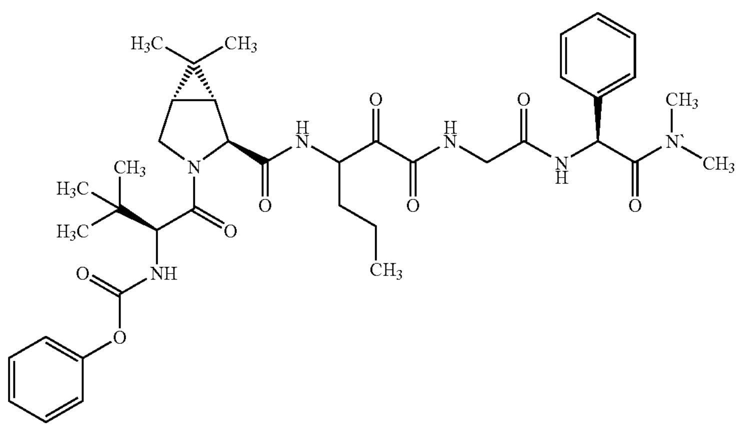 | 732 | A |
| 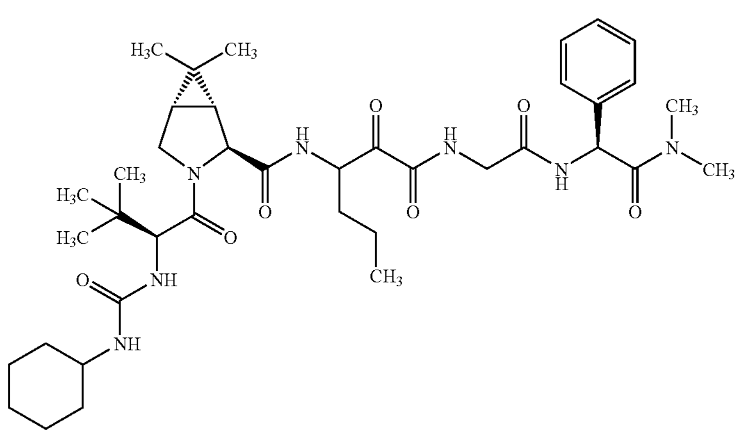 | 738 | A |

TABLE 5-continued

| STRUCTURE | MW | Ki* Range |
|---|---|---|
| 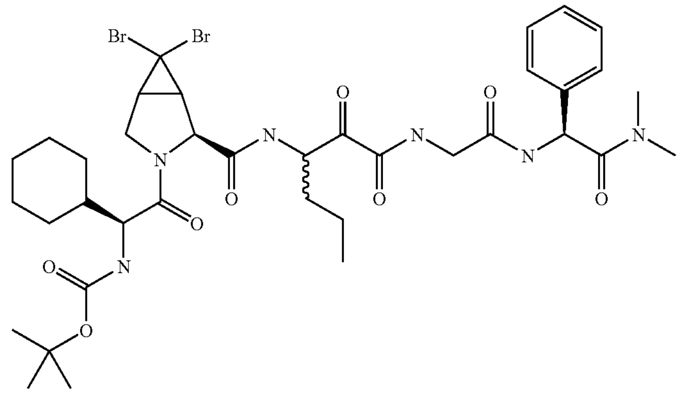 | 869 | A |
| | 785 | A |
| | 785 | A |
| | 785 | A |

TABLE 5-continued

| STRUCTURE | MW | Ki* Range |
|---|---|---|
| 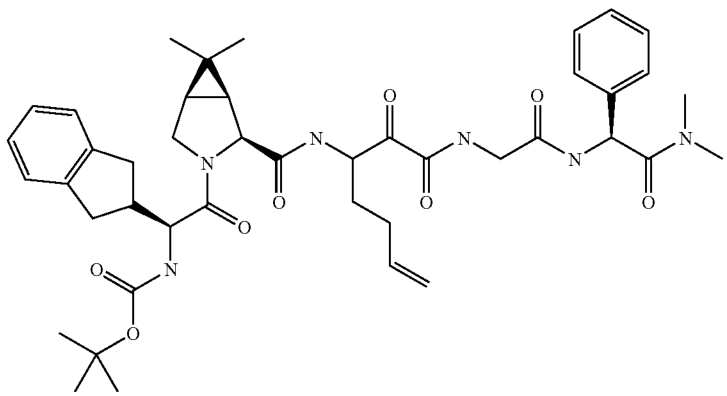 | 785 | A |
| 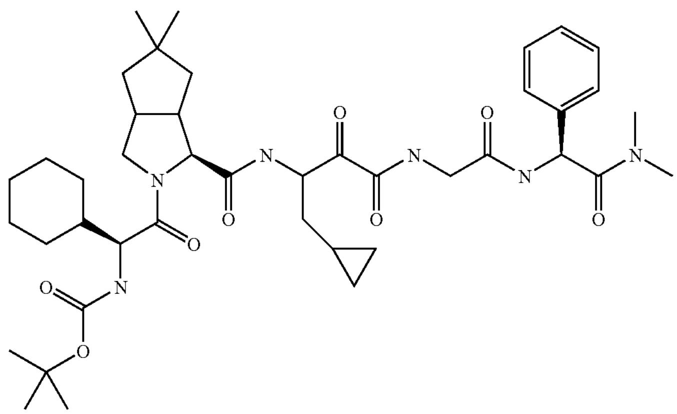 | 781 | A |
| 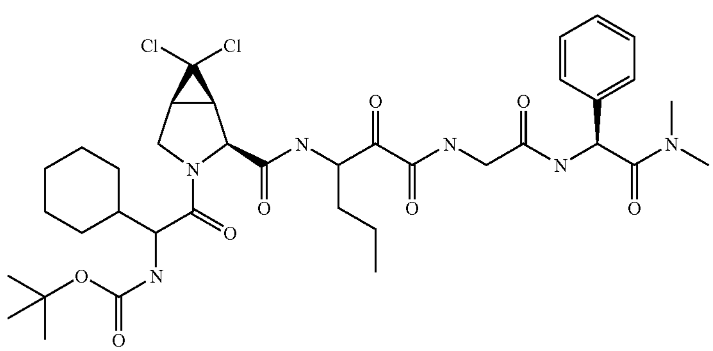 | 780 | A |
| 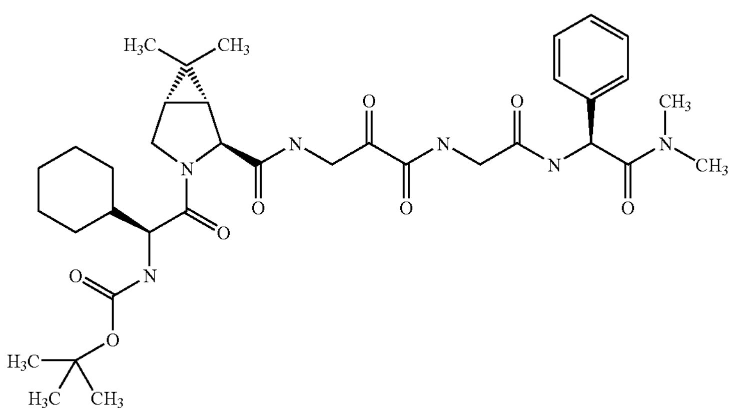 | 697 | C |

TABLE 5-continued

| STRUCTURE | MW | Ki* Range |
|---|---|---|
| 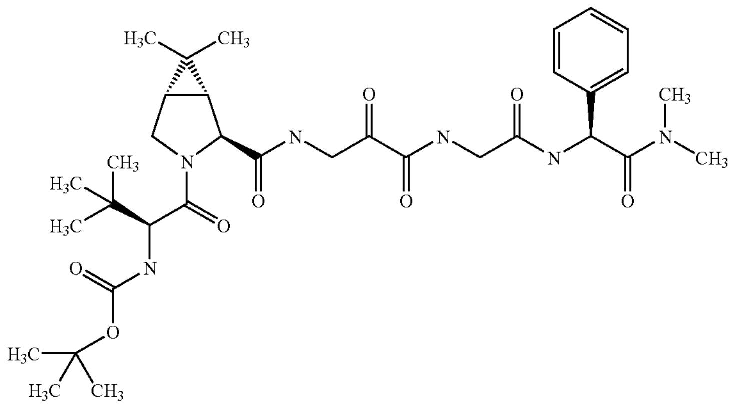 | 671 | C |
| 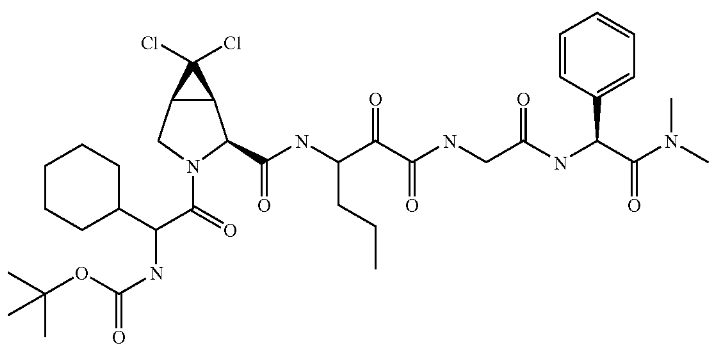 | 780 | A |
| 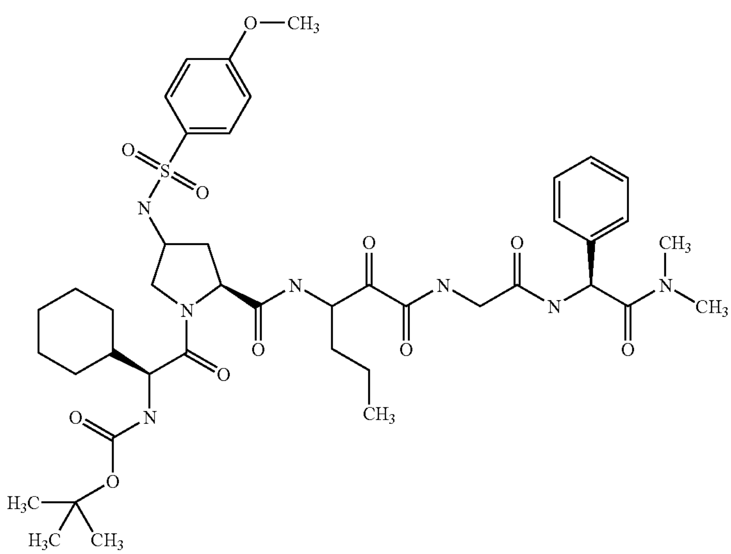 | 884 | A |

TABLE 5-continued
| STRUCTURE | MW | Ki* Range |
|---|---|---|
| 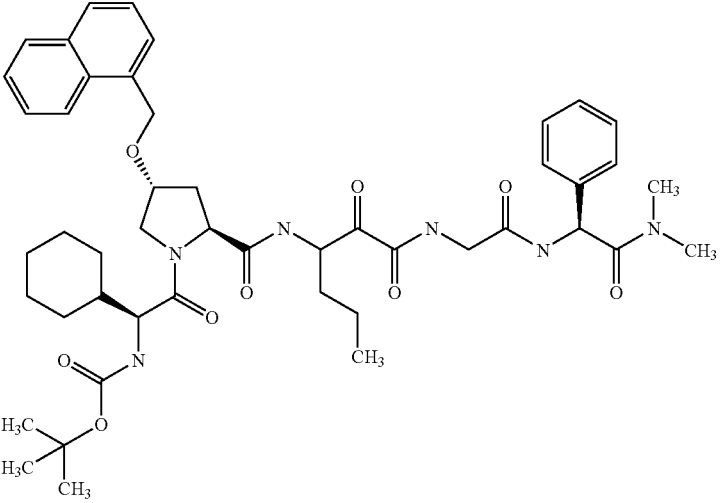 | 855 | A |
| 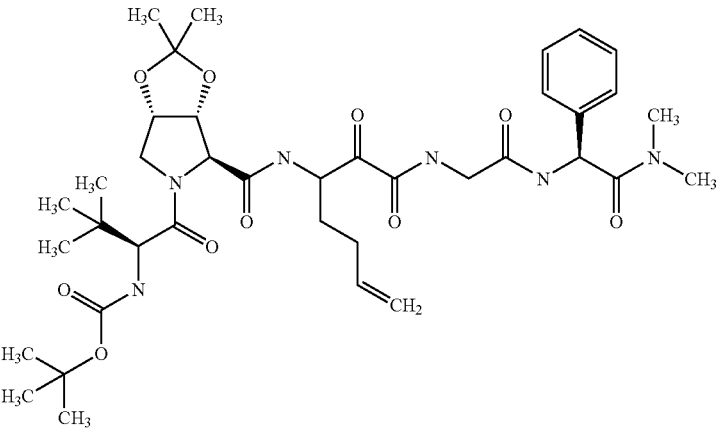 | 757 | B |
| 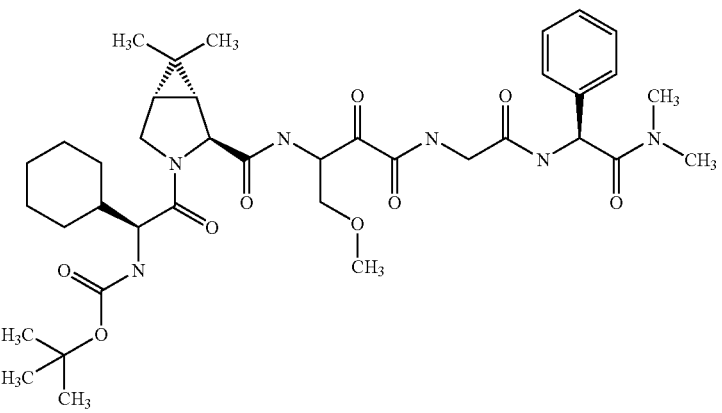 | 741 | B |

TABLE 5-continued

| STRUCTURE | MW | Ki* Range |
|---|---|---|
| 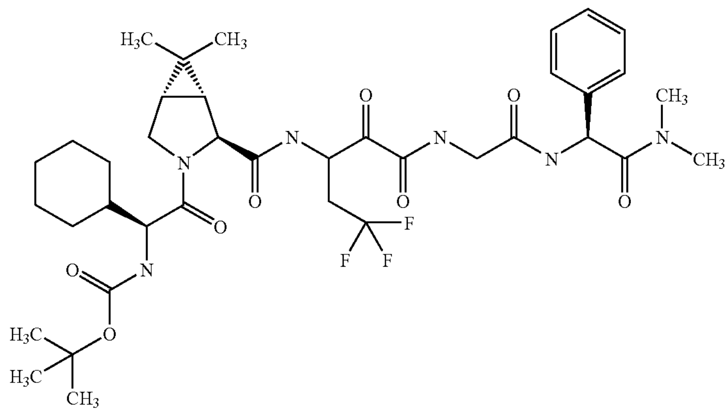 | 779 | B |
| 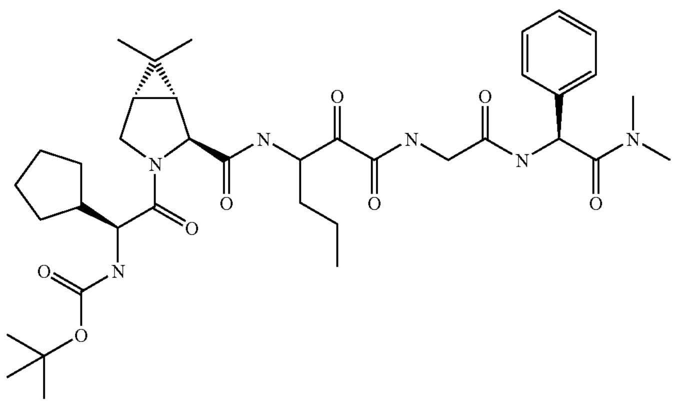 | 725 | A |
| 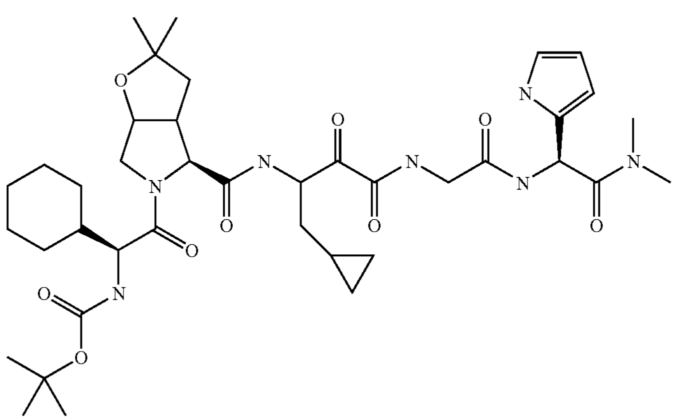 | 787 | A |

TABLE 5-continued

| STRUCTURE | MW | Ki* Range |
|---|---|---|
| 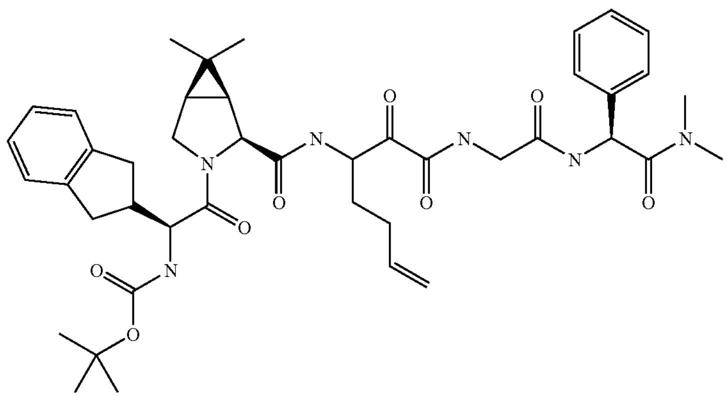 | 785 | A |
| | 737 | A |
| | 737 | A |
| 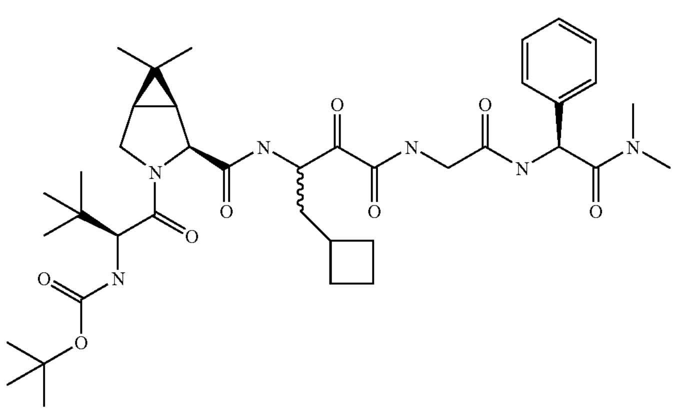 | 739 | A |

TABLE 5-continued

| STRUCTURE | MW | Ki* Range |
|---|---|---|
| 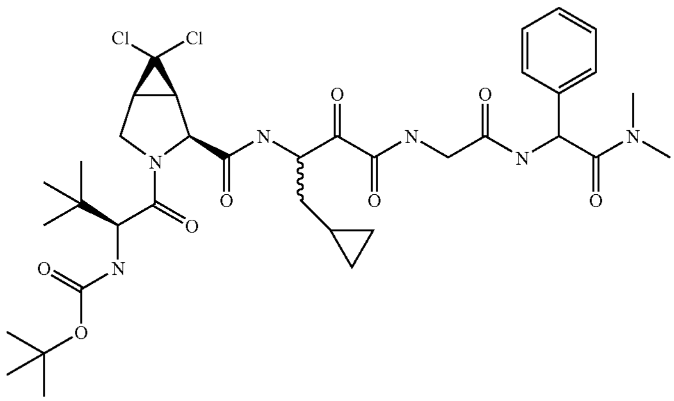 | 855 | A |
| 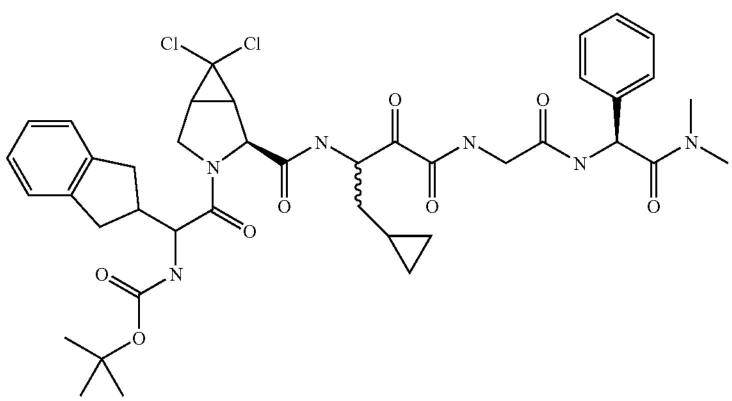 | 826 | A |
| 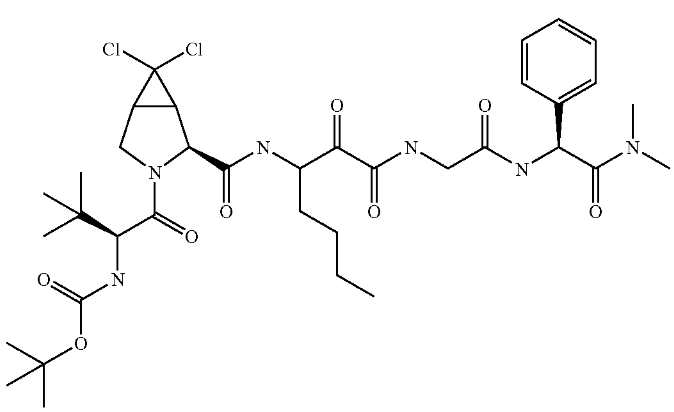 | 857 | A |

TABLE 5-continued

| STRUCTURE | MW | Ki* Range |
|---|---|---|
| 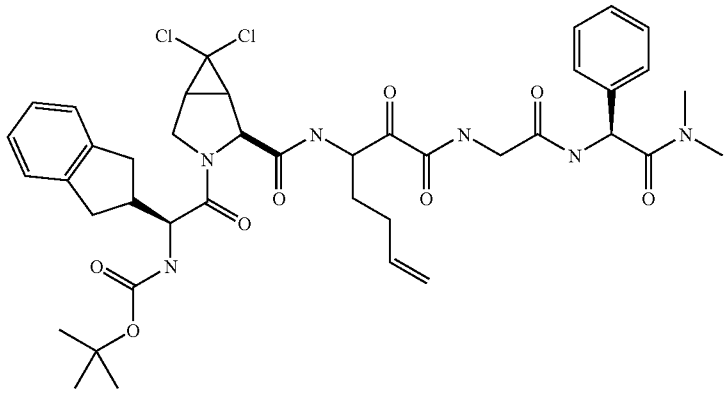 | 826 | A |
| 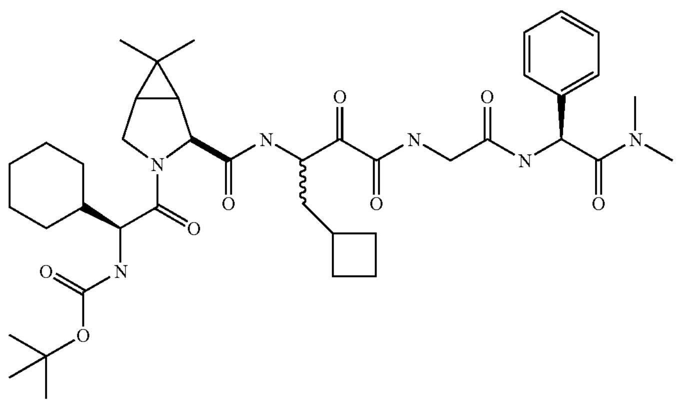 | 765 | A |
| 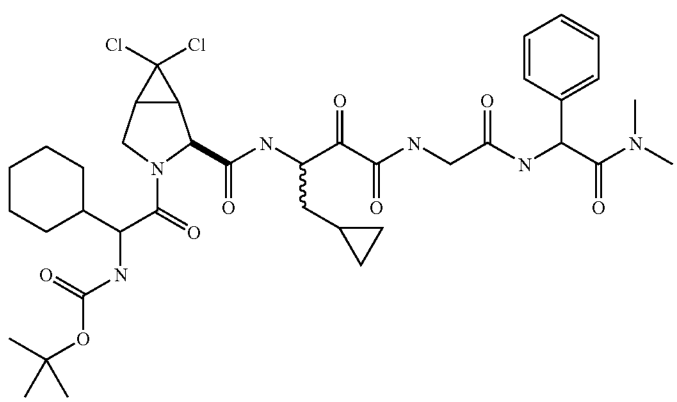 | 792 | A |
| 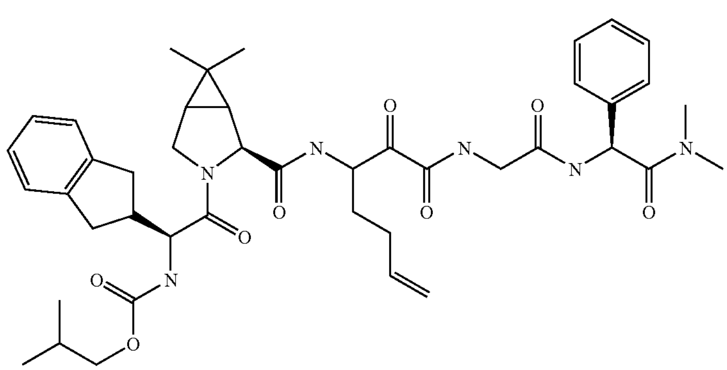 | 799 | A |

TABLE 5-continued

| STRUCTURE | MW | Ki* Range |
|---|---|---|
| 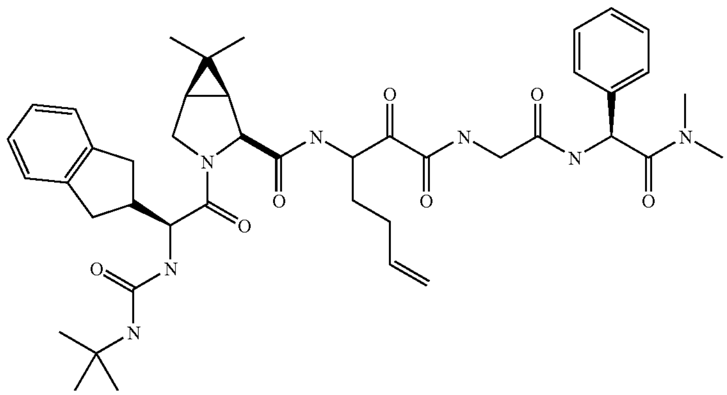 | 784 | A |
| 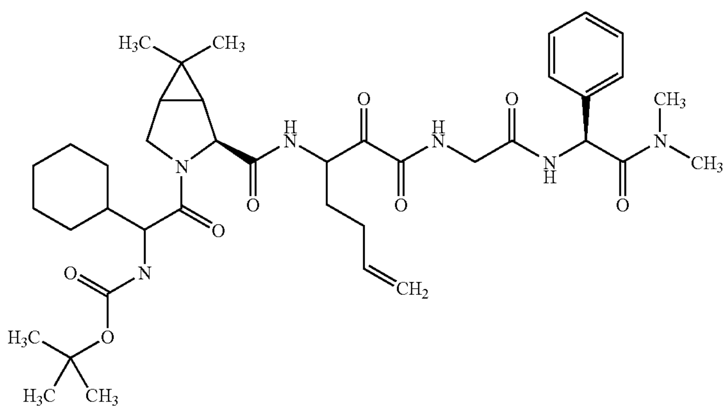 | 750 | A |
| 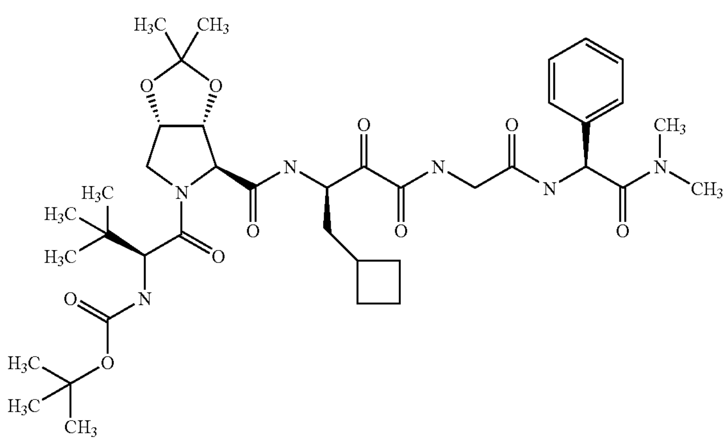 | 771 | A |

TABLE 5-continued

| STRUCTURE | MW | Ki* Range |
|---|---|---|
| 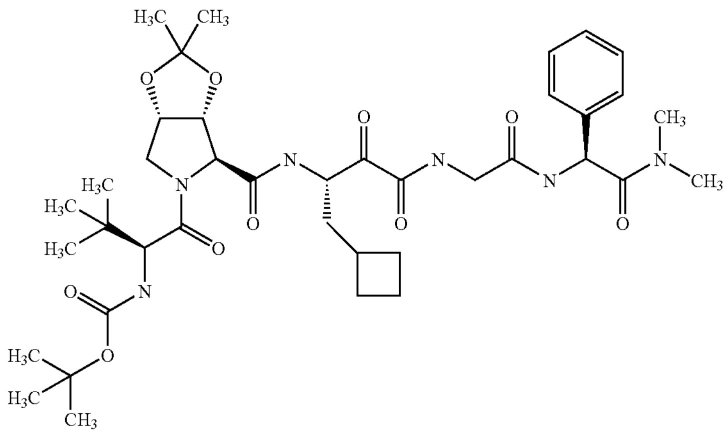 | 771 | A |
| 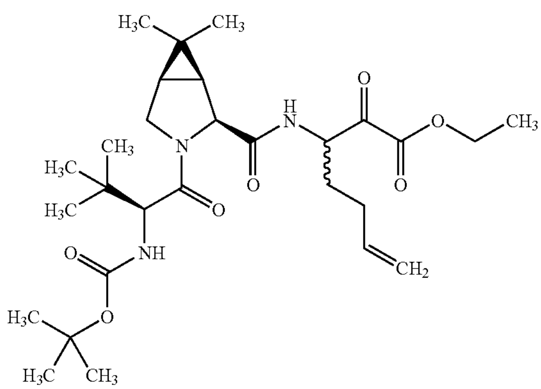 | 536 | C |
| 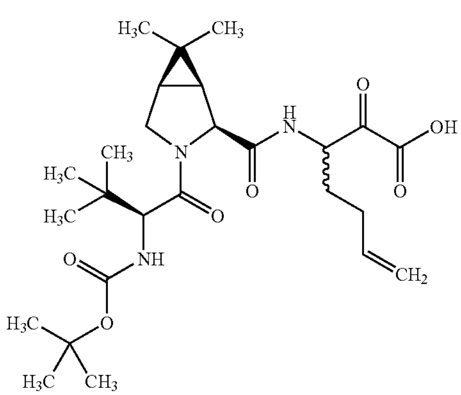 | 508 | B |

TABLE 5-continued

| STRUCTURE | MW | Ki* Range |
|---|---|---|
| 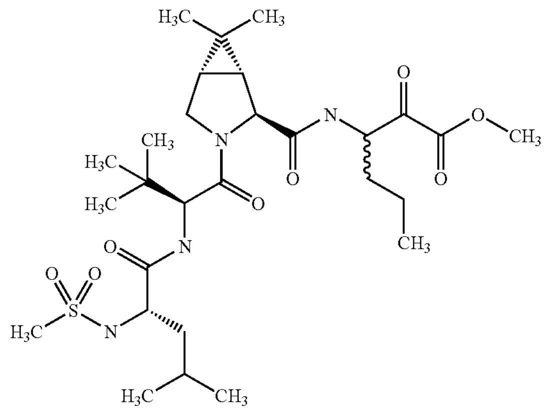 | 601 | C |
| 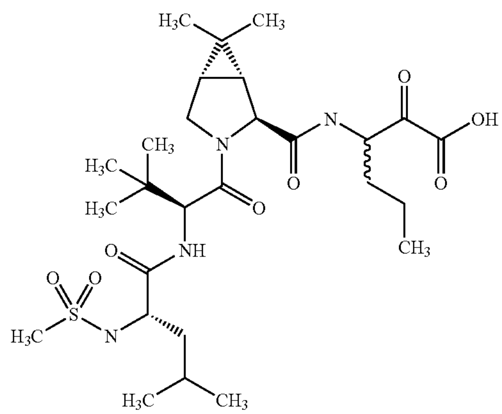 | 587 | B |
| 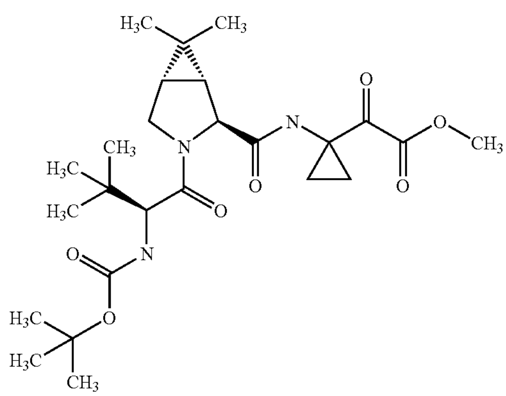 | 494 | C |
| 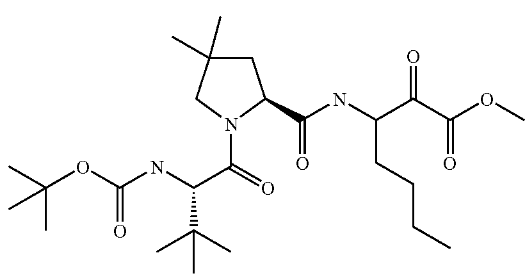 | 512 | C |

TABLE 5-continued
| STRUCTURE | MW | Ki* Range |
|---|---|---|
| 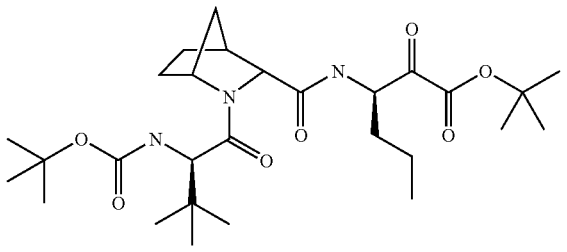 | 538 | C |
| 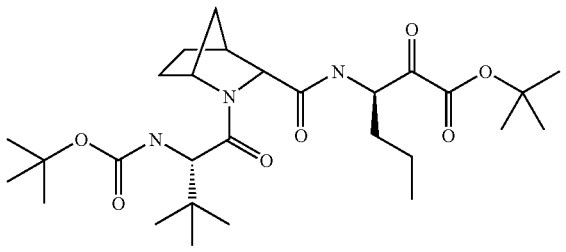 | 538 | C |
| 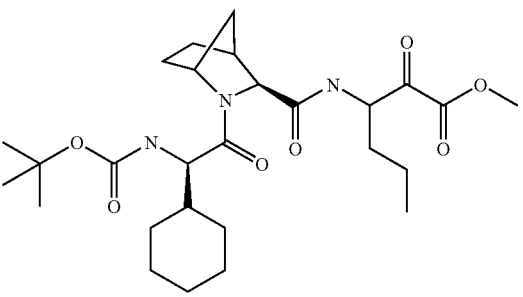 | 522 | C |
| 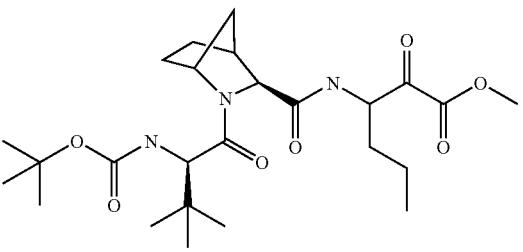 | 496 | C |
| 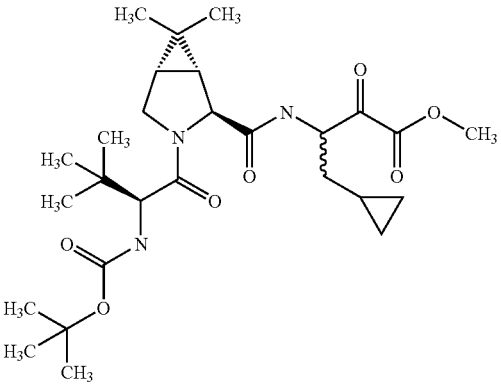 | 522 | C |

TABLE 5-continued

| STRUCTURE | MW | Ki* Range |
|---|---|---|
| 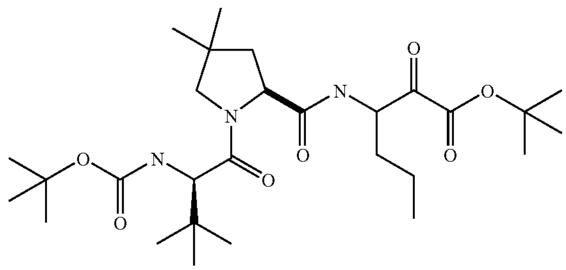 | 540 | C |
| 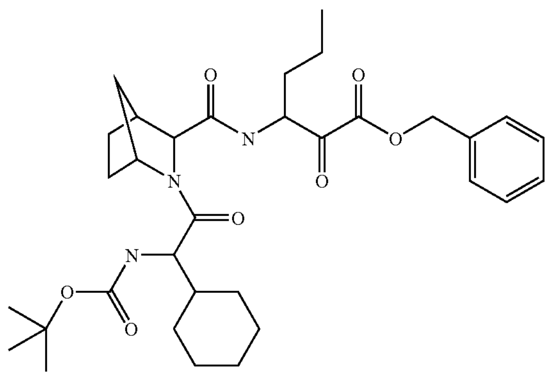 | 598 | C |
| 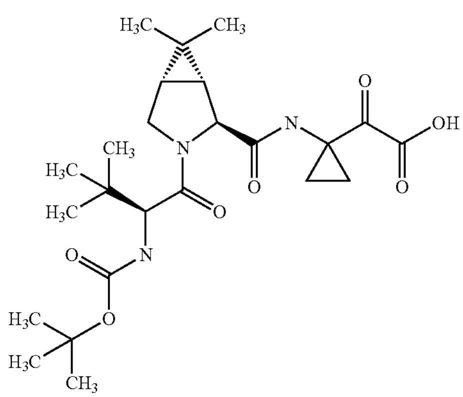 | 480 | C |
| 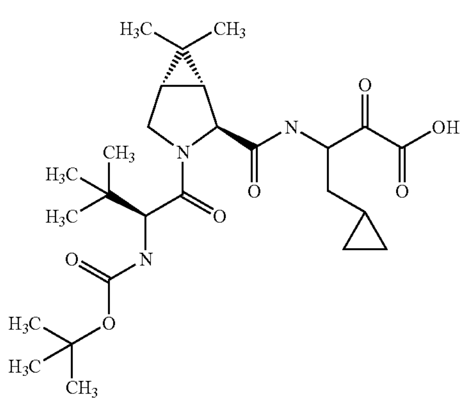 | 508 | B |

TABLE 5-continued

| STRUCTURE | MW | Ki* Range |
|---|---|---|
| 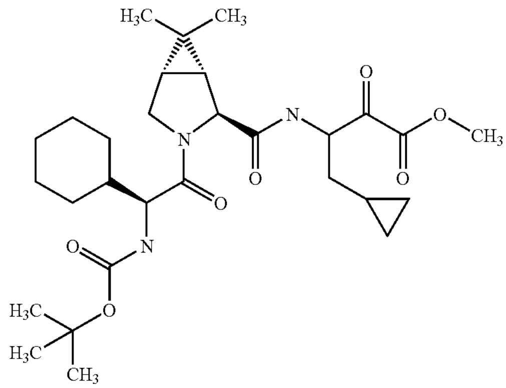 | 548 | C |
| 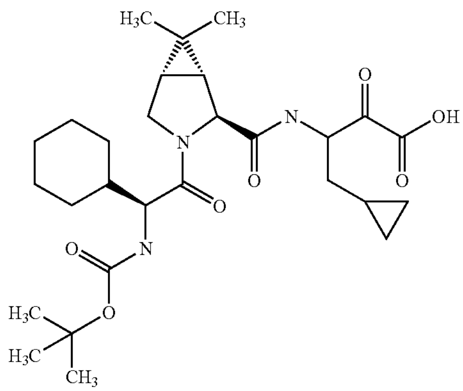 | 534 | B |
| 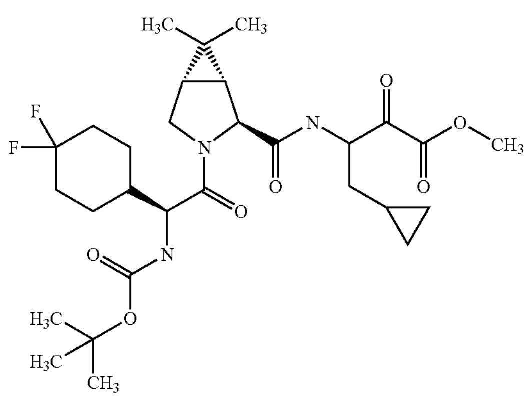 | 584 | C |
| 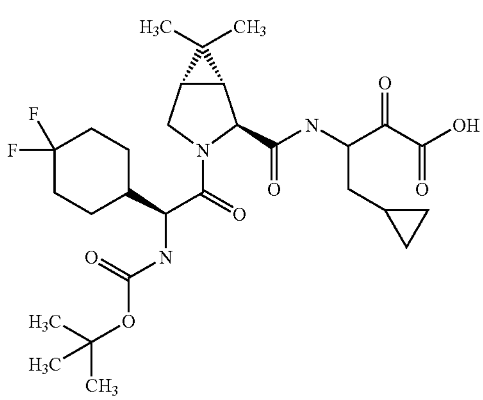 | 570 | B |

TABLE 5-continued
| STRUCTURE | MW | Ki* Range |
|---|---|---|
| 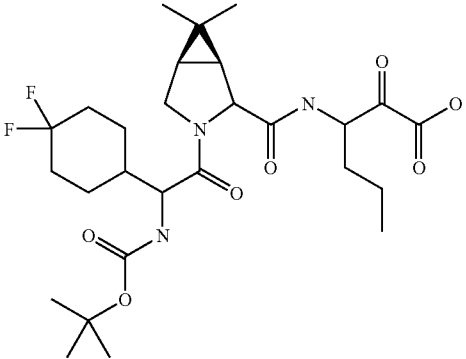 | 558 | C |
| 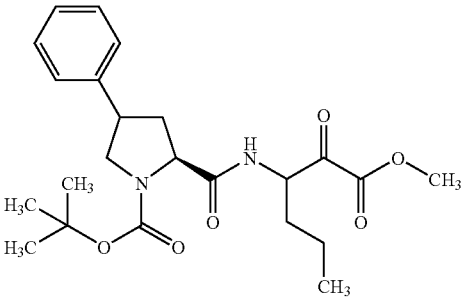 | 433 | C |
| 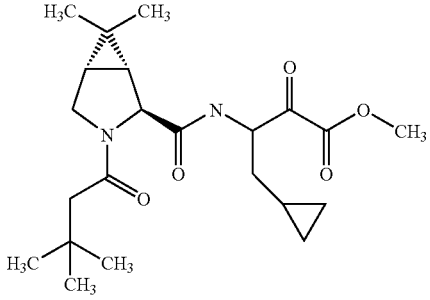 | 407 | C |
| 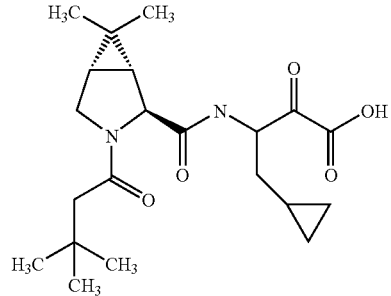 | 393 | C |

TABLE 5-continued

| STRUCTURE | MW | Ki* Range |
|---|---|---|
| 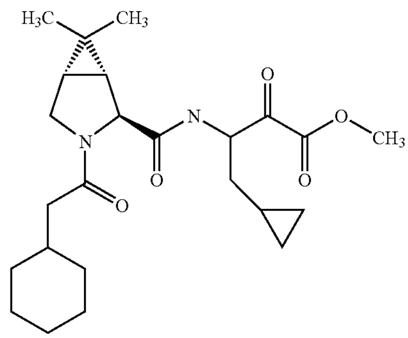 | 433 | C |
| 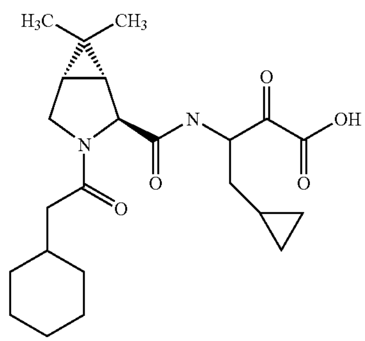 | 419 | C |
| 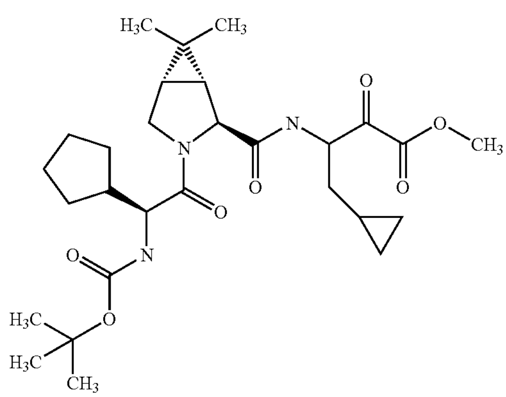 | 534 | C |
| 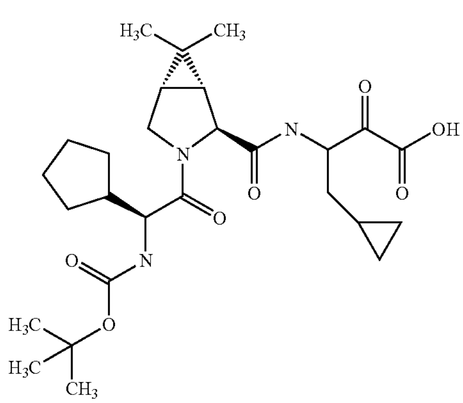 | 520 | B |

TABLE 5-continued

| STRUCTURE | MW | Ki* Range |
|---|---|---|
| 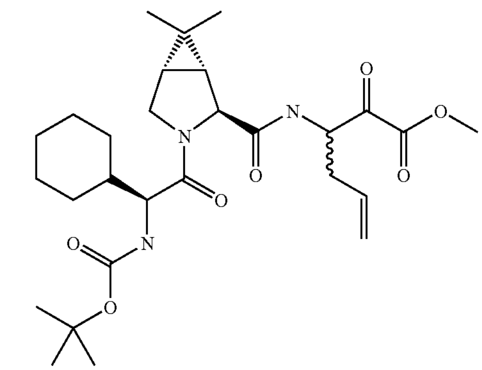 | 534 | C |
| 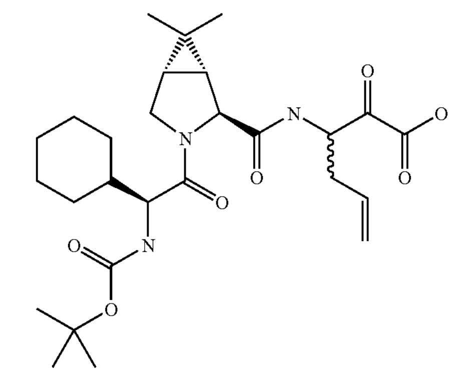 | 520 | B |
| 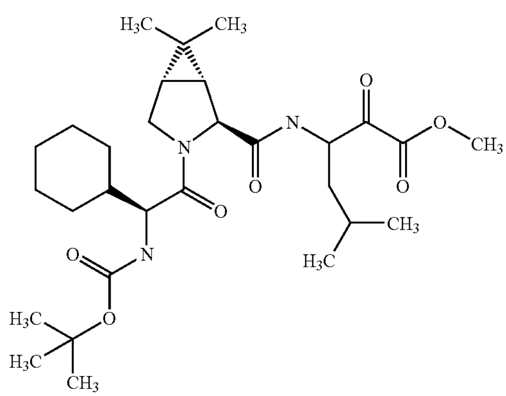 | 550 | C |
| 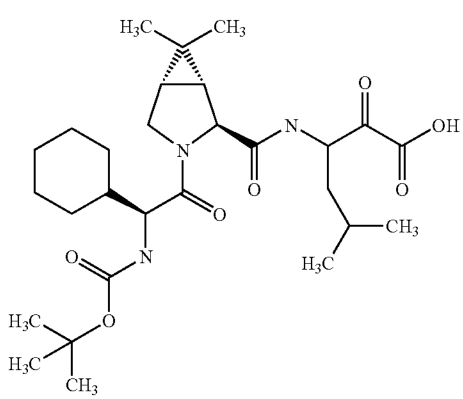 | 536 | C |

TABLE 5-continued

| STRUCTURE | MW | Ki* Range |
|---|---|---|
| 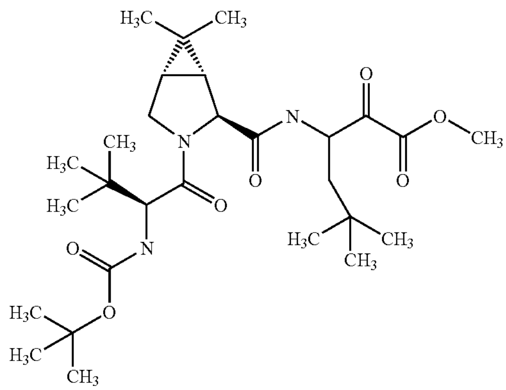 | 538 | C |
| 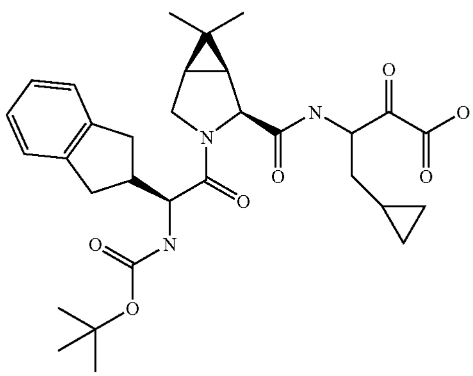 | 568 | B |
| 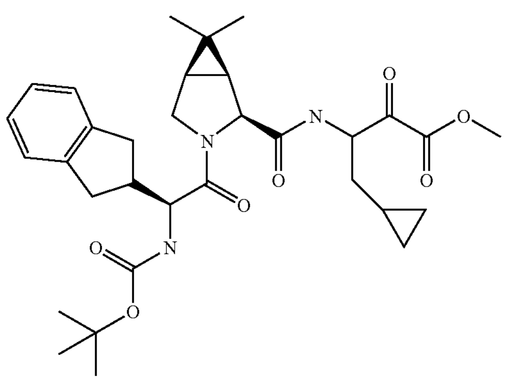 | 582 | C |
| 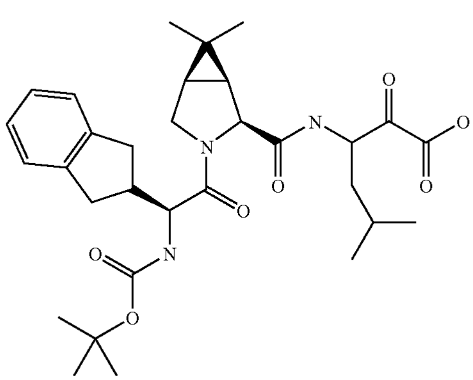 | 570 | C |

TABLE 5-continued

| STRUCTURE | MW | Ki* Range |
|---|---|---|
| 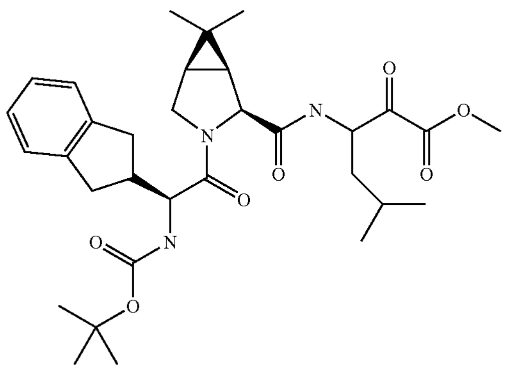 | 584 | C |
| 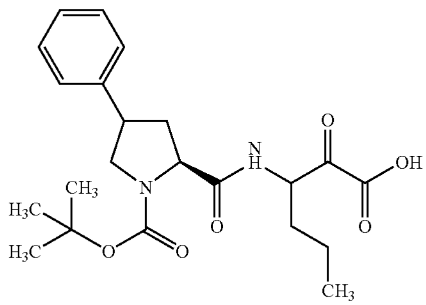 | 418 | C |
| 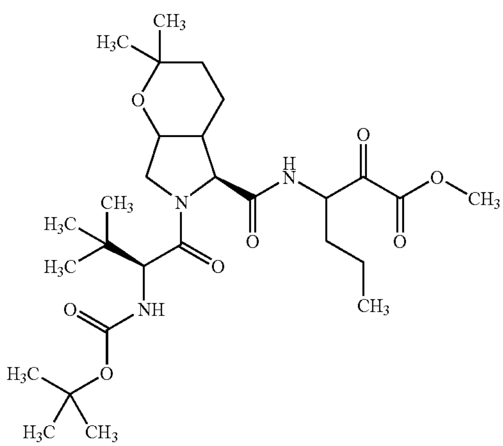 | 554 | C |
| 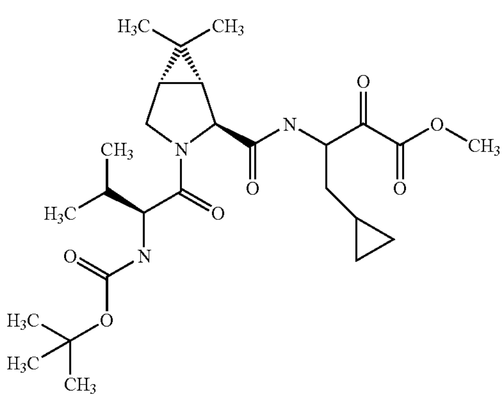 | 508 | C |

TABLE 5-continued

| STRUCTURE | MW | Ki* Range |
|---|---|---|
| 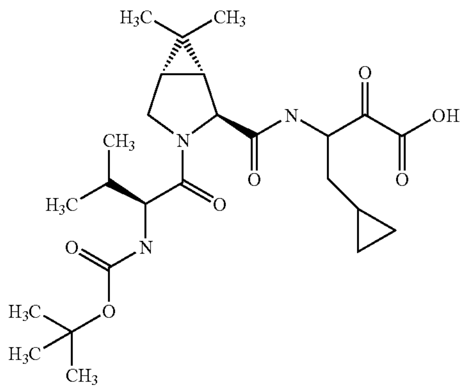 | 494 | B |
| 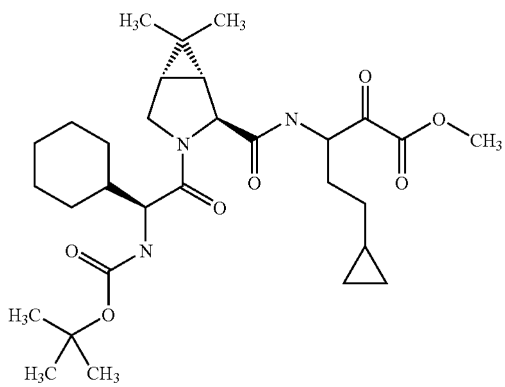 | 562 | C |
| 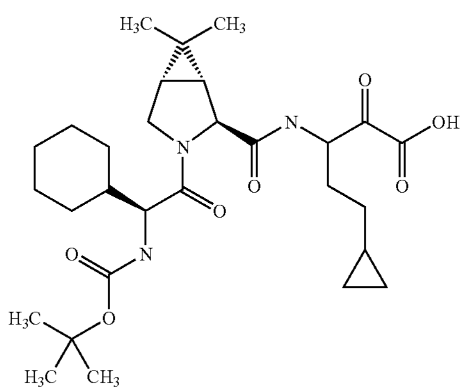 | 548 | A |
| 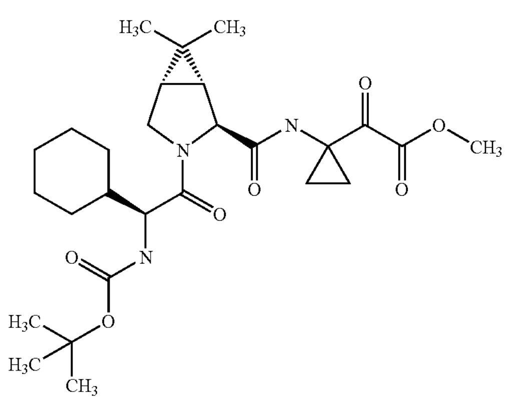 | 520 | C |

TABLE 5-continued
| STRUCTURE | MW | Ki* Range |
|---|---|---|
| 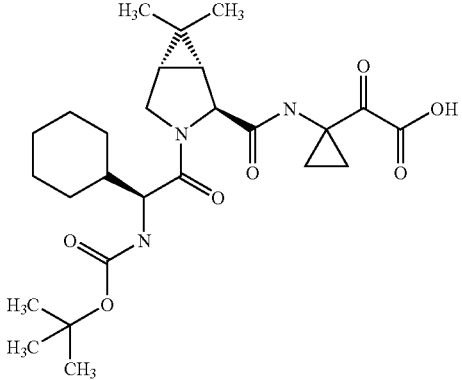 | 506 | C |
| 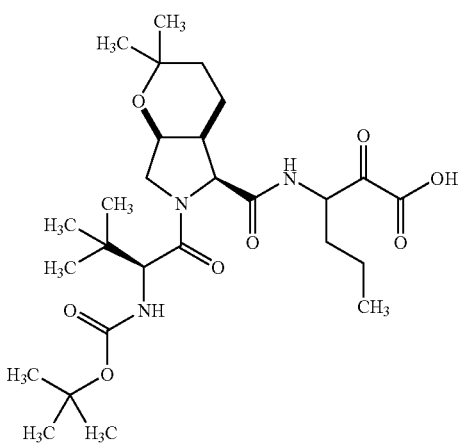 | 540 | C |
| 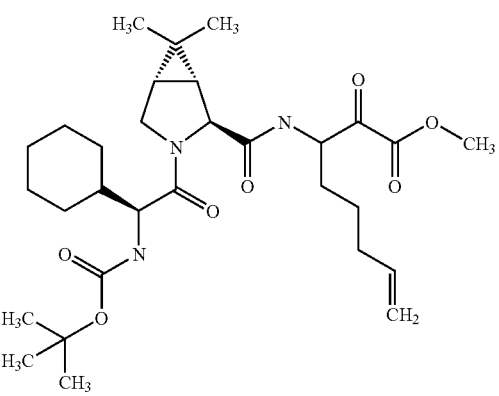 | 562 | C |

TABLE 5-continued

| STRUCTURE | MW | Ki* Range |
|---|---|---|
| 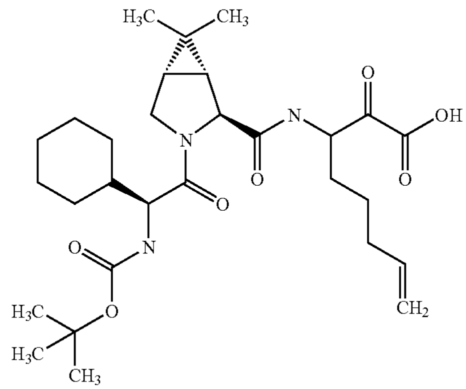 | 548 | B |
| 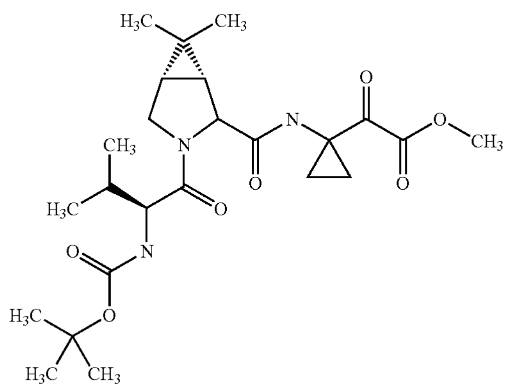 | 480 | C |
| 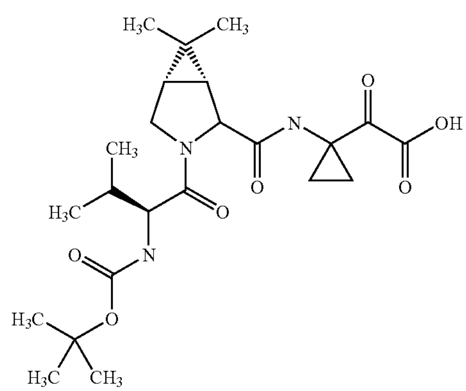 | 466 | C |
| 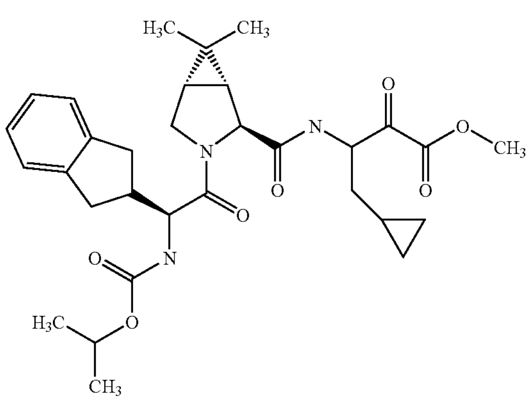 | 568 | C |

TABLE 5-continued

| STRUCTURE | MW | Ki* Range |
|---|---|---|
| 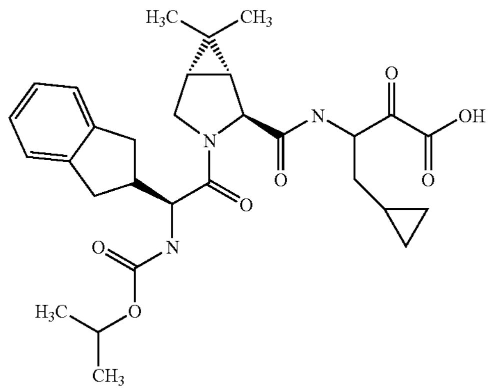 | 554 | B |
| 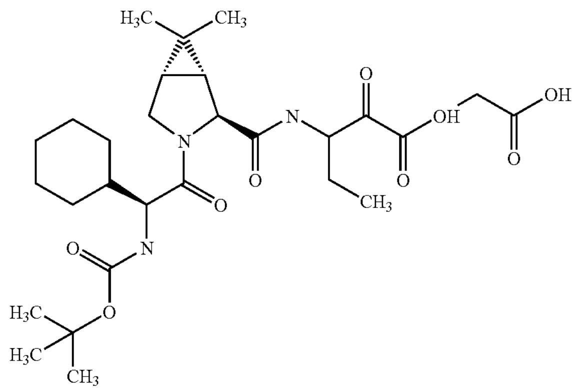 | 508 | B |
| 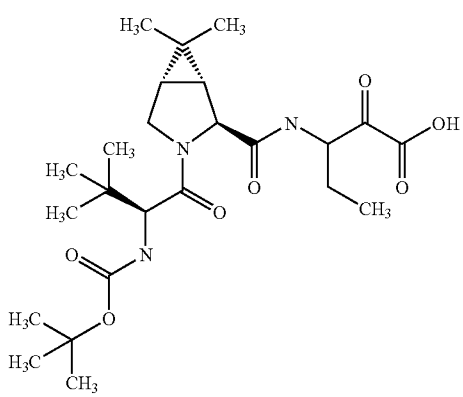 | 482 | C |
| 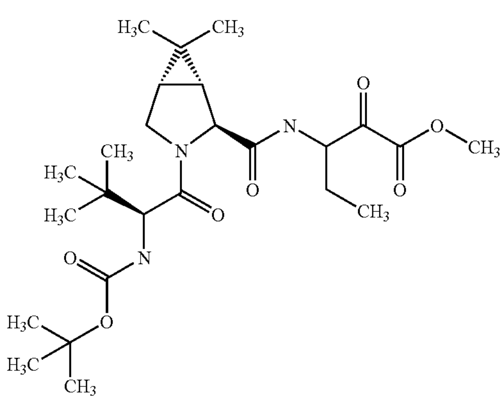 | 496 | C |

TABLE 5-continued

| STRUCTURE | MW | Ki* Range |
|---|---|---|
| 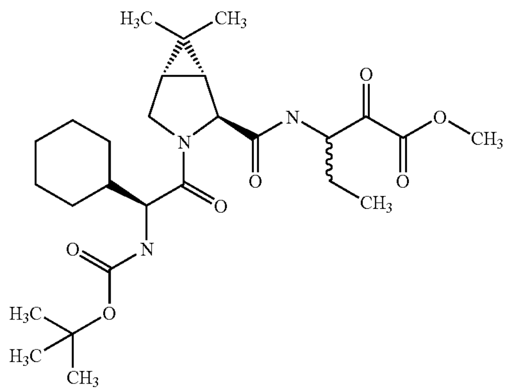 | 522 | C |
| 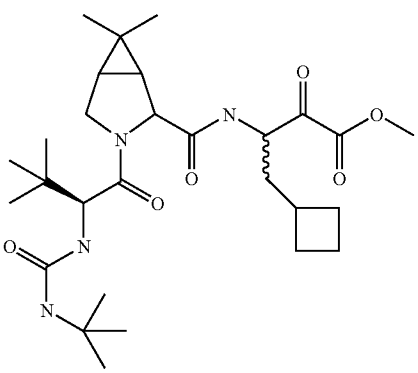 | 535 | C |
| 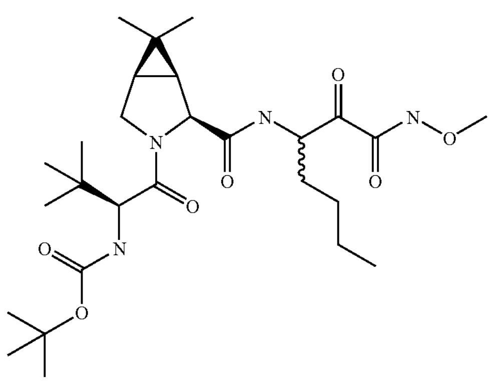 | 539 | B |
| 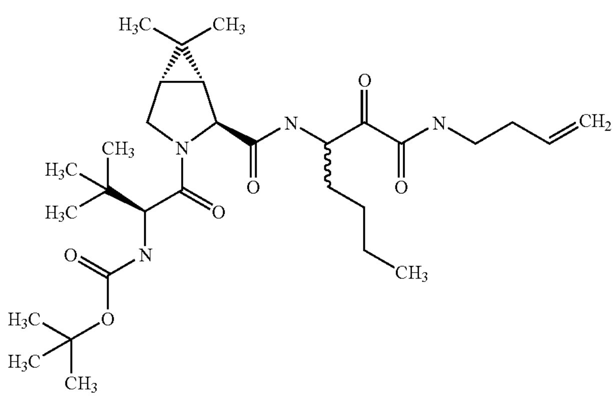 | 563 | B |

TABLE 5-continued
| STRUCTURE | MW | Ki* Range |
|---|---|---|
| 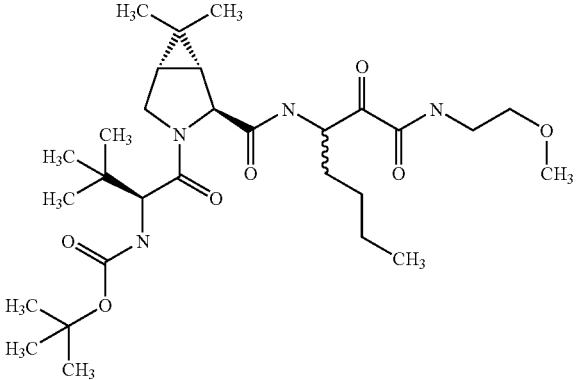 | 567 | C |
| 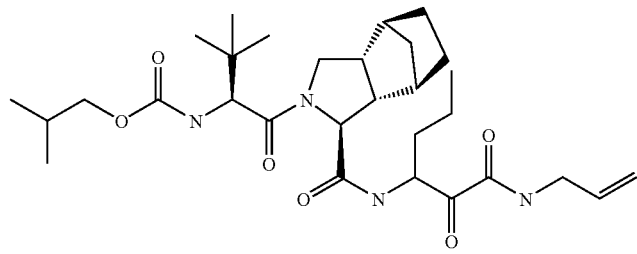 | 561 | C |
| 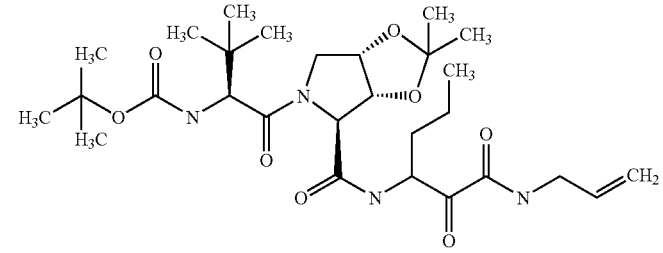 | 567 | C |
| 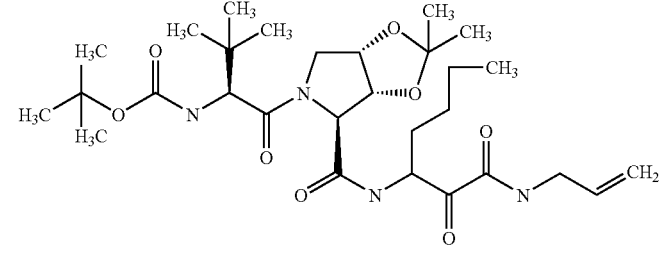 | 581 | C |
| 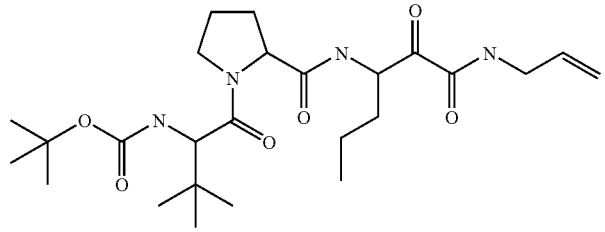 | 495 | C |

TABLE 5-continued

| STRUCTURE | MW | Ki* Range |
|---|---|---|
| 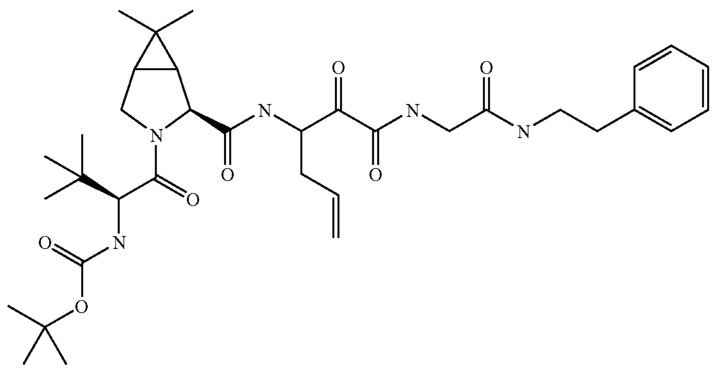 | 654 | B |
| 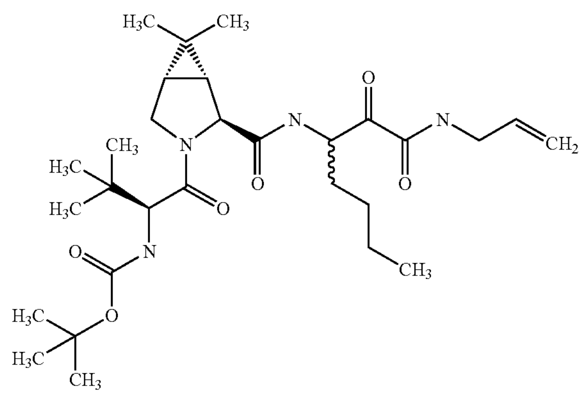 | 549 | C |
| 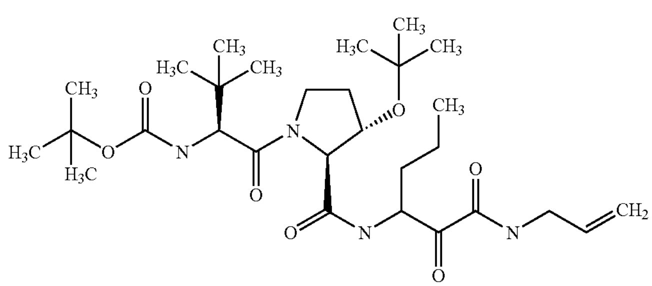 | 567 | C |
| 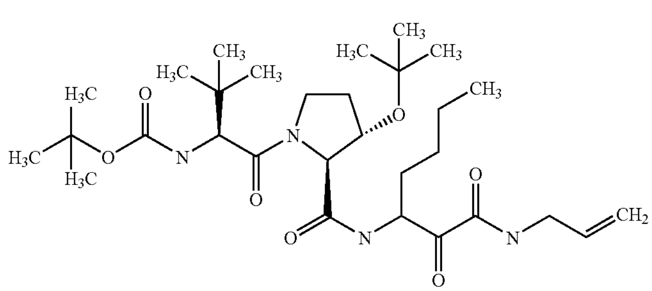 | 581 | C |

TABLE 5-continued
| STRUCTURE | MW | Ki* Range |
|---|---|---|
| 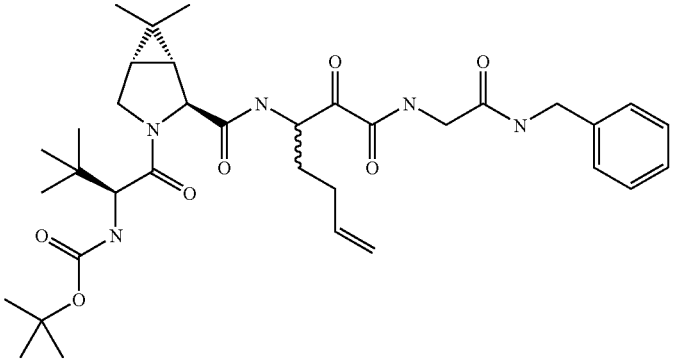 | 654 | C |
| 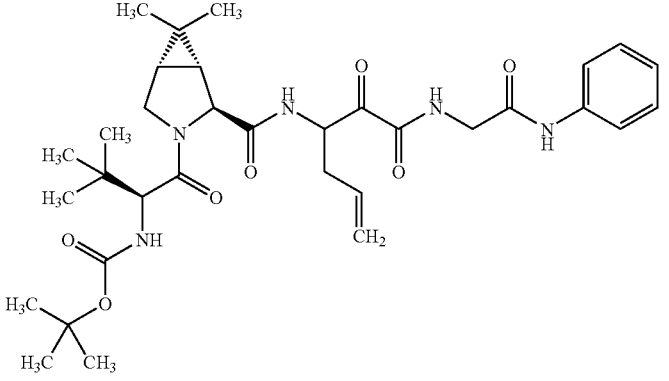 | 626 | B |
| 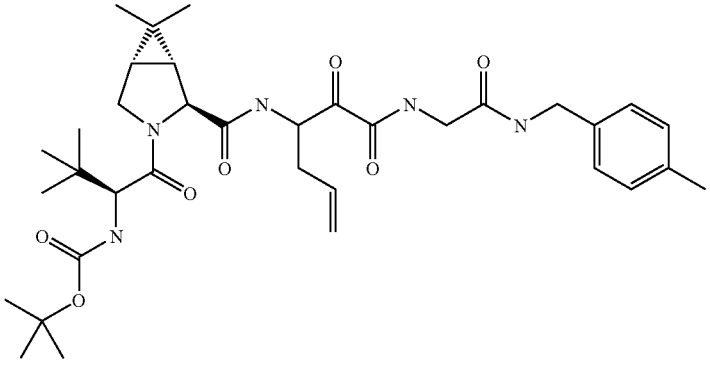 | 654 | A |
| 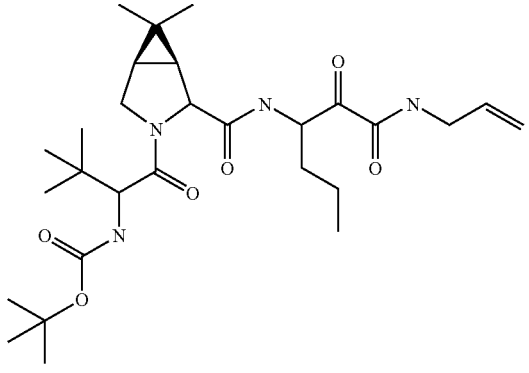 | 535 | C |

TABLE 5-continued

| STRUCTURE | MW | Ki* Range |
|---|---|---|
| 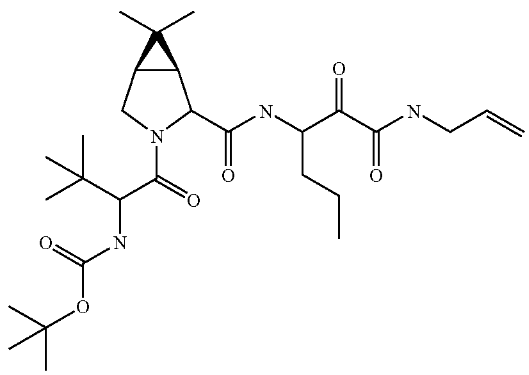 | 535 | B |
| | 523 | C |
| | 523 | C |
| 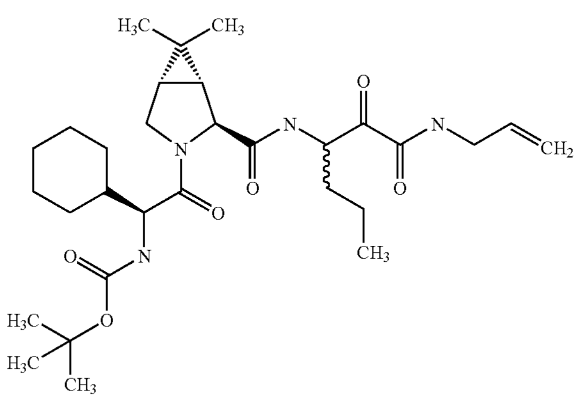 | 561 | B |
| 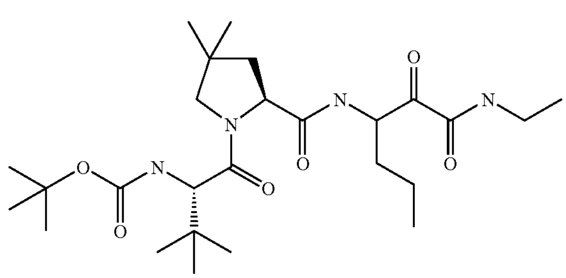 | 511 | C |

TABLE 5-continued
| STRUCTURE | MW | Ki* Range |
|---|---|---|
| 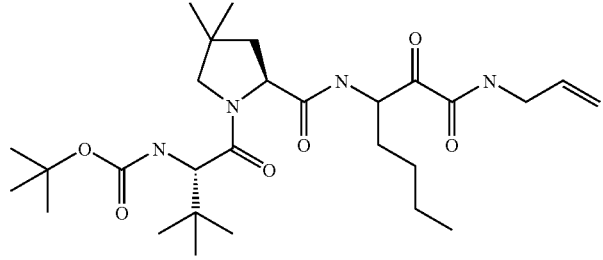 | 537 | C |
| 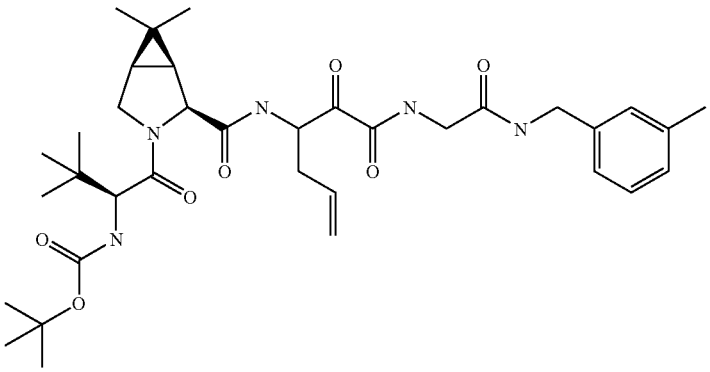 | 654 | B |
| 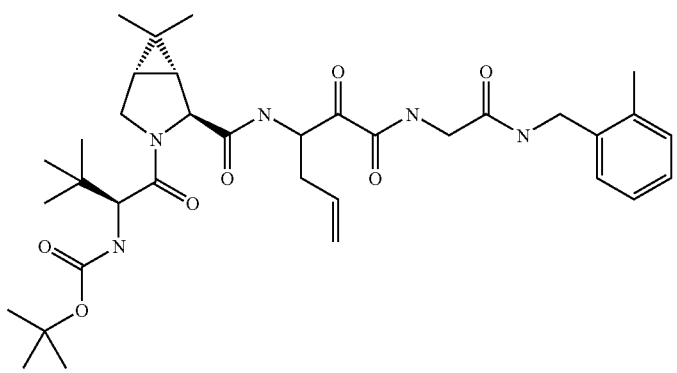 | 654 | A |
| 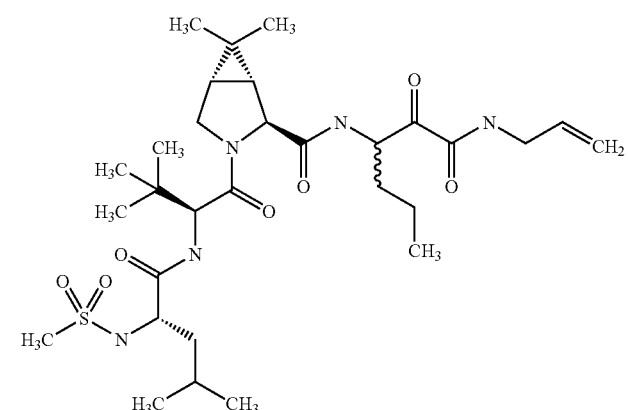 | 626 | B |

TABLE 5-continued
| STRUCTURE | MW | Ki* Range |
|---|---|---|
| 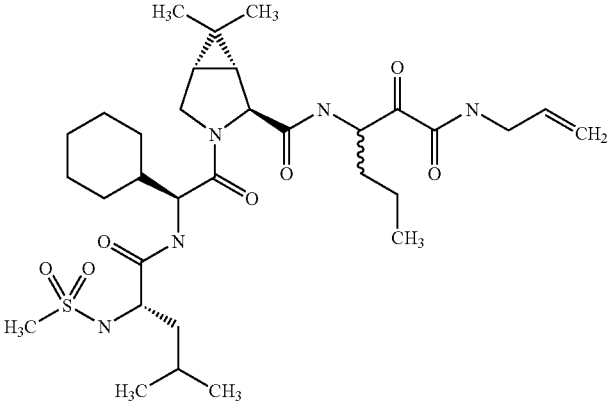 | 652 | B |
| 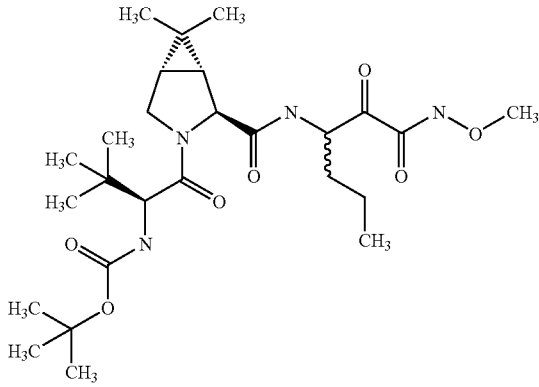 | 525 | C |
| 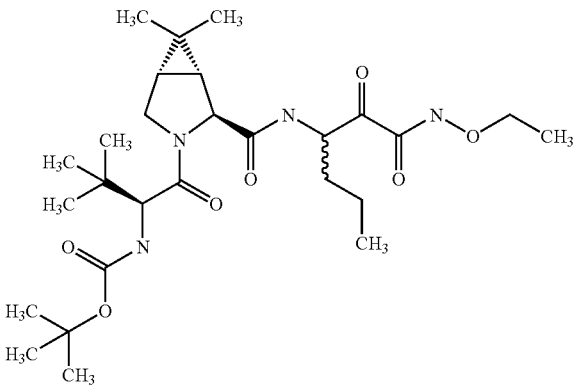 | 539 | C |
| 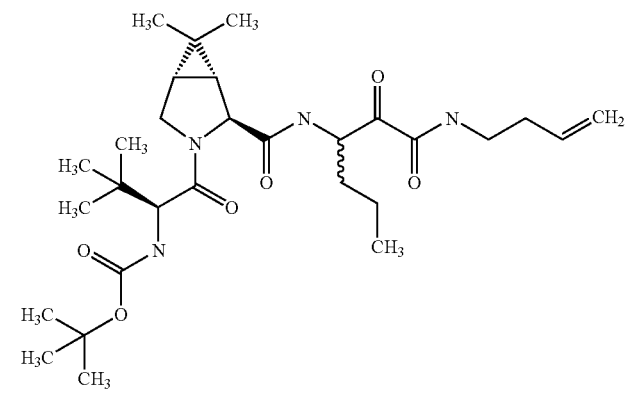 | 549 | C |

TABLE 5-continued

| STRUCTURE | MW | Ki* Range |
|---|---|---|
| 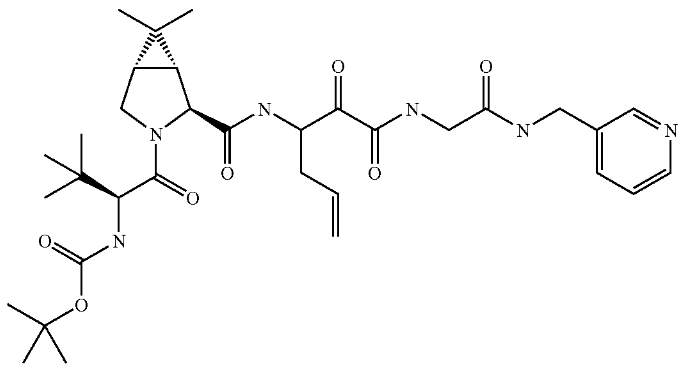 | 641 | B |
| 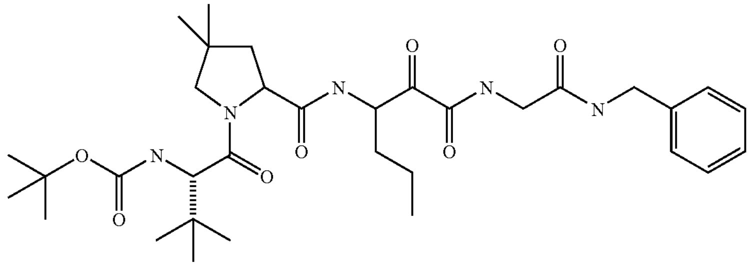 | 630 | C |
| | 653 | B |
| | 653 | B |

TABLE 5-continued
| STRUCTURE | MW | Ki* Range |
|---|---|---|
| 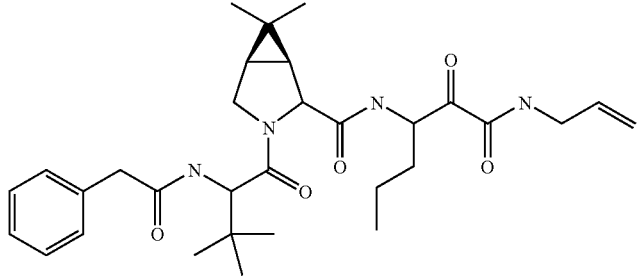 | 553 | C |
| 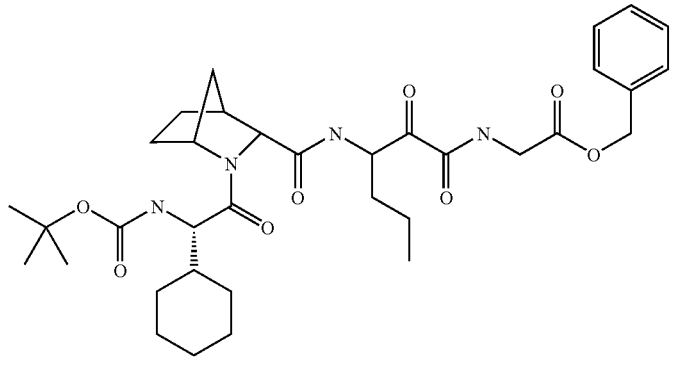 | 655 | C |
| 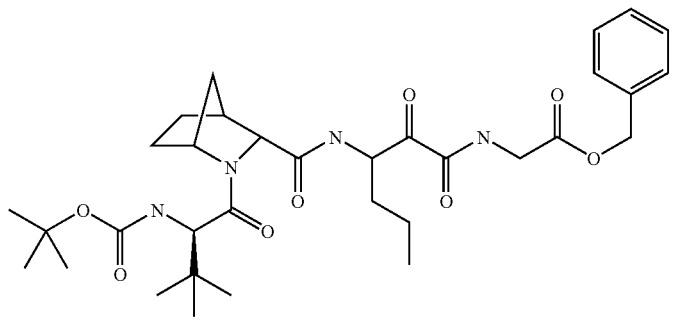 | 629 | C |
| 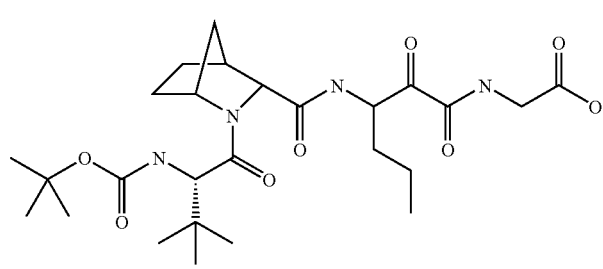 | 539 | C |
| 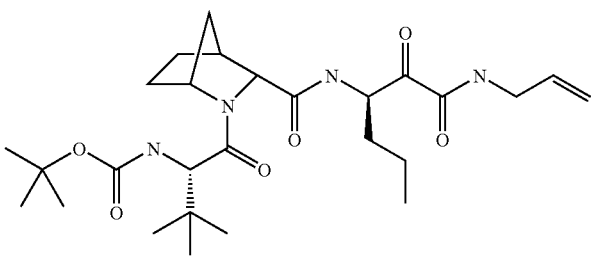 | 521 | C |

TABLE 5-continued

| STRUCTURE | MW | Ki* Range |
|---|---|---|
| 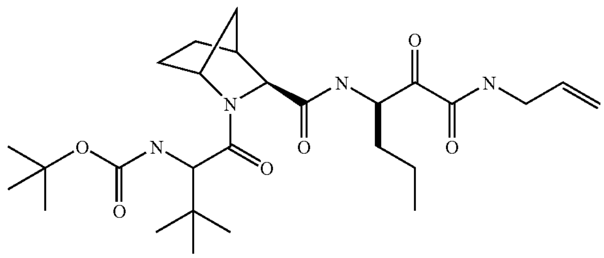 | 521 | C |
| | 547 | C |
| | 547 | C |
| 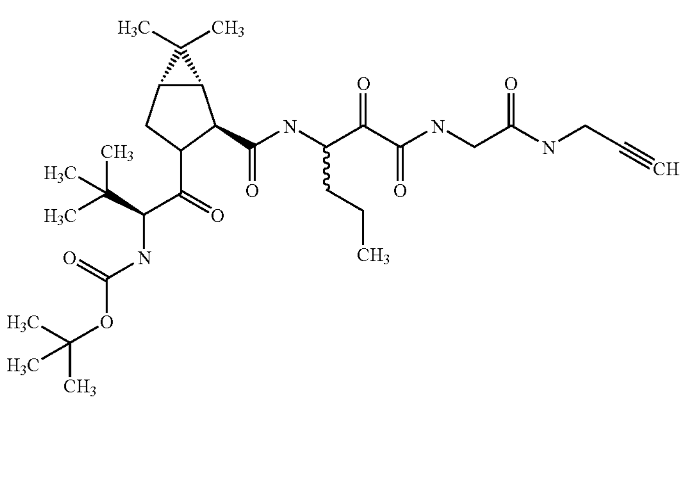 | 590 | B |

TABLE 5-continued

| STRUCTURE | MW | Ki* Range |
|---|---|---|
| 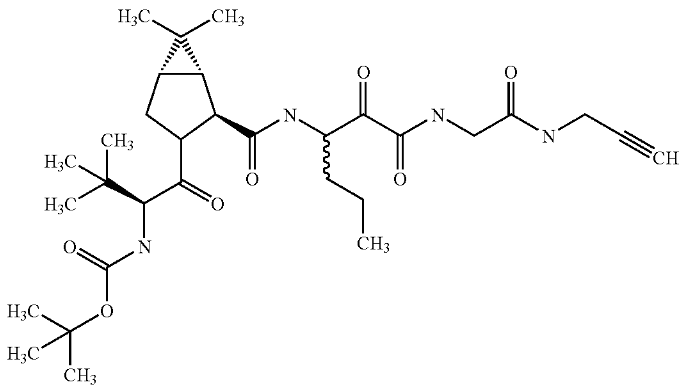 | 590 | B |
| 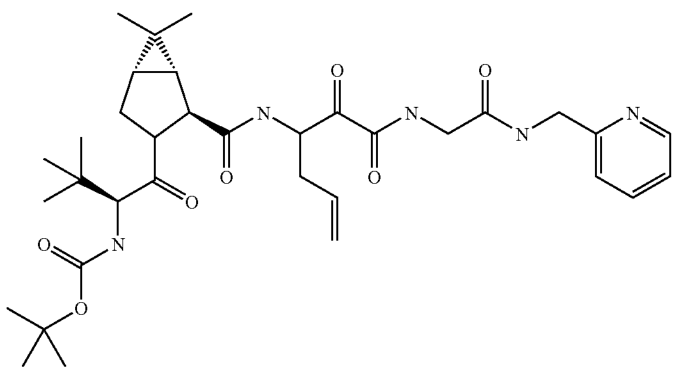 | 641 | B |
| 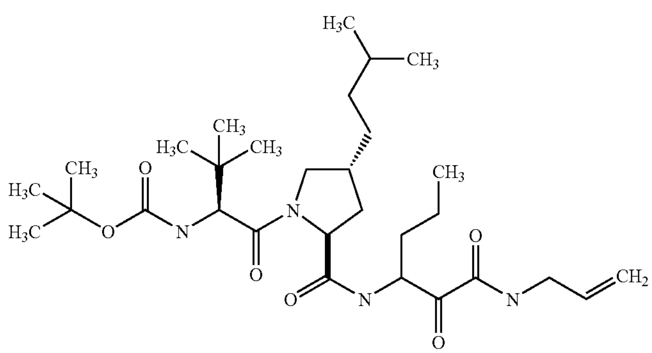 | 565 | C |
| 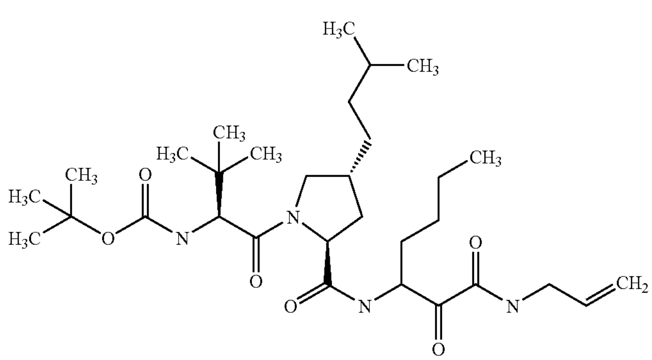 | 579 | C |

TABLE 5-continued

| STRUCTURE | MW | Ki* Range |
|---|---|---|
| 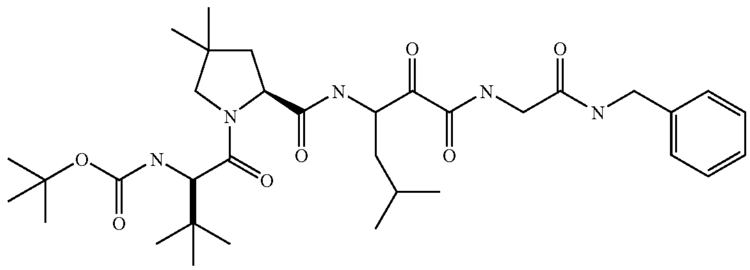 | 644 | C |
| 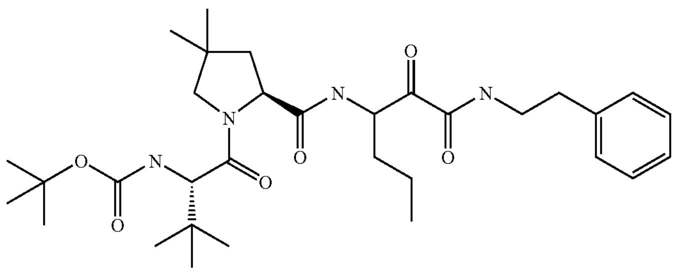 | 587 | C |
| 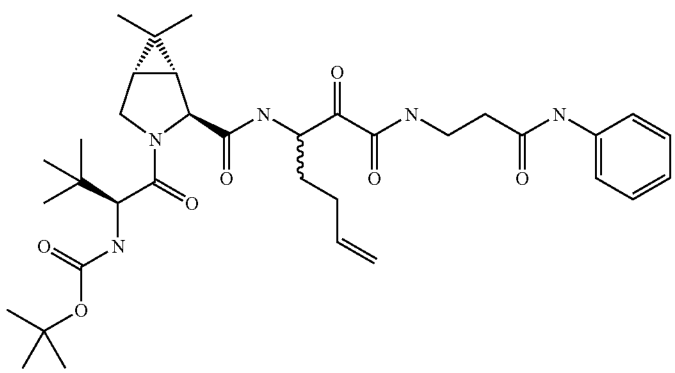 | 654 | B |
| 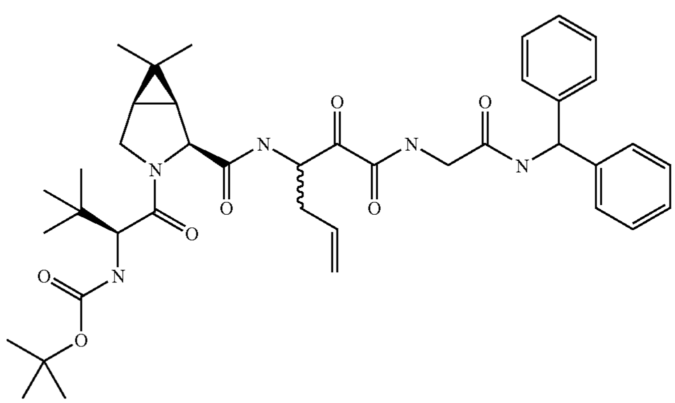 | 716 | B |

TABLE 5-continued
| STRUCTURE | MW | Ki* Range |
|---|---|---|
| 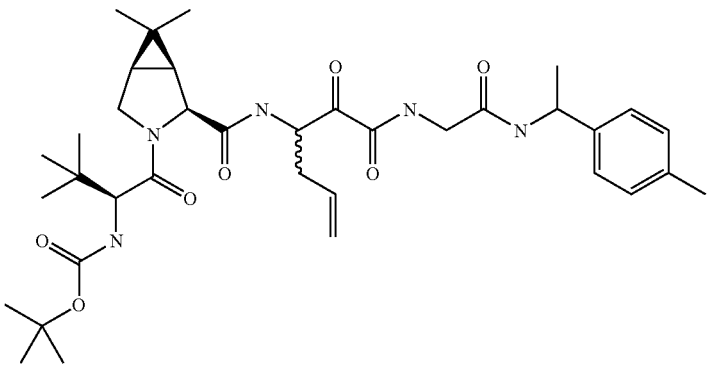 | 668 | B |
| 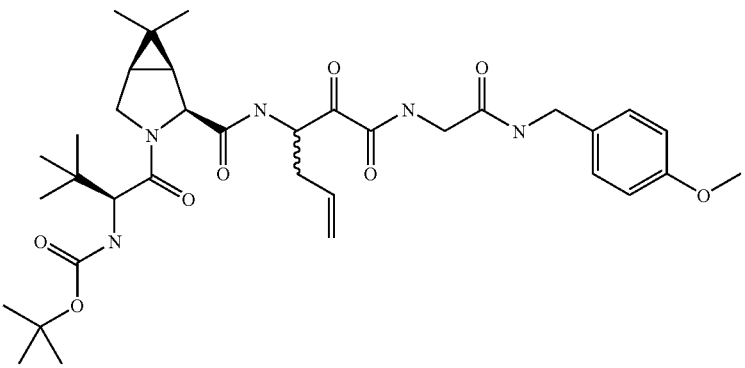 | 670 | A |
| 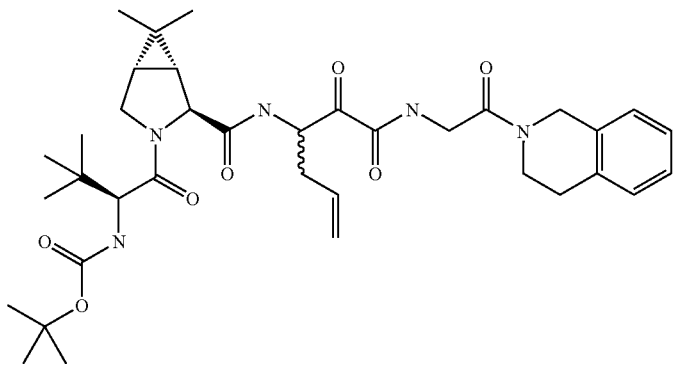 | 666 | C |
| 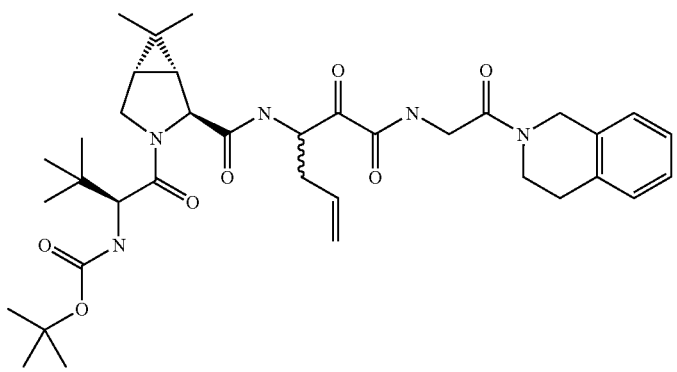 | 666 | C |

TABLE 5-continued
| STRUCTURE | MW | Ki* Range |
|---|---|---|
| 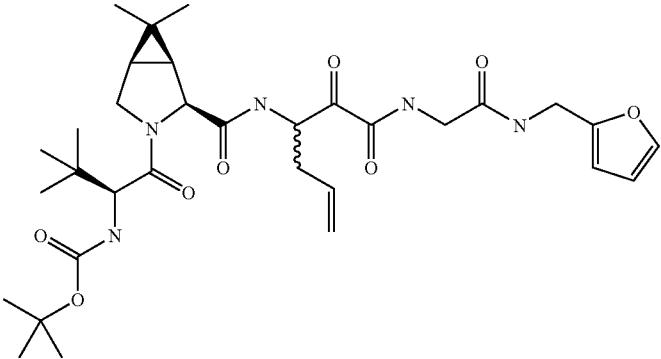 | 630 | B |
| 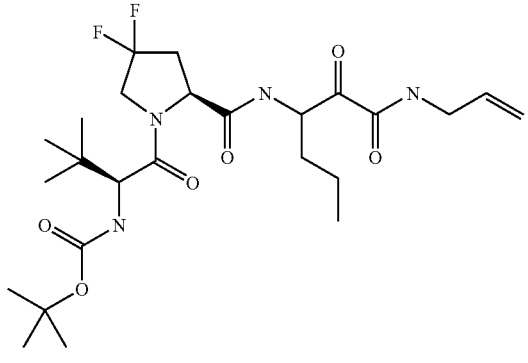 | 531 | C |
| 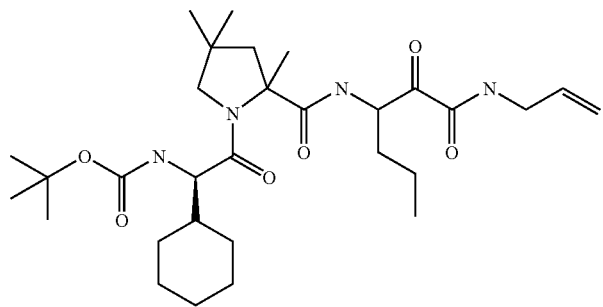 | 563 | C |
| 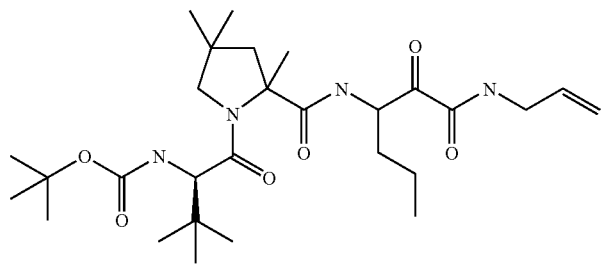 | 537 | C |

TABLE 5-continued

| STRUCTURE | MW | Ki* Range |
|---|---|---|
| 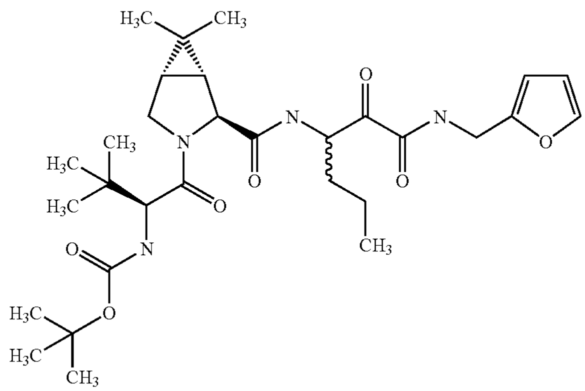 | 575 | B |
| 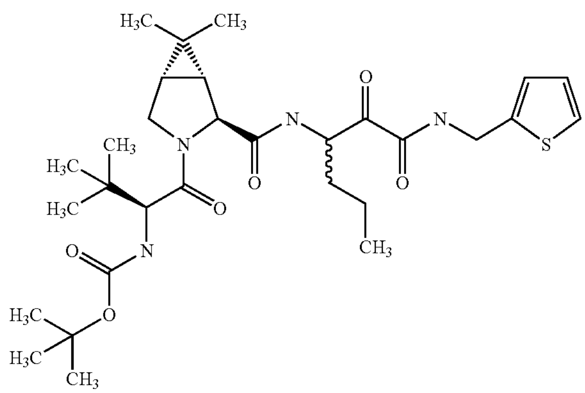 | 591 | B |
| | 586 | C |
| | 586 | C |

TABLE 5-continued

| STRUCTURE | MW | Ki* Range |
|---|---|---|
| 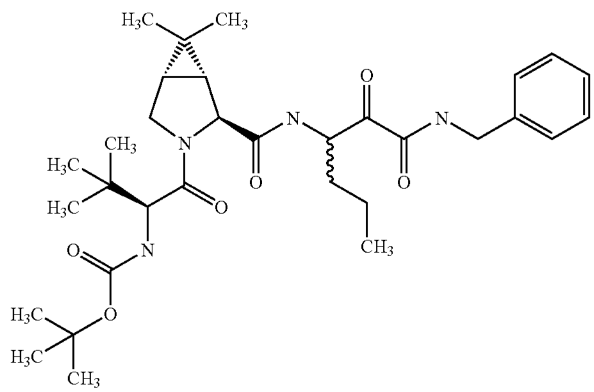 | 585 | B |
| 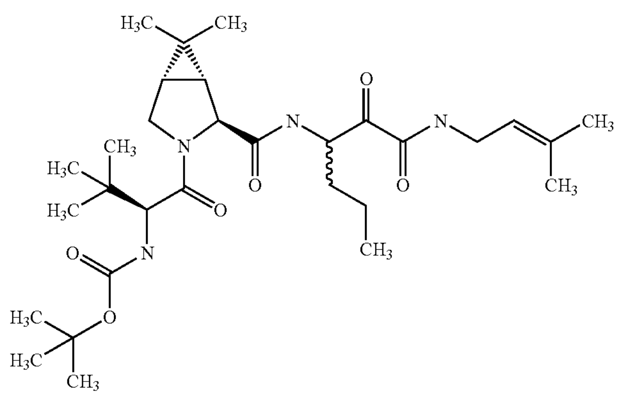 | 563 | B |
| 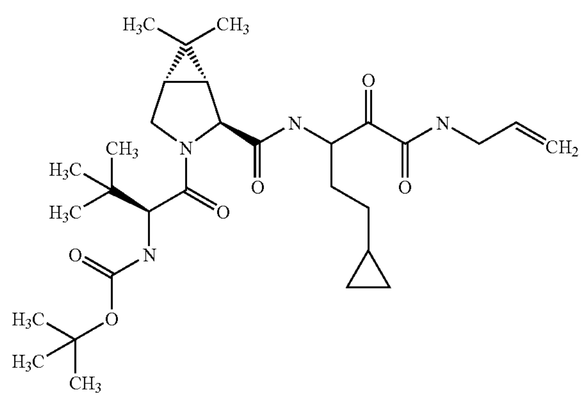 | 547 | B |
| 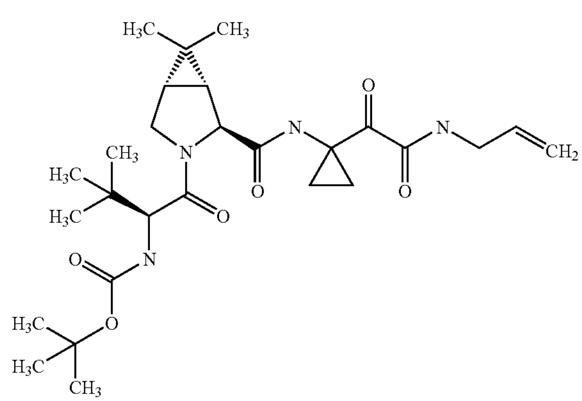 | 519 | C |

TABLE 5-continued

| STRUCTURE | MW | Ki* Range |
|---|---|---|
| 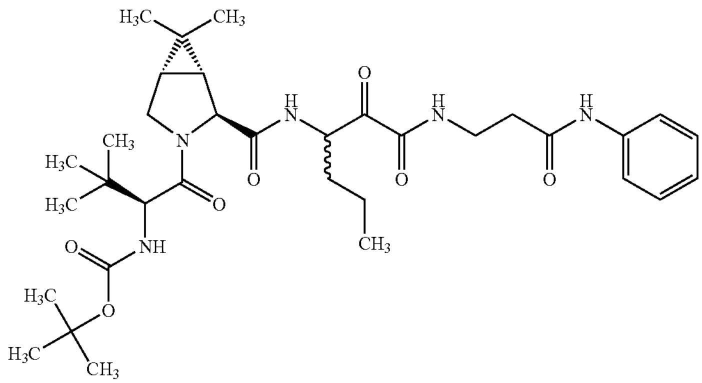 | 640 | B |
| 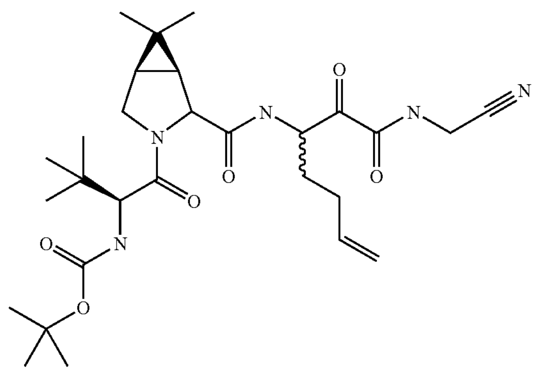 | 546 | B |
| 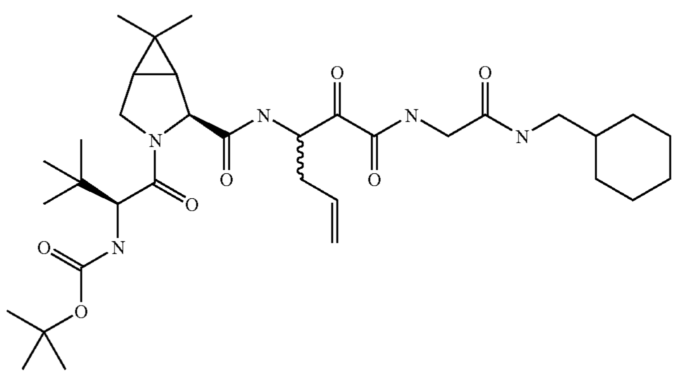 | 646 | B |
| 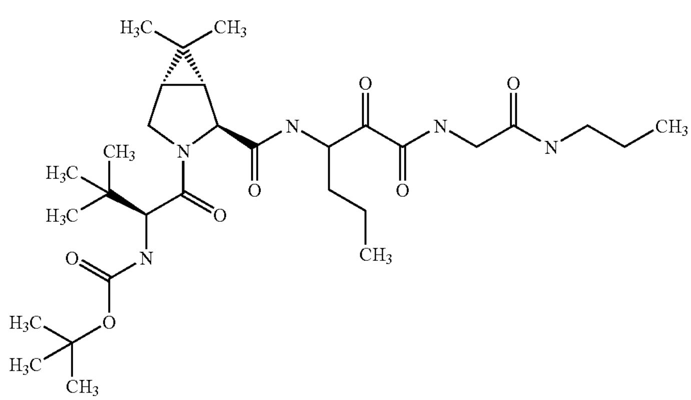 | 594 | C |

TABLE 5-continued

| STRUCTURE | MW | Ki* Range |
|---|---|---|
| 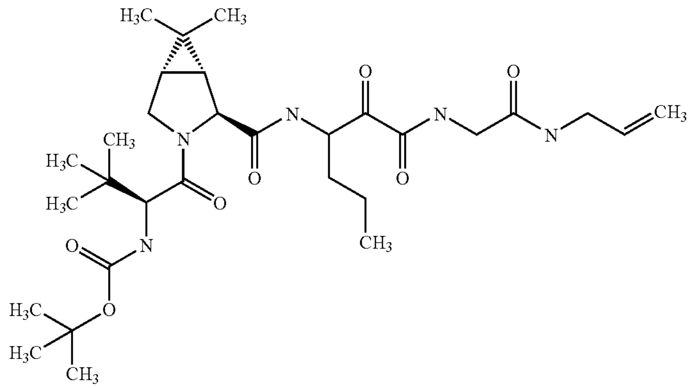 | 592 | B |
| 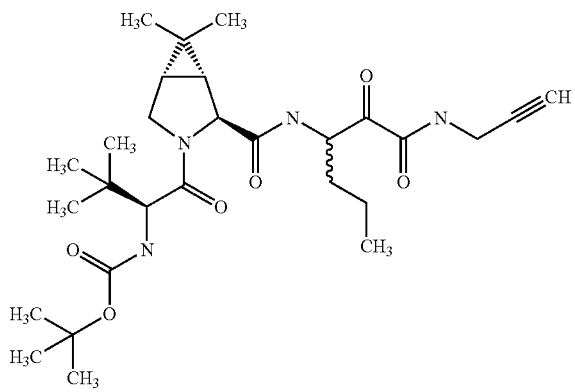 | 533 | C |
| 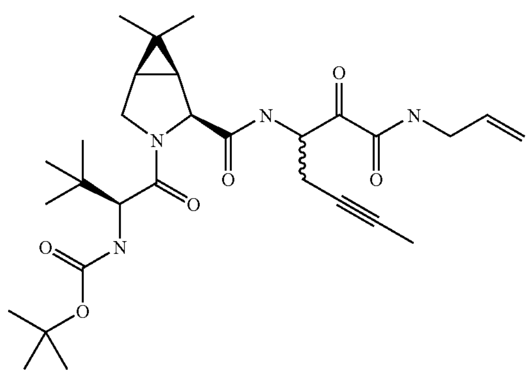 | 545 | C |
| 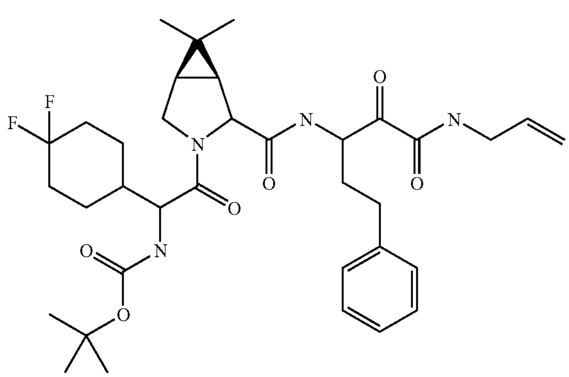 | 659 | B |

TABLE 5-continued

| STRUCTURE | MW | Ki* Range |
|---|---|---|
| 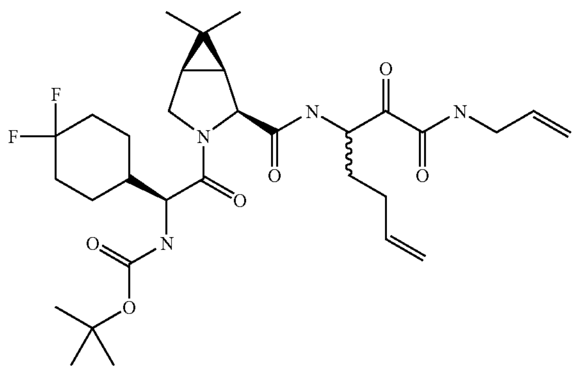 | 609 | A |
| 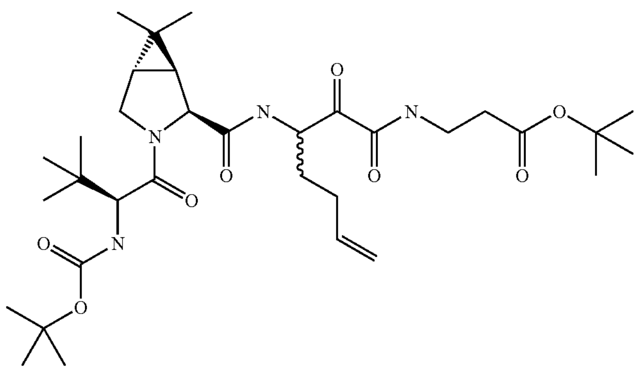 | 635 | B |
| 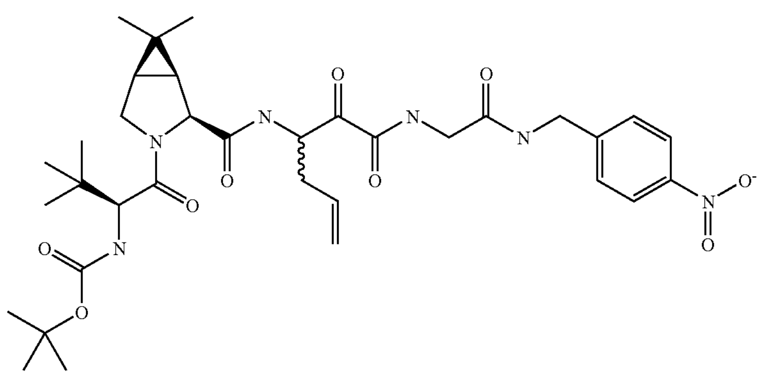 | 685 | B |
| 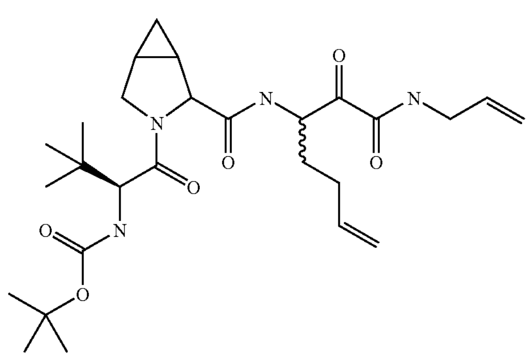 | 519 | C |

TABLE 5-continued

| STRUCTURE | MW | Ki* Range |
|---|---|---|
| 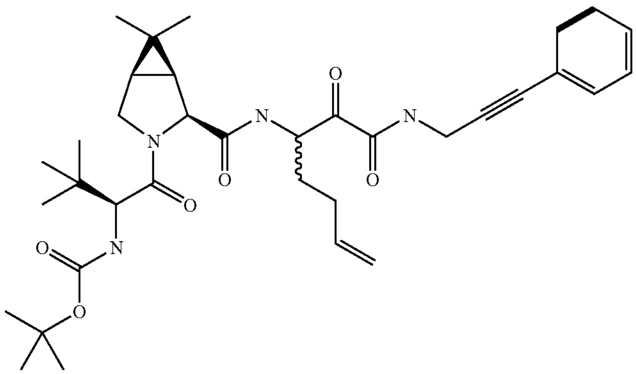 | 621 | B |
| 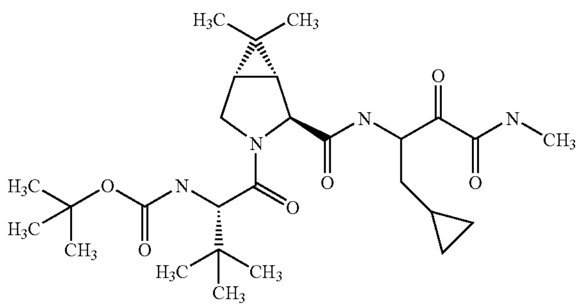 | 521 | B |
| 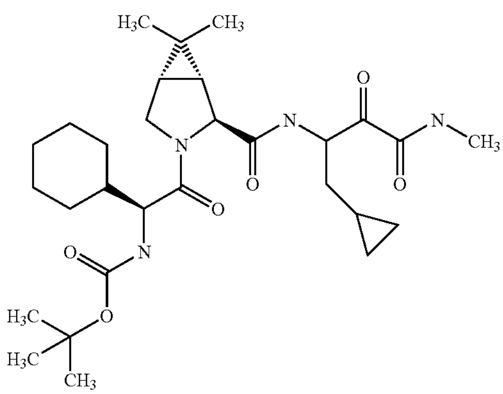 | 547 | B |
| 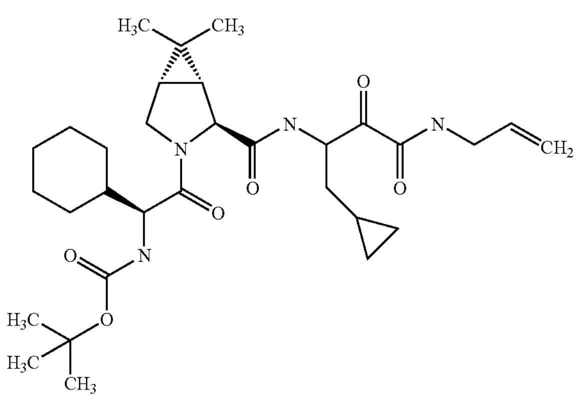 | 573 | B |

TABLE 5-continued
| STRUCTURE | MW | Ki* Range |
|---|---|---|
| 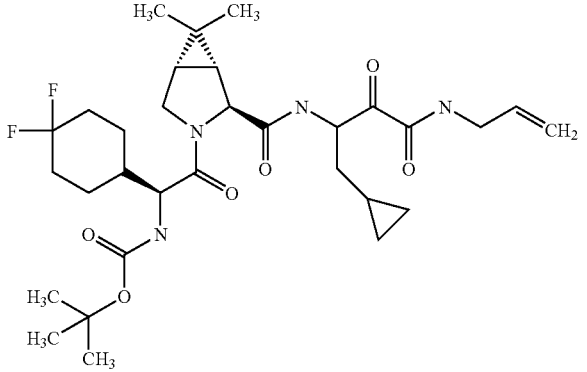 | 609 | B |
| 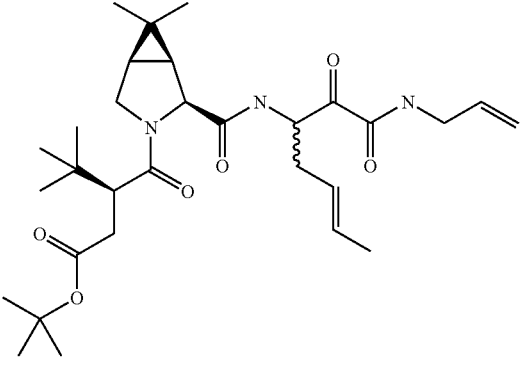 | 547 | B |
| 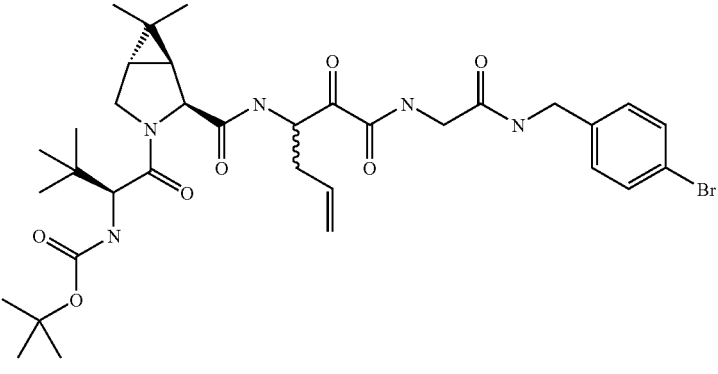 | 719 | B |
| 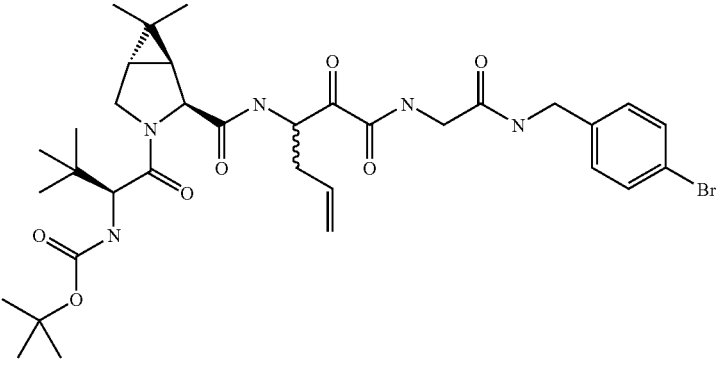 | 719 | C |

TABLE 5-continued

| STRUCTURE | MW | Ki* Range |
|---|---|---|
| 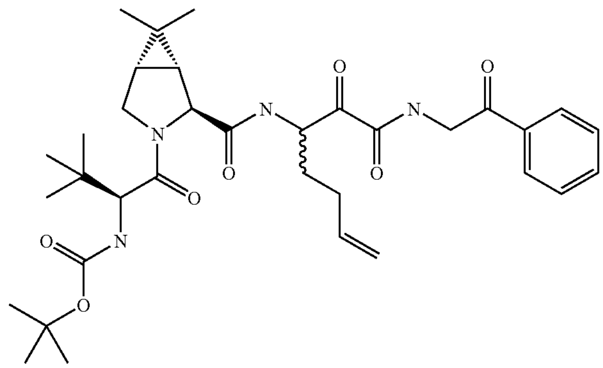 | 653 | B |
| 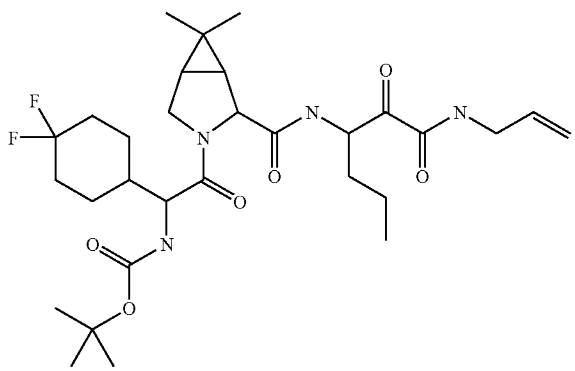 | 597 | B |
| 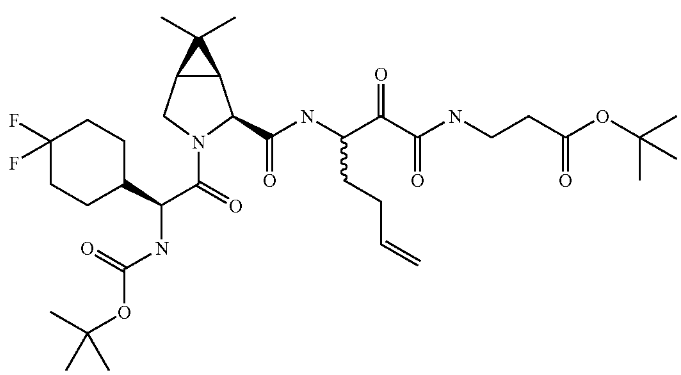 | 697 | A |
| 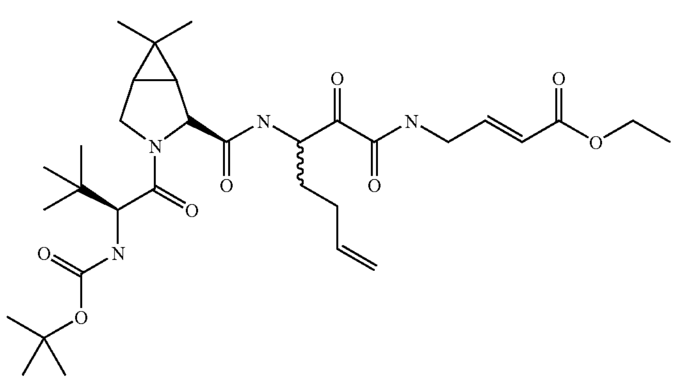 | 619 | B |

TABLE 5-continued

| STRUCTURE | MW | Ki* Range |
|---|---|---|
| 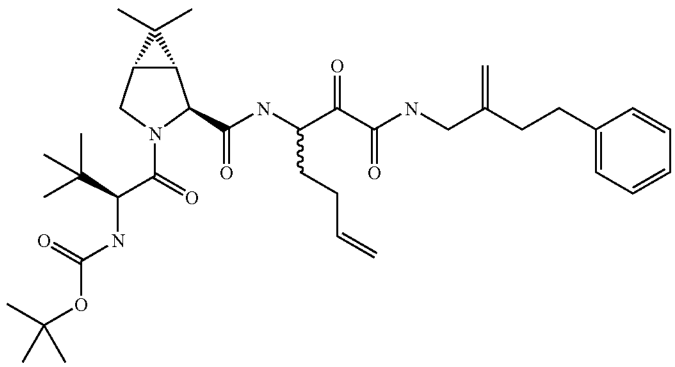 | 651 | C |
| 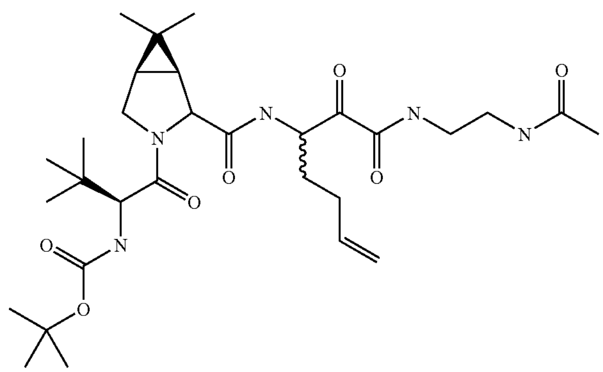 | 592 | B |
| 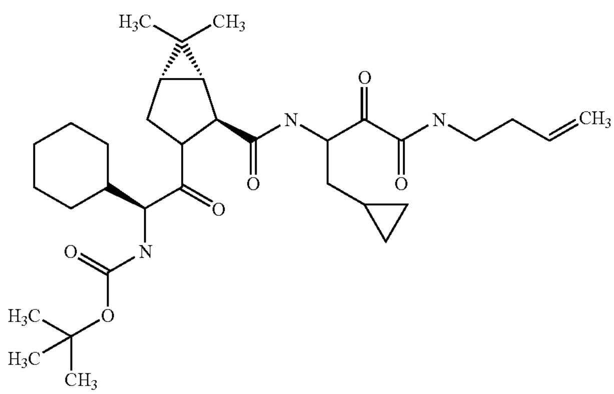 | 587 | C |
| 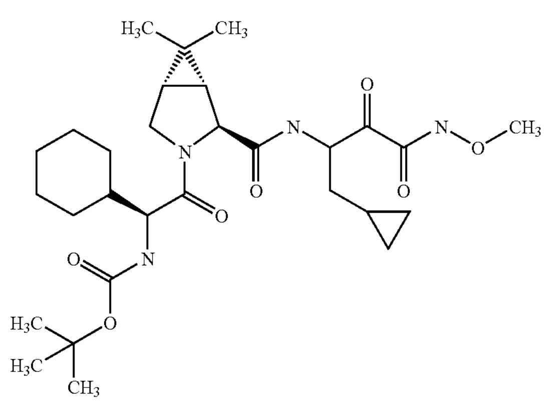 | 563 | B |

TABLE 5-continued
| STRUCTURE | MW | Ki* Range |
|---|---|---|
| 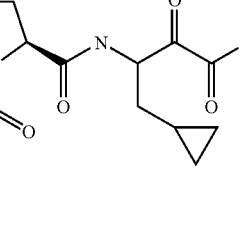 | 589 | C |
| 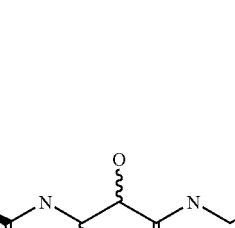 | 621 | C |
| 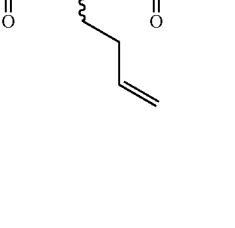 | 519 | C |
| 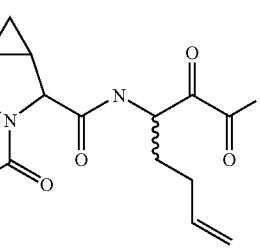 | 597 | B |

TABLE 5-continued
| STRUCTURE | MW | Ki* Range |
|---|---|---|
| 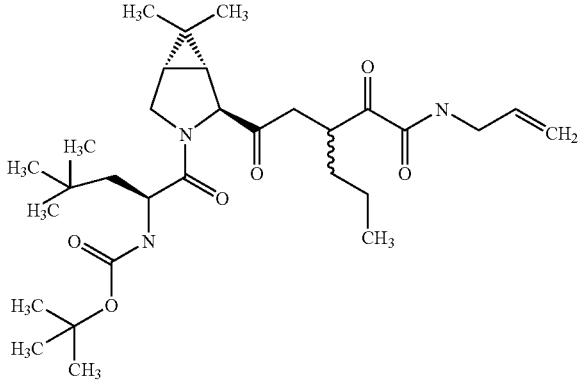 | 549 | C |
| 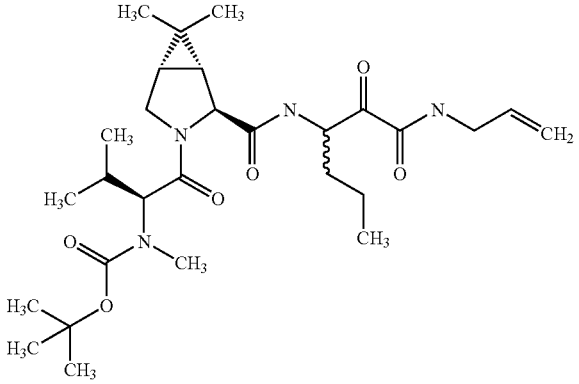 | 535 | C |
| 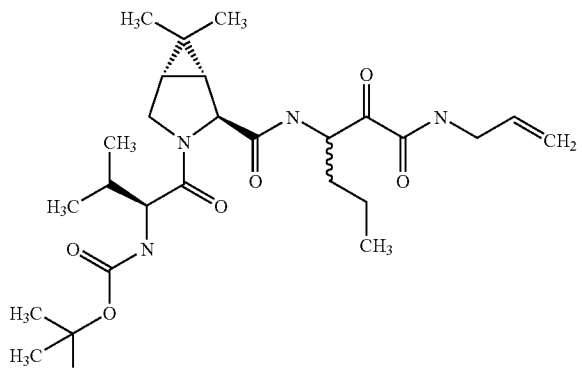 | 521 | B |
| 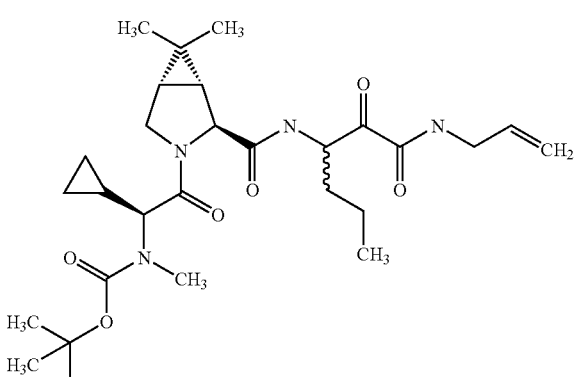 | 519 | C |

TABLE 5-continued

| STRUCTURE | MW | Ki* Range |
|---|---|---|
| 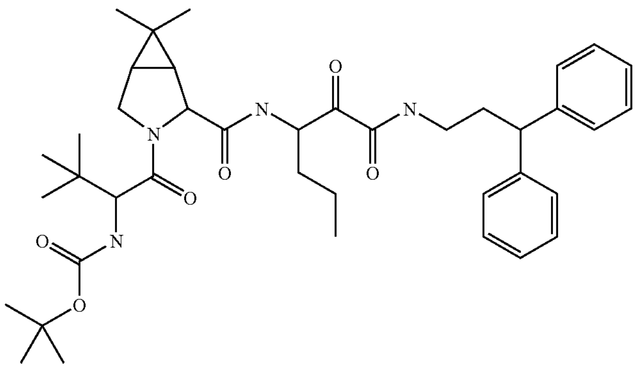 | 689 | C |
| 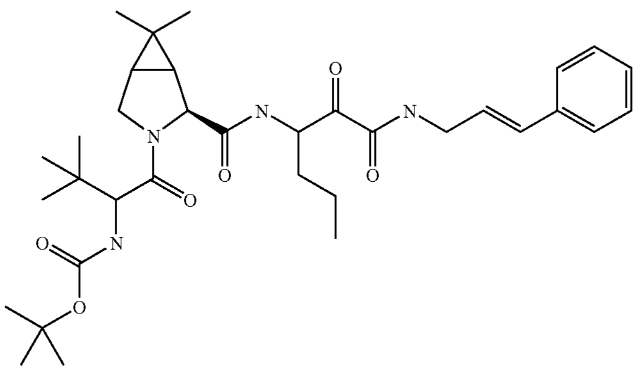 | 611 | C |
| 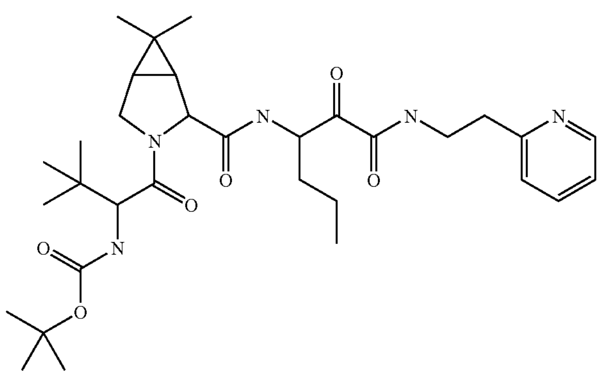 | 600 | C |
| 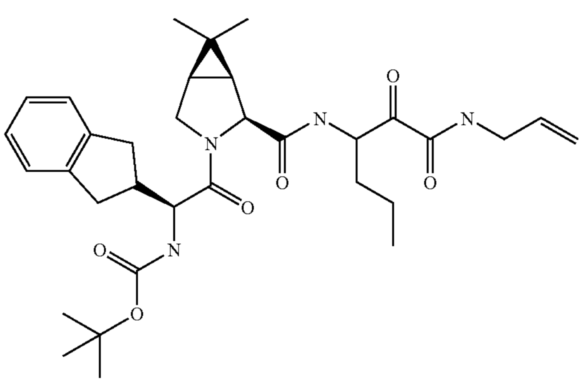 | 595 | B |

TABLE 5-continued

| STRUCTURE | MW | Ki* Range |
|---|---|---|
| 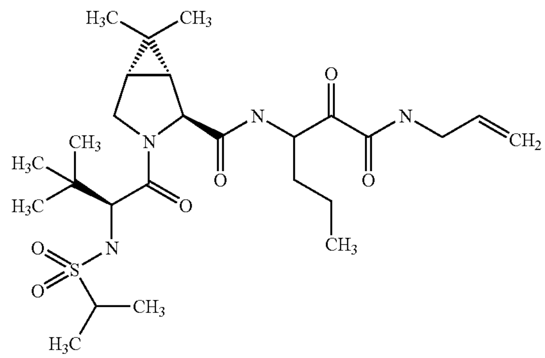 | 541 | C |
| 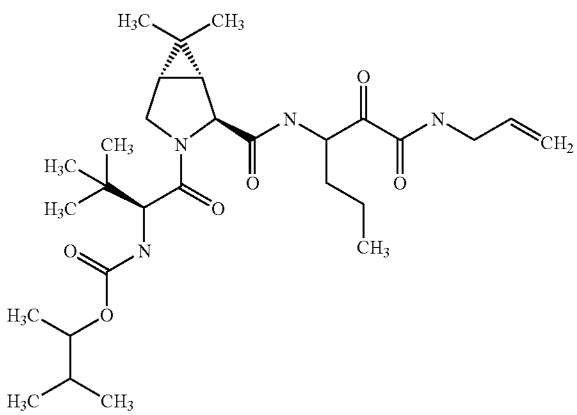 | 549 | B |
| 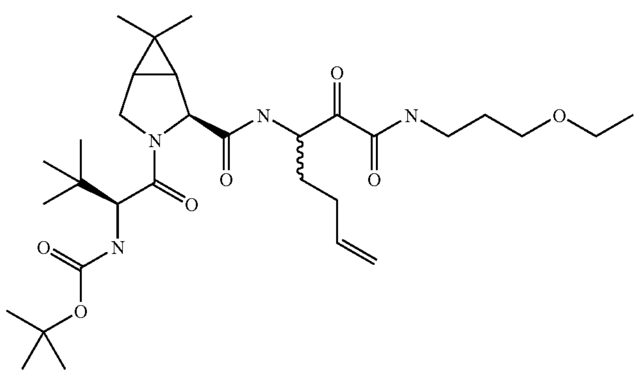 | 593 | C |
| 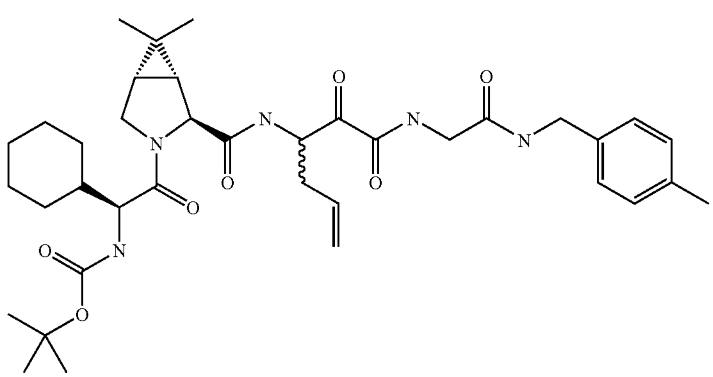 | 680 | B |

TABLE 5-continued
| STRUCTURE | MW | Ki* Range |
|---|---|---|
| 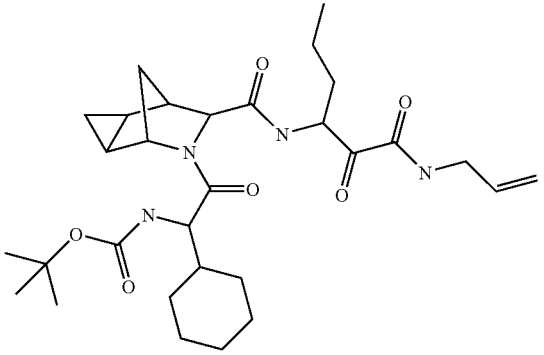 | 559 | C |
| 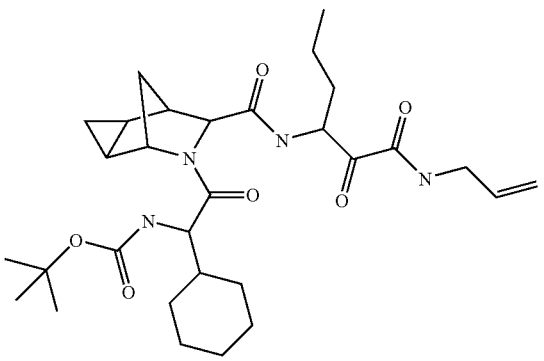 | 559 | C |
| 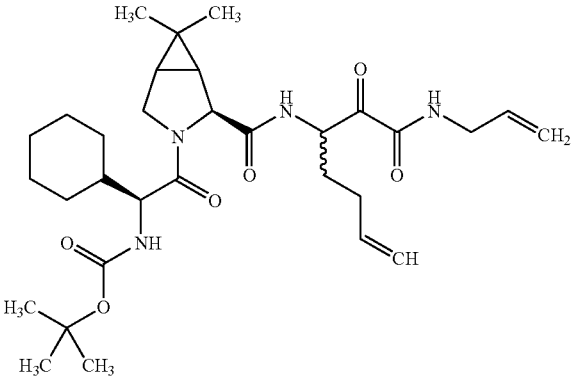 | 573 | B |
| 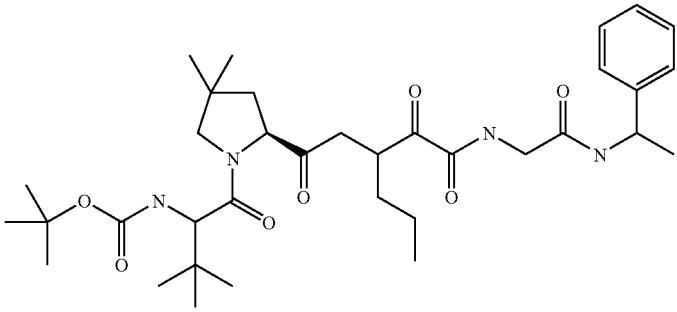 | 644 | C |

TABLE 5-continued

| STRUCTURE | MW | Ki* Range |
|---|---|---|
| 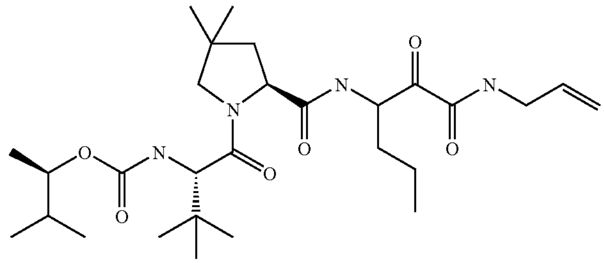 | 537 | C |
| 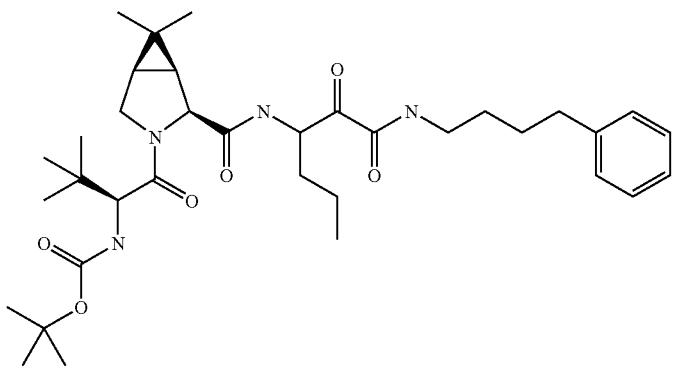 | 627 | C |
| 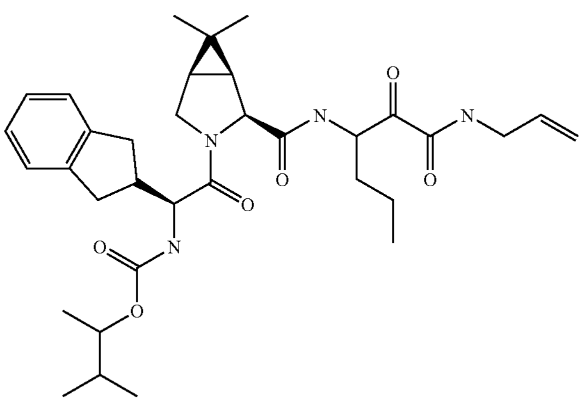 | 609 | B |
| 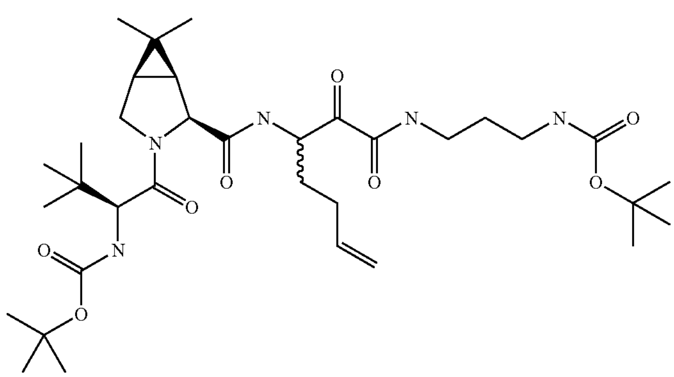 | 664 | B |

TABLE 5-continued

| STRUCTURE | MW | Ki* Range |
|---|---|---|
| 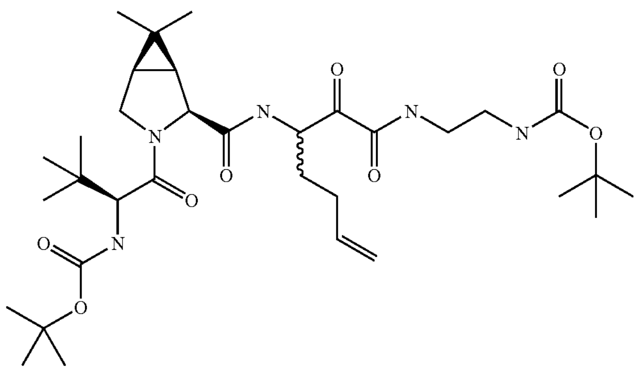 | 650 | C |
| | 661 | B |
| 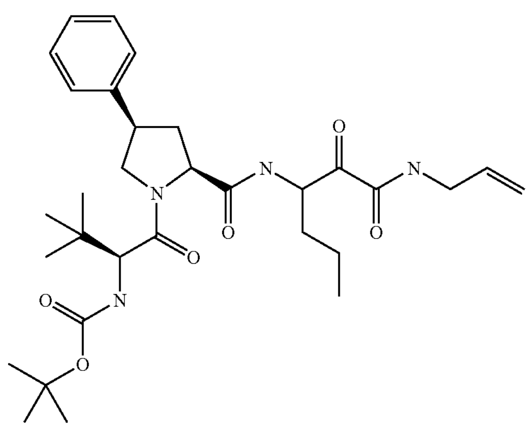 | 571 | C |
| | 661 | B |

TABLE 5-continued

| STRUCTURE | MW | Ki* Range |
|---|---|---|
| 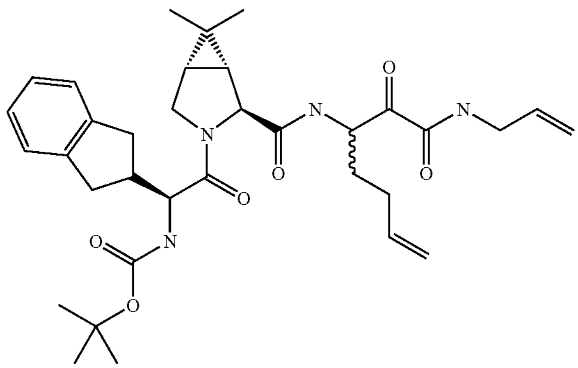 | 607 | B |
| 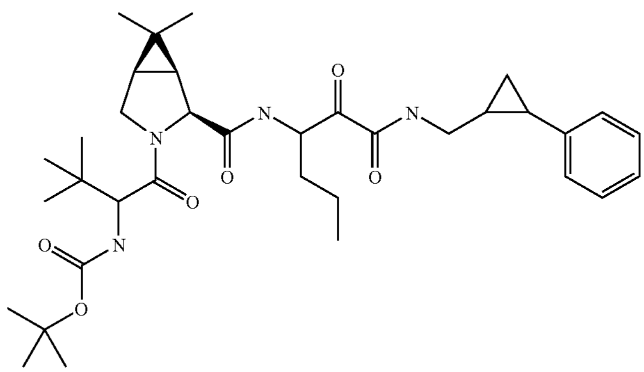 | 625 | C |
| | 575 | B |
| | 575 | B |

TABLE 5-continued
| STRUCTURE | MW | Ki* Range |
|---|---|---|
|  | 575 | B |
|  | 575 | B |
| 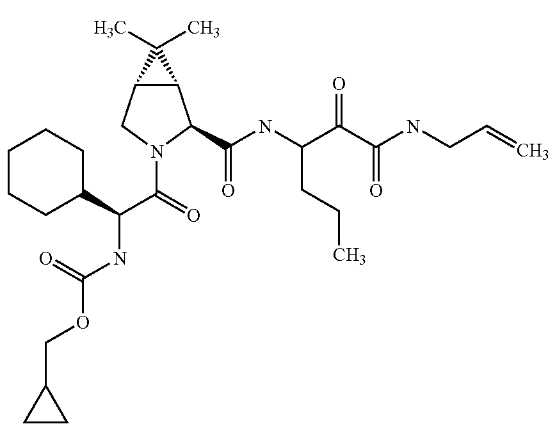 | 559 | B |

TABLE 5-continued

| STRUCTURE | MW | Ki* Range |
|---|---|---|
| 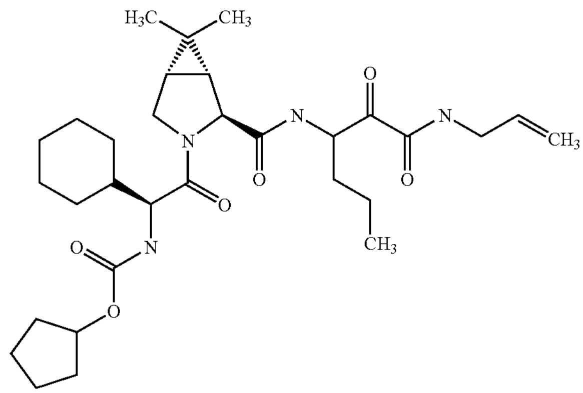 | 573 | B |
| 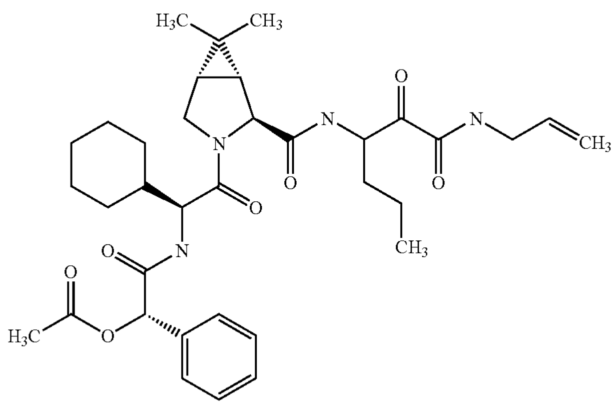 | 637 | B |
| 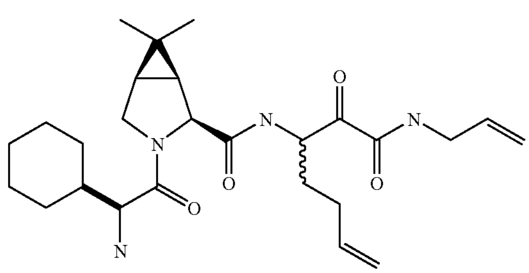 | 473 | C |
| 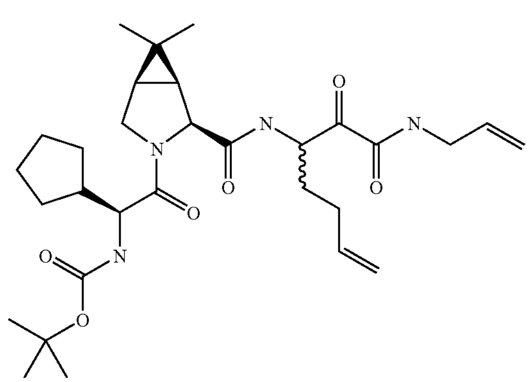 | 559 | B |

TABLE 5-continued

| STRUCTURE | MW | Ki* Range |
|---|---|---|
| 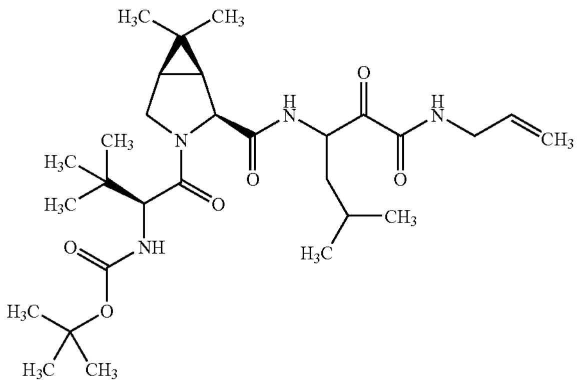 | 549 | C |
| 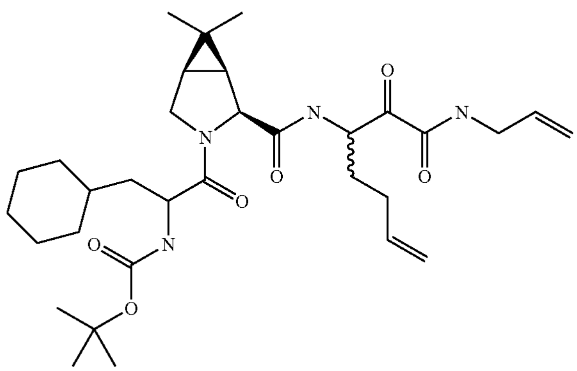 | 587 | C |
| | 547 | C |
| | 547 | B |

TABLE 5-continued

| STRUCTURE | MW | Ki* Range |
|---|---|---|
| | 573 | C |
| | 573 | C |
| 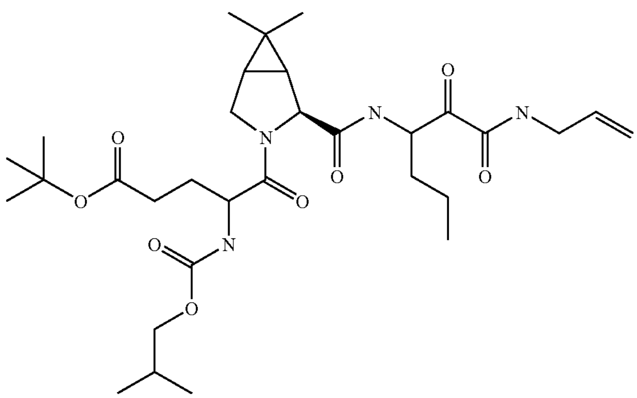 | 607 | C |
| 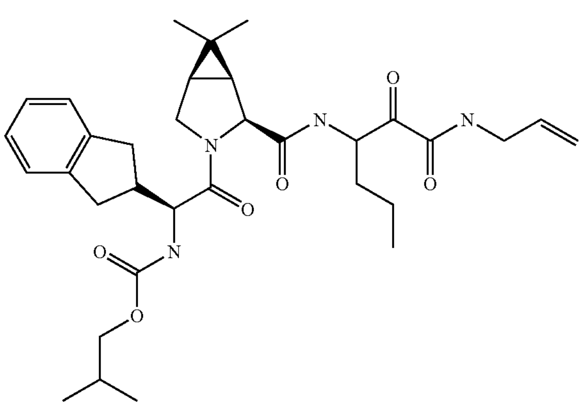 | 595 | B |

TABLE 5-continued
| STRUCTURE | MW | Ki* Range |
|---|---|---|
| 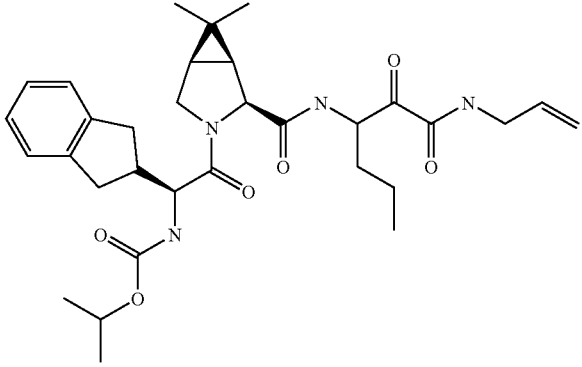 | 581 | B |
| 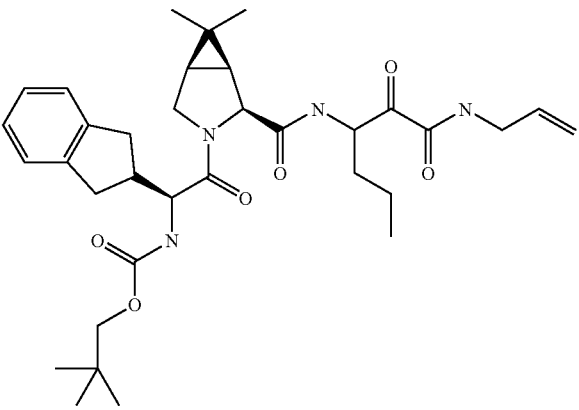 | 609 | B |
| 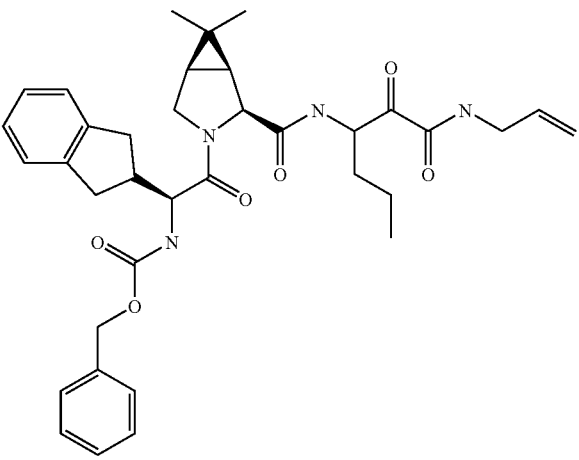 | 629 | C |

TABLE 5-continued

| STRUCTURE | MW | Ki* Range |
|---|---|---|
| 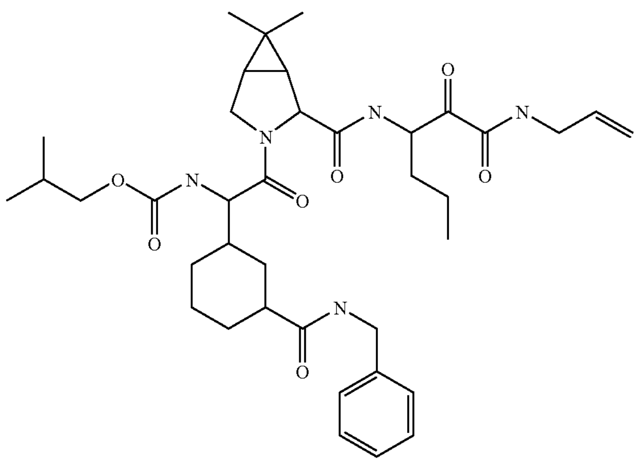 | 694 | C |
| 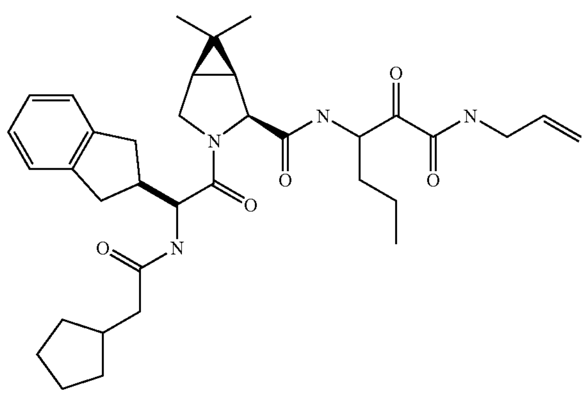 | 605 | C |
| 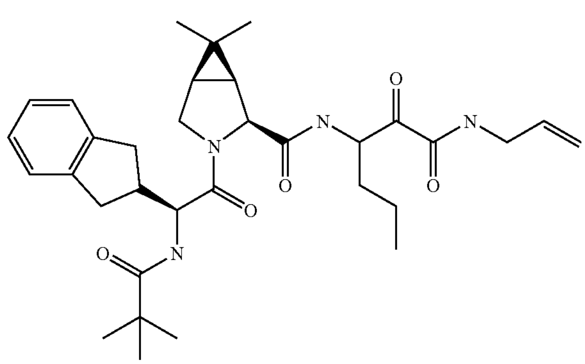 | 579 | C |

TABLE 5-continued

| STRUCTURE | MW | Ki* Range |
|---|---|---|
| 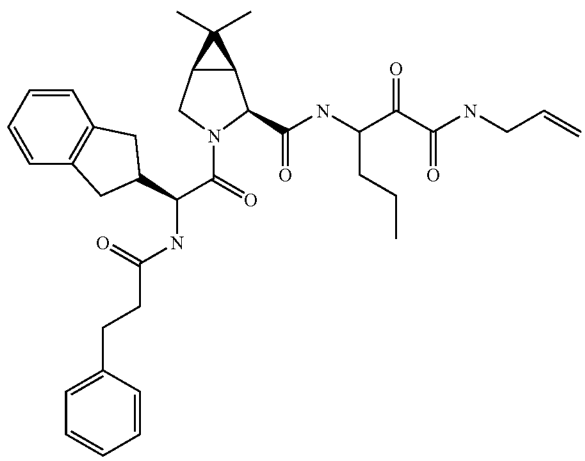 | 627 | C |
| 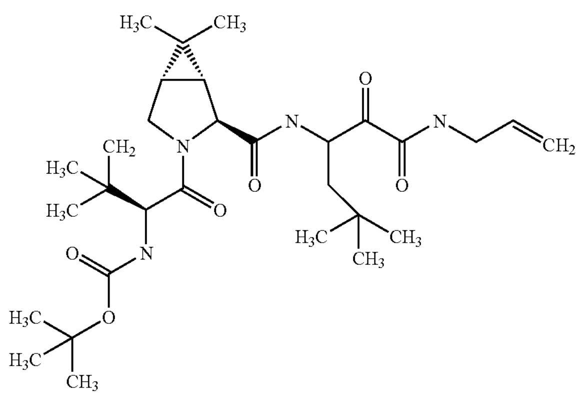 | 563 | C |
| 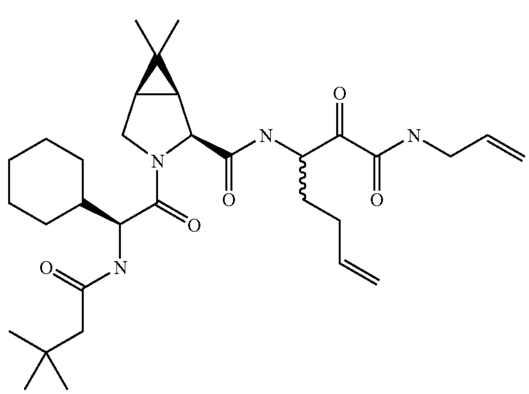 | 571 | C |

TABLE 5-continued
| STRUCTURE | MW | Ki* Range |
|---|---|---|
| 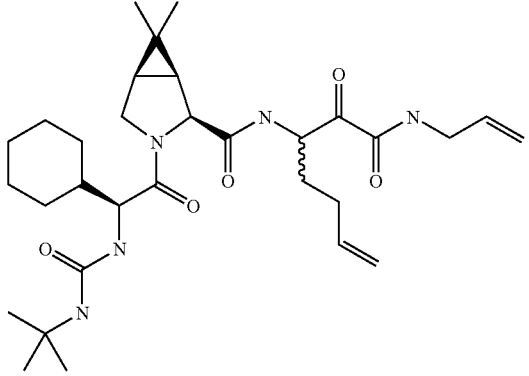 | 572 | B |
| 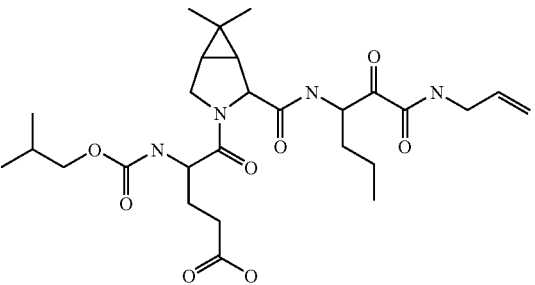 | 551 | C |
| 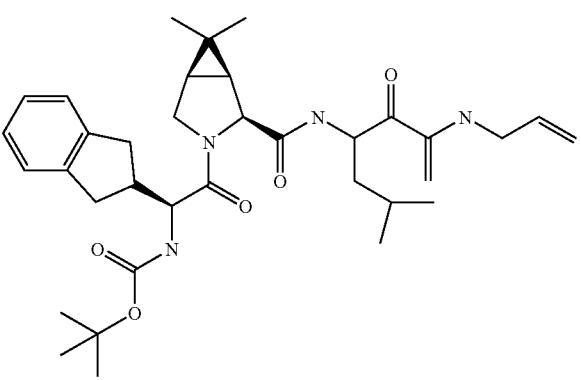 | 609 | C |
| 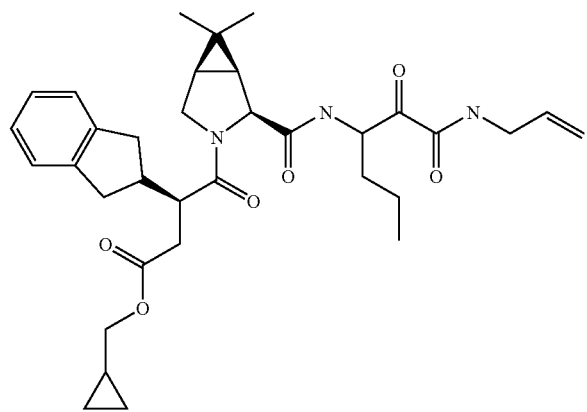 | 593 | B |

TABLE 5-continued

| STRUCTURE | MW | Ki* Range |
|---|---|---|
| | 593 | C |
| 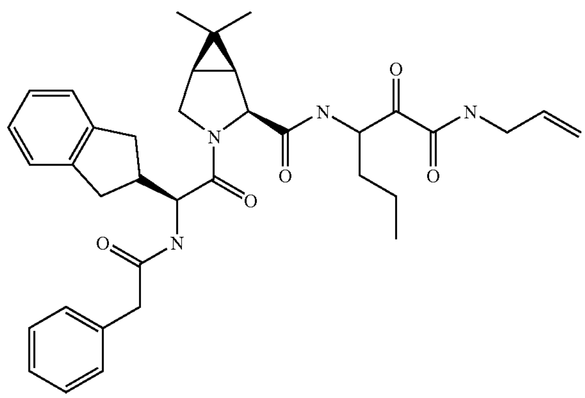 | 613 | C |
| | 593 | B |
| 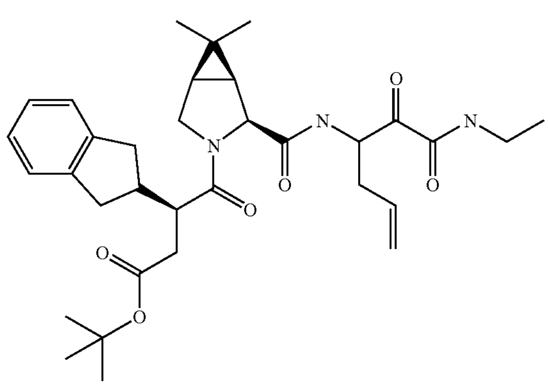 | 581 | C |

TABLE 5-continued

| STRUCTURE | MW | Ki* Range |
|---|---|---|
| | 571 | 6 |
| 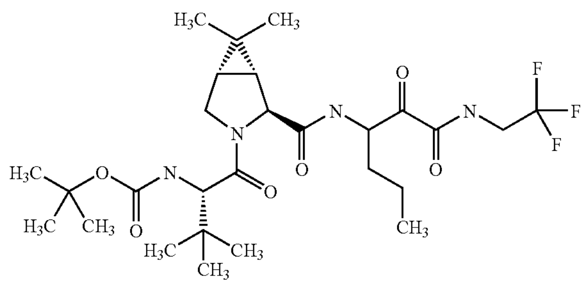 | 577 | C |
| 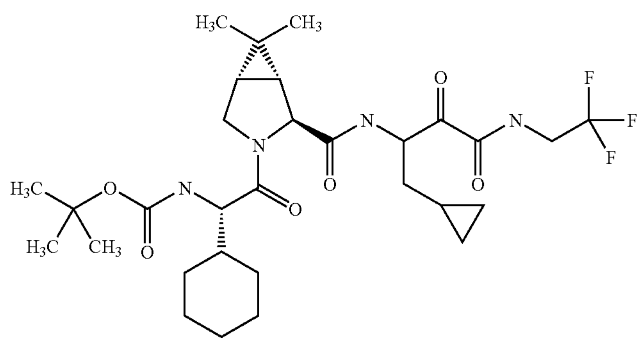 | 615 | C |
| | 571 | C |

TABLE 5-continued

| STRUCTURE | MW | Ki* Range |
|---|---|---|
| 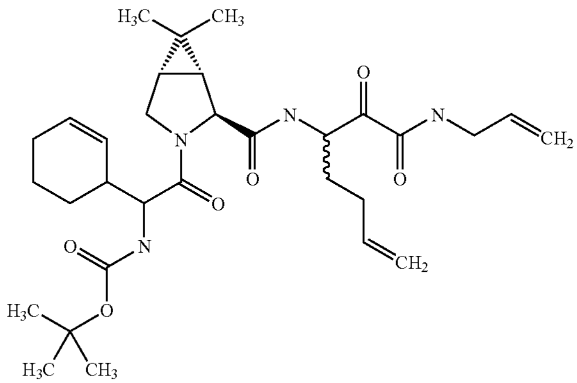 | 571 | C |
| 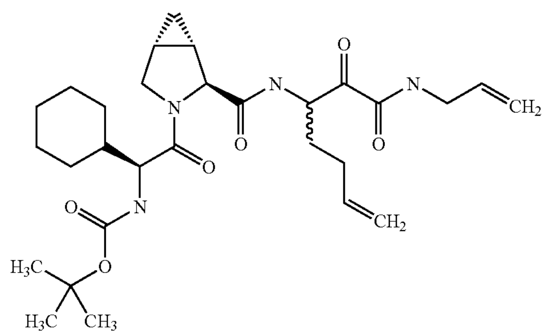 | 545 | C |
| 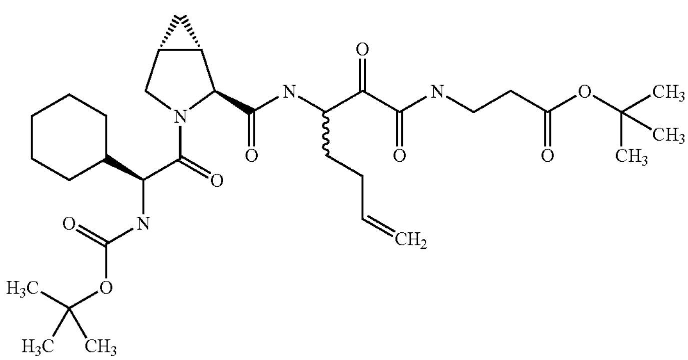 | 633 | C |
| 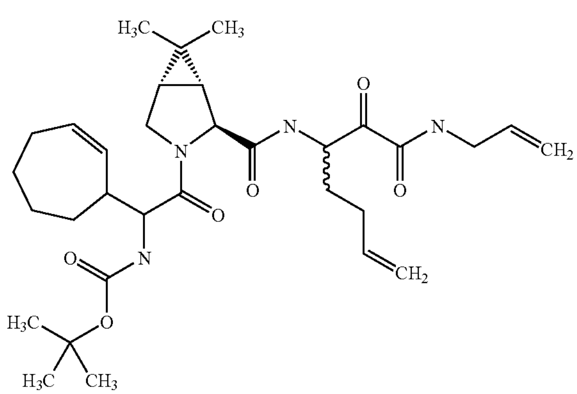 | 585 | B |

TABLE 5-continued

| STRUCTURE | MW | Ki* Range |
|---|---|---|
| 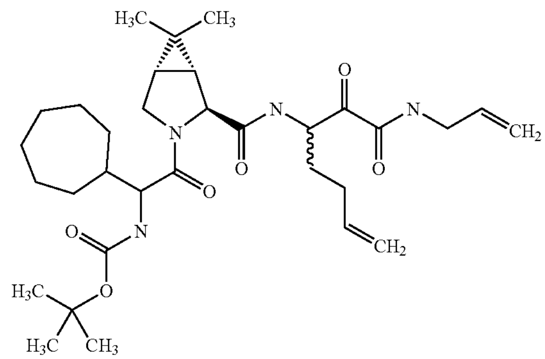 | 587 | B |
| 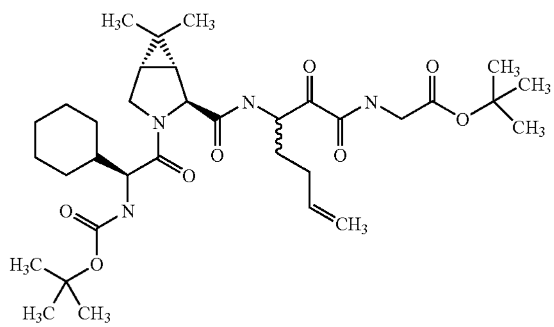 | 647 | B |
| 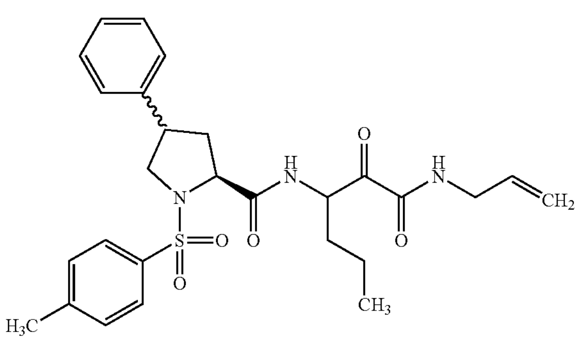 | 512 | C |
| 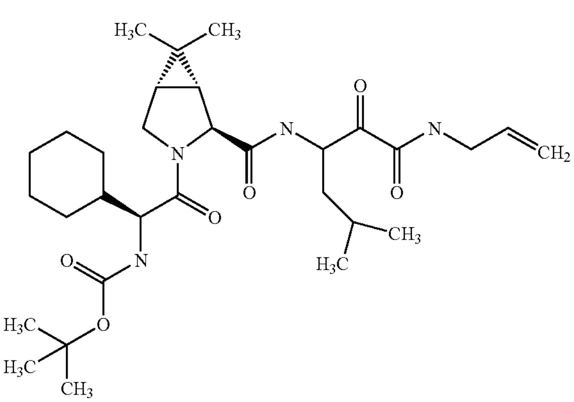 | 575 | C |

TABLE 5-continued
| STRUCTURE | MW | Ki* Range |
|---|---|---|
| 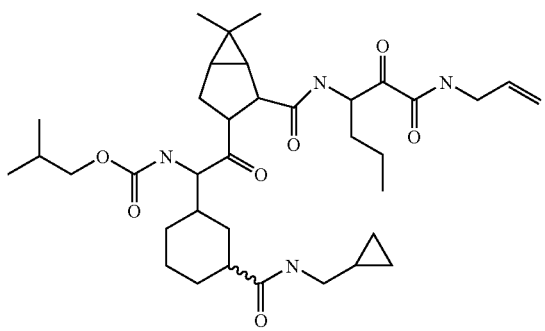 | 658 | C |
| 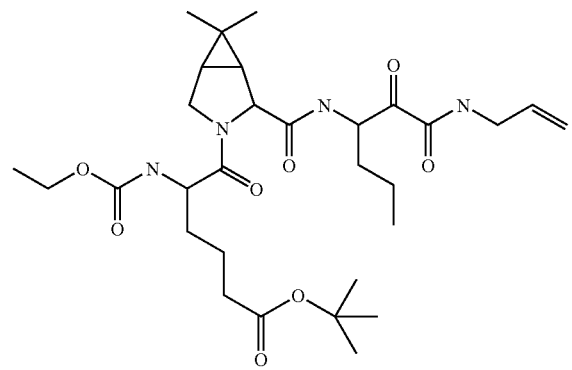 | 621 | C |
| 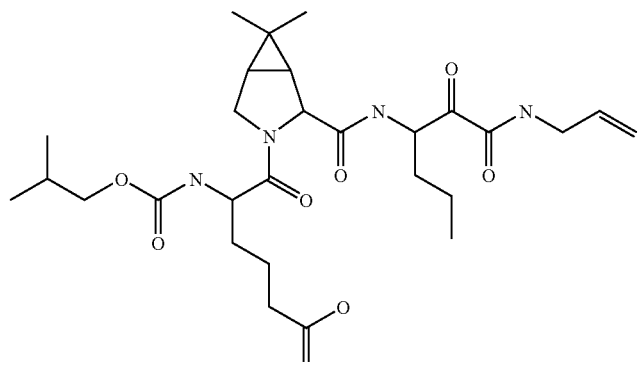 | 565 | C |
| 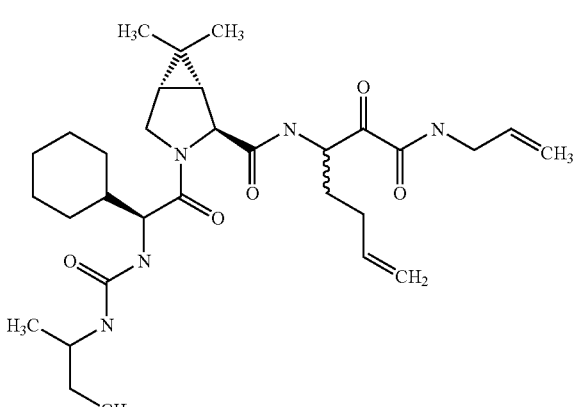 | 572 | A |

TABLE 5-continued

| STRUCTURE | MW | Ki* Range |
|---|---|---|
| | 587 | A |
| | 587 | B |
| 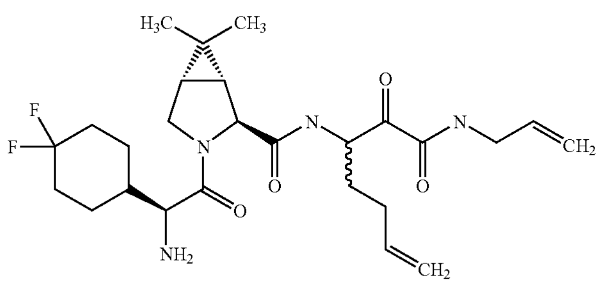 | 509 | C |
| 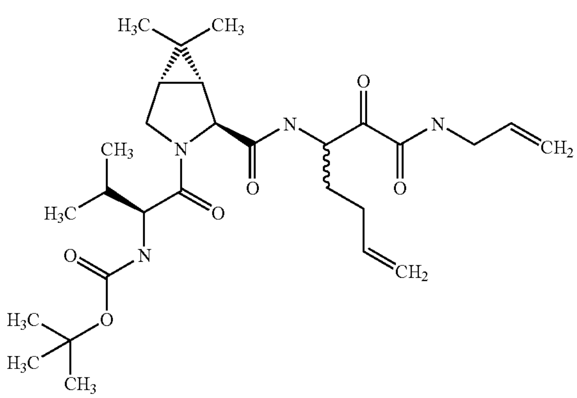 | 533 | C |

TABLE 5-continued

| STRUCTURE | MW | Ki* Range |
|---|---|---|
| 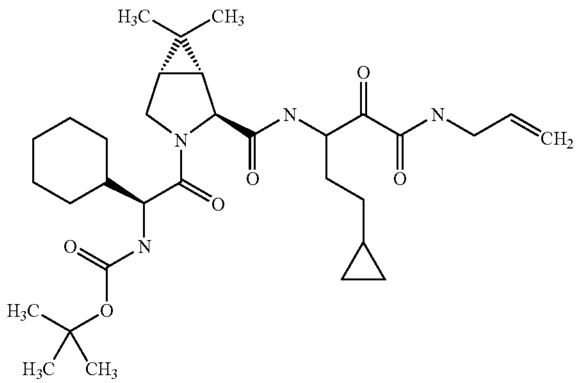 | 587 | B |
| 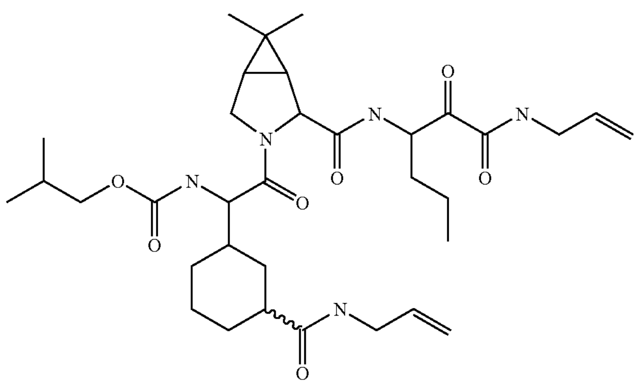 | 644 | C |
| 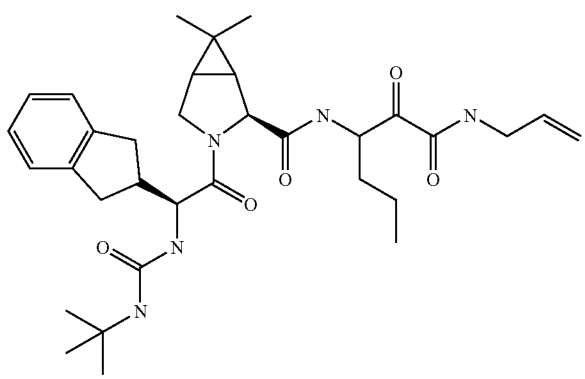 | 594 | B |
| 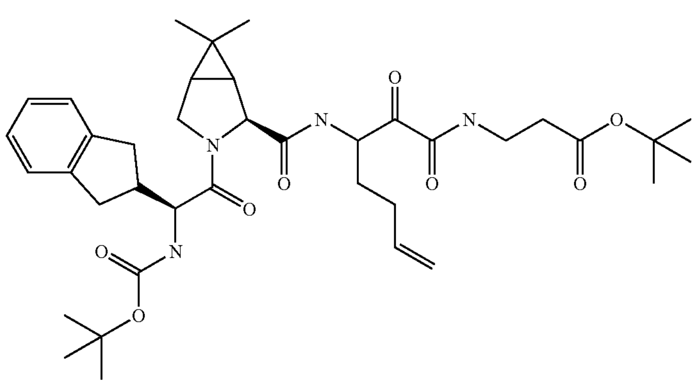 | 695 | B |

TABLE 5-continued

| STRUCTURE | MW | Ki* Range |
|---|---|---|
| 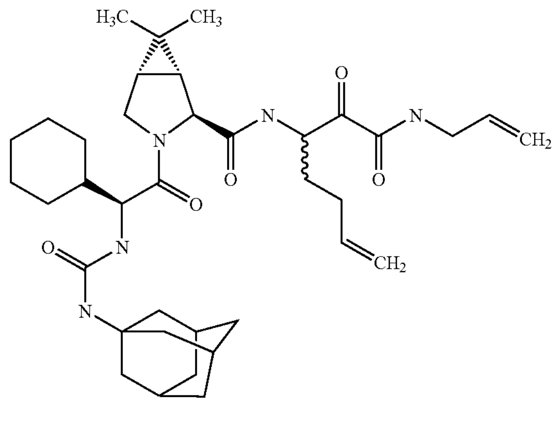 | 650 | B |
| 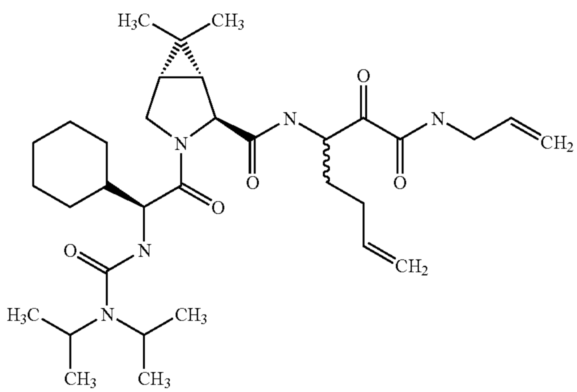 | 600 | B |
| 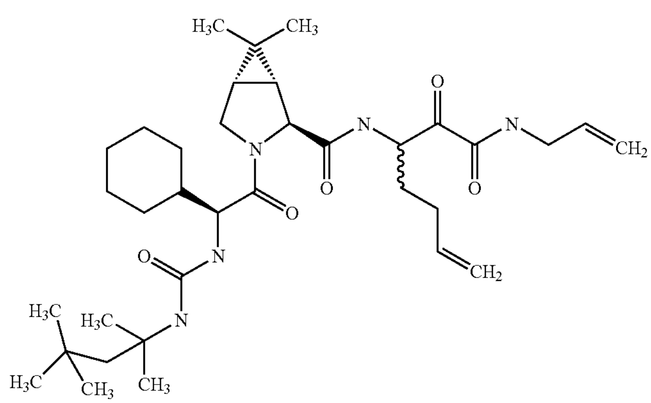 | 628 | A |

TABLE 5-continued

| STRUCTURE | MW | Ki* Range |
|---|---|---|
| 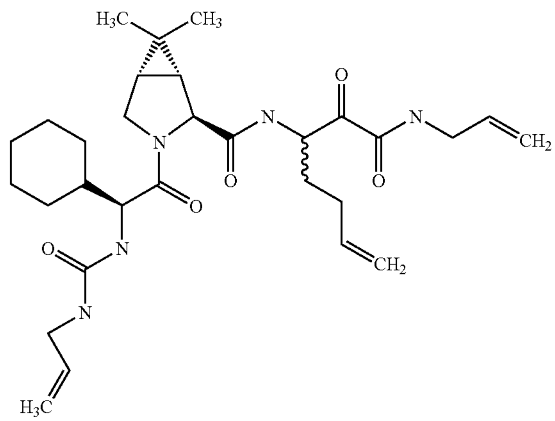 | 556 | B |
| 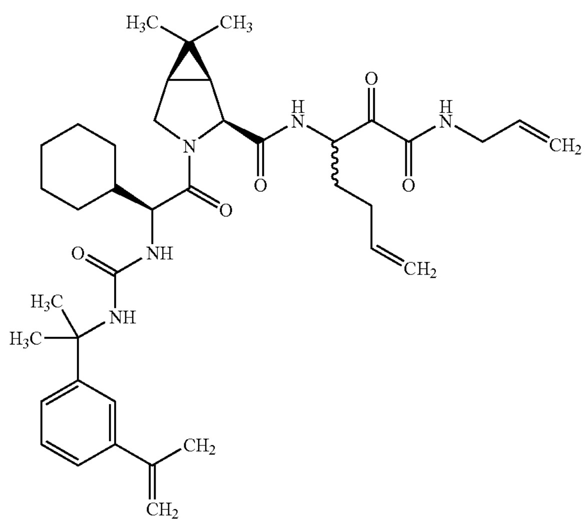 | 674 | B |
| 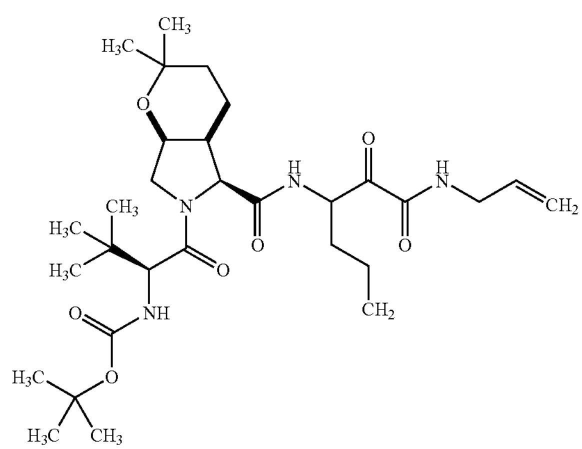 | 579 | C |

TABLE 5-continued

| STRUCTURE | MW | Ki* Range |
|---|---|---|
| 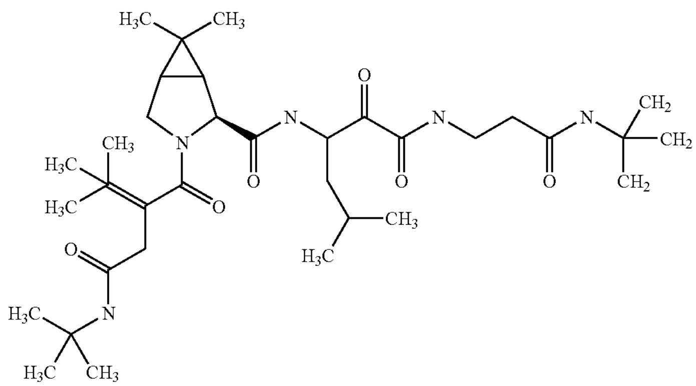 | 637 | C |
| 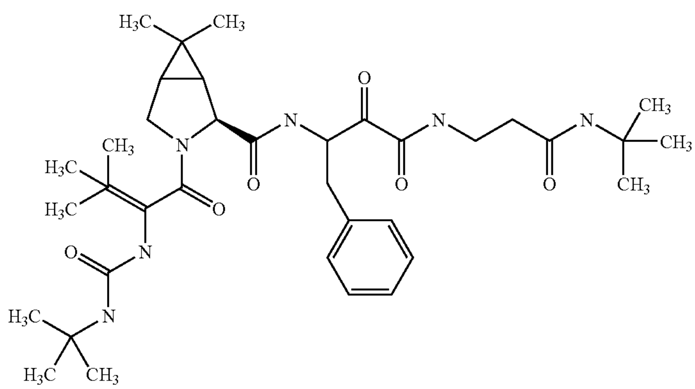 | 671 | C |
| 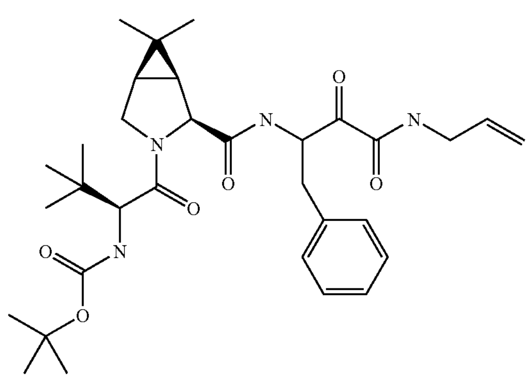 | 583 | C |
| 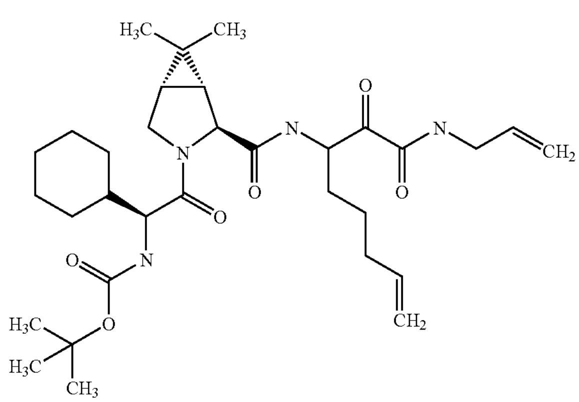 | 587 | B |

TABLE 5-continued

| STRUCTURE | MW | Ki* Range |
|---|---|---|
| 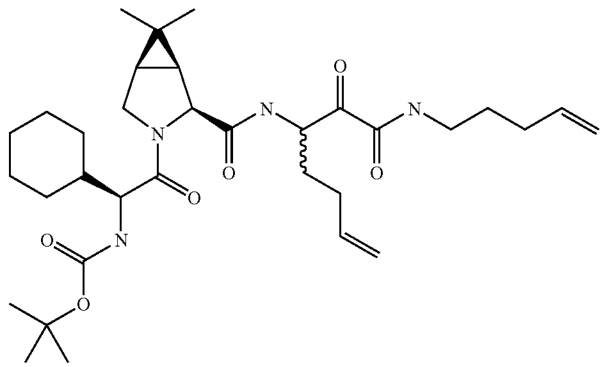 | 601 | B |
| 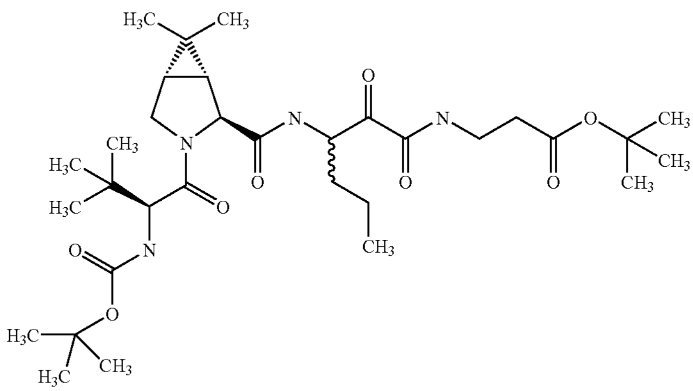 | 623 | B |
| 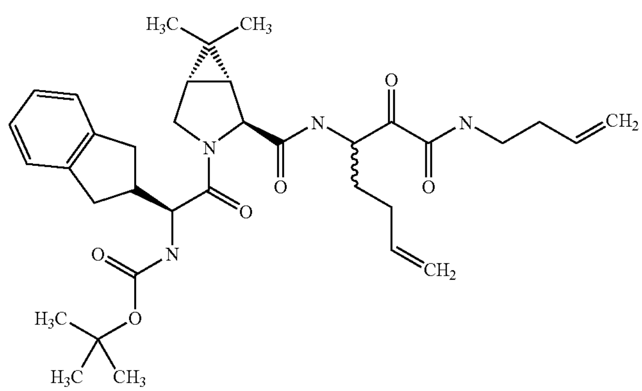 | 621 | A |
| 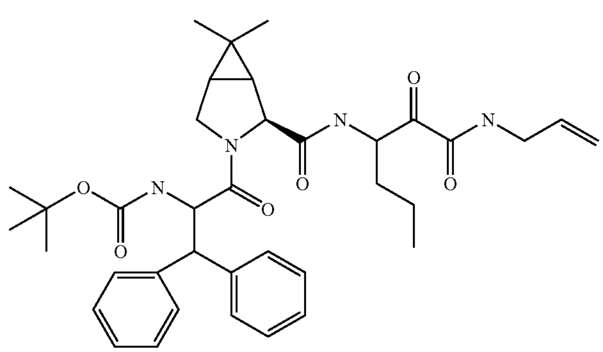 | 645 | C |

TABLE 5-continued

| STRUCTURE | MW | Ki* Range |
|---|---|---|
| 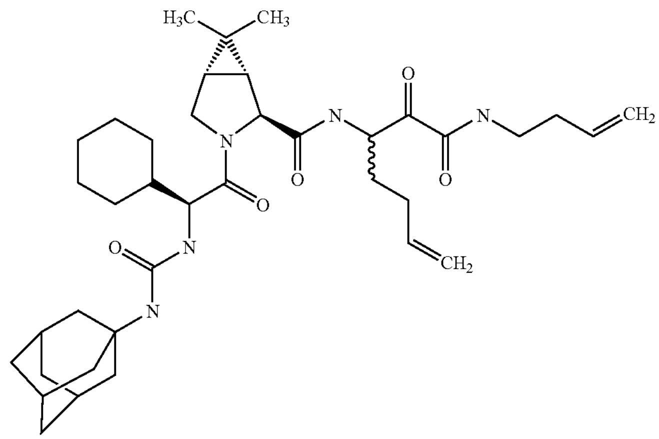 | 664 | B |
| 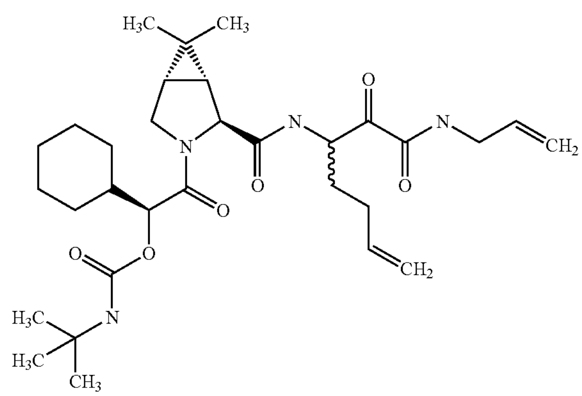 | 573 | C |
| 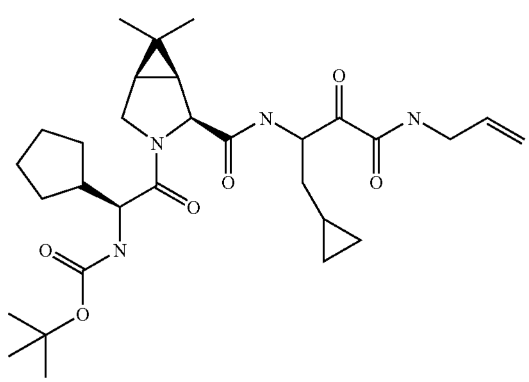 | 559 | C |

TABLE 5-continued
| STRUCTURE | MW | Ki* Range |
|---|---|---|
| 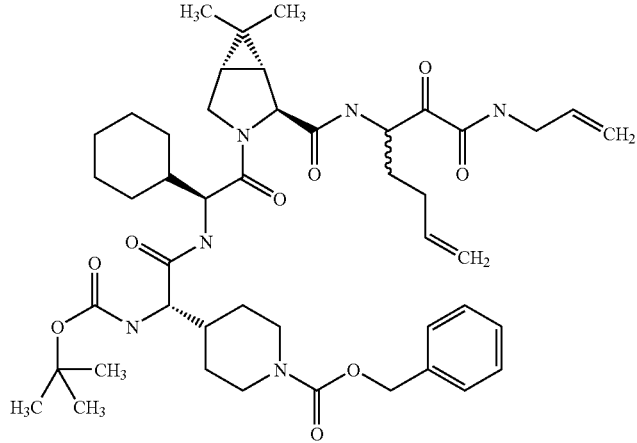 | 847 | B |
| 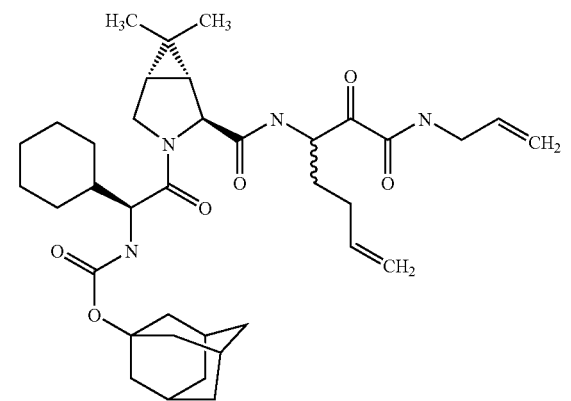 | 651 | B |
| 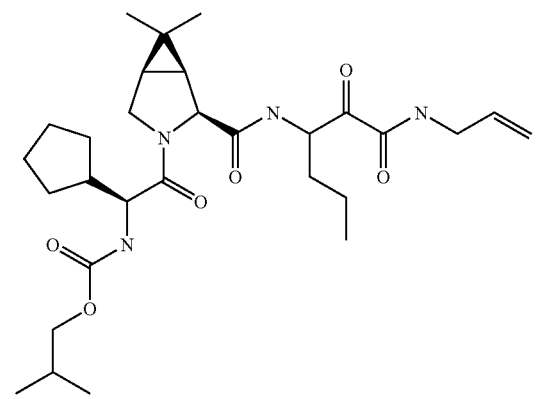 | 547 | C |

TABLE 5-continued
| STRUCTURE | MW | Ki* Range |
|---|---|---|
| 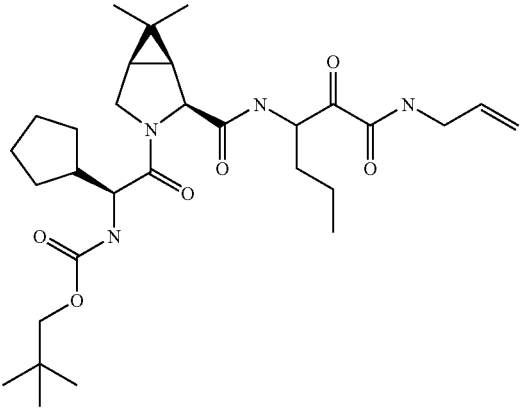 | 561 | B |
| 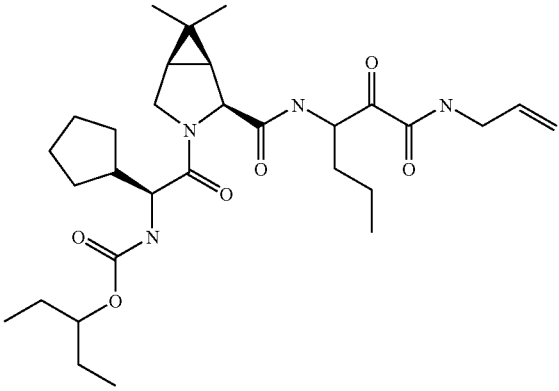 | 561 | B |
| 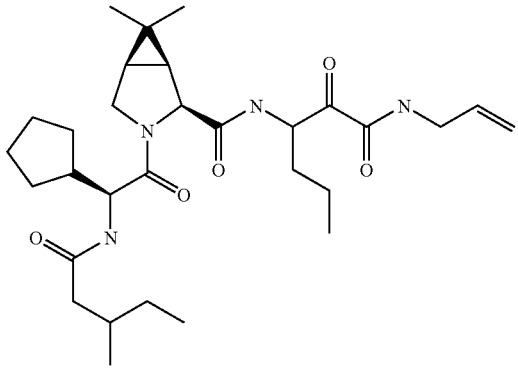 | 546 | C |
| 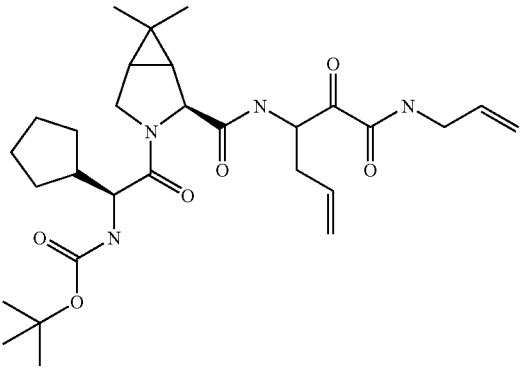 | 545 | C |

TABLE 5-continued
| STRUCTURE | MW | Ki* Range |
|---|---|---|
| 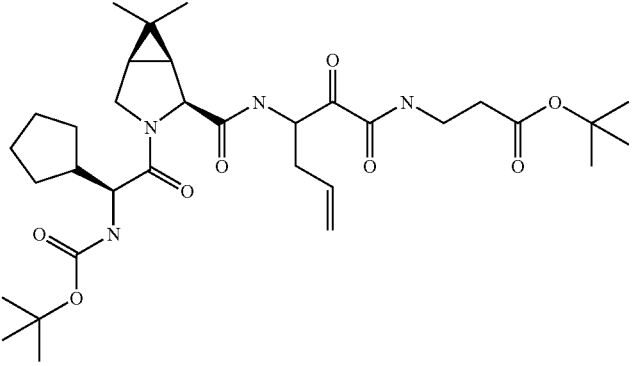 | 633 | B |
| 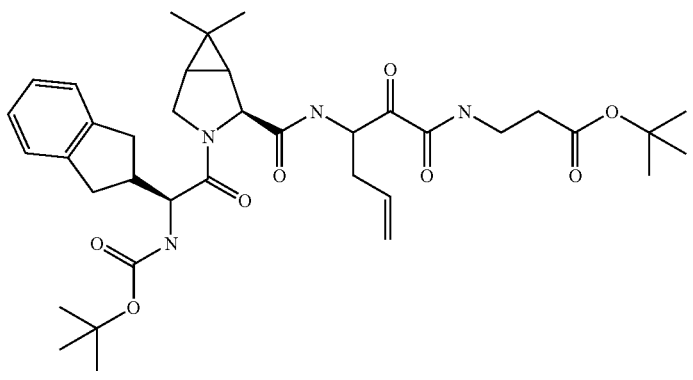 | 681 | C |
| 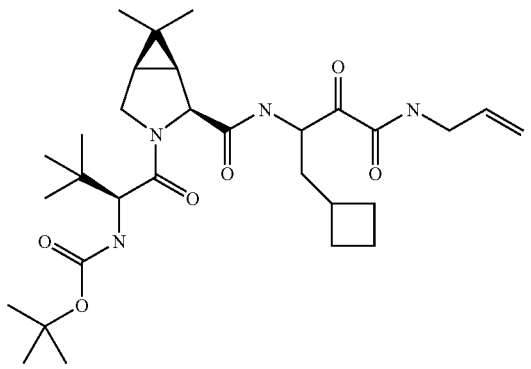 | 561 | C |
| 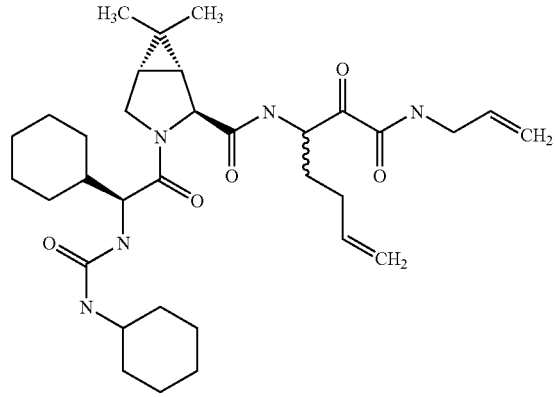 | 598 | B |

TABLE 5-continued
| STRUCTURE | MW | Ki* Range |
|---|---|---|
| 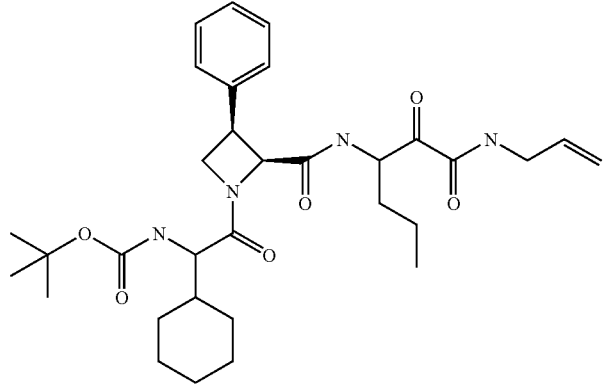 | 583 | C |
| 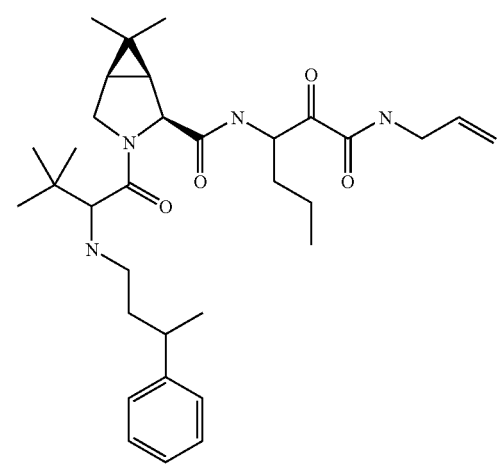 | 567 | C |
| 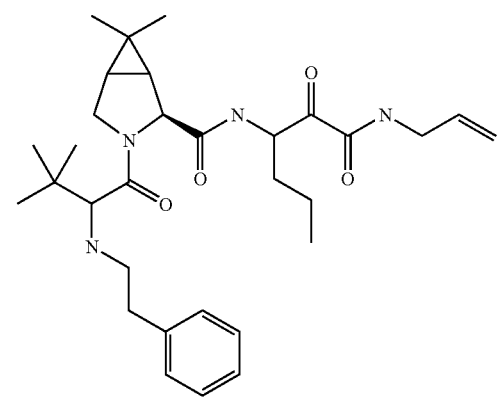 | 539 | C |

TABLE 5-continued

| STRUCTURE | MW | Ki* Range |
|---|---|---|
| 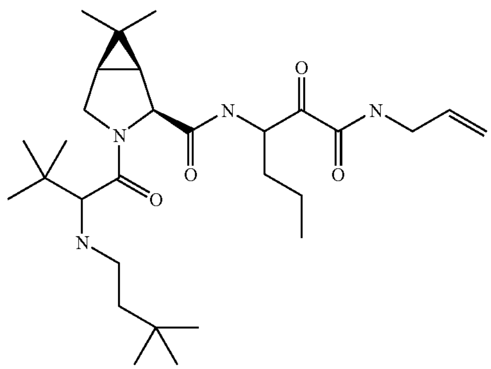 | 519 | C |
| 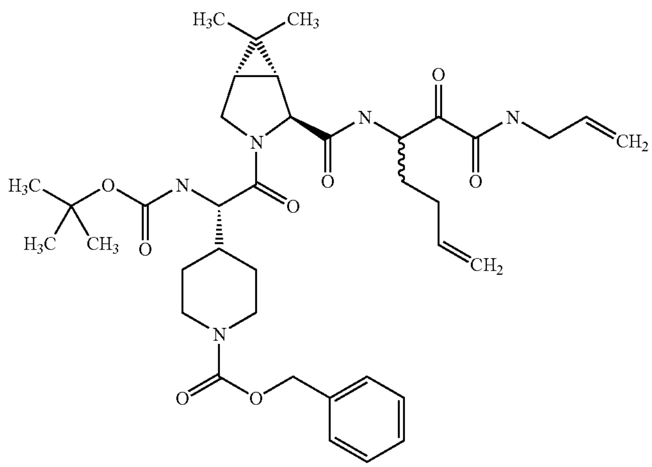 | 708 | B |
| 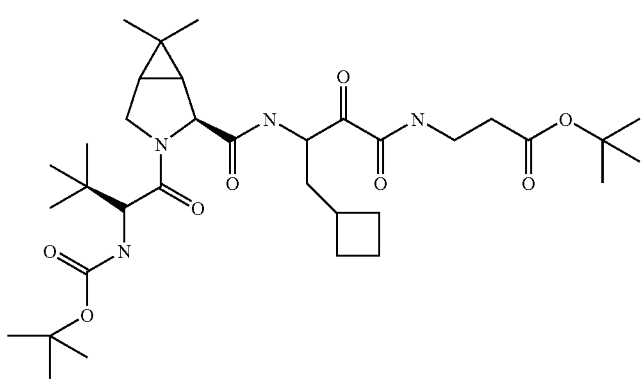 | 649 | C |
| 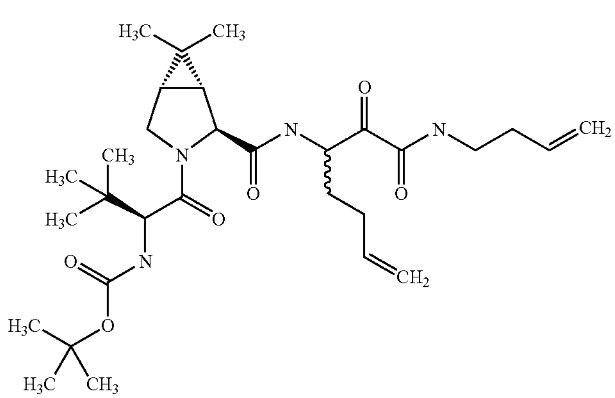 | 561 | B |

TABLE 5-continued

| STRUCTURE | MW | Ki* Range |
|---|---|---|
| 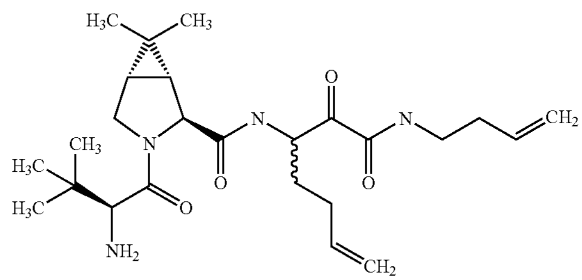 | 461 | C |
| 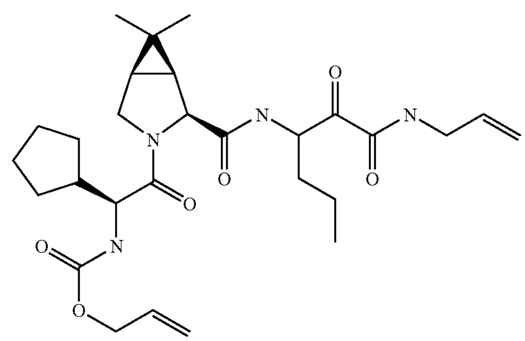 | 531 | C |
| | 606 | A |
| | 606 | A |

TABLE 5-continued

| STRUCTURE | MW | Ki* Range |
|---|---|---|
| 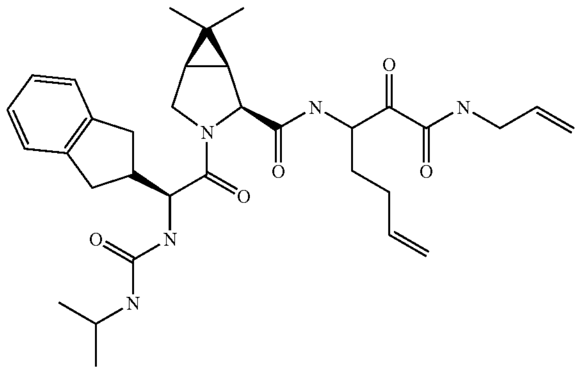 | 592 | A |
| 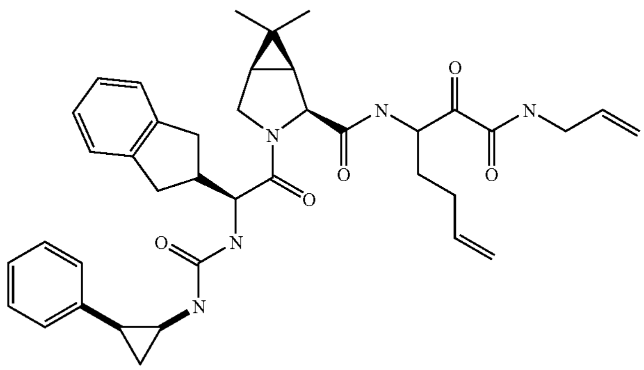 | 666 | C |
| 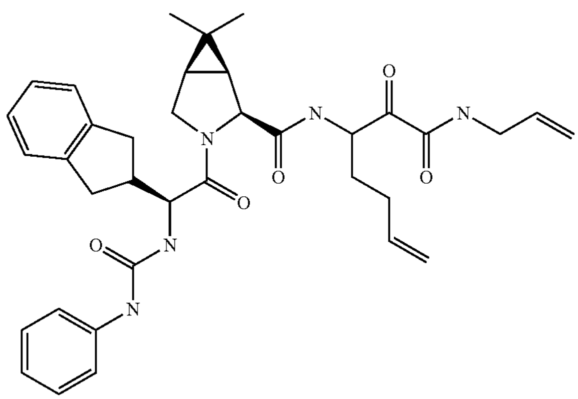 | 626 | B |
| 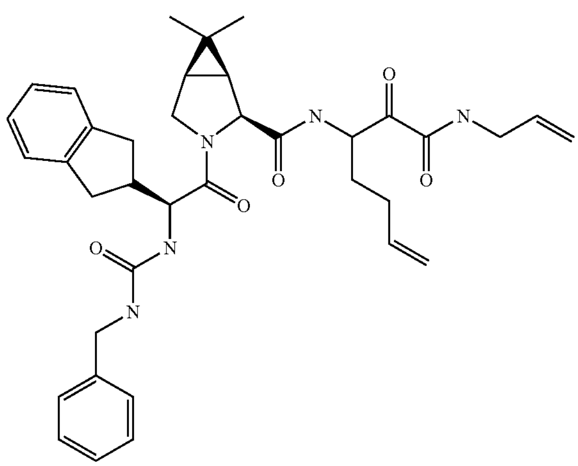 | 640 | B |

TABLE 5-continued
| STRUCTURE | MW | Ki* Range |
|---|---|---|
| 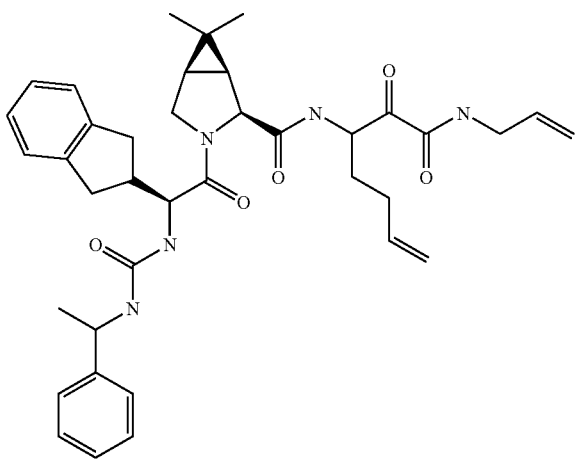 | 654 | B |
| 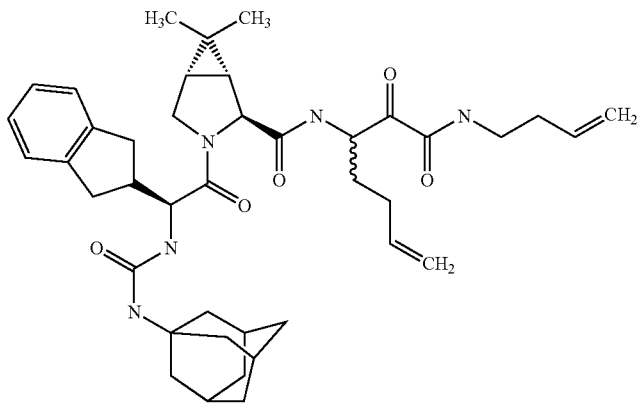 | 698 | B |
| 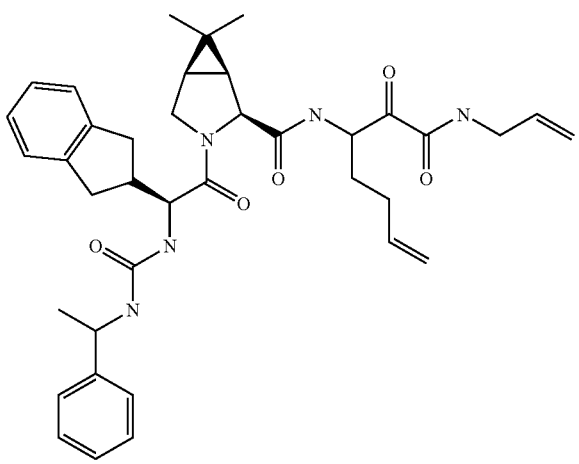 | 654 | B |

TABLE 5-continued
| STRUCTURE | MW | Ki* Range |
|---|---|---|
| 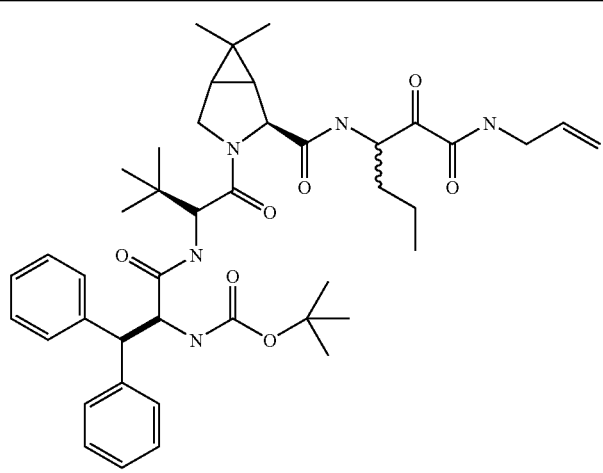 | 758 | C |
| 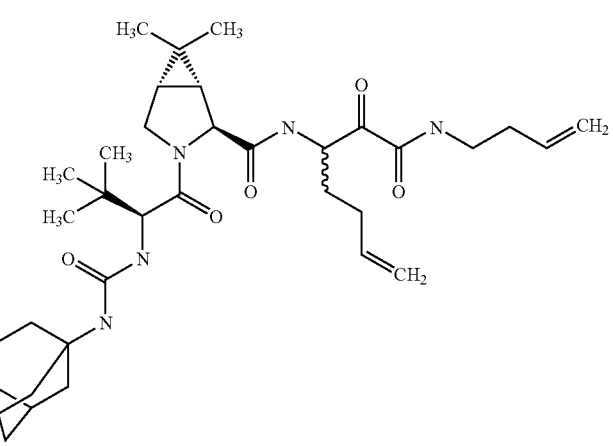 | 638 | A |
| 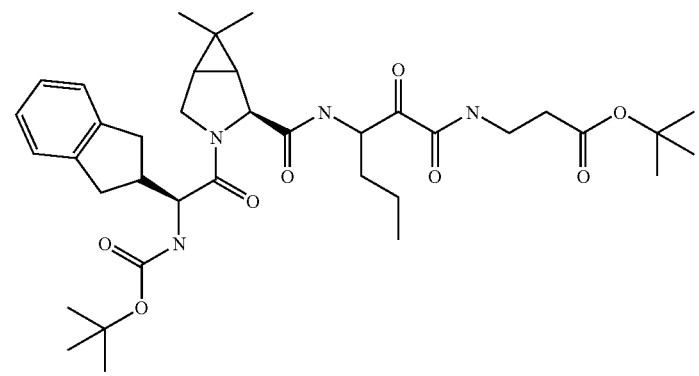 | 683 | B |

TABLE 5-continued

| STRUCTURE | MW | Ki* Range |
|---|---|---|
| 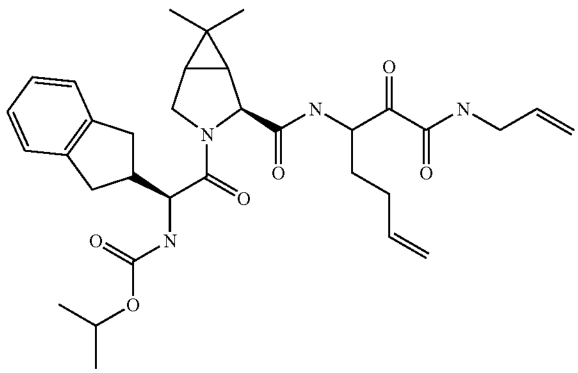 | 593 | A |
| 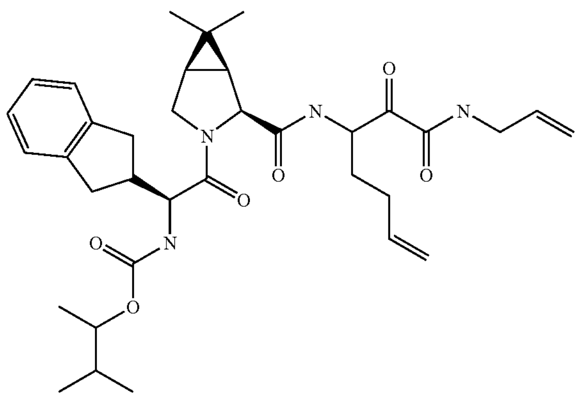 | 621 | A |
| 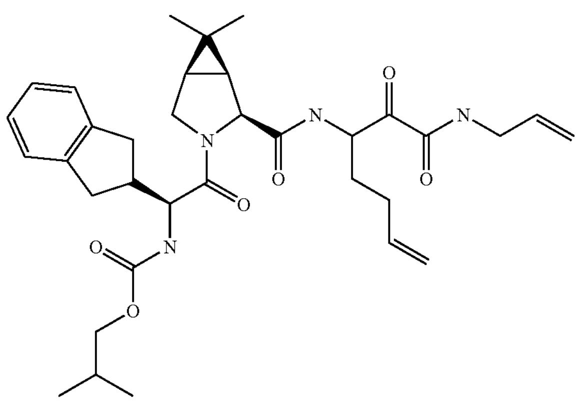 | 607 | B |
| 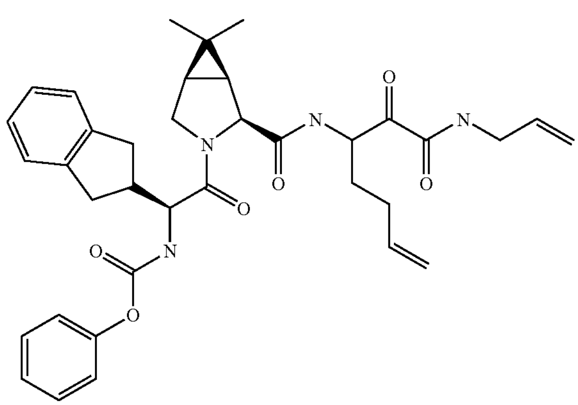 | 627 | B |

TABLE 5-continued

| STRUCTURE | MW | Ki* Range |
|---|---|---|
| 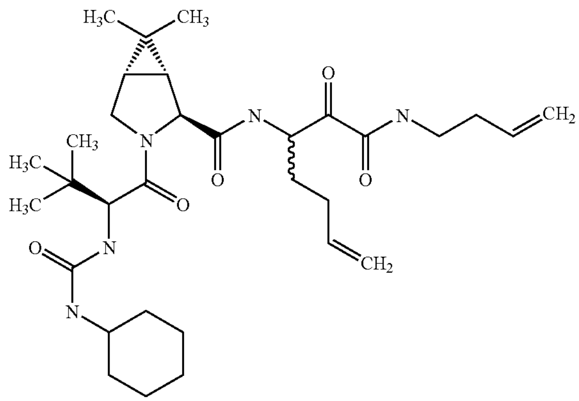 | 586 | A |
| 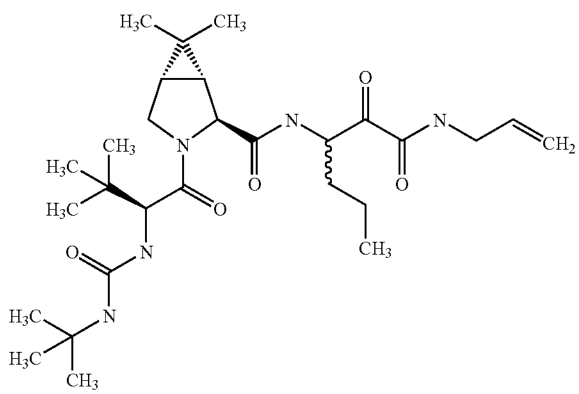 | 534 | B |
| 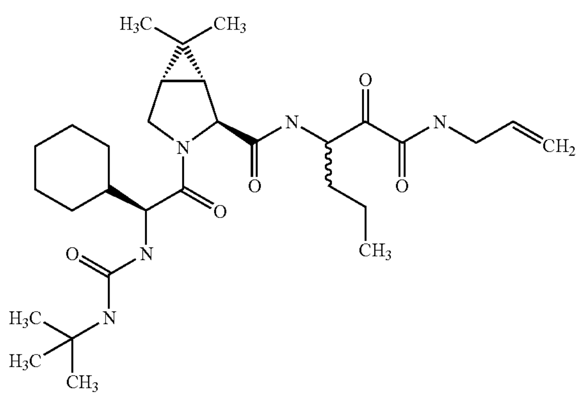 | 560 | C |
| 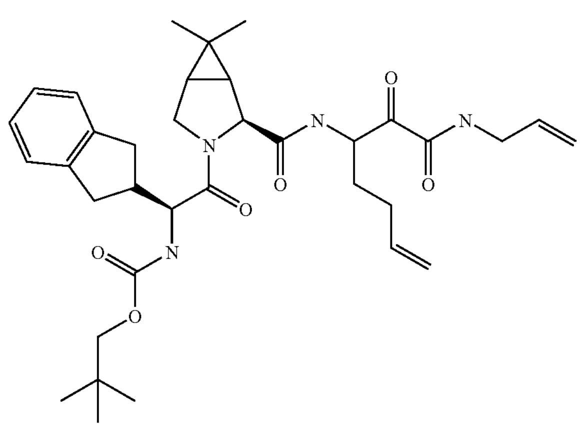 | 621 | A |

TABLE 5-continued

| STRUCTURE | MW | Ki* Range |
|---|---|---|
| 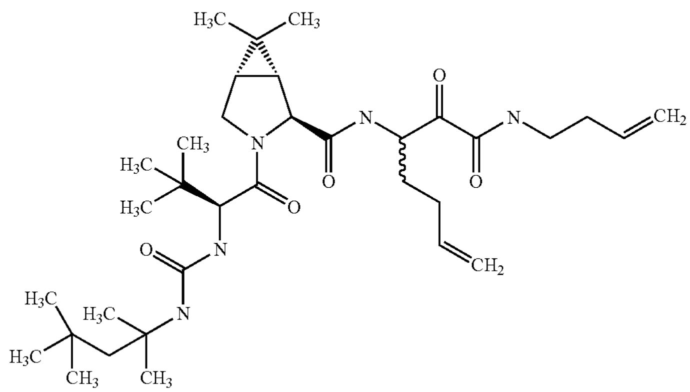 | 616 | B |
| 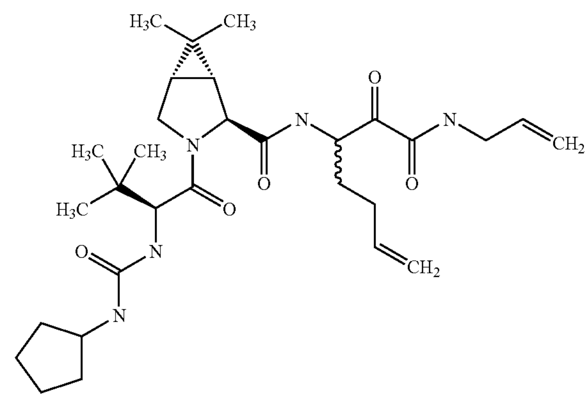 | 572 | A |
| 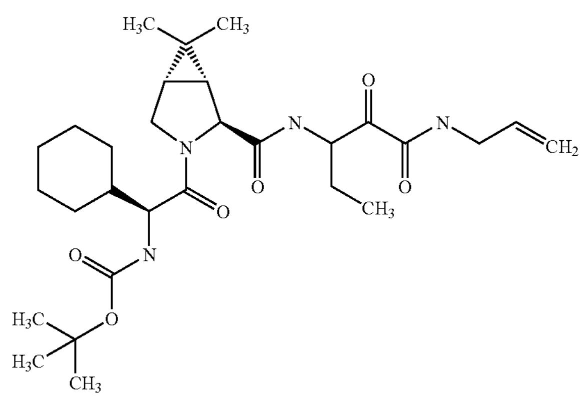 | 547 | C |
| 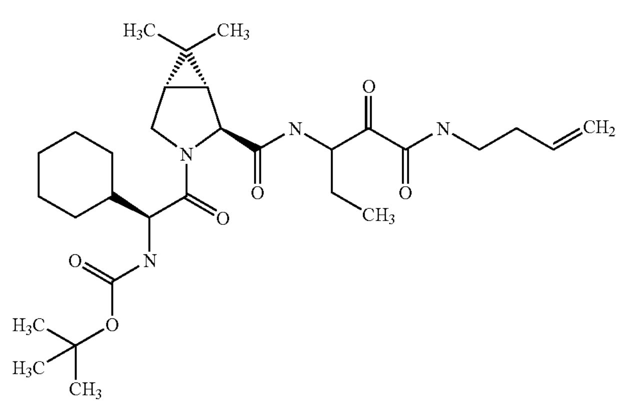 | 561 | C |

TABLE 5-continued

| STRUCTURE | MW | Ki* Range |
|---|---|---|
| 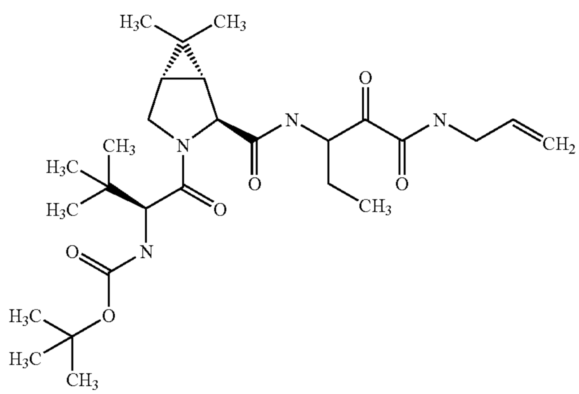 | 521 | C |
| 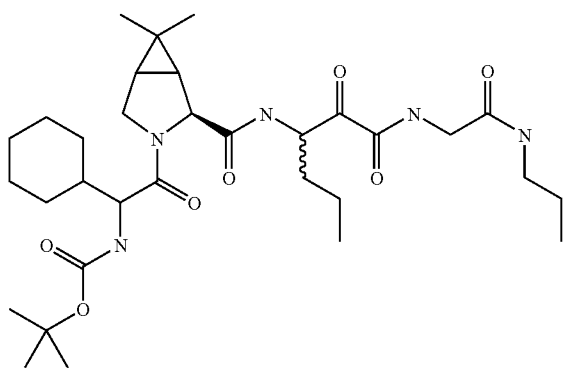 | 620 | B |
| 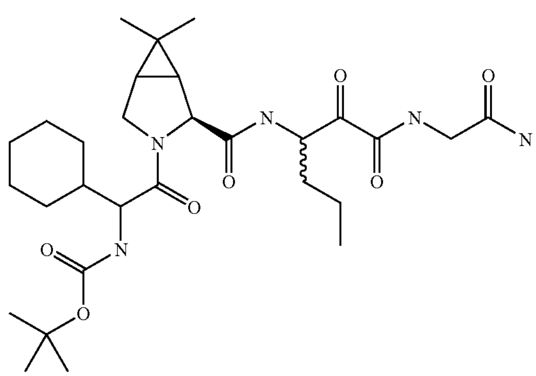 | 578 | B |
| 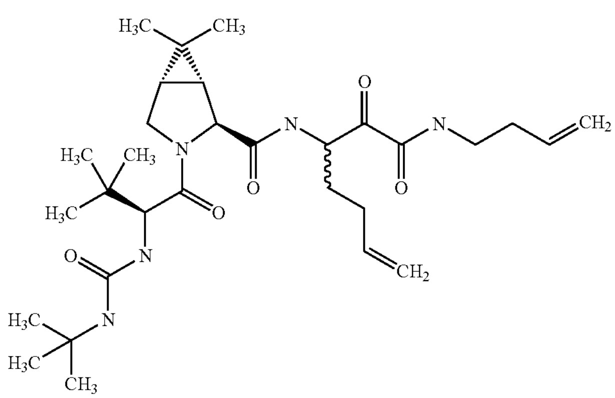 | 560 | A |

TABLE 5-continued

| STRUCTURE | MW | Ki* Range |
|---|---|---|
| 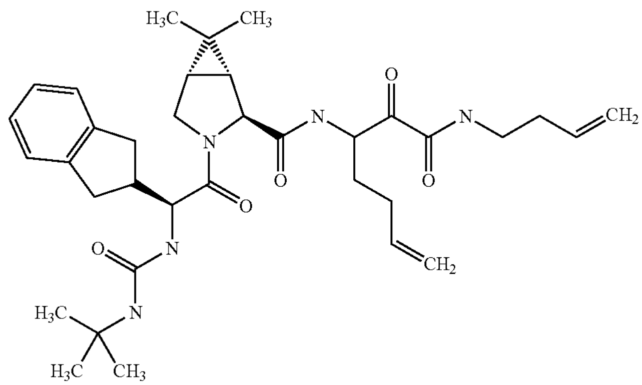 | 620 | A |
| 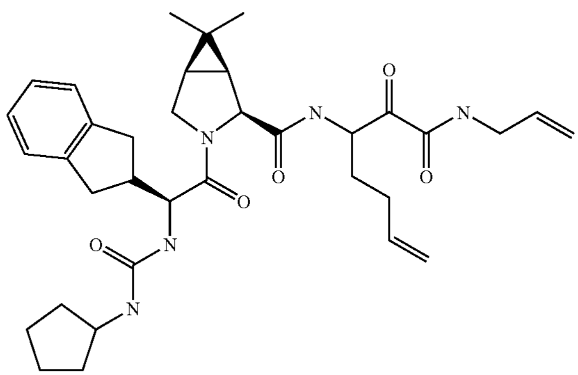 | 618 | B |
| 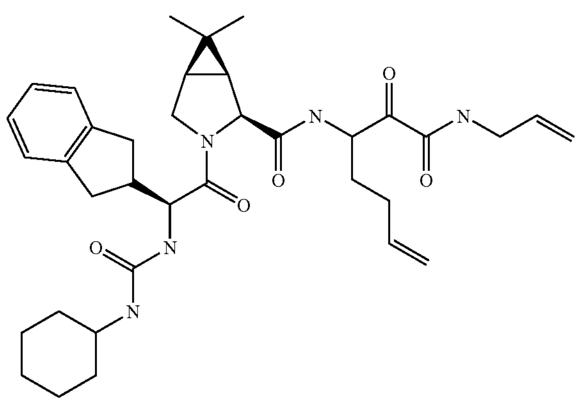 | 632 | B |
| 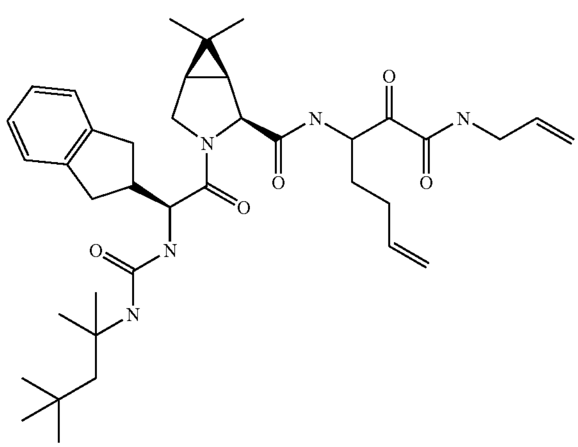 | 662 | B |

TABLE 5-continued
| STRUCTURE | MW | Ki* Range |
|---|---|---|
| 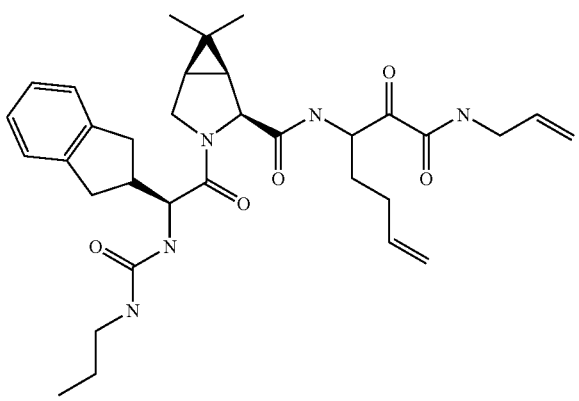 | 592 | B |
| 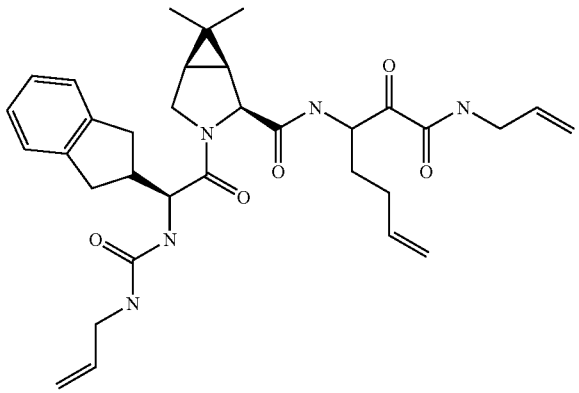 | 590 | B |
| 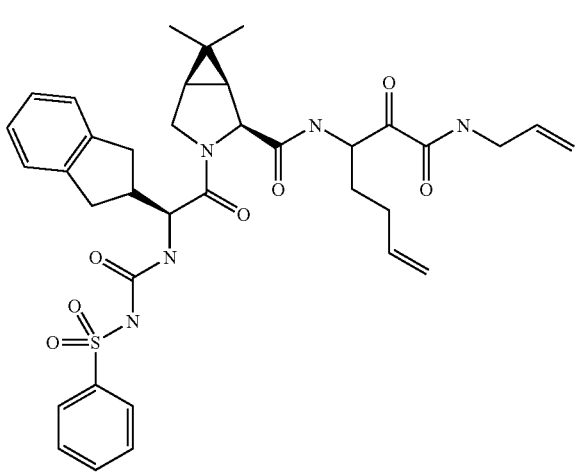 | 690 | B |

TABLE 5-continued
| STRUCTURE | MW | Ki* Range |
|---|---|---|
| 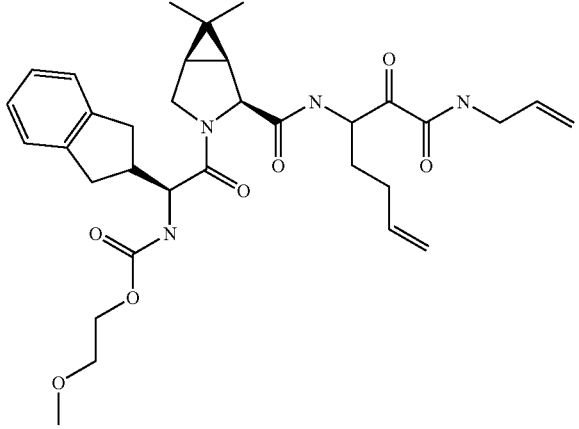 | 609 | B |
| 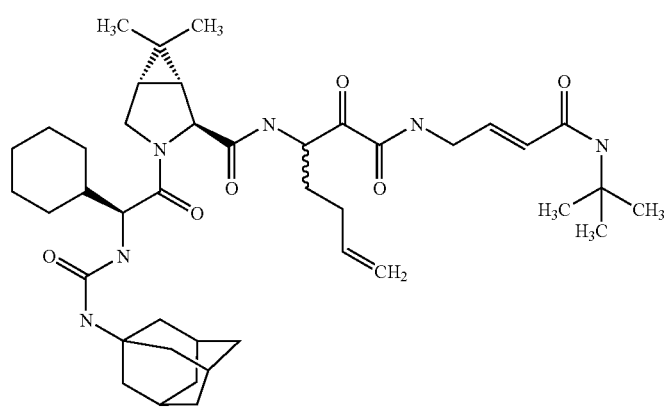 | 749 | B |
| 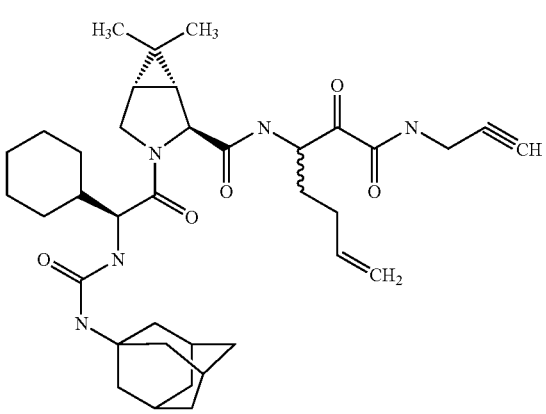 | 648 | A |

TABLE 5-continued

| STRUCTURE | MW | Ki* Range |
|---|---|---|
| | 783 | B |
| | 783 | B |
| 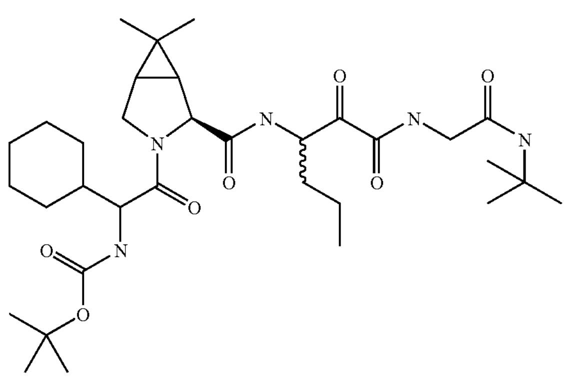 | 634 | C |
| 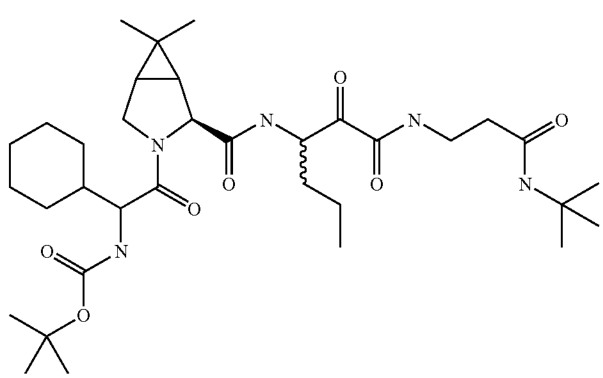 | 648 | C |

TABLE 5-continued

| STRUCTURE | MW | Ki* Range |
|---|---|---|
| 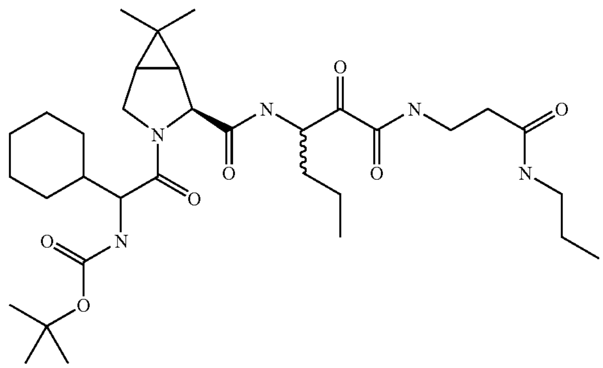 | 634 | C |
| 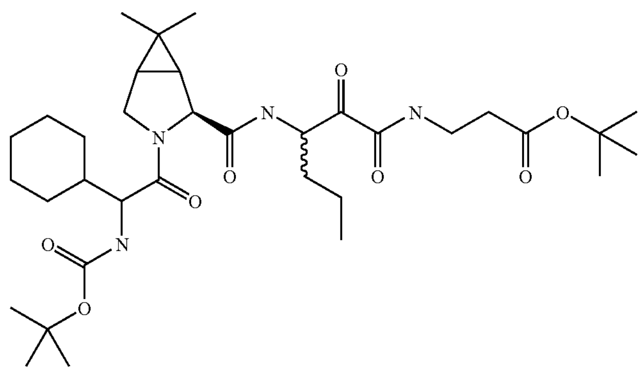 | 649 | C |
| 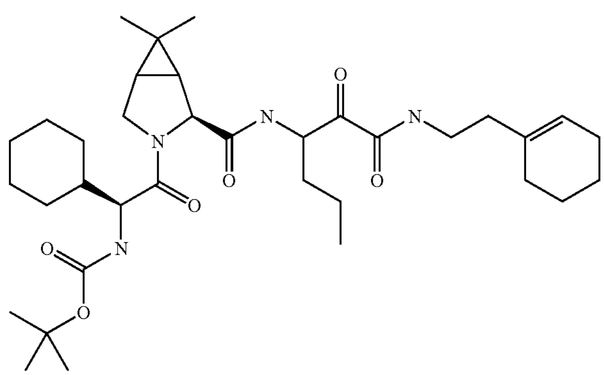 | 629 | C |
| 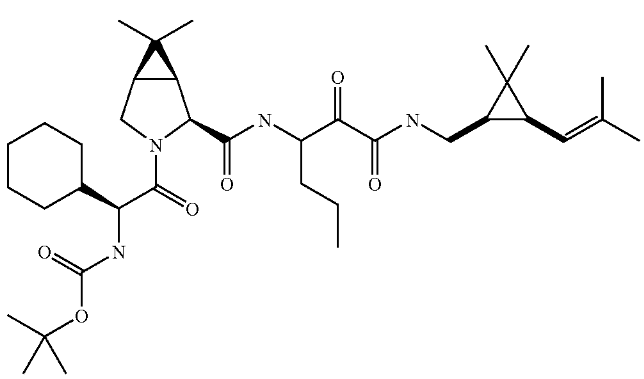 | 657 | C |

TABLE 5-continued

| STRUCTURE | MW | Ki* Range |
|---|---|---|
| 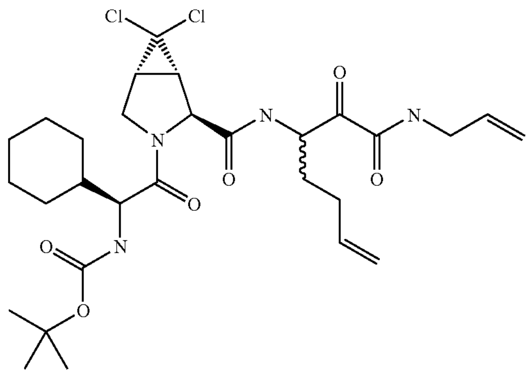 | 614 | A |
| | 702 | B |
| | 702 | A |
| 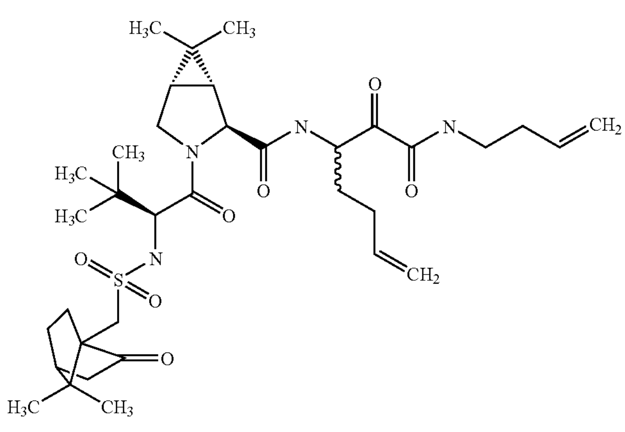 | 675 | B |

TABLE 5-continued

| STRUCTURE | MW | Ki* Range |
|---|---|---|
| 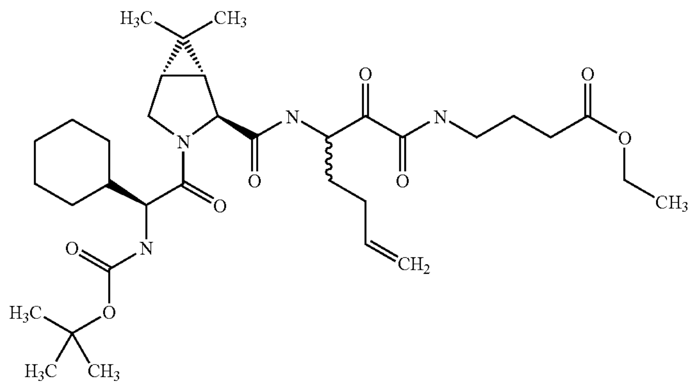 | 647 | B |
| 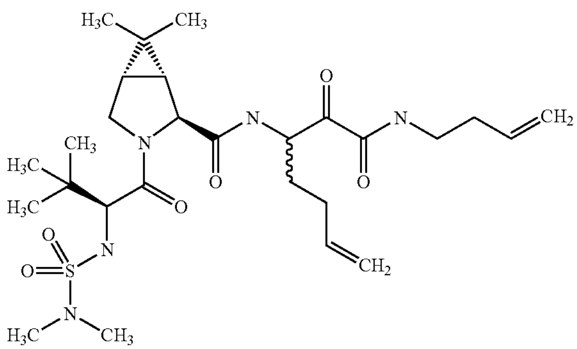 | 568 | C |
| 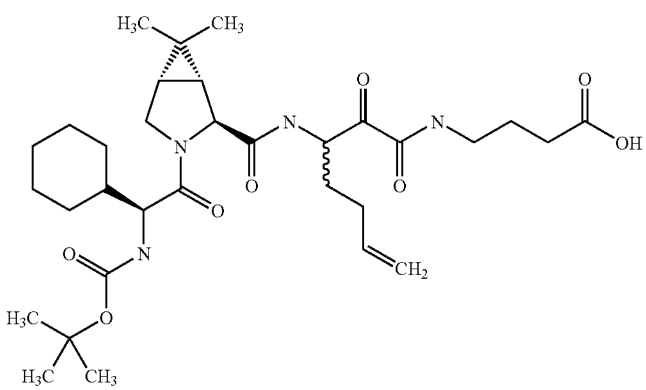 | 619 | C |
| 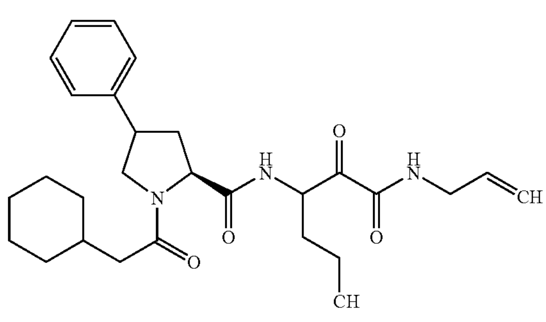 | 482 | C |

TABLE 5-continued
| STRUCTURE | MW | Ki* Range |
|---|---|---|
| 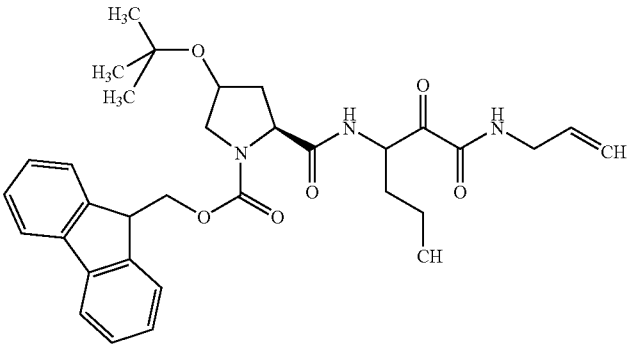 | 576 | C |
| 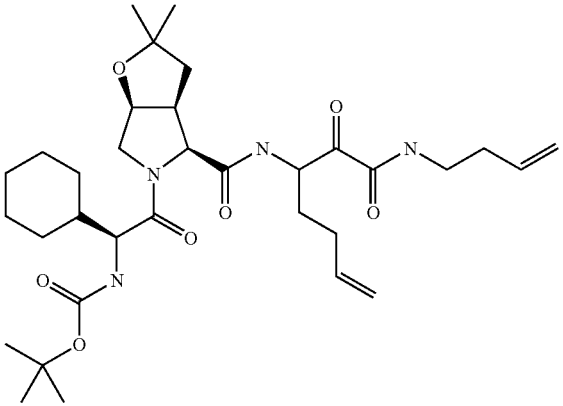 | 617 | B |
| 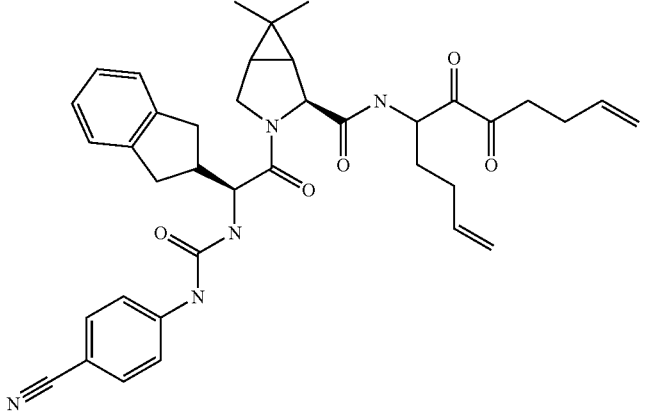 | 651 | C |
| 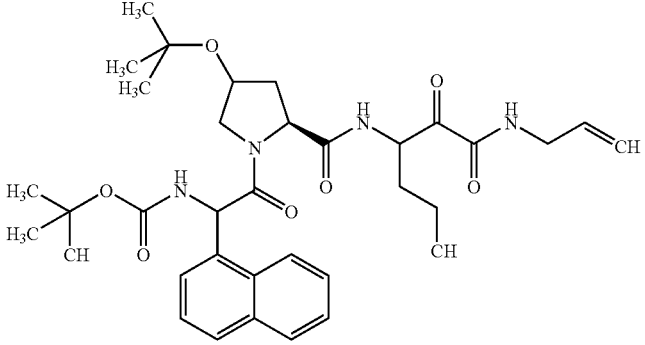 | 637 | C |

TABLE 5-continued

| STRUCTURE | MW | Ki* Range |
|---|---|---|
| 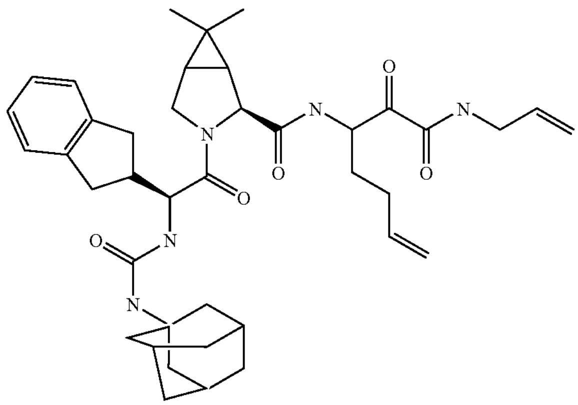 | 684 | B |
| 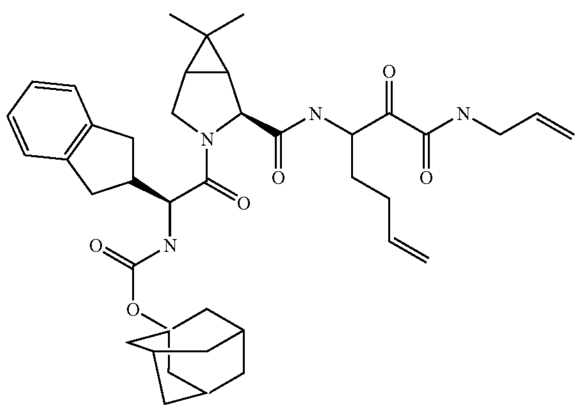 | 685 | B |
| 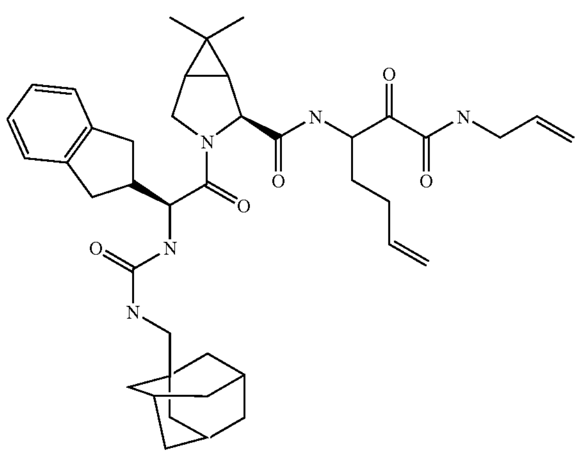 | 698 | B |

TABLE 5-continued
| STRUCTURE | MW | Ki* Range |
|---|---|---|
| 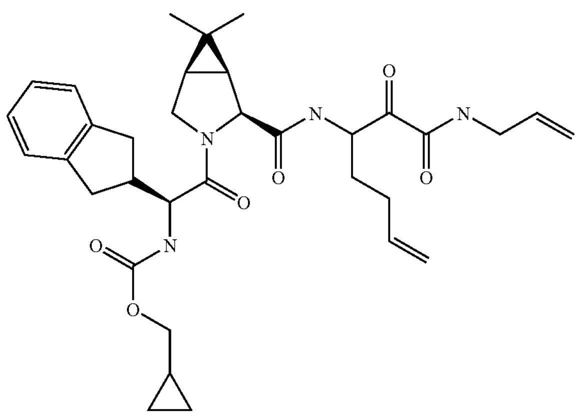 | 605 | B |
| 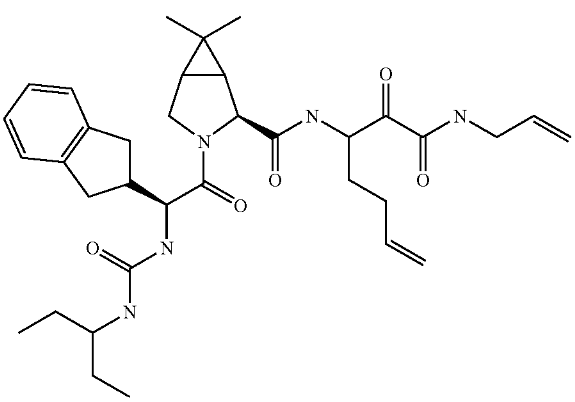 | 620 | B |
| 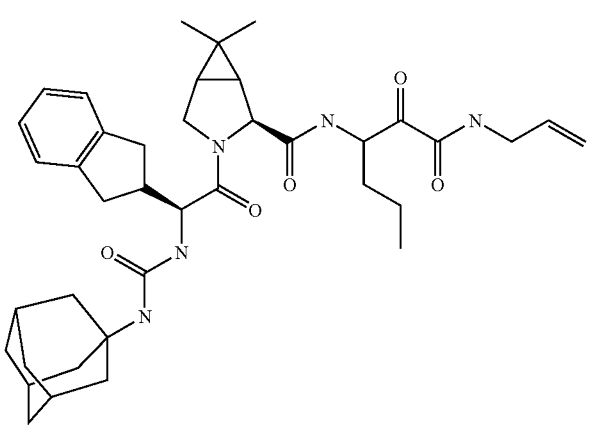 | 672 | C |

TABLE 5-continued

| STRUCTURE | MW | Ki* Range |
|---|---|---|
| 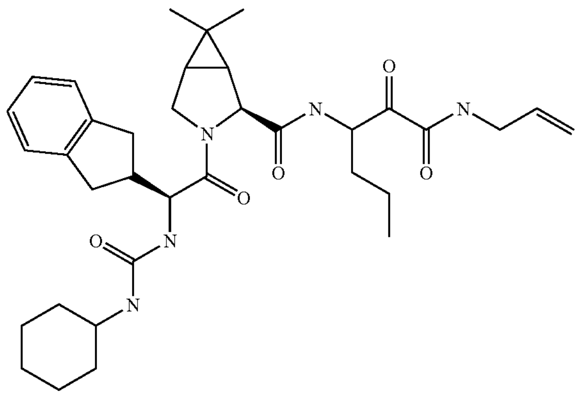 | 620 | B |
| 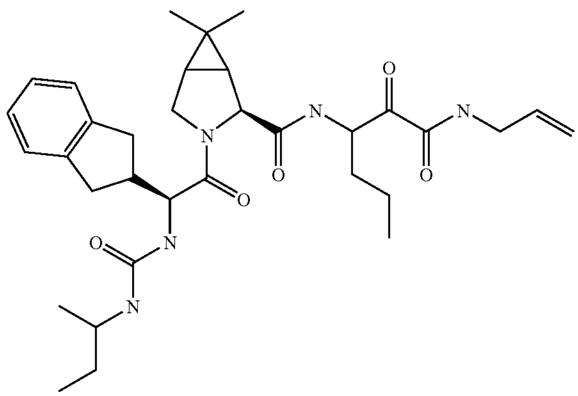 | 594 | B |
| 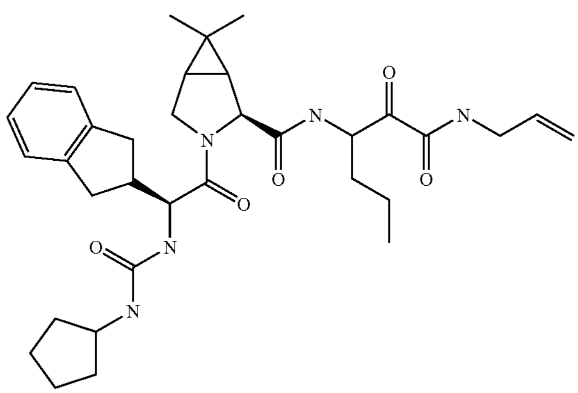 | 606 | B |
| 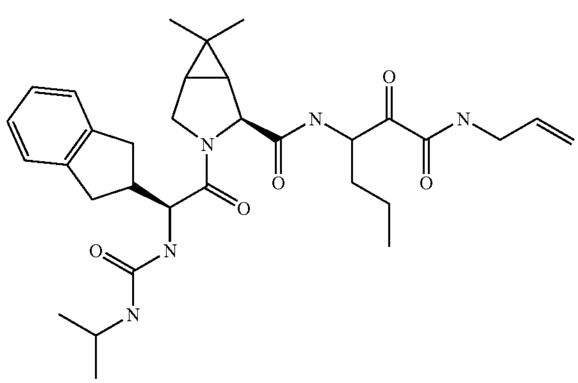 | 580 | C |

TABLE 5-continued

| STRUCTURE | MW | Ki* Range |
|---|---|---|
| 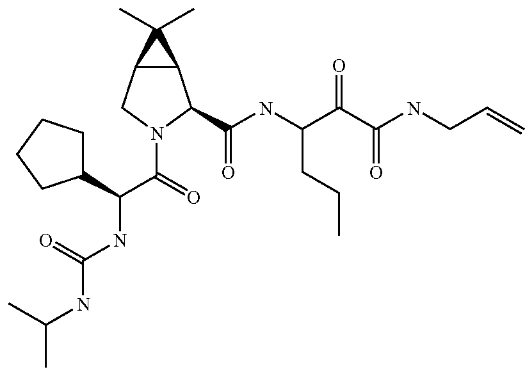 | 532 | B |
| 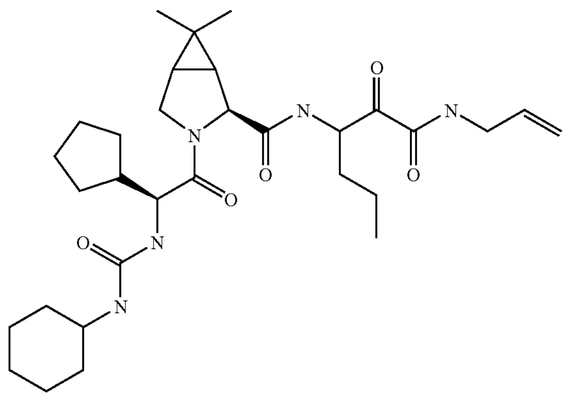 | 572 | B |
| 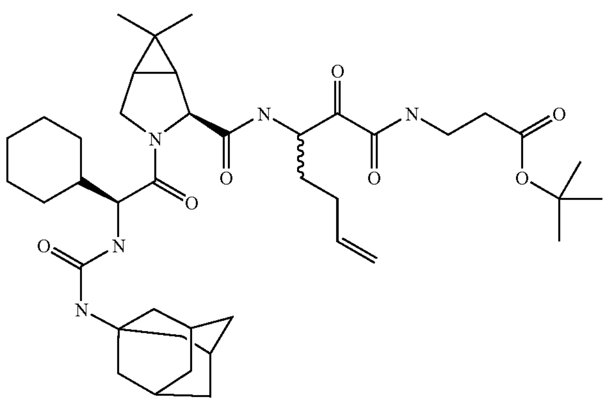 | 738 | A |
| 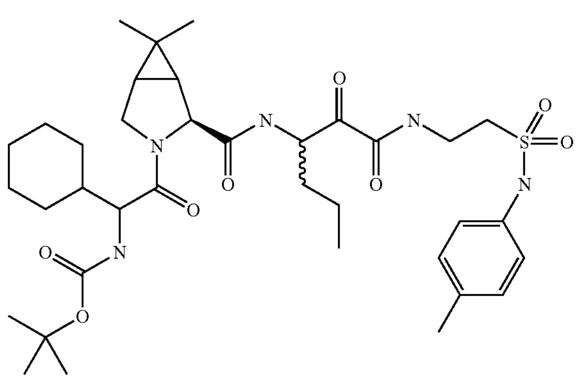 | 718 | B |

TABLE 5-continued
| STRUCTURE | MW | Ki* Range |
|---|---|---|
| 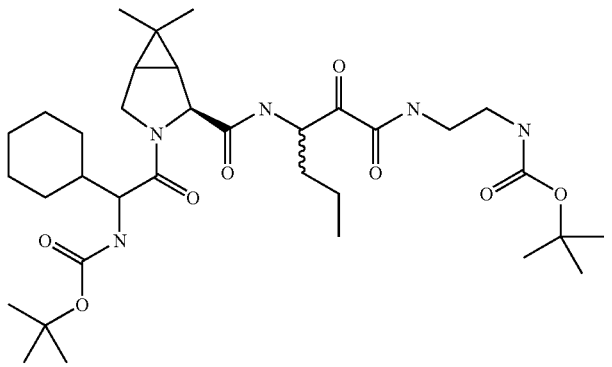 | 664 | B |
| 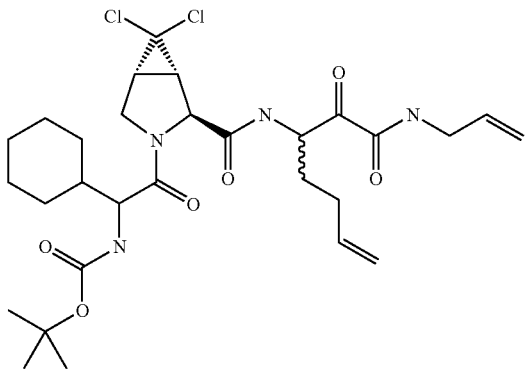 | 614 | B |
| 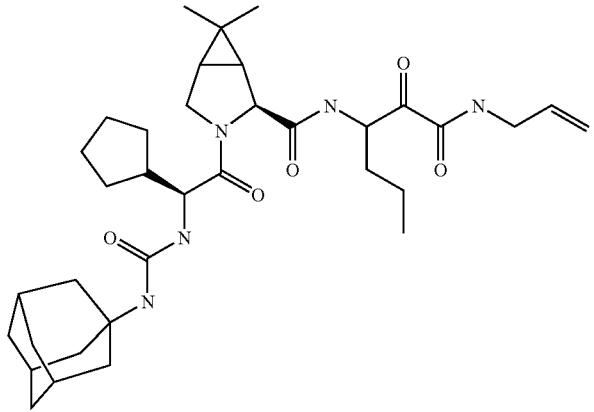 | 624 | B |
| 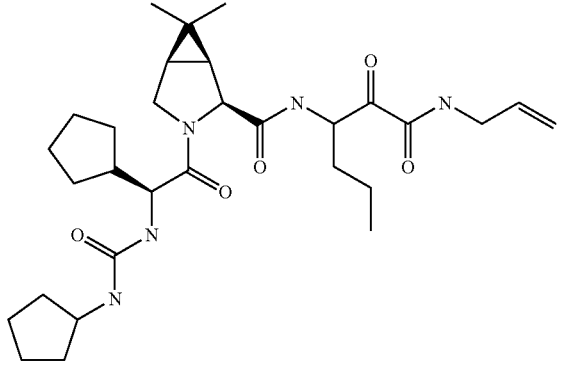 | 558 | B |

TABLE 5-continued

| STRUCTURE | MW | Ki* Range |
|---|---|---|
| 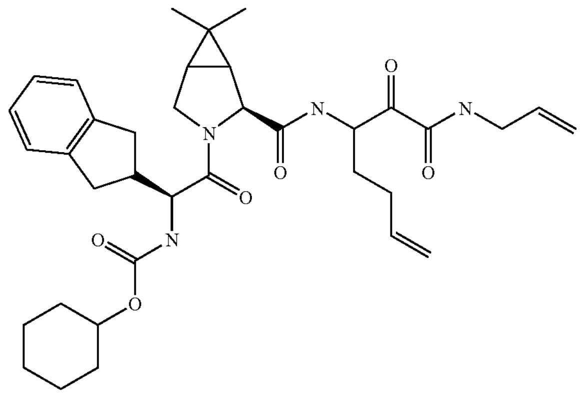 | 633 | B |
| 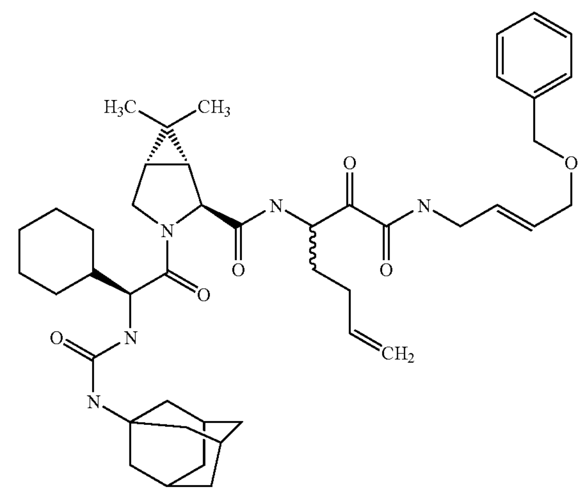 | 770 | C |
| 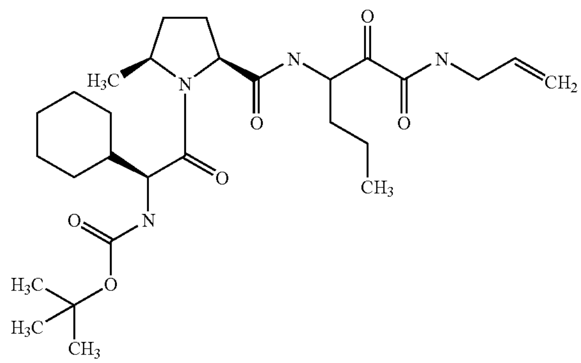 | 535 | C |
| 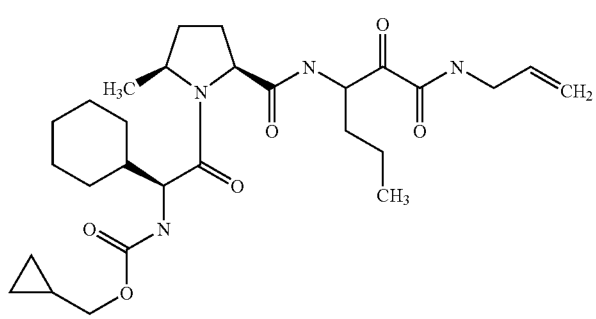 | 533 | C |

TABLE 5-continued
| STRUCTURE | MW | Ki* Range |
|---|---|---|
| 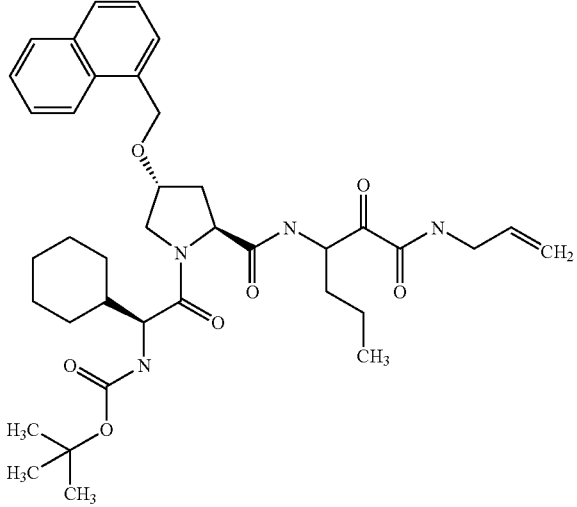 | 677 | C |
| 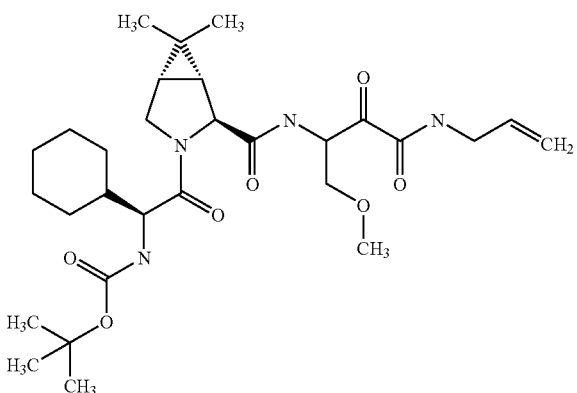 | 563 | B |
| 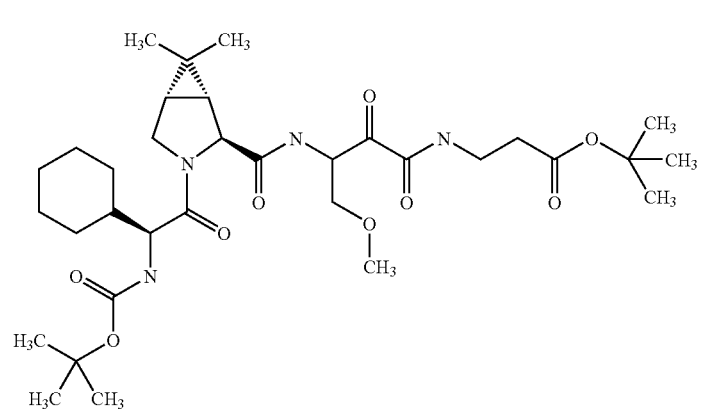 | 651 | A |

TABLE 5-continued
| STRUCTURE | MW | Ki* Range |
|---|---|---|
| 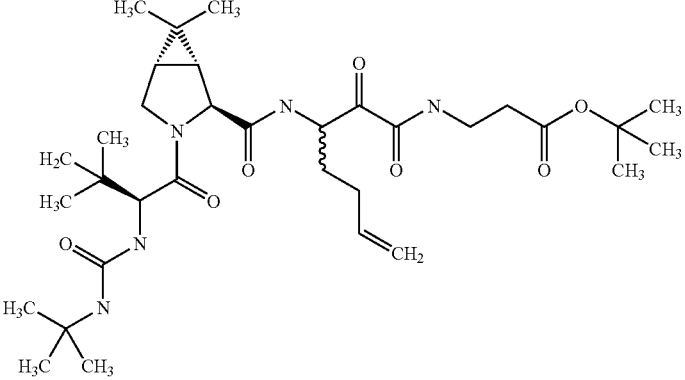 | 634 | A |
| 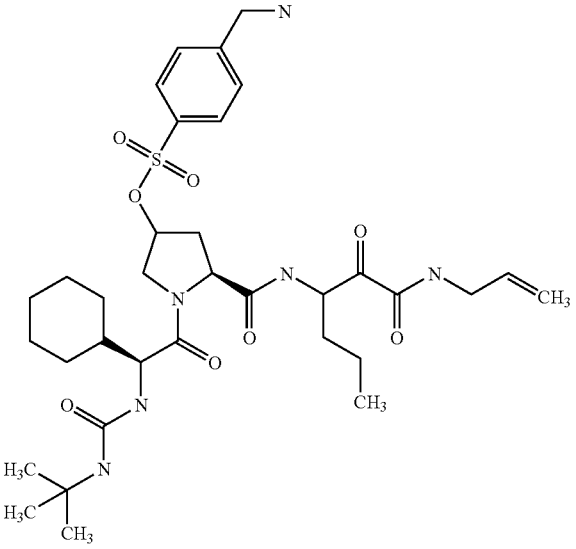 | 706 | C |
| 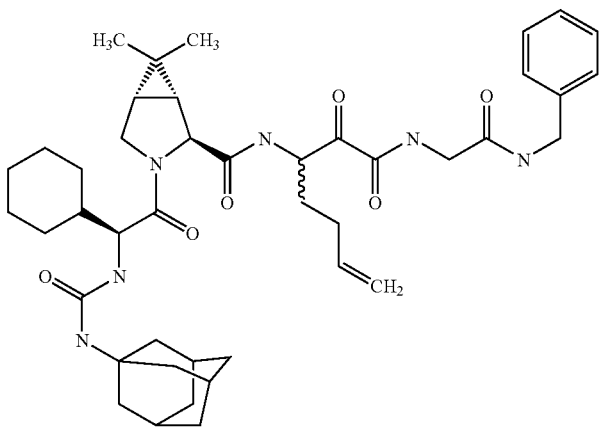 | 757 | A |

TABLE 5-continued

| STRUCTURE | MW | Ki* Range |
|---|---|---|
| 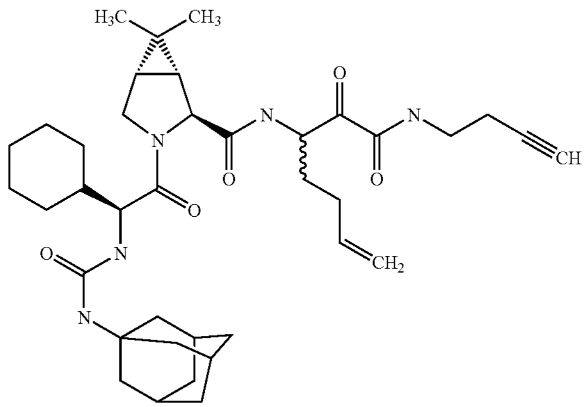 | 662 | A |
| 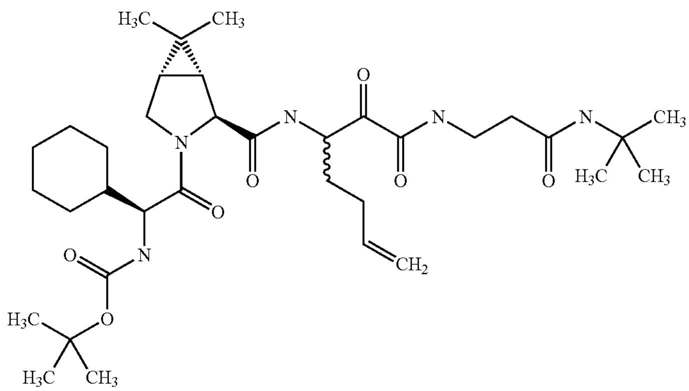 | 660 | A |
| | 648 | A |
| | 648 | C |

TABLE 5-continued
| STRUCTURE | MW | Ki* Range |
|---|---|---|
| 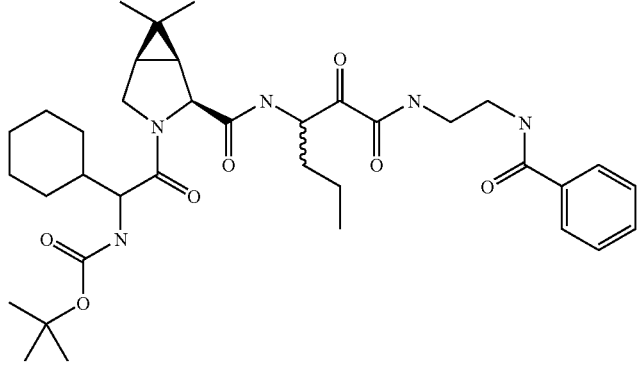 | 668 | B |
| 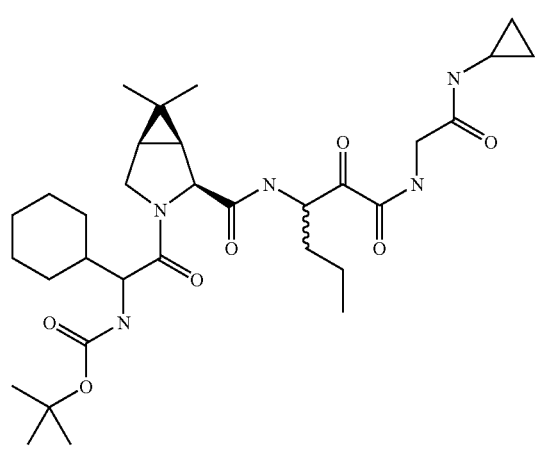 | 618 | A |
| 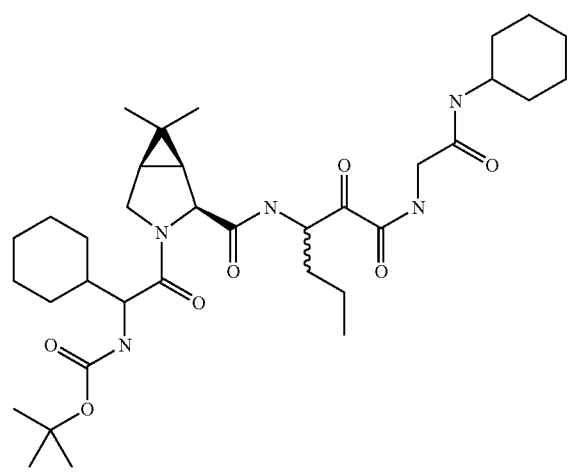 | 660 | B |

TABLE 5-continued

| STRUCTURE | MW | Ki* Range |
|---|---|---|
| 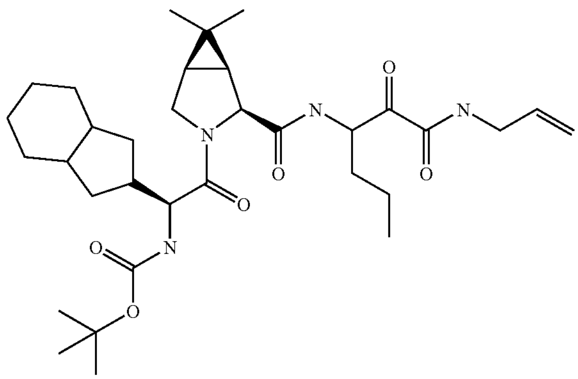 | 601 | B |
| 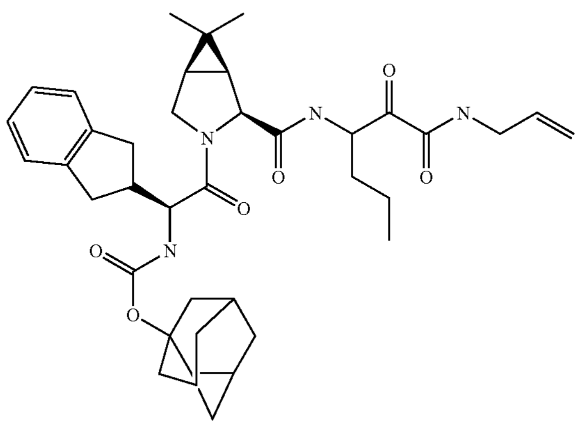 | 673 | B |
| 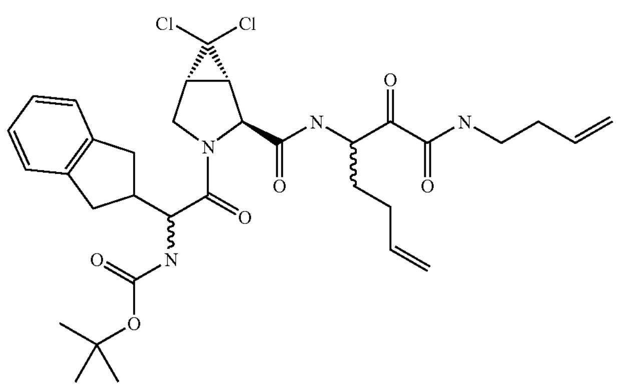 | 662 | A |
| 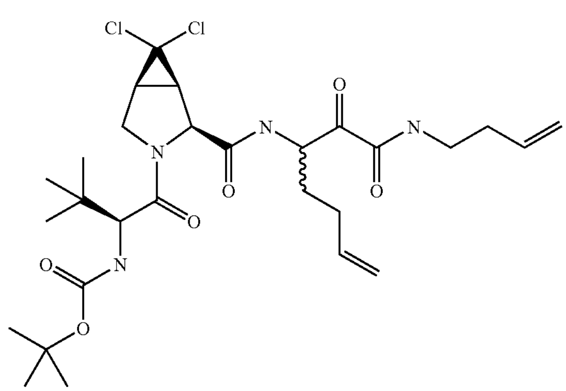 | 602 | A |

TABLE 5-continued
| STRUCTURE | MW | Ki* Range |
|---|---|---|
| 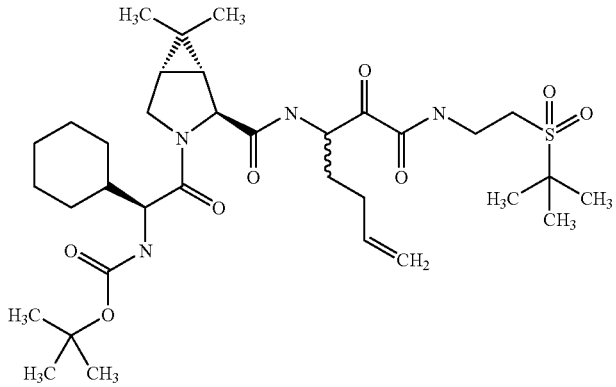 | 681 | A |
|  | 681 | C |
| 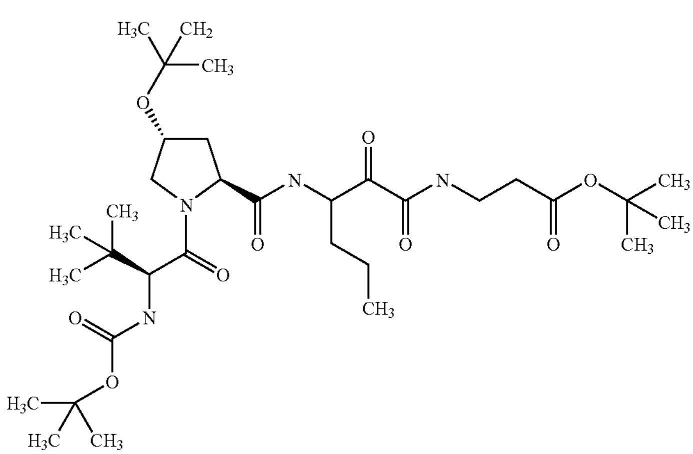 | 655 | C |

TABLE 5-continued

| STRUCTURE | MW | Ki* Range |
|---|---|---|
| 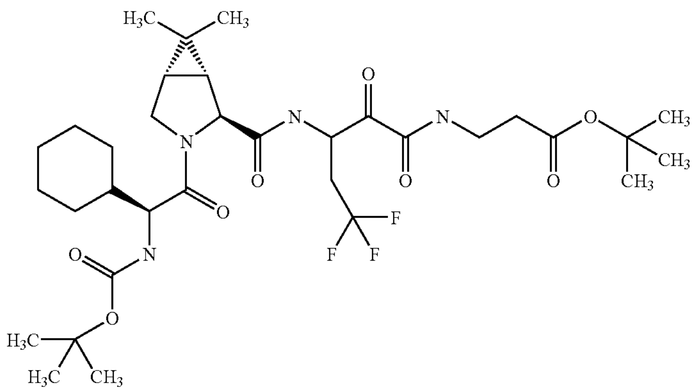 | 689 | B |
| 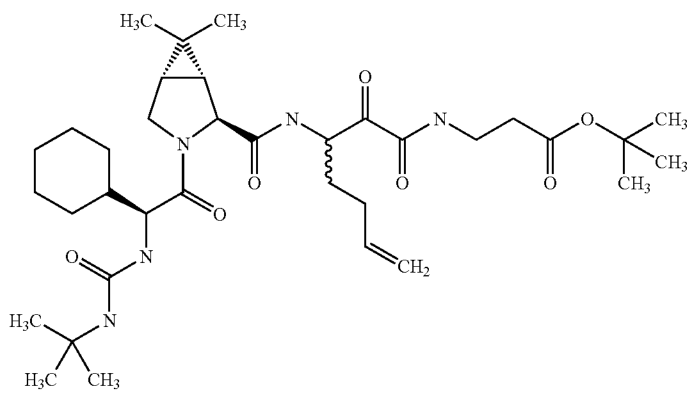 | 660 | A |
| 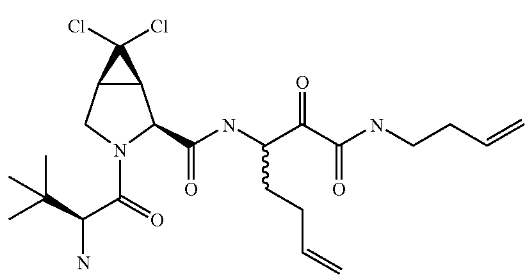 | 538 | C |
| 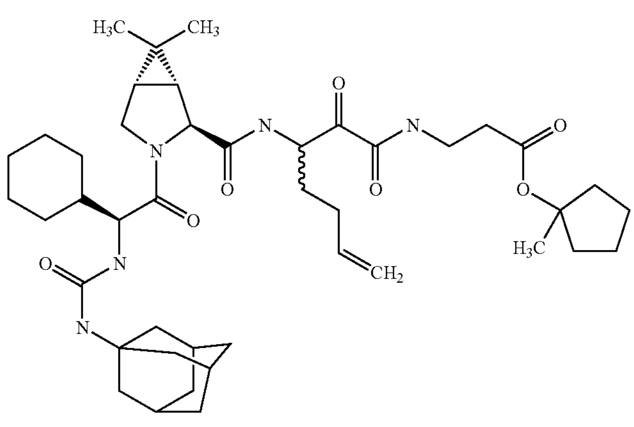 | 764 | A |

TABLE 5-continued

| STRUCTURE | MW | Ki* Range |
|---|---|---|
| 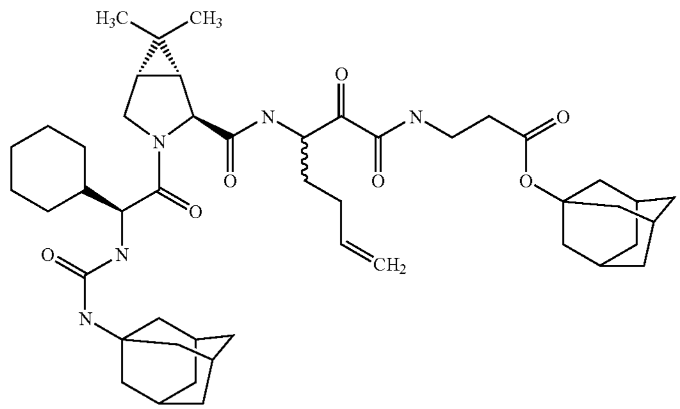 | 816 | C |
| 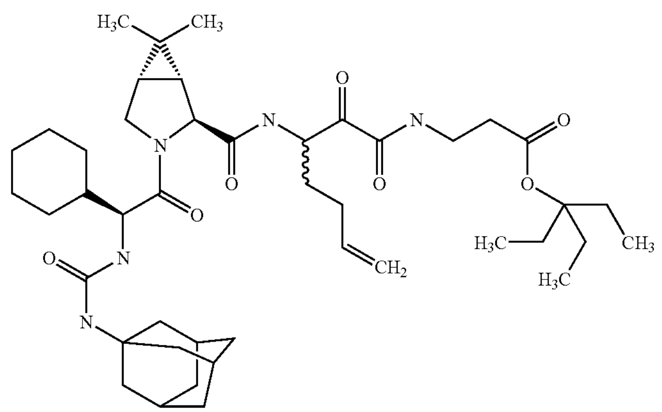 | 780 | B |
| 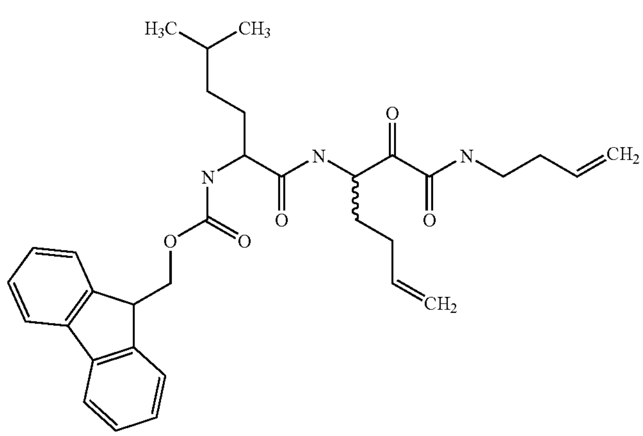 | 560 | C |

TABLE 5-continued

| STRUCTURE | MW | Ki* Range |
|---|---|---|
| 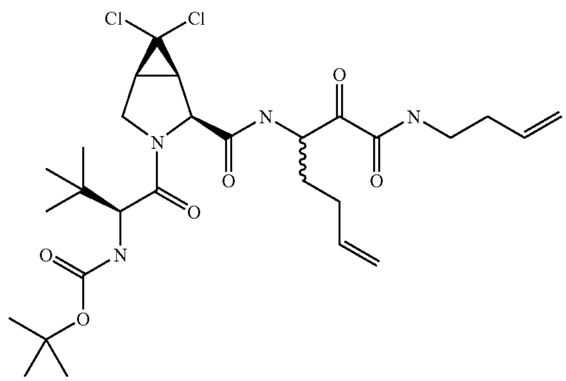 | 602 | C |
| 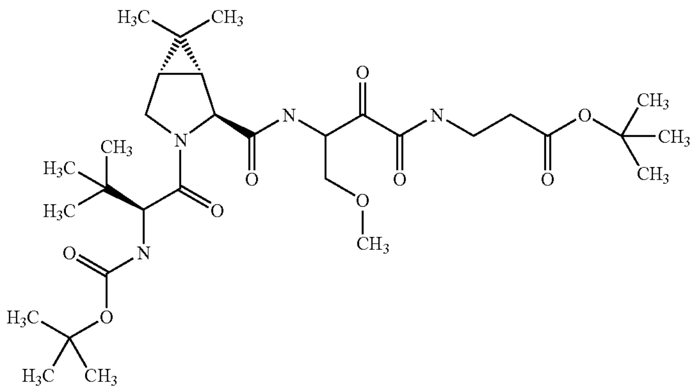 | 625 | B |
| 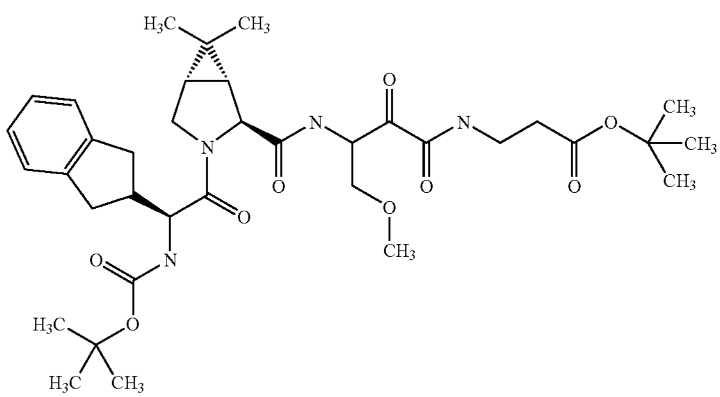 | 685 | B |
| 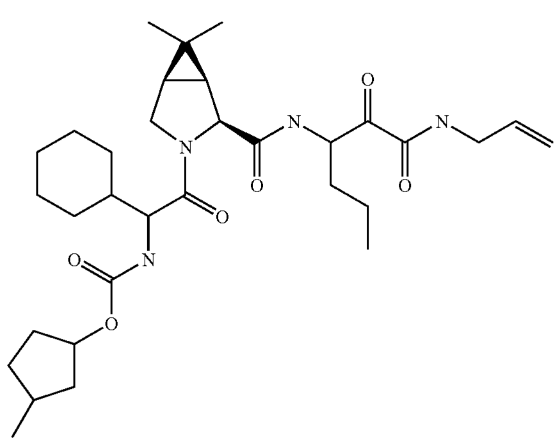 | 587 | A |

TABLE 5-continued

| STRUCTURE | MW | Ki* Range |
|---|---|---|
| 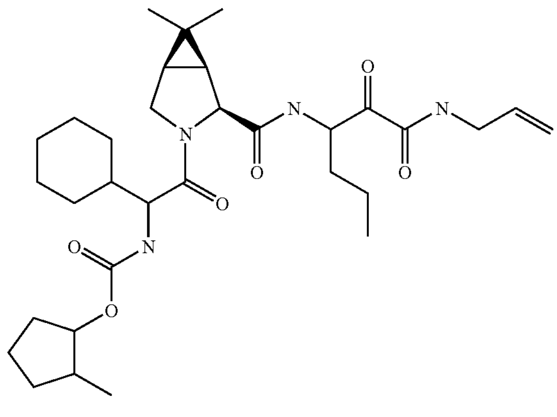 | 587 | A |
| 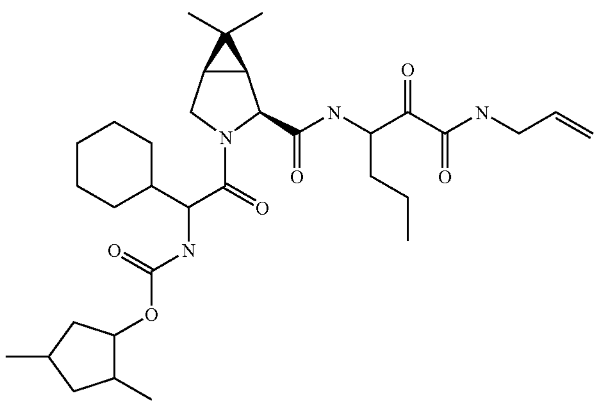 | 601 | A |
| 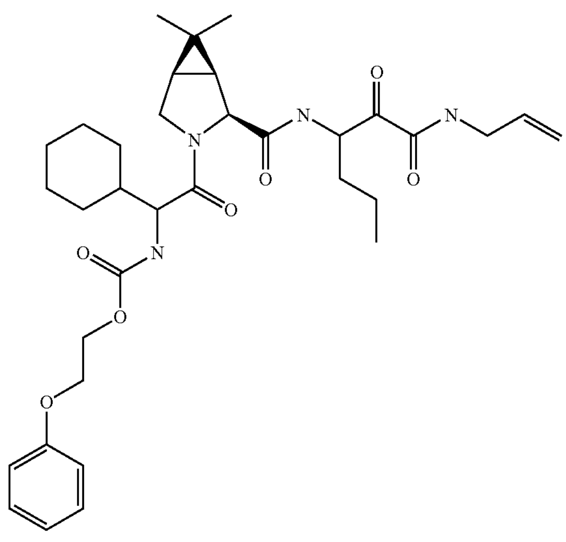 | 625 | B |

TABLE 5-continued

| STRUCTURE | MW | Ki* Range |
|---|---|---|
| 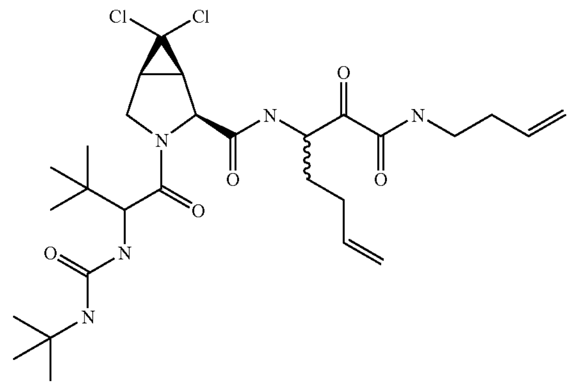 | 601 | A |
| 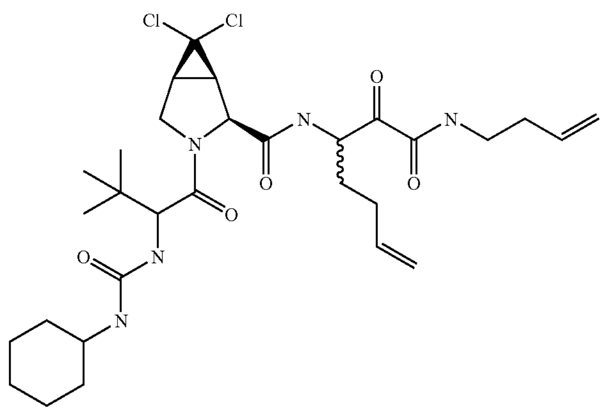 | 627 | B |
| 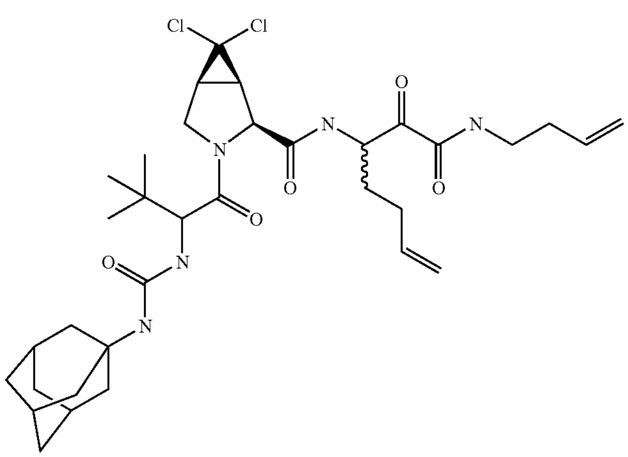 | 679 | A |

TABLE 5-continued

| STRUCTURE | MW | Ki* Range |
|---|---|---|
| 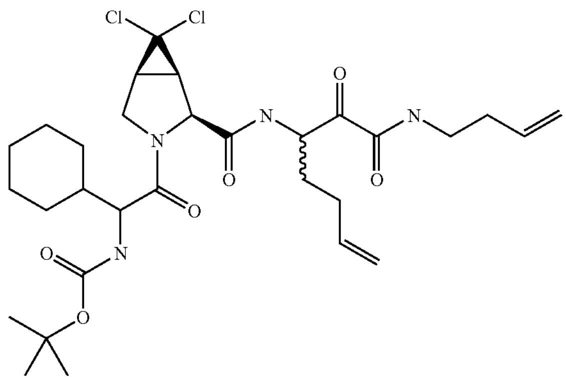 | 628 | A |
| 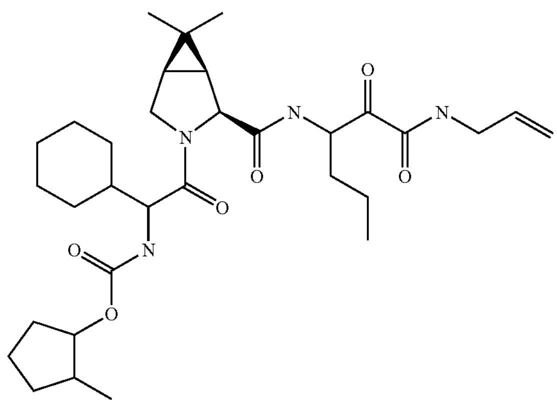 | 587 | A |
| 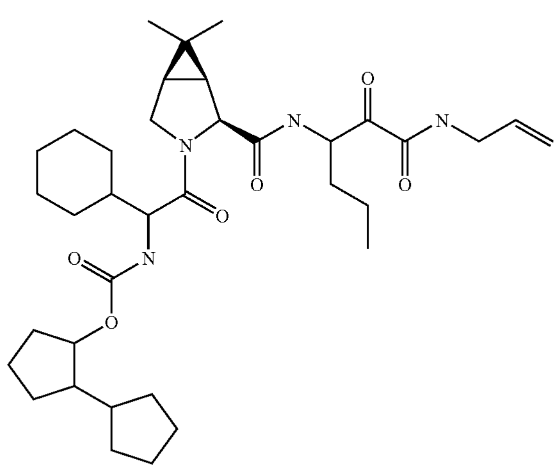 | 641 | A |

TABLE 5-continued

| STRUCTURE | MW | Ki* Range |
|---|---|---|
| 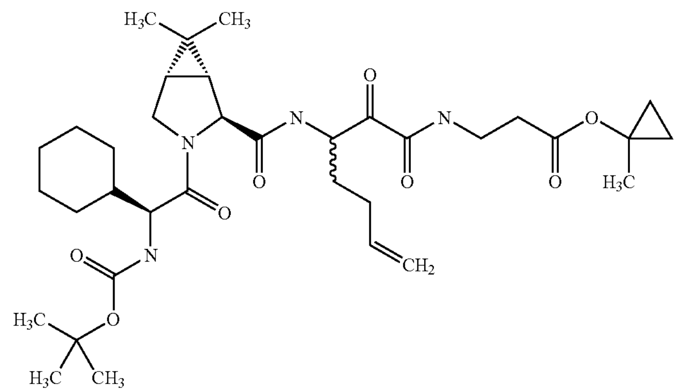 | 659 | A |
| 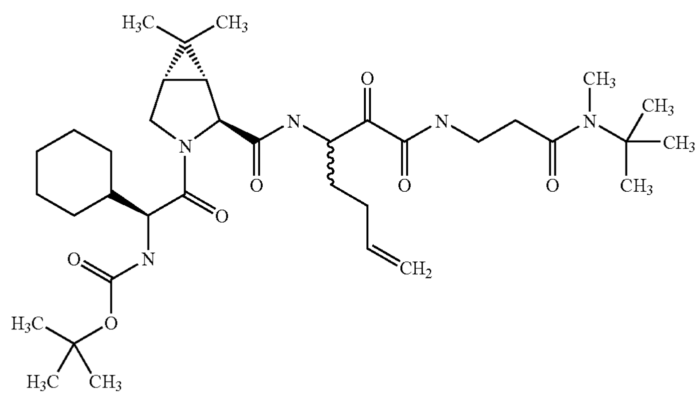 | 674 | A |
| 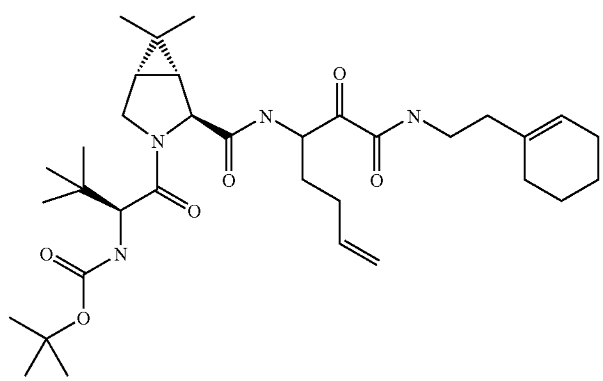 | 615 | B |
| 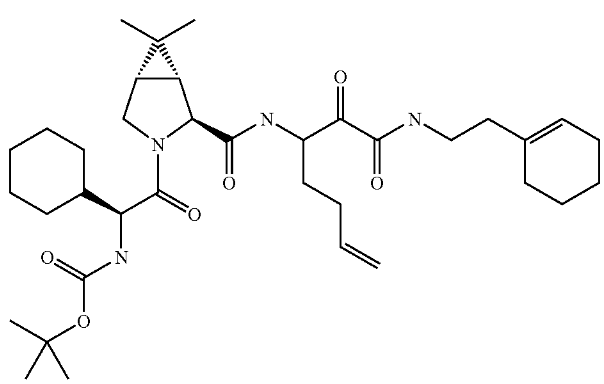 | 641 | B |

TABLE 5-continued

| STRUCTURE | MW | Ki* Range |
|---|---|---|
| 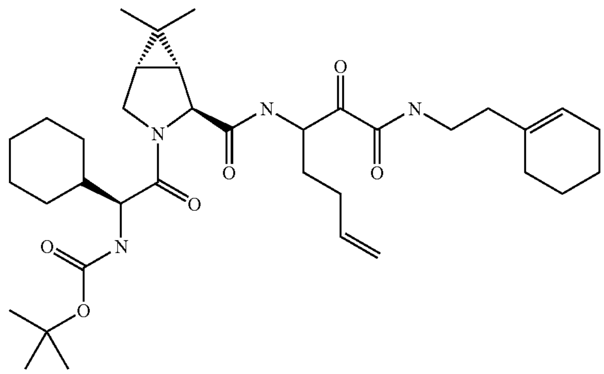 | 641 | B |
| 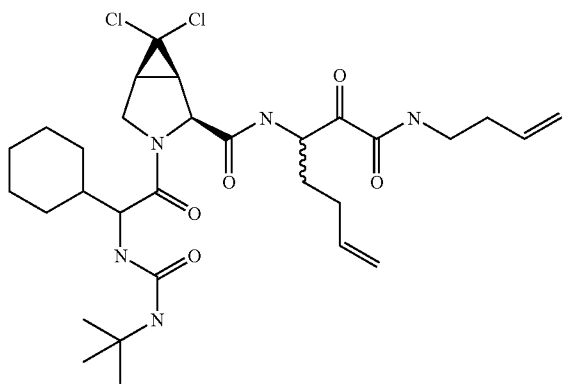 | 627 | A |
| 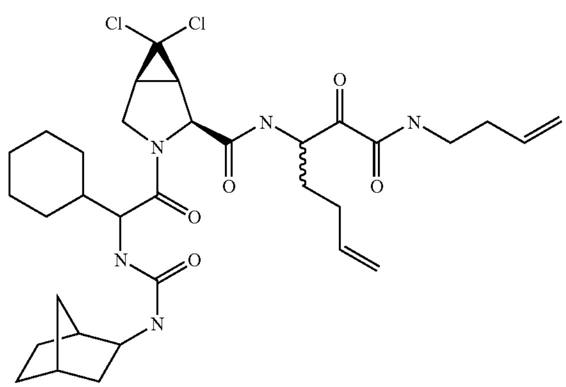 | 665 | A |
| 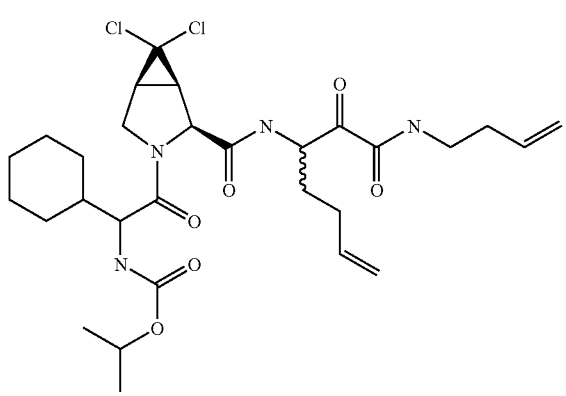 | 614 | A |

TABLE 5-continued
| STRUCTURE | MW | Ki* Range |
|---|---|---|
| 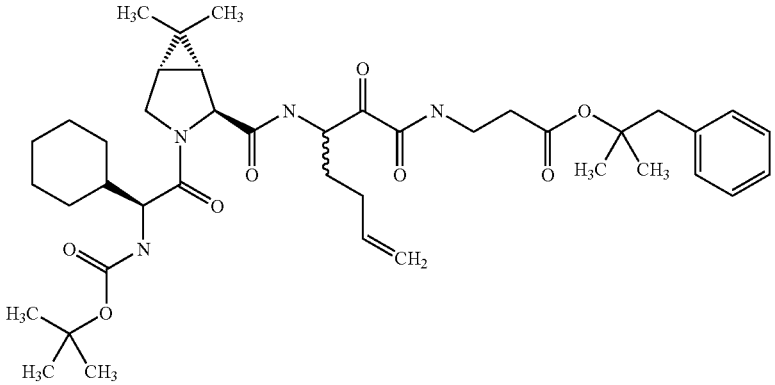 | 737 | B |
| 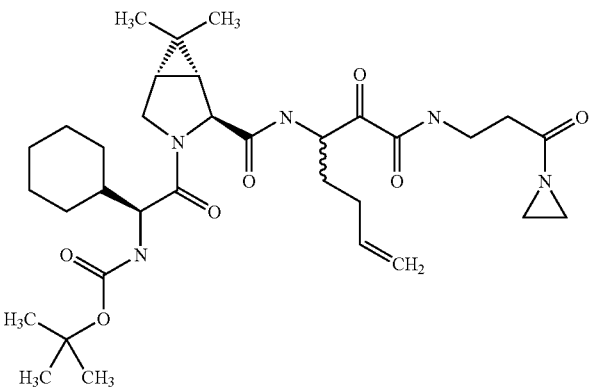 | 666 | A |
| 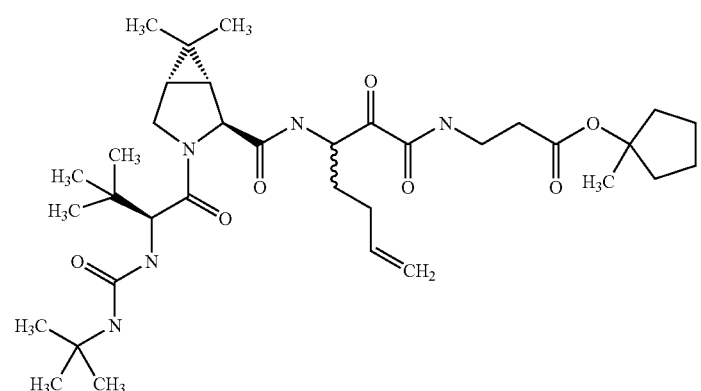 | 660 | A |
| 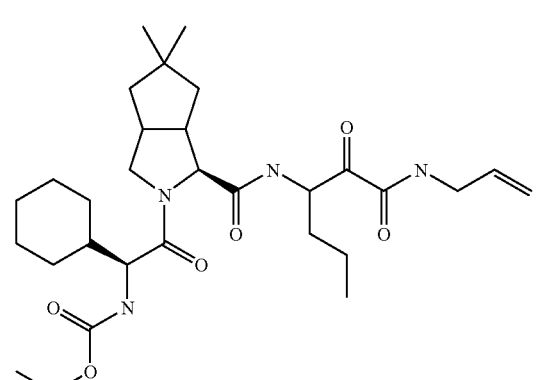 | 591 | C |

TABLE 5-continued

| STRUCTURE | MW | Ki* Range |
|---|---|---|
| 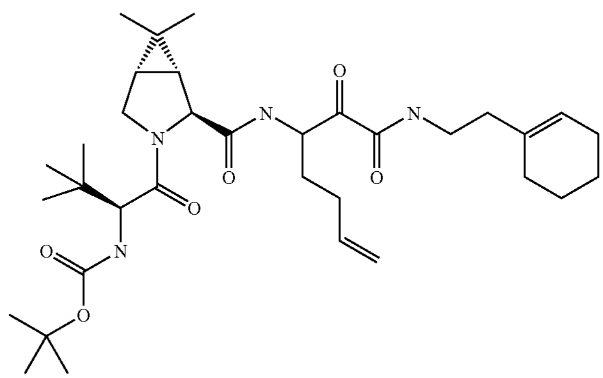 | 615 | C |
| 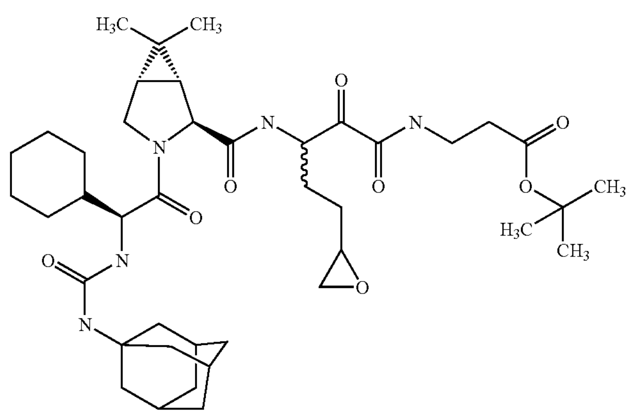 | 754 | B |
| 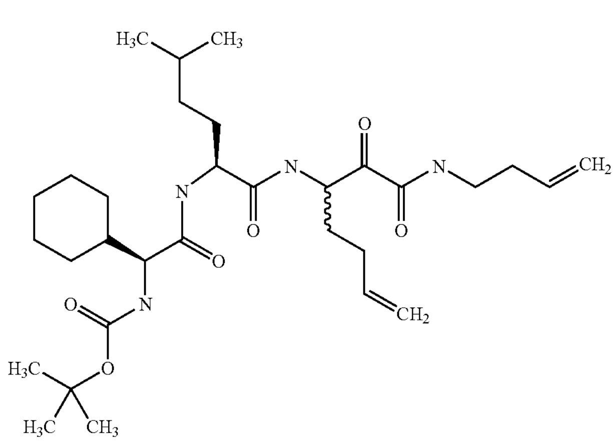 | 577 | C |

TABLE 5-continued

| STRUCTURE | MW | Ki* Range |
|---|---|---|
| 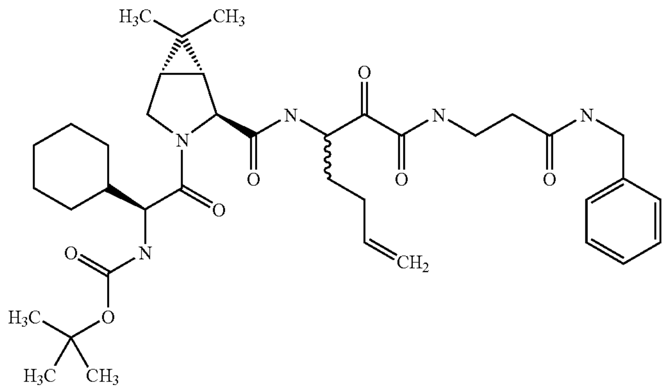 | 694 | A |
| 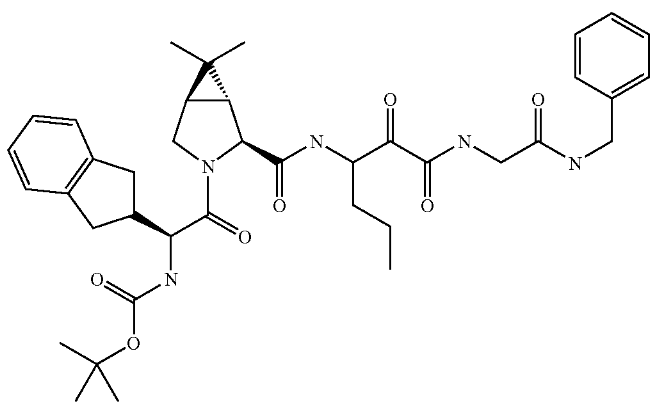 | 702 | A |
| 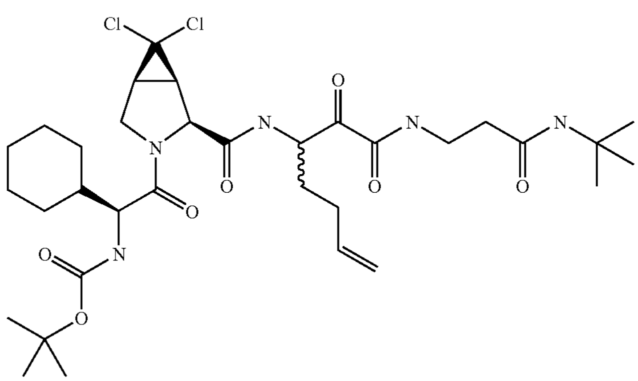 | 701 | A |
| 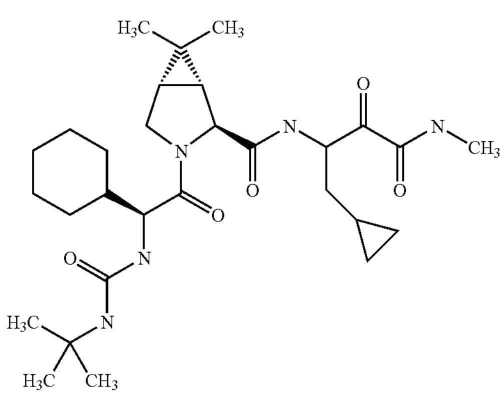 | 546 | B |

TABLE 5-continued

| STRUCTURE | MW | Ki* Range |
|---|---|---|
| 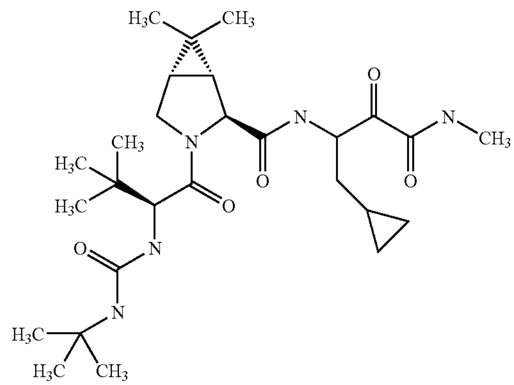 | 520 | B |
| 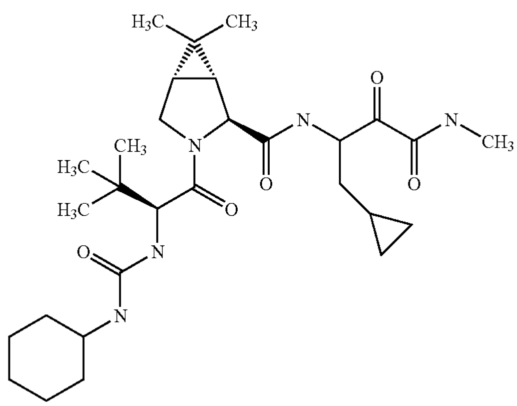 | 546 | B |
| 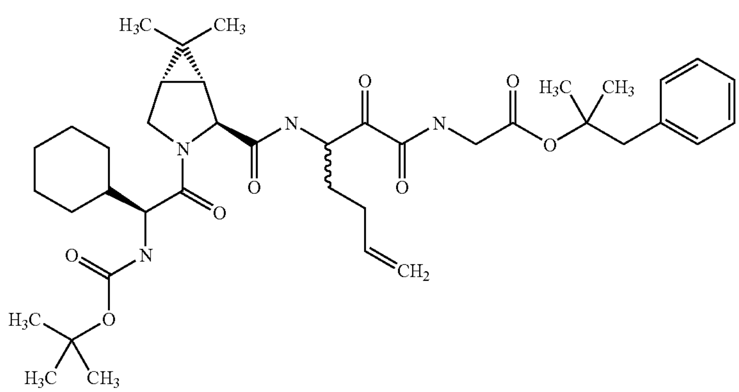 | 723 | B |
| 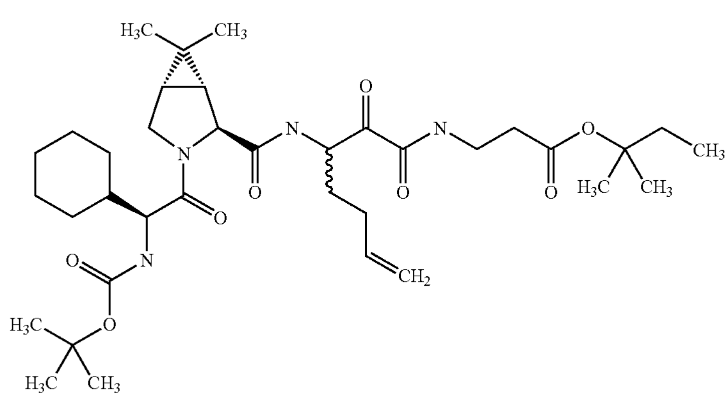 | 675 | A |

TABLE 5-continued
| STRUCTURE | MW | Ki* Range |
|---|---|---|
| 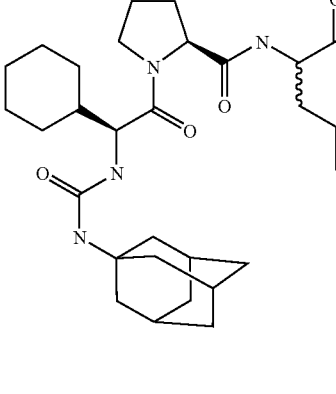 | 771 | B |
| 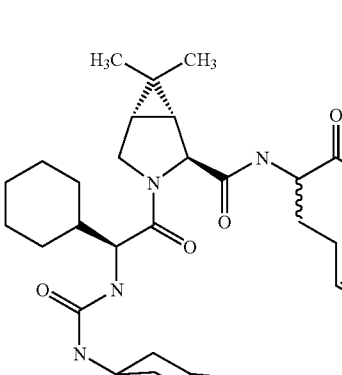 | 847 | C |
| 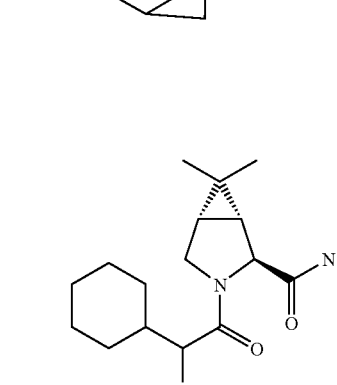 | 641 | A |

TABLE 5-continued
| STRUCTURE | MW | Ki* Range |
|---|---|---|
| 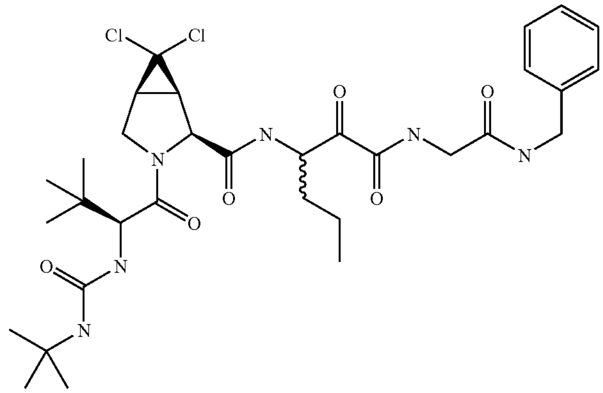 | 682 | A |
| 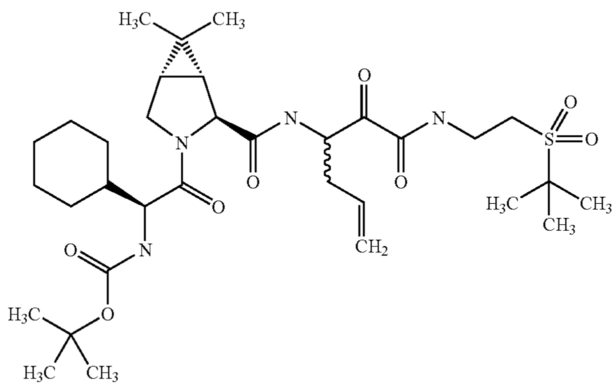 | 667 | B |
| 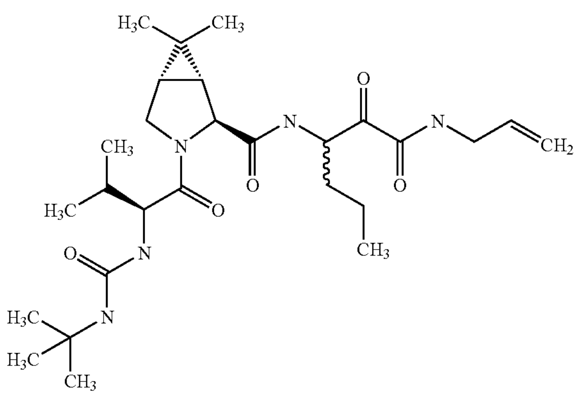 | 520 | B |
| 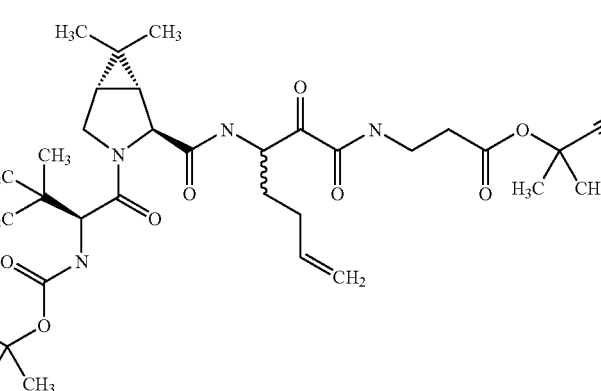 | 645 | B |

TABLE 5-continued

| STRUCTURE | MW | Ki* Range |
|---|---|---|
| 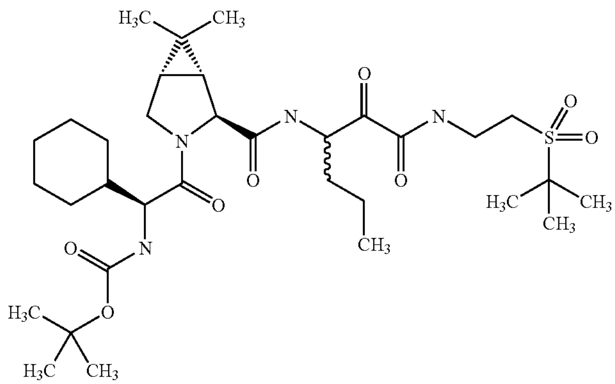 | 669 | C |
| 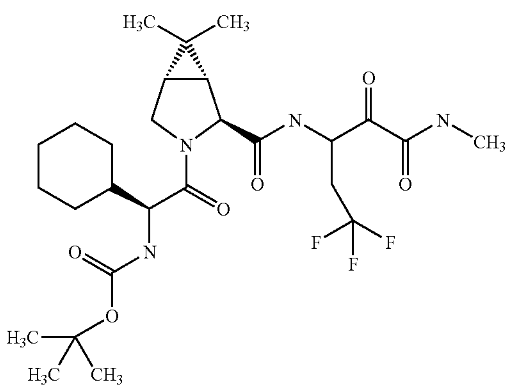 | 575 | A |
| 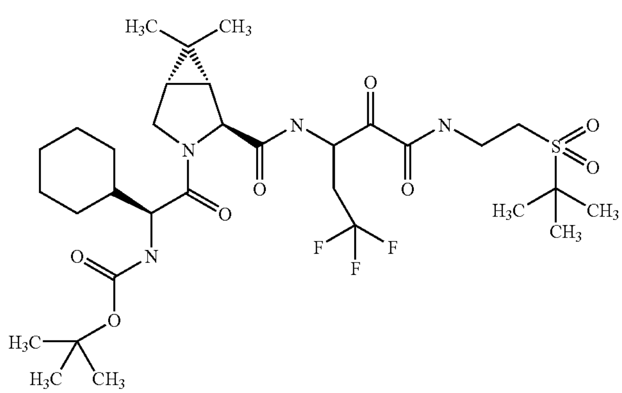 | 709 | B |
| 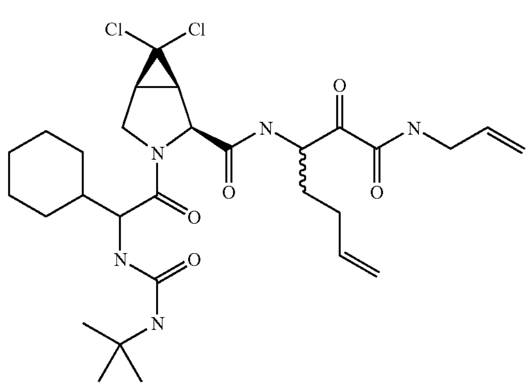 | 613 | A |

TABLE 5-continued

| STRUCTURE | MW | Ki* Range |
|---|---|---|
| 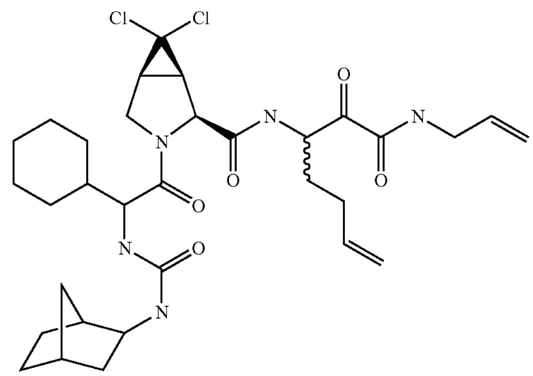 | 651 | C |
| 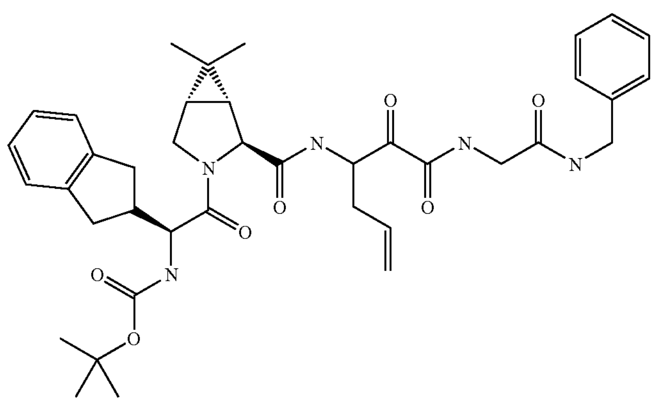 | 700 | A |
| 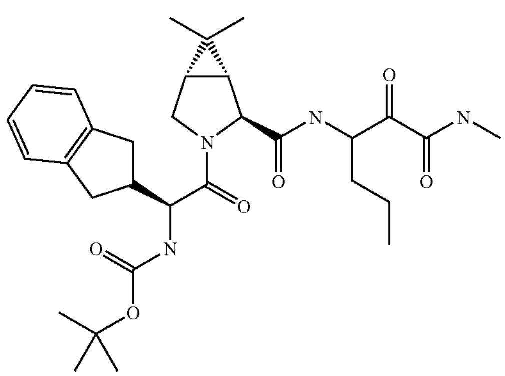 | 569 | A |
| 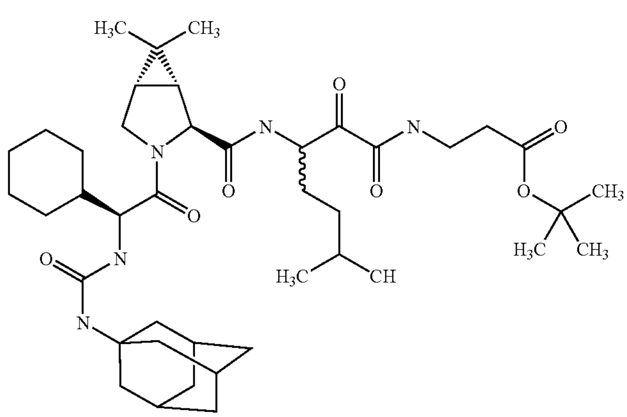 | 756 | B |

TABLE 5-continued

| STRUCTURE | MW | Ki* Range |
|---|---|---|
| 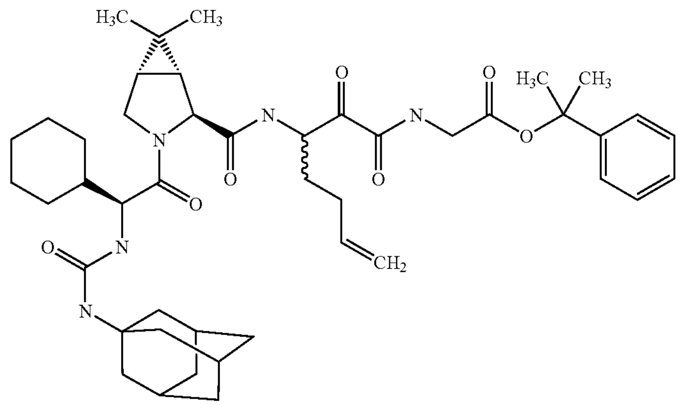 | 786 | A |
| 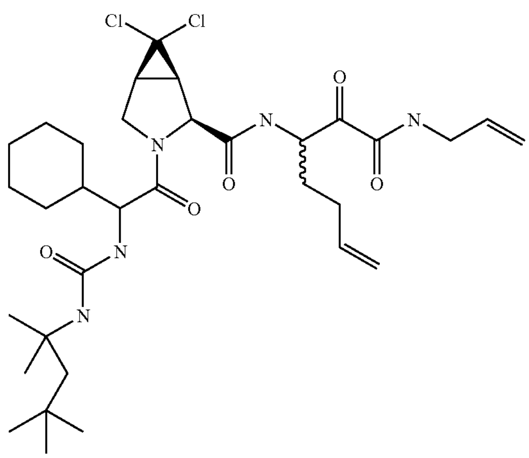 | 669 | B |
| | 601 | A |
| | 601 | B |

TABLE 5-continued

| STRUCTURE | MW | Ki* Range |
|---|---|---|
| 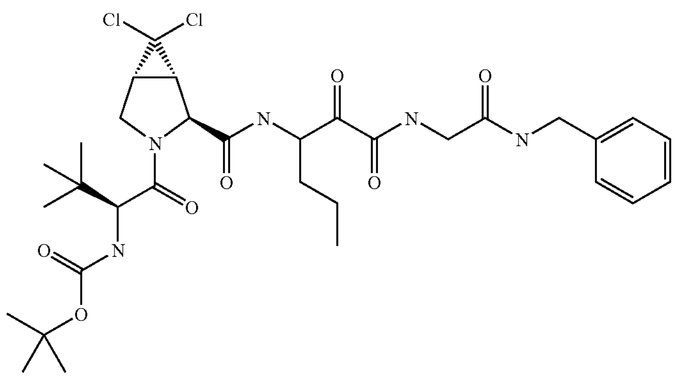 | 683 | A |
| 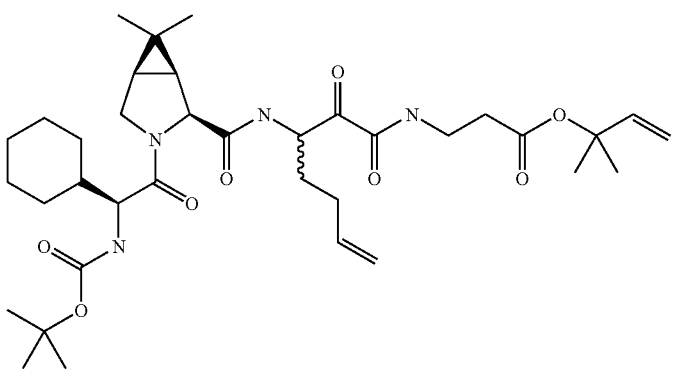 | 673 | A |
| 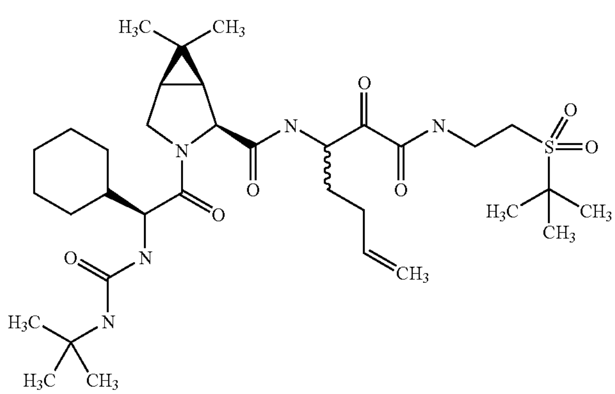 | 680 | A |
| 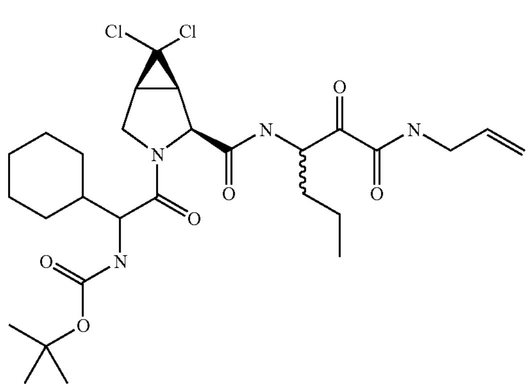 | 602 | A |

TABLE 5-continued
| STRUCTURE | MW | Ki* Range |
|---|---|---|
| 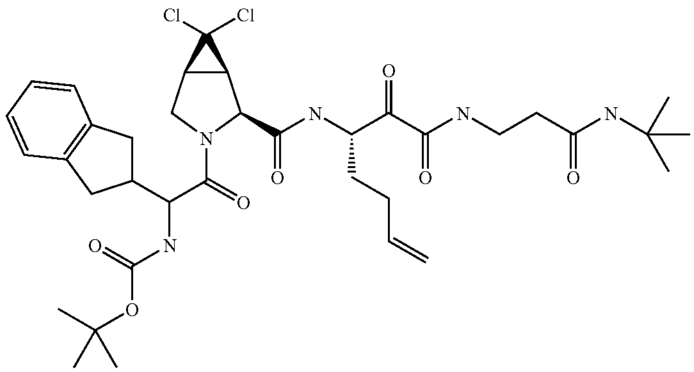 | 735 | A |
| 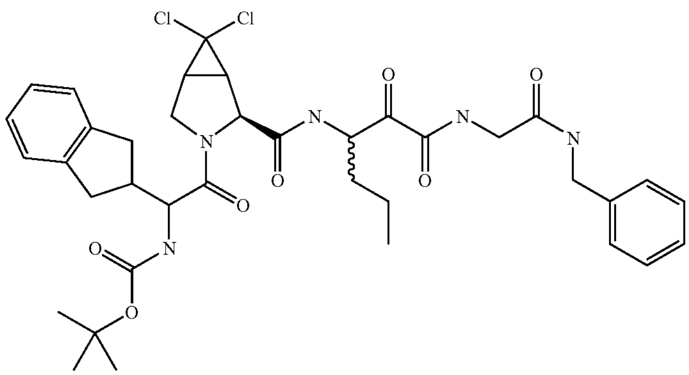 | 743 | A |
| 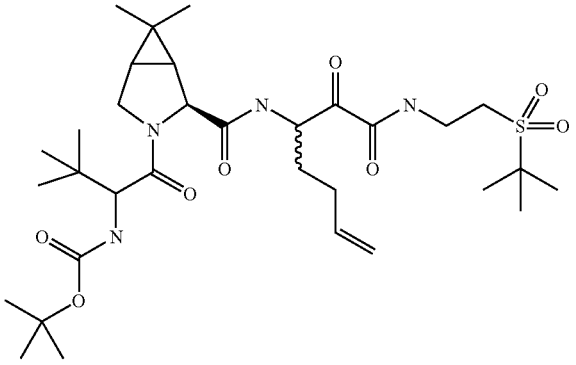 | 655 | B |
| 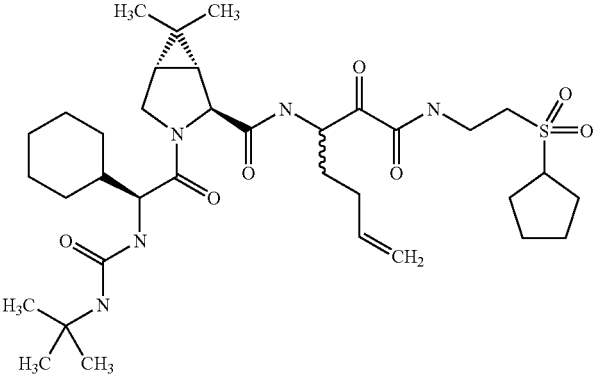 | 692 | A |

TABLE 5-continued

| STRUCTURE | MW | Ki* Range |
|---|---|---|
|  | 639 | A |
|  | 639 | A |
| 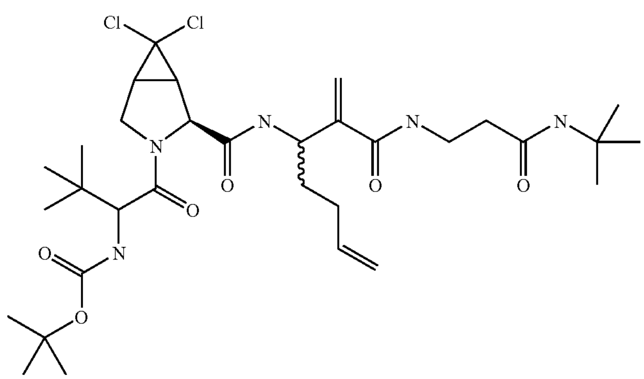 | 675 | A |
| 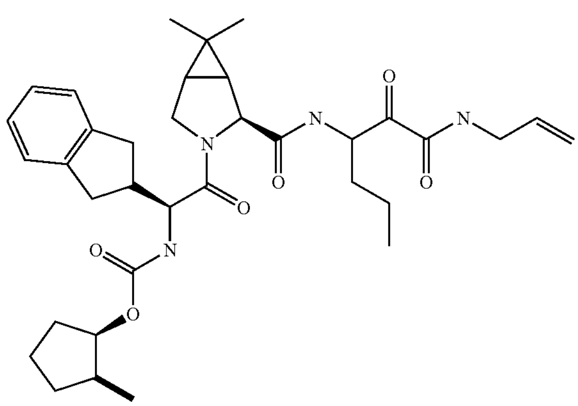 | 621 | A |

TABLE 5-continued

| STRUCTURE | MW | Ki* Range |
|---|---|---|
| 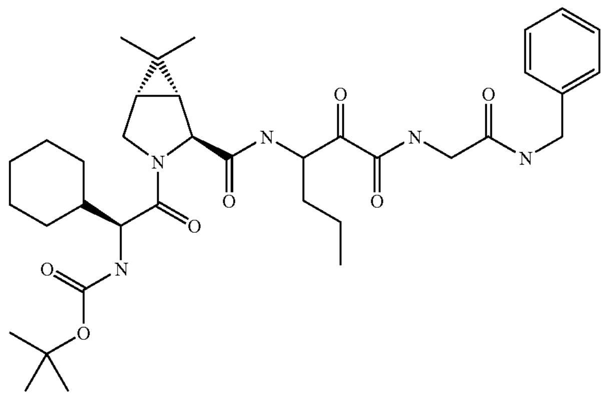 | 668 | A |
| 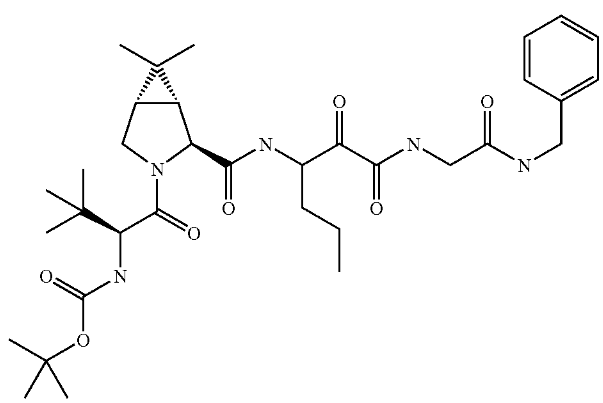 | 642 | A |
| 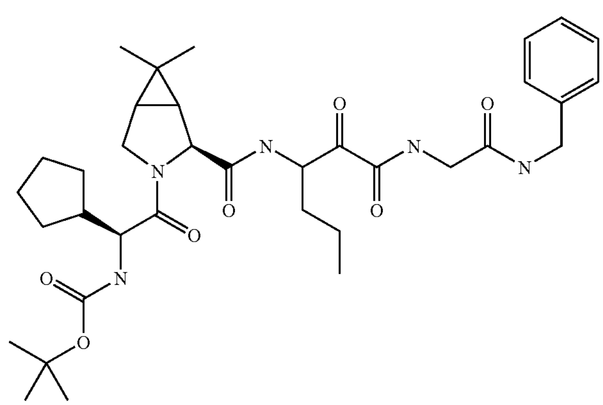 | 654 | A |

TABLE 5-continued

| STRUCTURE | MW | Ki* Range |
|---|---|---|
| 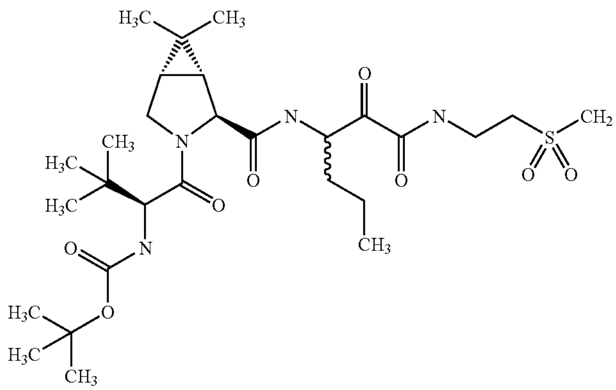 | 601 | C |
| 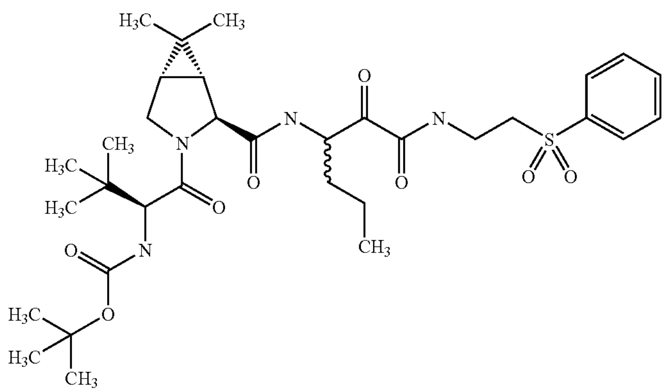 | 663 | B |
| 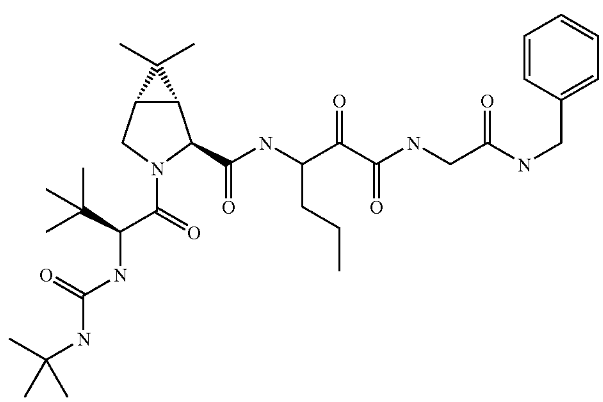 | 641 | A |
| 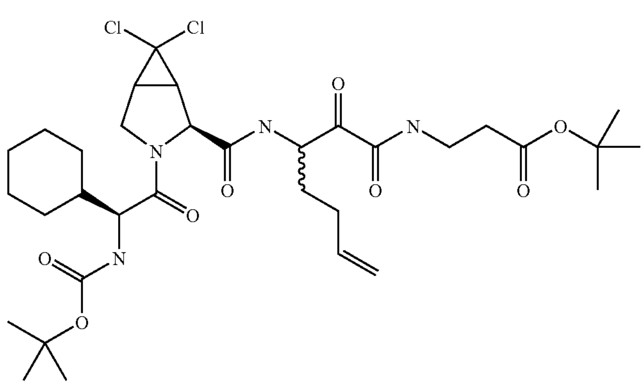 | 702 | A |

TABLE 5-continued

| STRUCTURE | MW | Ki* Range |
|---|---|---|
| 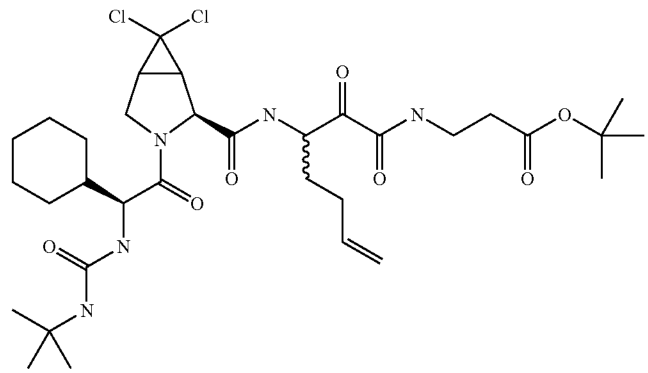 | 701 | A |
| 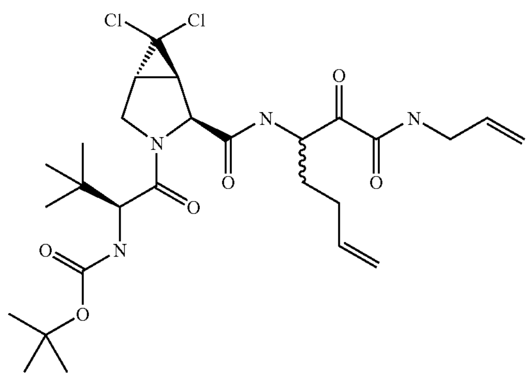 | 588 | B |
| 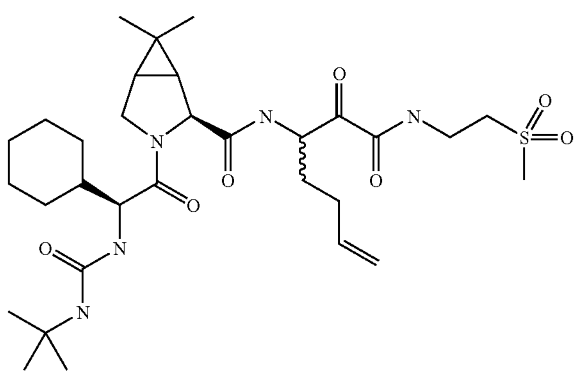 | 638 | A |
| 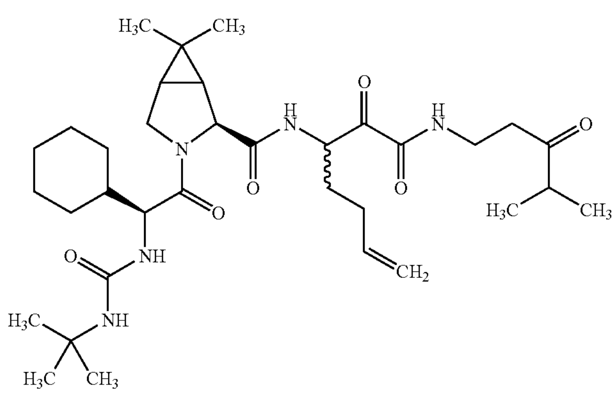 | 630 | A |

TABLE 5-continued

| STRUCTURE | MW | Ki* Range |
|---|---|---|
| 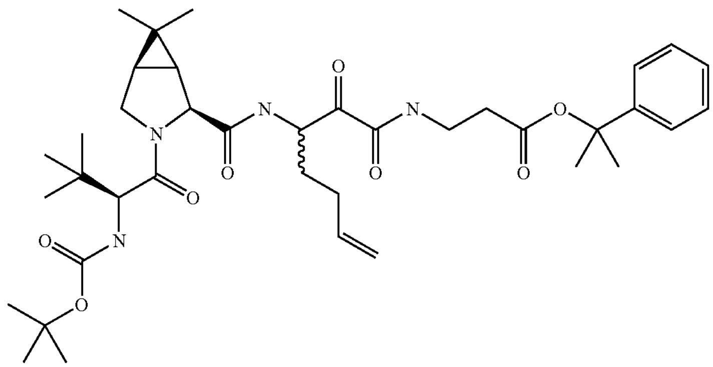 | 697 | A |
| 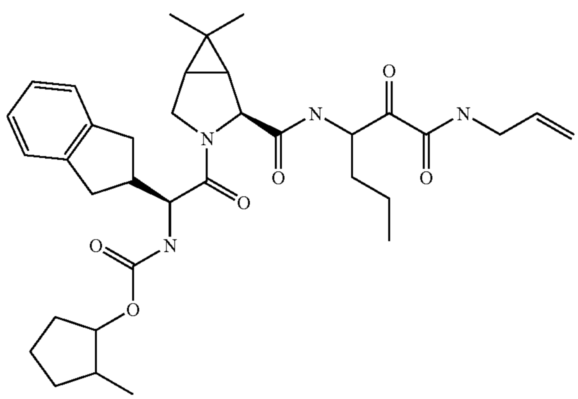 | 621 | A |
| 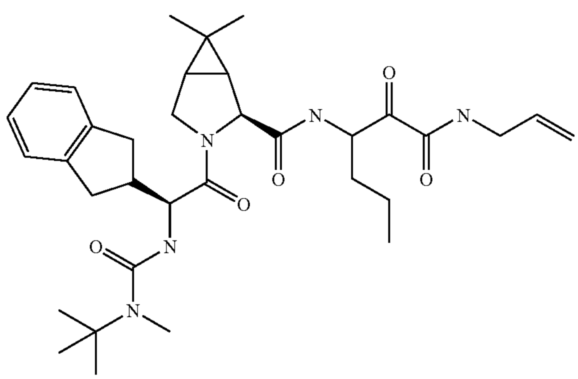 | 608 | B |
| 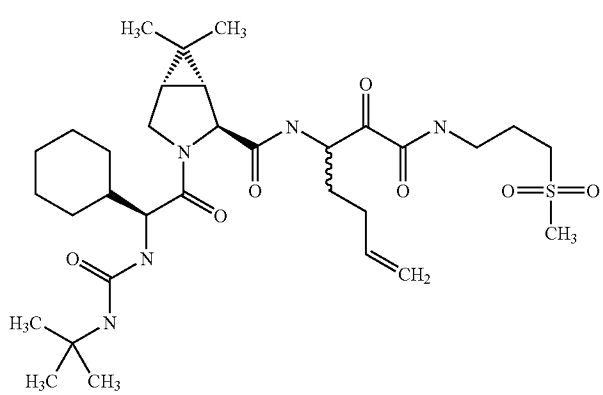 | 652 | B |

TABLE 5-continued
| STRUCTURE | MW | Ki* Range |
|---|---|---|
| 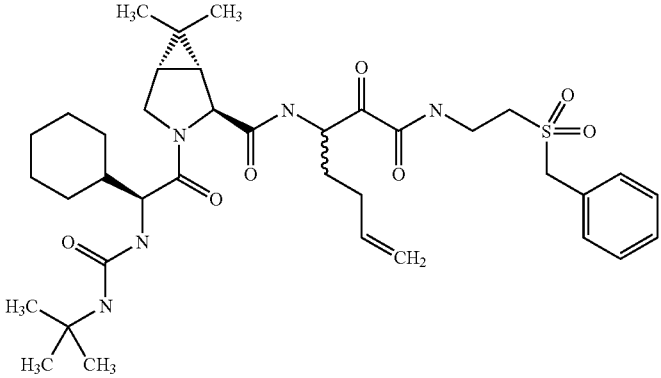 | 714 | A |
| 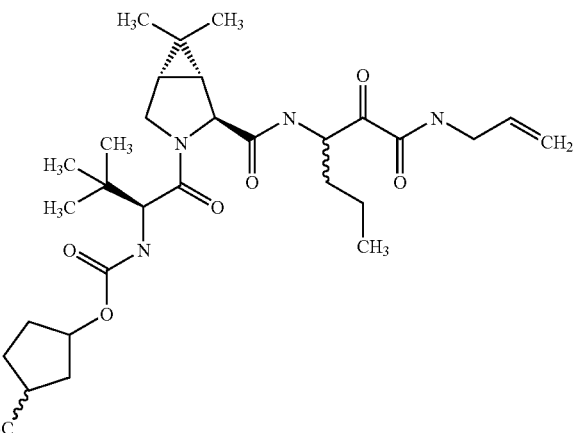 | 561 | B |
| 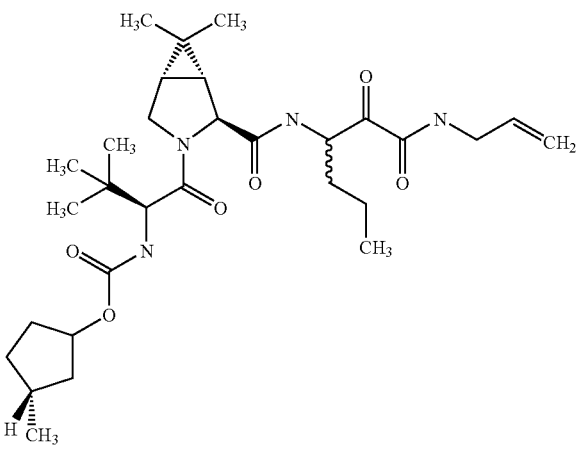 | 561 | B |

TABLE 5-continued
| STRUCTURE | MW | Ki* Range |
|---|---|---|
| 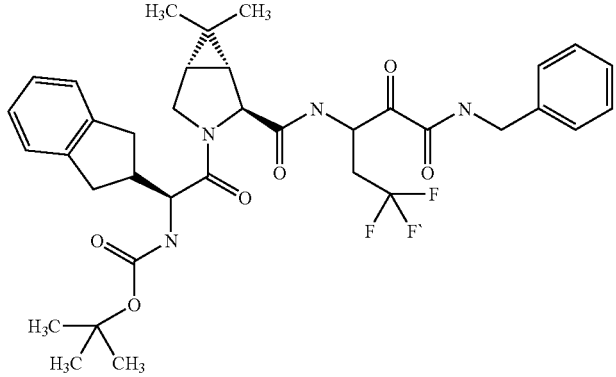 | 685 | B |
| 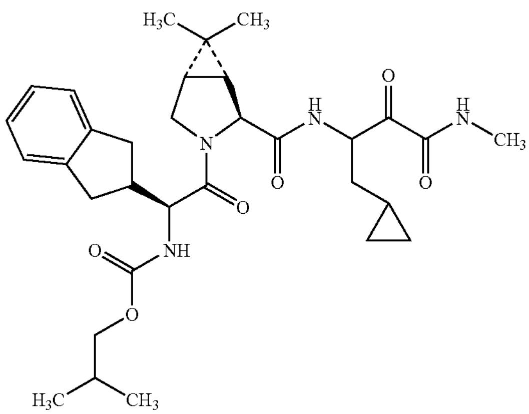 | 580 | A |
| 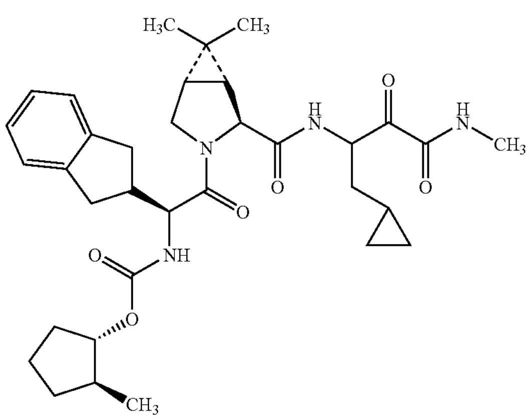 | 606 | A |
| 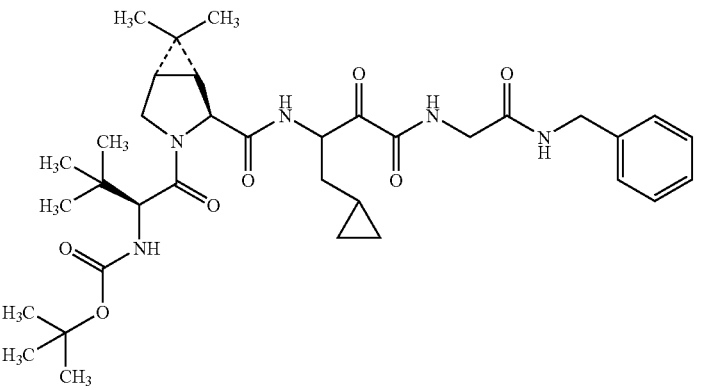 | 653 | A |

TABLE 5-continued
| STRUCTURE | MW | Ki* Range |
|---|---|---|
| 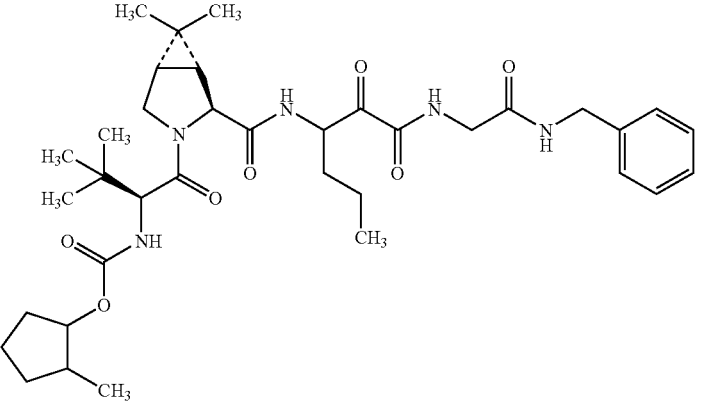 | 667 | A |
TABLE 6
| STRUCTURE | MW | Ki* (nM) |
|---|---|---|
| 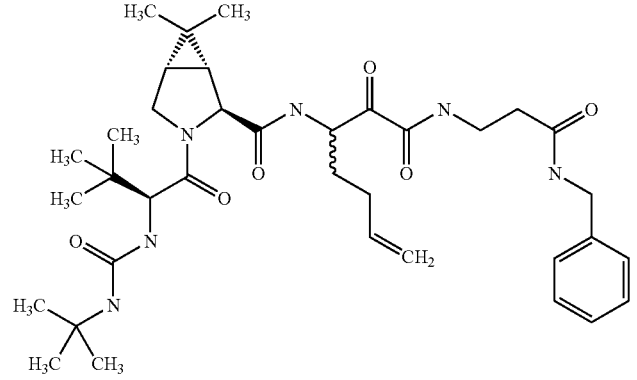 | 666.87 | A |
| 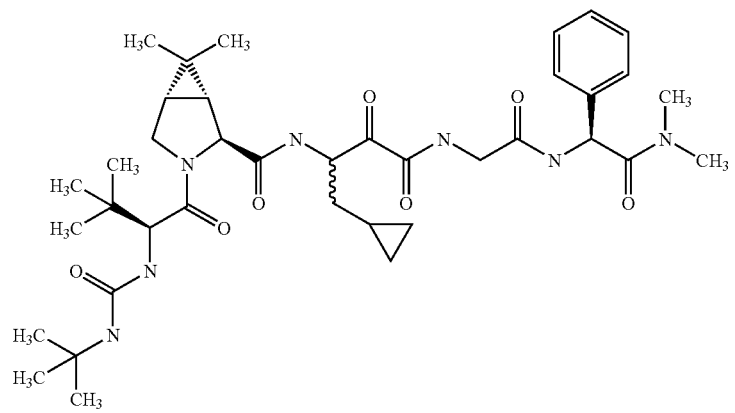 | 723.92 | A |

TABLE 6-continued
| STRUCTURE | MW | Ki* (nM) |
|---|---|---|
| 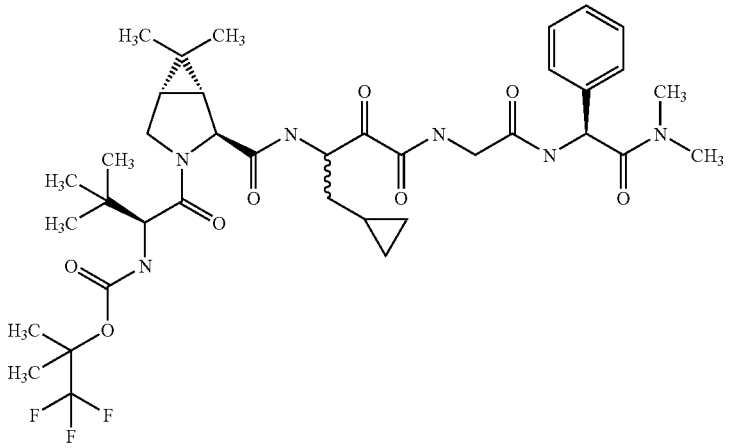 | 778.88 | A |
| 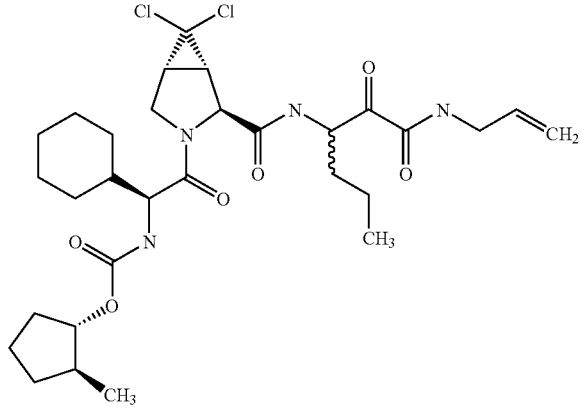 | 627.61 | A |
| 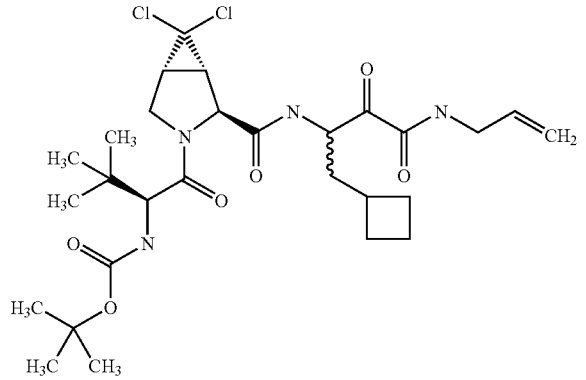 | 601.58 | B |

TABLE 6-continued
| STRUCTURE | MW | Ki* (nM) |
|---|---|---|
| 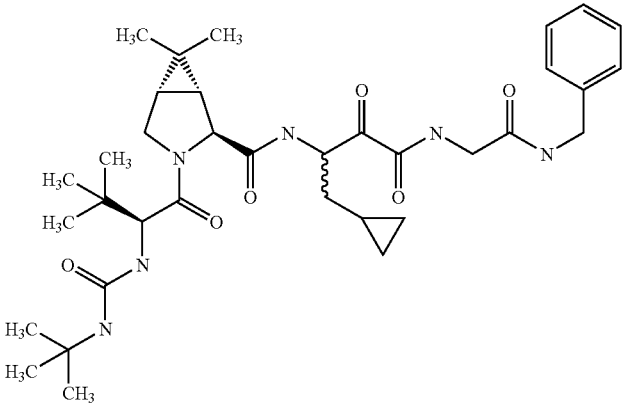 | 652.84 | A |
| 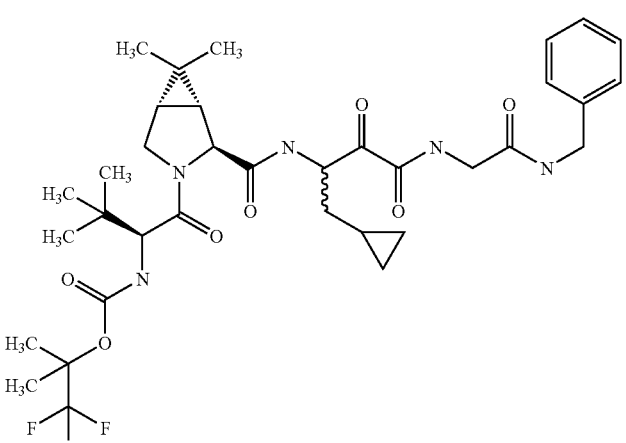 | 707.80 | A |
| 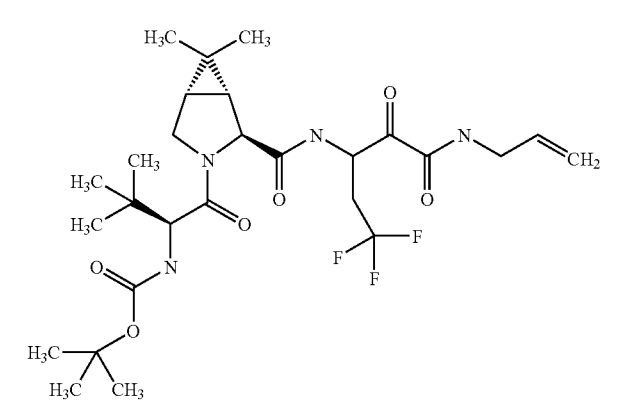 | 574.65 | B |

TABLE 6-continued
| STRUCTURE | MW | Ki* (nM) |
|---|---|---|
| 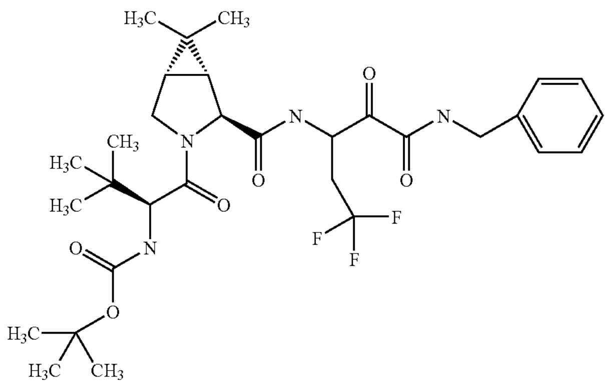 | 624.71 | B |
| 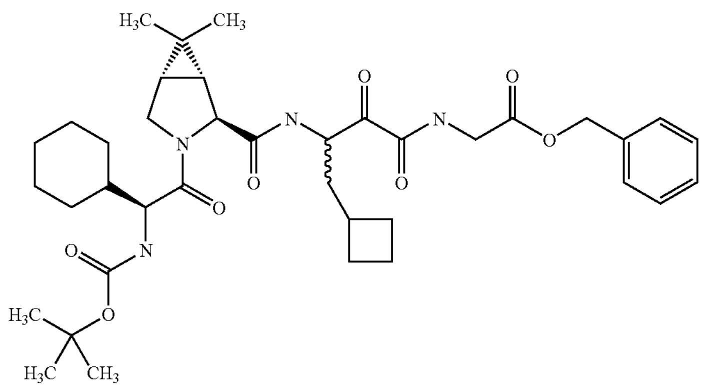 | 694.88 | A |
| 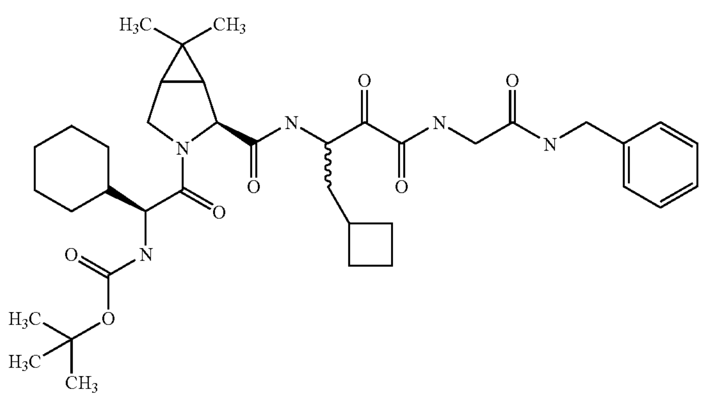 | 693.89 | B |
| 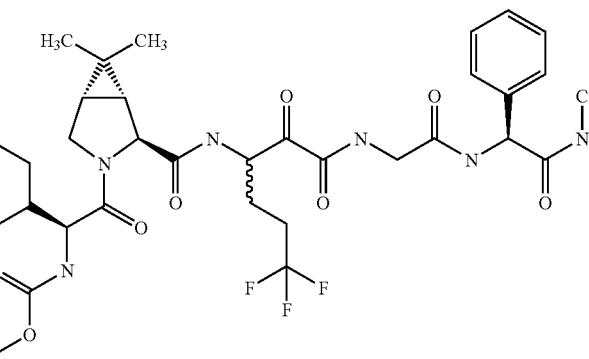 | 792.90 | A |

TABLE 6-continued

| STRUCTURE | MW | Ki* (nM) |
|---|---|---|
| 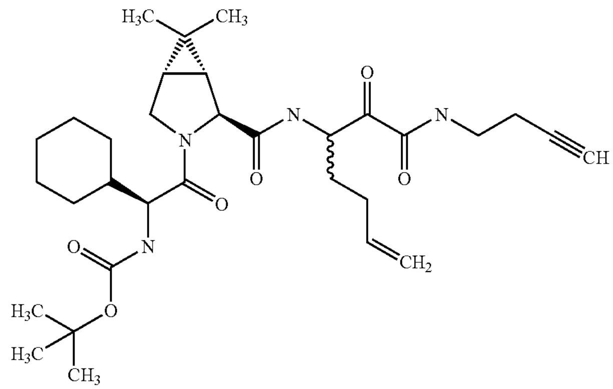 | 584.76 | A |
| 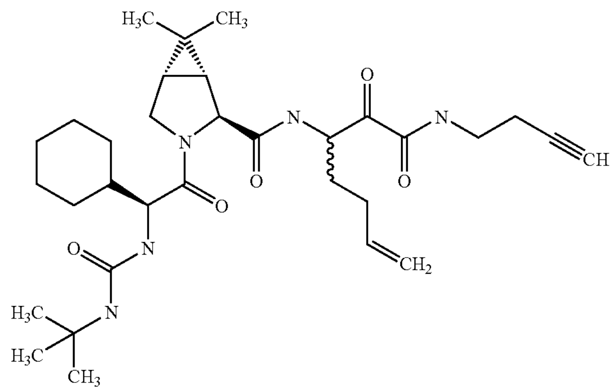 | 583.78 | A |
| 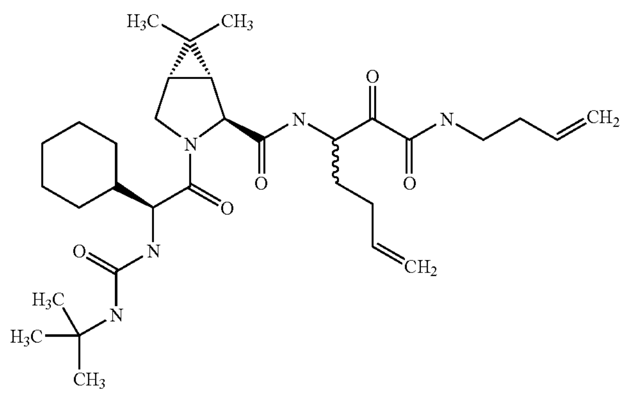 | 585.79 | A |
| 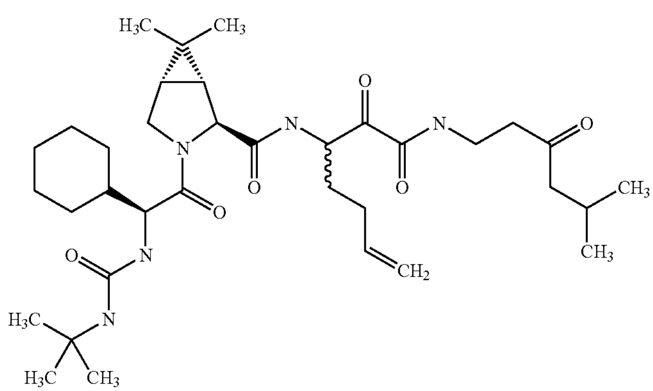 | 643.87 | A |

TABLE 6-continued

| STRUCTURE | MW | Ki* (nM) |
|---|---|---|
| | 574.72 | B |
| | 574.72 | B |
| 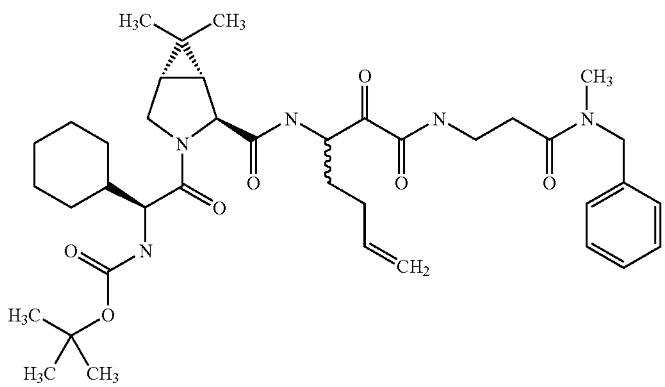 | 693.89 | B |
| 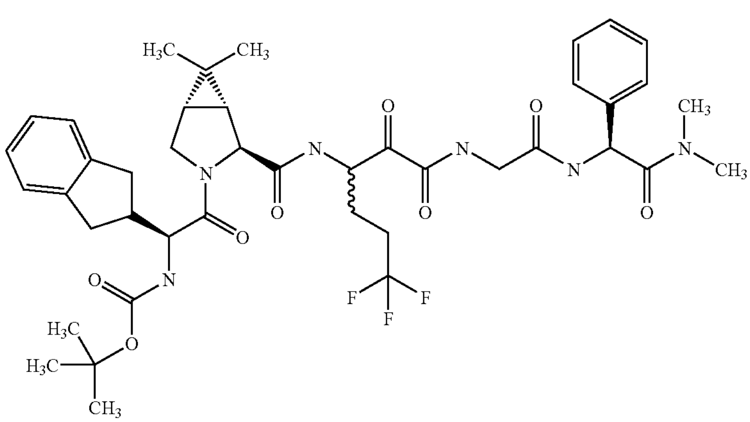 | 826.92 | A |

TABLE 6-continued
| STRUCTURE | MW | Ki* (nM) |
|---|---|---|
| 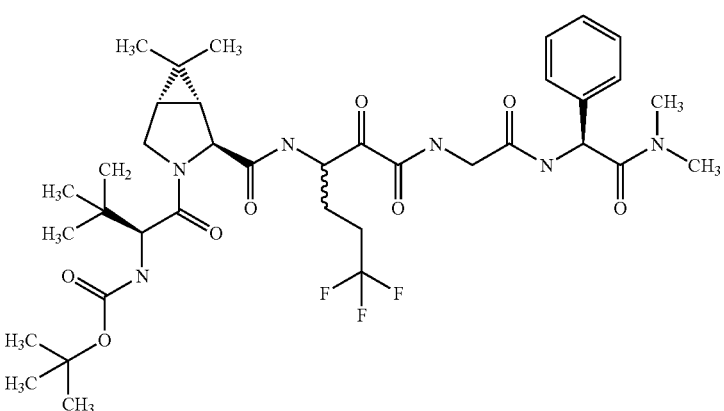 | 766.87 | A |
| 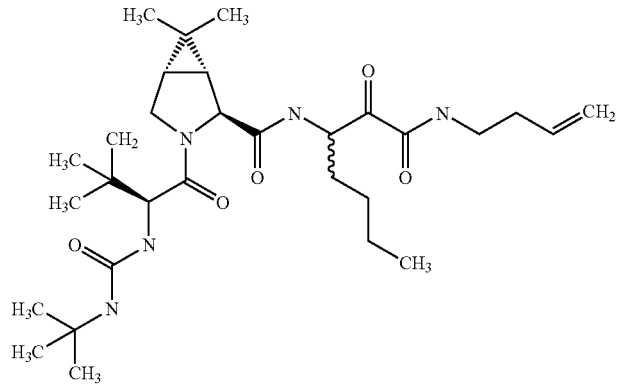 | 561.77 | B |
| 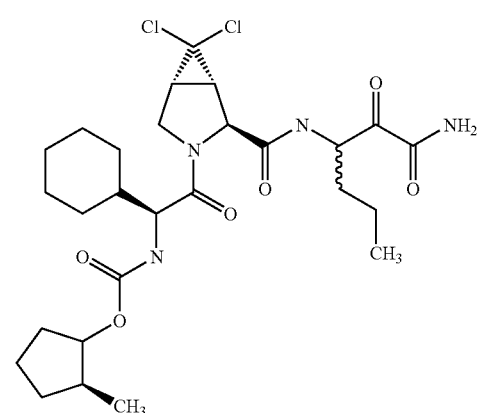 | 587.55 | A |

TABLE 6-continued

| STRUCTURE | MW | Ki* (nM) |
|---|---|---|
| 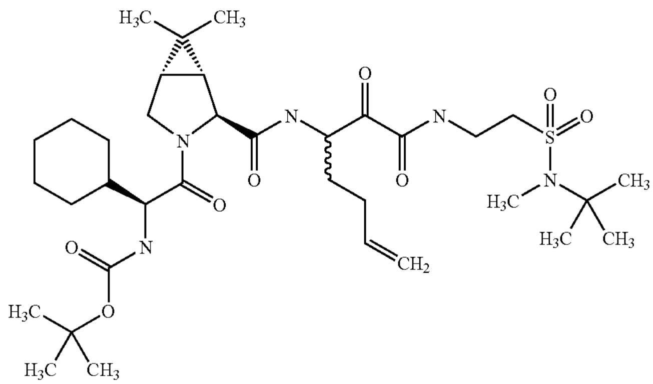 | 709.95 | A |
| 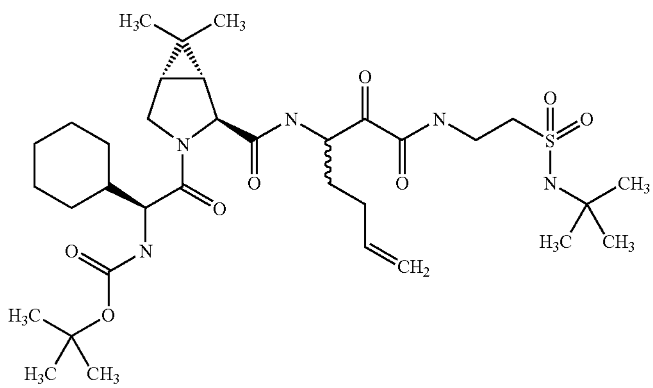 | 695.93 | B |
| 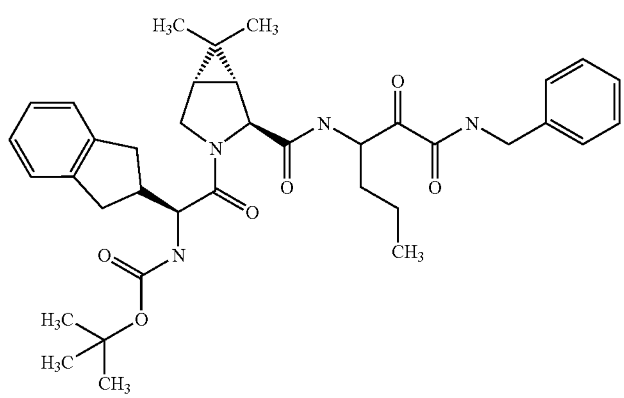 | 644.82 | B |
| 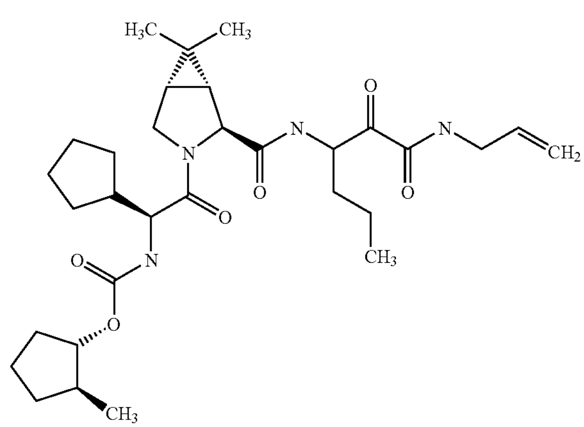 | 572.75 | A |

TABLE 6-continued
| STRUCTURE | MW | Ki* (nM) |
|---|---|---|
| 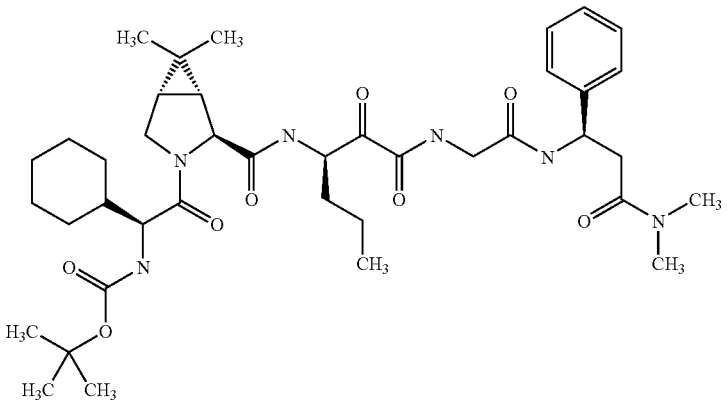 | 752.96 | A |
| 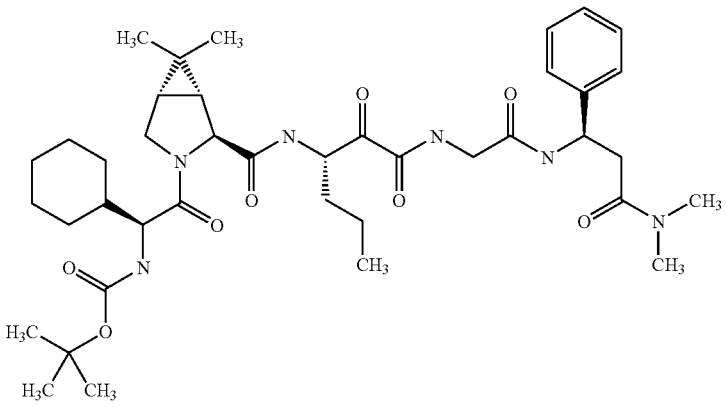 | 752.96 | A |
| 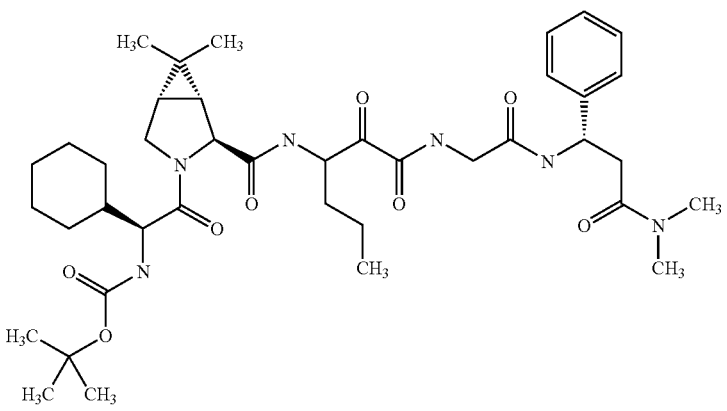 | 752.96 | A |

TABLE 6-continued
| STRUCTURE | MW | Ki* (nM) |
|---|---|---|
| 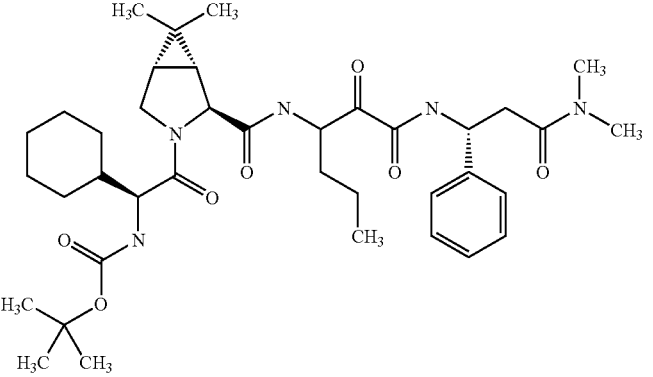 | 695.91 | C |
| 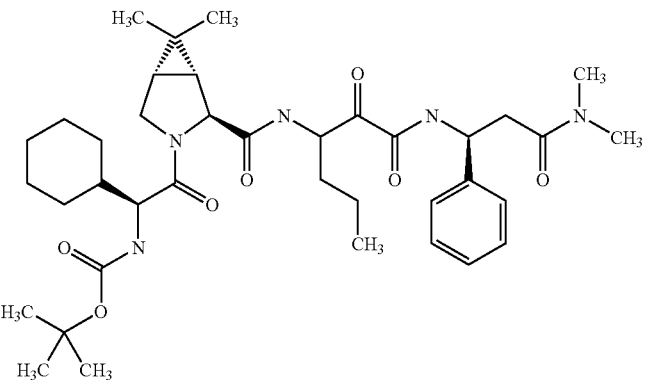 | 695.91 | B |
| 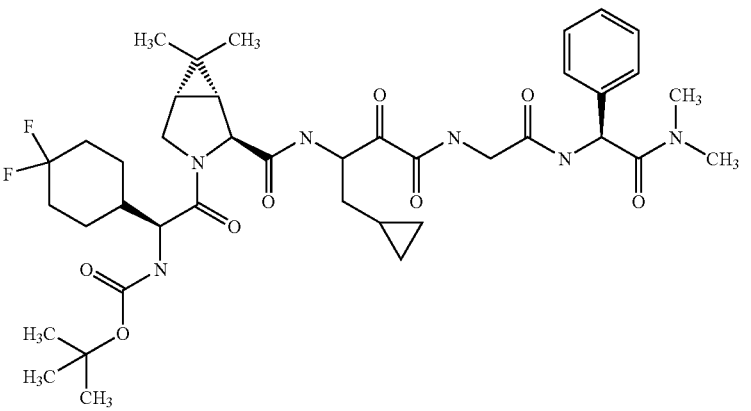 | 786.92 | A |

TABLE 6-continued
| STRUCTURE | MW | Ki* (nM) |
|---|---|---|
| 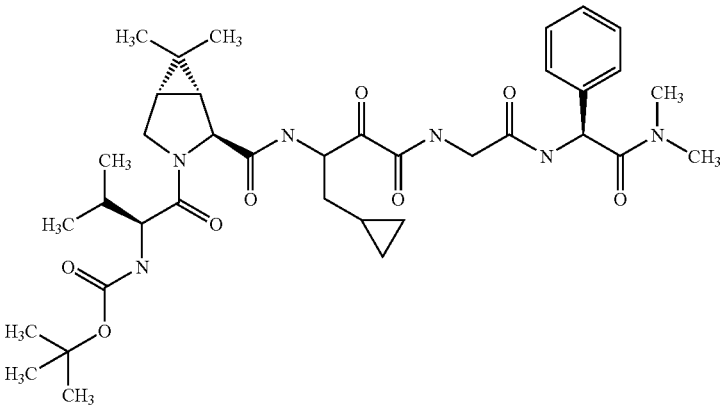 | 710.88 | A |
| 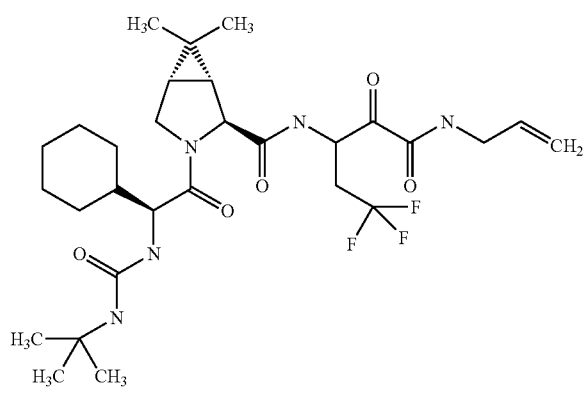 | 599.70 | A |
| 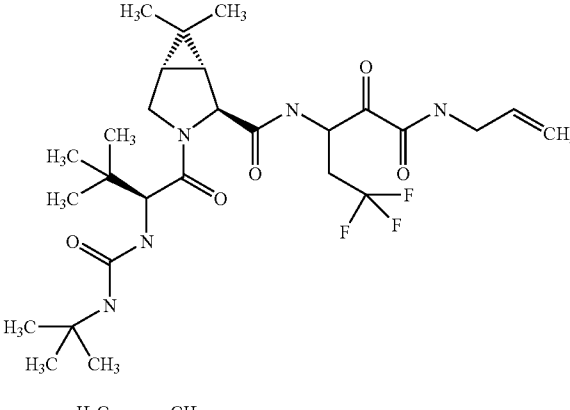 | 573.66 | B |
| 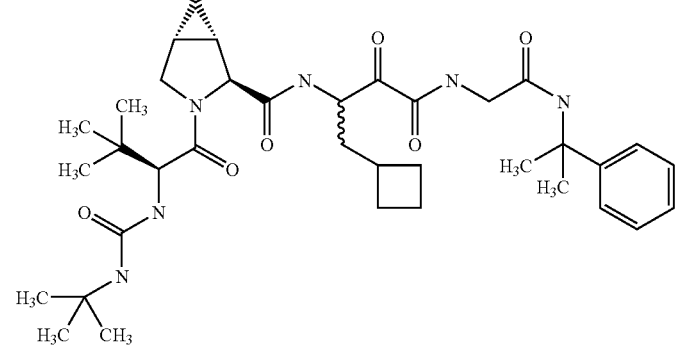 | 694.92 | B |

TABLE 6-continued
| STRUCTURE | MW | Ki* (nM) |
|---|---|---|
| 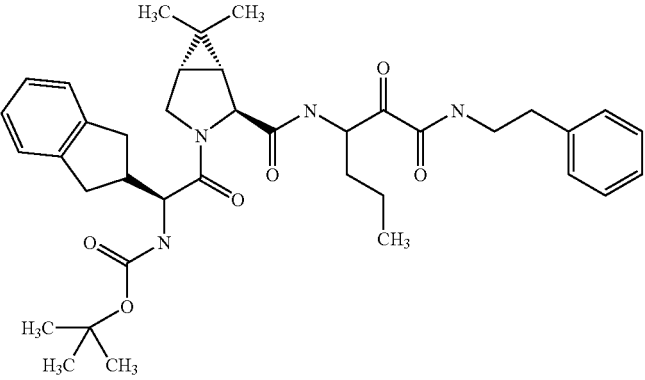 | 658.85 | B |
| 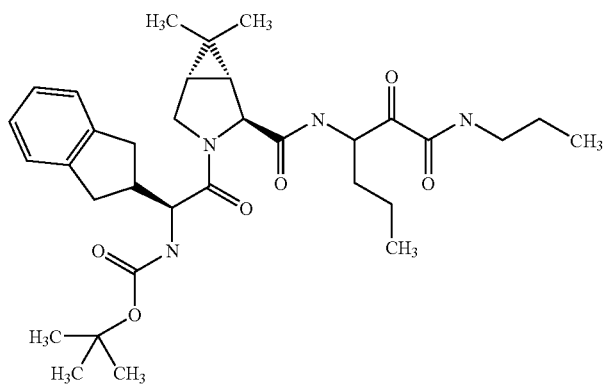 | 596.77 | B |
| 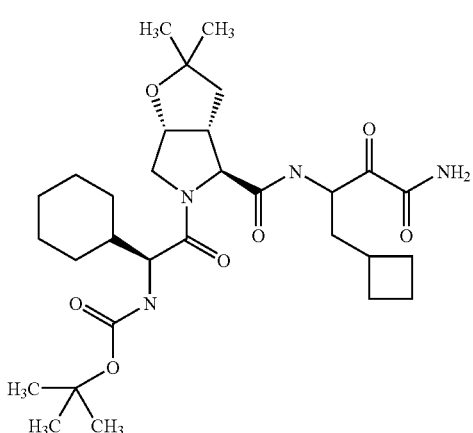 | 576.74 | B |

TABLE 6-continued
| STRUCTURE | MW | Ki* (nM) |
|---|---|---|
| 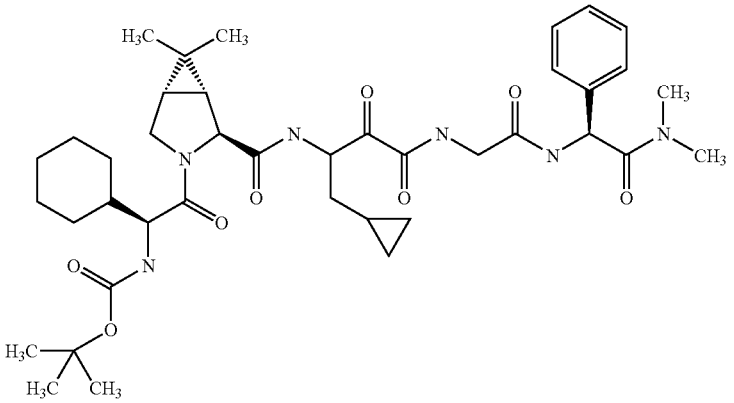 | 750.94 | A |
| 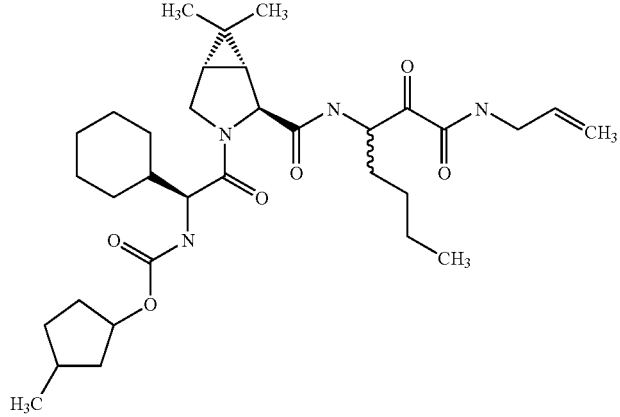 | 600.81 | B |
| 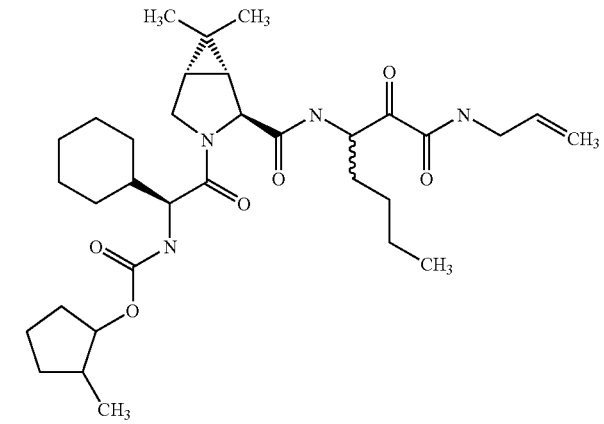 | 600.81 | B |

TABLE 6-continued

| STRUCTURE | MW | Ki* (nM) |
|---|---|---|
| 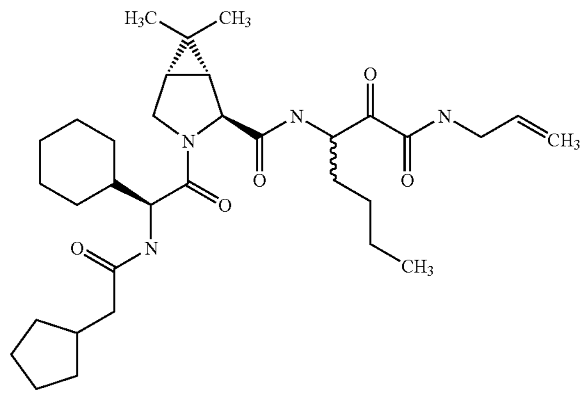 | 584.81 | B |
| 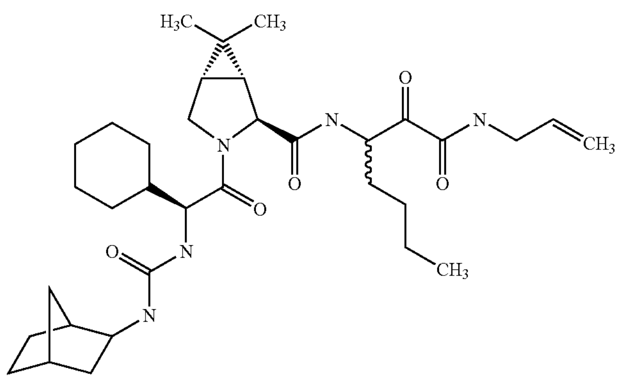 | 611.83 | A |
| 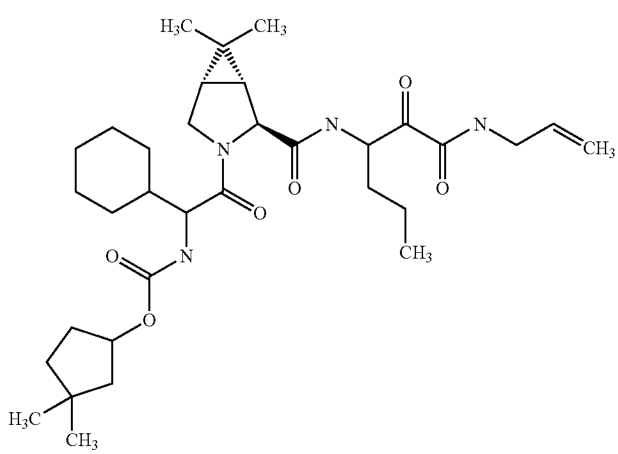 | 600.81 | B |

TABLE 6-continued
| STRUCTURE | MW | Ki* (nM) |
|---|---|---|
| 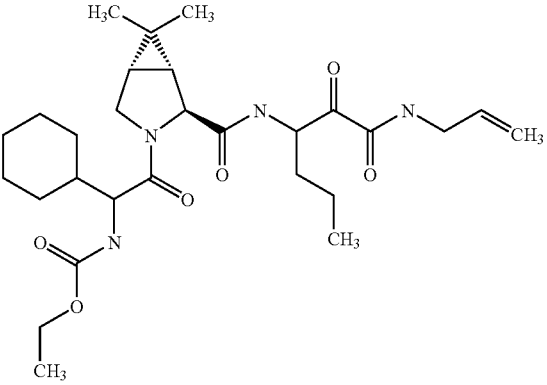 | 532.69 | B |
| 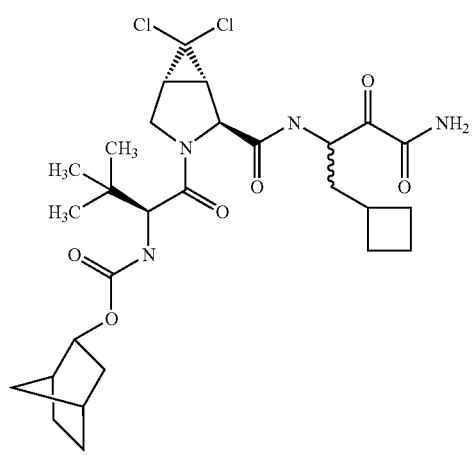 | 599.56 | A |
| 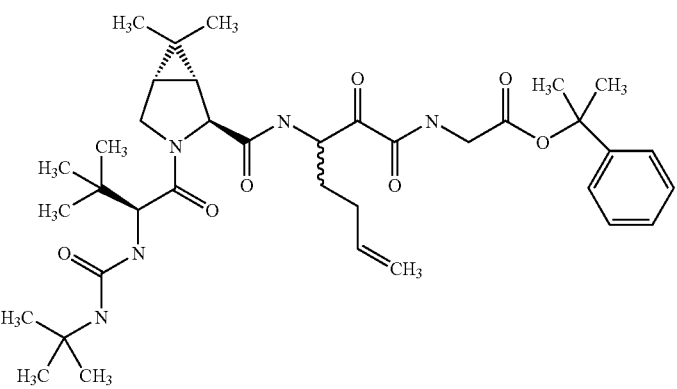 | 681.88 | A |

TABLE 6-continued

| STRUCTURE | MW | Ki* (nM) |
|---|---|---|
| 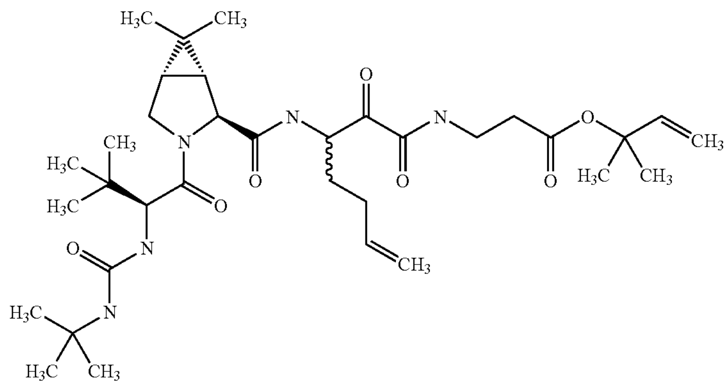 | 645.85 | A |
| 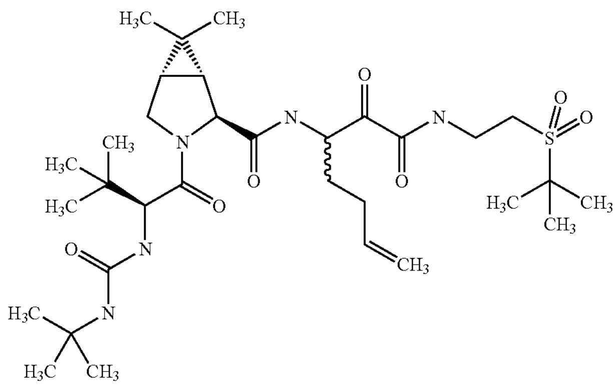 | 653.89 | B |
| 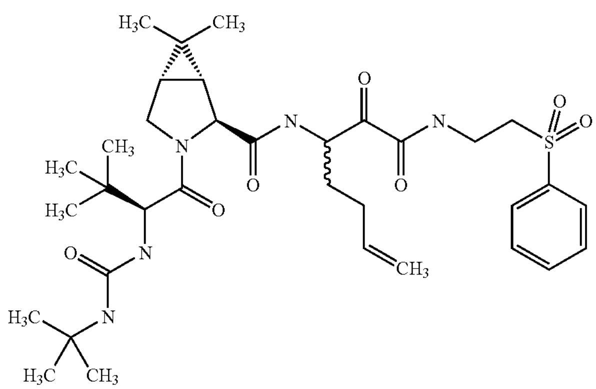 | 673.88 | A |
| 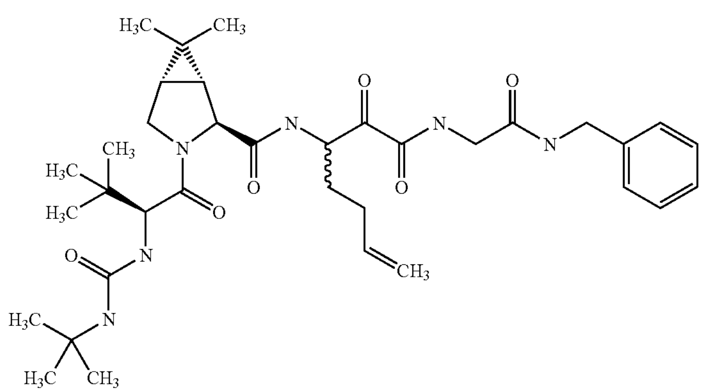 | 652.84 | A |

TABLE 6-continued

| STRUCTURE | MW | Ki* (nM) |
|---|---|---|
| 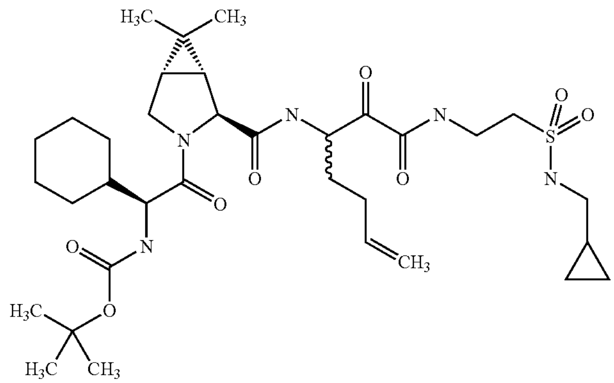 | 693.91 | A |
| 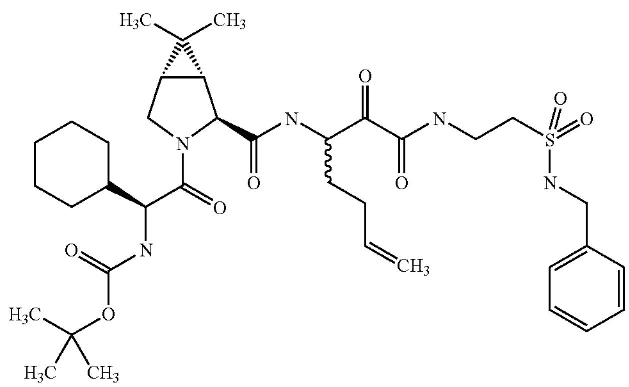 | 729.94 | A |
| 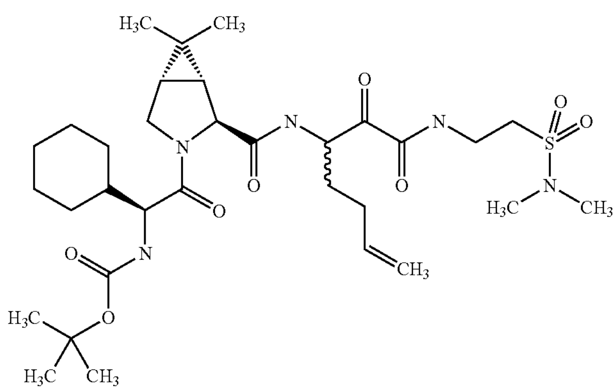 | 667.87 | A |
| 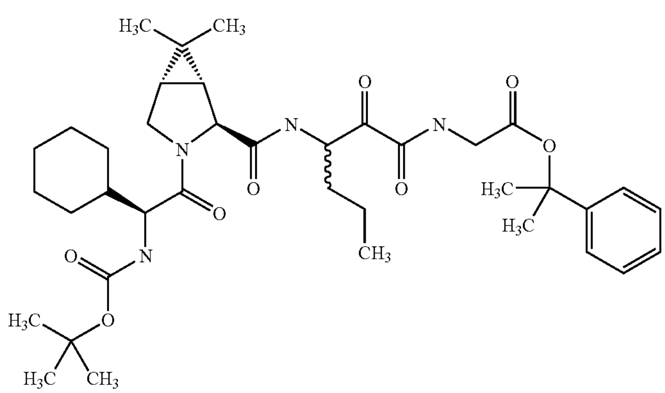 | 696.89 | A |

TABLE 6-continued

| STRUCTURE | MW | Ki* (nM) |
|---|---|---|
| 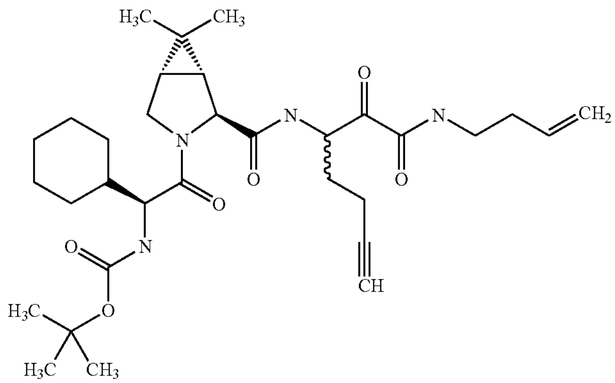 | 584.76 | A |
| 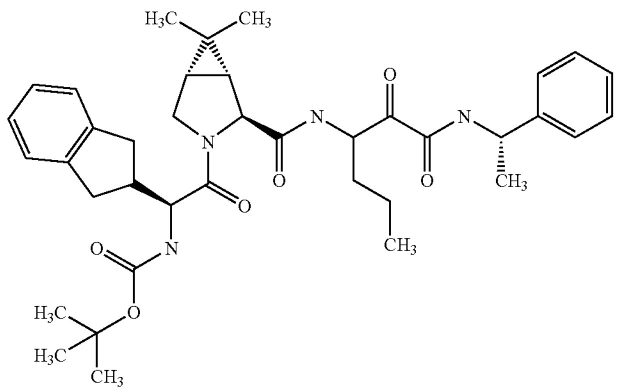 | 658.85 | A |
| 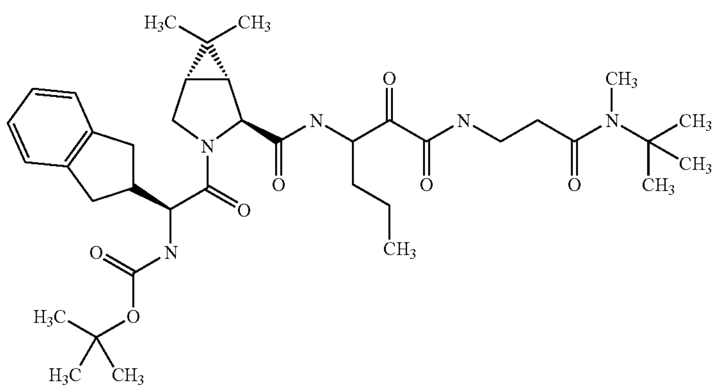 | 695.91 | B |
| 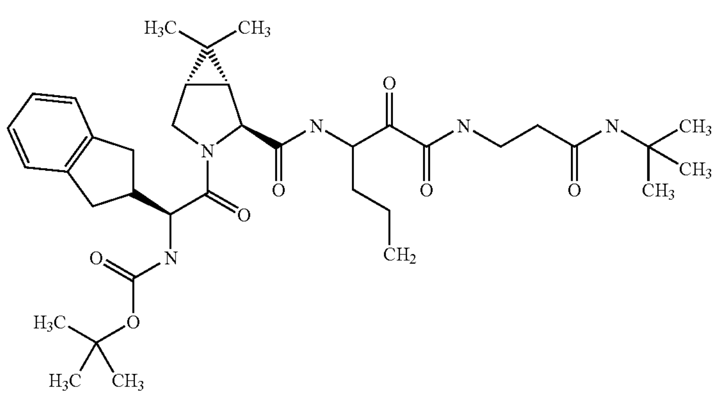 | 681.88 | B |

TABLE 6-continued

| STRUCTURE | MW | Ki* (nM) |
|---|---|---|
| 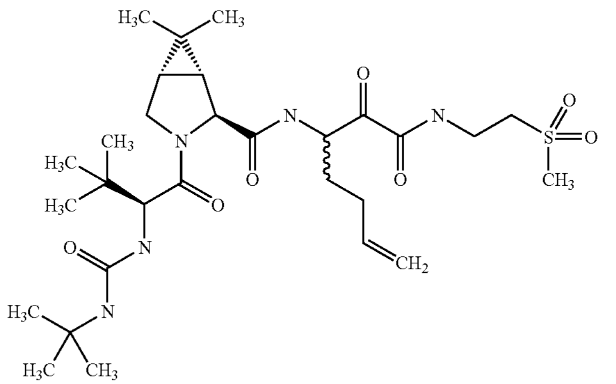 | 611.81 | B |
| 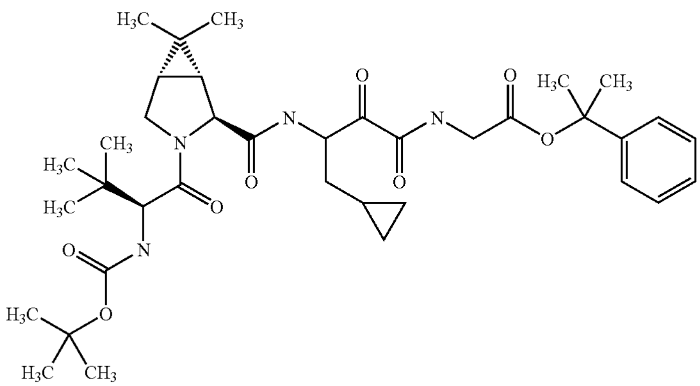 | 682.87 | A |
| 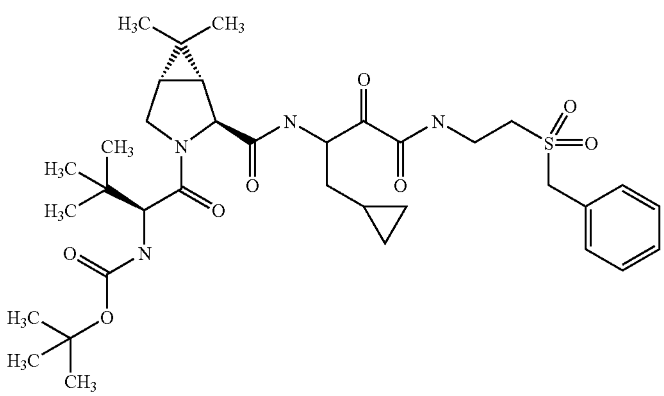 | 688.89 | A |
| 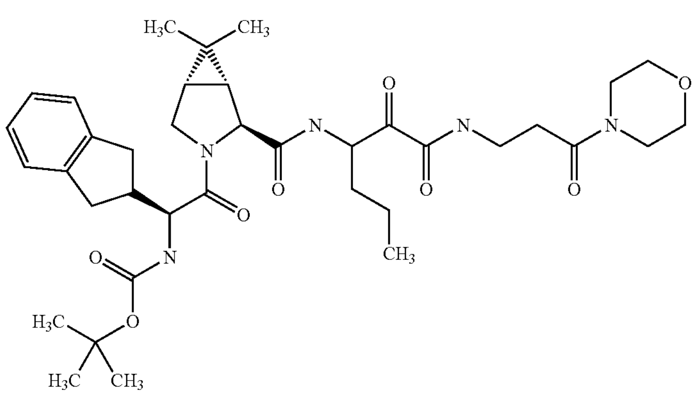 | 695.86 | B |

TABLE 6-continued

| STRUCTURE | MW | Ki* (nM) |
|---|---|---|
| 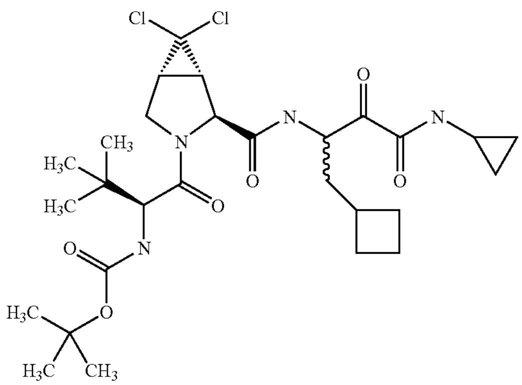 | 601.58 | B |
| 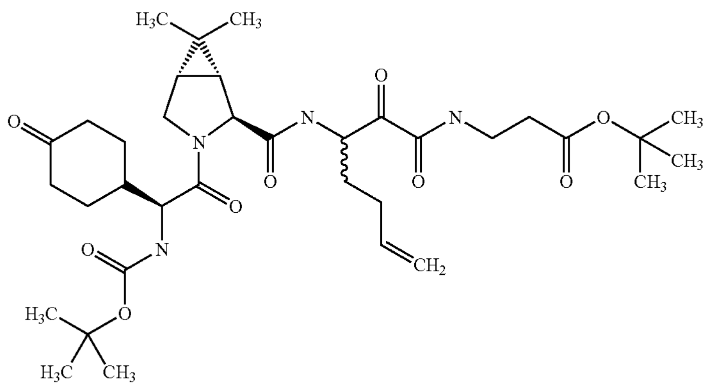 | 674.84 | A |
| 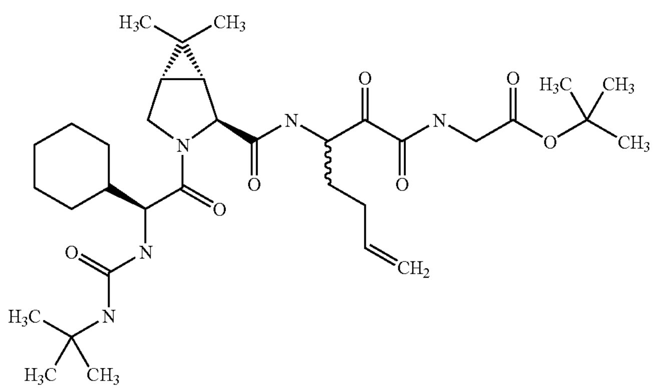 | 645.85 | B |
| 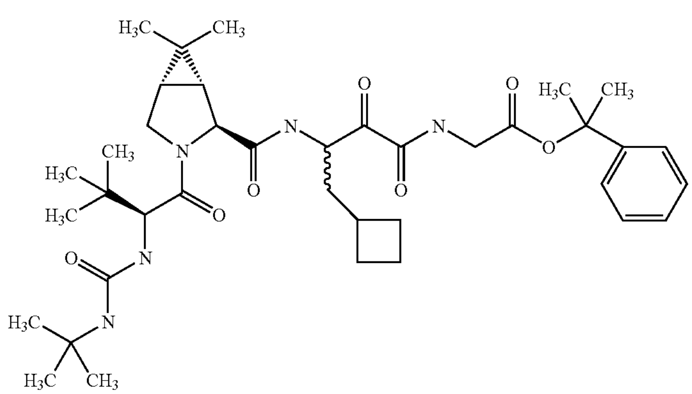 | 695.91 | A |

TABLE 6-continued

| STRUCTURE | MW | Ki* (nM) |
|---|---|---|
| 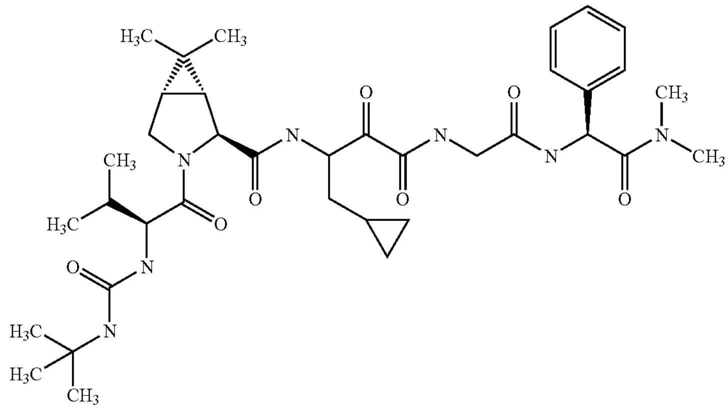 | 709.89 | A |
| 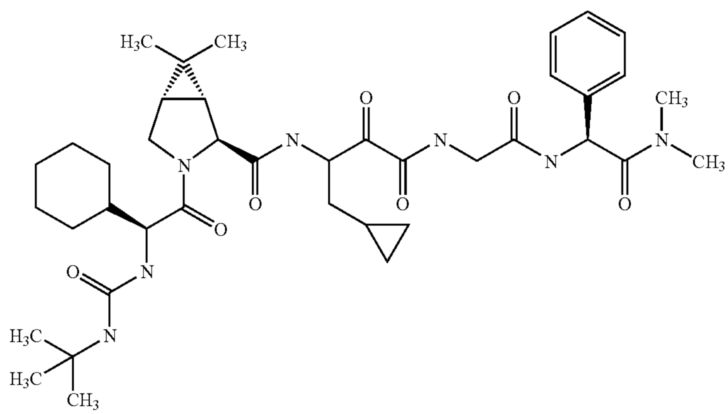 | 749.96 | A |
| 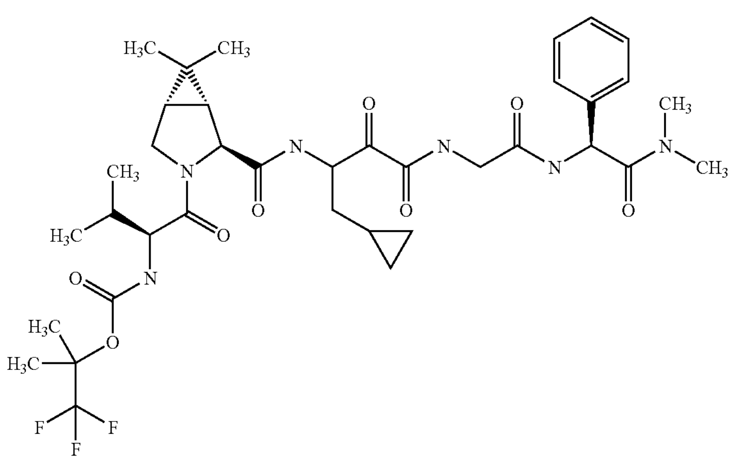 | 764.85 | A |

TABLE 6-continued
| STRUCTURE | MW | Ki* (nM) |
|---|---|---|
| 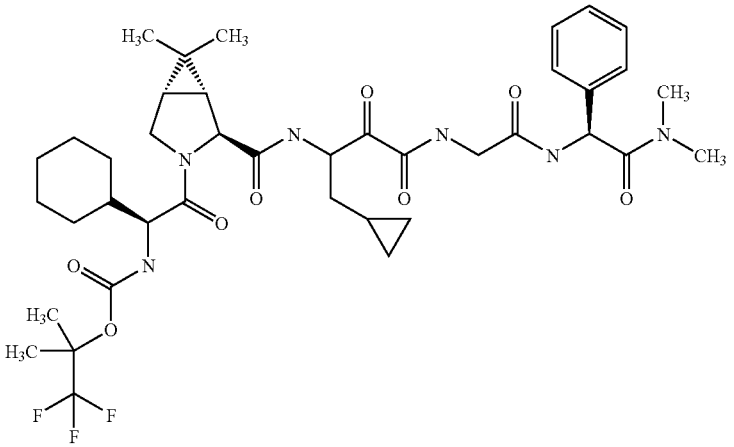 | 804.92 | A |
| 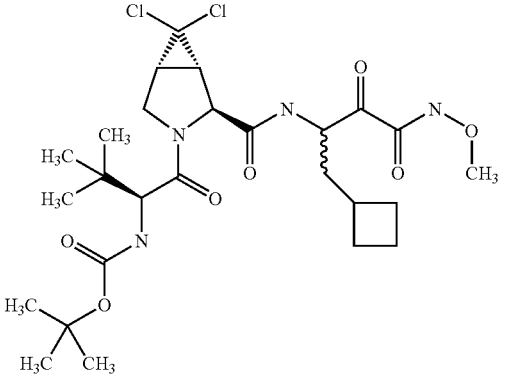 | 591.54 | A |
| 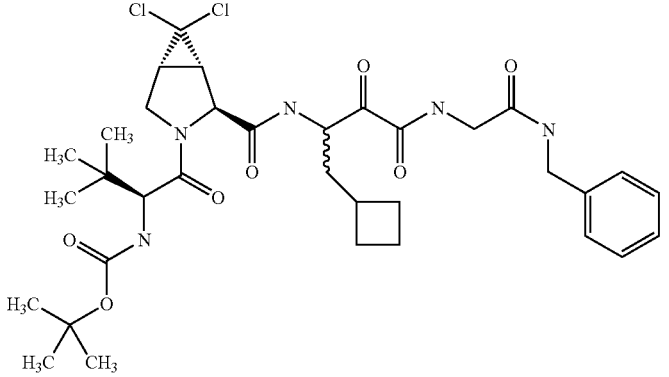 | 708.69 | C |

TABLE 6-continued
| STRUCTURE | MW | Ki* (nM) |
|---|---|---|
| 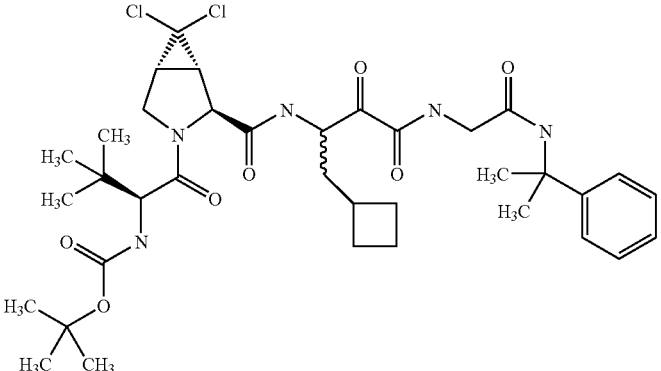 | 736.74 | C |
| 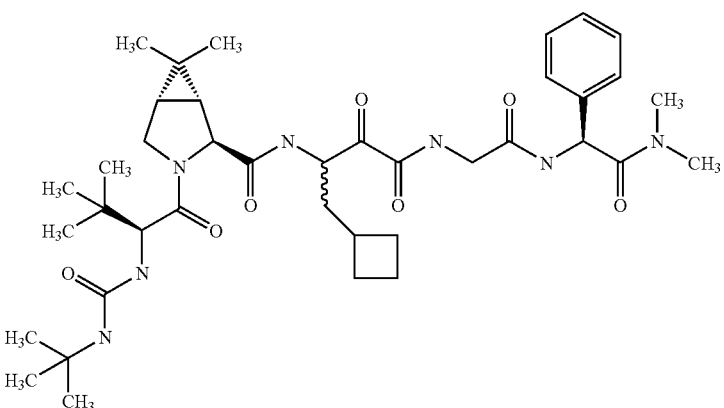 | 737.95 | A |
| 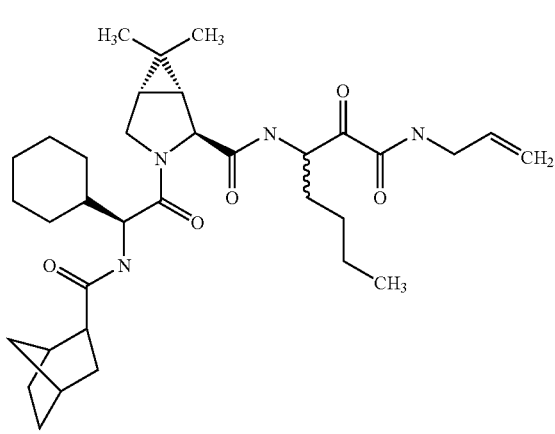 | 596.82 | B |

TABLE 6-continued

| STRUCTURE | MW | Ki* (nM) |
|---|---|---|
| 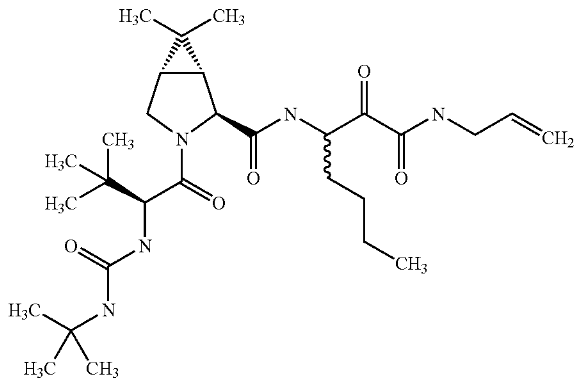 | 547.74 | B |
| 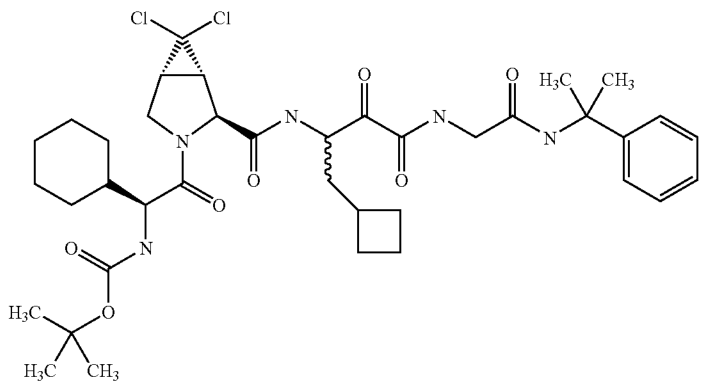 | 762.78 | C |
| 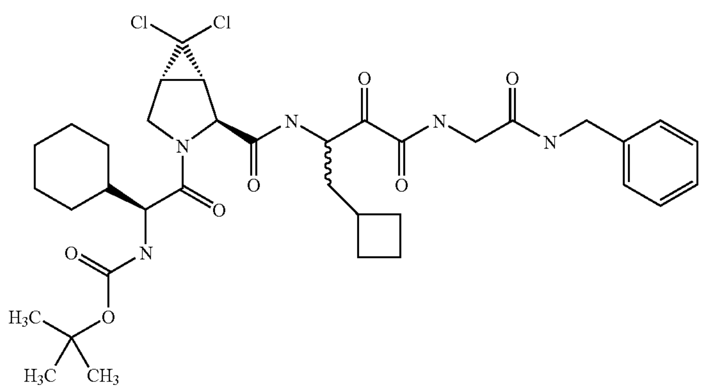 | 734.73 | A |
| 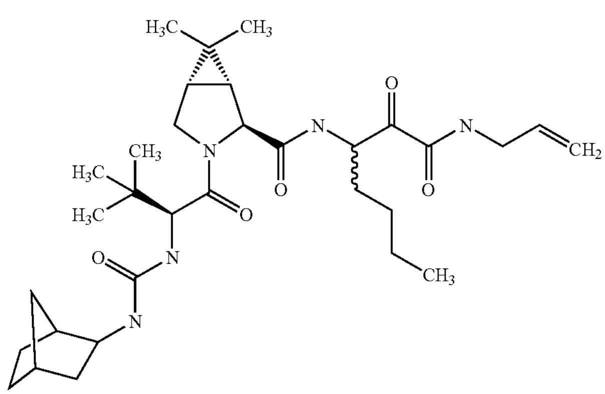 | 585.79 | B |

TABLE 6-continued
| STRUCTURE | MW | Ki* (nM) |
|---|---|---|
| 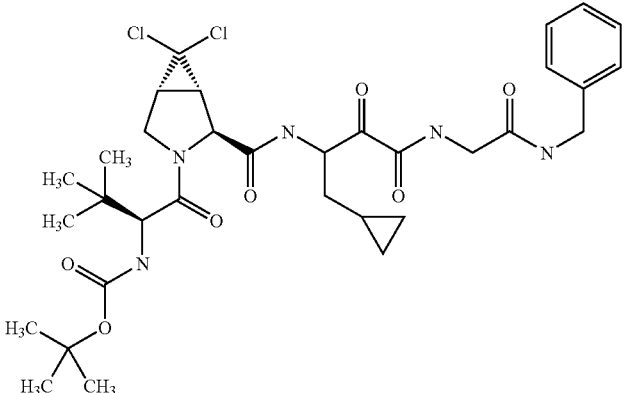 | 694.66 | A |
| 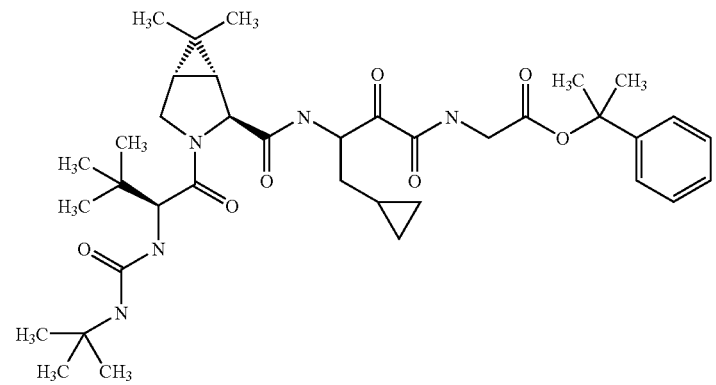 | 681.88 | A |
| 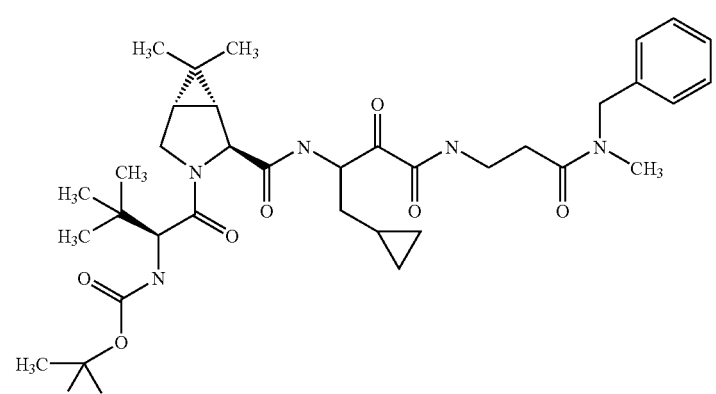 | 681.88 | B |

TABLE 6-continued

| STRUCTURE | MW | Ki* (nM) |
|---|---|---|
| 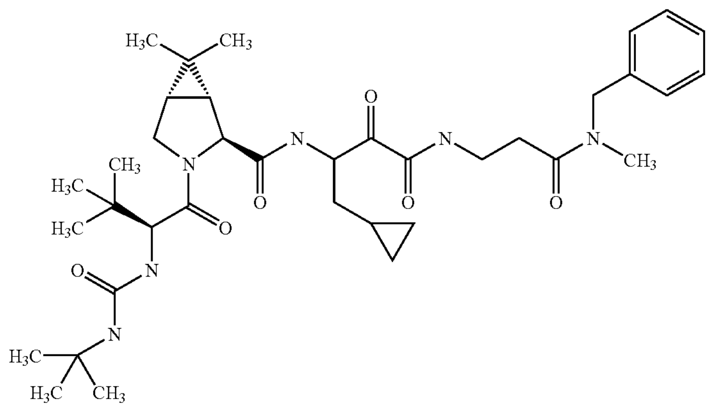 | 680.90 | B |
| 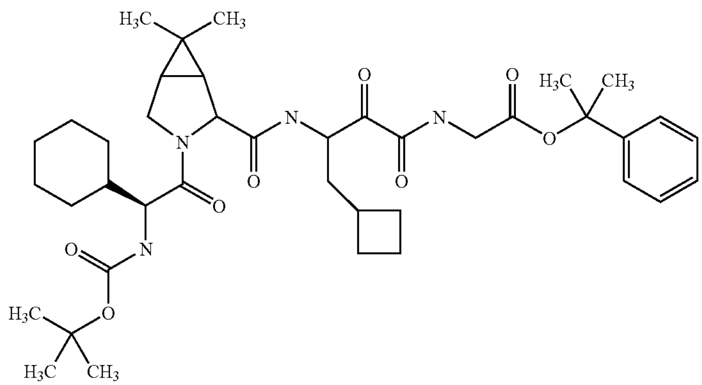 | 722.93 | C |
| 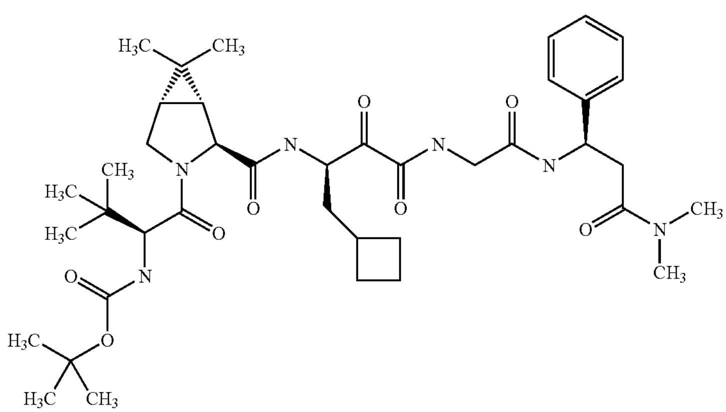 | 752.96 | A |

TABLE 6-continued

| STRUCTURE | MW | Ki* (nM) |
|---|---|---|
| | 752.96 | A |
| | 752.96 | A |
| 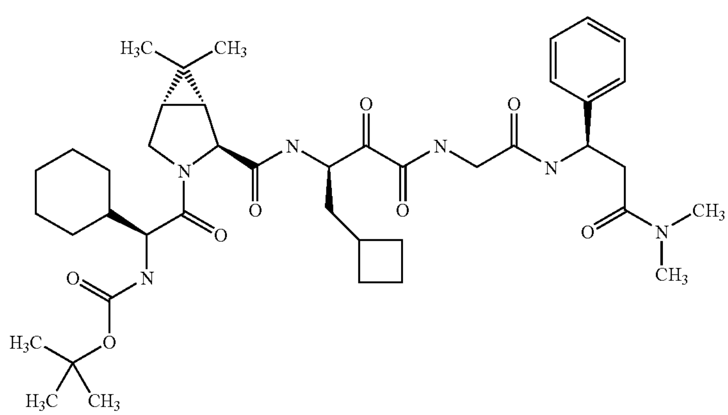 | 779.00 | A |

TABLE 6-continued
| STRUCTURE | MW | Ki* (nM) |
|---|---|---|
| 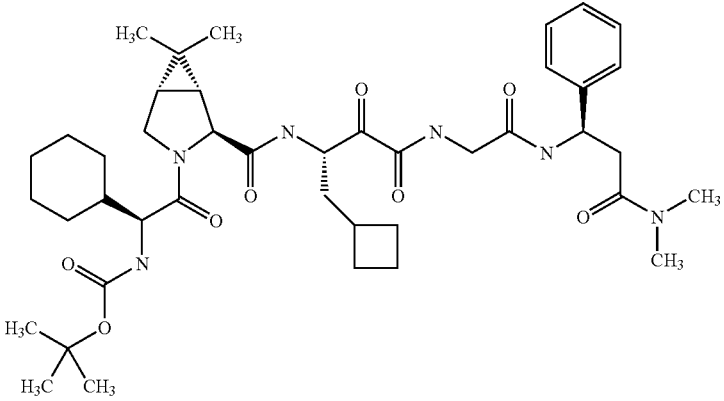 | 779.00 | A |
| 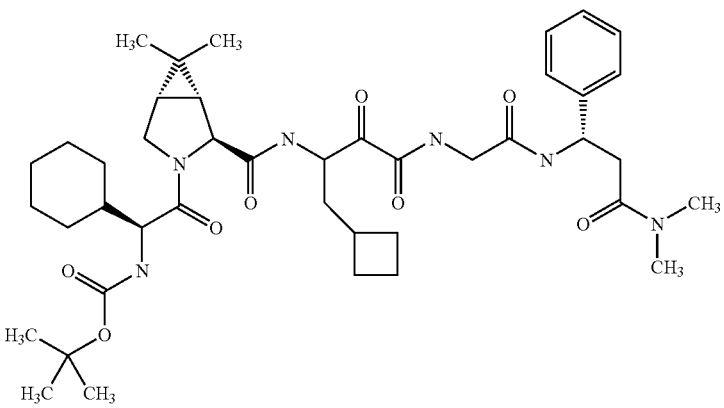 | 779.00 | A |
| 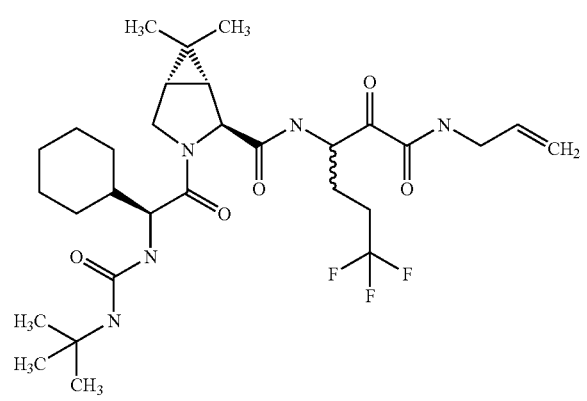 | 613.73 | C |

TABLE 6-continued

| STRUCTURE | MW | Ki* (nM) |
|---|---|---|
| 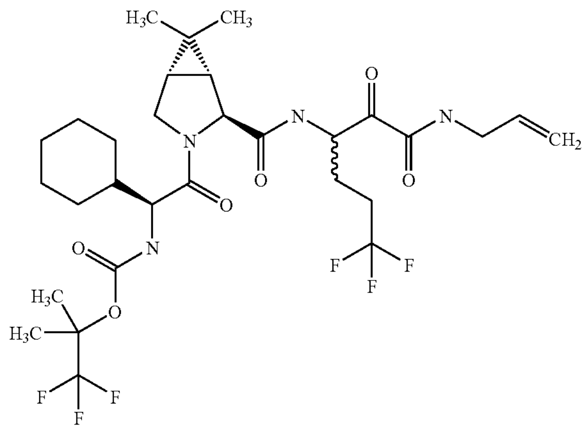 | 668.68 | A |
| 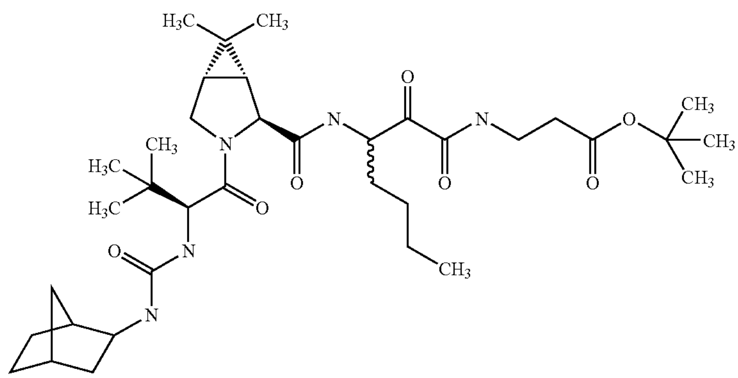 | 673.90 | B |
| 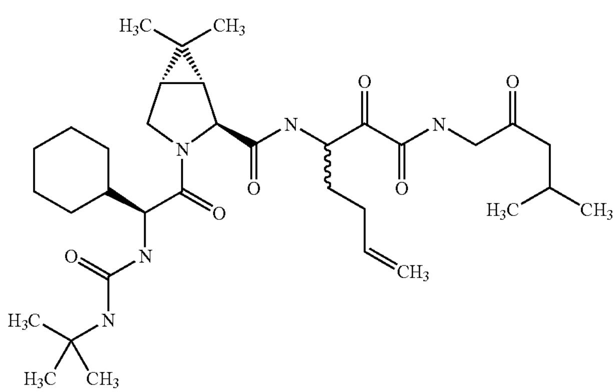 | 629.85 | B |
| 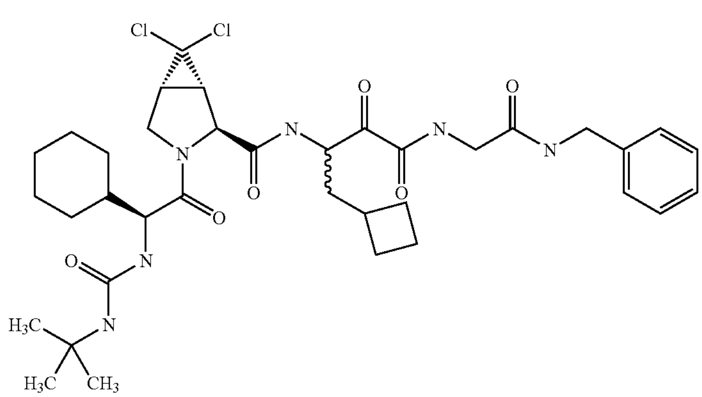 | 733.74 | B |

TABLE 6-continued
| STRUCTURE | MW | Ki* (nM) |
|---|---|---|
| 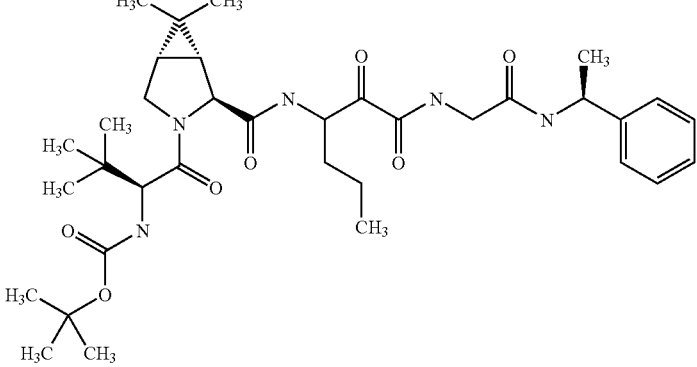 | 655.84 | B |
| 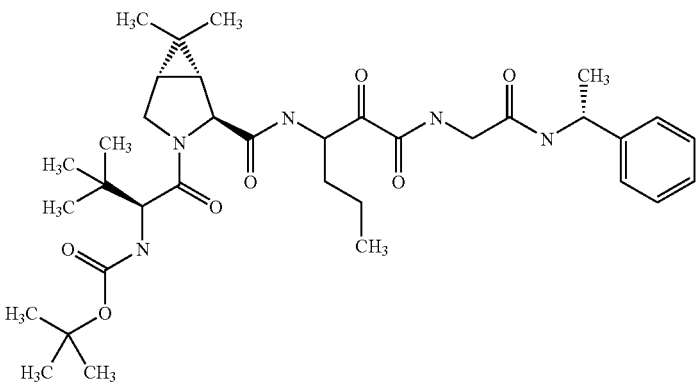 | 655.84 | B |
| 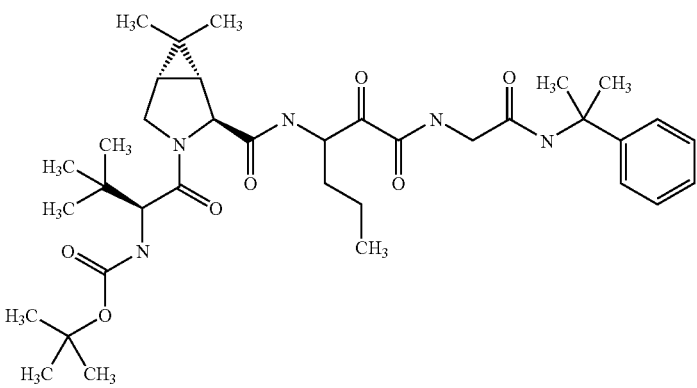 | 669.87 | B |
| 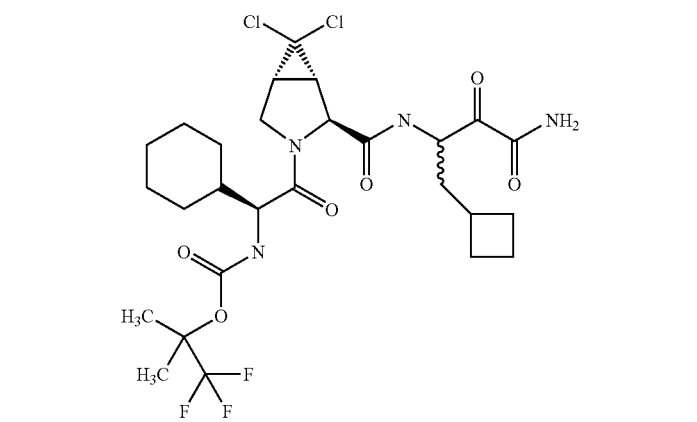 | 641.52 | B |

TABLE 6-continued
| STRUCTURE | MW | Ki* (nM) |
|---|---|---|
| 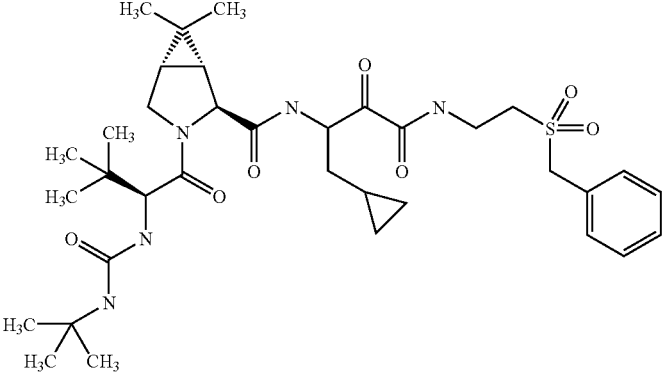 | 687.91 | A |
| 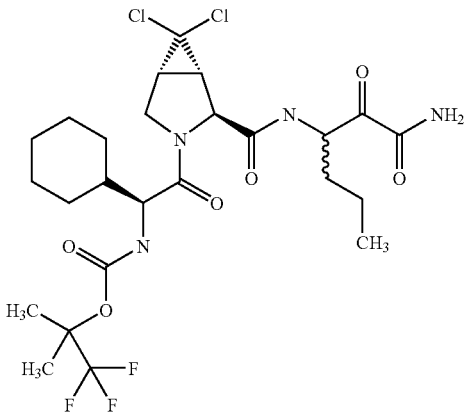 | 615.48 | A |
| 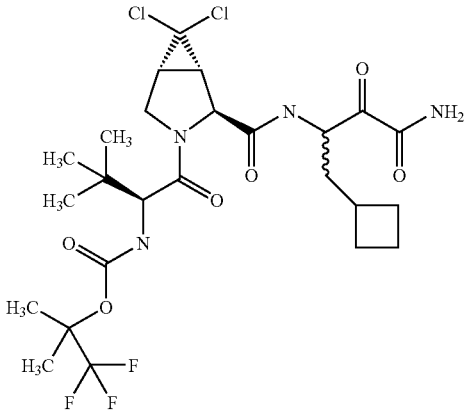 | 615.48 | A |

TABLE 6-continued

| STRUCTURE | MW | Ki* (nM) |
|---|---|---|
| | 694.92 | B |
| 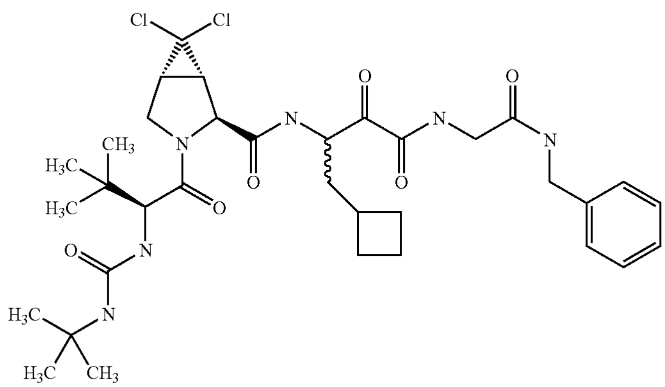 | 707.70 | A |
| | 694.92 | A |
| 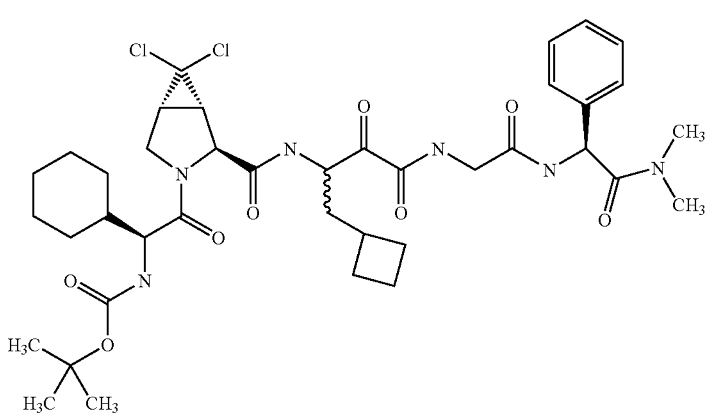 | 805.81 | A |

TABLE 6-continued
| STRUCTURE | MW | Ki* (nM) |
|---|---|---|
| 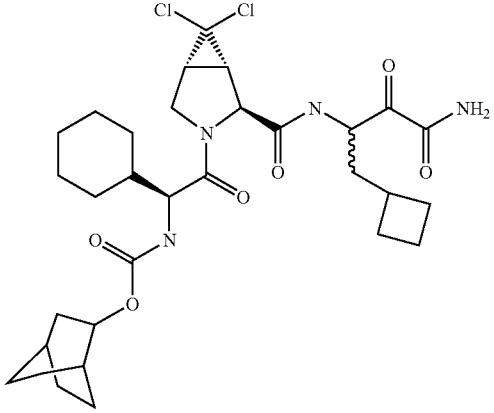 | 625.60 | A |
| 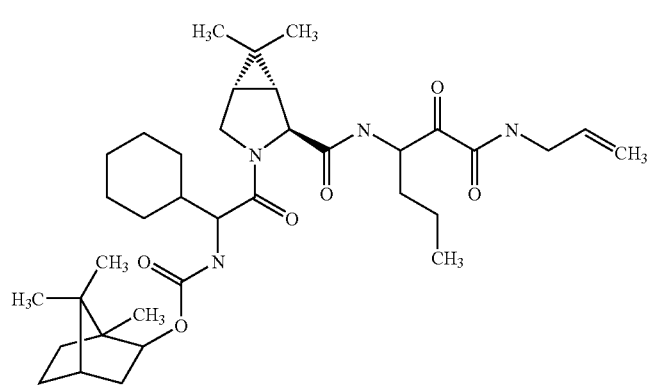 | 640.87 | B |
| 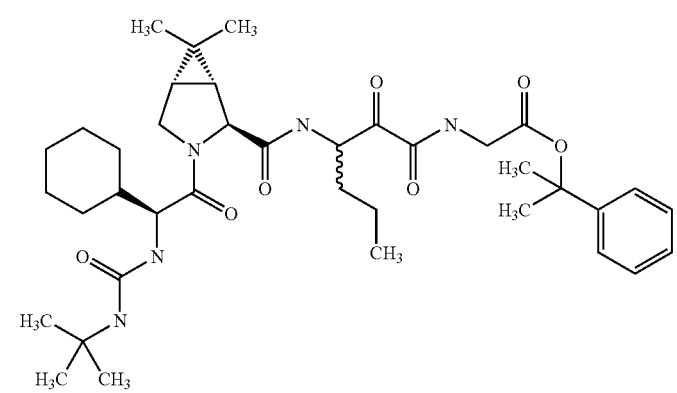 | 695.91 | A |

TABLE 6-continued
| STRUCTURE | MW | Ki* (nM) |
|---|---|---|
| 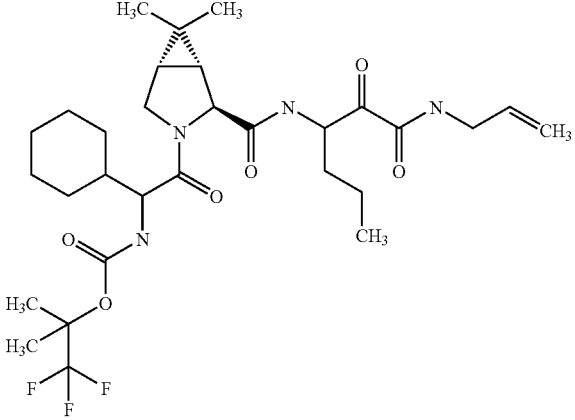 | 614.71 | B |
| 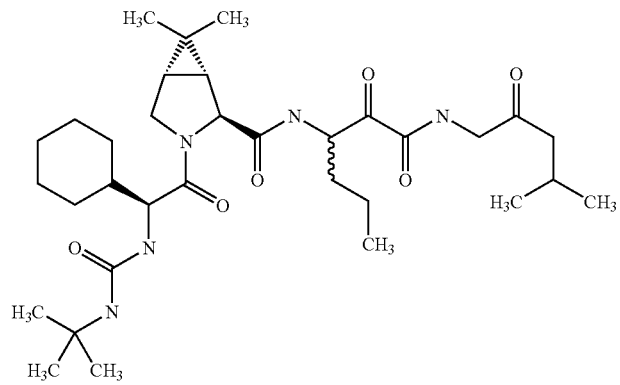 | 617.84 | B |
| 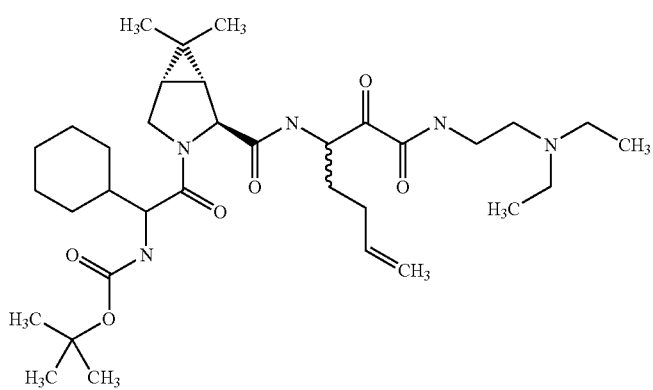 | 631.86 | C |

TABLE 6-continued

| STRUCTURE | MW | Ki* (nM) |
|---|---|---|
| 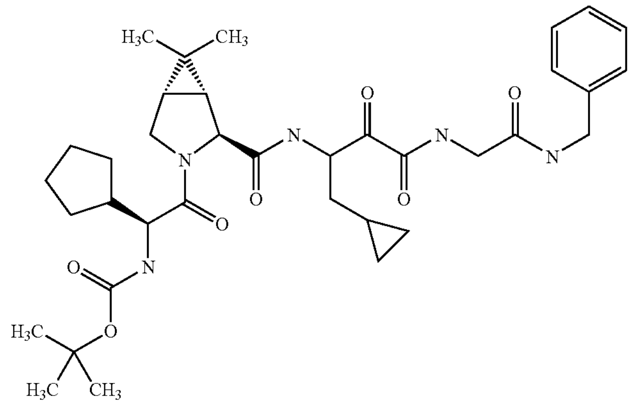 | 665.84 | A |
| 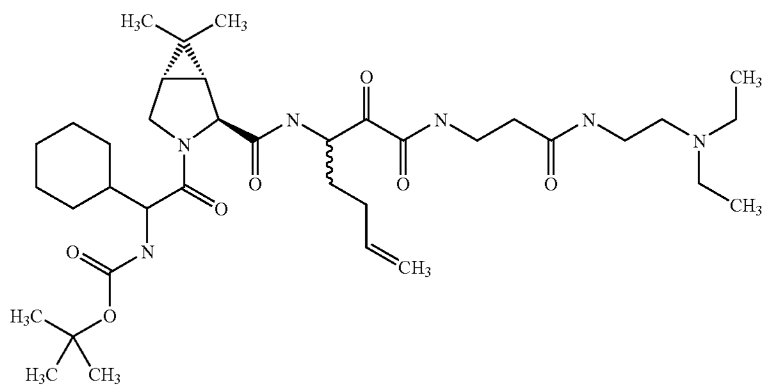 | 702.94 | C |
| 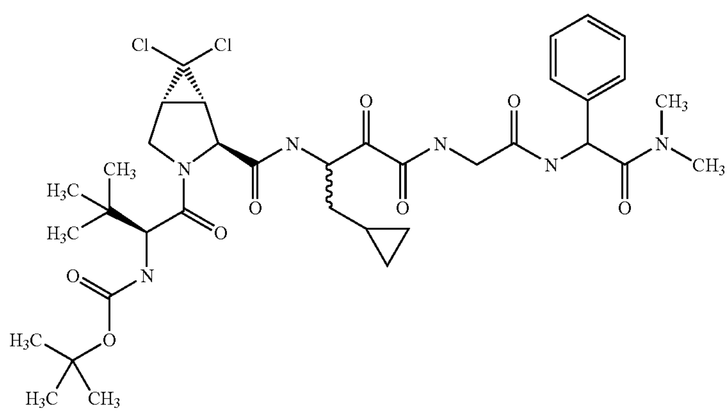 | 765.74 | A |
| 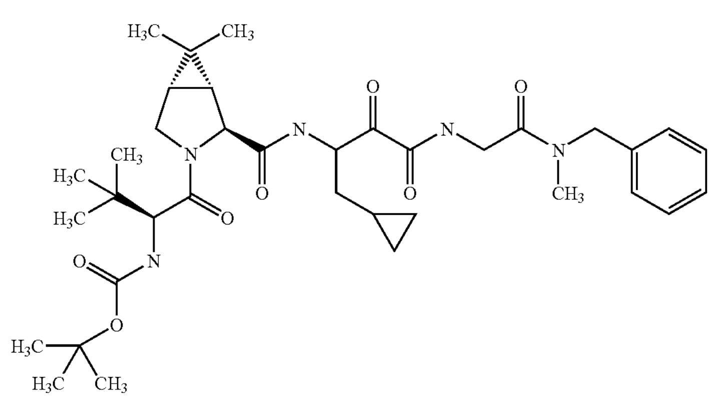 | 667.85 | C |

TABLE 6-continued

| STRUCTURE | MW | Ki* (nM) |
|---|---|---|
| 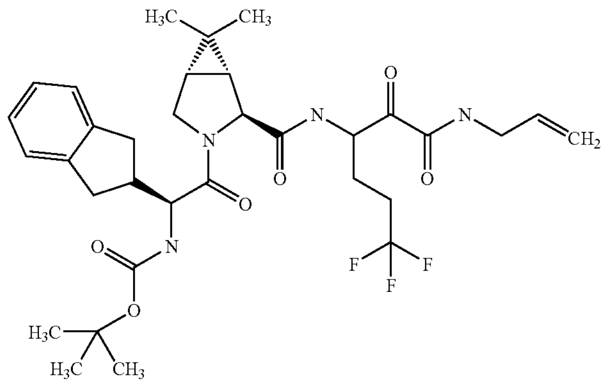 | 648.73 | A |
| 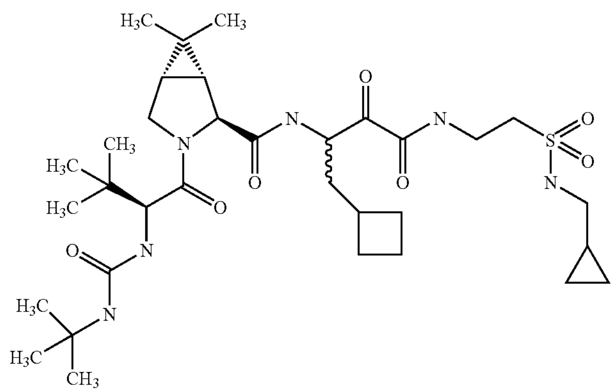 | 680.91 | B |
| 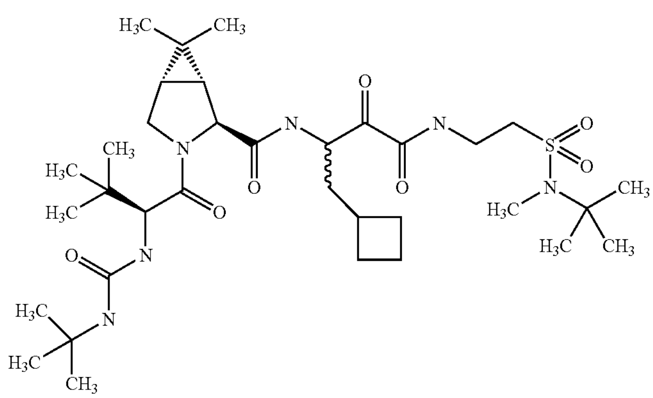 | 696.96 | C |
| 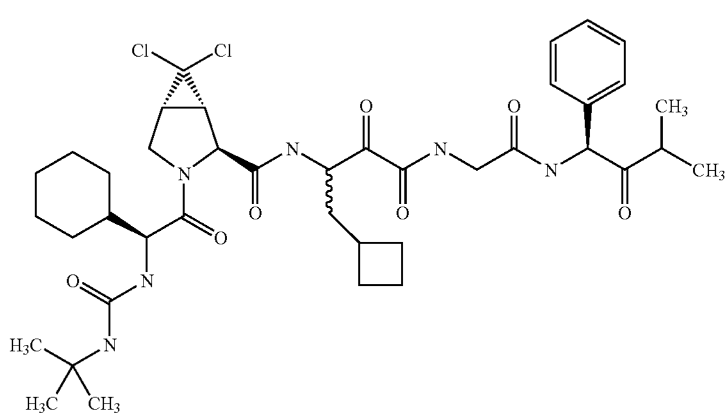 | 804.82 | A |

TABLE 6-continued

| STRUCTURE | MW | Ki* (nM) |
|---|---|---|
| 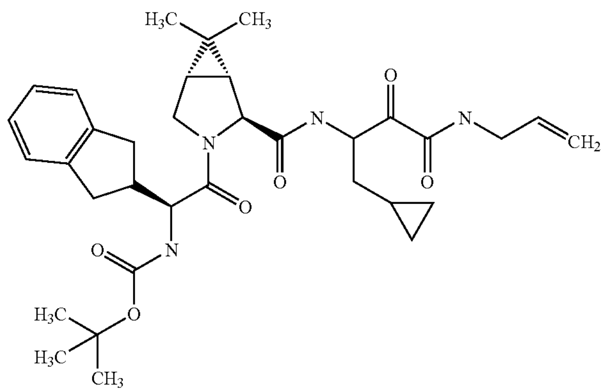 | 606.77 | B |
| 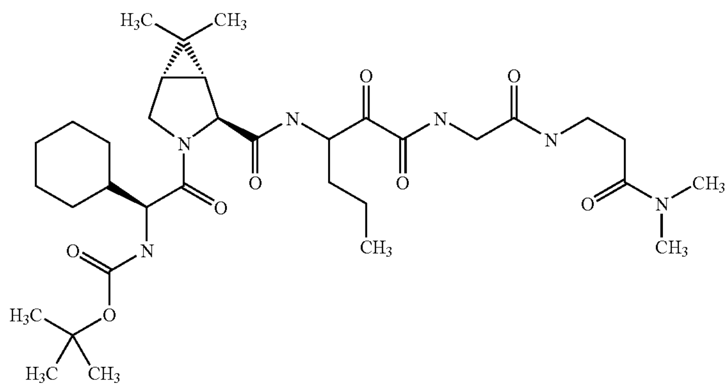 | 676.86 | A |
| 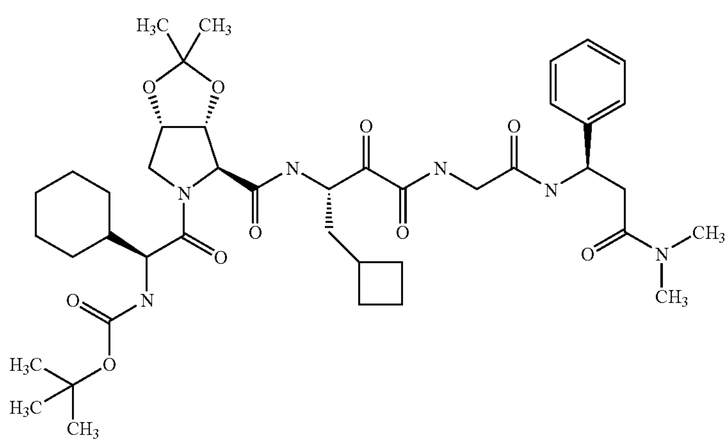 | 811.00 | A |

TABLE 6-continued
| STRUCTURE | MW | Ki* (nM) |
|---|---|---|
| 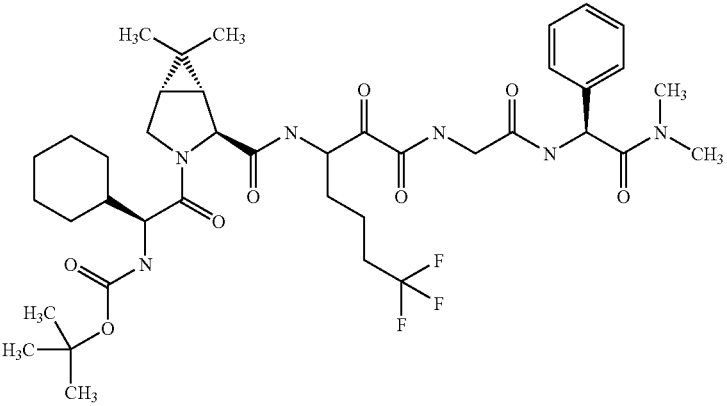 | 806.93 | A |
| 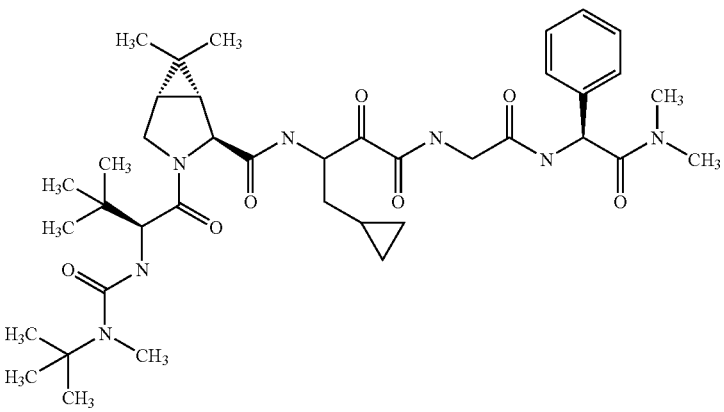 | 737.95 | A |
| 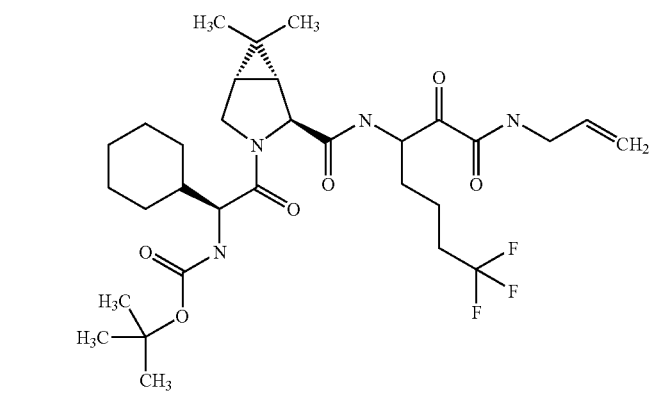 | 628.74 | B |
| 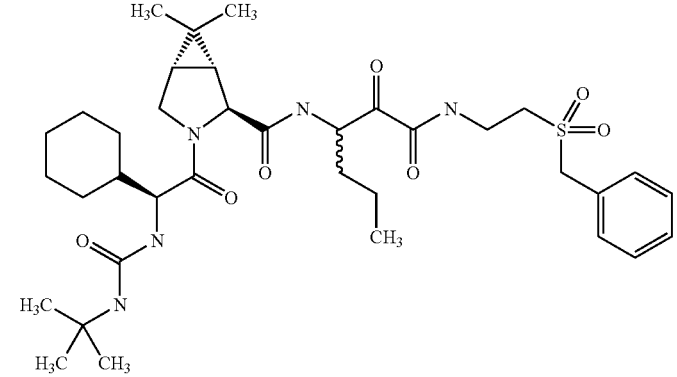 | 701.93 | A |

TABLE 6-continued

| STRUCTURE | MW | Ki* (nM) |
|---|---|---|
| 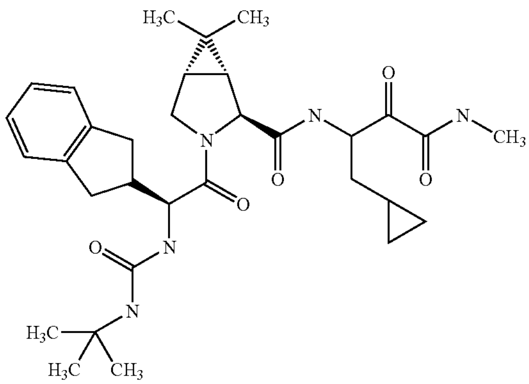 | 579.75 | B |
| 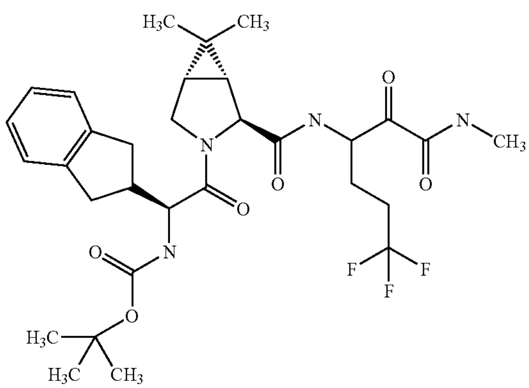 | 622.69 | B |
| 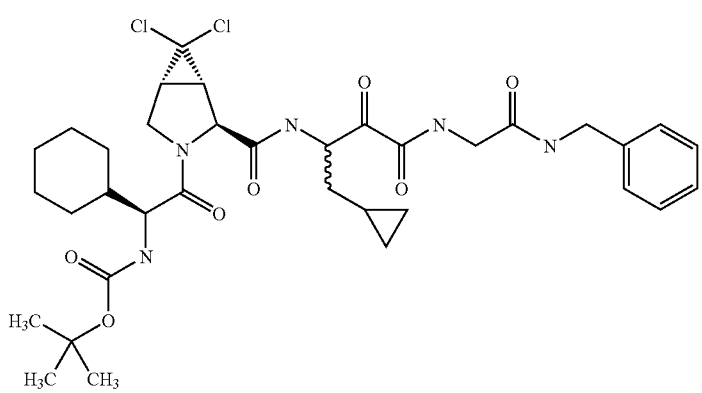 | 720.70 | A |
| 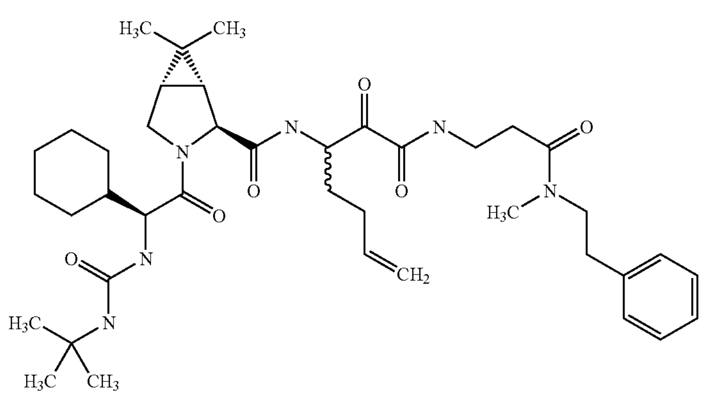 | 720.96 | A |

TABLE 6-continued

| STRUCTURE | MW | Ki* (nM) |
|---|---|---|
| 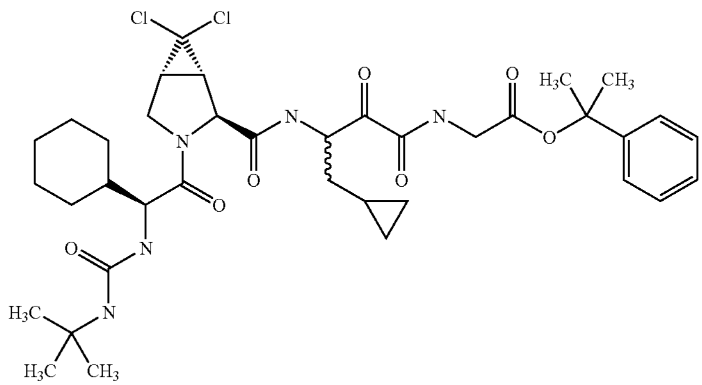 | 748.75 | A |
| | 681.88 | B |
| | 681.88 | B |

TABLE 6-continued
| STRUCTURE | MW | Ki* (nM) |
|---|---|---|
| 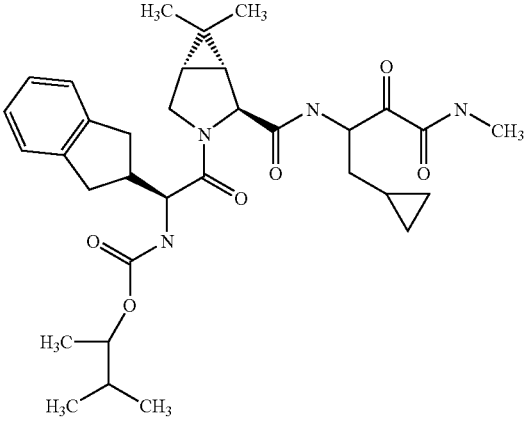 | 594.76 | A |
| 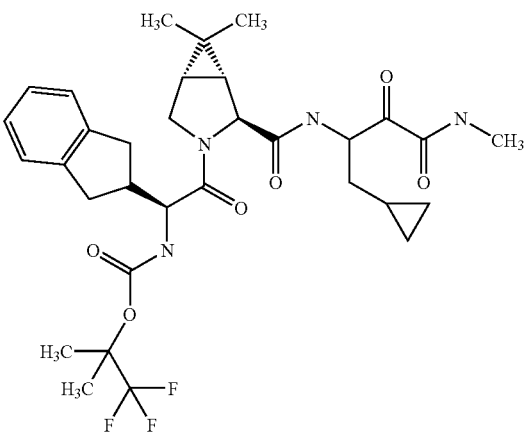 | 634.70 | A |
| 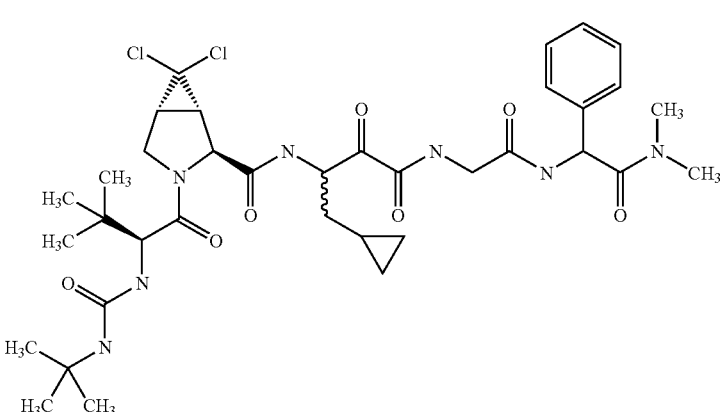 | 764.76 | A |

TABLE 6-continued
| STRUCTURE | MW | Ki* (nM) |
|---|---|---|
| 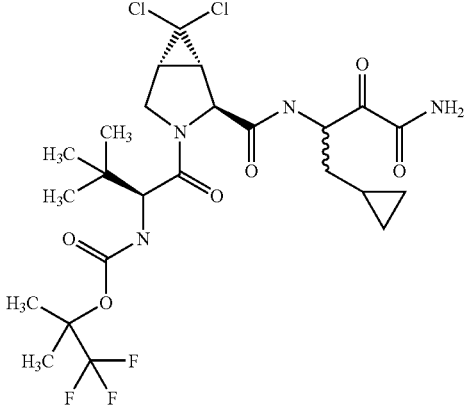 | 601.46 | A |
| 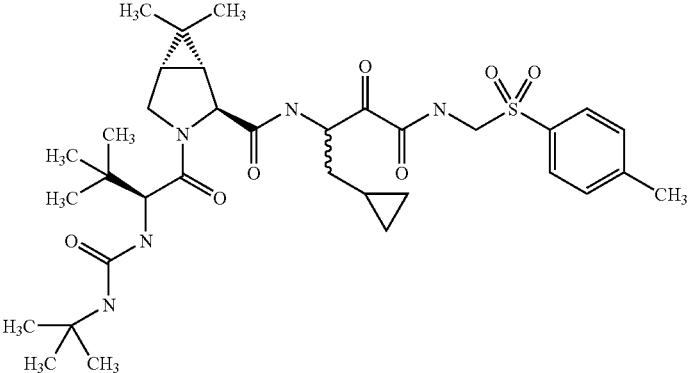 | 673.88 | A |
| 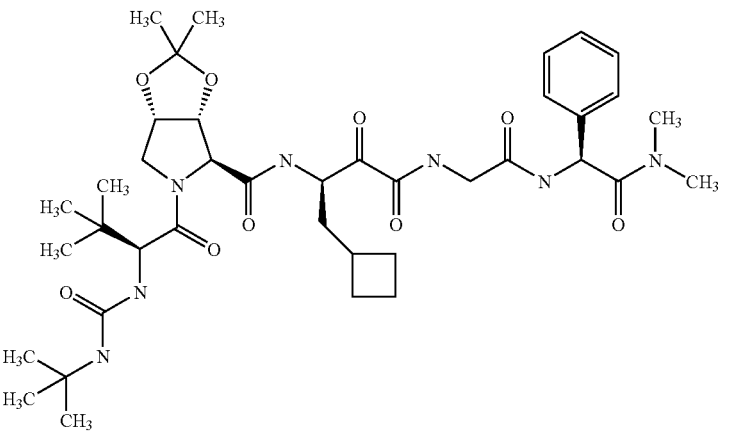 | 769.95 | B |

TABLE 6-continued

| STRUCTURE | MW | Ki* (nM) |
|---|---|---|
| 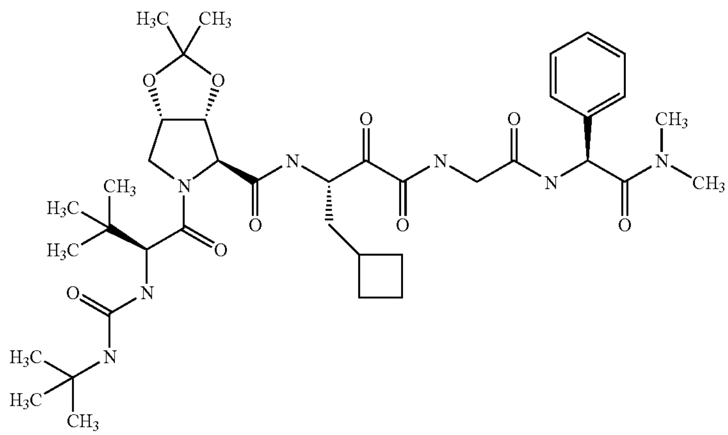 | 769.95 | A |
| 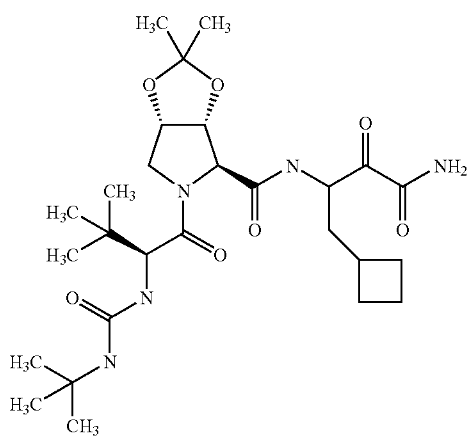 | 551.69 | B |
| 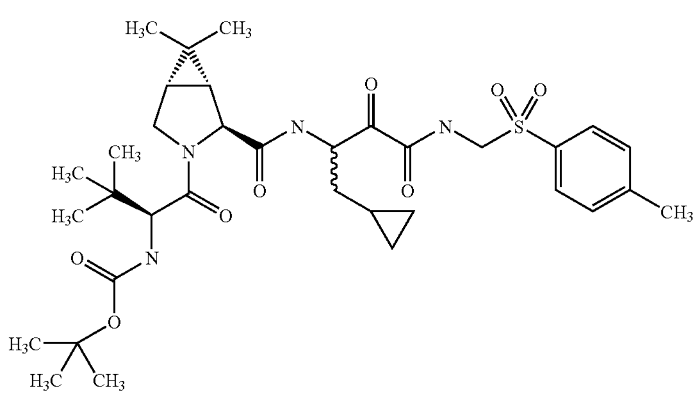 | 674.86 | B |

TABLE 6-continued
| STRUCTURE | MW | Ki* (nM) |
|---|---|---|
| 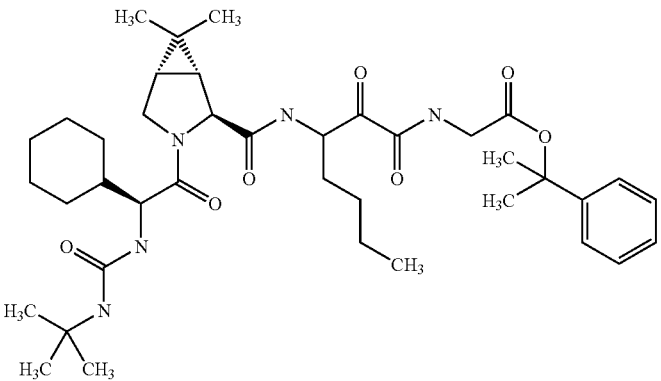 | 709.93 | A |
| 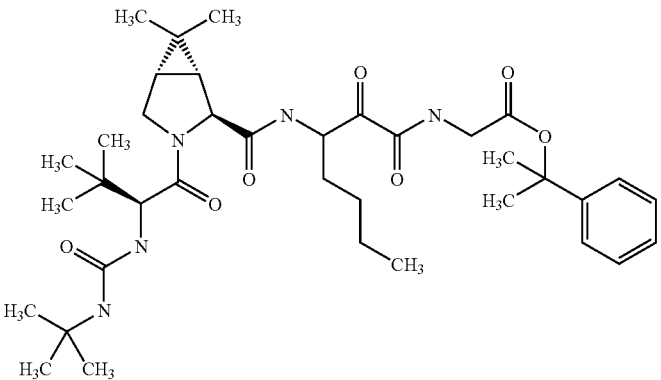 | 683.90 | B |
| 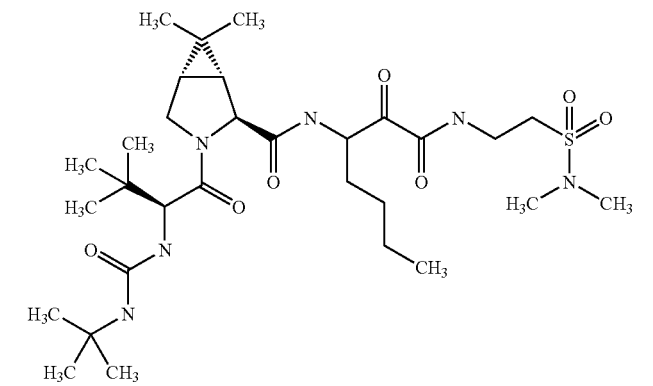 | 642.87 | B |
| 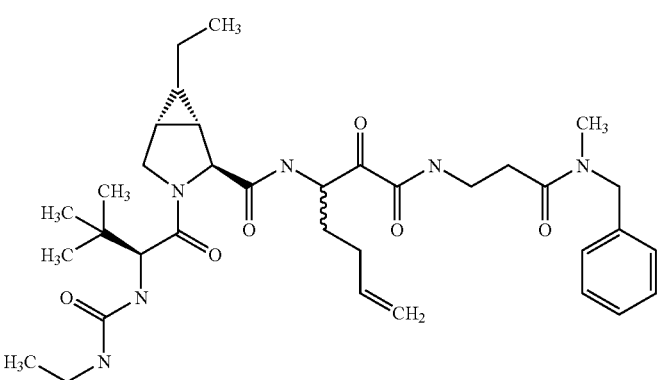 | 680.90 | B |

TABLE 6-continued

| STRUCTURE | MW | Ki* (nM) |
|---|---|---|
| 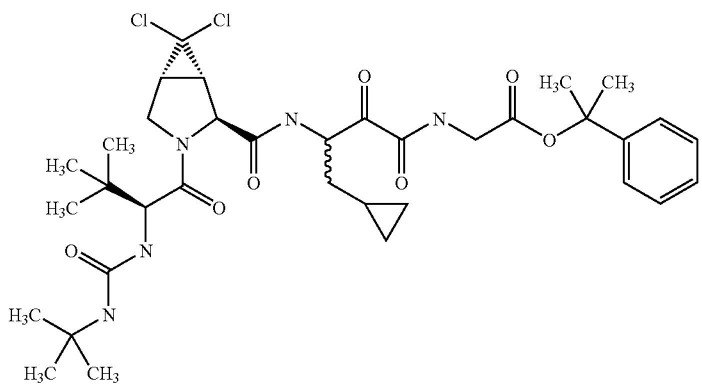 | 722.72 | A |
| 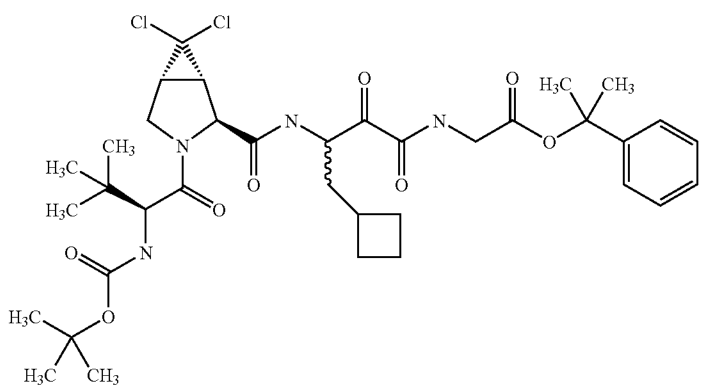 | 737.73 | B |
| 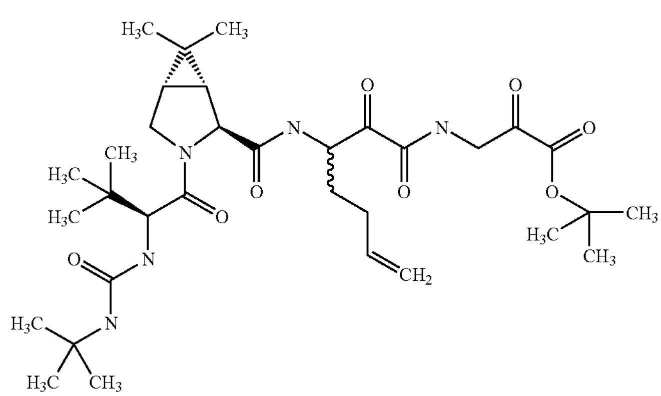 | 647.82 | B |
| 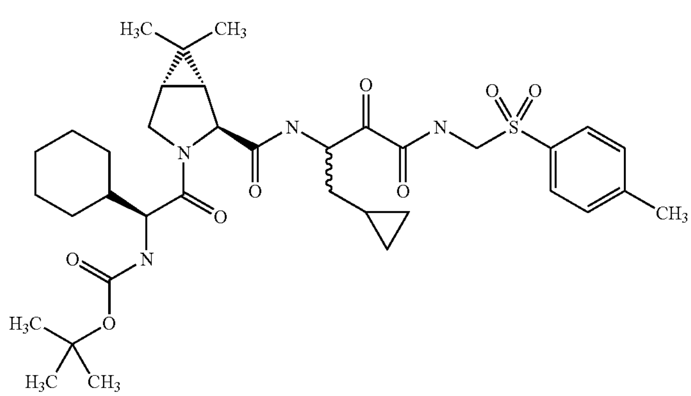 | 700.90 | A |

TABLE 6-continued
| STRUCTURE | MW | Ki* (nM) |
|---|---|---|
| 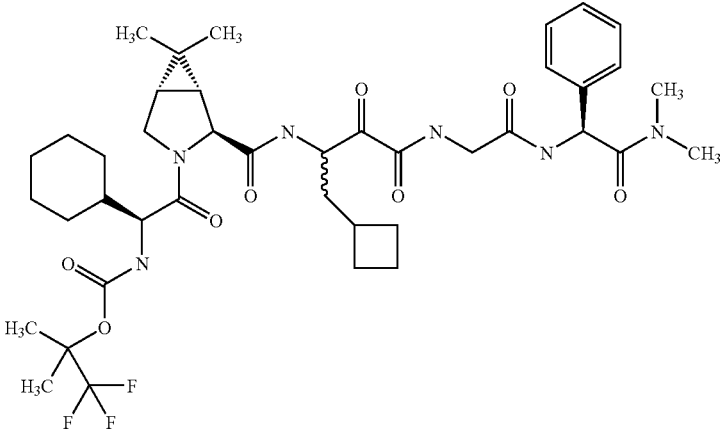 | 818.94 | A |
| 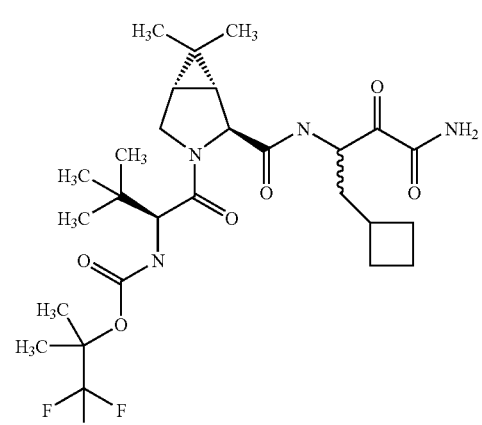 | 574.65 | B |
| 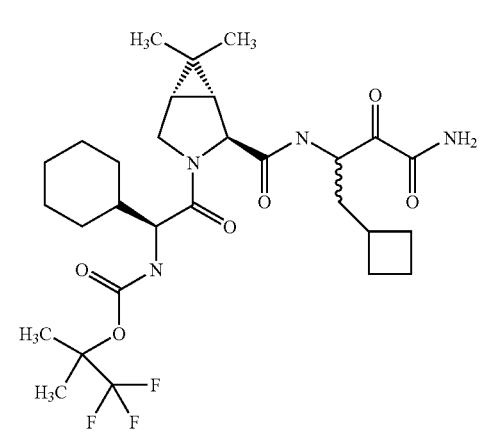 | 600.68 | A |

TABLE 6-continued
| STRUCTURE | MW | Ki* (nM) |
|---|---|---|
| 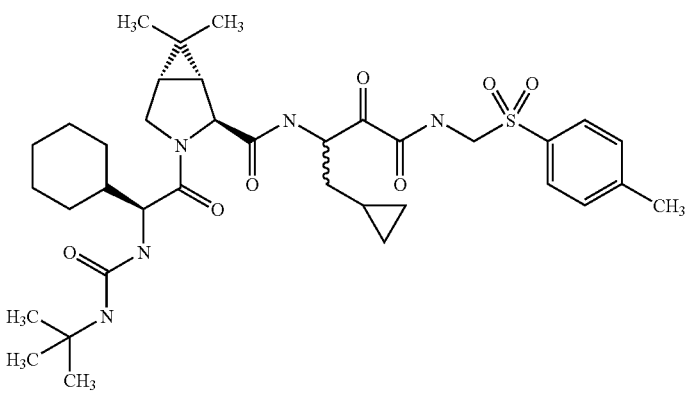 | 699.92 | B |
| 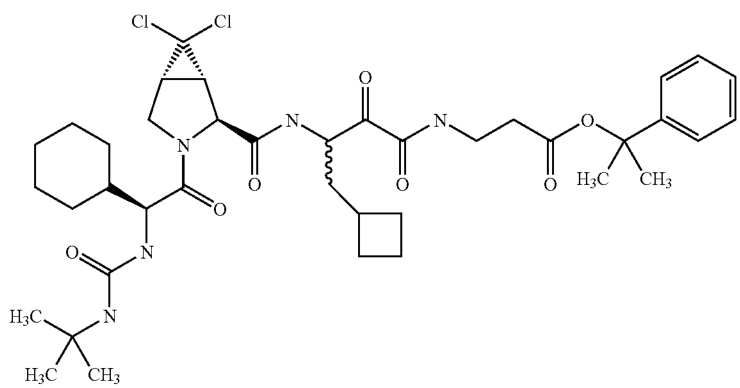 | 776.81 | B |
| 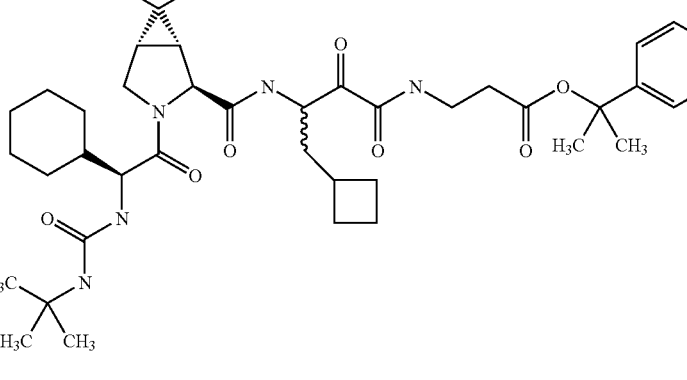 | 635.85 | A |
| 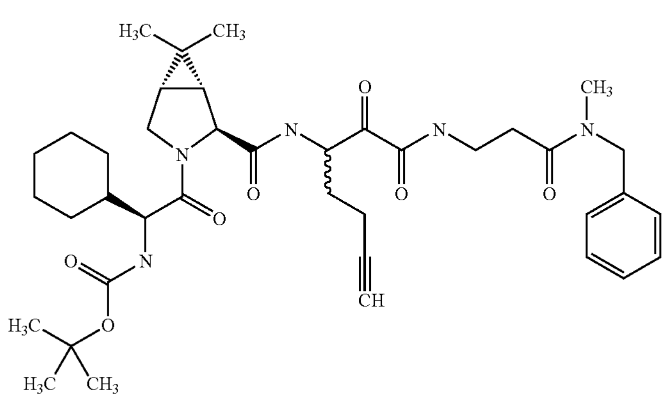 | 705.90 | A |

TABLE 6-continued

| STRUCTURE | MW | Ki* (nM) |
|---|---|---|
| 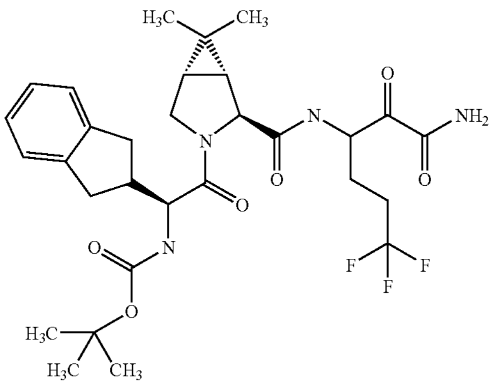 | 608.66 | A |
| 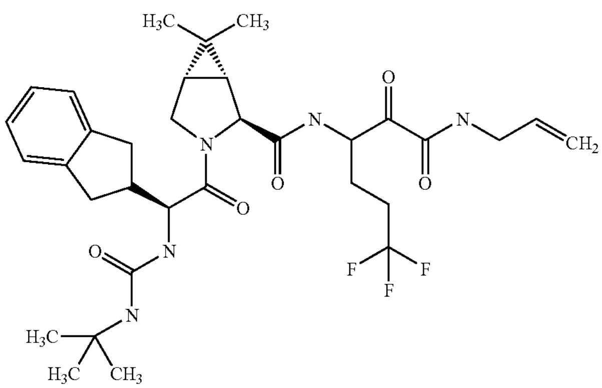 | 647.74 | A |
| 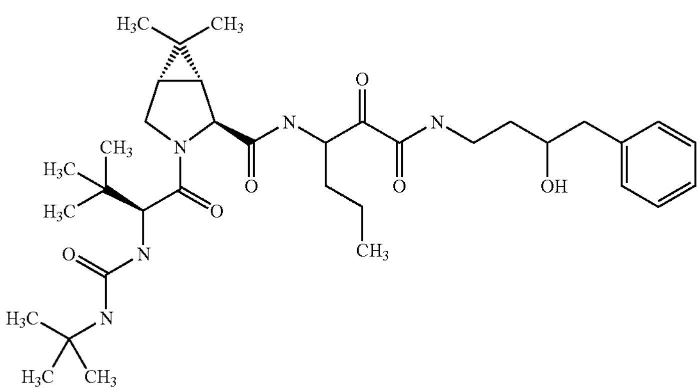 | 641.86 | B |
| 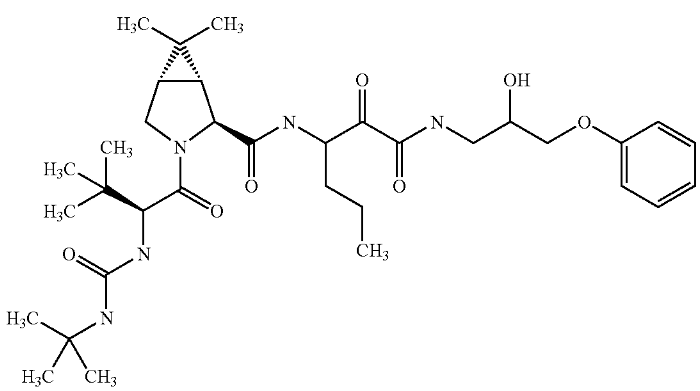 | 643.83 | B |

TABLE 6-continued
| STRUCTURE | MW | Ki* (nM) |
|---|---|---|
| 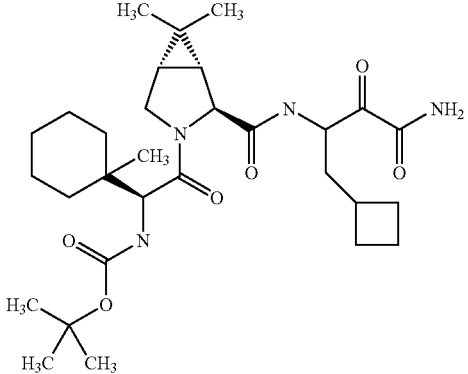 | 560.74 | B |
| 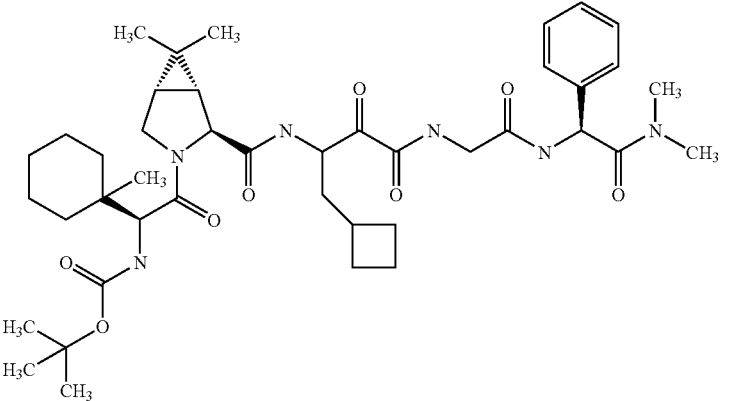 | 779.00 | A |
| 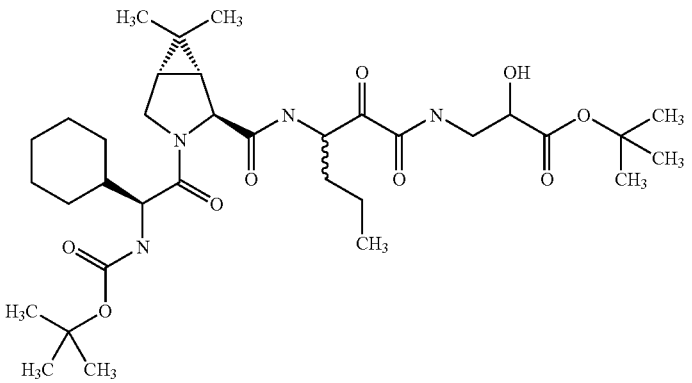 | 664.85 | A |

TABLE 6-continued

| STRUCTURE | MW | Ki* (nM) |
|---|---|---|
| 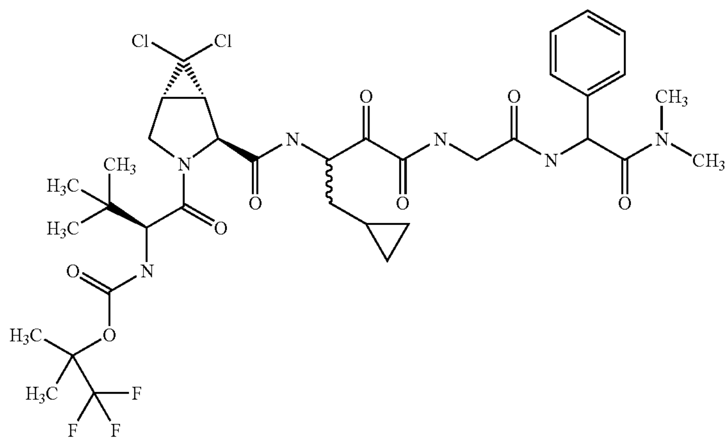 | 819.71 | A |
| 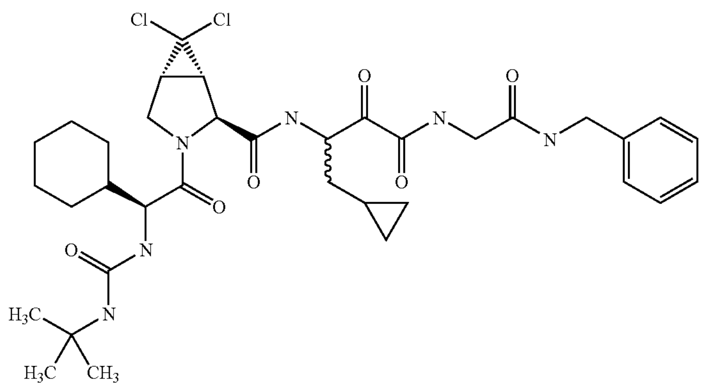 | 719.72 | A |
| 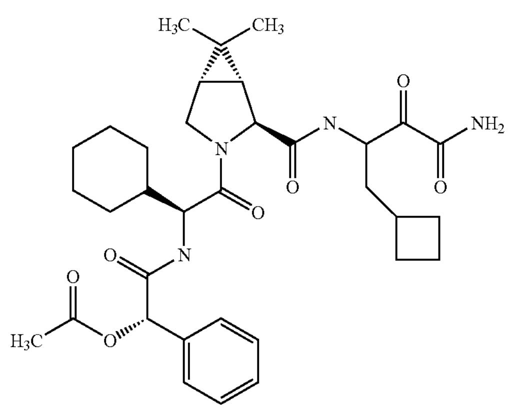 | 622.77 | A |

TABLE 6-continued

| STRUCTURE | MW | Ki* (nM) |
|---|---|---|
| | 787.00 | A |
| | 787.00 | A |
| 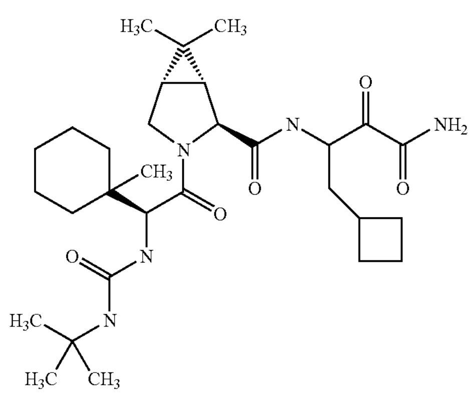 | 559.76 | A |

TABLE 6-continued
| STRUCTURE | MW | Ki* (nM) |
|---|---|---|
| 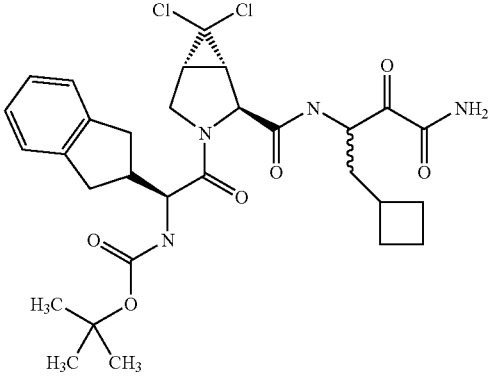 | 621.57 | A |
| 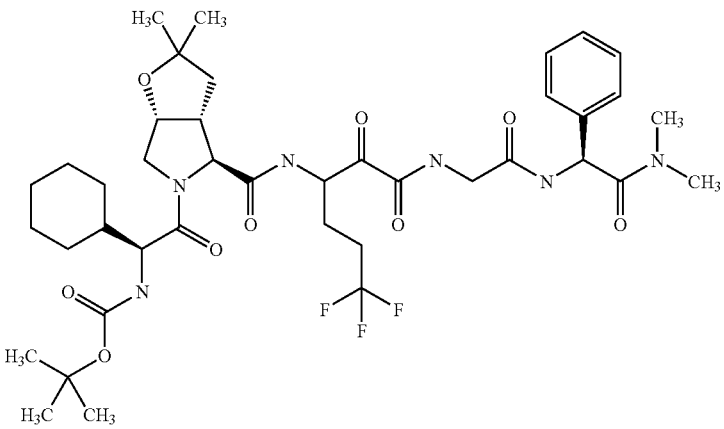 | 822.93 | A |
| 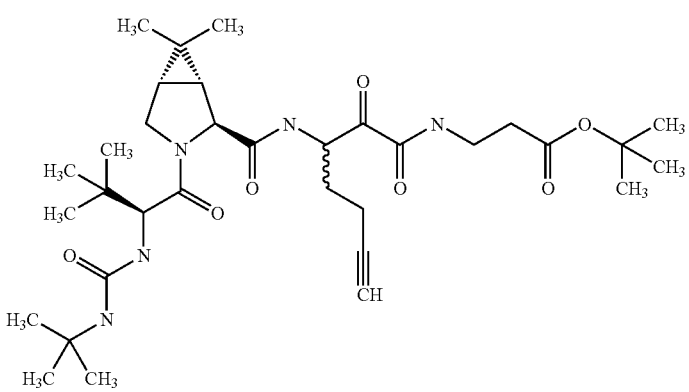 | 631.82 | A |

TABLE 6-continued
| STRUCTURE | MW | Ki* (nM) |
|---|---|---|
| 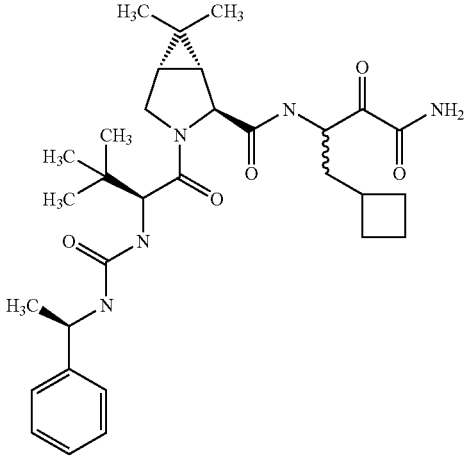 | 567.74 | B |
| 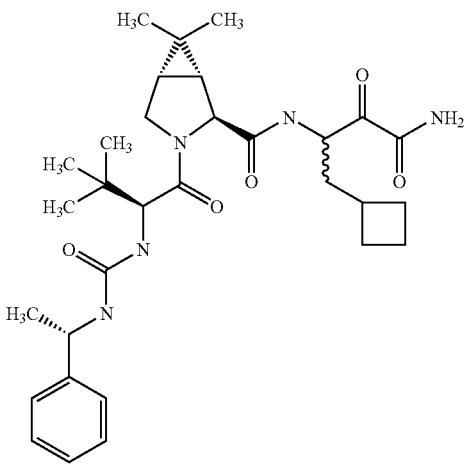 | 567.74 | A |
| 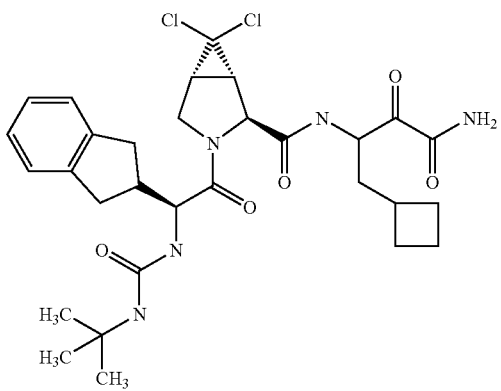 | 620.58 | A |

TABLE 6-continued

| STRUCTURE | MW | Ki* (nM) |
|---|---|---|
| 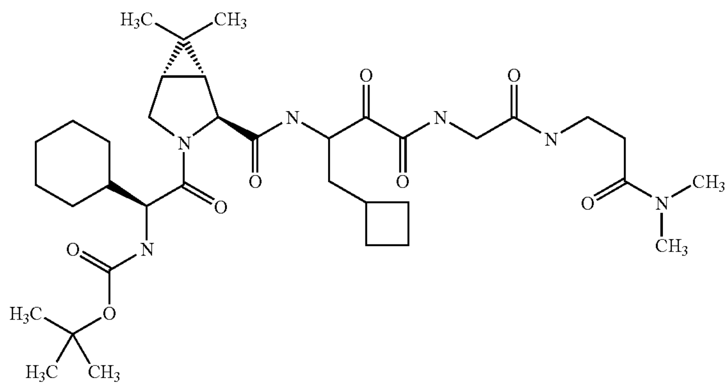 | 702.90 | A |
| 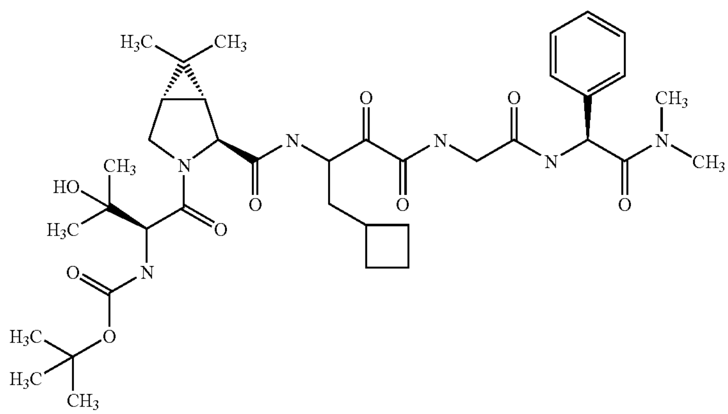 | 740.91 | A |
| 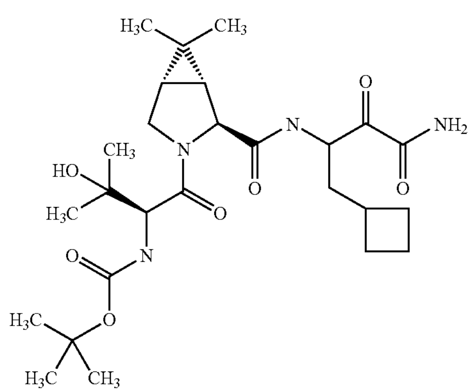 | 522.65 | B |
| 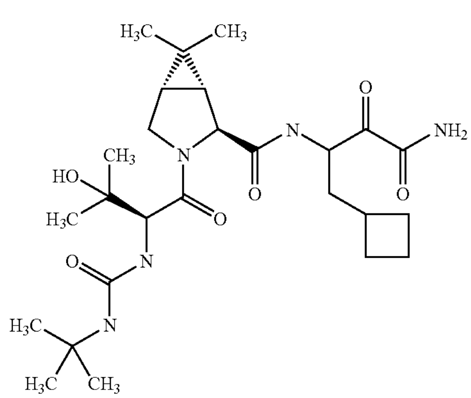 | 521.66 | B |

TABLE 6-continued
| STRUCTURE | MW | Ki* (nM) |
|---|---|---|
| 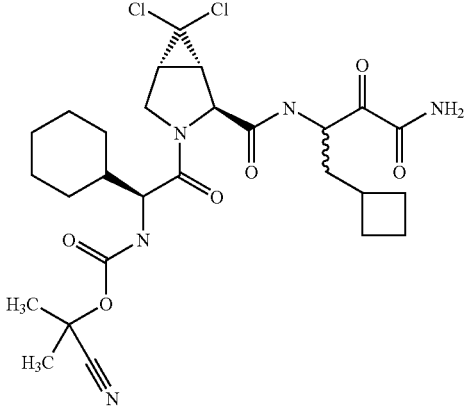 | 598.53 | B |
| 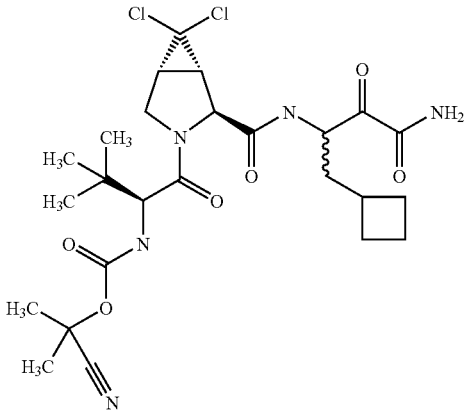 | 572.49 | B |
| 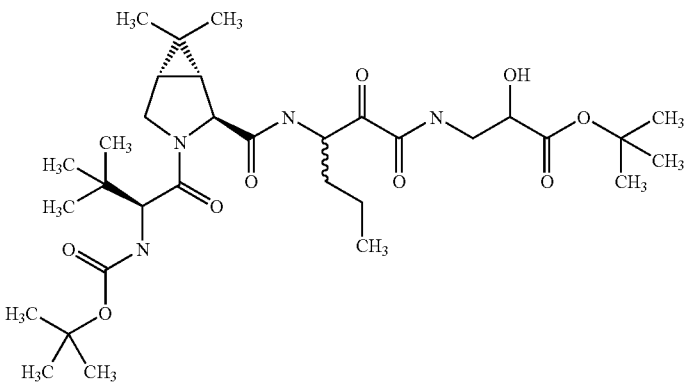 | 638.81 | B |

TABLE 6-continued
| STRUCTURE | MW | Ki* (nM) |
|---|---|---|
| 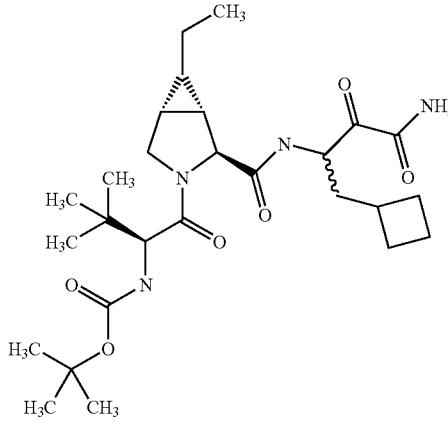 | 520.68 | C |
| 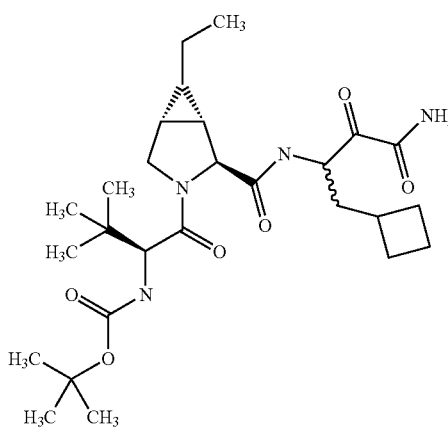 | 520.68 | B |
| 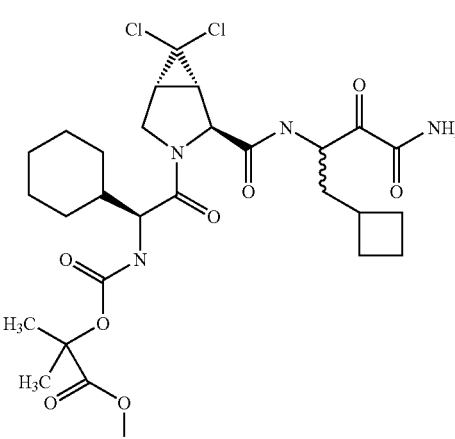 | 631.56 | B |

TABLE 6-continued
| STRUCTURE | MW | Ki* (nM) |
|---|---|---|
| 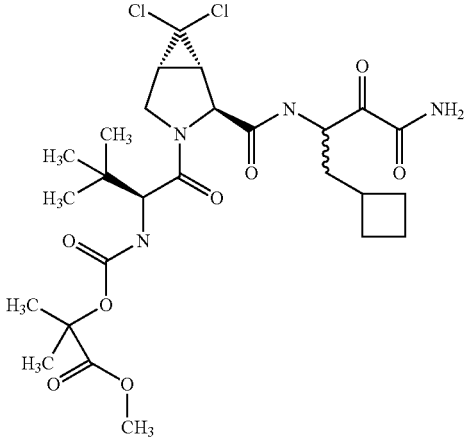 | 605.52 | B |
| 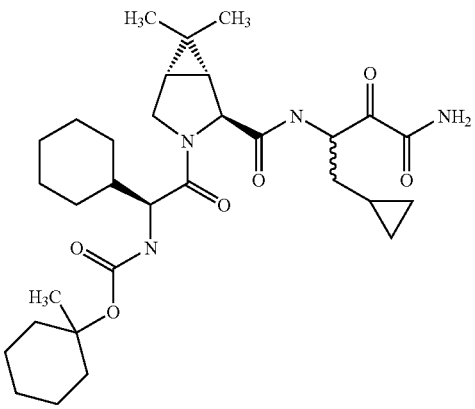 | 571.77 | A |
| 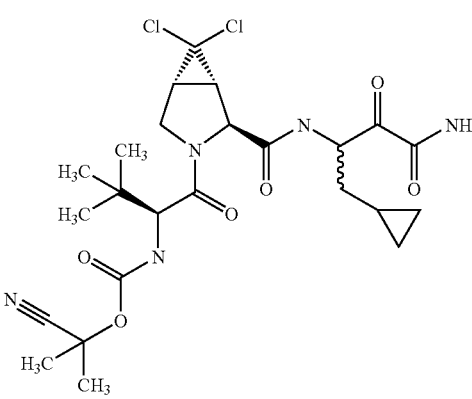 | 558.47 | A |

TABLE 6-continued

| STRUCTURE | MW | Ki* (nM) |
|---|---|---|
| 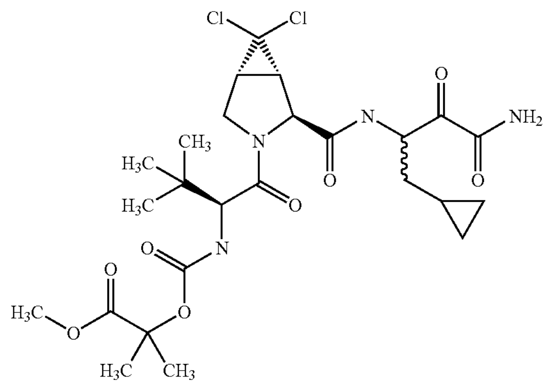 | 591.49 | A |
| 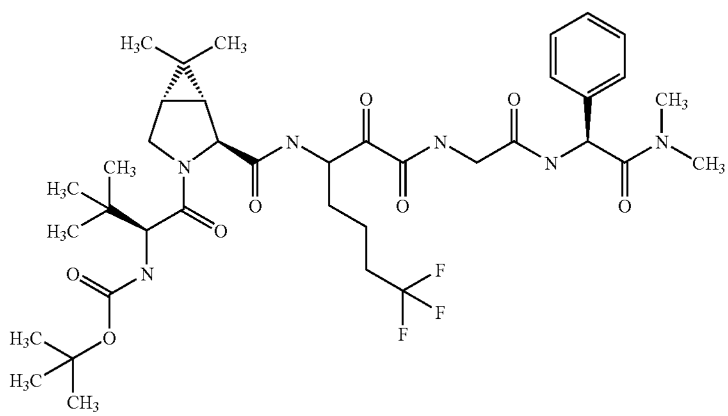 | 780.89 | A |
| 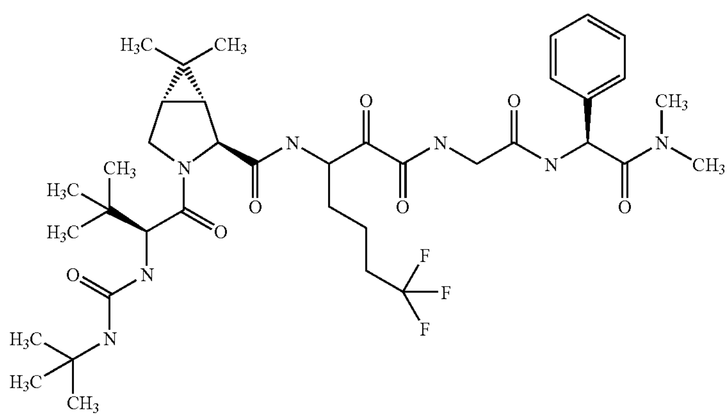 | 779.91 | A |
| 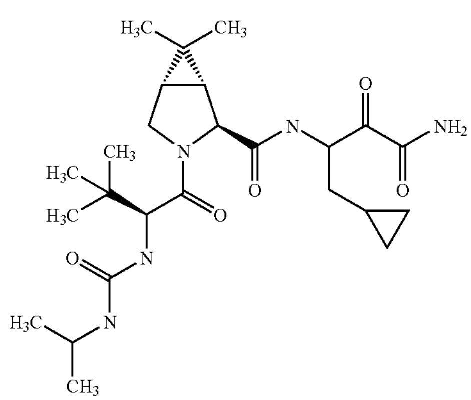 | 491.64 | B |

TABLE 6-continued
| STRUCTURE | MW | Ki* (nM) |
|---|---|---|
| 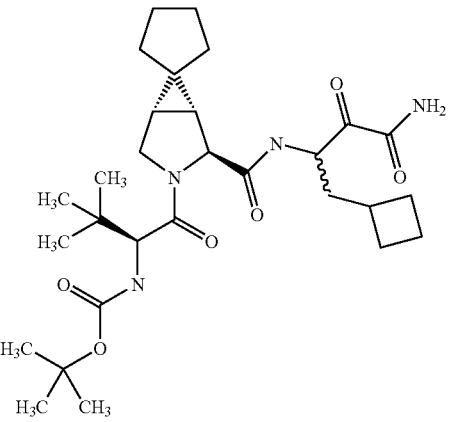 | 546.71 | B |
| 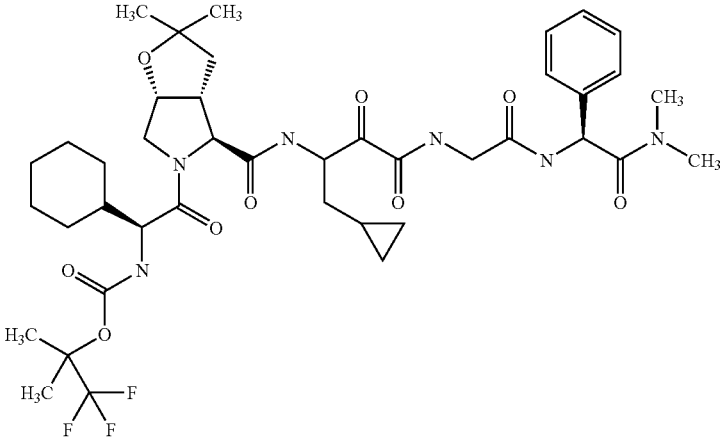 | 834.94 | A |
| 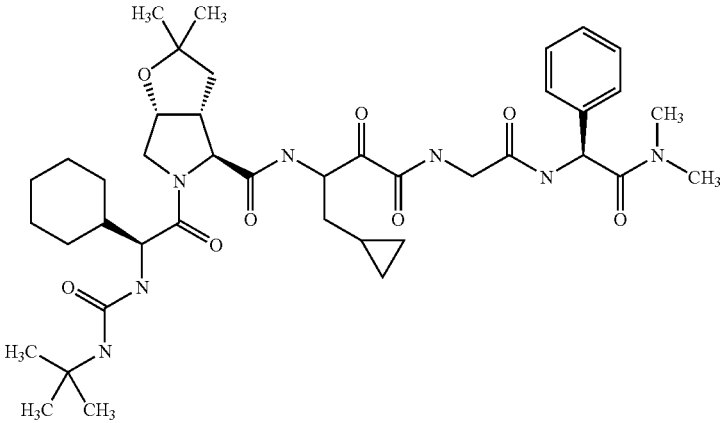 | 779.99 | A |

TABLE 6-continued
| STRUCTURE | MW | Ki* (nM) |
|---|---|---|
| 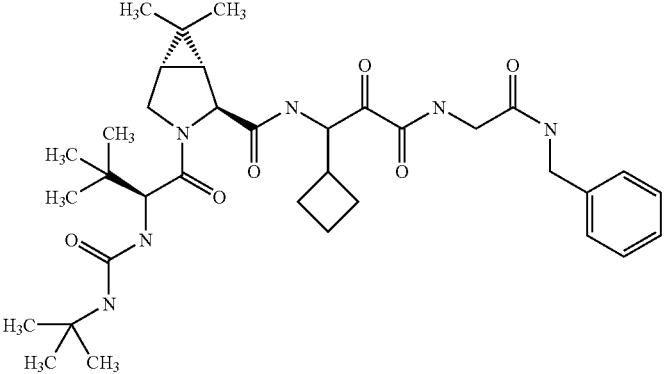 | 652.84 | A |
| 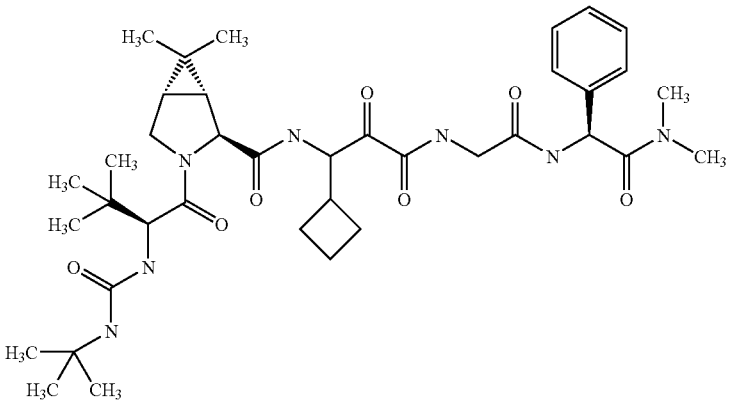 | 723.92 | A |
| 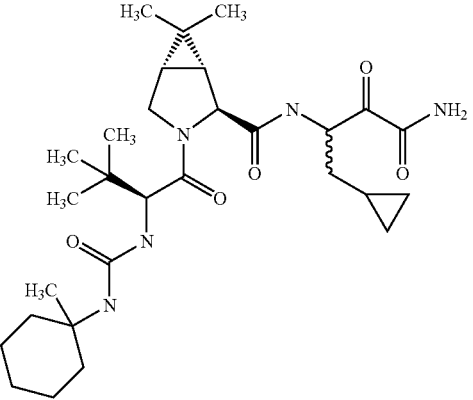 | 545.73 | A |

TABLE 6-continued
| STRUCTURE | MW | Ki* (nM) |
|---|---|---|
| 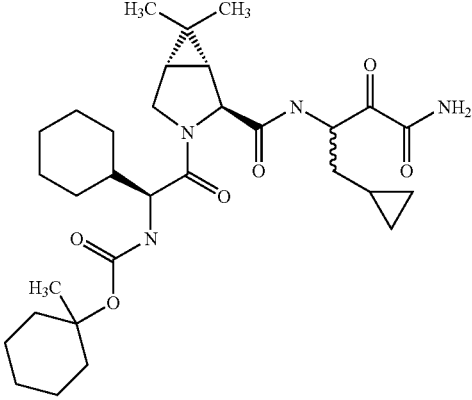 | 572.75 | A |
| 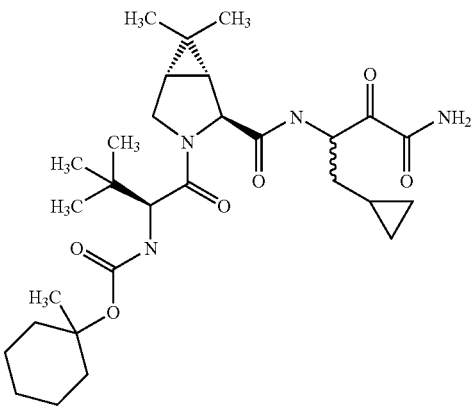 | 546.71 | A |
| 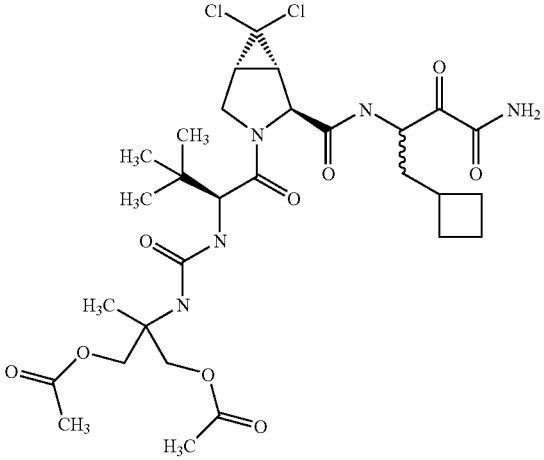 | 676.60 | B |

TABLE 6-continued
| STRUCTURE | MW | Ki* (nM) |
|---|---|---|
| 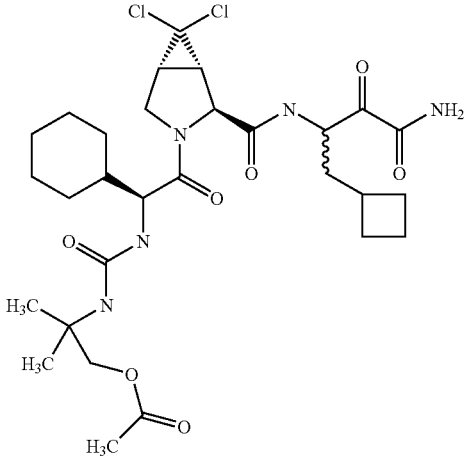 | 644.60 | B |
| 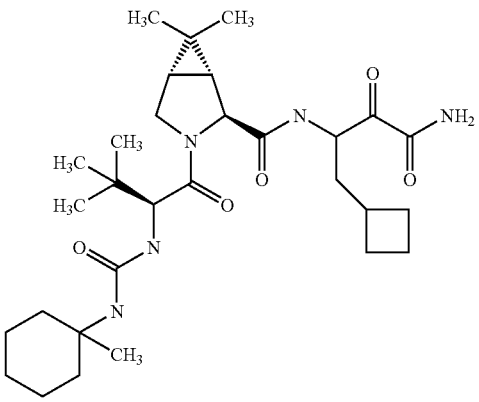 | 559.76 | A |
| 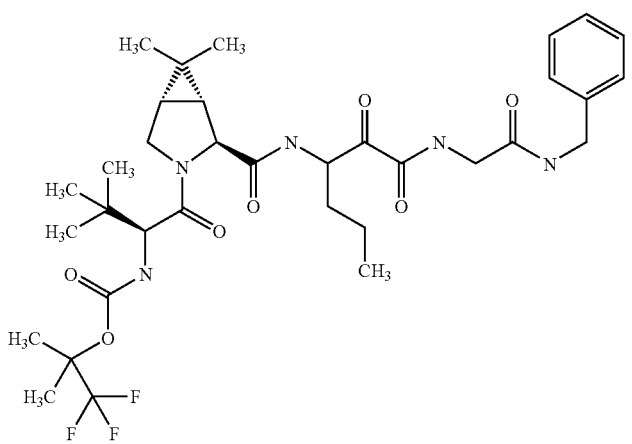 | 695.79 | A |

TABLE 6-continued
| STRUCTURE | MW | Ki* (nM) |
|---|---|---|
| 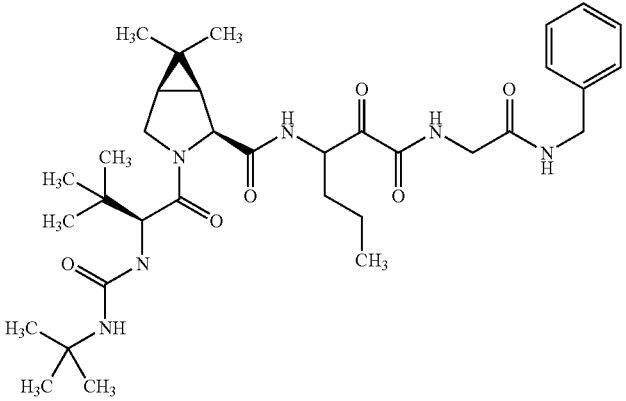 | 654.86 | A |
| 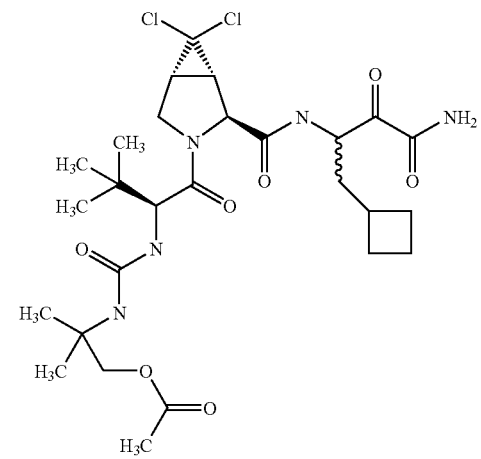 | 618.56 | B |
| 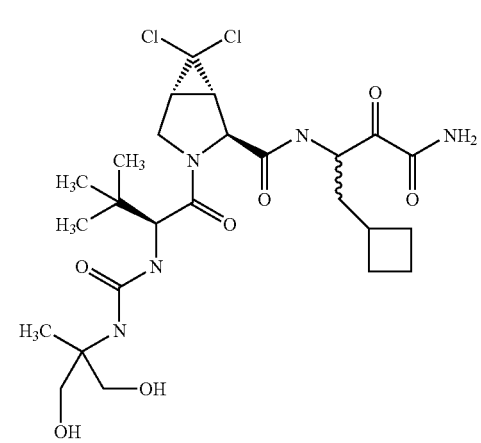 | 592.53 | B |

TABLE 6-continued
| STRUCTURE | MW | Ki* (nM) |
|---|---|---|
| 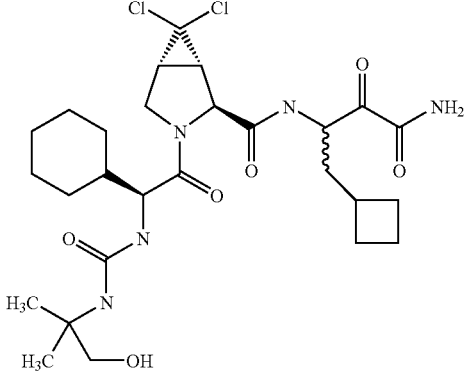 | 602.56 | B |
| 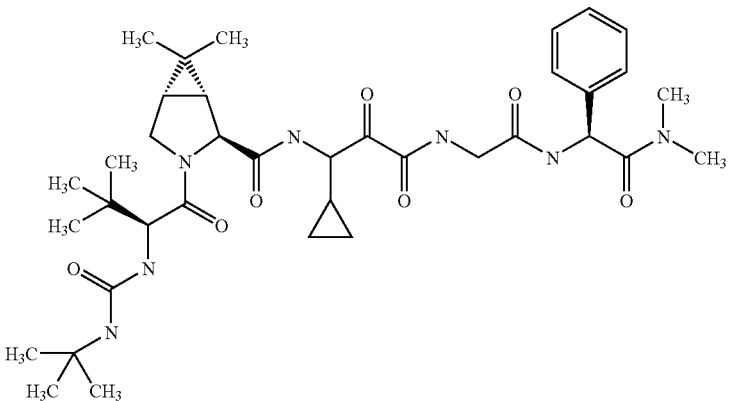 | 709.89 | A |
| 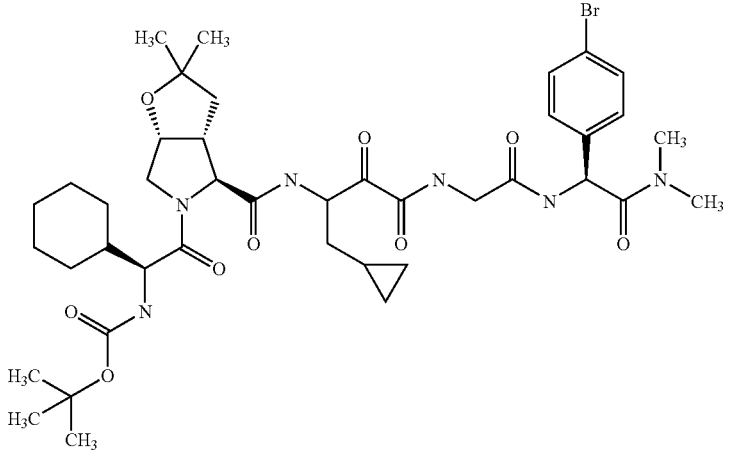 | 859.87 | A |

TABLE 6-continued
| STRUCTURE | MW | Ki* (nM) |
|---|---|---|
| 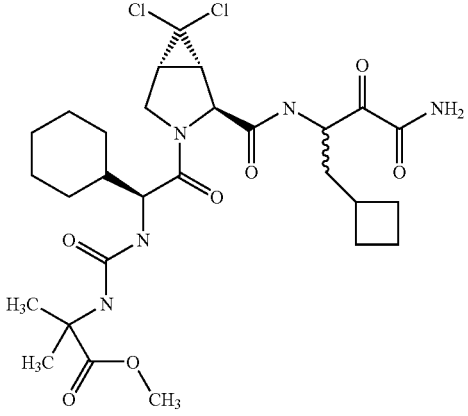 | 630.57 | A |
| 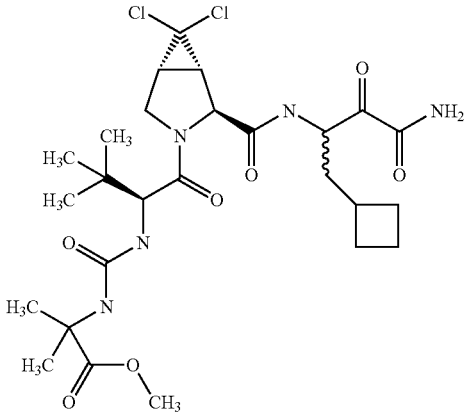 | 604.54 | A |
| 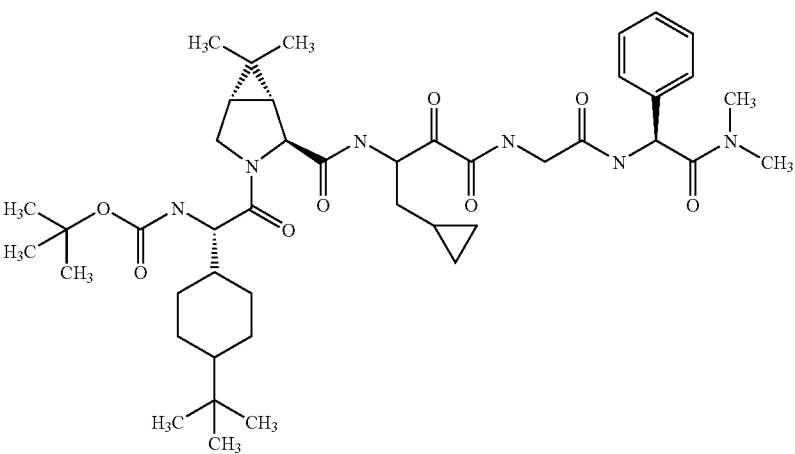 | 807.05 | A |

TABLE 6-continued
| STRUCTURE | MW | Ki* (nM) |
|---|---|---|
| 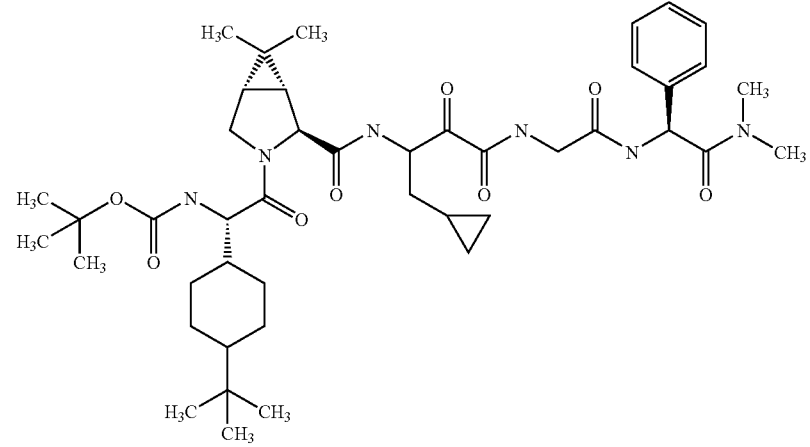 | 807.05 | A |
| 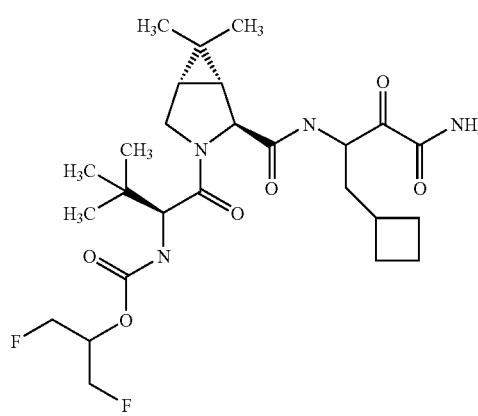 | 542.63 | B |
| 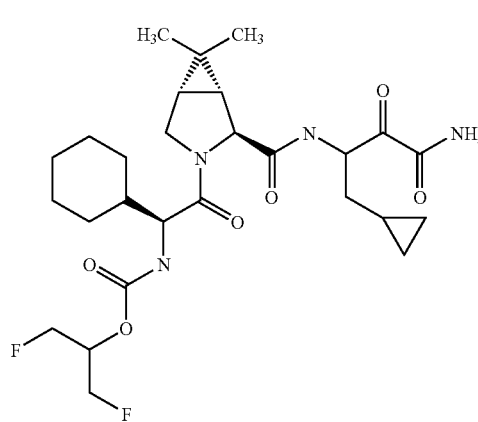 | 554.64 | A |

TABLE 6-continued
| STRUCTURE | MW | Ki* (nM) |
|---|---|---|
| 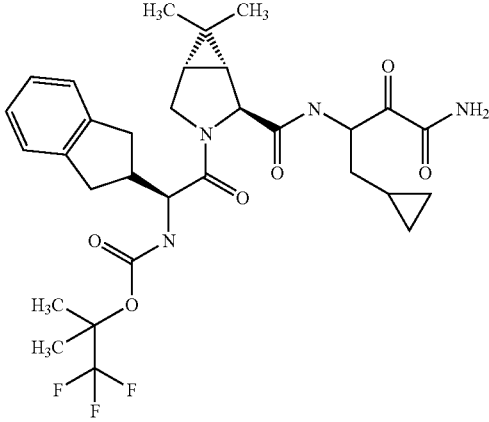 | 620.68 | A |
| 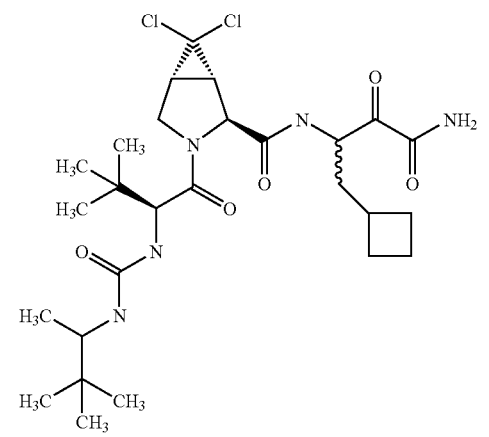 | 588.58 | A |
| 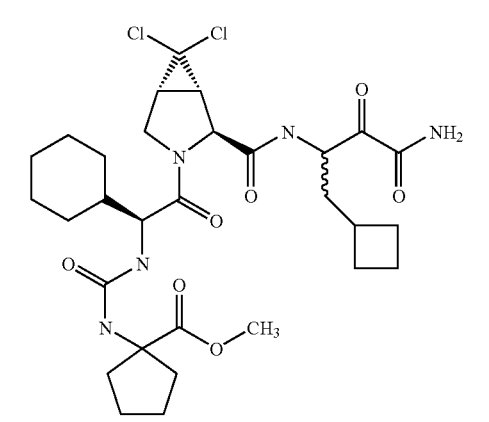 | 656.61 | B |

TABLE 6-continued

| STRUCTURE | MW | Ki* (nM) |
|---|---|---|
| 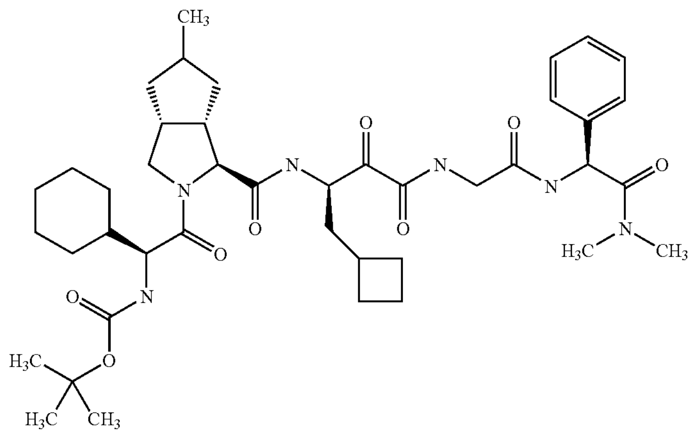 | 779.00 | A |
| 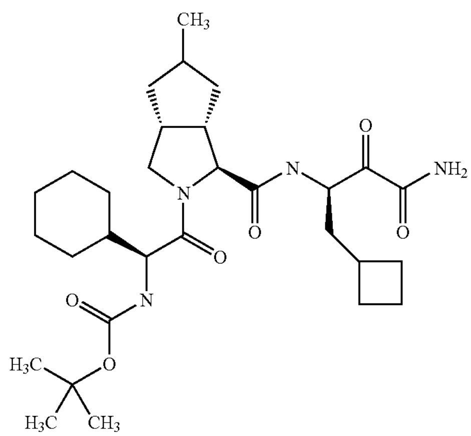 | 560.74 | B |
| 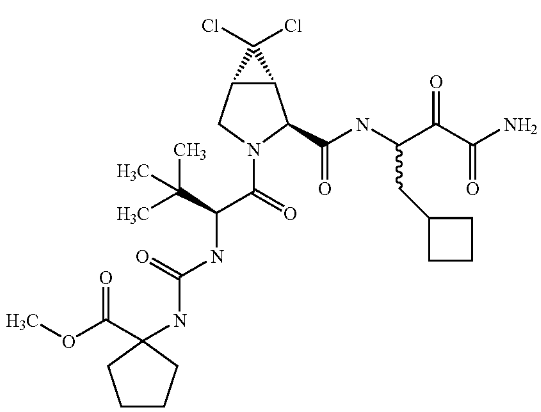 | 630.57 | B |

TABLE 6-continued
| STRUCTURE | MW | Ki* (nM) |
|---|---|---|
| 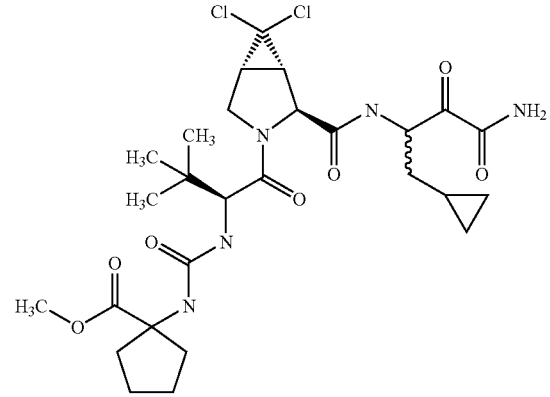 | 616.55 | B |
| 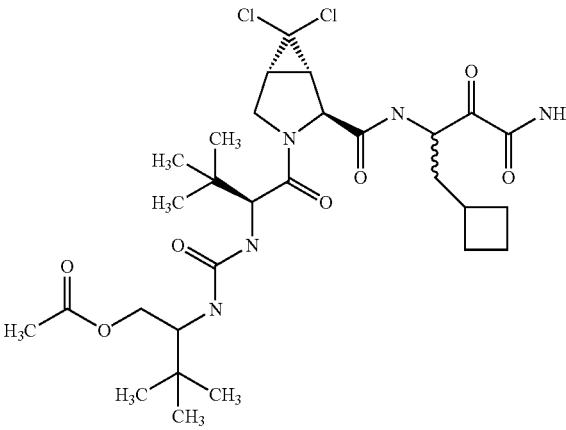 | 646.62 | A |
| 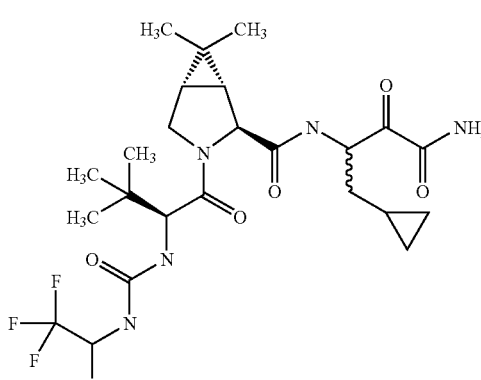 | 545.61 | B |

TABLE 6-continued
| STRUCTURE | MW | Ki* (nM) |
|---|---|---|
| 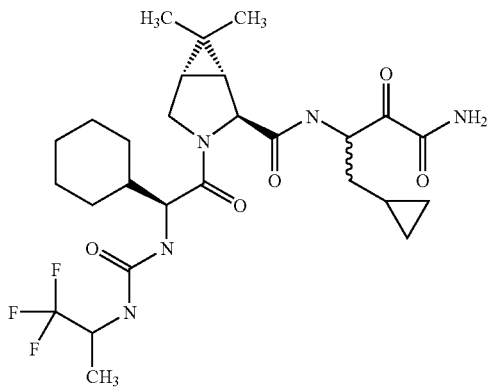 | 571.65 | B |
| 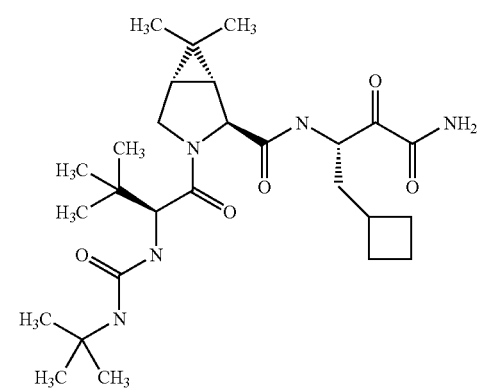 | 519.69 | A |
| 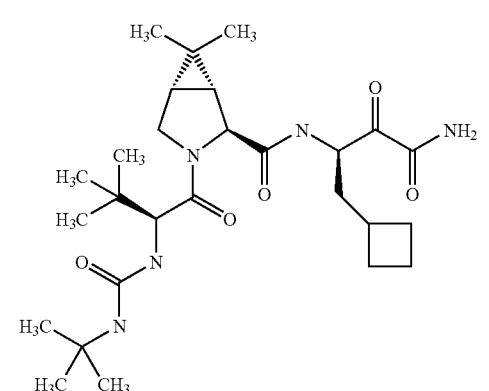 | 519.69 | B |
| 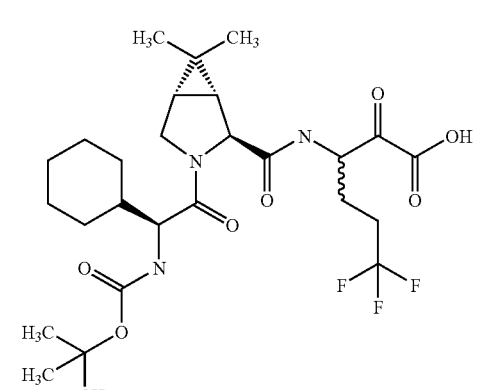 | 575.63 | A |

TABLE 6-continued

| STRUCTURE | MW | Ki* (nM) |
|---|---|---|
| 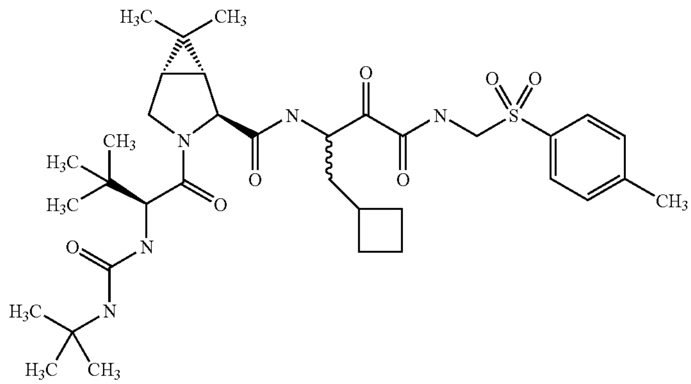 | 687.91 | B |
| 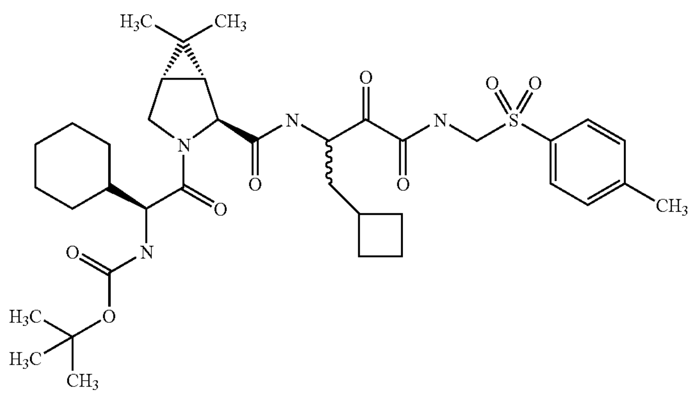 | 714.93 | B |
| 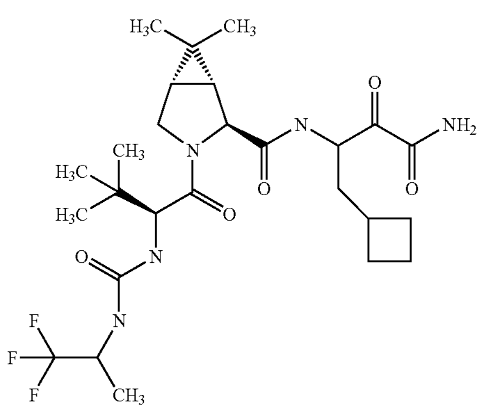 | 559.63 | A |

TABLE 6-continued
| STRUCTURE | MW | Ki* (nM) |
|---|---|---|
| 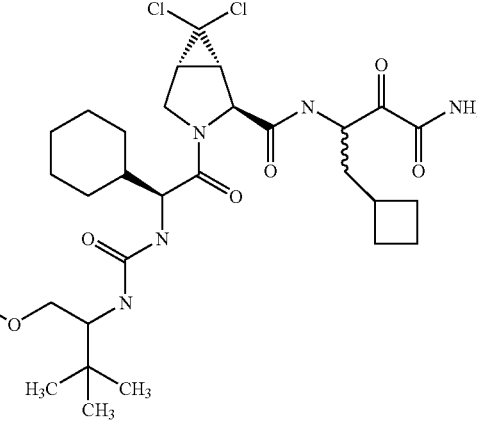 | 672.66 | A |
| 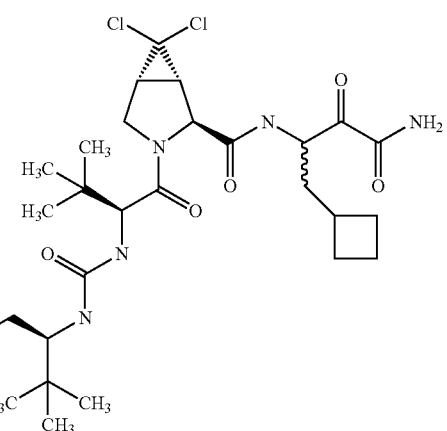 | 604.58 | B |
| 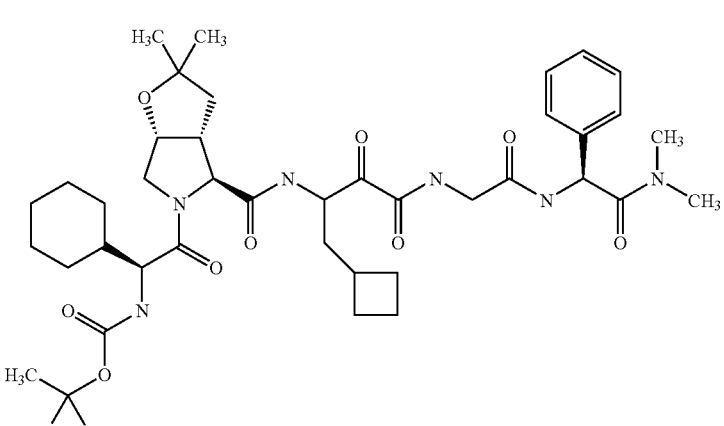 | 795.00 | A |

TABLE 6-continued
| STRUCTURE | MW | Ki* (nM) |
|---|---|---|
| 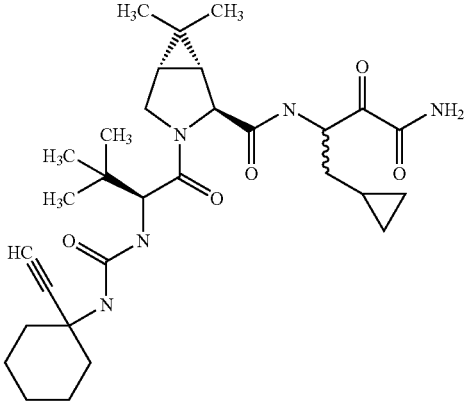 | 555.72 | A |
| 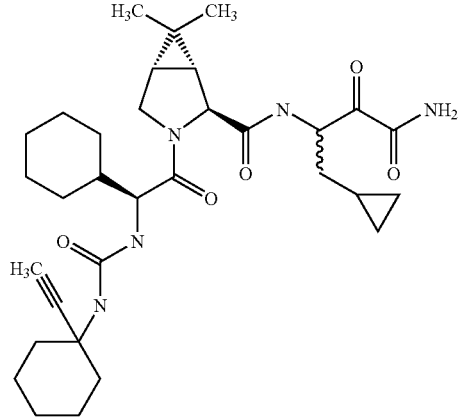 | 581.76 | A |
| 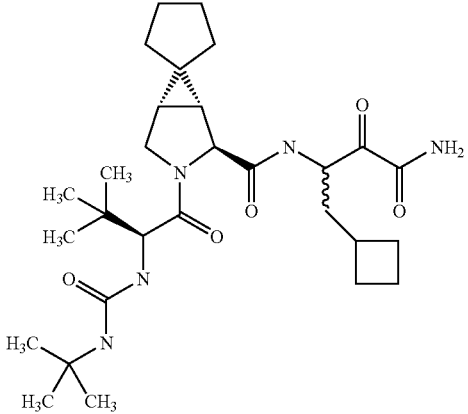 | 545.73 | B |

TABLE 6-continued
| STRUCTURE | MW | Ki* (nM) |
|---|---|---|
| 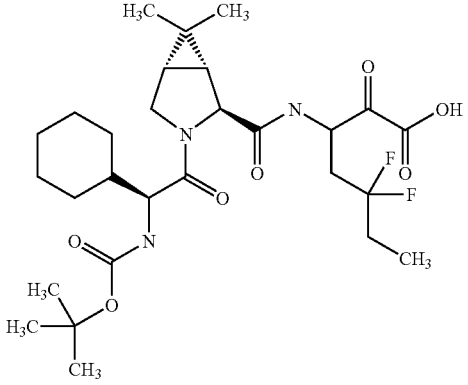 | 571.67 | B |
| 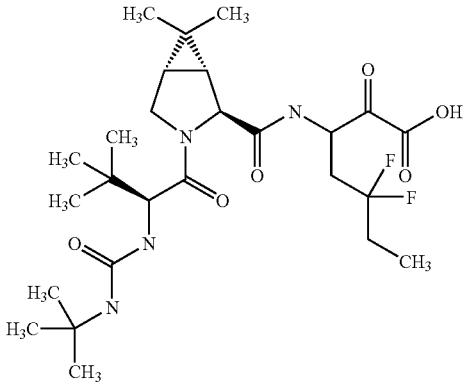 | 544.65 | B |
| 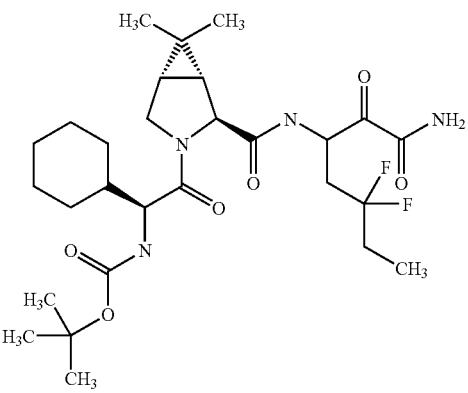 | 570.68 | B |
| 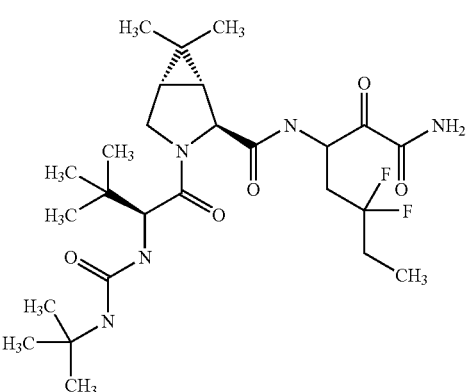 | 543.66 | B |

TABLE 6-continued
| STRUCTURE | MW | Ki* (nM) |
|---|---|---|
| 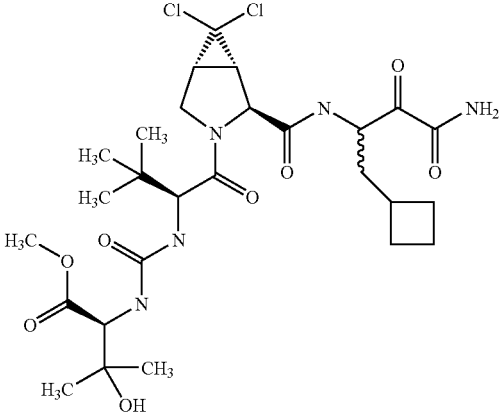 | 634.56 | B |
| 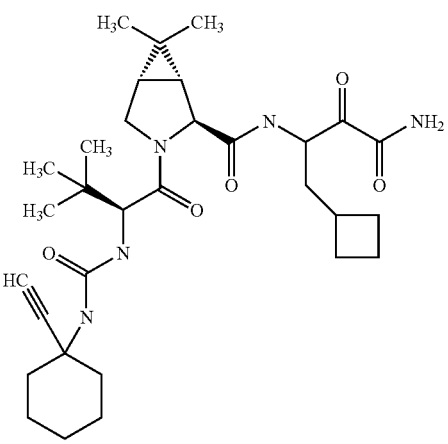 | 569.75 | A |
| 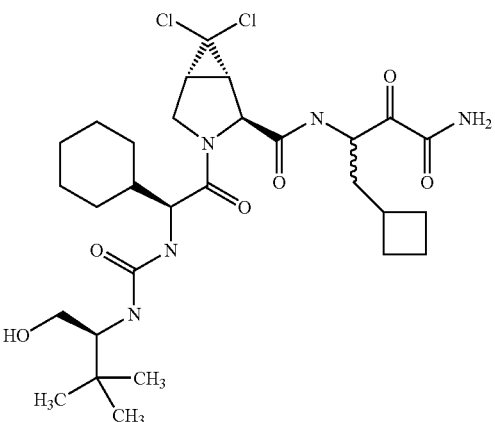 | 630.62 | B |

TABLE 6-continued

| STRUCTURE | MW | Ki* (nM) |
|---|---|---|
| | 561.51 | C |
| | 561.51 | A |
| 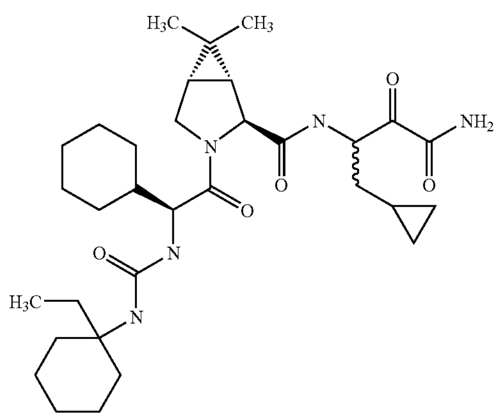 | 585.79 | A |
| 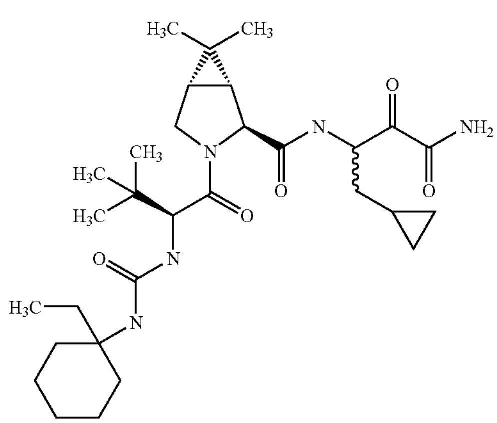 | 559.76 | A |

TABLE 6-continued
| STRUCTURE | MW | Ki* (nM) |
|---|---|---|
| 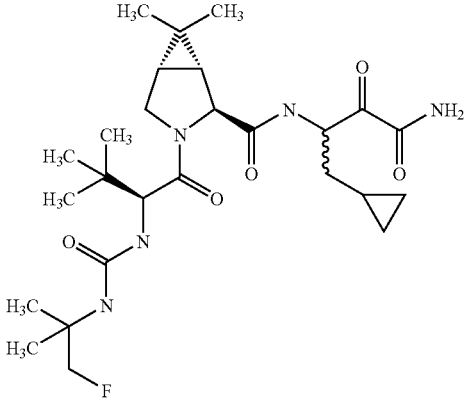 | 523.65 | A |
| 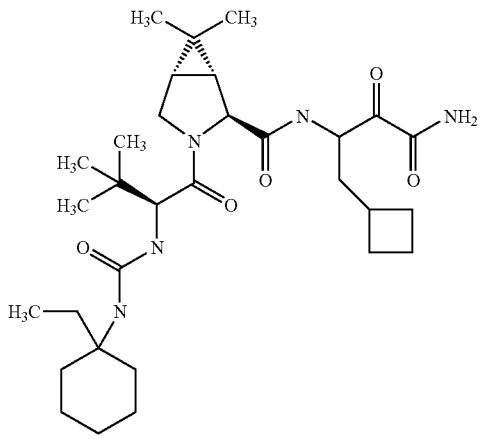 | 573.78 | A |
| 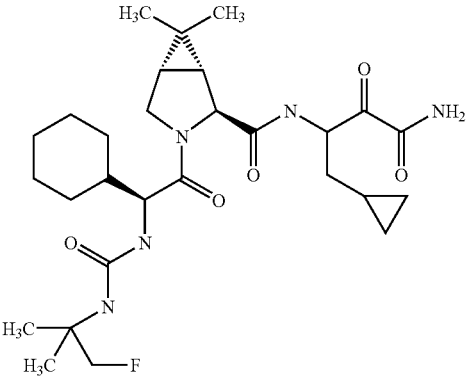 | 549.69 | A |

TABLE 6-continued
| STRUCTURE | MW | Ki* (nM) |
|---|---|---|
| 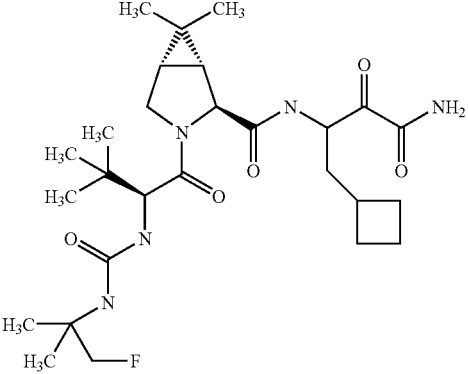 | 537.68 | A |
| 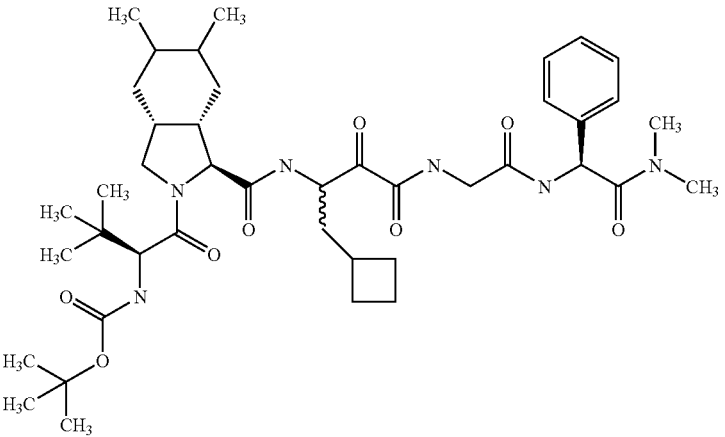 | 781.01 | A |
| 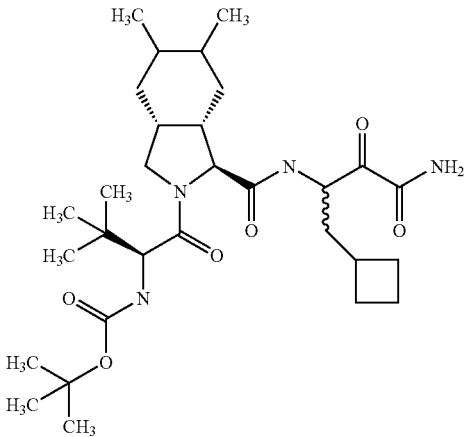 | 562.76 | B |

TABLE 6-continued
| STRUCTURE | MW | Ki* (nM) |
|---|---|---|
| 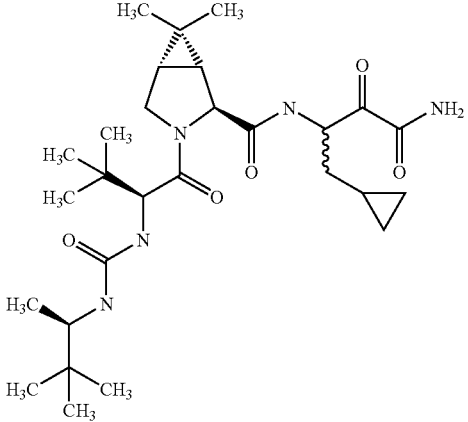 | 533.72 | A |
| 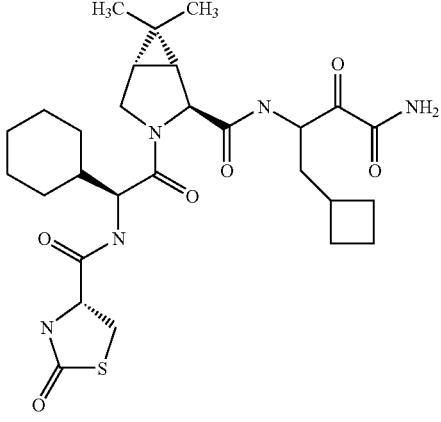 | 575.73 | A |
| 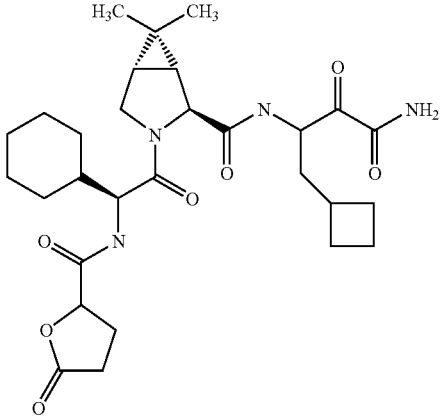 | 558.68 | A |

TABLE 6-continued
| STRUCTURE | MW | Ki* (nM) |
|---|---|---|
| 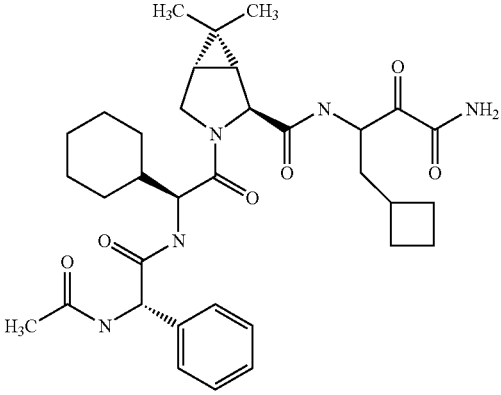 | 621.78 | A |
| 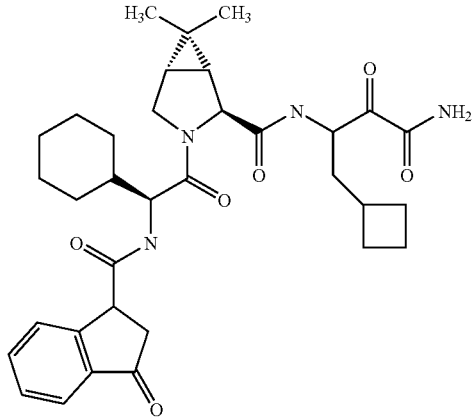 | 604.75 | B |
| 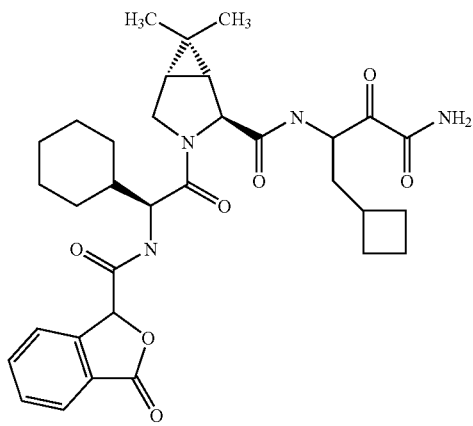 | 606.73 | A |

TABLE 6-continued
| STRUCTURE | MW | Ki* (nM) |
|---|---|---|
| 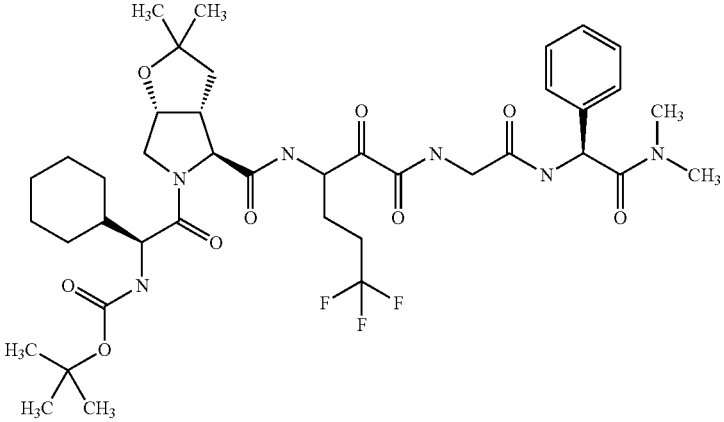 | 822.93 | A |
| 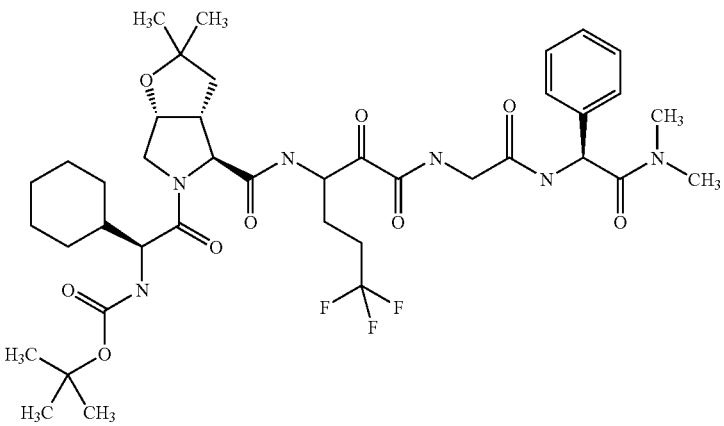 | 822.93 | A |
| 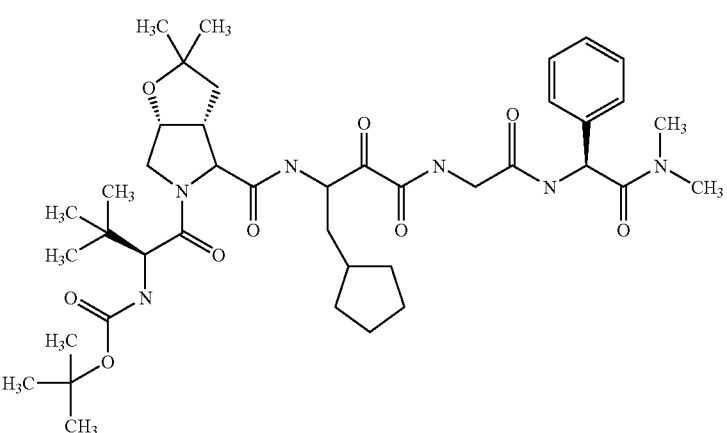 | 782.99 | A |

TABLE 6-continued
| STRUCTURE | MW | Ki* (nM) |
|---|---|---|
| 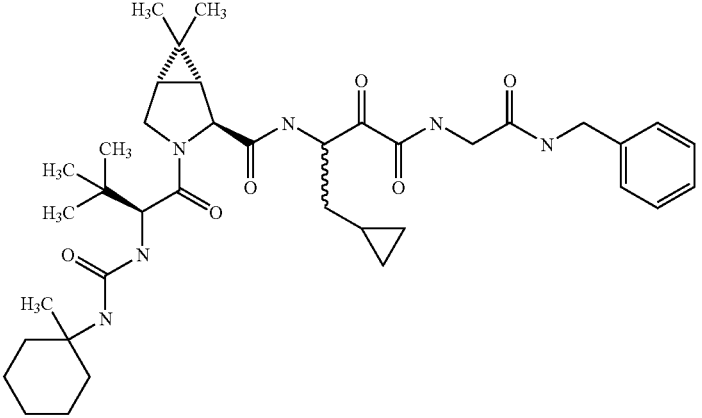 | 692.91 | A |
| 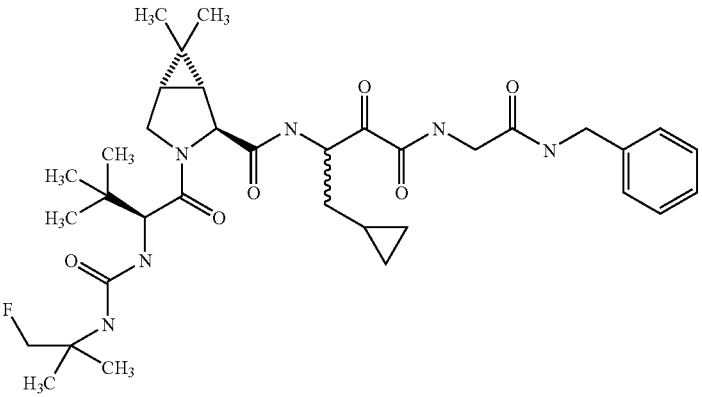 | 670.83 | A |
| 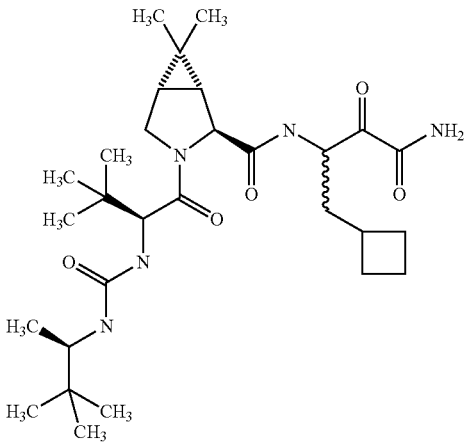 | 547.74 | A |

TABLE 6-continued
| STRUCTURE | MW | Ki* (nM) |
|---|---|---|
| 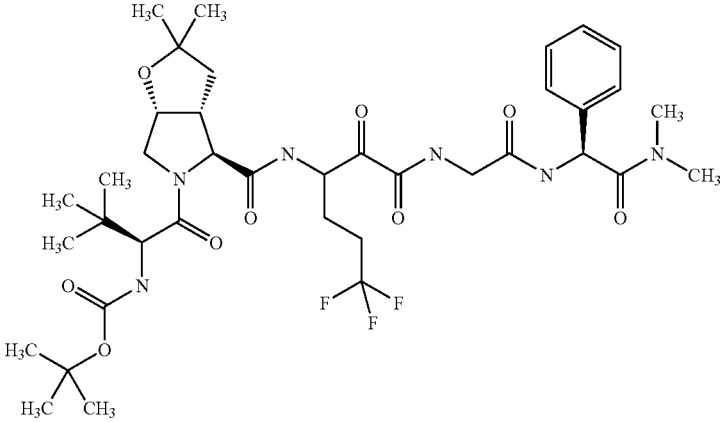 | 796.89 | A |
| 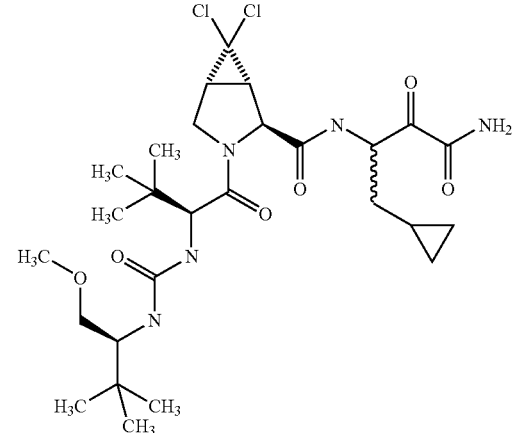 | 604.58 | A |
| 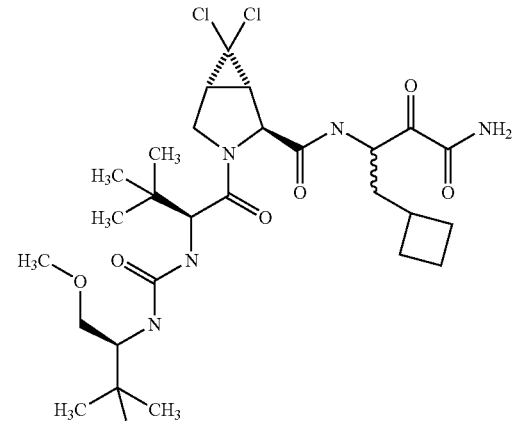 | 618.61 | A |

TABLE 6-continued
| STRUCTURE | MW | Ki* (nM) |
|---|---|---|
| 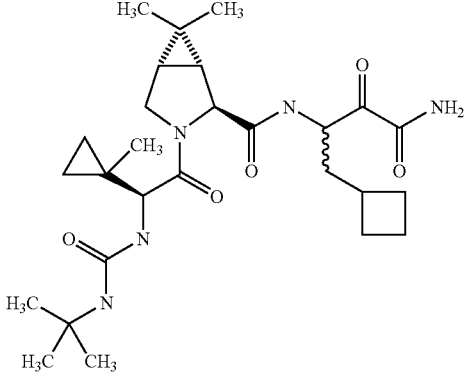 | 517.67 | B |
| 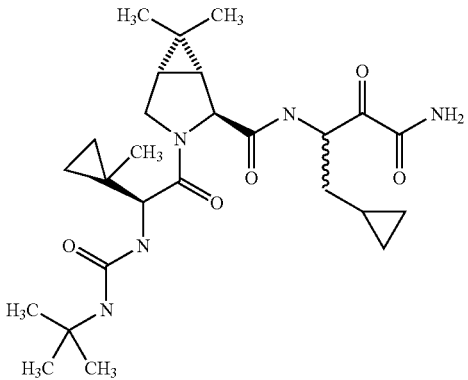 | 503.65 | B |
| 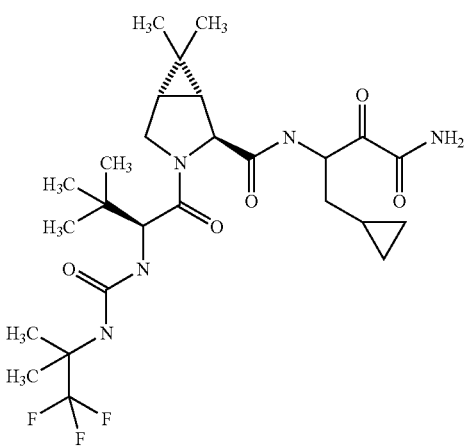 | 559.63 | A |

TABLE 6-continued
| STRUCTURE | MW | Ki* (nM) |
|---|---|---|
| 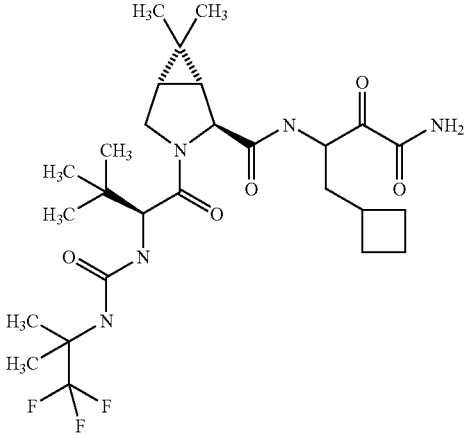 | 573.66 | A |
| 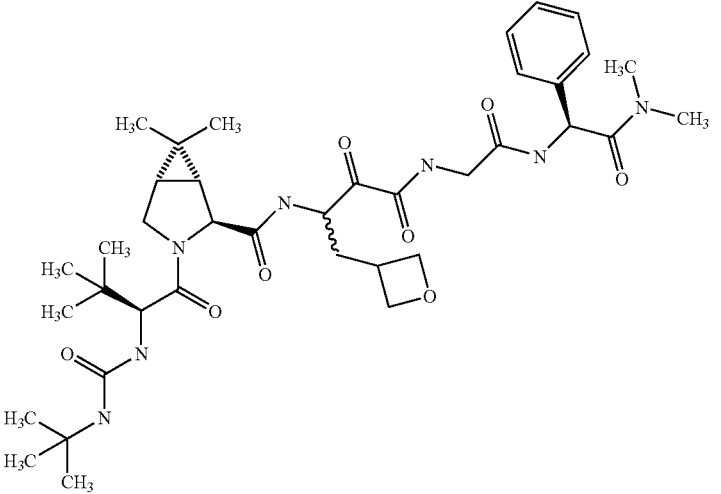 | 739.92 | A |
| 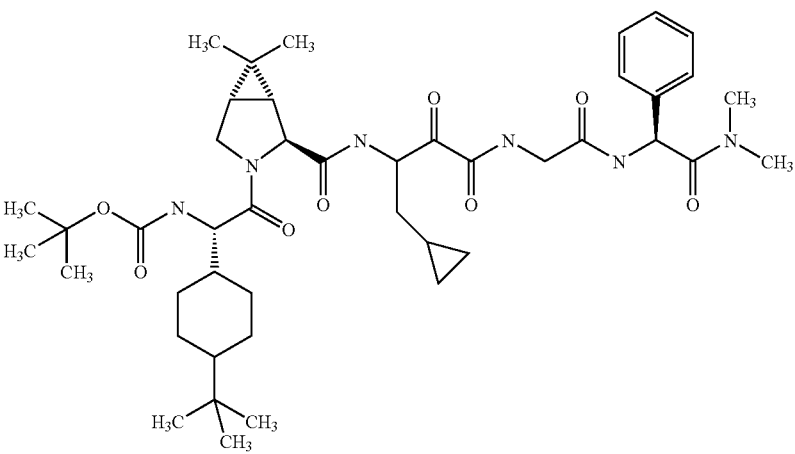 | 807.05 | A |

TABLE 6-continued
| STRUCTURE | MW | Ki* (nM) |
|---|---|---|
| 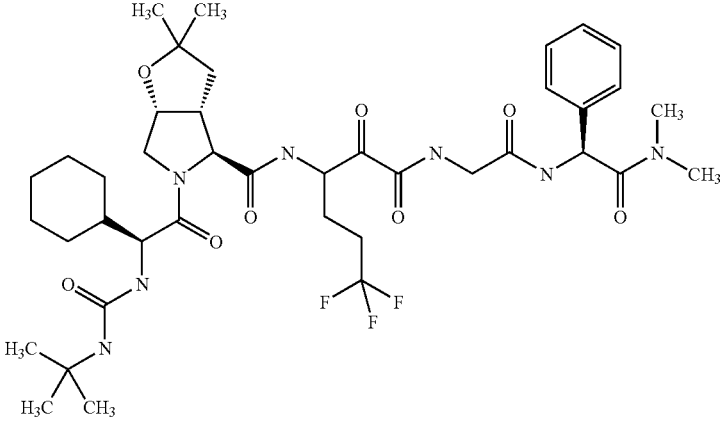 | 821.95 | A |
| 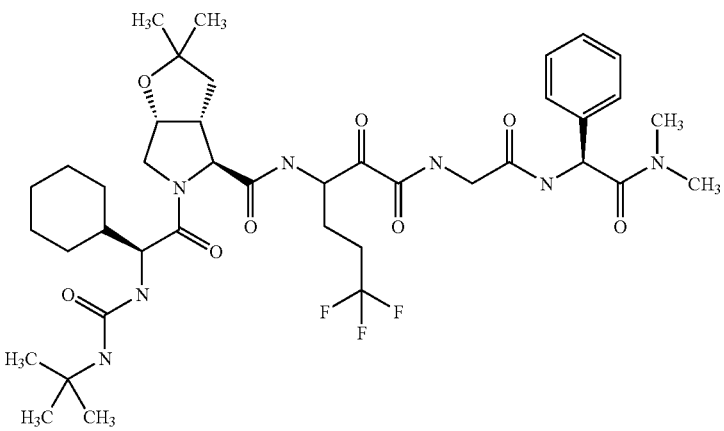 | 821.95 | A |
| 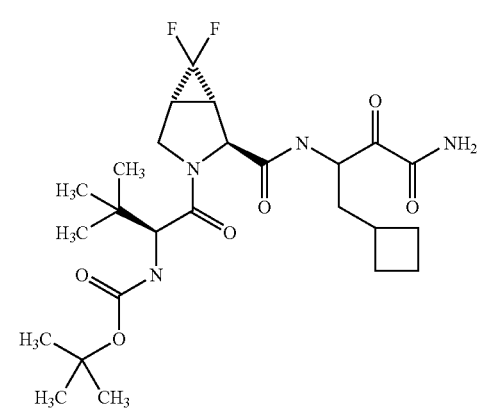 | 528.60 | B |

TABLE 6-continued
| STRUCTURE | MW | Ki* (nM) |
|---|---|---|
| 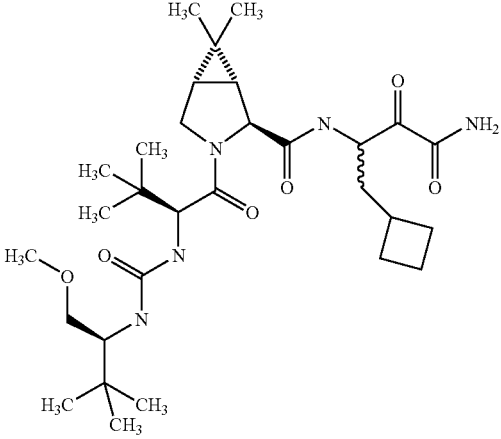 | 577.77 | B |
| 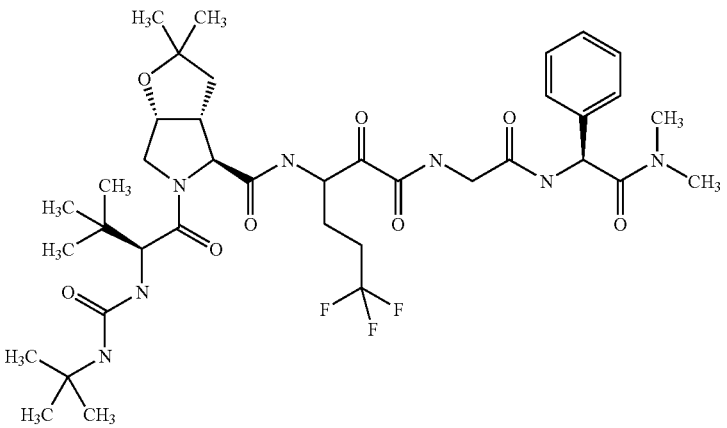 | 795.91 | A |
| 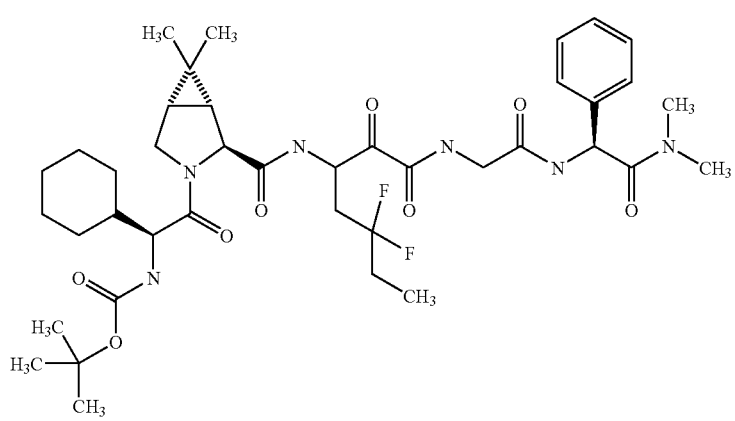 | 788.94 | A |

TABLE 6-continued
| STRUCTURE | MW | Ki* (nM) |
|---|---|---|
| 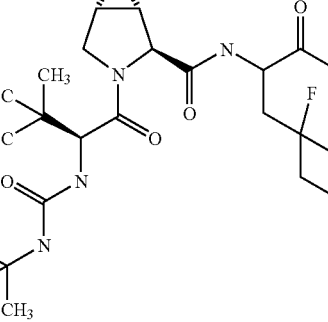 | 761.92 | A |
| 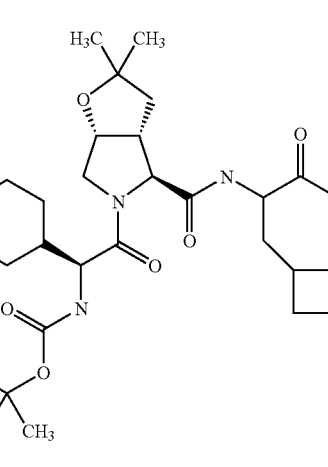 | 795.00 | A |
| 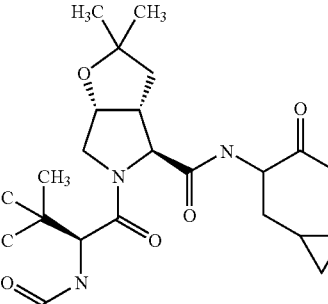 | 760.96 | A |

TABLE 6-continued

| STRUCTURE | MW | Ki* (nM) |
|---|---|---|
| 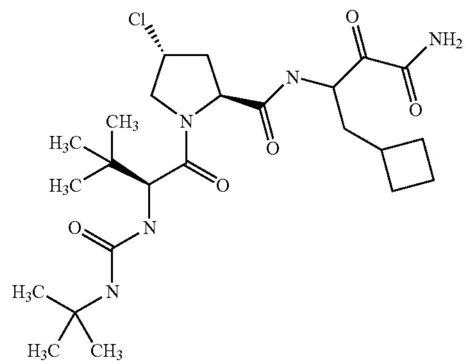 | 514.07 | B |
| 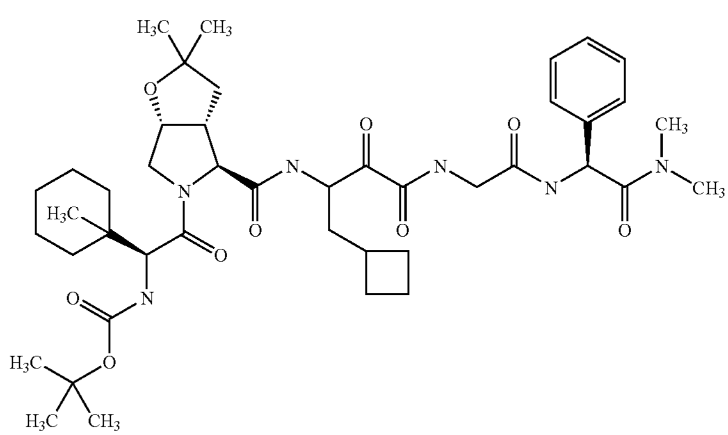 | 809.02 | A |
| 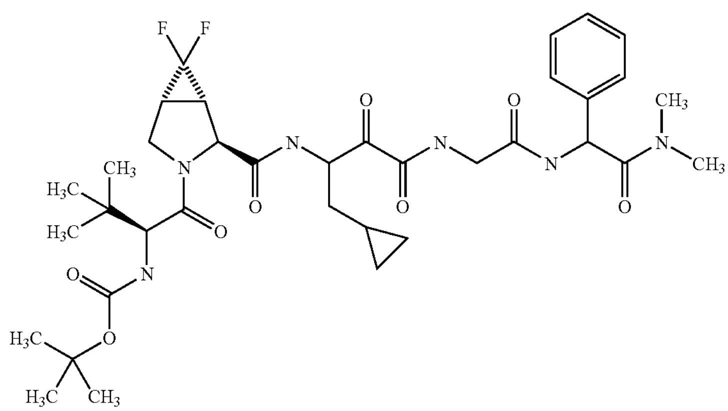 | 732.83 | A |

TABLE 6-continued
| STRUCTURE | MW | Ki* (nM) |
|---|---|---|
| 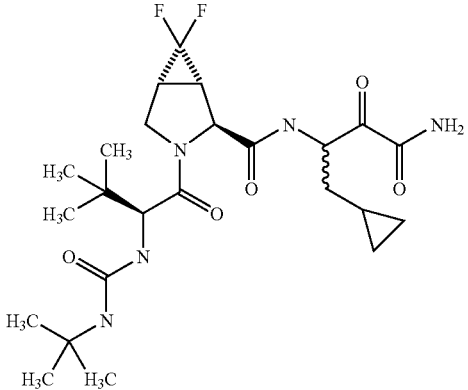 | 513.59 | B |
| 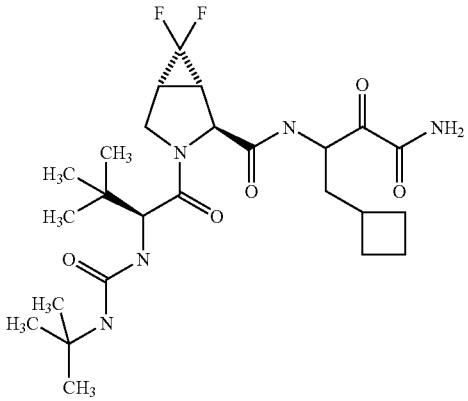 | 527.62 | B |
| 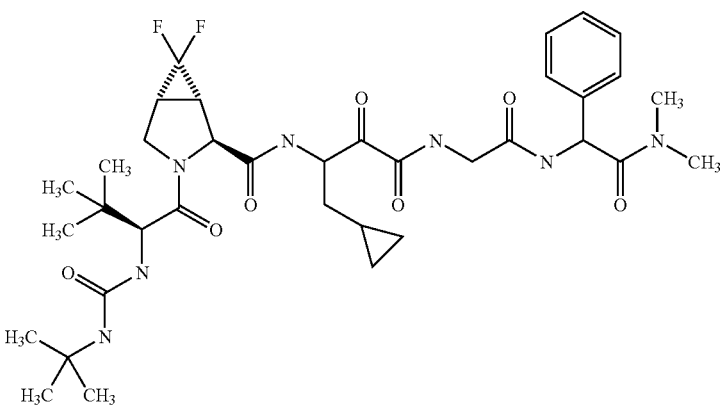 | 731.85 | A |

TABLE 6-continued
| STRUCTURE | MW | Ki* (nM) |
|---|---|---|
| 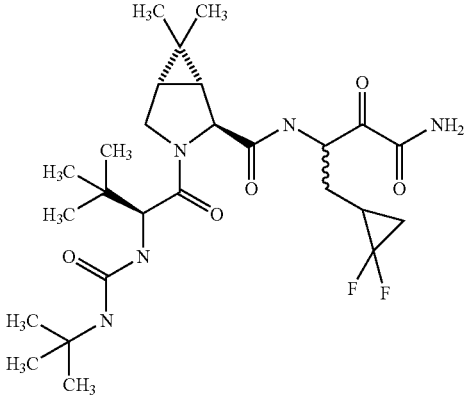 | 541.64 | A |
| 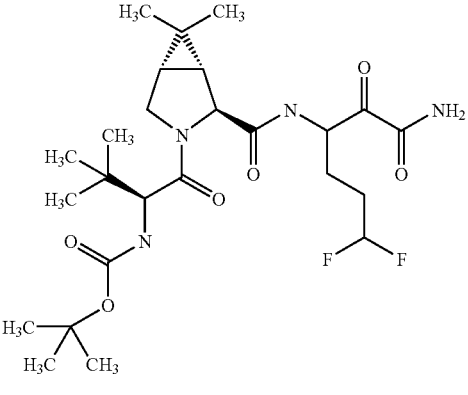 | 530.62 | B |
| 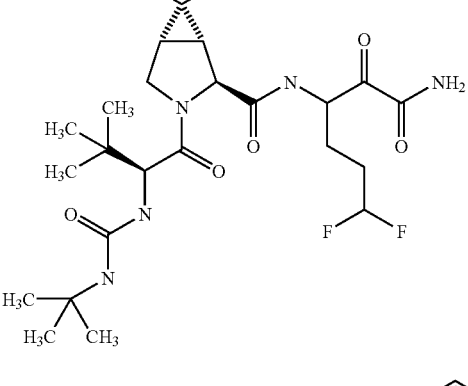 | 529.63 | B |
| 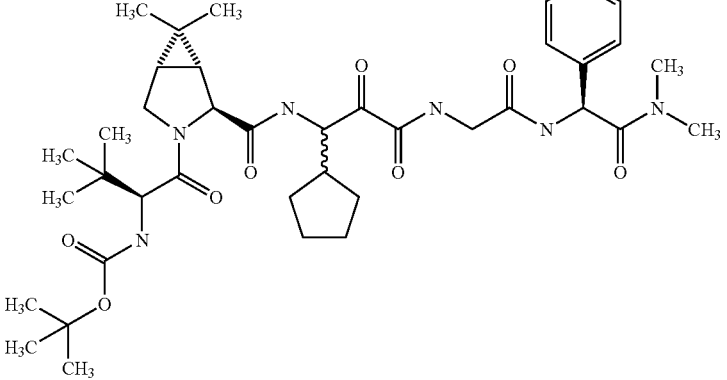 | 738.93 | A |

TABLE 6-continued
| STRUCTURE | MW | Ki* (nM) |
|---|---|---|
| 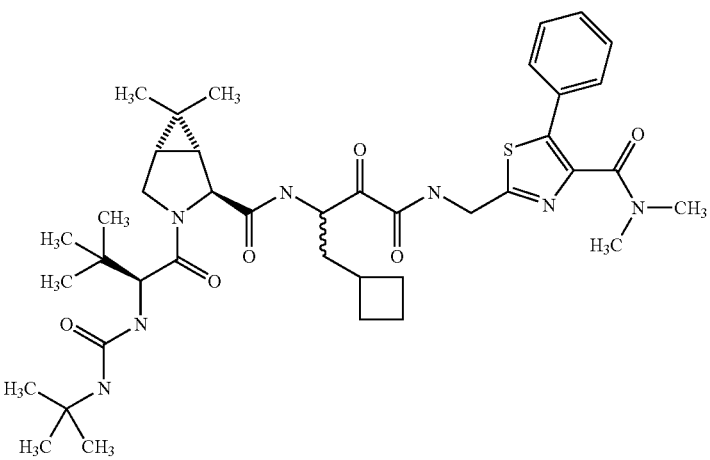 | 764.01 | B |
| 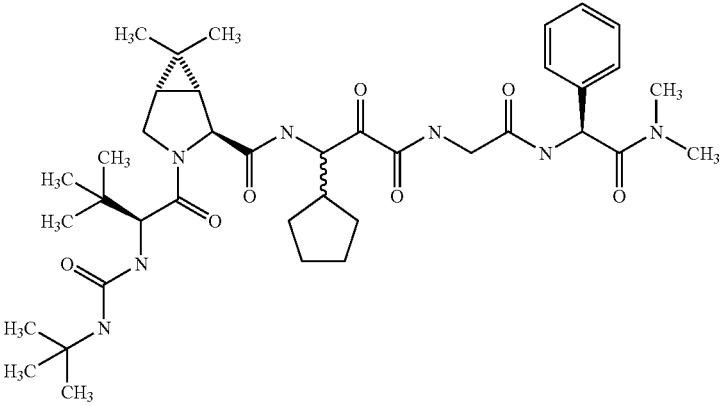 | 737.95 | A |
| 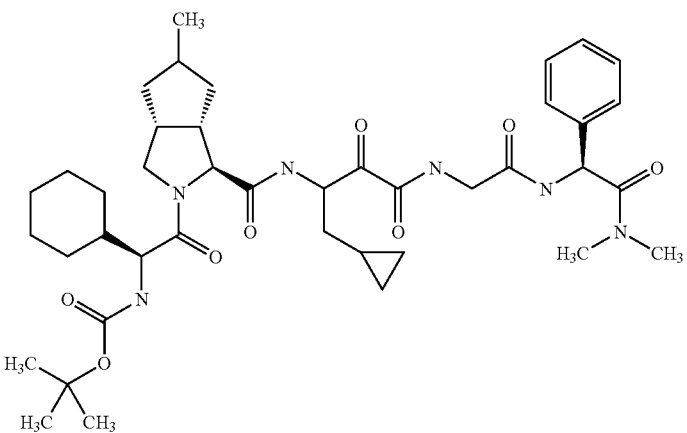 | 764.97 | A |

TABLE 6-continued
| STRUCTURE | MW | Ki* (nM) |
|---|---|---|
| 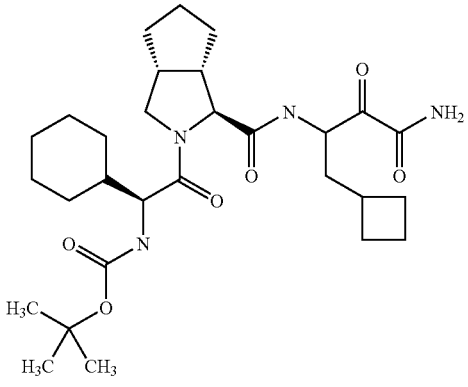 | 546.71 | B |
| 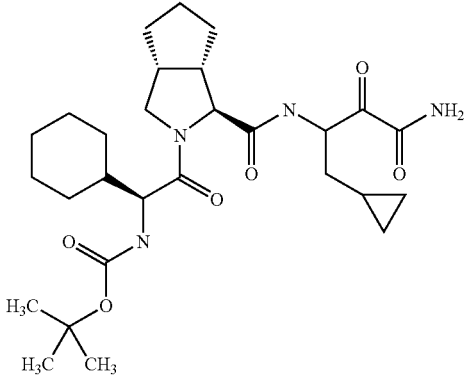 | 532.69 | B |
| 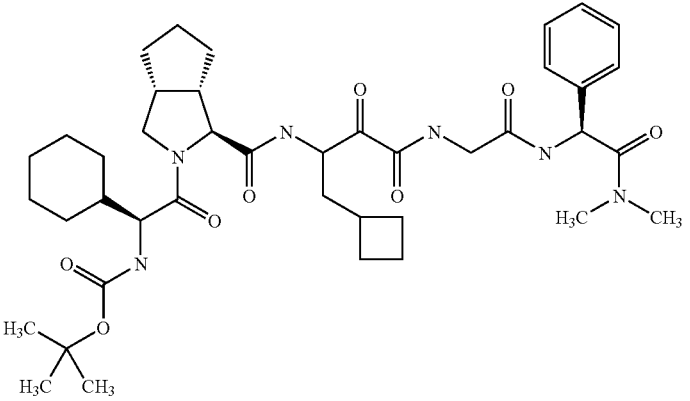 | 764.97 | A |
| 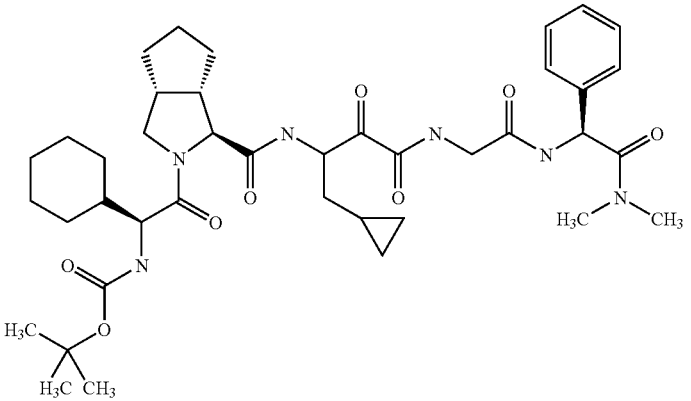 | 750.94 | A |

TABLE 6-continued

| STRUCTURE | MW | Ki* (nM) |
|---|---|---|
| | 800.95 | A |
| | 800.95 | A |
| 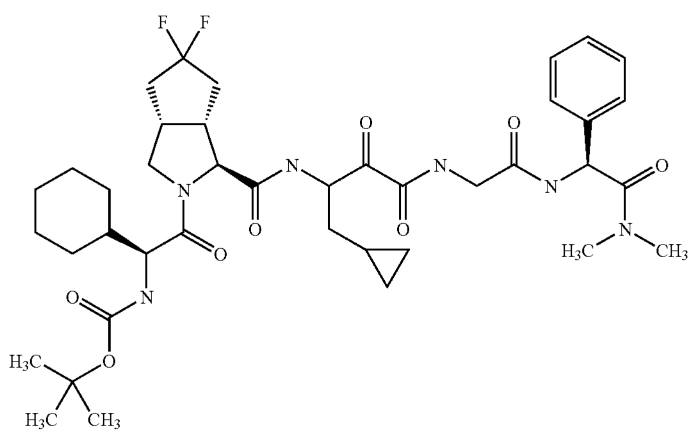 | 786.92 | A |

TABLE 6-continued
| STRUCTURE | MW | Ki* (nM) |
|---|---|---|
| 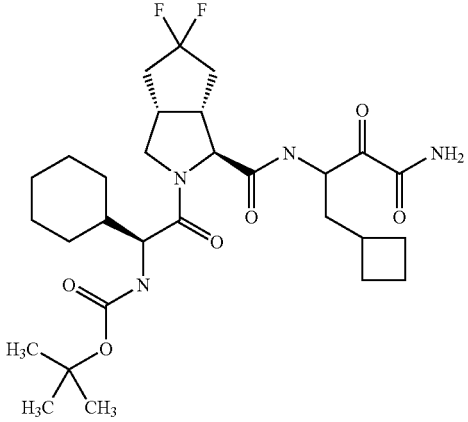 | 582.69 | B |
| 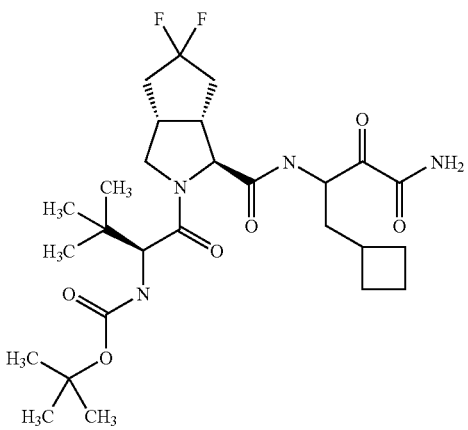 | 556.66 | B |
| 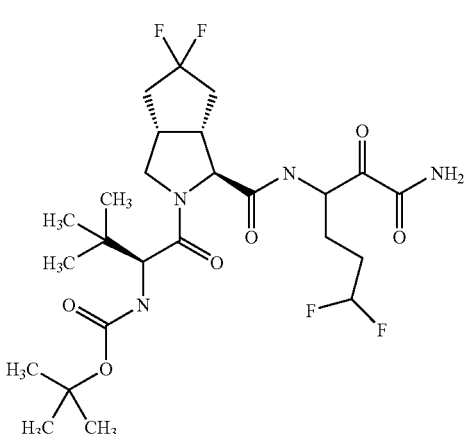 | 566.60 | B |

TABLE 6-continued

| STRUCTURE | MW | Ki* (nM) |
|---|---|---|
| 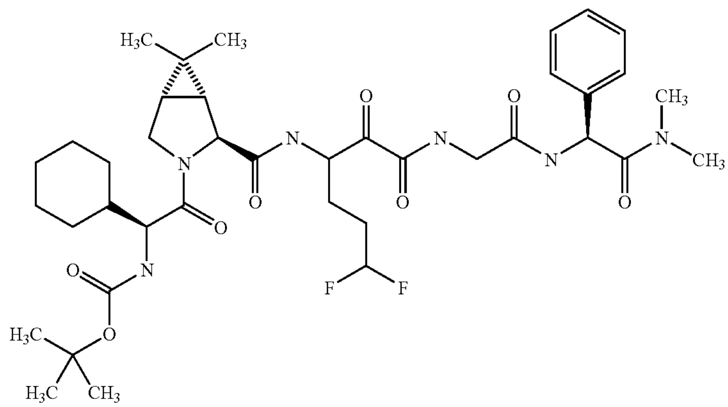 | 774.91 | A |
| 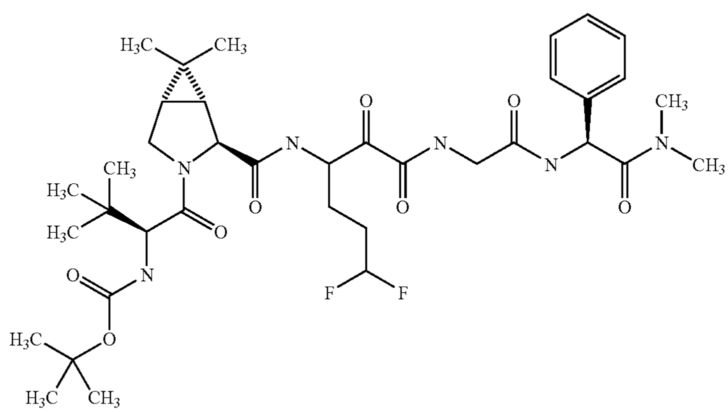 | 748.88 | A |
| 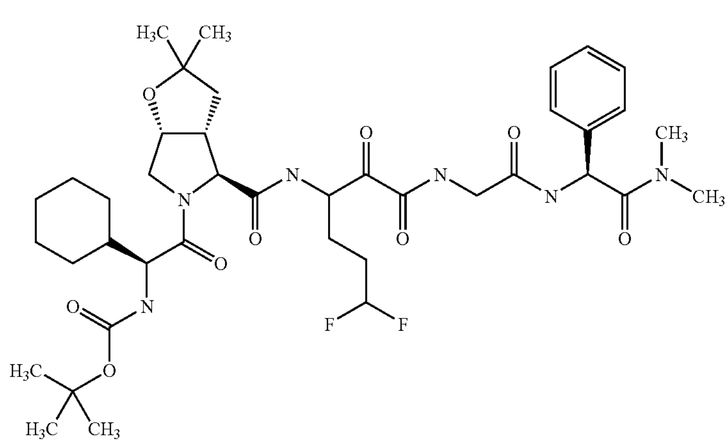 | 804.94 | A |

TABLE 6-continued

| STRUCTURE | MW | Ki* (nM) |
|---|---|---|
| 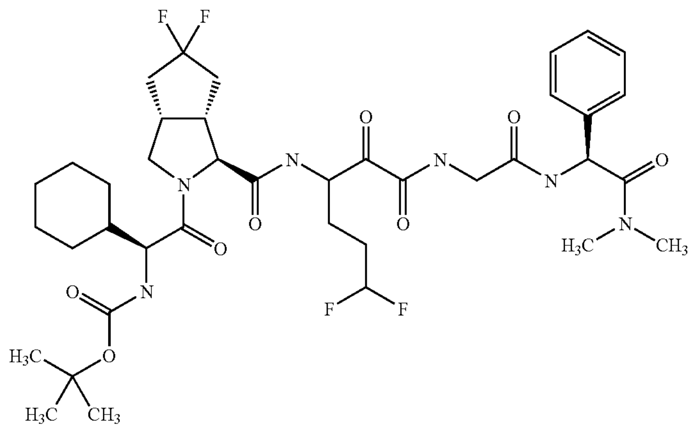 | 810.89 | A |
| 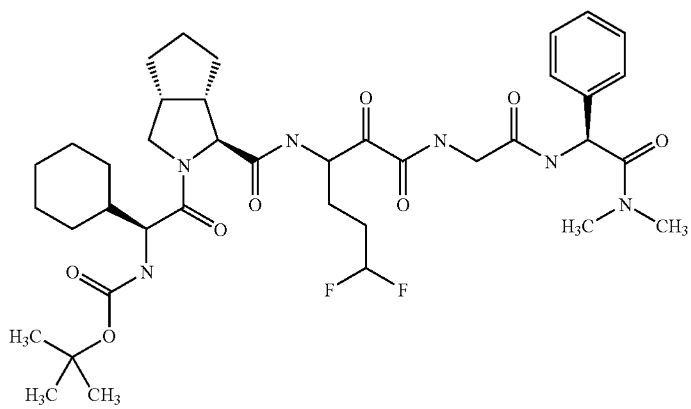 | 774.91 | A |
| 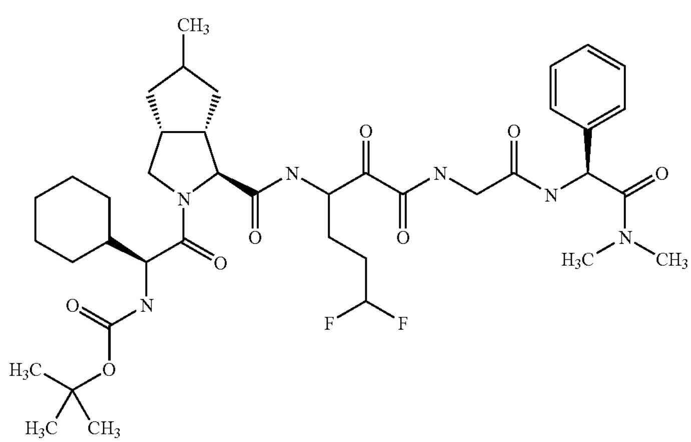 | 788.94 | A |

TABLE 6-continued
| STRUCTURE | MW | Ki* (nM) |
|---|---|---|
| 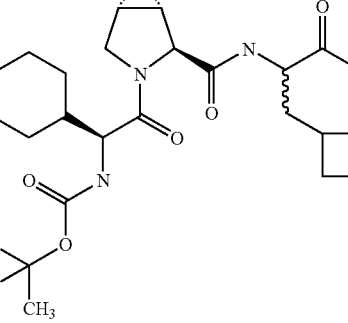 | 766.94 | A |
| 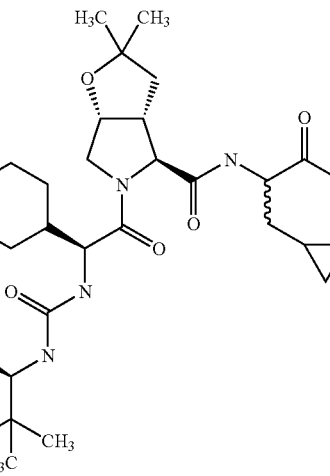 | 808.04 | A |
| 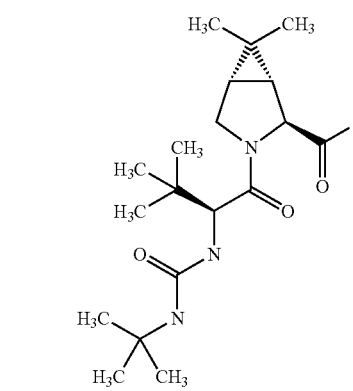 | 537.68 | B |

TABLE 6-continued

| STRUCTURE | MW | Ki* (nM) |
|---|---|---|
| 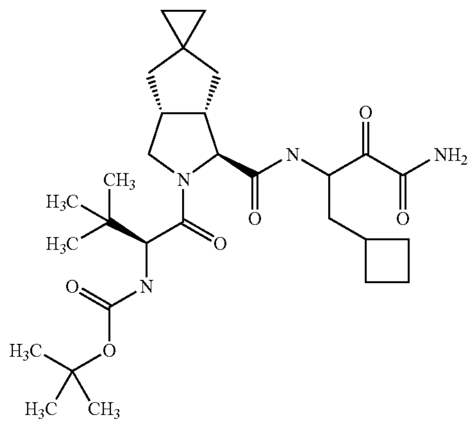 | 546.71 | B |
| 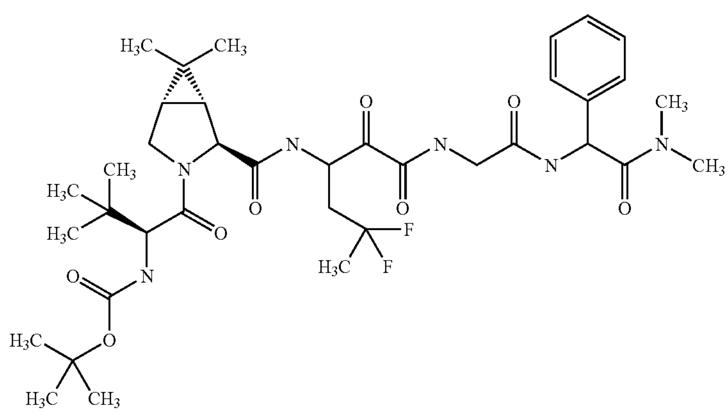 | 748.88 | B |
| 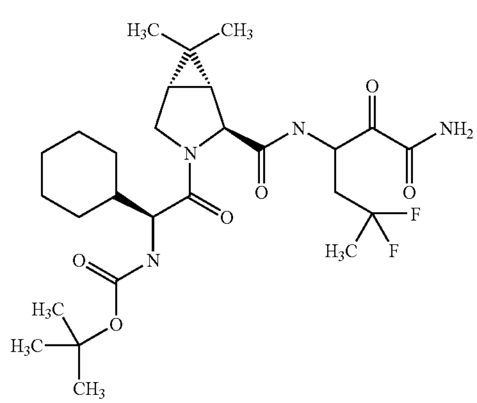 | 556.66 | B |

TABLE 6-continued
| STRUCTURE | MW | Ki* (nM) |
|---|---|---|
| 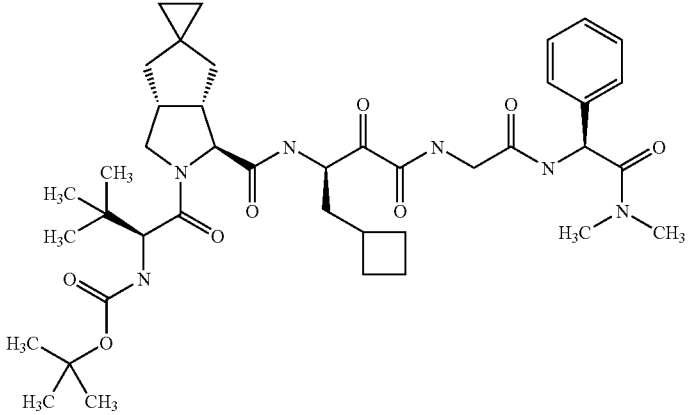 | 764.97 | B |
| 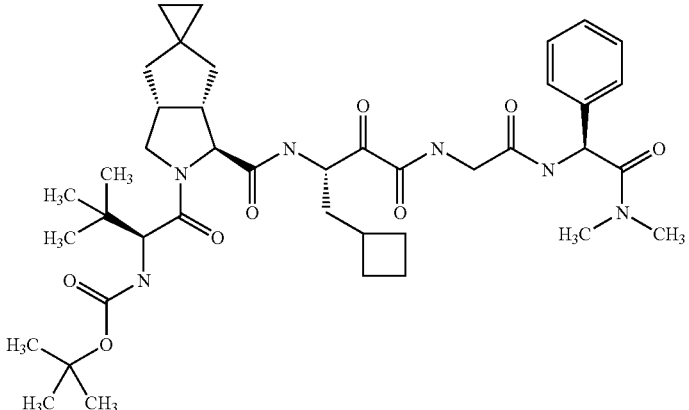 | 764.97 | A |
| 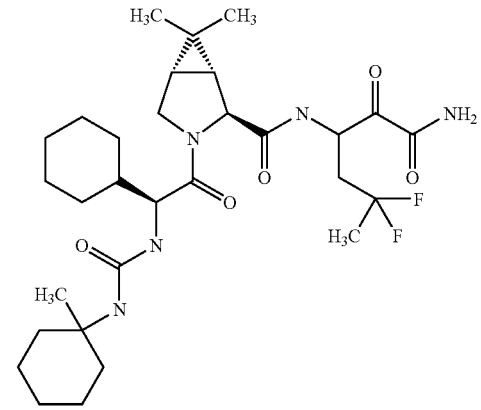 | 595.74 | B |

TABLE 6-continued

| STRUCTURE | MW | Ki* (nM) |
|---|---|---|
| 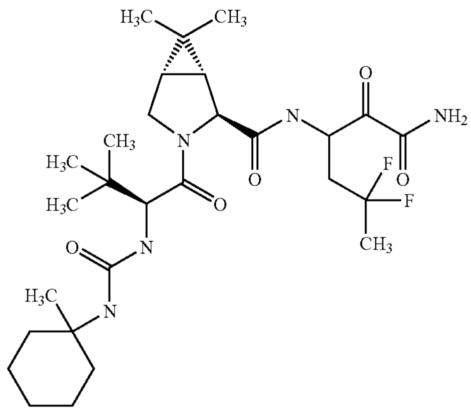 | 569.70 | A |
| 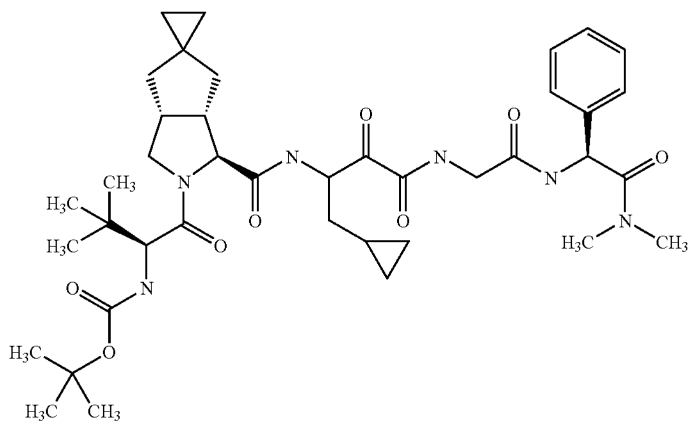 | 750.94 | A |
| 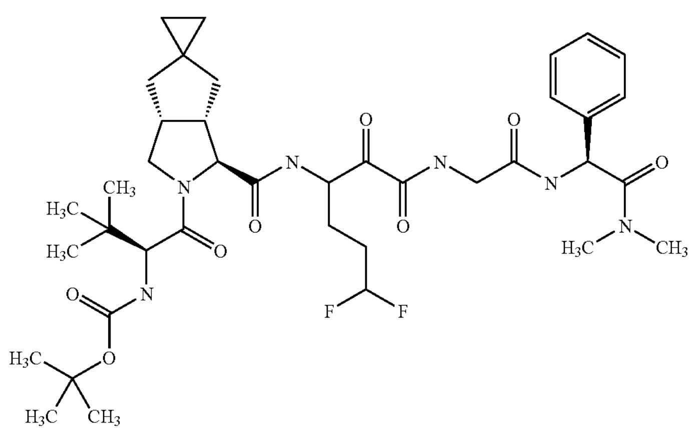 | 774.91 | A |

TABLE 6-continued
| STRUCTURE | MW | Ki* (nM) |
|---|---|---|
| 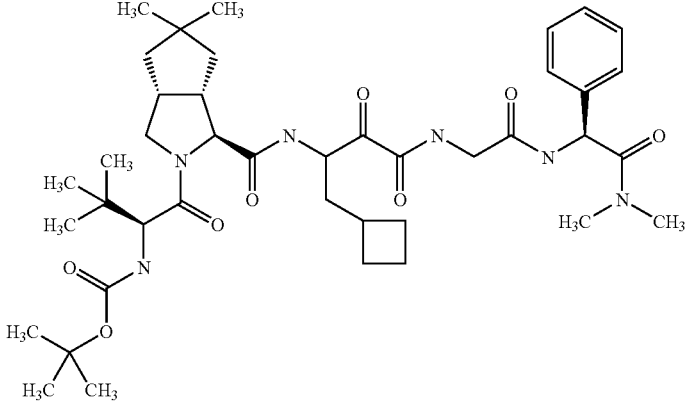 | 766.99 | A |
| 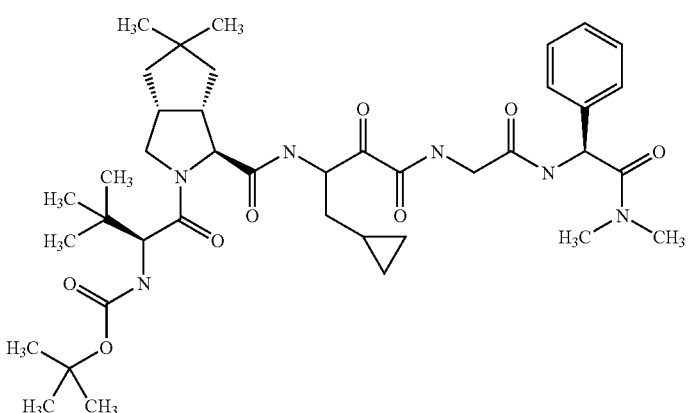 | 752.96 | A |
| 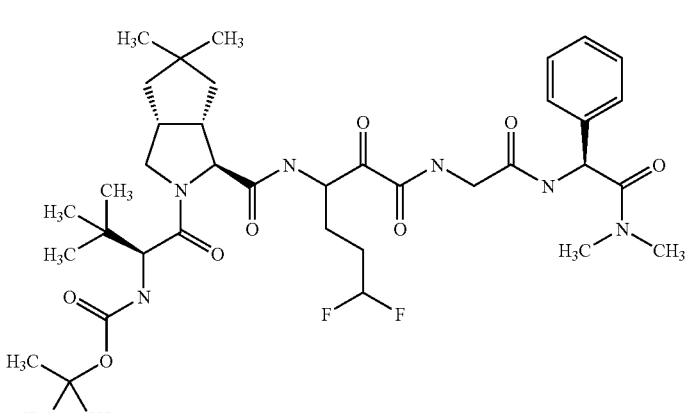 | 776.93 | A |

TABLE 6-continued
| STRUCTURE | MW | Ki* (nM) |
|---|---|---|
| 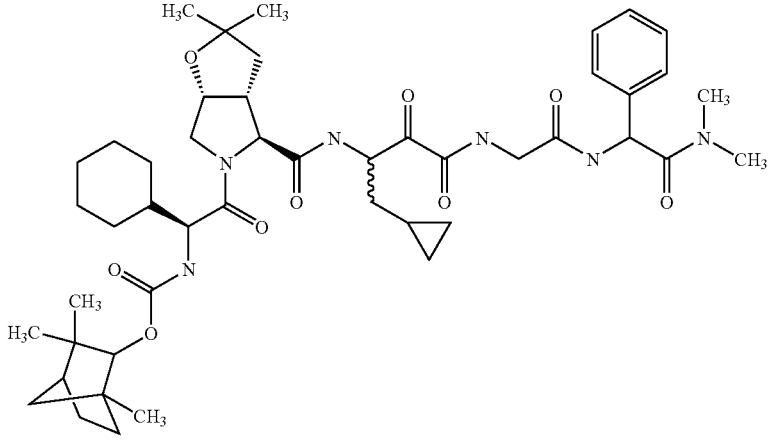 | 861.10 | A |
| 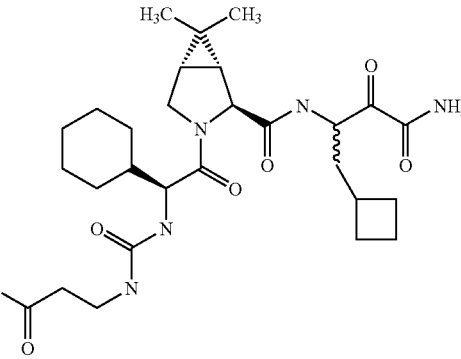 | 589.74 | A |
| 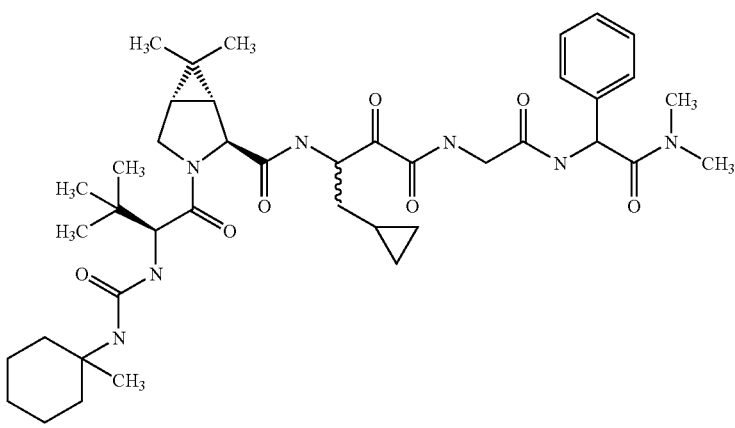 | 763.99 | A |

TABLE 6-continued
| STRUCTURE | MW | Ki* (nM) |
|---|---|---|
| 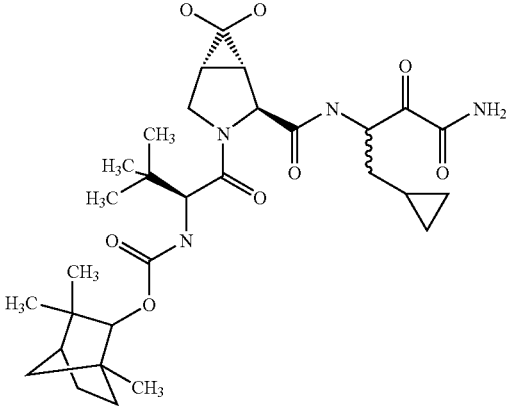 | 627.61 | A |
| 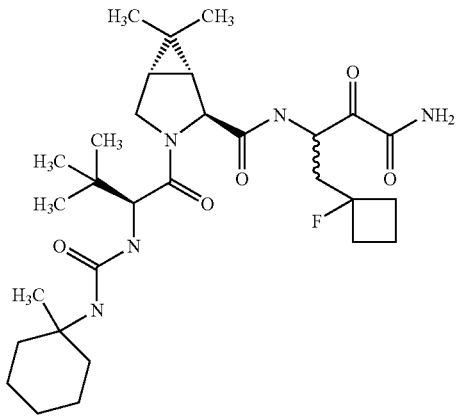 | 577.75 | A |
| 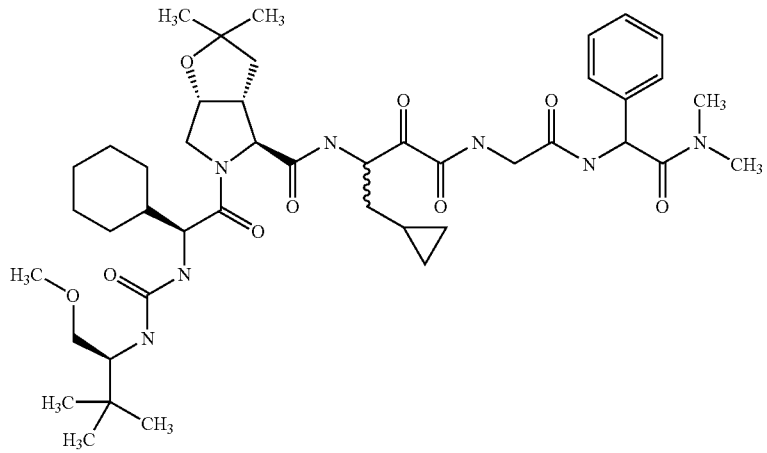 | 838.07 | A |

TABLE 6-continued
| STRUCTURE | MW | Ki* (nM) |
|---|---|---|
| 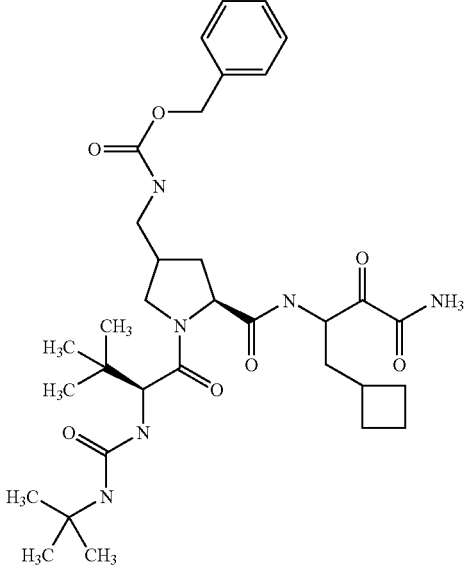 | 642.80 | B |
| 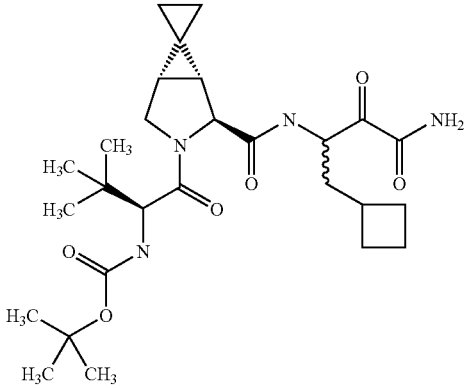 | 518.66 | B |
| 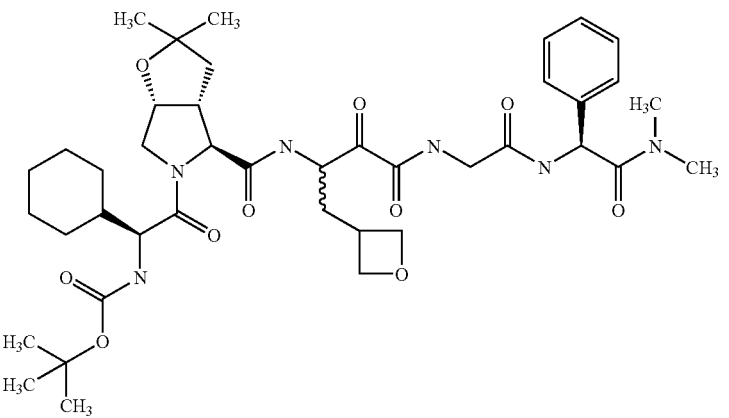 | 796.97 | A |

TABLE 6-continued

| STRUCTURE | MW | Ki* (nM) |
|---|---|---|
| 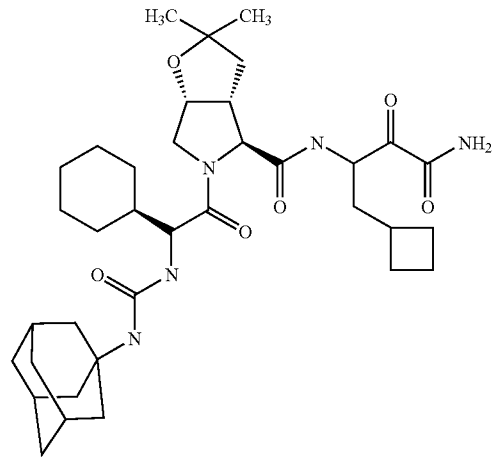 | 653.87 | B |
| 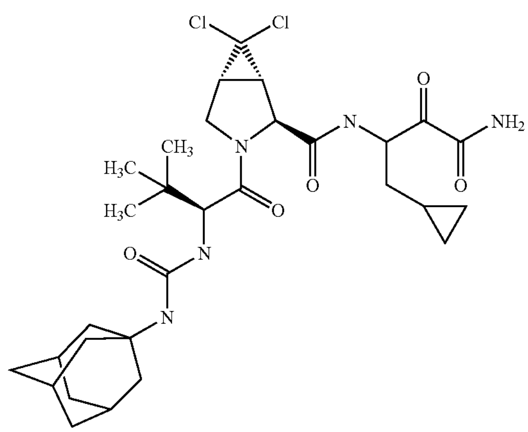 | 624.61 | A |
| 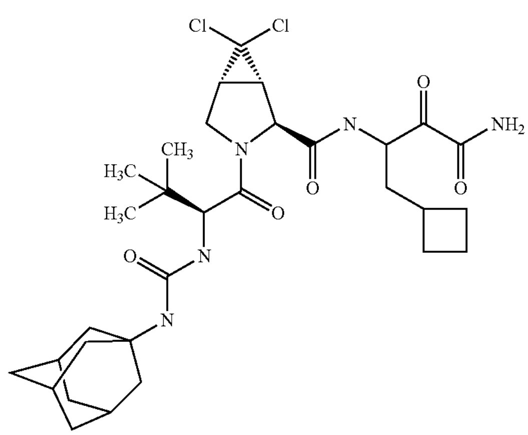 | 638.64 | A |

TABLE 6-continued

| STRUCTURE | MW | Ki* (nM) |
|---|---|---|
| 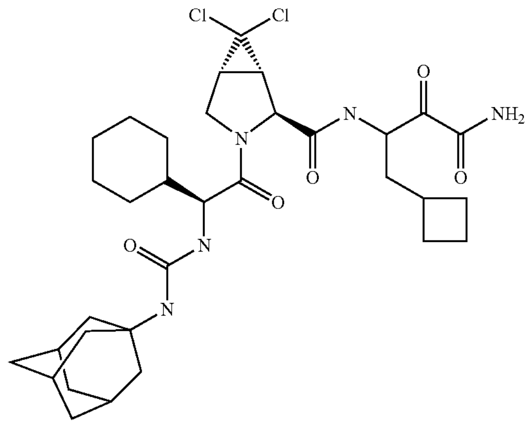 | 664.68 | A |
| 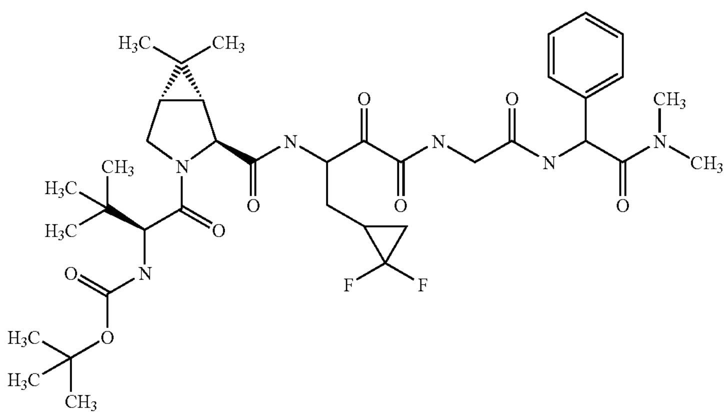 | 760.89 | A |
| 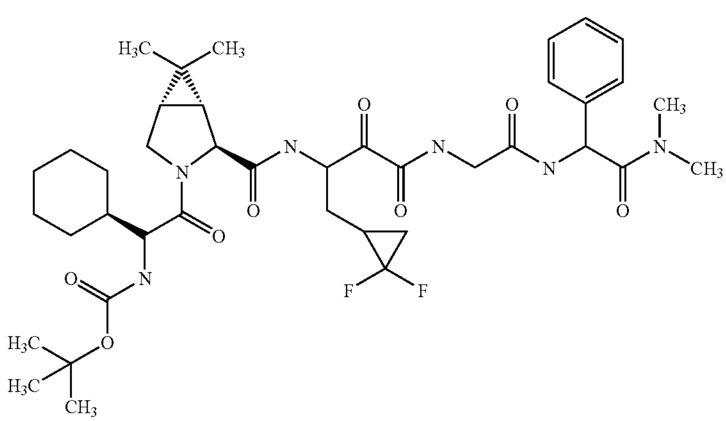 | 786.92 | A |

TABLE 6-continued
| STRUCTURE | MW | Ki* (nM) |
|---|---|---|
| 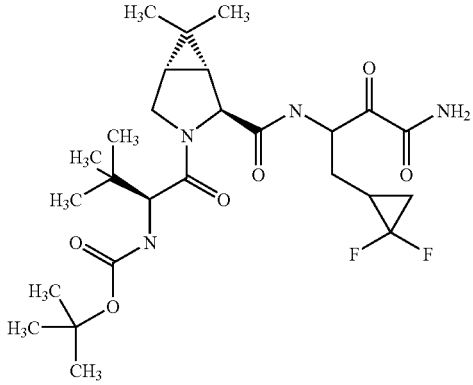 | 542.63 | A |
| 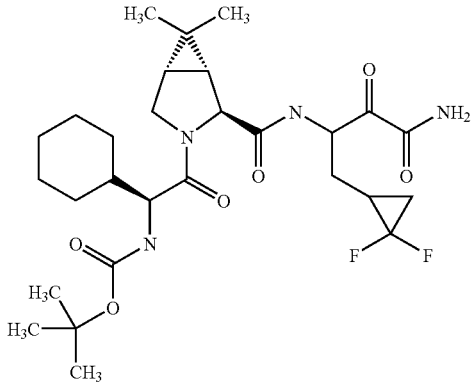 | 568.67 | A |
| 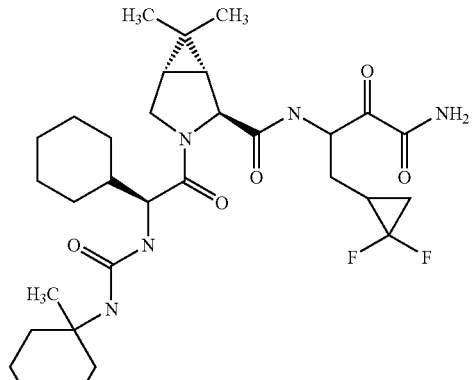 | 607.75 | A |

TABLE 6-continued
| STRUCTURE | MW | Ki* (nM) |
|---|---|---|
| 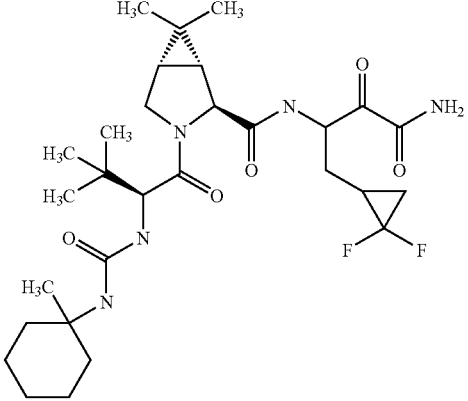 | 581.71 | A |
| 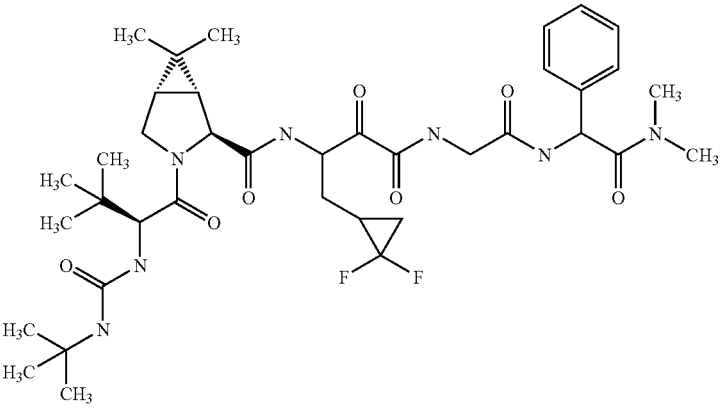 | 759.90 | A |
| 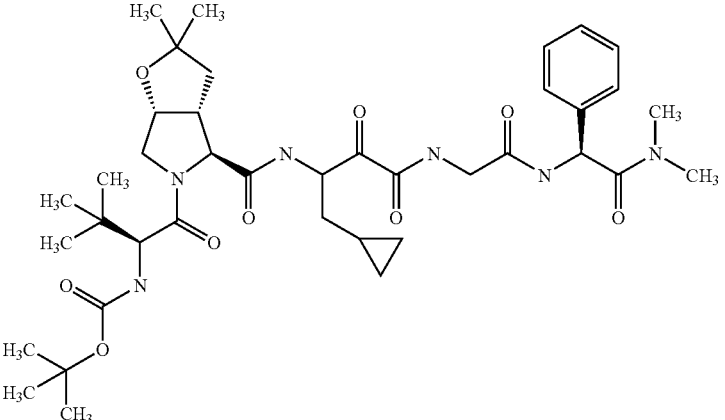 | 756.90 | A |

TABLE 6-continued

| STRUCTURE | MW | Ki* (nM) |
|---|---|---|
| 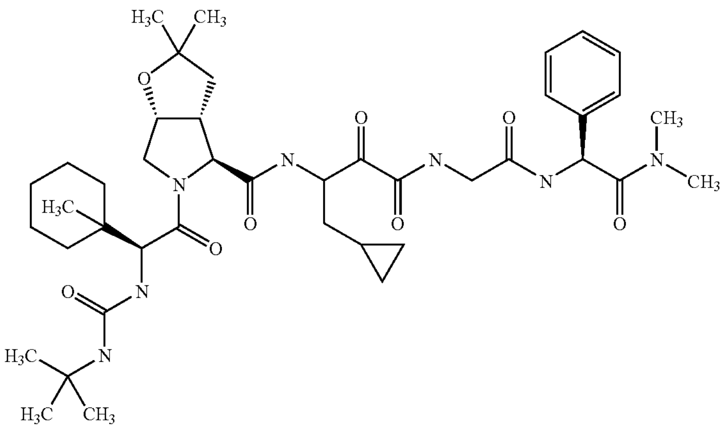 | 795.00 | A |
| 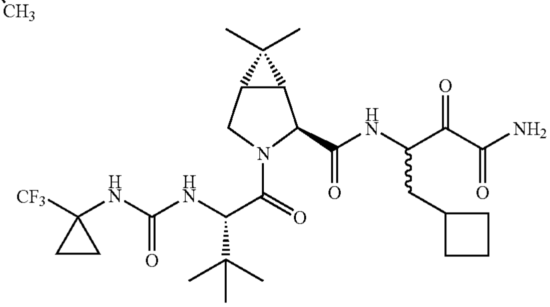 | 571.63 | A |

What is claimed is:

1. A pharmaceutical composition containing at least one antiviral agent, and at least one compound, or enantiomer, stereoisomer, rotamer, tautomer, racemate or prodrug of said compound, or pharmaceutically acceptable salts or solvates of said compound, or of said prodrug, said compound being selected from the group consisting of the compounds of the formulas 1-21:

1.

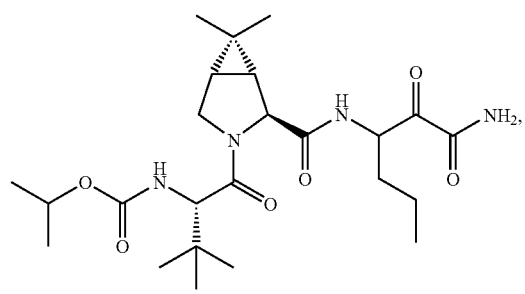

2.

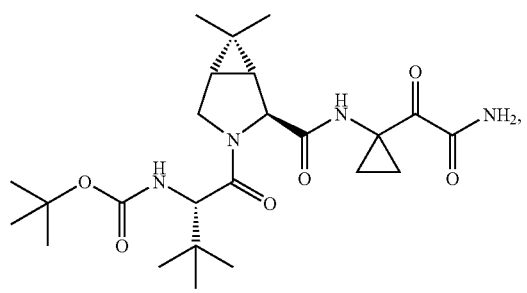

-continued

3.

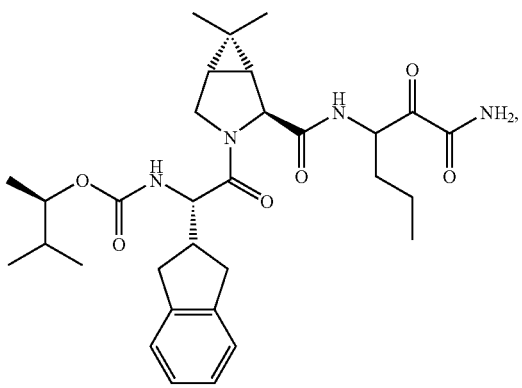

4.

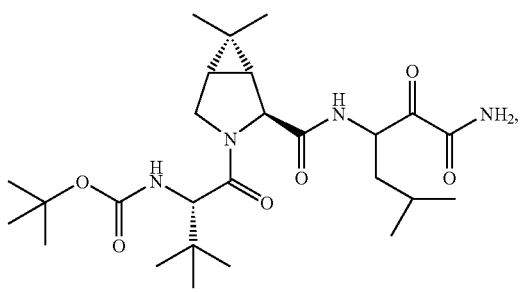

-continued
5.
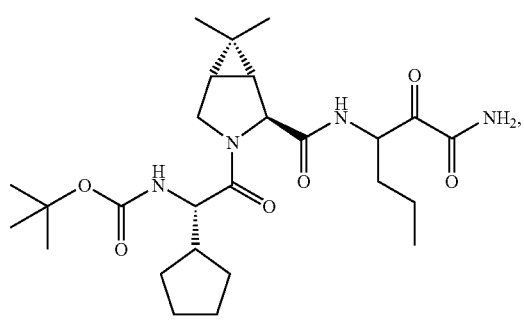
6.
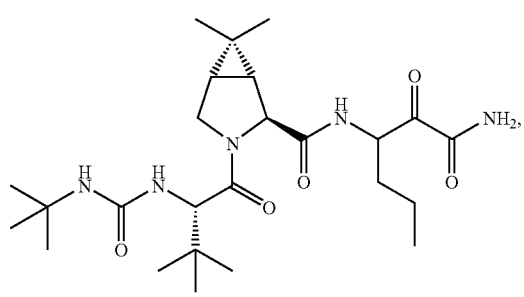
7.
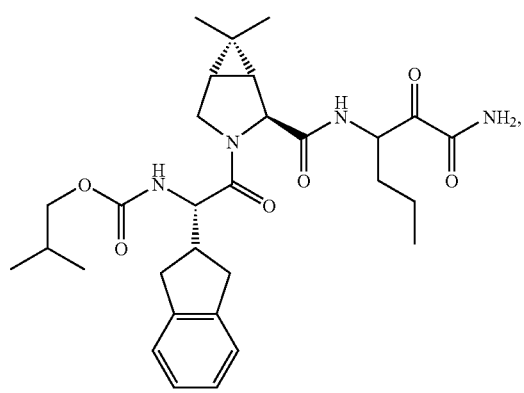
8.
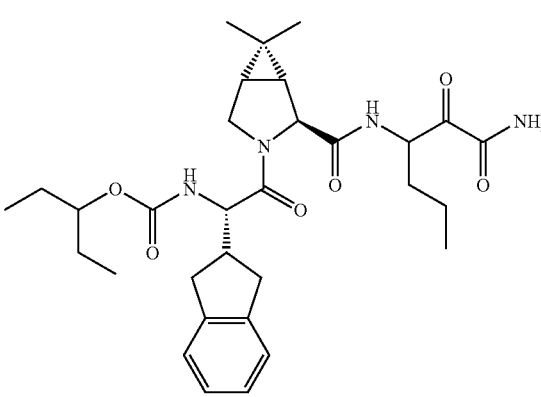
-continued
9.
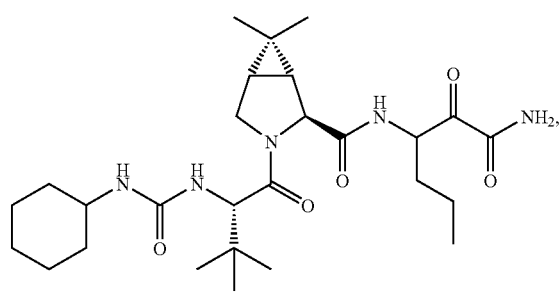
10.
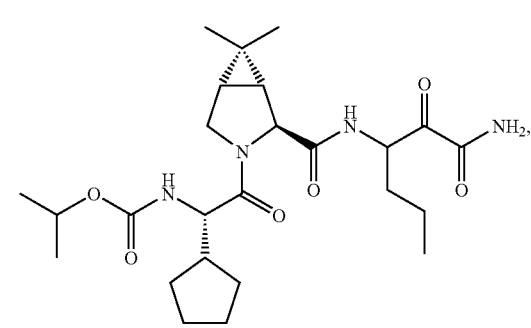
11.
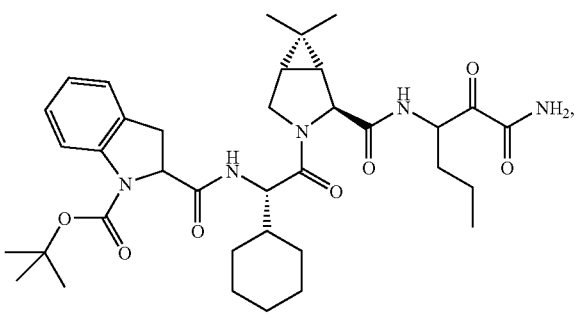
12.
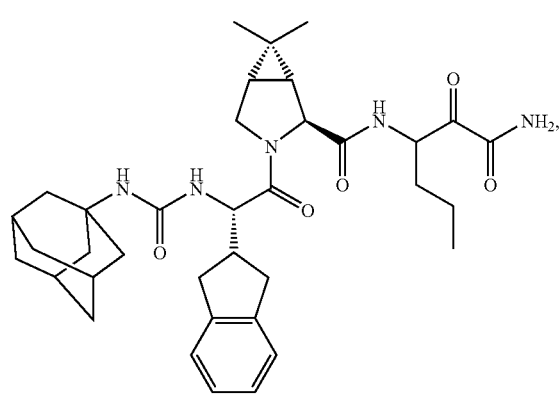

13.
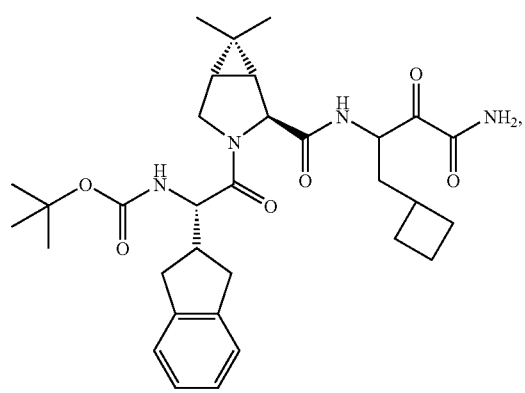
14.
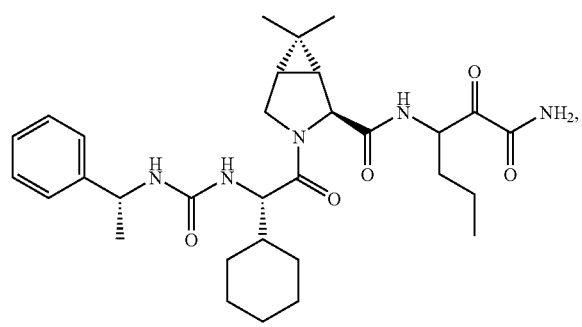
15.
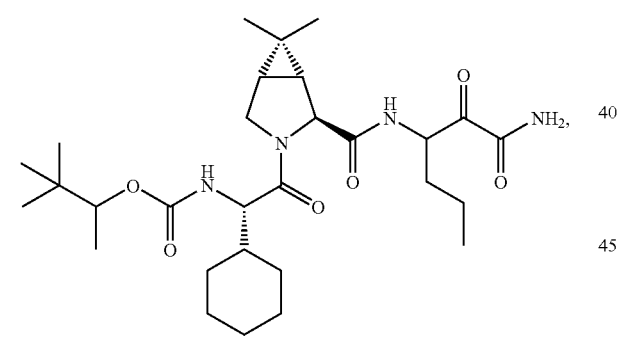
16.
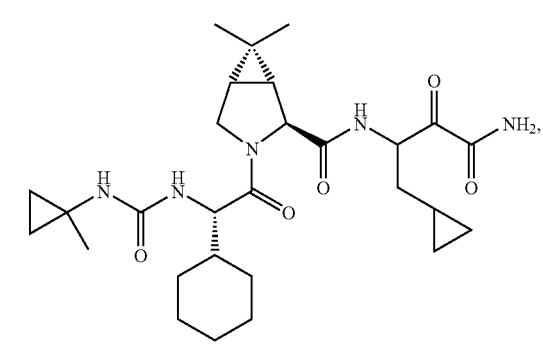
17.
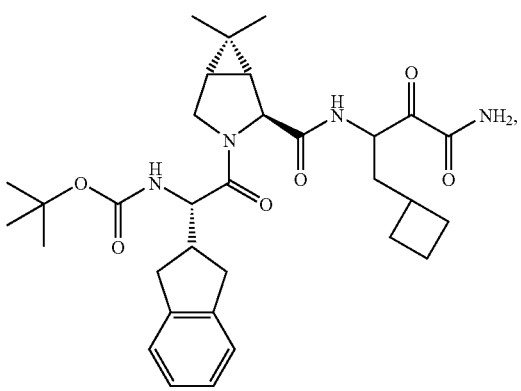
18.
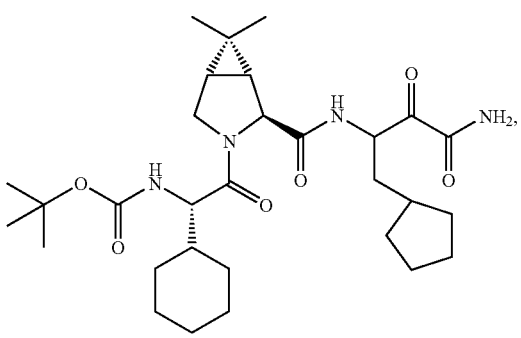
19.
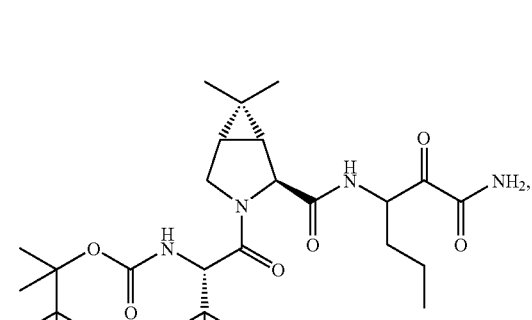
20.
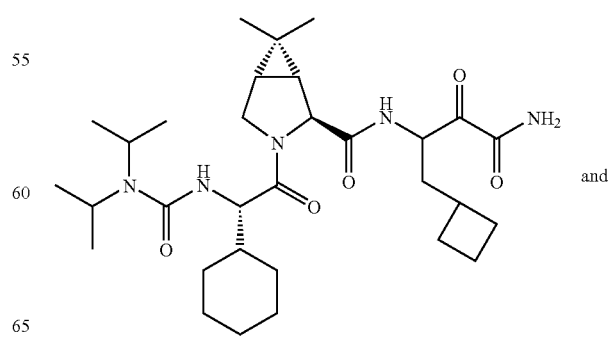
and -continued

21.

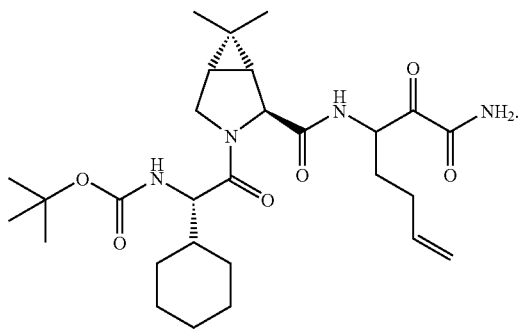

2. The pharmaceutical composition of claim 1, further containing at least one interferon or PEG-interferon alpha conjugate.

3. The pharmaceutical composition of claim 2, wherein said antiviral agent is ribavirin and said interferon is α-interferon.

4. The pharmaceutical composition of claim 2, wherein said antiviral agent is ribavirin and said interferon is interferon alpha-2a or interferon alpha-2b.

5. A method of inhibition of hepatitis C virus (HCV) replication, comprising administering to a patient in need thereof an effective amount of the pharmaceutical composition of claim 1.

6. A method of inhibition of hepatitis C virus (HCV) replication, comprising administering to a patient in need thereof an effective amount of the pharmaceutical composition of claim 4.

* * * * *